US012673946B2

(12) United States Patent
Shishido et al.

(10) Patent No.: US 12,673,946 B2
(45) Date of Patent: Jul. 7, 2026

(54) PYRIMIDIN-4(3H)-ONE DERIVATIVES AS TRPV4 ANTAGONISTS

(71) Applicant: RaQualia Pharma Inc., Aichi (JP)

(72) Inventors: Yuji Shishido, Aichi (JP); Tadashi Inoue, Aichi (JP); Tatsuya Yamagishi, Aichi (JP); Kazuo Ando, Aichi (JP); Yutaka Fukumoto, Aichi (JP); Ryohei Magara, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 761 days.

(21) Appl. No.: 17/921,203

(22) PCT Filed: Apr. 30, 2021

(86) PCT No.: PCT/JP2021/017277
§ 371 (c)(1),
(2) Date: Oct. 25, 2022

(87) PCT Pub. No.: WO2021/221169
PCT Pub. Date: Nov. 4, 2021

(65) Prior Publication Data

US 2023/0339934 A1 Oct. 26, 2023

Related U.S. Application Data

(60) Provisional application No. 63/017,891, filed on Apr. 30, 2020.

(51) Int. Cl.
*A61K 31/519* (2006.01)
*C07D 471/04* (2006.01)
*C07D 487/04* (2006.01)

(52) U.S. Cl.
CPC ......... *C07D 471/04* (2013.01); *C07D 487/04* (2013.01)

(58) Field of Classification Search
CPC ............................ A61K 31/519; C07D 487/04
USPC ....................................... 514/258.1; 544/279
See application file for complete search history.

(56) References Cited

U.S. PATENT DOCUMENTS 7,928,099 B2 * 4/2011 Andrews ................. A61P 15/00 514/215
2015/0038483 A1 2/2015 Yukimasa et al.
2016/0200721 A1 7/2016 Yukimasa et al.
2017/0066759 A1 3/2017 Yukimasa et al.
2019/0077769 A1 3/2019 Ma et al.
2021/0300859 A1 9/2021 Takamura et al.

FOREIGN PATENT DOCUMENTS

CN 101652367 2/2010
RU 2 718 913 4/2020
WO 2008/117169 10/2008
WO 2011/119701 9/2011
WO 2011/119704 9/2011
WO 2012/174340 12/2012
WO 2012/174342 12/2012
WO 2013/012500 1/2013
WO 2013/146754 10/2013
WO 2015/046193 4/2015
WO 2018/055524 3/2018
WO 2018/055526 3/2018
WO 2018/055527 3/2018
WO 2019/244937 12/2019

OTHER PUBLICATIONS

International Preliminary Report on Patentability issued Oct. 27, 2022 in International (PCT) Application No. PCT/JP2021/017277.
International Search Report dated Jul. 13, 2021 in International (PCT) Application No. PCT/JP2021/017277.
Registry on STN, CAS RN 859481-30-4, Aug. 10, 2005, 1 page.
Registry on STN, CAS RN 1043636-31-2, Aug. 26, 2008, 1 page.
Registry on STN, CAS RN 859091-90-0, Aug. 9, 2005, 1 page.
Registry on STN, CAS RN 856403-50-4, Jul. 21, 2005, 1 page.
Registry on STN, CAS RN 855216-09-0, Jul. 14, 2005, 1 page.
Registry on STN, CAS RN 858296-20-5, Aug. 4, 2005, 1 page.
Registry on STN, CAS RN 1044548-30-2, Aug. 28, 2008, 1 page.
Registry on STN, CAS RN 858550-42-2, Aug. 5, 2005, 1 page.
Liedtke, W., et al., "Vanilloid Receptor-Related Osmotically Activated Channel (VR-OAC), a Candidate Vertebrate Osmoreceptor", Cell, Oct. 27, 2000, vol. 103, pp. 525-535.
Watanabe, H., et al., "Anandamide and arachidonic acid use epoxyeicosatrienoic acids to activate TRPV4 channels", Nature, Jul. 24, 2003, vol. 424, pp. 434-438.
Watanabe, H., et al., "Heat-evoked Activation of TRPV4 Channels in a HEK293 Cell Expression System and in Native Mouse Aorta Endothelial Cells", The Journal of Biological Chemistry, Dec. 6, 2022, vol. 277, No. 49, pp. 47044-47051.
Watanabe, H., et al., "Activation of TRPV4 Channels (hVRL-2/mTRP12) by Phorbol Derivatives", The Journal of Biological Chemistry, Apr. 19, 2022, vol. 277, No. 16, pp. 13569-13577.

(Continued)

*Primary Examiner* — Douglas M Willis
(74) *Attorney, Agent, or Firm* — Wenderoth, Lind & Ponack, L.L.P.

(57) ABSTRACT

This invention relates to pyrimidin-4(3H)-one derivatives of formula (I), (I)

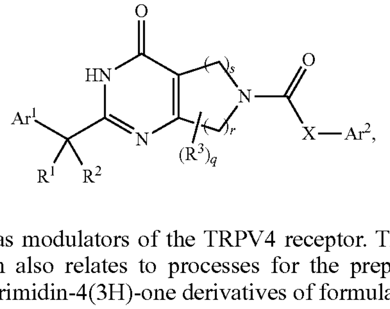

that act as modulators of the TRPV4 receptor. The present invention also relates to processes for the preparation of novel pyrimidin-4(3H)-one derivatives of formula (I) and to their use in the treatment of a wide range of diseases, syndromes, and disorders, in particular, for the treatment of inflammation, pain, and urological diseases or disorders.

23 Claims, No Drawings

(56) References Cited

OTHER PUBLICATIONS

Todaka, H., et al., "Warm Temperature-sensitive Transient Receptor Potential Vanilloid 4 (TRPV4) Plays an Essential Role in Thermal Hyperalgesia", The Journal of Biological Chemistry, Aug. 20, 2004, vol. 279, No. 34, pp. 35133-35138.
Lee, H., et al., "Altered Thermal Selection Behavior in Mice Lacking Transient Receptor Potential Vanilloid 4", The Journal of Neuroscience, Feb. 2, 2005, vol. 25, No. 5, pp. 1304-1310.
Alessandri-Haber, N., et al., "A Transient Receptor Potential Vanilloid 4-Dependent Mechanism of Hyperalgesia Is Engaged by Concerted Action of Inflammatory Mediators", The Journal of Neuroscience, Apr. 5, 2006, vol. 26, No. 14, pp. 3864-3874.
Alessandri-Haber, N., et al., "Transient Receptor Potential Vanilloid 4 Is Essential in Chemotherapy-Induced Neuropathic Pain in the Rat", The Journal of Neuroscience, May 5, 2004, vol. 24, No. 18, pp. 4444-4452.
Alessandri-Haber, N., et al., "Interaction of Transient Receptor Potential Vanilloid 4, Integrin, and Src Tyrosine Kinase in Mechanical Hyperalgesia", The Journal of Neuroscience, Jan. 30, 2008, vol. 28, No. 5, pp. 1046-1057.
Cenac, N., et al., "Transient Receptor Potential Vanilloid-4 Has a Major Role in Visceral Hypersensitivity Symptoms", Gastroenterology, 2008, vol. 135, pp. 937-946.
Everaerts, W., et al., "Inhibition of the cation channel TRPV4 improves bladder function in mice and rats with cyclophosphamide-induced cystitis", PNAS, Nov. 2, 2010, vol. 107, No. 44, pp. 19084-19089.
Mizuno, N., et al., "Impaired osmotic sensation in mice lacking TRPV4", Am J Physiol Cell Physiol, 2003, vol. 285, pp. C96-C101.
Köhler, R., et al., "Evidence for a Functional Role of Endothelial Transient Receptor Potential V4 in Shear Stress-Induced Vasodilatation", Arterioscler Thromb Vasc Biol., 2006, vol. 26, pp. 1495-1502.
Gevaert, T., et al., "Deletion of the transient receptor potential cation channel TRPV4 impairs murine bladder voiding", The Journal of Clinical Investigation, Nov. 2007, vol. 117, No. 11, pp. 3453-3462.
Thorneloe, K.S., et al., "N-((1S)-1-{[4-((2S)-2-{[(2,4-Dichlorophenyl)sulfonyl]amino}-3-hydroxypropanoyl)-1-piperazinyl]carbonyl}-3-methylbutyl)-1-benzothiophene-2-carboxamide (GSK1016790A), a Novel and Potent Transient Receptor Potential Vanilloid 4 Channel Agonist Induces Urinary Bladder Contraction and Hyperactivity: Part I", The Journal Of Pharmacology And Experimental Therapeutics, Sep. 2008, vol. 326, No. 2, pp. 432-442.
Masuyama, R., et al., "TRPV4-Mediated Calcium Influx Regulates Terminal Differentiation of Osteoclasts", Cell Metabolism, Sep. 3, 2008, vol. 8, pp. 257-265.
Cortright, D.N., et al., "TRP Channels and Pain", Current Pharmaceutical Design, 2009, vol. 15, pp. 1736-1749.
Jia, Y., et al., "Role of TRPV receptors in respiratory diseases", Biochimica et Biophysica Acta, 2007, vol. 1772, pp. 915-927.
Inoue, R., et al., "Mechanosensitive TRP channels in cardiovascular pathophysiology", Pharmacology & Therapeutics 2009, vol. 123, pp. 371-385.
Hsu, Y., et al., "TRP channels in kidney disease", Biochimica et Biophysica Acta, 2007, vol. 1772, pp. 928-936.
Casas, S., et al., "Calcium elevation in mouse pancreatic beta cells evoked by extracellular human islet amyloid polypeptide involves activation of the mechanosensitive ion channel TRPV4", Diabetologia, 2008, vol. 51, pp. 2252-2562.
Brierley, S.M., et al., "A selective role for TRPV4 ion channels in visceral sensory pathways", Gastroenterology, Jun. 2008, vol. 134, No. 7, pp. 2059-2069.
STN CAS Registry Nos. 1173064-88-4, 1172754-62-9, 1043645-14-2, 859132-94-8, 859119-11-2, 857867-17-5, 857866-38-7, 854615-60-4, 853359-58-7, 853356-83-9, 853217-92-2 (Dates entered: Jun. 29, 2005 to Aug. 5, 2009), 5 pages.
Extended European Search Report issued Apr. 18, 2024 in corresponding European Patent Application No. 21796562.3.
Registry on STN, Mar. 21, 2010, 3 pages: RN 1212485-50-1, RN 1212480-30-2, RN 1212462-15-1, RN 1212461-98-7, RN 1212455-00-9, RN 1212447-97-6.
Registry on STN, Jun. 29, 2005, 12 pages: RN 853251-83-9, RN 853250-96-1, RN 853249-31-7, RN 853244-82-3, RN 853239-45-9, RN 853238-62-7, RN 853237-52-2, RN 853235-30-0, RN 853224-51-8, RN 853221-52-0, RN 853221-51-9, RN 853221-50-8, RN 853219-84-8, RN 853219-83-7, RN 853219-82-6, RN 853219-81-5, RN 853219-80-4, RN 853218-93-6, RN 853218-80-1, RN 853218-22-1, RN 853218-21-0, RN 853218-20-9, RN 853218-19-6, RN 853218-18-5, RN 853218-17-4.
Office Action issued Oct. 23, 2024 in corresponding Russian Application No. 2022131009, with English-language translation.
Lazar, Janos et al., "Saturated Heterocycles, Part 172. Synthesis of 2,6-Disubstituted-5,6,7,8-tetrahydropyrido[4,3-d]pyrimidine Derivatives", J. Heterocyclic Chem., vol. 27, 1990, pp. 1885-1892.
Registry on STN, RN 1171745-47-3, Aug. 2, 2009.
Registry on STN, RN 1171705-15-9, Aug. 2, 2009.
Registry on STN, RN 1171681-64-3, Aug. 2, 2009.
Registry on STN, RN 1171549-67-9, Aug. 2, 2009.
Registry on STN, RN 1170220-19-5, Jul. 29, 2009.
Registry on STN, RN 1107706-41-1, Feb. 18, 2009.
Registry on STN, RN 1081463-17-3, Dec. 8, 2008.
Registry on STN, RN 1081326-66-0, Dec. 7, 2008.
Registry on STN, RN 1081180-02-0, Dec. 7, 2008.
Registry on STN, RN 1045583-07-0, Sep. 1, 2008.
Registry on STN, RN 1045521-60-5, Sep. 1, 2008.
Registry on STN, RN 1045520-08-8, Sep. 1, 2008.
Registry on STN, RN 1045519-99-0, Sep. 1, 2008.
Registry on STN, RN 1045516-65-1, Sep. 1, 2008.
Registry on STN, RN 1045516-57-1, Sep. 1, 2008.
Registry on STN, RN 1045492-34-9, Sep. 1, 2008.
Registry on STN, RN 1045059-67-3, Aug. 31, 2008.
Registry on STN, RN 1045054-94-1, Aug. 31, 2008.
Registry on STN, RN 1045053-61-9, Aug. 31, 2008.
Registry on STN, RN 1045037-77-1, Aug. 31, 2008.
Registry on STN, RN 1044568-77-5, Aug. 28, 2008.
Registry on STN, RN 1044546-43-1, Aug. 28, 2008.
Registry on STN, RN 1044536-78-8, Aug. 28, 2008.
Registry on STN, RN 1043643-50-0, Aug. 26, 2008.
Registry on STN, RN 1043643-49-7, Aug. 26, 2008.
Registry on STN, RN 1043635-82-0, Aug. 26, 2008.
Registry on STN, RN 1043608-83-8, Aug. 26, 2008.
Registry on STN, RN 1043594-59-7, Aug. 26, 2008.
Registry on STN, RN 861991-94-8, Aug. 29, 2005.
Registry on STN, RN 861692-76-4, Aug. 24, 2005.
Registry on STN, RN 861691-41-0, Aug. 24, 2005.
Registry on STN, RN 860128-73-0, Aug. 15, 2005.
Registry on STN, RN 860083-25-6, Aug. 12, 2005.
Registry on STN, RN 860074-82-4, Aug. 12, 2005.
Registry on STN, RN 859467-40-6, Aug. 10, 2005.
Registry on STN, RN 859384-21-7, Aug. 10, 2005.
Registry on STN, RN 859355-39-8, Aug. 10, 2005.
Registry on STN, RN 859350-48-4, Aug. 10, 2005.
Registry on STN, RN 859116-23-7, Aug. 9, 2005.
Registry on STN, RN 859091-47-7, Aug. 9, 2005.
Registry on STN, RN 858970-23-7, Aug. 8, 2005.
Registry on STN, RN 858923-21-4, Aug. 8, 2005.
Registry on STN, RN 858913-98-1, Aug. 8, 2005.
Registry on STN, RN 858912-93-3, Aug. 8, 2005.
Registry on STN, RN 858778-35-5, Aug. 7, 2005.
Registry on STN, RN 858720-10-2, Aug. 7, 2005.
Registry on STN, RN 858529-56-3, Aug. 5, 2005.
Registry on STN, RN 858301-11-8, Aug. 4, 2005.
Registry on STN, RN 858086-27-8, Aug. 3, 2005.
Registry on STN, RN 858061-93-5, Aug. 3, 2005.
Registry on STN, RN 858060-10-3, Aug. 3, 2005.
Registry on STN, RN 857889-72-6, Aug. 1, 2005.
Registry on STN, RN 857667-56-2, Jul. 29, 2005.
Registry on STN, RN 856394-34-8, Jul. 21, 2005.
Registry on STN, RN 856390-31-3, Jul. 21, 2005.

(56) References Cited

OTHER PUBLICATIONS

Registry on STN, RN 856229-53-3, Jul. 20, 2005.
Registry on STN, RN 856146-43-5, Jul. 20, 2005.
Registry on STN, RN 856138-40-4, Jul. 20, 2005.
Registry on STN, RN 855663-86-4, Jul. 18, 2005.
Registry on STN, RN 855512-56-0, Jul. 15, 2005.
Registry on STN, RN 855442-46-5, Jul. 15, 2005.
Registry on STN, RN 855175-92-7, Jul. 14, 2005.
Registry on STN, RN 855137-26-7, Jul. 14, 2005.
Registry on STN, RN 854978-34-0, Jul. 13, 2005.
Registry on STN, RN 854956-97-1, Jul. 13, 2005.
Registry on STN, RN 854606-08-9, Jul. 12, 2005.
Registry on STN, RN 854605-32-6, Jul. 12, 2005.
Registry on STN, RN 854510-71-7, Jul. 11, 2005.
Registry on STN, RN 854502-40-2, Jul. 11, 2005.
Registry on STN, RN 854440-12-3, Jul. 11, 2005.
Registry on STN, RN 854411-45-3, Jul. 11, 2005.
Registry on STN, RN 854336-79-1, Jul. 10, 2005.
Registry on STN, RN 854335-88-9, Jul. 10, 2005.
Registry on STN, RN 854321-25-8, Jul. 10, 2005.
Registry on STN, RN 854308-93-3, Jul. 10, 2005.
Registry on STN, RN 854249-02-8, Jul. 8, 2005.
Registry on STN, RN 854237-78-8, Jul. 8, 2005.
Registry on STN, RN 854191-71-2, Jul. 8, 2005.
Registry on STN, RN 854174-94-0, Jul. 8, 2005.
Registry on STN, RN 854094-72-7, Jul. 7, 2005.
Registry on STN, RN 854079-15-5, Jul. 7, 2005.
Registry on STN, RN 853722-42-6, Jul. 4, 2005.
Registry on STN, RN 853721-49-0, Jul. 4, 2005.
Registry on STN, RN 853719-40-1, Jul. 4, 2005.
Registry on STN, RN 853702-30-4, Jul. 4, 2005.
Registry on STN, RN 853692-34-9, Jul. 4, 2005.
Registry on STN, RN 853345-57-0, Jun. 30, 2005.
Registry on STN, RN 853250-96-1, Jun. 29, 2005.

* cited by examiner

PYRIMIDIN-4(3H)-ONE DERIVATIVES AS TRPV4 ANTAGONISTS

CROSS-REFERENCE TO RELATED APPLICATIONS

This application is a U.S. national stage application of International Application No. PCT/JP2021/017277, filed Apr. 30, 2021, which claims benefit of U.S. Provisional Application No. 63/017,891, filed Apr. 30, 2020, which is incorporated by reference herein in its entirety.

TECHNICAL FIELD

This invention relates to pyrimidin-4(3H)-one derivatives that act as modulators of the TRPV4 receptor. The present invention also relates to processes for the preparation of novel pyrimidin-4(3H)-one derivatives and to their use in the treatment of a wide range of diseases, syndromes, and disorders, in particular for the treatment of inflammatory, pain, and urological diseases or disorders.

BACKGROUND ART

Transient receptor potential 4 (TRPV4) is a $Ca^{2+}$-permeable non-selective cation channel belonging to the vanilloid subfamily of the TRP channels. TRPV4 was originally identified as a channel activated by hypotonicity-induced cell swelling, but it is also activated by a wide variety of physical and chemical stimuli, including heat (>24-27° C.), mechano-stimuli, endogenous substances such as arachidonic acid and its cytochrome P450-derived metabolites (epoxyeicosatrienoic acids), endocannabinoids (anandamide and 2-arachidonoylglycerol), as well as synthetic-phorbol derivatives (e.g. 4alpha-PDD) (NPL1: Liedtke, W., et al., Cell, 2000, 103, 525-535; NPL2: Watanabe, H., et al., Nature, 2003, 424, 434-438; NPL3: Watanabe, H., et al., J Biol Chem, 2002, 277, 47044-47051; and NPL4: Watanabe, H., et al., J Biol Chem, 2002, 277, 13569-13577). TRPV4 is a multimodal channel regulated by diverse stimuli and functions as an integrator summing the effects of contributions of all activators.

TRPV4 channels are expressed in pain pathways including dorsal root ganglia and trigeminal ganglia neurons. The use of TRPV4 knockout mice and TRPV4 knockdown studies has implicated TRPV4 in both inflammatory and neuropathy-induced pain states. TRPV4 knockout mice display reduced thermal hyperalgesia after inflammation induced by carrageenan or complete Freund's adjuvant (NPL5: Tadaka, H., et al., J Biol Chem, 2004, 279, 35133-35138). Intrathecal injection of TRPV4 antisense oligonucleotide (ODN) reduces the mechanical hyperalgesia induced by carrageenan or inflammatory mediators (NPL6: Lee, H., et al., J Neurosci, 2005, 25, 1304-1310). Similarly, TRPV4 knockout mice display reduced mechanical hyperalgesia associated with chemotherapy or diabetes-induced neuropathy (NPL7: Alessandri-Haber, N., et al., J Neurosci, 2006, 26, 3864-3874). Intrathecal administration of TRPV4 antisense ODN markedly reduces the mechanical hyperalgesia and enhanced nociceptive behavior responses to hypotonic stimulation in chemotherapy, alcoholism, diabetes and HIV therapy-induced neuropathy models (NPL8: Alessandri-Haber, N., et al., J Neurosci, 2004, 24, 4444-4452; and NPL9: Alessandri-Haber, N., et al., J Neurosci, 2008, 28, 1046-1057). TRPV4 is enriched in colonic sensory neurons. The behavioral responses to noxious colonic distention are substantially reduced in TRPV4 knockout mice. Inflammatory mediator- (e.g. PAR2 agonists, serotonin, and histamine) induced hyperalgesia and allodynia to colorectal distension is also significantly inhibited by TRPV4 knockdown (NPL10: Cenac, N., et al., Gastroenterology, 2008, 135, 937-946).

TRPV4 is highly expressed in the urothelial cells and plays a role in sensing the bladder filling. The development of cystitis-induced bladder dysfunction is strongly impaired in TRPV4 knockout mice. TRPV4 antagonist increased functional bladder capacity and reduced micturition frequency in mice and rats with cystitis (NPL11: Everaerts, W., et al., Proc Natl Acad Sci USA, 2010, 107, 19084-19089).

TRPV4 has a wide distribution in diverse peripheral tissues, including the lung, spleen, testis, fat, brain, cochlea, skin, smooth muscle, kidney, liver, vascular endothelium, central nervous system, peripheral nervous system, and bone. Using TRPV4 knockout/knockdown strategies, TRPV4 has been implicated in numerous physiological processes, including osmotic homeostasis, thermo- and mechano-sensation, vasoregulation, tuning of neuronal excitability, bladder voiding, and bone formation (NPL12: Mizuno, N., et al., Am J Physiol Cell Physiol, 2003, 285, C96-101.; NPL5: Tadaka, H., et al., J Biol Chem, 2004, 279, 35133-35138; NPL7: Alessandri-Haber, N., et al., J Neurosci, 2006, 26, 3864-3874; NPL13: Koehler, R., et al. Arterioscler Thromb Vasc Biol, 2006, 26, 1495-1502; NPL14: Gevaert, T., et al., J Clin Invest, 2007, 117, 3453-3462; NPL15: Thorneloe, K. S., et al. J Pharmacol Exp Ther, 2008, 326, 432-442; and NPL16: Masuyama, R., et al., Cell Metab, 2008, 8, 257-265).

The compounds having TRPV4 inhibitory activity are disclosed in Patent Literature 1 to 10. However, the compounds of the present invention are not disclosed in any documents.

CITATION LIST

Patent Literature

{PL1} WO2019244937
{PL2} WO2018055527
{PL3} WO2018055526
{PL4} WO2018055524
{PL5} WO2013012500
{PL6} WO2012174342
{PL7} WO2012174340
{PL8} WO2011119701
{PL9} WO2013146754
{PL10} WO2015046193

Non-Patent Literature

{NPL1} Liedtke, W., et al., Cell, 2000, 103, 525-535
{NPL2} Watanabe, H., et al., Nature, 2003, 424, 434-438
{NPL3} Watanabe, H., et al., J Biol Chem, 2002, 277, 47044-47051
{NPL4} Watanabe, H., et al., J Biol Chem, 2002, 277, 13569-13577
{NPL5} Tadaka, H., et al., J Biol Chem, 2004, 279, 35133-35138
{NPL6} Lee, H., et al., J Neurosci, 2005, 25, 1304-1310
{NPL7} Alessandri-Haber, N., et al., J Neurosci, 2006, 26, 3864-3874
{NPL8} Alessandri-Haber, N., et al., J Neurosci, 2004, 24, 4444-4452
{NPL9} Alessandri-Haber, N., et al., J Neurosci, 2008, 28, 1046-1057

{NPL10} Cenac, N., et al., Gastroenterology, 2008, 135, 937-946

{NPL11} Everaerts, W., et al., Proc Natl Acad Sci USA, 2010, 107, 19084-19089

{NPL12} Mizuno, N., et al., Am J Physiol Cell Physiol, 2003, 285, C96-101

{NPL13} Koehler, R., et al. Arterioscler Thromb Vasc Biol, 2006, 26, 1495-1502

{NPL14} Gevaert, T., et al., J Clin Invest, 2007, 117, 3453-3462

{NPL15} Thorneloe, K. S., et al. J Pharmacol Exp Ther, 2008, 326, 432-442

{NPL16} Masuyama, R., et al., Cell Metab, 2008, 8, 257-265

{NPL17} Cortright, D. N., et al., Curr Pharm Des, 2009, 15, 1736-1749

{NPL18} Jia, Y. et al., Biochim Biophys Acta, 2007, 1772, 915-927

{NPL19} Inoue, R., et al., Pharmacol Ther, 2009, 123, 371-385

{NPL20} Hsu, Y. J., et al., Biochim Biophys Acta, 2007, 1772, 928-936

{NPL21} Casas, S., et al., Diabetologia, 2008, 51, 2252-2562

{NPL22} Brierley, S. M., et al., Gastroenterology, 2008, 134, 2059-2069

SUMMARY OF INVENTION

Technical Problem

There is a need in the art for TRPV4 antagonists that can be used to treat a disease, syndrome, condition, or disorder in a mammal in which the disease, syndrome, condition, or disorder is affected by the modulation of TRPV4 channels, such chronic pain, neuropathic pain including diabetic neuropathy, postoperative pain, osteoarthritis, rheumatoid arthritic pain, cancer pain, neuralgia, neuropathies, algesia, nerve injury, cardiovascular disease, kidney disease, diabetes, irritable bowel syndrome, inflammatory bowel disease, inflammatory disorders including asthma, chronic obstructive pulmonary disease (COPD) and chronic obstructive airway disease (COAD), urological diseases or disorders including detrusor overactivity or overactive bladder, urinary incontinence (NPL17: Cortright, D. N., et al., Curr Pharm Des, 2009, 15, 1736-1749; NPL18: Jia, Y. et al., Biochim Biophys Acta, 2007, 1772, 915-927; NPL19: Inoue, R., et al., Pharmacol Ther, 2009, 123, 371-385; NPL20: Hsu, Y. J., et al., Biochim Biophys Acta, 2007, 1772, 928-936; NPL21: Casas, S., et al., Diabetologia, 2008, 51, 2252-2562; NPL22: Brierley, S. M., et al., Gastroenterology, 2008, 134, 2059-2069; NPL15: Thorneloe, K. S., et al. J Pharmacol Exp Ther, 2008, 326, 432-442; and NPL16: Masuyama, R., et al., Cell Metab, 2008, 8, 257-265).

Solution to Problem

With respect to other compounds disclosed in the art, the compounds of the present invention may show less toxicity, preferable absorption and distribution, preferable solubility, preferable plasma protein binding, less drug-drug interaction, preferable metabolic stability, reduced inhibitory activity at HERG channel, and/or reduced QT prolongation.

The gist of the present invention is as follows:

[1] A compound of the following formula (I):

{Chem. 1}

(I)

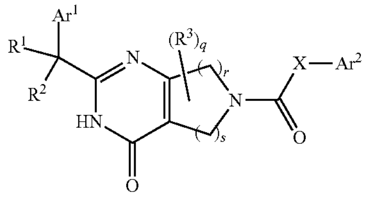

wherein $R^1$ and $R^2$ are independently selected from the group consisting of: hydrogen, hydroxyl, halogen, $(C_1\text{-}C_6)$alkyl, $(C_1\text{-}C_6)$haloalkyl, $(C_1\text{-}C_6)$alkoxy, $(C_1\text{-}C_6)$haloalkoxy, $(C_3\text{-}C_7)$cycloalkyl, and phenyl$(C_0\text{-}C_4)$alkyl; wherein the said $(C_3\text{-}C_7)$cycloalkyl or phenyl$(C_0\text{-}C_4)$alkyl is optionally substituted with 1 to 4 substituents independently selected from the group consisting of: halogen, hydroxyl, $(C_1\text{-}C_6)$alkyl, $(C_1\text{-}C_6)$haloalkyl, $(C_1\text{-}C_6)$alkoxy, and $(C_1\text{-}C_6)$haloalkoxy; or alternatively $R^1$ and $R^2$, together with the atom to which they are attached, may form a 3 to 8 membered ring which may contain 0 to 4 heteroatoms independently selected from oxygen, sulfur, and nitrogen; wherein the said 3 to 8 membered ring is optionally substituted with 1 to 6 substituents independently selected from the group consisting of: halogen, hydroxyl, $(C_1\text{-}C_6)$alkyl, $(C_1\text{-}C_6)$haloalkyl, $—SO_2(C_1\text{-}C_6)$alkyl, $—SO_2(C_1\text{-}C_6)$haloalkyl, $—C(═O)(C_1\text{-}C_6)$alkyl, and $—C(═O)(C_1\text{-}C_6)$haloalkyl; preferably $R^1$ and $R^2$ are independently selected from the group consisting of: hydrogen, $(C_1\text{-}C_6)$alkyl, $(C_1\text{-}C_6)$haloalkyl, $(C_1\text{-}C_6)$alkoxy, $(C_1\text{-}C_6)$haloalkoxy, and $(C_3\text{-}C_7)$cycloalkyl; or alternatively $R^1$ and $R^2$, together with the atom to which they are attached, may form a 3 to 8 membered carbon ring;

$R^3$ is independently selected from the group consisting of: hydrogen, fluoride, methyl, ethyl, and $(C_1\text{-}C_6)$haloalkyl; preferably $R^3$ is independently selected from the group consisting of: hydrogen, fluoride, and methyl;

X is selected from the group consisting of: a chemical bond, $—N(R^4)—$, $—(C(R^5)(R^6))_n—$, $—(C_3\text{-}C_8)$cycloalkyl-, $—C(R^5)═C(R^6)—$, $—C(═O)—$, $—CR^4(N(R^5)(R^6))—$, $—[(C(R^5)(R^6))_nO]—$, $—[(C(R^5)(R^6))_nN(R^4)]—$, $—[(C(R^5)(R^6))_nS]—$, and $—[N(R^4)(C(R^5)(R^6))_n]—$; preferably X is selected from the group consisting of: a chemical bond, $—(C(R^5)(R^6)—(CH_2)_m)—$, $—(C_3\text{-}C_8)$cycloalkyl-, $—CH═CH—$, and $—CH_2O—$; m is 0, 1, 2, or 3; more preferably X is selected from the group consisting of: a chemical bond, $—C(R^5)(R^6)CH_2—$, $—C(R^5)(R^6)—$, -cyclopropyl-, $—CH═CH—$, and $—CH_2O—$; further more preferably X is selected from the group consisting of: a chemical bond, $—CH_2—$, $—CF_2—$, $—CH_2CH_2—$, $—CH(OH)—$, and $—CH(Me)$-;

$R^4$ is hydrogen or $(C_1\text{-}C_6)$ alkyl;

$R^5$ and $R^6$ are independently selected from the group consisting of: hydrogen, halogen, hydroxyl, $(C_1\text{-}C_6)$alkyl, $(C_1\text{-}C_6)$alkoxy, hydroxyl$(C_1\text{-}C_6)$alkyl, $(C_1\text{-}C_6)$alkoxy$(C_1\text{-}C_6)$alkyl, $(C_1\text{-}C_6)$haloalkyl, and $(C_1\text{-}C_6)$haloalkoxy; preferably $R^5$ and $R^6$ are independently selected from the group consisting of: hydrogen, halogen, hydroxyl, and $(C_1\text{-}C_6)$alkyl; more preferably $R^5$ and $R^6$ are independently selected from the group consisting of: hydrogen, fluorine, hydroxyl, and methyl;

when $R^5$ is two or more than two, $R^5$ is same or different;

when $R^6$ is two or more than two, $R^6$ is same or different;

n is 1, 2, 3, or 4; preferably n is 1 or 2;

q is 1, 2, 3, or 4; preferably q is 1 or 2;

r is 1, 2, 3, or 4; preferably r is 1 or 2;

s is 1, 2, 3, or 4; preferably s is 1 or 2;

$Ar^1$ is selected from aryl and heteroaryl which are optionally substituted with 1 to 6 substituents independently selected from the group consisting of: hydrogen, halogen, cyano, nitro, hydroxyl, —C(═O)$R^7$, —C(═O)$NR^7R^8$, —$NHSO_2R^7$, —$SO_2NR^7R^8$, $(C_1\text{-}C_6)$alkylthio-, $(C_1\text{-}C_6)$haloalkylthio-, $(C_1\text{-}C_6)$alkylsulfinyl, $(C_1\text{-}C_6)$alkylsulfonyl, —$NR^7R^8$, tri$(C_1\text{-}C_6)$alkylsilyl, $(C_1\text{-}C_6)$alkyl, $(C_3\text{-}C_7)$cycloalkyl, $(C_3\text{-}C_7)$cycloalkoxy, $(C_1\text{-}C_6)$alkoxy, $(C_1\text{-}C_6)$alkenyl, aryl$(C_0\text{-}C_4)$alkyl, heteroaryl$(C_0\text{-}C_4)$alkyl, aryl$(C_0\text{-}C_6)$alkoxy, heterocyclyl$(C_0\text{-}C_4)$alkyl, heterocyclyl$(C_0\text{-}C_6)$alkoxy, heteroaryl$(C_0\text{-}C_6)$alkoxy and substituent group Q; wherein the said $(C_1\text{-}C_6)$alkyl, $(C_3\text{-}C_7)$cycloalkyl, $(C_3\text{-}C_7)$cycloalkoxy, $(C_1\text{-}C_6)$alkoxy, $(C_1\text{-}C_6)$alkenyl, aryl$(C_0\text{-}C_4)$alkyl, heteroaryl$(C_0\text{-}C_4)$alkyl, aryl$(C_0\text{-}C_6)$alkoxy, heterocyclyl$(C_0\text{-}C_4)$alkyl, heterocyclyl$(C_0\text{-}C_6)$alkoxy, or heteroaryl$(C_0\text{-}C_6)$alkoxy is optionally substituted with 1 to 6 substituents independently selected from the group consisting of: halogen, hydroxyl, cyano, $(C_1\text{-}C_6)$alkyl, $(C_3\text{-}C_7)$cycloalkyl, $(C_1\text{-}C_6)$haloalkyl, $(C_1\text{-}C_6)$alkoxy, $(C_1\text{-}C_6)$alkoxy$(C_1\text{-}C_6)$alkyl, $(C_1\text{-}C_6)$alkoxy$(C_1\text{-}C_6)$alkoxy, $(C_1\text{-}C_6)$haloalkoxy, phenyl, —$NR^aR^b$, $R^aR^b$N$(C_1\text{-}C_6)$alkyl, $R^aR^b$N$(C_1\text{-}C_6)$alkoxy, —C(═O)$NR^aR^b$, —C(═O)$R^a$, —$SO_2(C_1\text{-}C_6)$alkyl, —$SO_2NR^aR^b$, and $R^aR^b$NC(═O)$(C_1\text{-}C_6)$alkoxy;

wherein the said $(C_3\text{-}C_7)$cycloalkyl is optionally substituted with hydroxyl or cyano; wherein the substituent group Q is {Chem. 2}

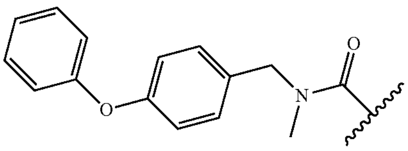
,

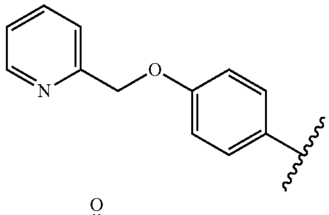
,

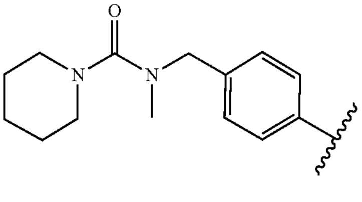
,

-continued

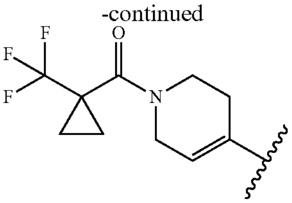
,

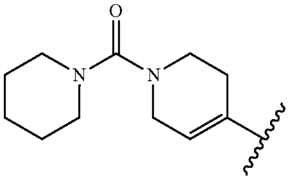
,

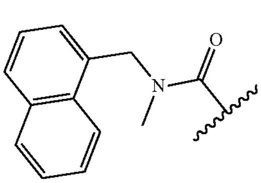
,
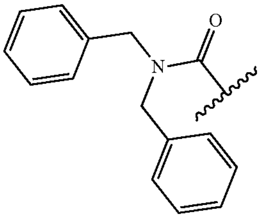
,

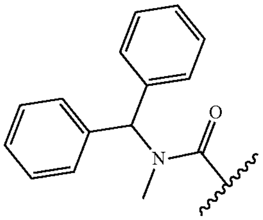
,

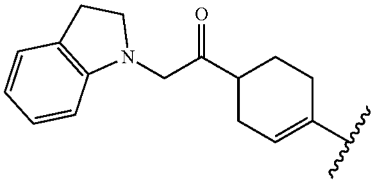
,

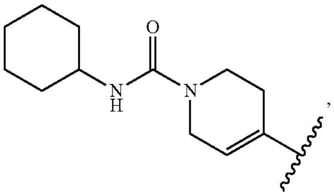
,

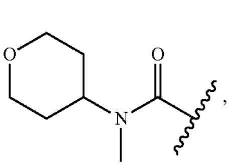
,
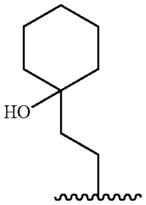
,

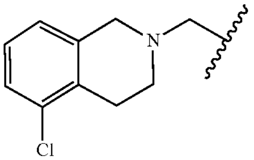
,

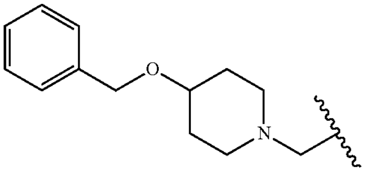
,

-continued
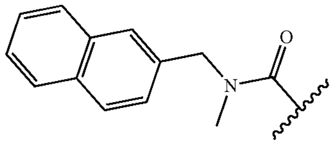,
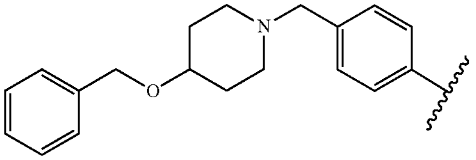,
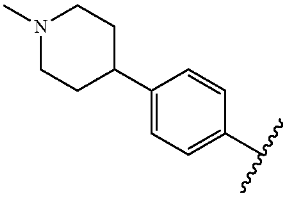,
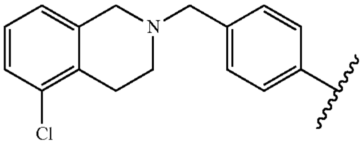,
{Chem. 3}
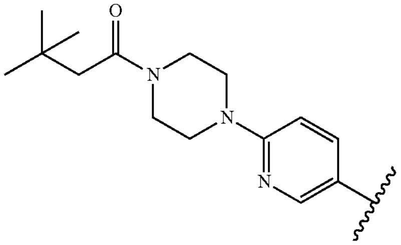,
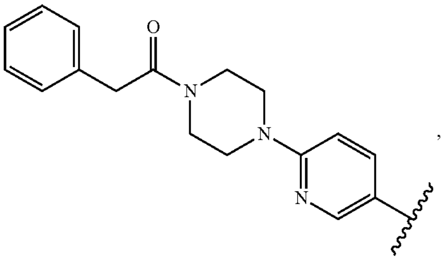,
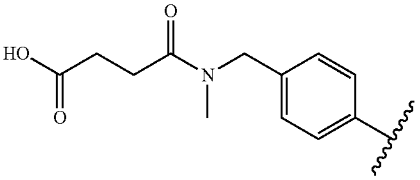,
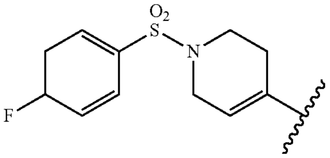,
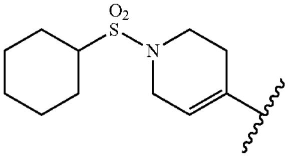,
-continued
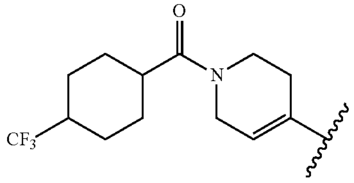,
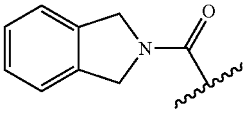,
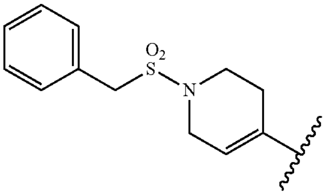,
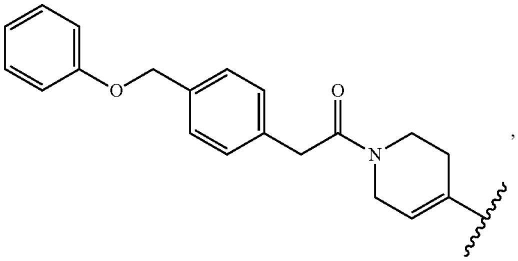,
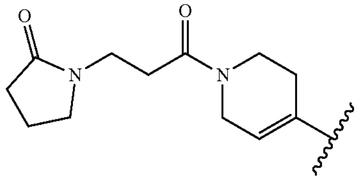,
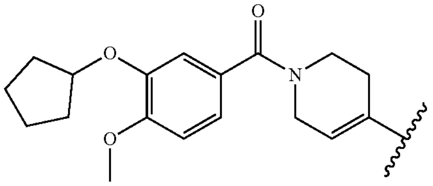,
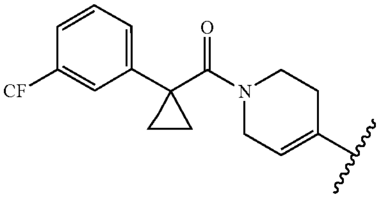,
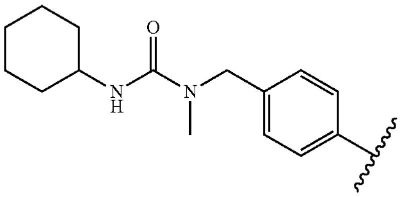, -continued

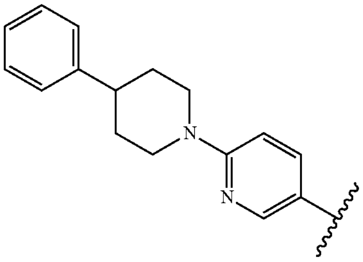

,

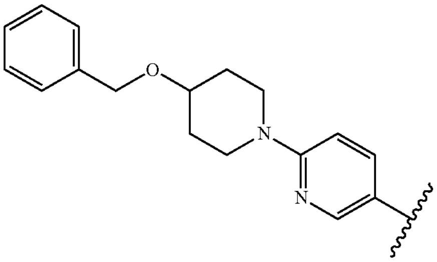

,

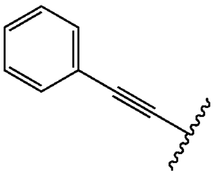

,

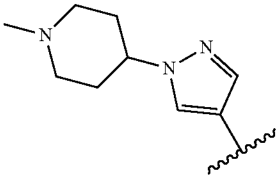

,

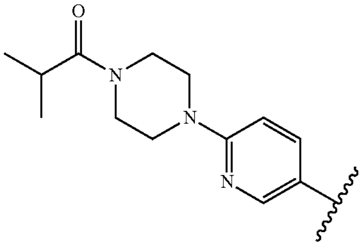

,

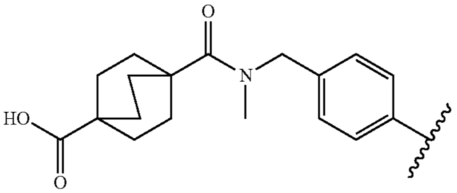

,

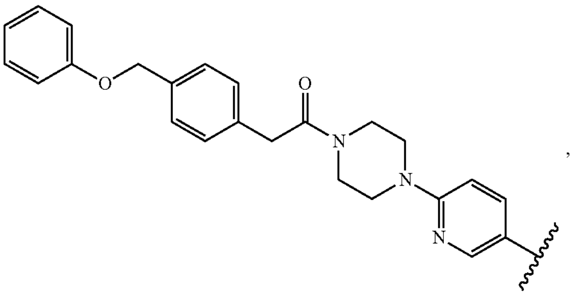

,

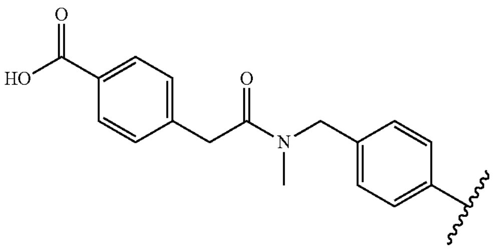

,

-continued

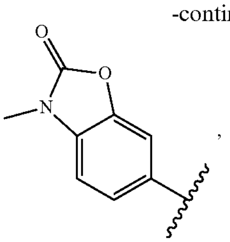

,

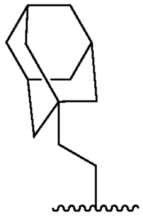

, or

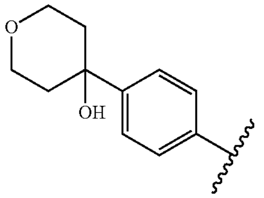

;

in which the substituent group Q may be optionally substituted with halogen, hydroxyl, or $(C_1-C_6)$alkyl;

preferably aryl is phenyl or naphthyl, and preferably heteroaryl is unsaturated or partially saturated mono- or bi-cyclic 5 to 15-membered ring with 1-4 heteroatoms independently selected from O, N, and S, or carbonyl; more preferably aryl is phenyl and more preferably heteroaryl is 5 to 6-membered ring with 1-4 heteroatoms independently selected from O, N, and S, or 9 to 10-membered heteroaromatic ring with 1-4 heteroatoms independently selected from O, N, and S; further more preferably aryl is phenyl and further more preferably heteroaryl is 5 to 6-membered heteroaromatic ring with 1-4 heteroatoms independently selected from O, N, and S; further more preferably heteroaryl is pyridinyl, pyrimidinyl, pyridazinyl, pyrazinyl, pyrrolyl, furanyl, thiophenyl, imidazolyl, pyrazolyl, oxazolyl, isoxazoyl, thiazolyl, isothiazolyl, indolyl, benzimidazolyl, benzofuranyl, benzothiophenyl, imidazopyridinyl, indazolyl, oxadiazolyl, benzoisoxazolyl, quinazolinyl, quinoxalinyl, quinolinyl, or isoquinolinyl;

$R^7$ and $R^8$ are independently selected from the group consisting of: hydrogen, hydroxyl, $(C_1-C_6)$alkyl, $(C_1-C_6)$alkoxy, $(C_1-C_6)$haloalkyl, $(C_1-C_6)$haloalkoxy, $(C_3-C_7)$cycloalkyl, heterocyclyl, hydroxy$(C_1-C_6)$alkyl, $(C_1-C_6)$alkoxy$(C_1-C_6)$alkyl, $(C_1-C_6)$haloalkoxy$(C_1-C_6)$alkyl, benzyl, $H_2N(C_1-C_6)$alkyl, $(C_1-C_6)$alkylNH$(C_1-C_6)$alkyl, and $[(C_1-C_6)alkyl]_2N(C_1-C_6)$alkyl; or $R^7$ and $R^8$, together with nitrogen atom to which they are attached, may form a 3 to 10 membered ring which may contain a heteroatom selected from oxygen, sulfur, and nitrogen; wherein the said 3 to 10 membered ring is optionally substituted with 1 to 6 substituents independently selected from the group consisting of: halogen, hydroxyl, oxo, $(C_1-C_6)$alkyl, $(C_1-C_6)$alkoxy, $(C_1-C_6)$haloalkyl, $—SO_2(C_1-C_6)$alkyl, $—SO_2(C_1-C_6)$haloalkyl, $—C(=O)(C_1-C_6)$alkyl, and $—C(=O)$ $(C_1-C_6)$haloalkyl;

$R^a$ and $R^b$ are independently selected from the group consisting of: hydrogen, $(C_1-C_6)$alkyl, $(C_1-C_6)$haloalkyl, hydroxy$(C_1-C_6)$alkyl, $(C_1-C_6)$alkoxy$(C_1-C_6)$alkyl, $(C_3-C_7)$cycloalkyl, phenyl$(C_0-C_6)$alkyl, $(C_1-C_6)$haloalkoxy$(C_1-C_6)$alkyl, $H_2N(C_1-C_6)$alkyl, $(C_1-C_6)$alkylNH$(C_1-C_6)$alkyl, and $[(C_1-C_6)alkyl]_2N(C_1-C_6)$alkyl; or $R^a$ and $R^b$, together with nitrogen atom to which they are attached, may form a 3 to 7 membered ring which may contain a heteroatom selected from oxygen, sulfur, and nitrogen; wherein the said 3 to 7 membered ring is optionally substituted with 1 to 3 substituents independently selected from $(C_1-C_6)$alkyl;

$Ar^2$ is selected from aryl and heteroaryl which are optionally substituted with 1 to 6 substituents independently selected from the group consisting of: hydrogen, halogen, cyano, nitro, hydroxyl, —$COR^9$, —$CONR^9R^{10}$, —$NHSO_2R^9$, —$SO_2NR^9R^{10}$, $(C_1-C_6)$alkylthio-, $(C_1-C_6)$alkylsulfinyl, $(C_1-C_6)$alkylsulfonyl, —$NR^9R^{10}$, tri$(C_1-C_6)$alkylsilyl, $(C_1-C_6)$haloalkylthio-, —$SF_5$, $(C_1-C_6)$alkyl, $(C_3-C_7)$cycloalkyl, $(C_3-C_7)$cycloalkoxy, $(C_1-C_6)$alkoxy, aryl$(C_0-C_4)$alkyl, heteroaryl$(C_0-C_4)$alkyl, aryl$(C_0-C_6)$alkoxy, phenoxy, heteroaryl$(C_0-C_6)$alkoxy, heterocyclyl$(C_0-C_4)$alkyl, and heterocyclyl$(C_0-C_6)$alkoxy; wherein the said $(C_1-C_6)$alkyl, $(C_3-C_7)$cycloalkyl, $(C_3-C_7)$cycloalkoxy, $(C_1-C_6)$alkoxy, aryl$(C_0-C_4)$alkyl, heteroaryl$(C_0-C_4)$alkyl, aryl$(C_0-C_6)$alkoxy, phenoxy, heteroaryl$(C_0-C_6)$alkoxy, heterocyclyl$(C_0-C_4)$alkyl, or heterocyclyl$(C_0-C_6)$alkoxy is optionally substituted with 1 to 6 substituents independently selected from the group consisting of: halogen, hydroxyl, $(C_1-C_6)$alkyl, $(C_3-C_7)$cycloalkyl, $(C_1-C_6)$haloalkyl, $(C_1-C_6)$alkoxy, $(C_1-C_6)$alkoxy$(C_1-C_6)$alkoxy, $(C_1-C_6)$haloalkoxy, —$NR^cR^d$, $R^cR^dN(C_1-C_6)$alkyl, $R^cR^dN(C_1-C_6)$alkoxy, —C(═O)$NR^cR^d$, $R^cR^d$NC(═O)$(C_1-C_6)$alkoxy, benzyloxy, and cyano; preferably aryl is phenyl or naphthyl, and preferably heteroaryl is unsaturated or partially saturated mono- or bi-cyclic 5 to 15-membered ring with 1-4 heteroatoms independently selected from O, N, and S, or carbonyl; more preferably aryl is phenyl and more preferably heteroaryl is 5 to 6-membered ring with 1-4 heteroatoms independently selected from O, N, and S, or 9 to 10-membered heteroaromatic ring with 1-4 heteroatoms independently selected from O, N, and S; further more preferably aryl is phenyl and further more preferably heteroaryl is 5 to 6-membered heteroaromatic ring with 1-4 heteroatoms independently selected from O, N, and S; further more preferably heteroaryl is pyridinyl, pyrimidinyl, pyridazinyl, pyrazinyl, pyrrolyl, furanyl, thiophenyl, imidazolyl, pyrazolyl, oxazolyl, isoxazoyl, thiazolyl, isothiazolyl, indolyl, benzimidazolyl, benzofuranyl, benzothiophenyl, imidazopyridinyl, indazolyl, oxadiazolyl, benzoisoxazolyl, quinazolinyl, quinoxalinyl, quinolinyl, or isoquinolinyl;

$R^9$ and $R^{10}$ are independently selected from the group consisting of: hydrogen, $(C_1-C_6)$alkyl, $(C_1-C_6)$haloalkyl, hydroxy$(C_1-C_6)$alkyl, $(C_1-C_6)$alkoxy$(C_1-C_6)$alkyl, $(C_1-C_6)$haloalkoxy$(C_1-C_6)$alkyl, $H_2N(C_1-C_6)$alkyl, $(C_1-C_6)$alkylNH$(C_1-C_6)$alkyl, and $[(C_1-C_6)alkyl]_2N(C_1-C_6)$alkyl; or $R^9$ and $R^{10}$, together with nitrogen atom to which they are attached, may form a 3 to 10 membered ring which may contain a heteroatom selected from oxygen, sulfur, and nitrogen; wherein the said 3 to 10 membered ring is optionally substituted with 1 to 6 substituents independently selected from the group consisting of: halogen, hydroxyl, oxo, $(C_1-C_6)$alkyl, $(C_1-C_6)$alkoxy, $(C_1-C_6)$haloalkyl, —$SO_2(C_1-C_6)$alkyl, —$SO_2(C_1-C_6)$haloalkyl, —C(═O)$(C_1-C_6)$alkyl, and —C(═O)$(C_1-C_6)$haloalkyl; and $R^c$ and $R^d$ are independently selected from the group consisting of: hydrogen, $(C_1-C_6)$alkyl, $(C_1-C_6)$haloalkyl, hydroxy$(C_1-C_6)$alkyl, $(C_1-C_6)$alkoxy$(C_1-C_6)$alkyl, $(C_1-C_6)$haloalkoxy$(C_1-C_6)$alkyl, $H_2N(C_1-C_6)$alkyl, $(C_1-C_6)$alkylNH$(C_1-C_6)$alkyl, and $[(C_1-C_6)alkyl]_2N(C_1-C_6)$alkyl; or $R^c$ and $R^d$, together with nitrogen atom to which they are attached, may form a 3 to 7 membered ring which may contain a heteroatom selected from oxygen, sulfur, and nitrogen;

or a pharmaceutically acceptable salt thereof;

[2] The compound of the formula (I), according to [1], wherein $R^1$ and $R^2$ are independently selected from the group consisting of: hydrogen, $(C_1-C_6)$alkyl, $(C_1-C_6)$haloalkyl, $(C_1-C_6)$alkoxy, $(C_1-C_6)$haloalkoxy, and $(C_3-C_7)$cycloalkyl; or alternatively $R^1$ and $R^2$, together with the atom to which they are attached, may form a 3 to 8 membered carbon ring;

X is selected from the group consisting of: a chemical bond, —$C(R^5)(R^6)$—$(CH_2)_m$)—, —$(C_3-C_8)$cycloalkyl-, —CH═CH—, and —$CH_2O$—;

m is 0, 1, 2, or 3; and $R^5$ and $R^6$ are independently selected from the group consisting of: hydrogen, halogen, hydroxyl, and $(C_1-C_6)$alkyl;

or a pharmaceutically acceptable salt thereof;

[3] The compound of the formula (I), according to [1] or [2], wherein $R^1$ and $R^2$ are independently selected from the group consisting of: hydrogen, $(C_1-C_6)$alkyl, $(C_1-C_6)$haloalkyl, $(C_1-C_6)$alkoxy, $(C_1-C_6)$haloalkoxy, and $(C_3-C_7)$cycloalkyl; or alternatively $R^1$ and $R^2$, together with the atom to which they are attached, may form a 3 to 8 membered carbon ring;

X is selected from the group consisting of: a chemical bond and —$CR^5R^6$—; $R^5$ and $R^6$ are independently selected from the group consisting of: hydrogen, halogen, hydroxyl, $(C_1-C_6)$alkyl, and $(C_1-C_6)$alkoxy;

q is 1, 2, or 3;

r is 1, 2, or 3;

s is 1, 2, or 3;

$Ar^1$ is selected from aryl and heteroaryl which are optionally substituted with 1 to 6 substituents independently selected from the group consisting of: hydrogen, halogen, hydroxyl, cyano, —C(═O)$R^7$, —C(═O)$NR^7R^8$, —$NR^7R^8$, —$NHSO_2R^7$, —$SO_2NR^7R^8$, $(C_1-C_6)$alkyl, $(C_3-C_7)$cycloalkyl, $(C_1-C_6)$alkoxy, phenyl, heteroaryl, phenoxy, and heterocyclyl; wherein the said $(C_1-C_6)$alkyl, $(C_3-C_7)$cycloalkyl, $(C_1-C_6)$alkoxy, phenyl, heteroaryl, phenoxy, or heterocyclyl is optionally substituted with 1 to 6 substituents independently selected from the group consisting of: halogen, hydroxyl, cyano, $(C_1-C_6)$alkyl, $(C_3-C_7)$cycloalkyl, $(C_1-C_6)$haloalkyl, $(C_1-C_6)$alkoxy, —$NR^aR^b$, —C(═O)$NR^aR^b$, —C(═O)$R^a$;

$R^7$ and $R^8$ are independently selected from the group consisting of: hydrogen, hydroxyl, $(C_1-C_6)$alkyl, $(C_1-C_6)$haloalkyl, and $(C_3-C_7)$cycloalkyl; or $R^7$ and $R^8$, together with nitrogen atom to which they are attached, may form a 3 to 7 membered ring which may contain a heteroatom selected from oxygen, sulfur, and nitrogen; wherein the said 3 to 7 membered ring is optionally substituted with 1 to 6 substituents independently selected from the group consisting of: halogen, hydroxyl, $(C_1-C_6)$alkyl, $(C_1-C_6)$alkoxy, and $(C_1-C_6)$haloalkyl;

$R^a$ and $R^b$ are independently selected from the group consisting of: hydrogen, $(C_1-C_6)$alkyl, $(C_1-C_6)$haloalkyl, and $(C_3-C_7)$cycloalkyl; or $R^a$ and $R^b$, together with nitrogen atom to which they are attached, may form a 3 to 7 membered ring which may contain a heteroatom selected from oxygen, sulfur, and nitrogen; wherein the said 3 to 7 membered ring is optionally substituted with 1 to 3 substituents independently selected from methyl and ethyl;

$Ar^2$ is selected from aryl and heteroaryl which are optionally substituted with 1 to 6 substituents independently selected from the group consisting of: hydrogen, halogen, hydroxyl, cyano, —$COR^9$, —$CONR^9R^{10}$, —$NHSO_2R^9$, —$SO_2NR^9R^{10}$, —$NR^9R^{10}$, $(C_1-C_6)$haloalkylthio-, —$SF_5$, $(C_1-C_6)$alkyl, $(C_3-C_7)$cycloalkyl, $(C_3-C_7)$cycloalkoxy, $(C_1-C_6)$alkoxy, phenyl, heteroaryl, phenoxy, and heterocyclyl; wherein the said $(C_1-C_6)$alkyl, $(C_3-C_7)$cycloalkyl, $(C_3-C_7)$cycloalkoxy, $(C_1-C_6)$alkoxy, phenyl, heteroaryl, phenoxy, or heterocyclyl is optionally substituted with 1 to 6 substituents independently selected from the group consisting of: halogen, hydroxyl, $(C_1-C_6)$alkyl, $(C_3-C_7)$cycloalkyl, $(C_1-C_6)$haloalkyl, $(C_1-C_6)$alkoxy, $(C_1-C_6)$haloalkoxy, —$NR^cR^d$, and —C(═O)$NR^cR^d$; and $R^c$ and $R^d$ are independently selected from the group consisting of: hydrogen, $(C_1-C_6)$alkyl, $(C_1-C_6)$haloalkyl, and hydroxy$(C_1-C_6)$alkyl; or $R^c$ and $R^d$, together with nitrogen atom to which they are attached, may form a 3 to 7 membered ring which may contain a heteroatom selected from oxygen, sulfur, and nitrogen;

or a pharmaceutically acceptable salt thereof;

[4] The compound of the formula (I), according to one of [1] to [3], wherein;

$R^1$ and $R^2$ are independently selected from the group consisting of: hydrogen, methyl, and ethyl; or alternatively $R^1$ and $R^2$, together with the atom to which they are attached, may form a 3 to 6 membered carbon ring;

$Ar^1$ is selected from aryl and heteroaryl which are optionally substituted with 1 to 6 substituents independently selected from the group consisting of: hydrogen, halogen, hydroxyl, cyano, —C(═O)$R^7$, —C(═O)$NR^7R^8$, —$NR^7R^8$, —$NHSO_2R^7$, —$SO_2NR^7R^8$, $(C_1-C_6)$alkyl, $(C_3-C_7)$cycloalkyl, $(C_1-C_6)$alkoxy, phenyl, naphthyl, phenoxy, pyridinyl, pyrimidinyl, pyridazinyl, pyrazinyl, pyrrolyl, furanyl, benzofuranyl, thiophenyl, benzothiophenyl, imidazolyl, benzimidazolyl, indolyl, pyrazolyl, oxazolyl, isoxazoyl, thiazolyl, isothiazolyl, phenoxy, pyrrolidinyl, piperidinyl, piperazinyl, morpholinyl, azetidinyl, tetrahydropyranyl, tetrahydrofuranyl, oxetanyl, and aziridinyl; wherein the said $(C_1-C_6)$ alkyl, $(C_3-C_7)$cycloalkyl, $(C_1-C_6)$alkoxy, phenyl, phenoxy, pyridinyl, pyrimidinyl, pyridazinyl, pyrazinyl, imidazolyl, pyrazolyl, furanyl, benzofuranyl, thiophenyl, benzothiophenyl, imidazolyl, benzimidazolyl, indolyl, pyrazolyl, oxazolyl, isoxazoyl, thiazolyl, isothiazolyl, phenoxy, pyrrolidinyl, piperidinyl, piperazinyl, morpholinyl, azetidinyl, tetrahydropyranyl, tetrahydrofuranyl, oxetanyl, or aziridinyl is optionally substituted with 1 to 6 substituents independently selected from the group consisting of: halogen, hydroxyl, cyano, $(C_1-C_6)$alkyl, and $(C_1-C_6)$haloalkyl;

wherein the said aryl is phenyl or naphthyl;

wherein the said heteroaryl is pyridinyl, pyrimidinyl, pyridazinyl, pyrazinyl, pyrrolyl, furanyl, thiophenyl, imidazolyl, pyrazolyl, oxazolyl, isoxazoyl, thiazolyl, isothiazolyl, indolyl, benzimidazolyl, benzofuranyl, benzothiophenyl, imidazopyridinyl, indazolyl, oxadiazolyl, benzoisoxazolyl, quinazolinyl, quinoxalinyl, quinolinyl or isoquinolinyl;

$R^7$ and $R^8$ are independently selected from the group consisting of: hydrogen, hydroxyl, $(C_1-C_6)$alkyl, $(C_1-C_6)$alkoxy, $(C_1-C_6)$haloalkyl, $(C_1-C_6)$haloalkoxy, and $(C_3-C_7)$cycloalkyl;

$Ar^2$ is selected from aryl and heteroaryl which are optionally substituted with 1 to 6 substituents independently selected from the group consisting of: hydrogen, halogen, hydroxyl, cyano, —$SCF_3$, $SF_5$, $(C_1-C_6)$alkyl, $(C_1-C_6)$haloalkyl, $(C_1-C_6)$alkoxy, $(C_1-C_6)$haloalkoxy, phenyl, naphthyl, phenoxy, pyridinyl, oxazolyl, pyridazinyl, pyrazinyl, pyrrolyl, benzothiophenyl, furanyl, benzofuranyl, quinolinyl, isoquinolinyl, thiophenyl, pyrimidinyl, pyrazolyl, imidazolyl, benzimidazolyl, and indolyl; wherein the said phenyl, naphthyl, phenoxy, pyridinyl, oxazolyl, pyridazinyl, pyrazinyl, pyrrolyl, benzothiophenyl, furanyl, benzofuranyl, quinolinyl, isoquinolinyl, thiophenyl, pyrimidinyl, pyrazolyl, imidazolyl, benzimidazolyl, or indolyl is optionally substituted with 1 to 6 substituents independently selected from the group consisting of: hydrogen, halogen, hydroxyl, cyano, —$SCF_3$, $SF_5$, $(C_1-C_6)$alkyl, $(C_1-C_6)$haloalkyl, $(C_1-C_6)$alkoxy, and $(C_1-C_6)$haloalkoxy;

wherein the said aryl is phenyl or naphthyl;

wherein the said heteroaryl is pyridinyl, pyrimidinyl, pyridazinyl, pyrazinyl, pyrrolyl, furanyl, thiophenyl, imidazolyl, pyrazolyl, oxazolyl, isoxazoyl, thiazolyl, isothiazolyl, indolyl, benzimidazolyl, benzofuranyl, benzothiophenyl, imidazopyridinyl, indazolyl, oxadiazolyl, benzoisoxazolyl, quinazolinyl, quinoxalinyl, quinolinyl or isoquinolinyl; or a pharmaceutically acceptable salt thereof;

[5] A compound of the following formula (I-a):

{Chem. 4}

(I-a)

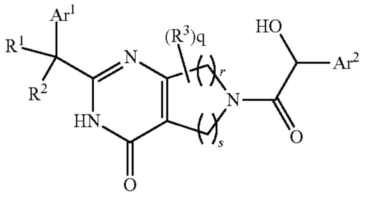

wherein $R^1$ and $R^2$ are independently selected from the group consisting of: hydrogen, hydroxyl, halogen, $(C_1-C_6)$ alkyl, $(C_1-C_6)$haloalkyl, $(C_1-C_6)$alkoxy, $(C_1-C_6)$haloalkoxy, $(C_3-C_7)$cycloalkyl, and phenyl$(C_0-C_4)$alkyl; wherein the said $(C_3-C_7)$cycloalkyl or phenyl $(C_0-C_4)$alkyl is optionally substituted with 1 to 4 substituents independently selected from the group consisting of: halogen, hydroxyl, $(C_1-C_6)$alkyl, $(C_1-C_6)$haloalkyl, $(C_1-C_6)$alkoxy, and $(C_1-C_6)$haloalkoxy; or alternatively $R^1$ and $R^2$, together with the atom to which they are attached, may form a 3 to 8 membered carbon ring; the said 3 to 8 membered ring is optionally substituted with 1 to 6 substituents independently selected from the group consisting of: halogen, hydroxyl, $(C_1-C_6)$alkyl, $(C_1-C_6)$haloalkyl, —$SO_2(C_1-C_6)$alkyl, —$SO_2(C_1-C_6)$haloalkyl, —C(═O)$(C_1-C_6)$alkyl, and —C(═O)$(C_1-C_6)$haloalkyl; preferably $R^1$ and $R^2$ are independently selected from the group consisting of: hydrogen, $(C_1-C_6)$alkyl, $(C_1-C_6)$haloalkyl, $(C_1-C_6)$alkoxy, $(C_1-C_6)$haloalkoxy, and $(C_3-C_7)$cycloalkyl; or alternatively $R^1$ and $R^2$, together with the atom to which they are attached, may form a 3 to 8 membered carbon ring;

$R^3$ is independently selected from the group consisting of: hydrogen, fluoride, methyl, ethyl, and $(C_1-C_6)$ haloalkyl; preferably $R^3$ is independently selected from the group consisting of: hydrogen, fluoride, and methyl;

q is 1, 2, 3, or 4; preferably q is 1 or 2;

r is 1, 2, 3, or 4; preferably r is 1 or 2;

s is 1, 2, 3, or 4; preferably s is 1 or 2;

$Ar^1$ is selected from aryl and heteroaryl which are optionally substituted with 1 to 6 substituents independently selected from the group consisting of: hydrogen, halogen, cyano, nitro, hydroxyl, —C(═O)$R^7$, —C(═O)$NR^7R^8$, —$NHSO_2R^7$, —$SO_2NR^7R^8$, $(C_1-C_6)$alkylthio-, $(C_1-C_6)$haloalkylthio-, $(C_1-C_6)$alkylsulfinyl, $(C_1-C_6)$alkylsulfonyl, —$NR^7R^8$, tri$(C_1-C_6)$alkylsilyl, $(C_1-C_6)$alkyl, $(C_3-C_7)$cycloalkyl, $(C_3-C_7)$cycloalkoxy, $(C_1-C_6)$alkoxy, $(C_1-C_6)$alkenyl, aryl$(C_0-C_4)$alkyl, heteroaryl$(C_0-C_4)$alkyl, aryl$(C_0-C_6)$alkoxy, heterocyclyl$(C_0-C_4)$alkyl, heterocyclyl$(C_0-C_6)$alkoxy, heteroaryl$(C_0-C_6)$alkoxy and substituent group Q; wherein the said $(C_1-C_6)$alkyl, $(C_3-C_7)$cycloalkyl, $(C_3-C_7)$cycloalkoxy, $(C_1-C_6)$alkoxy, $(C_1-C_6)$alkenyl, aryl$(C_0-C_4)$alkyl, heteroaryl$(C_0-C_4)$alkyl, aryl$(C_0-C_6)$alkoxy, heterocyclyl$(C_0-C_4)$alkyl, heterocyclyl$(C_0-C_6)$alkoxy, or heteroaryl$(C_0-C_6)$alkoxy is optionally substituted with 1 to 6 substituents independently selected from the group consisting of: halogen, hydroxyl, cyano, $(C_1-C_6)$alkyl, $(C_3-C_7)$cycloalkyl, $(C_1-C_6)$haloalkyl, $(C_1-C_6)$alkoxy, $(C_1-C_6)$alkoxy$(C_1-C_6)$alkyl, $(C_1-C_6)$alkoxy$(C_1-C_6)$alkoxy, $(C_1-C_6)$haloalkoxy, phenyl, —$NR^aR^b$, $R^aR^bN(C_1-C_6)$alkyl, $R^aR^bN(C_1-C_6)$alkoxy, —C(═O)$NR^aR^b$, —C(═O)$R^a$, —$SO_2(C_1-C_6)$alkyl, —$SO_2NR^aR^b$, and $R^aR^bNC(═O)(C_1-C_6)$alkoxy; wherein the said $(C_3-C_7)$cycloalkyl is optionally substituted with hydroxyl or cyano; wherein the substituent group Q is {Chem. 5}

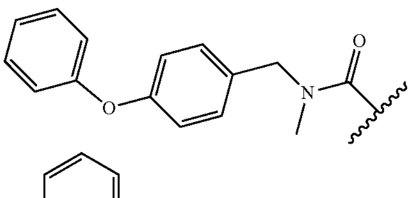
,
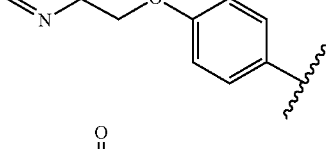
,
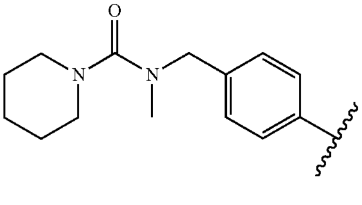
,

-continued

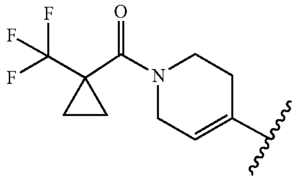
,
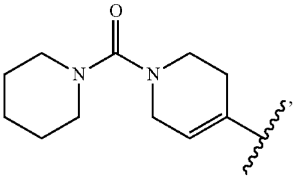
,
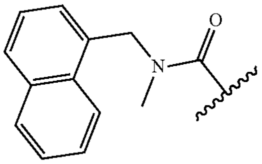
,
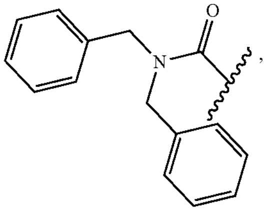
,
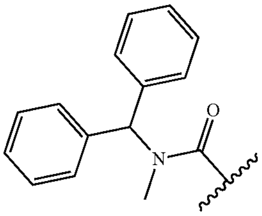
,
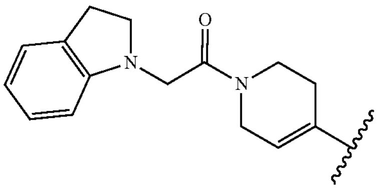
,
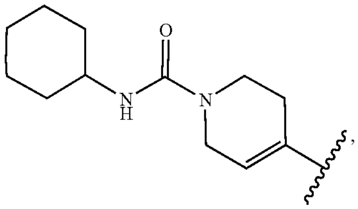
,
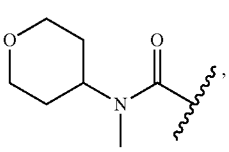
,
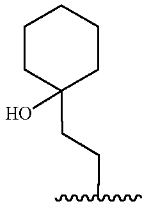
,
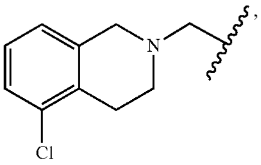
,
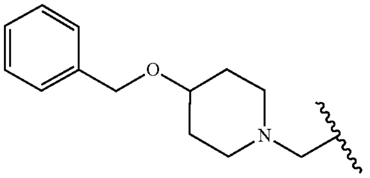
,
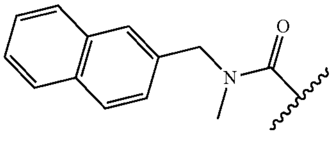
, -continued
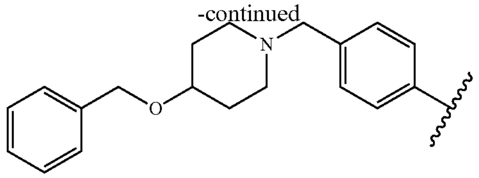,
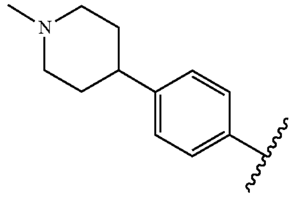,
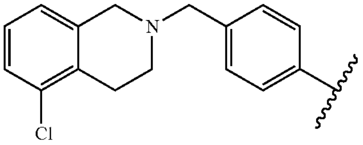,
{Chem. 6}
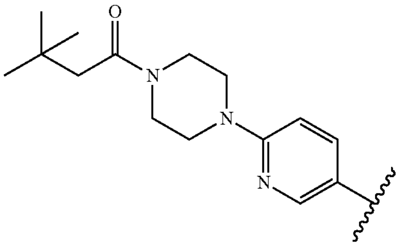,
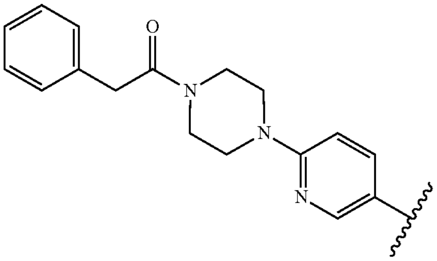,
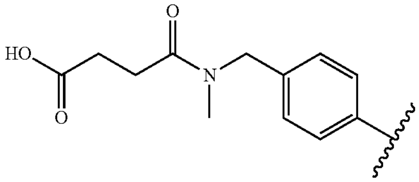,
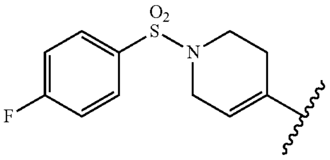,
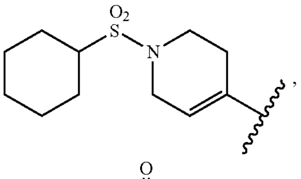,
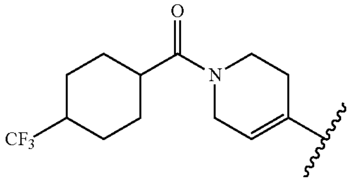,
-continued
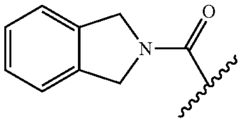
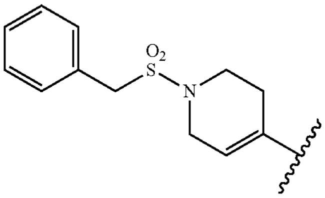,
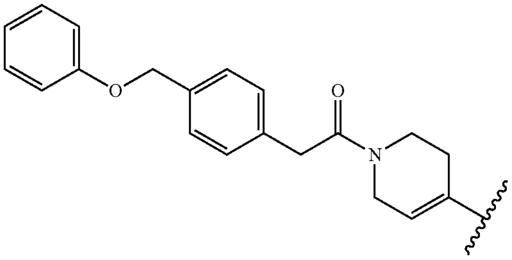,
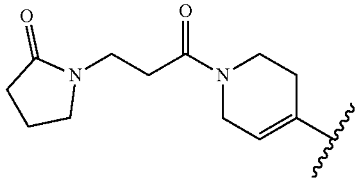,
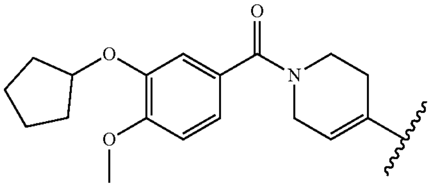,
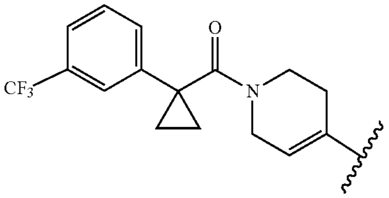,
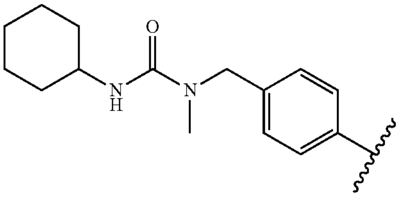,
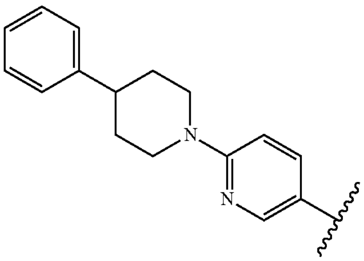, -continued

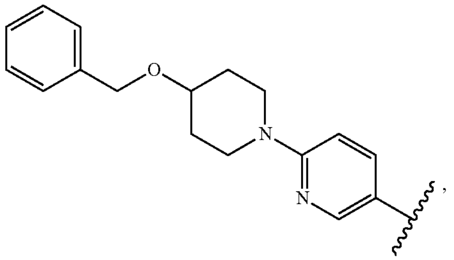
,

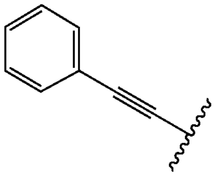
,

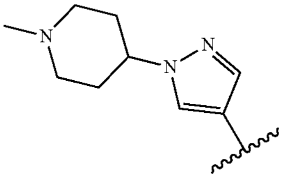
,

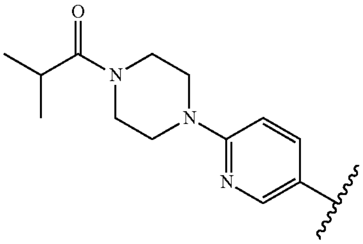
,

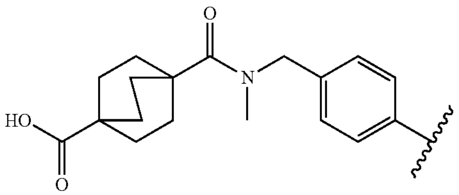
,

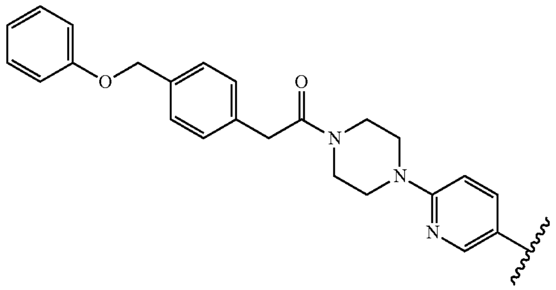
,

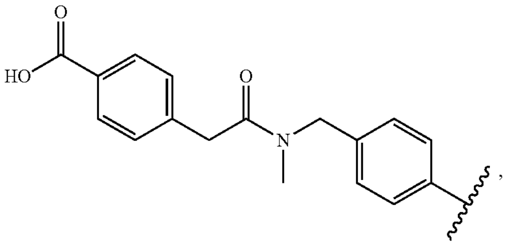
,

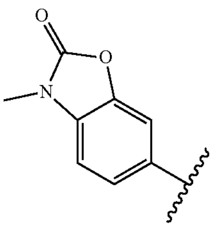
,

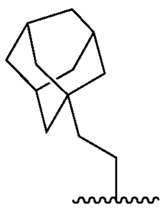
, or

-continued

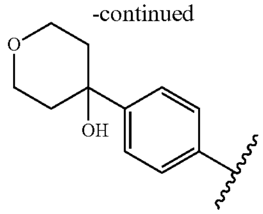
;

in which the substituent group Q may be optionally substituted with halogen, hydroxyl, or ($C_1$-$C_6$)alkyl;

preferably aryl is phenyl or naphthyl, and preferably heteroaryl is unsaturated or partially saturated mono- or bi-cyclic 5 to 15-membered ring with 1-4 heteroatoms independently selected from O, N, and S, or carbonyl; more preferably aryl is phenyl and more preferably heteroaryl is 5 to 6-membered ring with 1-4 heteroatoms independently selected from O, N, and S, or 9 to 10-membered heteroaromatic ring with 1-4 heteroatoms independently selected from O, N, and S; further more preferably aryl is phenyl and further more preferably heteroaryl is 5 to 6-membered heteroaromatic ring with 1-4 heteroatoms independently selected from O, N, and S; further more preferably heteroaryl is pyridinyl, pyrimidinyl, pyridazinyl, pyrazinyl, pyrrolyl, furanyl, thiophenyl, imidazolyl, pyrazolyl, oxazolyl, isoxazoyl, thiazolyl, isothiazolyl, indolyl, benzimidazolyl, benzofuranyl, benzothiophenyl, imidazopyridinyl, indazolyl, oxadiazolyl, benzoisoxazolyl, quinazolinyl, quinoxalinyl, quinolinyl, or isoquinolinyl;

$R^7$ and $R^8$ are independently selected from the group consisting of: hydrogen, hydroxyl, ($C_1$-$C_6$)alkyl, ($C_1$-$C_6$)alkoxy, ($C_1$-$C_6$)haloalkyl, ($C_3$-$C_7$)cycloalkyl, heterocyclyl, hydroxy($C_1$-$C_6$)alkyl, ($C_1$-$C_6$)alkoxy($C_1$-$C_6$)alkyl, ($C_1$-$C_6$)haloalkoxy($C_1$-$C_6$)alkyl, benzyl, $H_2N$($C_1$-$C_6$)alkyl, ($C_1$-$C_6$)alkylNH($C_1$-$C_6$)alkyl, and [($C_1$-$C_6$)alkyl]$_2$N($C_1$-$C_6$)alkyl; or $R^7$ and $R^8$, together with nitrogen atom to which they are attached, may form a 3 to 10 membered ring which may contain a heteroatom selected from oxygen, sulfur, and nitrogen; wherein the said 3 to 10 membered ring is optionally substituted with 1 to 6 substituents independently selected from the group consisting of: halogen, hydroxyl, oxo, ($C_1$-$C_6$)alkyl, ($C_1$-$C_6$)alkoxy, ($C_1$-$C_6$)haloalkyl, —$SO_2$($C_1$-$C_6$)alkyl, —$SO_2$($C_1$-$C_6$)haloalkyl, —C(═O)($C_1$-$C_6$)alkyl, and —C(═O)($C_1$-$C_6$)haloalkyl;

$R^a$ and $R^b$ are independently selected from the group consisting of: hydrogen, ($C_1$-$C_6$)alkyl, ($C_1$-$C_6$)haloalkyl, hydroxy($C_1$-$C_6$)alkyl, ($C_1$-$C_6$)alkoxy($C_1$-$C_6$)alkyl, ($C_3$-$C_7$)cycloalkyl, phenyl($C_0$-$C_6$)alkyl, ($C_1$-$C_6$)haloalkoxy($C_1$-$C_6$)alkyl, $H_2N$($C_1$-$C_6$)alkyl, ($C_1$-$C_6$)alkylNH($C_1$-$C_6$)alkyl, and [($C_1$-$C_6$)alkyl]$_2$N($C_1$-$C_6$)alkyl; or $R^a$ and $R^b$, together with nitrogen atom to which they are attached, may form a 3 to 7 membered ring which may contain an atom selected from oxygen, sulfur, and nitrogen; wherein the said 3 to 7 membered ring is optionally substituted with 1 to 3 substituents independently selected from ($C_1$-$C_6$)alkyl;

$Ar^2$ is selected from aryl and heteroaryl which are optionally substituted with 1 to 6 substituents independently selected from the group consisting of: hydrogen, halogen, cyano, nitro, hydroxyl, —$COR^9$, —$CONR^9R^{10}$, —$NHSO_2R^9$, —$SO_2NR^9R^{10}$, ($C_1$-

$C_6$)alkylthio, ($C_1$-$C_6$)alkylsulfinyl, ($C_1$-$C_6$)alkylsulfonyl, —$NR^9R^{10}$, tri($C_1$-$C_6$)alkylsilyl, ($C_1$-$C_6$) haloalkylthio-, —$SF_5$, ($C_1$-$C_6$)alkyl, ($C_3$-$C_7$) cycloalkyl, ($C_3$-$C_7$)cycloalkoxy, ($C_1$-$C_6$)alkoxy, aryl ($C_0$-$C_4$)alkyl, heteroaryl($C_0$-$C_4$)alkyl, aryl($C_0$-$C_6$) alkoxy, phenoxy, heteroaryl($C_0$-$C_6$)alkoxy, heterocyclyl($C_0$-$C_4$)alkyl, and heterocyclyl($C_0$-$C_6$) alkoxy; wherein the said ($C_1$-$C_6$)alkyl, ($C_3$-$C_7$)cycloalkyl, ($C_3$-$C_7$)cycloalkoxy, ($C_1$-$C_6$)alkoxy, aryl ($C_0$-$C_4$)alkyl, heteroaryl($C_0$-$C_4$)alkyl, aryl($C_0$-$C_6$) alkoxy, phenoxy, heteroaryl($C_0$-$C_6$)alkoxy, heterocyclyl($C_0$-$C_4$)alkyl, or heterocyclyl($C_0$-$C_6$) alkoxy is optionally substituted with 1 to 6 substituents independently selected from the group consisting of: halogen, hydroxyl, ($C_1$-$C_6$)alkyl, ($C_3$-$C_7$) cycloalkyl, ($C_1$-$C_6$)haloalkyl, ($C_1$-$C_6$)alkoxy, ($C_1$-$C_6$)alkoxy($C_1$-$C_6$)alkoxy, ($C_1$-$C_6$)haloalkoxy, —$NR^cR^d$, $R^cR^d$N($C_1$-$C_6$)alkyl, $R^cR^d$N($C_1$-$C_6$) alkoxy, —C(═O)$NR^cR^d$, $R^cR^d$NC(═O)($C_1$-$C_6$) alkoxy, benzyloxy, and cyano; preferably aryl is phenyl or naphthyl, and preferably heteroaryl is unsaturated or partially saturated mono- or bi-cyclic 5 to 15-membered ring with 1-4 heteroatoms independently selected from O, N, and S, or carbonyl; more preferably aryl is phenyl and more preferably heteroaryl is 5 to 6-membered ring with 1-4 heteroatoms independently selected from O, N, and S, or 9 to 10-membered heteroaromatic ring with 1-4 heteroatoms independently selected from O, N, and S; further more preferably aryl is phenyl and further more preferably heteroaryl is 5 to 6-membered heteroaromatic ring with 1-4 heteroatoms independently selected from O, N, and S; further more preferably heteroaryl is pyridinyl, pyrimidinyl, pyridazinyl, pyrazinyl, pyrrolyl, furanyl, thiophenyl, imidazolyl, pyrazolyl, oxazolyl, isoxazoyl, thiazolyl, isothiazolyl, indolyl, benzimidazolyl, benzofuranyl, benzothiophenyl, imidazopyridinyl, indazolyl, oxadiazolyl, benzoisoxazolyl, quinazolinyl, quinoxalinyl, quinolinyl, or isoquinolinyl;

$R^9$ and $R^{10}$ are independently selected from the group consisting of: hydrogen, ($C_1$-$C_6$)alkyl, ($C_1$-$C_6$)haloalkyl, hydroxy($C_1$-$C_6$)alkyl, ($C_1$-$C_6$)alkoxy($C_1$-$C_6$)alkyl, ($C_1$-$C_6$)haloalkoxy($C_1$-$C_6$)alkyl, $H_2$N($C_1$-$C_6$)alkyl, ($C_1$-$C_6$)alkylNH($C_1$-$C_6$)alkyl, and [($C_1$-$C_6$)alkyl]$_2$N($C_1$-$C_6$)alkyl; or $R^9$ and $R^{10}$, together with nitrogen atom to which they are attached, may form a 3 to 10 membered ring which may contain a heteroatom selected from oxygen, sulfur, and nitrogen; wherein the said 3 to 10 membered ring is optionally substituted with 1 to 6 substituents independently selected from the group consisting of: halogen, hydroxyl, oxo, ($C_1$-$C_6$)alkyl, ($C_1$-$C_6$) alkoxy, ($C_1$-$C_6$)haloalkyl, —$SO_2$($C_1$-$C_6$)alkyl, —$SO_2$($C_1$-$C_6$)haloalkyl, —C(═O)($C_1$-$C_6$)alkyl, and —C(═O)($C_1$-$C_6$)haloalkyl; and $R^c$ and $R^d$ are independently selected from the group consisting of: hydrogen, ($C_1$-$C_6$)alkyl, ($C_1$-$C_6$)haloalkyl, hydroxy($C_1$-$C_6$)alkyl, ($C_1$-$C_6$)alkoxy($C_1$-$C_6$)alkyl, ($C_1$-$C_6$)haloalkoxy($C_1$-$C_6$)alkyl, $H_2$N($C_1$-$C_6$)alkyl, ($C_1$-$C_6$)alkylNH($C_1$-$C_6$)alkyl, and [($C_1$-$C_6$)alkyl]$_2$N($C_1$-$C_6$)alkyl; or $R^c$ and $R^d$, together with nitrogen atom to which they are attached, may form a 3 to 7 membered ring which may contain a heteroatom selected from oxygen, sulfur, and nitrogen;

or a pharmaceutically acceptable salt thereof;

[6] A compound according to [1] to [5], which is selected from:

(R)-2-(1-phenylcyclopropyl)-6-(2-phenylpropanoyl)-5,6,7,8-tetrahydropyrido[4,3-d]pyrimidin-4(3H)-one;

(S)-2-(1-phenylcyclopropyl)-6-(2-phenylpropanoyl)-5,6,7,8-tetrahydropyrido[4,3-d]pyrimidin-4(3H)-one;

(R)-6-(2-(4-isobutylphenyl)propanoyl)-2-(1-phenylcyclopropyl)-5,6,7,8-tetrahydropyrido[4,3-d]pyrimidin-4(3H)-one;

(S)-6-(2-(4-isobutylphenyl)propanoyl)-2-(1-phenylcyclopropyl)-5,6,7,8-tetrahydropyrido[4,3-d]pyrimidin-4(3H)-one;

(R)-2-(1-(4-fluorophenyl)cyclopropyl)-6-(2-(4-isobutylphenyl)propanoyl)-5,6,7,8-tetrahydropyrido[4,3-d]pyrimidin-4(3H)-one;

(R)-2-(1-(4-chlorophenyl)cyclopropyl)-6-(2-(4-isobutylphenyl)propanoyl)-5,6,7,8-tetrahydropyrido[4,3-d]pyrimidin-4(3H)-one;

6-(2-(3,5-difluorophenyl)propanoyl)-2-(1-phenylcyclopropyl)-5,6,7,8-tetrahydropyrido[4,3-d]pyrimidin-4(3H)-one;

6-(2-(4-chlorophenyl)propanoyl)-2-(1-phenylcyclopropyl)-5,6,7,8-tetrahydropyrido[4,3-d]pyrimidin-4(3H)-one;

6-(2-(3,5-difluorophenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(4-(trifluoromethyl)phenyl)propanoyl)-5,6,7,8-tetrahydropyrido[4,3-d]pyrimidin-4(3H)-one;

6-(2-(4-fluorophenyl)propanoyl)-2-(1-phenylcyclopropyl)-5,6,7,8-tetrahydropyrido[4,3-d]pyrimidin-4(3H)-one;

6-(2-(4-isopropylphenyl)acetyl)-2-(1-phenylcyclopropyl)-5,6,7,8-tetrahydropyrido[4,3-d]pyrimidin-4(3H)-one;

6-(2-(3,5-difluorophenyl)propanoyl)-2-(1-(4-fluorophenyl)cyclopropyl)-5,6,7,8-tetrahydropyrido[4,3-d]pyrimidin-4(3H)-one;

6-(2-(4-(tert-butyl)phenoxy)acetyl)-2-(1-phenylcyclopropyl)-5,6,7,8-tetrahydropyrido[4,3-d]pyrimidin-4(3H)-one;

6-(2-(1H-indol-3-yl)acetyl)-2-(1-phenylcyclopropyl)-5,6,7,8-tetrahydropyrido[4,3-d]pyrimidin-4(3H)-one;

6-(2-(5-fluoro-1H-indol-3-yl)acetyl)-2-(1-phenylcyclopropyl)-5,6,7,8-tetrahydropyrido[4,3-d]pyrimidin-4(3H)-one;

6-(2-(benzo[d]isoxazol-3-yl)acetyl)-2-(1-phenylcyclopropyl)-5,6,7,8-tetrahydropyrido[4,3-d]pyrimidin-4(3H)-one;

6-(2-(5-methyl-2-phenyloxazol-4-yl)acetyl)-2-(1-phenylcyclopropyl)-5,6,7,8-tetrahydropyrido[4,3-d]pyrimidin-4(3H)-one;

6-(3-(3-phenyl-1,2,4-oxadiazol-5-yl)propanoyl)-2-(1-phenylcyclopropyl)-5,6,7,8-tetrahydropyrido[4,3-d]pyrimidin-4(3H)-one;

2-(1-phenylcyclopropyl)-6-(2-(quinoxalin-6-yl)acetyl)-5,6,7,8-tetrahydropyrido[4,3-d]pyrimidin-4(3H)-one;

6-(2,2-difluoro-2-phenylacetyl)-2-(1-phenylcyclopropyl)-5,6,7,8-tetrahydropyrido[4,3-d]pyrimidin-4(3H)-one;

6-(2-fluoro-2-phenylacetyl)-2-(1-phenylcyclopropyl)-5,6,7,8-tetrahydropyrido[4,3-d]pyrimidin-4(3H)-one;

6-(2-(5-chloro-1H-benzo[d]imidazol-2-yl)acetyl)-2-(1-phenylcyclopropyl)-5,6,7,8-tetrahydropyrido[4,3-d]pyrimidin-4(3H)-one;

6-(2-(2-hydroxyphenyl)acetyl)-2-(1-phenylcyclopropyl)-5,6,7,8-tetrahydropyrido[4,3-d]pyrimidin-4(3H)-one;

6-(2-(2-methoxyphenyl)acetyl)-2-(1-phenylcyclopropyl)-5,6,7,8-tetrahydropyrido[4,3-d]pyrimidin-4(3H)-one;

6-(3-(1H-indol-3-yl)propanoyl)-2-(1-phenylcyclopropyl)-5,6,7,8-tetrahydropyrido[4,3-d]pyrimidin-4(3H)-one;

6-(3-(3-(4-methoxyphenyl)-1,2,4-oxadiazol-5-yl)propanoyl)-2-(1-phenylcyclopropyl)-5,6,7,8-tetrahydropyrido[4,3-d]pyrimidin-4(3H)-one;

6-(2-(1H-indazol-1-yl)acetyl)-2-(1-phenylcyclopropyl)-5,6,7,8-tetrahydropyrido[4,3-d]pyrimidin-4(3H)-one;

4-(2-oxo-2-(4-oxo-2-(1-phenylcyclopropyl)-3,5,7,8-tetrahydropyrido[4,3-d]pyrimidin-6(4H)-yl)ethyl)-2H-benzo[b][1,4]oxazin-3(4H)-one;

(E)-6-(3-(3-chlorophenyl)acryloyl)-2-(1-phenylcyclopropyl)-5,6,7,8-tetrahydropyrido[4,3-d]pyrimidin-4(3H)-one;

6-((1R*,2R*)-2-phenylcyclopropane-1-carbonyl)-2-(1-phenylcyclopropyl)-5,6,7,8-tetrahydropyrido[4,3-d]pyrimidin-4(3H)-one;

6-((1R*,2R*)-2-(2,5-difluorophenyl)cyclopropane-1-carbonyl)-2-(1-phenylcyclopropyl)-5,6,7,8-tetrahydropyrido[4,3-d]pyrimidin-4(3H)-one;

(R)-6-(2-hydroxy-2-phenylacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-phenylcyclopropyl)-5,6,7,8-tetrahydropyrido[4,3-d]pyrimidin-4(3H)-one;

(R)-(−)-6-(2-(2,3-difluorophenyl)-2-hydroxyacetyl)-2-(1-phenylcyclopropyl)-5,6,7,8-tetrahydropyrido[4,3-d]pyrimidin-4(3H)-one;

(S)-(+)-6-(2-(2,3-difluorophenyl)-2-hydroxyacetyl)-2-(1-phenylcyclopropyl)-5,6,7,8-tetrahydropyrido[4,3-d]pyrimidin-4(3H)-one;

(R)-(−)-6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one;

(S)-(+)-6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one;

(R)-(−)-2-(1-(4-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-(−)-6-(2-(2,3-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one;

(−)-2-(1-(4-fluorophenyl)cyclopropyl)-6-(2-hydroxy-2-(m-tolyl)acetyl)-5,6,7,8-tetrahydropyrido[4,3-d]pyrimidin-4(3H)-one;

(−)-2-(1-(4-chlorophenyl)cyclopropyl)-6-(2-hydroxy-2-(m-tolyl)acetyl)-5,6,7,8-tetrahydropyrido[4,3-d]pyrimidin-4(3H)-one;

(S)-6-(2-hydroxy-2-phenylacetyl)-2-(1-phenylcyclopropyl)-5,6,7,8-tetrahydropyrido[4,3-d]pyrimidin-4(3H)-one;

6-(2-(2-chlorophenyl)-2-hydroxyacetyl)-2-(1-phenylcyclopropyl)-5,6,7,8-tetrahydropyrido[4,3-d]pyrimidin-4(3H)-one;

6-(2-(4-chlorophenyl)-2-hydroxyacetyl)-2-(1-phenylcyclopropyl)-5,6,7,8-tetrahydropyrido[4,3-d]pyrimidin-4(3H)-one;

(S)-6-(2-(2-chlorophenyl)-2-hydroxyacetyl)-2-(1-phenylcyclopropyl)-5,6,7,8-tetrahydropyrido[4,3-d]pyrimidin-4(3H)-one;

(R)-6-(2-(2-chlorophenyl)-2-hydroxyacetyl)-2-(1-phenylcyclopropyl)-5,6,7,8-tetrahydropyrido[4,3-d]pyrimidin-4(3H)-one;

6-(2-(2,3-difluorophenyl)-2-hydroxyacetyl)-2-(1-phenylcyclopropyl)-5,6,7,8-tetrahydropyrido[4,3-d]pyrimidin-4(3H)-one;

6-(2-(3,4-difluorophenyl)-2-hydroxyacetyl)-2-(1-phenylcyclopropyl)-5,6,7,8-tetrahydropyrido[4,3-d]pyrimidin-4(3H)-one;

6-(2-(2,4-difluorophenyl)-2-hydroxyacetyl)-2-(1-phenylcyclopropyl)-5,6,7,8-tetrahydropyrido[4,3-d]pyrimidin-4(3H)-one;

6-(2-(2,6-difluorophenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-3-phenylpropanoyl)-2-(1-phenylcyclopropyl)-5,6,7,8-tetrahydropyrido[4,3-d]pyrimidin-4(3H)-one;

(R)-6-(2-hydroxy-4-phenylbutanoyl)-2-(1-phenylcyclopropyl)-5,6,7,8-tetrahydropyrido[4,3-d]pyrimidin-4(3H)-one;

6-(2-(3-fluoro-4-methoxyphenyl)-2-hydroxyacetyl)-2-(1-phenylcyclopropyl)-5,6,7,8-tetrahydropyrido[4,3-d]pyrimidin-4(3H)-one;

6-(2-(3-chlorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(6-methylpyridin-2-yl)acetyl)-2-(1-phenylcyclopropyl)-5,6,7,8-tetrahydropyrido[4,3-d]pyrimidin-4(3H)-one;

6-(2-(3-fluorophenyl)-2-hydroxyacetyl)-2-(1-phenylcyclopropyl)-5,6,7,8-tetrahydropyrido[4,3-d]pyrimidin-4(3H)-one;

6-(2-(3-fluorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-(3-fluoro-4-methoxyphenyl)-2-hydroxyacetyl)-2-(1-(4-fluorophenyl)cyclopropyl)-5,6,7,8-tetrahydropyrido[4,3-d]pyrimidin-4(3H)-one;

2-(1-(4-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-6-(2-(2-chlorophenyl)-2-hydroxyacetyl)-2-(1-(4-chlorophenyl)cyclopropyl)-5,6,7,8-tetrahydropyrido[4,3-d]pyrimidin-4(3H)-one;

2-(1-(4-chlorophenyl)cyclopropyl)-6-(2-(3,5-difluorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(4-chlorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-hydroxy-2-(4-(trifluoromethyl)phenyl)acetyl)-2-(1-phenylcyclopropyl)-5,6,7,8-tetrahydropyrido[4,3-d]pyrimidin-4(3H)-one;

6-(2-(2,5-difluorophenyl)-2-hydroxyacetyl)-2-(1-phenylcyclopropyl)-5,6,7,8-tetrahydropyrido[4,3-d]pyrimidin-4(3H)-one;

6-(2-(2,3-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(3-fluorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(2,3-difluorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

(R)-6-(2-hydroxy-2-(naphthalen-2-yl)acetyl)-2-(1-phenylcyclopropyl)-5,6,7,8-tetrahydropyrido[4,3-d]pyrimidin-4(3H)-one;

6-(2-hydroxy-2-(3-methoxyphenyl)acetyl)-2-(1-phenylcyclopropyl)-5,6,7,8-tetrahydropyrido[4,3-d]pyrimidin-4(3H)-one;

6-(2-hydroxy-2-(m-tolyl)acetyl)-2-(1-phenylcyclopropyl)-5,6,7,8-tetrahydropyrido[4,3-d]pyrimidin-4(3H)-one;

(R)-4-(1-(6-(2-(3-chlorophenyl)-2-hydroxyacetyl)-4-oxo-3,4,5,6,7,8-hexahydropyrido[4,3-d]pyrimidin-2-yl)cyclopropyl)benzonitrile;

4-(1-(6-(2-(2,3-difluorophenyl)-2-hydroxyacetyl)-4-oxo-3,4,5,6,7,8-hexahydropyrido[4,3-d]pyrimidin-2-yl)cyclopropyl)benzonitrile;

(S)-2-(1-(4-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(S)-6-(2-(2,3-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-hydroxy-2-(3-hydroxyphenyl)acetyl)-2-(1-phenylcyclopropyl)-5,6,7,8-tetrahydropyrido[4,3-d]pyrimidin-4(3H)-one;

6-(2-(3-bromophenyl)-2-hydroxyacetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3-bromo-2-fluorophenyl)-2-hydroxyacetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(S)-2-(1-(3-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(p-tolyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(p-tolyl)cyclopropyl)-5,6,7,8-tetrahydropyrido[4,3-d]pyrimidin-4(3H)-one;

6-(2-hydroxy-2-(3-isopropoxyphenyl)acetyl)-2-(1-phenylcyclopropyl)-5,6,7,8-tetrahydropyrido[4,3-d]pyrimidin-4(3H)-one;

(R)-2-(1-(2-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(2-chlorophenyl)cyclopropyl)-5,6,7,8-tetrahydropyrido[4,3-d]pyrimidin-4(3H)-one;

6-(2-(3-(cyclopentyloxy)phenyl)-2-hydroxyacetyl)-2-(1-phenylcyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(3,5-difluorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3,5-difluorophenyl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(3,4-difluorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3,4-difluorophenyl)cyclopropyl)-5,6,7,8-tetrahydropyrido[4,3-d]pyrimidin-4(3H)-one;

6-(2-hydroxy-2-(3-(trifluoromethoxy)phenyl)acetyl)-2-(1-phenylcyclopropyl)-5,6,7,8-tetrahydropyrido[4,3-d]pyrimidin-4(3H)-one;

6-(2-(3,5-dichlorophenyl)-2-hydroxyacetyl)-2-(1-phenylcyclopropyl)-5,6,7,8-tetrahydropyrido[4,3-d]pyrimidin-4(3H)-one;

6-(2-(2,3-dichlorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(2,2,2-trifluoroethoxy)phenyl)acetyl)-2-(1-phenylcyclopropyl)-5,6,7,8-tetrahydropyrido[4,3-d]pyrimidin-4(3H)-one;

6-(2-(2-fluoro-3-methoxyphenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(trifluoromethyl)phenyl)acetyl)-2-(1-phenylcyclopropyl)-5,6,7,8-tetrahydropyrido[4,3-d]pyrimidin-4(3H)-one;

2-(1-(4-fluorophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-hydroxy-2-(m-tolyl)acetyl)-2-(1-phenylcyclopropyl)-5,6,7,8-tetrahydropyrido[4,3-d]pyrimidin-4(3H)-one;

6-(2-(3-cyclopropylphenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(6-methylpyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(oxazol-5-yl)phenyl)acetyl)-2-(1-phenylcyclopropyl)-5,6,7,8-tetrahydropyrido[4,3-d]pyrimidin-4(3H)-one;

3-(1-hydroxy-2-oxo-2-(4-oxo-2-(1-phenylcyclopropyl)-3,5,7,8-tetrahydropyrido[4,3-d]pyrimidin-6(4H)-yl)ethyl)benzonitrile;

6-(2-hydroxy-2-(3-(pyrimidin-5-yl)phenyl)acetyl)-2-(1-phenylcyclopropyl)-5,6,7,8-tetrahydropyrido[4,3-d]pyrimidin-4(3H)-one;

6-(2-hydroxy-2-(3-(2-methoxypyrimidin-5-yl)phenyl)acetyl)-2-(1-phenylcyclopropyl)-5,6,7,8-tetrahydropyrido[4,3-d]pyrimidin-4(3H)-one;

6-(2-(3-(1,3-dimethyl-1H-pyrazol-4-yl)phenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(pyridin-3-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(oxazol-5-yl)phenyl)acetyl)-2-(1-phenylcyclopropyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(pyridin-3-yl)phenyl)acetyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(oxazol-5-yl)phenyl)acetyl)-5,6,7,8-tetrahydropyrido[4,3-d]pyrimidin-4(3H)-one;

2-fluoro-3-(1-hydroxy-2-oxo-2-(4-oxo-2-(1-phenylcyclopropyl)-3,5,7,8-tetrahydropyrido[4,3-d]pyrimidin-6(4H)-yl)ethyl)benzonitrile;

6-(2-(3,5-difluorophenyl)-2-hydroxyacetyl)-2-(1-phenylcyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one;

(S)-6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(pyridin-2-yl)cyclopropyl)-5,6,7,8-tetrahydropyrido[4,3-d]pyrimidin-4(3H)-one;

6-(2-(2,3-difluorophenyl)-2-hydroxyacetyl)-2-(1-(pyridin-3-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(pyridin-3-yl)cyclopropyl)-5,6,7,8-tetrahydropyrido[4,3-d]pyrimidin-4(3H)-one;

6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(thiophen-2-yl)cyclopropyl)-5,6,7,8-tetrahydropyrido[4,3-d]pyrimidin-4(3H)-one;

6-(2-(3,5-difluorophenyl)-2-hydroxyacetyl)-2-(1-(thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(thiophen-2-yl)cyclopropyl)-5,6,7,8-tetrahydropyrido[4,3-d]pyrimidin-4(3H)-one;

(R)-2-(1-benzylcyclopropyl)-6-(2-(3-chlorophenyl)-2-hydroxyacetyl)-5,6,7,8-tetrahydropyrido[4,3-d]pyrimidin-4(3H)-one;

2-(1-benzylcyclopropyl)-6-(2-(2,3-difluorophenyl)-2-hydroxyacetyl)-5,6,7,8-tetrahydropyrido[4,3-d]pyrimidin-4(3H)-one;

6-(2-hydroxy-2-(m-tolyl)acetyl)-2-(1-(thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(2-methylthiazol-4-yl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(thiazol-4-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(thiazol-4-yl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(thiazol-5-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(thiazol-5-yl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(5-methylthiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-methylthiophen-2-yl)cyclopropyl)-5,6,7,8-tetrahydropyrido[4,3-d]pyrimidin-4(3H)-one;

(R)-2-(1-(4-bromothiophen-2-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(4-methylthiazol-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-methylthiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-phenylthiophen-2-yl)cyclopropyl)-5,6,7,8-tetrahydropyrido[4,3-d]pyrimidin-4(3H)-one;

6-((R)-2-(3-chlorophenyl)-2-hydroxyacetyl)-2-((R/S)-1-phenylethyl)-5,6,7,8-tetrahydropyrido[4,3-d]pyrimidin-4(3H)-one;

(R)-6-(2-(3-chlorophenyl)-2-hydroxyacetyl)-2-(2-phenylpropan-2-yl)-5,6,7,8-tetrahydropyrido[4,3-d]pyrimidin-4(3H)-one;

6-(2-(2,3-difluorophenyl)-2-hydroxyacetyl)-2-(2-phenylpropan-2-yl)-5,6,7,8-tetrahydropyrido[4,3-d]pyrimidin-4(3H)-one;

6-(2-(3,5-difluorophenyl)-2-hydroxyacetyl)-2-(2-phenylpropan-2-yl)-5,6,7,8-tetrahydropyrido[4,3-d]pyrimidin-4(3H)-one;

(R)-6-(2-(2-chlorophenyl)-2-hydroxyacetyl)-2-(2-phenylpropan-2-yl)-5,6,7,8-tetrahydropyrido[4,3-d]pyrimidin-4(3H)-one;

6-(2-(2,3-difluorophenyl)-2-hydroxyacetyl)-2-(1-phenylcyclobutyl)-5,6,7,8-tetrahydropyrido[4,3-d]pyrimidin-4(3H)-one;

(R)-6-(2-(2-chlorophenyl)-2-hydroxyacetyl)-2-(1-phenylcyclobutyl)-5,6,7,8-tetrahydropyrido[4,3-d]pyrimidin-4(3H)-one;

6-(2-(3,5-difluorophenyl)-2-hydroxyacetyl)-2-(1-phenylcyclobutyl)-5,6,7,8-tetrahydropyrido[4,3-d]pyrimidin-4(3H)-one;

(R)-6-(2-(3-chlorophenyl)-2-hydroxyacetyl)-2-(1-phenylcyclobutyl)-5,6,7,8-tetrahydropyrido[4,3-d]pyrimidin-4(3H)-one;

7-(2-(2,3-difluorophenyl)-2-hydroxyacetyl)-2-(1-phenylcyclopropyl)-3,5,6,7,8,9-hexahydro-4H-pyrimido[4,5-d]azepin-4-one;

(R)-7-(2-(3-chlorophenyl)-2-hydroxyacetyl)-2-(1-phenylcyclopropyl)-3,5,6,7,8,9-hexahydro-4H-pyrimido[4,5-d]azepin-4-one;

(R)-6-(2-(2-chlorophenyl)-2-hydroxyacetyl)-2-(1-phenylcyclopropyl)-3,5,6,7-tetrahydro-4H-pyrrolo[3,4-d]pyrimidin-4-one;

(R)-7-(2-(3-chlorophenyl)-2-hydroxyacetyl)-2-(1-phenylcyclopropyl)-5,6,7,8-tetrahydropyrido[3,4-d]pyrimidin-4(3H)-one;

7-(2-(2,3-difluorophenyl)-2-hydroxyacetyl)-2-(1-phenylcyclopropyl)-5,6,7,8-tetrahydropyrido[3,4-d]pyrimidin-4(3H)-one;

(R)-6-(2-(2,3-difluorophenyl)-2-hydroxyacetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-phenylcyclopropyl)-3,5,6,7,8,9-hexahydro-4H-pyrimido[5,4-c]azepin-4-one;

(R)-8-(2-(2,3-difluorophenyl)-2-hydroxyacetyl)-2-(1-phenylcyclopropyl)-3,5,6,7,8,9-hexahydro-4H-pyrimido[4,5-c]azepin-4-one;

(R)-8-(2-(3-chlorophenyl)-2-hydroxyacetyl)-2-(1-phenylcyclopropyl)-3,5,6,7,8,9-hexahydro-4H-pyrimido[4,5-c]azepin-4-one;

6-(2-hydroxy-2-(2-(pyrrolidin-1-yl)pyridin-4-yl)acetyl)-2-(1-phenylcyclopropyl)-5,6,7,8-tetrahydropyrido[4,3-d]pyrimidin-4(3H)-one;

6-(2-hydroxy-2-(2-(piperidin-1-yl)pyridin-4-yl)acetyl)-2-(1-phenylcyclopropyl)-5,6,7,8-tetrahydropyrido[4,3-d]pyrimidin-4(3H)-one;

6-(2-(2-(azepan-1-yl)pyridin-4-yl)-2-hydroxyacetyl)-2-(1-phenylcyclopropyl)-5,6,7,8-tetrahydropyrido[4,3-d]pyrimidin-4(3H)-one;

(R)-5-(1-(6-(2-(3-chlorophenyl)-2-hydroxyacetyl)-4-oxo-3,4,5,6,7,8-hexahydropyrido[4,3-d]pyrimidin-2-yl)cyclopropyl)thiophene-3-carbonitrile;

4-oxo-2-(1-phenylcyclopropyl)-N-(3-(trifluoromethyl)phenyl)-3,5,7,8-tetrahydropyrido[4,3-d]pyrimidine-6(4H)-carboxamide;

6-(1H-benzo[d]imidazole-2-carbonyl)-2-(1-phenylcyclopropyl)-5,6,7,8-tetrahydropyrido[4,3-d]pyrimidin-4(3H)-one;

6-(5,6-difluoro-1H-benzo[d]imidazole-2-carbonyl)-2-(1-phenylcyclopropyl)-5,6,7,8-tetrahydropyrido[4,3-d]pyrimidin-4(3H)-one;

6-(5,6-difluoro-1H-benzo[d]imidazole-2-carbonyl)-2-(2-phenylpropan-2-yl)-5,6,7,8-tetrahydropyrido[4,3-d]pyrimidin-4(3H)-one;

2-benzyl-6-(5,6-difluoro-1H-benzo[d]imidazole-2-carbonyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(thiophen-2-yl)cyclopropyl)-5,6,7,8-tetrahydropyrido[4,3-d]pyrimidin-4(3H)-one;

(R)-2-(1-(4-bromothiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-phenylcyclopropyl)-3,5,6,7,8,9-hexahydro-4H-pyrimido[5,4-c]azepin-4-one;

6-(2-(5-chloro-2-fluorophenyl)-2-hydroxyacetyl)-2-(1-phenylcyclopropyl)-5,6,7,8-tetrahydropyrido[4,3-d]pyrimidin-4(3H)-one;

6-(2-(3-chloro-5-fluorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-isopropylphenyl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-cyclohexylthiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-(pyridin-4-yl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-(pyridin-3-yl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-phenylcyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(thiophen-2-yl)cyclopropyl)-5,6,7,8-tetrahydropyrido[4,3-d]pyrimidin-4(3H)-one;

6-(2-hydroxy-2-(3-((trifluoromethyl)thio)phenyl)acetyl)-2-(1-phenylcyclopropyl)-5,6,7,8-tetrahydropyrido[4,3-d]pyrimidin-4(3H)-one;

6-(2-(3-bromophenyl)-2-hydroxyacetyl)-2-(1-phenylcyclopropyl)-5,6,7,8-tetrahydropyrido[4,3-d]pyrimidin-4(3H)-one;

6-(2-(2-chloro-3-fluorophenyl)-2-hydroxyacetyl)-2-(1-phenylcyclopropyl)-5,6,7,8-tetrahydropyrido[4,3-d]pyrimidin-4(3H)-one;

(R)-2-(1-(4-(benzyloxy)phenyl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(4-(tetrahydro-2H-pyran-4-yl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-phenylcyclopropyl)-3,5,6,7,8,9-hexahydro-4H-pyrimido[5,4-c]azepin-4-one;

(R)-2-(1-(3-fluorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(4-(1-methyl-1H-pyrazol-4-yl)thiophen-2-yl)cyclopropyl)-5,6,7,8-tetrahydropyrido[4,3-d]pyrimidin-4(3H)-one;

6-(4-hydroxy-2-naphthoyl)-2-(1-phenylcyclopropyl)-5,6,7,8-tetrahydropyrido[4,3-d]pyrimidin-4(3H)-one;

6-(2-hydroxy-2-(2-(trifluoromethyl)phenyl)acetyl)-2-(1-phenylcyclopropyl)-5,6,7,8-tetrahydropyrido[4,3-d]pyrimidin-4(3H)-one;

6-(2-(2,3-dihydrobenzofuran-7-yl)-2-hydroxyacetyl)-2-(1-phenylcyclopropyl)-5,6,7,8-tetrahydropyrido[4,3-d]pyrimidin-4(3H)-one;

6-(2-(2-fluoro-3-methylphenyl)-2-hydroxyacetyl)-2-(1-phenylcyclopropyl)-5,6,7,8-tetrahydropyrido[4,3-d]pyrimidin-4(3H)-one;

6-(2-(3-chloro-4-fluorophenyl)-2-hydroxyacetyl)-2-(1-phenylcyclopropyl)-5,6,7,8-tetrahydropyrido[4,3-d]pyrimidin-4(3H)-one;

6-(2-(3-chloro-2,4-difluorophenyl)-2-hydroxyacetyl)-2-(1-phenylcyclopropyl)-5,6,7,8-tetrahydropyrido[4,3-d]pyrimidin-4(3H)-one;

6-(3-(1H-indol-1-yl)propanoyl)-2-(1-phenylcyclopropyl)-5,6,7,8-tetrahydropyrido[4,3-d]pyrimidin-4(3H)-one;

6-(2-(5-chlorothiophen-2-yl)-2-hydroxyacetyl)-2-(1-phenylcyclopropyl)-5,6,7,8-tetrahydropyrido[4,3-d]pyrimidin-4(3H)-one;

6-(2-(4-cyclopropylphenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(4-(trifluoromethyl)phenyl)acetyl)-5,6,7,8-tetrahydropyrido[4,3-d]pyrimidin-4(3H)-one;

6-(2-(4-chlorophenyl)acetyl)-2-(1-phenylcyclopropyl)-5,6,7,8-tetrahydropyrido[4,3-d]pyrimidin-4(3H)-one;

6-(2-(3-chlorophenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(3-(trifluoromethyl)phenyl)acetyl)-5,6,7,8-tetrahydropyrido[4,3-d]pyrimidin-4(3H)-one;

(R)-6-(3-hydroxy-3-phenylpropanoyl)-2-(1-phenylcyclopropyl)-5,6,7,8-tetrahydropyrido[4,3-d]pyrimidin-4(3H)-one;

6-(2-(3-(difluoromethyl)phenyl)-2-hydroxyacetyl)-2-(1-phenylcyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-phenylcyclopropyl)-5,6,7,8-tetrahydropyrido[4,3-d]pyrimidin-4(3H)-one;

6-(2-(4-(tert-butyl)phenyl)acetyl)-2-(1-phenylcyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3,5-dichlorophenyl)-2-hydroxyacetyl)-2-(1-phenylcyclopropyl)-3,5,6,7,8,9-hexahydro-4H-pyrimido[5,4-c]azepin-4-one;

(R)-2-(1-(4-(1H-pyrazol-4-yl)thiophen-2-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(thiophen-3-yl)cyclopropyl)-5,6,7,8-tetrahydropyrido[4,3-d]pyrimidin-4(3H)-one;

6-(2-(3-chlorophenyl)-2,2-difluoroacetyl)-2-(1-phenylcyclopropyl)-5,6,7,8-tetrahydropyrido[4,3-d]pyrimidin-4(3H)-one;

6-(2-(4-chloro-2-fluorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(5-(trifluoromethyl)pyridin-3-yl)acetyl)-2-(1-phenylcyclopropyl)-5,6,7,8-tetrahydropyrido[4,3-d]pyrimidin-4(3H)-one;

6-(2-(2-fluoro-5-(trifluoromethyl)phenyl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(naphthalen-1-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(naphthalen-1-ylmethyl)-5,6,7,8-tetrahydropyrido[4,3-d]pyrimidin-4(3H)-one;

(R)-6-(2-(3-chlorophenyl)-2-hydroxyacetyl)-2-(1-(naphthalen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;

(R)-8-(2-(3-chlorophenyl)-2-hydroxyacetyl)-2-(1-(thiophen-2-yl)cyclopropyl)-3,5,6,7,8,9-hexahydro-4H-pyrimido[4,5-c]azepin-4-one;

(R)-8-(2-hydroxy-2-(3-(trifluoromethyl)phenyl)acetyl)-2-(1-phenylcyclopropyl)-3,5,6,7,8,9-hexahydro-4H-pyrimido[4,5-c]azepin-4-one;

(R)-6-(2-(2,3-difluorophenyl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(2-chlorophenyl)-2-hydroxyacetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-hydroxy-2-(6-(trifluoromethyl)pyridin-2-yl)acetyl)-2-(1-phenylcyclopropyl)-5,6,7,8-tetrahydropyrido[4,3-d]pyrimidin-4(3H)-one;

6-(2-hydroxy-2-(2-(trifluoromethyl)pyridin-4-yl)acetyl)-2-(1-phenylcyclopropyl)-5,6,7,8-tetrahydropyrido[4,3-d]pyrimidin-4(3H)-one;

6-(6-chloro-1H-indole-2-carbonyl)-2-(1-phenylcyclopropyl)-5,6,7,8-tetrahydropyrido[4,3-d]pyrimidin-4(3H)-one;

2-(1-phenylcyclopropyl)-6-(5-(trifluoromethyl)-1H-benzo[d]imidazole-2-carbonyl)-5,6,7,8-tetrahydropyrido[4,3-d]pyrimidin-4(3H)-one;

6-(3-(2-fluorophenyl)-1H-pyrazole-5-carbonyl)-2-(1-phenylcyclopropyl)-5,6,7,8-tetrahydropyrido[4,3-d]pyrimidin-4(3H)-one;

6-(2-(2-chlorophenyl)acetyl)-2-(1-phenylcyclopropyl)-5,6,7,8-tetrahydropyrido[4,3-d]pyrimidin-4(3H)-one;

6-(3-(2-chlorophenyl)propanoyl)-2-(1-phenylcyclopropyl)-5,6,7,8-tetrahydropyrido[4,3-d]pyrimidin-4(3H)-one;

6-(2-(2-chlorophenoxy)acetyl)-2-(1-phenylcyclopropyl)-5,6,7,8-tetrahydropyrido[4,3-d]pyrimidin-4(3H)-one;

2-(1-phenylcyclopropyl)-6-(2-(2-(trifluoromethyl)phenyl)acetyl)-5,6,7,8-tetrahydropyrido[4,3-d]pyrimidin-4(3H)-one;

6-(3-(3-chlorophenyl)propanoyl)-2-(1-phenylcyclopropyl)-5,6,7,8-tetrahydropyrido[4,3-d]pyrimidin-4(3H)-one;

6-(2-(3-chlorophenoxy)acetyl)-2-(1-phenylcyclopropyl)-5,6,7,8-tetrahydropyrido[4,3-d]pyrimidin-4(3H)-one;

6-(2-hydroxy-2-(3-(pentafluoro-(lambda)$^{6}$-sulfaneyl)phenyl)acetyl)-2-(1-phenylcyclopropyl)-5,6,7,8-tetrahydropyrido[4,3-d]pyrimidin-4(3H)-one;

6-(2-(4-chloro-3-fluorophenyl)-2-hydroxyacetyl)-2-(1-phenylcyclopropyl)-5,6,7,8-tetrahydropyrido[4,3-d]pyrimidin-4(3H)-one;

6-(2-hydroxy-3-(o-tolyloxy)propanoyl)-2-(1-phenylcyclopropyl)-5,6,7,8-tetrahydropyrido[4,3-d]pyrimidin-4(3H)-one;

6-(2-(3,4-dichlorophenyl)-2-hydroxyacetyl)-2-(1-phenylcyclopropyl)-5,6,7,8-tetrahydropyrido[4,3-d]pyrimidin-4(3H)-one;

6-(2-(3-acetylphenyl)-2-hydroxyacetyl)-2-(1-phenylcyclopropyl)-5,6,7,8-tetrahydropyrido[4,3-d]pyrimidin-4(3H)-one;

6-(2-(3-ethylphenyl)-2-hydroxyacetyl)-2-(1-phenylcyclopropyl)-5,6,7,8-tetrahydropyrido[4,3-d]pyrimidin-4(3H)-one;

(R)-2-(1-(3-bromothiophen-2-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(6-phenylpyridin-3-yl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-3,5,6,7,8,9-hexahydro-4H-pyrimido[5,4-c]azepin-4-one;

6-(2-(2-fluoro-3-methylphenyl)-2-hydroxyacetyl)-2-(1-phenylcyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-chlorophenyl)cyclopropyl)-5,6,7,8-tetrahydropyrido[4,3-d]pyrimidin-4(3H)-one;

(R)-2-(1-(3-bromophenyl)cyclopropyl)-6-(2-(3-chlorophenyl)-2-hydroxyacetyl)-5,6,7,8-tetrahydropyrido[4,3-d]pyrimidin-4(3H)-one;

6-(2-(2,5-dichlorophenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(p-tolyl)acetyl)-2-(1-phenylcyclopropyl)-5,6,7,8-tetrahydropyrido[4,3-d]pyrimidin-4(3H)-one;

6-(2-hydroxy-2-(3-isopropylphenyl)acetyl)-2-(1-phenylcyclopropyl)-3,5,6,7,8,9-hexahydro-4H-pyrimido[5,4-c]azepin-4-one;

6-(2-(3-(difluoromethyl)phenyl)-2-hydroxyacetyl)-2-(1-phenylcyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-phenylcyclopropyl)-3,5,6,7,8,9-hexahydro-4H-pyrimido[5,4-c]azepin-4-one;

2-(1-phenylcyclopropyl)-6-(2-(4-(trifluoromethoxy)phenyl)acetyl)-5,6,7,8-tetrahydropyrido[4,3-d]pyrimidin-4(3H)-one;

6-(2-(4-phenoxyphenyl)acetyl)-2-(1-phenylcyclopropyl)-5,6,7,8-tetrahydropyrido[4,3-d]pyrimidin-4(3H)-one;

6-(2-(3-chloro-2-methoxyphenyl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-phenylpyridin-3-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-chlorothiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-chlorothiophen-2-yl)cyclopropyl)-5,6,7,8-tetrahydropyrido[4,3-d]pyrimidin-4(3H)-one;

(R)-2-(1-([1,1'-biphenyl]-3-yl)cyclopropyl)-6-(2-(3-chlorophenyl)-2-hydroxyacetyl)-5,6,7,8-tetrahydropyrido[4,3-d]pyrimidin-4(3H)-one;

(R)-2-(1-(4-bromophenyl)cyclopropyl)-6-(2-(3-chlorophenyl)-2-hydroxyacetyl)-5,6,7,8-tetrahydropyrido[4,3-d]pyrimidin-4(3H)-one;

(R)-2-(1-([1,1'-biphenyl]-4-yl)cyclopropyl)-6-(2-(3-chlorophenyl)-2-hydroxyacetyl)-5,6,7,8-tetrahydropyrido[4,3-d]pyrimidin-4(3H)-one;

6-(2-hydroxy-2-(naphthalen-1-yl)acetyl)-2-(1-phenylcyclopropyl)-5,6,7,8-tetrahydropyrido[4,3-d]pyrimidin-4(3H)-one;

6-(2-(3-chloro-2-methylphenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(2-methylpyridin-3-yl)phenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(quinolin-3-yl)acetyl)-5,6,7,8-tetrahydropyrido[4,3-d]pyrimidin-4(3H)-one;

2-(1-phenylcyclopropyl)-6-(2-(4-(pyridin-2-yl)phenyl)acetyl)-5,6,7,8-tetrahydropyrido[4,3-d]pyrimidin-4(3H)-one;

2-(1-phenylcyclopropyl)-6-(2-(3-(trifluoromethoxy)phenyl)acetyl)-5,6,7,8-tetrahydropyrido[4,3-d]pyrimidin-4(3H)-one;

6-(2-([1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-phenoxyphenyl)cyclopropyl)-5,6,7,8-tetrahydropyrido[4,3-d]pyrimidin-4(3H)-one;

6-(2-hydroxy-2-(3-(5-methylpyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(4-methylpyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(6-methoxypyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(4'-methyl-[1,1'-biphenyl]-3-yl)acetyl)-2-(1-phenylcyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(2-methylpyridin-4-yl)phenyl)acetyl)-2-(1-phenylcyclopropyl)-5,6,7,8-tetrahydropyrido[4,3-d]pyrimidin-4(3H)-one;

6-(2-hydroxy-2-(3-(2-methylpyrimidin-5-yl)phenyl)acetyl)-2-(1-phenylcyclopropyl)-5,6,7,8-tetrahydropyrido[4,3-d]pyrimidin-4(3H)-one;

6-(2-(3-(6-(dimethylamino)pyridin-3-yl)phenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(6-(trifluoromethyl)pyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

6-(2-(3-(1-cyclopropyl-1H-pyrazol-4-yl)phenyl)-2-hydroxyacetyl)-2-(1-phenylcyclopropyl)-5,6,7,8-tetrahydropyrido[4,3-d]pyrimidin-4(3H)-one;

6-(2-(3-(5-chlorothiophen-2-yl)phenyl)-2-hydroxyacetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-hydroxy-2-(3-isopropylphenyl)acetyl)-5,6,7,8-tetrahydropyrido[4,3-d]pyrimidin-4(3H)-one;

2-(1-(3-chlorophenyl)cyclopropyl)-6-(2-hydroxy-2-(3-isopropylphenyl)acetyl)-5,6,7,8-tetrahydropyrido[4,3-d]pyrimidin-4(3H)-one;

6-(2-hydroxy-2-(3-isopropylphenyl)acetyl)-2-(1-(thiophen-2-yl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(3-fluorophenyl)cyclopropyl)-5,6,7,8-tetrahydropyrido[4,3-d]pyrimidin-4(3H)-one;

2-(1-(3-chlorophenyl)cyclopropyl)-6-(2-(2-fluoro-3-(trifluoromethyl)phenyl)-2-hydroxyacetyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(thiophen-2-yl)cyclopropyl)-5,6,7,8-tetrahydropyrido[4,3-d]pyrimidin-4(3H)-one;

2-(1-(3-fluorophenyl)cyclopropyl)-6-(2-hydroxy-2-(3-((trifluoromethyl)thio)phenyl)acetyl)-5,6,7,8-tetrahydropyrido[4,3-d]pyrimidin-4(3H)-one;

2-(1-(3-chlorophenyl)cyclopropyl)-6-(2-hydroxy-2-(3-((trifluoromethyl)thio)phenyl)acetyl)-5,6,7,8-tetrahydropyrido[4,3-d]pyrimidin-4(3H)-one;

6-(2-hydroxy-2-(3-((trifluoromethyl)thio)phenyl)acetyl)-2-(1-(thiophen-2-yl)cyclopropyl)-5,6,7,8-tetrahydropyrido[4,3-d]pyrimidin-4(3H)-one;

6-(2-hydroxy-2-(3-((trifluoromethyl)thio)phenyl)acetyl)-2-(1-phenylcyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3-(pentafluoro-(lambda)$^6$-sulfaneyl)phenyl)acetyl)-5,6,7,8-tetrahydropyrido[4,3-d]pyrimidin-4(3H)-one;

2-(1-(3-chlorophenyl)cyclopropyl)-6-(2-hydroxy-2-(3-(pentafluoro-(lambda)$^6$-sulfaneyl)phenyl)acetyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-(thiophen-2-yl)cyclopropyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;

6-(2-hydroxy-2-(2-phenylpyridin-4-yl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-cyclohexylphenyl)cyclopropyl)-5,6,7,8-tetrahydropyrido[4,3-d]pyrimidin-4(3H)-one;

6-(2-(2-fluoro-3-(trifluoromethyl)phenyl)acetyl)-2-(1-phenylcyclopropyl)-5,6,7,8-tetrahydropyrido[4,3-d]pyrimidin-4(3H)-one;

6-(2-(3-cyclopropylphenyl)acetyl)-2-(1-phenylcyclopropyl)-5,6,7,8-tetrahydropyrido[4,3-d]pyrimidin-4(3H)-one;

6-(2-hydroxy-2-(1-methyl-1H-indol-3-yl)acetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

(R)-2-(1-(4-ethylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(4-cyclopentylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(2-methyl-3-(trifluoromethyl)phenyl)acetyl)-2-(1-phenylcyclopropyl)-5,6,7,8-tetrahydropyrido[4,3-d]pyrimidin-4(3H)-one;

6-(2-(2-chloro-3-(trifluoromethyl)phenyl)-2-hydroxyacetyl)-2-(1-phenylcyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(thiophen-2-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3-fluoro-5-(trifluoromethyl)phenyl)-2-hydroxyacetyl)-2-(1-phenylcyclopropyl)-5,6,7,8-tetrahydropyrido[4,3-d]pyrimidin-4(3H)-one;

6-(2-(3-chloro-5-(trifluoromethyl)phenyl)-2-hydroxyacetyl)-2-(1-phenylcyclopropyl)-5,6,7,8-tetrahydropyrido[4,3-d]pyrimidin-4(3H)-one;

2-(1-phenylcyclopropyl)-6-(2-(3-(trifluoromethyl)phenyl)acetyl)-3,5,6,7,8,9-hexahydro-4H-pyrimido[5,4-c]azepin-4-one;

6-(2-(3-chlorophenyl)-2,2-difluoroacetyl)-2-(1-phenylcyclopropyl)-3,5,6,7,8,9-hexahydro-4H-pyrimido[5,4-c]azepin-4-one;

6-(2-hydroxy-2-(3-((trifluoromethyl)thio)phenyl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-phenoxyphenyl)cyclopropyl)-5,6,7,8-tetrahydropyrido[4,3-d]pyrimidin-4(3H)-one;

(R)-2-(1-(4-cycloheptylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-hydroxy-2-(2'-(trifluoromethyl)-[2,4'-bipyridin]-4-yl)acetyl)-2-(1-phenylcyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-chlorophenyl)cyclopropyl)-5,6,7,8-tetrahydropyrido[4,3-d]pyrimidin-4(3H)-one;

6-(2-(4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(4'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(4'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3'-methyl-[1,1'-biphenyl]-3-yl)acetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(4'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;

6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

6-(2-(3-(5-chlorothiophen-3-yl)phenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-methyl-5-(trifluoromethyl)phenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(3-(trifluoromethyl)phenyl)propanoyl)-3,5,6,7,8,9-hexahydro-4H-pyrimido[5,4-c]azepin-4-one;

6-(2-hydroxy-2-(3'-methoxy-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(4'-methoxy-[1,1'-biphenyl]-3-yl)acetyl)-2-(1-phenylcyclopropyl)-5,6,7,8-tetrahydropyrido[4,3-d]pyrimidin-4(3H)-one;

6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

3'-(1-hydroxy-2-oxo-2-(4-oxo-2-(1-phenylcyclopropyl)-3,5,7,8-tetrahydropyrido[4,3-d]pyrimidin-6(4H)-yl)ethyl)-[1,1'-biphenyl]-3-carbonitrile;

6-(2-(4'-ethoxy-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(4'-isopropoxy-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(2'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

6-(2-(3-(benzo[b]thiophen-3-yl)phenyl)-2-hydroxyacetyl)-2-(1-phenylcyclopropyl)-5,6,7,8-tetrahydropyrido[4,3-d]pyrimidin-4(3H)-one;

6-(2-(3-(5,6-dimethylpyridin-3-yl)phenyl)-2-hydroxyacetyl)-2-(1-phenylcyclopropyl)-5,6,7,8-tetrahydropyrido[4,3-d]pyrimidin-4(3H)-one;

6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(4'-(difluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-chloro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(5-bromopyridin-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4-bromothiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(prop-1-en-2-yl)phenyl)cyclopropyl)-3,5,6,7,8,9-hexahydro-4H-pyrimido[5,4-c]azepin-4-one;

(R)-2-(1-(3-cyclohexylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3-chlorophenyl)-2,2-difluoroacetyl)-2-(1-(thiophen-2-yl)cyclopropyl)-3,5,6,7,8,9-hexahydro-4H-pyrimido[5,4-c]azepin-4-one;

6-(2-(2-fluoro-3-(trifluoromethyl)phenyl)acetyl)-2-(1-phenylcyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-phenylcyclopropyl)-5,6,7,8-tetrahydropyrido[4,3-d]pyrimidin-4(3H)-one;

6-(2,2-difluoro-2-(3-(trifluoromethyl)phenyl)acetyl)-2-(1-phenylcyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-fluorophenyl)cyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;

2-(1-(3-fluorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;

6-(2-(3-chlorophenyl)-2,2-difluoroacetyl)-2-(1-(3-chlorophenyl)cyclopropyl)-5,6,7,8-tetrahydropyrido[4,3-d]pyrimidin-4(3H)-one;

6-(2-(3-chlorophenyl)-2,2-difluoroacetyl)-2-(1-(3-fluorophenyl)cyclopropyl)-3,5,6,7,8,9-hexahydro-4H-pyrimido[5,4-c]azepin-4-one;

2-(1-(3-chlorophenyl)cyclopropyl)-6-(2,2-difluoro-2-(3-(trifluoromethyl)phenyl)acetyl)-5,6,7,8-tetrahydropyrido[4,3-d]pyrimidin-4(3H)-one;

6-(2,2-difluoro-2-(3-(trifluoromethyl)phenyl)acetyl)-2-(1-(3-fluorophenyl)cyclopropyl)-3,5,6,7,8,9-hexahydro-4H-pyrimido[5,4-c]azepin-4-one;

2-(1-(3-chlorophenyl)cyclopropyl)-6-(2-(3-cyclopropylphenyl)-2-hydroxyacetyl)-5,6,7,8-tetrahydropyrido[4,3-d]pyrimidin-4(3H)-one;

6-(2-(3-cyclopropylphenyl)-2-hydroxyacetyl)-2-(1-phenylcyclopropyl)-3,5,6,7,8,9-hexahydro-4H-pyrimido[5,4-c]azepin-4-one;

6-(2-(3-cyclopropylphenyl)-2-hydroxyacetyl)-2-(1-(thiophen-2-yl)cyclopropyl)-3,5,6,7,8,9-hexahydro-4H-pyrimido[5,4-c]azepin-4-one;
6-(2-(3-cyclopropylphenyl)-2-hydroxyacetyl)-2-(1-(3-fluorophenyl)cyclopropyl)-3,5,6,7,8,9-hexahydro-4H-pyrimido[5,4-c]azepin-4-one;
(R)-2-(1-(4-ethylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(4-cyclopentylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
2-(1-(3-chlorophenyl)cyclopropyl)-6-(2-(2-fluoro-3-(trifluoromethyl)phenyl)-2-hydroxyacetyl)-3,5,6,7,8,9-hexahydro-4H-pyrimido[5,4-c]azepin-4-one;
2-(1-(3-chlorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;
2-(1-(3-chlorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;
6-(2-(3-chlorophenyl)-2,2-difluoroacetyl)-2-(1-(3-chlorophenyl)cyclopropyl)-3,5,6,7,8,9-hexahydro-4H-pyrimido[5,4-c]azepin-4-one;
2-(1-(3-chlorophenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one;
(R)-2-(1-(4-(1-acetylpiperidin-4-yl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;
(R)-2-(1-(3-(4,4-difluorocyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
6-(2-(6-chloropyridin-2-yl)-2-hydroxyacetyl)-2-(1-phenylcyclopropyl)-5,6,7,8-tetrahydropyrido[4,3-d]pyrimidin-4(3H)-one;
6-(2-hydroxy-2-(6-(3-(trifluoromethyl)phenyl)pyridin-2-yl)acetyl)-2-(1-phenylcyclopropyl)-5,6,7,8-tetrahydropyrido[4,3-d]pyrimidin-4(3H)-one;
6-(2-hydroxy-2-(2'-(trifluoromethyl)-[2,4'-bipyridin]-6-yl)acetyl)-2-(1-phenylcyclopropyl)-5,6,7,8-tetrahydropyrido[4,3-d]pyrimidin-4(3H)-one;
6-(2-(6-(3-chlorophenyl)pyridin-2-yl)-2-hydroxyacetyl)-2-(1-phenylcyclopropyl)-5,6,7,8-tetrahydropyrido[4,3-d]pyrimidin-4(3H)-one;
6-(2-hydroxy-2-(6-(3-(trifluoromethoxy)phenyl)pyridin-2-yl)acetyl)-2-(1-phenylcyclopropyl)-5,6,7,8-tetrahydropyrido[4,3-d]pyrimidin-4(3H)-one;
(R)-2-(1-(3-chlorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-(3-chlorophenyl)-2-hydroxyacetyl)-2-(1-(3-chlorophenyl)cyclopropyl)-3,5,6,7,8,9-hexahydro-4H-pyrimido[5,4-c]azepin-4-one;
6-(2-(3-chloro-2-fluorophenyl)-2-hydroxyacetyl)-2-(1-(3-chlorophenyl)cyclopropyl)-3,5,6,7,8,9-hexahydro-4H-pyrimido[5,4-c]azepin-4-one;
6-(2-(3-(tert-butyl)phenyl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(piperidin-4-yl)thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(1-methylpiperidin-4-yl)thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(2-isopropylpyridin-4-yl)cyclopropyl)-3,5,6,7,8,9-hexahydro-4H-pyrimido[5,4-c]azepin-4-one;
2-(1-(3-chlorophenyl)cyclopropyl)-6-(2-(3-cyclopropylphenyl)-2-hydroxyacetyl)-3,5,6,7,8,9-hexahydro-4H-pyrimido[5,4-c]azepin-4-one;
6-(2-(2'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3',5'-bis(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-((dimethylamino)methyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-2-(1-(3-acetylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-methoxyphenyl)cyclopropyl)-3,5,6,7,8,9-hexahydro-4H-pyrimido[5,4-c]azepin-4-one;
6-(1H-benzo[d]imidazole-2-carbonyl)-2-(1-(3-chlorophenyl)cyclopropyl)-3,5,6,7,8,9-hexahydro-4H-pyrimido[5,4-c]azepin-4-one;
6-(2-(6-(cyclohex-1-en-1-yl)pyridin-2-yl)-2-hydroxyacetyl)-2-(1-phenylcyclopropyl)-5,6,7,8-tetrahydropyrido[4,3-d]pyrimidin-4(3H)-one;
6-(2-hydroxy-2-(3-(2,2,2-trifluoroethoxy)phenyl)acetyl)-2-(1-phenylcyclopropyl)-3,5,6,7,8,9-hexahydro-4H-pyrimido[5,4-c]azepin-4-one;
6-(2-hydroxy-2-(1'-methyl-1',2',3',6'-tetrahydro-[2,4'-bipyridin]-6-yl)acetyl)-2-(1-phenylcyclopropyl)-5,6,7,8-tetrahydropyrido[4,3-d]pyrimidin-4(3H)-one;
(R)-2-(1-(3-chlorophenyl)cyclopropyl)-6-(2-(2,3-difluorophenyl)-2-hydroxyacetyl)-3,5,6,7,8,9-hexahydro-4H-pyrimido[5,4-c]azepin-4-one;
6-(2-(6-cyclohexylpyridin-2-yl)-2-hydroxyacetyl)-2-(1-phenylcyclopropyl)-5,6,7,8-tetrahydropyrido[4,3-d]pyrimidin-4(3H)-one;
2-(1-(3-chlorophenyl)cyclopropyl)-6-(2-hydroxy-2-(3-(2,2,2-trifluoroethoxy)phenyl)acetyl)-3,5,6,7,8,9-hexahydro-4H-pyrimido[5,4-c]azepin-4-one;
6-(2-(2'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(6-isopropylpyridin-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-phenylthiophen-2-yl)cyclopropyl)-3,5,6,7,8,9-hexahydro-4H-pyrimido[5,4-c]azepin-4-one;
2-(1-phenylcyclopropyl)-6-(2-(3-((trifluoromethyl)thio)phenyl)acetyl)-3,5,6,7,8,9-hexahydro-4H-pyrimido[5,4-c]azepin-4-one;
6-(2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;

6-(2-amino-2-(3-(trifluoromethyl)phenyl)acetyl)-2-(1-phenylcyclopropyl)-3,5,6,7,8,9-hexahydro-4H-pyrimido[5,4-c]azepin-4-one;
2-(1-(3-chlorophenyl)cyclopropyl)-6-(2-hydroxy-2-(2-(trifluoromethyl)phenyl)acetyl)-3,5,6,7,8,9-hexahydro-4H-pyrimido[5,4-c]azepin-4-one;
2-(1-(3-chlorophenyl)cyclopropyl)-6-(2-hydroxy-2-(4-(trifluoromethyl)phenyl)acetyl)-3,5,6,7,8,9-hexahydro-4H-pyrimido[5,4-c]azepin-4-one;
6-(2-methyl-2-(3-(trifluoromethyl)phenyl)propanoyl)-2-(1-phenylcyclopropyl)-3,5,6,7,8,9-hexahydro-4H-pyrimido[5,4-c]azepin-4-one;
6-(2-hydroxy-2-(3'-hydroxy-5'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;
6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-hydroxy-2-(3'-((trifluoromethyl)thio)-[1,1'-biphenyl]-3-yl)acetyl)-2-(1-phenylcyclopropyl)-5,6,7,8-tetrahydropyrido[4,3-d]pyrimidin-4(3H)-one;
6-(2-hydroxy-2-(2'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;
(R)-2-(1-([1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(thiazol-5-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(3-methoxypropyl)thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-phenethylthiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;
6-(2-(6-(3-(tert-butyl)phenyl)pyridin-2-yl)-2-hydroxyacetyl)-2-(1-phenylcyclopropyl)-5,6,7,8-tetrahydropyrido[4,3-d]pyrimidin-4(3H)-one;
6-(2-(6-(3-cyclopropylphenyl)pyridin-2-yl)-2-hydroxyacetyl)-2-(1-phenylcyclopropyl)-5,6,7,8-tetrahydropyrido[4,3-d]pyrimidin-4(3H)-one;
6-(2-(3-bromophenyl)-2-hydroxyacetyl)-2-(1-phenylcyclopropyl)-3,5,6,7,8,9-hexahydro-4H-pyrimido[5,4-c]azepin-4-one;
2-(1-phenylcyclopropyl)-6-(1-(3-(trifluoromethyl)phenyl)cyclopropane-1-carbonyl)-3,5,6,7,8,9-hexahydro-4H-pyrimido[5,4-c]azepin-4-one;
6-(2-hydroxy-2-(3-(trifluoromethyl)phenyl)propanoyl)-2-(1-phenylcyclopropyl)-3,5,6,7,8,9-hexahydro-4H-pyrimido[5,4-c]azepin-4-one;
6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;
6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;
6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(2-(tetrahydro-2H-pyran-4-yl)ethyl)thiophen-2-yl)cyclopropyl)-3,5,6,7,8,9-hexahydro-4H-pyrimido[5,4-c]azepin-4-one;
(R)-2-(1-(4-(2-cyclopropylethyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(pyridin-3-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(pyrimidin-5-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-methyl-1H-pyrazol-4-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(isothiazol-4-yl)phenyl)cyclopropyl)-3,5,6,7,8,9-hexahydro-4H-pyrimido[5,4-c]azepin-4-one;
6-((R)-2-hydroxy-2-(3-(trifluoromethyl)phenyl)acetyl)-2-(1-(4'-(trifluoromethyl)-2',3',4',5'-tetrahydro-[1,1'-biphenyl]-3-yl)cyclopropyl)-3,5,6,7,8,9-hexahydro-4H-pyrimido[5,4-c]azepin-4-one;
6-((R)-2-hydroxy-2-(3-(trifluoromethyl)phenyl)acetyl)-2-(1-(3-(1,1,1-trifluoropropan-2-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-isobutylphenyl)cyclopropyl)-3,5,6,7,8,9-hexahydro-4H-pyrimido[5,4-c]azepin-4-one;
(R)-2-(1-(3-(4,4-dimethylcyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(3-hydroxy-3-methylbutyl)thiophen-2-yl)cyclopropyl)-3,5,6,7,8,9-hexahydro-4H-pyrimido[5,4-c]azepin-4-one;
(R)-2-(1-(4-(3,3-dimethylbutyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;
(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;
(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N, N-dimethylthiophene-3-carboxamide;
1-(2-(1-(3-chlorophenyl)cyclopropyl)-4-oxo-3,5,7,8-tetrahydropyrido[4,3-d]pyrimidin-6(4H)-yl)-2-(3-(trifluoromethyl)phenyl)ethane-1,2-dione;
(R)-6-(2-hydroxy-2-(3-(trifluoromethyl)phenyl)acetyl)-2-(1-(3-(hydroxymethyl)phenyl)cyclopropyl)-3,5,6,7,8,9-hexahydro-4H-pyrimido[5,4-c]azepin-4-one;

6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3',4'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3',5'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2',5'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-fluoro-[1,1'-biphenyl]-3-yl)-2-hydroxyacetyl)-2-(1-(3-fluorophenyl)cyclopropyl)-5,6,7,8-tetrahydropyrido[4,3-d]pyrimidin-4(3H)-one;

2-(1-(3-chlorophenyl)cyclopropyl)-6-(2-(3'-fluoro-[1,1'-biphenyl]-3-yl)-2-hydroxyacetyl)-5,6,7,8-tetrahydropyrido[4,3-d]pyrimidin-4(3H)-one;

6-(2-(3'-fluoro-[1,1'-biphenyl]-3-yl)-2-hydroxyacetyl)-2-(1-(thiophen-2-yl)cyclopropyl)-5,6,7,8-tetrahydropyrido[4,3-d]pyrimidin-4(3H)-one;

6-(2-(3'-fluoro-[1,1'-biphenyl]-3-yl)-2-hydroxyacetyl)-2-(1-(3-fluorophenyl)cyclopropyl)-3,5,6,7,8,9-hexahydro-4H-pyrimido[5,4-c]azepin-4-one;

2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

6-(2-hydroxy-2-(3-phenoxyphenyl)acetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-hydroxy-2-(3-phenoxyphenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(2-(oxetan-3-yl)ethyl)thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(trifluoromethyl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(piperidin-1-ylmethyl)phenyl)cyclopropyl)-3,5,6,7,8,9-hexahydro-4H-pyrimido[5,4-c]azepin-4-one;

(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)nicotinonitrile;

(R)-2-(1-(3-(6-(dimethylamino)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-dimethyl-[1,1'-biphenyl]-3-carboxamide;

6-(2-(3-chlorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;

6-(2-(3'-fluoro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-fluoro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(5'-fluoro-2'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2',3'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(4'-chloro-3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-([1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;

6-(2-(2',4'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(5-bromopyridin-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(5-(3-(trifluoromethyl)phenyl)pyridin-3-yl)acetyl)-2-(1-phenylcyclopropyl)-5,6,7,8-tetrahydropyrido[4,3-d]pyrimidin-4(3H)-one;

6-(2-(5-(3-chlorophenyl)pyridin-3-yl)-2-hydroxyacetyl)-2-(1-phenylcyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

2-(1-(4-(2-((3S,5S)-adamantan-1-yl)ethyl)thiophen-2-yl)cyclopropyl)-6-((RS)-2-hydroxy-2-(3-(trifluoromethyl)phenyl)acetyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(trifluoromethoxy)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-methoxypyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-6-oxo-1,6-dihydropyridin-3-yl)phenyl)cyclopropyl)-3,5,6,7,8,9-hexahydro-4H-pyrimido[5,4-c]azepin-4-one;

(R)-2-(1-(3'-((dimethylamino)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(5-(3-fluorophenyl)pyridin-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(2'-(trifluoromethyl)-[3,4'-bipyridin]-5-yl)acetyl)-2-(1-phenylcyclopropyl)-5,6,7,8-tetrahydropyrido[4,3-d]pyrimidin-4(3H)-one;

6-(2-(6-(3-fluorophenyl)pyridin-2-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(1-(2,2,2-trifluoroethyl)piperidin-4-yl)phenyl)cyclopropyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-sulfonamide;

(R)-6-(2-hydroxy-2-(3-(trifluoromethyl)phenyl)acetyl)-2-(1-(4'-(4-hydroxytetrahydro-2H-pyran-4-yl)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-pyrazol-5-yl)phenyl)cyclopropyl)-3,5,6,7,8,9-hexahydro-4H-pyrimido[5,4-c]azepin-4-one;

(R)-2-(1-(3-(1-cyclopropyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(1-(difluoromethyl)-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-pyrazol-3-yl)phenyl)cyclopropyl)-3,5,6,7,8,9-hexahydro-4H-pyrimido[5,4-c]azepin-4-one;

(R)-2-(1-(3-(1-cyclobutyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-methoxyethyl)-1H-pyrazol-4-yl)phenyl)cyclopropyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-dimethyl-[1,1'-biphenyl]-4-sulfonamide;

6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(oxazol-5-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3'-(methylsulfonyl)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(pyridin-4-yl)phenyl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)-6-(2-hydroxy-2-(3-(trifluoromethyl)phenyl)acetyl)-2-(1-(4-(isoindoline-2-carbonyl)thiophen-2-yl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-fluorophenyl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(thiophen-2-yl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(3-fluorophenyl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

6-(2-(4"-chloro-[1,1':4',1"-terphenyl]-3-yl)-2-hydroxyacetyl)-2-(1-phenylcyclopropyl)-5,6,7,8-tetrahydropyrido[4,3-d]pyrimidin-4(3H)-one;

6-(2-(2-fluoro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2,3'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2-fluoro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(2-(methylamino)pyridin-4-yl)phenyl)cyclopropyl)-3,5,6,7,8,9-hexahydro-4H-pyrimido[5,4-c]azepin-4-one;

(R)-2-(1-(4'-(dimethylamino)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-(pyrrolidin-1-yl)pyrimidin-5-yl)phenyl)cyclopropyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-3-methylbenzo[d]oxazol-2(3H)-one;

(R)-6-(2-hydroxy-2-(3-(trifluoromethyl)phenyl)acetyl)-2-(1-(3'-(piperidine-1-carbonyl)-[1,1'-biphenyl]-3-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

6-(2-hydroxy-2-(3'-(2-methoxyethoxy)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;

6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

6-(2-hydroxy-2-(3'-(trifluoromethyl)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

2-(1-(3-fluorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

6-(2-hydroxy-2-(3'-(trifluoromethoxy)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

2-(1-(3-chlorophenyl)cyclopropyl)-6-(2-hydroxy-2-(3-phenoxyphenyl)acetyl)-5,6,7,8-tetrahydropyrido[4,3-d]pyrimidin-4(3H)-one;

6-(2-hydroxy-2-(3-phenoxyphenyl)acetyl)-2-(1-phenylcyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3-phenoxyphenyl)acetyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(2-fluoro-3-(2-(trifluoromethyl)pyridin-4-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-cyclohexylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one; 2-(1-(3-fluorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-methylpiperidin-1-yl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-methylpiperazin-1-yl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-((4-methylpiperazin-1-yl)methyl)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-methoxypyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(1-methylpiperidin-4-yl)-1H-pyrazol-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(1-methylpiperidin-4-yl)-[1,1'-biphenyl]-3-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-cyclopentylpyridin-3-yl)cyclopropyl)-5,6,7,8-tetrahydropyrido[4,3-d]pyrimidin-4(3H)-one;

(R)-2-(1-(5-cyclopentylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(3-cyclopentylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(3-isopropylphenyl)cyclopropyl)-3,5,6,7,8,9-hexahydro-4H-pyrimido[5,4-c]azepin-4-one;

6-(2-hydroxy-2-(3-((trifluoromethyl)thio)phenyl)acetyl)-2-(1-(3-isopropylphenyl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl) acetyl)-2-(1-(3-isopropylphenyl)cyclopropyl)-3,5,6,7,8, 9-hexahydro-4H-pyrimido[5,4-c]azepin-4-one;

6-(2-hydroxy-2-(3'-(trifluoromethyl)-[1,1'-biphenyl]-3-yl) acetyl)-2-(1-(3-isopropylphenyl)cyclopropyl)-3,5,6,7,8, 9-hexahydro-4H-pyrimido[5,4-c]azepin-4-one;

(R)-6-(2-(3-chlorophenyl)-2-hydroxyacetyl)-2-(1-(4-(thiazol-5-yl)thiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-phenylthiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(pyridin-3-yl)thiophen-2-yl)cyclopropyl)-5,6,7,8-tetrahydropyrido[4,3-d]pyrimidin-4(3H)-one;

6-(2-hydroxy-2-(3-(2-(trifluoromethyl)pyridin-4-yl)phenyl) acetyl)-2-(1-(3-isopropylphenyl)cyclopropyl)-3,5,6,7,8, 9-hexahydro-4H-pyrimido[5,4-c]azepin-4-one;

(R)-2-(1-([3,3'-bipyridin]-5-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-(isothiazol-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

6-(2-hydroxy-2-(2-phenoxyphenyl)acetyl)-2-(1-phenylcyclopropyl)-5,6,7,8-tetrahydropyrido[4,3-d]pyrimidin-4 (3H)-one;

2-(1-(3-chlorophenyl)cyclopropyl)-6-(2-hydroxy-2-(2-phenoxyphenyl)acetyl)-3,5,6,7,8,9-hexahydro-4H-pyrimido [5,4-c]azepin-4-one;

(R)-6-(2-hydroxy-2-(3-(trifluoromethyl)phenyl)acetyl)-2-(1-(3-(1-(2-phenylacetyl)piperidin-4-yl)phenyl)cyclopropyl)-3,5,6,7,8,9-hexahydro-4H-pyrimido[5,4-c]azepin-4-one;

(R)-2-(1-(3-(1-(3,3-dimethylbutanoyl)piperidin-4-yl)phenyl)cyclopropyl)-6-(2-hydroxy-2-(3-(trifluoromethyl) phenyl)acetyl)-3,5,6,7,8,9-hexahydro-4H-pyrimido[5,4-c]azepin-4-one;

(R)-2-(1-(3-(1-benzoylpiperidin-4-yl)phenyl)cyclopropyl)-6-(2-hydroxy-2-(3-(trifluoromethyl)phenyl)acetyl)-3,5,6, 7,8,9-hexahydro-4H-pyrimido[5,4-c]azepin-4-one;

(R)-6-(2-hydroxy-2-(3-(trifluoromethyl)phenyl)acetyl)-2-(1-(3-(1-(3-phenylpropanoyl)piperidin-4-yl)phenyl)cyclopropyl)-3,5,6,7,8,9-hexahydro-4H-pyrimido[5,4-c] azepin-4-one;

2-(1-(3-chlorophenyl)cyclopropyl)-6-(2-hydroxy-2-(4-phenoxyphenyl)acetyl)-3,5,6,7,8,9-hexahydro-4H-pyrimido [5,4-c]azepin-4-one;

6-(2-(3-(benzyloxy)phenyl)-2-hydroxyacetyl)-2-(1-phenylcyclopropyl)-5,6,7,8-tetrahydropyrido[4,3-d]pyrimidin-4 (3H)-one;

6-(2-(3-(benzyloxy)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(pyridin-3-yl)thiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-2-(1-(3-bromophenyl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-([1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3-(isothiazol-4-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(pyridin-3-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(2',3',4', 5'-tetrahydro-[1,1'-biphenyl]-3-yl)cyclopropyl)-3,5,6,7,8, 9-hexahydro-4H-pyrimido[5,4-c]azepin-4-one;

(R)-6-(2-(3-chlorophenyl)-2-hydroxyacetyl)-2-(1-(3-(prop-1-en-2-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-(tetrahydro-2H-pyran-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-(tetrahydro-2H-pyran-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(tetrahydro-2H-pyran-4-yl)phenyl)cyclopropyl)-3, 5,6,7,8,9-hexahydro-4H-pyrimido[5,4-c]azepin-4-one;

(R)-2-(1-([3,3'-bipyridin]-5-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(5-(isothiazo-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(6-(methylamino)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(pyrrolidin-1-yl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(pyrrolidin-1-ylmethyl)-[1,1'-biphenyl]-3-yl)cyclopropyl)-3,5,6,7,8,9-hexahydro-4H-pyrimido[5,4-c]azepin-4-one;

6-(2-hydroxy-2-(3-(3-(trifluoromethyl)phenoxy)phenyl) acetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-hydroxy-2-(3-(3-(trifluoromethyl)phenoxy)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(4-(4,4-difluorocyclohexyl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-cyclopentylthiophen-2-yl)cyclopropyl)-5,6,7,8-tetrahydropyrido[4,3-d]pyrimidin-4(3H)-one;

(R)-2-(1-(4-(4,4-difluorocyclohexyl)thiophen-2-yl)cyclopropyl)-6-(2-hydroxy-2-(3-(trifluoromethyl)phenyl) acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(tetrahydro-2H-pyran-4-yl)thiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(pyridin-3-yl)thiophen-2-yl)cyclopropyl)-3,5,6,7,8,9-hexahydro-4H-pyrimido[5,4-c]azepin-4-one;

(R)-2-(1-(4-(4,4-difluorocyclohexyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(3-isopropylphenyl)cyclopropyl)-3,5,6,7,8,9-hexahydro-4H-pyrimido[5,4-c]azepin-4-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(tetrahydro-2H-pyran-4-yl)thiophene-3-carboxamide;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropyl-N-methylthiophene-3-carboxamide;

(R)-6-(2-hydroxy-2-(3-(trifluoromethyl)phenyl)acetyl)-2-(1-(4-(piperidine-1-carbonyl)thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(2-(1-hydroxycyclohexyl)ethyl)thiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-isopropylphenyl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-(quinolin-3-yl)phenyl)acetyl)-5,6,7,8-tetrahydropyrido[4,3-d]pyrimidin-4(3H)-one;

6-(2-hydroxy-2-(3-(quinolin-3-yl)phenyl)acetyl)-2-(1-phenylcyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-(quinolin-3-yl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-indazol-5-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-indazol-4-yl)phenyl)cyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(benzo[b]thiophen-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(5-(4,4-difluorocyclohexyl)pyridin-3-yl)cyclopropyl)-5,6,7,8-tetrahydropyrido[4,3-d]pyrimidin-4(3H)-one;

(R)-2-(1-(5-(4,4-difluorocyclohexyl)pyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(S)-6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(S)-6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;

(R)-6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclopentylphenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-(pyridin-3-yl)phenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-(isothiazol-4-yl)phenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-isopropylphenyl)cyclopropyl)-5,6,7,8-tetrahydropyrido[4,3-d]pyrimidin-4(3H)-one;

(R)-2-(1-(3-cyclopentylphenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(tetrahydro-2H-pyran-4-yl)phenyl)cyclopropyl)-5,6,7,8-tetrahydropyrido[4,3-d]pyrimidin-4(3H)-one;

(R)-2-(1-([1,1'-biphenyl]-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(pyridin-3-yl)phenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(isothiazol-4-yl)phenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-phenoxyphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-phenoxyphenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3-((trifluoromethyl)thio)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(4-phenoxyphenyl)acetyl)-2-(1-phenylcyclopropyl)-5,6,7,8-tetrahydropyrido[4,3-d]pyrimidin-4(3H)-one;

(R)-6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

(S)-6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;

(R)-6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2-phenoxypyridin-4-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(3-chlorophenyl)-2,2-difluoroacetyl)-2-(1-(4-isopropylthiophen-2-yl)cyclopropyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-(4-isopropylthiophen-2-yl)cyclopropyl)-5,6,7,8-tetrahydropyrido[4,3-d]pyrimidin-4(3H)-one;

(S)-6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(S)-6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(5-(trifluoromethyl)pyridin-3-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(6-(trifluoromethyl)pyridin-2-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(quinolin-6-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(isoquinolin-6-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(quinolin-7-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(quinolin-4-yl)phenyl)acetyl)-2-(1-phenylcyclopropyl)-5,6,7,8-tetrahydropyrido[4,3-d]pyrimidin-4(3H)-one;

(R)-6-(2-(3-(benzofuran-2-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(3-(2,2-difluorobenzo[d][1,3]dioxol-5-yl)phenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(4'-(pyridin-2-ylmethoxy)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclopentylphenyl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;
(R)-6-(2-(3'-fluoro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;
(R)-6-(2-(3-(6-(benzyloxy)pyridin-3-yl)phenyl)-2-hydroxyacetyl)-2-(1-phenylcyclopropyl)-5,6,7,8-tetrahydropyrido[4,3-d]pyrimidin-4(3H)-one;
2-(1-(3-chlorophenyl)cyclopropyl)-6-(2-hydroxy-2-(3-(3-(trifluoromethyl)phenoxy)phenyl)acetyl)-5,6,7,8-tetrahydropyrido[4,3-d]pyrimidin-4(3H)-one;
6-(2-hydroxy-2-(3-(3-(trifluoromethyl)phenoxy)phenyl)acetyl)-2-(1-phenylcyclopropyl)-3,5,6,7,8,9-hexahydro-4H-pyrimido[5,4-c]azepin-4-one;
6-(2-(3-(benzyloxy)phenyl)-2-hydroxyacetyl)-2-(1-phenylcyclopropyl)-3,5,6,7,8,9-hexahydro-4H-pyrimido[5,4-c]azepin-4-one;
(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-N,N-dimethylnicotinamide;
(R)-6-(2-hydroxy-2-(3-(trifluoromethyl)phenyl)acetyl)-2-(1-(3-(1-(1-(trifluoromethyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;
(R)-6-(2-(3'-fluoro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;
(R)-6-(2-hydroxy-2-(3'-(trifluoromethyl)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;
(R)-6-(2-hydroxy-2-(3'-(trifluoromethoxy)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;
(R)-2-(1-(4'-(tert-butyl)-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;
(R)-6-(2-(3-chlorophenyl)-2-hydroxyacetyl)-2-(1-(4'-fluoro-[1,1'-biphenyl]-3-yl)cyclopropyl)-3,5,6,7,8,9-hexahydro-4H-pyrimido[5,4-c]azepin-4-one;
(R)-2-(1-(4'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;
(R)-6-(2-(3-chlorophenyl)-2-hydroxyacetyl)-2-(1-(3-(1-cyclopropyl-1H-pyrazol-4-yl)phenyl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(3-(2-methoxypyridin-4-yl)phenyl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(4'-(trifluoromethyl)-[1,1'-biphenyl]-3-yl)cyclopropyl)-3,5,6,7,8,9-hexahydro-4H-pyrimido[5,4-c]azepin-4-one;
8-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[4,5-c]azepin-4-one;
(R)-6-(2-(3-chlorophenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(4-cyclopentylthiophen-2-yl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;
6-(2-(3-(benzyloxy)phenyl)-2-hydroxyacetyl)-2-(1-(3-chlorophenyl)cyclopropyl)-5,6,7,8-tetrahydropyrido[4,3-d]pyrimidin-4(3H)-one;
(R)-2-(1-(3'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;
(R)-6-(2-(3-chlorophenyl)-2-hydroxyacetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one;
(R)-3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-3-carbonitrile;
2-(1-(3-chlorophenyl)cyclopropyl)-6-(2-(3-(trifluoromethyl)phenyl)propanoyl)-3,5,6,7,8,9-hexahydro-4H-pyrimido[5,4-c]azepin-4-one;
2-(1-(3-fluorophenyl)cyclopropyl)-6-(2-(3-(trifluoromethyl)phenyl)propanoyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(6-(4-isobutyrylpiperazin-1-yl)pyridin-3-yl)phenyl)cyclopropyl)-3,5,6,7,8,9-hexahydro-4H-pyrimido[5,4-c]azepin-4-one;
(R)-2-(1-(3-(6-(4-(3,3-dimethylbutanoyl)piperazin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(6-(4-(2-phenylacetyl)piperazin-1-yl)pyridin-3-yl)phenyl)cyclopropyl)-3,5,6,7,8,9-hexahydro-4H-pyrimido[5,4-c]azepin-4-one;
(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)picolinonitrile;
(R)-2-(1-(4'-((dimethylamino)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4'-(pyridin-2-ylmethoxy)-[1,1'-biphenyl]-3-yl)cyclopropyl)-3,5,6,7,8,9-hexahydro-4H-pyrimido[5,4-c]azepin-4-one;
(R)-6-(2-hydroxy-2-(4'-(trifluoromethoxy)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;
(R)-6-(2-hydroxy-2-(4'-(trifluoromethyl)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;
(R)-6-(2-(4'-(tert-butyl)-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;
(R)-6-(2-(4'-fluoro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;
(R)-6-(2-(4'-chloro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;
(R)-6-(2-hydroxy-2-(3-(6-(trifluoromethyl)pyridin-3-yl)phenyl)acetyl)-2-(1-(5-isopropylpyridin-3-yl)cyclopropyl)-5,6,7,8-tetrahydropyrido[4,3-d]pyrimidin-4(3H)-one;
(R)-6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(5-isopropylpyridin-3-yl)cyclopropyl)-3,5,6,7,8,9-hexahydro-4H-pyrimido[5,4-c]azepin-4-one;

6-(2-(2-(benzyloxy)phenyl)acetyl)-2-(1-(3-chlorophenyl)cyclopropyl)-3,5,6,7,8,9-hexahydro-4H-pyrimido[5,4-c]azepin-4-one;

6-(2-(4-(benzyloxy)phenyl)acetyl)-2-(1-(3-chlorophenyl)cyclopropyl)-3,5,6,7,8,9-hexahydro-4H-pyrimido[5,4-c]azepin-4-one;

6-(2-([1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(3-isopropylphenyl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-chlorophenyl)-2,2-difluoroacetyl)-2-(1-(3-isopropylphenyl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(5-phenylpyridin-3-yl)cyclopropyl)-5,6,7,8-tetrahydropyrido[4,3-d]pyrimidin-4(3H)-one;

6-(2-(3-chlorophenyl)-2,2-difluoroacetyl)-2-(1-(5-phenylpyridin-3-yl)cyclopropyl)-5,6,7,8-tetrahydropyrido[4,3-d]pyrimidin-4(3H)-one;

6-(2,2-difluoro-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

6-(2-(3-chlorophenyl)-2,2-difluoroacetyl)-2-(1-(5-isopropylpyridin-3-yl)cyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-hydroxy-2-(3-(2-(trifluoromethyl)pyridin-4-yl)phenyl)acetyl)-2-(1-(3-isopropylphenyl)cyclopropyl)-5,6,7,8-tetrahydropyrido[4,3-d]pyrimidin-4(3H)-one;

6-(2,2-difluoro-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(1-methyl-1H-indazol-4-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(1-methyl-1H-indazol-4-yl)cyclopropyl)-3,5,6,7,8,9-hexahydro-4H-pyrimido[5,4-c]azepin-4-one;

(S)-6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;

6-(2-([1,1'-biphenyl]-2-yl)acetyl)-2-(1-(3-chlorophenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-methyl-1H-indazol-4-yl)phenyl)cyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-methyl-1H-indazol-5-yl)phenyl)cyclopropyl)-3,5,6,7,8,9-hexahydro-4H-pyrimido[5,4-c]azepin-4-one;

(R)-1-(3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-4-yl)cyclopropane-1-carbonitrile;

(R)-3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-3-sulfonamide;

(R)-6-(2-(3-chlorophenyl)-2-hydroxyacetyl)-2-(1-(3-(4,4-difluorocyclohexyl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(indolin-1-yl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(3-isopropylphenyl)cyclopropyl)-3,5,6,7,8,9-hexahydro-4H-pyrimido[5,4-c]azepin-4-one;

(R)-4-(((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)(methyl)amino)-4-oxobutanoic acid;

(R)-6-(2-(3-chlorophenyl)-2-hydroxyacetyl)-2-(1-(2-phenoxypyridin-4-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-(isothiazol-4-yl)pyridin-3-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-(isothiazo-4-yl)pyridin-3-yl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-(trifluoromethyl)pyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(trifluoromethyl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(5-(trifluoromethyl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(piperidine-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)—N-((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)-N-methylpiperidine-1-carboxamide;

(R)-6-(2-(3-(cyclopent-1-en-1-yl)phenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(naphthalen-1-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(naphthalen-2-yl)phenyl)cyclopropyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3',4'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-5'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

8,8-difluoro-2-(1-phenylcyclopropyl)-6-(2-(3-(trifluoromethyl)phenyl)acetyl)-5,6,7,8-tetrahydropyrido[4,3-d]pyrimidin-4(3H)-one;

(R)—N, N-dibenzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

(R)—N-benzhydryl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(4-phenoxybenzyl)thiophene-3-carboxamide;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(naphthalen-1-ylmethyl)thiophene-3-carboxamide;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-diisopropylthiophene-3-carboxamide;

6-((R)-2-hydroxy-2-(3-(trifluoromethyl)phenyl)acetyl)-2-(1-(3-(1-((trans)-4-(trifluoromethyl)cyclohexane-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(4-(phenoxymethyl)phenyl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methylindolin-5-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(3-(2-oxopyrrolidin-1-yl)propanoyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-(1-(2,2,2-trifluoroethyl)-1,2,3,6-tetrahydropyridin-4-yl)phenyl)cyclopropyl)-3,5,6,7,8,9-hexahydro-4H-pyrimido[5,4-c]azepin-4-one;

(R)-2-(1-(3-(1-(benzylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(1-(cyclohexylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(1-((4-fluorophenyl)sulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(2',3'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(2',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-5-chloro-3'-(1-hydroxy-2-oxo-2-(4-oxo-2-(1-phenylcyclopropyl)-3,5,7,8-tetrahydropyrido[4,3-d]pyrimidin-6(4H)-yl)ethyl)-[1,1'-biphenyl]-3-carbonitrile;

(R)-6-(2-hydroxy-2-(3'-isopropoxy-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3',5'-di-tert-butyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(3,4-dihydro-2H-benzo[b][1,4]dioxepin-7-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3-(benzo[b]thiophen-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3-(benzo[b]thiophen-2-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-phenoxyphenyl)cyclopropyl)-3,5,6,7,8,9-hexahydro-4H-pyrimido[5,4-c]azepin-4-one;

6-(2-(3-chloro-2-fluorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;

6-(2-(3-chloro-2-fluorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;

6-(2-(3-chloro-2-fluorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;

(R)-2-(1-(3-(benzofuran-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3-(benzo[b]thiophen-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3-(benzofuran-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(2'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3',4'-dimethyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3',5'-dimethyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(2,3-dihydrobenzofuran-5-yl)phenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3'-isopropyl-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(4'-chloro-3'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(1-(3-(trifluoromethyl)phenyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-2-(1-(3-(1-(3-(cyclopentyloxy)-4-methoxybenzoyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)—N-cyclohexyl-4-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-3,6-dihydropyridine-1(2H)-carboxamide;

(R)-3-cyclohexyl-1-((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)-1-methylurea;

(R)-6-(2-hydroxy-2-(3-(trifluoromethyl)phenyl)acetyl)-2-(1-(3-(6-(4-phenylpiperidin-1-yl)pyridin-3-yl)phenyl)cyclopropyl)-3,5,6,7,8,9-hexahydro-4H-pyrimido[5,4-c]azepin-4-one;

(R)-2-(1-(3-(6-(4-(benzyloxy)piperidin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-4-(2-(((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)(methyl)amino)-2-oxoethyl)benzoic acid;

(R)-4-(((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)(methyl)carbamoyl)bicyclo[2.2.2]octane-1-carboxylic acid;

(R)-6-(2-hydroxy-2-(3-(trifluoromethyl)phenyl)acetyl)-2-(1-(3-(6-(4-(2-(4-(phenoxymethyl)phenyl)acetyl)piperazin-1-yl)pyridin-3-yl)phenyl)cyclopropyl)-3,5,6,7,8,9-hexahydro-4H-pyrimido[5,4-c]azepin-4-one;

(R)-2-(1-(3-chlorophenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3-(2-(trifluoromethyl)pyridin-4-yl)phenyl)acetyl)-3,5,6,7,8,9-hexahydro-4H-pyrimido[5,4-c]azepin-4-one;

(R)-6-(2-(3'-(benzyloxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-5'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3-(benzo[b]thiophen-3-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(3-(6-(benzyloxy)pyridin-3-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3-(benzo[b]thiophen-2-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3-(2,2-difluorobenzo[d][1,3]dioxol-5-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3-(benzofuran-2-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-4'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-(benzyloxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-(trifluoromethyl)pyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2-phenyloxazol-5-yl)cyclopropyl)-3,5,6,7,8,9-hexahydro-4H-pyrimido[5,4-c]azepin-4-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)—N-benzyl-N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

(R)—N, N-dicyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(naphthalen-2-ylmethyl)thiophene-3-carboxamide;

(R)—N-(tert-butyl)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

6-(2-(3'-fluoro-[1,1'-biphenyl]-3-yl)acetyl)-2-(1-phenylcyclopropyl)-3,5,6,7,8,9-hexahydro-4H-pyrimido[5,4-c]azepin-4-one;

2-(1-phenylcyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

2-(1-phenylcyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-2-(1-(3-cyclohexylphenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-2-(1-(3-cyclohexylphenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-2-(1-(3-cyclohexylphenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzyloxy)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(benzyloxy)phenyl)cyclopropyl)-6-(2-(3-chlorophenyl)-2-hydroxyacetyl)-3,5,6,7,8,9-hexahydro-4H-pyrimido[5,4-c]azepin-4-one;

(S)-6-(2-hydroxy-2-(3-(trifluoromethyl)phenyl)acetyl)-2-(1-phenylcyclopropyl)-5,6,7,8-tetrahydropyrido[4,3-d]pyrimidin-4(3H)-one;

(S)-6-(2-hydroxy-2-(3-(trifluoromethyl)phenyl)acetyl)-2-(1-phenylcyclopropyl)-3,5,6,7,8,9-hexahydro-4H-pyrimido[5,4-c]azepin-4-one;

(S)-2-(1-(3-chlorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3',4'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(4'-chloro-3'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(2',3'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(2',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-5-chloro-3'-(1-hydroxy-2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

(R)-6-(2-hydroxy-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(3'-cyclopropyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',4'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',5'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3'-isopropyl-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(4'-chloro-3'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(2'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3'-((trifluoromethyl)thio)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-8-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[4,5-c]azepin-4-one;

(R)-8-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[4,5-c]azepin-4-one;

(R)-8-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[4,5-c]azepin-4-one;

(R)-8-(2-hydroxy-2-(3'-isopropyl-[1,1'-biphenyl]-3-yl)acetyl)-2-(1-phenylcyclopropyl)-3,5,6,7,8,9-hexahydro-4H-pyrimido[4,5-c]azepin-4-one;

(R)-2-(1-(4'-((5-chloro-3,4-dihydroisoquinolin-2(1H)-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4'-((4-(benzyloxy)piperidin-1-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-6-(2-(3-(benzo[b]thiophen-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-2-(1-(3-(benzo[b]thiophen-5-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(benzo[d]thiazol-6-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(benzo[d]thiazol-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-phenyloxazol-5-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(5-phenylthiazol-2-yl)phenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3-(6-(trifluoromethyl)pyridin-2-yl)phenyl)acetyl)-5,6,7,8-tetrahydropyrido[4,3-d]pyrimidin-4(3H)-one;

(R)-5-chloro-3'-(2-(2-(1-(3-chlorophenyl)cyclopropyl)-4-oxo-3,5,7,8-tetrahydropyrido[4,3-d]pyrimidin-6(4H)-yl)-1-hydroxy-2-oxoethyl)-[1,1'-biphenyl]-3-carbonitrile;

(R)-2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-6-(2-(3'-chloro-4'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

(R)-6-(2-(3'-chloro-5'-(trifluoromethoxy)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-chloro-5'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

6-(2,2-difluoro-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

6-(2,2-difluoro-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-(tert-butyl)-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

6-(2,2-difluoro-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-cyclopropyl-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

(R)-2-(1-(2'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-2-carbonitrile;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;

(R)-6-(2-hydroxy-2-(3-(trifluoromethyl)phenyl)acetyl)-2-(1-(2'-methyl-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3'-methyl-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-methyl-[1,1'-biphenyl]-3-yl)cyclopropyl)-3,5,6,7,8,9-hexahydro-4H-pyrimido[5,4-c]azepin-4-one;

(R)-2-(1-(3',4'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3',5'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3'-isopropyl-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3'-cyclopropyl-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(3-phenoxyphenyl)cyclopropyl)-3,5,6,7,8,9-hexahydro-4H-pyrimido[5,4-c]azepin-4-one;

(R)-4-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-3-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,4-dicarbonitrile;

2-(1-(3-chlorophenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-isopropoxy-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

2-(1-(5-phenylpyridin-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(2',3',4',5'-tetrahydro-[1,1'-biphenyl]-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-isopropylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-5-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,5-dicarbonitrile;

(R)-2-(1-(4-cyclohexylthiophen-2-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(4-cyclohexylthiophen-2-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3-(benzo[b]thiophen-3-yl)phenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

2-(1-(3-chlorophenyl)cyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(2-(3'-isopropyl-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-(3-(6-(trifluoromethyl)pyridin-2-yl)phenyl)acetyl)-3,5,6,7,8,9-hexahydro-4H-pyrimido[5,4-c]azepin-4-one;

6-(2-(3'-chloro-5'-fluoro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

6-(2-([1,1'-biphenyl]-4-yl)acetyl)-2-(1-(3-chlorophenyl)cyclopropyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

(R)-2-(1-(5-cyclohexylpyridin-3-yl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(4'-chloro-3'-methyl-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-(3-(2,2-difluorobenzo[d][1,3]dioxol-5-yl)phenyl)-2-hydroxyacetyl)-3,5,6,7,8,9-hexahydro-4H-pyrimido[5,4-c]azepin-4-one;

(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-3-carbonitrile;

(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-4-carbonitrile;

(R)-2-(1-(3-chlorophenyl)cyclopropyl)-6-(2-hydroxy-2-(4'-(trifluoromethyl)-[1,1'-biphenyl]-3-yl)acetyl)-3,5,6,7,8,9-hexahydro-4H-pyrimido[5,4-c]azepin-4-one;

(R)-2-(1-(3-chlorophenyl)cyclopropyl)-6-(2-hydroxy-2-(4'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(4'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

6-(2-([1,1'-biphenyl]-4-yloxy)acetyl)-2-(1-(3-chlorophenyl)cyclopropyl)-3,5,6,7,8,9-hexahydro-4H-pyrimido[5,4-c]azepin-4-one;

6-([1,1'-biphenyl]-3-carbonyl)-2-(1-(3-chlorophenyl)cyclopropyl)-3,5,6,7,8,9-hexahydro-4H-pyrimido[5,4-c]azepin-4-one;

6-([1,1'-biphenyl]-4-carbonyl)-2-(1-(3-chlorophenyl)cyclopropyl)-3,5,6,7,8,9-hexahydro-4H-pyrimido[5,4-c]azepin-4-one;

6-(2-([1,1'-biphenyl]-3-yloxy)acetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(3-phenoxybenzoyl)-3,5,6,7,8,9-hexahydro-4H-pyrimido[5,4-c]azepin-4-one;

2-(1-(3-chlorophenyl)cyclopropyl)-6-(4-phenoxybenzoyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

2-(1-(4-phenylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

8-(2-(3'-chloro-[1,1'-biphenyl]-3-yl)acetyl)-2-(1-phenylcyclopropyl)-3,5,6,7,8,9-hexahydro-4H-pyrimido[4,5-c]azepin-4-one;

2-(1-phenylcyclopropyl)-8-(2-(3'-(trifluoromethyl)-[1,1'-biphenyl]-3-yl)acetyl)-3,5,6,7,8,9-hexahydro-4H-pyrimido[4,5-c]azepin-4-one;

2-(1-(4-isopropylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

6-(2-(3'-chloro-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

2-(1-(3-isopropylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-(3-(trifluoromethyl)phenyl)acetyl)-3,5,6,7,8,9-hexahydro-4H-pyrimido[5,4-c]azepin-4-one;

2-(1-(3-chlorophenyl)cyclopropyl)-6-(2-(2-fluoro-3-(trifluoromethyl)phenyl)acetyl)-3,5,6,7,8,9-hexahydro-4H-pyrimido[5,4-c]azepin-4-one;

2-(1-(3-chlorophenyl)cyclopropyl)-6-(2-(3-(trifluoromethoxy)phenyl)acetyl)-3,5,6,7,8,9-hexahydro-4H-pyrimido[5,4-c]azepin-4-one;

2-(1-(3-chlorophenyl)cyclopropyl)-6-(2-(3-((trifluoromethyl)thio)phenyl)acetyl)-3,5,6,7,8,9-hexahydro-4H-pyrimido[5,4-c]azepin-4-one;

2-(1-(3-chlorophenyl)cyclopropyl)-6-(2-(3-(pentafluoro-(lambda)$^6$-sulfaneyl)phenyl)acetyl)-3,5,6,7,8,9-hexahydro-4H-pyrimido[5,4-c]azepin-4-one;

2-(1-(3-chlorophenyl)cyclopropyl)-6-(2-(naphthalen-2-yl)acetyl)-3,5,6,7,8,9-hexahydro-4H-pyrimido[5,4-c]azepin-4-one;

2-(1-(3-chlorophenyl)cyclopropyl)-6-(2-(3-cyclopropylphenyl)acetyl)-3,5,6,7,8,9-hexahydro-4H-pyrimido[5,4-c]azepin-4-one;

(E)-2-(1-(3-chlorophenyl)cyclopropyl)-6-(3-(3-(trifluoromethyl)phenyl)acryloyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-cyclohexylphenyl)cyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-cyclohexylphenyl)cyclopropyl)-5,6,7,8-tetrahydropyrido[4,3-d]pyrimidin-4(3H)-one;

6-(2-(3-(benzofuran-3-yl)phenyl)acetyl)-2-(1-(3-chlorophenyl)cyclopropyl)-3,5,6,7,8,9-hexahydro-4H-pyrimido[5,4-c]azepin-4-one;

5-chloro-3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-3-carbonitrile;

2-(1-(3-chlorophenyl)cyclopropyl)-6-(2-(naphthalen-1-yl)acetyl)-3,5,6,7,8,9-hexahydro-4H-pyrimido[5,4-c]azepin-4-one;

2-(1-(3-chlorophenyl)cyclopropyl)-6-(3-(3-(trifluoromethyl)phenyl)propanoyl)-3,5,6,7,8,9-hexahydro-4H-pyrimido[5,4-c]azepin-4-one;

6-(2-(3-(benzyloxy)phenyl)acetyl)-2-(1-(3-chlorophenyl)cyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-chloro-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3-bromophenyl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-(benzo[b]thiophen-3-yl)phenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-[1,1'-biphenyl]-3-yl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-(tert-butyl)-[1,1'-biphenyl]-3-yl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-5'-fluoro-[1,1'-biphenyl]-3-yl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;

3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-4-carbonitrile;

6-(2-(4'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

6-(2-(4'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

3'-(2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-4-carbonitrile;

6-(2-(4'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

2-(1-phenylcyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

2-(1-phenylcyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

6-(2-(4'-chloro-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3-(benzofuran-3-yl)phenyl)acetyl)-2-(1-phenylcyclopropyl)-3,5,6,7,8,9-hexahydro-4H-pyrimido[5,4-c]azepin-4-one;

5-chloro-3'-(2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

2-(1-(3-chlorophenyl)cyclopropyl)-6-(2-(2-phenoxyphenyl)acetyl)-3,5,6,7,8,9-hexahydro-4H-pyrimido[5,4-c]azepin-4-one;

2-(1-(3-chlorophenyl)cyclopropyl)-6-(2-(3-phenoxyphenyl)acetyl)-3,5,6,7,8,9-hexahydro-4H-pyrimido[5,4-c]azepin-4-one;

6-(2-(3-(tert-butyl)phenyl)acetyl)-2-(1-(3-chlorophenyl)cyclopropyl)-3,5,6,7,8,9-hexahydro-4H-pyrimido[5,4-c]azepin-4-one;

6-(2-(3-(tert-butyl)phenyl)acetyl)-2-(1-phenylcyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-(3'-(trifluoromethoxy)-[1,1'-biphenyl]-3-yl)acetyl)-5,6,7,8-tetrahydropyrido[4,3-d]pyrimidin-4(3H)-one;

6-(2-(3'-(tert-butyl)-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

3'-(2-(2-(1-(3-chlorophenyl)cyclopropyl)-4-oxo-3,5,7,8-tetrahydropyrido[4,3-d]pyrimidin-6(4H)-yl)-2-oxoethyl)-[1,1'-biphenyl]-4-carbonitrile;

6-(2-(4'-(tert-butyl)-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-(4'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-(4'-(trifluoromethoxy)-[1,1'-biphenyl]-3-yl)acetyl)-5,6,7,8-tetrahydropyrido[4,3-d]pyrimidin-4(3H)-one;

6-(2-(4'-chloro-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

6-(2-(3-(benzofuran-3-yl)phenyl)acetyl)-2-(1-(3-chlorophenyl)cyclopropyl)-5,6,7,8-tetrahydropyrido[4,3-d]pyrimidin-4(3H)-one;

5-chloro-3'-(2-(2-(1-(3-chlorophenyl)cyclopropyl)-4-oxo-3,5,7,8-tetrahydropyrido[4,3-d]pyrimidin-6(4H)-yl)-2-oxoethyl)-[1,1'-biphenyl]-3-carbonitrile;

6-(2-(2-phenoxyphenyl)acetyl)-2-(1-phenylcyclopropyl)-3,5,6,7,8,9-hexahydro-4H-pyrimido[5,4-c]azepin-4-one;

6-(2-(3-phenoxyphenyl)acetyl)-2-(1-phenylcyclopropyl)-3,5,6,7,8,9-hexahydro-4H-pyrimido[5,4-c]azepin-4-one;

6-(2-(2-(benzyloxy)phenyl)acetyl)-2-(1-phenylcyclopropyl)-3,5,6,7,8,9-hexahydro-4H-pyrimido[5,4-c]azepin-4-one;

6-(2-(3-(benzyloxy)phenyl)acetyl)-2-(1-phenylcyclopropyl)-3,5,6,7,8,9-hexahydro-4H-pyrimido[5,4-c]azepin-4-one;

2-(1-(3-chlorophenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-(3-(trifluoromethyl)phenoxy)acetyl)-3,5,6,7,8,9-hexahydro-4H-pyrimido[5,4-c]azepin-4-one; and (R)-6-(2-hydroxy-2-(3-(trifluoromethyl)phenyl)acetyl)-2-(1-(4-(phenylethynyl)thiophen-2-yl)cyclopropyl)-3,5,6,7,8,9-hexahydro-4H-pyrimido[5,4-c]azepin-4-one;

or a pharmaceutically acceptable salt thereof;

[7] The compound according to [6], which is selected from:

(R)-6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-phenoxyphenyl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(2-methoxypyridin-4-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-methyl-1H-indazol-5-yl)phenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;

(R)-2-(1-([1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(prop-1-en-2-yl)phenyl)cyclopropyl)-3,5,6,7,8,9-hexahydro-4H-pyrimido[5,4-c]azepin-4-one;

(R)-3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-3-carbonitrile;

(R)-6-(2-hydroxy-2-(3-(trifluoromethyl)phenyl)acetyl)-2-(1-(3-(isothiazol-4-yl)phenyl)cyclopropyl)-3,5,6,7,8,9-hexahydro-4H-pyrimido[5,4-c]azepin-4-one;

(R)-2-(1-(3-(6-(4-(benzyloxy)piperidin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(6-(trifluoromethyl)pyridin-2-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-methoxypyridin-4-yl)phenyl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

(R)-5-chloro-3'-(1-hydroxy-2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

(R)-6-(2-hydroxy-2-(3-(trifluoromethyl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-4-carbonitrile;

6-(2-(3-chlorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2,2,2-trifluoroethyl)piperidin-4-yl)phenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-phenylcyclopropyl)-3,5,6,7,8,9-hexahydro-4H-pyrimido[5,4-c]azepin-4-one;

(R)-5-chloro-3'-(1-hydroxy-2-oxo-2-(4-oxo-2-(1-phenylcyclopropyl)-3,5,7,8-tetrahydropyrido[4,3-d]pyrimidin-6(4H)-yl)ethyl)-[1,1'-biphenyl]-3-carbonitrile;

(R)-2-(1-(3-(4,4-difluorocyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(2',3',4',5'-tetrahydro-[1,1'-biphenyl]-3-yl)cyclopropyl)-3,5,6,7,8,9-hexahydro-4H-pyrimido[5,4-c]azepin-4-one;

(R)-1-(3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-4-yl)cyclopropane-1-carbonitrile;

(R)-6-(2-hydroxy-2-(3-(trifluoromethyl)phenyl)acetyl)-2-(1-(3-(6-(trifluoromethyl)pyridin-3-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4'-fluoro-[1,1'-biphenyl]-3-yl)cyclopropyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3-chlorophenyl)-2,2-difluoroacetyl)-2-(1-(3-chlorophenyl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(trifluoromethyl)phenyl)cyclopropyl)-3,5,6,7,8,9-hexahydro-4H-pyrimido[5,4-c]azepin-4-one;

(R)—N-cyclohexyl-4-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-3,6-dihydropyridine-1(2H)-carboxamide;

(R)-2-(1-(4-cyclopentylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(4,4-dimethylcyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;

6-(2,2-difluoro-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-hydroxy-2-(3'-isopropyl-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(isothiazol-4-yl)phenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(2-(pyrrolidin-1-yl)pyrimidin-5-yl)phenyl)cyclopropyl)-3,5,6,7,8,9-hexahydro-4H-pyrimido[5,4-c]azepin-4-one;

(R)-6-(2-(3-(2,2-difluorobenzo[d][1,3]dioxol-5-yl)phenyl)-2-hydroxyacetyl)-2-(1-phenylcyclopropyl)-3,5,6,7,8,9-hexahydro-4H-pyrimido[5,4-c]azepin-4-one;

(R)-2-(1-(5-cyclopentylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(3-fluorophenyl)cyclopropyl)-3,5,6,7,8,9-hexahydro-4H-pyrimido[5,4-c]azepin-4-one;

2-(1-(3-chlorophenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-methyl-1H-indazol-4-yl)phenyl)cyclopropyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

(R)-6-(2-(3-(benzo[b]thiophen-2-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-(benzofuran-2-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(1-(3-(trifluoromethyl)phenyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-2-(1-(3-chlorophenyl)cyclopropyl)-6-(2-(3-(2,2-difluorobenzo[d][1,3]dioxol-5-yl)phenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(prop-1-en-2-yl)phenyl)cyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-phenylthiophen-2-yl)cyclopropyl)-3,5,6,7,8,9-hexahydro-4H-pyrimido[5,4-c]azepin-4-one;

(R)-2-(1-(4-ethylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-cyclopropyl-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3',4'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(4'-chloro-3'-methyl-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(4-bromothiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-((R)-2-hydroxy-2-(3-(trifluoromethyl)phenyl)acetyl)-2-(1-(3-(1,1,1-trifluoropropan-2-yl)phenyl)cyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-phenylcyclopropyl)-3,5,6,7,8,9-hexahydro-4H-pyrimido[5,4-c]azepin-4-one;

(R)-2-(1-(3-(1-cyclopropyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-methoxypyridin-3-yl)phenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3-(2-(trifluoromethyl)pyridin-4-yl)phenyl)acetyl)-3,5,6,7,8,9-hexahydro-4H-pyrimido[5,4-c]azepin-4-one;

(R)-2-(1-(3-cyclopentylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(pyridin-3-yl)phenyl)cyclopropyl)-3,5,6,7,8,9-hexahydro-4H-pyrimido[5,4-c]azepin-4-one;

2-(1-phenylcyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3'-(piperidine-1-carbonyl)-[1,1'-biphenyl]-3-yl)cyclopropyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

6-(2-(3-chloro-2-fluorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-2-(1-(5-cyclohexylpyridin-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4-cyclopentylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-(3-chlorophenyl)-2-hydroxyacetyl)-2-(1-(3-cyclopentylphenyl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

(R)-2-(1-(4-cycloheptylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(6-(4-methylpiperidin-1-yl)pyridin-3-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(isothiazol-4-yl)phenyl)cyclopropyl)-3,5,6,7,8,9-hexahydro-4H-pyrimido[5,4-c]azepin-4-one;

2-(1-(3-chlorophenyl)cyclopropyl)-6-(2-(2-fluoro-3-(trifluoromethyl)phenyl)-2-hydroxyacetyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(pyridin-2-ylmethoxy)-[1,1'-biphenyl]-3-yl)cyclopropyl)-3,5,6,7,8,9-hexahydro-4H-pyrimido[5,4-c]azepin-4-one;

(R)-5-chloro-3'-(2-(2-(1-(3-chlorophenyl)cyclopropyl)-4-oxo-3,5,7,8-tetrahydropyrido[4,3-d]pyrimidin-6(4H)-yl)-1-hydroxy-2-oxoethyl)-[1,1'-biphenyl]-3-carbonitrile;

(R)-6-(2-hydroxy-2-(3-(trifluoromethyl)phenyl)acetyl)-2-(1-(3-(trifluoromethoxy)phenyl)cyclopropyl)-3,5,6,7,8,9-hexahydro-4H-pyrimido[5,4-c]azepin-4-one;

(R)-2-(1-(4-cyclohexylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-(3-chlorophenyl)-2-hydroxyacetyl)-2-(1-(4-cyclopentylthiophen-2-yl)cyclopropyl)-3,5,6,7,8,9-hexahydro-4H-pyrimido[5,4-c]azepin-4-one;

(R)-6-(2-(4'-chloro-3'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-hydroxy-2-(3-(3-(trifluoromethyl)phenoxy)phenyl)acetyl)-2-(1-phenylcyclopropyl)-3,5,6,7,8,9-hexahydro-4H-pyrimido[5,4-c]azepin-4-one;

(R)-2-(1-(3-(benzofuran-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3-(1-(3-(cyclopentyloxy)-4-methoxybenzoyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(cyclopent-1-en-1-yl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;

(R)-2-(1-(4'-(dimethylamino)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclohexylphenyl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3-(benzofuran-2-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-(4,4-difluorocyclohexyl)phenyl)cyclopropyl)-3,5,6,7,8,9-hexahydro-4H-pyrimido[5,4-c]azepin-4-one;

(R)-4-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-6-(2-(3-chlorophenyl)-2-hydroxyacetyl)-2-(1-(3-cyclohexylphenyl)cyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-isobutylphenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-(3-phenylpropanoyl)piperidin-4-yl)phenyl)cyclopropyl)-3,5,6,7,8,9-hexahydro-4H-pyrimido[5,4-c]azepin-4-one;
(R)-2-(1-(3-(1-cyclobutyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(3-(6-(dimethylamino)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3'-(trifluoromethoxy)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(5-phenylpyridin-3-yl)cyclopropyl)-5,6,7,8-tetrahydropyrido[4,3-d]pyrimidin-4(3H)-one;
(R)-3-cyclohexyl-1-((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)-1-methylurea;
6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;
(R)-6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;
(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)picolinonitrile;
(R)-6-(2-(3-(2,2-difluorobenzo[d][1,3]dioxol-5-yl)phenyl)-2-hydroxyacetyl)-2-(1-phenylcyclopropyl)-5,6,7,8-tetrahydropyrido[4,3-d]pyrimidin-4(3H)-one;
(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-3-carbonitrile;
(R)-6-(2-hydroxy-2-(3-(trifluoromethyl)phenyl)acetyl)-2-(1-(3-(5-phenylthiazol-2-yl)phenyl)cyclopropyl)-3,5,6,7,8,9-hexahydro-4H-pyrimido[5,4-c]azepin-4-one;
(R)-2-(1-(3-(benzofuran-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;
(R)-6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;
(R)-2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;
(R)-6-(2-hydroxy-2-(3-(2-(trifluoromethyl)pyridin-4-yl)phenyl)acetyl)-2-(1-(3-isopropylphenyl)cyclopropyl)-3,5,6,7,8,9-hexahydro-4H-pyrimido[5,4-c]azepin-4-one;
(R)-2-(1-(3-(benzyloxy)phenyl)cyclopropyl)-6-(2-(3-chlorophenyl)-2-hydroxyacetyl)-3,5,6,7,8,9-hexahydro-4H-pyrimido[5,4-c]azepin-4-one;
6-(2-(3'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;
(R)-6-(2-(3-(6-(benzyloxy)pyridin-3-yl)phenyl)-2-hydroxyacetyl)-2-(1-phenylcyclopropyl)-3,5,6,7,8,9-hexahydro-4H-pyrimido[5,4-c]azepin-4-one;
(R)-6-(2-(3'-chloro-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;
(R)-6-(2-(3'-fluoro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;
6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;
(R)-2-(1-(4-(4,4-difluorocyclohexyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
6-((R)-2-hydroxy-2-(3-(trifluoromethyl)phenyl)acetyl)-2-(1-(3-(1-((trans)-4-(trifluoromethyl)cyclohexane-1-carbonyl)-1,2,3,6-tetrahydropyridin-4-yl)phenyl)cyclopropyl)-3,5,6,7,8,9-hexahydro-4H-pyrimido[5,4-c]azepin-4-one;
(R)-6-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-3-methylbenzo[d]oxazol-2(3H)-one;
(R)-6-(2-hydroxy-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;
(R)-6-(2-(3'-chloro-5'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-(3'-fluoro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;
(R)-6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
(R)-6-(2-(3'-chloro-4'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(2'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-2-(1-(3-chlorophenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;
6-(2-(3-chlorophenyl)-2,2-difluoroacetyl)-2-(1-(3-fluorophenyl)cyclopropyl)-3,5,6,7,8,9-hexahydro-4H-pyrimido[5,4-c]azepin-4-one;
(R)-6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-(3-chlorophenyl)-2-hydroxyacetyl)-2-(1-(5-cyclopentylpyridin-3-yl)cyclopropyl)-5,6,7,8-tetrahydropyrido[4,3-d]pyrimidin-4(3H)-one;
6-(2-(3-chloro-2-fluorophenyl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-hydroxy-2-(3-(2-(trifluoromethyl)pyridin-4-yl)phenyl)acetyl)-2-(1-(3-isopropylphenyl)cyclopropyl)-5,6,7,8-tetrahydropyrido[4,3-d]pyrimidin-4(3H)-one;
(R)-2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;
6-(2-(3-chloro-2-fluorophenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-2-(1-([1,1'-biphenyl]-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(2-(trifluoromethyl)pyridin-4-yl)phenyl)cyclopropyl)-3,5,6,7,8,9-hexahydro-4H-pyrimido[5,4-c]azepin-4-one;

6-(2-(3-chloro-2-fluorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

5-chloro-3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-3-carbonitrile;

(R)-6-(2-hydroxy-2-(3-(trifluoromethyl)phenyl)acetyl)-2-(1-(3'-(methylsulfonyl)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3'-isopropoxy-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-hydroxy-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-((R)-2-hydroxy-2-(3-(trifluoromethyl)phenyl)acetyl)-2-(1-(4'-(trifluoromethyl)-2',3',4',5'-tetrahydro-[1,1'-biphenyl]-3-yl)cyclopropyl)-3,5,6,7,8,9-hexahydro-4H-pyrimido[5,4-c]azepin-4-one;

(R)-6-(2-(3'-(benzyloxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-hydroxy-2-(3-(2-(trifluoromethyl)pyridin-4-yl)phenyl)acetyl)-2-(1-(3-isopropylphenyl)cyclopropyl)-3,5,6,7,8,9-hexahydro-4H-pyrimido[5,4-c]azepin-4-one;

(R)-2-(1-(3-(benzo[d]thiazol-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)-6-(2-hydroxy-2-(3-(trifluoromethyl)phenyl)acetyl)-2-(1-(3-isopropylphenyl)cyclopropyl)-5,6,7,8-tetrahydropyrido[4,3-d]pyrimidin-4(3H)-one;

5-chloro-3'-(2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

(R)-6-(2-(3-(benzo[b]thiophen-3-yl)phenyl)-2-hydroxyacetyl)-2-(1-phenylcyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-fluorophenyl)cyclopropyl)-3,5,6,7,8,9-hexahydro-4H-pyrimido[5,4-c]azepin-4-one;

(R)-2-(1-(3-(benzo[b]thiophen-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-2-(1-(3-(1-(benzylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-phenoxyphenyl)cyclopropyl)-3,5,6,7,8,9-hexahydro-4H-pyrimido[5,4-c]azepin-4-one;

6-(2-(2-fluoro-3-(trifluoromethyl)phenyl)acetyl)-2-(1-phenylcyclopropyl)-3,5,6,7,8,9-hexahydro-4H-pyrimido[5,4-c]azepin-4-one;

6-(2-(4'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(4-(phenoxymethyl)phenyl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(3',5'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(isothiazol-4-yl)phenyl)cyclopropyl)-5,6,7,8-tetrahydropyrido[4,3-d]pyrimidin-4(3H)-one;

(R)-2-(1-(5-cyclohexylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-2-(1-(4-(3,3-dimethylbutyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(2'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(pyrrolidin-1-yl)pyridin-3-yl)phenyl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(4'-(tert-butyl)-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;
6-(2-(3-(benzyloxy)phenyl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(tetrahydro-2H-pyran-4-yl)phenyl)cyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;
(R)-2-(1-([1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
2-(1-(3-fluorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;
6-(2-(3-chlorophenyl)-2,2-difluoroacetyl)-2-(1-(thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-(piperidine-1-carbonyl)-1,2,3,6-tetrahydropyridin-4-yl)phenyl)cyclopropyl)-3,5,6,7,8,9-hexahydro-4H-pyrimido[5,4-c]azepin-4-one;
(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-diisopropylthiophene-3-carboxamide;
(R)-2-(1-(3-bromophenyl)cyclopropyl)-6-(2-(3-chlorophenyl)-2-hydroxyacetyl)-3,5,6,7,8,9-hexahydro-4H-pyrimido[5,4-c]azepin-4-one;
6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;
(R)-6-(2-(3'-cyclopropyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
2-(1-(3-chlorophenyl)cyclopropyl)-6-(2-(3-(6-(trifluoromethyl)pyridin-2-yl)phenyl)acetyl)-3,5,6,7,8,9-hexahydro-4H-pyrimido[5,4-c]azepin-4-one;
2-(1-(3-chlorophenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;
6-(2-(3-chlorophenyl)-2,2-difluoroacetyl)-2-(1-phenylcyclopropyl)-3,5,6,7,8,9-hexahydro-4H-pyrimido[5,4-c]azepin-4-one;
2-(1-(4-(2-((3S,5S)-adamantan-1-yl)ethyl)thiophen-2-yl)cyclopropyl)-6-((RS)-2-hydroxy-2-(3-(trifluoromethyl)phenyl)acetyl)-3,5,6,7,8,9-hexahydro-4H-pyrimido[5,4-c]azepin-4-one;
(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,4-dicarbonitrile;
6-(2-hydroxy-2-(3-(quinolin-3-yl)phenyl)acetyl)-2-(1-phenylcyclopropyl)-3,5,6,7,8,9-hexahydro-4H-pyrimido[5,4-c]azepin-4-one;
(R)-2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;
6-(2-(3-(benzyloxy)phenyl)-2-hydroxyacetyl)-2-(1-phenylcyclopropyl)-3,5,6,7,8,9-hexahydro-4H-pyrimido[5,4-c]azepin-4-one;
(R)-6-(2-hydroxy-2-(3'-((trifluoromethyl)thio)-[1,1'-biphenyl]-3-yl)acetyl)-2-(1-phenylcyclopropyl)-3,5,6,7,8,9-hexahydro-4H-pyrimido[5,4-c]azepin-4-one;
(R)-6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;
6-(2-hydroxy-2-(6-(3-(trifluoromethyl)phenyl)pyridin-2-yl)acetyl)-2-(1-phenylcyclopropyl)-5,6,7,8-tetrahydropyrido[4,3-d]pyrimidin-4(3H)-one;
(R)-2-(1-(4-cyclohexylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;
(R)-3-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;
6-(2-(3-(benzyloxy)phenyl)acetyl)-2-(1-(3-chlorophenyl)cyclopropyl)-3,5,6,7,8,9-hexahydro-4H-pyrimido[5,4-c]azepin-4-one;
6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3'-chloro-4'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;
2-(1-(3-chlorophenyl)cyclopropyl)-6-(2-(2-fluoro-3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(6-(4-phenylpiperidin-1-yl)pyridin-3-yl)phenyl)cyclopropyl)-3,5,6,7,8,9-hexahydro-4H-pyrimido[5,4-c]azepin-4-one;
6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;
(R)-6-(2-(4'-chloro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;
(R)-6-(2-hydroxy-2-(3'-(trifluoromethoxy)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(6-(4-(2-(4-(phenoxymethyl)phenyl)acetyl)piperazin-1-yl)pyridin-3-yl)phenyl)cyclopropyl)-3,5,6,7,8,9-hexahydro-4H-pyrimido[5,4-c]azepin-4-one;
6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3'-chloro-5'-(trifluoromethoxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(2-(tetrahydro-2H-pyran-4-yl)ethyl)thiophen-2-yl)cyclopropyl)-3,5,6,7,8,9-hexahydro-4H-pyrimido[5,4-c]azepin-4-one;
(R)-6-(2-(3'-fluoro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;
(R)-6-(2-hydroxy-2-(3'-(trifluoromethyl)-[1,1'-biphenyl]-3-yl)acetyl)-2-(1-(3-phenoxyphenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(pyridin-4-yl)phenyl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-3'-(1-(6-(2-hydroxy-2-(3-(trifluoromethyl)phenyl) acetyl)-4-oxo-4,5,6,7,8,9-hexahydro-3H-pyrimido[5,4-c] azepin-2-yl)cyclopropyl)-N,N-dimethyl-[1,1'-biphenyl]-4-sulfonamide;

(R)-6-(2-(3-chlorophenyl)-2-hydroxyacetyl)-2-(1-(3-(1-cyclopropyl-1H-pyrazol-4-yl)phenyl)cyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzyloxy)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(3-chloro-2-fluorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3',4'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

2-(1-phenylcyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

8-(2-hydroxy-2-(3'-(trifluoromethyl)-[1,1'-biphenyl]-3-yl) acetyl)-2-(1-phenylcyclopropyl)-3,5,6,7,8,9-hexahydro-4H-pyrimido[4,5-c]azepin-4-one;

6-(2-hydroxy-2-(6-(3-(trifluoromethoxy)phenyl)pyridin-2-yl)acetyl)-2-(1-phenylcyclopropyl)-5,6,7,8-tetrahydropyrido[4,3-d]pyrimidin-4(3H)-one;

(R)-2-(1-(3-cyclohexylphenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-phenoxyphenyl)cyclopropyl)-5,6,7,8-tetrahydropyrido[4,3-d]pyrimidin-4(3H)-one;

(R)-2-(1-(4'-((4-(benzyloxy)piperidin-1-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3-chlorophenyl)-2,2-difluoroacetyl)-2-(1-(3-isopropylphenyl)cyclopropyl)-3,5,6,7,8,9-hexahydro-4H-pyrimido[5,4-c]azepin-4-one;

(R)-6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-5-(1-(6-(2-hydroxy-2-(3-(trifluoromethyl)phenyl) acetyl)-4-oxo-4,5,6,7,8,9-hexahydro-3H-pyrimido[5,4-c] azepin-2-yl)cyclopropyl)-N-methyl-N-(naphthalen-1-ylmethyl)thiophene-3-carboxamide;

2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-cyclopropyl-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

6-(2-([1,1'-biphenyl]-3-yl)acetyl)-2-(1-(3-chlorophenyl)cyclopropyl)-3,5,6,7,8,9-hexahydro-4H-pyrimido[5,4-c] azepin-4-one;

6-(2,2-difluoro-2-(3'-(trifluoromethyl)-[1,1'-biphenyl]-3-yl) acetyl)-2-(1-phenylcyclopropyl)-3,5,6,7,8,9-hexahydro-4H-pyrimido[5,4-c]azepin-4-one;

(R)-5-(3-(1-(6-(2-hydroxy-2-(3-(trifluoromethyl)phenyl) acetyl)-4-oxo-4,5,6,7,8,9-hexahydro-3H-pyrimido[5,4-c] azepin-2-yl)cyclopropyl)phenyl)nicotinonitrile;

6-(2-(2-fluoro-3-(trifluoromethyl)phenyl)-2-hydroxyacetyl)-2-(1-(5-phenylpyridin-3-yl)cyclopropyl)-5,6,7,8-tetrahydropyrido[4,3-d]pyrimidin-4(3H)-one;

(R)-6-(2-hydroxy-2-(3'-isopropyl-[1,1'-biphenyl]-3-yl) acetyl)-2-(1-phenylcyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-phenylacetyl)piperidin-4-yl)phenyl)cyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-2-(1-(4-ethylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(3-cyclopentylphenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4'-methyl-[1,1'-biphenyl]-3-yl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-(quinolin-3-yl)phenyl)acetyl)-5,6,7,8-tetrahydropyrido[4,3-d] pyrimidin-4(3H)-one;

6-(2-(2-(benzyloxy)phenyl)acetyl)-2-(1-(3-chlorophenyl) cyclopropyl)-3,5,6,7,8,9-hexahydro-4H-pyrimido[5,4-c] azepin-4-one;

(R)-6-(2-(3-chlorophenyl)-2-hydroxyacetyl)-2-(1-(5-cyclohexylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(1-methyl-1H-indazol-5-yl)phenyl)cyclopropyl)-3,5,6,7,8,9-hexahydro-4H-pyrimido[5,4-c]azepin-4-one;

(R)-2-(1-(3-(1-(difluoromethyl)-1H-pyrazol-4-yl)phenyl) cyclopropyl)-6-(2-hydroxy-2-(3-(trifluoromethyl)phenyl) acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3'-isopropyl-[1,1'-biphenyl]-3-yl) acetyl)-2-(1-(thiophen-2-yl)cyclopropyl)-3,5,6,7,8,9-hexahydro-4H-pyrimido[5,4-c]azepin-4-one;

(R)-2-(1-(3-(1-benzoylpiperidin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3-(tert-butyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-2-(1-(3-cyclohexylphenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(4-hydroxytetrahydro-2H-pyran-4-yl)-[1,1'-biphenyl]-3-yl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(4'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-methoxyethyl)-1H-pyrazol-4-yl)phenyl)cyclopropyl)-3,5,6,7,8,9-hexahydro-4H-pyrimido[5,4-c]azepin-4-one;

3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-4-carbonitrile;

(R)-6-(2-hydroxy-2-(3-(trifluoromethyl)phenyl)acetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4'-(trifluoromethyl)-[1,1'-biphenyl]-3-yl)cyclopropyl)-3,5,6,7,8,9-hexahydro-4H-pyrimido[5,4-c]azepin-4-one;

(R)-2-(1-(4-(2-cyclopropylethyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-(benzo[b]thiophen-2-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-indazol-4-yl)phenyl)cyclopropyl)-3,5,6,7,8,9-hexahydro-4H-pyrimido[5,4-c]azepin-4-one;

(R)-6-(2-hydroxy-2-(4'-(trifluoromethoxy)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3'-(trifluoromethyl)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

(R)-2-(1-(5-cyclohexylpyridin-3-yl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-2-(1-(3-chlorophenyl)cyclopropyl)-6-(2-hydroxy-2-(4'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(1-(cyclohexylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(2-fluoro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(4'-(trifluoromethyl)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-(2',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3'-(tert-butyl)-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2'-methyl-[1,1'-biphenyl]-3-yl)cyclopropyl)-3,5,6,7,8,9-hexahydro-4H-pyrimido[5,4-c]azepin-4-one;

(R)-6-(2-(3',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2,2-difluoro-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(tetrahydro-2H-pyran-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(methylamino)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methylindolin-5-yl)phenyl)cyclopropyl)-3,5,6,7,8,9-hexahydro-4H-pyrimido[5,4-c]azepin-4-one;

(R)-2-(1-(4'-((5-chloro-3,4-dihydroisoquinolin-2(1H)-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-phenethylthiophen-2-yl)cyclopropyl)-3,5,6,7,8,9-hexahydro-4H-pyrimido[5,4-c]azepin-4-one;

6-(2-(3-(benzyloxy)phenyl)acetyl)-2-(1-phenylcyclopropyl)-3,5,6,7,8,9-hexahydro-4H-pyrimido[5,4-c]azepin-4-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(4-phenoxybenzyl)thiophene-3-carboxamide;

(R)—N-benzyl-N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

2-(1-(3-chlorophenyl)cyclopropyl)-6-(2-hydroxy-2-(3-(quinolin-3-yl)phenyl)acetyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,5-dicarbonitrile;

(R)-6-(2-(3-(benzo[b]thiophen-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(2-(1-hydroxycyclohexyl)ethyl)thiophen-2-yl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3-(6-(trifluoromethyl)pyridin-2-yl)phenyl)acetyl)-5,6,7,8-tetrahydropyrido[4,3-d]pyrimidin-4(3H)-one;

(R)-6-(2-(3-chlorophenyl)-2-hydroxyacetyl)-2-(1-(3-phenoxyphenyl)cyclopropyl)-5,6,7,8-tetrahydropyrido[4,3-d]pyrimidin-4(3H)-one;

6-(2-hydroxy-2-(3-((trifluoromethyl)thio)phenyl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-2-(1-(3-(benzo[d]thiazol-6-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;

(R)—N-((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)-N-methylpiperidine-1-carboxamide;

6-(2-(2-fluoro-3-(trifluoromethyl)phenyl)-2-hydroxyacetyl)-2-(1-phenylcyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-isopropoxy-[1,1'-biphenyl]-3-yl)acetyl)-3,5,6,7,8,9-hexahydro-4H-pyrimido[5,4-c]azepin-4-one;

(R)-5-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-5'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(4'-(trifluoromethyl)-[1,1'-biphenyl]-3-yl)acetyl)-3,5,6,7,8,9-hexahydro-4H-pyrimido[5,4-c]azepin-4-one;

(R)—N-benzhydryl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)-6-(2-hydroxy-2-(3-(trifluoromethyl)phenyl)acetyl)-2-(1-(3-(naphthalen-2-yl)phenyl)cyclopropyl)-3,5,6,7,8,9-hexahydro-4H-pyrimido[5,4-c]azepin-4-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)-2-(1-(3-cyclohexylphenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-(benzyloxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-(1-(3,3-dimethylbutanoyl)piperidin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(6-(trifluoromethyl)pyridin-3-yl)phenyl)acetyl)-2-(1-(5-isopropylpyridin-3-yl)cyclopropyl)-5,6,7,8-tetrahydropyrido[4,3-d]pyrimidin-4(3H)-one;

(R)-6-(2-(3-(benzo[b]thiophen-3-yl)phenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

6-(2,2-difluoro-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;

(R)-2-(1-(3-(1-((4-fluorophenyl)sulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4'-(tert-butyl)-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

6-(2-hydroxy-2-(2'-(trifluoromethyl)-[2,4'-bipyridin]-6-yl)acetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(5-(trifluoromethyl)pyridin-3-yl)phenyl)cyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-phenylcyclopropyl)-3,5,6,7,8,9-hexahydro-4H-pyrimido[5,4-c]azepin-4-one;

(R)—N, N-dibenzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

2-(1-(4-isopropylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

(R)-2-(1-(3-(6-(4-(3,3-dimethylbutanoyl)piperazin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3-(tert-butyl)phenyl)-2-hydroxyacetyl)-2-(1-(3-fluorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-hydroxy-2-(2-phenoxyphenyl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-5-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(4'-chloro-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-chloro-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-cyclohexylphenyl)cyclopropyl)-5,6,7,8-tetrahydropyrido[4,3-d]pyrimidin-4(3H)-one;

6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-(3-cyclopropylphenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclopentylphenyl)cyclopropyl)-5,6,7,8-tetrahydropyrido[4,3-d]pyrimidin-4(3H)-one;

6-(2-(3'-chloro-5'-fluoro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(thiazol-5-yl)phenyl)cyclopropyl)-3,5,6,7,8,9-hexahydro-4H-pyrimido[5,4-c]azepin-4-one;

(R)—N, N-dicyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

6-(2,2-difluoro-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

(R)-6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3-(benzofuran-3-yl)phenyl)acetyl)-2-(1-phenylcyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-(3-phenoxyphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(pyridin-3-yl)phenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-6-(2-(3-chlorophenyl)-2-hydroxyacetyl)-2-(1-(4-(4,4-difluorocyclohexyl)thiophen-2-yl)cyclopropyl)-5,6,7,8-tetrahydropyrido[4,3-d]pyrimidin-4(3H)-one;

(R)-2-(1-(3-(benzo[b]thiophen-3-yl)phenyl)cyclopropyl)-6-(2-(3-bromophenyl)-2-hydroxyacetyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-2-(1-(4-(4,4-difluorocyclohexyl)thiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-(3',5'-bis(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-isopropylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-2-carbonitrile;

(R)-6-(2-(3-chlorophenyl)-2-hydroxyacetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(indolin-1-yl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(4'-chloro-3'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

(R)-6-(2-(4'-chloro-3'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

2-(1-(3-chlorophenyl)cyclopropyl)-6-(2-(3-((trifluoromethyl)thio)phenyl)acetyl)-3,5,6,7,8,9-hexahydro-4H-pyrimido[5,4-c]azepin-4-one;

2-(1-(3-chlorophenyl)cyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-phenylthiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3'-methyl-[1,1'-biphenyl]-3-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;

6-(2-hydroxy-2-(5-(3-(trifluoromethyl)phenyl)pyridin-3-yl)acetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-2-(1-(3-cyclohexylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

6-(2-(3-(benzofuran-3-yl)phenyl)acetyl)-2-(1-(3-chlorophenyl)cyclopropyl)-3,5,6,7,8,9-hexahydro-4H-pyrimido[5,4-c]azepin-4-one;

6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-(4-isopropylthiophen-2-yl)cyclopropyl)-5,6,7,8-tetrahydropyrido[4,3-d]pyrimidin-4(3H)-one;

(R)-6-(2-(4'-fluoro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(5-phenylpyridin-3-yl)cyclopropyl)-5,6,7,8-tetrahydropyrido[4,3-d]pyrimidin-4(3H)-one;

2-(1-(3-chlorophenyl)cyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

2-(1-phenylcyclopropyl)-6-(2-(3-((trifluoromethyl)thio)phenyl)acetyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;

(R)-2-(1-(3'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(3-methoxypropyl)thiophen-2-yl)cyclopropyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)-6-(2-(4'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(naphthalen-2-ylmethyl)thiophene-3-carboxamide;

6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-(trifluoromethyl)pyridin-3-yl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(2-(oxetan-3-yl)ethyl)thiophen-2-yl)cyclopropyl)-3,5,6,7,8,9-hexahydro-4H-pyrimido[5,4-c]azepin-4-one;

(R)-2-(1-(3',5'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(1-(trifluoromethyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-8-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[4,5-c]azepin-4-one;

(R)-2-(1-(3',4'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(3-chlorophenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-6-(2-(4'-chloro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(4'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(4-phenylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-[1,1'-biphenyl]-3-yl)-2-hydroxyacetyl)-3,5,6,7,8,9-hexahydro-4H-pyrimido[5,4-c]azepin-4-one;

6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-phenylcyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

6-(2-(4'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(5-phenylpyridin-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-8-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[4,5-c]azepin-4-one;

(R)-6-(2-hydroxy-2-(3-(trifluoromethyl)phenyl)acetyl)-2-(1-(3-(pyridin-3-yl)phenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(6-(4-isobutyrylpiperazin-1-yl)pyridin-3-yl)phenyl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(1-methyl-1H-pyrazol-5-yl)phenyl)cyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(2-phenyloxazol-5-yl)phenyl)cyclopropyl)-3,5,6,7,8,9-hexahydro-4H-pyrimido[5,4-c]azepin-4-one;

6-(2-(2-(benzyloxy)phenyl)acetyl)-2-(1-phenylcyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-pyrazol-4-yl)phenyl)cyclopropyl)-3,5,6,7,8,9-hexahydro-4H-pyrimido[5,4-c]azepin-4-one;

6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3-chlorophenyl)-2,2-difluoroacetyl)-2-(1-(4-isopropylthiophen-2-yl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

2-(1-(3-isopropylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-(1-(2,2,2-trifluoroethyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-(2-phenylacetyl)piperazin-1-yl)pyridin-3-yl)phenyl)cyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3-(tert-butyl)phenyl)acetyl)-2-(1-(3-chlorophenyl)cyclopropyl)-3,5,6,7,8,9-hexahydro-4H-pyrimido[5,4-c]azepin-4-one;

(R)-6-(2-(2',3'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-5'-fluoro-[1,1'-biphenyl]-3-yl)-2-hydroxyacetyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-isopropylphenyl)cyclopropyl)-5,6,7,8-tetrahydropyrido[4,3-d]pyrimidin-4(3H)-one;

2-(1-(3-chlorophenyl)cyclopropyl)-6-(2-(3-(trifluoromethyl)phenyl)acetyl)-3,5,6,7,8,9-hexahydro-4H-pyrimido[5,4-c]azepin-4-one;

6-(2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;

6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-(3-(trifluoromethyl)phenyl)propanoyl)-3,5,6,7,8,9-hexahydro-4H-pyrimido[5,4-c]azepin-4-one;

6-(2-(3-(tert-butyl)phenyl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-cyclohexylthiophen-2-yl)cyclopropyl)-5,6,7,8-tetrahydropyrido[4,3-d]pyrimidin-4(3H)-one;

6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)acetyl)-2-(1-(3-cyclohexylphenyl)cyclopropyl)-3,5,6,7,8,9-hexahydro-4H-pyrimido[5,4-c]azepin-4-one;

6-(2-(2'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(2',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-(tert-butyl)-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-isopropylpyridin-3-yl)cyclopropyl)-5,6,7,8-tetrahydropyrido[4,3-d]pyrimidin-4(3H)-one;

2-(1-(3-chlorophenyl)cyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3',5'-di-tert-butyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-(benzo[b]thiophen-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(4'-chloro-3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-(3'-isopropyl-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2-isopropylpyridin-4-yl)cyclopropyl)-3,5,6,7,8,9-hexahydro-4H-pyrimido[5,4-c]azepin-4-one;

(R)-2-(1-([1,1'-biphenyl]-3-yl)cyclopropyl)-6-(2-(3-chlorophenyl)-2-hydroxyacetyl)-5,6,7,8-tetrahydropyrido[4,3-d]pyrimidin-4(3H)-one;

2-(1-phenylcyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

6-(2-(3-(tert-butyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(oxazol-5-yl)phenyl)cyclopropyl)-3,5,6,7,8,9-hexahydro-4H-pyrimido[5,4-c]azepin-4-one;

2-(1-(3-chlorophenyl)cyclopropyl)-6-(2-(2-phenoxyphenyl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-fluorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3-phenoxyphenyl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

2-(1-(3-chlorophenyl)cyclopropyl)-6-(2-(3-cyclopropylphenyl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(5-isopropylpyridin-3-yl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3'-fluoro-[1,1'-biphenyl]-3-yl)acetyl)-2-(1-phenylcyclopropyl)-3,5,6,7,8,9-hexahydro-4H-pyrimido[5,4-c]azepin-4-one;

(R)-8-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[4,5-c]azepin-4-one;

6-(2-hydroxy-2-(3-((trifluoromethyl)thio)phenyl)acetyl)-2-(1-(thiophen-2-yl)cyclopropyl)-3,5,6,7,8,9-hexahydro-4H-pyrimido[5,4-c]azepin-4-one;

(R)-2-(1-(3-chlorophenyl)cyclopropyl)-6-(2-(2,3-difluorophenyl)-2-hydroxyacetyl)-3,5,6,7,8,9-hexahydro-4H-pyrimido[5,4-c]azepin-4-one;

6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

(R)-2-(1-(3-(benzo[b]thiophen-3-yl)phenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-(tert-butyl)-[1,1'-biphenyl]-3-yl)-2-hydroxyacetyl)-3,5,6,7,8,9-hexahydro-4H-pyrimido[5,4-c]azepin-4-one;

2-(1-(2',3',4',5'-tetrahydro-[1,1'-biphenyl]-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

(R)-6-(2-(3-(6-(benzyloxy)pyridin-3-yl)phenyl)-2-hydroxyacetyl)-2-(1-phenylcyclopropyl)-5,6,7,8-tetrahydropyrido[4,3-d]pyrimidin-4(3H)-one;

(E)-2-(1-(3-chlorophenyl)cyclopropyl)-6-(3-(3-(trifluoromethyl)phenyl)acryloyl)-3,5,6,7,8,9-hexahydro-4H-pyrimido[5,4-c]azepin-4-one;

(R)-6-(2-(3-chlorophenyl)-2-hydroxyacetyl)-2-(1-(4-cyclopentylthiophen-2-yl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3-(benzo[b]thiophen-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

2-(1-(3-chlorophenyl)cyclopropyl)-6-(2-(3-(pentafluoro-(lambda)$^6$-sulfaneyl)phenyl)acetyl)-3,5,6,7,8,9-hexahydro-4H-pyrimido[5,4-c]azepin-4-one;

(R)-2-(1-(5-(4,4-difluorocyclohexyl)pyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2,2-difluoro-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

2-(1-(3-chlorophenyl)cyclopropyl)-6-(2-(3'-fluoro-[1,1'-biphenyl]-3-yl)-2-hydroxyacetyl)-5,6,7,8-tetrahydropyrido[4,3-d]pyrimidin-4(3H)-one;

6-(2-(3-chloro-2-fluorophenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

2-(1-(3-chlorophenyl)cyclopropyl)-6-(2-(3'-(trifluoromethoxy)-[1,1'-biphenyl]-3-yl)acetyl)-5,6,7,8-tetrahydropyrido[4,3-d]pyrimidin-4(3H)-one;

(R)-6-(2-(3-(benzofuran-3-yl)phenyl)-2-hydroxyacetyl)-2-(1-phenylcyclopropyl)-5,6,7,8-tetrahydropyrido[4,3-d]pyrimidin-4(3H)-one;

(R)-2-(1-(3-(benzo[b]thiophen-3-yl)phenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(3-(tert-butyl)phenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-(5-(3-chlorophenyl)pyridin-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-(3-(trifluoromethyl)phenyl)propanoyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-dimethyl-[1,1'-biphenyl]-3-carboxamide;

6-(2-(3-chloro-2-fluorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(thiophen-2-yl)cyclopropyl)-3,5,6,7,8,9-hexahydro-4H-pyrimido[5,4-c]azepin-4-one;

6-(2-hydroxy-2-(3'-((trifluoromethyl)thio)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-(4,4-difluorocyclohexyl)pyridin-3-yl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

6-(2-(3-(benzyloxy)phenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3-bromophenyl)-2-hydroxyacetyl)-2-(1-phenylcyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

(R)-6-(2-(3'-chloro-5'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-phenylcyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one 6-(2-hydroxy-2-(3-((trifluoromethyl)thio)phenyl)acetyl)-2-(1-phenylcyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(3-isopropylphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-isopropylphenyl)cyclopropyl)-5,6,7,8-tetrahydropyrido[4,3-d]pyrimidin-4(3H)-one;

2-(1-(3-chlorophenyl)cyclopropyl)-6-(2-hydroxy-2-(3-(3-(trifluoromethyl)phenoxy)phenyl)acetyl)-3,5,6,7,8,9-hexahydro-4H-pyrimido[5,4-c]azepin-4-one (R)-6-(2-hydroxy-2-(3-(trifluoromethyl)phenyl)acetyl)-2-(1-(3-(naphthalen-1-yl)phenyl)cyclopropyl)-3,5,6,7,8,9-hexahydro-4H-pyrimido[5,4-c]azepin-4-one;

6-(2-(6-(3-cyclopropylphenyl)pyridin-2-yl)-2-hydroxyacetyl)-2-(1-phenylcyclopropyl)-5,6,7,8-tetrahydropyrido[4,3-d]pyrimidin-4(3H)-one;

6-(2-(4"-chloro-[1,1':4',1"-terphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-(naphthalen-1-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-(methylamino)pyridin-4-yl)phenyl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;

(R)-6-(2-(3',4'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(4-bromothiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-hydroxy-2-(3-(3-(trifluoromethyl)phenoxy)phenyl)acetyl)-2-(1-phenylcyclopropyl)-5,6,7,8-tetrahydropyrido[4,3-d]pyrimidin-4(3H)-one;

6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

2-(1-phenylcyclopropyl)-8-(2-(3'-(trifluoromethyl)-[1,1'-biphenyl]-3-yl)acetyl)-3,5,6,7,8,9-hexahydro-4H-pyrimido[4,5-c]azepin-4-one;

6-(2-(3-chloro-2-fluorophenyl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(pyrimidin-5-yl)phenyl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(5-(trifluoromethyl)pyridin-3-yl)phenyl)acetyl)-2-(1-phenylcyclopropyl)-3,5,6,7,8,9-hexahydro-4H-pyrimido[5,4-c]azepin-4-one;

6-(2-(4'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(2-phenoxypyridin-4-yl)cyclopropyl)-3,5,6,7,8,9-hexahydro-4H-pyrimido[5,4-c]azepin-4-one;

6-(2-(2-fluoro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-3,5,6,7,8,9-hexahydro-4H-pyrimido[5,4-c]azepin-4-one; and 6-(2-(2-fluoro-3-(2-(trifluoromethyl)pyridin-4-yl)phenyl)-2-hydroxyacetyl)-2-(1-phenylcyclopropyl)-5,6,7,8-tetrahydropyrido[4,3-d]pyrimidin-4(3H)-one;

or a pharmaceutically acceptable salt thereof;

[8] A single enantiomer of a compound selected from the group consisting of:

6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-hydroxy-2-(m-tolyl)acetyl)-2-(1-phenylcyclopropyl)-5,6,7,8-tetrahydropyrido[4,3-d]pyrimidin-4(3H)-one;

6-(2-(3-bromo-2-fluorophenyl)-2-hydroxyacetyl)-2-(1-phenylcyclopropyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-5,6,7,8-tetrahydropyrido[4,3-d]pyrimidin-4(3H)-one;

2-fluoro-3-(1-hydroxy-2-oxo-2-(4-oxo-2-(1-phenylcyclopropyl)-3,5,7,8-tetrahydropyrido[4,3-d]pyrimidin-6(4H)-yl)ethyl)benzonitrile;

6-(2-(3,5-difluorophenyl)-2-hydroxyacetyl)-2-(1-phenylcyclopropyl)-5,6,7,8-tetrahydropyrido[4,3-d]pyrimidin-4(3H)-one; and 6-(2-hydroxy-2-(m-tolyl)acetyl)-2-(1-(thiophen-2-yl)cyclopropyl)-5,6,7,8-tetrahydropyrido[4,3-d]pyrimidin-4(3H)-one;

or a pharmaceutically acceptable salt thereof;

[9] A pharmaceutical composition comprising a compound, or a pharmaceutically acceptable salt thereof, according to any one of [1] to [8], and a pharmaceutically acceptable carrier;

[10] The pharmaceutical composition according to [9], further comprising another pharmacologically active agent;

[11] A method for the treatment of a condition or disorder mediated by TRPV4 receptor antagonistic activity, in an animal including a human, which comprises administering to an animal in need of such treatment a therapeutically effective amount of a compound thereof, or a pharmaceutically acceptable salt thereof, according to any one of [1] to [8];

[12] The method according to [11], wherein said condition or disorder is one or more selected from the group consisting of: inflammatory, pain, and urological diseases or disorders, and combinations thereof;

[13] The method according to [11], wherein said condition or disorder is one or more selected from the group consisting of: chronic pain; neuropathic pain including diabetic neuropathy; postoperative pain; osteoarthritis; rheumatoid arthritic pain; cancer pain; neuralgia; neuropathies; algesia, nerve injury; migraine; cluster and tension headaches; ischaemia; irritable bowel syndrome; inflammatory bowel disease; neurodegeneration; fibromyalgia; stroke; itch; psychiatric disorders including anxiety, anxiety for other stress-related disorders and depression; inflammatory disorders including asthma, chronic obstructive pulmonary disease (COPD) and chronic obstructive airway disease (COAD); pulmonary hypertension; and urological diseases or disorders including detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms; and combinations thereof;

[14] A compound according to any one of [1] to [8], or a pharmaceutically acceptable salt thereof for use in the treatment of a condition or disorder mediated by TRPV4 receptor antagonistic activity;

[15] A use of a compound according to any one of [1] to [8], or a pharmaceutically acceptable salt, solvate, or composition thereof for the manufacture of a medicament for the treatment of a condition or disorder mediated by TRPV4 receptor antagonistic activity;

[16] The use according to [15], wherein said condition or disorder is one or more selected form the group consisting of: inflammatory, pain, and urological diseases or disorders, and combinations thereof;

[17] The use according to [15], wherein said condition or disorder is one or more selected form the group consisting of: chronic pain; neuropathic pain including diabetic neuropathy; postoperative pain; osteoarthritis; rheumatoid arthritic pain; cancer pain; neuralgia; neuropathies; algesia, nerve injury; migraine; cluster and tension headaches; ischaemia; irritable bowel syndrome; inflammatory bowel disease; neurodegeneration; fibromyalgia; stroke; itch; psychiatric disorders including anxiety, anxiety for other stress-related disorders and depression; inflammatory disorders including asthma, chronic obstructive pulmonary disease (COPD) and chronic obstructive airway disease (COAD); pulmonary hypertension; and urological diseases or disorders including detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms; and combinations thereof.

[18] A process for preparing a pharmaceutical composition comprising mixing a compound or a pharmaceutically acceptable salt thereof, according to any one of [1] to [8], and a pharmaceutically acceptable carrier or excipient.

[19] A compound represented by the following formula (I-d):

{Chem. 7}

(I-d)

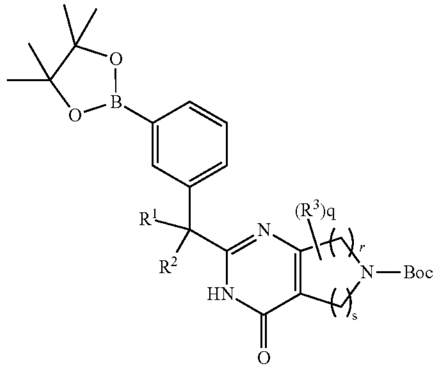

wherein $R^1$ and $R^2$ are independently selected from the group consisting of: hydrogen, hydroxyl, halogen, $(C_1\text{-}C_6)$alkyl, $(C_1\text{-}C_6)$haloalkyl, $(C_1\text{-}C_6)$alkoxy, $(C_1\text{-}C_6)$haloalkoxy, $(C_3\text{-}C_7)$cycloalkyl, and phenyl$(C_0\text{-}C_4)$alkyl; wherein the said $(C_3\text{-}C_7)$cycloalkyl or phenyl$(C_0\text{-}C_4)$alkyl is optionally substituted with 1 to 4 substituents independently selected from the group consisting of: halogen, hydroxyl, $(C_1\text{-}C_6)$alkyl, $(C_1\text{-}C_6)$haloalkyl, $(C_1\text{-}C_6)$alkoxy, and $(C_1\text{-}C_6)$haloalkoxy; or alternatively $R^1$ and $R^2$, together with the atom to which they are attached, may form a 3 to 8 membered ring which may contain 0 to 4 heteroatoms independently selected from oxygen, sulfur, and nitrogen; wherein the said 3 to 8 membered ring is optionally substituted with 1 to 6 substituents independently selected from the group consisting of: halogen, hydroxyl, $(C_1\text{-}C_6)$alkyl, $(C_1\text{-}C_6)$haloalkyl, $—SO_2(C_1\text{-}C_6)$alkyl, $—SO_2(C_1\text{-}C_6)$haloalkyl, $—C(═O)(C_1\text{-}C_6)$alkyl, and $—C(═O)(C_1\text{-}C_6)$haloalkyl;

$R^3$ is independently selected from the group consisting of: hydrogen, fluoride, methyl, ethyl, and $(C_1\text{-}C_6)$haloalkyl;

q is 1, 2, 3, or 4;

r is 1, 2, 3, or 4;

s is 1, 2, 3, or 4;

or a pharmaceutically acceptable salt thereof.

[20] A compound which is selected from the group consisting of:

(R)-2-(1-(5-bromopyridin-3-yl)cyclopropyl)-6-(2-(3-chlorophenyl)-2-hydroxyacetyl)-5,6,7,8-tetrahydropyrido[4,3-d]pyrimidin-4(3H)-one;

(R)-2-(1-(3-bromophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(5-bromopyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(4-bromothiophen-2-yl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3-bromophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(2-bromopyridin-4-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(6-bromopyridin-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-bromophenyl)-2-hydroxyacetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3-bromophenyl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-(3-bromophenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(3-bromophenyl)acetyl)-2-(1-phenylcyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-cyclohexylphenyl)cyclopropyl)-3,5,6,7,8,9-hexahydro-4H-pyrimido[5,4-c]azepin-4-one;

6-(2-(3-bromophenyl)-2,2-difluoroacetyl)-2-(1-phenylcyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3-bromophenyl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-phenoxyphenyl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(4-phenylthiophen-2-yl)cyclopropyl)-3,5,6,7,8,9-hexahydro-4H-pyrimido[5,4-c]azepin-4-one;

6-(2-(3-bromophenyl)acetyl)-2-(1-(3-chlorophenyl)cyclopropyl)-3,5,6,7,8,9-hexahydro-4H-pyrimido[5,4-c]azepin-4-one;

2-(1-(3-bromophenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3-bromophenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

6-(2-(3-bromophenyl)acetyl)-2-(1-(3-chlorophenyl)cyclopropyl)-5,6,7,8-tetrahydropyrido[4,3-d]pyrimidin-4(3H)-one;

2-(1-(3-bromophenyl)cyclopropyl)-6-(2-(3'-chloro-[1,1'-biphenyl]-3-yl)acetyl)-3,5,6,7,8,9-hexahydro-4H-pyrimido[5,4-c]azepin-4-one;

2-(1-(3-bromophenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one; and 2-(1-(3-bromophenyl)cyclopropyl)-6-(2-(3'-chloro-[1,1'-biphenyl]-3-yl)acetyl)-5,6,7,8-tetrahydropyrido[4,3-d]pyrimidin-4(3H)-one;

or a pharmaceutically acceptable salt thereof.

Advantageous Effects of Invention

The compounds of the present invention show the TRPV4 receptor antagonistic activity. The compounds of the present invention may show less toxicity, preferable absorption and distribution, preferable solubility, less protein binding affinity other than TRPV4 receptor, less drug-drug interaction, and preferable metabolic stability.

DESCRIPTION OF EMBODIMENTS

As used herein, the term "alkyl" as a group or part of a group e.g. alkoxy or hydroxyalkyl refers to a straight or branched alkyl group in all isomeric forms. The term "$C_1$-$C_4$ alkyl" refers to an alkyl group, as defined above, containing at least 1 carbon atom, and at most 4 carbon atoms. Examples of such alkyl groups include methyl, ethyl, propyl, iso-propyl, n-butyl, iso-butyl, sec-butyl, or tert-butyl. Examples of such alkoxy groups include methoxy, ethoxy, propoxy, iso-propoxy, butoxy, iso-butoxy, sec-butoxy and tert-butoxy.

The term "cycloalkyl", as used herein, means a mono- or bicyclic ring, but not limited to, cyclopropyl, cyclobutyl, cyclopentyl, cyclohexyl, cycloheptyl, norbornyl, and adamantyl groups and the like.

The term "halogen", as used herein, refers to fluorine (F), chlorine (Cl), bromine (Br), or iodine (I) and the term "halo" refers to the halogen: fluoro (—F), chloro (—Cl), bromo (—Br) and iodo (—I).

The term "haloalkyl", as used herein, means an alkyl radical which is substituted by halogen atom(s) as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

The term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The term "alkoxy", as used herein, means an O-alkyl group wherein "alkyl" is defined above.

The term "alkylthio", as used herein, means a straight or branched alkylthio group, and includes, for example, a methylthio group, an ethylthio group, a propylthio group, an isopropylthio group, a n-butylthio group, a sec-butylthio group, a tert-butylthio group, a pentylthio group, an isopentylthio group, a neopentylthio group, a n-hexylthio group, an isohexylthio group, a sec-hexylthio group, and the like.

The term “haloalkylthio”, as used herein, means a group wherein at least one hydrogen atom of the straight or branched alkylthio group is substituted with a halogen atom, and includes, for example, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, and the like.

The term “aryl”, as used herein, means unsaturated or partially saturated mono- or bi-cyclic 5 to 15-membered ring which consists of carbon atoms. Examples of such aryl include, but are not limited to, phenyl, naphthyl, indanyl, indenyl, 1,2,3,4-tetrahydronaphthyl, 1,2-dihydronaphthyl, 2,3-dihydro-1H-indenyl, cyclohexenyl, cyclopentenyl, (1S, 4S)-bicyclo[2.2.2]oct-2-enyl, and (1R,4S)-bicyclo[2.2.1]hept-2-enyl and the like. In this specification, preferable aryl is 6-10 membered unsaturated aryl, more preferable aryl is phenyl or naphthyl.

The term “heteroaryl”, as used herein, means unsaturated or partially saturated mono- or bi-cyclic 5 to 15-membered ring with 1-4 heteroatoms independently selected from O, N, and S, or carbonyl, preferably unsaturated or partially saturated mono- or bi-cyclic 5 to 10-membered ring with 1-4 heteroatoms independently selected from O, N, and S, or carbonyl, more preferably unsaturated 5-6 membered ring with 1-4 heteroatoms independently selected from O, N, and S, or unsaturated or partially saturated 9 to 10-membered ring with 1-4 heteroatoms independently selected from O, N, and S, or carbonyl. Examples of such heteroaryl include, but are not limited to, thiophenyl, thiazolyl, isoxazolyl, pyrazolyl, pyrazyl, tetrazolyl, furanyl, pyrrolyl, imidazolyl, oxazolyl, isothiazolyl, triazolyl, thiadiazolyl, pyridyl, pyrimidyl, pyridazinyl, pyrazinyl, pyranyl, triazinyl, 3,6-dihydro-2H-pyran, 1,2,3,6-tetrahydropyridyl, benzofuranyl, benzothiophenyl, benzotriazolyl, benzoxazolyl, indolyl, indazolyl, benzoimidazolyl, pyrrolopyridyl, 2,3-dihydro-pyrrolo[2,3-b]pyridyl, 2,3-dihydro-1H-pyrrolo[2,3-c]pyridyl, pyrrolopyrimidinyl, pyrazolopyridyl, pyrazolopyrimidinyl, imidazopyridinyl, furopyridyl, benzoisoxazolyl, imidazopyrazinyl, imidazopyridazinyl, imidazopyrimidinyl, quinolyl, isoquinolyl, quinoxalyl, quinazolinyl, phthalazinyl, quinoxalinyl, naphthyridinyl, pyridopyrimidinyl, 2,3-dihydro-[1,4]dioxino[2,3-b]pyridyl, 2,3-dihydro-[1,4]dioxino[2,3-c]pyridyl, 1H-indolyl, 1H-pyrrolo[2,3-b]pyridyl, 1H-pyrrolo[2,3-c]pyridyl, 1H-pyrrolo[3,2-c]pyridyl, 1H-pyrrolo[3,2-b]pyridyl, 7H-pyrrolo[2,3-d]pyrimidyl, 7H-pyrrolo[2,3-c]pyridazinyl, 1H-indazolyl, 2H-indazolyl, 1H-pyrazolo[3,4-b]pyridyl, 1H-pyrazolo[3,4-c]pyridyl, 1H-pyrazolo[4,3-c]pyridyl, 1H-pyrazolo[4,3-b]pyridyl, 1H-pyrazolo[3,4-d]pyrimidyl, 1H-benzo[d]imidazolyl, 3H-imidazo[4,5-b]pyridyl, 1H-imidazo[4,5-b]pyridyl, 9H-purinyl, 1H-imidazo[4,5-d]pyridazinyl, 1H-imidazo[4,5-b]pyrazinyl, imidazo[1,2-a]pyridyl, imidazo[1,5-a]pyridyl, imidazo[1,2-a]pyrazinyl, imidazo[1,2-b]pyridazinyl, pyrazolo[1,5-a]pyridyl, pyrazolo[1,5-a]pyrimidyl, furo[3,2-c]pyridyl, benzo[d]isoxazolyl, 2,3-dihydro-1H-indenyl, indolinyl, isoindolinyl, indolin-2-one-yl, isoindolin-1-one-yl, 1H-benzo[d]imidazol-2(3H)-one-yl, benzo[d]oxazol-2(3H)-one-yl, 1H-pyrrolo[2,3-b]pyridin-2(3H)-one-yl, 1H-imidazo[4,5-b]pyridin-2(3H)-one-yl, quinolyl, isoquinolyl, quinazolinyl, phthalazinyl, 2,6-naphthyridinyl, 2,7-naphthyridinyl, quinoxalinyl, pyrido[3,4-d]pyrimidyl, pyrido[2,3-d]pyrimidyl, 1,2,3,4-tetrahydroquinolyl, 1,2,3,4-tetrahydroisoquinolyl, 3,4-dihydro-2H-benzo[b][1,4]oxazinyl, 2,3-dihydro-[1,4]dioxino[2,3-b]pyridyl, 3,4-dihydroquinolin-2(1H)-one-yl, 2H-benzo[b][1,4]oxazin-3(4H)-one-yl, quinolin-2(1H)-one-yl, benzo[d][1,3]dioxolyl, or 4,5-dihydro-1H-benzo[b]azepin-2(3H)-one-yl, and N-oxides thereof and S-oxides thereof and the like. Preferable heteroaryl is 5 to 6-membered heteroaromatic ring with 1-4 heteroatoms independently selected from O, N, and S, or 9 to 10-membered heteroaromatic ring with 1-4 heteroatoms independently selected from O, N, and S, more preferable heteroaryl is 5 to 6-membered N-containing heteroaromatic ring, further more preferable heteroaryl is benzoimidazolyl, dihydroisoquinolyl, indolyl, indazolyl, pyrazolyl, pyrazinyl, pyridazinyl, pyridyl, quinolyl, isoquinolyl and thiazolyl.

The term “heterocyclyl”, as used herein includes both unsaturated and saturated heterocyclic moieties, wherein the unsaturated heterocyclic moieties (i.e. “heteroaryl”) include, but not limited to, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, furazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, 3,6-dihydro-2H-pyranyl, 1,2,3,6-tetrahydropyridinyl, tetrahydro-2H-thiopyran 1,1-dioxide, and N-oxides thereof, and wherein the saturated heterocyclic moieties include, but not limited to, azetidinyl, 1,4-dioxanyl, hexahydroazepinyl, piperazinyl, piperidinyl, pyridin-2-onyl, pyrrolidinyl, morpholinyl, tetrahydrofuranyl, tetrahydropyranyl, thiomorpholinyl, triazolopyrimidyl, tetrahydrothienyl, pyrrolidinonyl, 3,4-dihydro-2H-pyrido[3,2-b][1,4]oxazinyl, 2-oxo-2,5,6,7-tetrahydro-1H-cyclopentapyridyl, 4,5,6,7-tetrahydro-indazolyl, 5,6,7,8-tetrahydro-1,6-naphthyridyl, 1,4-oxazepanyl, and N-oxides thereof and S-oxides thereof. In this specification, preferable heterocyclyl is 3 to 8-membered heterocyclyl with 1-4 heteroatoms independently selected from O, N, and S, or carbonyl, more preferable heterocyclyl is 4-6 membered saturated mono heterocyclyl with 1-4 heteroatoms selected from O, N, and S, or carbonyl, further more preferable heterocyclyl is 5-6 membered saturated mono heterocyclyl with 1-3 heteroatoms selected from O, N, and S, or carbonyl.

The term “protecting group”, as used herein, means a hydroxyl or amino protecting group which is selected from typical hydroxyl or amino protecting groups described in Protective Groups in Organic Synthesis edited by T. W. Greene et al. (John Wiley & Sons, 1991).

The term “animal subject”, as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formulae (I) and (I-a) and their pharmaceutically acceptable salts.

In certain of the compounds of formulae (I) and (I-a), there may be some chiral carbon atoms. In such cases, compounds of formulae (I) and (I-a) exist as stereoisomers. The invention extends to all optical isomers such as stereoisomeric forms of the compounds of formulae (I) and (I-a) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds of formulae (I) and (I-a) herein can exist in various tautomeric forms and it is to be understood that the invention encompasses all such tautomeric forms.

{Chem. 8}

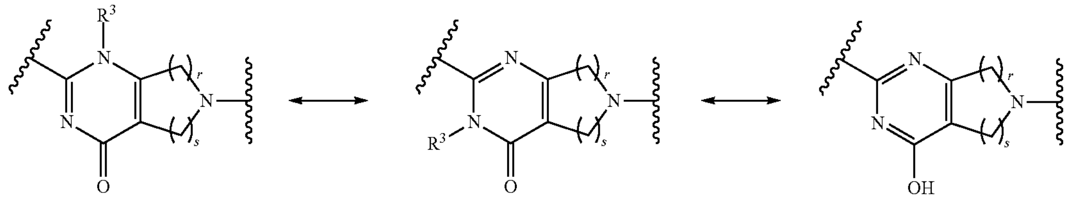

Further, the symbol letter is written the corresponding English word in the present specification.

For example, the symbols a, P, b and A are written alpha, beta, delta, and lambda.

Included within the scope of the "compounds of the invention" are all salts, solvates, hydrates, complexes, polymorphs, radiolabeled derivatives, stereoisomers and optical isomers of the compounds of formulae (I) and (I-a).

The compounds of formulae (I) and (I-a) can form acid addition salts thereof. It will be appreciated that for use in medicine the salts of the compounds of formulae (I) and (I-a) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formulae (I) and (I-a) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

The compounds of formulae (I) and (I-a) and salts thereof may be prepared in crystalline or non-crystalline form, and, Certain of the compounds of formulae (I) and (I-a) may have a carbon-carbon double bond. In such cases, a compound of formula (I) or (I-a) may exist as an E-isomer, a Z-isomer or a mixture of E- and Z-isomers.

Certain of the compounds of formulae (I) and (I-a) may exist as a stereoisomer which should be recognized as a cis/trans isomer. In such cases, the compounds of formulae (I) and (I-a) may exist as a cis-isomer, a trans-isomer, or a mixture of cis- and trans-isomers.

Formulae, chemical structures or chemical names without specifying a stereochemistry herein include all the above isomers which may exist, unless otherwise specified.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{3}H$, $^{11}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances, isotopically labeled compounds of the invention can generally be prepared by carrying out the procedures disclosed in the Schemes and/or in the Examples below, then substituting a readily available isotopically labeled reagent for a non-isotopically labeled reagent.

The potencies and efficacies of the compounds of this invention for TRPV4 can be determined by reporter assay performed on the human cloned receptor as described herein. Compounds of formulae (I) and (I-a) have demonstrated antagonistic activity at the TRPV4 receptor, using the functional assay described herein.

Compounds of formulae (I) and (I-a) and pharmaceutically acceptable salts thereof are therefore of use in the treatment of conditions or disorders which are mediated via the TRPV4 receptor. In particular the compounds of formulae (I) and (I-a) and pharmaceutically acceptable salts thereof are of use in the treatment of a wide range of diseases, syndromes, and disorders, in particular for the treatment of inflammatory, pain, and urological diseases or disorders, such as chronic pain, neuropathic pain including diabetic neuropathy, postoperative pain, osteoarthritis, rheumatoid arthritic pain, cancer pain, neuralgia, neuropathies, algesia, nerve injury, migraine, cluster and tension headaches, ischaemia, irritable bowel syndrome, inflammatory bowel disease, neurodegeneration, fibromyalgia, stroke, itch, psychiatric disorders including anxiety and depression and inflammatory disorders including asthma, chronic obstructive pulmonary disease (COPD) and chronic obstructive airway disease (COAD), pulmonary hypertension, anxiety, including other stress-related disorders, urological diseases or disorders including detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms, and combinations thereof.

Activities of the compounds of formulae (I) and (I-a) for each diseases, syndromes, and disorders described above can be confirmed in the suitable model known to skilled in the arts. For example, activities of compounds of formulae (I) and (I-a) for neuropathic pain have been confirmed in chronic constriction injury (CCI)-induced model, such as static allodynia model.

It is to be understood that "treatment" as used herein includes prophylaxis as well as alleviation of established symptoms.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compounds or pharmaceutically acceptable salts thereof.

For parenteral administration, fluid unit dosage forms are prepared utilizing a compound of formula (I) or (I-a) or a pharmaceutically acceptable salt thereof and a sterile vehicle. Formulations for injection may be presented in unit dosage form e.g. in ampoules or in multi-dose, utilizing a compound of formula (I) or (I-a) or a pharmaceutically acceptable salt thereof and a sterile vehicle, optionally with an added preservative. The compositions may take such forms as suspensions, solutions or emulsions in oily or aqueous vehicles, and may contain formulated agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter-sterilized before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formulae (I) and (I-a) or pharmaceutically acceptable salts thereof may also be formulated in rectal compositions such as suppositories or retention enemas, e.g. containing conventional suppository bases such as cocoa butter or other glycerides.

The compounds of formulae (I) and (I-a) or pharmaceutically acceptable salts may also be formulated as depot preparations. Such long acting formulations may be administered by implantation (for example subcutaneously or intramuscularly) or by intramuscular injection. Thus, for example, the compounds of formulae (I) and (I-a) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formulae (I) and (I-a) or pharmaceutically acceptable salts thereof may be formulated as solutions for administration via a suitable metered or unitary dose device or alternatively as a powder mix with a suitable carrier for administration using a suitable delivery device. Thus compounds of formulae (I) and (I-a) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formulae (I) and (I-a) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

A TRPV4 antagonist may be usefully combined with another pharmacologically active compound, or with two or more other pharmacologically active compounds, particularly in the treatment of inflammatory, pain, and urological diseases or disorders. For example, a TRPV4 antagonist, particularly a compound of formula (I) or (I-a), or a pharmaceutically acceptable salt or solvate thereof, as defined above, may be administered simultaneously, sequentially or separately in combination with one or more agents.

Thus, for example, for the treatment or prevention of pain and/or inflammation, a compound of the present invention may be used in conjunction with other analgesics, such as acetaminophen (paracetamol), aspirin and other NSAIDs, including selective cyclooxygenase-2 (Cox-2) inhibitors and 5-lipoxygenase inhibitors, as well as opioid analgesics, especially morphine, oxycodone, fentanyl and tramadol, NR2B antagonists, bradykinine (BK1 and/or BK2) antagonists, 5-HT agonist and antagonists including 5-$HT_3$ antagonists, 5-$HT_{2A}$ antagonists, and 5-$HT_{1B/1D}$ agonist such as eletriptan, and sumatriptan, sedative agents (barbiturate, benzodiazepine, etc.), anticonvulsants such as oxcarbazepine and carbamazepine, antidepressants (such as TCAs, SSRIs, SNRIs, NRIs, neurokinin-1 antagonist, etc.), spinal blocks, alpha-2-delta ligands such as gabapentin and pregabalin, asthma treatments (such as bata-2 adrenergic receptor agonist or leukotriene D4 antagonist (e.g. montelukast), Transient receptor potential subtypes (V1, V3, A1, M8) antagonists, NMDA receptor antagonist, Sodium ($Na^+$)-dependent channels (Nav1.3, Nav1.7, Nav1.8), calcium ($Ca^{2+}$)-dependent channels (N-type, T-type), acid-sensing ion channel (ASIC3, ASIC1a) antagonist, large conductance $Ca^{2+}$-dependent $K^+$ channel activators, CGRP (calcitonine gene-related peptide) antagonist, cannabinoid (CB1 and/or CB2 agonists), P2X (ion channel-type ATP receptor) antagonist, cholinergic (nicotinic) analgesic, alpha adrenergic such as doxazosin and clonidine, prostaglandin E2 subtype 4 (EP4) antagonist, leukotriene B4 antagonist, corticosteroids, methotrexate, tumor necrosis (TNF) receptor antagonists, anti-TNF alpha antibodies, anti-$C_5$ antibodies, NGF antibodies and interleukin-1 (IL-1) receptor antagonists. Specific agents include dexbrompheniramine plus pseudoephedrine, loratadine, oxymetazoline, ipratropium, albuterol, beclomethasone, mexiletine.

Thus, for example, for the treatment or prevention of urinary incontinence, a compound of the present invention may be used in conjunction with other medication designed to treat this condition or disorder, such as estrogen replacement therapy, progesterone congeners, electrical stimulation, calcium channel blocker, antispasmodic agents, cholinergic antagonist, antimuscarinic drugs such as oxybutynin, tolterodine, and darifenacin, tricyclic antidepressants, SNRIs, beta adrenoreceptor agonists, phosphodiesterase inhibitors, potassium channel openers, transient receptor potential subtypes (V1, V3, A1, M8) agonist and antagonists, nociceptin/orphanin FQ agonist, neurokinin (NK1 and NK2) antagonist, P2X3 antagonists, musculotrophic drugs and sacral neuromodulation.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors.

A therapeutically effective amount of a compound of formula (I) or (I-a) or a pharmaceutical acceptable salt thereof includes a dose range from about 0.05 mg to about 3000 mg, in particular from about 1 mg to about 1000 mg, and more particularly, from about 10 mg to about 500 mg of active ingredient in a regimen of about once a day or more than once a day, for example two, three or four times a day for an average (70 kg) human; although, it is apparent to one skilled in the art that the therapeutically effective amount for active compounds of the invention will vary with the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of the inventive compound as the active ingredient.

Advantageously, the compounds of formulae (I) and (I-a) may be administered in a single daily dose, or the total daily dosage may be administered in divided doses of two, three and four times daily.

Optimal dosages of the compounds of formulae (I) and (I-a) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level.

The above dosages are thus exemplary of the average case. There can be, of course, individual instances wherein higher or lower dosage ranges are used, and such are within the scope of this invention.

Compounds of formulae (I) and (I-a) may be administered in any of the foregoing compositions and dosage regimens or by means of those compositions and dosage regimens established in the art whenever the compounds of formulae (I) and (I-a) are required for a subject in need thereof.

As antagonists of the TRPV4 ion channel, the compounds of formulae (I) and (I-a) are useful in methods for treating and preventing a disease, a syndrome, a condition, or a disorder in a subject, including an animal, for example, a mammal and a human in which the disease, the syndrome, the condition, or the disorder is affected by the modulation of TRPV4 receptors. Such methods comprise, consist of, and consist essentially of administering to a subject, including an animal, for example, a mammal and a human in need of such treatment or prevention a therapeutically effective amount of a compound, salt, or solvate of formula (I) or (I-a). In particular, the compounds of formulae (I) and (I-a) are useful for preventing or treating pain, or diseases, syndromes, conditions, or disorders causing such pain, or pulmonary or vascular dysfunction. More particularly, the compounds of formulae (I) and (I-a) are useful for preventing or treating inflammatory pain, inflammatory hypersensitivity conditions, neuropathic pain, anxiety, depression, and cardiovascular disease, including peripheral vascular disease, vascular hypertension, pulmonary hypertension, Raynaud's disease, and coronary artery disease, by administering to a subject in need thereof a therapeutically effective amount of the compounds of formula (I) or (I-a).

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a mammal in need of such treatment a therapeutically effective amount of a compound, salt or solvate of formula (I) or (I-a).

A further embodiment of the present invention is directed to a method for treating inflammatory visceral hyperalgesia in which an enhanced visceral irritability exists, comprising, consisting of, and/or consisting essentially of the step of administering to a subject in need of such treatment a therapeutically effective amount of a compound, salt or solvate of formula (I) or (I-a).

Examples of an inflammatory hypersensitivity condition or disorder include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

Examples of anxiety include social anxiety, post traumatic stress disorder, phobias, social phobia, special phobias, panic disorder, obsessive compulsive disorder, acute stress disorder, separation anxiety disorder, and generalized anxiety disorder.

Examples of depression include major depression, bipolar disorder, seasonal affective disorder, post natal depression, manic depression, and bipolar depression.

General Synthesis

Throughout the instant application, the following abbreviations are used with the following meanings:

DMF: N,N-Dimethylformamide
THF: Tetrahydrofuran
DMSO: Dimethylsulfoxide
NMP: N-methylpyrrolidone
EtOAc: Ethyl acetate
Me: Methyl
MeOH: Methanol
EtOH: Ethanol
BuOH: Butanol
DCM: Dichloromethane
DIPEA: N,N-Diisopropylethylamine
DME: 1,2-dimethoxyethane
TFA: Trifluoroacetic acid
MeCN: Acetonitrile
$Et_3N$: Triethylamine
DMAP: 4-Dimethylaminopyridine
EDC: 1-Ethyl-3-(3-dimethylaminopropyl)carbodiimide Hydrochloride
HOBT: 1-Hydroxybenzotriazole
HBTU: O-(Benzotriazol-1-yl)-N,N,N',N'-tetramethyluronium Hexafluorophosphate HATU: O-(7-Azabenzotriazol-1-yl)-N,N,N',N'-tetramethyluronium Hexafluorophosphate BOP: (Benzotriazol-1-yloxy)tris(dimethylamino) phosphonium Hexafluorophosphate $T_3P$: Propylphosphonic Acid Anhydride (Cyclic Trimer)

$Pd(dba)_3$: Tris(dibenzylideneacetone)dipalladium(0)

$Pd(Amphos)Cl_2$: Bis(di-tert-butyl(4-dimethylaminophenyl)phosphine)dichloropalladium(II)

$PdCl_2(dppf)$-DCM: [1,1'-Bis(diphenylphosphino)ferrocene]dichloropalladium (II), Dichloromethane Adduct $Pd(PPh_3)_4$: Tetrakis(triphenylphosphine)palladium (0)

XantPhos Pd G3: [2'-(Amino-κN)[1,1'-biphenyl]-2-yl-κC][[5-(diphenylphosphino)-9,9-dimethyl-9H-xanthen-4-yl]diphenylphosphine-κP](methanesulfonato-κO)palladium SCX: Strong Cation Exchanger SFC: Supercritical fluid chromatography $Zn(CN)_2$: Zinc cyanide HPLC: High performance liquid chromatography tR: Retention time MHz: Megahertz NMR: Nuclear Magnetic Resonance TLC: Thin layer chromatography rt: room temperature ee: enantio excess, enantiomeric excess or enantiomer excess eq.: quantitative obs: observed mp: melting point The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, DMA, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, DCM, dichloroethane and chloroform are preferred.

EXAMPLES

The invention is illustrated in the following non-limiting examples in which, unless stated otherwise: all reagents are commercially available, all operations are carried out at room or ambient temperature, that is, in the range of about 18 to 25° C.; evaporation of solvent is carried out using a rotary evaporator under reduced pressure with a bath temperature of up to about 60° C.; reactions are monitored by thin layer chromatography (TLC)(Merck silica gel 60 $F_{254}$ precoated TLC plates or Merck $NH_2$ $F_{254}$ precoated HPTLC plates) or LC-MS and reaction times are given for illustration only; the structure and purity of all isolated compounds are assured by at least one of the following techniques: LC-MS and nuclear magnetic resonance (NMR). Microwave reaction is conducted by Initiator+ (registered trademark)(Biotage). Yields are given for illustrative purposes only. The column chromatography system is conducted by Yamazen and Biotage (Isolera one). Flash column chromatography is carried out using Merck silica gel 60 (230-400 mesh ASTM), Fuji Silysia Chromatorex (registered trademark) NH-DH1020, Biotage silica (32-63 mm, KP-Sil), Biotage amino bounded silica (35-75 mm, KP-NH), Wakogel (registered trademark) C-300HGT, Hi-Flash (registered trademark) column (YAMAZEN, silica gel, 40 micro meters, 60 angstrom), Hi-Flash (registered trademark) column (YAMAZEN, amino, 40 micro meters, 60 angstrom).

LC-MS analysis for intermediates and Examples are carried out by Waters 2695 Alliance HPLC with ZQ 2000 mass spectrometer and 2996 PDA detector. Analytical conditions (method-A to method-L, method-A1 and method-B1) are as follows.

Conditions for Method-A, Method-B, and Method-C:

| | | |
|---|---|---|
| Column | Waters XTerra C18 2.1 × 30 mm, 3.5 micrometer | |
| Column temperature | 45° C. | |
| Flow rate | 0.5 mL/min | |
| PDA detection | 210-400 nm scan (Extracted wave length: 254 nm) | |
| MS detection | ESI positive & negative mode | |
| Mobile phases | A: | MeCN (HPLC grade) |
| | B: | 0.5% aqueous $HCO_2H$ |
| | C: | 0.2% aqueous $NH_3$ |
| | D: | $H_2O$ (Milli-Q water) |

Method-A

| Time (min) | A(%) | B(%) | C(%) | D(%) |
|---|---|---|---|---|
| 0 | 4 | 4.8 | 4.8 | 86.4 |
| 2 | 96 | 0.2 | 0.2 | 3.6 |

run time: 4 min

| Method-B | | | | |
|---|---|---|---|---|
| Time (min) | A(%) | B(%) | C(%) | D(%) |
| 0 | 4 | 0 | 4.8 | 91.2 |
| 2 | 96 | 0 | 0.2 | 3.8 |

run time: 4 min

| Method-C | | | | |
|---|---|---|---|---|
| Time (min) | A(%) | B(%) | C(%) | D(%) |
| 0 | 32 | 3.4 | 3.4 | 61.2 |
| 2 | 96 | 0.2 | 0.2 | 3.6 |

run time: 4 min

Conditions for Method-A1 and Method-B1:

| | | |
|---|---|---|
| Column | Agilent Poroshell HPH-C18/C8, 2.1 × 30 mm, 2.7 micrometer | |
| Column temperature | 45° C. | |
| Flow rate | 0.7 mL/min | |
| PDA detection | 210-400 nm scan (Extracted wave length: 254 nm) | |
| MS detection | ESI positive & negative mode | |
| Mobile phases | A: | MeCN (HPLC grade) |
| | B: | 0.5% aqueous $HCO_2H$ |
| | C: | 0.2% aqueous $NH_3$ |
| | D: | $H_2O$ (Milli-Q water) |

| Method-A-1 | | | | |
|---|---|---|---|---|
| Time (min) | A(%) | B(%) | C(%) | D(%) |
| 0 | 5 | 2.5 | 2.5 | 90 |
| 1.5 | 95 | 2.5 | 2.5 | 0 |
| 3 | 95 | 2.5 | 2.5 | 0 |

run time: 3 min

| Method-B-1 | | | | |
|---|---|---|---|---|
| Time (min) | A(%) | B(%) | C(%) | D(%) |
| 0 | 5 | 0 | 5 | 90 |
| 1.5 | 95 | 0 | 5 | 0 |
| 3 | 95 | 0 | 5 | 0 |

run time: 3 min

Conditions for Method-D and Method-E:

| | | |
|---|---|---|
| Column | Waters SunFire C18 4.6 × 50 mm, 5 micrometer | |
| Column temperature: | 45° C. | |
| Flow rate: | 0.8 mL/min | |
| PDA detection: | 210-400 nm scan (Extracted wave length: 215 nm) | |
| MS detection: | ESI positive & negative mode | |
| Mobile phases | A: | MeCN (HPLC grade) |
| | B: | 0.5% aqueous $HCO_2H$ |
| | C: | 0.2% aqueous $NH_3$ |
| | D | $H_2O$ (Milli-Q water) |

| Method-D | | | | |
|---|---|---|---|---|
| Time (min) | A(%) | B(%) | C(%) | D(%) |
| 0 | 5 | 2.5 | 2.5 | 90 |
| 0.5 | 5 | 2.5 | 2.5 | 90 |
| 3.5 | 95 | 2.5 | 2.5 | 0 |
| 4 | 95 | 2.5 | 2.5 | 0 |

run time: 4.5 min

| Method-E | | | | |
|---|---|---|---|---|
| Time (min) | A(%) | B(%) | C(%) | D(%) |
| 0 | 5 | 0 | 5 | 90 |
| 0.5 | 5 | 0 | 5 | 90 |
| 3.5 | 95 | 0 | 5 | 0 |
| 4 | 95 | 0 | 5 | 0 |

run time: 4.5 min

Conditions for Method-F and Method-G and Method-H:

| | |
|---|---|
| Column | Waters XBridge C18/C8 2.1 × 50 mm, 3.5 micrometer |
| Column temperature: | 45° C. |
| Flow rate: | 0.8 mL/min |
| PDA detection: | 210-400 nm scan (Extracted wave length: 220 nm) |
| MS detection: | ESI positive & negative mode |
| Mobile phases | A: MeCN (HPLC grade) |
| | B: 0.5% aqueous $HCO_2H$ |
| | C: 0.2% aqueous $NH_3$ |
| | D: $H_2O$ (Milli-Q water) |

| Method-F | | | | |
|---|---|---|---|---|
| Time (min) | A(%) | B(%) | C(%) | D(%) |
| 0 | 10 | 2.5 | 2.5 | 85 |
| 0.5 | 10 | 2.5 | 2.5 | 85 |
| 3.5 | 95 | 2.5 | 2.5 | 0 |
| 4.5 | 95 | 2.5 | 2.5 | 0 |

run time: 4.5 min

| Method-G | | | | |
|---|---|---|---|---|
| Time (min) | A(%) | B(%) | C(%) | D(%) |
| 0 | 10 | 5 | 0 | 85 |
| 0.5 | 10 | 5 | 0 | 85 |
| 3.5 | 95 | 5 | 0 | 0 |
| 4.5 | 95 | 5 | 0 | 0 |

run time: 4.5 min

| Method-H | | | | |
|---|---|---|---|---|
| Time (min) | A(%) | B(%) | C(%) | D(%) |
| 0 | 10 | 0 | 5 | 85 |
| 0.5 | 10 | 0 | 5 | 85 |
| 3.5 | 95 | 0 | 5 | 0 |
| 4.5 | 95 | 0 | 5 | 0 |

run time: 4.5 min

UPLC-MS analysis for intermediates and Examples are carried out by Waters ACQUITY UPLC H-Class with QDa mass spectrometer and ACQUITY PDA detector. Analytical conditions (method-I, method-J and method-K) are as follows.

Conditions for Method-I, Method-J, and Method-K:

| | | |
|---|---|---|
| Column | Waters ACQUITY UPLC BEH C18/C8, 2.1 × 50 mm, 1.7 micrometer | |
| Column temperature | 45° C./55° C. | |
| Flow rate | 1 mL/min | |
| PDA detection | 210-400 nm scan (Extracted wave length: 210 nm or 254 nm) | |
| MS detection | ESI positive & negative mode | |
| Mobile phases | A: | MeCN (HPLC grade) |
| | B: | 0.5% aqueous $HCO_2H$ |
| | C: | 0.2% aqueous $NH_3$ |
| | D: | $H_2O$ (Milli-Q water) |

| Method-I | | | | |
|---|---|---|---|---|
| Time (min) | A(%) | B(%) | C(%) | D(%) |
| 0 | 5 | 2.5 | 2.5 | 90 |
| 0.3 | 95 | 2.5 | 2.5 | 0 |
| 0.7 | 95 | 2.5 | 2.5 | 0 |

run time: 0.7 min

| Method-J | | | | |
|---|---|---|---|---|
| Time (min) | A(%) | B(%) | C(%) | D(%) |
| 0 | 5 | 5 | 0 | 90 |
| 0.3 | 95 | 5 | 0 | 0 |
| 0.7 | 95 | 5 | 0 | 0 |

run time: 0.7 min

| Method-K | | | | |
|---|---|---|---|---|
| Time (min) | A(%) | B(%) | C(%) | D(%) |
| 0 | 5 | 0 | 5 | 90 |
| 0.3 | 95 | 0 | 5 | 0 |
| 0.7 | 95 | 0 | 5 | 0 |

run time: 0.7 min

The optical purity for intermediates and compounds of Examples are measured out by Waters Alliance 2695 with 2996 PDA detector. Analytical conditions (Method-L) are as follows.

Conditions for Method-L:

| | |
|---|---|
| Column | Daicel Chiralpak AD-H, 4.6 × 250 mm |
| Column temperature | 40° C. |
| Flow rate | 1.0 mL/min |
| UV Detector | 275 nm |
| Run time | 25 min |
| Solvents | n-Hexane:isopropanol:diethylamine = 55:45:0.1 |

The purification of compounds (=examples) using HPLC (preparative LC-MS) or SFC (preparative SFC-MS) is performed by the following apparatus and conditions.

The pre-purification for the HPLC (preparative LC-MS) is carried out using a strong cation exchange cartridge (ISOLUTE (registered trademark) SCX-2, 1 g/6 mL, Biotage), or strong anion exchange cartridge (ISOLUTE (registered trademark) PE-AX, 1 g/6 mL, Biotage).

HPLC:

Apparatus: Waters MS-trigger AutoPurification (registered trademark) system

Column: Waters XBridge C8, 19 mm×50 mm, 5 micrometer particle or Waters XBridge C18, 19 mm×50 mm, 5 micrometer particle Mobile phase 1: (A) 0.05% (v/v) ammonia aqueous solution, (B) MeOH or MeCN Mobile phase 2: (A) 0.05% (v/v) formic acid aqueous solution, (B) MeOH or MeCN Mobile phase 3: (A) 10 mM ammonium formate aqueous solution, (B) MeCN/water=90/10 (v/v)

Flow rate: 20 mL/min

Gradient: A/B (95/5) to A/B (5/95) in 5 or 7 or 10 min

SFC:

Apparatus: Waters Prep15 SFC system with ACQUITY QDa Detector

Column: Waters Torus 2-PIC, 10 mm×150 mm, 5 micrometer particle; Waters Torus DEA, 10 mm×150 mm, 5 micrometer particle; Waters Torus DIOL, 10 mm×150 mm, 5 micrometer particle; Waters Torus 1-AA, 10 mm×150 mm, 5 micrometer particle Mobile phase: (A) Carbon dioxide ($CO_2$), (B) MeOH or 10 mM ammonia in MeOH Flow rate: 15 mL/min Gradient: A/B (95/5) to A/B (60/40) in 7 or 10 min Temperature: 40° C.

Pressure: 120 bar (1740 psi)

Mass spectral data (ESI) are obtained by Waters Alliance HPLC system with ZQ mass spectrometer and UV detector.

The chemical purity of the each Example is assured as greater than 80% by at least one quality check (QC) method. Details of the conditions are described in the section of the "Condition for determining HPLC-QC retention time for Example compounds" in the Examples, and the results are shown in the Tables 1 to 93-4.

Conditions for Determining HPLC Retention Time:

QC Method-A:

Apparatus: Waters Acquity Ultra Performance LC with PDA Detector and ZQ mass spectrometer Column: YMC Triart C18, 2.1×100 mm, 1.9 micrometer particle Column Temperature: 60° C.

PDA detection: 200-400 nm scan

MS detection: ESI positive/negative mode

Mobile Phase:

QC-A1 (neutral method)

A: 10 mM ammonium acetate aqueous solution

B: acetonitrile

QC-A2 (basic method)

A: 0.05% (v/v) ammonia aqueous solution

B: acetonitrile

| Time(min) | A (%) | B (%) |
|---|---|---|
| 0 | 90 | 10 |
| 0.05 | 90 | 10 |
| 1.9 | 5 | 95 |
| 2.5 | 5 | 95 |
| 2.51 | 90 | 10 |
| | run time | 3 min |
| | Flow rate | 0.75 mL/min |

QC Method-B:

Apparatus: Waters ACQUITY UPLC H-Class PLUS with PDA Detector and SQ Detector 2 mass spectrometer Column: YMC Triart C18, 2.1×100 mm, 1.9 micrometer particle Column Temperature: 60° C.

PDA detection: 200-400 nm scan

MS detection: ESI positive/negative mode

Mobile phase:

QC-B1 (neutral method)

A: 10 mM ammonium acetate aqueous solution

B: acetonitrile

QC-B2 (basic method)

A: 0.05% (v/v) ammonia aqueous solution

B: acetonitrile

| Time(min) | A (%) | B (%) |
|---|---|---|
| 0 | 90 | 10 |
| 1.6 | 5 | 95 |
| 2.2 | 5 | 95 |
| 2.21 | 90 | 10 |
| | run time | 3 min |
| | Flow rate | 0.75 mL/min |

QC Method-C:

Apparatus: Waters 2795 Alliance HPLC with 2996 PDA Detector and ZQ 2000 mass spectrometer Column: Waters Xbridge C18, 2.1×50 mm, 3.5 micrometer particle Column Temperature: 45° C.

PDA detection: 210-400 nm scan

MS detection: ESI positive/negative mode

Mobile Phase:

QC-C (neutral Method)

A: $H_2O$ (Milli-Q water)

B: acetonitrile

C: 1% aqueous $HCO_2H$

D: 1% aqueous $NH_3$

| Time(min) | A (%) | B (%) | C (%) | D (%) |
|---|---|---|---|---|
| 0 | 82.5 | 10 | 5 | 2.5 |
| 0.2 | 82.5 | 10 | 5 | 2.5 |
| 4.8 | 0 | 92.5 | 5 | 2.5 |
| 5.3 | 0 | 92.5 | 5 | 2.5 |
| 5.31 | 82.5 | 10 | 5 | 2.5 |
| 6 | 82.5 | 10 | 5 | 2.5 |
| | run time | 6 min | | |
| | Flow rate | 0.8 mL/min | | |

QC Method-D:

Apparatus: Waters Acquity Ultra Performance LC on TUV Detector and ZQ mass spectrometer Column: Waters ACQUITY C18, 2.1×100 mm, 1.7 micrometer particle Column Temperature: 60° C.

PDA detection: 210 nm scan

MS detection: ESI positive/negative mode

Solvents:

A1: 10 mM ammonium acetate aqueous solution

B1: Acetonitrile

| Time (min) | A1 (%) | B1 (%) |
|---|---|---|
| 0 | 95 | 5 |
| 0.1 | 95 | 5 |

-continued

| Time (min) | A1 (%) | B1 (%) |
|---|---|---|
| 1.8 | 5 | 95 |
| 2.3 | 95 | 5 |

run flow: 3.0 min/flow 0.7 mL/min

NMR data is determined at 270 MHz (JEOL JNM-LA 270 spectrometer), 300 MHz (JEOL JNM-LA300) and 400 MHz (JEOL JNM-ECZ400S) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; microL (microliter(s)), microg (microgram(s)), microm (micrometer(s)), M (mol(s) per liter), L (liter(s)), mL (milliliter(s)), g (gram(s)), mg (milligram(s)), mol (moles), mmol (millimoles).

The description of ESI positive/negative mode is noted as M+1/M−1.

The mp data is measured at SEIKO TG/DTA6200R system. The optical rotation is measured at JASCO P-1020 polarimeter.

All of the pyrimidin-4(3H)-one derivatives of the formula (I) can be prepared by the procedures described in the general methods presented below or by the specific methods described in the Example synthesis part and Intermediate synthesis part, or by routine modifications thereof. The present invention also encompasses any one or more of these processes for preparing the pyrimidin-4(3H)-one derivatives of formula (I), in addition to any novel intermediates used therein.

In the following general methods, descriptors ($R^1$, $R^2$, $R^3$, q, r, s, $Ar^1$, $Ar^2$, and X) are as previously defined for the compound of the formula (I) unless otherwise stated. All starting materials in the following general syntheses may be commercially available or obtained by the conventional methods known to those skilled in the art, otherwise noted in the Intermediate synthesis part.

General Synthesis

Scheme-1: Sythesis of compound of formula (I) via compound formula (II)

{Chem. 9}

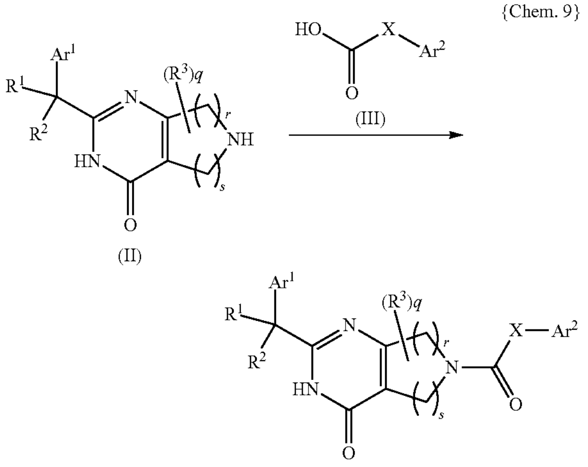

(II)

(I)

In this Scheme-1, an amide compound of formula (I) can be prepared by the coupling reaction of an amine compound of formula (II) with the acid compound or acid chloride of formula (III) in the presence or absence of a coupling reagent in an inert solvent. This reaction can be also carried out via activated carboxylic derivatives. Suitable coupling reagents are those typically used in peptide synthesis including, for example, not limited to, phosgene, triphosgene, ethyl chloroformate, isobutyl chloroformate, diphenyl phosphoryl azide (DPPA), diethyl phosphoryl cyanide (DEPC), carbodiimides [e.g., N,N'-dicyclohexylcarbodiimide (DCC), 1-ethyl-3-(3-dimethylaminopropyl)carbodiimide hydrochloride (EDCl)], imidazolium derived reagents [e.g., 1,1'-carbonyldiimidazole (CDI), 2-chloro-1,3-dimethylimidazolidinium hexafluorophosphate (CIP)], phosphonium salts [e.g., Benzotriazol-1-yl-oxy-tris(dimethylamino)phosphonium hexafluorophosphate (BOP), Benzotriazol-1-yl-oxy-tripyrrolidinophosphonium hexafluorophosphate (PyBOP (registered trademark)), Bromo-tripyrrolidinophosphonium hexafluorophosphate (PyBrop (registered trademark)), uronium and guanidinium salts [e.g., O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(6-chlorobenzotriazol-1-yl)-N,N,N',N'-tetramethyluronium hexafluorophosphate (HCTU)], miscellaneous coupling reagents [e.g., 2-chloro-4,6-dimethoxy-1,3,5-triazine (CDMT), (2-bromo-1-ethylpyridinium tetrafluoroborate) (BEP), 2-bromo-1-methylpyridinium iodide (BMPI)]. The reaction can be carried out in the presence of a base such as, 1-hydroxybenzotriazole (HOBt), 1-hydroxy-7-azabenzotriazole (HOAt), N,N-diisopropylethylamine, N-methylmorpholine or triethylamine. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone; nitromethane; DMF; NMP; sulfolane; DMSO; 2-butanone; acetonitrile; halogenated hydrocarbons, such as DCM, dichloroethane, chloroform; and ethers, such as THF and 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., and, more preferably from about 0° C. to 60° C. The time required for the reaction can also vary widely, depending on many factors, notably the reaction temperature and the nature of the reagents and solvent employed. However, provided that the reaction is effected under the preferred conditions outlined above, a period of from 5 minutes to 1 week, more preferably from 30 minutes to 24 hrs, will usually suffice. Alternatively, a compound of formula (II) can first be converted to an acylhalide derivative by reaction with halogenating agents such as oxalylchloride, phosphorus oxychloride and thionyl chloride. The resulting acylhalide derivative can then be reacted with an amine compound of formula (II) as described above to provide a compound of formula (I). A compound of racemic formula (I) is separated to their optical active form using chiral column including, for example, not limited to, Daicel Chiralpak AD-H, AS-H, IA, IB, IC, Daicel Chiralcel OJ-H, OD-H, OK, OG, OA, OC and OB-H as the eluent including, for example, not limited to, n-Hexane, EtOAc, EtOH, isopropanol, acetonitrile, 1,4-dioxane, THF, MeOH, methyl tert-butyl ether and DCM, as the additive including, for example, not limited to, ethanolamine, butylamine, diethylamine, formic acid, acetic acid and trifluoroacetic acid at a temperature of from 0° C. to 40° C.

Scheme-2: Synthesis of compound of formula (II) via compound of formula (IV)

{Chem. 10}

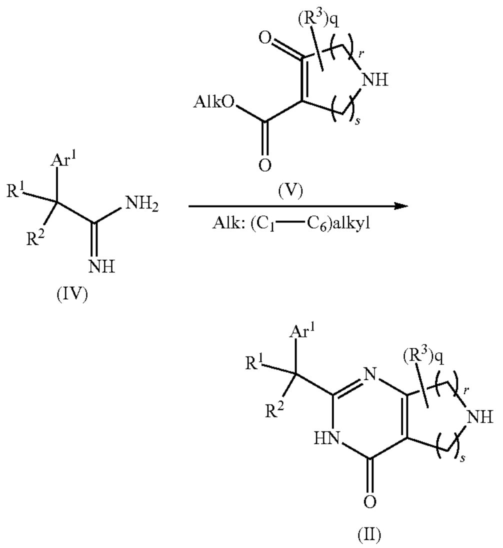

(II)

In this Scheme-2, the corresponding amine derivatives of formula (II) can be prepared by the cyclization reaction of a compound of formula (V) with an amidine compound of formula (IV) in the presence of base in an inert solvent.

In this Scheme-2, compounds of the formula (II) can be prepared by reaction of a compound of formula (V) and an amidine compound of formula (IV), for example, in the presence of a suitable base such as sodium methoxide, sodium ethoxide, potassium tert-butoxide or potassium carbonate in an organic solvent as methanol, ethanol or tert-buthanol. Typically, 1.0 equivalent of amidine (IV) is reacted with 1.0 to 1.1 equivalent of compound (V) and 1.0 to 4.5 equivalent of sodium methoxide in methanol at the range from ambient temperature to reflux condition.

Scheme-3: Synthesis of compound of formula (II) via compound formula (IV)

{Chem. 11}

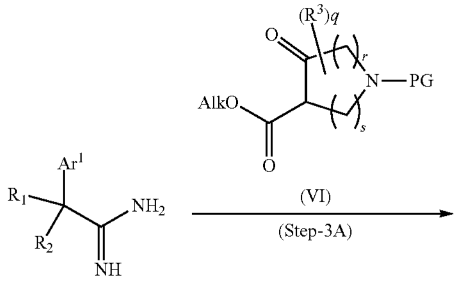

(IV)

-continued

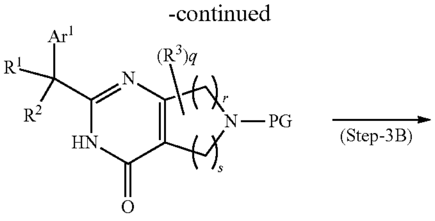

(VII)

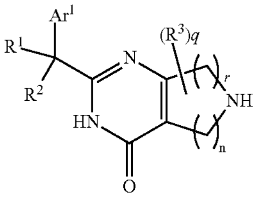

(II)

PG is a suitable protecting group, such as benzyl, tert-butyl carbamoyl (Boc), benzyl carbamoyl (Cbz) or ethyl carbamoyl. Alk is $(C_{1-6})$alkyl group.

In this Scheme-3, a corresponding amine derivative of formula (II) can be prepared by the cyclization reaction of an N-protected compound of formula (VI) with an amidine compound of formula (IV) in the presence of base in an inert solvent, followed by the deprotection of an N-protected compound of formula (VII).

In Step-3A, compounds of the formula (VII) can be prepared from an amidine compound of the formula (IV) and an N-protected compound of formula (VI) by the method described in Scheme-2.

In Step-3B, compounds of formula (II) can be prepared by deprotection of compounds of formula (VII) using standard methodology as described in "Protecting Groups in Organic Synthesis" by T. W. Greene and P. Wutz. More specifically, when PG is Boc, compounds of formula (VII) are typically treated with a suitable acid such as 4M to 6M hydrochloric acid or trifluoroacetic acid in a suitable solvent such as dichloromethane, methanol, ethyl acetate or 1,4-dioxane at ambient temperatures for 1 to 18 hrs. When PG is benzyl-carbamoyl, compounds of formula (VII) are typically reacted in a hydrogen atmosphere with a suitable palladium catalyst in a solvent such as ethanol. The compounds of formula (II) can also be prepared from compounds of formula (VII) with a suitable hydrogen transfer agent such as 1-methyl-1,4-cyclohexadiene in the presence of a suitable metal catalyst such as 10% palladium on charcoal in a solvent such as ethanol. Alternatively, compounds of formula (VII) can be treated with 48% aqueous hydrogen bromide at ambient temperature for 3 hrs.

Scheme-4: Synthesis compound of formula (IV) via compound of formula (VIII)

{Chem. 12}

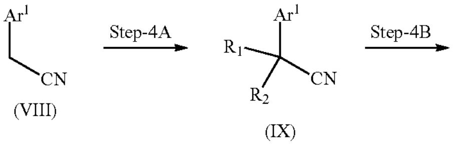

(VIII) (IX)

-continued

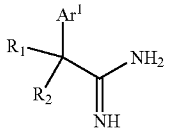

(IV)

In this Scheme-4, a nitrile derivative of formula (VIII) can be converted to a compound of formula (IX) by alkylation using alkyl halide in present of an inorganic base, such as sodium hydroxide, in an inert solvent. Further, a compound of formula (IX) can be converted to amidine derivative of formula (IV) in a single step by reaction with methylchloroaluminium amide prepared from trimethylaluminium and ammonium chloride in a suitable solvent.

In Step-4A, compounds of the formula (IX) can be prepared from a compound of the formula (VIII) by alkylation reaction under, for example, known alkylation conditions in the presence of a base in an inert solvent. A preferred base is selected from, for example, but not limited to: an alkaline earth metal hydroxide, alkoxide, carbonate, halide or hydride, such as sodium hydroxide, potassium hydroxide, sodium methoxide, potassium tert-butoxide, sodium hydride, lithium diisopropylamide or sodium bis (trimethylsilyl)amide. Examples of suitable inert aqueous, non-aqueous organic solvents include; water; ethers, such as diethyl ether, THF or 1,4-dioxane; acetone; DMF; DMSO; halogenated hydrocarbons, such as DCM, 1,2-dichloroethane or chloroform; hydrocarbons, such as hexane, heptane or toluene; or mixtures thereof. In the case of the water-organic co-solvent mixture, a preferred phase transfer catalyst is selected from tetraalkylammonium halide, such as tetrabutylammonium bromide and benzyltrialkylammonium halide, such as benzyltrimethylammonium chloride. The reaction can be carried out at a temperature of from −78° C. to 150° C. The reaction times are, in general, from 5 minutes to 96 hrs, more preferable from 30 minutes to 24 hrs.

In Step-4B, compounds of the formula (IV) can be prepared from a compound of the formula (IX) by the methodology described in the literature (for example, Eur. J. Med. Chem. 1981, 16, 175 or Tetrahedron Letters 1995, 36, 8761). Typically, a compound of formula (IX) is stirred in a saturated ethanolic hydrogen chloride solution and the resulting mixture is treated with a saturated ethanolic ammonia solution. Alternatively compounds of the formula (IV) can be prepared from compounds of the formula (IX) in the presence of the reagent (methylchloroaluminium) prepared from trimethylaluminium and ammonium chloride in a suitable organic solvent such as toluene at 80° C. for 18 hrs.

Scheme-5: Synthesis of compound of formula (I-b) via compound of formula (X)

{Chem. 13}

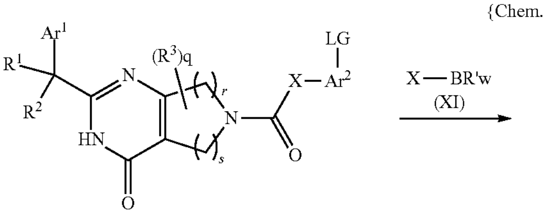

(X)

-continued

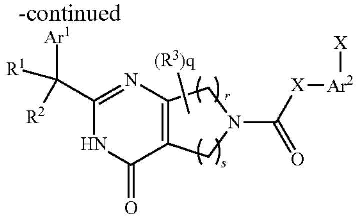

(I-b)

In this Scheme-5, LG presents a suitable leaving group such as O-trifluoromethanesulfonate, O-tosylate, O-mesylate, iodide, bromide, or chloride and X of metal reagent (XI) is selected from, for example, but not limited to: ($C_1$-$C_{10}$)alkyl, ($C_1$-$C_{10}$)alkenyl, ($C_3$-$C_{10}$)cycloalkyl, ($C_3$-$C_{10}$)cycloalkenyl, aryl, and heteroaryl derivatives with non-substituted or substituted groups. Compounds of formula (I-b) can be prepared by the cross coupling reaction of compounds of formula (X) with a boronic (or boronic ester) compound of formula (XI) in organic solvent or water-organic co-solvent mixture under cross coupling conditions in the presence of a suitable transition metal catalyst and in the presence or absence of a base. In a representation of $R'_wB$, R' means OH, O-low alkyl or fluorine, and w is 2 or 3, B is boron atom. As the concrete representation of substituent, $B(OH)_2$, B(O-lower alkyl)$_2$, B(lower alkyl)$_2$, potassium trifluoroborate ($BF_3^-$)($BF_3K$) are described, but when B(O-lower alkyl)$_2$ may form the cyclic ring between the lower alkyl groups.

Examples of suitable transition metal catalysts include: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(I) trifluoromethanesulfonate, copper (II) acetate, copper(II) bromide, copper(II) chloride, copper(II) iodide, copper(II) oxide, copper(II) trifluoromethanesulfonate, palladium(II) acetate, palladium(II) chloride, bis(acetonitrile)dichloropalladium(II), bis(dibenzylideneacetone)palladium(0), tris(dibenzylideneacetone) dipalladium(0) and [1,1'-bis(diphenylphosphino)ferrocene] palladium(II) dichloride. Preferred catalysts are tetrakis (triphenylphosphine)palladium(0), bis(triphenylphosphine) palladium(II) chloride, palladium(II) acetate, palladium(II) chloride, bis(acetonitrile)dichloropalladium(II), bis(dibenzylideneacetone)palladium(0), tris(dibenzylideneacetone) dipalladium(0), [1,1-bis(diphenylphosphino)ferrocene]palladium(II) dichloride, and bis(di-tert-butyl(4-dimethylaminophenyl)phosphine)dichloropalladium(II).

Examples of suitable organic solvent for the anhydrous solvent and the water-organic co-solvent mixture include: THF; 1,4-dioxane; DME; DMF; acetonitrile; alcohols, such as methanol or ethanol; halogenated hydrocarbons, such as DCM, 1,2-dichloroethane, chloroform or carbon tetrachloride; and diethylether. This reaction can be carried out in the presence or absence of a base such as potassium hydroxide, sodium hydroxide, lithium hydroxide, sodium bicarbonate, sodium carbonate, potassium carbonate and potassium phosphate. This reaction can be carried out in the presence of a suitable additive agent.

Examples of such additive agents include: triphenylphosphine, tri-tert-butylphosphine, 1,1'-bis(diphenylphosphino) ferrocene, tri-2-furylphosphine, tri-o-tolylphosphine, 2-(dichlorohexylphosphino)biphenyl, triphenylarsine, tetrabutylammonium chloride, tetrabutylammonium fluoride, lithium acetate, lithium chloride, triethylamine, potassium or sodium methoxide, sodium hydroxide, cesium carbonate, tripotassium phosphate, sodium carbonate, sodium bicarbonate, and/or sodium iodide. The reaction can be carried out at a temperature of from 0° C. to 200° C., more preferably from 20° C. to 150° C. Reaction times are, in general, from 5 minutes to 96 h, more preferably from 30 minutes to 24 h. In an alternative case, the reaction can be carried out in a microwave system in the presence of a base in an inert solvent. The reaction can be carried out at a temperature in the range of from 100° C. to 200° C., preferably in the range of from 120° C. to 150° C. Reaction times are, in general, from 10 minutes to 3 h, preferably from 15 minutes to 1 h.

The preferred conditions in the preparation of examples are as follows:

1) Starting Material (1.0 eq.), boronic acid derivative (1.0 to 3.0 eq.), palladium (II) acetate (0.2 eq.), triphenylphosphine (0.4 eq.), 1,4-dioxane-saturated sodium hydrogen carbonate aqueous solution (1:1 v/v), 100-150° C., 1-6 hrs or Microwave (100-150° C., 10 min. to 1 hr)
2) Starting Material (1.0 eq.), boronic acid derivative (1.0 to 3.0 eq.), Pd(amphos)$Cl_2$ (0.1 to 0.5 eq.), potassium carbonate (2.0 to 4.0 eq.), 1,4-dioxane-water (1:1 to 3:1 v/v), 80-150° C., 1-6 hrs or Microwave (100-150° C., 10 min. to 1 hr)
3) Starting Material (1.0 eq.), boronic acid derivative (1.0 to 3.0 eq.), $Pd(PPh3)_4$ (0.1 to 0.5 eq.), potassium carbonate (2.0 to 4.0 eq.), DMF, 80-150° C., 1-6 hrs or Microwave (100-150° C., 10 min. to 1 hr)

Other than a Suzuki-Miyaura cross coupling shown above, Still cross coupling reaction using trialkyltin instead of $R'_wB$ substituent, and Negishi coupling reaction using zinc-halogen, wherein as a halogen, chlorine, bromine, and iodine are cited, instead of $R'_wB$ substituent can be used.

The ethynyl compounds of formula (I-b) are synthesized by Sonogashira reaction from the compounds of formula (XI) and substituted ethynyl derivatives in place of compounds of formula (XI) under the above cross coupling conditions.

The cyano derivatives of formula (I-b) are synthesized by using zinc cyanide in place of compounds of formula (XI) under the above cross coupling conditions.

Scheme-6: Synthesis of compound of formula (I-c) via compound of formula (XII)

{Chem. 14}

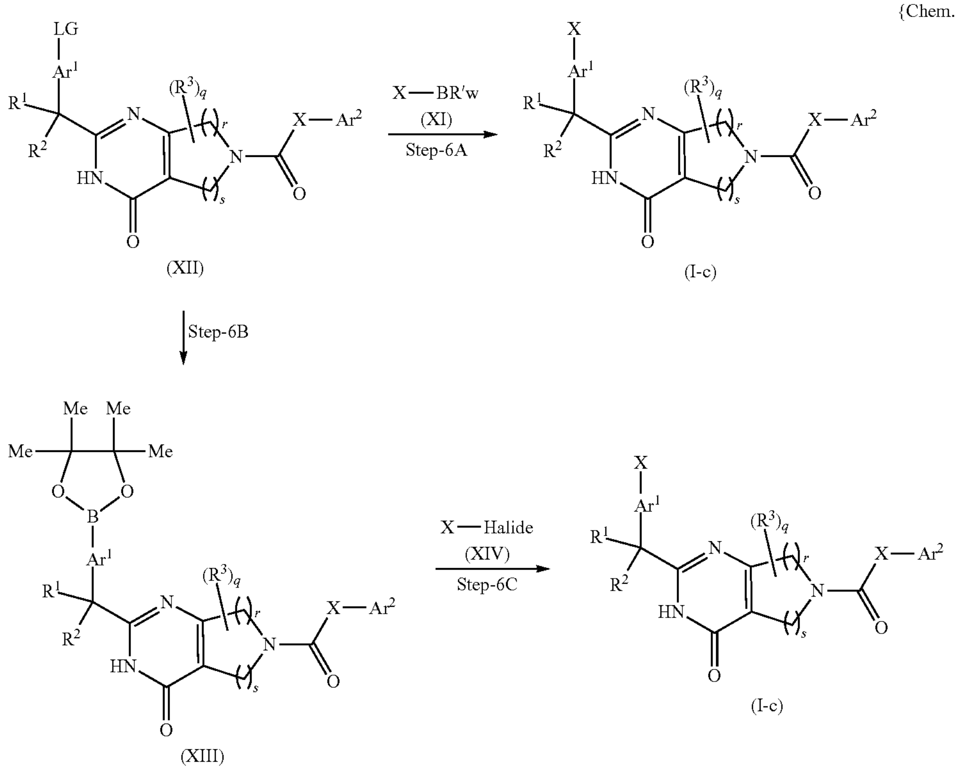

(XII) (I-c) (XIII) (I-c)

In scheme-6, a compound of the formula (I-c) can be prepared by the cross coupling reaction of a compound of formula (XII) with a boronic (or boronic ester) compound of formula (XI) according to the general synthesis in scheme-5. Furthermore, a compound of the formula (I-b) can also be prepared by the same cross coupling reaction from a halide compound of formula (XIV) with a boronic (or boronic ester) compound of formula (XIII) converted from the halide compound of formula (XII). Typically, the compound of the formula (XIII) can be prepared by the cross coupling reaction from a compound of the formula (XII) with bis(pinacolato)diboron in the presence of potassium acetate and [1,1'-Bis(diphenylphosphino)ferrocene]dichloropalladium (II), Dichloromethane Adduct in a suitable solvent such as 1,4-dioxane at 80° C. for 1 to 6 hrs.

In step-6A, the ethynyl compounds of formula (I-b) are synthesized by Sonogashira reaction from the compounds of formula (XI) and substituted ethynyl derivatives in place of compounds of formula (XI) under the above cross coupling conditions.

The cyano derivatives of formula (I-b) are synthesized by using zinc cyanide in place of compounds of formula (XI) under the above cross coupling conditions.

Scheme-7: Synthesis compound of formula (XVI) via compound of formula (XV)

{Chem. 15}

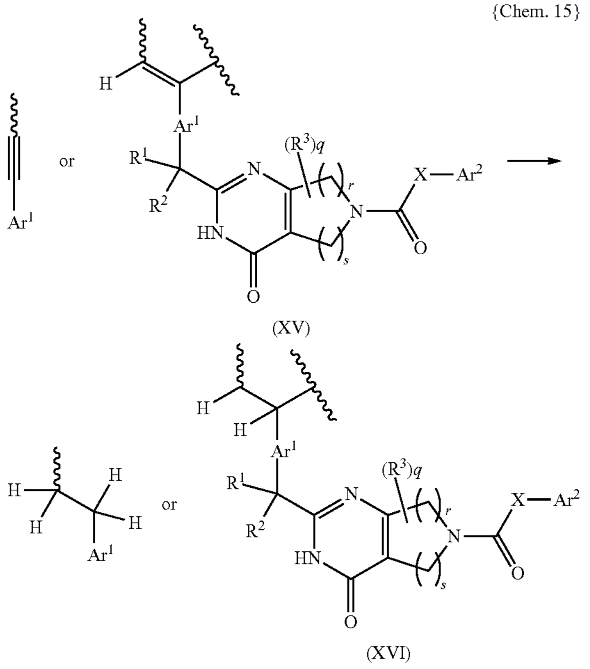

or (XV) or (XVI)

When above X moiety in formula (I-b) includes a part of unsaturated or triple bond as shown in formula (XV), compound of formula (XV) can be converted to saturated compound of formula (XVI) by hydrogenation reaction in the presence of hydrogen gas and a suitable metal catalyst such as 5 to 10% palladium on carbon, palladium hydroxide on carbon and platinum (IV) oxide in a solvent such as methanol, ethanol and THF.

Scheme-8: Synthesis of compound of formula (I-c) via compound of formula (XVII)

{Chem. 16}

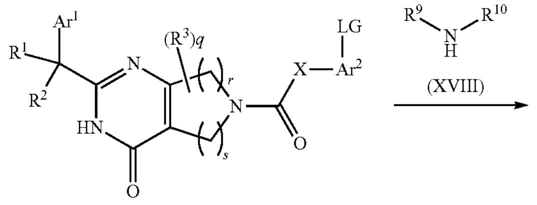

(XVII)

-continued

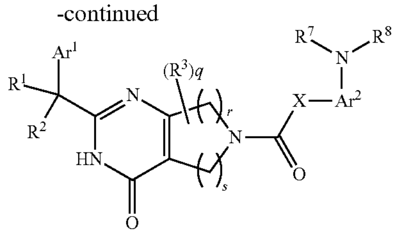

(I-c)

In this Scheme-8, compounds of the formula (I-c) can be prepared by substitution reaction of a compound of formula (XVII) with amine ($HNR^9R^{10}$)(XVIII). Typically, compounds of formula (I-c) may be prepared by addition of the required primary or secondary amine ($HNR^9R^{10}$)(XVIII) in a suitable solvent as tetrahydrofuran, acetonitrile, N,N-dimethylacetamide or 1-methyl-2-pyrrolidinone at either ambient or elevated temperatures. A microwave oven may be used to increase reaction rates.

Scheme-9: Synthesis of compound of formula (XXI) via compound of formula (XIX)

{Chem. 17}

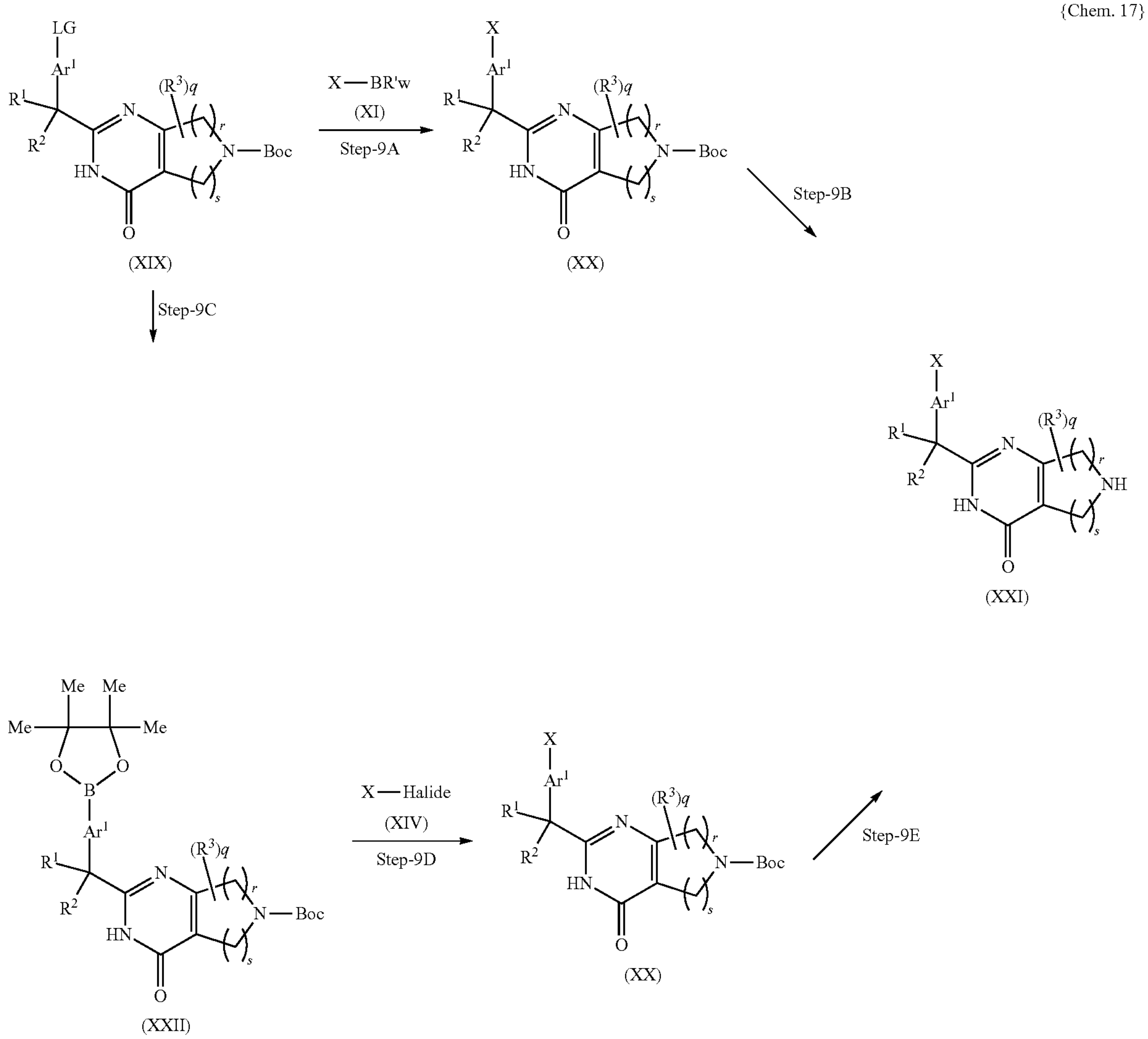

(XIX)

(XX)

(XXI)

(XXII)

(XX)

In this Scheme-9, an N-Boc derivative of the formula (XX) can be prepared according to same general synthesis described in scheme-5. A compound of the formula (XX) can be prepared by the cross coupling reaction of a compound of formula (XIX) with a boronic (or boronic ester) compound of formula (XI). Furthermore, a compound of the general formula (XX) can also be prepared by the same cross coupling reaction from a halide compound of formula (XIV) with a boronic ester compound of formula (XXII) converted from the compound of formula (XIX). Finally, an N-Boc compound of the general formula (XX) can be converted to an N—H compound of the general formula (XXI) according to N-Boc deprotective condition in scheme-3

Scheme-10: Synthesis of compound of formula (XII) via compound of formula (X)

{Chem. 18}

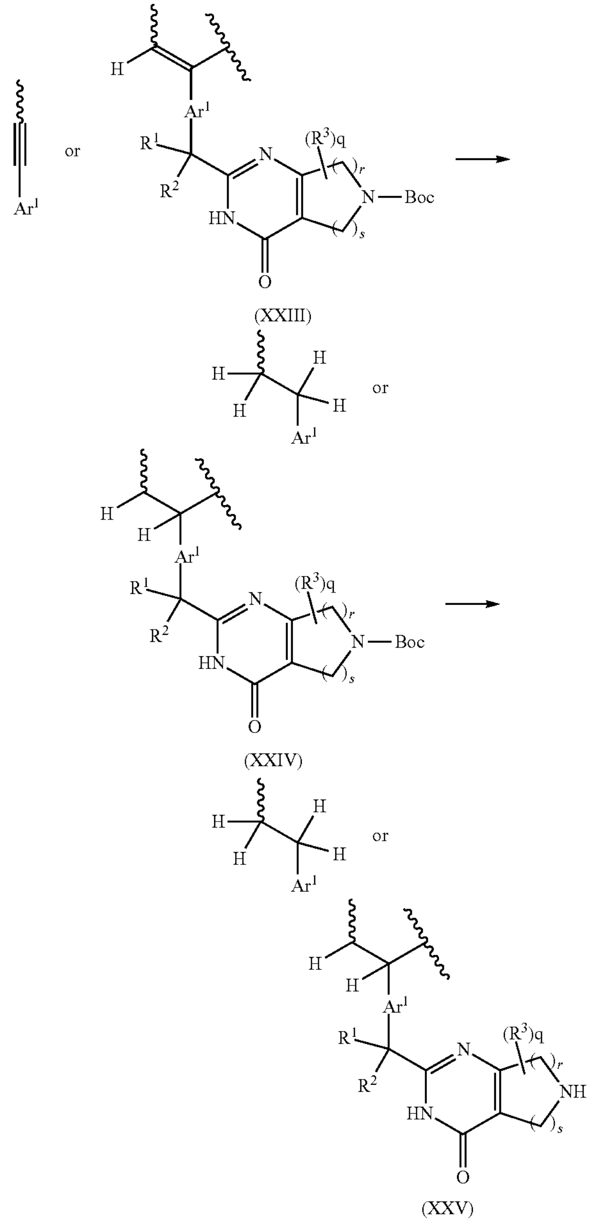

(XXIII) or (XXIV) or (XXV)

When above X moiety in formula (XX) includes a part of unsaturated or triple bond as shown in formula (XXIII), compound of formula (XXIII) can be converted to saturated compound of formula (XXIV) by hydrogenation reaction in the presence of hydrogen gas and a suitable metal catalyst such as 5 to 10% palladium on carbon, palladium hydroxide on carbon and platinum (IV) oxide in a solvent such as methanol, ethanol and THF. Finally, an N-Boc compound of the formula (XXIV) can be converted to an N—H compound of the formula (XXV) according to N-Boc deprotective condition in scheme-3.

Scheme-11: Synthesis of compound of formula (XXVII) via compound of formula (XXVI)

{Chem. 19}

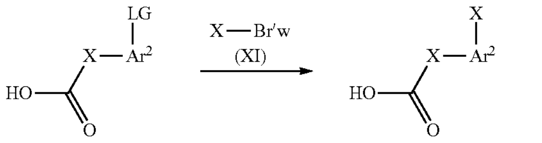

(XXVI) (XXVII)

In this Scheme-11, an acid compound of the general formula (XXVII) can be prepared according to same general synthesis described in scheme-5.

Scheme-12: Synthesis of a compound of formula (XXX) via compound of formula (XXVIII)

{Chem. 20}

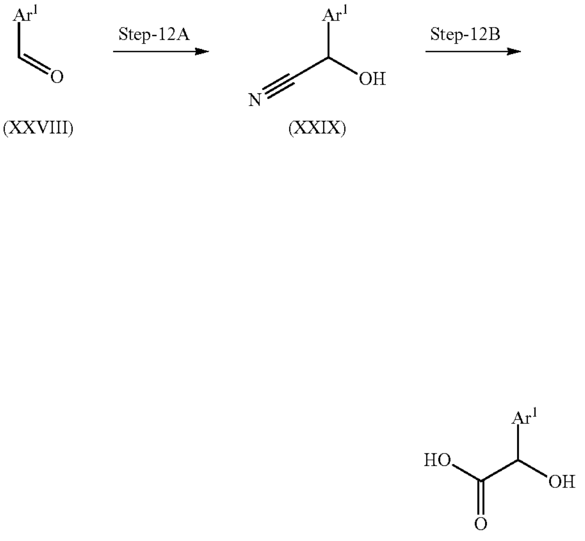

(XXVIII) (XXIX) (XXX)

In this Scheme-12, a compound of the general formula (XXX) can be prepared by acid hydrolysis of a cyanohydrin compound of the general formula (XXIX) in step-12A. A cyanohydrin compound of the general formula (XXIX) can be prepared from a compound of the general formula (XXVIII) and trimethylsilyl cyanide in the presence of a suitable lewis acid (for example, titanium tetraisopropoxide) in step-12-B.

Scheme-13: Synthesis of a compound of formula (XXXII) via compound of formula (XXXI)

{Chem. 21}

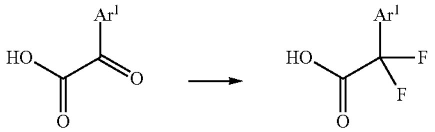

(XXXI) (XXXII)

In this Scheme-13, a compound of the general formula (XXXII) can be prepared by the fluorination reaction of a compound of the general formula (XXXI) in the presence of a suitable fluorination reagent (for example, N,N-diethylaminosulfur trifluoride).

Compound Preparation

The synthesis of the compounds of the general formulae (I) and (I-a) and pharmaceutically acceptable derivatives and salts thereof may be accomplished as outline above in Schemes 1 to 13. In the following description, the groups are as defined above for compounds of formulae (I) and (I-a) unless otherwise indicated. Starting materials are commercially available or are made from commercially available starting materials using methods known to those skilled in the art. The naming program used is ChemDraw Ver. 18.2.

Intermediate-1 (INT-1)

2-(1-phenylcyclopropyl)-5,6,7,8-tetrahydropyrido[4,3-d]pyrimidin-4(3H)-one (INT-1)

{Chem. 22}

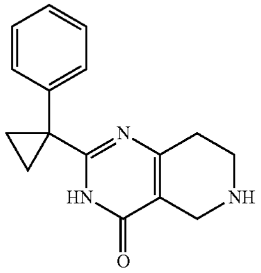

Step-1A: Synthesis of 1-phenylcyclopropanecarboximidamide monohydrochloride (INT-1-A)

{Chem. 23}

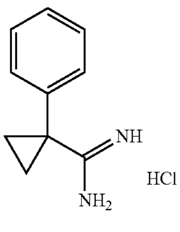

To a stirred suspension of ammonium chloride (2.02 g, 37.7 mmol) in toluene (15 mL) is added a 2.0 M trimethylaluminium solution in toluene (17.5 mL, 34.9 mmol) dropwise under nitrogen with ice-cooling. The mixture is allowed to warm to rt and stirring continued until the evolution of methane ceased (2 hrs). Then, to this is added a solution of 1-phenylcyclopropanecarbonitrile (3.0 g, 21.0 mmol) in toluene (10 mL) and the reaction mixture is heated at 80° C. overnight. After cooling to rt, the mixture is poured into silica gel (20 g) in DCM (50 mL) and stirred at rt for 15 min. The mixture is filtered through a pad of celite and the filter cake is washed with DCM then further washed with MeOH (50 mL×2). The filtrate is evaporated in vacuo to give the crude product (white solid), which is charged into amino silica gel (about 30 g). The crude product is purified by column chromatography on amine silica gel (250 g) eluting with DCM:MeOH (20:1 to 10:1 v/v) to give 1-phenylcyclopropanecarboximidamide (2.37 g, pale yellow oil), which is dissolved in methanol (30 mL) and treated with 10% HCl-MeOH (40 mL). The mixture is evaporated in vacuo to give the titled compound (2.91 g) as a white solid.

$^1$H-NMR (300 MHz, DMSO-$d_6$): delta 9.07 (4H, br.s), 7.50-7.29 (5H, m), 1.53-1.45 (2H, m), 1.30-1.22 (2H, m).

LC-MS (Method-A) m/z: M+1 obs 161.16, tR=1.09 min.

Step-1B: Synthesis of 2-(1-phenylcyclopropyl)-5,6,7,8-tetrahydropyrido[4,3-d]pyrimidin-4(3H)-one (INT-1)

{Chem. 24}

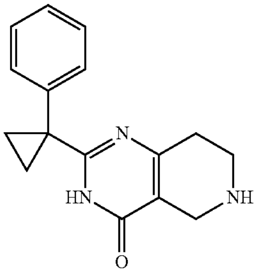

To a stirred solution of sodium methoxide (2.63 g, 48.6 mmol) in dry MeOH (15 mL) (prepared from powdered sodium methoxide) is added dropwise a solution of methyl 4-oxopiperidine-3-carboxylate monohydrochloride (2.47 g, 11.9 mmol) in methanol (20 mL) with ice-cooling. After 15 min, to this is added a solution of INT-1-A (2.13 g, 10.8 mmol) in methanol (20 mL) with ice-cooling. Then, the mixture is refluxed for 15 hrs. After cooling to rt, the solvent is evaporated in vacuo and the residue is quenched with water (8 mL). The mixture is azeotroped with toluene (50 mL×2) to give crude product (pale yellow solid), which is charged with amine silica gel (ca 40 g). The mixture is purified by column chromatography on amine silica gel (250 g) (chromatorex) eluting with DCM-MeOH (20:1 to 10:1 v/v) to give the titled compound (2.6 g, 90% yield) as a white solid.

$^1$H-NMR (300 MHz, DMSO-$d_6$): delta 7.34-7.19 (5H, m), 3.44 (2H, s), 2.92-2.83 (2H, m), 2.47-2.38 (2H, m), 1.46-

1.39 (2H, m), 1.22-1.16 (2H, m) (two signals of NH proton are not observed).

LC-MS (Method-A) m/z: M+1 obs 268.23, M−1 obs 266.26, tR=2.09 min.

The following carboximidamide derivatives (INT-2-1 to INT-2-35) (free or hydrochloride salt) are prepared according to the procedure (step-1A) of intermediate-1 from the known or synthesized acetonitrile (INT-3-1 to INT-3-8) derivatives in Tables 1-1 to 1-6.

TABLE 1-1

| Structure | Chemical Name | $^{1}$H-NMR & LC-MS (m/z) |
|---|---|---|
| 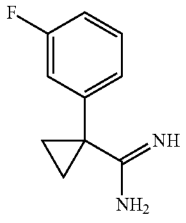 INT-2-1 | 1-(3-fluorophenyl)cyclopropane-carboximidamide | (300 MHz, $CDCl_3$): δ 7.36-7.24 (1H, m), 7.20-6.92 (3H, m), 4.69 (3H, br.s), 1.42-1.35 (2H, m), 1.18-1.11 (2H, m). LC-MS (Method-A) m/z: M + 1 obs 179.24, tR = 1.10 min. |
| 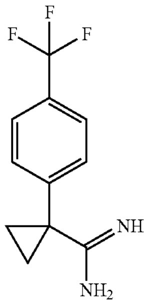 INT-2-2 | 1-(4-(trifluoromethyl)phenyl)-cyclopropanecarboximidamide | (300 MHz, $CDCl_3$): δ 7.52 (2H, d, J = 8.1 Hz), 7.40 (2H, d, J = 8.1 Hz), 3.89 (3H, br.s), 1.85-1.81 (2H, m), 1.49-1.45 (2H, m). |
| 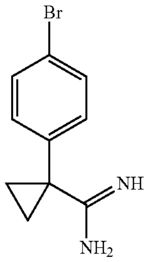 INT-2-3 | 1-(4-bromophenyl)cyclopropane-carboximidamide | (300 MHz, DMSO-$d_6$): δ 7.56-7.51 (2H, m), 7.34-7.26 (2H, m), 4.47 (3H, br.s), 1.39-1.35 (2H, m), 1.13-1.09 (2H, m). |
| 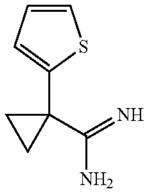 INT-2-4 | 1-(thiophen-2-yl)cyclopropane-carboximidamide | (270 MHz, $CDCl_3$): δ 7.23-7.18 (1H, m), 7.05-7.00 (1H, m), 6.97-6.91 (1H, m), 4.64 (3H, br.s), 1.50-1.43 (2H, m), 1.28-1.22 (2H, m). LC-MS (Method-A) m/z: M + 1 obs 169.14, tR = 0.75 min. |
| 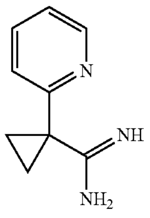 INT-2-5 | 1-(pyridin-2-yl)cyclopropane-carboximidamide | (300 MHz, $CDCl_3$): δ 8.55-8.48 (1H, m), 7.67-7.58 (1H, m), 7.48-7.42 (1H, m), 7.18-7.10 (1H, m), 5.17 (3H, br.s), 1.44-1.30 (4H, m). LC-MS (Method-A) m/z: M + 1 obs 162.22, tR = 0.60 min. |

TABLE 1-1-continued

| Structure | Chemical Name | $^1$H-NMR & LC-MS (m/z) |
|---|---|---|
| 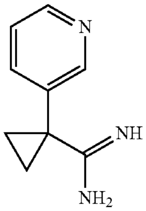 INT-2-6 | 1-(pyridin-3-yl)cyclopropane-carboximidamide | (300 MHz, $CDCl_3$): δ 8.65-8.60 (1H, m), 8.55-8.50 (1H, m), 7.72-7.65 (1H, m), 7.30-7.24 (1H, m), 4.92 (3H, br.s), 1.47-1.40 (2H, m), 1.20-1.14 (2H, m). LC-MS (Method-A) m/z: M + 1 obs 162.22, tR = 0.54 min. |

TABLE 1-2

| | | |
|---|---|---|
| 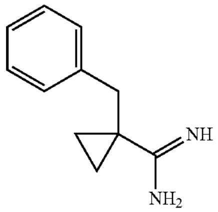 INT-2-7 | 1-benzylcyclopropane-carboximidamide | The structure is confirmed at the next step. |
| 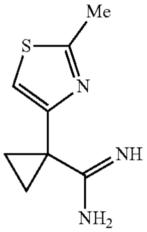 INT-2-8 | 1-(2-methylthiazol-4-yl) cyclopropane-1-carboximidamide | (300 MHz, $CDCl_3$): δ 6.95 (1H, s), 4.40 (3H, br.s), 2.69 (3H, s), 1.40-1.20 (4H, m). |
| 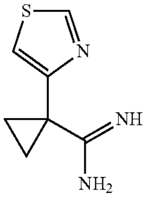 INT-2-9 | 1-(thiazol-4-yl)cyclopropane-1-carboximidamide | (300 MHz, DMSO-$d_6$): δ 9.00 (1H, d, J = 1.5 Hz), 7.43 (1H, d, J = 1.5 Hz), 5.98 (3H, br.s), 1.30-1.23 (2H, m), 1.15-1.09 (2H, m). LC-MS (Method-A) m/z: M + 1 obs 168.24, tR = 0.54 min. |
| 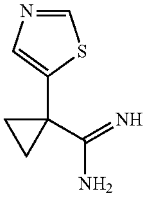 INT-2-10 | 1-(thiazol-5-yl)cyclopropane-1-carboximidamide | (300 MHz, $CDCl_3$): δ 8.73 (1H, s), 7.79 (1H, s), 1.57-1.50 (2H, m), 1.30-1.23 (2H, m), (three signals of NH proton are not observed). |

TABLE 1-2-continued

| | | |
|---|---|---|
| 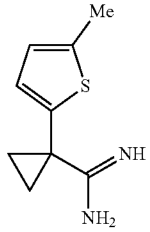 INT-2-11 | 1-(5-methylthiophen-2-yl)cyclopropane-1-carboximidamide | (300 MHz, $CDCl_3$): δ 6.82-6.77 (1H, m), 6.60-6.55 (1H, m), 4.21 (3H, br.s), 2.44 (3H, s), 1.45-1.38 (2H, m), 1.25-1.18 (2H, m). |
| 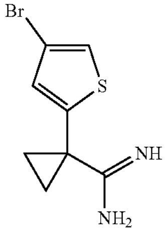 INT-2-12 | 1-(4-bromothiophen-2-yl) cyclopropane-1-carboximidamide | (300 MHz, $CDCl_3$): δ 7.11 (1H, d, J = 1.5 Hz), 6.94 (1H, d, J = 1.5 Hz), 3.73 (3H, br.s), 1.51-1.43 (2H, m), 1.27-1.20 (2H, m). |

TABLE 1-3

| | | |
|---|---|---|
| 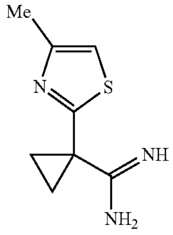 INT-2-13 | 1-(4-methylthiazol-2-yl) cyclopropane-1-carboximidamide | (300 MHz, $CDCl_3$): δ 6.75 (1H, s), 4.70 (3H, br.s), 2.42 (3H, s), 1.62-1.53 (2H, m), 1.45-1.36 (2H, m). |
| 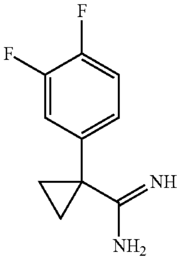 INT-2-14 | 1-(3,4-difluorophenyl)cyclopropane-1-carboximidamide | (300 MHz, $CDCl_3$): δ 7.25-7.05 (3H, m), 4.74 (3H, br.s), 1.45-1.35 (2H, m), 1.20-1.10 (2H, m). |
| 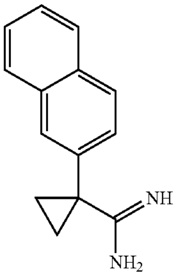 INT-2-15 | 1-(naphthalen-2-yl)cyclopropanecarboximidamide | LC-MS (Method-A1) m/z: M + 1 obs 211.32, tR = 1.68 min. |

TABLE 1-3-continued

| | | |
|---|---|---|
| 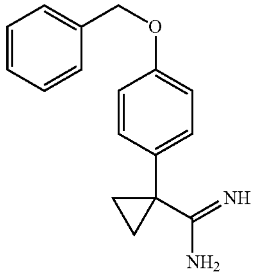 INT-2-16 | 1-(4-(benzyloxy)phenyl)cyclopropane-carboximidamide | LC-MS (Method-A1) m/z: M + 1 obs 267.2, tR = 1.97 min. |
| 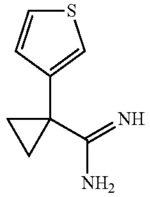 INT-2-17 | 1-(thiophen-3-yl)cyclopropanecarboximidamide | LC-MS (Method-A1) m/z: M + 1 obs 167.18, tR = 0.45 min. |
| 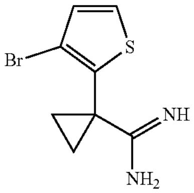 INT-2-18 | 1-(3-bromothiophen-2-yl)cyclopropanecarboximidamide | The structure is confirmed at the next step. |

TABLE 1-4

| | | |
|---|---|---|
| 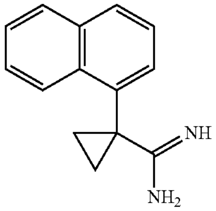 INT-2-19 | 1-(naphthalen-1-yl)cyclopropanecarboximidamide | LC-MS (Method-A1) m/z: M + 1 obs 211.38, tR = 1.67 min. |
| 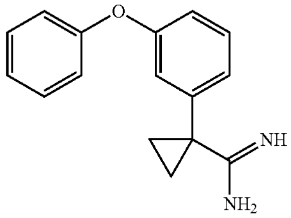 INT-2-20 | 1-(3-phenoxyphenyl)cyclopropanecar-boximidamide | (400 MHz, $CDCl_3$): δ 7.37-7.28 (3H, m), 7.14-7.08 (2H, m), 7.03-6.98 (3H, m), 6.89 (1H, dq, J = 8.1, 1.2 Hz), 4.46-3.54 (2H, br.s), 1.35 (2H, dd, J = 6.8, 4.7 Hz), 1.14 (2H, dd, J = 6.8, 4.7 Hz), (one signal of NH proton are not observed). LC-MS (Method-I) m/z: M + 1 obs 253.17, tR = 0.48 min. |

TABLE 1-4-continued

| | | |
|---|---|---|
| 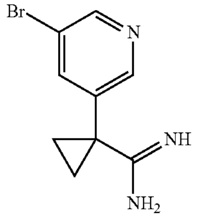<br>INT-2-21 | 1-(5-bromopyridin-3-yl)cyclopropanecarboximidamide | (400 MHz, DMSO-$d_6$): δ 9.00 (2H, s), 8.70 (1H, d, J = 2.3 Hz), 8.66-8.64 (1H, m), 8.16-8.13 (1H, m), 1.57-1.54 (2H, m), 1.46-1.42 (2H, m), (one signal of NH proton are not observed).<br>LC-MS (Method-I) m/z: M + 1 obs 240.04, 242.04, tR = 0.37 min. |
| 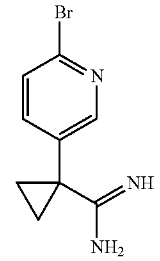<br>INT-2-22 | 1-(6-bromopyridin-3-yl)cyclopropanecarboximidamide | LC-MS (Method-A1) m/z: M + 1 obs 240.13, 242.14, tR = 0.56 min. |
| 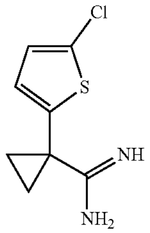<br>INT-2-23 | 1-(5-chlorothiophen-2-yl)cyclopropanecarboximidamide | LC-MS (Method-I) m/z: M + 1 obs 201.03, tR = 0.43 min. |
| 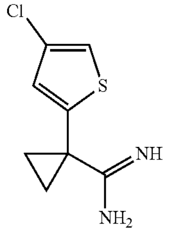<br>INT-2-24 | 1-(4-chlorothiophen-2-yl)cyclopropanecarboximidamide | LC-MS (Method-I) m/z: M + 1 obs 201.03, tR = 0.39 min. |

TABLE 1-5

| | | |
|---|---|---|
| 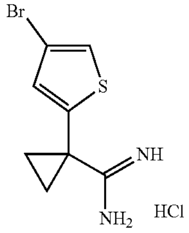<br>INT-2-25 | 1-(4-bromothiophen-2-yl)cyclopropane-1-carboximidamide hydrochloride | (400 MHz, DMSO-$d_6$): δ 9.06 (3H, br.s), 7.65 (1H, d, J = 1.8 Hz), 7.21 (1H, d, J = 1.8 Hz), 1.63-1.58 (2H, m), 1.43-1.38 (2H, m).<br>LC-MS (Method-B1) m/z: M + 1 obs 245.1, tR = 2.48 min. |

TABLE 1-5-continued

| | | |
|---|---|---|
| 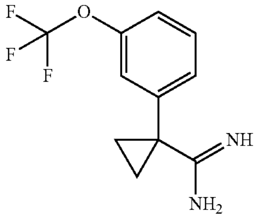 INT-2-26 | 1-(3-(trifluoromethoxy)phenyl)cyclopropanecarboximidamide | LC-MS (Method-I) m/z: M + 1 obs 245.11, tR = 0.47 min. |
| 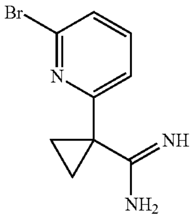 INT-2-27 | 1-(6-bromopyridin-2-yl)cyclopropanecarboximidamide | LC-MS (Method-I) m/z: M + 1 obs 240.03, 242.04, tR = 0.39 min. |
| 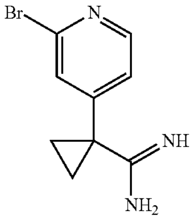 INT-2-28 | 1-(2-bromopyridin-4-yl)cyclopropanecarboximidamide | LC-MS (Method-I) m/z: M + 1 obs 240.17, 242.15, tR = 0.42 min. |
| 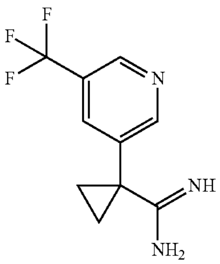 INT-2-29 | 1-(5-(trifluoromethyl)pyridin-3-yl)cyclopropanecarboximidamide | (400 MHz, $CDCl_3$): δ 8.81-8.79 (2H, m), 7.88 (1H, dd, J = 1.8, 1.8 Hz), 1.52 (2H, dd, J = 6.9, 5.0 Hz), 1.23 (2H, dd, J = 6.9, 5.0 Hz), (three signals of NH proton are not observed). LC-MS (Method-I) m/z: M + 1 obs 230.10, tR = 0.41 min. |
| 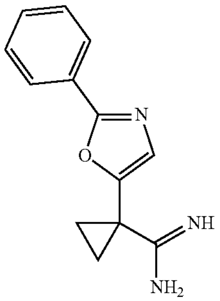 INT-2-30 | 1-(2-phenyloxazol-5-yl)cyclopropanecarboximidamide | (400 MHz, $CDCl_3$): δ 8.03-7.99 (2H, m), 7.47-7.44 (3H, m), 7.04 (1H, s), 1.48 (2H, dd, J = 7.2, 4.7 Hz), 1.31 (2H, dd, J = 7.2, 4.7 Hz), (three signals of NH proton are not observed). LC-MS (Method-1) m/z: M + 1 obs 228.11, tR = 0.44 min. |

TABLE 1-6

| | | |
|---|---|---|
| 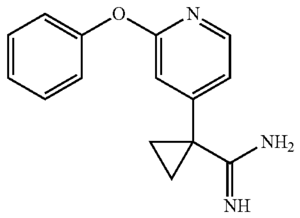 INT-2-31 | 1-(2-phenoxypyridin-4-yl)cyclopropanecarboximidamide | (400 MHz, $CDCl_3$): δ 8.17 (1H, d, J = 2.4 Hz), 7.69 (1H, dd, J = 8.5, 2.4 Hz), 7.43-7.39 (2H, m), 7.24-7.20 (1H, m), 7.13 (2H, d, J = 7.3 Hz), 6.88 (1H, d, J = 8.2 Hz), 1.41 (2H, dd, J = 6.8, 4.7 Hz), 1.12 (2H, dd, J = 6.8, 4.7 Hz), (three signals of NH proton are not observed). LC-MS (Method-I) m/z: M + 1 obs 254.19, tR = 0.46 min. |
| 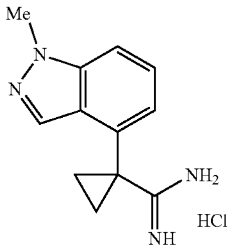 INT-2-32 | 1-(1-methyl-1H-indazol-4-yl)cyclopropane-1-carboximidamide hydrochloride | (400 MHz, DMSO-$d_6$): δ 8.92 (2H, brs), 8.71 (2H, brs), 8.29 (1H, s), 7.66 (1H, d, J = 8.2 Hz), 7.40 (1H, dd, J = 8.2, 7.3 Hz), 7.31 (1H, d, J = 6.9 Hz), 4.06 (3H, s), 1.80-1.56 (2H, m), 1.50-1.30 (2H, m). |
| 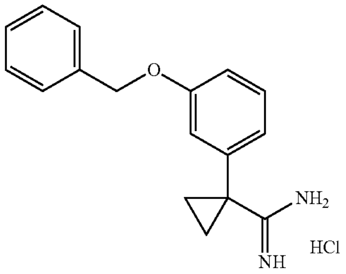 INT-2-33 | 1-(3-(benzyloxy)phenyl)cyclopropane-1-carboximidamide hydrochloride | (400 MHz, $CDCl_3$): δ 9.29 (2H, brs), 7.51-7.37 (4H, m), 7.37-7.29 (2H, m), 7.11 (2H, brs), 7.05-6.89 (3H, m), 5.07 (2H, s), 2.16-1.92 (2H, m), 1.66-1.43 (2H, m). LC-MS (Method-I) m/z: M + 1 obs 267.2, M − 1 obs 265.1, tR = 0.52 min. |
| 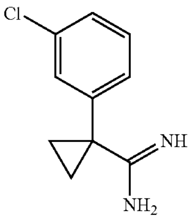 INT-2-34 | 1-(3-chlorophenyl)cyclopropane-1-carboximidamide | (400 MHz, $CDCl_3$): δ 7.36-7.33 (1H, m), 7.28-7.22 (3H, m), 4.22 (3H, br.s), 1.41-1.36 (2H, m), 1.17-1.12 (2H, m). |
| 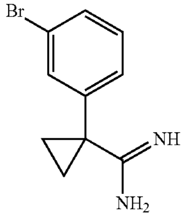 INT-2-35 | 1-(3-bromophenyl)cyclopropane-1-carboximidamide | (400 MHz, $CDCl_3$): δ 7.52-7.50 (1H, m), 7.43-7.39 (1H, m), 7.32-7.28 (1H, m), 7.24-7.18 (1H, m), 4.12 (3H, br.s), 1.40-1.35 (2H, m), 1.17-1.10 (2H, m). |

Intermediate-3-1 (INT-3-1)

Synthesis of 1-(thiazol-4-yl)cyclopropanecarbonitrile

{Chem. 25}

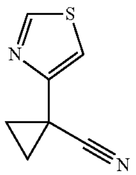

To a mixture of 2-(thiazol-4-yl)acetonitrile (1.90 g, 15.3 mmol), 1-bromo-2-chloroethane (2.55 ml, 30.6 mmol) and benzyltriethylammonium chloride (70 mg, 2 mol %) in toluene (10 ml) is added 50% aqueous NaOH (4.28 g, 107 mmol) in water (4.3 ml). The reaction mixture is heated at 60° C. for 18 hrs. After cooling to rt, the mixture is diluted with cold-water and ethyl acetate, the aqueous layer is extracted with ethyl acetate (×2). The combine solution is washed with brine, dried over sodium sulfate, filtered and concentrated in vacuo to give crude product. The crude product is purified by column chromatography on silica gel (250 g) eluting with n-hexane-ethyl acetate (4:1 v/v) to give the titled compound (832 mg) as a white solid.

$^1$H-NMR (300 MHz, $CDCl_3$): delta 8.68 (1H, d, J=2.2 Hz), 7.41 (1H, d, J=2.2 Hz), 1.78-1.71 (4H, m).

The following cyclopropane derivatives (INT-3-2 to INT-3-4) are prepared according to the procedure of intermediate-3-1 or intermediate-3-5 from the known acetonitrile derivatives in Table 2.

TABLE 2

| Structure | Chemical Name | $^1$H-NMR & LC-MS (m/z) |
|---|---|---|
| 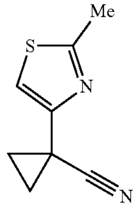 INT-3-2 | 1-(2-methylthiazol-4-yl)cyclopropane-1-carbonitrile | (300 MHz, $CDCl_3$): δ 7.15 (1H, s), 2.63 (3H, s), 1.73-1.62 (4H, m). |
| 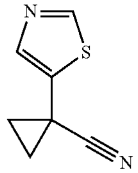 INT-3-3 | 1-(thiazol-5-yl)cyclopropane-1-carbonitrile | (300 MHz, $CDCl_3$): δ 8.73 (1H, s), 7.82 (1H, s), 1.88-1.80 (2H, m), 1.52-1.48 (2H, m). |
| 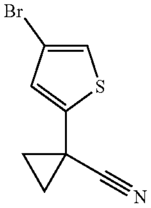 INT-3-4 | 1-(4-bromothiophen-2-yl)cyclopropane-1-carbonitrile | (300 MHz, $CDCl_3$): δ 7.11 (1H, d, J = 1.5 Hz), 6.98 (1H, d, J = 1.5 Hz), 1.82-1.75 (2H, m), 1.47-1.40 (2H, m). |

Intermediate-3-5 (INT-3-5)

Synthesis of 1-(5-methylthiophen-2-yl)cyclopropanecarbonitrile

{Chem. 26}

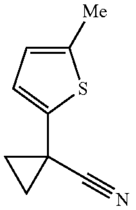

To a 60% sodium hydride (458 mg, 11.46 mmol) is added DMSO (5 ml) at rt and the mixture is stirred at rt for 15 min. To this is added a solution of 2-(5-methylthiophen-2-yl)acetonitrile (629 mg, 4.58 mmol) in DMSO (3 ml) at rt. After 15 min., to this is added 1,2-dibromoethane (593 microl, 6.88 mmol) via a syringe at rt and the reaction mixture is heated at 60° C. for 2 hrs. After cooling to rt, the mixture is quenched with water (20 ml) and extracted with ethyl acetate-toluene (8:1) (×2). The combined solution is washed with water and brine, dried over sodium sulfate, filtered and concentrated in vacuo to give crude product, which is purified by column chromatography on silica gel (250 g) eluting with n-hexane-ethyl acetate (10:1 v/v) to give the titled compound (585 mg) as a yellow oil.

$^1$H-NMR (300 MHz, $CDCl_3$): delta 6.83 (1H, d, J=3.7 Hz), 6.60-6.55 (1H, m), 2.43 (3H, s), 1.73-1.65 (2H, m), 1.42-1.34 (2H, m).

The following cyclopropane derivatives (INT-3-6 to INT-3-8) are prepared according to the procedure of intermediate-3-1 or intermediate-3-5 from the known acetonitrile derivatives in Table 3.

TABLE 3

| Structure | Chemical Name | $^1$H-NMR & LC-MS (m/z) |
|---|---|---|
| 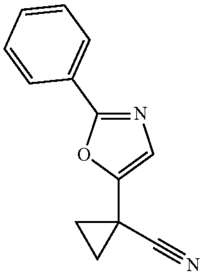 INT-3-6 | 1-(2-phenyloxazol-5-yl)cyclopropanecarbonitrile | (400 MHz, $CDCl_3$): δ 8.01-7.97 (2H, m), 7.48-7.45 (3H, m), 7.10 (1H, s), 1.79 (2H, dd, J = 7.9, 4.9 Hz), 1.59 (2H, dd, J = 7.9, 4.9 Hz). LC-MS (Method-I) m/z: M + 1 obs 211.10, tR = 0.54 min. |
| 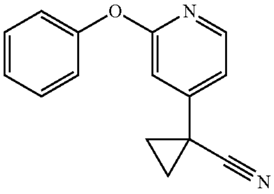 INT-3-7 | 1-(2-phenoxypyridin-4-yl)cyclopropanecarbonitrile | (400 MHz, $CDCl_3$): δ 8.13 (1H, d, J = 2.7 Hz), 7.66 (1H, dd, J = 8.7, 2.7 Hz), 7.44-7.39 (2H, m), 7.25-7.20 (1H, m), 7.15-7.10 (2H, m), 6.90 (1H, d, J = 8.7 Hz), 1.73 (2H, dd, J = 7.4, 5.2 Hz), 1.37 (2H, dd, J = 7.4, 5.2 Hz). LC-MS (Method-I) m/z: M + 1 obs 237.15, tR = 0.54 min. |
| 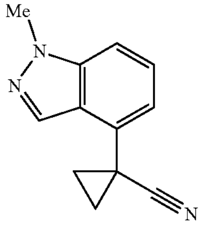 INT-3-8 | 1-(1-methyl-1H-indazol-4-yl)cyclopropane-1-carbonitrile | (400 MHz, $CDCl_3$): δ 8.24 (1H, s), 7.46-7.30 (2H, m), 7.07 (1H, dd, J = 6.6, 1.1 Hz), 4.10 (3H, s), 1.78 (2H, dd, J = 7.3, 5.0 Hz), 1.53 (2H, dd, J = 7.3, 5.0 Hz). LC-MS (Method-I) m/z: M + 1 obs 198.1, tR = 0.50 min. |

The following pyrimidin-4(3H)-one derivatives (INT-4-1 to INT-4-35) are prepared according to the procedure (step-1B) of intermediate-1 from the known or synthesized carboximidamide (INT-1-A, INT-2-1 to INT-2-21, INT-2-23, 2-24, 2-34 or 2-35) derivatives and known alpha-ketoester derivatives in Tables 4-1 to 4-7.

TABLE 4-1

| Structure | Chemical Name | $^1$H-NMR & LC-MS (m/z) |
|---|---|---|
| 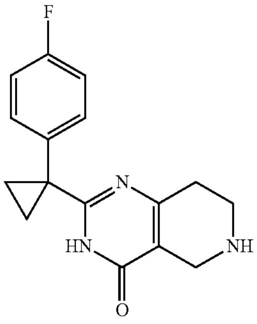 INT-4-1 | 2-(1-(4-fluorophenyl)cyclopropyl)-5,6,7,8-tetrahydropyrido[4,3-d]-pyrimidin-4(3H)-one | (300 MHz, DMSO-$d_6$): δ 7.40-7.32 (2H, m), 7.19-7.08 (2H, m), 3.44 (2H, s), 2.92-2.82 (2H, m), 2.46-2.38 (2H, m), 1.48-1.38 (2H, m), 1.20-1.14 (2H, m), (two signals of NH proton are not observed). |

TABLE 4-1-continued

| Structure | Chemical Name | $^1$H-NMR & LC-MS (m/z) |
| --- | --- | --- |
| 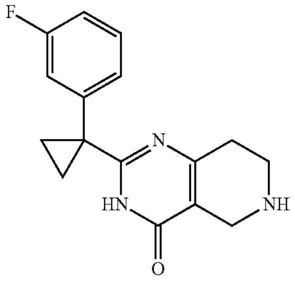 INT-4-2 | 2-(1-(3-fluorophenyl)cyclopropyl)-5,6,7,8-tetrahydropyrido[4,3-d]-pyrimidin-4(3H)-one | (300 MHz, DMSO-$d_6$): δ 7.40-7.29 (1H, m), 7.16-7.00 (3H, m), 3.45 (2H, br.s), 2.93-2.82 (2H, m) 2.43 (2H, br.s), 1.49-1.40 (2H, m), 1.28-1.20 (2H, m), (two signals of NH proton are not observed). LC-MS (Method-B) m/z: M + 1 obs 286.14, M − 1 obs 284.17, tR = 1.75 min. |
| 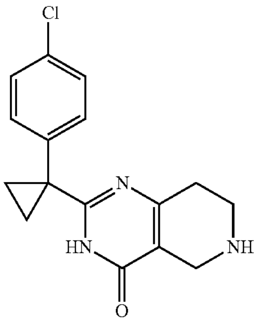 INT-4-3 | 2-(1-(4-chlorophenyl)cyclopropyl)-5,6,7,8-tetrahydropyrido[4,3-d]-pyrimidin-4(3H)-one | (270 MHz, DMSO-$d_6$): δ 7.40-7.25 (4H, m), 3.44 (2H, s), 2.92-2.82 (2H, m), 2.46-2.37 (2H, m), 1.48-1.40 (2H, m), 1.23-1.15 (2H, m), (two signals of NH proton are not observed). LC-MS (Method-A) m/z: M + 1 obs 302.06, M − 1 obs 300.03, tR = 2.30 min. |
| 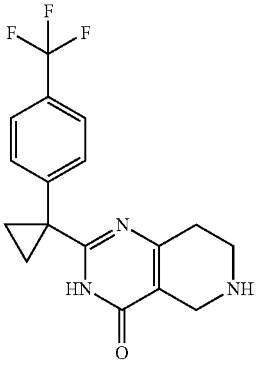 INT-4-4 | 2-(1-(4-(trifluoromethyl)phenyl)-cyclopropyl)-5,6,7,8-tetrahydro-pyrido-[4,3-d]pyrimidin-4(3H)-one | (300 MHz, DMSO-$d_6$): δ 7.67 (2H, d, J = 8.0 Hz), 7.44 (2H, d, J = 8.0 Hz), 3.43 (2H, m), 2.88 (2H, t, J = 5.9 Hz), 2.43 (2H, br.s), 1.54-1.50 (2H, m), 1.30-1.26 (2H, m), (two signals of NH proton are not observed). LC-MS (Method-B) m/z: M + 1 + MeCN obs 377.15, M − 1 obs 334.19, tR = 2.36 min. |
| 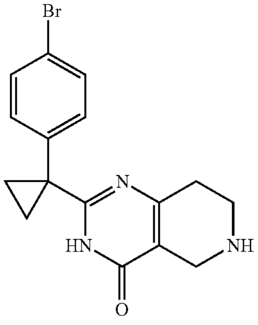 INT-4-5 | 2-(1-(4-bromophenyl)cyclopropyl)-5,6,7,8-tetrahydropyrido[4,3-d]-pyrimidin-4(3H)-one | (300 MHz, DMSO-$d_6$): δ 7.93 (1H, s), 7.49 (2H, d, J = 8.0 Hz), 7.25 (2H, d, J = 8.0 Hz), 3.74 (2H, m), 3.27 (2H, br.s), 2.78 (2H, br.s), 1.50-1.46 (2H, m), 1.25-1.21 (2H, m), (one signal of NH proton is not observed). LC-MS (Method-B) m/z: M + 1 obs 348.05, M − 1 obs 346.10, tR = 2.33 min. |

TABLE 4-2

| | | |
|---|---|---|
| 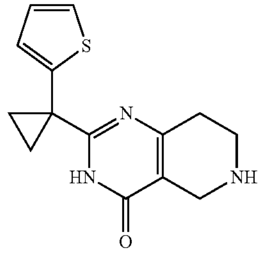 INT-4-6 | 2-(1-(thiophen-2-yl)cyclopropyl)-5,6,7,8-tetrahydropyrido[4,3-d]-pyrimidin-4(3H)-one | (270 MHz, DMSO-$d_6$): δ 7.40-7.34 (1H, m), 7.05-6.90 (2H, m), 3.44 (2H, s), 2.95-2.80 (2H, m), 2.50-2.35 (2H, m), 1.57-1.45 (2H, m), 1.30-1.20 (2H, m), (two signals of NH proton are not observed). LC-MS (Method-A) m/z: M + 1 obs 274.16, tR = 1.89 min. |
| 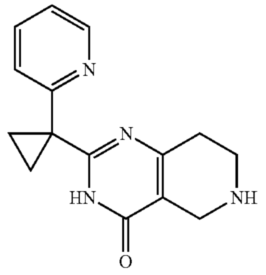 INT-4-7 | 2-(1-(pyridin-2-yl)cyclopropyl)-5,6,7,8-tetrahydropyrido[4,3-d]-pyrimidin-4(3H)-one | (300 MHz, DMSO-$d_6$): δ 8.48-8.42 (1H, m), 7.73-7.64 (1H, m), 7.25-7.16 (1H, m), 7.06-6.98 (1H, m), 3.49 (2H, s), 2.95-2.85 (2H, m), 2.48-2.40 (2H, m), 1.54-1.41 (4H, m), (two signals of NH proton are not observed). LC-MS (Method-A) m/z: M + 1 obs 269.20, tR = 0.84 min. |
| 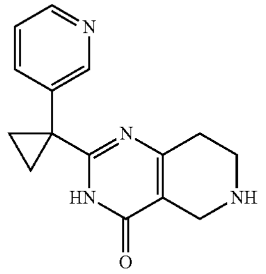 INT-4-8 | 2-(1-(pyridin-3-yl)cyclopropyl)-5,6,7,8-tetrahydropyrido[4,3-d]-pyrimidin-4(3H)-one | (300 MHz, DMSO-$d_6$): δ 8.53-8.48 (1H, m), 8.46-8.42 (1H, m), 7.73-7.65 (1H, m), 7.37-7.29 (1H, m), 3.44 (2H, s), 2.91-2.82 (2H, m), 2.48-2.37 (2H, m), 1.55-1.46 (2H, m), 1.30-1.22 (2H, m), (two signals of NH proton are not observed). LC-MS (Method-A) m/z: M + 1 obs 269.14, M − 1 obs 267.15, tR = 0.52 min. |
| 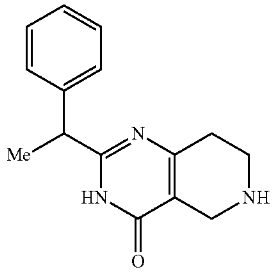 INT-4-9 | 2-(1-phenylethyl)-5,6,7,8-tetrahydropyrido[4,3-d]pyrimidin-4(3H)-one | (270 MHz, DMSO-$d_6$): δ 7.40-7.15 (5H, m), 4.05-3.93 (1H, m), 3.44 (2H, s), 2.96-2.80 (2H, m), 2.60-2.38 (2H, m), 1.55-1.45 (3H, m), (two signals of NH proton are not observed). LC-MS (Method-A) m/z: M + 1 obs 256.16, M − 1 obs 254.13, tR = 1.72 min. |
| 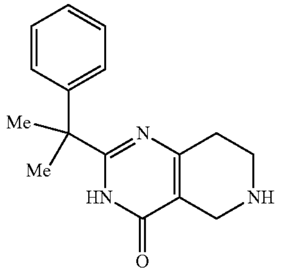 INT-4-10 | 2-(2-phenylpropan-2-yl)-5,6,7,8-tetrahydropyrido[4,3-d]pyrimidin-4(3H)-one | (300 MHz, DMSO-$d_6$): δ 7.38-7.17 (5H, m), 3.45 (2H, s), 2.96-2.86 (2H, m), 2.54-2.45 (2H, m), 1.62 (6H, s), (two signals of NH proton are not observed). LC-MS (Method-A) m/z: M + 1 obs 270.21, tR = 2.24 min. |

TABLE 4-3

| | | |
|---|---|---|
| 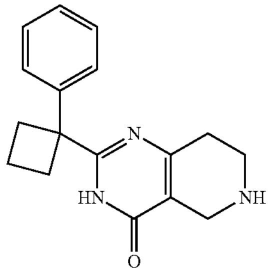<br>INT-4-11 | 2-(1-phenylcyclobutyl)-5,6,7,8-tetrahydropyrido[4,3-d]pyrimidin-4(3H)-one | (270 MHz, DMSO-$d_6$): δ 7.39-7.14 (5H, m), 3.77-3.75 (2H, m), 3.15-3.11 (2H, m), 2.99-2.86 (2H, m), 2.72-2.59 (4H, m), 2.07-1.89 (2H, m), (two signals of NH proton are not observed).<br>LC-MS (Method-B) m/z: M + 1 obs 282.23, M − 1 obs 280.23, tR = 2.38 min. |
| 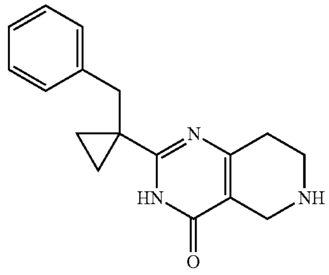<br>INT-4-12 | 2-(1-benzylcyclopropyl)-5,6,7,8-tetrahydropyrido[4,3-d]pyrimidin-4(3H)-one | LC-MS (Method-B) m/z: M + 1 obs 282.13, tR = 2.13 min. |
| 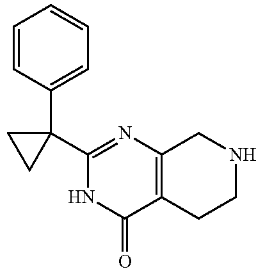<br>INT-4-13 | 2-(1-phenylcyclopropyl)-5,6,7,8-tetrahydropyrido[3,4-d]pyrimidin-4(3H)-one | (300 MHz, $CDCl_3$): δ 7.44-7.24 (5H, m), 3.74-3.67 (2H, m), 3.09-3.03 (2H, m), 2.53-2.45 (2H, m), 1.77-1.73 (2H, m), 1.36-1.32 (2H, m), (two signals of NH proton are not observed).<br>LC-MS (Method-B) m/z: M + 1 obs 268.23, M − 1 obs 266.24, tR = 2.15 min. |
| 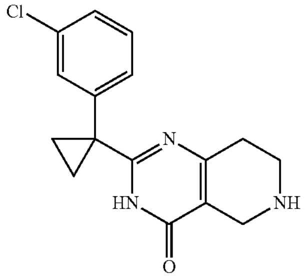<br>INT-4-14 | 2-(1-(3-chlorophenyl)cyclopropyl)-5,6,7,8-tetrahydropyrido[4,3-d]pyrimidin-4(3H)-one | (300 MHz, DMSO-$d_6$): δ 7.38-7.20 (4H, m), 3.44 (2H, br.s), 2.92-2.83 (2H, m), 2.47-2.38 (2H, m), 1.48-1.40 (2H, m), 1.27-1.19 (2H, m), (two signals of NH proton are not observed). |
| 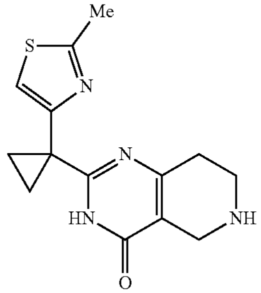<br>INT-4-15 | 2-(1-(2-methylthiazol-4-yl)cyclopropyl)-5,6,7,8-tetrahydropyrido[4,3-d]pyrimidin-4(3H)-one | (300 MHz, DMSO-$d_6$): δ 7.23 (1H, s), 3.85 (2H, br.s), 3.32 (2H, br.s), 2.85-2.76 (2H, m), 2.64 (3H, s), 1.58-1.50 (2H, m), 1.44-1.36 (2H, m), (two signals of NH proton are not observed). |

TABLE 4-4

| | | |
|---|---|---|
| 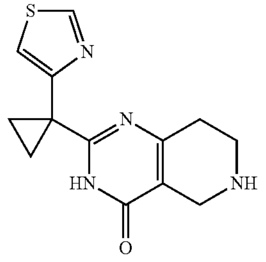<br>INT-4-16 | 2-(1-(thiazol-4-yl)cyclopropyl)-5,6,7,8-tetrahydropyrido[4,3-d]pyrimidin-4(3H)-one | (300 MHz, DMSO-$d_6$): δ 9.03 (1H, d, J = 1.5 Hz), 7.34 (1H, d, J = 1.5 Hz), 3.47 (2H, br.s), 2.93-2.85 (2H, m), 2.47-2.38 (2H, m), 1.54-1.48 (2H, m), 1.41-1.34 (2H, m), (two signals of NH proton are not observed). |
| 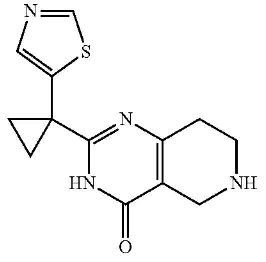<br>INT-4-17 | 2-(1-(thiazol-5-yl)cyclopropyl)-5,6,7,8-tetrahydropyrido[4,3-d]pyrimidin-4(3H)-one | (300 MHz, DMSO-$d_6$): δ 9.13 (1H, s), 7.90 (1H, s), 3.84 (2H, br.s), 3.32 (2H, br.s), 2.85-2.76 (2H, m), 1.74-1.67 (2H, m), 1.48-1.41 (2H, m), (two signals of NH proton are not observed). |
| 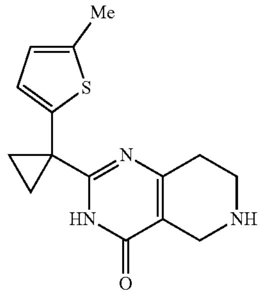<br>INT-4-18 | 2-(1-(5-methylthiophen-2-yl)cyclopropyl)-5,6,7,8-tetrahydropyrido[4,3-d]pyrimidin-4(3H)-one | (300 MHz, DMSO-$d_6$): δ 6.80 (1H, d, J = 3.7 Hz), 6.63-6.58 (1H, m), 3.44 (2H, br.s), 2.91-2.83 (2H, m), 2.47-2.38 (2H, m), 2.36 (3H, s), 1.50-1.43 (2H, m), 1.24-1.17 (2H, m), (two signals of NH proton are not observed). |
| 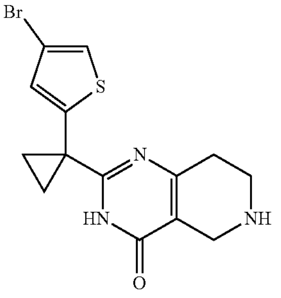<br>INT-4-19 | 2-(1-(4-bromothiophen-2-yl)cyclopropyl)-5,6,7,8-tetrahydropyrido[4,3-d]pyrimidin-4(3H)-one | (300 MHz, DMSO-$d_6$): δ 7.51 (1H, d, J = 1.5 Hz), 7.01 (1H, d, J = 1.5 Hz), 3.46 (2H, br.s), 2.92-2.84 (2H, m), 2.47-2.38 (2H, m), 1.59-1.52 (2H, m), 1.34-1.26 (2H, m), (two signals of NH proton are not observed). |
| 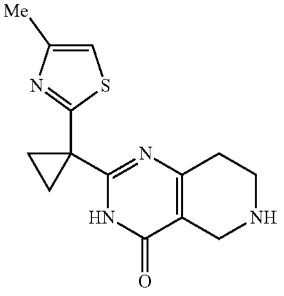<br>INT-4-20 | 2-(1-(4-methylthiazol-2-yl)cyclopropyl)-5,6,7,8-tetrahydropyrido[4,3-d]pyrimidin-4(3H)-one | (300 MHz, DMSO-$d_6$): δ 7.10 (1H, d, J = 1.5 Hz), 3.50 (2H, br.s), 2.95-2.88 (2H, m), 2.50-2.42 (2H, m), 2.30 (3H, s), 1.74-1.68 (2H, m), 1.54-1.48 (2H, m), (two signals of NH proton are not observed). |

TABLE 4-5

| | | |
|---|---|---|
| 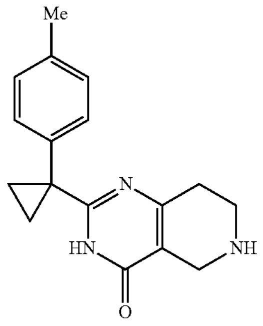 INT-4-21 | 2-(1-(p-tolyl)cyclopropyl)-5,6,7,8-tetrahydropyrido[4,3-d]pyrimidin-4(3H)-one | (300 MHz, DMSO-$d_6$): δ 7.18 (2H, d, J = 8.1 Hz), 7.10 (2H, d, J = 8.1 Hz), 3.43 (2H, br.s), 2.90-2.83 (2H, m), 2.45-2.38 (2H, m), 2.26 (3H, s), 1.43-1.35 (2H, m), 1.17-1.10 (2H, m), (two signals of NH proton are not observed). |
| 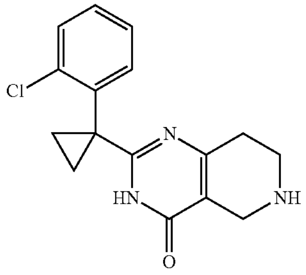 INT-4-22 | 2-(1-(2-chlorophenyl)cyclopropyl)-5,6,7,8-tetrahydropyrido[4,3-d]pyrimidin-4(3H)-one | (300 MHz, DMSO-$d_6$): δ 7.55-7.47 (1H, m), 7.45-7.38 (1H, m), 7.35-7.28 (2H, m), 3.43 (2H, br.s), 2.87-2.80 (2H, m), 2.35-2.28 (2H, m), 1.77-1.70 (2H, m), 1.28-1.22 (2H, m), (two signals of NH proton are not observed). |
| 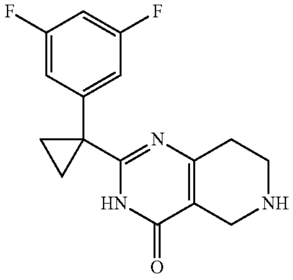 INT-4-23 | 2-(1-(3,5-difluorophenyl)cyclopropyl)-5,6,7,8-tetrahydropyrido[4,3-d]pyrimidin-4(3H)-one | (300 MHz, $CDCl_3$): δ 6.97-6.78 (3H, m), 3.78 (2H, br.s), 3.17-3.09 (2H, m), 2.67-2.59 (2H, m), 1.80-1.74 (2H, m), 1.37-1.30 (2H, m), (two signals of NH proton are not observed). |
| 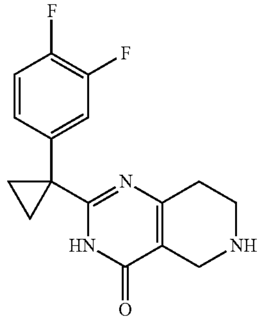 INT-4-24 | 2-(1-(3,4-difluorophenyl)cyclopropyl)-5,6,7,8-tetrahydropyrido[4,3-d]pyrimidin-4(3H)-one | (300 MHz, DMSO-$d_6$): δ 7.45-7.28 (2H, m), 7.18-7.10 (1H, m), 3.44 (2H, br.s), 2.92-2.83 (2H, m), 2.47-2.37 (2H, m), 1.50-1.42 (2H, m), 1.27-1.18 (2H, m), (two signals of NH proton are not observed). |

TABLE 4-5-continued

| | | |
|---|---|---|
| 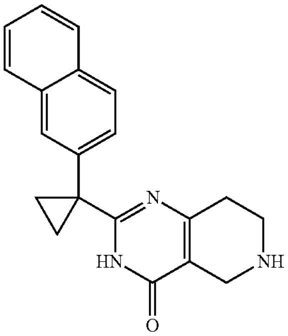 INT-4-25 | 2-(1-(naphthalen-2-yl)cyclopropyl)-5,6,7,8-tetrahydropyrido[4,3-d]pyrimidin-4(3H)-one | (400 MHz, $CDCl_3$): δ 7.91-7.86 (3H, m), 7.82 (1H, q, J = 3.0 Hz), 7.57-7.52 (2H, m), 7.47 (1H, dd, J = 8.2, 1.8 Hz), 3.74 (2H, t, J = 1.8 Hz), 3.11 (2H, t, J = 5.7 Hz), 2.63-2.61 (2H, m), 1.85 (2H, dd, J = 7.0, 4.0 Hz), 1.45 (2H, dd, J = 7.0, 4.0 Hz), (two signals of NH proton are not observed). LC-MS (Method-A1) m/z: M + 1 obs 318.15, tR = 1.63 min. |

TABLE 4-6

| | | |
|---|---|---|
| 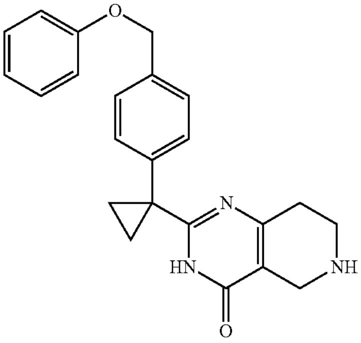 INT-4-26 | 2-(1-(4-(benzyloxy)phenyl)cyclopropyl)-5,6,7,8-tetrahydropyrido[4,3-d]pyrimidin-4(3H)-one | (400 MHz, $CDCl_3$): δ 7.47-7.29 (7H, m), 7.02-6.98 (2H, m), 5.09 (2H, s), 3.74 (2H, t, J = 1.8 Hz), 3.09 (2H, t, J = 5.7 Hz), 2.59-2.56 (2H, m), 1.74 (2H, dd, J = 7.0, 4.0 Hz), 1.30 (2H, dd, J = 7.0, 4.0 Hz), (two signals of NH proton are not observed). LC-MS (Method-A1) m/z: M + 1 obs 374.25, tR = 1.94 min. |
| 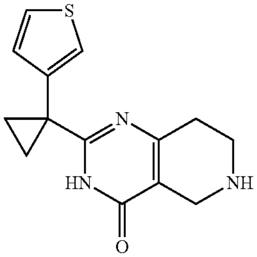 INT-4-27 | 2-(1-(thiophen-3-yl)cyclopropyl)-5,6,7,8-tetrahydropyrido[4,3-d]pyrimidin-4(3H)-one | (400 MHz, $CDCl_3$): δ 7.41 (1H, dd, J = 4.9, 2.9 Hz), 7.30 (1H, dd, J = 2.9, 1.1 Hz), 7.06 (1H, dd, J = 4.9, 1.1 Hz), 3.75 (2H, t, J = 1.8 Hz), 3.10 (2H, t, J = 5.7 Hz), 2.60-2.57 (2H, m), 1.74 (2H, dd, J = 7.0, 4.0 Hz), 1.32 (2H, dd, J = 7.0, 4.0 Hz), (two signals of NH proton are not observed). LC-MS (Method-A1) m/z: M + 1 obs 274.32, tR = 0.82 min. |
| 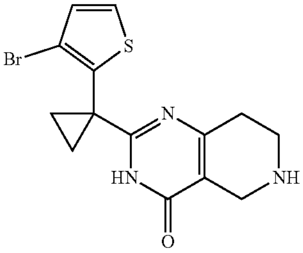 INT-4-28 | 2-(1-(3-bromothiophen-2-yl)cyclopropyl)-5,6,7,8-tetrahydropyrido[4,3-d]pyrimidin-4(3H)-one | LC-MS (Method-I) m/z: M + 1 obs 351.97, tR = 0.42 min. |

TABLE 4-6-continued

| | | |
|---|---|---|
| 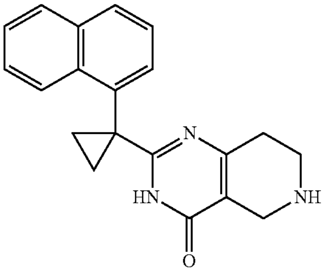 INT-4-29 | 2-(1-(naphthalen-1-yl)cyclopropyl)-5,6,7,8-tetrahydropyrido[4,3-d]pyrimidin-4(3H)-one | LC-MS (Method-A1) m/z: M + 1 obs 318.15, tR = 1.77 min. |
| 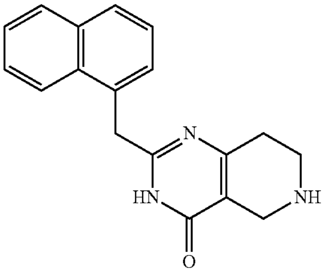 INT-4-30 | 2-(naphthalen-1-ylmethyl)-5,6,7,8-tetrahydropyrido[4,3-d]pyrimidin-4(3H)-one | (400 MHz, $CDCl_3$): δ 7.92-7.89 (3H, m), 7.55-7.41 (4H, m), 4.44 (2H, s), 3.75-3.71 (2H, br.s), 3.15 (2H, t, J = 5.8 Hz), 2.74 (2H, m), (two signals of NH proton are not observed). LC-MS (Method-A1) m/z: M + 1 obs 292.17, tR = 1.50 min. |

TABLE 4-7

| | | |
|---|---|---|
| 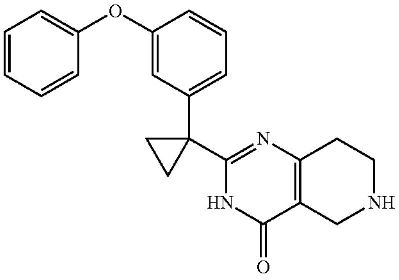 INT-4-31 | 2-(1-(3-phenoxyphenyl)cyclopropyl)-5,6,7,8-tetrahydropyrido[4,3-d]pyrimidin-4(3H)-one | (400 MHz, $CD_3OD$): δ 7.37-7.30 (4H, m), 7.14-7.07 (2H, m), 6.99-6.96 (2H, m), 6.87 (1H, d, J = 8.2 Hz), 3.66 (2H, s), 3.06 (2H, t, J = 5.3 Hz), 2.66-2.59 (2H, m), 1.57-1.51 (2H, m), 1.32-1.27 (2H, m), (two signals of NH proton are not observed). LC-MS (Method-A1) m/z: M + 1 obs 360.24, tR = 1.90 min. |
| 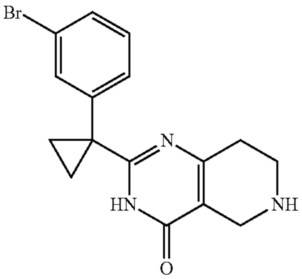 INT-4-32 | 2-(1-(3-bromophenyl)cyclopropyl)-5,6,7,8-tetrahydropyrido[4,3-d]pyrimidin-4(3H)-one | (400 MHz, $CD_3OD$): δ 7.47 (1H, t, J = 1.8 Hz), 7.40-7.37 (1H, m), 7.29-7.27 (1H, m), 7.21 (1H, t, J = 8.0 Hz), 3.63 (2H, t, J = 1.6 Hz), 3.03 (2H, t, J = 5.9 Hz), 2.61 (2H, t, J = 5.9 Hz), 1.52 (2H, dd, J = 7.1, 4.8 Hz), 1.29 (2H, dd, J = 7.1, 4.8 Hz), (two signals of NH proton are not observed). LC-MS (Method-I) m/z: M + 1 obs 346.05, tR = 0.43 min. |

TABLE 4-7-continued

| | | |
|---|---|---|
| 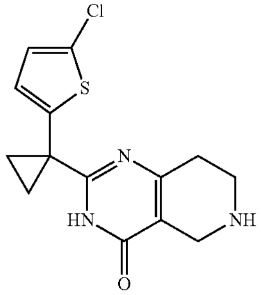<br>INT-4-33 | 2-(1-(5-chlorothiophen-2-yl)cyclopropyl)-5,6,7,8-tetrahydropyrido[4,3-d]pyrimidin-4(3H)-one | (400 MHz, $CD_3OD$): δ 6.87 (1H, d, J = 3.7 Hz), 6.82 (1H, d, J = 3.7 Hz), 3.68 (2H, s), 3.09 (2H, t, J = 5.8 Hz), 2.65 (2H, t, J = 5.8 Hz), 1.63 (2H, dd, J = 7.2, 4.7 Hz), 1.38 (2H, dd, J = 7.2, 4.7 Hz), (two signals of NH proton are not observed). LC-MS (Method-I) m/z: M + 1 obs 308.03, tR = 0.43 min. |
| 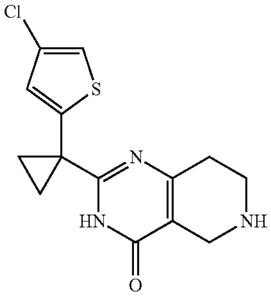<br>INT-4-34 | 2-(1-(4-chlorothiophen-2-yl)cyclopropyl)-5,6,7,8-tetrahydropyrido[4,3-d]pyrimidin-4(3H)-one | (400 MHz, $CD_3OD$): δ 7.15 (1H, d, J = 1.8 Hz), 6.92 (1H, d, J = 1.8 Hz), 3.68 (2H, s), 3.08 (2H, t, J = 5.8 Hz), 2.65 (2H, t, J = 5.8 Hz), 1.63 (2H, dd, J = 7.2, 4.7 Hz), 1.37 (2H, dd, J = 7.2, 4.7 Hz), (two signals of NH proton are not observed). LC-MS (Method-I) m/z: M + 1 obs 308.05, tR = 0.41 min. |
| 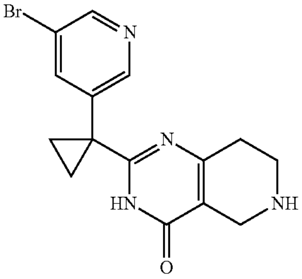<br>INT-4-35 | 2-(1-(5-bromopyridin-3-yl)cyclopropyl)-5,6,7,8-tetrahydropyrido[4,3-d]pyrimidin-4(3H)-one | (400 MHz, $CD_3OD$): δ 8.53 (1H, d, J = 2.1 Hz), 8.48 (1H, d, J = 2.1 Hz), 8.00 (1H, t, J = 2.1 Hz), 3.71 (2H, s), 3.11 (2H, t, J = 5.8 Hz), 2.66 (2H, t, J = 5.8 Hz), 1.64 (2H, dd, J = 7.2, 4.9 Hz), 1.38 (2H, dd, J = 7.2, 4.9 Hz), (two signals of NH proton are not observed). LC-MS (Method-I) m/z: M + 1 obs 347.01, tR = 0.38 min. |

The following pyrimidin-4(3H)-one derivatives (INT-5-1 to INT-5-27) are prepared according to the procedure (step-1B) of intermediate-1 from the known or synthesized carboximidamide (INT-1-A, INT-2-1, 2-4, 2-12, 2-20, 2-21, 2-22, or INT-2-25 to INT-2-35) derivatives and known N-protected alpha-ketoester derivatives in Tables 5-1 to 5-5.

TABLE 5-1

| Structure | Chemical Name | $^1$H-NMR & LC-MS (m/z) |
|---|---|---|
| 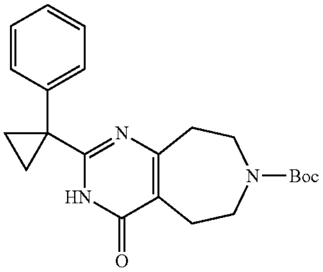<br>INT-5-1 | tert-butyl 4-oxo-2-(1-phenylcyclopropyl)-5,6,8,9-tetrahydro-3H-pyrimido[4,5-d]azepine-7(4H)-carboxylate | (300 MHz, $CDCl_3$): δ 8.62 (1H, s), 7.41-7.39 (5H, m), 3.59-3.51 (4H, m), 2.89-2.81 (4H, m), 1.79-1.76 (2H, m), 1.48 (9H, s), 1.36-1.33 (2H, m). LC-MS (Method-B) m/z: M + 1 obs 382.18, M − 1 obs 380.23, tR = 2.93 min. |

TABLE 5-1-continued

| Structure | Chemical Name | $^1$H-NMR & LC-MS (m/z) |
|---|---|---|
| 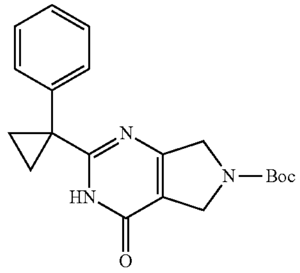 INT-5-2 | tert-butyl 4-oxo-2-(1-phenylcyclopropyl)-5,7-dihydro-3H-pyrrolo[3,4-d]pyrimidine-6(4H)-carboxylate | (300 MHz, $CDCl_3$): δ 7.43 (5H, s), 4.49 (4H, s), 1.85-1.81 (2H, m), 1.59-1.43 (11H, m), (one signal of NH proton is not observed). LC-MS (Method-B) m/z M + 1 obs 354.04, M − 1 obs 352.00, tR = 2.42 min. |
| 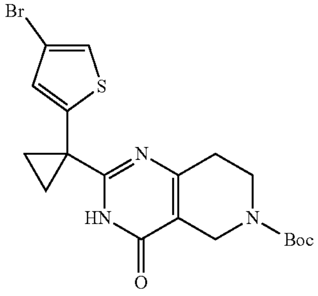 INT-5-3 | tert-butyl 2-(1-(4-bromothiophen-2-yl)cyclopropyl)-4-oxo-3,5,7,8-tetrahydropyrido[4,3-d]pyrimidine-6(4H)-carboxylate | (400 MHz, $CDCl_3$): δ 8.99-8.89 (1H, br. s), 7.25 (1H, d, J = 1.6 Hz), 7.04 (1H, d, J = 1.6 Hz), 4.31 (2H, s), 3.64 (2H, t, J = 5.5 Hz), 2.63 (2H, t, J = 5.5 Hz), 1.87 (2H, dd, J = 7.3, 4.1 Hz), 1.48-1.44 (m, 11H). LC-MS (Method-B) m/z: M + 1 obs 452.2, M − obs 450.2, tR = 2.80 min. |
| 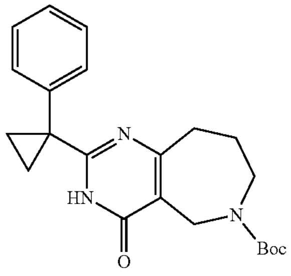 INT-5-4 | tert-butyl 4-oxo-2-(1-phenylcyclopropyl)-3,4,5,7,8,9-hexahydro-6H-pyrimido[5,4-c]azepine-6-carboxylate | (300 MHz, $CDCl_3$): δ 7.41 (5H, (br. s), 4.39 (2H, br. s), 3.61 (2H, br. s), 2.80 (2H, br. s), 1.95-1.83 (2H, m), 1.78 (2H, br. s), 1.48-1.30 (11H, m), (one signal of NH proton is not observed). |
| 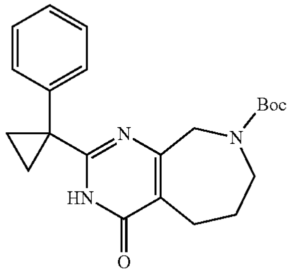 INT-5-5 | tert-butyl 4-oxo-2-(1-phenylcyclopropyl)-3,4,5,6,7,9-hexahydro-8H-pyrimido[4,5-c]azepine-8-carboxylate | (300 MHz, $CDCl_3$): δ 7.43-7.37 (5H, m), 4.45-4.30 (2H, m), 3.65-3.50 (2H, m), 2.73-2.60 (2H, m), 1.93-1.74 (4H, m), 1.50-1.30 (11H, m), (one signal of NH proton is not observed). |

TABLE 5-2

| | | |
|---|---|---|
| 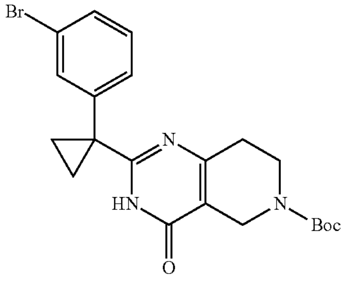 INT-5-6 | tert-butyl 2-(1-(3-bromophenyl)cyclopropyl)-4-oxo-3,5,7,8-tetrahydropyrido[4,3-d]pyrimidine-6(4H)-carboxylate | (400 MHz, $CDCl_3$): δ 8.68-8.57 (1H, br. s), 7.56-7.52 (2H, m), 7.35-7.28 (2H, m), 4.29 (2H, s), 3.64 (2H, t, J = 5.5 Hz), 2.64 (2H, t, J = 5.3 Hz), 1.78 (2H, dd, J = 7.0, 4.0 Hz), 1.47 (9H, s), 1.35 (2H, q, J = 7.0, 4.0 Hz). LC-MS (Method-I) m/z: M + 1 obs 446.17, tR = 0.57 min. |
| 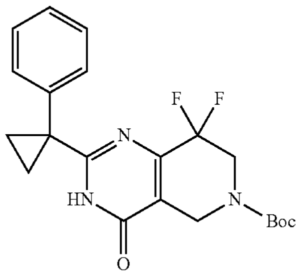 INT-5-7 | tert-butyl 8,8-difluoro-4-oxo-2-(1-phenylcyclopropyl)-3,5,7,8-tetrahydropyrido[4,3-d]pyrimidine-6(4H)-carboxylate | (400 MHz, $CDCl_3$): δ 8.77 (1H, br. s), 7.48-7.38 (5H, m), 4.40 (2H, br. s), 4.04-3.94 (2H, m), 1.95-1.90 (2H, m), 1.50-1.42 (11H, m). LC-MS (Method-B1) m/z: M + 1 obs 404.01, tR = 1.87 min. |
| 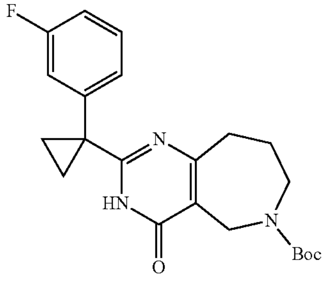 INT-5-8 | tert-butyl 2-(1-(3-fluorophenyl)cyclopropyl)-4-oxo-3,4,5,7,8,9-hexahydro-6H-pyrimido[5,4-c]azepine-6-carboxylate | (400 MHz, $CDCl_3$): δ 8.62 (1H, br. s), 7.44-7.35 (1H, m), 7.23-7.17 (1H, m), 7.14-7.05 (2H, m), 4.40 (2H, s), 3.62 (2H, br. s), 2.80 (2H, br. s), 1.94-1.85 (2H, m), 1.79 (2H, br. s), 1.48-1.30 (11H, m). LC-MS (Method-B1) m/z: M + 1 obs 400.26, tR = 2.12 min. |
| 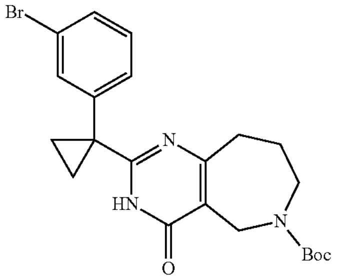 INT-5-9 | tert-butyl 2-(1-(3-bromophenyl)cyclopropyl)-4-oxo-3,4,5,7,8,9-hexahydro-6H-pyrimido[5,4-c]azepine-6-carboxylate | (400 MHz, $CDCl_3$): δ 8.68 (1H, br. s), 7.60-7.50 (2H, m), 7.40-7.20 (2H, m), 4.40 (2H, s), 3.62 (2H, br. s), 2.80 (2H, br. s), 1.94-1.85 (2H, m), 1.79 (2H, br. s), 1.50-1.30 (11H, m). LC-MS (Method-B1) m/z: M + 1 obs 460.0, tR = 2.27 min. |
| 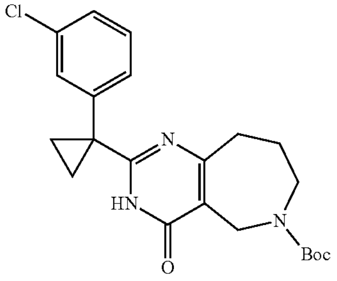 INT-5-10 | tert-butyl 2-(1-(3-chlorophenyl)cyclopropyl)-4-oxo-3,4,5,7,8,9-hexahydro-6H-pyrimido[5,4-c]azepine-6-carboxylate | (400 MHz, $CDCl_3$): δ 8.71 (1H, br. s), 7.43-7.28 (4H, m), 4.40 (2H, s), 3.63 (2H, br. s), 2.80 (2H, br. s), 1.94-1.85 (2H, m), 1.79 (2H, br. s), 1.48-1.30 (11H, m). LC-MS (Method-H) m/z: M + 1 obs 415.99, tR = 2.13 min. |

TABLE 5-2-continued

| | | |
|---|---|---|
| 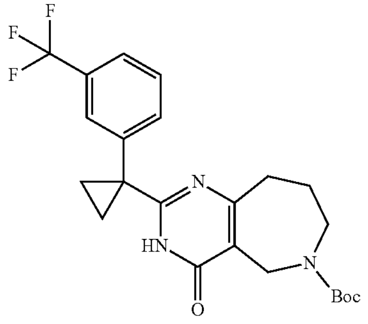 INT-5-11 | tert-butyl 4-oxo-2-(1-(3-(trifluoromethyl)phenyl) cyclopropyl)-3,4,5,7,8,9-hexahydro-6H-pyrimido[5,4-c]azepine-6-carboxylate | (400 MHz, $CDCl_3$): δ 8.64-8.49 (1H, br), 7.67-7.52 (m, 4H), 4.39 (2H, s), 3.67-3.53 (2H, br. s), 2.87-2.74 (2H, br. s), 1.93-1.87 (2H, m), 1.86-1.78 (2H, br. s), 1.40-1.32 (m, 11H). LC-MS (Method-I) m/z: M − 1 obs 448.29, tR = 0.58 min. |

TABLE 5-3

| | | |
|---|---|---|
| 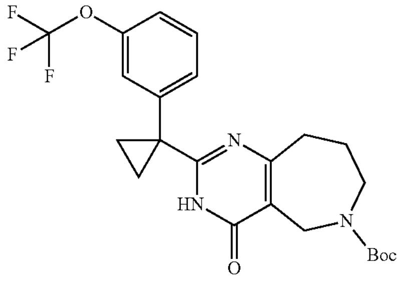 INT-5-12 | tert-butyl 4-oxo-2-(1-(3-(trifluoromethoxy)phenyl) cyclopropyl)-3,4,5,7,8,9-hexahydro-6H-pyrimido[5,4-c]azepine-6-carboxylate | LC-MS (Method-I) m/z: M + 1 obs 466.26, tR = 0.58 min. |
| 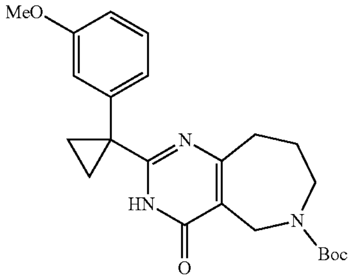 INT-5-13 | tert-butyl 2-(1-(3-methoxyphenyl)cyclopropyl)-4-oxo-3,4,5,7,8,9-hexahydro-6H-pyrimido[5,4-c]azepine-6-carboxylate | (400 MHz, $CDCl_3$): δ 8.70-8.56 (1H, br), 7.38-7.31 (1H, m), 6.98 (1H, d, J = 7.3 Hz), 6.92-6.90 (2H, m), 4.39 (2H, s), 3.82 (3H, s), 3.68-3.50 (2H, br. s), 2.85-2.75 (2H, m), 1.92-1.84 (m, 2H), 1.81-1.72 (2H, br. s), 1.40 (9H, s), 1.34-1.32 (2H, m). LC-MS (Method-A1) m/z: M + 1 obs 412.28, tR = 2.14 min. |
| 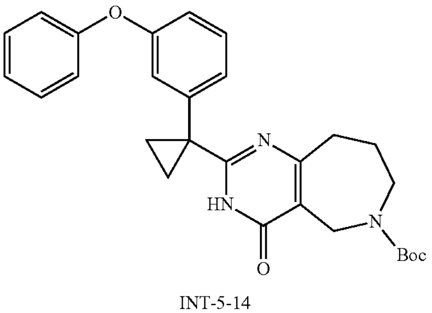 [SMILES: CC(C)(C)OC(=O)N1CCCc2nc(C3(c4cccc(Oc5ccccc5)c4)CC3)[nH]c(=O)c2C1] INT-5-14 | tert-butyl 4-oxo-2-(1-(3-phenoxyphenyl)cyclopropyl)-3,4,5,7,8,9-hexahydro-6H-pyrimido[5,4-c]azepine-6-carboxylate | (400 MHz, $CDCl_3$): δ 8.72-8.57 (1H, br. s), 7.41-7.33 (3H, m), 7.18-7.14 (1H, m), 7.11 (1H, d, J = 7.8 Hz), 7.08-7.04 (3H, m), 6.96 (1H, d, J = 7.3 Hz), 4.40 (2H, s), 3.66-3.50 (2H, br. s), 2.83-2.73 (2H, br. s), 1.91-1.82 (2H, m), 1.80-1.71 (2H, br. s), 1.45-1.41 (11H, m). LC-MS (Method-I) m/z: M + 1 obs 474.31, tR = 0.62 min. |

TABLE 5-3-continued

| | | |
|---|---|---|
| 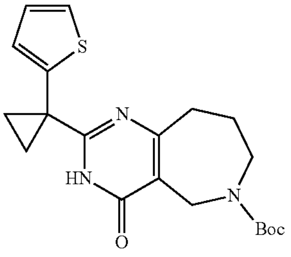<br>INT-5-15 | tert-butyl 4-oxo-2-(1-(thiophen-2-yl)cyclopropyl)-3,4,5,7,8,9-hexahydro-6H-pyrimido[5,4-c]azepine-6-carboxylate | (400 MHz, $CDCl_3$): δ 8.92 (1H, br. s), 7.37-7.30 (1H, m), 7.15-7.09 (1H, m), 7.07-7.00 (1H, m), 4.41 (2H, s), 3.62 (2H, br. s), 2.79 (2H, br. s), 1.94-1.83 (4H, m), 1.50-1.38 (11H, m). LC-MS (Method-B1) m/z: M + 1 obs 388.13, tR = 2.00 min. |
| 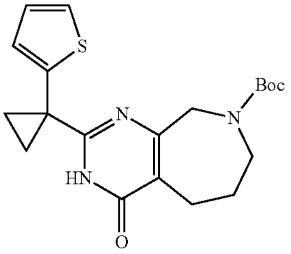<br>INT-5-16 | tert-butyl 4-oxo-2-(1-(thiophen-2-yl)cyclopropyl)-3,4,5,7,8,9-hexahydro-8H-pyrimido[4,5-c]azepine-8-carboxylate | LC-MS (Method-B1): m/z: M + 1 obs 388.13, tR = 2.00 min. |

TABLE 5-4

| | | |
|---|---|---|
| 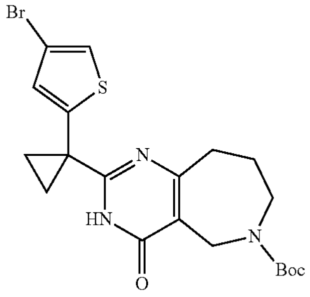<br>INT-5-17 | tert-butyl 2-(1-(4-bromothiophen-2-yl)cyclopropyl)-4-oxo-3,4,5,7,8,9-hexahydro-6H-pyrimido[5,4-c]azepine-6-carboxylate | (400 MHz, $CDCl_3$): δ 9.03 (1H, br. s), 7.24 (1H, s), 7.04 (1H, s), 4.41 (2H, s), 3.62 (2H, br. s), 2.79 (2H, br. s), 1.93-1.83 (4H, m), 1.48-1.38 (11H, m). LC-MS (Method-B1) m/z: M + 1 obs 466.0, tR = min. |
| 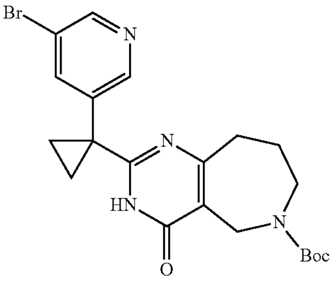<br>INT-5-18 | tert-butyl 2-(1-(5-bromopyridin-3-yl)cyclopropyl)-4-oxo-3,4,5,7,8,9-hexahydro-6H-pyrimido[5,4-c]azepine-6-carboxylate | (400 MHz, $CDCl_3$): δ 8.71-8.66 (1H, br), 8.60 (1H, d, J = 1.8 Hz), 7.89 (1H, t, J = 1.8 Hz), 4.40 (2H, s), 3.67-3.54 (2H, br), 2.85-2.74 (2H, br), 1.93-1.87 (2H, m), 1.86-1.75 (2H, br) 1.40-1.38 (11H, m), (one signal of NH proton is not observed). LC-MS (Method-I) m/z: M + 1 obs 461.17, tR = 0.52 min. |

TABLE 5-4-continued

| | | |
|---|---|---|
| 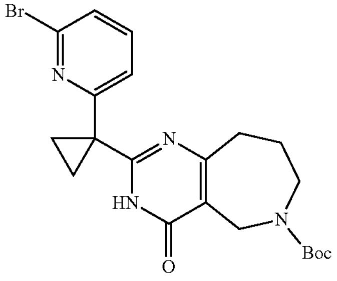 INT-5-19 | tert-butyl 2-(1-(6-bromopyridin-2-yl)cyclopropyl)-4-oxo-3,4,5,7,8,9-hexahydro-6H-pyrimido[5,4-c]azepine-6-carboxylate | LC-MS (Method-A1) m/z: M + 1 obs 461.19, tR = 2.14 min. |
| 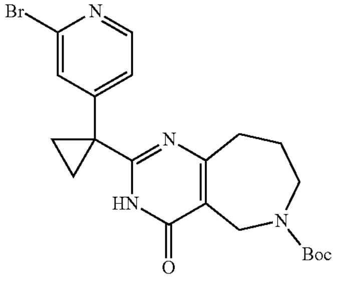 INT-5-20 | tert-butyl 2-(1-(2-bromopyridin-4-yl)cyclopropyl)-4-oxo-3,4,5,7,8,9-hexahydro-6H-pyrimido[5,4-c]azepine-6-carboxylate | (400 MHz, $CDCl_3$): δ 8.38 (1H, d, J = 5.0 Hz), 7.47 (1H, d, J = 1.3 Hz), 7.24 (1H, dd, J = 5.0, 1.3 Hz), 4.47-4.36 (2H, br. s), 3.69-3.53 (2H, br. s), 2.87-2.75 (2H, br. s), 1.94-1.88 (2H, m), 1.83-1.73 (2H, br. s), 1.40-1.36 (11H, m), (one signal of NH proton is not observed). LC-MS (Method-A1) m/z: M + 1 obs 461.19, tR = 2.17 min. |
| 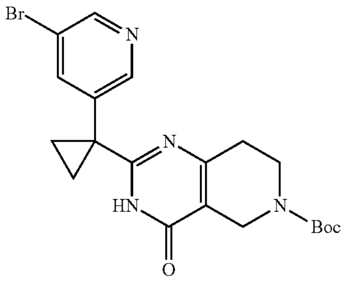 INT-5-21 | tert-butyl 2-(1-(5-bromopyridin-3-yl)cyclopropyl)-4-oxo-3,5,7,8-tetrahydropyrido[4,3-d]pyrimidine-6(4H)-carboxylate | (400 MHz, $CDCl_3$): δ 8.70-8.63 (1H, br. s), 8.59 (1H, d, J = 2.0 Hz), 7.88 (1H, t, J = 2.0 Hz), 4.30 (2H, s), 3.68-3.58 (2H, m), 2.69-2.59 (2H, m), 1.48 (9H, s), 1.84-1.75 (2H, br. s), 1.39-1.31 (2H, br. s), (one signal of NH proton is not observed). LC-MS (Method-I) m/z: M + 1 obs 447.14, tR = 0.51 min. |
| 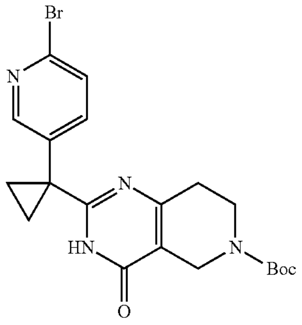 INT-5-22 | tert-butyl 2-(1-(6-bromopyridin-3-yl)cyclopropyl)-4-oxo-3,5,7,8-tetrahydropyrido[4,3-d]pyrimidine-6(4H)-carboxylate | (400 MHz, $CDCl_3$): δ 8.43 (1H, d, J = 1.8 Hz), 7.59 (1H, dd, J = 8.2, 1.8 Hz), 7.54 (1H, d, J = 8.2 Hz), 4.30 (2H, s), 3.65 (2H, t, J = 5.4 Hz), 2.65 (2H, t, J = 5.4 Hz), 1.85-1.79 (2H, br. s), 1.48 (9H, s), 1.34 (2H, dd, J = 7.3, 4.1 Hz), (one signal of NH proton is not observed). LC-MS (Method-I) m/z: M + 1 obs 447.13, tR = 0.52 min. |

TABLE 5-5

| | | |
|---|---|---|
| 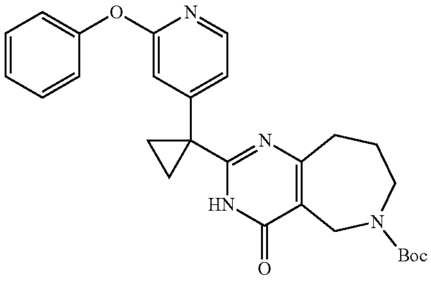 INT-5-23 | tert-butyl 4-oxo-2-(1-(2-phenoxypyridin-4-yl)cyclopropyl)-3,4,5,7,8,9-hexahydro-6H-pyrimido[5,4-c]azepine-6-carboxylate | (400 MHz, $CDCl_3$): δ 8.22 (1H, d, J = 2.4 Hz), 7.71 (1H, dd, J = 8.5, 2.4 Hz), 7.45-7.42 (2H, m), 7.26-7.23 (1H, m), 7.19-7.17 (2H, m), 6.95 (1H, d, J = 7.8 Hz), 4.39 (2H, s), 3.67-3.50 (2H, br. s), 2.85-2.72 (2H, br. s), 1.91-1.86 (2H, m), 1.84-1.74 (2H, br. s), 1.46-1.40 (11H, m), (one signal of NH proton is not observed). LC-MS (Method-I) m/z: M + 1 obs 475.31, tR = 0.58 min. |
| 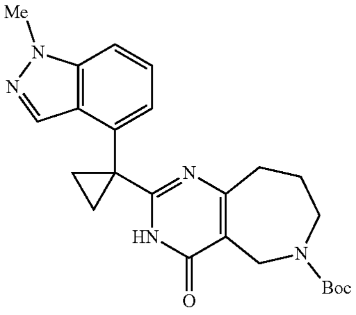 INT-5-24 | tert-butyl 2-(1-(1-methyl-1H-indazol-4-yl)cyclopropyl)-4-oxo-3,4,5,7,8,9-hexahydro-6H-pyrimido[5,4-c]azepine-6-carboxylate | (400 MHz, $CDCl_3$): δ 8.48 (s, 1H), 7.98 (d, J = 13.7 Hz, 1H), 7.57-7.34 (m, 2H), 7.20 (d, J = 6.4 Hz, 1H), 4.36 (s, 2H), 4.12 (s, 3H), 3.62 (s, 2H), 2.83 (s, 2H), 1.92 (s, 2H), 1.59 (s, 2H), 1.55-1.31 (m, 11H) LC-MS (Method-I) m/z: M + 1 obs 436.3, M − 1 obs 434.3, tR = 0.55 min |
| 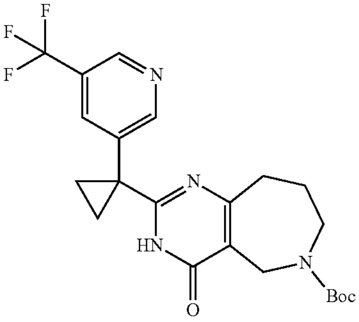 INT-5-25 | tert-butyl 4-oxo-2-(1-(5-(trifluoromethyl)pyridin-3-yl)cyclopropyl)-5,7,8,9-tetrahydro-3H-pyrimido[5,4-c]azepine-6(4H)-carboxylate | LC-MS (Method-I) m/z: M + 1 obs 451.24, tR = 0.55 min. |
| 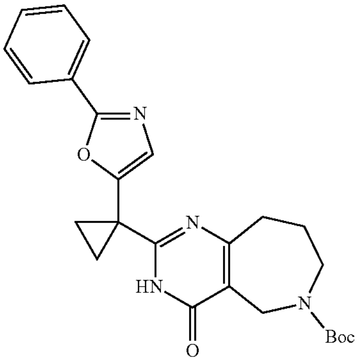 INT-5-26 | tert-butyl 4-oxo-2-(1-(2-phenyloxazol-5-yl)cyclopropyl)-3,4,5,7,8,9-hexahydro-6H-pyrimido[5,4-c]azepine-6-carboxylate | The structure is confirmed at the next step. |

TABLE 5-5-continued

| | | |
|---|---|---|
| 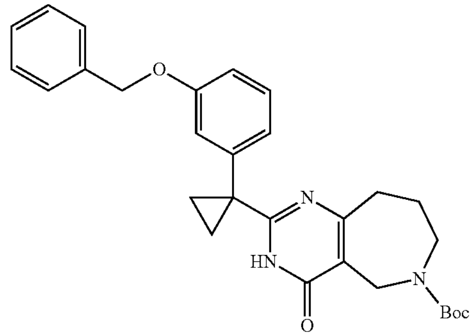 INT-5-27 | tert-butyl 2-(1-(3-(benzyloxy)phenyl)cyclo-propyl)-4-oxo-3,4,5,7,8,9-hexahydro-6H-pyrimido[5,4-c]azepine-6-carboxylate | (400 MHz, $CDCl_3$): δ 8.65 (1H, br. s), 7.71-7.29 (6H, m), 7.18-6.85 (3H, m), 5.06 (2H, s), 4.66-4.25 (2H, m), 3.90-3.41 (2H, m), 3.06-2.55 (2H, m), 2.02-1.84 (2H, m), 1.84-1.68 (2H, m), 1.43 (9H, br. s), 1.36-1.29 (2H, m). LC-MS (Method-I) m/z: M + 1 obs 488.3, M − 1 obs 486.3, tR = 0.62 min. |

Intermediate-6-1 (INT-6-1)

Synthesis of tert-butyl 4-oxo-2-(1-(3-(prop-1-en-2-yl)phenyl)cyclopropyl)-3,5,7,8-tetrahydropyrido[4,3-d]pyrimidine-6(4H)-carboxylate (INT-6-1)

{Chem. 27}

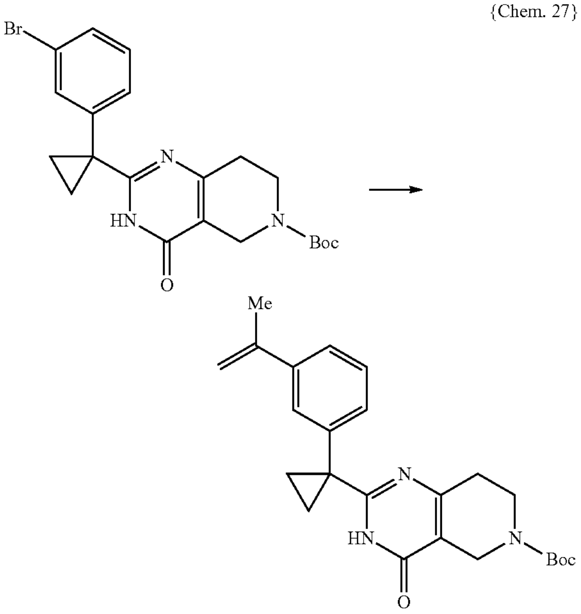

The mixture of INT-5-6 (466 mg, 1.04 mmol), 4,4,5,5-tetramethyl-2-(prop-1-en-2-yl)-1,3,2-dioxaborolane (947 mg, 5.64 mmol), palladium (II) acetate (70.3 mg, 0.313 mmol) and triphenylphosphine (164 mg, 0.626 mmol) in 1,4-dioxane (2 mL) and saturated aqueous sodium bicarbonate (2 mL) is stirred at 80° C. for 1 hr. After cooled down to rt, the mixture is extracted with ethyl acetate and the organic layer is dried over sodium sulfate, filtered and concentrated in vacuo to give crude product, which is purified by column chromatography on silica gel (25 g) eluting with a gradient of 24 to 100% ethyl acetate in n-hexane to give the titled compound (245 mg, 58% yield) as a brown amorphous solid.

$^1$H-NMR (400 MHz, $CDCl_3$): delta 8.61 (1H, s), 7.49-7.46 (2H, m), 7.41-7.36 (1H, m), 7.31-7.28 (1H, m), 5.38 (1H, s), 5.15-5.14 (1H, m), 4.29 (2H, s), 3.65 (2H, t, J=5.7 Hz), 2.65-2.65 (2H, m), 2.15 (3H, d, J=0.9 Hz), 1.79 (2H, dd, J=6.8, 4.0 Hz), 1.47 (9H, s), 1.37 (2H, dd, J=6.8, 4.0 Hz).

LC-MS (Method-1) m/z: M+1 obs 408.29, tR=0.61 min.

The following pyrimidin-4(3H)-one derivatives (INT-6-2 to INT-6-17) are prepared according to the procedure of intermediate-6-1 from the synthesized halide derivatives (INT-5-3, INT-5-6, INT-5-9, INT-5-17, INT-5-18 or INT-5-21) and known boronic acid derivatives in Tables 6-1 to 6-3.

TABLE 6-1

| Structure | Chemical Name | $^1$H-NMR & LC-MS (m/z) |
|---|---|---|
| 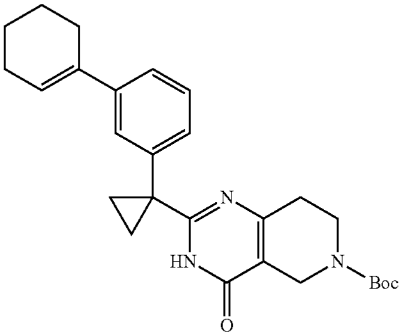 INT-6-2 | tert-butyl 4-oxo-2-(1-(2',3',4',5'-tetrahydro-[1,1'-biphenyl]-3-yl)cyclopropyl)-3,5,7,8-tetrahydropyrido[4,3-d]pyrimidine-6(4H)-carboxylate | (400 MHz, $CDCl_3$): δ 8.67-8.59 (1H, br.s), 7.39-7.33 (3H, m), 7.26-7.20 (1H, m), 6.17-6.11 (1H, m), 4.29 (2H, s), 3.64 (2H, t, J = 5.5 Hz), 2.69-2.58 (2H, m), 2.43-2.35 (2H, m), 2.25-2.16 (2H, m), 1.82-1.76 (3H, m), 1.70-1.62 (3H, m), 1.47 (9H, s), 1.36 (2H, dd, J = 7.1, 3.9 Hz). LC-MS (Method-I) m/z: M + 1 obs 448.34, tR = 0.67 min. |

TABLE 6-1-continued

| Structure | Chemical Name | $^1$H-NMR & LC-MS (m/z) |
|---|---|---|
| 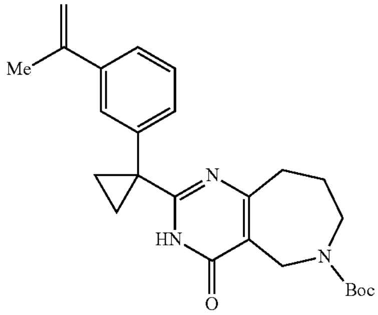 INT-6-3 | tert-butyl 4-oxo-2-(1-(3-(prop-1-en-2-yl)phenyl)cyclopropyl)-3,4,5,7,8,9-hexahydro-6H-pyrimido[5,4-c]azepine-6-carboxylate | LC-MS (Method-I) m/z: M + 1 obs 422.31, tR = 0.60 min. |
| 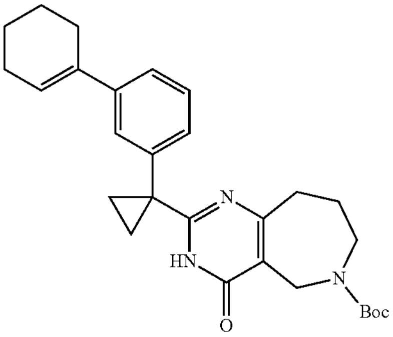 INT-6-4 | tert-butyl 4-oxo-2-(1-(2',3',4',5'-tetrahydro-[1,1'-biphenyl]-3-yl)cyclopropyl)-3,4,5,7,8,9-hexahydro-6H-pyrimido[5,4-c]azepine-6-carboxylate | LC-MS (Method-K) m/z: M + 1 obs 462.3, tR = 0.63 min. |
| 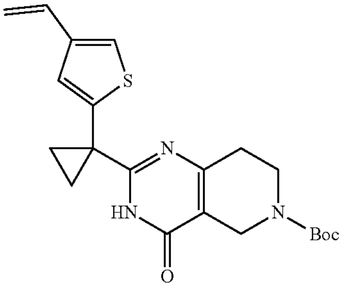 INT-6-5 | tert-butyl 4-oxo-2-(1-(4-vinylthiophen-2-yl)cyclopropyl)-3,5,7,8-tetrahydropyrido[4,3-d]pyrimidine-6(4H)-carboxylate | LC-MS (Method-I) m/z: M + 1 obs 400.23, tR = 0.58 min. |
| 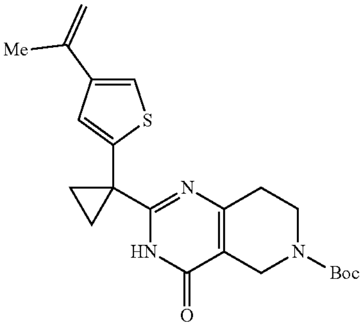 INT-6-6 | tert-butyl 4-oxo-2-(1-(4-(prop-1-en-2-yl)thiophen-2-yl)cyclopropyl)-3,5,7,8-tetrahydropyrido[4,3-d]pyrimidine-6(4H)-carboxylate | (400 MHz, $CDCl_3$): δ 9.00-8.91 (1H, br.s), 7.26 (1H, d, J = 1.4 Hz), 7.17 (1H, d, J = 1.4 Hz), 5.31 (1H, s), 5.07-5.06 (1H, m), 4.31 (2H, s), 3.64 (2H, t, J = 5.7 Hz), 2.67-2.59 (2H, m), 2.10 (3H, s), 1.86 (2H, dd, J = 7.3, 3.7 Hz), 1.50-1.45 (11H, m). LC-MS (Method-I) m/z: M + 1 obs 414.26, tR = 0.60 min. |

TABLE 6-2

| | | |
|---|---|---|
| 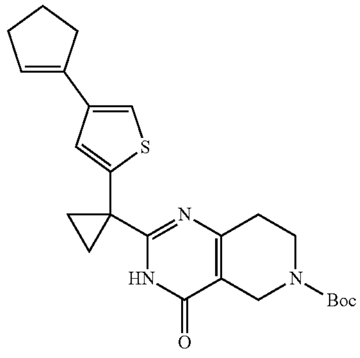 INT-6-7 | tert-butyl 2-(1-(4-(cyclopent-1-en-1-yl)thiophen-2-yl)cyclopropyl)-4-oxo-3,5,7,8-tetrahydropyrido[4,3-d]pyrimidine-6(4H)-carboxylate | LC-MS (Method-1) m/z: M + 1 obs 440.30, tR = 0.64 min. |
| 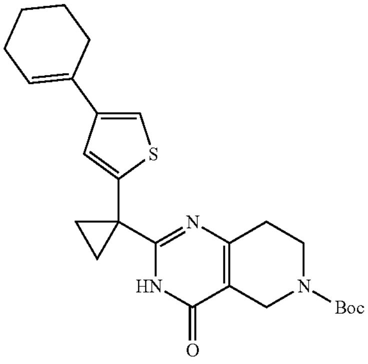 INT-6-8 | tert-butyl 2-(1-(4-(cyclohex-1-en-1-yl)thiophen-2-yl)cyclopropyl)-4-oxo-3,5,7,8-tetrahydropyrido[4,3-d]pyrimidine-6(4H)-carboxylate | (400 MHz, $CDCl_3$): δ 9.05-8.92 (1H, br.s), 7.23 (1H, d, J = 1.2 Hz), 7.04 (1H, d, J = 1.2 Hz), 6.15-6.13 (1H, m), 4.30 (2H, s), 3.64 (2H, t, J = 5.7 Hz), 2.68-2.58 (2H, m), 2.37-2.34 (2H, m), 2.20-2.18 (2H, m), 1.84 (2H, dd, J = 7.1, 3.9 Hz), 1.80-1.74 (2H, m), 1.64-1.61 (2H, m), 1.48-1.45 (11H, m). LC-MS (Method-I) m/z: M + 1 obs 454.29, tR = 0.68 min. |
| 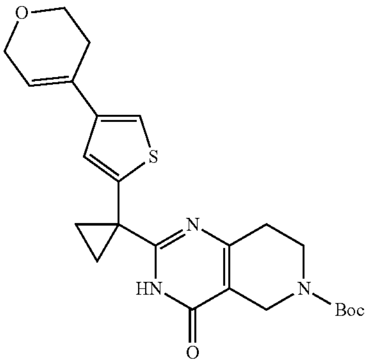 INT-6-9 | tert-butyl 2-(1-(4-(3,6-dihydro-2H-pyran-4-yl)thiophen-2-yl)cyclopropyl)-4-oxo-3,5,7,8-tetrahydropyrido[4,3-d]pyrimidine-6(4H)-carboxylate | (400 MHz, $CDCl_3$): δ 8.98-8.91 (1H, br.s), 7.22 (1H, d, J = 1.4 Hz), 7.10 (1H, d, J = 1.4 Hz), 6.08-6.07 (1H, m), 4.31-4.30 (4H, m), 3.92 (2H, t, J = 5.7 Hz), 3.64 (2H, t, J = 5.7 Hz), 2.67-2.59 (2H, m), 2.48-2.47 (2H, m), 1.86 (2H, dd, J = 7.1, 3.9 Hz), 1.48-1.46 (11H, m). LC-MS (Method-A1) m/z: M + 1 obs 456.18, tR = 2.27 min. |
| 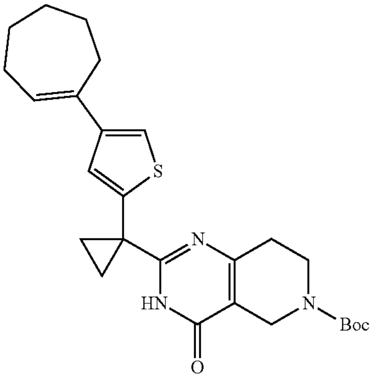 INT-6-10 | tert-butyl 2-(1-(4-(cyclohept-1-en-1-yl)thiophen-2-yl)cyclopropyl)-4-oxo-3,5,7,8-tetrahydropyrido[4,3-d]pyrimidine-6(4H)-carboxylate | (400 MHz, $CDCl_3$): δ 9.03-8.95 (1H, br.s), 7.16 (1H, d, J = 1.4 Hz), 7.03 (1H, d, J = 1.4 Hz), 6.22 (1H, t, J = 6.6 Hz), 4.31 (2H, s), 3.64 (2H, t, J = 5.9 Hz), 2.67-2.59 (2H, m), 2.56-2.53 (2H, m), 2.28 (2H, dd, J = 11.2, 6.6 Hz), 1.85-1.79 (4H, m), 1.66-1.52 (4H, m), 1.48-1.44 (11H, m). LC-MS (Method-1) m/z: M + 1 obs 468.30, tR = 0.48 min. |

TABLE 6-2-continued

| | | |
|---|---|---|
| 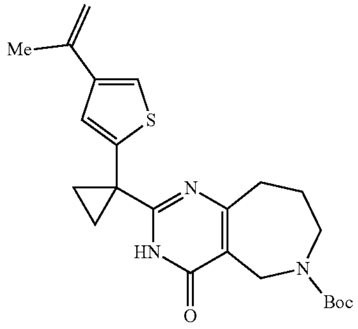 INT-6-11 | tert-butyl 4-oxo-2-(1-(4-(prop-1-en-2-yl)thiophen-2-yl)cyclopropyl)-3,4,5,7,8,9-hexahydro-6H-pyrimido[5,4-c]azepine-6-carboxylate | LC-MS (Method-I) m/z: M + 1 obs 428.26, tR = 0.61 min. |

TABLE 6-3

| | | |
|---|---|---|
| 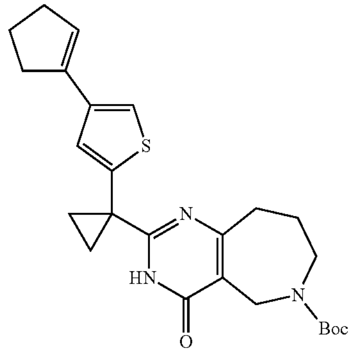 INT-6-12 | tert-butyl 2-(1-(4-(cyclopent-1-en-1-yl)thiophen-2-yl)cyclopropyl)-4-oxo-3,4,5,7,8,9-hexahydro-6H-pyrimido[5,4-c]azepine-6-carboxylate | The structure is confirmed at the next step. |
| 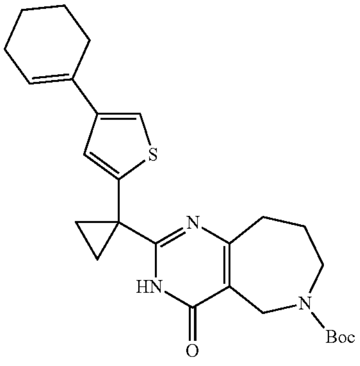 INT-6-13 | tert-butyl 2-(1-(4-(cyclohex-1-en-1-yl)thiophen-2-yl)cyclopropyl)-4-oxo-3,4,5,7,8,9-hexahydro-6H-pyrimido[5,4-c]azepine-6-carboxylate | LC-MS (Method-I) m/z: M + 1 obs 468.30, tR = 0.66 min. |

TABLE 6-3-continued

| | | |
|---|---|---|
| 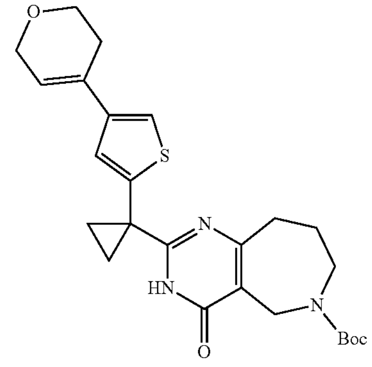<br>INT-6-14 | tert-butyl 2-(1-(4-(3,6-dihydro-2H-pyran-4-yl)thiophen-2-yl)cyclopropyl)-4-oxo-3,4,5,7,8,9-hexahydro-6H-pyrimido[5,4-c]azepine-6-carboxylate | The structure is confirmed at the next step. |
| 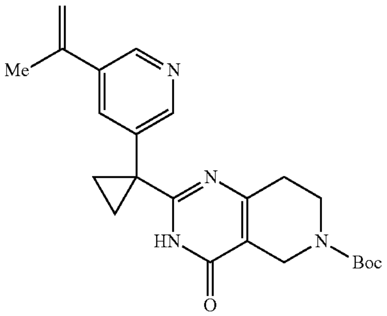<br>INT-6-15 | tert-butyl 4-oxo-2-(1-(5-(prop-1-en-2-yl)pyridin-3-yl)cyclopropyl)-3,5,7,8-tetrahydropyrido[4,3-d]pyrimidine-6(4H)-carboxylate | (400 MHz, $CDCl_3$): δ 8.74 (1H, d, J = 1.9 Hz), 8.56 (1H, d, J = 1.9 Hz), 7.73 (1H, t, J = 1.9 Hz), 5.46 (1H, s), 5.25 (1H, s), 4.30 (2H, s), 3.65 (2H, t, J = 5.7 Hz), 2.70-2.61 (2H, br.s), 2.18 (3H, s), 1.87-1.80 (2H, m), 1.47 (9H, s), 1.38 (2H, dd, J = 7.1, 4.3 Hz), (one signal of NH proton is not observed). LC-MS (Method-I) m/z: M + 1 obs 409.29, tR = 0.54 min. |
| 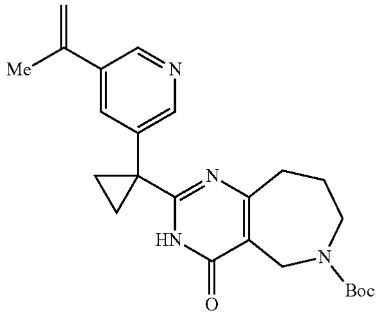<br>INT-6-16 | tert-butyl 4-oxo-2-(1-(5-(prop-1-en-2-yl)pyridin-3-yl)cyclopropyl)-3,4,5,7,8,9-hexahydro-6H-pyrimido[5,4-c]azepine-6-carboxylate | (400 MHz, $CDCl_3$): δ 8.73 (1H, d, J = 1.8 Hz), 8.57 (1H, d, J = 1.8 Hz), 7.74 (1H, t, J = 1.8 Hz), 5.46 (1H, s), 5.25 (1H, s), 4.40 (2H, s), 3.70-3.50 (2H, br.s), 2.89-2.74 (2H, br.s), 2.18 (3H, s), 1.93-1.85 (4H, m), 1.40-1.37 (11H, m), (one signal of NH proton is not observed). LC-MS (Method-I) m/z: M + 1 obs 423.33, tR = 0.53 min. |
| 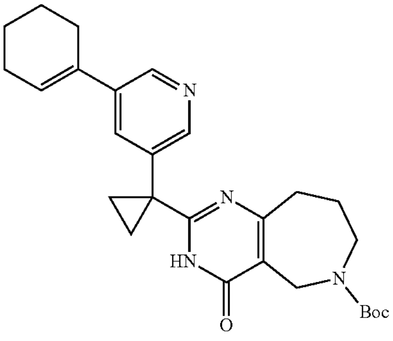<br>INT-6-17 | tert-butyl 2-(1-(5-(cyclohex-1-en-1-yl)pyridin-3-yl)cyclopropyl)-4-oxo-3,4,5,7,8,9-hexahydro-6H-pyrimido[5,4-c]azepine-6-carboxylate | (400 MHz, $CDCl_3$): δ 8.67-8.62 (1H, br.s), 8.53-8.47 (1H, br.s), 7.65 (1H, t, J = 2.1 Hz), 6.23-6.21 (1H, m), 4.39 (2H, s), 3.67-3.53 (2H, br.s), 2.85-2.74 (2H, br.s), 2.41-2.38 (2H, m), 2.27-2.22 (2H, m), 1.92-1.78 (6H, m), 1.71-1.65 (2H, m), 1.40-1.35 (11H, m), (one signal of NH proton is not observed). LC-MS (Method-I) m/z: M + 1 obs 463.36, tR = 0.58 min. |

Intermediate-7-1 (INT-7-1)

Synthesis of tert-butyl 2-(1-(3-isopropylphenyl) cyclopropyl)-4-oxo-3,5,7,8-tetrahydropyrido[4,3-d] pyrimidine-6(4H)-carboxylate (INT-7-1)

{Chem. 28}

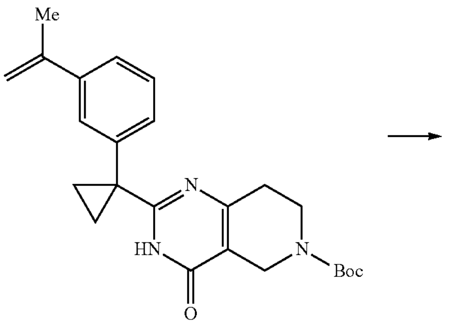

-continued

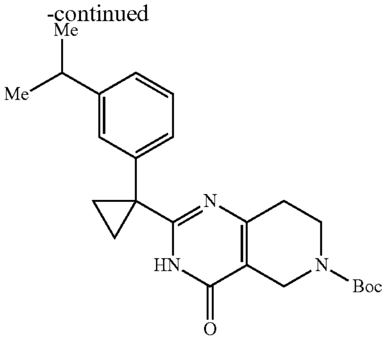

The mixture of INT-6-1 (245 mg, 0.601 mmol) and Pd/C (Pd 10%) (49 mg) in MeOH (1 mL) is stirred overnight at room temperture under hydrogen atmosphere. The reaction mixture is filtered through celite pad to give the MeOH solution of titled compound. The solution is used in the next reaction without further purification.

LC-MS (Method-1) m/z: M+1 obs 410.30, tR=0.63 min.

The following pyrimidin-4(3H)-one derivatives (INT-7-2 to INT-7-17) are prepared according to the procedure of intermediate-7-1 or the general synthesis in scheme-10 from the synthesized vinyl derivatives (INT-6-2 to INT-6-17) in Tables 7-1 to 7-3.

TABLE 7-1

| Structure | Chemical Name | LC-MS (m/z) |
|---|---|---|
| 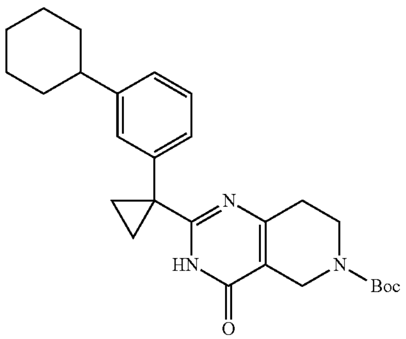 INT-7-2 | tert-butyl 2-(1-(3-cyclohexylphenyl) cyclopropyl)-4-oxo-3,5,7,8-tetrahydropyrido[4,3-d]pyrimidine-6(4H)-carboxylate | LC-MS (Method-A1) m/z: M + 1 obs 450.32, tR = 2.61 min. |
| 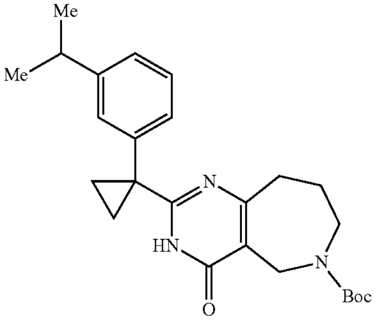 INT-7-3 | tert-butyl 2-(1-(3-isopropylphenyl)cyclopropyl)-4-oxo-3,4,5,7,8,9-hexahydro-6H-pyrimido[5,4-c]azepine-6-carboxylate | LC-MS (Method-I) m/z: M + 1 obs 424.39, tR = 0.62 min. |

TABLE 7-1-continued

| Structure | Chemical Name | LC-MS (m/z) |
|---|---|---|
| 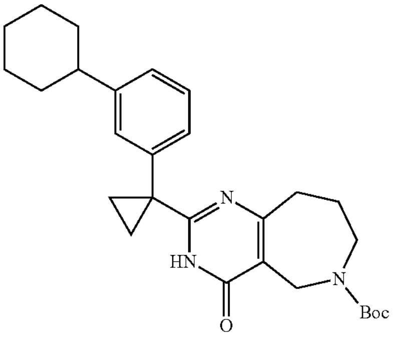 INT-7-4 | tert-butyl 2-(1-(3-cyclohexylphenyl) cyclopropyl)-4-oxo-3,4,5,7,8,9-hexahydro-6H-pyrimido[5,4-c]azepine-6-carboxylate | LC-MS (Method-I) m/z: M + 1 obs 464.4, tR = 0.66 min. |
| 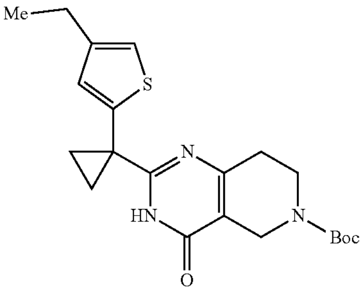 INT-7-5 | tert-butyl 2-(1-(4-ethylthiophen-2-yl)cyclopropyl)-4-oxo-3,5,7,8-tetrahydropyrido[4,3-d]pyrimidine-6(4H)-carboxylate | LC-MS (Method-A1) m/z: M + 1 obs 402.27, tR = 2.34 min. |
| 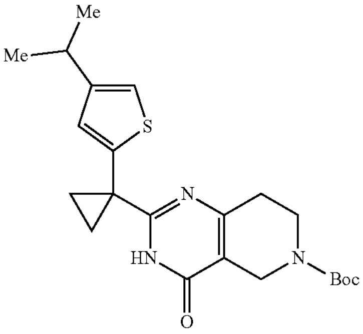 INT-7-6 | tert-butyl 2-(1-(4-isopropylthiophen-2-yl)cyclopropyl)-4-oxo-3,5,7,8-tetrahydropyrido[4,3-d]pyrimidine-6(4H)-carboxylate | LC-MS (Method-A1) m/z: M + 1 obs 416.01, tR = 2.37 min. |

TABLE 7-2

| | | |
|---|---|---|
| 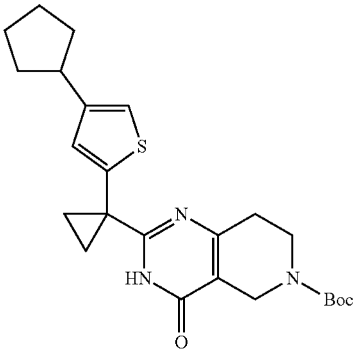 INT-7-7 | tert-butyl 2-(1-(4-cyclopentylthiophen-2-yl)cyclopropyl)-4-oxo-3,5,7,8-tetrahydropyrido[4,3-d]pyrimidine-6(4H)-carboxylate | LC-MS (Method-A1) m/z: M + 1 obs 442.27, tR = 2.54 min. |

TABLE 7-2-continued

| | | |
|---|---|---|
| 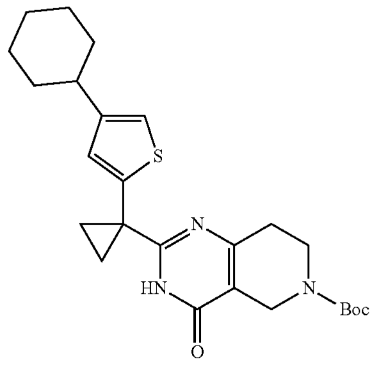<br>INT-7-8 | tert-butyl 2-(1-(4-cyclohexylthiophen-2-yl)cyclopropyl)-4-oxo-3,5,7,8-tetrahydropyrido[4,3-d]pyrimidine-6(4H)-carboxylate | LC-MS (Method-A1) m/z: M + 1 obs 456.21, tR = 2.71 min. |
| 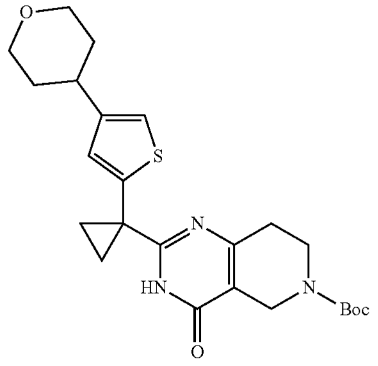<br>INT-7-9 | tert-butyl 4-oxo-2-(1-(4-(tetrahydro-2H-pyran-4-yl)thiophen-2-yl)cyclopropyl)-3,5,7,8-tetrahydropyrido[4,3-d]pyrimidine-6(4H)-carboxylate | LC-MS (Method-A1) m/z: M + 1 obs 458.18, tR = 2.27 min. |
| 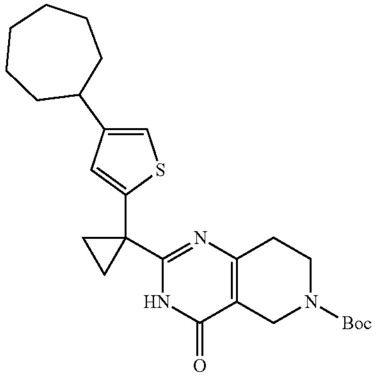<br>INT-7-10 | tert-butyl 2-(1-(4-cycloheptylthiophen-2-yl)cyclopropyl)-4-oxo-3,5,7,8-tetrahydropyrido[4,3-d]pyrimidine-6(4H)-carboxylate | LC-MS (Method-A1) m/z: M + 1 obs 470.30, tR = 2.81 min. |
| 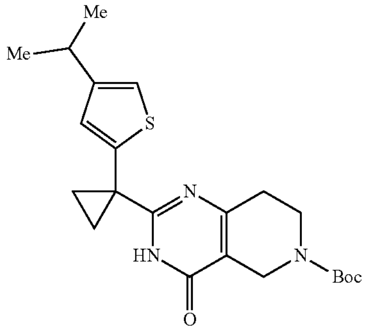<br>INT-7-11 | tert-butyl 2-(1-(4-isopropylthiophen-2-yl)cyclopropyl)-4-oxo-3,4,5,7,8,9-hexahydro-6H-pyrimido[5,4-c]azepine-6-carboxylate | LC-MS (Method-A1) m/z: M + 1 obs 430.37, tR = 2.41 min. |

TABLE 7-3

| | | |
|---|---|---|
| 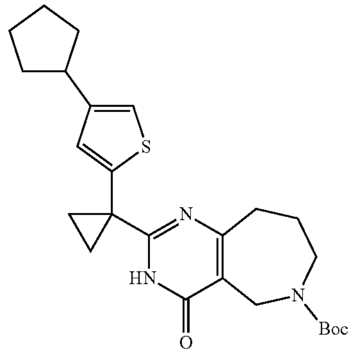 INT-7-12 | tert-butyl 2-(1-(4-cyclopentylthiophen-2-yl)cyclopropyl)-4-oxo-3,4,5,7,8,9-hexahydro-6H-pyrimido[5,4-c]azepine-6-carboxylate | LC-MS (Method-I) m/z: M + 1 obs 356.2, M − 1 obs 354.2, tR = 0.55 min. |
| 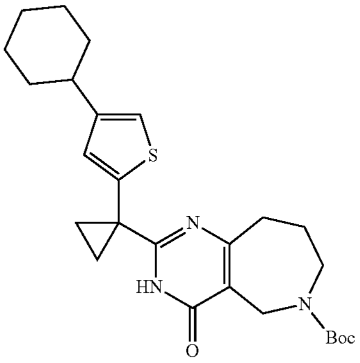 INT-7-13 | tert-butyl 2-(1-(4-cyclohexylthiophen-2-yl)cyclopropyl)-4-oxo-3,4,5,7,8,9-hexahydro-6H-pyrimido[5,4-c]azepine-6-carboxylate | LC-MS (Method-I) m/z: M + 1 obs 470.42, tR = 2.68 min. |
| 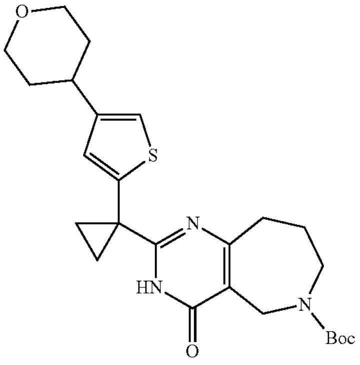 INT-7-14 | tert-butyl 4-oxo-2-(1-(4-(tetrahydro-2H-pyran-4-yl)thiophen-2-yl)cyclopropyl)-3,4,5,7,8,9-hexahydro-6H-pyrimido[5,4-c]azepine-6-carboxylate | LC-MS (Method-I) m/z: M + 1 obs 472.3, M − 1 obs 470.3, tR = 0.57 min. |
| 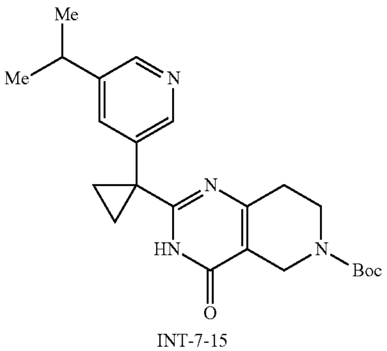 [SMILES: CC(C)c1cncc(C2(c3nc4c(c(=O)[nH]3)CN(C(=O)OC(C)(C)C)CC4)CC2)c1] INT-7-15 | tert-butyl 2-(1-(5-isopropylpyridin-3-yl)cyclopropyl)-4-oxo-3,5,7,8-tetrahydropyrido[4,3-d]pyrimidine-6(4H)-carboxylate | LC-MS (Method-I) m/z: M + 1 obs 411.31, tR = 0.55 min. |

TABLE 7-3-continued

| | | |
|---|---|---|
| 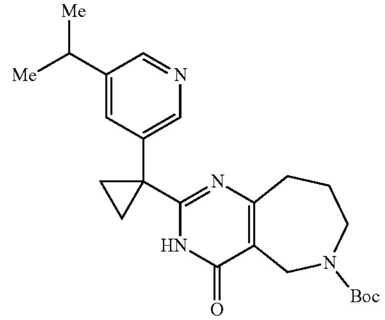 INT-7-16 | tert-butyl 2-(1-(5-isopropylpyridin-3-yl)cyclopropyl)-4-oxo-3,4,5,7,8,9-hexahydro-6H-pyrimido[5,4-c]azepine-6-carboxylate | LC-MS (Method-I) m/z: M + 1 obs 425.33, tR = 0.53 min. |
| 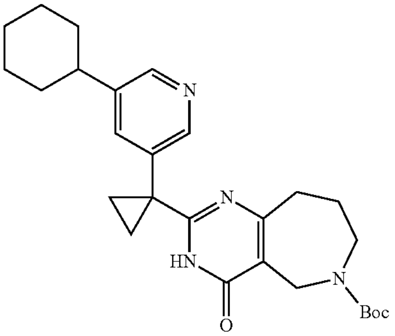 INT-7-17 | tert-butyl 2-(1-(5-cyclohexylpyridin-3-yl)cyclopropyl)-4-oxo-3,4,5,7,8,9-hexahydro-6H-pyrimido[5,4-c]azepine-6-carboxylate | LC-MS (Method-I) m/z: M + 1 obs 465.36, tR = 2.34 min. |

Intermediate-8-1 (INT-8-1)

Synthesis of 2-(1-phenylcyclopropyl)-6,7,8,9-tetrahydro-3H-pyrimido[4,5-d]azepin-4(5H)-one·hydrochloride (INT-8-1)

{Chem. 29}

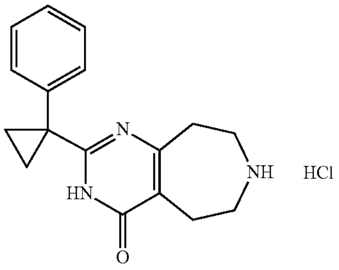

To a solution of INT-5-1 (0.98 g, 2.57 mmol) in MeOH (20 mL) is added 4M HCl-dioxane solution (2.8 mL) at room temperature. The mixture is stirred at 60° C. for 2 hrs. The reaction mixture is concentrated under reduced pressure to give the titled compound (1.10 g) as a yellow solid.

$^1$H-NMR (300 MHz, DMSO-$d_6$): delta 7.30-7.19 (5H, m), 2.76 (4H, s), 2.66 (4H, s), 1.46-1.42 (2H, m), 1.20-1.16 (2H, m), (two signals of NH proton are not observed).

LC-MS (Method-B) m/z: M+1 obs 282.23, M−1 obs 280.26, tR=2.30 min.

Intermediate-8-2 (INT-8-2)

Synthesis of 2-(1-phenyicyclopropyl)-6,7-dihydro-3H-pyrrolo[3,4-d]pyrimidin-4(5H)-one hydrochloride (INT-8-2)

{Chem. 30}

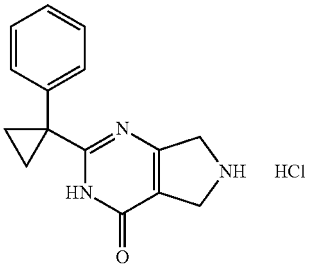

The titled compound is prepared according to the procedure described in INT-8-1 from above INT-5-2 (230 mg, 0.651 mmol) and 4M HCl-dioxane solution (0.7 mL) to give the titled compound (228 mg) as a yellow solid.

$^1$H-NMR (300 MHz, $CD_3OD$): delta 7.42-7.28 (5H, m), 4.45 (4H, s), 1.68-1.64 (2H, s), 1.44-1.40 (2H, m), (two signals of NH proton are not observed).

LC-MS (Method-B) m/z: M+1 obs 254.23, M−1 obs 252.27, tR=0.96 min.

The following pyrimidin-4(3H)-one derivatives (INT-8-3 to INT-8-41) are prepared according to the procedure of INT-8-1 from the synthesized N-Boc pyrimidin-4(3H)-one derivatives (INT-5-4, INT-5-5, INT-5-7 to INT-5-20, INT-5-23 to INT-5-27, INT-6-3, INT-7-1 to INT-7-17) in Tables 8-1 to 8-7.

TABLE 8-1

| Structure | Chemical Name | $^1$H-NMR & LC-MS (m/z) |
|---|---|---|
| 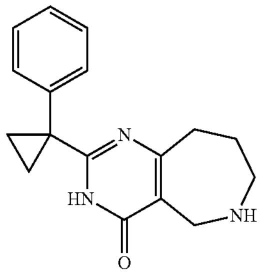 INT-8-3 | 2-(1-phenylcyclopropyl)-3,5,6,7,8,9-hexahydro-4H-pyrimido[5,4-c]azepin-4-one | (300 MHz, $CDCl_3$): δ 7.44-7.36 (5H, m), 3.86 (2H, br.s), 3.20-3.10 (2H, m), 2.93-2.83 (2H, m), 1.82-1.70 (4H, m), 1.38-1.30 (2H, m), (two signals of NH proton are not observed). |
| 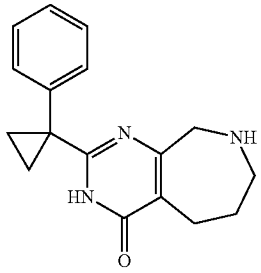 INT-8-4 | 2-(1-phenylcyclopropyl)-3,5,6,7,8,9-hexahydro-4H-pyrimido[4,5-c]azepin-4-one | (300 MHz, $CDCl_3$): δ 7.44-7.36 (5H, m), 3.85 (2H, br.s), 3.17-3.10 (2H, m), 2.82-2.74 (2H, m), 1.80-1.65 (4H, m), 1.36-1.30 (2H, m), (two signals of NH proton are not observed). |
| 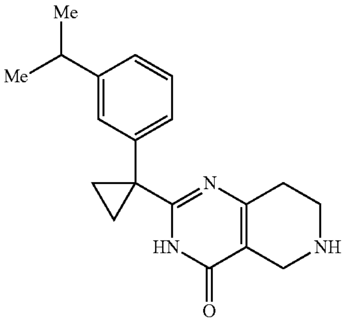 INT-8-5 | 2-(1-(3-isopropylphenyl)cyclopropyl)-5,6,7,8-tetrahydropyrido[4,3-d]pyrimidin-4(3H)-one | LC-MS (Method-I) m/z: M + 1 obs 310.16, tR = 0.48 min. |
| 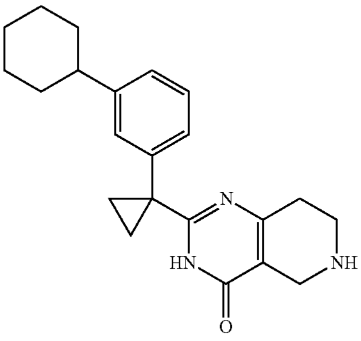 INT-8-6 | 2-(1-(3-cyclohexylphenyl) cyclopropyl)-5,6,7,8-tetrahydropyrido[4,3-d]pyrimidin-4(3H)-one | LC-MS (Method-I) m/z: M + 1 obs 350.22, tR = 0.53 min. |

TABLE 8-1-continued

| Structure | Chemical Name | $^1$H-NMR & LC-MS (m/z) |
|---|---|---|
| 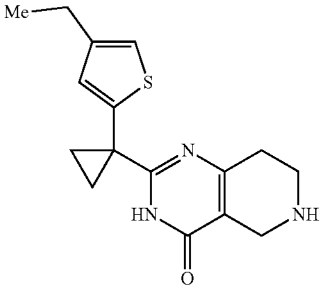 INT-8-7 | 2-(1-(4-ethylthiophen-2-yl)cyclopropyl)-5,6,7,8-tetrahydropyrido[4,3-d]pyrimidin-4(3H)-one | LC-MS (Method-I) m/z: M + 1 obs 302.15, tR = 0.45 min. |

TABLE 8-2

| | | |
|---|---|---|
| 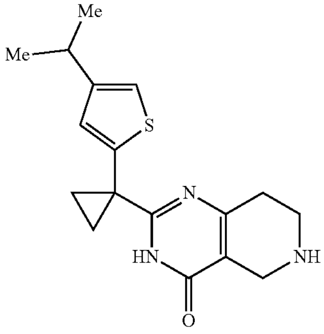 [SMILES: CC(C)c1csc(C2(c3nc4c(c(=O)[nH]3)CNCC4)CC2)c1] INT-8-8 | 2-(1-(4-isopropylthiophen-2-yl)cyclopropyl)-5,6,7,8-tetrahydropyrido[4,3-d]pyrimidin-4(3H)-one | LC-MS (Method-I) m/z: M + 1 obs 316.09, tR = 1.83 min. |
| 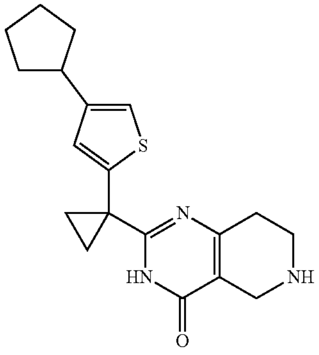 [SMILES: O=c1[nH]c(C2(c3cc(C4CCCC4)cs3)CC2)nc2c1CNCC2] INT-8-9 | 2-(1-(4-cyclopentylthiophen-2-yl)cyclopropyl)-5,6,7,8-tetrahydropyrido[4,3-d]pyrimidin-4(3H)-one | LC-MS (Method-I) m/z: M + 1 obs 342.16, tR = 0.51 min. |

TABLE 8-2-continued
| | | |
|---|---|---|
| 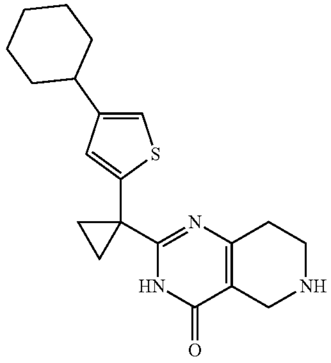 [SMILES: O=c1[nH]c(C2(c3cc(C4CCCCC4)cs3)CC2)nc2c1CNCC2]<br>INT-8-10 | 2-(1-(4-cyclohexylthiophen-2-yl)cyclopropyl)-5,6,7,8-tetrahydropyrido[4,3-d]pyrimidin-4(3H)-one | LC-MS (Method-A1) m/z: M + 1 obs 356.07, tR = 2.07 min. |
| 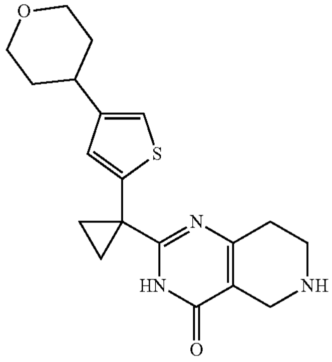 [SMILES: O=c1[nH]c(C2(c3cc(C4CCOCC4)cs3)CC2)nc2c1CNCC2]<br>INT-8-11 | 2-(1-(4-(tetrahydro-2H-pyran-4-yl)thiophen-2-yl)cyclopropyl)-5,6,7,8-tetrahydropyrido[4,3-d]pyrimidin-4(3H)-one | LC-MS (Method-A1) m/z: M + 1 obs 358.01, tR = 1.67 min. |
| 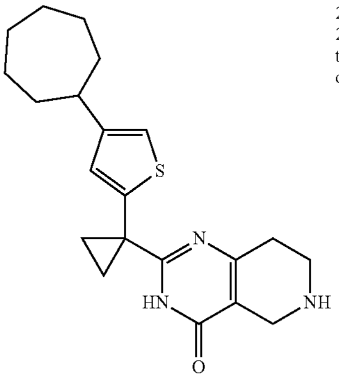<br>INT-8-12 | 2-(1-(4-cycloheptylthiophen-2-yl)cyclopropyl)-5,6,7,8-tetrahydropyrido[4,3-d]pyrimidin-4(3H)-one | LC-MS (Method-I) m/z: M + 1 obs 370.25, tR = 0.56 min. |

TABLE 8-3

| | | |
|---|---|---|
| 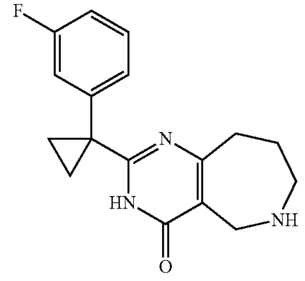 [SMILES: O=c1[nH]c(C2(c3cccc(F)c3)CC2)nc2c1CNCCC2] INT-8-13 | 2-(1-(3-fluorophenyl)cyclopropyl)-3,5,6,7,8,9-hexahydro-4H-pyrimido[5,4-c]azepin-4-one | (400 MHz, $CDCl_3$): δ 7.42-7.35 (1H, m), 7.20-7.16 (1H, m), 7.12-7.04 (2H, m), 3.87 (2H, s), 3.18-3.12 (2H, m), 2.90-2.84 (2H, m), 1.80-1.72 (4H, m), 1.35-1.30 (2H, m), (two signals of NH proton are not observed). LC-MS (Method-H) m/z: M + 1 obs 300.26, tR = 2.00 min. |
| 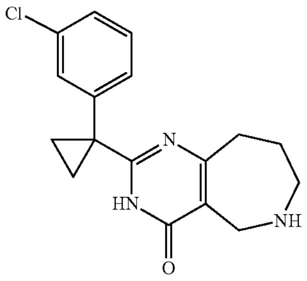 [SMILES: O=c1[nH]c(C2(c3cccc(Cl)c3)CC2)nc2c1CNCCC2] INT-8-14 | 2-(1-(3-chlorophenyl)cyclopropyl)-3,5,6,7,8,9-hexahydro-4H-pyrimido[5,4-c]azepin-4-one | (400 MHz, $CDCl_3$): δ 7.40-7.38 (1H, m), 7.36-7.34 (2H, m), 7.30-7.26 (1H, m), 3.87 (2H, s), 3.18-3.12 (2H, m), 2.90-2.84 (2H, m), 1.80-1.72 (4H, m), 1.34-1.30 (2H, m), (two signals of NH proton are not observed). LC-MS (Method-H) m/z: M + 1 obs 316.19, tR = 2.00 min. |
| 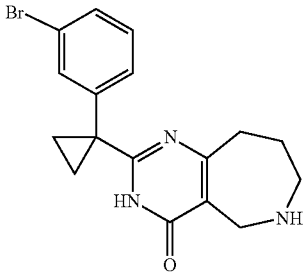 [SMILES: O=c1[nH]c(C2(c3cccc(Br)c3)CC2)nc2c1CNCCC2] INT-8-15 | 2-(1-(3-bromophenyl)cyclopropyl)-3,5,6,7,8,9-hexahydro-4H-pyrimido[5,4-c]azepin-4-one | (400 MHz, $CDCl_3$): δ 7.56-7.49 (2H, m), 7.35-7.26 (2H, m), 3.87 (2H, s), 3.18-3.12 (2H, m), 2.90-2.85 (2H, m), 1.80-1.72 (4H, m), 1.34-1.30 (2H, m), (two signals of NH proton are not observed). LC-MS (Method-B1) m/z: M + 1 obs 359.9, tR = 1.75 min. |
| 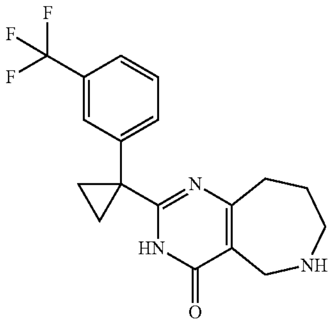 [SMILES: O=c1[nH]c(C2(c3cccc(C(F)(F)F)c3)CC2)nc2c1CNCCC2] INT-8-16 | 2-(1-(3-(trifluoromethyl)phenyl)cyclopropyl)-3,5,6,7,8,9-hexahydro-4H-pyrimido[5,4-c]azepin-4-one | LC-MS (Method-I) m/z: M + 1 obs 350.13, tR = 0.49 min. |

TABLE 8-3-continued

| | | |
|---|---|---|
| 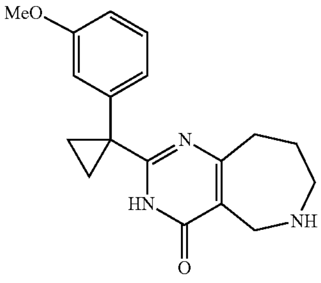 [SMILES: COc1cccc(C2(c3nc4c(c(=O)[nH]3)CNCCC4)CC2)c1] INT-8-17 | 2-(1-(3-methoxyphenyl)cyclopropyl)-3,5,6,7,8,9-hexahydro-4H-pyrimido[5,4-c]azepin-4-one | LC-MS (Method-I) m/z: M + 1 obs 312.17, tR = 0.44 min. |

TABLE 8-4

| | | |
|---|---|---|
| 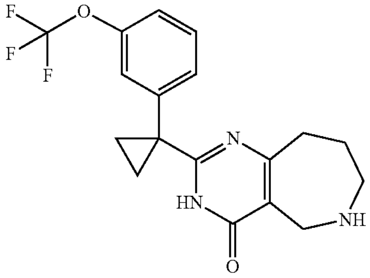 [SMILES: O=c1[nH]c(C2(c3cccc(OC(F)(F)F)c3)CC2)nc2c1CNCCC2] INT-8-18 | 2-(1-(3-(trifluoromethoxy)phenyl)cyclopropyl)-3,5,6,7,8,9-hexahydro-4H-pyrimido[5,4-c]azepin-4-one | LC-MS (Method-I) m/z: M + 1 obs 366.17, tR = 0.49 min. |
| 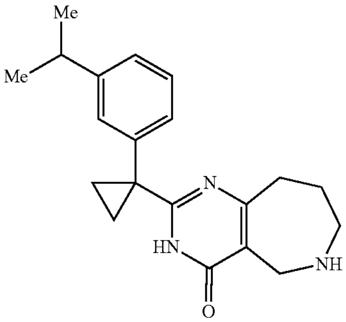 [SMILES: CC(C)c1cccc(C2(c3nc4c(c(=O)[nH]3)CNCCC4)CC2)c1] INT-8-19 | 2-(1-(3-isopropylphenyl)cyclopropyl)-3,5,6,7,8,9-hexahydro-4H-pyrimido[5,4-c]azepin-4-one | LC-MS (Method-I) m/z: M + 1 obs 324.23, tR = 0.50 min. |
| 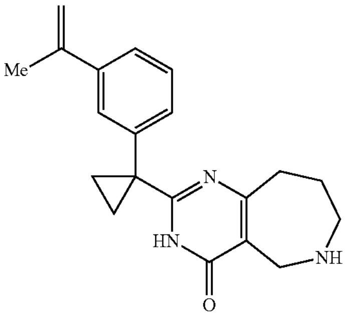 [SMILES: C=C(C)c1cccc(C2(c3nc4c(c(=O)[nH]3)CNCCC4)CC2)c1] INT-8-20 | 2-(1-(3-(prop-1-en-2-yl)phenyl)cyclopropyl)-3,5,6,7,8,9-hexahydro-4H-pyrimido[5,4-c]azepin-4-one | LC-MS (Method-K) m/z: M + 1 obs 322.2, tR = 0.50 min. |

TABLE 8-4-continued

| | | |
|---|---|---|
| 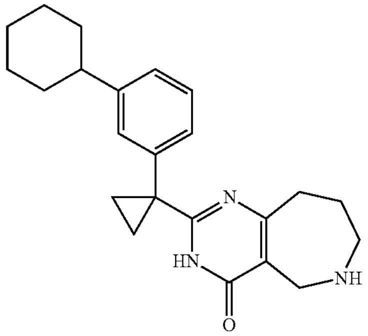 [SMILES: O=c1[nH]c(C2(c3cccc(C4CCCCC4)c3)CC2)nc2c1CNCCC2] INT-8-21 | 2-(1-(3-cyclohexylphenyl)cyclopropyl)-3,5,6,7,8,9-hexahydro-4H-pyrimido[5,4-c]azepin-4-one | LC-MS (Method-K) m/z: M + 1 obs 364.2, tR = 0.59 min. |
| 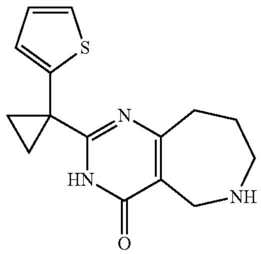 [SMILES: O=c1[nH]c(C2(c3cccs3)CC2)nc2c1CNCCC2] INT-8-22 | 2-(1-(thiophen-2-yl)cyclopropyl)-3,5,6,7,8,9-hexahydro-4H-pyrimido[5,4-c]azepin-4-one | (400 MHz, $CDCl_3$): δ 7.34-7.31 (1H, m), 7.12-7.09 (1H, m), 7.05-7.01 (1H, m), 3.88 (2H, s), 3.18-3.12 (2H, m), 2.89-2.84 (2H, m), 1.90-1.84 (2H, m), 1.79-1.71 (2H, m), 1.47-1.42 (2H, m), (two signals of NH proton are not observed). LC-MS (Method-H) m/z: M + 1 obs 288.15, tR = 1.23 min. |

TABLE 8-5

| | | |
|---|---|---|
| 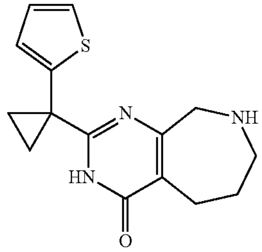 [SMILES: O=c1[nH]c(C2(c3cccs3)CC2)nc2c1CCCNC2] INT-8-23 | 2-(1-(thiophen-2-yl)cyclopropyl)-3,5,6,7,8,9-hexahydro-4H-pyrimido[4,5-c]azepin-4-one | (400 MHz, $CDCl_3$): δ 7.34-7.31 (1H, m), 7.12-7.08 (1H, m), 7.05-7.01 (1H, m), 3.84 (2H, s), 3.16-3.10 (2H, m), 2.82-2.77 (2H, m), 1.88-1.84 (2H, m), 1.74-1.66 (2H, m), 1.46-1.42 (2H, m), (two signals of NH proton are not observed). LC-MS (Method-H) m/z: M + 1 obs 288.15, tR = 0.92 min. |
| 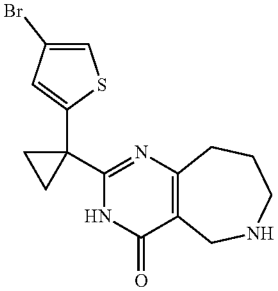 [SMILES: O=c1[nH]c(C2(c3cc(Br)cs3)CC2)nc2c1CNCCC2] INT-8-24 | 2-(1-(4-bromothiophen-2-yl)cyclopropyl)-3,5,6,7,8,9-hexahydro-4H-pyrimido[5,4-c]azepin-4-one | (400 MHz, DMSO-$d_6$): δ 9.08-8.96 (2H, br.s), 7.56 (1H, d, J = 1.6 Hz), 7.05 (1H, d, J = 1.6 Hz), 4.18-4.12 (2H, m), 3.37-3.27 (2H, m), 2.92-2.90 (2H, m), 1.87-1.83 (2H, m), 1.62 (2H, dd, J = 7.4, 4.7 Hz), 1.40 (2H, dd, J = 7.4, 4.7 Hz). LC-MS (Method-I) m/z: M + 1 obs 366.05, tR = 0.43 min. |

TABLE 8-5-continued
| | | |
|---|---|---|
| 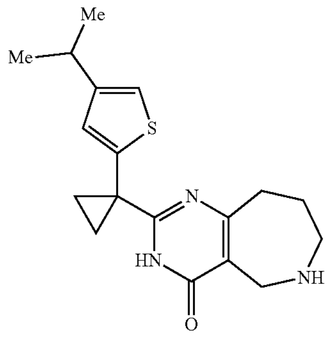 [SMILES: CC(C)c1csc(C2(c3nc4c(c(=O)[nH]3)CNCCC4)CC2)c1] INT-8-25 | 2-(1-(4-isopropylthiophen-2-yl)cyclopropyl)-3,5,6,7,8,9-hexahydro-4H-pyrimido[5,4-c]azepin-4-one | LC-MS (Method-I) m/z: M + 1 obs 330.12, tR = 0.50 min. |
| 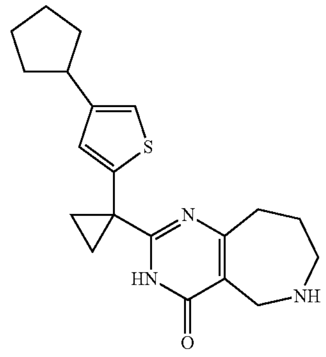 [SMILES: O=c1[nH]c(C2(c3cc(C4CCCC4)cs3)CC2)nc2c1CNCCC2] INT-8-26 | 2-(1-(4-cyclopentylthiophen-2-yl)cyclopropyl)-3,5,6,7,8,9-hexahydro-4H-pyrimido[5,4-c]azepin-4-one | LC-MS (Method-I) m/z: M + 1 obs 370.2, M−1 obs 368.3, tR = 0.53 min. |
| 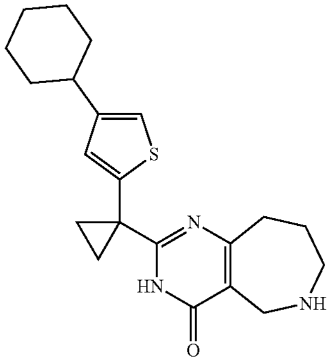 INT-8-27 | 2-(1-(4-cyclohexylthiophen-2-yl)cyclopropyl)-3,5,6,7,8,9-hexahydro-4H-pyrimido[5,4-c]azepin-4-one | LC-MS (Method-I) m/z: M + 1 obs 370.23, tR = 0.56 min. |

TABLE 8-6

| | | |
|---|---|---|
| 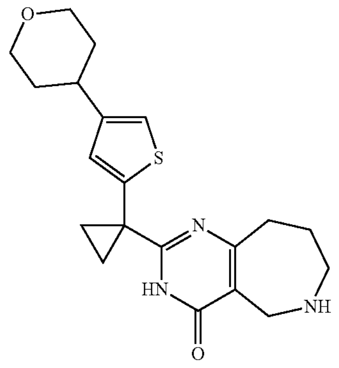 [SMILES: O=c1[nH]c(C2(c3cc(C4CCOCC4)cs3)CC2)nc2c1CNCCC2] INT-8-28 | 2-(1-(4-(tetrahydro-2H-pyran-4-yl)thiophen-2-yl)cyclopropyl)-3,5,6,7,8,9-hexahydro-4H-pyrimido[5,4-c]azepin-4-one | LC-MS (Method-I) m/z: M + 1 obs 372.2, M − 1 obs 370.3, tR = 0.53 min. |
| 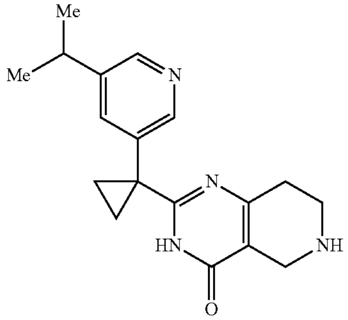 [SMILES: CC(C)c1cncc(C2(c3nc4c(c(=O)[nH]3)CNCC4)CC2)c1] INT-8-29 | 2-(1-(5-isopropylpyridin-3-yl)cyclopropyl)-5,6,7,8-tetrahydropyrido[4,3-d]pyrimidin-4(3H)-one | LC-MS (Method-I) m/z: M + 1 obs 311.19, tR = 0.43 min. |
| 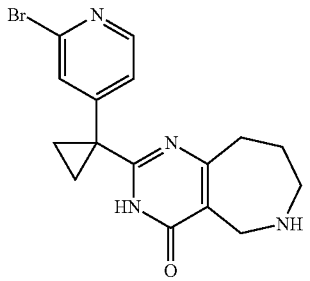 [SMILES: O=c1[nH]c(C2(c3ccnc(Br)c3)CC2)nc2c1CNCCC2] INT-8-30 | 2-(1-(2-bromopyridin-4-yl)cyclopropyl)-3,5,6,7,8,9-hexahydro-4H-pyrimido[5,4-c]azepin-4-one | LC-MS (Method-I) m/z: M + 1 obs 361.09, tR = 0.40 min. |
| 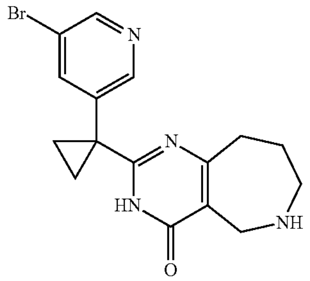 [SMILES: O=c1[nH]c(C2(c3cncc(Br)c3)CC2)nc2c1CNCCC2] INT-8-31 | 2-(1-(5-bromopyridin-3-yl)cyclopropyl)-3,5,6,7,8,9-hexahydro-4H-pyrimido[5,4-c]azepin-4-one | LC-MS (Method-I) m/z: M + 1 obs 361.08, tR = 0.40 min. |

TABLE 8-6-continued

| | | |
|---|---|---|
| 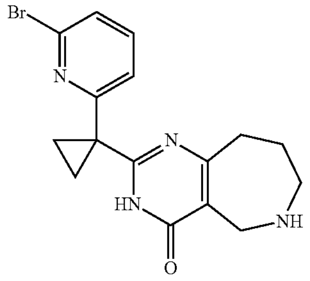 [SMILES: O=c1[nH]c(C2(c3cccc(Br)n3)CC2)nc2c1CNCCC2] INT-8-32 | 2-(1-(6-bromopyridin-2-yl)cyclopropyl)-3,5,6,7,8,9-hexahydro-4H-pyrimido[5,4-c]azepin-4-one | LC-MS (Method-I) m/z: M + 1 obs 361.08, tR = 0.44 min. |
| 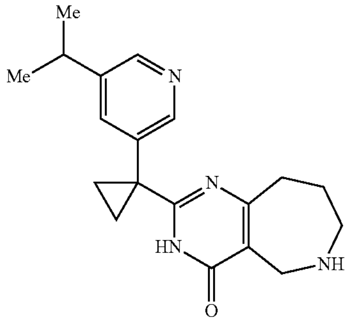 INT-8-33 | 2-(1-(5-isopropylpyridin-3-yl)cyclopropyl)-3,5,6,7,8,9-hexahydro-4H-pyrimido[5,4-c]azepin-4-one | LC-MS (Method-I) m/z: M + 1 obs 325.15, tR = 1.60 min. |
| 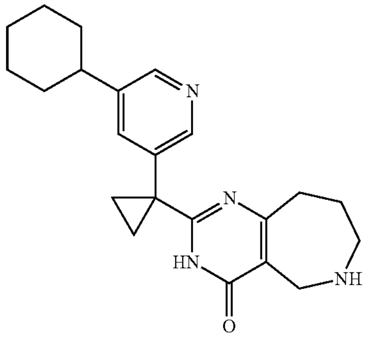 INT-8-34 | 2-(1-(5-cyclohexylpyridin-3-yl)cyclopropyl)-3,5,6,7,8,9-hexahydro-4H-pyrimido[5,4-c]azepin-4-one | LC-MS (Method-I) m/z: M + 1 obs 365.26, tR = 0.48 min. |

TABLE 8-7

| | | |
|---|---|---|
| 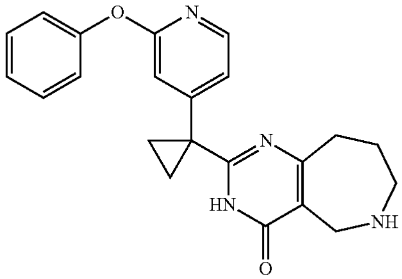 [SMILES: O=c1[nH]c(C2(c3ccnc(Oc4ccccc4)c3)CC2)nc2c1CNCCC2] INT-8-35 | 2-(1-(2-phenoxypyridin-4-yl)cyclopropyl)-6,7,8,9-tetrahydro-3H-pyrimido[5,4-c]azepin-4(5H)-one | LC-MS (Method-I) m/z: M + 1 obs 375.23, tR = 0.48 min. |

TABLE 8-7-continued

| | | |
|---|---|---|
| 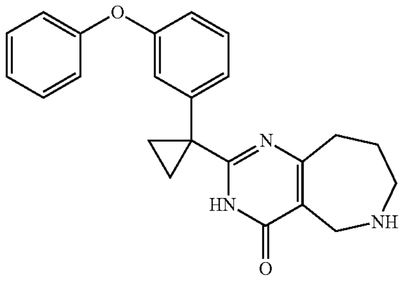 [SMILES: O=c1[nH]c(C2(c3cccc(Oc4ccccc4)c3)CC2)nc2c1CNCCC2]<br>INT-8-36 | 2-(1-(3-phenoxyphenyl)cyclopropyl)-6,7,8,9-tetrahydro-3H-pyrimido[5,4-c]azepin-4(5H)-one | LC-MS (Method-I) m/z: M + 1 obs 374.21, tR = 0.53 min. |
| 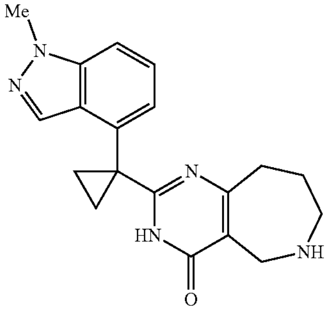 [SMILES: Cn1ncc2c(C3(c4nc5c(c(=O)[nH]4)CNCCC5)CC3)cccc21]<br>INT-8-37 | 2-(1-(1-methyl-1H-indazol-4-yl)cyclopropyl)-3,5,6,7,8,9-hexahydro-4H-pyrimido[5,4-c]azepin-4-one | LC-MS (Method-I) m/z: M + 1 obs 336.1, tR = 0.38 min. |
| 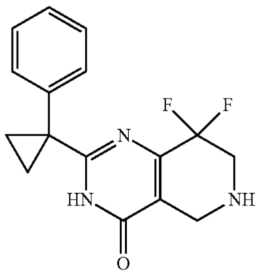 [SMILES: O=c1[nH]c(C2(c3ccccc3)CC2)nc2c1CNCC2(F)F]<br>INT-8-38 | 8,8-difluoro-2-(1-phenylcyclopropyl)-5,6,7,8-tetrahydropyrido[4,3-d]pyrimidin-4(3H)-one | (400 MHz, $CDCl_3$): δ 7.36-7.23 (5H, m), 4.02-3.92 (4H, m), 3.45 (2H, br.s), 1.54-1.47 (2H, m), 1.33-1.27 (2H, m).<br>LC-MS (Method-B1) m/z: M + 1 obs 304.06, tR = 0.65 min. |
| 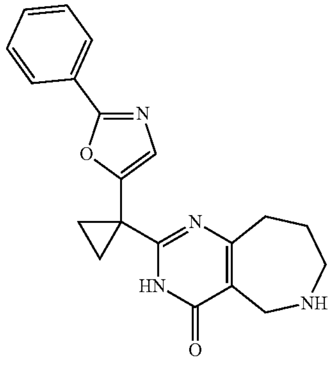 [SMILES: O=c1[nH]c(C2(c3cnc(-c4ccccc4)o3)CC2)nc2c1CNCCC2]<br>INT-8-39 | 2-(1-(2-phenyloxazol-5-yl)cyclopropyl)-6,7,8,9-tetrahydro-3H-pyrimido[5,4-c]azepin-4(5H)-one | LC-MS (Method-I) m/z: M − 1 obs 347.22, tR = 0.47 min. |

TABLE 8-7-continued

| | | |
|---|---|---|
| 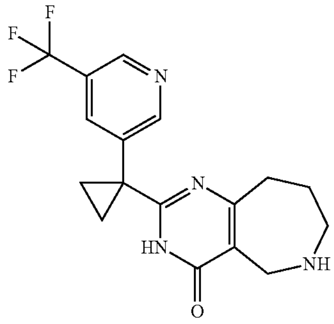 [SMILES: O=c1[nH]c(C2(c3cncc(C(F)(F)F)c3)CC2)nc2c1CNCCC2]<br>INT-8-40 | 2-(1-(5-(trifluoromethyl)pyridin-3-yl)cyclopropyl)-6,7,8,9-tetrahydro-3H-pyrimido[5,4-c]azepin-4(5H)-one | LC-MS (Method-I) m/z: M + 1 obs 351.14, tR = 0.45 min. |
| 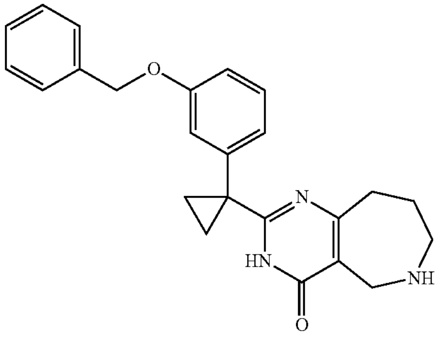 [SMILES: O=c1[nH]c(C2(c3cccc(OCc4ccccc4)c3)CC2)nc2c1CNCCC2]<br>INT-8-41 | 2-(1-(3-(benzyloxy)phenyl)cyclopropyl)-3,5,6,7,8,9-hexahydro-4H-pyrimido[5,4-c]azepin-4-one | (400 MHz, DMSO-$d_6$): δ 9.01 (1H, s), 7.55-7.29 (5H, m), 7.24 (1H, td, J = 8.0, 2.1 Hz), 6.98-6.82 (3H, m), 5.08 (2H, s), 4.29-4.01 (2H, m), 3.41-3.19 (2H, m), 3.03-2.81 (2H, m), 2.04-1.70 (2H, m), 1.66-1.37 (2H, m), 1.37-1.09 (2H, m), (one signal of NH proton is not observed).<br>LC-MS (Method-I) m/z: M + 1 obs 388.2, M-1 obs 386.3, tR = 0.58 min. |

Intermediate-9-1 (INT-9-1)

Synthesis of 4-(1-(4-oxo-3,4,5,6,7,8-hexahydropyrido[4,3-d]pyrimidin-2-yl)cyclopropyl)benzonitrile (INT-9-1)

{Chem. 31}

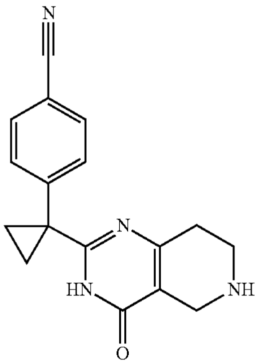

Step-9-1-A: Synthesis of tert-butyl 2-(1-(4-bromophenyl)cyclopropyl)-4-oxo-3,4,7,8-tetrahydropyrido[4,3-d]pyrimidine-6(5H)-carboxylate (INT-9-1-A)

{Chem. 32}

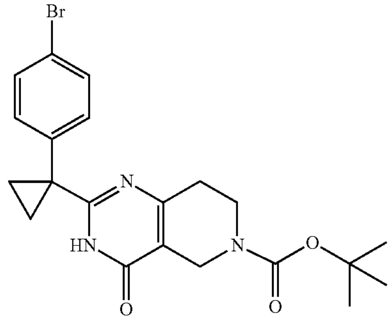

To a stirred solution of INT-4-5 (653 mg, 1.89 mmol) in DCM (10 mL) is added di-tert-butyl dicarbonate (494 mg, 2.26 mmol) and triethylamine (382 mg, 3.77 mmol). The mixture is stirred at rt for 2 hrs. After the removal of solvent in vacuo, the purification is carried out by column chromatography on silica gel (pre-packed column: YAMAZEN; Hi-Flash Column; 30 g) eluting with a gradient of 10 to 80% EtOAc in n-hexane to give the titled compound (549 mg, 65% yield) as a white amorphous solid.

$^1$H-NMR (300 MHz, $CDCl_3$): delta 7.55 (2H, d, J=8.0 Hz), 7.35-7.21 (2H, m), 4.29 (2H, s), 3.66-3.63 (2H, m), 2.65 (2H, br.s), 1.79-1.76 (2H, m), 1.48 (9H, s), 1.34-1.31 (2H, m), (the signal of NH proton is not observed).

LC-MS (Method-B) m/z: M+1 obs 448.09, M−1 446.15, tR=2.88 min.

Step-9-1-B: Synthesis of tert-butyl 2-(1-(4-cyanophenyl)cyclopropyl)-4-oxo-3,4,7,8-tetrahydropyrido[4,3-d]pyrimidine-6(5H)-carboxylate (INT-9-1-B)

{Chem. 33}

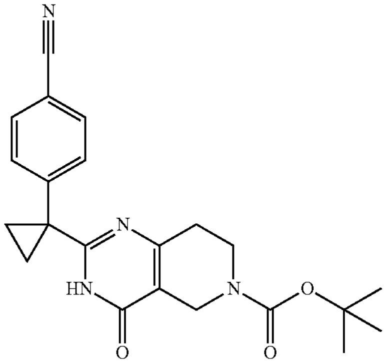

To a solution of INT-9-1-A (400 mg, 0.896 mmol) in DMF (10 mL) is added $Zn(CN)_2$ (0.421 g, 3.58 mmol) and $Pd(PPh_3)_4$ (104 mg, 0.090 mmol) and the resulting mixture is irradiated at 160° C. for 1 hr under microwave. The reaction mixture is filtered through a pad of celite and the filter cake is washed with ethyl acetate. The combined solution is washed with 2M NaOH aqueous solution, brine and dried over sodium sulfate, filtered. The filtrate is concentrated in vacuo to give the crude product, which is purified with column chromatography on silica gel eluting with a gradient of 10 to 80% EtOAc in n-hexane to give the titled compound (234 mg, 67% yield) as a white solid.

$^1$H-NMR (270 MHz, $CDCl_3$): delta 7.69 (2H, d, J=7.9 Hz), 7.52 (2H, d, J=7.9 Hz), 4.29 (2H, s), 3.68-3.64 (2H, m), 2.67 (2H, br.s), 2.00-1.36 (13H, m), (the signal of NH proton is not observed).

LC-MS (Method-B) m/z: M+1 obs 393.17, M−1 obs 393.17, tR=2.55 min.

Step-9-1-C: Synthesis of 4-(1-(4-oxo-3,4,5,6,7,8-hexahydropyrido[4,3-d]pyrimidin-2-yl)cyclopropyl)benzonitrile (INT-9-1)

The titled compound is prepared according to the procedure of INT-8-1 from INT-9-1-B (234 mg, 0.596 mmol) and 4M HCl-dioxane solution (0.65 mL). The purification is carried out by column chromatography on amine gel (pre-packed column: YAMAZEN; Hi-Flash Column; 15 g) eluting with DCM-MeOH (40:1 v/v) to give the titled compound (240 mg, 99% yield) as a white amorphous solid.

$^1$H-NMR (300 MHz, DMSO-$d_6$): delta 9.43 (1H, br.s), 7.78 (2H, d, J=8.1 Hz), 7.40 (2H, d, J=8.1 Hz), 3.85 (2H, br.s), 3.33 (2H, m), 2.76 (2H, br.s), 1.58-1.54 (2H, m), 1.36-1.32 (2H, m), (the signal of NH proton is not observed).

LC-MS (Method-B) m/z: M+1 obs 293.18, M−1 obs 291.20, tR=1.78 min.

Intermediate-9-3 (INT-9-3)

Synthesis of tert-butyl 4-oxo-2-(1-(4-phenylthiophen-2-yl)cyclopropyl)-3,5,7,8-tetrahydropyrido[4,3-d]pyrimidine-6(4H)-carboxylate (INT-9-3)

{Chem. 34}

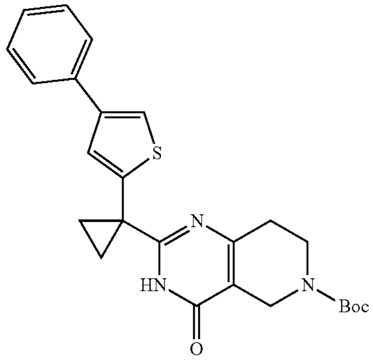

A mixture of INT-5-3 (30 mg, 0.066 mmol), phenyl boronic acid (24.3 mg, 0.199 mmol), palladium(II) acetate (1.49 mg, 0.0066 mmol), triphenylphosphine (3.48 mmol, 0.013 mmol) and potassium carbonate (18.3 mg, 0.133 mmol) in DMF (0.5 mL) is irradiated at 150° C. for 25 minute under microwave. The reaction mixture is diluted with water and extracted with EtOAc. The separated organic layer is washed with brine and dried over sodium sulfate, filtered and concentrated in vacuo to give the crude product, which is purified with column chromatography on silica gel eluting with a gradient of 15 to 100% EtOAc in n-hexane to give the titled compound (25.9 mg, 87% yield) as a white solid. The NMR data is noted in Tables 9-1 to 9-3.

The following pyrimidin-4(3H)-one derivatives (INT-9-2 and INT-9-15) are prepared according to the procedure of INT-9-3 or the general synthesis in scheme-9 from the synthesized halide (INT-9-1-A, INT-5-3, 5-6, 5-9, 5-17, 5-18, 5-21 and INT-5-22) derivatives in Tables 9-1 to 9-3.

TABLE 9-1

| Structure | Chemical Name | $^1$H-NMR & LC-MS (m/z) |
|---|---|---|
| 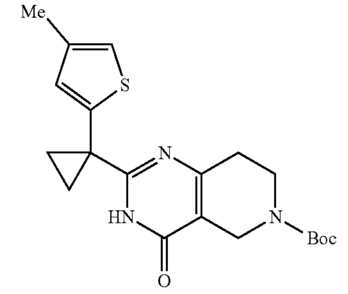 [SMILES: Cc1csc(C2(c3nc4c(c(=O)[nH]3)CN(C(=O)OC(C)(C)C)CC4)CC2)c1] INT-9-2 | tert-butyl 2-(1-(4-methylthiophen-2-yl)cyclopropyl)-4-oxo-3,5,7,8-tetrahydropyrido[4,3-d]pyrimidine-6(4H)-carboxylate | (300 MHz, $CDCl_3$): δ 9.01 (1H, br.s), 7.26 (1H, s), 6.90 (1H, s), 4.31 (2H, br.s), 3.70-3.60 (2H, m), 2.70-2.59 (2H, m), 1.90-1.80 (2H, m), 1.60 (3H, s), 1.54-1.40 (11H, m). LC-MS (Method-B) m/z: M + 1 obs 388.3, M-1 obs 386.3, tR = 3.00 min. |
| 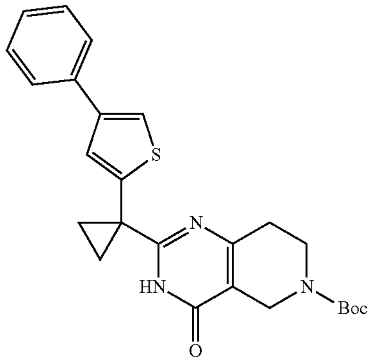 [SMILES: CC(C)(C)OC(=O)N1CCc2nc(C3(c4cc(-c5ccccc5)cs4)CC3)[nH]c(=O)c2C1] INT-9-3 | tert-butyl 4-oxo-2-(1-(4-phenylthiophen-2-yl)cyclopropyl)-3,5,7,8-tetrahydropyrido[4,3-d]pyrimidine-6(4H)-carboxylate | (300 MHz, $CDCl_3$): δ 7.75-7.30 (7H, m), 4.31 (2H, s), 3.64 (2H, t, J = 5.8 Hz), 2.69-2.60 (2H, m), 1.93-1.85 (2H, m), 1.55-1.45 (11H, m), (one signal of NH proton is not observed). |
| 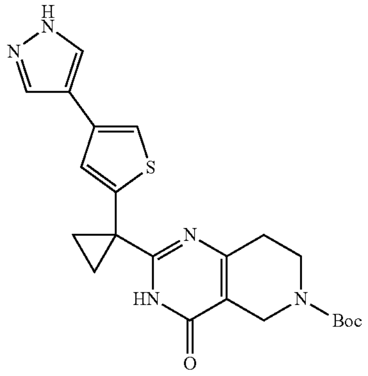 [SMILES: CC(C)(C)OC(=O)N1CCc2nc(C3(c4cc(-c5cn[nH]c5)cs4)CC3)[nH]c(=O)c2C1] INT-9-4 | tert-butyl 2-(1-(4-(1H-pyrazol-4-yl)thiophen-2-yl)cyclopropyl)-4-oxo-3,5,7,8-tetrahydropyrido[4,3-d]pyrimidine-6(4H)-carboxylate | LC-MS (Method-A1) m/z: M − 1 obs 438.27, tR = 2.09 min. |
| 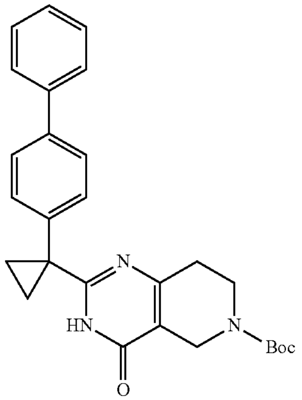 [SMILES: CC(C)(C)OC(=O)N1CCc2nc(C3(c4ccc(-c5ccccc5)cc4)CC3)[nH]c(=O)c2C1] INT-9-5 | tert-butyl 2-(1-([1,1'-biphenyl]-4-yl)cyclopropyl)-4-oxo-3,5,7,8-tetrahydropyrido[4,3-d]pyrimidine-6(4H)-carboxylate | (400 MHz, $CDCl_3$): δ 8.83-8.67 (1H, br), 7.64-7.57 (4H, m), 7.49-7.45 (4H, m), 7.41-7.37 (1H, m), 4.30 (2H, s), 3.65 (2H, t, J = 5.5 Hz), 2.70-2.61 (2H, m), 1.81 (2H, dd, J = 6.9, 3.9 Hz), 1.47 (9H, s), 1.40 (2H, dd, J = 6.9, 3.9 Hz). LC-MS (Method-I) m/z: M + 1 obs 444.30, tR = 0.61 min. |

TABLE 9-1-continued

| Structure | Chemical Name | $^1$H-NMR & LC-MS (m/z) |
|---|---|---|
| 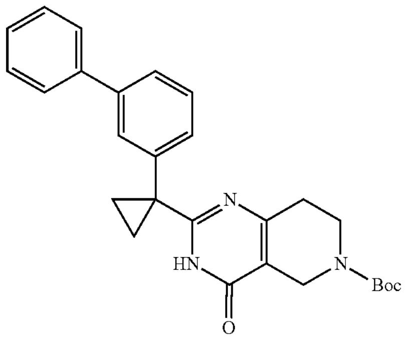 INT-9-6 | tert-butyl 2-(1-([1,1'-biphenyl]-3-yl)cyclopropyl)-4-oxo-3,4,7,8-tetrahydropyrido[4,3-d]pyrimidine-6(5H)-carboxylate | (400 MHz, $CDCl_3$): δ 7.62-7.55 (4H, m), 7.52-7.44 (3H, m), 7.41-7.36 (2H, m), 4.29 (2H, s), 3.66-3.63 (2H, m), 2.66 (2H, s), 1.82 (2H, dd, J = 7.0, 4.0 Hz), 1.47 (9H, s), 1.42 (2H, dd, J = 7.0, 4.0 Hz), (one signal of NH proton is not observed). LC-MS (Method-I) m/z: M + 1 obs 444.30, tR = 0.61 min. |

TABLE 9-2

| | | |
|---|---|---|
| 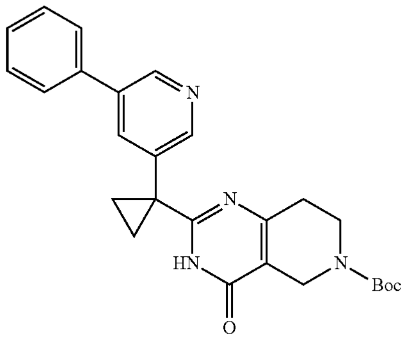 [SMILES: CC(C)(C)OC(=O)N1CCc2nc(C3(c4cncc(-c5ccccc5)c4)CC3)[nH]c(=O)c2C1] INT-9-7 | tert-butyl 4-oxo-2-(1-(5-phenylpyridin-3-yl)cyclopropyl)-3,5,7,8-tetrahydropyrido[4,3-d]pyrimidine-6(4H)-carboxylate | (400 MHz, $CDCl_3$): δ 8.88 (1H, d, J = 2.1 Hz), 8.65 (1H, d, J = 2.1 Hz), 7.88 (1H, t, J = 2.1 Hz), 7.59-7.57 (2H, m), 7.52-7.41 (3H, m), 4.30 (2H, s), 3.65 (2H, t, J = 5.7 Hz), 2.71-2.62 (2H, m), 1.88 (2H, dd, J = 7.0, 4.2 Hz), 1.47 (9H, s), 1.43 (2H, dd, J = 7.0, 4.2 Hz), (one signal of NH proton is not observed). LC-MS (Method-I) m/z: M + 1 obs 445.29, tR = 0.54 min. |
| 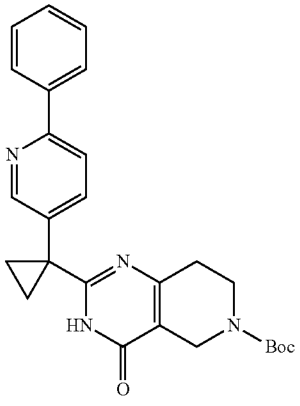 [SMILES: CC(C)(C)OC(=O)N1CCc2nc(C3(c4ccc(-c5ccccc5)nc4)CC3)[nH]c(=O)c2C1] INT-9-8 | tert-butyl 4-oxo-2-(1-(6-phenylpyridin-3-yl)cyclopropyl)-3,5,7,8-tetrahydropyrido[4,3-d]pyrimidine-6(4H)-carboxylate | (400 MHz, $CDCl_3$): δ 8.73 (1H, t, J = 1.6 Hz), 8.00-7.98 (2H, m), 7.78-7.77 (2H, m), 7.51-7.41 (3H, m), 4.28 (2H, s), 3.61 (2H, t, J = 5.5 Hz), 2.67-2.59 (2H, m), 1.86-1.80 (2H, m), 1.48 (9H, s), 1.40 (2H, dd, J = 7.1, 3.9 Hz), (one signal of NH proton is not observed). LC-MS (Method-I) m/z: M + 1 obs 445.27, tR = 0.55 min. |

TABLE 9-2-continued

| | | |
|---|---|---|
| 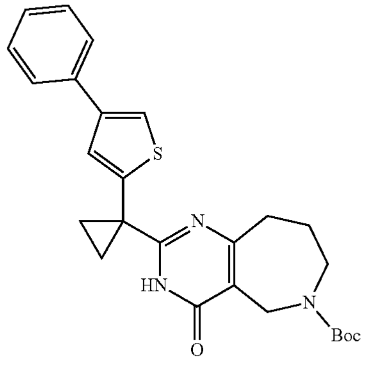 [SMILES: CC(C)(C)OC(=O)N1CCCc2nc(C3(c4cc(-c5ccccc5)cs4)CC3)[nH]c(=O)c2C1]<br>INT-9-9 | tert-butyl 4-oxo-2-(1-(4-phenylthiophen-2-yl)cyclopropyl)-3,4,5,7,8,9-hexahydro-6H-pyrimido[5,4-c]azepine-6-carboxylate | LC-MS (Method-K) m/z: M + 1 obs 464.3, tR = 0.60 min. |
| 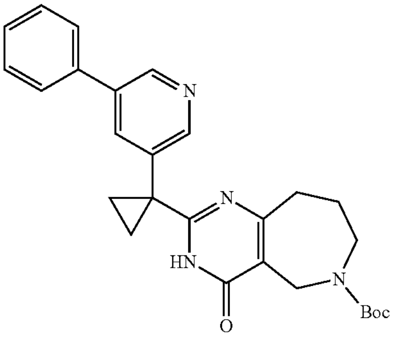 [SMILES: CC(C)(C)OC(=O)N1CCCc2nc(C3(c4cncc(-c5ccccc5)c4)CC3)[nH]c(=O)c2C1]<br>INT-9-10 | tert-butyl 4-oxo-2-(1-(5-phenylpyridin-3-yl)cyclopropyl)-3,4,5,7,8,9-hexahydro-6H-pyrimido[5,4-c]azepine-6-carboxylate | (400 MHz, $CDCl_3$): δ 8.89-8.82 (1H, br), 8.66 (1H, d, J = 2.0 Hz), 7.90 (1H, t, J = 2.0 Hz), 7.59-7.57 (2H, m), 7.51-7.42 (3H, m), 4.38 (2H, s), 3.66-3.52 (2H, br.s), 2.86-2.74 (2H, br.s), 1.95-1.87 (4H, m), 1.41-1.39 (11H, m), (one signal of NH proton is not observed). LC-MS (Method-I) m/z: M + 1 obs 459.30, tR = 0.54 min. |
| 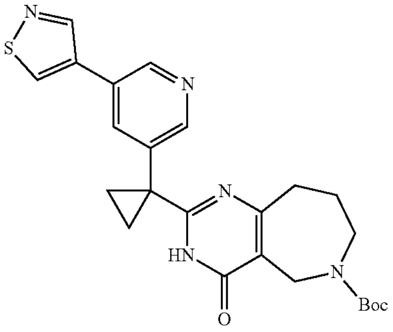 [SMILES: CC(C)(C)OC(=O)N1CCCc2nc(C3(c4cncc(-c5cnsc5)c4)CC3)[nH]c(=O)c2C1]<br>INT-9-11 | tert-butyl 2-(1-(5-(isothiazol-4-yl)pyridin-3-yl)cyclopropyl)-4-oxo-3,4,5,7,8,9-hexahydro-6H-pyrimido[5,4-c]azepine-6-carboxylate | (400 MHz, $CDCl_3$): δ 8.88-8.87 (2H, m), 8.80 (1H, s), 8.67 (1H, s), 7.92 (1H, s), 4.39 (2H, s), 3.69-3.52 (2H, m), 2.91-2.71 (2H, br.s), 1.91-1.89 (4H, m), 1.44-1.39 (11H, m), (one signal of NH proton is not observed). LC-MS (Method-I) m/z: M + 1 obs 466.22, tR = 0.51 min. |

TABLE 9-3

| | | |
|---|---|---|
| 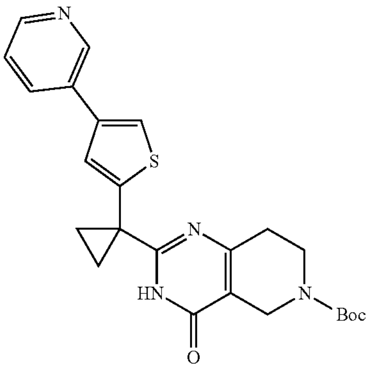 [SMILES: CC(C)(C)OC(=O)N1CCc2nc(C3(c4cc(-c5cccnc5)cs4)CC3)[nH]c(=O)c2C1]<br>INT-9-12 | tert-butyl 4-oxo-2-(1-(4-(pyridin-3-yl)thiophen-2-yl)cyclopropyl)-3,5,7,8-tetrahydropyrido[4,3-d]pyrimidine-6(4H)-carboxylate | (400 MHz, $CDCl_3$): δ 8.82 (1H, d, J = 1.8 Hz), 8.56 (1H, dd, J = 5.0, 1.4 Hz), 7.85-7.82 (1H, m), 7.50 (1H, d, J = 1.6 Hz), 7.38 (1H, d, J = 1.6 Hz), 7.37-7.32 (1H, m), 4.30 (2H, s), 3.65 (2H, t, J = 5.5 Hz), 2.65-2.65 (2H, m), 1.90 (2H, dd, J = 7.2, 4.0 Hz), 1.52 (2H, dd, J = 7.2, 4.0 Hz), 1.47 (s, 9H), (one signal of NH proton are not observed). LC-MS (Method-A1) m/z: M + 1 obs 451.00, tR = 2.14 min. |

TABLE 9-3-continued

| | | |
|---|---|---|
| 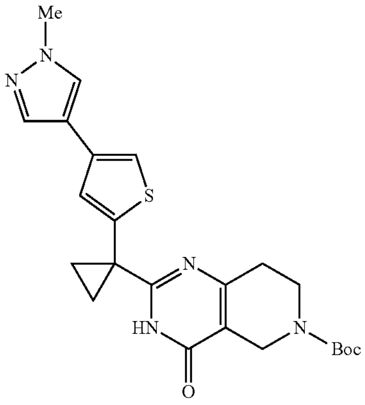 [SMILES: Cn1cc(-c2csc(C3(c4nc5c(c(=O)[nH]4)CN(C(=O)OC(C)(C)C)CC5)CC3)c2)cn1] INT-9-13 | tert-butyl 2-(1-(4-(1-methyl-1H-pyrazol-4-yl)thiophen-2-yl)cyclopropyl)-4-oxo-3,5,7,8-tetrahydropyrido[4,3-d]pyrimidine-6(4H)-carboxylate | LC-MS (Method-A1) m/z: M − 1 obs 452.27, tR = 2.15 min. |
| 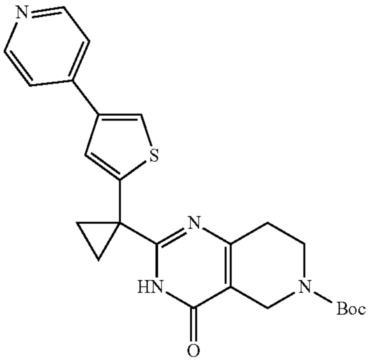 INT-9-14 | tert-butyl 4-oxo-2-(1-(4-(pyridin-4-yl)thiophen-2-yl)cyclopropyl)-3,5,7,8-tetrahydropyrido[4,3-d]pyrimidine-6(4H)-carboxylate | (400 MHz, $CDCl_3$): δ 8.62 (2H, d, J = 4.6 Hz), 7.62 (1H, s), 7.43-7.41 (3H, m), 4.28 (2H, s), 3.70-3.56 (2H, br), 2.69-2.56 (2H, s), 1.95-1.81 (2H, s), 1.50-1.47 (11H, m), (one signal of NH proton are not observed). LC-MS (Method-A1) m/z: M + 1 obs 451.04, tR = 2.00 min. |
| 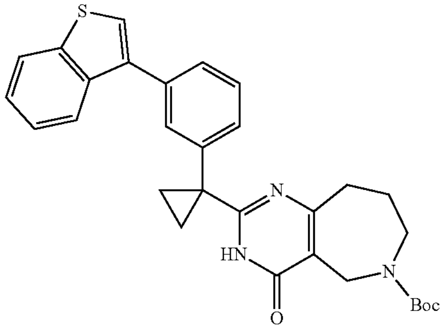 [SMILES: CC(C)(C)OC(=O)N1CCCc2nc(C3(c4cccc(-c5csc6ccccc56)c4)CC3)[nH]c(=O)c2C1] INT-9-15 | tert-butyl 2-(1-(3-(benzo[b]thiophen-3-yl)phenyl)cyclopropyl)-4-oxo-3,4,5,7,8,9-hexahydro-6H-pyrimido[5,4-c]azepine-6-carboxylate | LC-MS (Method-B1) m/z: M + 1 obs 513.93, M − 1 obs 511.99, tR = 2.53 min. |

Intermediate-9-16 (INT-9-16)

Synthesis of tert-butyl 2-(1-(3-(benzo[b]thiophen-5-yl)phenyl)cyclopropyl)-4-oxo-3,4,5,7,8,9-hexahydro-6H-pyrimido[5,4-c]azepine-6-carboxylate {Chem. 35}

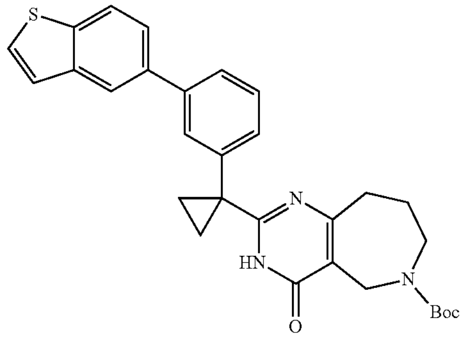

Step-9-12-A: tert-butyl 4-oxo-2-(1-(3-(4,4,5,5-tetramethyl-1,3,2-dioxaborolan-2-yl)phenyl)cyclopropyl)-3,4,5,7,8,9-hexahydro-6H-pyrimido[5,4-c]azepine-6-carboxylate (INT-9-16-A)

{Chem. 36}

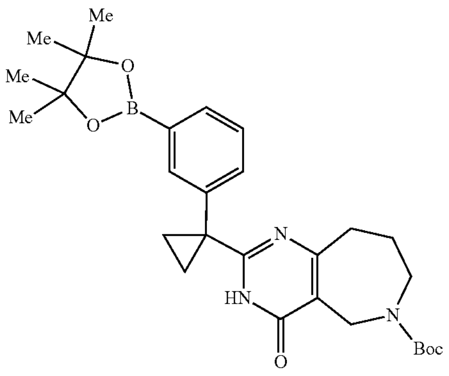

A mixture of INT-5-9 (200 mg, 0.434 mmol), 4,4,4',4',5,5,5',5'-octamethyl-2,2'-bi(1,3,2-dioxaborolane) (132 mg, 0.521 mmol), $PdCl_2$(dppf)-DCM (35.5 mg, 0.43 mmol) and potassium acetate (128 mg, 1.30 mmol) in 1,4-dioxane (4 mL) is stirred at 80° C. for 1 hr. After cooling to room temperature, the mixture is diluted with water and extracted with ethyl acetate. The combined organic layer is washed with brine, dried over sodium sulfate, filtered and concentrated in vacuo to give crude product. The crude product is purified by column chromatography on silica gel (10 g) eluting with a gradient of 25 to 100% ethyl acetate in n-hexane to give the titled compound (220 mg, quantitive yield) as a white solid.

LC-MS (Method-1) m/z: M+1 obs 508.3, M−1 obs 506.3, tR=0.64 min.

Step-9-16-B: Synthesis of tert-butyl 2-(1-(3-(benzo[b]thiophen-5-yl)phenyl)cyclopropyl)-4-oxo-3,4,5,7,8,9-hexahydro-6H-pyrimido[5,4-c]azepine-6-carboxylate (INT-9-16)

A mixture of INT-9-16-A (20 mg, 0.039 mmol), 5-bromobenzo[b]thiophene (12.6 mg, 0.059 mmol), palladium(II) acetate (0.885 mg, 0.00394 mmol) and triphenylphosphine (2.07 mg, 0.00788 mmol) in 1,4-dioxane (0.5 mL) and saturated aqueous sodium bicarbonate (0.5 mL) is stirred at 100° C. for 2 hrs. After cooling to room temperature, the mixture is diluted with water and extracted with ethyl acetate. The combined organic layer is washed with brine, dried over sodium sulfate, filtered and concentrated in vacuo to give crude product. The crude product is purified by column chromatography on silica gel (10 g) eluting with a gradient of 20 to 80% ethyl acetate in n-hexane to give the titled compound (9 mg, 45% yield) as a white solid.

$^1$H-NMR (400 MHz, $CDCl_3$): delta 8.06-7.97 (1H, m), 7.94 (1H, d, J=8.2 Hz), 7.72-7.62 (2H, m), 7.55 (1H, dd, J=8.5, 1.6 Hz), 7.49 (2H, d, J=5.5 Hz), 7.39 (2H, d, J=5.5 Hz), 4.39 (2H, s), 3.71-3.51 (2H, m), 2.85-2.72 (2H, m), 1.96-1.85 (2H, m), 1.85-1.71 (2H, m), 1.52-1.31 (11H, m), one signal of NH proton is not observed.

LC-MS (Method-1) m/z: M+1 obs 514.3, M−1 obs 512.3, tR=0.64 min.

The following pyrimidin-4(3H)-one derivatives (INT-9-17 and INT-9-20) are prepared according to the procedure (Step-9-16-B) of INT-9-16 from the known halide derivatives and INT-9-16-A in Table 10.

TABLE 10

| Structure | Chemical Name | $^1$H-NMR & LC-MS (m/z) |
|---|---|---|
| 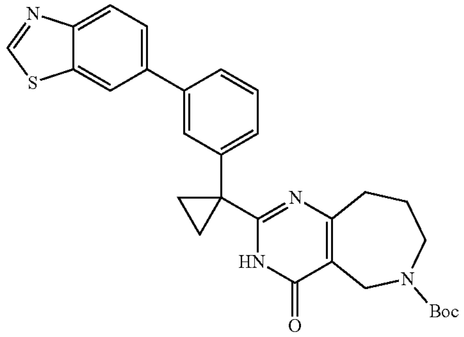 [SMILES: CC(C)(C)OC(=O)N1CCCc2nc(C3(c4cccc(-c5ccc6ncsc6c5)c4)CC3)[nH]c(=O)c2C1] INT-9-17 | tert-butyl 2-(1-(3-(benzo[d]thiazol-5-yl)phenyl)cyclopropyl)-4-oxo-3,4,5,7,8,9-hexahydro-6H-pyrimido[5,4-c]azepine-6-carboxylate | (400 MHz, $CDCl_3$): δ 9.02 (1H, s), 8.20 (1H, d, J = 8.2 Hz), 8.14 (1H, d, J = 1.8 Hz), 7.72 (1H, dd, J = 8.2, 1.8 Hz), 7.70-7.64 (2H, m), 7.59-7.47 (1H, m), 7.47-7.35 (1H, m), 4.51-4.28 (2H, m), 3.73-3.51 (2H, m), 2.95-2.66 (2H, m), 2.01-1.87 (2H, m), 1.86-1.72 (2H, m), 1.49-1.19 (11H, m), (NH proton is not observed). LC-MS (Method-I) m/z: M + 1 obs 515.2, M − 1 obs 513.3, tR = 0.58 min. |

TABLE 10-continued

| Structure | Chemical Name | $^1$H-NMR & LC-MS (m/z) |
|---|---|---|
| 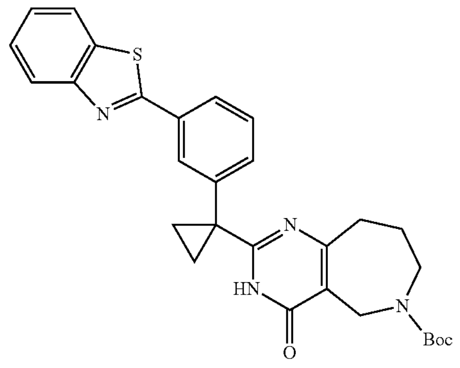 [SMILES: CC(C)(C)OC(=O)N1CCCc2nc(C3(c4cccc(-c5nc6ccccc6s5)c4)CC3)[nH]c(=O)c2C1] INT-9-18 | tert-butyl 2-(1-(3-(benzo[d]thiazol-2-yl)phenyl)cyclopropyl)-4-oxo-3,4,5,7,8,9-hexahydro-6H-pyrimido[5,4-c]azepine-6-carboxylate | (400 MHz, $CDCl_3$): δ 8.27-8.15 (1H, m), 8.07 (1H, d, J = 7.8 Hz), 8.05-8.00 (1H, m), 7.92 (1H, d, J = 7.8 Hz), 7.59-7.37 (4H, m), 4.38 (2H, s), 3.69-3.50 (2H, m), 2.86-2.71 (2H, m), 1.96-1.87 (2H, m), 1.87-1.80 (2H, m), 1.51-1.31 (11H, m), (one signal of NH proton is not observed). LC-MS (Method-I) m/z: M + 1 obs 515.3, M − 1 obs 513.3, tR = 0.62 min. |
| 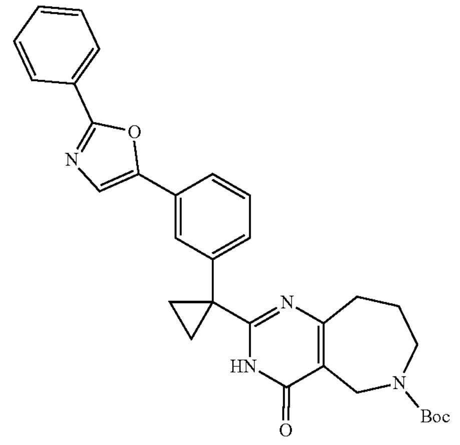 [SMILES: CC(C)(C)OC(=O)N1CCCc2nc(C3(c4cccc(-c5cnc(-c6ccccc6)o5)c4)CC3)[nH]c(=O)c2C1] INT-9-19 | tert-butyl 4-oxo-2-(1-(3-(2-phenyloxazol-5-yl)phenyl)cyclopropyl)-3,4,5,7,8,9-hexahydro-6H-pyrimido[5,4-c]azepine-6-carboxylate | (400 MHz, $CDCl_3$): δ 8.19-8.08 (2H, m), 7.81-7.70 (2H, m), 7.55-7.45 (5H, m), 7.42-7.35 (1H, m), 4.40 (2H, s), 3.74-3.52 (2H, m), 2.95-2.72 (2H, m), 1.99-1.88 (2H, m), 1.88-1.80 (2H, m), 1.49-1.31 (11H, m), (one signal of NH proton is not observed). LC-MS (Method-I) m/z: M + 1 obs 525.3, M − 1 obs 523.3, tR = 0.62 min. |
| 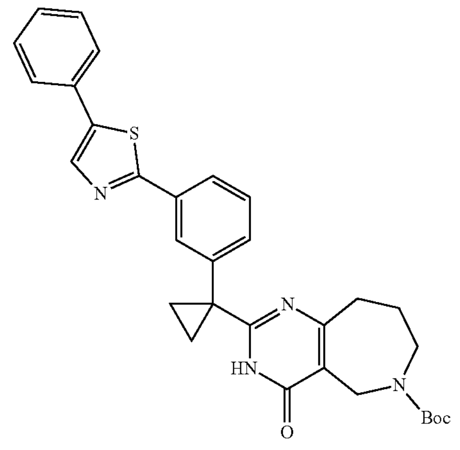 [SMILES: CC(C)(C)OC(=O)N1CCCc2nc(C3(c4cccc(-c5ncc(-c6ccccc6)s5)c4)CC3)[nH]c(=O)c2C1] INT-9-20 | tert-butyl 4-oxo-2-(1-(3-(5-phenylthiazol-2-yl)phenyl)cyclopropyl)-3,4,5,7,8,9-hexahydro-6H-pyrimido[5,4-c]azepine-6-carboxylate | LC-MS (Method-I) m/z: M + 1 obs 541.2, M − 1 obs 539.3, tR = 0.65 min. |

The following pyrimidin-4(3H)-one derivatives (INT-10-1 to INT-10-20) are prepared according to the procedure of INT-8-1 from INT-9-2 to INT-9-20, INT-9-16-A in Tables 11-1 to 11-4.

TABLE 11-1

| Structure | Chemical Name | LC-MS (m/z) |
|---|---|---|
| 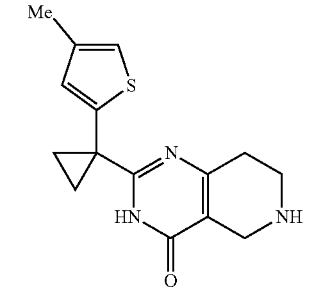 [SMILES: Cc1csc(C2(c3nc4c(c(=O)[nH]3)CNCC4)CC2)c1] INT-10-1 | 2-(1-(4-methylthiophen-2-yl)cyclopropyl)-5,6,7,8-tetrahydropyrido[4,3-d]pyrimidin-4(3H)-one | LC-MS (Method-B) m/z: M + 1 obs 288.3, M − 1 obs 286.3, tR = 2.31 min. |
| 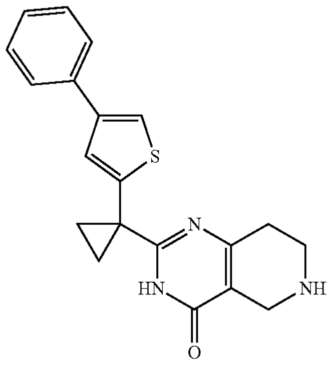 [SMILES: O=c1[nH]c(C2(c3cc(-c4ccccc4)cs3)CC2)nc2c1CNCC2] INT-10-2 | 2-(1-(4-phenylthiophen-2-yl)cyclopropyl)-5,6,7,8-tetrahydropyrido[4,3-d]pyrimidin-4(3H)-one | LC-MS (Method-A1) m/z: M + 1 obs 350.01, tR = 1.87 min. |
| 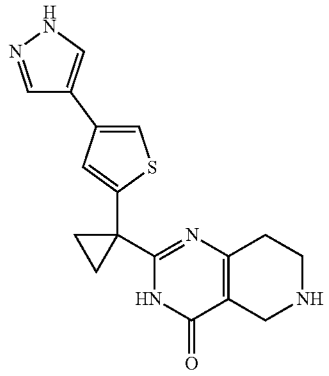 [SMILES: O=c1[nH]c(C2(c3cc(-c4cn[nH]c4)cs3)CC2)nc2c1CNCC2] INT-10-3 | 2-(1-(4-(1H-pyrazol-4-yl)thiophen-2-yl)cyclopropyl)-5,6,7,8-tetrahydropyrido[4,3-d]pyrimidin-4(3H)-one | LC-MS (Method-A1) m/z: M + 1 obs 340.19, tR = 1.53 min. |
| 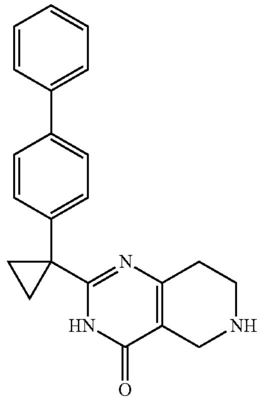 [SMILES: O=c1[nH]c(C2(c3ccc(-c4ccccc4)cc3)CC2)nc2c1CNCC2] INT-10-4 | 2-(1-([1,1'-biphenyl]-4-yl)cyclopropyl)-5,6,7,8-tetrahydropyrido[4,3-d]pyrimidin-4(3H)-one | LC-MS (Method-A1) m/z: M + 1 obs 344.30, tR = 1.94 min. |

TABLE 11-1-continued
| Structure | Chemical Name | LC-MS (m/z) |
|---|---|---|
| 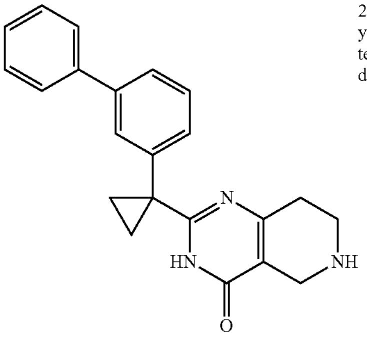 INT-10-5 | 2-(1-([1,1'-biphenyl]-3-yl)cyclopropyl)-5,6,7,8-tetrahydropyrido[4,3-d]pyrimidin-4(3H)-one | LC-MS (Method-A1) m/z: M + 1 obs 344.23, tR = 1.90 min. |
TABLE 11-2
| | | |
|---|---|---|
| 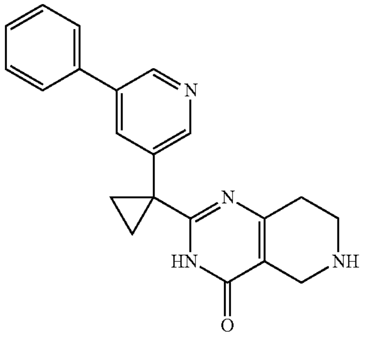 [SMILES: O=c1[nH]c(C2(c3cncc(-c4ccccc4)c3)CC2)nc2c1CNCC2] INT-10-6 | 2-(1-(5-phenylpyridin-3-yl)cyclopropyl)-5,6,7,8-tetrahydropyrido[4,3-d]pyrimidin-4(3H)-one | LC-MS (Method-I) m/z: M + 1 obs 345.15, tR = 0.45 min. |
| 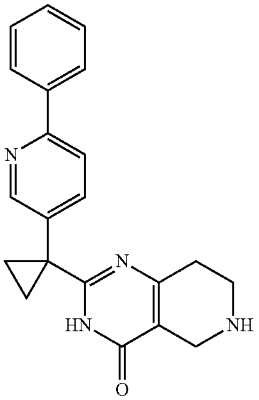 [SMILES: O=c1[nH]c(C2(c3ccc(-c4ccccc4)nc3)CC2)nc2c1CNCC2] INT-10-7 | 2-(1-(6-phenylpyridin-3-yl)cyclopropyl)-5,6,7,8-tetrahydropyrido[4,3-d]pyrimidin-4(3H)-one | LC-MS (Method-I) m/z: M + 1 obs 345.14, tR = 0.43 min. |

TABLE 11-2-continued

| | | |
|---|---|---|
| 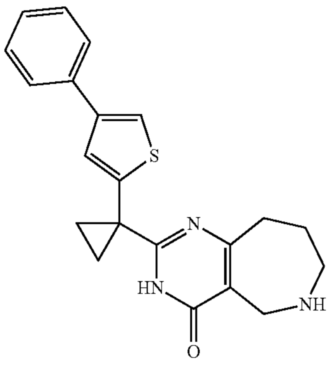 [SMILES: O=c1[nH]c(C2(c3cc(-c4ccccc4)cs3)CC2)nc2c1CNCCC2] INT-10-8 | 2-(1-(4-phenylthiophen-2-yl)cyclopropyl)-3,5,6,7,8,9-hexahydro-4H-pyrimido[5,4-c]azepin-4-one | LC-MS (Method-K) m/z: M + 1 obs 364.2, tR = 0.51 min. |
| 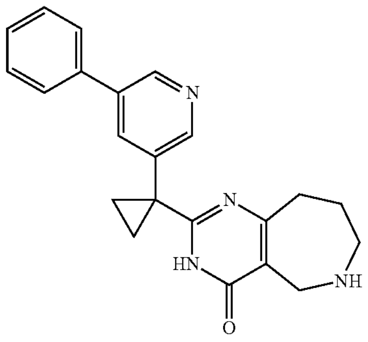 [SMILES: O=c1[nH]c(C2(c3cncc(-c4ccccc4)c3)CC2)nc2c1CNCCC2] INT-10-9 | 2-(1-(5-phenylpyridin-3-yl)cyclopropyl)-3,5,6,7,8,9-hexahydro-4H-pyrimido[5,4-c]azepin-4-one | LC-MS (Method-I) m/z: M + 1 obs 345.19, tR = 0.44 min. |
| 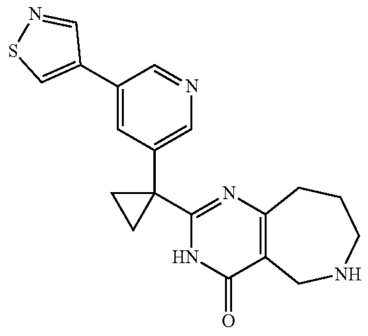 [SMILES: O=c1[nH]c(C2(c3cncc(-c4cnsc4)c3)CC2)nc2c1CNCCC2] INT-10-10 | 2-(1-(5-(isothiazol-4-yl)pyridin-3-yl)cyclopropyl)-3,5,6,7,8,9-hexahydro-4H-pyrimido[5,4-c]azepin-4-one | LC-MS (Method-I) m/z: M + 1 obs 366.17, tR = 0.42 min. |

TABLE 11-3

| | | |
|---|---|---|
| 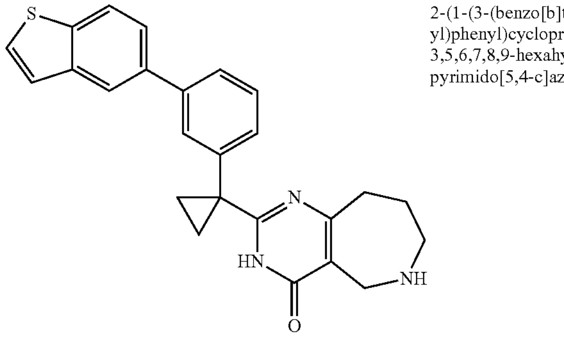 INT-10-11 | 2-(1-(3-(benzo[b]thiophen-5-yl)phenyl)cyclopropyl)-3,5,6,7,8,9-hexahydro-4H-pyrimido[5,4-c]azepin-4-one | LC-MS (Method-I) m/z: M + 1 obs 414.2, M − 1 obs 412.3, tR = 0.57 min. |

TABLE 11-3-continued
| | | |
|---|---|---|
| 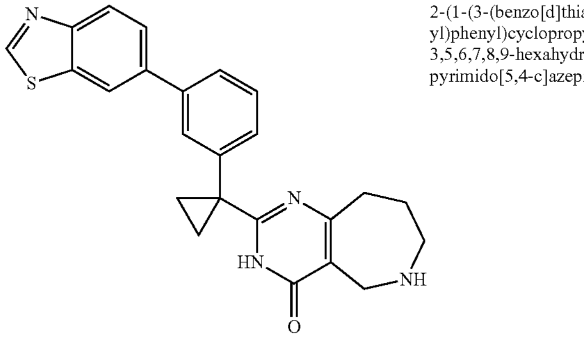 INT-10-12 | 2-(1-(3-(benzo[d]thiazol-5-yl)phenyl)cyclopropyl)-3,5,6,7,8,9-hexahydro-4H-pyrimido[5,4-c]azepin-4-one | LC-MS (Method-I) m/z: M + 1 obs 415.2, M − 1 obs 413.3, tR = 0.50 min. |
| 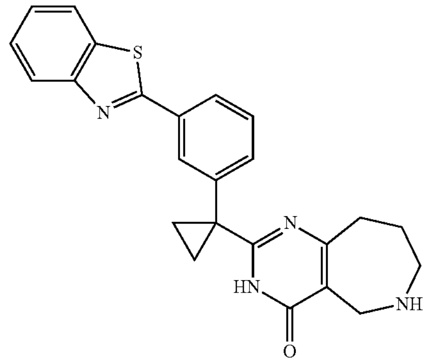 [SMILES: O=c1[nH]c(C2(c3cccc(-c4nc5ccccc5s4)c3)CC2)nc2c1CNCCC2] INT-10-13 | 2-(1-(3-(benzo[d]thiazol-2-yl)phenyl)cyclopropyl)-3,5,6,7,8,9-hexahydro-4H-pyrimido[5,4-c]azepin-4-one | LC-MS (Method-I) m/z: M + 1 obs 415.2, M − 1 obs 413.3, tR = 0.54 min. |
| 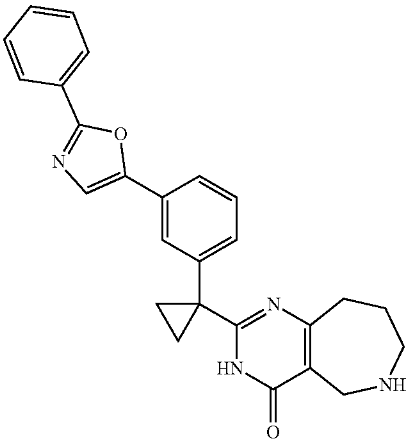 [SMILES: O=c1[nH]c(C2(c3cccc(-c4cnc(-c5ccccc5)o4)c3)CC2)nc2c1CNCCC2] INT-10-14 | 2-(1-(3-(2-phenyloxazol-5-yl)phenyl)cyclopropyl)-3,5,6,7,8,9-hexahydro-4H-pyrimido[5,4-c]azepin-4-one | LC-MS (Method-I) m/z: M + 1 obs 425.3, M − 1 obs 423.3, tR = 0.54 min. |

TABLE 11-3-continued
| | | |
|---|---|---|
| 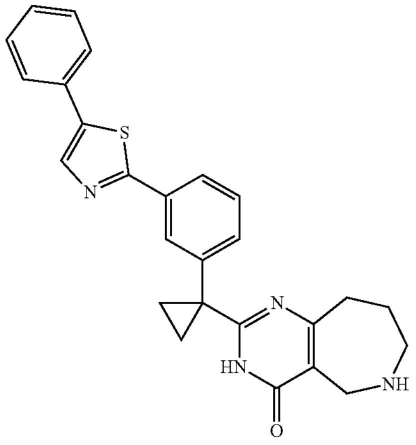 [SMILES: O=c1[nH]c(C2(c3cccc(-c4ncc(-c5ccccc5)s4)c3)CC2)nc2c1CNCCC2] INT-10-15 | 2-(1-(3-(5-phenylthiazol-2-yl)phenyl)cyclopropyl)-3,5,6,7,8,9-hexahydro-4H-pyrimido[5,4-c]azepin-4-one | LC-MS (Method-I) m/z: M + 1 obs 441.2, M − 1 obs 439.2, tR = 0.57 min. |
TABLE 11-4
| | | |
|---|---|---|
| 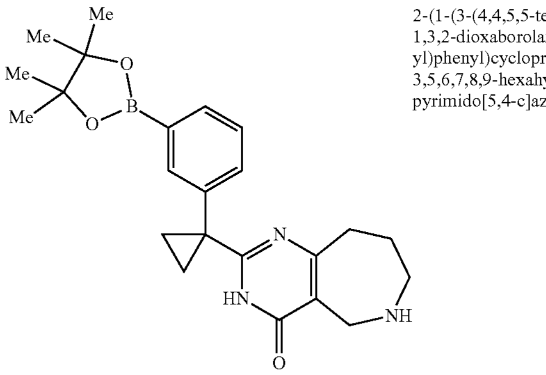 INT-10-16 | 2-(1-(3-(4,4,5,5-tetramethyl-1,3,2-dioxaborolan-2-yl)phenyl)cyclopropyl)-3,5,6,7,8,9-hexahydro-4H-pyrimido[5,4-c]azepin-4-one | LC-MS (Method-I) m/z: M + 1 obs 408.3, tR = 0.53 min. |
| 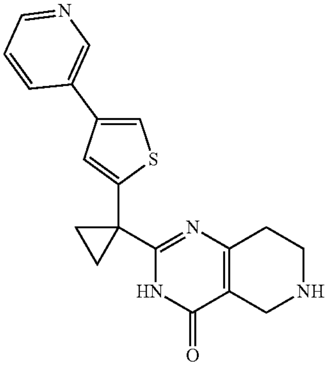 [SMILES: O=c1[nH]c(C2(c3cc(-c4cccnc4)cs3)CC2)nc2c1CNCC2] INT-10-17 | 2-(1-(4-(pyridin-3-yl)thiophen-2-yl)cyclopropyl)-5,6,7,8-tetrahydropyrido[4,3-d]pyrimidin-4(3H)-one | LC-MS (Method-I) m/z: M + 1 obs 351.00, tR = 1.33 min. |

TABLE 11-4-continued
| | | |
|---|---|---|
| 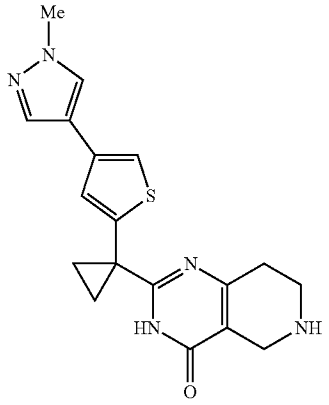 [SMILES: Cn1cc(-c2csc(C3(c4nc5c(c(=O)[nH]4)CNCC5)CC3)c2)cn1] INT-10-18 | 2-(1-(4-(1-methyl-1H-pyrazol-4-yl)thiophen-2-yl)cyclopropyl)-5,6,7,8-tetrahydropyrido[4,3-d]pyrimidin-4(3H)-one | LC-MS (Method-A1) m/z: M + 1 obs 354.17, tR = 1.60 min. |
| 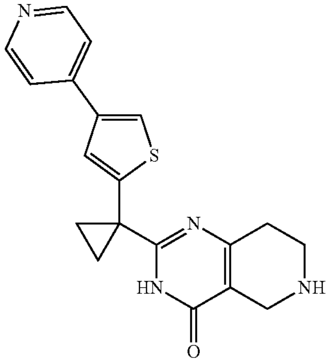 [SMILES: O=c1[nH]c(C2(c3cc(-c4ccncc4)cs3)CC2)nc2c1CNCC2] INT-10-19 | 2-(1-(4-(pyridin-4-yl)thiophen-2-yl)cyclopropyl)-5,6,7,8-tetrahydropyrido[4,3-d]pyrimidin-4(3H)-one | LC-MS (Method-A1) m/z: M + 1 obs 351.00, tR = 1.09 min. |
| 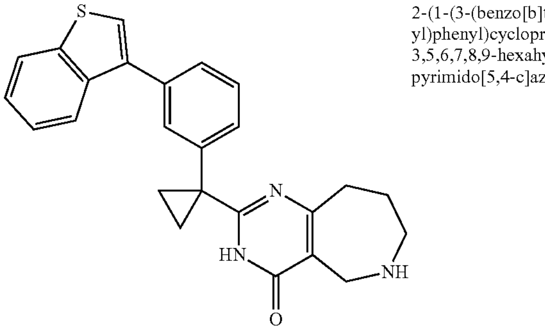 INT-10-20 | 2-(1-(3-(benzo[b]thiophen-3-yl)phenyl)cyclopropyl)-3,5,6,7,8,9-hexahydro-4H-pyrimido[5,4-c]azepin-4-one | LC-MS (Method-B1) m/z: M + 1 obs 414.01, M − 1 obs 412.01, tR = 2.15 min. |

Intermediate-11-25 (INT-11-25)

Synthesis of (R)-6-(2-(3-bromophenyl)-2-hydroxy-acetyl)-2-(1-(3-chlorophenyl)cyclopropyl)-3,5,6,7,8,9-hexahydro-4H-pyrimido[5,4-c]azepin-4-one {Chem. 37}

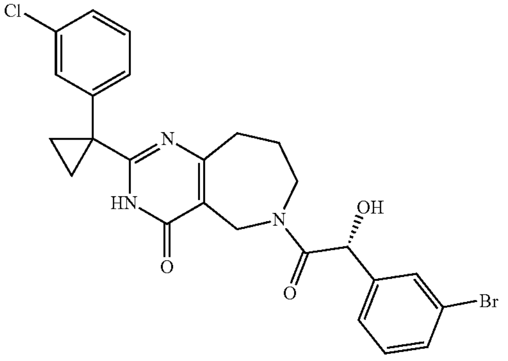

A mixture of (R)-2-(3-bromophenyl)-2-hydroxyacetic acid (100 mg, 0.433 mmol), INT-8-14 (144 mg, 0.454 mmol), HATU (197 mg, 0.519 mmol) and DIPEA (0.226 mL, 1.30 mmol) in DMF (8 mL) is stirred at rt for 15 hrs. The mixture is quenched with water (5 mL) and extracted with EtOAc-toluene (10:1 v/v)(100 mL). The separated organic layer is washed with water, brine, dried over magnesium sulfate, filtered and concentrated in vacuo to give crude product, which was purified by column chromatography on silica gel (30 g) eluting with a gradient of 20 to 100% EtOAc in n-hexane to give the title compound (246 mg) as a white amorphous solid.

LC-MS data is noted in Table 12-1 to 12-10.

The following pyrimidin-4(3H)-one derivatives (INT-11-1 to INT-11-51) are prepared according to the procedure of INT-11-25 by amidation of the synthesized amine derivatives and the known or synthesized acid derivatives in Tables 12-1 to 12-10.

TABLE 12-1

| Structure | amine | acid | LC-MS (m/z) |
|---|---|---|---|
| 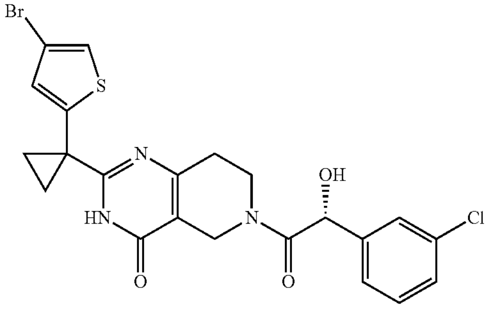 INT-11-1 | INT-4-19 | 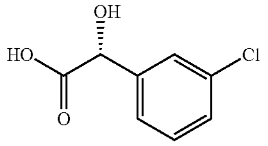 | (= Ex-6-18) LC-MS (HPLC-QC) m/z: M + 1 obs 518.1, tR = 1.67 min. |
| 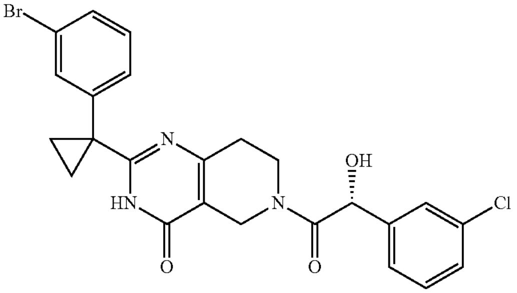 INT-11-2 | INT-4-32 | 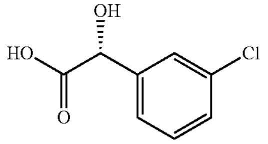 | (= Ex-14-26) LC-MS (HPLC-QC) m/z: M + 1 obs 514.0, tR = 1.70 min. |

TABLE 12-1-continued
| Structure | amine | acid | LC-MS (m/z) |
|---|---|---|---|
| 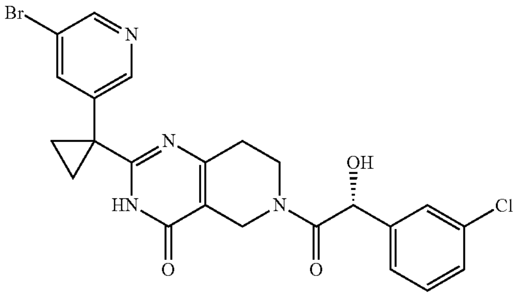 INT-11-3 | INT-4-35 | 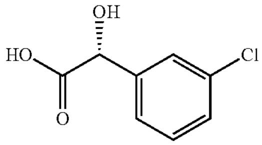 | LC-MS (Method-K) m/z: M + 1 obs 515.1, tR = 0.40 min. |
| 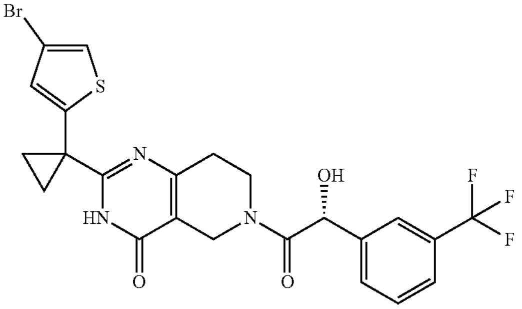 INT-11-4 | INT-4-19 | 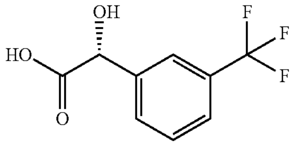 [SMILES: O=C(O)[C@H](O)c1cccc(C(F)(F)F)c1] | (= Ex-15-9) LC-MS (HPLC-QC) m/z: M + 1 obs 554.0, tR = 1.73 min. |
| 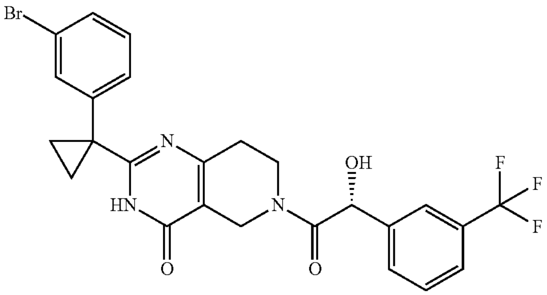 INT-11-5 | INT-4-32 | 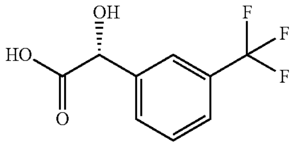 [SMILES: O=C(O)[C@H](O)c1cccc(C(F)(F)F)c1] | LC-MS (Method-K) m/z: M + 1 obs 548.1, tR = 0.50 min. |
| 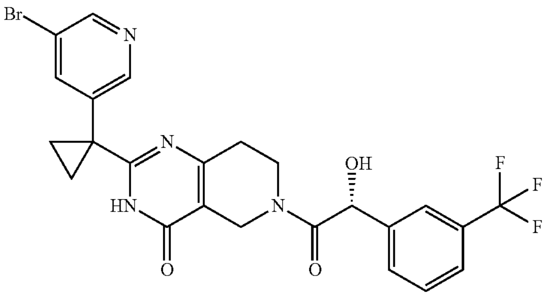 INT-11-6 | INT-4-35 | 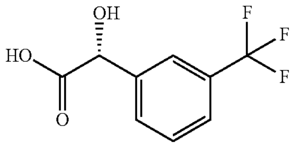 [SMILES: O=C(O)[C@H](O)c1cccc(C(F)(F)F)c1] | LC-MS (Method-K) m/z: M + 1 obs 549.0, tR = 0.44 min. |

TABLE 12-2
| | | | |
|---|---|---|---|
| 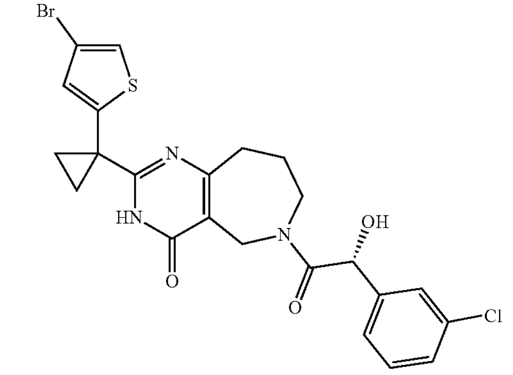 INT-11-7 | INT-8-24 | 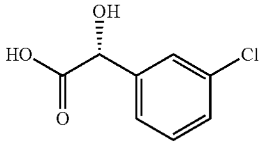 | LC-MS (Method-I) m/z: M + 1 obs 534.1, M − 1 obs 532.1, tR = 0.54 min. |
| 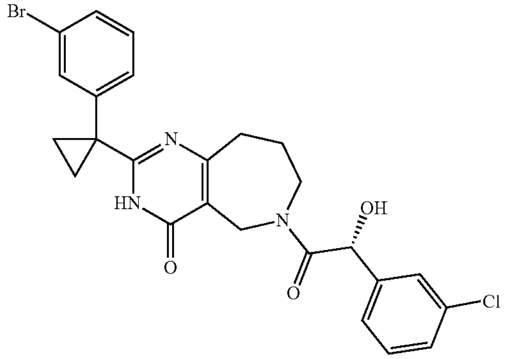 INT-11-8 | INT-8-15 | 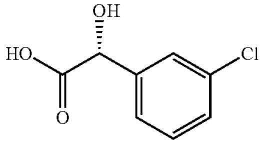 | (= Ex-17-87) LC-MS (HPLC-QC) m/z: M + 1 obs 527.9, tR = 1.73 min. |
| 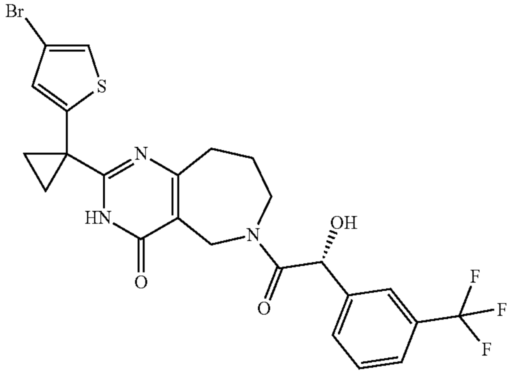 INT-11-9 | INT-8-24 | 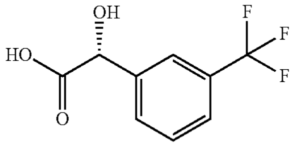 [SMILES: O=C(O)[C@H](O)c1cccc(C(F)(F)F)c1] | (= Ex-18-2) LC-MS (HPLC-QC) m/z: M + 1 obs 568.0, tR = 1.78 min. |
| 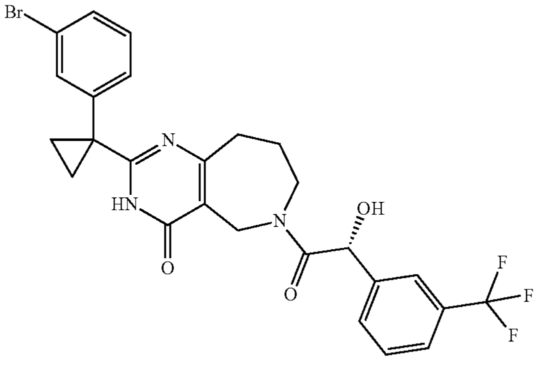 INT-11-10 | INT-8-15 | 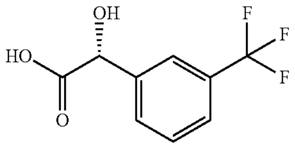 [SMILES: O=C(O)[C@H](O)c1cccc(C(F)(F)F)c1] | LC-MS (Method-K) m/z: M + 1 obs 562.1, tR = 0.53 min. |

TABLE 12-2-continued
| | | | |
|---|---|---|---|
| 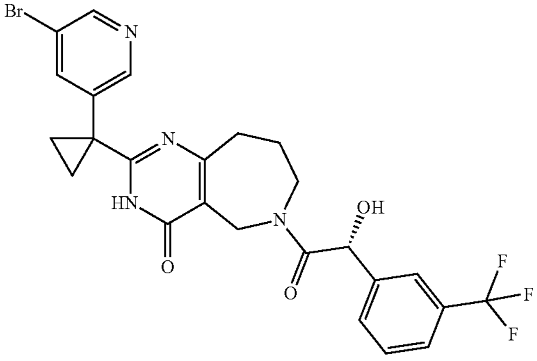 INT-11-11 | INT-8-31 | 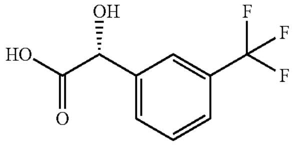 [SMILES: O=C(O)[C@H](O)c1cccc(C(F)(F)F)c1] | (= Ex-19-6) LC-MS (HPLC-QC) m/z: M + 1 obs 563.1, tR = 1.53 min. |
TABLE 12-3
| | | | |
|---|---|---|---|
| 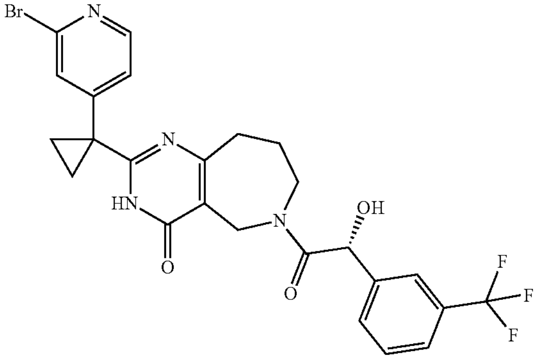 INT-11-12 | INT-8-30 | 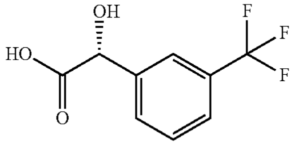 [SMILES: O=C(O)[C@H](O)c1cccc(C(F)(F)F)c1] | LC-MS (Method-I) m/z: M + 1 obs 563.07, tR = 0.51 min. |
| 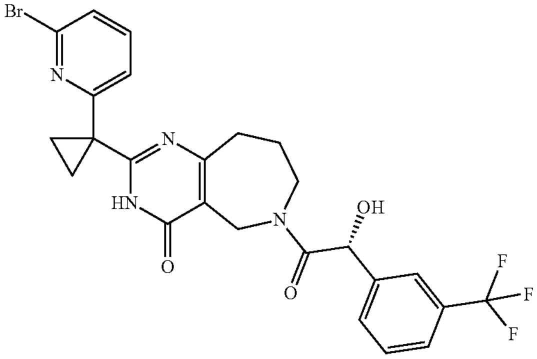 INT-11-13 | INT-8-32 | 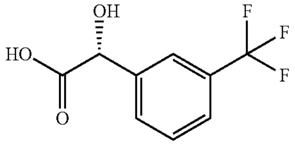 [SMILES: O=C(O)[C@H](O)c1cccc(C(F)(F)F)c1] | LC-MS (Method-I) m/z: M + 1 obs 563.04, tR = 0.49 min. |

TABLE 12-3-continued
| | | | |
|---|---|---|---|
| 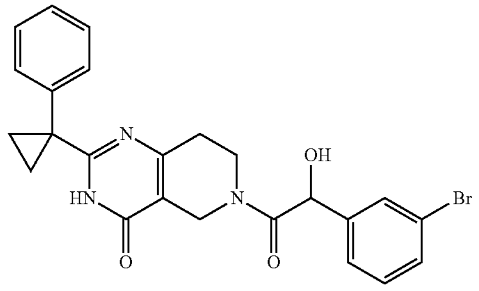 INT-11-14 | INT-1 | 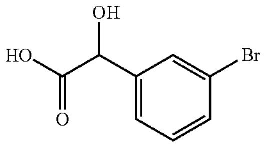 | (= Ex-14-44) LC-MS (HPLC-QC) m/z: M + 1 obs 480.1, tR = 1.58 min. |
| 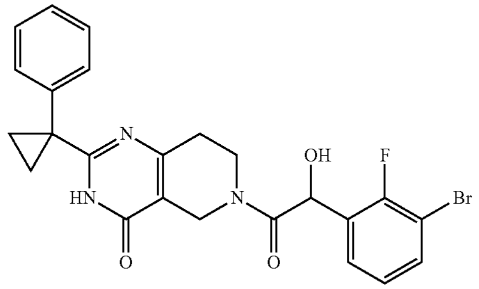 INT-11-15 | INT-1 | 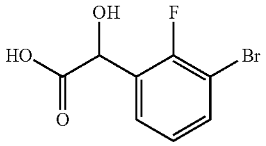 | LC-MS (Method-H) m/z: M + 1 obs 497.9, tR = 2.60 min. |
| 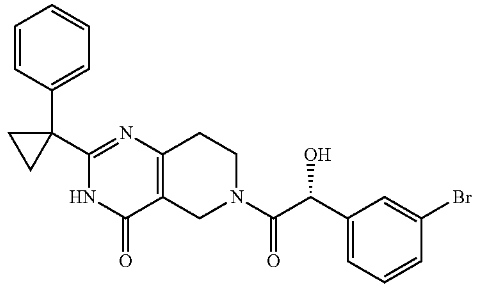 INT-11-16 | INT-1 | 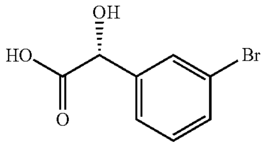 | LC-MS (Method-H) m/z: M + 1 obs 479.9, tR = 1.87 min. |
| 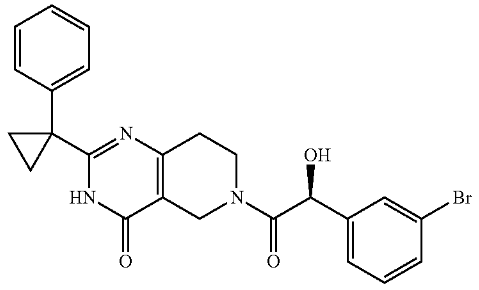 INT-11-17 | INT-1 | 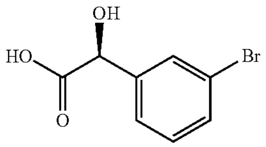 [SMILES: O=C(O)[C@@H](O)c1cccc(Br)c1] | LC-MS (Method-H) m/z: M + 1 obs 479.9, tR = 1.82 min. |

TABLE 12-4
| | | | |
|---|---|---|---|
| 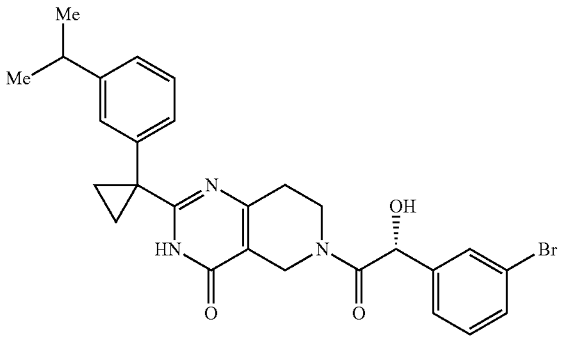<br>INT-11-18 | INT-8-5 | 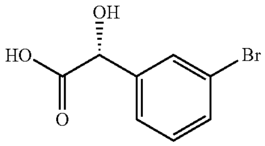 | LC-MS (Method-K) m/z: M + 1 obs 522.2, tR = 0.57 min. |
| 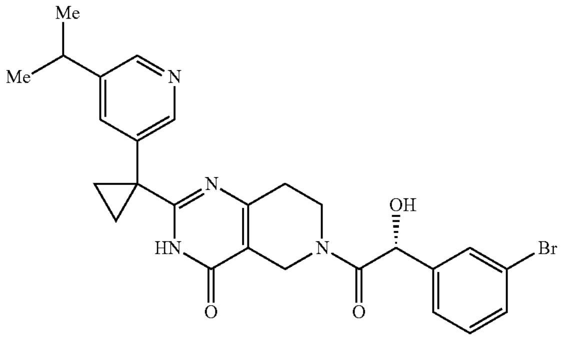<br>INT-11-19 | INT-8-29 | 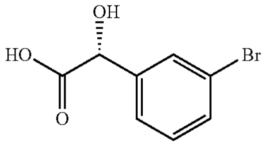 | LC-MS (Method-I) m/z: M + 1 obs 523.1, M − 1 obs 521.2, tR = 0.51 min. |
| 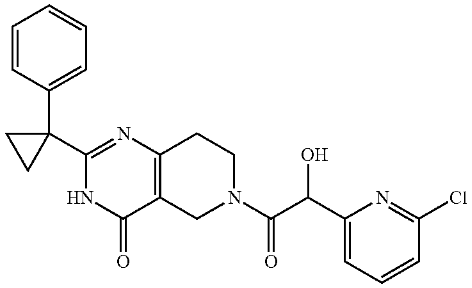<br>INT-11-20 | INT-1 | 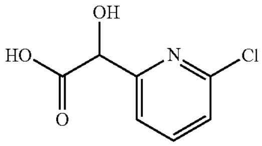 [SMILES: O=C(O)C(O)c1cccc(Cl)n1] | (= Ex-14-84) LC-MS (HPLC-QC) m/z: M + 1 obs 437.1, tR = 1.43 min. |
| 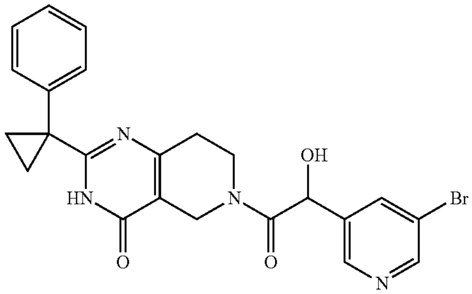<br>INT-11-21 | INT-1 | 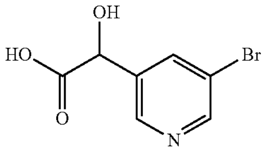 [SMILES: O=C(O)C(O)c1cncc(Br)c1] | (= Ex-14-58) LC-MS (HPLC-QC) m/z: M + 1 obs 480.9, tR = 1.36 min. |

TABLE 12-4-continued
| | | | |
|---|---|---|---|
| 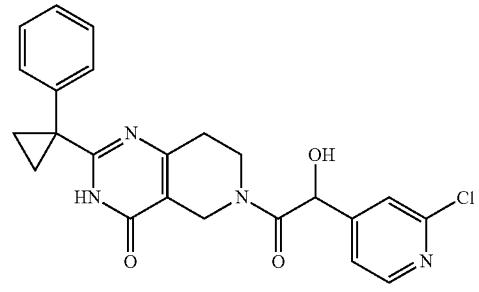<br>INT-11-22 | INT-1 | 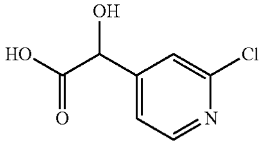<br>INT-24-1 | LC-MS (Method-H) m/z: M + 1 obs 437.24, tR = 2.05 min. |
| 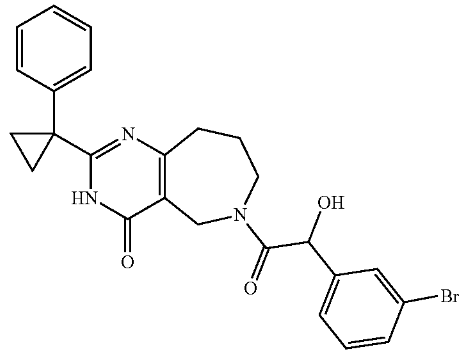<br>INT-11-23 | INT-8-3 | 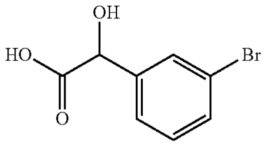 | (= Ex-17-55) LC-MS (HPLC-QC) m/z: M + 1 obs 494.0, tR = 1.62 min. |
TABLE 12-5
| | | | |
|---|---|---|---|
| 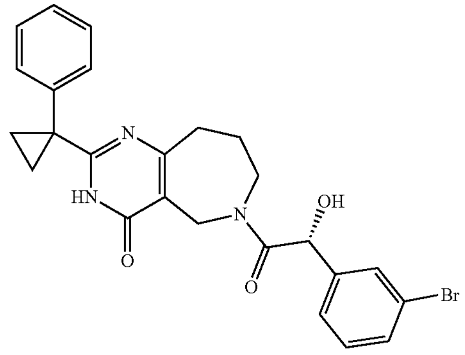 [SMILES: O=C([C@H](O)c1cccc(Br)c1)N1CCCc2nc(C3(c4ccccc4)CC3)[nH]c(=O)c2C1]<br>INT-11-24 | INT-8-3 | 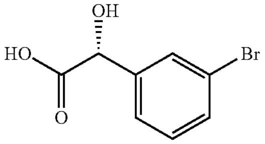 | (= Ex-17-77) LC-MS (HPLC-QC) m/z: M + 1 obs 493.9, tR = 1.60 min. |
| 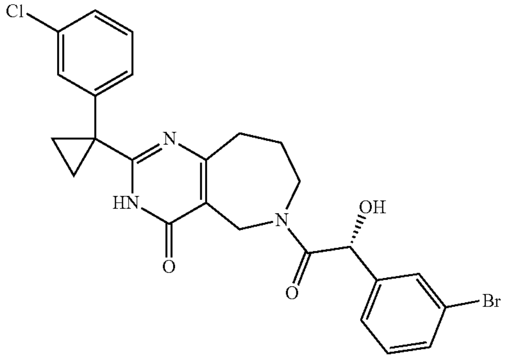 [SMILES: O=C([C@H](O)c1cccc(Br)c1)N1CCCc2nc(C3(c4cccc(Cl)c4)CC3)[nH]c(=O)c2C1]<br>INT-11-25 | INT-8-14 | 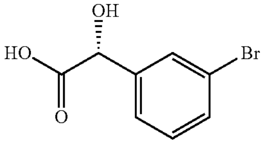 | LC-MS (Method-H) m/z: M + 1 obs 527.8, tR = 2.85 min. |

TABLE 12-5-continued
| | | | |
|---|---|---|---|
| 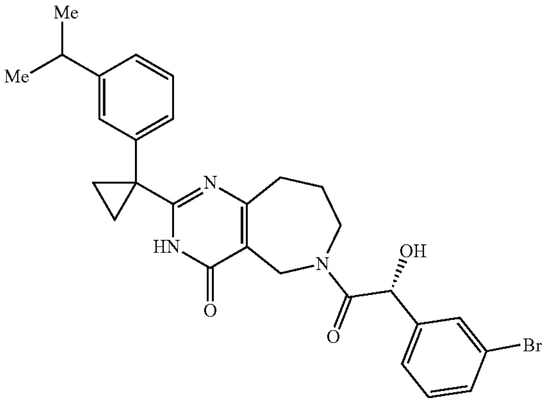 [SMILES: CC(C)c1cccc(C2(c3nc4c(c(=O)[nH]3)CN(C(=O)[C@H](O)c3cccc(Br)c3)CCC4)CC2)c1]<br>INT-11-26 | INT-8-19 | 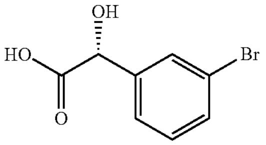 | LC-MS (Method-K) m/z: M + 1 obs 536.2, tR = 0.59 min. |
| 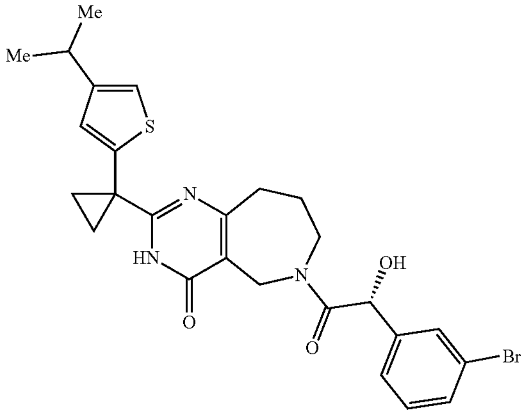 [SMILES: CC(C)c1csc(C2(c3nc4c(c(=O)[nH]3)CN(C(=O)[C@H](O)c3cccc(Br)c3)CCC4)CC2)c1]<br>INT-11-27 | INT-8-25 | 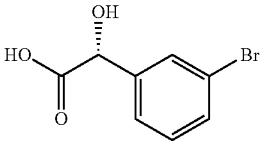 | LC-MS (Method-I) m/z: M + 1 obs 542.12, tR = 0.60 min. |
| 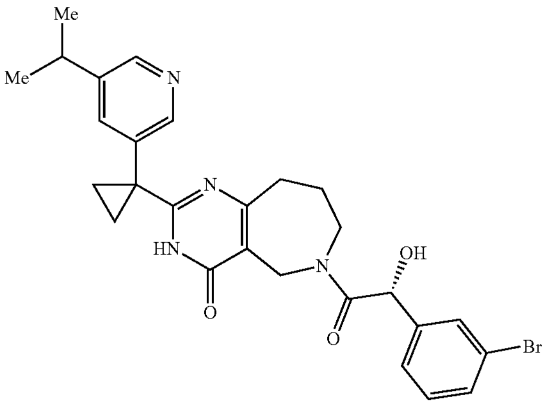 [SMILES: CC(C)c1cncc(C2(c3nc4c(c(=O)[nH]3)CN(C(=O)[C@H](O)c3cccc(Br)c3)CCC4)CC2)c1]<br>INT-11-28 | INT-8-33 | 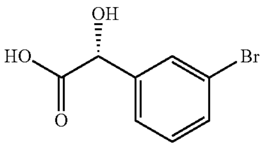 | LC-MS (Method-I) m/z: M + 1 obs 537.1, M − 1 obs 535.2, tR = 0.52 min. |

TABLE 12-6
| | | | |
|---|---|---|---|
| 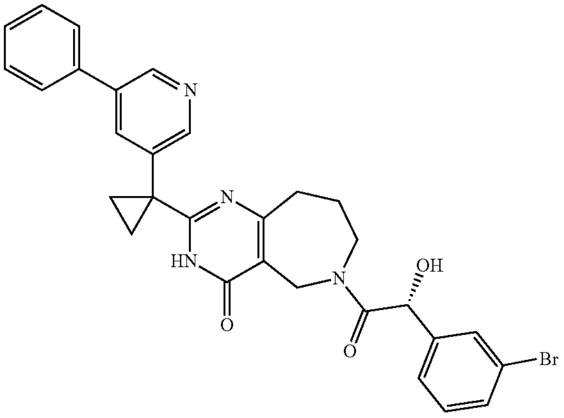 [SMILES: O=C([C@H](O)c1cccc(Br)c1)N1CCCc2nc(C3(c4cncc(-c5ccccc5)c4)CC3)[nH]c(=O)c2C1] INT-11-29 | INT-10-9 | 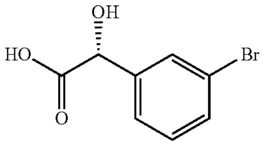 | LC-MS (Method-K) m/z: M + 1 obs 571.1, tR = 0.48 min. |
| 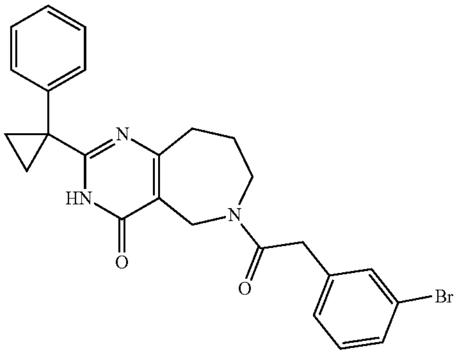 [SMILES: O=C(Cc1cccc(Br)c1)N1CCCc2nc(C3(c4ccccc4)CC3)[nH]c(=O)c2C1] INT-11-30 | INT-8-3 | 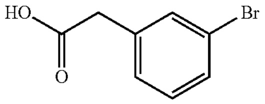 | LC-MS (Method-I) m/z: M + 1 obs 478.15, tR = 0.55 min. |
| 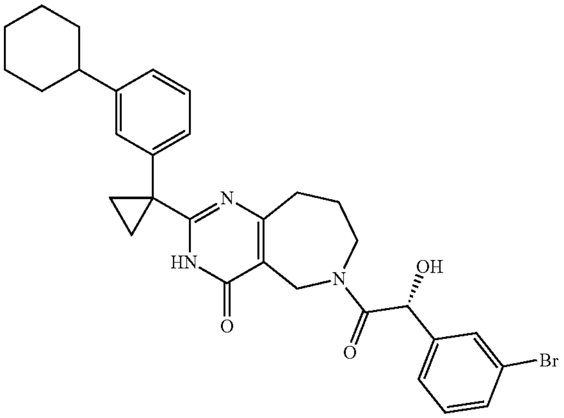 [SMILES: O=C([C@H](O)c1cccc(Br)c1)N1CCCc2nc(C3(c4cccc(C5CCCCC5)c4)CC3)[nH]c(=O)c2C1] INT-11-31 | INT-8-21 | 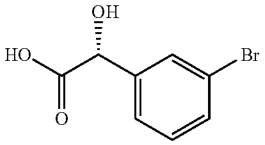 | LC-MS (Method-K) m/z: M + 1 obs 576.2, tR = 0.63 min. |
| 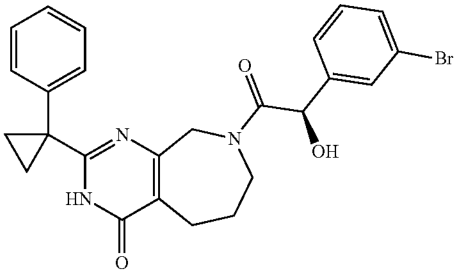 [SMILES: O=C([C@H](O)c1cccc(Br)c1)N1CCCc2c(nc(C3(c4ccccc4)CC3)[nH]c2=O)C1] INT-11-32 | INT-8-4 | 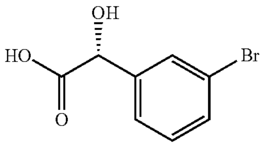 | LC-MS (Method-H) m/z: M + 1 obs 493.8, tR = 2.05 min. |

TABLE 12-6-continued
| | | | |
|---|---|---|---|
| 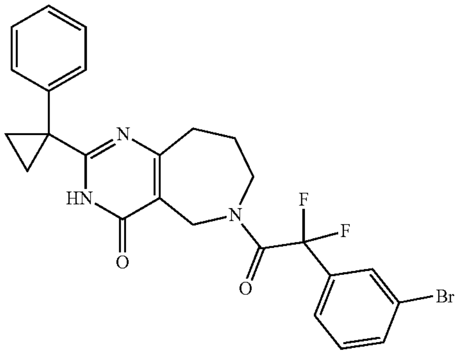 [SMILES: O=C(N1CCCc2nc(C3(c4ccccc4)CC3)[nH]c(=O)c2C1)C(F)(F)c1cccc(Br)c1]<br>INT-11-33 | INT-8-3 | 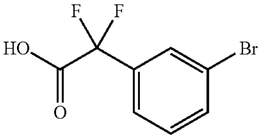 | LC-MS (Method-I) m/z: M + 1 obs 514.1, M − 1 obs 512.2, tR = 0.59 min. |
TABLE 12-7
| | | | |
|---|---|---|---|
| 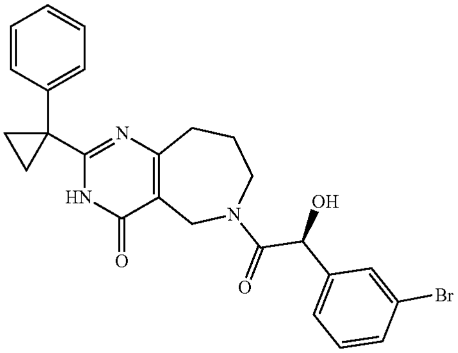 [SMILES: O=C([C@@H](O)c1cccc(Br)c1)N1CCCc2nc(C3(c4ccccc4)CC3)[nH]c(=O)c2C1]<br>INT-11-34 | INT-8-3 | 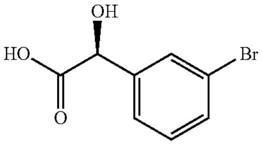 [SMILES: O=C(O)[C@@H](O)c1cccc(Br)c1] | LC-MS (Method-K) m/z: M + 1 obs 494.2, tR = 0.52 min. |
| 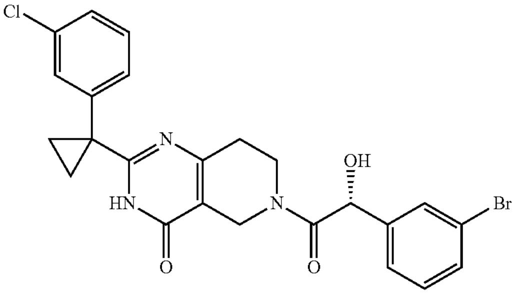 [SMILES: O=C([C@H](O)c1cccc(Br)c1)N1CCc2nc(C3(c4cccc(Cl)c4)CC3)[nH]c(=O)c2C1]<br>INT-11-35 | INT-4-14 | 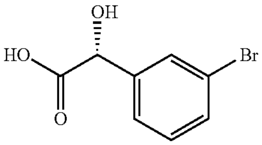 | LC-MS (Method-K) m/z: M + 1 obs 516.9, tR = 0.55 min. |
| 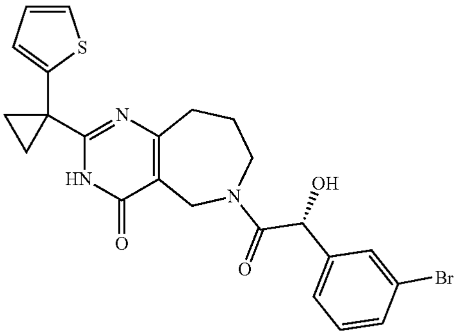 [SMILES: O=C([C@H](O)c1cccc(Br)c1)N1CCCc2nc(C3(c4cccs4)CC3)[nH]c(=O)c2C1]<br>INT-11-36 | INT-8-22 | 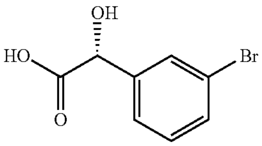 | LC-MS (Method-B1) m/z: M + 1 obs 499.9, M − 1 obs 497.9, tR = 1.85 min. |

TABLE 12-7-continued
| | | | |
|---|---|---|---|
| 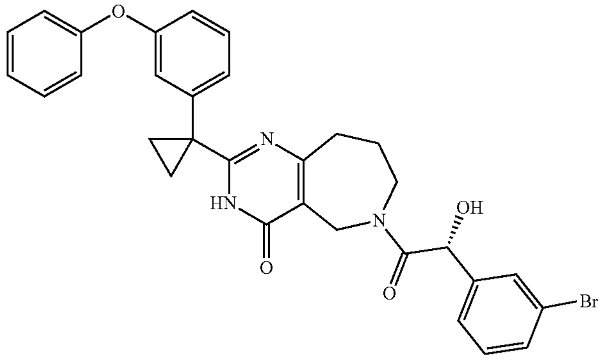 [SMILES: O=C([C@H](O)c1cccc(Br)c1)N1CCCc2nc(C3(c4cccc(Oc5ccccc5)c4)CC3)[nH]c(=O)c2C1] INT-11-37 | INT-8-36 | 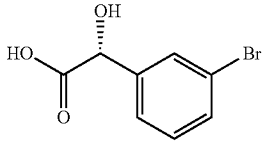 | LC-MS (Method-I) m/z: M + 1 obs 586.15, tR = 0.60 min. |
| 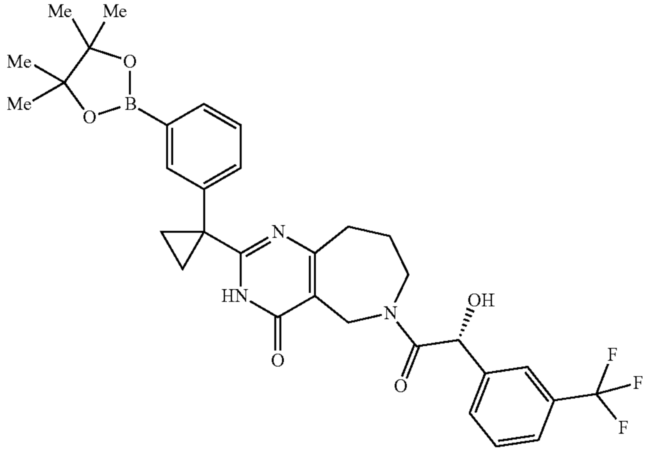 [SMILES: CC1(C)OB(c2cccc(C3(c4nc5c(c(=O)[nH]4)CN(C(=O)[C@H](O)c4cccc(C(F)(F)F)c4)CCC5)CC3)c2)OC1(C)C] INT-11-38 | INT-10-16 | 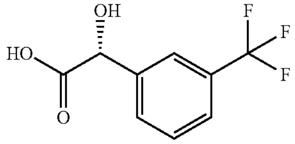 [SMILES: O=C(O)[C@H](O)c1cccc(C(F)(F)F)c1] | LC-MS (Method-I) m/z: M + 1 obs 610.28, tR = 0.62 min. |
TABLE 12-8
| | | | |
|---|---|---|---|
| 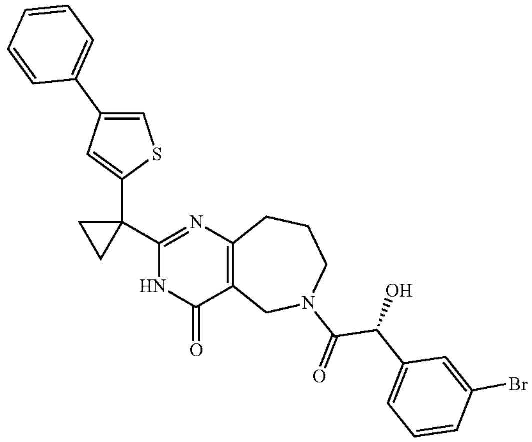 [SMILES: O=C([C@H](O)c1cccc(Br)c1)N1CCCc2nc(C3(c4cc(-c5ccccc5)cs4)CC3)[nH]c(=O)c2C1] INT-11-39 | INT-10-8 | 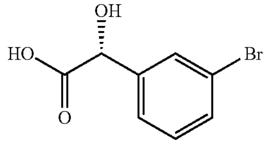 | LC-MS (Method-K) m/z: M + 1 obs 578.0, tR = 0.56 min. |

TABLE 12-8-continued
| | | | |
|---|---|---|---|
| 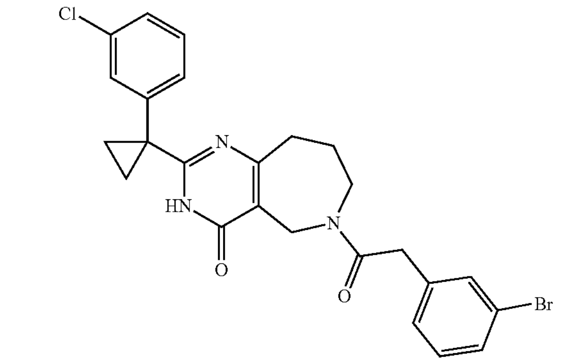 [SMILES: O=C(Cc1cccc(Br)c1)N1CCCc2nc(C3(c4cccc(Cl)c4)CC3)[nH]c(=O)c2C1]<br>INT-11-40 | INT-8-14 | 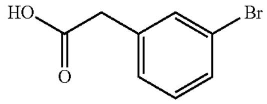 | LC-MS (Method-K) m/z: M + 1 obs 514.0, tR = 0.63 min. |
| 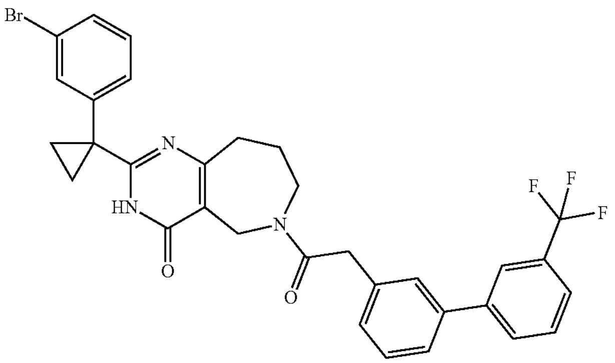 [SMILES: O=C(Cc1cccc(-c2cccc(C(F)(F)F)c2)c1)N1CCCc2nc(C3(c4cccc(Br)c4)CC3)[nH]c(=O)c2C1]<br>INT-11-41 | INT-8-15 | 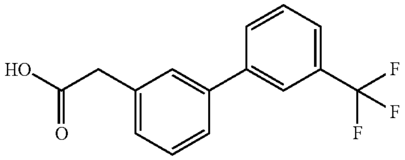 [SMILES: O=C(O)Cc1cccc(-c2cccc(C(F)(F)F)c2)c1] | LC-MS (Method-K) m/z: M − 1 obs 622.2, tR = 0.62 min. |
| 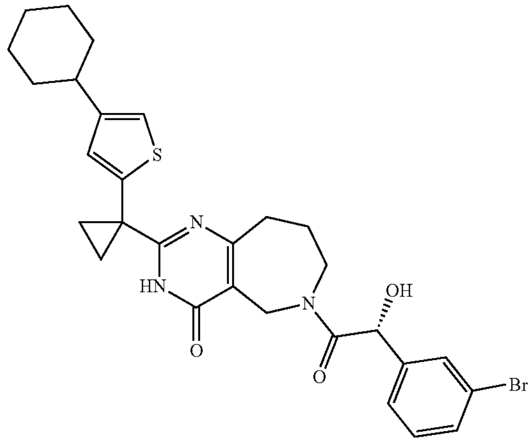 [SMILES: O=C([C@H](O)c1cccc(Br)c1)N1CCCc2nc(C3(c4cc(C5CCCCC5)cs4)CC3)[nH]c(=O)c2C1]<br>INT-11-42 | INT-8-27 | 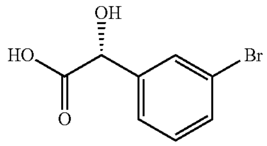 | LC-MS (Method-I) m/z: M + 1 obs 582.17, tR = 0.66 min. |

TABLE 12-8-continued
| | | | |
|---|---|---|---|
| 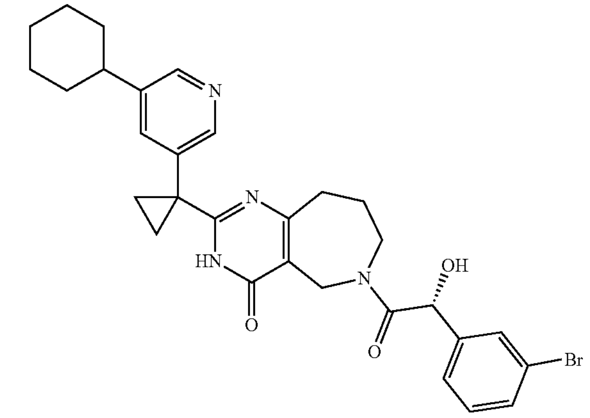 [SMILES: O=C([C@H](O)c1cccc(Br)c1)N1CCCc2nc(C3(c4cncc(C5CCCCC5)c4)CC3)[nH]c(=O)c2C1]<br>INT-11-43 | INT-8-34 | 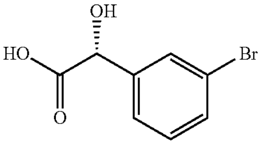 | LC-MS (Method-I) m/z: M + 1 obs 577.2, M − 1 obs 575.2, tR = 0.57 min. |
TABLE 12-9
| | | | |
|---|---|---|---|
| 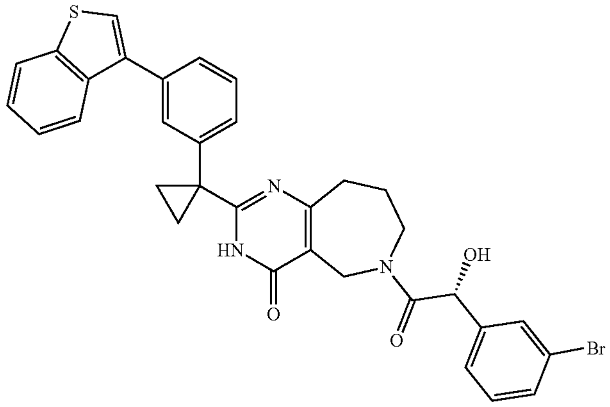 [SMILES: O=C([C@H](O)c1cccc(Br)c1)N1CCCc2nc(C3(c4cccc(-c5csc6ccccc56)c4)CC3)[nH]c(=O)c2C1]<br>INT-11-44 | INT-10-20 | 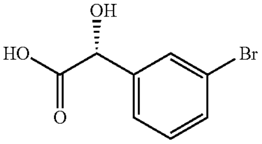 | LC-MS (Method-K) m/z: M + H obs 628.0, tR = 0.64 min. |
| 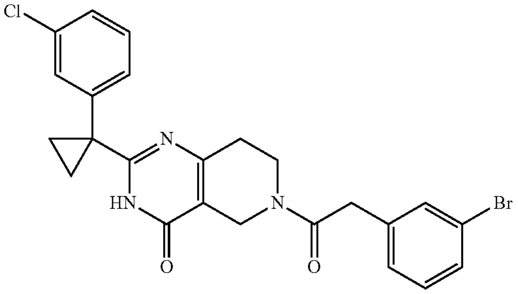 [SMILES: O=C(Cc1cccc(Br)c1)N1CCc2nc(C3(c4cccc(Cl)c4)CC3)[nH]c(=O)c2C1]<br>INT-11-45 | INT-4-14 | 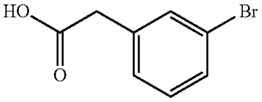 | LC-MS (Method-K) m/z: M + H obs 500.1, tR = 0.56 min. |

TABLE 12-9-continued
| | | | |
|---|---|---|---|
| 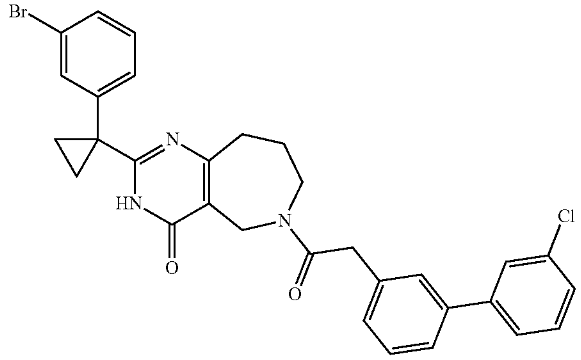<br>INT-11-46 | INT-8-15 | 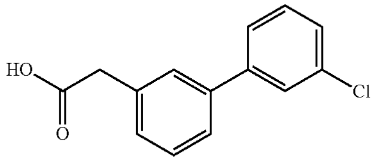 [SMILES: O=C(O)Cc1cccc(-c2cccc(Cl)c2)c1] | LC-MS (Method-K) m/z: M + 1 obs 590.0, tR = 0.59 min |
| 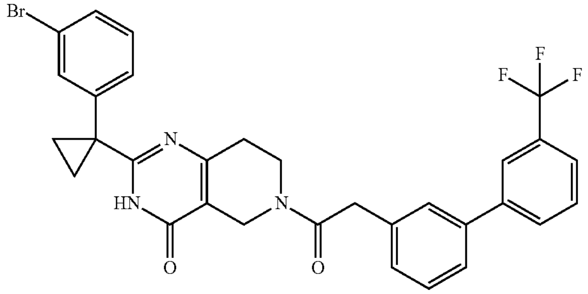 [SMILES: O=C(Cc1cccc(-c2cccc(C(F)(F)F)c2)c1)N1CCc2nc(C3(c4cccc(Br)c4)CC3)[nH]c(=O)c2C1]<br>INT-11-47 | INT-4-32 | 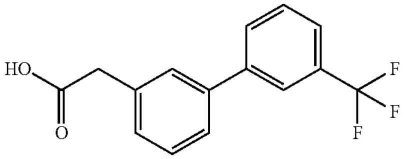 [SMILES: O=C(O)Cc1cccc(-c2cccc(C(F)(F)F)c2)c1] | LC-MS (Method-K) m/z: M + 1 obs 610.1, tR = 0.57 min |
| 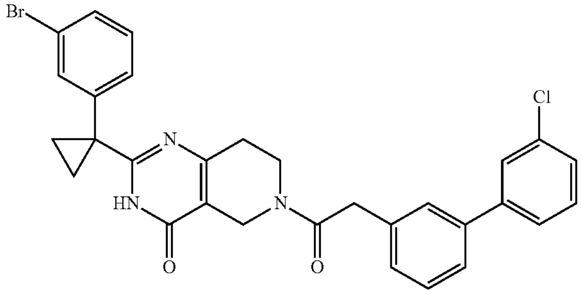 [SMILES: O=C(Cc1cccc(-c2cccc(Cl)c2)c1)N1CCc2nc(C3(c4cccc(Br)c4)CC3)[nH]c(=O)c2C1]<br>INT-11-48 | INT-4-32 | 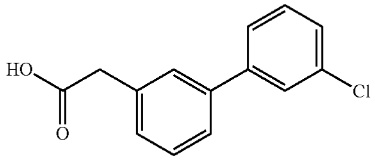 [SMILES: O=C(O)Cc1cccc(-c2cccc(Cl)c2)c1] | LC-MS (Method-K) m/z: M + 1 obs 576.0, tR = 0.57 min |
TABLE 12-10
| | | | |
|---|---|---|---|
| 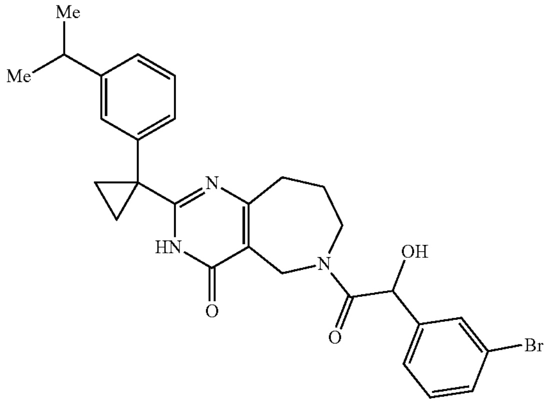 [SMILES: CC(C)c1cccc(C2(c3nc4c(c(=O)[nH]3)CN(C(=O)C(O)c3cccc(Br)c3)CCC4)CC2)c1]<br>INT-11-49 | INT-8-19 | 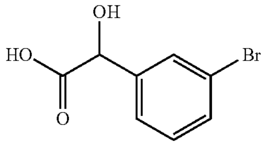 [SMILES: O=C(O)C(O)c1cccc(Br)c1] | LC-MS (Method-K) m/z: M + 1 obs 536.2, tR = 0.59 min. |

TABLE 12-10-continued
| | | | |
|---|---|---|---|
| 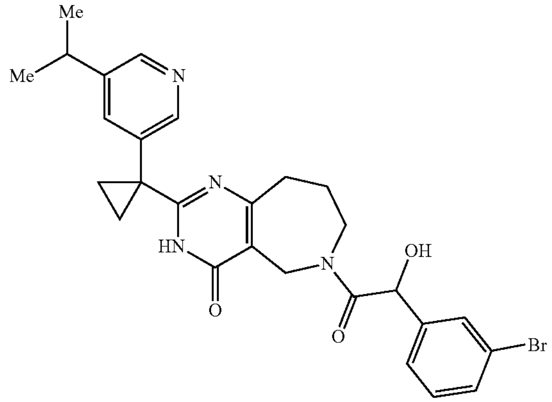 [SMILES: CC(C)c1cncc(C2(c3nc4c(c(=O)[nH]3)CN(C(=O)C(O)c3cccc(Br)c3)CCC4)CC2)c1]<br>INT-11-50 | INT-8-33 | 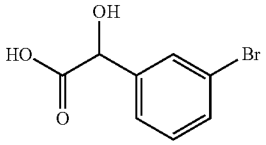 | LC-MS (Method-I) m/z: M + 1 obs 537.1, M − 1 obs 535.2, tR = 0.52 min. |
| 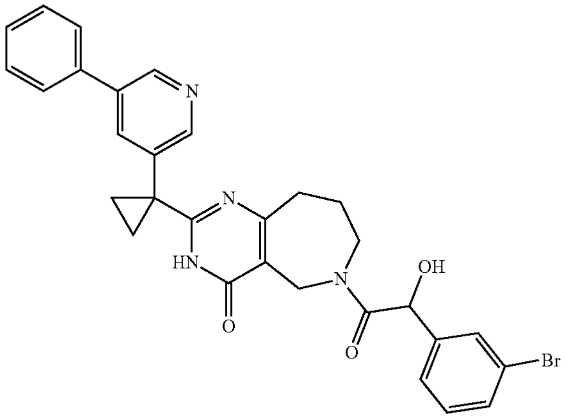<br>INT-11-51 | INT-10-9 | 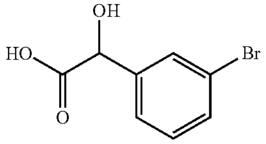 | LC-MS (Method-K) m/z: M + 1 obs 571.1, tR = 0.48 min. |
Intermediate-12-1 (INT-12-1)
Synthesis of (R)-6-(2-(3-chlorophenyl)-2-hydroxyacetyl)-2-(1-(4-(cyclopent-1-en-1-yl)thiophen-2-yl)cyclopropyl)-5,6,7,8-tetrahydropyrido[4,3-d]pyrimidin-4(3H)-one
{Chem. 38}
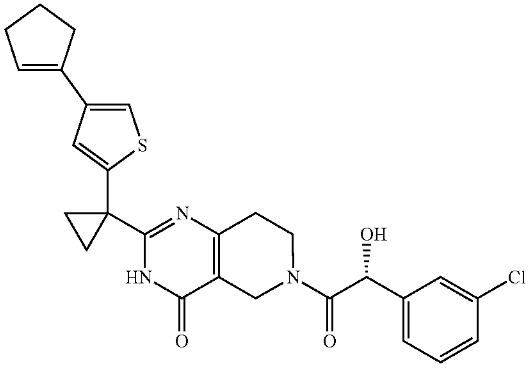

The mixture of INT-11-1 (25 mg, 0.041 mmol), cyclopent-1-en-1-ylboronic acid (14.0 mg, 0.057 mmol), palladium (II) acetate (1.84 mg, 0.0082 mmol) and triphenylphosphine (4.31 mg, 0.016 mmol) in 1,4-dioxane (1 mL) and saturated aqueous sodium bicarbonate (0.5 mL) is stirred at 100° C. for 1 hr. After cooled down to rt, the mixture is extracted with ethyl acetate and the separated organic layer is concentrated in vacuo to give the crude compound, which is purified by a strong anion exchange cartridge (ISOLUTE(registered trademark) SCX-2) to give the titled compound (14.7 mg) as a brown solid. The compound is used in the next reaction without further purification.

LC-MS (Method-I) m/z: M+1 obs 508.20, tR=0.59 min.

The following pyrimidin-4(3H)-one derivative (INT-12-2) is prepared according to the procedure of intermediate-12-1 from INT-11-1 and 2-(4,4-difluorocyclohex-1-en-1-yl)-4,4,5,5-tetramethyl-1,3,2-dioxaborolane in Table 13.

TABLE 13

| Structure | Chemical Name | LC-MS (m/z) |
|---|---|---|
| 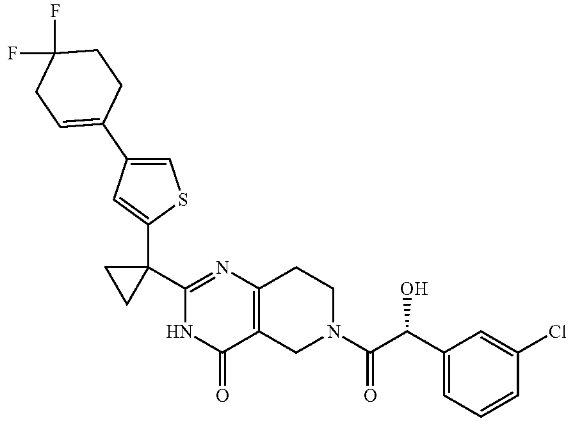 [SMILES: O=C([C@H](O)c1cccc(Cl)c1)N1CCc2nc(C3(c4cc(C5=CCC(F)(F)CC5)cs4)CC3)[nH]c(=O)c2C1] INT-12-2 | (R)-6-(2-(3-chlorophenyl)-2-hydroxyacetyl)-2-(1-(4-(4,4-difluorocyclohex-1-en-1-yl)thiophen-2-yl)cyclopropyl)-5,6,7,8-tetrahydropyrido[4,3-d]pyrimidin-4(3H)-one | LC-MS (Method-I) m/z: M + 1 obs 558.16, tR = 0.56 min. |

The following pyrimidin-4(3H)-one derivative (INT-13-1) is prepared according to the procedure of intermediate-12-1 from INT-11-2 and cyclopentene-1-boronic acid in Table 14.

TABLE 14

| Structure | Chemical Name | LC-MS (m/z) |
|---|---|---|
| 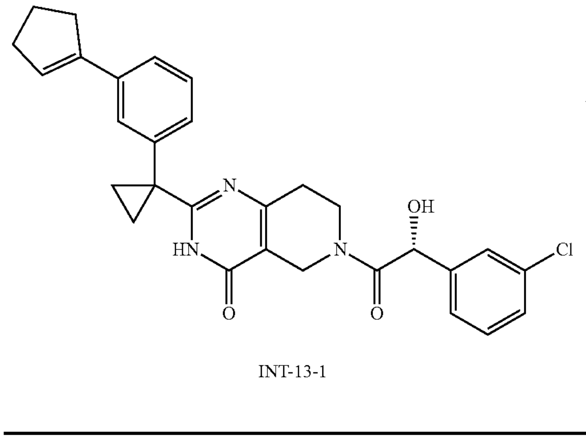 INT-13-1 | (R)-6-(2-(3-chlorophenyl)-2-hydroxyacetyl)-2-(1-(3-(cyclopent-1-en-1-yl)phenyl)cyclopropyl)-5,6,7,8-tetrahydropyrido[4,3-d]pyrimidin-4(3H)-one | LC-MS (Method-K) m/z: M + 1 obs 502.2, tR = 0.56 min. |

The following pyrimidin-4(3H)-one derivatives (INT-14-1 to INT-14-5) are prepared according to the procedure of intermediate-12-1 from the known boronic acid derivatives and INT-11-3 in Table 15.

TABLE 15

| Structure | Chemical Name | LC-MS (m/z) |
|---|---|---|
| 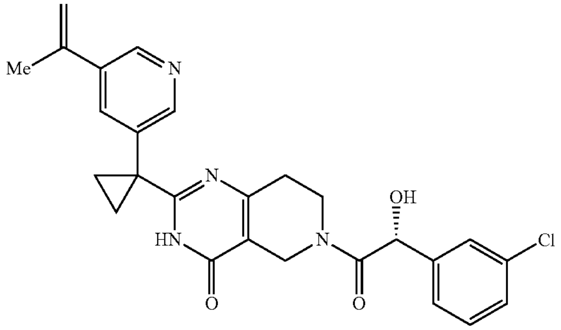 [SMILES: C=C(C)c1cncc(C2(c3nc4c(c(=O)[nH]3)CN(C(=O)[C@H](O)c3cccc(Cl)c3)CC4)CC2)c1] INT-14-1 | (R)-6-(2-(3-chlorophenyl)-2-hydroxyacetyl)-2-(1-(5-(prop-1-en-2-yl)pyridin-3-yl)cyclopropyl)-5,6,7,8-tetrahydropyrido[4,3-d]pyrimidin-4(3H)-one | LC-MS (Method-K) m/z: M + 1 obs 477.2, tR = 0.40 min. |
| 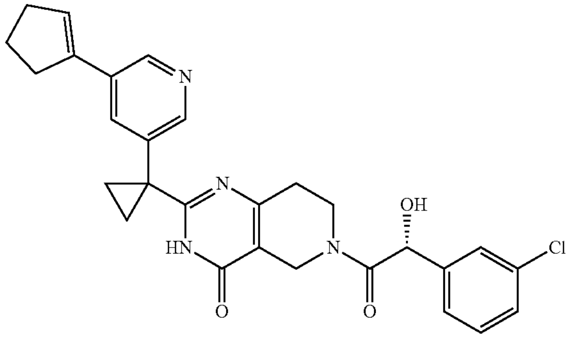 [SMILES: O=C([C@H](O)c1cccc(Cl)c1)N1CCc2nc(C3(c4cncc(C5=CCCC5)c4)CC3)[nH]c(=O)c2C1] INT-14-2 | (R)-6-(2-(3-chlorophenyl)-2-hydroxyacetyl)-2-(1-(5-(cyclopent-1-en-1-yl)pyridin-3-yl)cyclopropyl)-5,6,7,8-tetrahydropyrido[4,3-d]pyrimidin-4(3H)-one | LC-MS (Method-K) m/z: M + 1 obs 503.2, tR = 0.44 min. |
| 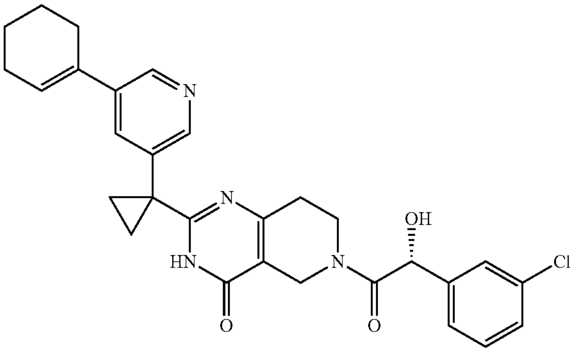 [SMILES: O=C([C@H](O)c1cccc(Cl)c1)N1CCc2nc(C3(c4cncc(C5=CCCCC5)c4)CC3)[nH]c(=O)c2C1] INT-14-3 | (R)-6-(2-(3-chlorophenyl)-2-hydroxyacetyl)-2-(1-(5-(cyclohex-1-en-1-yl)pyridin-3-yl)cyclopropyl)-5,6,7,8-tetrahydropyrido[4,3-d]pyrimidin-4(3H)-one | LC-MS (Method-K) m/z: M + 1 obs 517.2, tR = 0.48 min. |
| 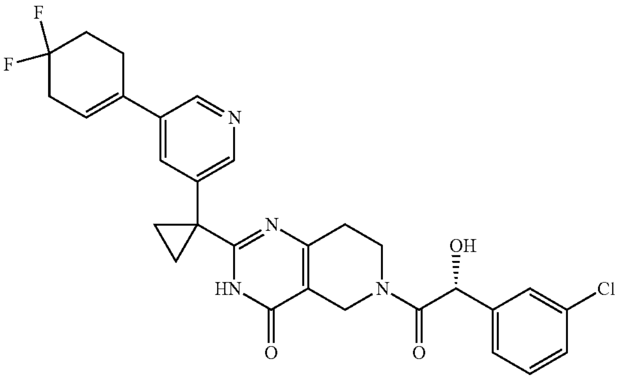 [SMILES: O=C([C@H](O)c1cccc(Cl)c1)N1CCc2nc(C3(c4cncc(C5=CCC(F)(F)CC5)c4)CC3)[nH]c(=O)c2C1] INT-14-4 | (R)-6-(2-(3-chlorophenyl)-2-hydroxyacetyl)-2-(1-(5-(4,4-difluorocyclohex-1-en-1-yl)pyridin-3-yl)cyclopropyl)-5,6,7,8-tetrahydropyrido[4,3-d]pyrimidin-4(3H)-one | LC-MS (Method-K) m/z: M + 1 obs 553.2, tR = 0.44 min. |

TABLE 15-continued

| Structure | Chemical Name | LC-MS (m/z) |
|---|---|---|
| 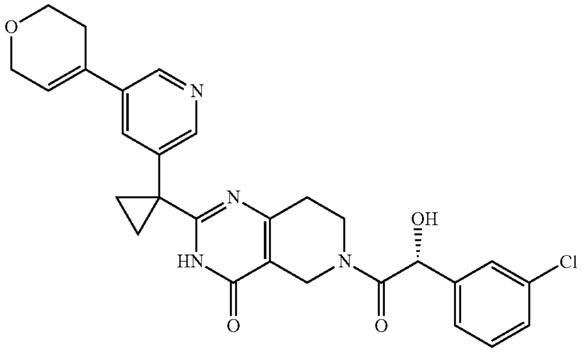 [SMILES: O=C([C@H](O)c1cccc(Cl)c1)N1CCc2nc(C3(c4cncc(C5=CCOCC5)c4)CC3)[nH]c(=O)c2C1] INT-14-5 | (R)-6-(2-(3-chlorophenyl)-2-hydroxyacetyl)-2-(1-(5-(3,6-dihydro-2H-pyran-4-yl)pyridin-3-yl)cyclopropyl)-5,6,7,8-tetrahydropyrido[4,3-d]pyrimidin-4(3H)-one | The structure is confirmed at the next step. |

The following pyrimidin-4(3H)-one derivatives (INT-15-1 to INT-15-3) are prepared according to the procedure of intermediate-12-1 from the known boronic acid derivatives and INT-11-4 in Table 16.

TABLE 16

| Structure | Chemical Name | LC-MS (m/z) |
|---|---|---|
| 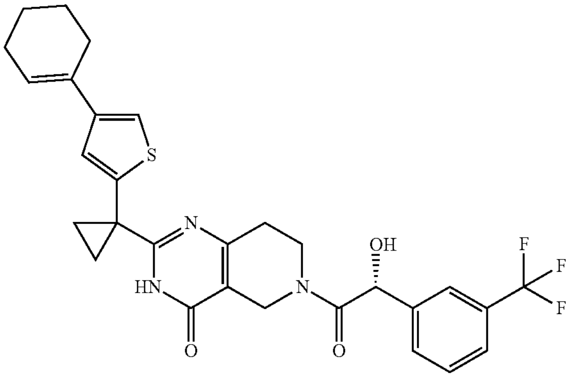 [SMILES: O=C([C@H](O)c1cccc(C(F)(F)F)c1)N1CCc2nc(C3(c4cc(C5=CCCCC5)cs4)CC3)[nH]c(=O)c2C1] INT-15-1 | (R)-2-(1-(4-(cyclohex-1-en-1-yl)thiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one | LC-MS (Method-I) m/z: M + 1 obs 556.21, tR = 0.62 min. |
| 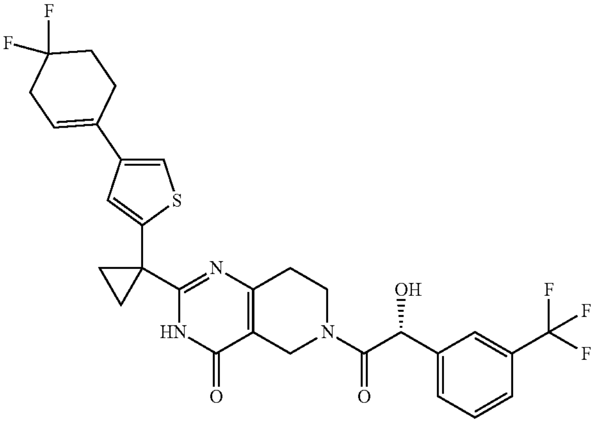 [SMILES: O=C([C@H](O)c1cccc(C(F)(F)F)c1)N1CCc2nc(C3(c4cc(C5=CCC(F)(F)CC5)cs4)CC3)[nH]c(=O)c2C1] INT-15-2 | (R)-2-(1-(4-(4,4-difluorocyclohex-1-en-1-yl)thiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one | LC-MS (Method-I) m/z: M + 1 obs 592.21, tR = 0.56 min. |

TABLE 16-continued

| Structure | Chemical Name | LC-MS (m/z) |
| --- | --- | --- |
| 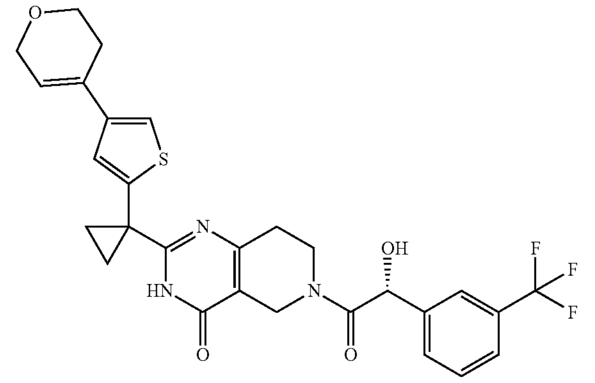 [SMILES: O=C([C@H](O)c1cccc(C(F)(F)F)c1)N1CCc2nc(C3(c4cc(C5=CCOCC5)cs4)CC3)[nH]c(=O)c2C1] INT-15-3 | (R)-2-(1-(4-(3,6-dihydro-2H-pyran-4-yl)thiophen-2-yl)cyclopropyl)-6-(2-hydroxy-2-(3-(trifluoromethyl)phenyl) acetyl)-5,6,7,8-tetrahydropyrido[4,3-d]pyrimidin-4(3H)-one | LC-MS (Method-I) m/z: M + 1 obs 558.19, tR = 0.53 min. |

The following pyrimidin-4(3H)-one derivatives (INT-16-1 to INT-16-3) are prepared according to the procedure of intermediate-12-1 from the known boronic acid derivatives and INT-11-5 in Table 17.

TABLE 17

| Structure | Chemical Name | LC-MS (m/z) |
| --- | --- | --- |
| 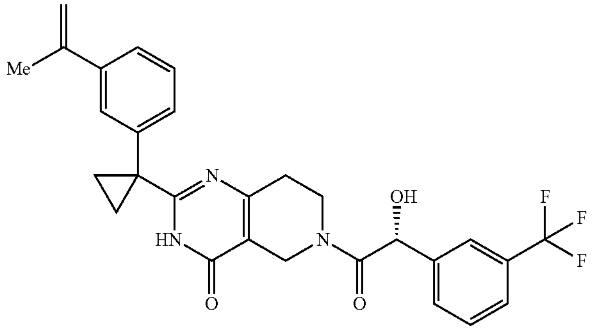 [SMILES: C=C(C)c1cccc(C2(c3nc4c(c(=O)[nH]3)CN(C(=O)[C@H](O)c3cccc(C(F)(F)F)c3)CC4)CC2)c1] INT-16-1 | (R)-6-(2-hydroxy-2-(3-(trifluoromethyl)phenyl) acetyl)-2-(1-(3-(prop-1-en-2-yl)phenyl)cyclopropyl)-5,6,7,8-tetrahydropyrido[4,3-d]pyrimidin-4(3H)-one | LC-MS (Method-K) m/z: M + 1 obs 510.2, tR = 0.62 min. |
| 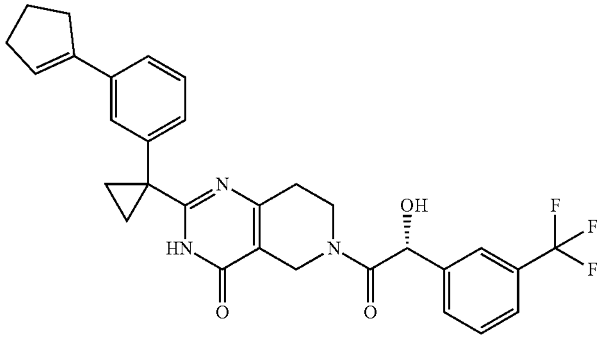 [SMILES: O=C([C@H](O)c1cccc(C(F)(F)F)c1)N1CCc2nc(C3(c4cccc(C5=CCCC5)c4)CC3)[nH]c(=O)c2C1] INT-16-2 | (R)-2-(1-(3-(cyclopent-1-en-1-yl)phenyl)cyclopropyl)-6-(2-hydroxy-2-(3-(trifluoromethyl)phenyl) acetyl)-5,6,7,8-tetrahydropyrido[4,3-d]pyrimidin-4(3H)-one | LC-MS (Method-K) m/z: M + 1 obs 536.2, tR = 0.64 min. |

TABLE 17-continued

| Structure | Chemical Name | LC-MS (m/z) |
|---|---|---|
| 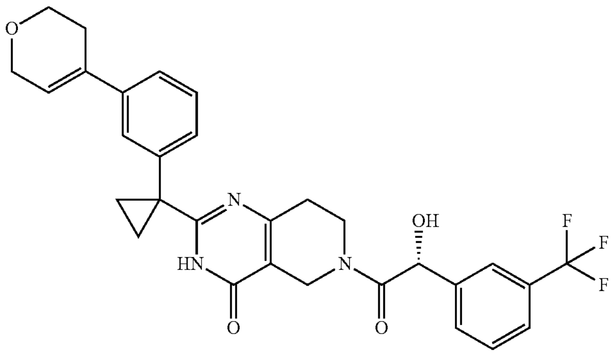 [SMILES: O=C([C@H](O)c1cccc(C(F)(F)F)c1)N1CCc2nc(C3(c4cccc(C5=CCOCC5)c4)CC3)[nH]c(=O)c2C1] INT-16-3 | (R)-2-(1-(3-(3,6-dihydro-2H-pyran-4-yl)phenyl)cyclopropyl)-6-(2-hydroxy-2-(3-(trifluoromethyl)phenyl)acetyl)-5,6,7,8-tetrahydropyrido[4,3-d]pyrimidin-4(3H)-one | LC-MS (Method-K) m/z: M + 1 obs 552.2, tR = 0.58 min. |

Intermediate-17-1 (INT-17-1)

Synthesis of (R)-6-(2-hydroxy-2-(3-(trifluoromethyl)phenyl)acetyl)-2-(1-(5-(prop-1-en-2-yl)pyridin-3-yl)cyclopropyl)-5,6,7,8-tetrahydropyrido[4,3-d]pyrimidin-4(3H)-one {Chem. 39}

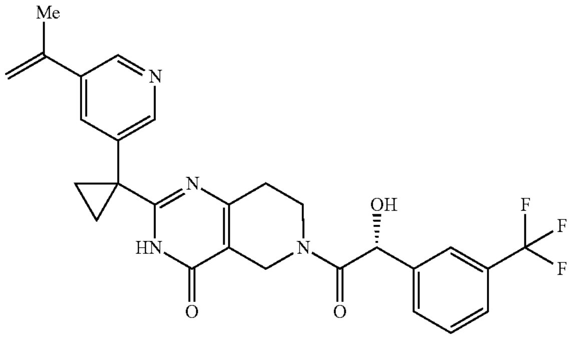

The title compound (18 mg) is prepared in quantitive yield by the similar manner to INT-12-1 using INT-11-6 (18.1 mg, 0.033 mmol) and 4,4,5,5-tetramethyl-2-(prop-1-en-2-yl)-1,3,2-dioxaborolane (9.98 mg, 0.059 mmol).

LC-MS (Method-K) m/z: M+1 obs 511.2, tR=0.41 min.

The following pyrimidin-4(3H)-one derivatives (INT-17-2 to INT-17-5) are prepared according to the procedure of intermediate-12-1 from the known boronic acid derivatives and INT-11-6 in Table 18.

TABLE 18

| Structure | Chemical Name | $^1$H-NMR & LC-MS (m/z) |
|---|---|---|
| 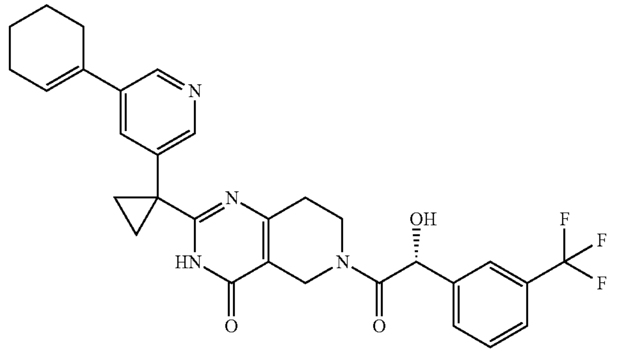 [SMILES: O=C([C@H](O)c1cccc(C(F)(F)F)c1)N1CCc2nc(C3(c4cncc(C5=CCCCC5)c4)CC3)[nH]c(=O)c2C1] INT-17-2 | (R)-2-(1-(5-(cyclohex-1-en-1-yl)pyridin-3-yl)cyclopropyl)-6-(2-hydroxy-2-(3-(trifluoromethyl)phenyl) acetyl)-5,6,7,8-tetrahydropyrido[4,3-d]pyrimidin-4(3H)-one | LC-MS (Method-K) m/z: M + 1 obs 551.2, tR = 0.50 min. |
| 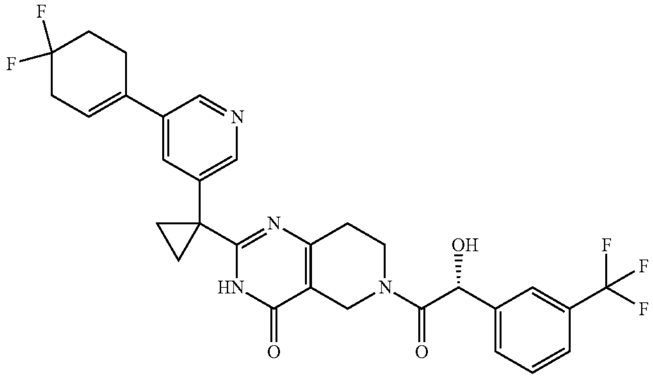 [SMILES: O=C([C@H](O)c1cccc(C(F)(F)F)c1)N1CCc2nc(C3(c4cncc(C5=CCC(F)(F)CC5)c4)CC3)[nH]c(=O)c2C1] INT-17-3 | (R)-2-(1-(5-(4,4-difluorocyclohex-1-en-1-yl)pyridin-3-yl)cyclopropyl)-6-(2-hydroxy-2-(3-(trifluoromethyl)phenyl) acetyl)-5,6,7,8-tetrahydropyrido[4,3-d]pyrimidin-4(3H)-one | LC-MS (Method-K) m/z: M + 1 obs 587.3, tR = 0.44 min. |
| 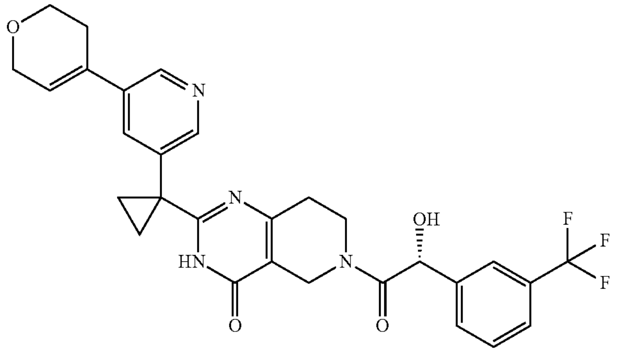 [SMILES: O=C([C@H](O)c1cccc(C(F)(F)F)c1)N1CCc2nc(C3(c4cncc(C5=CCOCC5)c4)CC3)[nH]c(=O)c2C1] INT-17-4 | (R)-2-(1-(5-(3,6-dihydro-2H-pyran-4-yl)pyridin-3-yl)cyclopropyl)-6-(2-hydroxy-2-(3-(trifluoromethyl)phenyl) acetyl)-5,6,7,8-tetrahydropyrido[4,3-d]pyrimidin-4(3H)-one | The structure is confirmed at the next step. |

TABLE 18-continued

| Structure | Chemical Name | ¹H-NMR & LC-MS (m/z) |
|---|---|---|
| 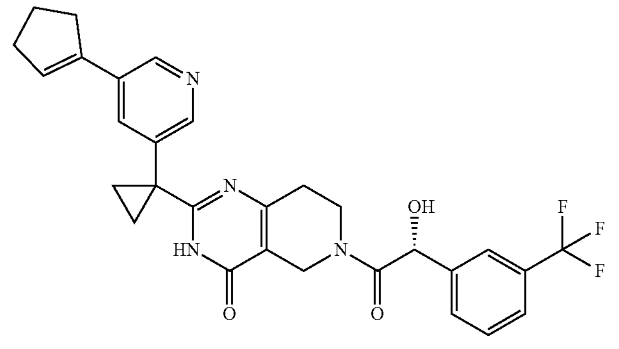 [SMILES: O=C([C@H](O)c1cccc(C(F)(F)F)c1)N1CCc2nc(C3(c4cncc(C5=CCCC5)c4)CC3)[nH]c(=O)c2C1] INT-17-5 | (R)-2-(1-(5-(cyclopent-1-en-1-yl)pyridin-3-yl)cyclopropyl)-6-(2-hydroxy-2-(3-(trifluoromethyl)phenyl) acetyl)-5,6,7,8-tetrahydropyrido[4,3-d]pyrimidin-4(3H)-one | LC-MS (Method-K) m/z: M + 1 obs 537.3, tR = 0.45 min. |

Intermediate-18-1 (INT-18-1)(=Ex-40-4)

Synthesis of (R)-6-(2-(3-chlorophenyl)-2-hydroxy-acetyl)-2-(1-(3-(prop-1-en-2-yl)phenyl)cyclopropyl)-3,5,6,7,8,9-hexahydro-4H-pyrimido[5,4-c]azepin-4-one (INT-18-1)

{Chem. 40}

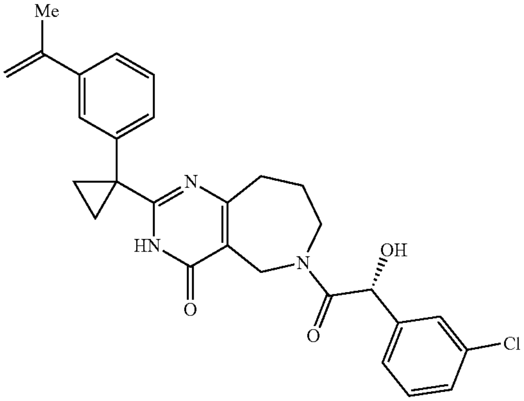

The mixture of INT-11-8 (25.0 mg, 0.047 mmol), 4,4,5,5-tetramethyl-2-(prop-1-en-2-yl)-1,3,2-dioxaborolane (9.53 mg, 0.057 mmol), palladium (II) acetate (2.12 mg, 0.0095 mmol) and triphenylphosphine (4.96 mg, 0.019 mmol) in 1,4-dioxane (1 mL) and saturated aqueous sodium bicarbonate (0.5 mL) is stirred at 100° C. for 3 hrs. After cooled down to rt, the mixture is extracted with ethyl acetate and the separated organic layer is concentrated in vacuo to give the crude compound, which is purified by a strong anion exchange cartridge (ISOLUTE(registered trademark) SCX-2) to give the titled compound (18.9 mg) as a slightly yellow viscous oil. The compound is used in the next reaction without further purification.

LC-MS (Method-H) m/z: M+1 obs 489.99, tR=3.17 min.

The following pyrimidin-4(3H)-one derivatives (INT-18-2 to INT-18-4) are prepared according to the procedure of intermediate-18-1 from the known boronic acid derivatives and INT-11-8 in Table 19.

TABLE 19

| Structure | Chemical Name | LC-MS (m/z) |
|---|---|---|
| 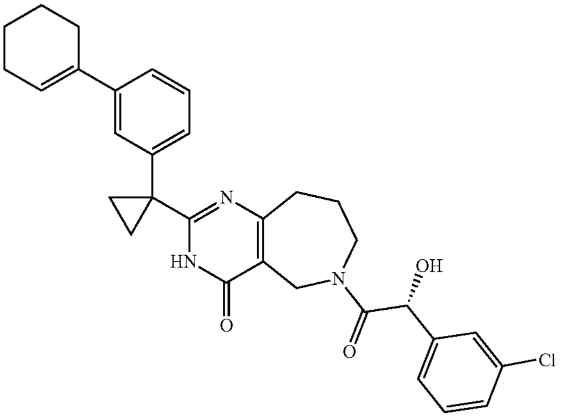 INT-18-2 | (R)-6-(2-(3-chlorophenyl)-2-hydroxyacetyl)-2-(1-(2',3',4',5'-tetrahydro-[1,1'-biphenyl]-3-yl)cyclopropyl)-3,5,6,7,8,9-hexahydro-4H-pyrimido[5,4-c]azepin-4-one | LC-MS (Method-H) m/z: M + 1 obs 530.03, tR = 3.50 min. |

TABLE 19-continued

| Structure | Chemical Name | LC-MS (m/z) |
|---|---|---|
| 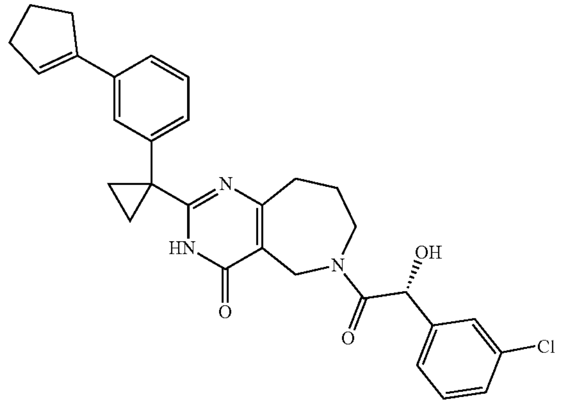 [SMILES: O=C([C@H](O)c1cccc(Cl)c1)N1CCCc2nc(C3(c4cccc(C5=CCCC5)c4)CC3)[nH]c(=O)c2C1] INT-18-3 | (R)-6-(2-(3-chlorophenyl)-2-hydroxyacetyl)-2-(1-(3-(cyclopent-1-en-1-yl)phenyl)cyclopropyl)-3,5,6,7,8,9-hexahydro-4H-pyrimido[5,4-c]azepin-4-one | LC-MS (Method-H) m/z: M + 1 obs 515.99, tR = 3.38 min. |
| 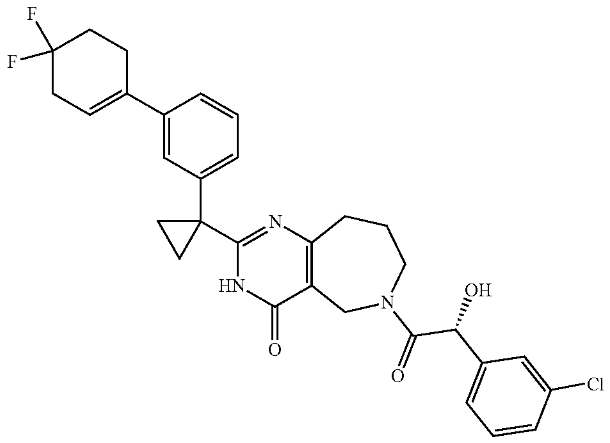 [SMILES: O=C([C@H](O)c1cccc(Cl)c1)N1CCCc2nc(C3(c4cccc(C5=CCC(F)(F)CC5)c4)CC3)[nH]c(=O)c2C1] INT-18-4 | (R)-6-(2-(3-chlorophenyl)-2-hydroxyacetyl)-2-(1-(4',4'-difluoro-2',3',4',5'-tetrahydro-[1,1'-biphenyl]-3-yl)cyclopropyl)-3,5,6,7,8,9-hexahydro-4H-pyrimido[5,4-c]azepin-4-one | LC-MS (Method-H) m/z: M + 1 obs 566.02, tR = 3.23 min. |

The following pyrimidin-4(3H)-one derivatives (INT-19-1 to INT-19-6) are prepared according to the procedure of intermediate-18-1 from the known boronic acid derivatives and INT-11-9 in Tables 20-1 and 20-2.

TABLE 20-1

| Structure | Chemical Name | LC-MS (m/z) |
|---|---|---|
| 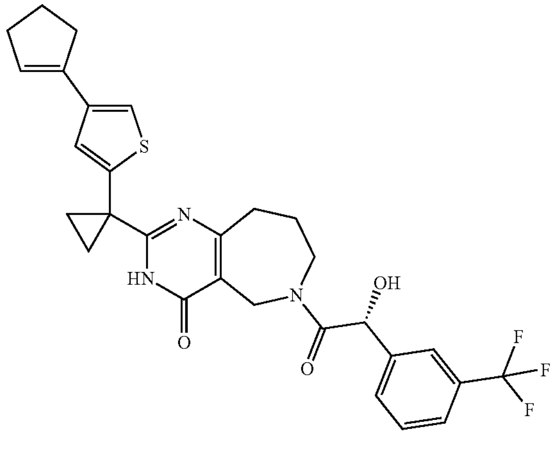 [SMILES: O=C([C@H](O)c1cccc(C(F)(F)F)c1)N1CCCc2nc(C3(c4cc(C5=CCCC5)cs4)CC3)[nH]c(=O)c2C1] INT-19-1 | (R)-2-(1-(4-(cyclopent-1-en-1-yl)thiophen-2-yl)cyclopropyl)-6-(2-hydroxy-2-(3-(trifluoromethyl) phenyl)acetyl)-3,5,6,7,8,9-hexahydro-4H-pyrimido[5,4-c]azepin-4-one | LC-MS (Method-I) m/z: M + 1 obs 556.19, tR = 0.61 min. |

TABLE 20-1-continued

| Structure | Chemical Name | LC-MS (m/z) |
| --- | --- | --- |
| 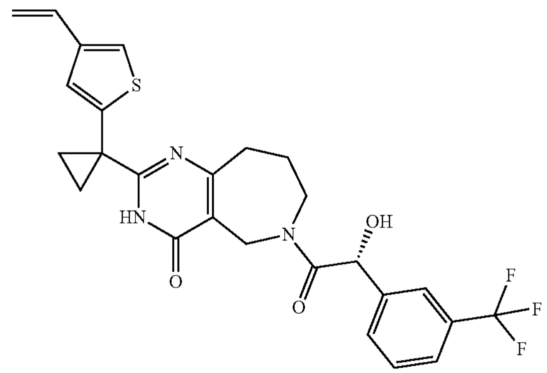 [SMILES: C=Cc1csc(C2(c3nc4c(c(=O)[nH]3)CN(C(=O)[C@H](O)c3cccc(C(F)(F)F)c3)CCC4)CC2)c1] INT-19-2 | (R)-6-(2-hydroxy-2-(3-(trifluoromethyl)phenyl)acetyl)-2-(1-(4-vinylthiophen-2-yl)cyclopropyl)-3,5,6,7,8,9-hexahydro-4H-pyrimido[5,4-c]azepin-4-one | LC-MS (Method-I) m/z: M + 1 obs 516.15, tR = 0.56 min. |
| 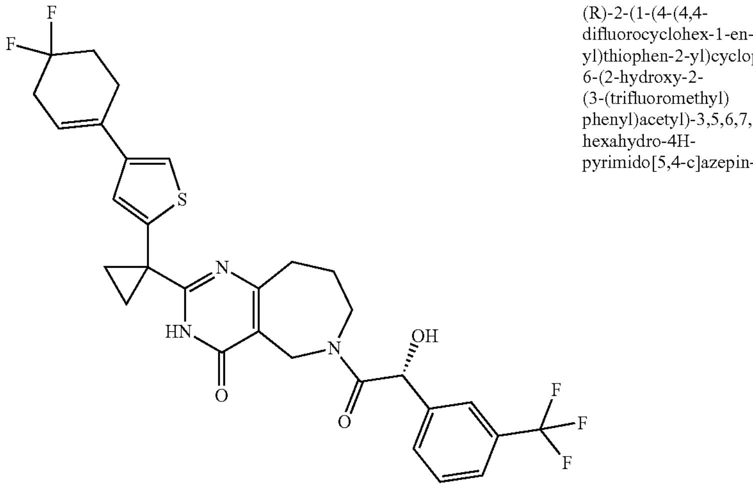 INT-19-3 | (R)-2-(1-(4-(4,4-difluorocyclohex-1-en-1-yl)thiophen-2-yl)cyclopropyl)-6-(2-hydroxy-2-(3-(trifluoromethyl) phenyl)acetyl)-3,5,6,7,8,9-hexahydro-4H-pyrimido[5,4-c]azepin-4-one | LC-MS (Method-I) m/z: M + 1 obs 606.22, tR = 0.58 min. |
| 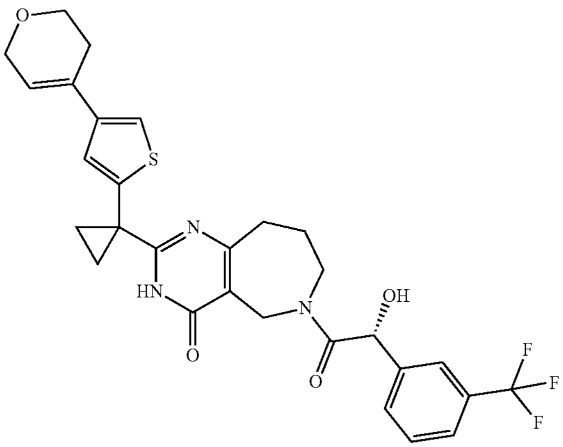 [SMILES: O=C([C@H](O)c1cccc(C(F)(F)F)c1)N1CCCc2nc(C3(c4cc(C5=CCOCC5)cs4)CC3)[nH]c(=O)c2C1] INT-19-4 | (R)-2-(1-(4-(3,6-dihydro-2H-pyran-4-yl)thiophen-2-yl)cyclopropyl)-6-(2-hydroxy-2-(3-(trifluoromethyl) phenyl)acetyl)-3,5,6,7,8,9-hexahydro-4H-pyrimido[5,4-c]azepin-4-one | LC-MS (Method-I) m/z: M + 1 obs 572.21, tR = 0.54 min. |

TABLE 20-2
| | | |
|---|---|---|
| 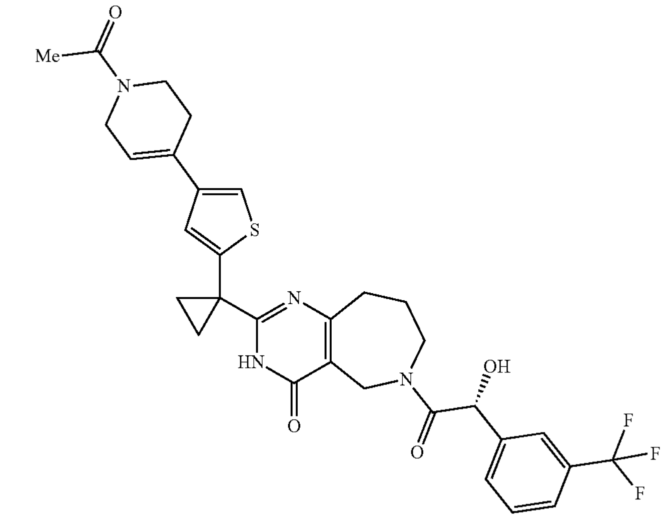 [SMILES: CC(=O)N1CC=C(c2csc(C3(c4nc5c(c(=O)[nH]4)CN(C(=O)[C@H](O)c4cccc(C(F)(F)F)c4)CCC5)CC3)c2)CC1]<br>INT-19-5 | (R)-2-(1-(4-(1-acetyl-1,2,3,6-tetrahydropyridin-4-yl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one | LC-MS (Method-I) m/z: M + 1 obs 613.26, tR = 0.51 min. |
| 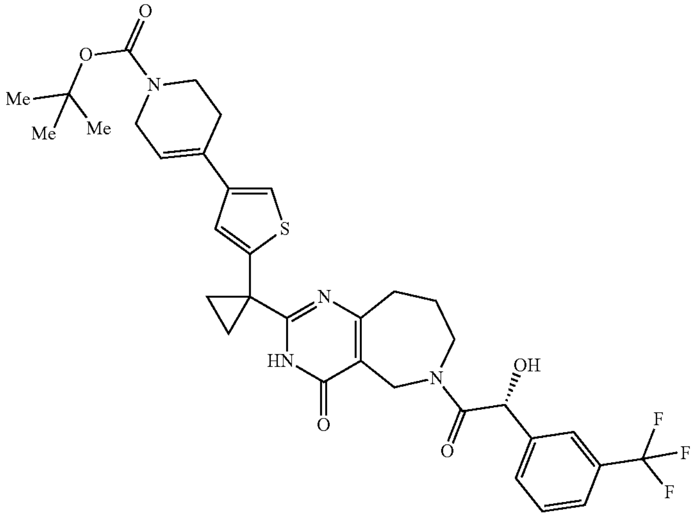 [SMILES: CC(C)(C)OC(=O)N1CC=C(c2csc(C3(c4nc5c(c(=O)[nH]4)CN(C(=O)[C@H](O)c4cccc(C(F)(F)F)c4)CCC5)CC3)c2)CC1]<br>INT-19-6 | tert-butyl (R)-4-(5-(1-(6-(2-hydroxy-2-(3-(trifluoromethyl) phenyl)acetyl)-4-oxo-4,5,6,7,8,9-hexahydro-3H-pyrimido[5,4-c]azepin-2-yl)cyclopropyl)thiophen-3-yl)-3,6-dihydropyridine-1(2H)-carboxylate | LC-MS (Method-I) m/z: M + 1 obs 671.33, tR = 0.60 min. |

Intermediate-20-1 (INT-20-1)

Synthesis of 2-(1-(4-(adamantan-1-ylethynyl)thiophen-2-yl)cyclopropyl)-6-((R)-2-hydroxy-2-(3-(trifluoromethyl)phenyl)acetyl)-6,7,8,9-tetrahydro-3H-pyrimido[5,4-c]azepin-4(5H)-one (INT-20-1)

{Chem. 41}

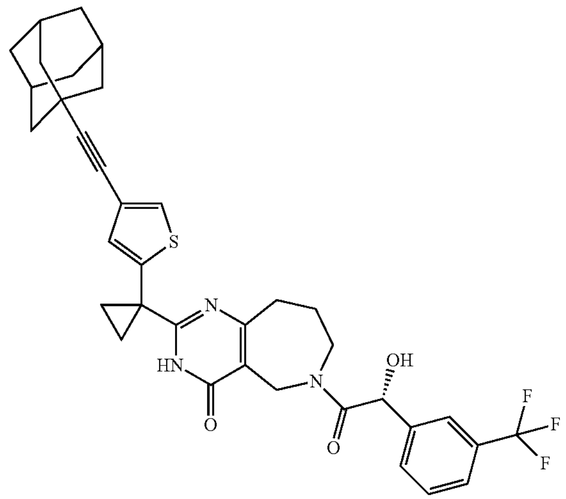

The mixture of INT-11-9 (25.0 mg, 0.044 mmol), 1-ethynyladamantane (106 mg, 0.66 mmol), copper (I) iodide (3.35 mg, 0.018 mmol), palladium (II) acetate (3.95 mg, 0.018 mmol), triphenylphosphine (9.23 mg, 0.035 mmol) and tripotassium phosphate (46.7 mg, 0.22 mmol) in 1,4-dioxane (1 mL) is stirred at 100° C. for 3 hrs. The mixture is filtered through silica gel pad (eluting with EtOAc) and the filtrate is concentrated in vacuo to give the crude compound, which is purified by a strong anion exchange cartridge (ISOLUTE (registered trademark) SCX-2) to give the titled compound (28.2 mg) as a brown gum. The compound is used in the next reaction without further purification.

LC-MS (Method-I) m/z: M+1 obs 648.35, tR=0.66 min.

The following pyrimidin-4(3H)-one derivatives (INT-20-2 to INT-20-9) are prepared according to the procedure of intermediate-20-1 from the known 1-ethynyl derivatives and INT-11-9 in Tables 21-1 and 21-2.

TABLE 21-1

| Structure | Chemical Name | LC-MS (m/z) |
|---|---|---|
| 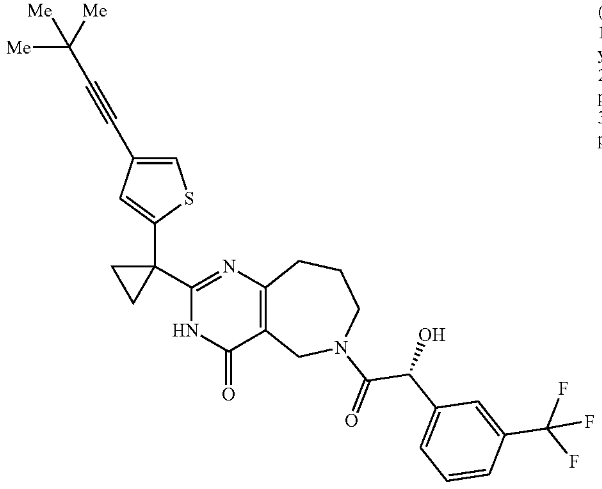 INT-20-2 | (R)-2-(1-(4-(3,3-dimethylbut-1-yn-1-yl)thiophen-2-yl)cyclopropyl)-6-(2-hydroxy-2-(3-(trifluoromethyl) phenyl)acetyl)-3,5,6,7,8,9-hexahydro-4H-pyrimido[5,4-c]azepin-4-one | LC-MS (Method-I) m/z: M + 1 obs 570.21, tR = 0.62 min. |

TABLE 21-1-continued

| Structure | Chemical Name | LC-MS (m/z) |
|---|---|---|
| 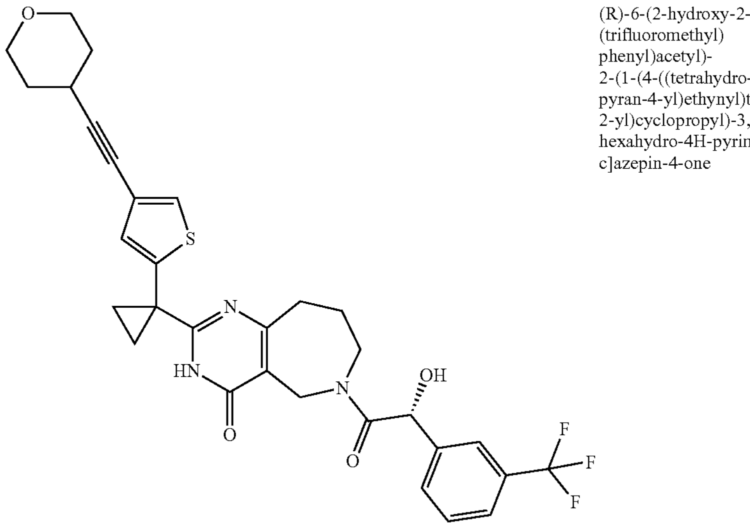 INT-20-3 | (R)-6-(2-hydroxy-2-(3-(trifluoromethyl) phenyl)acetyl)-2-(1-(4-((tetrahydro-2H-pyran-4-yl)ethynyl)thiophen-2-yl)cyclopropyl)-3,5,6,7,8,9-hexahydro-4H-pyrimido[5,4-c]azepin-4-one | LC-MS (Method-I) m/z: M + 1 obs 598.21, tR = 0.56 min. |
| 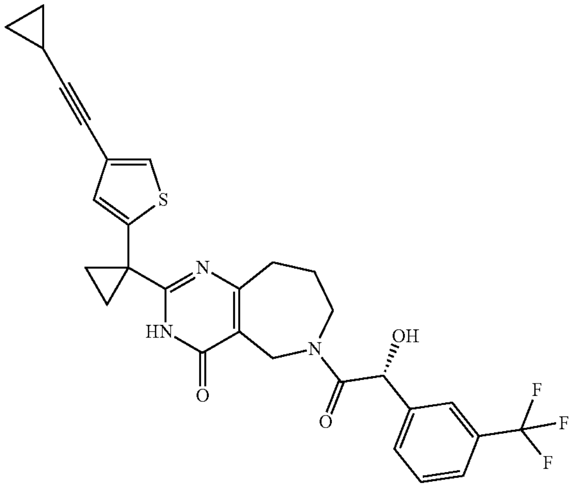 [SMILES: O=C([C@H](O)c1cccc(C(F)(F)F)c1)N1CCCc2nc(C3(c4cc(C#CC5CC5)cs4)CC3)[nH]c(=O)c2C1] INT-20-4 | (R)-2-(1-(4-(cyclopropylethynyl) thiophen-2-yl)cyclopropyl)-6-(2-hydroxy-2-(3-(trifluoromethyl) phenyl)acetyl)-3,5,6,7,8,9-hexahydro-4H-pyrimido[5,4-c]azepin-4-one | LC-MS (Method-I) m/z: M + 1 obs 54.16, tR = 0.58 min. |

TABLE 21-1-continued
| Structure | Chemical Name | LC-MS (m/z) |
|---|---|---|
| 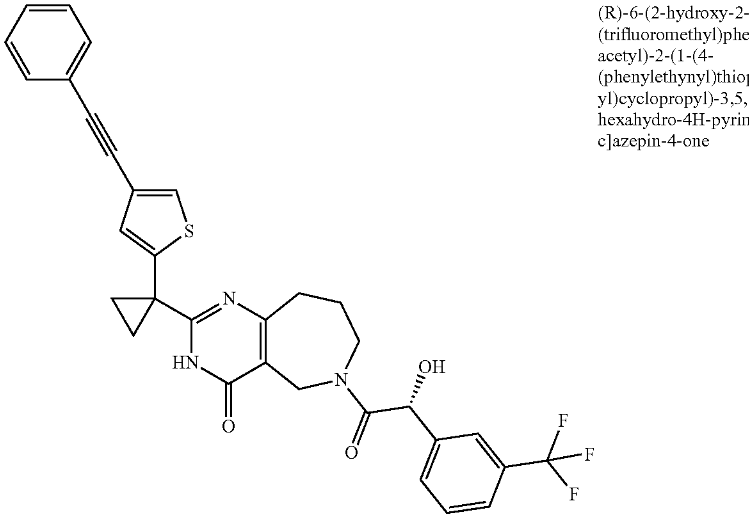 INT-20-5 | (R)-6-(2-hydroxy-2-(3-(trifluoromethyl)phenyl) acetyl)-2-(1-(4-(phenylethynyl)thiophen-2-yl)cyclopropyl)-3,5,6,7,8,9-hexahydro-4H-pyrimido[5,4-c]azepin-4-one | LC-MS (Method-I) m/z: M + 1 obs 590.16, tR = 0.60 min. |
TABLE 21-2
| | | |
|---|---|---|
| 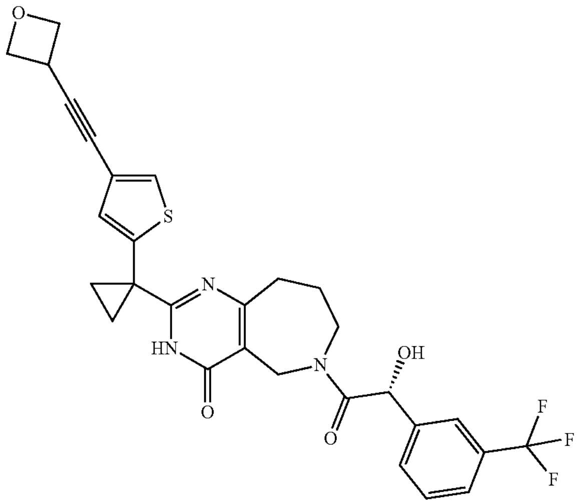 [SMILES: O=C([C@H](O)c1cccc(C(F)(F)F)c1)N1CCCc2nc(C3(c4cc(C#CC5COC5)cs4)CC3)[nH]c(=O)c2C1] INT-20-6 | (R)-6-(2-hydroxy-2-(3-(trifluoromethyl)phenyl) acetyl)-2-(1-(4-(oxetan-3-ylethynyl)thiophen-2-yl)cyclopropyl)-3,5,6,7,8,9-hexahydro-4H-pyrimido[5,4-c]azepin-4-one | LC-MS (Method-I) m/z: M + 1 obs 570.15, tR = 0.53 min. |

TABLE 21-2-continued

| | | |
|---|---|---|
| 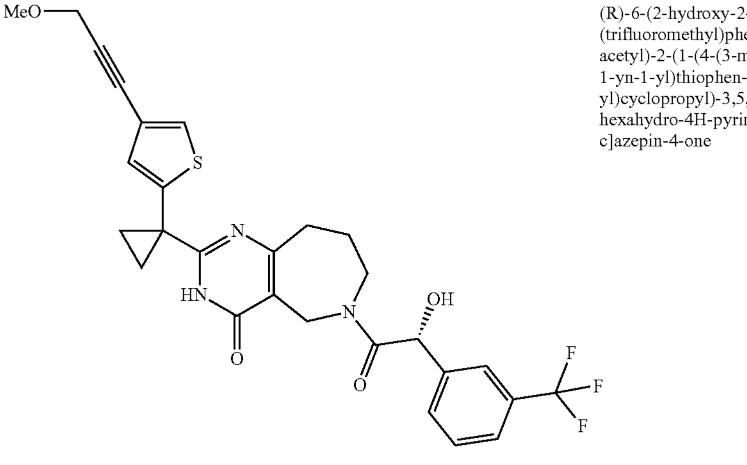 INT-20-7 | (R)-6-(2-hydroxy-2-(3-(trifluoromethyl)phenyl) acetyl)-2-(1-(4-(3-methoxyprop-1-yn-1-yl)thiophen-2-yl)cyclopropyl)-3,5,6,7,8,9-hexahydro-4H-pyrimido[5,4-c]azepin-4-one | LC-MS (Method-I) m/z: M + 1 obs 558.19, tR = 0.55 min. |
| 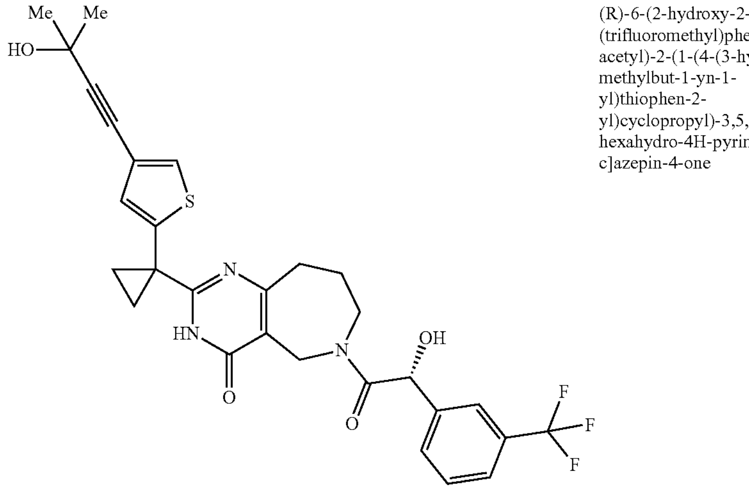 INT-20-8 | (R)-6-(2-hydroxy-2-(3-(trifluoromethyl)phenyl) acetyl)-2-(1-(4-(3-hydroxy-3-methylbut-1-yn-1-yl)thiophen-2-yl)cyclopropyl)-3,5,6,7,8,9-hexahydro-4H-pyrimido[5,4-c]azepin-4-one | LC-MS (Method-I) m/z: M + 1 obs 572.20, tR = 0.52 min. |
| 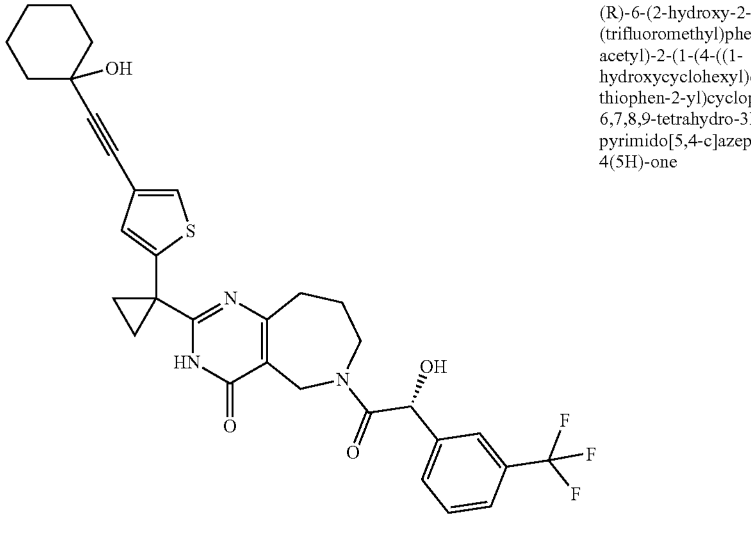 INT-20-9 | (R)-6-(2-hydroxy-2-(3-(trifluoromethyl)phenyl) acetyl)-2-(1-(4-((1-hydroxycyclohexyl)ethynyl) thiophen-2-yl)cyclopropyl)-6,7,8,9-tetrahydro-3H-pyrimido[5,4-c]azepin-4(5H)-one | LC-MS (Method-I) m/z: M − 1 obs 610.34, tR = 0.57 min. |

Intermediate-21-1 (INT-21-1)

Synthesis of (R)-2-(1-(3-(cyclopent-1-en-1-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one {Chem. 42}

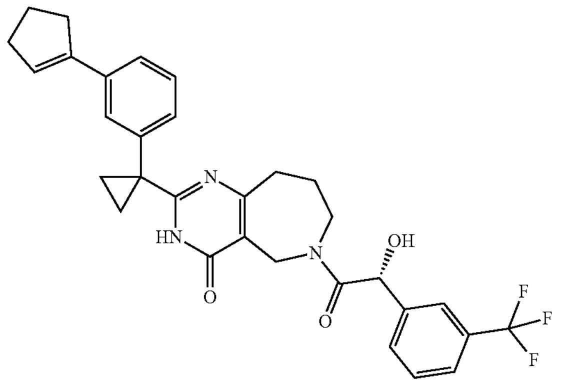

The title compound (15 mg) is prepared in 83% yield by the similar manner to INT-18-1 using INT-11-10 (18.6 mg, 0.033 mmol) and cyclopentene-1-boronic acid (5.17 mg, 0.046 mmol).

LC-MS (Method-K) m/z: M+1 obs 550.3, tR=0.58 min.

The following pyrimidin-4(3H)-one derivatives (INT-21-2 to INT-21-12) are prepared according to the procedure of intermediate-18-1 from the known boronic acid derivatives and INT-11-10 in Tables 22-1 to 22-3.

TABLE 22-1

| Structure | Chemical Name | $^1$H-NMR & LC-MS (m/z) |
|---|---|---|
| 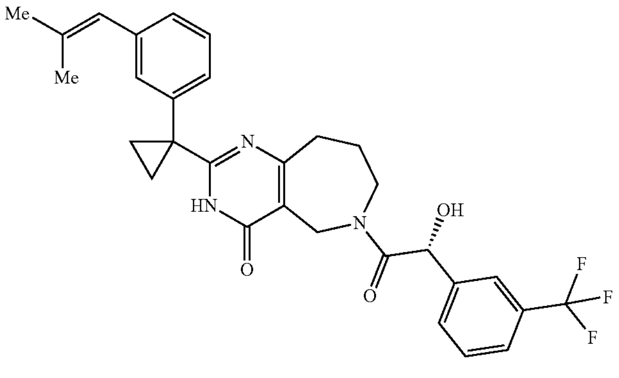 [SMILES: CC(C)=Cc1cccc(C2(c3nc4c(c(=O)[nH]3)CN(C(=O)[C@H](O)c3cccc(C(F)(F)F)c3)CCC4)CC2)c1] INT-21-2 | (R)-6-(2-hydroxy-2-(3-(trifluoromethyl)phenyl)acetyl)-2-(1-(3-(2-methylprop-1-en-1-yl)phenyl)cyclopropyl)-3,5,6,7,8,9-hexahydro-4H-pyrimido[5,4-c]azepin-4-one | LC-MS (Method-K) m/z: M + 1 obs 538.2, tR = 0.59 min. |

TABLE 22-1-continued

| Structure | Chemical Name | $^1$H-NMR & LC-MS (m/z) |
|---|---|---|
| 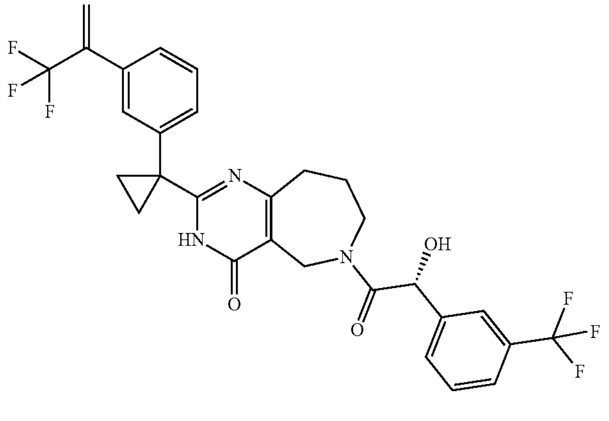 [SMILES: C=C(c1cccc(C2(c3nc4c(c(=O)[nH]3)CN(C(=O)[C@H](O)c3cccc(C(F)(F)F)c3)CCC4)CC2)c1)C(F)(F)F] INT-21-3 | (R)-6-(2-hydroxy-2-(3-(trifluoromethyl)phenyl) acetyl)-2-(1-(3-(3,3,3-trifluoroprop-1-en-2-yl)phenyl)cyclopropyl)-3,5,6,7,8,9-hexahydro-4H-pyrimido[5,4-c]azepin-4-one | LC-MS (Method-K) m/z: M + 1 obs 578.2, tR = 0.57 min. |
| 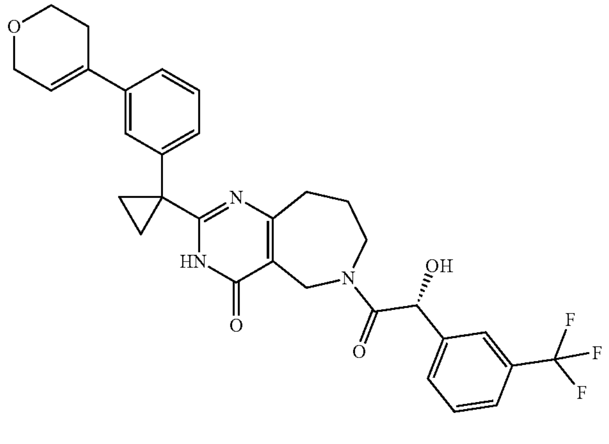 [SMILES: O=C([C@H](O)c1cccc(C(F)(F)F)c1)N1CCCc2nc(C3(c4cccc(C5=CCOCC5)c4)CC3)[nH]c(=O)c2C1] INT-21-4 | (R)-2-(1-(3-(3,6-dihydro-2H-pyran-4-yl)phenyl)cyclopropyl)-6-(2-hydroxy-2-(3-(trifluoromethyl)phenyl) acetyl)-3,5,6,7,8,9-hexahydro-4H-pyrimido[5,4-c]azepin-4-one | The structure is confirmed at the next step. |
| 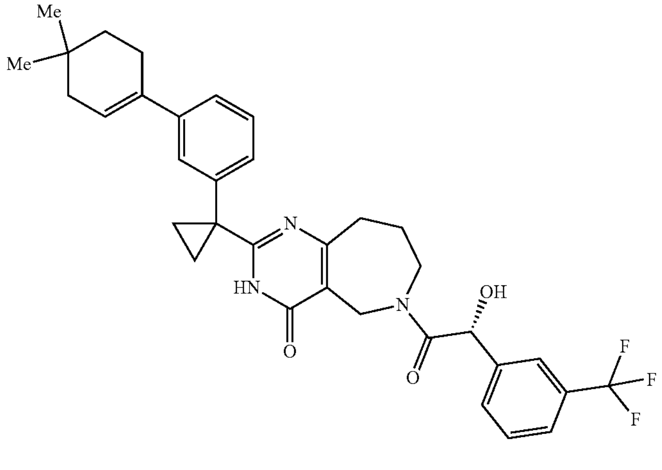 [SMILES: CC1(C)CC=C(c2cccc(C3(c4nc5c(c(=O)[nH]4)CN(C(=O)[C@H](O)c4cccc(C(F)(F)F)c4)CCC5)CC3)c2)CC1] INT-21-5 | (R)-2-(1-(4',4'-dimethyl-2',3',4',5'-tetrahydro-[1,1'-biphenyl]-3-yl)cyclopropyl)-6-(2-hydroxy-2-(3-(trifluoromethyl)phenyl) acetyl)-3,5,6,7,8,9-hexahydro-4H-pyrimido[5,4-c]azepin-4-one | LC-MS (Method-K) m/z: M + 1 obs 592.3, tR = 0.62 min. |

TABLE 22-1-continued

| Structure | Chemical Name | $^1$H-NMR & LC-MS (m/z) |
|---|---|---|
| 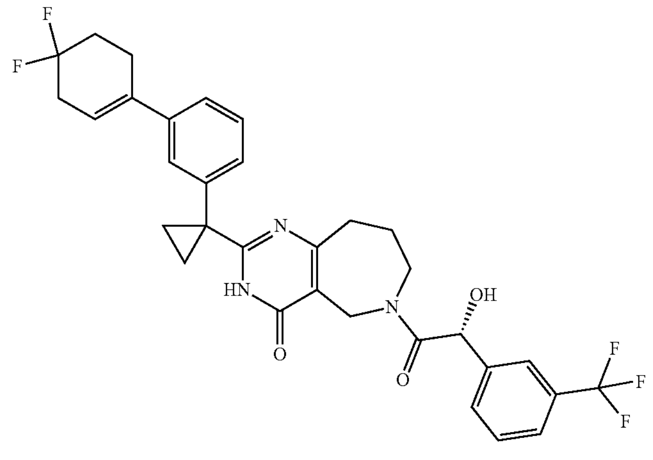 [SMILES: O=C([C@H](O)c1cccc(C(F)(F)F)c1)N1CCCc2nc(C3(c4cccc(C5=CCC(F)(F)CC5)c4)CC3)[nH]c(=O)c2C1] INT-21-6 | (R)-2-(1-(4',4'-difluoro-2',3',4',5'-tetrahydro-[1,1'-biphenyl]-3-yl)cyclopropyl)-6-(2-hydroxy-2-(3-(trifluoromethyl)phenyl) acetyl)-3,5,6,7,8,9-hexahydro-4H-pyrimido[5,4-c]azepin-4-one | LC-MS (Method-K) m/z: M + 1 obs 600.3, tR = 0.57 min. |

TABLE 22-2

| | | |
|---|---|---|
| 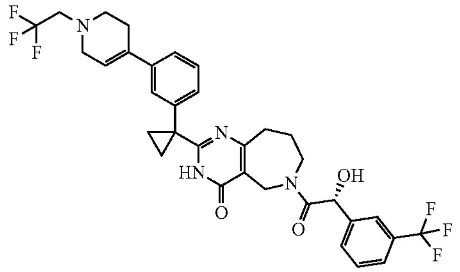 [SMILES: O=C([C@H](O)c1cccc(C(F)(F)F)c1)N1CCCc2nc(C3(c4cccc(C5=CCN(CC(F)(F)F)CC5)c4)CC3)[nH]c(=O)c2C1] INT-21-7 | (R)-6-(2-hydroxy-2-(3-(trifluoromethyl)phenyl) acetyl)-2-(1-(3-(1-(2,2,2-trifluoroethyl)-1,2,3,6-tetrahydropyridin-4-yl)phenyl)cyclopropyl)-3,5,6,7,8,9-hexahydro-4H-pyrimido[5,4-c]azepin-4-one | LC-MS (Method-K) m/z: M + 1 obs 647.3, tR = 0.62 min. |
| 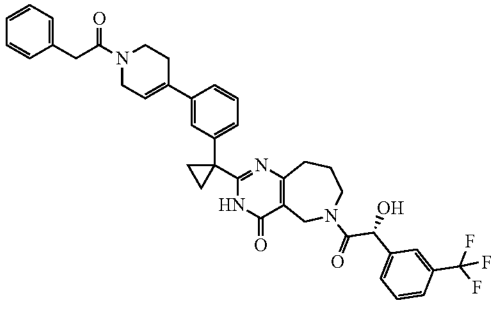 [SMILES: O=C(Cc1ccccc1)N1CC=C(c2cccc(C3(c4nc5c(c(=O)[nH]4)CN(C(=O)[C@H](O)c4cccc(C(F)(F)F)c4)CCC5)CC3)c2)CC1] INT-21-8 | (R)-6-(2-hydroxy-2-(3-(trifluoromethyl)phenyl)acetyl)-2-(1-(3-(1-(2-phenylacetyl)-1,2,3,6-tetrahydropyridin-4-yl)phenyl)cyclopropyl)-3,5,6,7,8,9-hexahydro-4H-pyrimido[5,4-c]azepin-4-one | LC-MS (Method-K) m/z: M + 1 obs 683.4, tR = 0.54 min. |
| 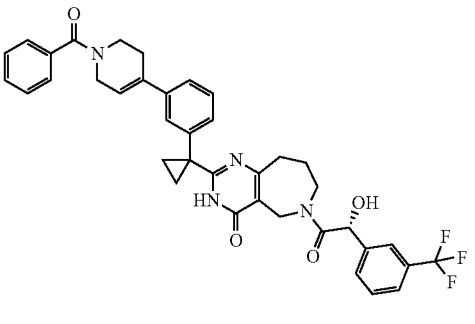 [SMILES: O=C(c1ccccc1)N1CC=C(c2cccc(C3(c4nc5c(c(=O)[nH]4)CN(C(=O)[C@H](O)c4cccc(C(F)(F)F)c4)CCC5)CC3)c2)CC1] | (R)-2-(1-(3-(1-benzoyl-1,2,3,6-tetrahydropyridin-4-yl)phenyl)cyclopropyl)-6-(2-hydroxy-2-(3-(trifluoromethyl) phenyl)acetyl)-3,5,6,7,8,9-hexahydro-4H-pyrimido[5,4-c]azepin-4-one | LC-MS (Method-K) m/z: M + 1 obs 669.3, tR = 0.53 min. |

TABLE 22-2-continued

| | | |
|---|---|---|
| INT-21-9 | | |
| 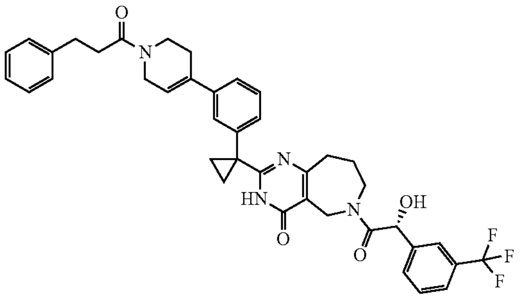 [SMILES: O=C(CCc1ccccc1)N1CC=C(c2cccc(C3(c4nc5c(c(=O)[nH]4)CN(C(=O)[C@H](O)c4cccc(C(F)(F)F)c4)CCC5)CC3)c2)CC1] | (R)-6-(2-hydroxy-2-(3-(trifluoromethyl)phenyl) acetyl)-2-(1-(3-(1-(3-phenylpropanoyl)-1,2,3,6-tetrahydropyridin-4-yl)phenyl)cyclopropyl)-3,5,6,7,8,9-hexahydro-4H-pyrimido[5,4-c]azepin-4-one | LC-MS (Method-K) m/z: M + 1 obs 697.4, tR = 0.55 min. |
| INT-21-10 | | |
| 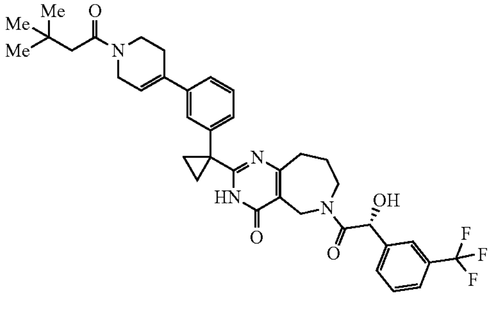 [SMILES: CC(C)(C)CC(=O)N1CC=C(c2cccc(C3(c4nc5c(c(=O)[nH]4)CN(C(=O)[C@H](O)c4cccc(C(F)(F)F)c4)CCC5)CC3)c2)CC1] | (R)-2-(1-(3-(1-(3,3-dimethylbutanoyl)-1,2,3,6-tetrahydropyridin-4-yl)phenyl)cyclopropyl)-6-(2-hydroxy-2-(3-(trifluoromethyl) phenyl)acetyl)-3,5,6,7,8,9-hexahydro-4H-pyrimido[5,4-c]azepin-4-one | LC-MS (Method-K) m/z: M + 1 obs 663.3, tR = 0.56 min. |
| INT-21-11 | | |

TABLE 22-3

| | | |
|---|---|---|
| 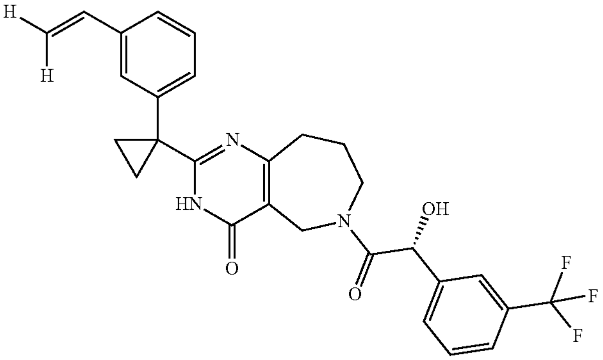 [SMILES: C=Cc1cccc(C2(c3nc4c(c(=O)[nH]3)CN(C(=O)[C@H](O)c3cccc(C(F)(F)F)c3)CCC4)CC2)c1] | (R)-6-(2-hydroxy-2-(3-(trifluoromethyl) phenyl) acetyl)-2-(1-(3-vinylphenyl) cyclopropyl)-3,5,6,7,8,9-hexahydro-4H-pyrimido[5,4-c] azepin-4-one | NMR (400 MHZ, $CDCl_3$): δ 8.61 (1H, br.s), 7.72-7.64 (2H, m), 7.61-7.38 (5H, m), 7.31-7.26 (1H, m), 6.72 (1H, dd, J = 17.8, 11.0 Hz), 5.81 (1H, d, J = 17.8 Hz), 5.35 (1H, d, J = 11.4 Hz), 5.32 (1H, d, J = 7.3 Hz), 4.64-4.59 (2H, m), 4.33 (1H, ddd, J = 13.7, 5.0, 4.6 Hz), 3.92 (1H, d, J = 16.9 Hz), 3.40 (1H, ddd, J = 13.7, 9.6, 3.7 Hz), 2.81-2.77 (2H, m), 2.02-1.75 (4H, m), 1.42-1.35 (2H, m). LC-MS (Method-K) m/z: M + 1 obs 510.2, tR = 0.56 min. |
| INT-21-12 | | |

The following pyrimidin-4(3H)-one derivatives (INT-21-13 to INT-21-19) are prepared according to the procedure of intermediate-18-1 from the known boronic acid derivatives and INT-11-41, INT-11-46 to INT-11-48 in Tables 23-1 and 23-2.

TABLE 23-1

| Structure | Chemical Name | LC-MS (m/z) |
|---|---|---|
| 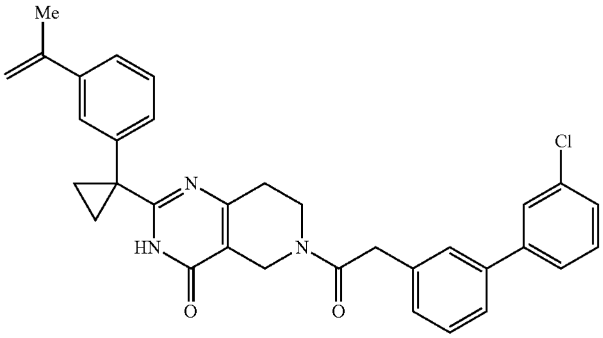 [SMILES: C=C(C)c1cccc(C2(c3nc4c(c(=O)[nH]3)CN(C(=O)Cc3cccc(-c5cccc(Cl)c5)c3)CC4)CC2)c1] INT-21-13 | 6-(2-(3'-chloro-[1,1'-biphenyl]-3-yl)acetyl)-2-(1-(3-(prop-1-en-2-yl)phenyl)cyclopropyl)-5,6,7,8-tetrahydropyrido[4,3-d]pyrimidin-4(3H)-one | LC-MS (Method-K) m/z: M + 1 obs 536.2, tR = 0.59 min. |
| 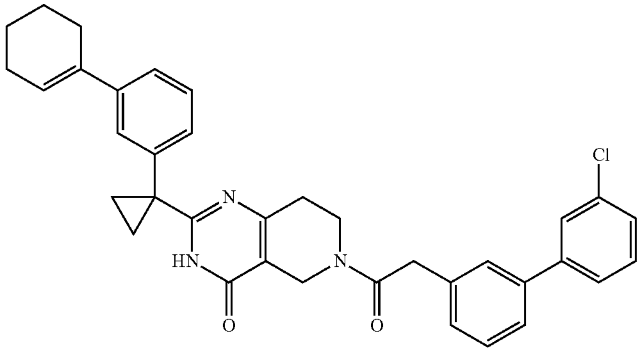 [SMILES: O=C(Cc1cccc(-c2cccc(Cl)c2)c1)N1CCc2nc(C3(c4cccc(C5=CCCCC5)c4)CC3)[nH]c(=O)c2C1] INT-21-14 | 6-(2-(3'-chloro-[1,1'-biphenyl]-3-yl)acetyl)-2-(1-(2',3',4',5'-tetrahydro-[1,1'-biphenyl]-3-yl)cyclopropyl)-5,6,7,8-tetrahydropyrido[4,3-d]pyrimidin-4(3H)-one | LC-MS (Method-K) m/z: M + 1 obs 576.3, tR = 0.64 min. |
| 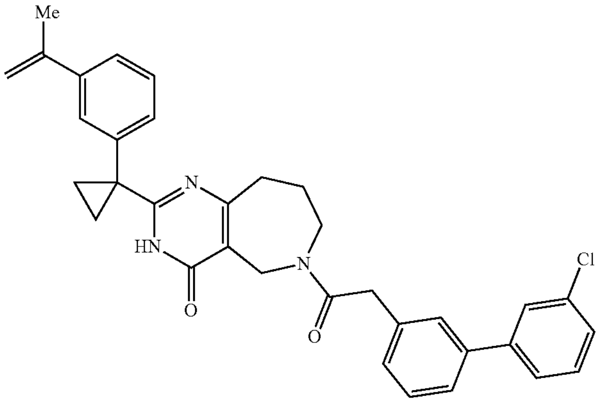 [SMILES: C=C(C)c1cccc(C2(c3nc4c(c(=O)[nH]3)CN(C(=O)Cc3cccc(-c5cccc(Cl)c5)c3)CCC4)CC2)c1] INT-21-15 | 6-(2-(3'-chloro-[1,1'-biphenyl]-3-yl)acetyl)-2-(1-(3-(prop-1-en-2-yl)phenyl)cyclopropyl)-3,5,6,7,8,9-hexahydro-4H-pyrimido[5,4-c]azepin-4-one | LC-MS (Method-K) m/z: M + 1 obs 550.2, tR = 0.61 min. |

TABLE 23-1-continued

| Structure | Chemical Name | LC-MS (m/z) |
|---|---|---|
| 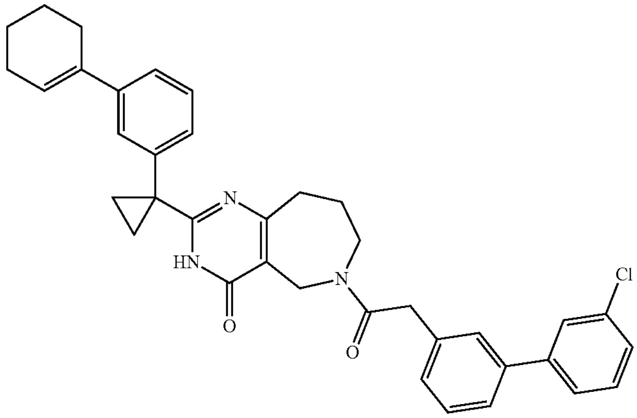 [SMILES: O=C(Cc1cccc(-c2cccc(Cl)c2)c1)N1CCCc2nc(C3(c4cccc(C5=CCCCC5)c4)CC3)[nH]c(=O)c2C1]<br>INT-21-16 | 6-(2-(3'-chloro-[1,1'-biphenyl]-3-yl)acetyl)-2-(1-(2',3',4',5'-tetrahydro-[1,1'-biphenyl]-3-yl)cyclopropyl)-3,5,6,7,8,9-hexahydro-4H-pyrimido[5,4-c]azepin-4-one | LC-MS (Method-K) m/z: M + 1 obs 590.3, tR = 0.65 min. |
| 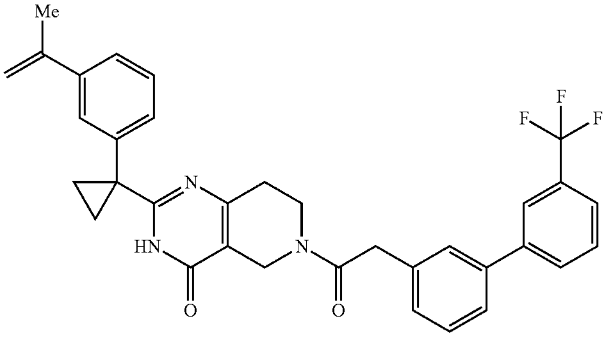 [SMILES: C=C(C)c1cccc(C2(c3nc4c(c(=O)[nH]3)CN(C(=O)Cc3cccc(-c5cccc(C(F)(F)F)c5)c3)CC4)CC2)c1]<br>INT-21-17 | 2-(1-(3-(prop-1-en-2-yl)phenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one | LC-MS (Method-K) m/z: M + 1 obs 570.3, tR = 0.59 min. |

TABLE 23-2

| | | |
|---|---|---|
| 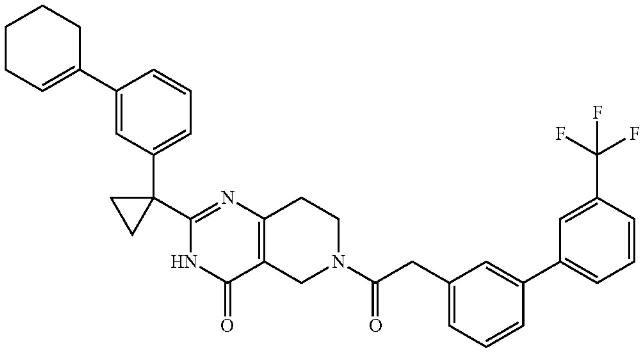 [SMILES: O=C(Cc1cccc(-c2cccc(C(F)(F)F)c2)c1)N1CCc2nc(C3(c4cccc(C5=CCCCC5)c4)CC3)[nH]c(=O)c2C1]<br>INT-21-18 | 2-(1-(2',3',4',5'-tetrahydro-[1,1'-biphenyl]-3-yl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one | LC-MS (Method-K) m/z: M + 1 obs 610.3, tR = 0.64 min. |

TABLE 23-2-continued

| | | |
|---|---|---|
| 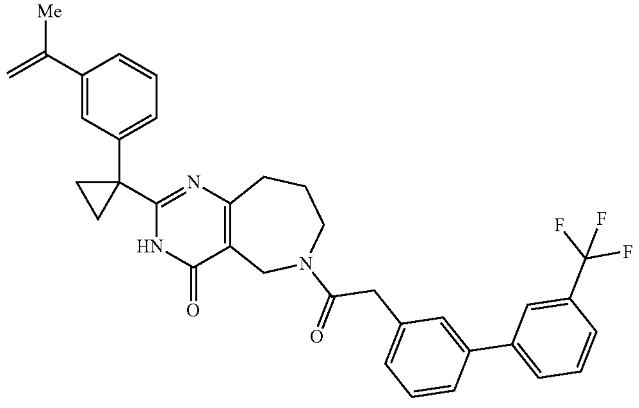 [SMILES: C=C(C)c1cccc(C2(c3nc4c(c(=O)[nH]3)CN(C(=O)Cc3cccc(-c5cccc(C(F)(F)F)c5)c3)CCC4)CC2)c1] INT-21-19 | 2-(1-(3-(prop-1-en-2-yl)phenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one | LC-MS (Method-K) m/z: M + 1 obs 584.3, tR = 0.63 min. |

Intermediate-22-1 (INT-22-1)

Synthesis of (R)-6-(2-hydroxy-2-(3-(trifluoromethyl)phenyl)acetyl)-2-(1-(6-(prop-1-en-2-yl)pyridin-2-yl)cyclopropyl)-3,5,6,7,8,9-hexahydro-4H-pyrimido[5,4-c]azepin-4-one {Chem. 43}

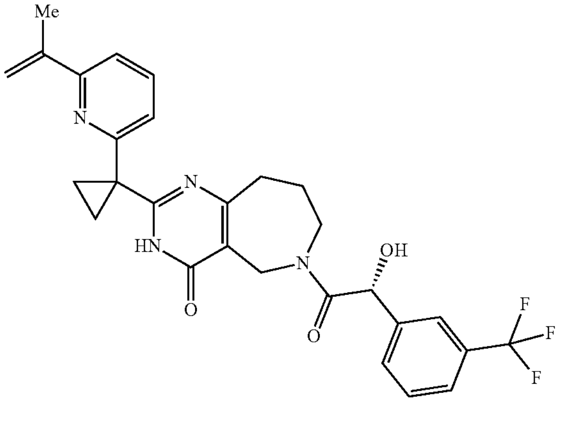

The mixture of INT-11-13 (34.8 mg, 0.062 mmol), 4,4,5,5-tetramethyl-2-(prop-1-en-2-yl)-1,3,2-dioxaborolane (56.6 mg, 0.34 mmol), palladium (II) acetate (2.8 mg, 0.012 mmol) and triphenylphosphine (6.5 mg, 0.025 mmol) in 1,4-dioxane (0.5 mL) and saturated aqueous sodium bicarbonate (0.5 mL) is stirred at 100° C. for 2 hrs. After cooled down to rt, the mixture is extracted with ethyl acetate and the separated organic layer is concentrated in vacuo to give the crude product, which is purified by a strong anion exchange cartridge (ISOLUTE(registered trademark) SCX-2) to give the titled compound (26.3 mg) as a brown solid. The compound is used in the next reaction without further purification.

LC-MS (Method-I) m/z: M+1 obs 525.19, tR=0.57 min.

Intermediate-23-1 (INT-23-1)

Synthesis of (R)-6-(2-hydroxy-2-(3-(trifluoromethyl)phenyl)acetyl)-2-(1-(2-(prop-1-en-2-yl)pyridin-4-yl)cyclopropyl)-3,5,6,7,8,9-hexahydro-4H-pyrimido[5,4-c]azepin-4-one (INT-23-1)

{Chem. 44}

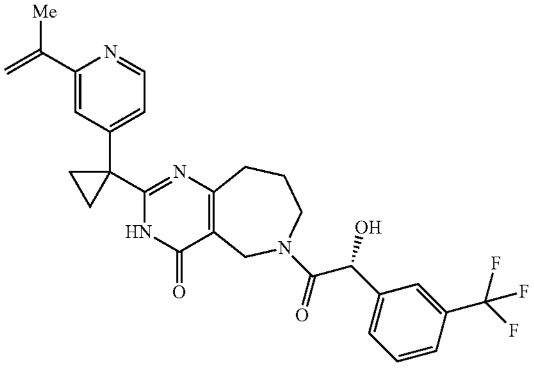

The mixture of INT-11-12 (34.0 mg, 0.060 mmol), 4,4,5,5-tetramethyl-2-(prop-1-en-2-yl)-1,3,2-dioxaborolane (54.8 mg, 0.33 mmol), palladium (II) acetate (2.7 mg, 0.012 mmol) and triphenylphosphine (6.3 mg, 0.024 mmol) in 1,4-dioxane (0.5 mL) and saturated aqueous sodium bicarbonate (0.5 mL) is stirred overnight at 100° C. After cooled down to rt, the mixture is extracted with ethyl acetate and the separated organic layer is concentrated in vacuo to give the crude product, which is purified by a strong anion exchange cartridge (ISOLUTE(registered trademark) SCX-2) to give the titled compound (26.9 mg) as a brown solid. The compound is used in the next reaction without further purification.

LC-MS (Method-I) m/z: M+1 obs 525.21, tR=0.52 min.

Intermediate-24-1 (INT-24-1)

Synthesis of 2-(2-chloropyridin-4-yl)-2-hydroxyacetic acid (INT-24-1)

{Chem. 45}

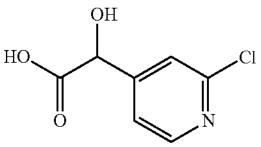

Step-24-1-A: Synthesis of 2-(2-chloropyridin-4-yl)-2-hydroxyacetonitrile (INT-24-1-A)

{Chem. 46}

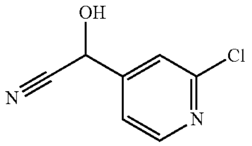

To a solution of 2-chloroisonicotinaldehyde (600 mg, 4.24 mmol) in DCM (5 mL) is added titanium isopropoxide (1.21 g, 4.24 mmol) at 0° C. The reaction mixture is stirred at rt for 30 min. Trimethylsilyl cyanide (841 mg, 8.48 mmol) is added to the mixture and the resulting solution is stirred at rt for 18 hrs. The mixture is quenched with 2M hydrochloric acid aqueous solution and extracted with DCM (×2). The combined solution is washed with brine, dried over sodium sulfate, filtered and concentrated in vacuo to give the crude product, which is triturated with DCM and filtered to give the titled compound (467 mg, 65% yield) as a brown solid.

$^1$H-NMR (300 MHz, DMSO-$d_6$): delta 8.48 (1H, d, J=5.1 Hz), 7.55 (1H, s), 7.50 (1H, d, J=5.1 Hz), 7.46 (1H, d, J=6.6 Hz), 5.90 (1H, d, J=6.6 Hz).

LCMS (Method-A) m/z: M−1 obs 167.1, tR=1.42 min.

Step-24-1-B: Synthesis of 2-(2-chloropyridin-4-yl)-2-hydroxyacetic acid (INT-24-1)

{Chem. 47}

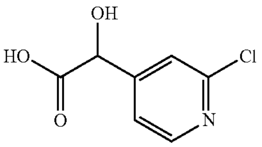

To a solution of INT-24-1-A (467 mg, 2.77 mmol) in toluene (1 mL) is added 37% aqueous hydrochloric acid (5 mL) at rt. The reaction mixture is stirred at 70° C. for 3 hrs. After cooling to rt, the reaction mixture is diluted with a mixture of EtOAc-$H_2O$ (1:1 v/v). The mixture is extracted with EtOAc (×2). The combined solution is washed with brine, dried over sodium sulfate, filtered and concentrated in vacuo to give the titled compound (252 mg). This is used for next reaction without the further purification.

LCMS (Method-A) m/z: M+1 obs 188.1, tR=0.54 min.

The following hydroxyacetonitrile derivatives (INT-24-2-A to INT-24-7-A) are prepared according to the procedure of intermediate-24-1-A from the known aldehyde derivatives in Table 24.

TABLE 24

| Structure | Chemical Name | $^1$H-NMR & LC-MS (m/z) |
|---|---|---|
| 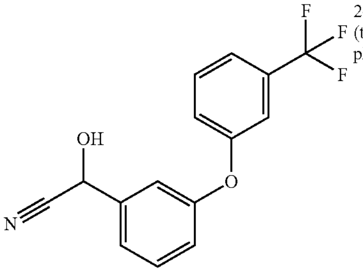 INT-24-2-A | 2-hydroxy-2-(3-(3-(trifluoromethyl)phenoxy)phenyl)acetonitrile | (400 MHz, CDCl3) δ 7.50-7.41 (3H, m), 7.39-7.33 (1H, m), 7.27-7.26 (1H, m), 7.23-7.17 (2H, m), 7.09-7.06 (1H, m), 5.56 (1H, d, J = 6.9 Hz), 2.71 (1H, d, J = 6.9 Hz). |
| 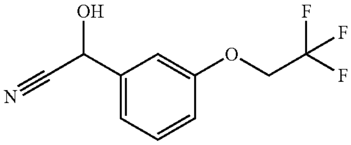 [SMILES: N#CC(O)c1cccc(OCC(F)(F)F)c1] INT-24-3-A | 2-hydroxy-2-(3-(2,2,2-trifluoroethoxy)phenyl)acetonitrile | (300 MHz, $CDCl_3$) 7.43 (1H, t, J = 7.3 Hz), 7.25 (1H, m), 7.15 (1H, s), 7.02 (1H, m), 5.56 (1H, d, J = 6.6 Hz), 4.40 (2H, q, J = 8.0 Hz), 2.75 (1H, d, J = 6.6 Hz). |
| 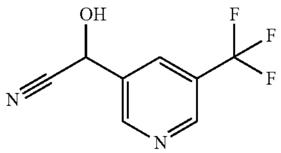 [SMILES: N#CC(O)c1cncc(C(F)(F)F)c1] INT-24-4-A | 2-hydroxy-2-(5-(trifluoromethyl)pyridin-3-yl)acetonitrile | (400 MHz, $CDCl_3$) δ 9.00 (1H, d, J = 1.4 Hz), 8.97 (1H, d, J = 1.4 Hz), 8.20 (1H, s), 5.77 (1H, s), 4.29 (1H, br.s). LC-MS (Method-F) m/z: M + 1 obs 203.2, tR = 1.63 min. obs 203.2, tR = 1.63 min. |

TABLE 24-continued

| Structure | Chemical Name | $^1$H-NMR & LC-MS (m/z) |
|---|---|---|
| 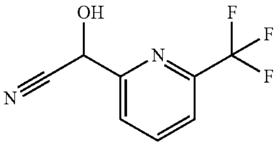 [SMILES: N#CC(O)c1cccc(C(F)(F)F)n1] INT-24-5-A | 2-hydroxy-2-(6-(trifluoromethyl)pyridin-2-yl)acetonitrile | (400 MHz, $CDCl_3$) δ 8.07 (1H, t, Hz), 7.76 (1H, d, J = 7.8 Hz), 5.66 (1H, d, J = 5.9 Hz), 4.59 (1H, d, J = 5.9 Hz). LC-MS (Method-F) m/z: M − 1 obs 201.1, tR = 1.75 min. |
| 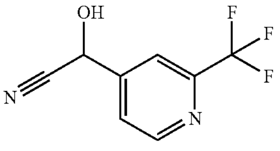 [SMILES: N#CC(O)c1ccnc(C(F)(F)F)c1] INT-24-6-A | 2-hydroxy-2-(2-(trifluoromethyl)pyridin-4-yl)acetonitrile | (400 MHz, $CDCl_3$) δ 8.85 (1H, d, J = 5.0 Hz), 7.89 (1H, s), 7.71 (1H, d, J = 5.0 Hz), 5.71 (1H, s), 3.66 (1H, br.s). LC-MS (ZQ-01, Neutral_QC) m/z: M − 1 obs 201.1, tR = 1.45 min. |
| 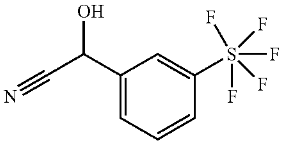 [SMILES: N#CC(O)c1cccc(S(F)(F)(F)(F)F)c1] INT-24-7-A | 2-hydroxy-2-(3-(pentafluoro-$\lambda^6$-sulfaneyl)phenyl) acetonitrile | (400 MHz, $CDCl_3$) δ 7.94 (1H, d, J = 1.8 Hz), 7.84 (1H, dd, J = 8.2, 1.8 Hz), 7.73 (1H, d, J = 7.7 Hz), 7.59 (1H, dd, J = 8.2, 7.7 Hz), 5.65 (1H, d, J = 6.4 Hz), 3.03 (1H, d, J = 6.4 Hz). |

The following hydroxyacetonitrile derivatives (INT-24-2 to INT-24-7) are prepared according to the procedure of intermediate-24-1-B from INT-24-2-A to INT-24-7-A in Table 25.

TABLE 25

| Structure | Chemical Name | 1H-NMR & LC-MS (m/z) |
|---|---|---|
| 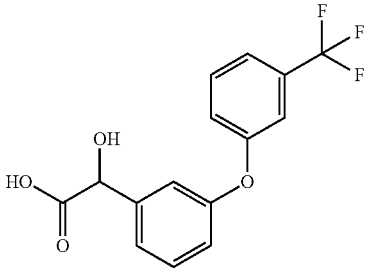 [SMILES: O=C(O)C(O)c1cccc(Oc2cccc(C(F)(F)F)c2)c1] INT-24-2 | 2-hydroxy-2-(3-(3-(trifluoromethyl)phenoxy)phenyl) acetic acid | LC-MS (Method-I) m/z: M − 1 obs 311.1, tR = 0.46 min. |
| 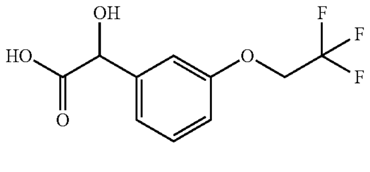 [SMILES: O=C(O)C(O)c1cccc(OCC(F)(F)F)c1] INT-24-3 | 2-hydroxy-2-(3-(2,2,2-trifluoroethoxy)phenyl)acetic acid | (300 MHz, DMSO-$d_6$) 12.62 (1H, br.s), 7.31 (1H, t, J = 8.1 Hz), 7.10-7.05 (2H, m), 6.98 (1H, dd, J = 7.3, 2.2 Hz), 5.83 (1H, br.s), 5.00 (1H, s), 4.73 (2H, q, J = 8.8 Hz). LC-MS (Method-A) m/z: M − 1 obs 249.3, tR = 2.32 min. |
| 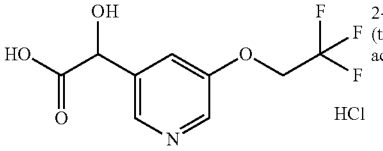 INT-24-4 | 2-hydroxy-2-(5-(trifluoromethyl)pyridin-3-yl)acetic acid hydrochoride | (400 MHz, DMSO-$d_6$) δ 8.94 (2H, s), 8.19 (1H, s), 5.34 (1H, s), (two signals of OH proton are not observed). LC-MS (Method-F) m/z: M + 1 obs 222.2, tR = 0.62 min. |

TABLE 25-continued

| Structure | Chemical Name | 1H-NMR & LC-MS (m/z) |
|---|---|---|
| 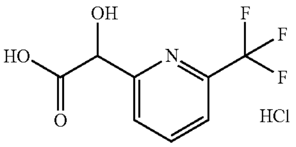 [SMILES: O=C(O)C(O)c1cccc(C(F)(F)F)n1 ; Cl] INT-24-5 | 2-hydroxy-2-(6-(trifluoromethyl)pyridin-2-yl)acetic acid hydrochoride | (400 MHz, DMSO-$d_6$) δ 8.10 (1H, t, J = 7.8 Hz), 7.83-7.77 (2H, m), 5.14 (1H, s), (two signals of OH proton are not observed). LC-MS (Method-F) m/z: M + 1 obs 222.1, tR = 0.38 min. |
| 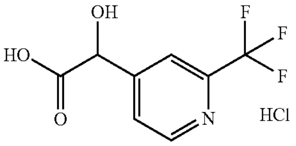 [SMILES: O=C(O)C(O)c1ccnc(C(F)(F)F)c1 ; Cl] INT-24-6 | 2-hydroxy-2-(2-(trifluoromethyl)pyridin-4-yl)acetic acid hydrochoride | (400 MHz, DMSO-$d_6$) δ 8.73 (1H, d, J = 5.0 Hz), 7.89 (1H, s), 7.74 (1H, d, J = 5.0 Hz), 5.28 (1H, s), (two signals of OH proton are not observed). LC-MS (Method-F) m/z: M + 1 obs 222.1, tR = 0.35 min. |
| 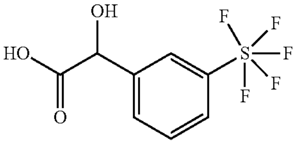 [SMILES: O=C(O)C(O)c1cccc(S(F)(F)(F)(F)F)c1] INT-24-7 | 2-hydroxy-2-(3-(pentafluoro-$\lambda^6$-sulfaneyl)phenyl)acetic acid | LC-MS (Method-F) m/z: M − 1 obs 277.2, tR = 0.35 min. |

Intermediate-25-1 (INT-25-1)

Synthesis of 2-(3'-fluoro-[1,1'-biphenyl]-3-yl)-2-hydroxyacetic acid (INT-25-1)

{Chem. 48}

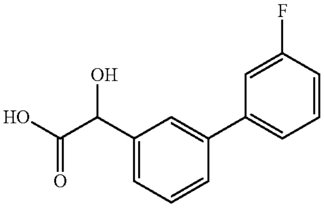

Step-25-1-A: Synthesis of methyl 2-(3'-fluoro-[1,1'-biphenyl]-3-yl)-2-hydroxyacetate (INT-25-1-A)

{Chem. 49}

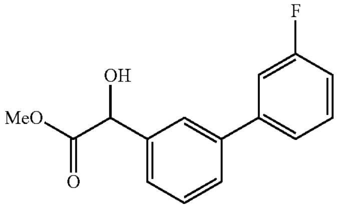

A mixture of methyl 2-(3-bromophenyl)-2-hydroxyacetate (430 mg, 1.76 mmol), (3-fluorophenyl)boronic acid (369 mg, 2.63 mmol), Pd(amphos)$Cl_2$ (124 mg, 0.18 mmol), saturated sodium hydrogen carbonate aqueous solution (2 mL) and 1,4-dioxane (8 mL) is stirred at 80° C. under nitrogen atmosphere for 2 hrs. After cooling to room temperature, the mixture is diluted with ethyl acetate (50 mL) and washed with water (40 mL). The organic layer is dried over sodium sulfate. After concentration in vacuo, the residue is purified by column chromatography on silica gel eluting with n-hexane-ethyl acetate (2:1 v/v) to give the titled compound (408 mg, 89% yield) as a colorless syrup.

$^1$H-NMR (400 MHz, $CDCl_3$): delta 7.66 (1H, d, J=1.8 Hz), 5.58-7.50 (1H, m), 7.48-7.39 (4H, m), 7.33-7.30 (1H, m), 7.10-7.05 (1H, m), 5.28 (1H, s), 3.82 (3H, s), 3.52 (1H, br s).

Step-25-1-B: Synthesis of 2-(3'-fluoro-[1,1'-biphenyl]-3-yl)-2-hydroxyacetic acid (INT-25-1)

A mixture of INT-25-1-A (408 mg, 1.57 mmol) and 2M NaOH aqueous solution (2 mL) in THF (2 mL) and MeOH (4 mL) is stirred at 60° C. for 1 hr. After removal of the organic solvent by evaporation, the residual solution is acidified by 0.5 M hydrogen chloride aqueous solution. This mixture is extracted with ethyl acetate (50 mL) and the separated organic layer is dried over sodium sulfate, filtered and concentrated under reduced pressure to give the titled compound (386 mg, quantitative yield) as a white solid.

LC-MS (Method-I) m/z: M−1 obs 245.1, tR=0.44 min.

The following biphenyl derivatives (INT-25-2-A to INT-25-5-A) are prepared according to the procedure of INT-25-1-A from methyl 2-(3-bromophenyl)-2-hydroxyacetate and the corresponding boronic acid derivatives in Table 26.

TABLE 26

| Structure | Chemical Name | 1H-NMR |
|---|---|---|
| 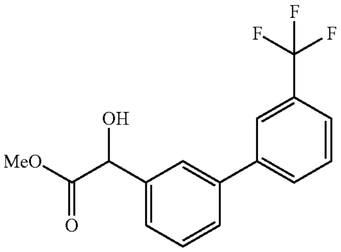 [SMILES: COC(=O)C(O)c1cccc(-c2cccc(C(F)(F)F)c2)c1] INT-25-2-A | methyl 2-hydroxy-2-(3'-(trifluoromethyl)-[1,1'-biphenyl]-3-yl)acetate | (400 MHz, $CDCl_3$) δ 7.85 (1H, s), 7.80 (1H, d, J = 7.3 Hz), 7.68-7.57 (4H, m), 7.53-7.47 (2H, m), 5.29 (1H, d, J = 5.0 Hz), 3.82 (3H, s), 3.55 (1H, d, J = 5.0 Hz). |
| 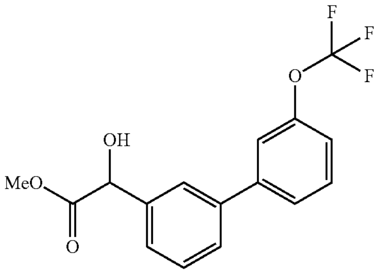 [SMILES: COC(=O)C(O)c1cccc(-c2cccc(OC(F)(F)F)c2)c1] INT-25-3-A | methyl 2-hydroxy-2-(3'-(trifluoromethoxy)-[1,1'-biphenyl]-3-yl)acetate | (400 MHz, $CDCl_3$) δ 7.66 (1H, d, J = 1.8 Hz), 7.58-7.51 (2H, m), 7.50-7.45 (4H, m), 7.26-7.22 (1H, m), 5.28 (1H, d, J = 5.1 Hz), 3.82 (3H, s), 3.53 (1H, d, J = 5.1 Hz). |
| 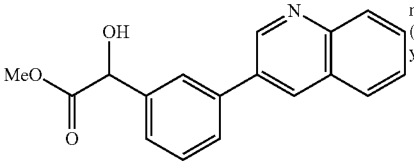 INT-25-4-A | methyl 2-hydroxy-2-(3-(quinolin-3-yl)phenyl)acetate | The structure is confirmed at the next step. |
| 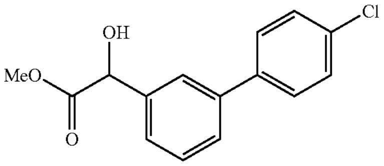 [SMILES: COC(=O)C(O)c1cccc(-c2ccc(Cl)cc2)c1] INT-25-5-A | methyl 2-(4'-chloro-[1,1'-biphenyl]-3-yl)-2-hydroxyacetate | (400 MHz, $CDCl_3$) δ 7.72-7.40 (8H, m), 5.24 (1H, s), 3.78 (3H, s), 3.49 (1H, br s). |

The following 2-hydroxyacetic acid derivatives (INT-25-2 to INT-25-5) are prepared according to the procedure of intermediate-25-1-1B from the synthesized biphenyl derivatives (INT-25-2-A to INT-25-5-A) in Table 27.

TABLE 27

| Structure | Chemical Name | LC-MS (m/z) |
|---|---|---|
| 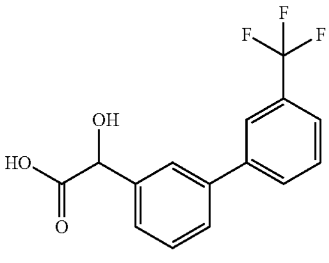 [SMILES: O=C(O)C(O)c1cccc(-c2cccc(C(F)(F)F)c2)c1] INT-25-2 | 2-hydroxy-2-(3'-(trifluoromethyl)-[1,1'-biphenyl]-3-yl)acetic acid | LC-MS (Method-I) m/z: M − 1 obs 295.1, tR = 0.42 min. |

TABLE 27-continued

| Structure | Chemical Name | LC-MS (m/z) |
| --- | --- | --- |
| 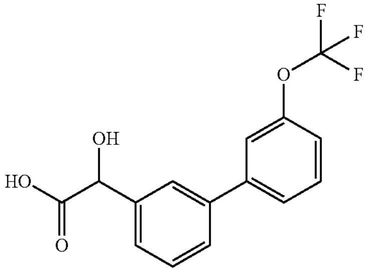 [SMILES: O=C(O)C(O)c1cccc(-c2cccc(OC(F)(F)F)c2)c1] INT-25-3 | 2-hydroxy-2-(3'-(trifluoromethoxy)-[1,1'-biphenyl]-3-yl)acetic acid | LC-MS (Method-1) m/z: M − 1 obs 311.1, tR = 0.45 min. |
| 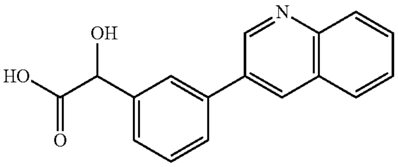 [SMILES: O=C(O)C(O)c1cccc(-c2cnc3ccccc3c2)c1] INT-25-4 | 2-hydroxy-2-(3-(quinolin-3-yl)phenyl)acetic acid | LC-MS (Method-I) m/z: M − 1 obs 278.1, tR = 0.39 min. |
| 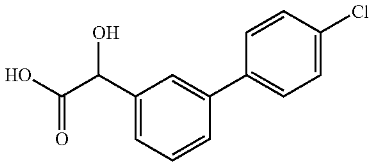 [SMILES: O=C(O)C(O)c1cccc(-c2ccc(Cl)cc2)c1] INT-25-5 | 2-(4'-chloro-[1,1'-biphenyl]-3-yl)-2-hydroxyacetic acid | LC-MS (Method-I) m/z: M − 1 obs 261.1, tR = 0.44 min. |

Intermediate-26-1 (INT-26-1)

Synthesis of (R)-2-(3'-chloro-[1,1'-biphenyl]-3-yl)-2-hydroxyacetic acid (INT-26-1)

{Chem. 50}

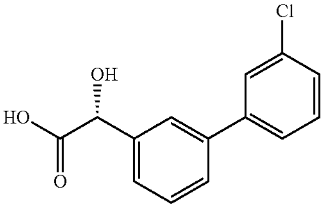

The mixture of (R)-2-(3-bromophenyl)-2-hydroxyacetic acid (20.0 mg, 0.087 mmol), (3-chlorophenyl)boronic acid (17.6 mg, 0.113 mmol), palladium (II) acetate (3.89 mg, 0.017 mmol) and triphenylphosphine (9.08 mg, 0.035 mmol) in dioxane (1 mL) and saturated aqueous sodium bicarbonate (0.5 mL) is stirred at 100° C. for 3 hrs. After cooled down to rt., the reaction mixture is concentrated in vacuo and the residue is diluted with MeCN (2 mL). The resulting mixture is filtrate through the pad of celite and the filtrate is purified by a strong cation exchange cartridge (ISOLUTE(registered trademark) PE-AX) to give the titled compound (19 mg, 0.072 mmol, 84% yield).

LC-MS (Method-K) m/z: M−1 obs 261.0, tR=0.40 min.

The following 2-hydroxyacetic acid derivative (INT-26-2 to INT-26-9) is prepared according to the procedure of intermediate-26-1 from (R)-2-(3-bromophenyl)-2-hydroxyacetic acid or 2-(3-bromophenyl)acetic acid and the corresponding boronic acid derivatives in Table 28.

TABLE 28

| Structure | Chemical Name | $^1$H-NMR & LC-MS (m/z) |
| --- | --- | --- |
| 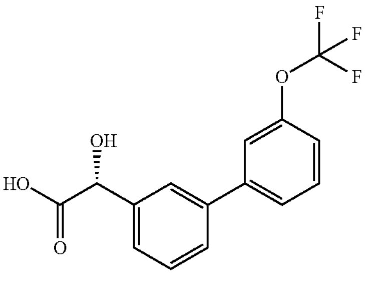 [SMILES: O=C(O)[C@H](O)c1cccc(-c2cccc(OC(F)(F)F)c2)c1] INT-26-2 | (R)-2-hydroxy-2-(3'-(trifluoromethoxy)-[1,1'-biphenyl]-3-yl)acetic acid | LC-MS (Method-K) m/z: M − 1 obs 311.1, tR = 0.41 min. |

TABLE 28-continued

| Structure | Chemical Name | $^1$H-NMR & LC-MS (m/z) |
|---|---|---|
| 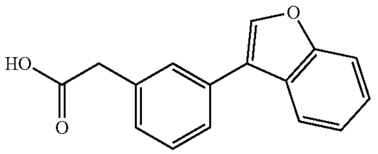 [SMILES: O=C(O)Cc1cccc(-c2coc3ccccc23)c1] INT-26-3 | 2-(3-(benzofuran-3-yl)phenyl)acetic acid | LC-MS (Method-I) m/z: M + HCOO obs 297.1, tR = 0.50 min. |
| 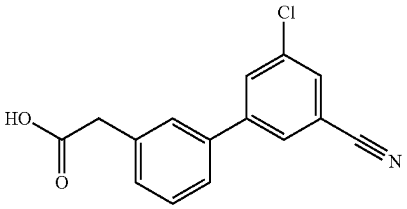 [SMILES: N#Cc1cc(Cl)cc(-c2cccc(CC(=O)O)c2)c1] INT-26-4 | 2-(3'-chloro-5'-cyano-[1,1'-biphenyl]-3-yl)acetic acid | LC-MS (Method-1) m/z: 2 × M − 1 obs 541.0, tR = 0.49 min. |
| 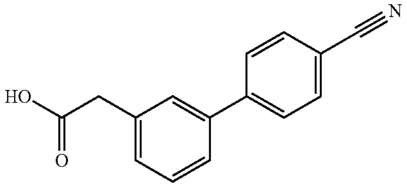 [SMILES: N#Cc1ccc(-c2cccc(CC(=O)O)c2)cc1] INT-26-5 | 2-(4'-cyano-[1,1'-biphenyl]-3-yl)acetic acid | LC-MS (Method-I) m/z: M + HCOO obs 282.1, tR = 0.50 min. |
| 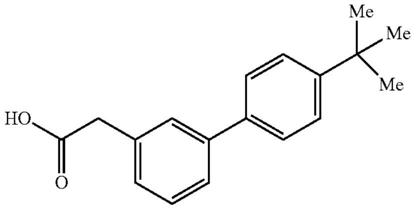 [SMILES: CC(C)(C)c1ccc(-c2cccc(CC(=O)O)c2)cc1] INT-26-6 | 2-(4'-(tert-butyl)-[1,1'-biphenyl]-3-yl)acetic acid | LC-MS (Method-I) m/z: M + HCOO obs 313.1, tR = 0.61 min. |
| 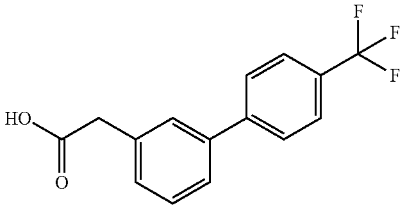 [SMILES: O=C(O)Cc1cccc(-c2ccc(C(F)(F)F)cc2)c1] INT-26-7 | 2-(4'-(trifluoromethyl)-[1,1'-biphenyl]-3-yl)acetic acid | LC-MS (Method-I) m/z: M + HCOO obs 325.1, tR = 0.56 min. |
| 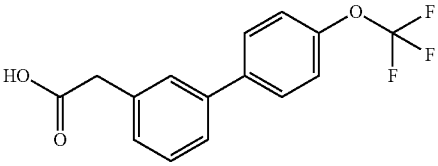 [SMILES: O=C(O)Cc1cccc(-c2ccc(OC(F)(F)F)cc2)c1] INT-26-8 | 2-(4'-(trifluoromethoxy)-[1,1'-biphenyl]-3-yl)acetic acid | LC-MS (Method-I) m/z: M + HCOO obs 341.1, tR = 0.57 min. |

TABLE 28-continued

| Structure | Chemical Name | $^1$H-NMR & LC-MS (m/z) |
|---|---|---|
| 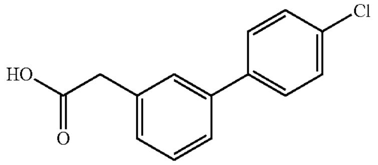 [SMILES: O=C(O)Cc1cccc(-c2ccc(Cl)cc2)c1] INT-26-9 | 2-(4'-chloro-[1,1'-biphenyl]-3-yl)acetic acid | LC-MS (Method-I) m/z: M + HCOO obs 291.1, tR = 0.56 min. |

Intermediate-27-1 (INT-27-1)

Synthesis of (R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl) thiophene-3-carboxylic acid (INT-27-1)

{Chem. 51}

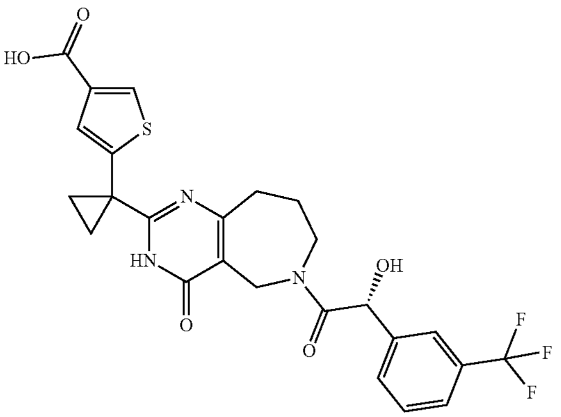

Step-27-1-A: ethyl (R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxylate (INT-27-1-A)

The mixture of INT-11-9 (143 mg, 0.252 mmol), molybdenum carbonyl (139 mg, 0.503 mmol), XantPhos Pd G3 (47.8 mg, 0.050 mmol) and 1,8-diazabicyclo[5.4.0]undec-7-ene (0.114 mL, 0.755 mmol) in EtOH (1 mL) is stirred at 80° C. for 3 hrs. After cooled down to rt, the mixture is filtered through silica gel pad (eluting with EtOAc) and concentrated in vacuo to give crude product, which is purified by column chromatography on silica gel (25 g) eluting with a gradient of 8-100% ethyl acetate in n-hexane to give the titled compound (59.8 mg, 42% yield) as a brown solid.

LC-MS (Method-I) m/z: M+1 obs 562.15, tR=0.57 min.

Step-27-1-B (R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxylic acid The solution of INT-27-1-A (91.9 mg, 0.164 mmol) in EtOH (1 mL) is added with 2M aqueous sodium hydroxide (1 mL). The reaction mixture is stirred at rt for 1 hr. After roughly concentrated, the mixture is acidified with 2M aqueous hydrogen chloride, extracted with ethyl acetate, dried over sodium sulfate, filtered and concentrated in vacuo to give the titled compound (90.9 mg, quantitative yield) as a brown amorphous solid.

LC-MS (Method-I) m/z: M+1 obs 534.10, tR=0.44 min.

Intermediate-28-1 (INT-28-1)

Synthesis of (4-(4,4,5,5-tetramethyl-1,3,2-dioxaborolan-2-yl)-3,6-dihydropyridin-1(2H)-yl)(1-(trifluoromethyl)cyclopropyl)methanone {Chem. 52}

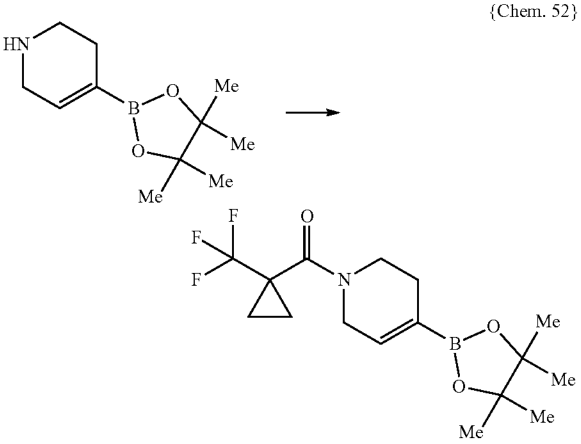

Propylphosphonic anhydride 50% solution in ethyl acetate (0.211 mL, 0.359 mmol) is added to a mixture of 4-(4,4,5,5-tetramethyl-1,3,2-dioxaborolan-2-yl)-1,2,3,6-tetrahydropyridine (50 mg, 0.239 mmol), diisopropyl ethylamine (155 mg, 1.20 mmol) and 1-(trifluoromethyl)cyclopropanecarboxylic acid (40.5 mg, 0.263 mmol) in THF (1 mL). The resulting mixture is stirred at rt for 3 hrs. The reaction mixture is reduced in vacuo and the residue is taken up in EtOAc (2 mL) and washed with water (1 mL). The organic layer is then separated and dried over sodium sulfate and concentrated in vacuo. The residue was purified by column chromatography on amine silica gel (eluting with ethyl acetate) to give the titled compound.

LC-MS (Method-K) m/z: M+1 obs 346.2, tR=0.58 min.

The following amide derivatives (INT-28-2 to INT-28-11) are prepared according to the procedure of intermediate-28-1 from 4-(4,4,5,5-tetramethyl-1,3,2-dioxaborolan-2-yl)-1,2,3,6-tetrahydropyridine and the corresponding acid derivatives in Tables 29-1 to 29-2.

TABLE 29-1

| Structure | Chemical Name | LC-MS (m/z) |
|---|---|---|
| 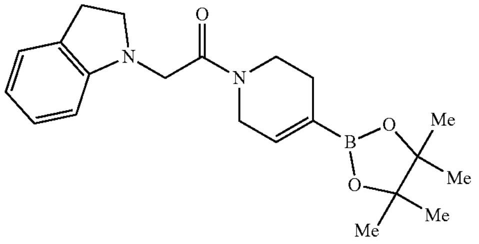 [SMILES: CC1(C)OB(C2=CCN(C(=O)CN3CCc4ccccc43)CC2)OC1(C)C] INT-28-2 | 2-(indolin-1-yl)-1-(4-(4,4,5,5-tetramethyl-1,3,2-dioxaborolan-2-yl)-3,6-dihydropyridin-1(2H)-yl)ethan-1-one | LC-MS (Method-H) m/z: M + 1 obs 369.1, tR = 3.32 min. |
| 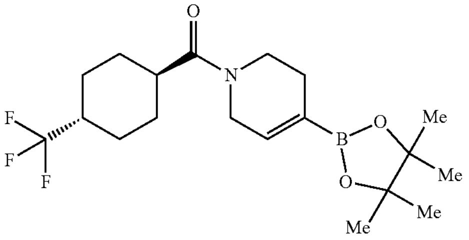 [SMILES: CC1(C)OB(C2=CCN(C(=O)[C@H]3CC[C@H](C(F)(F)F)CC3)CC2)OC1(C)C] INT-28-3 | (4-(4,4,5,5-tetramethyl-1,3,2-dioxaborolan-2-yl)-3,6-dihydropyridin-1(2H)-yl)((1r,4r)-4-(trifluoromethyl)cyclohexyl) methanone | LC-MS (Method-H) m/z: M + 1 obs 388.03, tR = 3.48 min. |
| 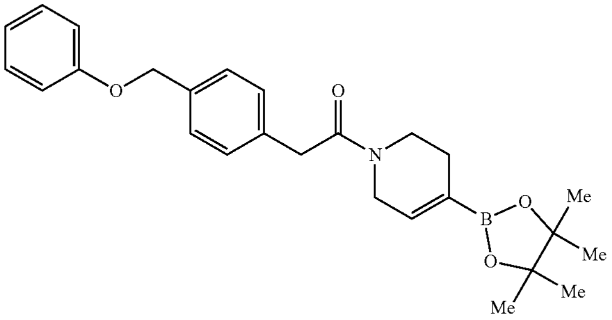 [SMILES: CC1(C)OB(C2=CCN(C(=O)Cc3ccc(COc4ccccc4)cc3)CC2)OC1(C)C] INT-28-4 | 2-(4-(phenoxymethyl)phenyl)-1-(4-(4,4,5,5-tetramethyl-1,3,2-dioxaborolan-2-yl)-3,6-dihydropyridin-1 (2H)-yl)ethan-1-one | LC-MS (Method-H) m/z: M + 1 obs 434.02, tR = 3.65 min. |
| 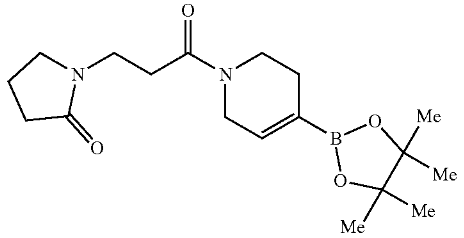 [SMILES: CC1(C)OB(C2=CCN(C(=O)CCN3CCCC3=O)CC2)OC1(C)C] INT-28-5 | 1-(3-oxo-3-(4-(4,4,5,5-tetramethyl-1,3,2-dioxaborolan-2-yl)-3,6-dihydropyridin-1(2H)-yl)propyl)pyrrolidin-2-one | LC-MS (Method-H) m/z: M + 1 obs 349.09, tR = 2.10 min. |
| 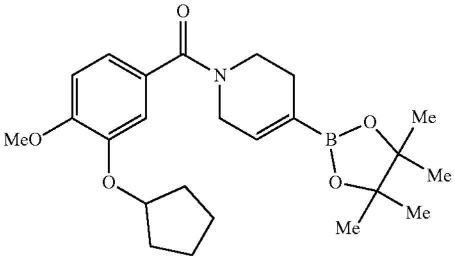 [SMILES: COc1ccc(C(=O)N2CC=C(B3OC(C)(C)C(C)(C)O3)CC2)cc1OC1CCCC1] INT-28-6 | (4-(cyclopentyloxy)-3-methoxyphenyl)(4-(4,4,5,5-tetramethyl-1,3,2-dioxaborolan-2-yl)-3,6-dihydropyridin-1(2H)-yl)methanone | LC-MS (Method-K) m/z: M + 1 obs 428.3, tR = 0.63 min. |

TABLE 29-1-continued

| Structure | Chemical Name | LC-MS (m/z) |
|---|---|---|
| 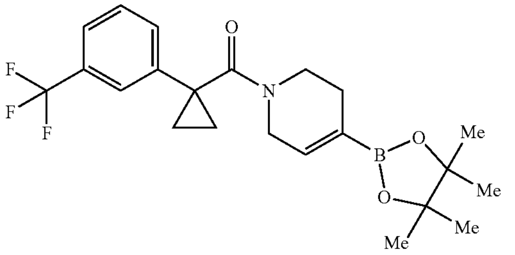 [SMILES: CC1(C)OB(C2=CCN(C(=O)C3(c4cccc(C(F)(F)F)c4)CC3)CC2)OC1(C)C] INT-28-7 | (4-(4,4,5,5-tetramethyl-1,3,2-dioxaborolan-2-yl)-3,6-dihydropyridin-1(2H)-yl)(1-(3-(trifluoromethyl)phenyl) cyclopropyl)methanone | LC-MS (Method-K) m/z: M + 1 obs 422.3, tR = 0.65 min. |

TABLE 29-2

| | | |
|---|---|---|
| 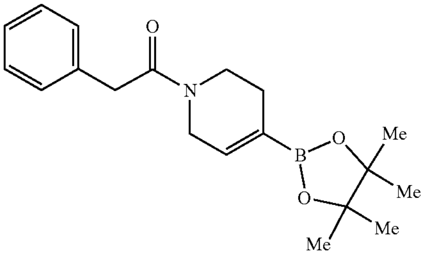 [SMILES: CC1(C)OB(C2=CCN(C(=O)Cc3ccccc3)CC2)OC1(C)C] INT-28-8 | 2-phenyl-1-(4-(4,4,5,5-tetramethyl-1,3,2-dioxaborolan-2-yl)-3,6-dihydropyridin-1(2H)-yl)ethan-1-one | LC-MS (Method-K) m/z: M + 1 obs 328.2, tR = 0.55 min. |
| 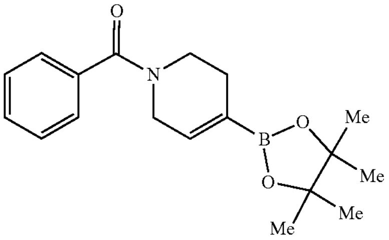 [SMILES: CC1(C)OB(C2=CCN(C(=O)c3ccccc3)CC2)OC1(C)C] INT-28-9 | phenyl(4-(4,4,5,5-tetramethyl-1,3,2-dioxaborolan-2-yl)-3,6-dihydropyridin-1(2H)-yl)methanone | LC-MS (Method-K) m/z: M + 1 obs 314.2, tR = 0.54 min. |
| 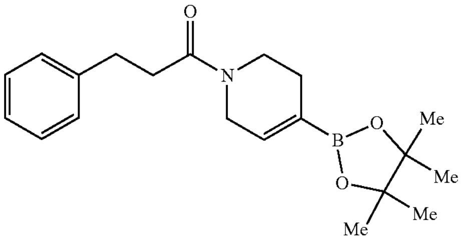 [SMILES: CC1(C)OB(C2=CCN(C(=O)CCc3ccccc3)CC2)OC1(C)C] INT-28-10 | 3-phenyl-1-(4-(4,4,5,5-tetramethyl-1,3,2-dioxaborolan-2-yl)-3,6-dihydropyridin-1(2H)-yl)propan-1-one | LC-MS (Method-K) m/z: M + 1 obs 342.2, tR = 0.56 min. |
| 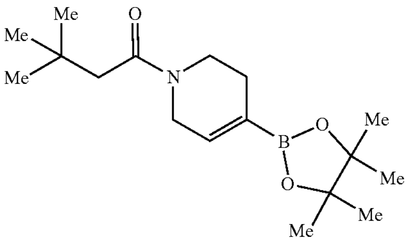 [SMILES: CC(C)(C)CC(=O)N1CC=C(B2OC(C)(C)C(C)(C)O2)CC1] INT-28-11 | 3,3-dimethyl-1-(4-(4,4,5,5-tetramethyl-1,3,2-dioxaborolan-2-yl)-3,6-dihydropyridin-1 (2H)-yl)butan-1-one | LC-MS (Method-K) m/z: M + 1 obs 308.3, tR = 0.57 min. |

Intermediate-29-1 (INT-29-1)

Synthesis of piperidin-1-yl(4-(4,4,5,5-tetramethyl-1,3,2-dioxaborolan-2-yl)-3,6-dihydropyridin-1(2H)-yl)methanone (INT-29-1)

{Chem. 53}

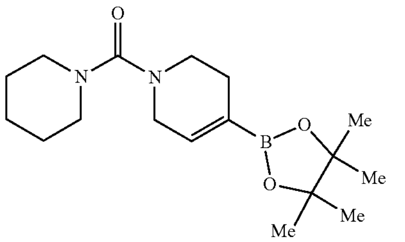

To a solution of 4-(4,4,5,5-tetramethyl-1,3,2-dioxaborolan-2-yl)-1,2,3,6-tetrahydropyridine (30 mg, 0.143 mmol) in dichloromethane (1 mL) are added triethylamine (0.10 mL, 0.717 mmol) and piperidine-1-carbonyl chloride (29.6 mg, 0.201 mmol). The resulting mixture is stirred at room temperature for 2 hrs, then diluted with dichloromethane (5 mL) and washed with water (2 mL). The organic layer is then separated, dried over sodium sulfate and concentrated in vacuo. The residue is purified by column chromatography on amine silica gel (eluting with ethyl acetate) to give the titled compound (13 mg, 28% yield).

LC-MS (Method-K) m/z: M+1 obs 321.3, tR=0.59 min.

Intermediate-30-1 (INT-30-1)

Synthesis of N-cyclohexyl-4-(4,4,5,5-tetramethyl-1,3,2-dioxaborolan-2-yl)-3,6-dihydropyridine-1(2H)-carboxamide (INT-30-1)

{Chem. 54}

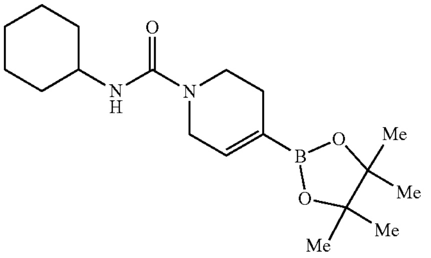

To a solution of 4-(4,4,5,5-tetramethyl-1,3,2-dioxaborolan-2-yl)-1,2,3,6-tetrahydropyridine (30 mg, 0.143 mmol) in THF (1 mL) is added triethylamine (0.10 mL, 0.717 mmol) and isocyanatocyclohexane (26.9 mg, 0.215 mmol). The resulting mixture is stirred at room temperature for 2 hrs, then diluted with ethyl acetate (2 mL) and washed with water (1 mL). The organic layer is then separated, dried over sodium sulfate and concentrated in vacuo. The residue was purified by column chromatography on amine silica gel (eluting with ethyl acetate) to give the titled compound (23 mg, 48.0% yield).

LC-MS (Method-K) m/z: M+1 obs 335.2, tR=0.59 min.

Intermediate-31-1 (INT-31-1)

Synthesis of 1-((4-fluorophenyl)sulfonyl)-4-(4,4,5,5-tetramethyl-1,3,2-dioxaborolan-2-yl)-1,2,3,6-tetrahydropyridine (INT-31-1)

{Chem. 55}

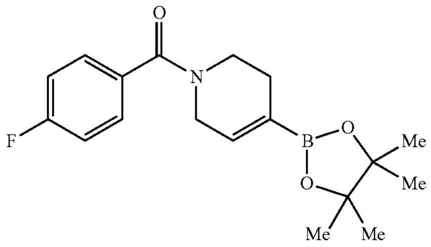

To a solution of 4-(4,4,5,5-tetramethyl-1,3,2-dioxaborolan-2-yl)-1,2,3,6-tetrahydropyridine (30 mg, 0.143 mmol) in dichloromethane (1 mL) are added triethylamine (0.10 mL, 0.717 mmol) and 4-fluorobenzene-1-sulfonyl chloride (41.9 mg, 0.215 mmol). The resulting mixture is stirred at rt for 2 hrs, then diluted with dichloromethane (5 mL) and washed with water (2 mL). The organic layer is then separated, dried over sodium sulfate and concentrated in vacuo. The residue is purified by column chromatography on amine silica gel (eluting with ethyl acetate) to give the titled compound (18 mg, 34% yield).

$^1$H-NMR (400 MHz, $CDCl_3$): delta 7.83-7.78 (2H, m), 7.23-7.17 (2H, m), 6.41-6.38 (1H, m), 3.67-3.65 (2H, m), 3.15 (2H, t, J=5.7 Hz), 2.33-2.29 (2H, m), 1.24 (12H, s).

LC-MS (Method-K) m/z: [$M+NH_4$-1] obs 384.2, tR=0.62 min.

The following sulfonamide derivatives (INT-31-2 to INT-31-3) are prepared according to the procedure of intermediate-31-1 from 4-(4,4,5,5-tetramethyl-1,3,2-dioxaborolan-2-yl)-1,2,3,6-tetrahydropyridine and the corresponding sulfonyl chloride derivatives in Table 30.

TABLE 30

| Structure | Chemical Name | $^1$H-NMR & LC-MS (m/z) |
|---|---|---|
| 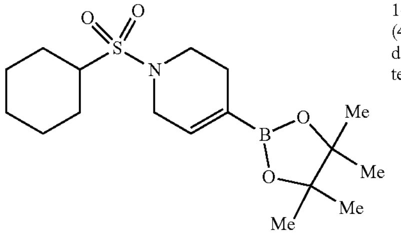 INT-31-2 | 1-(cyclohexylsulfonyl)-4-(4,4,5,5-tetramethyl-1,3,2-dioxaborolan-2-yl)-1,2,3,6-tetrahydropyridine | LC-MS (Method-K) m/z: M + 1 obs 356.2, tR = 0.58 min. |

TABLE 30-continued

| Structure | Chemical Name | $^1$H-NMR & LC-MS (m/z) |
|---|---|---|
| 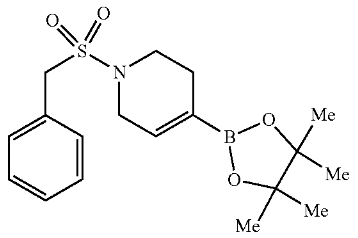 [SMILES: CC1(C)OB(C2=CCN(S(=O)(=O)Cc3ccccc3)CC2)OC1(C)C] INT-31-3 | 1-(benzylsulfonyl)-4-(4,4,5,5-tetramethyl-1,3,2-dioxaborolan-2-yl)-1,2,3,6-tetrahydropyridine | LC-MS (Method-K) m/z: (M + $NH_4$-1) obs 380.2, tR = 0.59 min. |

Intermediate-32-1 (INT-32-1)

Synthesis of 3,3-dimethyl-1-(4-(5-(4,4,5,5-tetramethyl-1,3,2-dioxaborolan-2-yl)pyridin-2-yl)piperazin-1-yl)butan-1-one (INT-32-1)

{Chem. 56}

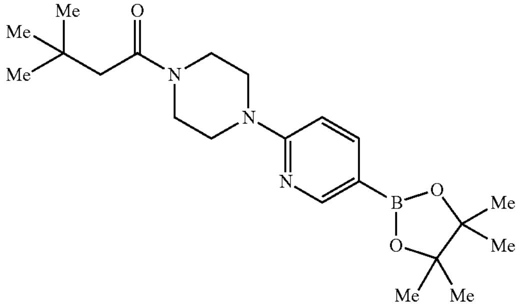

To a solution of 1-(5-(4,4,5,5-tetramethyl-1,3,2-dioxaborolan-2-yl)pyridin-2-yl)piperazine (25 mg, 0.086 mmol) in dichloromethane (1 mL) is added triethyamine (0.0301 mL, 0.216 mmol) and 3,3-dimethylbutanoyl chloride (14.0 mg, 0.104 mmol). The resulting mixture is stirred at rt for 1 hr, then diluted with dichloromethane (2 mL) and washed with water (2 mL). The organic layer is washed with brine (1 mL), dried over sodium sulfate and filtered. The resulting solution is concentrated in vacuo to give the titled compound (38 mg, quant, yield).

LC-MS (Method-K) m/z: M+1 obs 388.3, tR=0.59 min.

The following amide derivatives (INT-32-2 and INT-32-3) are prepared according to the procedure of intermediate-32-1 from 4-(4,4,5,5-tetramethyl-1,3,2-dioxaborolan-2-yl)-1,2,3,6-tetrahydropyridine and the known acid chloride derivatives in Table 31. The amide derivative (INT-32-4) is prepared according to the procedure of amidation using $T_3P$ reagent from the above boronic ester derivative and 2-(4-(phenoxymethyl)phenyl)acetic acid.

TABLE 31

| Structure | Chemical Name | $^1$H-NMR & LC-MS (m/z) |
|---|---|---|
| 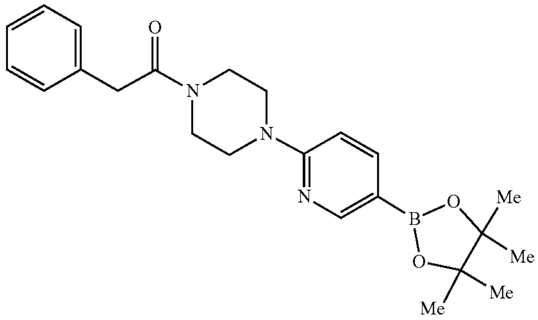 [SMILES: CC1(C)OB(c2ccc(N3CCN(C(=O)Cc4ccccc4)CC3)nc2)OC1(C)C] INT-32-2 | 2-phenyl-1-(4-(5-(4,4,5,5-tetramethyl-1,3,2-dioxaborolan-2-yl)pyridin-2-yl)piperazin-1-yl)ethan-1-one | LC-MS (Method-K) m/z: M + 1 obs 408.3, tR = 0.57 min |
| 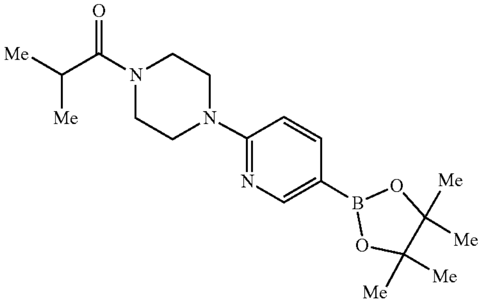 [SMILES: CC(C)C(=O)N1CCN(c2ccc(B3OC(C)(C)C(C)(C)O3)cn2)CC1] INT-32-3 | 2-methyl-1-(4-(5-(4,4,5,5-tetramethyl-1,3,2-dioxaborolan-2-yl)pyridin-2-yl)piperazin-1-yl)propan-1-one | LC-MS (Method-K) m/z: M + 1 obs 360.3, tR = 0.55 min. |

TABLE 31-continued

| Structure | Chemical Name | $^1$H-NMR & LC-MS (m/z) |
|---|---|---|
| 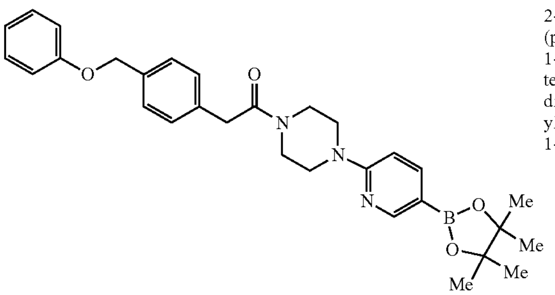 INT-32-4 | 2-(4-(phenoxymethyl)phenyl)-1-(4-(5-(4,4,5,5-tetramethyl-1,3,2-dioxaborolan-2-yl)pyridin-2-yl)piperazin-1-yl)ethan-1-one | LC-MS (Method-K) m/z: M + 1 obs 514.3, tR = 0.61 min |

Intermediate-33-1 (INT-33-1)

Synthesis of N-methyl-N-(4-(4,4,5,5-tetramethyl-1,3,2-dioxaborolan-2-yl)benzyl)piperidine-1-carboxamide (INT-33-1)

{Chem.57}

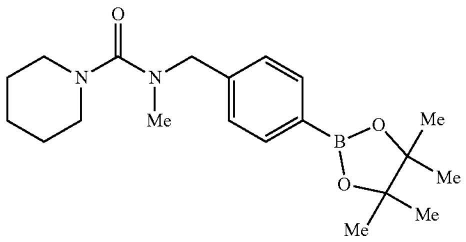

The title compound (17 mg) is prepared in 33% yield by the similar manner to INT-29-1 using N-methyl-1-(4-(4,4,5,5-tetramethyl-1,3,2-dioxaborolan-2-yl)phenyl)methanamine (35.5 mg, 0.143 mmol) in place of 4-(4,4,5,5-tetramethyl-1,3,2-dioxaborolan-2-yl)-1,2,3,6-tetrahydropyridine.

LC-MS (Method-K) m/z: M+1 obs 359.3, tR=0.61 min.

Intermediate-34-1 (INT-34-1)

Synthesis of 3-cyclohexyl-1-methyl-1-(4-(4,4,5,5-tetramethyl-1,3,2-dioxaborolan-2-yl)benzyl)urea (INT-34-1)

{Chem.58}

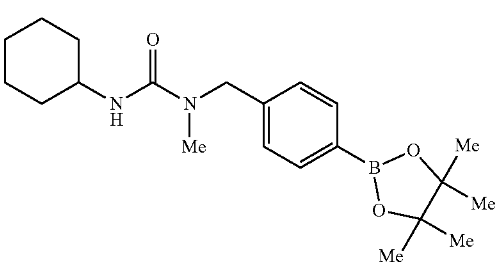

The title compound (38 mg) is prepared in 71% yield by the similar manner to INT-30-1 using N-methyl-1-(4-(4,4,5,5-tetramethyl-1,3,2-dioxaborolan-2-yl)phenyl)methanamine (35.5 mg, 0.143 mmol) in place of 4-(4,4,5,5-tetramethyl-1,3,2-dioxaborolan-2-yl)-1,2,3,6-tetrahydropyridine.

$^1$H-NMR (400 MHz, $CDCl_3$): delta 7.78 (2H, d, J=7.8 Hz), 7.24 (2H, d, J=8.2 Hz), 4.49 (2H, s), 4.20 (1H, d, J=7.8 Hz), 3.71-3.62 (1H, m), 2.85 (3H, s), 1.95-1.91 (2H, m), 1.69-1.57 (4H, m), 1.41-1.30 (1H, m), 1.34 (12H, s), 1.18-1.01 (3H, m).

LC-MS (Method-K) m/z: M+1 obs 373.3, tR=0.61 min.

Intermediate-35-1 (INT-35-1)

Synthesis of ethyl 4-(methyl(4-(4,4,5,5-tetramethyl-1,3,2-dioxaborolan-2-yl)benzyl)amino)-4-oxobutanoate (INT-35-1)

{Chem.59}

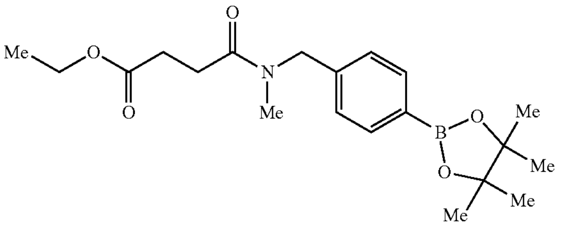

The title compound (49 mg) is prepared in 91% yield by the similar manner to INT-32-1 using ethyl 4-chloro-4-oxobutanoate (28.3 mg, 0.172 mmol) and N-methyl-1-(4-(4,4,5,5-tetramethyl-1,3,2-dioxaborolan-2-yl)phenyl)methanamine (35.5 mg, 0.143 mmol) in place of 1-(5-(4,4,5,5-tetramethyl-1,3,2-dioxaborolan-2-yl)pyridin-2-yl)piperazine.

LC-MS (Method-K) m/z: M+1 obs 376.2, tR=0.57 min.

The following amide derivatives (INT-35-2 and INT-35-3) are prepared according to the procedure of amidation using $T_3P$ reagent from 4-(N-methylaminomethyl)phenylboronic acid, pinacol ester and 2-(4-(methoxycarbonyl)phenyl)acetic acid or 4-(methoxycarbonyl)bicyclo[2.2.2]octane-1-carboxylic acid in Table 32.

TABLE 32

| Structure | Chemical Name | $^1$H-NMR & LC-MS (m/z) |
|---|---|---|
| 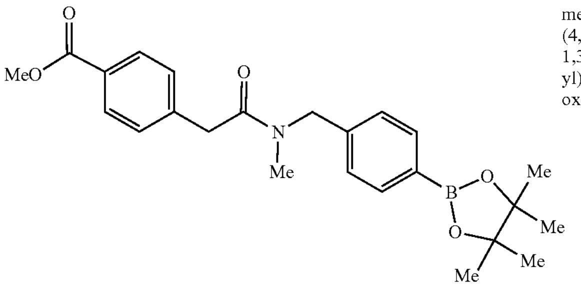 INT-35-2 | methyl 4-(2-(methyl(4-(4,4,5,5-tetramethyl-1,3,2-dioxaborolan-2-yl)benzyl)amino)-2-oxoethyl)benzoate | LC-MS (Method-K) m/z: M + 1 obs 424.3, tR = 0.60 min |
| 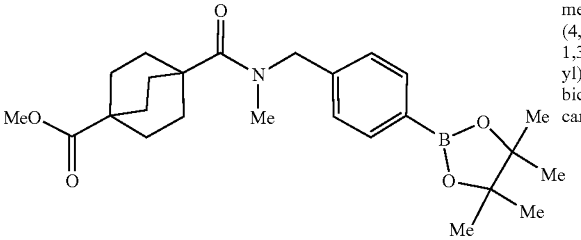 INT-35-3 | methyl 4-(methyl(4-(4,4,5,5-tetramethyl-1,3,2-dioxaborolan-2-yl)benzyl)carbamoyl) bicyclo[2.2.2]octane-1-carboxylate | LC-MS (Method-k) m/z: M + 1 obs 442.4, tR = 0.62 min. |

Intermediate-36-1 (INT-36-1)

Synthesis of 4-(benzyloxy)-1-(4-(4,4,5,5-tetramethyl-1,3,2-dioxaborolan-2-yl)benzyl)piperidine {Chem.60}

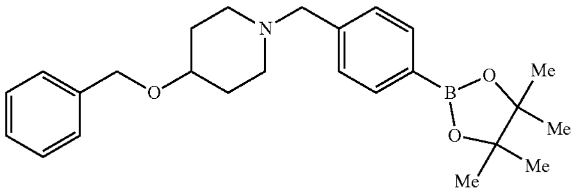

A solution of 2-(4-bromomethyl)-4,4,5,5-tetramethyl-1,3,2-dioxaborolane (20 mg, 0.067 mmol), 4-(benzyloxy)piperidine (14.2 mg, 0.074 mmol), and potassium carbonate (10.2 mg, 0.074 mmol) in acetonitrile (1 mL) is heated to 50° C. for 3 hrs. The reaction mixture is cooled and filterd with Millex (registered trademark) GP filter. The filtrate is concentrated to give the titled compound (26 mg, 95% yield).

LC-MS (Method-K) m/z: M+1 obs 408.3, tR=0.67 min.

The following amine derivative (INT-36-2) is prepared according to the procedure of intermediate-36-1 from 2-(4-(bromomethyl)phenyl)-4,4,5,5-tetramethyl-1,3,2-dioxaborolane and 5-chloro-1,2,3,4-tetrahydroisoquinoline in Table 33.

TABLE 33

| Structure | Chemical Name | $^1$H-NMR & LC-MS (m/z) |
|---|---|---|
| 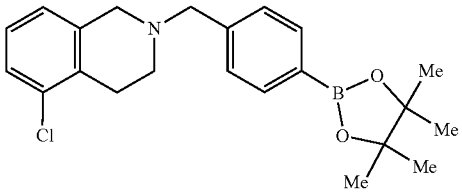 [SMILES: CC1(C)OB(c2ccc(CN3CCc4c(Cl)cccc4C3)cc2)OC1(C)C] INT-36-2 | 5-chloro-2-(4-(4,4,5,5-tetramethyl-1,3,2-dioxaborolan-2-yl)benzyl)-1,2,3,4-tetrahydroisoquinoline | LC-MS (Method-K) m/z: M + 1 obs 384.2, tR = 0.69 min |

Intermediate-37-1 (INT-37-1)

Synthesis of (6-(4-phenylpiperidin-1-yl)pyridin-3-yl)boronic acid (INT-37-1)

{Chem. 61}

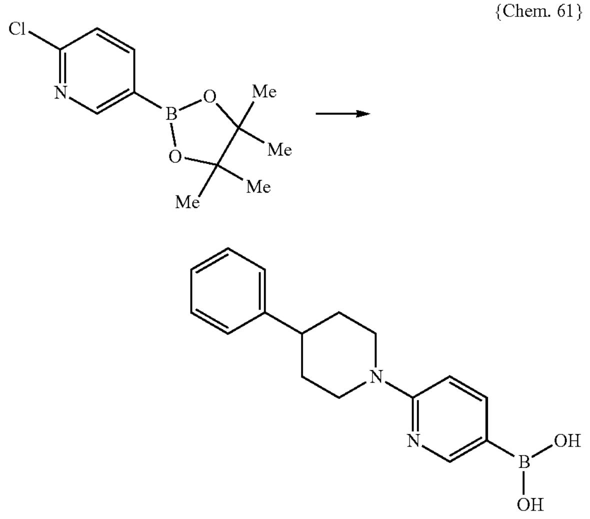

To a solution of 2-chloro-5-(4,4,5,5-tetramethyl-1,3,2-dioxaborolan-2-yl)pyridine (20 mg, 0.084 mmol) in NMP (1 mL) is added 4-phenylpiperidine (26.9 mg, 0.167 mmol) and DIPEA (0.0583 ml, 0.344 mmol), then the mixture is sealed in a microwave tube and heated in microwave reactor at 180° C. for 1.5 hrs. The reaction mixture was poured into 2 mL of water, and extracted with n-BuOH, the organic layer was concentrated and purified by a strong anion exchange cartridge (ISOLUTE(registered trademark) SCX-2) to give the titled compound (20 mg, 85% yield). This titled compound is isolated as the corresponding carboxylic boronic acid derivarive by hydrolysis in situ.

LC-MS (Method-I) m/z: M+1 obs 283.2, tR=0.53 min.

The following boronic acid derivative (INT-37-2) is prepared according to the procedure of intermediate-37-1 from 2-chloro-5-(4,4,5,5-tetramethyl-1,3,2-dioxaborolan-2-yl) pyridine and 4-(benzyloxy)piperidine in Table 34.

TABLE 34

| Structure | Chemical Name | $^1$H-NMR & LC-MS (m/z) |
|---|---|---|
| 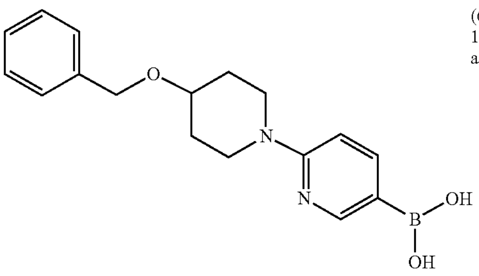 INT-37-2 | (6-(4-(benzyloxy)piperidin-1-yl)pyridin-3-yl)boronic acid | LC-MS (QD-03, basic 5-95 m/z): M + 1 obs 313.2, tR = 0.52 min. |

Intermediate-38-1 (INT-38-1) and Intermediate-38-2 (INT-38-2)

(R)-(−)-2-(2,3-difluorophenyl)-2-hydroxyacetic acid (INT-38-1) and (S)-(+)-2-(2,3-difluorophenyl)-2-hydroxyacetic acid (INT-38-2)

{Chem.63}

(-)- 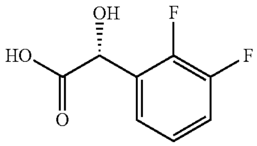

(+)- 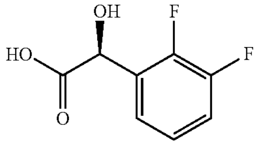

(R)-(−)-2-(2,3-difluorophenyl)-2-hydroxyacetic acid (INT-38-1) and (S)-(+)-2-(2,3-difluorophenyl)-2-hydroxyacetic acid (INT-38-2) are commercially available reagents. Alternatively, the racemic 2-(2,3-difluorophenyl)-2-hydroxyacetic acid is separated by HPLC using chiral column to give (−)-2-(2,3-difluorophenyl)-2-hydroxyacetic acid (INT-38-1) ($[\alpha]_D$ −131.4° (c=0.507, MeOH, 23.2° C.)) and (+)-2-(2,3-difluorophenyl)-2-hydroxyacetic acid (INT-38-2) ($[\alpha]_D$ 134.6° (c=0.507, MeOH, 23.2° C.)), respectively.

The chirality of obtained (−)-2-(2,3-difluorophenyl)-2-hydroxyacetic acid (INT-38-1) is determined to be (R)-form by X-ray structure analysis.

Intermediate-39-1 (INT-39-1) and Intermediate-39-2 (INT-39-2)

(R)-(−)-2-(3-bromophenyl)-2-hydroxyacetic acid (INT-39-1) and (S)-(+)-2-(3-bromophenyl)-2-hydroxyacetic acid (INT-39-2)

{Chem.63}

(-)- 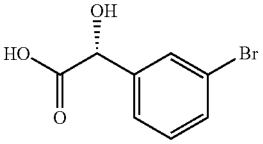

-continued

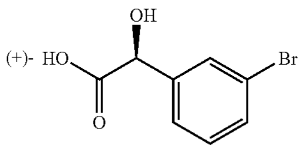

(R)-(−)-2-(3-bromophenyl)-2-hydroxyacetic acid (INT-39-1) and (S)-(+)-2-(3-bromophenyl)-2-hydroxyacetic acid (INT-39-2) are commercially available reagents. Alternatively, the racemic 2-(3-bromophenyl)-2-hydroxyacetic acid is separated by HPLC using chiral column to give (−)-2-(3-bromophenyl)-2-hydroxyacetic acid (INT-39-1) ($[\alpha]_D$ −98.1° (c=0.68, MeOH, 25.0° C.), 98.9% e.e) and (+)-2-(3-bromophenyl)-2-hydroxyacetic acid (INT-39-2) ($[\alpha]_D$ 88.3° (c=0.68, MeOH, 25.0° C.), 99.7% e.e.), respectively.

The chirality of obtained (−)-2-(3-bromophenyl)-2-hydroxyacetic acid (INT-39-1) is reported to be (R)-form by literatures. J. Am. Chem. Soc., 2002, 124, 9024-9025 Angew. Chem. Int. Ed. 2008, 47, 6643-6646.

Intermediate-40-1 (INT-40-1) and Intermediate-40-2 (INT-40-2)

(R)-(−)-2-hydroxy-2-(3-(trifluoromethyl)phenyl) acetic acid (INT-40-1) and (S)-(+)-2-(3-bromophenyl)-2-hydroxyacetic acid (INT-40-2)

{Chem.64}

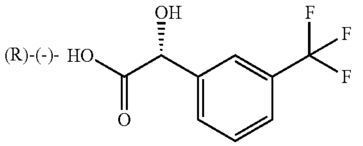

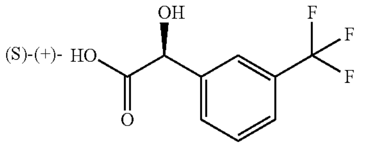

(R)-(−)-2-hydroxy-2-(3-(trifluoromethyl)phenyl)acetic acid (INT-40-1) and (S)-(+)-2-hydroxy-2-(3-(trifluoromethyl)phenyl)acetic acid (INT-40-2) are commercially available reagents (for example, (R)-(−)-2-hydroxy-2-(3-(trifluoromethyl)phenyl)acetic acid (Astatech, COA of Catalog #66997): $[\alpha]_D$ −96.23° (c=0.3, EtOH, 22.0° C.)). Alternatively, the racemic 2-hydroxy-2-(3-(trifluoromethyl)phenyl) acetic acid is separated by HPLC using chiral column to give (R)-(−)-2-hydroxy-2-(3-(trifluoromethyl)phenyl)acetic acid (INT-40-1)(97.0% e.e.) and (S)-(+)-2-hydroxy-2-(3-(trifluoromethyl)phenyl)acetic acid (INT-40-2) (88.1% e.e.), respectively.

Intermediate-41-1 (INT-41-1) and Intermediate-41-2 (INT-41-2)

Chiral 2-(3,5-difluorophenyl)-2-hydroxyacetic acid (INT-41-1 and INT-41-2)

{Chem.65}

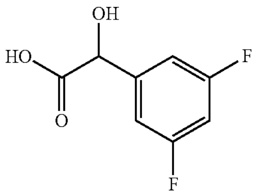

The racemic 2-(3,5-difluorophenyl)-2-hydroxyacetic acid (188 mg) is separated by HPLC system (column: OJ-H; Eluent: Hex/EtOH/TFA=95/5/0.1; Temp. 40° C.; Flow rate: 20 ml/min.) to give the both enantiomers of racemic 2-(3,5-difluorophenyl)-2-hydroxyacetic acid.

Former fraction: INT-41-1

88% e.e. (Method-L)

Later fraction: INT-41-2

>99% e.e. (Method-L)

Intermediate-42-1 (INT-42-1)

(−)-2-(3-bromo-2-fluorophenyl)-2-hydroxyacetic acid (INT-42-1)

{Chem.66}

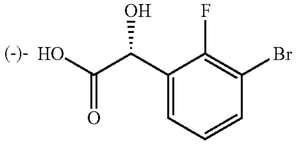

The racemic 2-(3-bromo-2-fluorophenyl)-2-hydroxyacetic acid (440 mg) is separated by HPLC system (column: OJ-H; Eluent: Hex/EtOH/TFA=93/7/0.1; Temp. 40° C.; Flow rate: 20 ml/min.) to give the (−)-enantiomer of 2-(3-bromo-2-fluorophenyl)-2-hydroxyacetic acid.

Former fraction: INT-42-1

98.3% e.e. (Method-L)

$[\alpha]_D$ −139.4° (c=0.251, MeOH)

Intermediate-43-1 (INT-43-1) and -43-2 (INT-43-2)

Chiral 2-(3-chloro-2-fluorophenyl)-2-hydroxyacetic acid (INT-43-1 and INT-43-2)

{Chem.67}

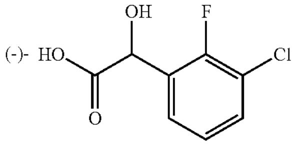

-continued

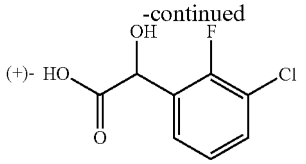

The racemic 2-(3-chloro-2-fluorophenyl)-2-hydroxy-acetic acid (250 mg) is separated by HPLC system (column: OJ-H; Eluent: Hex/EtOH/TFA=93/7/0.1; Temperature 40° C.; Flow rate: 20 mL/min.) to give the both enantiomers of racemic 2-(3-chloro-2-fluorophenyl)-2-hydroxyacetic acid.

Former fraction: INT-43-1

98.8% e.e. (Method-L)

[α]D −155.6° (c=0.473, MeOH, 23.9° C.)

Later fraction: INT-43-2

>99% e.e. (Method-L)

Intermediate-44-1 (INT-44-1)

(−)-2-hydroxy-2-(m-tolyl)acetic acid (INT-44-1)

{Chem. 68}

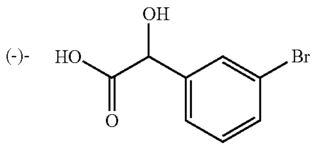

A 2-hydroxy-2-(m-tolyl)acetic acid (971 mg, 5.84 mmol) is added to a solution of phenylethylamine (708 mg, 5.84 mg) in IPA (10 mL). The mixture is stirred at 70° C. for 10 min and at room temperature for 1 hr. The resulting precipitate is collected by filtration, washed with small amount of IPA and dried at 70° C. in vacuo to give the product. This crude product is repeated the above operation 3 times. The obtained product is dissolved in ethyl acetate and acidified to pH<3 with 2M HCl aqueous solution. The mixture is extracted with ethyl acetate and the separated organic layer is concentrated in vacuo. The residue is triturated with toluene and filtered off to give the titled compound.

98% e.e. (Method-L)

$[\alpha]_D$ −130° (c=0.543, EtOH, 22.8° C.)

Example-1

(R)-2-(1-phenylcyclopropyl)-6-(2-phenylpropanoyl)-5,6,7,8-tetrahydropyrido[4,3-d]pyrimidin-4(3H)-one (Ex-1)

{Chem. 69}

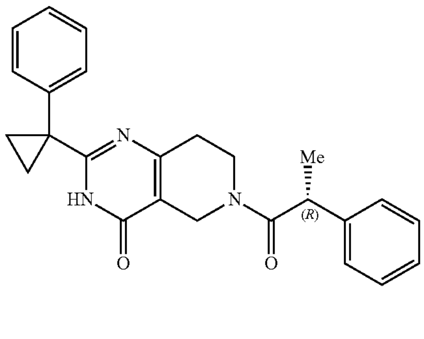

To a stirred solution of (R)-(−)-2-phenylpropionic acid (56 mg, 0.374 mmol) in DMF (5 mL) is added HBTU (170 mg, 0.449 mmol) in one portion at rt. After 10 min, to this is added intermediate-1 (INT-1) (100 mg, 0.374 mmol) and triethylamine (156 microL, 1.12 mmol) at rt. The reaction mixtures are stirred at rt for 18 hrs. After the quenching with water, the mixture is extracted with ethyl acetate-toluene (8:1 v/v mixture). The organic layer is separated and the aqueous layer is extracted with the same solvent. The combined solution is washed with water (×2), brine, dried over sodium sulfate, filtered and concentrated in vacuo to give crude product, which is purified by column chromatography on silica gel (Yamazen, Hi-Flash column, size L (26×100 mm), 30 g) eluting with n-hexane-ethyl acetate (1:2 to 1:3 v/v) to the titled compound (119 mg, 80% yield) as a white solid.

$[\alpha]^{25}_D$ −11.4° (c 0.371, MeOH)

$^1$H-NMR (270 MHz, DMSO-$d_6$, 75° C.): delta 11.83 (1H, br. s), 7.35-7.15 (10H, m), 4.37-4.05 (3H, m), 3.75-3.55 (2H, m), 2.55-2.40 (2H, m), 1.47-1.38 (2H, m), 1.32 (3H, d, J=6.6 Hz), 1.23-1.13 (2H, m).

LC-MS (Method-E) m/z: M+1 obs 400.18 M−1 obs 398.17, tR=2.98 min.

The compounds in Table 35 are prepared by a method similar to the one described for the preparation of Example-1. As is appreciated by those skilled in the art, these analogous examples may involve variation in general reaction conditions. After the amidation of acids with amines using the coupling reagent (HBTU, HATU or EDC-HOBt) in inert solvents (Acetonitrile, DMF, DCM or DCM-DMF mixtures), the crude product is purified by column chromatography on silica gel or SCX (strong cation exchange cartridge) [BondElute (registered trademark) SCX, 1 g/6 mL, Varian Inc.]. In the case of SCX purification, the residue is dissolved in a minimal amount of methanol, and passed through an SCX cartridge eluting with methanol, then 1M-ammonia/methanol to release the product. The further purification is carried out by preparative LC-MS or preparative SFC-MS system in usual manner, and HPLC retention time and observed MS are measured by HPLC-QC method.

All examples are identified as the described compounds with the chemical purity of greater than 80% by preparative LC-MS or preparative SFC-MS and HPLC-QC method. In Tables 35 to 93-4, HPLC retention time (min.) and observed MS (M+1 or M−1) are measured by at least one HPLC-QC method (QC mathod-A to method-D).

{Chem. 70}

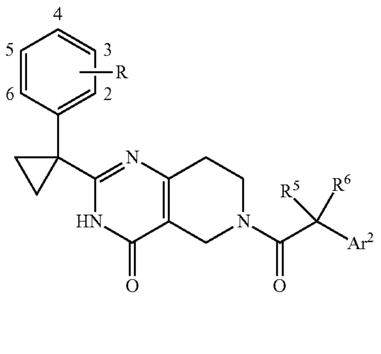

TABLE 35

| Ex. | Ar$^2$ | R | R$^5$ | R$^6$ | Retention time (min.) | Observed MS |
|---|---|---|---|---|---|---|
| 2-1 | phenyl | H | (S)—Me | H | 1.62 | 398.3 |
| 2-2 | 4-(isobutyl)phenyl | H | (R)—Me | H | 2.00 | 454.3 |
| 2-3 | 4-(isobutyl)phenyl | H | (S)—Me | H | 2.00 | 454.3 |
| 2-4 | 4-(isobutyl)phenyl | 4-F | (R)—Me | H | 1.98 | 472.1 |
| 2-5 | 4-(isobutyl)phenyl | 4-Cl | (R)—Me | H | 2.06 | 488.1 |
| 2-6 | 3,5-difluorophenyl | H | Me | H | 1.69 | 434.2 |
| 2-7 | 4-chlorophenyl | H | Me | H | 1.74 | 432.2 |
| 2-8 | 3,5-difluorophenyl | H | H | H | 1.60 | 420.2 |
| 2-9 | 4-(trifluoromethyl)phenyl | H | Me | H | 1.77 | 466.2 |
| 2-10 | 4-fluorophenyl | H | Me | H | 1.63 | 416.3 |
| 2-11 | 4-(isopropyl)phenyl | H | H | H | 1.79 | 426.4 |
| 2-12 | 3,5-difluorophenyl | 4-F | Me | H | 1.70 | 452.3 |
| 2-13 | 4-(tert-butyl)phenoxy | H | H | H | 1.87 | 456.3 |
| 2-14 | 1H-indol-3-yl | H | H | H | 1.50 | 423.3 |
| 2-15 | 5-fluoro-1H-indol-3-yl | H | H | H | 1.53 | 441.3 |
| 2-16 | benzo[d]isoxazol-3-yl | H | H | H | 1.54 | 425.3 |
| 2-17 | 5-methyl-2-phenyloxazol-4-yl | H | H | H | 1.65 | 465.3 |
| 2-18 | (3-phenyl-1,2,4-oxadiazol-5-yl)methyl | H | H | H | 1.64 | 466.2 |
| 2-19 | quinoxalin-6-yl | H | H | H | 1.33 | 436.3 |
| 2-20 | phenyl | H | F | F | 1.69 | 420.2 |
| 2-21 | phenyl | H | F | H | 1.54 | 402.3 |
| 2-22 | 5-chloro-1H-benzo[d]imidazol-2-yl | H | H | H | 1.46 | 458.2 |
| 2-23 | 2-hydroxyphenyl | H | H | H | 1.43 | 400.3 |
| 2-24 | 2-methoxyphenyl | H | H | H | 1.56 | 414.3 |
| 2-25 | (1H-indol-3-yl)methyl | H | H | H | 1.48 | 437.3 |
| 2-26 | ((4-methoxyphenyl)-1,2,4-oxadiazol-5-yl) methyl | H | H | H | 1.63 | 496.3 |
| 2-27 | 1H-indazol-1-yl | H | H | H | 1.49 | 424.3 |
| 2-28 | (2H-benzo[b][1,4]oxazin-3(4H)-one)-4-yl | H | H | H | 1.47 | 455.3 |

Examples 2-29, 2-30 and 2-31 are prepared according to the procedure described in amidation reaction of Example-1 from intermediate-1 (INT-1) and the corresponding acids. The purification is carried out by SCX cartridge and the further purification is carried out by preparative LC-MS or SFC-MS system in usual manner. The retention time and observed MS by HPLC-QC method are noted in Examples 2-29, 2-30 and 2-31.

Example-2-29

(E)-6-(3-(3-chlorophenyl)acryloyl)-2-(1-phenylcyclopropyl)-5,6,7,8-tetrahydropyrido[4,3-d]pyrimidin-4(3H)-one (Ex-2-29)

{Chem. 71}

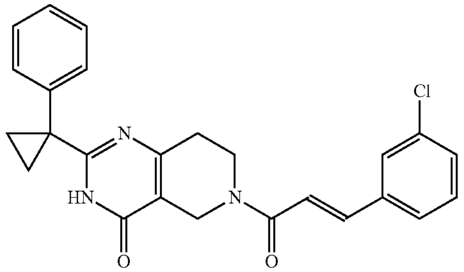

LC-MS (Method-HPLC-QC) m/z: M+1 obs 432.0, M−1 obs 430.2, tR=1.73 min.

Example-2-30

6-((1S*,2S*)-2-phenylcyclopropanecarbonyl)-2-(1-phenylcyclopropyl)-5,6,7,8-tetrahydropyrido[4,3-d]pyrimidin-4(3H)-one (Ex-2-30)

{Chem. 72}

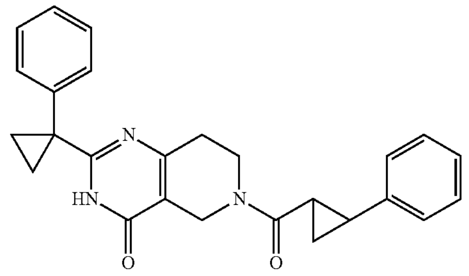

LC-MS (Method-HPLC-QC) m/z: M+1 obs 412.0, M−1 obs 410.3, tR=1.67 min.

Example-2-31

6-((1S*,2S*)-2-(2,5-difluorophenyl)cyclopropanecarbonyl)-2-(1-phenylcyclopropyl)-5,6,7,8-tetrahydropyrido[4,3-d]pyrimidin-4(3H)-one (Ex-2-31)

{Chem. 73}

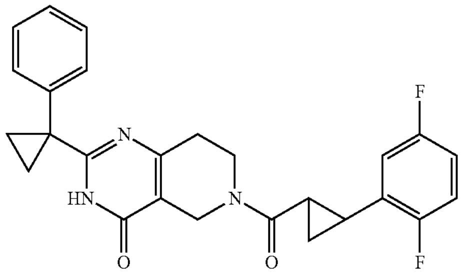

LC-MS (Method-HPLC-QC) m/z: M+1 obs 448.0, M−1 obs 446.3, tR=1.70 min.

Example-2-32

(R)-6-(2-hydroxy-2-phenylacetyl)-2-(1-phenylcyclopropyl)-5,6,7,8-tetrahydropyrido[4,3-d]pyrimidin-4(3H)-one (Ex-2-32)

{Chem. 74}

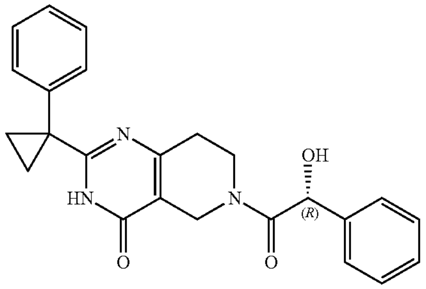

The titled compound is prepared according to the procedure described in amidation reaction of Example 1 from (R)-(−)-mandelic acid (61.5 mg, 0.40 mmol) and intermediate (INT-1) (108 mg, 0.40 mmol). The purification is carried out by column chromatography on silica gel (pre-packed column: 30 g) eluting with DCM-MeOH (40:1 v/v) to give the titled compound (75.9 mg, 47% yield) as a white solid.

$^1$H-NMR (270 MHz, DMSO-$d_6$, 75° C.): delta 11.86 (1H, br.s), 7.38-7.18 (10H, m), 5.54-5.47 (1H, m), 5.47-5.40 (1H, m), 4.36-4.12 (2H, m), 3.76-3.58 (2H, m), 2.39 (2H, br.s), 1.47-1.39 (2H, m), 1.22-1.14 (2H, m).

LC-MS (Method-A) m/z: M+1 obs 402.26, M−1 obs 400.26, tR=2.69 min.

Example-2-33

(R)-6-(2-(3-chlorophenyl)-2-hydroxyacetyl)-2-(1-phenylcyclopropyl)-5,6,7,8-tetrahydropyrido[4,3-d]pyrimidin-4(3H)-one (Ex-2-33)

{Chem. 75}

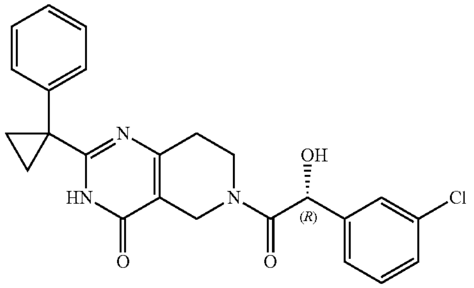

To a stirred solution of (R)-(−)-3-chloromandelic acid (36.6 mg, 0.196 mmol) and intermediate (INT-1) (50.0 mg, 0.187 mmol) in DCM (5 mL) are added $Et_3N$ (95.0 mg, 0.935 mmol), EDC (39.4 mg, 0.206 mmol) and HOBT (14.3 mg, 0.094 mmol) successively. The resulting solution stirred at room temperature for 1 h. The mixture is concentrated in vacuo to give the residue, which is purified by column chromatography on silica gel (pre-packed column: 14 g) eluting with DCM-MeOH (45:1 v/v) to give the crude product. The crude product is dissolved in methanol (3 mL). Potassium carbonate (19.4 mg, 0.140 mmol) is added to the mixture. The resulting solution stirred at 60° C. for 3 hrs. The mixture is concentrated in vacuo to give the residue, which is purified by column chromatography on silica gel (pre-packed column: 14 g) eluting with DCM-MeOH (45:1 v/v) to give the titled compound (55 mg, 68% yield) as a white solid.

$^1$H-NMR (270 MHz, DMSO-$d_6$, 80° C.): delta 11.85 (1H, brs), 7.40-7.20 (9H, m), 5.75 (1H, d, J=7.3 Hz), 5.48 (1H, d, J=6.6 Hz), 4.32 (1H, d, J=19.8 Hz), 4.21 (1H, d, J=19.8 Hz), 3.78-3.62 (2H, m), 2.49-2.43 (2H, m), 1.47-1.42 (2H, m), 1.22-1.17 (2H, m).

LC-MS (Method-E) m/z: M+1 obs 436.1, tR=2.71 min.

LCMS (Method-L) 98.1% e.e., tR=19.07 min.

Example-2-34

(R)-(−)-6-(2-(2,3-difluorophenyl)-2-hydroxyacetyl)-2-(1-phenylcyclopropyl)-5,6,7,8-tetrahydropyrido[4,3-d]pyrimidin-4(3H)-one (Ex-2-34)

{Chem. 76}

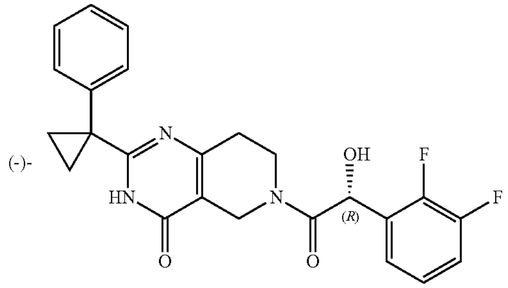

The titled compound is prepared according to the procedure described in Example-2-33 from (R)-(−)-2,3-difluoromandelic acid (INT-38-1)(24.3 mg, 0.129 mmol) and intermediate (INT-1) (30.0 mg, 0.112 mmol). The purification is carried out by column chromatography on silica gel (prepacked column: 14 g) eluting with DCM-MeOH (50:1 v/v) to give the titled compound (36 mg, 73% yield) as a white solid.

$[\alpha]^{24}_{D}$ −20.3° (c 0.314, MeOH)

$^1$H-NMR (270 MHz, DMSO-$d_6$, 80° C.): delta 11.84 (1H, brs), 7.30-7.05 (8H, m), 5.72 (1H, d, J=6.6 Hz), 5.66 (1H, d, J=6.6 Hz), 4.35-4.18 (2H, m), 3.79-3.62 (2H, m), 2.63-2.47 (2H, m), 1.48-1.43 (2H, m), 1.28-1.18 (2H, m).

LCMS (Method-E) m/z: M+1 obs 438.3, tR=2.79 min.

LCMS (Method-L)>99% e.e., tR=15.1 min.

Example-2-35

(S)-(+)-6-(2-(2,3-difluorophenyl)-2-hydroxyacetyl)-2-(1-phenylcyclopropyl)-5,6,7,8-tetrahydropyrido[4,3-d]pyrimidin-4(3H)-one (Ex-2-35)

{Chem. 77}

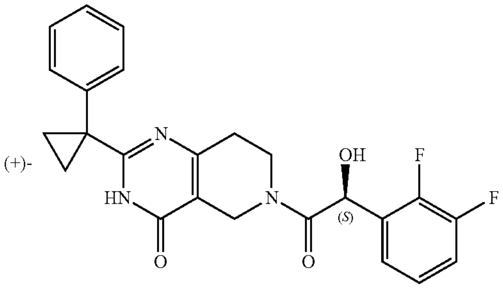

The titled compound is prepared according to the procedure described in Example-2-33 from (S)-(+)-2,3-difluoromandelic acid (INT-38-2) (25.0 mg, 0.135 mmol) and intermediate (INT-1) (30.0 mg, 0.112 mmol). The purification is carried out by column chromatography on silica gel (prepacked column: 14 g) eluting with DCM-MeOH (50:1 v/v) to give the titled compound (25 mg, 51% yield) as a white solid.

$[\alpha]^{25}_{D}$ +19.9° (c 0.256, MeOH)

$^1$H-NMR (270 MHz, DMSO-$d_6$, 80° C.): delta 11.86 (1H, br.s), 7.34-7.14 (8H, m), 5.76-5.68 (2H, m), 4.35-4.18 (2H, m), 3.79-3.64 (2H, m), 2.62-2.47 (2H, m), 1.48-1.43 (2H, m), 1.28-1.18 (2H, m).

LCMS (Method-E) m/z: M+1 obs 438.20, M−1 obs 436.12, tR=2.64 min.

LCMS (Method-L)>99% e.e., tR=9.26 min.

Example-2-36

(R)-(−)-6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one (Ex-2-36)

{Chem. 78}

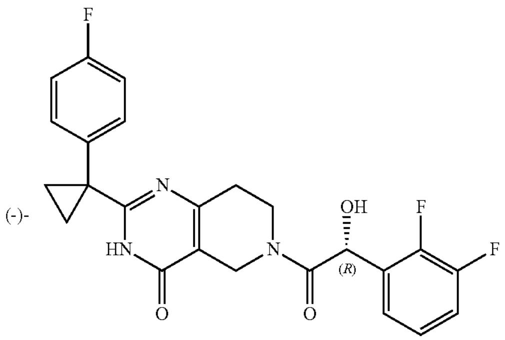

The titled compound is prepared according to the procedure described in Example-2-33 from (R)-(−)-2,3-difluoromandelic acid (INT-38-1)(24.3 mg, 0.129 mmol) and intermediate (INT-4-1)(32 mg, 0.112 mmol). The purification is carried out by column chromatography on silica gel (prepacked column: 14 g) eluting with DCM-MeOH (50:1 v/v) to give the titled compound (30 mg, 59% yield) as a white solid.

$[\alpha]^{24}_{D}$ −17.6° (c 0.359, MeOH)

$^1$H-NMR (270 MHz, DMSO-$d_6$, 80° C.): delta 11.89 (1H, brs), 7.40-7.00 (7H, m), 5.73 (1H, d, J=6.6 Hz), 5.66 (1H, d, J=6.6 Hz), 4.35-4.18 (2H, m), 3.78-3.62 (2H, m), 2.63-2.47 (2H, m), 1.48-1.44 (2H, m), 1.21-1.16 (2H, m).

LCMS (Method-E) m/z: M+1 obs 456.3, tR=2.63 min.

LCMS (Method-L)>99% e.e., tR=17.1 min.

Example-2-37

(S)-(+)-6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one (Ex-2-37)

{Chem. 79}

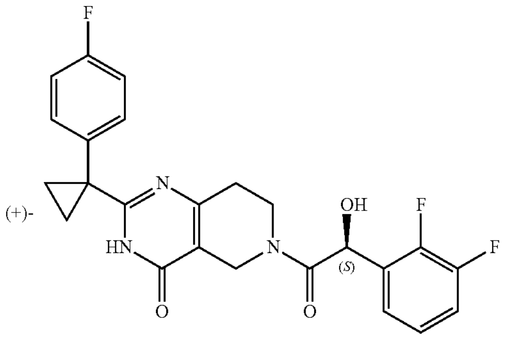

The titled compound is prepared according to the procedure described in Example-2-33 from (S)-(+)-2,3-difluoromandelic acid (INT-38-2) (24.3 mg, 0.129 mmol) and intermediate (INT-4-1) (32.0 mg, 0.112 mmol). The purification is carried out by column chromatography on silica gel (pre-packed column: 14 g) eluting with DCM-MeOH (50:1 v/v) to give the titled compound (35 mg, 68% yield) as a white solid.

$[\alpha]^{25}_D$ +23.7° (c 0.315, MeOH)

$^1$H-NMR (270 MHz, DMSO-$d_6$, 80° C.): delta 11.87 (1H, br.s), 7.39-7.04 (7H, m), 5.76-5.67 (2H, m), 4.35-4.18 (2H, m), 3.78-3.63 (2H, m), 2.63-2.47 (2H, m), 1.48-1.44 (2H, m), 1.21-1.16 (2H, m).

LCMS (Method-E) m/z: M+1 obs 456.17, M−1 obs 454.10, tR=2.63 min.

LCMS (Method-L)>99% e.e., tR=10.06 min.

Example-2-38

(R)-(−)-2-(1-(4-chlorophenyl)cyclopropyl)-6-(2-(2,3-difluorophenyl)-2-hydroxyacetyl)-5,6,7,8-tetrahydropyrido[4,3-d]pyrimidin-4(3H)-one (Ex-2-38)

{Chem. 80}

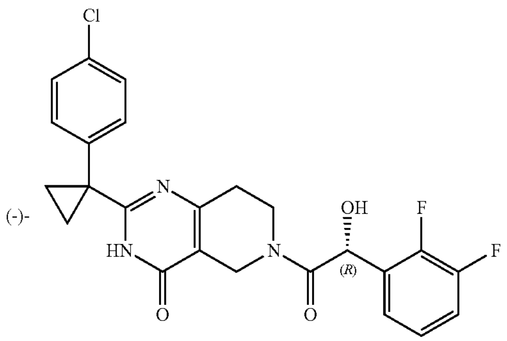

The titled compound is prepared according to the procedure described in Example-2-33 from (R)-(−)-2,3-difluoromandelic acid (INT-38-1) (24.3 mg, 0.129 mmol) and intermediate (INT-4-3) (34.0 mg, 0.112 mmol). The purification is carried out by column chromatography on silica gel (pre-packed column: 14 g) eluting with DCM-MeOH (50:1 v/v) to give the titled compound (39 mg, 74% yield) as a white solid.

$[\alpha]^{24}_D$ −19.0° (c 0.330, MeOH)

$^1$H-NMR (270 MHz, DMSO-$d_6$, 80° C.): delta 11.98 (1H, brs), 7.35-7.05 (7H, m), 5.73 (1H, d, J=6.6 Hz), 5.66 (1H, d, J=6.6 Hz), 4.35-4.19 (2H, m), 3.79-3.62 (2H, m), 2.63-2.48 (2H, m), 1.50-1.46 (2H, m), 1.23-1.18 (2H, m).

LCMS (Method-E) m/z: M+1 obs 472.2, tR=2.63 min.

Example-2-39

(R)-(−)-6-(2-(2,3-difluorophenyl)-2-hydroxyacetyl)-2-(1-(3-fluorophenyl)cyclopropyl)-5,6,7,8-tetrahydropyrido[4,3-d]pyrimidin-4(3H)-one (Ex-2-39)

{Chem. 81}

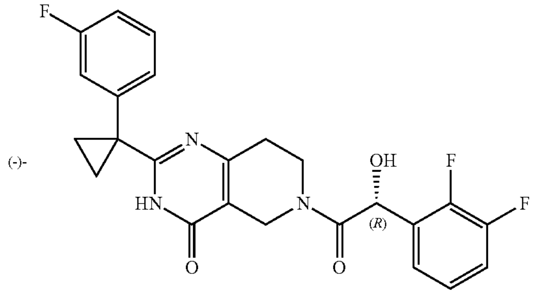

The titled compound is prepared according to the procedure described in Example-2-33 from (R)-(−)-2,3-difluoromandelic acid (INT-38-1) (24.3 mg, 0.129 mmol) and intermediate (INT-4-2) (32.0 mg, 0.112 mmol). The purification is carried out by column chromatography on silica gel (pre-packed column: 14 g) eluting with DCM-MeOH (50:1 v/v) to give the titled compound (31 mg, 61% yield) as a white solid.

$[\alpha]^{24}_D$ −17.7° (c 0.286, MeOH)

$^1$H-NMR (270 MHz, DMSO-$d_6$, 80° C.): delta 11.99 (1H, brs), 7.35-6.95 (7H, m), 5.72 (1H, d, J=6.6 Hz), 5.67 (1H, d, J=6.6 Hz), 4.36-4.19 (2H, m), 3.79-3.63 (2H, m), 2.63-2.47 (2H, m), 1.50-1.45 (2H, m), 1.26-1.22 (2H, m).

LCMS (Method-E) m/z: M+1 obs 456.3, tR=2.63 min.

Example-2-40

(Chiral)-6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one (Ex-2-40)

{Chem. 82}

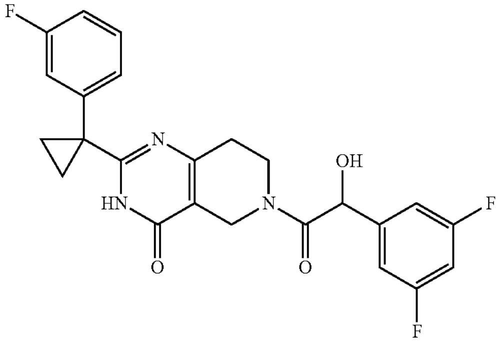

The titled compound is prepared according to the procedure described in Example-2-33 from 3,5-difluoro-mandelic acid (INT-41-1) (40.0 mg, 0.213 mmol) and intermediate (INT-4-2) (57.8 mg, 0.203 mmol). The purification is carried out by column chromatography on silica gel (pre-packed column: 14 g) with DCM-MeOH (50:1 v/v) to give the titled compound (25 mg, 27% yield) as a white solid.

$^1$H-NMR (270 MHz, DMSO-$d_6$, 80° C.): delta 12.01 (1H, brs), 7.32 (1H, m), 7.15-6.90 (6H, m), 5.95 (1H, d, J=6.6 Hz), 5.50 (1H, d, J=6.6 Hz), 4.36-4.21 (2H, m), 3.78-3.64 (2H, m), 2.50-2.47 (2H, m), 1.49-1.45 (2H, m), 1.26-1.21 (2H, m).

LCMS (Method-E) m/z: M+1 obs 456.1, tR=2.64 min.

LCMS (Method-L): 93% e.e., tR=11.0 min.

Example-2-41

(Chiral)-6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one (Ex-2-41)

{Chem. 83}

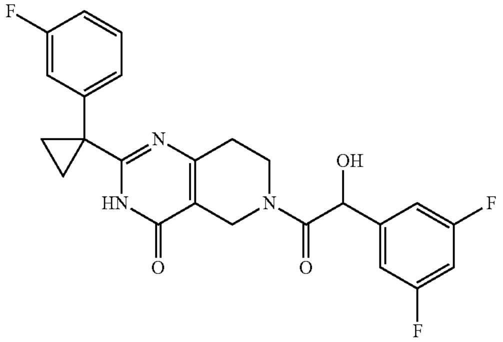

The titled compound is prepared according to the procedure described in Example 34 from 3,5-difluoro-mandelic acid (INT-41-2) (45.0 mg, 0.240 mmol) and intermediate (INT-4-2) (57.0 mg, 0.200 mmol). The purification is carried out by column chromatography on silica gel (pre-packed column: 14 g) with DCM-MeOH (50:1 v/v) to give the titled compound (31 mg, 34% yield) as a white solid.

$^1$H-NMR (270 MHz, DMSO-$d_6$, 80° C.): delta 12.04 (1H, br.s), 7.37-7.28 (1H, m), 7.11-7.00 (6H, m), 5.95 (1H, d, J=6.6 Hz), 5.50 (1H, d, J=6.6 Hz), 4.28 (2H, br.s), 3.78-3.64 (2H, m), 2.50-2.47 (2H, m), 1.49-1.45 (2H, m), 1.26-1.21 (2H, m).

LCMS (Method-E) m/z: M+1 obs 456.04, M−1 obs 454.03, tR=2.64 min.

LCMS (Method-L): 93% e.e., tR=6.31 min.

Example-2-42

(−)-2-(1-(4-fluorophenyl)cyclopropyl)-6-(2-hydroxy-2-(m-tolyl)acetyl)-5,6,7,8-tetrahydropyrido[4,3-d]pyrimidin-4(3H)-one (Ex-2-42)

{Chem. 84}

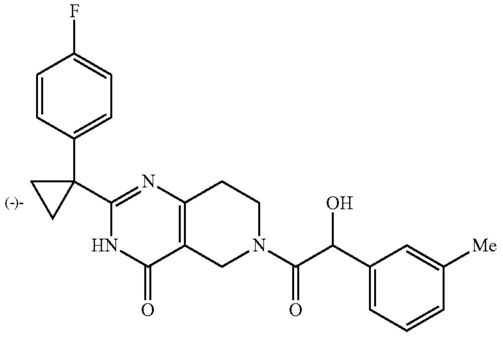

The titled compound is prepared according to the procedure described in Example-2-33 from (−)-3-methyl-mandelic acid (INT-44-1) (20.4 mg, 0.123 mmol) and intermediate (INT-4-1) (35.0 mg, 0.123 mmol). The purification is carried out by column chromatography on silica gel (pre-packed column: 14 g) eluting with DCM-MeOH (50:1 v/v) to give the titled compound (18 mg, 34% yield) as a white solid.

$[\alpha]^{25}_D$ −12.6° (c 0.311, MeOH)

$^1$H-NMR (270 MHz, DMSO-$d_6$, 80° C.): delta 11.85 (1H, brs), 7.45-7.00 (8H, m), 5.43-5.37 (2H, m), 4.33-4.14 (2H, m), 3.70-3.62 (2H, m), 2.50-2.39 (2H, m), 2.25 (3H, s), 1.45-1.41 (2H, m), 1.19-1.15 (2H, m).

LCMS (Method-E) m/z: M+1 obs 434.2, tR=2.71 min.

Example-2-43

(−)-2-(1-(4-chlorophenyl)cyclopropyl)-6-(2-hydroxy-2-(m-tolyl)acetyl)-5,6,7,8-tetrahydropyrido[4,3-d]pyrimidin-4(3H)-one (Ex-2-43)

{Chem. 85}

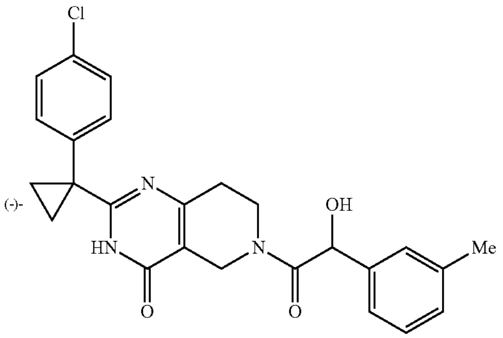

The titled compound is prepared according to the procedure described in Example-2-33 from (−)-3-methyl-mandelic acid (INT-44-1) (20.4 mg, 0.123 mmol) and intermediate (INT-4-3) (37.1 mg, 0.123 mmol). The purification is carried out by column chromatography on silica gel (pre-packed column: 14 g) eluting with DCM-MeOH (50:1 v/v) to give the titled compound (35 mg, 63% yield) as a white solid.

$[\alpha]^{25}_D$ −12.6° (c 0.332, MeOH)

$^1$H-NMR (270 MHz, DMSO-$d_6$, 80° C.): delta 11.93 (1H, brs), 7.45-7.00 (8H, m), 5.43-5.37 (2H, m), 4.33-4.15 (2H, m), 3.69-3.62 (2H, m), 2.50-2.47 (2H, m), 2.26 (3H, s), 1.47-1.43 (2H, m), 1.21-1.17 (2H, m).

LCMS (Method-E) m/z: M+1 obs 450.1, tR=2.91 min.

{Chem. 70}

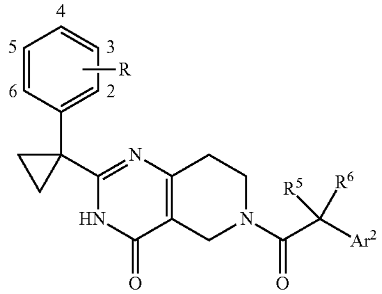

The following amide derivatives are prepared according to the procedure of Ex-1 from the 5,6,7,8-tetrahydropyrido [4,3-d]pyrimidin-4(3H)-one derivatives (INT-1, INT-4-1 to INT-4-4, INT-4-14, INT-4-21 to INT-4-24, INT-9-1) and the known or synthesized acid derivatives. The further purification is carried out by preparative LC-MS or SFC-MS system in usual manner. The retention time and observed MS by HPLC-QC method are summarized in Tables 36-1 and 36-2. The retention time and observed MS of Ex-3-44 to Ex-3-47 measured by Method-E condition are summarized in Tables 36-1 and 36-2.

TABLE 36-1

| Ex. | $Ar^2$ | R | $R^5$ | $R^6$ | Retention time (min.) | Observed MS |
|---|---|---|---|---|---|---|
| 3-1 | phenyl | H | (S)—OH | H | 1.44 | 400.2 |
| 3-2 | 2-chlorophenyl | H | OH | H | 1.52 | 434.2 |
| 3-3 | 4-chlorophenyl | H | OH | H | 1.56 | 434.1 |
| 3-4 | 2-chlorophenyl | H | (S)—OH | H | 1.52 | 434.2 |
| 3-5 | 2-chlorophenyl | H | (R)—OH | H | 1.52 | 434.2 |
| 3-6 | 2,3-difluorophenyl | H | OH | H | 1.50 | 436.1 |
| 3-7 | 3,4-difluorophenyl | H | OH | H | 1.51 | 436.2 |
| 3-8 | 2,4-difluorophenyl | H | OH | H | 1.50 | 436.2 |
| 3-9 | 2,6-difluorophenyl | H | OH | H | 1.46 | 436.2 |
| 3-10 | benzyl | H | (R)—OH | H | 1.42 | 414.3 |
| 3-11 | phenethyl | H | (R)—OH | H | 1.58 | 428.3 |
| 3-12 | 3-fluoro-4-methoxyphenyl | H | OH | H | 1.46 | 448.3 |
| 3-13 | 3-chlorophenyl | H | OH | H | 1.55 | 434.2 |
| 3-14 | 6-methylpyridin-2-yl | H | OH | H | 1.35 | 415.2 |
| 3-15 | 3-fluorophenyl | H | OH | H | 1.48 | 418.2 |
| 3-16 | 3-fluorophenyl | 4-F | OH | H | 1.50 | 436.1 |
| 3-17 | 3-fluoro-4-methoxyphenyl | 4-F | OH | H | 1.48 | 466.2 |
| 3-18 | 2,3-difluorophenyl | 4-Cl | OH | H | 1.61 | 470.2 |
| 3-19 | 2-chlorophenyl | 4-Cl | (R)—OH | H | 1.63 | 468.1 |
| 3-20 | 3,5-difluorophenyl | 4-Cl | OH | H | 1.63 | 470.2 |
| 3-21 | 3-chlorophenyl | 4-Cl | (R)—OH | H | 1.66 | 468.1 |
| 3-22 | 3-chlorophenyl | 4-F | (R)—OH | H | 1.57 | 452.2 |
| 3-23 | 2,3-difluorophenyl | 4-F | OH | H | 1.52 | 454.2 |
| 3-24 | 2-chlorophenyl | 4-F | (R)—OH | H | 1.55 | 452.2 |
| 3-25 | 3,5-difluorophenyl | 4-F | OH | H | 1.54 | 454.2 |
| 3-26 | 4-(trifluoromethyl)phenyl | H | OH | H | 1.63 | 468.1 |
| 3-27 | 2,5-difluorophenyl | H | OH | H | 1.49 | 436.1 |
| 3-28 | 2,3-difluorophenyl | 3-F | OH | H | 1.52 | 454.2 |
| 3-29 | 3,5-difluorophenyl | 3-F | OH | H | 1.54 | 454.2 |
| 3-30 | 2-chlorophenyl | 3-F | (R)—OH | H | 1.54 | 452.2 |
| 3-31 | 3-chlorophenyl | 3-F | (R)—OH | H | 1.56 | 452.2 |
| 3-32 | 2,3-difluorophenyl | $4\text{-}CF_3$ | OH | H | 1.65 | 504.2 |
| 3-33 | 3,5-difluorophenyl | $4\text{-}CF_3$ | OH | H | 1.66 | 504.2 |
| 3-34 | 2-chlorophenyl | $4\text{-}CF_3$ | (R)—OH | H | 1.67 | 502.2 |
| 3-35 | 3-chlorophenyl | $4\text{-}CF_3$ | (R)—OH | H | 1.69 | 502.2 |
| 3-36 | naphthalen-2-yl | H | (R)—OH | H | 1.60 | 450.3 |
| 3-37 | 3-methoxyphenyl | H | OH | H | 1.45 | 430.3 |
| 3-38 | 3-methylphenyl | H | (Chiral)-OH | H | 1.51 | 414.3 |
| 3-39 | 3-chlorophenyl | 4-CN | (R)—OH | H | 1.46 | 459.2 |
| 3-40 | 2,3-difluorophenyl | 4-CN | OH | H | 1.41 | 461.2 |
| 3-41 | 2,3-difluorophenyl | 4-Cl | (S)—OH | H | 1.61 | 470.2 |
| 3-42 | 2,3-difluorophenyl | 3-F | (S)—OH | H | 1.52 | 454.2 |
| 3-43 | 3-hydroxyphenyl | H | OH | H | 1.29 | 416.2 |
| 3-44 | 3-bromophenyl | H | OH | H | 2.80 | 479.9 |
| 3-45 | 3-bromophenyl | H | (R)—OH | H | 2.87 | 480.1 |
| 3-46 | 3-bromophenyl | 3-F | (R)—OH | H | 2.90 | 498.1 |

TABLE 36-2

| | | | | | | |
|---|---|---|---|---|---|---|
| 3-47 | 3-bromo-2-fluorophenyl | H | (Chiral)-OH | H | 2.89 | 498.2 |
| 3-48 | 2,3-difluorophenyl | 3-Cl | (R)—OH | H | 1.62 | 470.2 |
| 3-49 | 2,3-difluorophenyl | 3-Cl | (S)—OH | H | 1.62 | 470.2 |
| 3-50 | 3-chlorophenyl | 3-Cl | (R)—OH | H | 1.67 | 468.2 |
| 3-51 | 2,3-difluorophenyl | 4-Me | (R)—OH | H | 1.63 | 450.3 |
| 3-52 | 3-chlorophenyl | 4-Me | (R)—OH | H | 1.67 | 448.3 |
| 3-53 | 3-isopropoxyphenyl | H | OH | H | 1.62 | 458.3 |
| 3-54 | 2,3-difluorophenyl | 2-Cl | (R)—OH | H | 1.64 | 470.2 |
| 3-55 | 3-chlorophenyl | 2-Cl | (R)—OH | H | 1.69 | 468.2 |
| 3-56 | 3-(cyclopentyloxy)phenyl | H | OH | H | 1.77 | 484.3 |
| 3-57 | 2,3-difluorophenyl | 3,5-F | (R)—OH | H | 1.57 | 472.2 |
| 3-58 | 3-chlorophenyl | 3,5-F | (R)—OH | H | 1.61 | 470.2 |
| 3-59 | 2,3-difluorophenyl | 3,4-F | (R)—OH | H | 1.57 | 472.2 |
| 3-60 | 3-chlorophenyl | 3,4-F | (R)—OH | H | 1.62 | 470.3 |
| 3-61 | 3-(trifluoromethoxy)phenyl | H | OH | H | 1.66 | 484.3 |

TABLE 36-2-continued

| | | | | | | |
|---|---|---|---|---|---|---|
| 3-62 | 3,5-dichlorophenyl | H | OH | H | 1.70 | 468.3 |
| 3-63 | 2,3-dichlorophenyl | H | OH | H | 1.64 | 468.2 |
| 3-64 | 3-(2,2,2-trifluoroethoxy)phenyl | H | OH | H | 1.63 | 498.2 |
| 3-65 | 2-fluoro-3-methoxyphenyl | H | OH | H | 1.47 | 448.3 |
| 3-66 | 3-(trifluoromethyl)phenyl | H | OH | H | 1.62 | 468.3 |
| 3-67 | 3-(trifluoromethyl)phenyl | 4-F | OH | H | 1.64 | 486.2 |
| 3-68 | 3-chloro-2-fluorophenyl | H | OH | H | 1.59 | 452.2 |
| 3-69 | 3-chloro-2-fluorophenyl | H | (Chiral)-OH | H | 1.59 | 454.0 |
| 3-70 | 3-chloro-2-fluorophenyl | H | (Chiral)-OH | H | 1.59 | 454.0 |
| 3-71 | 3-(trifluoromethyl)phenyl | H | (R)—OH | H | 1.62 | 470.0 |
| 3-72 | 3-(trifluoromethyl)phenyl | 3-Cl | (R)—OH | H | 1.72 | 504.0 |
| 3-73 | 3-(trifluoromethyl)phenyl | 3-F | (R)—OH | H | 1.63 | 488.0 |

(Chiral)-OH of Ex-3-38, 3-47, 3-69 and 3-70 in Table 37 present single enantiomer prepared from the optically active mandelic acid. The examples are prepared by the amidation of amines with optically active acids in table 37.

TABLE 37

| Ex. | Amine | Acid |
|---|---|---|
| 3-38 | INT-1 | INT-44-1 |
| 3-47 | INT-1 | INT-42-1 |
| 3-69 | INT-1 | INT-43-1 |
| 3-70 | INT-1 | INT-43-2 |

Example-4-1

6-(2-hydroxy-2-(m-tolyl)acetyl)-2-(1-phenylcyclopropyl)-5,6,7,8-tetrahydropyrido[4,3-d]pyrimidin-4(3H)-one (Ex-4-1)

{Chem. 87}

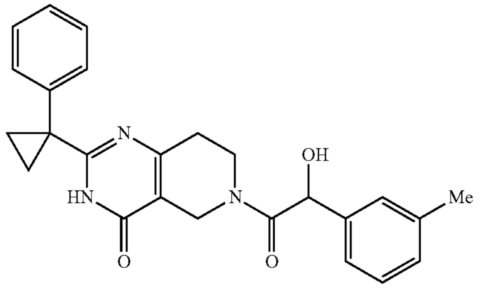

To a stirred solution of Ex-3-44 (57 mg, 0.12 mmol) and trimethylboroxine (15 mg, 0.12 mmol) in 1,4-dioxane (2 mL) are added tricyclohexylphosphine (3.3 mg, 0.012 mmol), $Pd_2(dba)_3$ (5.4 mg, 0.006 mmol) and 1.7 M potassium phosphate aqueous solution (0.098 mL) successively. The resulting solution is stirred at 150° C. for 45 min using microwave oven. The mixture is purified by column chromatography on silica gel (14 g) eluting with DCM-methanol (45:1 v/v) to give the crude product. The further purification is carried out by preparative LC-MS or SFC-MS system in usual manner. The retention time and observed MS by HPLC-QC method are summarized in Table 38.

Example-4-3

6-(2-hydroxy-2-(3-(6-methylpyridin-3-yl)phenyl)acetyl)-2-(1-phenylcyclopropyl)-5,6,7,8-tetrahydropyrido[4,3-d]pyrimidin-4(3H)-one (Ex-4-3)

{Chem. 88}

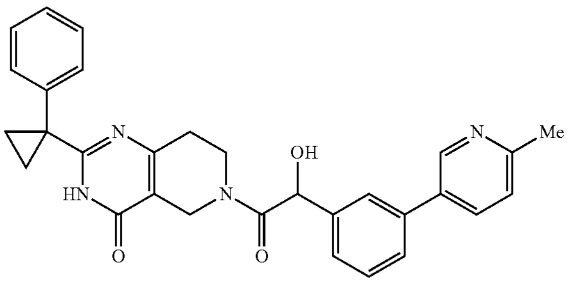

The mixture of Ex-3-44 (35 mg, 0.073 mmol), (6-methylpyridin-3-yl)boronic acid (9.98 mg, 0.073 mmol), tricyclohexylphosphine (2.04 mg, 10% mol) and $Pd_2(dba)_3$ (3.34 mg, 5% mol) in 1,4-dioxane (2 mL) is irradiated under microwave at 150° C. for 45 min. The mixture is purified by column chromatography on silica gel (14 g) eluting with DCM-methanol (50:1 v/v) to give the crude product. The further purification is carried out by preparative LC-MS od SFC-MS system in usual manner. The retention time and observed MS by HPLC-QC method are summarized in Table 38.

Example-4-5

3-(1-hydroxy-2-oxo-2-(4-oxo-2-(1-phenylcyclopropyl)-3,4,7,8-tetrahydropyrido[4,3-d]pyrimidin-6(5H)-yl)ethyl)benzonitrile (Ex-4-5)

{Chem. 89}

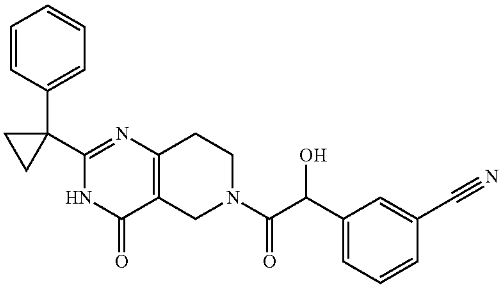

To a stirred solution of Ex-3-44 (60 mg, 0.13 mmol) and dicyanozinc (29 mg, 0.25 mmol) in 1,4-dioxane (3 mL) are added triphenylphosphine (13 mg, 0.050 mmol) and palladium acetate (2.8 mg, 0.012 mmol) successively. The resulting solution is stirred at 150° C. for 45 min using microwave oven. The mixture is purified by column chromatography on silica gel (14 g) eluting with DCM-MeOH (45:1 v/v) to give the crude product. The further purification is carried out by preparative LC-MS or SFC-MS system in usual manner. The retention time and observed MS by HPLC-QC method are summarized in Table 38.

{Chem. 90}

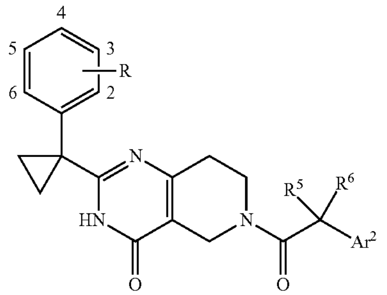

The following amide derivatives (Ex-4-2, Ex-4-4, Ex-4-6 to Ex-4-12) are prepared according to the procedure of Ex-4-3 from Ex-3-44 to Ex-3-46 and the known or synthesized boronic acid derivatives. Example 4-13 is prepared according to the procedure of Ex-4-5 from Ex-3-47 and dicyanozinc. The further purification is carried out by preparative LC-MS or SFC-MS system in usual manner. The retention time and observed MS by HPLC-QC method are summarized in Table 38.

TABLE 38

| Ex. | $Ar^2$ | R | $R^5$ | $R^6$ | Retention time (min.) | Observed MS |
|---|---|---|---|---|---|---|
| 4-1 | 3-methylphenyl | H | OH | H | 1.51 | 414.3 |
| 4-2 | 3-cyclopropylphenyl | H | OH | H | 1.60 | 440.3 |
| 4-3 | 3-(6-methylpyridin-3-yl)-phenyl | H | OH | H | 1.45 | 491.3 |
| 4-4 | 3-(oxazol-5-yl)phenyl | H | OH | H | 1.36 | 467.2 |
| 4-5 | 3-cyanophenyl | H | OH | H | 1.40 | 425.2 |
| 4-6 | 3-(pyrimidin-5-yl)phenyl | H | OH | H | 1.30 | 478.3 |
| 4-7 | 3-(2-methoxypyrimidin-5-yl)phenyl | H | OH | H | 1.42 | 508.3 |
| 4-8 | 3-(1,3-dimethyl-1H-pyrazol-4-yl)phenyl | H | OH | H | 1.39 | 494.3 |
| 4-9 | (3-(pyridin-3-yl)phenyl | H | (R)—OH | H | 1.41 | 477.3 |
| 4-10 | 3-(oxazol-5-yl)phenyl | H | (R)—OH | H | 1.38 | 467.2 |
| 4-11 | (3-(pyridin-3-yl)phenyl | 3-F | (R)—OH | H | 1.43 | 495.2 |
| 4-12 | 3-(oxazol-5-yl)phenyl | 3-F | (R)—OH | H | 1.40 | 485.2 |
| 4-13 | 3-cyano-2-fluorophenyl | H | (chiral)-OH | H | 1.45 | 443.3 |

Example 4-14 and Example 4-15

Chiral 6-(2-(3,5-difluorophenyl)-2-hydroxyacetyl)-2-(1-phenylcyclopropyl)-5,6,7,8-tetrahydropyrido[4,3-d]pyrimidin-4(3H-one (Ex-4-14 and Ex-4-15)

{Chem. 91}

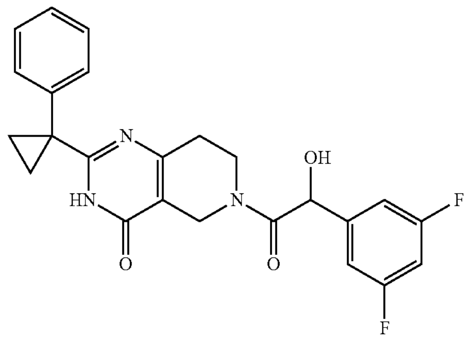

The racemic 6-(2-(3,5-difluorophenyl)-2-hydroxyacetyl)-2-(1-phenylcyclopropyl)-5,6,7,8-tetrahydropyrido[4,3-d]pyrimidin-4(3H)-one is separated by HPLC system (column: AD-H; Eluent: Hex/EtOH=65/35; Temp. 40° C.; Flow rate: 20 ml/min.) to give the both enantiomers of racemic 6-(2-(3,5-difluorophenyl)-2-hydroxyacetyl)-2-(1-phenylcyclopropyl)-5,6,7,8-tetrahydropyrido[4,3-d]pyrimidin-4(3H)-one.

Former Fraction (Ex-4-14)

LCMS (Method-HPLC-QC) m/z: M−1 obs 436.2, tR=1.52 min.

Chiral HPLC (AD-H, n-Hex/EtOH/DEA=55/45/0.1) 7.83 min, >99% e.e.

Later Fraction (Ex-4-15)

LCMS (Method-HPLC-QC) m/z: M−1 obs 436.2, tR=1.52 min.

Chiral HPLC (AD-H, n-Hex/EtOH/DEA=55/45/0.1) 16.88 min, >99% e.e.

Example-5-1

(R)-(−)-6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one (Ex-5-1)

{Chem. 92}

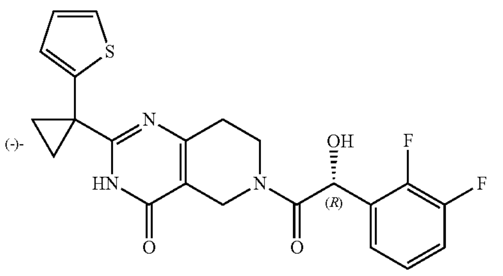

The titled compound is prepared according to the procedure described in Example-2-33 from (R)-(−)-2,3-difluoromandelic acid (INT-38-1)(24.3 mg, 0.129 mmol) and intermediate (INT-4-6)(31 mg, 0.112 mmol). The purification is carried out by column chromatography on silica gel (prepacked column: 14 g) eluting with DCM-MeOH (50:1 v/v) to give the titled compound (26 mg, 52% yield) as a white solid.

$[\alpha]^{24}_D$ −16.4° (c 0.324, MeOH)

$^1$H-NMR (270 MHz, DMSO-$d_6$, 80° C.): delta 11.90 (1H, brs), 7.35-6.95 (7H, m), 5.72 (1H, d, J=6.6 Hz), 5.67 (1H, d, J=6.6 Hz), 4.36-4.19 (2H, m), 3.79-3.62 (2H, m), 2.62-2.47 (2H, m), 1.58-1.54 (2H, m), 1.29-1.25 (2H, m).

LCMS (Method-E) m/z: M+1 obs 444.2, tR=2.43 min.

LCMS (Method-L)>99% e.e., tR=16.8 min.

Example-5-2

(+)-6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one (Ex-5-2)

{Chem. 93}

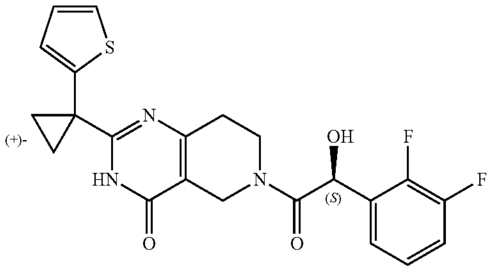

The titled compound is prepared according to the procedure described in Example-2-33 from (S)-(+)-2,3-difluoromandelic acid (INT-38-2) (25 mg, 0.135 mmol) and intermediate (INT-4-6) (31 mg, 0.112 mmol). The purification is carried out by column chromatography on silica gel (prepacked column: 14 g) eluting with DCM-MeOH (50:1 v/v) to give the titled compound (30 mg, 60% yield) as a white solid.

$[\alpha]^{25}_D$ +16.4° (c 0.311, MeOH)

$^1$H-NMR (270 MHz, DMSO-$d_6$, 80° C.): delta 11.92 (1H, br.s), 7.35-7.14 (4H, m), 7.02-7.00 (1H, m), 6.94-6.91 (1H, m), 5.77-5.68 (2H, m), 4.36-4.12 (2H, m), 3.81-3.65 (2H, m), 2.62-2.49 (2H, m), 1.58-1.53 (2H, m), 1.29-1.25 (2H, m).

LCMS (Method-E) m/z: M+1 obs 444.17, M−1 obs 442.09, tR=2.51 min.

LCMS (Method-L)>99% e.e., tR=10.5 min.

The following amide derivatives (Ex-6-1 to Ex-6-21) are prepared according to the procedure of Ex-1 from the 5,6,7,8-tetrahydropyrido[4,3-d]pyrimidin-4(3H)-one derivatives (INT-4-6 to INT-4-8, INT-4-12, INT-4-15 to INT-4-20, INT-10-1, INT-10-2) and the known or synthesized acid derivatives. The further purification is carried out by preparative LC-MS or SFC-MS system in usual manner. The retention time and observed MS by HPLC-QC method are summarized in Table 39.

{Chem. 94}

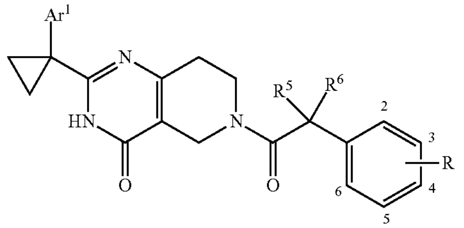

TABLE 39

| Ex. | Ar$^1$ | R$^5$ | R$^6$ | R | Retention time (min.) | Observed MS |
|---|---|---|---|---|---|---|
| 6-1 | 2-pyridinyl | (R)—OH | H | 3-Cl | 1.36 | 435.2 |
| 6-2 | 3-pyridinyl | OH | H | 2,3-F | 1.20 | 437.2 |
| 6-3 | 3-pyridinyl | (R)—OH | H | 3-Cl | 1.25 | 435.2 |
| 6-4 | thiophen-2-yl | OH | H | 2,3-F | 1.48 | 442.2 |
| 6-5 | thiophen-2-yl | (R)—OH | H | 2-Cl | 1.51 | 440.2 |
| 6-6 | thiophen-2-yl | OH | H | 3,5-F | 1.51 | 442.2 |
| 6-7 | thiophen-2-yl | (R)—OH | H | 3-Cl | 1.53 | 440.2 |
| 6-8 | benzyl | (R)—OH | H | 3-Cl | 1.57 | 448.3 |
| 6-9 | benzyl | OH | H | 2,3-F | 1.53 | 450.3 |
| 6-10 | thiophen-2-yl | (Chiral)-OH | H | 3-Me | 1.50 | 420.2 |
| 6-11 | 2-methylthiazol-4-yl | (R)—OH | H | 3-Cl | 1.45 | 455.2 |

TABLE 39-continued

| Ex. | $Ar^1$ | $R^5$ | $R^6$ | R | Retention time (min.) | Observed MS |
|---|---|---|---|---|---|---|
| 6-12 | thiazol-4-yl | (R)—OH | H | 2,3-F | 1.31 | 443.3 |
| 6-13 | thiazol-4-yl | (R)—OH | H | 3-Cl | 1.36 | 441.2 |
| 6-14 | thiazol-5-yl | (R)—OH | H | 2,3-F | 1.24 | 443.2 |
| 6-15 | thiazol-5-yl | (R)—OH | H | 3-Cl | 1.29 | 441.3 |
| 6-16 | 5-methylthiophen-2-yl | (R)—OH | H | 2,3-F | 1.62 | 456.3 |
| 6-17 | 5-methylthiophen-2-yl | (R)—OH | H | 3-Cl | 1.67 | 454.3 |
| 6-18 | 4-bromothiophen-2-yl | (R)—OH | H | 3-Cl | 1.67 | 518.1 |
| 6-19 | 4-methylthiazol-2-y | (R)—OH | H | 3-Cl | 1.55 | 455.2 |
| 6-20 | 4-methylthiophen-2-yl | (R)—OH | H | 3-Cl | 1.66 | 454.2 |
| 6-21 | 4-phenylthiophen-2-yl | (R)—OH | H | 3-Cl | 1.82 | 516.2 |

(Chiral)-OH of Ex-6-10 in Table 39 presents single enantiomer prepared from the optically active mandelic acids. The examples are prepared by the amidation of amine with optically active acid in Table 40.

TABLE 40

| Ex. | Amine | Acid |
|---|---|---|
| 6-10 | INT-4-6 | INT-44-1 |

Example-7-1

6-((R)-2-(3-chlorophenyl)-2-hydroxyacetyl)-2-((R/S)-1-phenylethyl)-5,6,7,8-tetrahydropyrido[4,3-d]pyrimidin-4(3H)-one (Ex-7-1)

{Chem. 95}

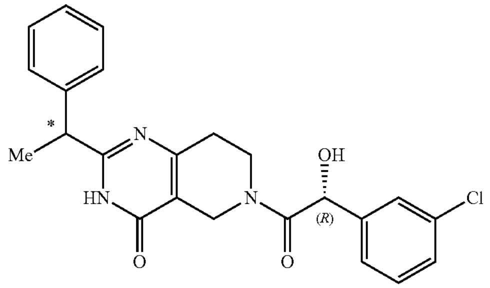

The titled compound is prepared according to the procedure described in Example-1 from (R)-(−)-3-chloromandelic acid (100 mg, 0.54 mmol) and intermediate (INT-4-9) (137 mg, 0.32 mmol). The purification is carried out by column chromatography on silica gel (pre-packed column: 45 g) eluting with DCM-MeOH (40:1-20:1 v/v) to give the titled compound (205 mg, 90% yield) as a slightly yellow solid.

$^1$H-NMR (270 MHz, DMSO-$d_6$, 70° C.): delta 12.14 (1H, br.s), 7.46-7.16 (9H, m), 5.83-5.75 (1H, m), 5.52-5.44 (1H, m), 4.36-4.15 (2H, m), 4.06-3.94 (1H, m), 3.78-3.62 (2H, m), 2.48 (2H, br.s), 1.51 (3H, d, J=7.3 Hz).

LCMS (Method-A) m/z: M+1 obs 424.09, M−1 obs 422.11, tR=2.84 min.

Example-8-1

(R)-6-(2-(3-chlorophenyl)-2-hydroxyacetyl)-2-(2-phenylpropan-2-yl)-5,6,7,8-tetrahydropyrido[4,3-d]pyrimidin-4(3H)-one (Ex-8-1)

{Chem. 96}

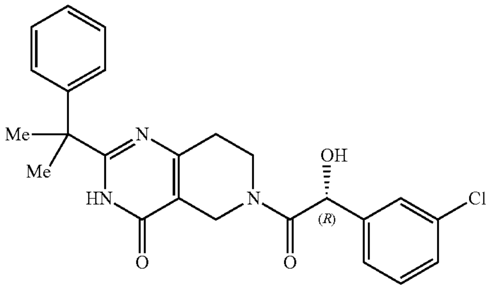

The titled compound is prepared according to the procedure described in Example-1 from (R)-(−)-3-chloromandelic acid (60.0 mg, 0.32 mmol) and intermediate (INT-4-10) (87 mg, 0.32 mmol). The purification is carried out by column chromatography on silica gel (pre-packed column: 30 g) eluting with DCM-methanol (40:1 v/v) to give the titled compound (127 mg, 90% yield) as a white solid.

$^1$H-NMR (270 MHz, DMSO-$d_6$, 75° C.): delta 11.63 (1H, br.s), 7.46-7.16 (9H, m), 5.83-5.74 (1H, m), 5.54-5.46 (1H, m), 4.38-4.18 (2H, m), 3.82-3.66 (2H, m), 2.47 (2H, br.s), 1.62 (6H, s).

LCMS (Method-A) m/z: M+1 obs 438.14, M−1 obs 436.18, tR=2.95 min.

The following amide derivatives (Ex-9-1 to Ex-9-7) are prepared according to the procedure of Ex-1 from the 5,6,7,8-tetrahydropyrido[4,3-d]pyrimidin-4(3H)-one derivatives (INT-4-10 and INT-4-11) and the known or synthesized acid derivatives. The further purification is carried out by preparative LC-MS or SFC-MS system in usual manner. The retention time and observed MS by HPLC-QC method are summarized in Table 41.

{Chem. 97}

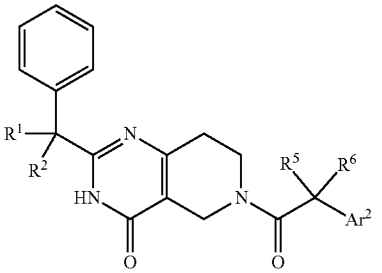

TABLE 41

| Ex. | $R^1$ and $R^2$ | $R^5$ | $R^6$ | $Ar^2$ | Retention time (min.) | Observed MS |
|---|---|---|---|---|---|---|
| 9-1 | $R^1 = R^2 = Me$ | OH | H | 2,3-difluorophenyl | 1.59 | 438.2 |
| 9-2 | $R^1 = R^2 = Me$ | OH | H | 3,5-difluorophenyl | 1.61 | 438.2 |
| 9-3 | $R^1 = R^2 = Me$ | (R)—OH | H | 2-chlorophenyl | 1.61 | 436.2 |
| 9-4 | cyclobutyl | OH | H | 2,3-difluorophenyl | 1.60 | 450.3 |
| 9-5 | cyclobutyl | (R)—OH | H | 2-chlorophenyl | 1.62 | 448.3 |
| 9-6 | cyclobutyl | OH | H | 3,5-difluorophenyl | 1.62 | 450.3 |
| 9-7 | cyclobutyl | (R)—OH | H | 3-chlorophenyl | 1.64 | 448.3 |

The following amide derivatives (Ex-10-1 to Ex-10-9) are prepared according to the procedure of Ex-1 from the pyrimidin-4(3H)-one derivatives (INT-4-13, INT-8-1 to INT-8-4) and the known or synthesized acid derivatives. The further purification is carried out by preparative LC-MS system in usual manner. The retention time and observed MS by HPLC-QC method are summarized in Table 42.

{Chem. 98}

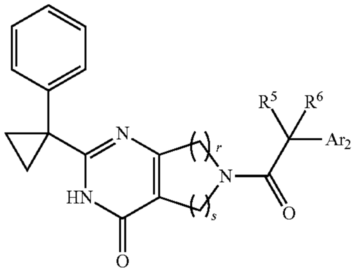

TABLE 42

| Ex. | r | S | $R^5$ | $R^6$ | $Ar^2$ | Retention time (min.) | Observed MS |
|---|---|---|---|---|---|---|---|
| 10-1 | 2 | 2 | OH | H | 2,3-difluorophenyl | 1.52 | 450.2 |
| 10-2 | 2 | 2 | (R)—OH | H | 3-chlorophenyl | 1.58 | 448.2 |
| 10-3 | 1 | 1 | (R)—OH | H | 2-chlorophenyl | 1.51 | 420.2 |
| 10-4 | 1 | 2 | (R)—OH | H | 3-chlorophenyl | 1.54 | 434.2 |
| 10-5 | 1 | 2 | OH | H | 2,3-difluorophenyl | 1.50 | 436.2 |
| 10-6 | 3 | 1 | (R)—OH | H | 2,3-difluorophenyl | 1.53 | 450.3 |
| 10-7 | 3 | 1 | (R)—OH | H | 3-chlorophenyl | 1.59 | 448.3 |
| 10-8 | 1 | 3 | (R)—OH | H | 2,3-difluorophenyl | 1.55 | 450.2 |
| 10-9 | 1 | 3 | (R)—OH | H | 3-chlorophenyl | 1.60 | 448.2 |

Example-11-1

6-(2-hydroxy-2-(2-(pyrrolidin-1-yl)pyridin-4-yl)acetyl)-2-(1-phenylcyclopropyl)-5,6,7,8-tetrahydropyrido[4,3-d]pyrimidin-4(3H)-one (Ex-11-1)

{Chem. 99}

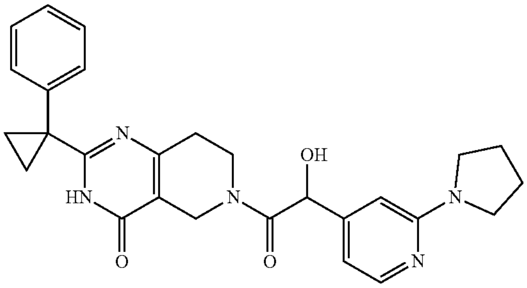

To a stirred solution of intermediate (INT-11-22) (30.0 mg, 0.096 mmol) in 1,4-dioxane (2 mL) is added pyrrolidine (147 mg, 2.06 mmol). The resulting solution is irradiated with microwave at 150° C. for 2 hrs using microwave oven.

After concentration in vacuo, the residue is purified by column chromatography on silica gel (14 g) elutin with DCM-MeOH (50:1 v/v) to give the titled product. The further purification is carried out by preparative LC-MS system in usual manner.

LCMS (Method-HPLC-QC) m/z: M+1 obs 472.1 M−1 obs 470.2, tR=1.41 min.

{Chem. 100}

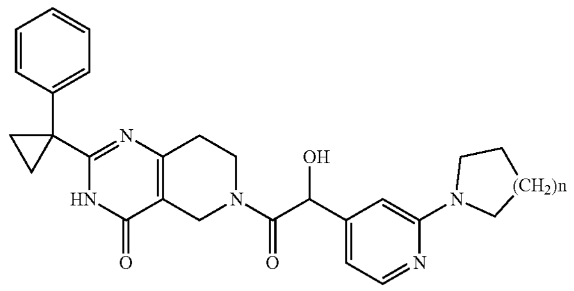

The following amide derivatives (Ex-11-2 and 11-3) are prepared according to the procedure of Ex-11-1 from INT-11-22 and piperidine or azepane.

TABLE 43

| Ex. | n | Retention time (min.) | Observed MS |
|---|---|---|---|
| 11-2 | 2 | 486.2 | 1.56 min |
| 11-3 | 3 | 500.2 | 1.62 min |

Example-12-1

4-oxo-2-(1-phenylcyclopropyl)-N-(3-(trifluoromethyl)phenyl)-3,4,7,8-tetrahydropyrido[4,3-d]pyrimidine-6(5H)-carboxamide (Ex-12-1)

{Chem. 101}

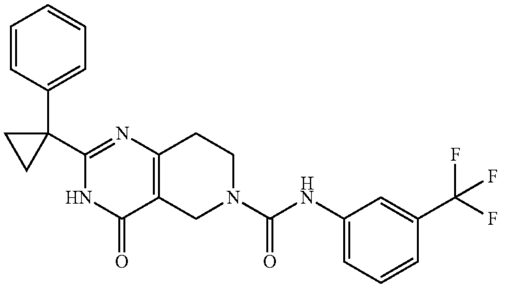

To a solution of intermediate-1 (INT-1)(27 mg, 0.1 mmol) in THF (1 mL) is added 3-(trifluoromethyl)phenyl isocyanate (21 mg, 0.11 mmol) and $Et_3N$ (20 mg, 0.200 mmol). The mixture is stirred at room temperature overnight. The reaction mixture is concentrated in vacuo. The residue is loaded onto an SCX cartridge (Varian BondElute, 1 g/6 mL) conditioned with 1 mL of MeOH, rinsed with 5 mL of MeOH and eluted with 5 mL of 1N $NH_3$/MeOH. Volatiles are removed by nitrogen flow to give a titled compound (28 mg, 62% yield) as a solid. The further purification is carried out by preparative LC-MS or SFC-MS system in usual manner.

LC-MS (Method-HPLC-QC) m/z: M+1 obs 455.0 M−1 obs 453.2, tR=1.70 min.

The following amide derivatives (Ex-13-1 to Ex-13-4) are prepared according to the procedure of Ex-1 from the known or synthesized 5,6,7,8-tetrahydropyrido[4,3-d]pyrimidin-4(3H)-one derivatives (INT-1 and INT-4-10) and the known acid derivatives. The further purification is carried out by preparative LC-MS or SFC-MS system in usual manner. The retention time and observed MS by HPLC-QC method are summarized in Table 44.

{Chem. 102}

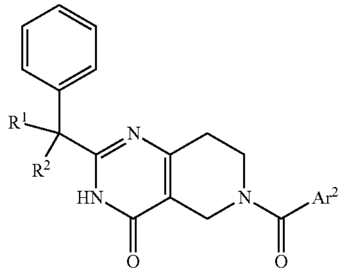

TABLE 44

| Ex. | $R^1$ and $R^2$ | $Ar^2$ | Retention time (min.) | Observed MS |
|---|---|---|---|---|
| 13-1 | cyclopropane | 1H-benzo[d]imidazole-2-yl | 1.52 | 410.2 |
| 13-2 | cyclopropane | 5,6-difluoro-1H-benzo[d]imidazole-2-yl | 1.61 | 446.2 |
| 13-3 | $R^1 = R^2 = Me$ | 5,6-difluoro-1H-benzo[d]imidazole-2-yl | 1.69 | 448.3 |
| 13-4 | $R^1 = R^2 = H$ | 5,6-difluoro-1H-benzo[d]imidazole-2-yl | 1.46 | 420.2 |

The following amide derivatives (Ex-14-1 to Ex-14-122) are prepared according to the procedure of Ex-1 or the general synthesis in scheme-1 from the synthesized amine drivatives and the known or synthesized acid derivatives in Tables 45-1 to 45-18. The further purification is carried out by preparative LC-MS or SFC-MS system in usual manner. The retention time and observed MS by HPLC-QC method are summarized in Tables 45-1 to 45-18.

TABLE 45-1

| Ex. | Acid (INT or Reagent) | Amine (INT) | Structure | Retention time | Observed MS |
|---|---|---|---|---|---|
| 14-1 | 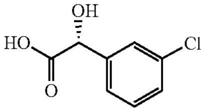 [SMILES: O=C(O)[C@H](O)c1cccc(Cl)c1] | INT-8-6 | 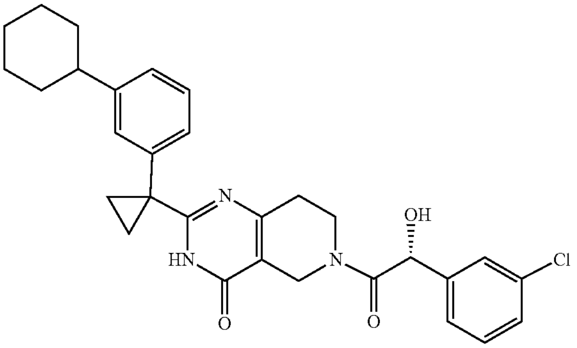 [SMILES: O=C([C@H](O)c1cccc(Cl)c1)N1CCc2nc(C3(c4cccc(C5CCCCC5)c4)CC3)[nH]c(=O)c2C1] | 2.11 min | 518.2 |
| 14-2 | 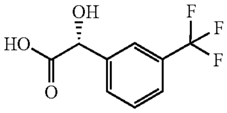 [SMILES: O=C(O)[C@H](O)c1cccc(C(F)(F)F)c1] | INT-4-31 | 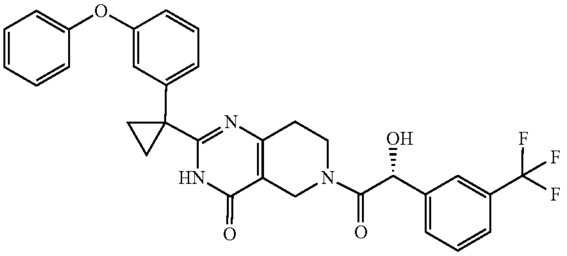 [SMILES: O=C([C@H](O)c1cccc(C(F)(F)F)c1)N1CCc2nc(C3(c4cccc(Oc5ccccc5)c4)CC3)[nH]c(=O)c2C1] | 1.89 min | 562.3 |
| 14-3 | INT-25-4 | INT-4-14 | 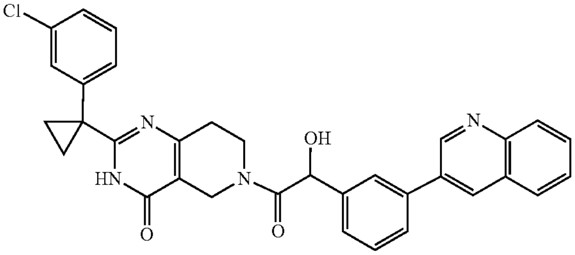 [SMILES: O=C(C(O)c1cccc(-c2cnc3ccccc3c2)c1)N1CCc2nc(C3(c4cccc(Cl)c4)CC3)[nH]c(=O)c2C1] | 1.71 min | 563.0 |
| 14-4 | 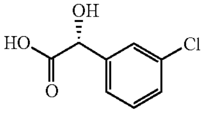 [SMILES: O=C(O)[C@H](O)c1cccc(Cl)c1] | INT-4-31 | 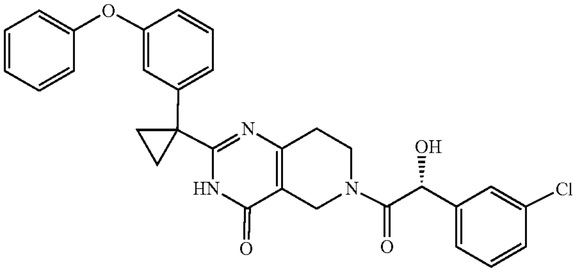 [SMILES: O=C([C@H](O)c1cccc(Cl)c1)N1CCc2nc(C3(c4cccc(Oc5ccccc5)c4)CC3)[nH]c(=O)c2C1] | 1.86 min | 528.1 |
| 14-5 | INT-25-3 | INT-4-14 | 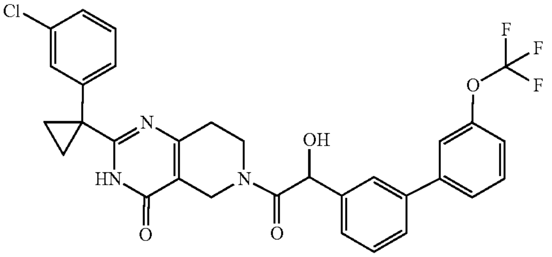 [SMILES: O=C(C(O)c1cccc(-c2cccc(OC(F)(F)F)c2)c1)N1CCc2nc(C3(c4cccc(Cl)c4)CC3)[nH]c(=O)c2C1] | 2.00 min | 596.2 |

TABLE 45-1-continued
| Ex. | Acid (INT or Reagent) | Amine (INT) | Structure | Retention time | Observed MS |
|---|---|---|---|---|---|
| 14-6 | INT-25-2 | INT-4-2 | 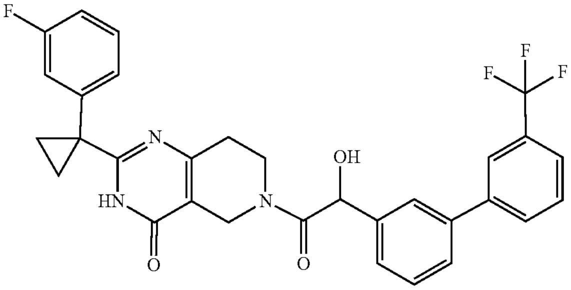 [SMILES: O=C(C(O)c1cccc(-c2cccc(C(F)(F)F)c2)c1)N1CCc2nc(C3(c4cccc(F)c4)CC3)[nH]c(=O)c2C1] | 1.88 min | 564.2 |
| 14-7 | INT-25-3 | INT-4-2 | 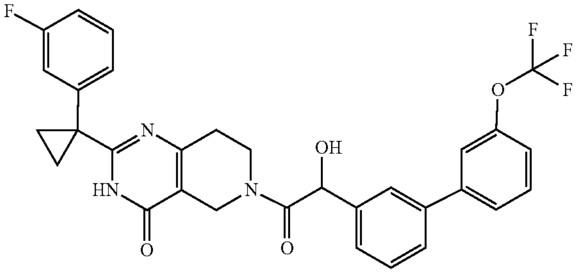 [SMILES: O=C(C(O)c1cccc(-c2cccc(OC(F)(F)F)c2)c1)N1CCc2nc(C3(c4cccc(F)c4)CC3)[nH]c(=O)c2C1] | 1.91 min | 580.2 |
TABLE 45-2
| | | | | | |
|---|---|---|---|---|---|
| 14-8 | INT-25-2 | INT-4-14 | 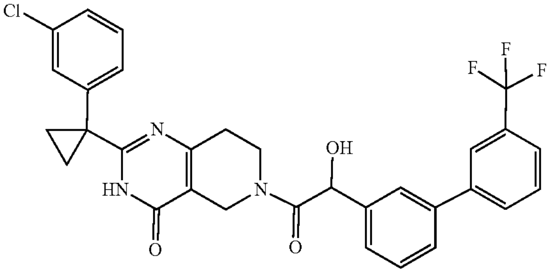 [SMILES: O=C(C(O)c1cccc(-c2cccc(C(F)(F)F)c2)c1)N1CCc2nc(C3(c4cccc(Cl)c4)CC3)[nH]c(=O)c2C1] | 1.96 min | 580.2 |
| 14-9 | INT-25-5 | INT-4-14 | 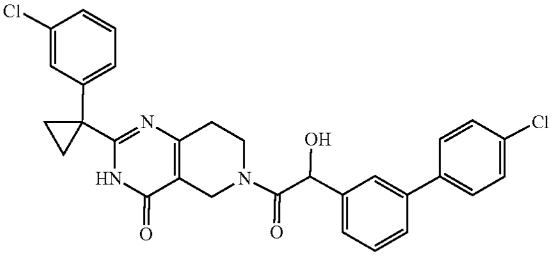 [SMILES: O=C(C(O)c1cccc(-c2ccc(Cl)cc2)c1)N1CCc2nc(C3(c4cccc(Cl)c4)CC3)[nH]c(=O)c2C1] | 1.95 min | 546.0 |

TABLE 45-2-continued
| | | | | |
|---|---|---|---|---|
| 14-10 | 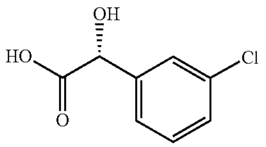 | INT-10-5 | 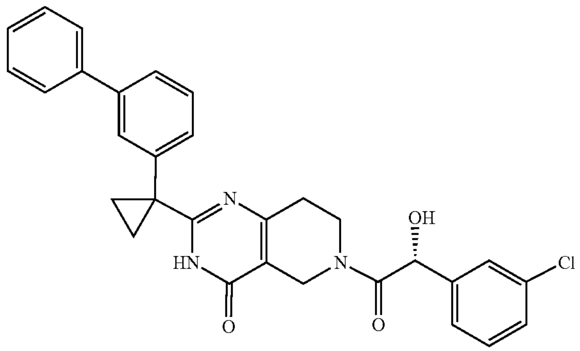 [SMILES: O=C([C@H](O)c1cccc(Cl)c1)N1CCc2nc(C3(c4cccc(-c5ccccc5)c4)CC3)[nH]c(=O)c2C1] | 1.87 min 512.2 |
| 14-11 | 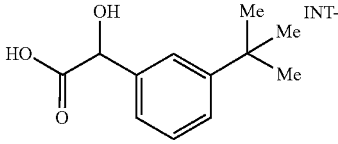 | INT-4-14 | 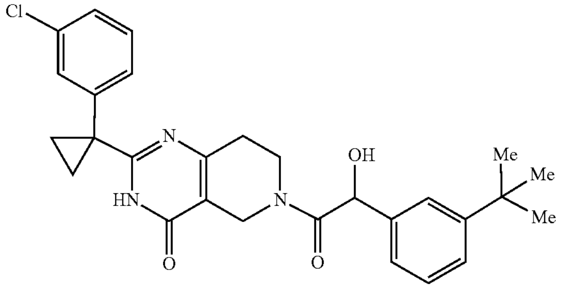 [SMILES: CC(C)(C)c1cccc(C(O)C(=O)N2CCc3nc(C4(c5cccc(Cl)c5)CC4)[nH]c(=O)c3C2)c1] | 1.86 min 492.2 |
| 14-12 | INT-25-1 | INT-4-14 | 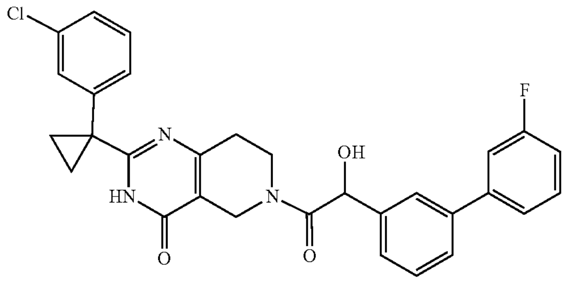 [SMILES: O=C(C(O)c1cccc(-c2cccc(F)c2)c1)N1CCc2nc(C3(c4cccc(Cl)c4)CC3)[nH]c(=O)c2C1] | 1.84 min 530.1 |
| 14-13 | 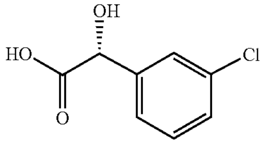 [SMILES: O=C(O)[C@H](O)c1cccc(Cl)c1] | INT-8-5 | 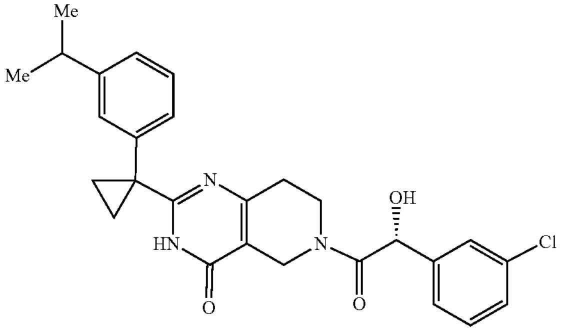 [SMILES: CC(C)c1cccc(C2(c3nc4c(c(=O)[nH]3)CN(C(=O)[C@H](O)c3cccc(Cl)c3)CC4)CC2)c1] | 1.86 min 478.2 |
| 14-14 | INT-24-2 | INT-1 | 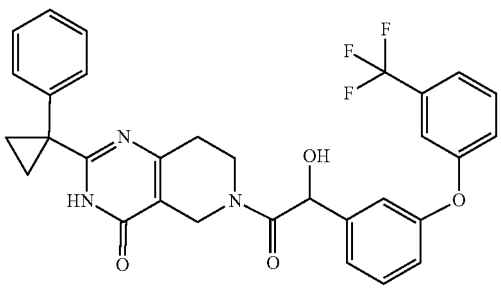 [SMILES: O=C(C(O)c1cccc(Oc2cccc(C(F)(F)F)c2)c1)N1CCc2nc(C3(c4ccccc4)CC3)[nH]c(=O)c2C1] | 1.89 min 562.0 |

TABLE 45-3
| | | | | |
|---|---|---|---|---|
| 14-15 | 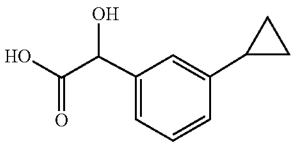 [SMILES: O=C(O)C(O)c1cccc(C2CC2)c1] | INT-4-14 | 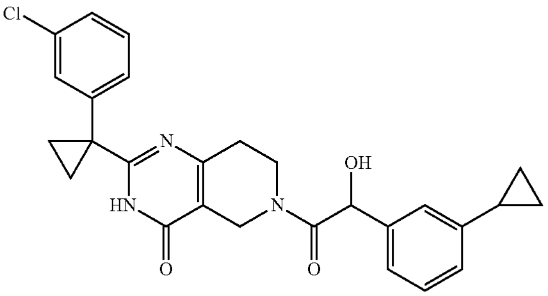 [SMILES: O=C(C(O)c1cccc(C2CC2)c1)N1CCc2nc(C3(c4cccc(Cl)c4)CC3)[nH]c(=O)c2C1] | 1.73 min 476.1 |
| 14-16 | 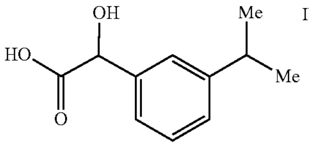 | INT-4-14 | 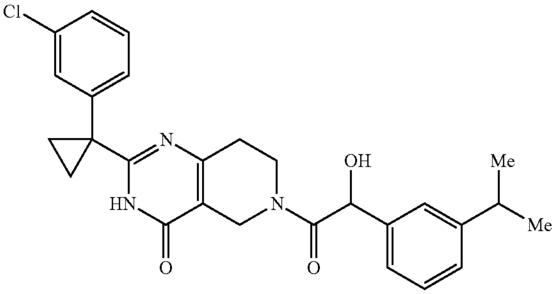 [SMILES: CC(C)c1cccc(C(O)C(=O)N2CCc3nc(C4(c5cccc(Cl)c5)CC4)[nH]c(=O)c3C2)c1] | 1.80 min 478.1 |
| 14-17 | 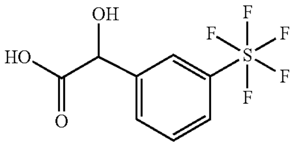 [SMILES: O=C(O)C(O)c1cccc(S(F)(F)(F)(F)F)c1] | INT-4-14 | 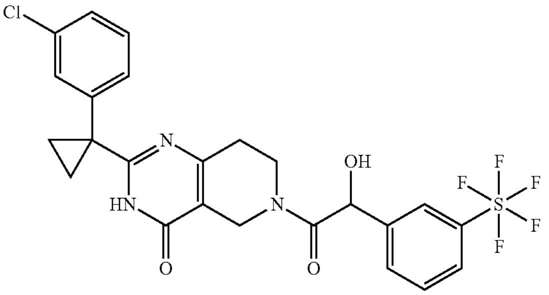 [SMILES: O=C(C(O)c1cccc(S(F)(F)(F)(F)F)c1)N1CCc2nc(C3(c4cccc(Cl)c4)CC3)[nH]c(=O)c2C1] | 1.78 min 562.1 |
| 14-18 | 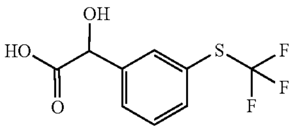 [SMILES: O=C(O)C(O)c1cccc(SC(F)(F)F)c1] | INT-4-14 | 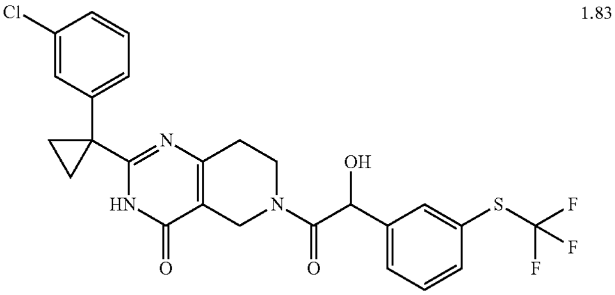 | 1.83 min 536.1 |
| 14-19 | INT-25-1 | INT-4-2 | 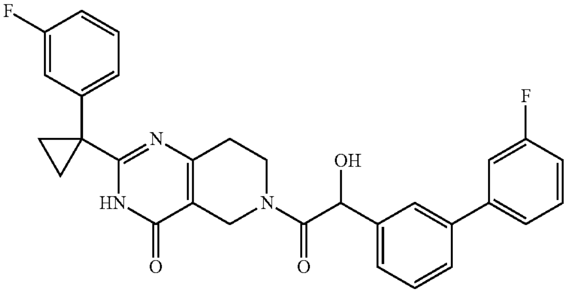 [SMILES: O=C(C(O)c1cccc(-c2cccc(F)c2)c1)N1CCc2nc(C3(c4cccc(F)c4)CC3)[nH]c(=O)c2C1] | 1.75 min 514.1 |

TABLE 45-3-continued
| | | | | |
|---|---|---|---|---|
| 14-20 | 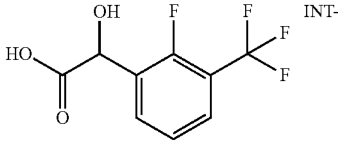 | INT-4-14 | 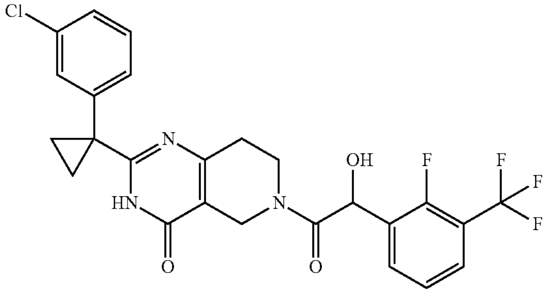 [SMILES: O=C(C(O)c1cccc(C(F)(F)F)c1F)N1CCc2nc(C3(c4cccc(Cl)c4)CC3)[nH]c(=O)c2C1] | 1.75 min 522.1 |
| 14-21 | 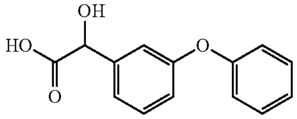 [SMILES: O=C(O)C(O)c1cccc(Oc2ccccc2)c1] | INT-4-14 | 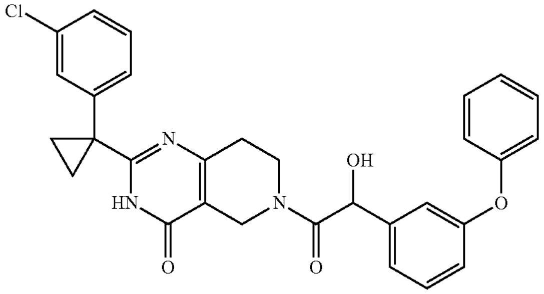 [SMILES: O=C(C(O)c1cccc(Oc2ccccc2)c1)N1CCc2nc(C3(c4cccc(Cl)c4)CC3)[nH]c(=O)c2C1] | 1.84 min 528.1 |
TABLE 45-4
| | | | | |
|---|---|---|---|---|
| 14-22 | 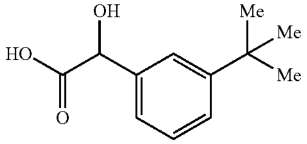 [SMILES: CC(C)(C)c1cccc(C(O)C(=O)O)c1] | INT-4-2 | 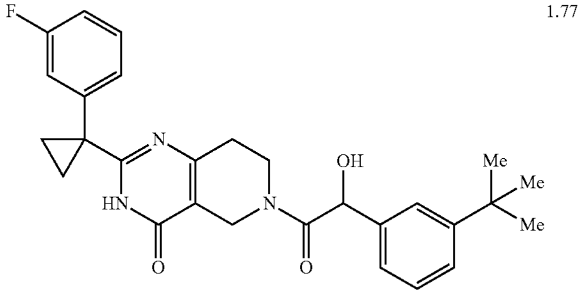 | 1.77 min 476.2 |
| 14-23 | 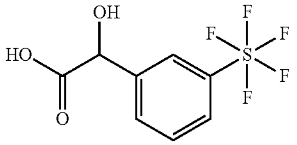 [SMILES: O=C(O)C(O)c1cccc(S(F)(F)(F)(F)F)c1] | INT-4-2 | 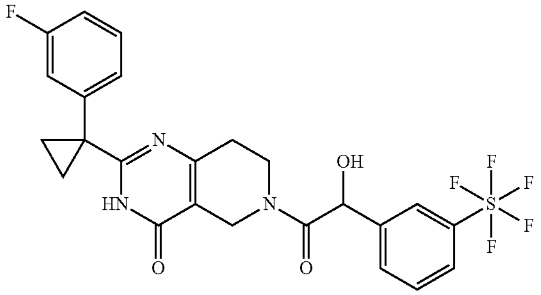 [SMILES: O=C(C(O)c1cccc(S(F)(F)(F)(F)F)c1)N1CCc2nc(C3(c4cccc(F)c4)CC3)[nH]c(=O)c2C1] | 1.69 min 546.1 |
| 14-24 | INT-25-5 | INT-4-2 | 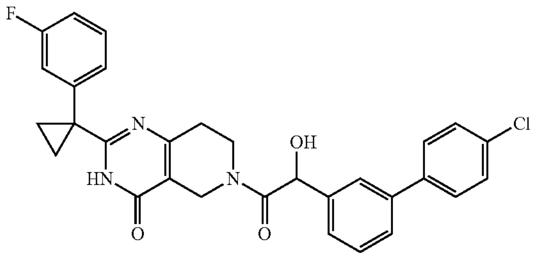 [SMILES: O=C(C(O)c1cccc(-c2ccc(Cl)cc2)c1)N1CCc2nc(C3(c4cccc(F)c4)CC3)[nH]c(=O)c2C1] | 1.86 min 530.0 |

TABLE 45-4-continued
| | | | | |
|---|---|---|---|---|
| 14-25 | 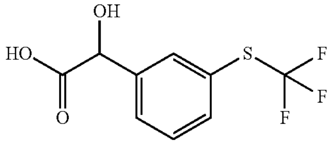 [SMILES: O=C(O)C(O)c1cccc(SC(F)(F)F)c1] | INT-1 | 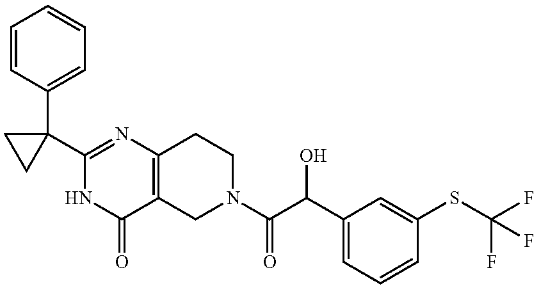 [SMILES: O=C(C(O)c1cccc(SC(F)(F)F)c1)N1CCc2nc(C3(c4ccccc4)CC3)[nH]c(=O)c2C1] | 1.73 min 502.1 |
| 14-26 | 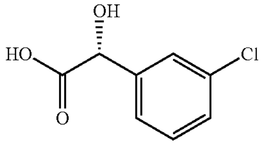 | INT-4-32 | 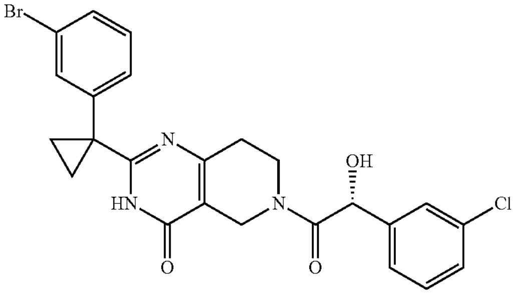 [SMILES: O=C([C@H](O)c1cccc(Cl)c1)N1CCc2nc(C3(c4cccc(Br)c4)CC3)[nH]c(=O)c2C1] | 1.70 min 514.0 |
| 14-27 | 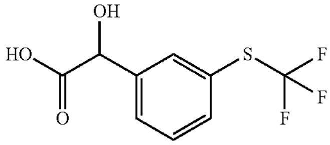 [SMILES: O=C(O)C(O)c1cccc(SC(F)(F)F)c1] | INT-4-2 | 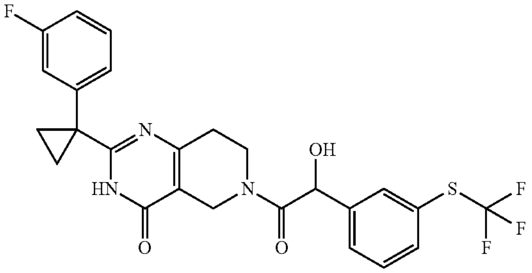 [SMILES: O=C(C(O)c1cccc(SC(F)(F)F)c1)N1CCc2nc(C3(c4cccc(F)c4)CC3)[nH]c(=O)c2C1] | 1.73 min 520.1 |
| 14-28 | 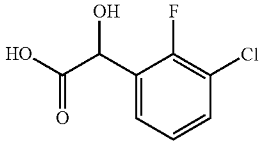 | INT-4-14 | 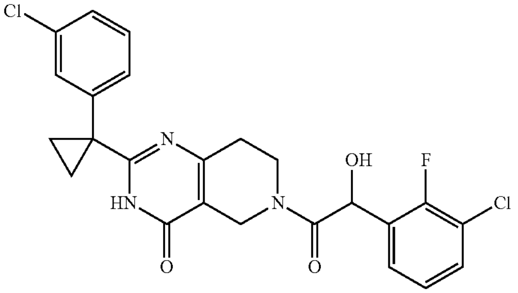 [SMILES: O=C(C(O)c1cccc(Cl)c1F)N1CCc2nc(C3(c4cccc(Cl)c4)CC3)[nH]c(=O)c2C1] | 1.70 min 488.1 |
TABLE 45-5
| | | | | |
|---|---|---|---|---|
| 14-29 | 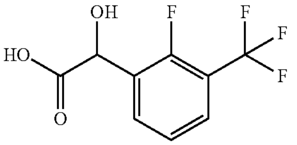 [SMILES: O=C(O)C(O)c1cccc(C(F)(F)F)c1F] | INT-4-2 | 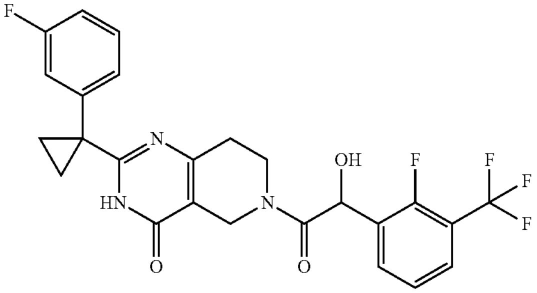 [SMILES: O=C(C(O)c1cccc(C(F)(F)F)c1F)N1CCc2nc(C3(c4cccc(F)c4)CC3)[nH]c(=O)c2C1] | 1.66 min 506.1 |

TABLE 45-5-continued
| | | | | |
|---|---|---|---|---|
| 14-30 | 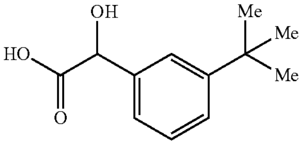 [SMILES: CC(C)(C)c1cccc(C(O)C(=O)O)c1] | INT-1 | 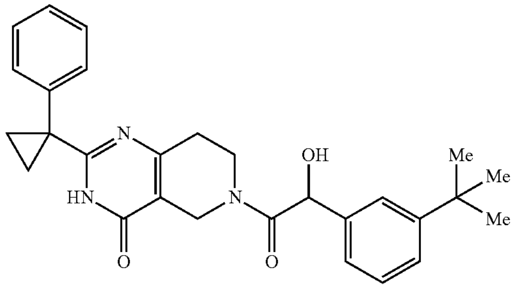 [SMILES: CC(C)(C)c1cccc(C(O)C(=O)N2CCc3nc(C4(c5ccccc5)CC4)[nH]c(=O)c3C2)c1] | 1.76 min 458.3 |
| 14-31 | 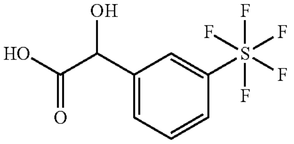 [SMILES: O=C(O)C(O)c1cccc(S(F)(F)(F)(F)F)c1] | INT-1 | 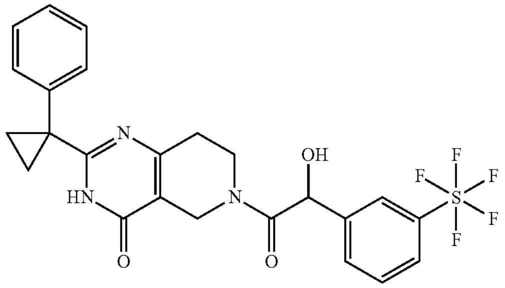 [SMILES: O=C(C(O)c1cccc(S(F)(F)(F)(F)F)c1)N1CCc2nc(C3(c4ccccc4)CC3)[nH]c(=O)c2C1] | 1.69 min 528.1 |
| 14-32 | 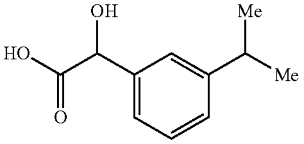 [SMILES: CC(C)c1cccc(C(O)C(=O)O)c1] | INT-4-2 | 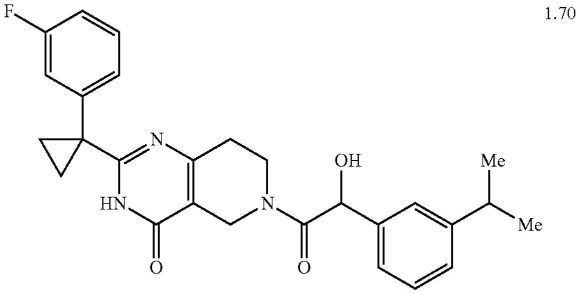 | 1.70 min 462.2 |
| 14-33 | 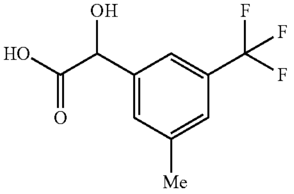 [SMILES: Cc1cc(C(O)C(=O)O)cc(C(F)(F)F)c1] | INT-1 | 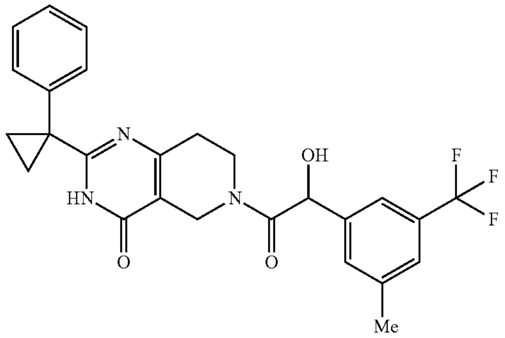 [SMILES: Cc1cc(C(O)C(=O)N2CCc3nc(C4(c5ccccc5)CC4)[nH]c(=O)c3C2)cc(C(F)(F)F)c1] | 1.70 min 484.2 |
| 14-34 | 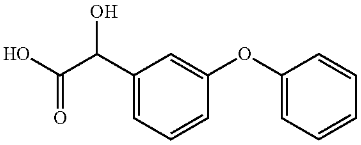 [SMILES: O=C(O)C(O)c1cccc(Oc2ccccc2)c1] | INT-1 | 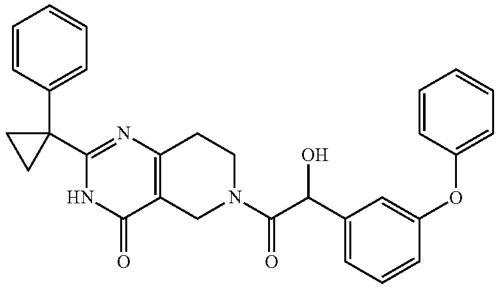 [SMILES: O=C(C(O)c1cccc(Oc2ccccc2)c1)N1CCc2nc(C3(c4ccccc4)CC3)[nH]c(=O)c2C1] | 1.74 min 494.1 |

TABLE 45-5-continued
| | | | | |
|---|---|---|---|---|
| 14-35 | 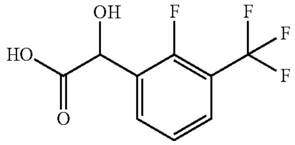 [SMILES: O=C(O)C(O)c1cccc(C(F)(F)F)c1F] | INT-1 | 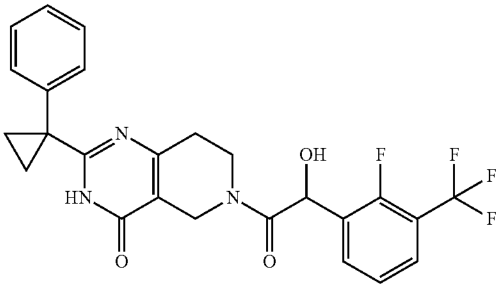 [SMILES: O=C(C(O)c1cccc(C(F)(F)F)c1F)N1CCc2nc(C3(c4ccccc4)CC3)[nH]c(=O)c2C1] | 1.65 min 488.1 |
TABLE 45-6
| | | | | |
|---|---|---|---|---|
| 14-36 | 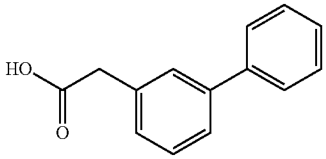 [SMILES: O=C(O)Cc1cccc(-c2ccccc2)c1] | INT-1 | 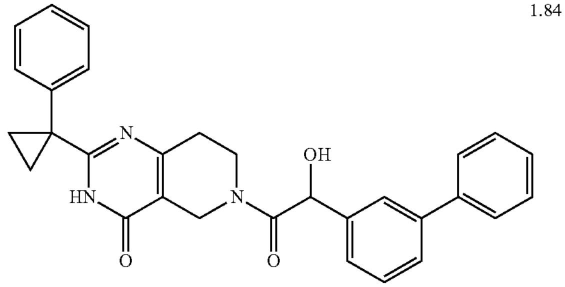 | 1.84 min 462.2 |
| 14-37 | 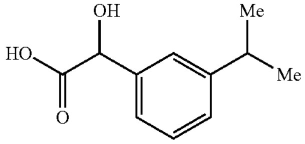 [SMILES: CC(C)c1cccc(C(O)C(=O)O)c1] | INT-1 | 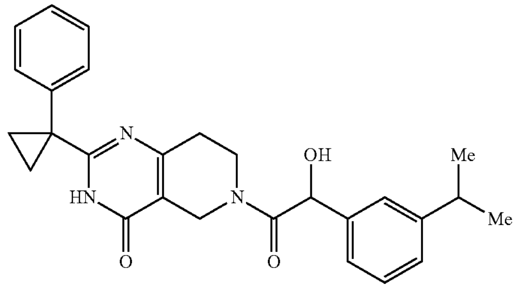 [SMILES: CC(C)c1cccc(C(O)C(=O)N2CCc3nc(C4(c5ccccc5)CC4)[nH]c(=O)c3C2)c1] | 1.70 min 444.2 |
| 14-38 | 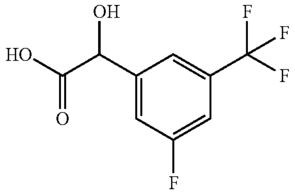 [SMILES: O=C(O)C(O)c1cc(F)cc(C(F)(F)F)c1] | INT-1 | 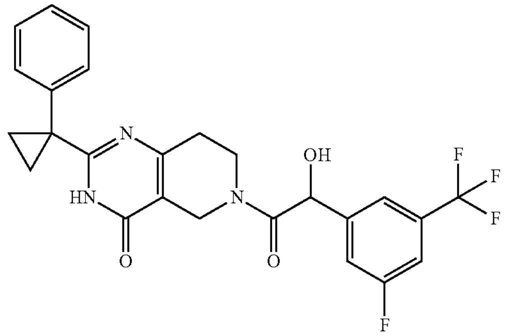 [SMILES: O=C(C(O)c1cc(F)cc(C(F)(F)F)c1)N1CCc2nc(C3(c4ccccc4)CC3)[nH]c(=O)c2C1] | 1.67 min 488.2 |
| 14-39 | 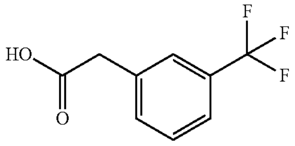 [SMILES: O=C(O)Cc1cccc(C(F)(F)F)c1] | INT-1 | 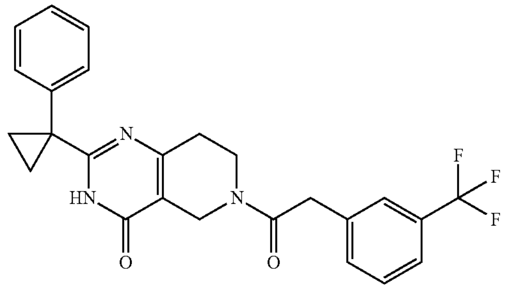 [SMILES: O=C(Cc1cccc(C(F)(F)F)c1)N1CCc2nc(C3(c4ccccc4)CC3)[nH]c(=O)c2C1] | 1.73 min 454.1 |

TABLE 45-6-continued
| | | | | |
|---|---|---|---|---|
| 14-40 | 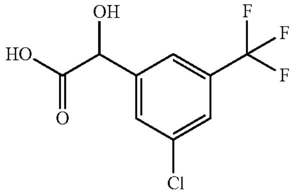 [SMILES: O=C(O)C(O)c1cc(Cl)cc(C(F)(F)F)c1] | INT-1 | 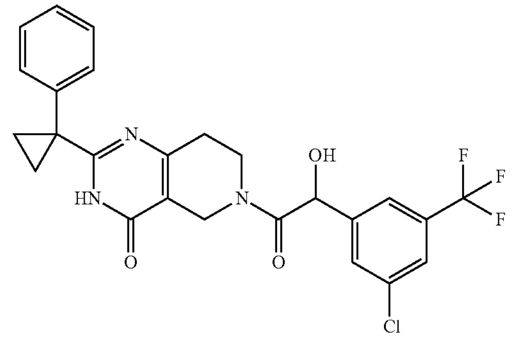 [SMILES: O=C(C(O)c1cc(Cl)cc(C(F)(F)F)c1)N1CCc2nc(C3(c4ccccc4)CC3)[nH]c(=O)c2C1] | 1.76 min 504.1 |
| 14-41 | 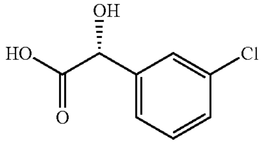 | INT-4-25 | 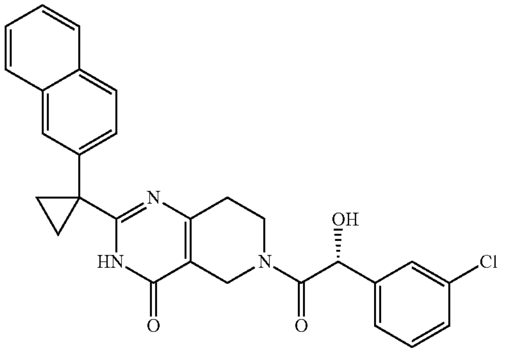 [SMILES: O=C([C@H](O)c1cccc(Cl)c1)N1CCc2nc(C3(c4ccc5ccccc5c4)CC3)[nH]c(=O)c2C1] | 1.78 min 486.1 |
TABLE 45-7
| | | | | |
|---|---|---|---|---|
| 14-42 | 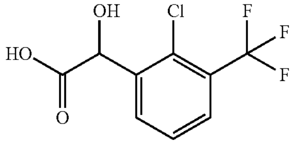 | INT-1 | 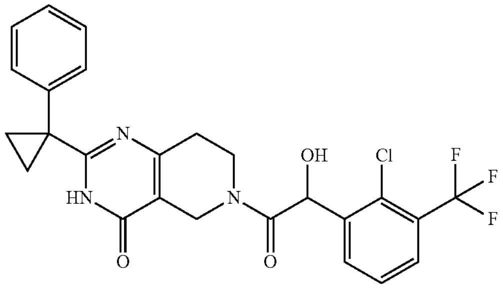 [SMILES: O=C(C(O)c1cccc(C(F)(F)F)c1Cl)N1CCc2nc(C3(c4ccccc4)CC3)[nH]c(=O)c2C1] | 1.69 min 504.1 |
| 14-43 | 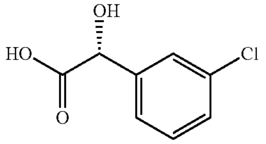 | INT-4-26 | 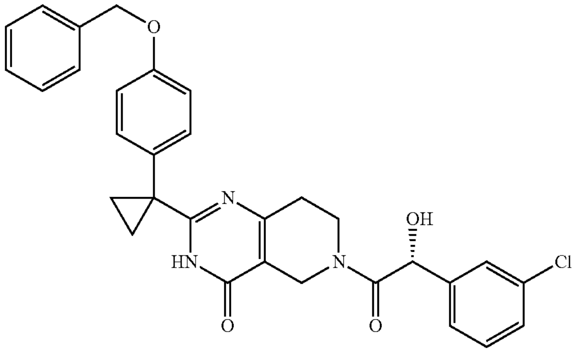 [SMILES: O=C([C@H](O)c1cccc(Cl)c1)N1CCc2nc(C3(c4ccc(OCc5ccccc5)cc4)CC3)[nH]c(=O)c2C1] | 1.88 min 542.1 |

TABLE 45-7-continued
| | | | | |
|---|---|---|---|---|
| 14-44 | 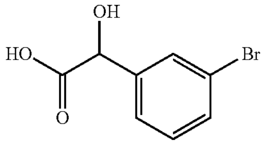 [SMILES: O=C(O)C(O)c1cccc(Br)c1] | INT-1 | 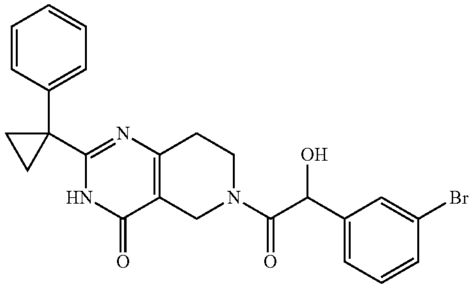 [SMILES: O=C(C(O)c1cccc(Br)c1)N1CCc2nc(C3(c4ccccc4)CC3)[nH]c(=O)c2C1] | 1.58 min 480.1 |
| 14-45 | 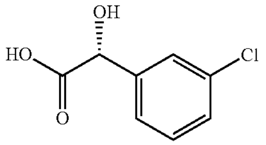 | INT-10-4 | 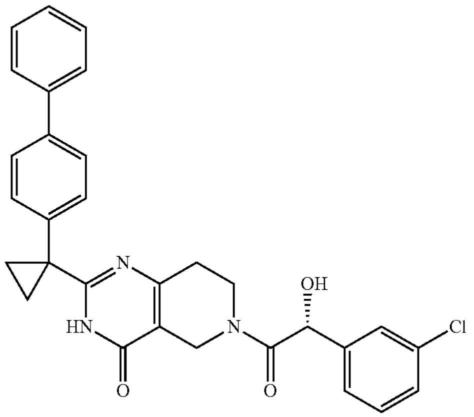 [SMILES: O=C([C@H](O)c1cccc(Cl)c1)N1CCc2nc(C3(c4ccc(-c5ccccc5)cc4)CC3)[nH]c(=O)c2C1] | 1.87 min 512.2 |
| 14-46 | 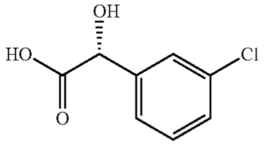 | INT-4-5 | 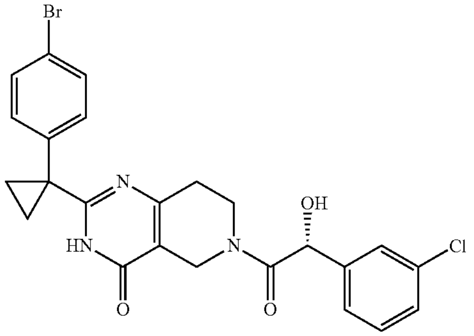 [SMILES: O=C([C@H](O)c1cccc(Cl)c1)N1CCc2nc(C3(c4ccc(Br)cc4)CC3)[nH]c(=O)c2C1] | 1.71 min 514.1 |
| 14-47 | 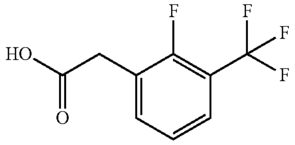 [SMILES: O=C(O)Cc1cccc(C(F)(F)F)c1F] | INT-1 | 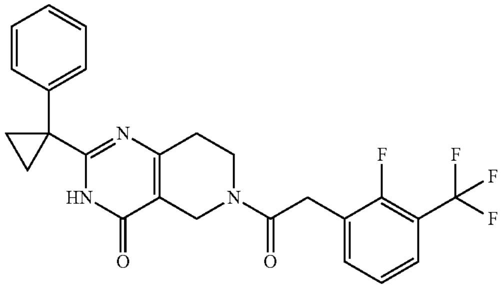 [SMILES: O=C(Cc1cccc(C(F)(F)F)c1F)N1CCc2nc(C3(c4ccccc4)CC3)[nH]c(=O)c2C1] | 1.75 min 472.1 |

TABLE 45-8
| | | | | |
|---|---|---|---|---|
| 14-48 | 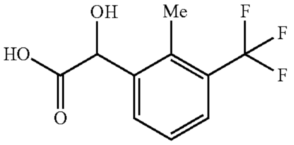 | INT-1 | 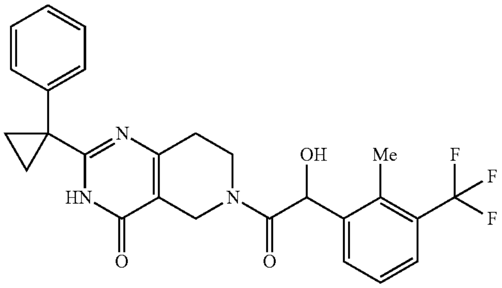 [SMILES: Cc1c(C(O)C(=O)N2CCc3nc(C4(c5ccccc5)CC4)[nH]c(=O)c3C2)cccc1C(F)(F)F] | 1.70 min 484.2 |
| 14-49 | 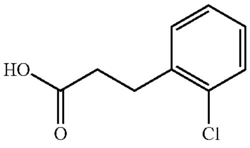 [SMILES: O=C(O)CCc1ccccc1Cl] | INT-1 | 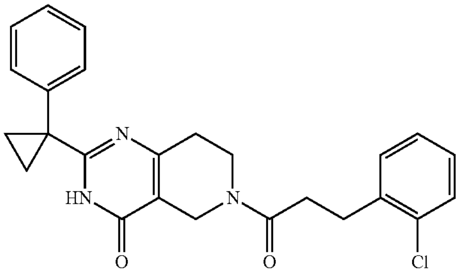 [SMILES: O=C(CCc1ccccc1Cl)N1CCc2nc(C3(c4ccccc4)CC3)[nH]c(=O)c2C1] | 1.70 min 434.1 |
| 14-50 | 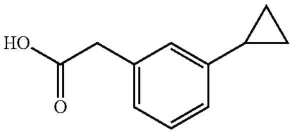 | INT-1 | 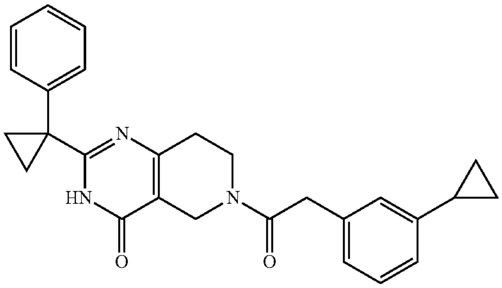 [SMILES: O=C(Cc1cccc(C2CC2)c1)N1CCc2nc(C3(c4ccccc4)CC3)[nH]c(=O)c2C1] | 1.74 min 426.2 |
| 14-51 | 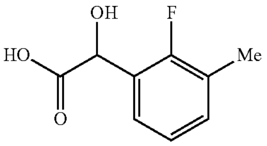 [SMILES: Cc1cccc(C(O)C(=O)O)c1F] | INT-1 | 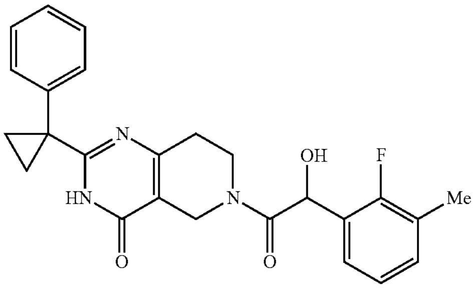 [SMILES: Cc1cccc(C(O)C(=O)N2CCc3nc(C4(c5ccccc5)CC4)[nH]c(=O)c3C2)c1F] | 1.54 min 434.1 |
| 14-52 | 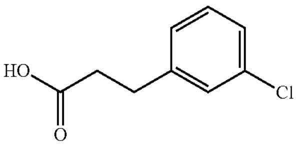 | INT-1 | 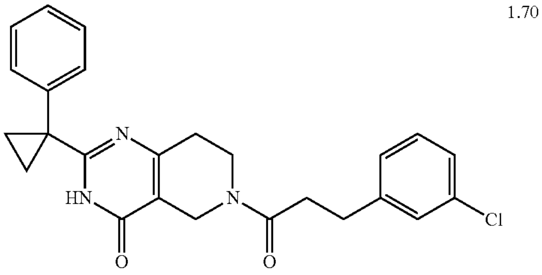 | 1.70 min 434.1 |

TABLE 45-8-continued
| | | | | |
|---|---|---|---|---|
| 14-53 | 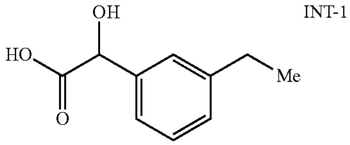 | INT-1 | 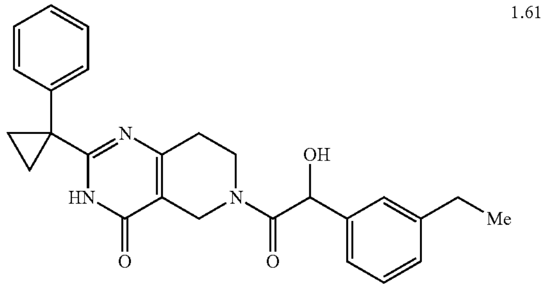 | 1.61 min 430.2 |
| 14-54 | 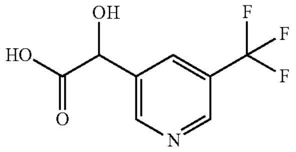 [SMILES: O=C(O)C(O)c1cncc(C(F)(F)F)c1] | INT-1 | 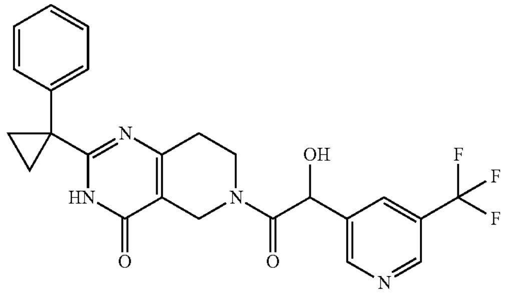 [SMILES: O=C(C(O)c1cncc(C(F)(F)F)c1)N1CCc2nc(C3(c4ccccc4)CC3)[nH]c(=O)c2C1] | 1.43 min 471.1 |
TABLE 45-9
| | | | | | |
|---|---|---|---|---|---|
| 14-55 | 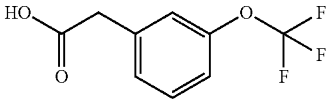 [SMILES: O=C(O)Cc1cccc(OC(F)(F)F)c1] | INT-1 | 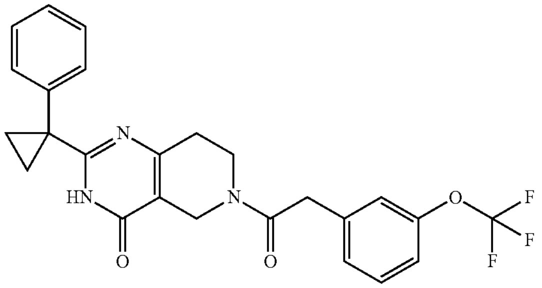 [SMILES: O=C(Cc1cccc(OC(F)(F)F)c1)N1CCc2nc(C3(c4ccccc4)CC3)[nH]c(=O)c2C1] | 1.76 min | 470.1 |
| 14-56 | 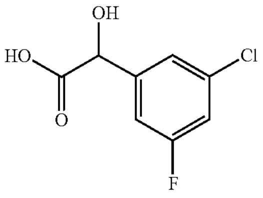 [SMILES: O=C(O)C(O)c1cc(F)cc(Cl)c1] | INT-1 | 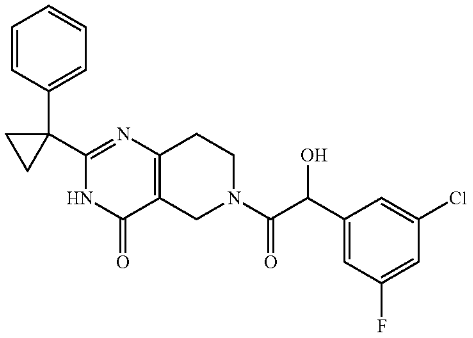 | 1.61 min | 454.1 |
| 14-57 | 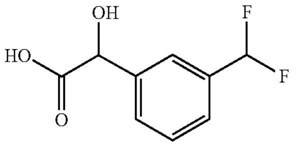 [SMILES: O=C(O)C(O)c1cccc(C(F)F)c1] | INT-1 | 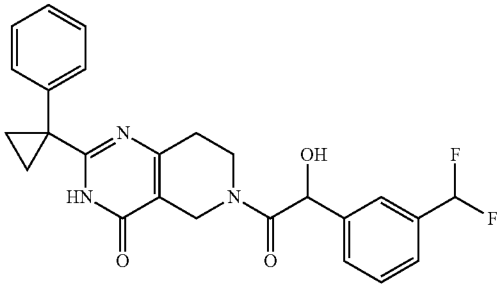 [SMILES: O=C(C(O)c1cccc(C(F)F)c1)N1CCc2nc(C3(c4ccccc4)CC3)[nH]c(=O)c2C1] | 1.50 min | 452.1 |

TABLE 45-9-continued
| | | | | | |
|---|---|---|---|---|---|
| 14-58 | 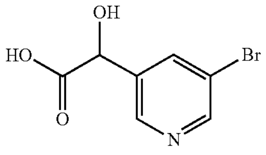 [SMILES: O=C(O)C(O)c1cncc(Br)c1] | INT-1 | 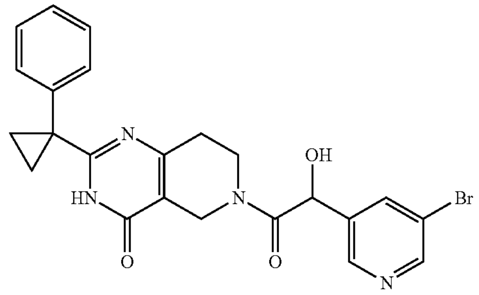 [SMILES: O=C(C(O)c1cncc(Br)c1)N1CCc2nc(C3(c4ccccc4)CC3)[nH]c(=O)c2C1] | 1.36 min | 480.9 |
| 14-59 | 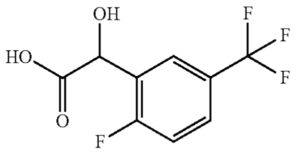 [SMILES: O=C(O)C(O)c1cc(C(F)(F)F)ccc1F] | INT-1 | 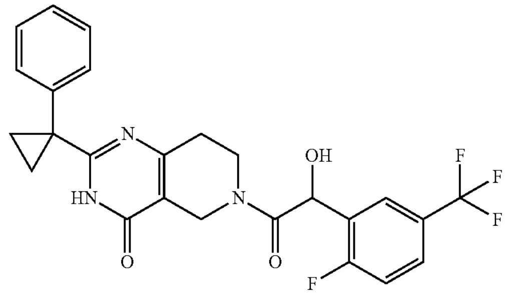 [SMILES: O=C(C(O)c1cc(C(F)(F)F)ccc1F)N1CCc2nc(C3(c4ccccc4)CC3)[nH]c(=O)c2C1] | 1.64 min | 488.1 |
| 14-60 | 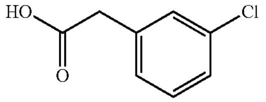 | INT-1 | 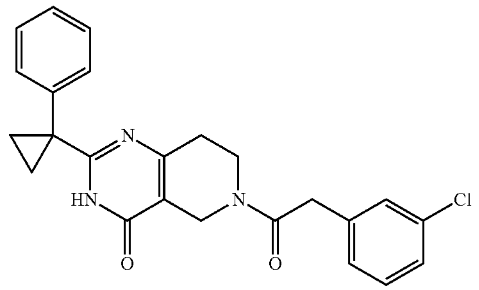 [SMILES: O=C(Cc1cccc(Cl)c1)N1CCc2nc(C3(c4ccccc4)CC3)[nH]c(=O)c2C1] | 1.68 min | 420.1 |
| 14-61 | 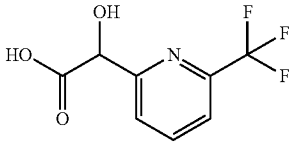 [SMILES: O=C(O)C(O)c1cccc(C(F)(F)F)n1] | INT-1 | 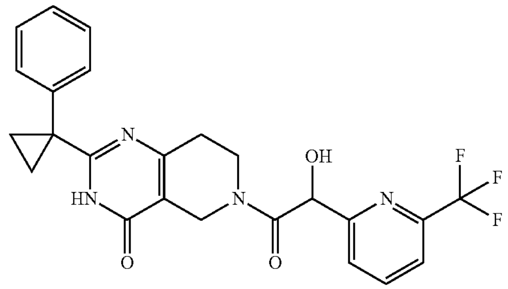 [SMILES: O=C(C(O)c1cccc(C(F)(F)F)n1)N1CCc2nc(C3(c4ccccc4)CC3)[nH]c(=O)c2C1] | 1.54 min | 471.1 |
TABLE 45-10
| | | | | | |
|---|---|---|---|---|---|
| 14-62 | 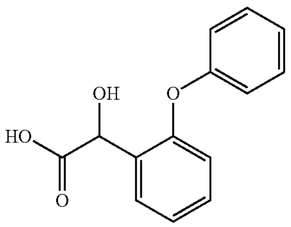 [SMILES: O=C(O)C(O)c1ccccc1Oc1ccccc1] | INT-1 | 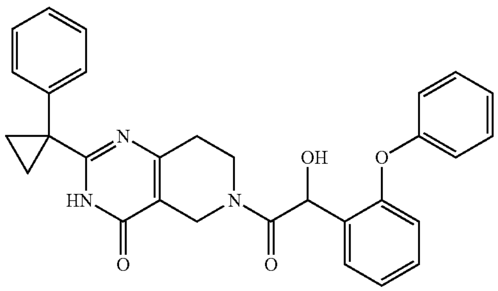 [SMILES: O=C(C(O)c1ccccc1Oc1ccccc1)N1CCc2nc(C3(c4ccccc4)CC3)[nH]c(=O)c2C1] | 1.73 min | 494.1 |

TABLE 45-10-continued
| | | | | | |
|---|---|---|---|---|---|
| 14-63 | 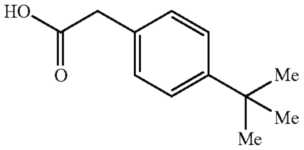 [SMILES: CC(C)(C)c1ccc(CC(=O)O)cc1] | INT-1 | 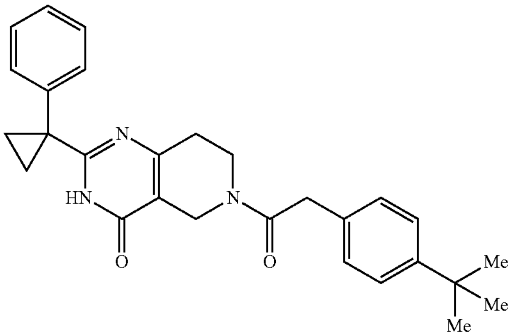 [SMILES: CC(C)(C)c1ccc(CC(=O)N2CCc3nc(C4(c5ccccc5)CC4)[nH]c(=O)c3C2)cc1] | 1.91 min | 442.2 |
| 14-64 | 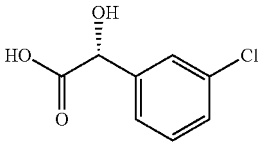 | INT-10-7 | 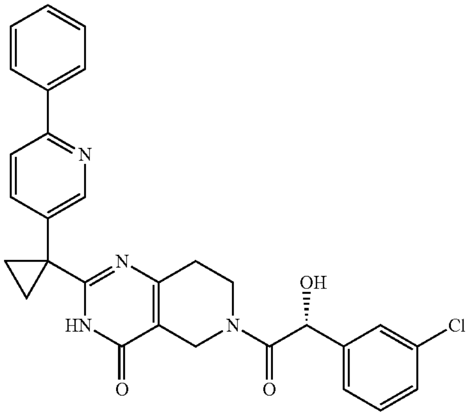 [SMILES: O=C([C@H](O)c1cccc(Cl)c1)N1CCc2nc(C3(c4ccc(-c5ccccc5)nc4)CC3)[nH]c(=O)c2C1] | 1.62 min | 513.1 |
| 14-65 | 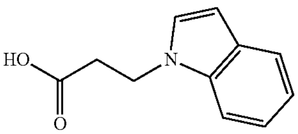 [SMILES: O=C(O)CCn1ccc2ccccc21] | INT-1 | 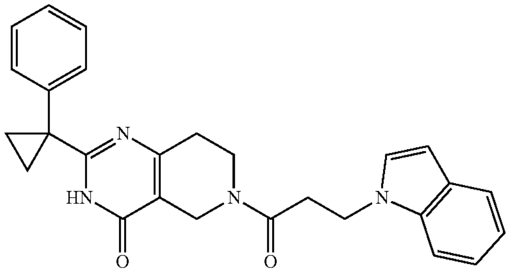 [SMILES: O=C(CCn1ccc2ccccc21)N1CCc2nc(C3(c4ccccc4)CC3)[nH]c(=O)c2C1] | 1.61 min | 439.2 |
| 14-66 | 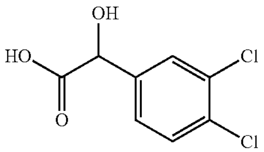 [SMILES: O=C(O)C(O)c1ccc(Cl)c(Cl)c1] | INT-1 | 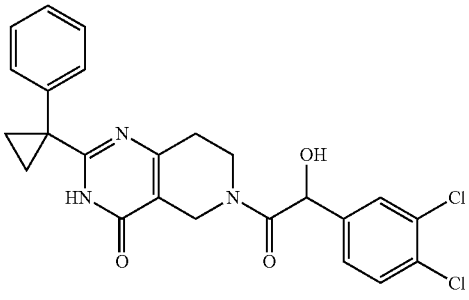 [SMILES: O=C(C(O)c1ccc(Cl)c(Cl)c1)N1CCc2nc(C3(c4ccccc4)CC3)[nH]c(=O)c2C1] | 1.69 min | 470.1 |

TABLE 45-10-continued
| | | | | | |
|---|---|---|---|---|---|
| 14-67 | 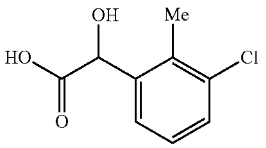 | INT-1 | 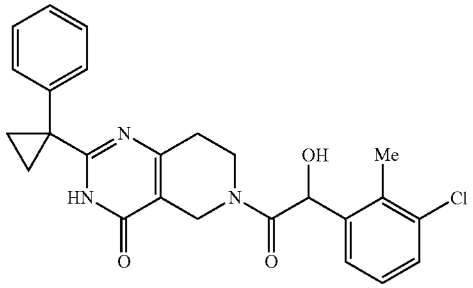 [SMILES: Cc1c(Cl)cccc1C(O)C(=O)N1CCc2nc(C3(c4ccccc4)CC3)[nH]c(=O)c2C1] | 1.64 min | 450.1 |
TABLE 45-11
| | | | | | |
|---|---|---|---|---|---|
| 14-68 | 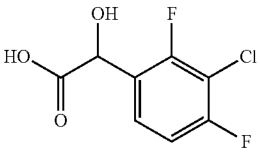 [SMILES: O=C(O)C(O)c1ccc(F)c(Cl)c1F] | INT-1 | 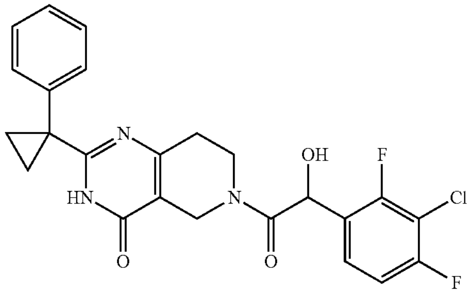 [SMILES: O=C(C(O)c1ccc(F)c(Cl)c1F)N1CCc2nc(C3(c4ccccc4)CC3)[nH]c(=O)c2C1] | 1.62 min | 472.1 |
| 14-69 | 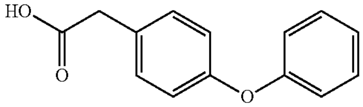 [SMILES: O=C(O)Cc1ccc(Oc2ccccc2)cc1] | INT-1 | 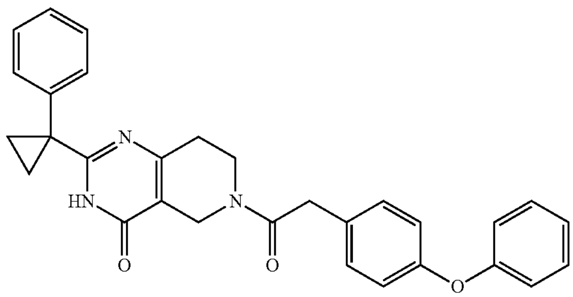 [SMILES: O=C(Cc1ccc(Oc2ccccc2)cc1)N1CCc2nc(C3(c4ccccc4)CC3)[nH]c(=O)c2C1] | 1.85 min | 478.2 |
| 14-70 | 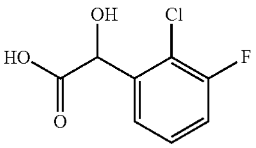 [SMILES: O=C(O)C(O)c1cccc(F)c1Cl] | INT-1 | 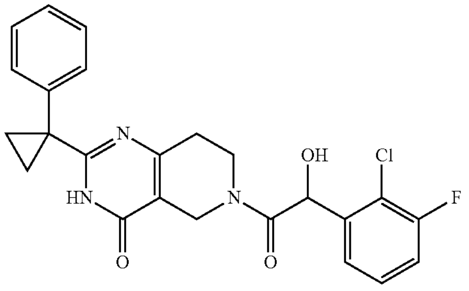 | 1.56 min | 454.1 |
| 14-71 | 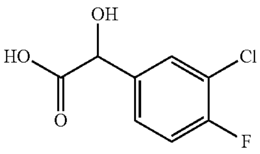 [SMILES: O=C(O)C(O)c1ccc(F)c(Cl)c1] | INT-1 | 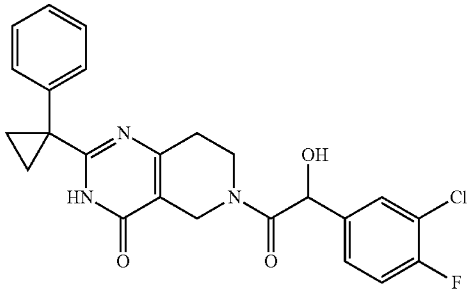 [SMILES: O=C(C(O)c1ccc(F)c(Cl)c1)N1CCc2nc(C3(c4ccccc4)CC3)[nH]c(=O)c2C1] | 1.59 min | 454.1 |

TABLE 45-11-continued
| | | | | | |
|---|---|---|---|---|---|
| 14-72 | 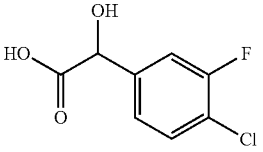 [SMILES: O=C(O)C(O)c1ccc(Cl)c(F)c1] | INT-1 | 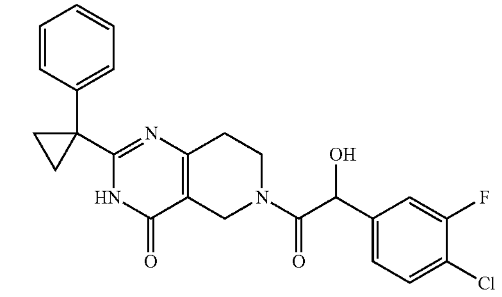 [SMILES: O=C(C(O)c1ccc(Cl)c(F)c1)N1CCc2nc(C3(c4ccccc4)CC3)[nH]c(=O)c2C1] | 1.61 min | 454.1 |
| 14-73 | 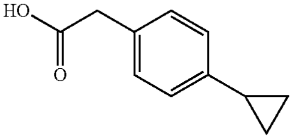 [SMILES: O=C(O)Cc1ccc(C2CC2)cc1] | INT-1 | 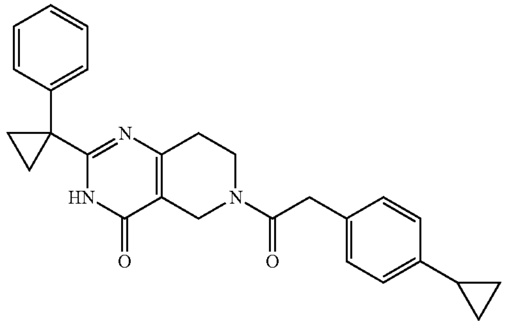 [SMILES: O=C(Cc1ccc(C2CC2)cc1)N1CCc2nc(C3(c4ccccc4)CC3)[nH]c(=O)c2C1] | 1.75 min | 426.2 |
| 14-74 | 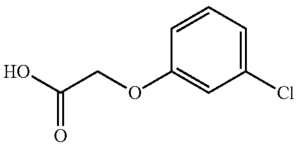 [SMILES: O=C(O)COc1cccc(Cl)c1] | INT-1 | 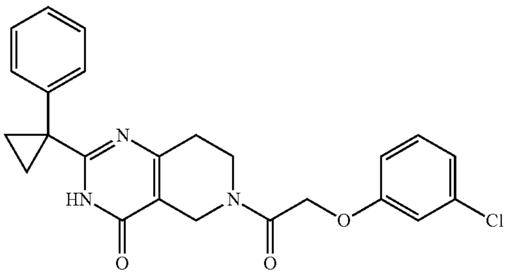 [SMILES: O=C(COc1cccc(Cl)c1)N1CCc2nc(C3(c4ccccc4)CC3)[nH]c(=O)c2C1] | 1.70 min | 436.1 |
TABLE 45-12
| | | | | | |
|---|---|---|---|---|---|
| 14-75 | 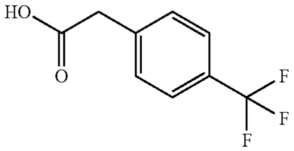 [SMILES: O=C(O)Cc1ccc(C(F)(F)F)cc1] | INT-1 | 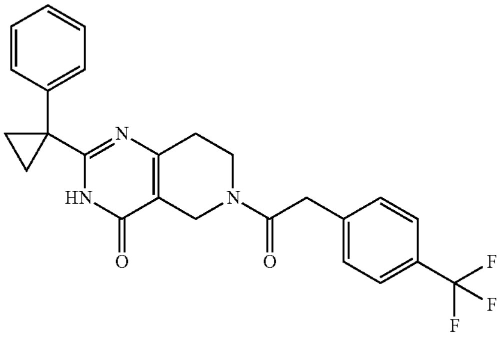 [SMILES: O=C(Cc1ccc(C(F)(F)F)cc1)N1CCc2nc(C3(c4ccccc4)CC3)[nH]c(=O)c2C1] | 1.74 min | 454.1 |

TABLE 45-12-continued
| | | | | | |
|---|---|---|---|---|---|
| 14-76 | 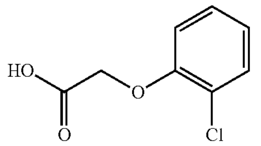 [SMILES: O=C(O)COc1ccccc1Cl] | INT-1 | 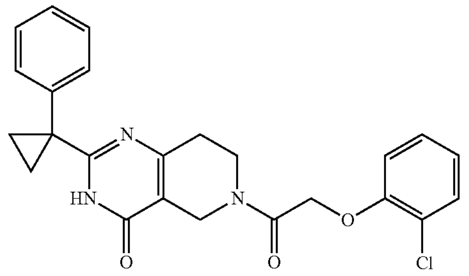 [SMILES: O=C(COc1ccccc1Cl)N1CCc2nc(C3(c4ccccc4)CC3)[nH]c(=O)c2C1] | 1.68 min | 436.1 |
| 14-77 | 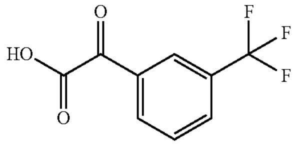 [SMILES: O=C(O)C(=O)c1cccc(C(F)(F)F)c1] | INT-4-14 | 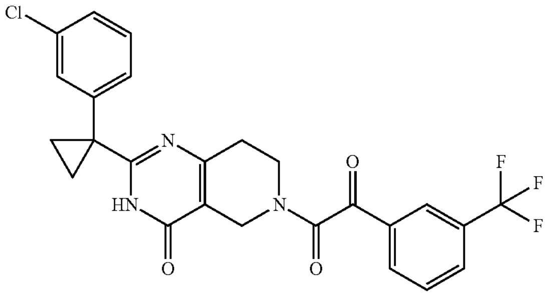 [SMILES: O=C(C(=O)N1CCc2nc(C3(c4cccc(Cl)c4)CC3)[nH]c(=O)c2C1)c1cccc(C(F)(F)F)c1] | 1.90 min | 502.0 |
| 14-78 | 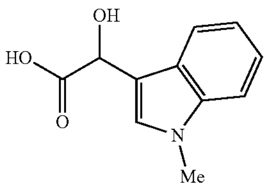 [SMILES: Cn1cc(C(O)C(=O)O)c2ccccc21] | INT-1 | 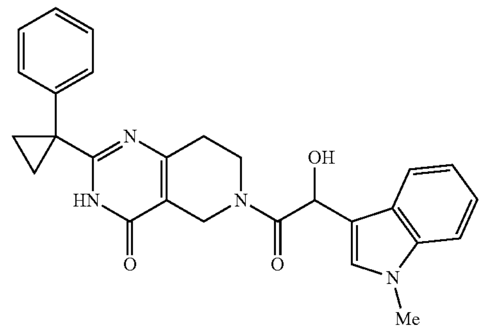 [SMILES: Cn1cc(C(O)C(=O)N2CCc3nc(C4(c5ccccc5)CC4)[nH]c(=O)c3C2)c2ccccc21] | 1.48 min | 455.2 |
| 14-79 | 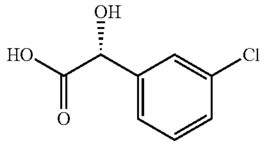 | INT-4-29 | 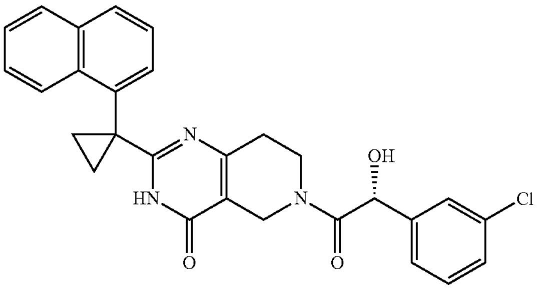 [SMILES: O=C([C@H](O)c1cccc(Cl)c1)N1CCc2nc(C3(c4cccc5ccccc45)CC3)[nH]c(=O)c2C1] | 1.84 min | 486.1 |
| 14-80 | 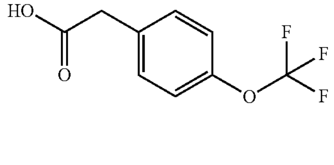 [SMILES: O=C(O)Cc1ccc(OC(F)(F)F)cc1] | INT-1 | 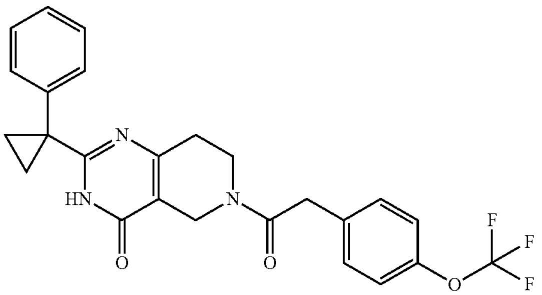 [SMILES: O=C(Cc1ccc(OC(F)(F)F)cc1)N1CCc2nc(C3(c4ccccc4)CC3)[nH]c(=O)c2C1] | 1.77 min | 470.1 |

TABLE 45-12-continued
| | | | | | |
|---|---|---|---|---|---|
| 14-81 | 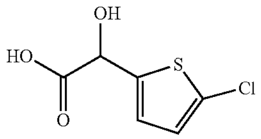 [SMILES: O=C(O)C(O)c1ccc(Cl)s1] | INT-1 | 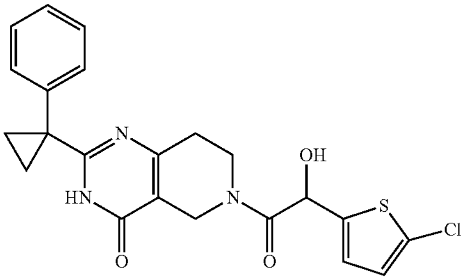 [SMILES: O=C(C(O)c1ccc(Cl)s1)N1CCc2nc(C3(c4ccccc4)CC3)[nH]c(=O)c2C1] | 1.57 min | 442.0 |
TABLE 45-13
| | | | | | |
|---|---|---|---|---|---|
| 14-82 | 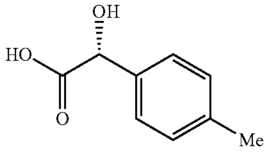 [SMILES: Cc1ccc([C@@H](O)C(=O)O)cc1] | INT-1 | 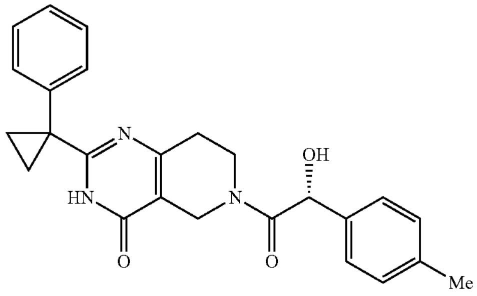 [SMILES: Cc1ccc([C@@H](O)C(=O)N2CCc3nc(C4(c5ccccc5)CC4)[nH]c(=O)c3C2)cc1] | 1.53 min | 416.2 |
| 14-83 | 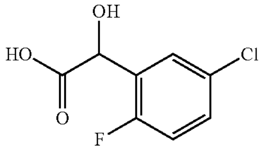 [SMILES: O=C(O)C(O)c1cc(Cl)ccc1F] | INT-1 | 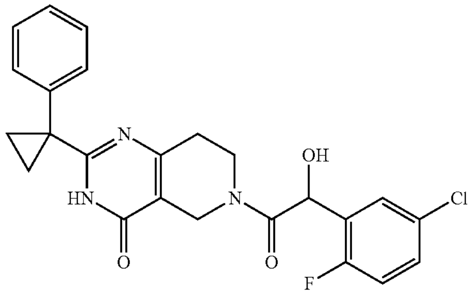 [SMILES: O=C(C(O)c1cc(Cl)ccc1F)N1CCc2nc(C3(c4ccccc4)CC3)[nH]c(=O)c2C1] | 1.57 min | 454.1 |
| 14-84 | 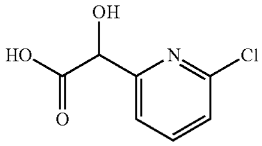 [SMILES: O=C(O)C(O)c1cccc(Cl)n1] | INT-1 | 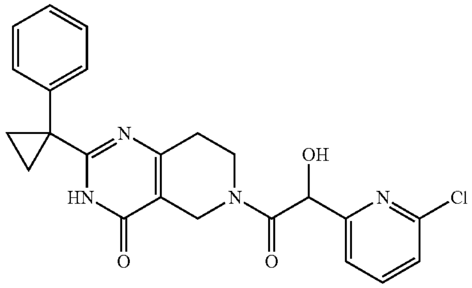 | 1.43 min | 437.1 |
| 14-85 | 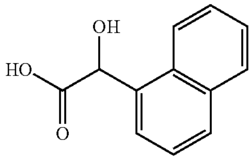 [SMILES: O=C(O)C(O)c1cccc2ccccc12] | INT-1 | 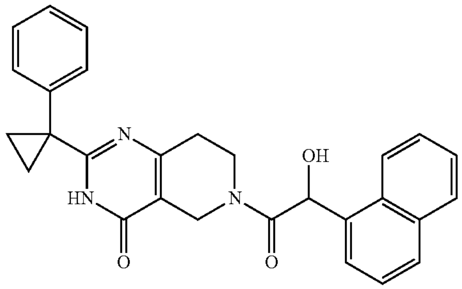 [SMILES: O=C(C(O)c1cccc2ccccc12)N1CCc2nc(C3(c4ccccc4)CC3)[nH]c(=O)c2C1] | 1.62 min | 452.2 |

TABLE 45-13-continued
| | | | | |
|---|---|---|---|---|
| 14-86 | 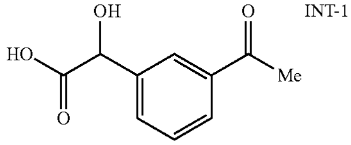 | INT-1 | 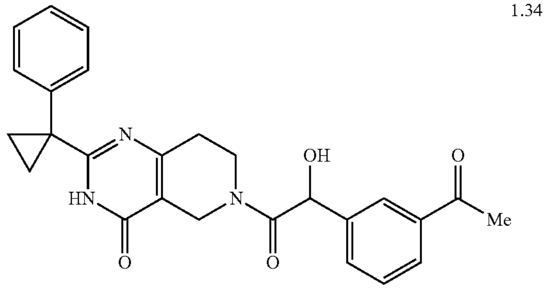 | 1.34 min 444.1 |
| 14-87 | 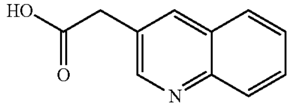 [SMILES: O=C(O)Cc1cnc2ccccc2c1] | INT-1 | 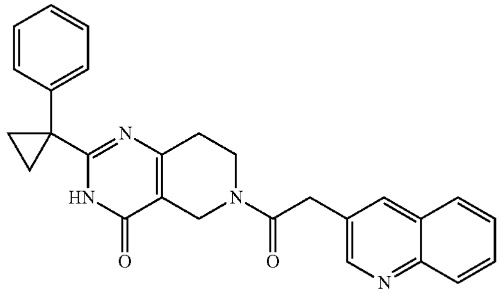 [SMILES: O=C(Cc1cnc2ccccc2c1)N1CCc2nc(C3(c4ccccc4)CC3)[nH]c(=O)c2C1] | 1.44 min 437.2 |
| 14-88 | 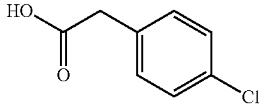 [SMILES: O=C(O)Cc1ccc(Cl)cc1] | INT-1 | 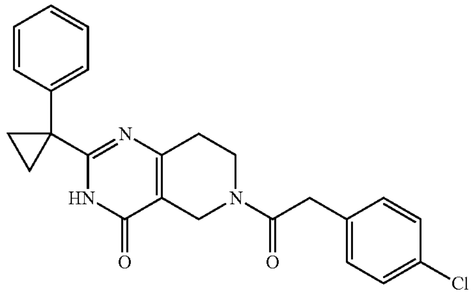 [SMILES: O=C(Cc1ccc(Cl)cc1)N1CCc2nc(C3(c4ccccc4)CC3)[nH]c(=O)c2C1] | 1.68 min 420.1 |
TABLE 45-14
| | | | | |
|---|---|---|---|---|
| 14-89 | 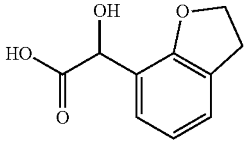 [SMILES: O=C(O)C(O)c1cccc2c1OCC2] | INT-1 | 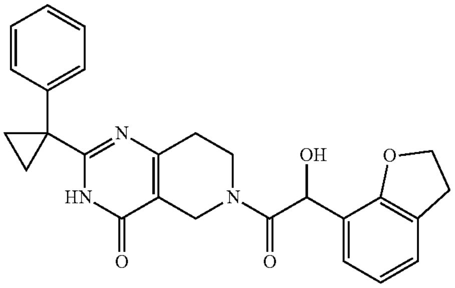 [SMILES: O=C(C(O)c1cccc2c1OCC2)N1CCc2nc(C3(c4ccccc4)CC3)[nH]c(=O)c2C1] | 1.46 min 444.1 |
| 14-90 | 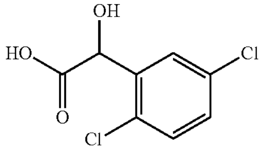 [SMILES: O=C(O)C(O)c1cc(Cl)ccc1Cl] | INT-1 | 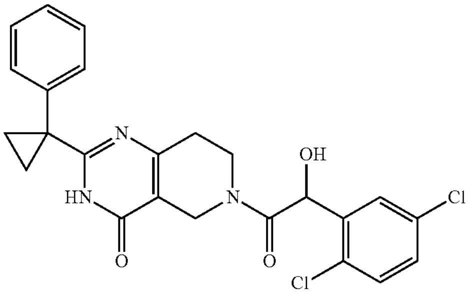 [SMILES: O=C(C(O)c1cc(Cl)ccc1Cl)N1CCc2nc(C3(c4ccccc4)CC3)[nH]c(=O)c2C1] | 1.64 min 470.0 |

TABLE 45-14-continued
| | | | | |
|---|---|---|---|---|
| 14-91 | 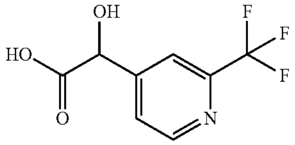 [SMILES: O=C(O)C(O)c1ccnc(C(F)(F)F)c1] | INT-1 | 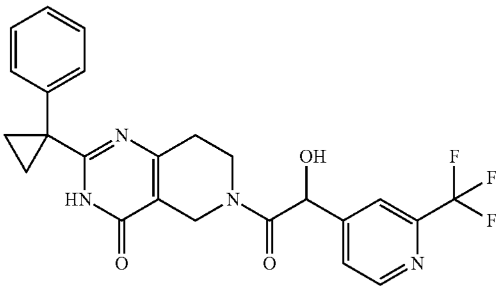 [SMILES: O=C(C(O)c1ccnc(C(F)(F)F)c1)N1CCc2nc(C3(c4ccccc4)CC3)[nH]c(=O)c2C1] | 1.45 min 471.1 |
| 14-92 | 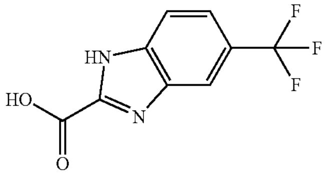 [SMILES: O=C(O)c1nc2cc(C(F)(F)F)ccc2[nH]1] | INT-1 | 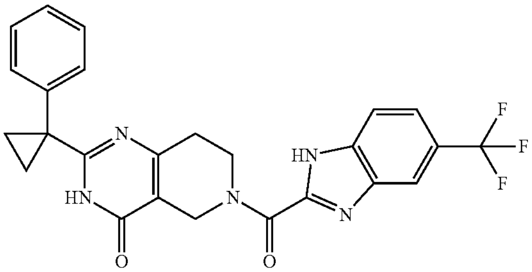 [SMILES: O=C(c1nc2cc(C(F)(F)F)ccc2[nH]1)N1CCc2nc(C3(c4ccccc4)CC3)[nH]c(=O)c2C1] | 1.77 min 480.1 |
| 14-93 | 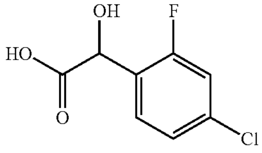 [SMILES: O=C(O)C(O)c1ccc(Cl)cc1F] | INT-1 | 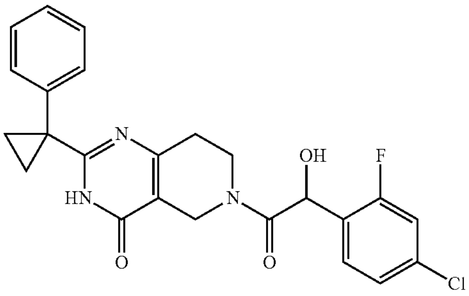 [SMILES: O=C(C(O)c1ccc(Cl)cc1F)N1CCc2nc(C3(c4ccccc4)CC3)[nH]c(=O)c2C1] | 1.60 min 454.1 |
| 14-94 | 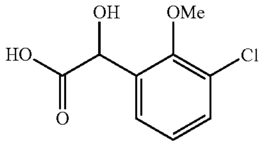 [SMILES: COc1c(Cl)cccc1C(O)C(=O)O] | INT-1 | 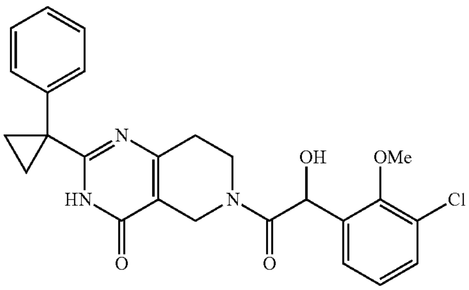 [SMILES: COc1c(Cl)cccc1C(O)C(=O)N1CCc2nc(C3(c4ccccc4)CC3)[nH]c(=O)c2C1] | 1.61 min 466.1 |
| 14-95 | 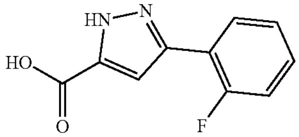 [SMILES: O=C(O)c1cc(-c2ccccc2F)n[nH]1] | INT-1 | 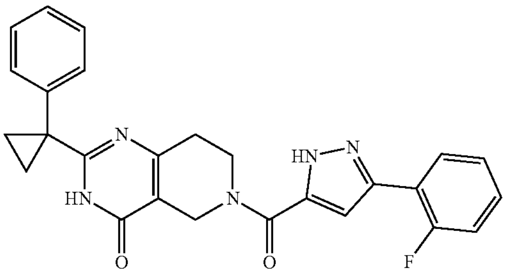 [SMILES: O=C(c1cc(-c2ccccc2F)n[nH]1)N1CCc2nc(C3(c4ccccc4)CC3)[nH]c(=O)c2C1] | 1.58 min 456.1 |

TABLE 45-15
| | | | | |
|---|---|---|---|---|
| 14-96 | 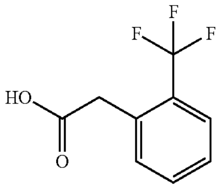 [SMILES: O=C(O)Cc1ccccc1C(F)(F)F] | INT-1 | 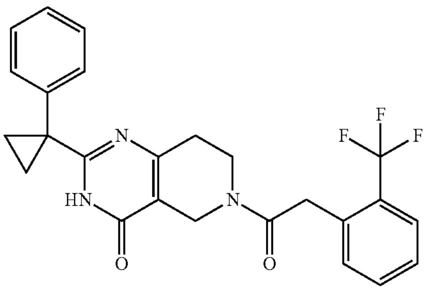 [SMILES: O=C(Cc1ccccc1C(F)(F)F)N1CCc2nc(C3(c4ccccc4)CC3)[nH]c(=O)c2C1] | 1.72 min 454.1 |
| 14-97 | 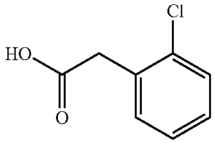 [SMILES: O=C(O)Cc1ccccc1Cl] | INT-1 | 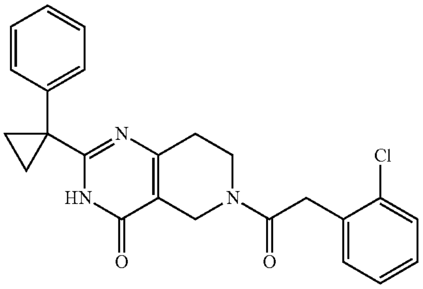 [SMILES: O=C(Cc1ccccc1Cl)N1CCc2nc(C3(c4ccccc4)CC3)[nH]c(=O)c2C1] | 1.66 min 420.1 |
| 14-98 | 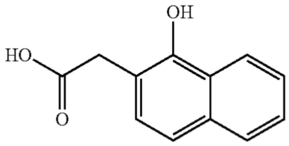 [SMILES: O=C(O)Cc1ccc2ccccc2c1O] | INT-1 | 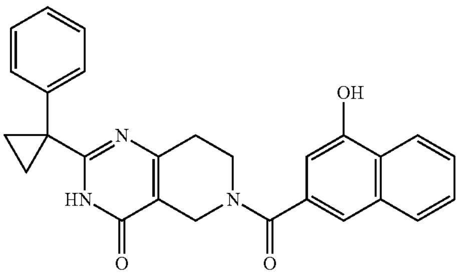 [SMILES: O=C(c1cc(O)c2ccccc2c1)N1CCc2nc(C3(c4ccccc4)CC3)[nH]c(=O)c2C1] | 1.59 min 438.1 |
| 14-99 | 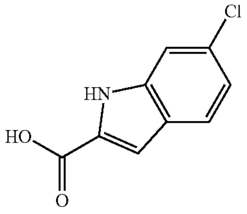 [SMILES: O=C(O)c1cc2ccc(Cl)cc2[nH]1] | INT-1 | 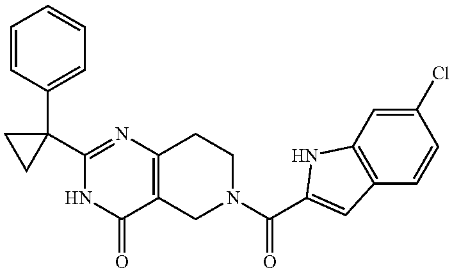 [SMILES: O=C(c1cc2ccc(Cl)cc2[nH]1)N1CCc2nc(C3(c4ccccc4)CC3)[nH]c(=O)c2C1] | 1.79 min 445.1 |
| 14-100 | 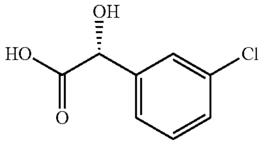 | INT-4-30 | 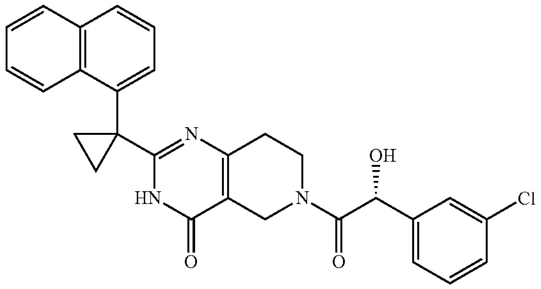 [SMILES: O=C([C@H](O)c1cccc(Cl)c1)N1CCc2nc(C3(c4cccc5ccccc45)CC3)[nH]c(=O)c2C1] | 1.58 min 460.1 |

TABLE 45-15-continued
| | | | | | |
|---|---|---|---|---|---|
| 14-101 | 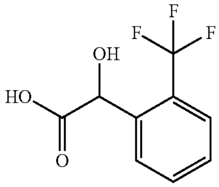 [SMILES: O=C(O)C(O)c1ccccc1C(F)(F)F] | INT-1 | 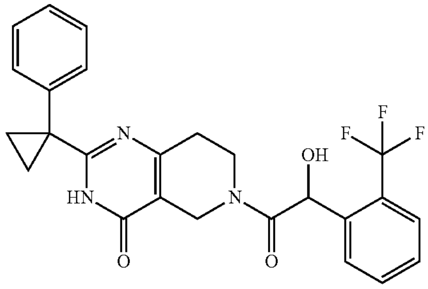 [SMILES: O=C(C(O)c1ccccc1C(F)(F)F)N1CCc2nc(C3(c4ccccc4)CC3)[nH]c(=O)c2C1] | 1.62 min | 470.1 |
| 14-102 | 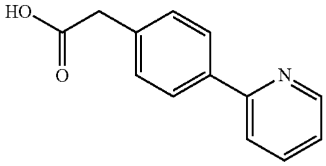 [SMILES: O=C(O)Cc1ccc(-c2ccccn2)cc1] | INT-1 | 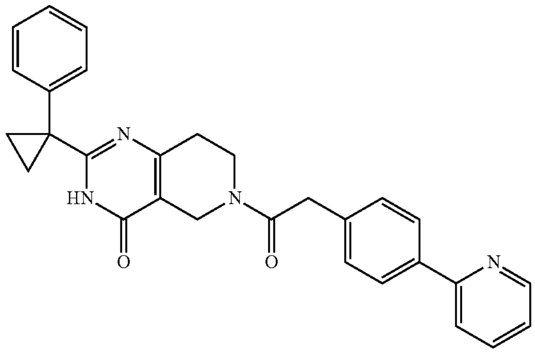 [SMILES: O=C(Cc1ccc(-c2ccccn2)cc1)N1CCc2nc(C3(c4ccccc4)CC3)[nH]c(=O)c2C1] | 1.56 min | 463.2 |
TABLE 45-16
| | | | | | |
|---|---|---|---|---|---|
| 14-103 | 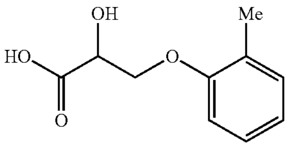 [SMILES: Cc1ccccc1OCC(O)C(=O)O] | INT-1 | 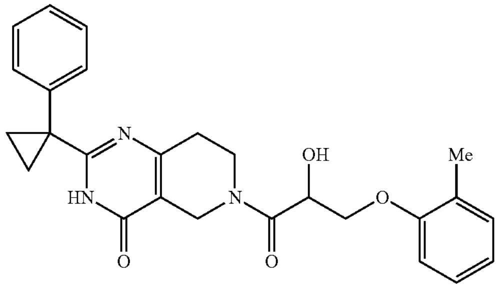 [SMILES: Cc1ccccc1OCC(O)C(=O)N1CCc2nc(C3(c4ccccc4)CC3)[nH]c(=O)c2C1] | 1.59 min | 446.2 |
| 14-104 | 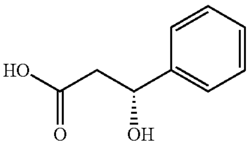 [SMILES: O=C(O)C[C@@H](O)c1ccccc1] | INT-1 | 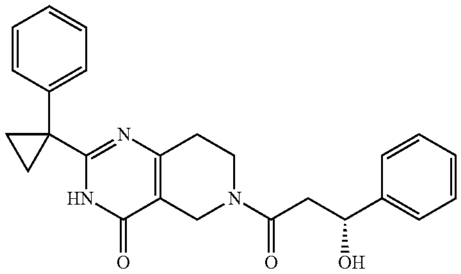 [SMILES: O=C(C[C@@H](O)c1ccccc1)N1CCc2nc(C3(c4ccccc4)CC3)[nH]c(=O)c2C1] | 1.37 min | 416.2 |
| 14-105 | 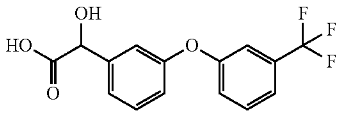 [SMILES: O=C(O)C(O)c1cccc(Oc2cccc(C(F)(F)F)c2)c1] | INT-4-14 | 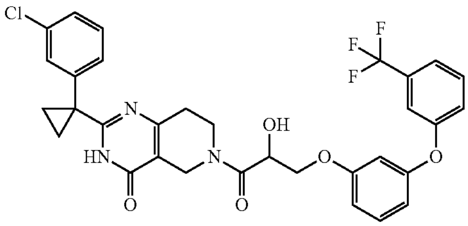 [SMILES: O=C(C(O)COc1cccc(Oc2cccc(C(F)(F)F)c2)c1)N1CCc2nc(C3(c4cccc(Cl)c4)CC3)[nH]c(=O)c2C1] | 1.96 min | 595.9 |

TABLE 45-16-continued
| | | | | | |
|---|---|---|---|---|---|
| 14-106 | 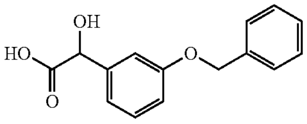 [SMILES: O=C(O)C(O)c1cccc(OCc2ccccc2)c1] | INT-4-14 | 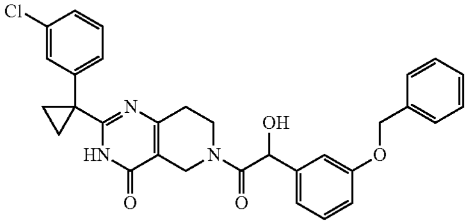 [SMILES: O=C(C(O)c1cccc(OCc2ccccc2)c1)N1CCc2nc(C3(c4cccc(Cl)c4)CC3)[nH]c(=O)c2C1] | 1.83 min | 542.0 |
| 14-107 | 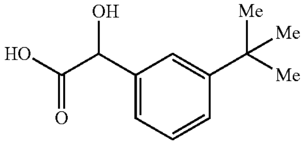 [SMILES: CC(C)(C)c1cccc(C(O)C(=O)O)c1] | INT-8-5 | 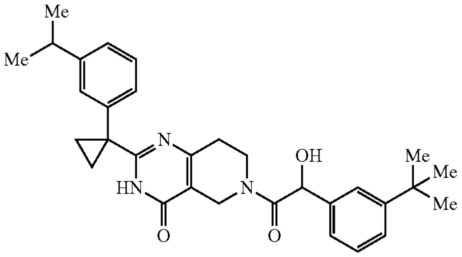 [SMILES: CC(C)c1cccc(C2(c3nc4c(c(=O)[nH]3)CN(C(=O)C(O)c3cccc(C(C)(C)C)c3)CC4)CC2)c1] | 2.02 min | 500.1 |
| 14-108 | 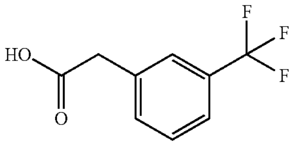 [SMILES: O=C(O)Cc1cccc(C(F)(F)F)c1] | INT-8-38 | 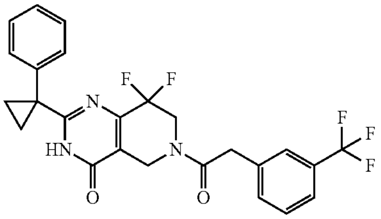 [SMILES: O=C(Cc1cccc(C(F)(F)F)c1)N1Cc2c(nc(C3(c4ccccc4)CC3)[nH]c2=O)C(F)(F)C1] | 1.86 min | 489.9 |
| 14-109 | 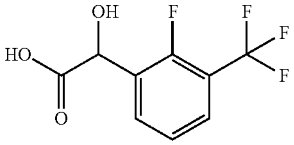 [SMILES: O=C(O)C(O)c1cccc(C(F)(F)F)c1F] | INT-8-5 | 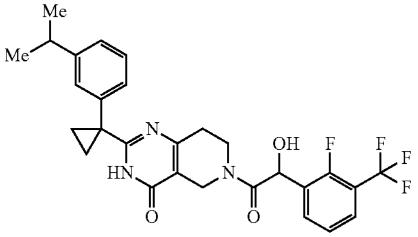 [SMILES: CC(C)c1cccc(C2(c3nc4c(c(=O)[nH]3)CN(C(=O)C(O)c3cccc(C(F)(F)F)c3F)CC4)CC2)c1] | 1.89 min | 530.0 |
TABLE 45-17
| | | | | | |
|---|---|---|---|---|---|
| 14-110 | 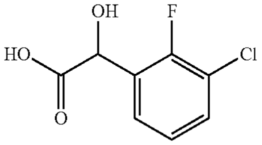 | INT-8-5 | 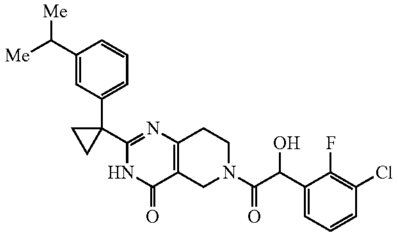 [SMILES: CC(C)c1cccc(C2(c3nc4c(c(=O)[nH]3)CN(C(=O)C(O)c3cccc(Cl)c3F)CC4)CC2)c1] | 1.86 min | 495.9 |
| 14-111 | 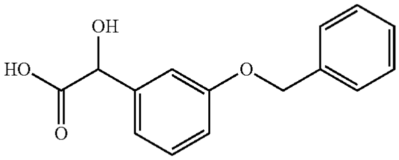 [SMILES: O=C(O)C(O)c1cccc(OCc2ccccc2)c1] | INT-1 | 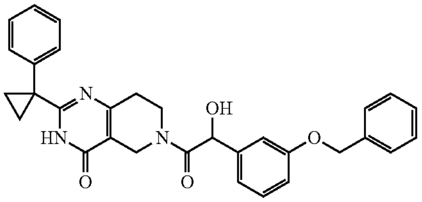 [SMILES: O=C(C(O)c1cccc(OCc2ccccc2)c1)N1CCc2nc(C3(c4ccccc4)CC3)[nH]c(=O)c2C1] | 1.74 min | 508.1 |

TABLE 45-17-continued
| | | | | | |
|---|---|---|---|---|---|
| 14-112 | 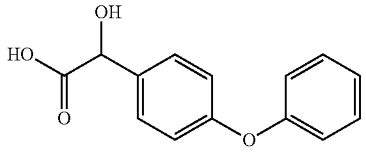 [SMILES: O=C(O)C(O)c1ccc(Oc2ccccc2)cc1] | INT-1 | 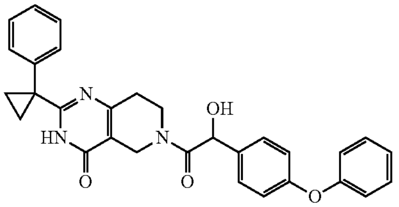 [SMILES: O=C(C(O)c1ccc(Oc2ccccc2)cc1)N1CCc2nc(C3(c4ccccc4)CC3)[nH]c(=O)c2C1] | 1.73 min | 494.0 |
| 14-113 | 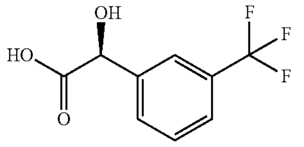 [SMILES: O=C(O)[C@@H](O)c1cccc(C(F)(F)F)c1] | INT-1 | 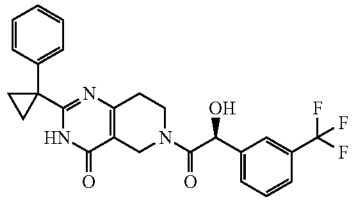 [SMILES: O=C([C@@H](O)c1cccc(C(F)(F)F)c1)N1CCc2nc(C3(c4ccccc4)CC3)[nH]c(=O)c2C1] | 1.61 min | 469.9 |
| 14-114 | 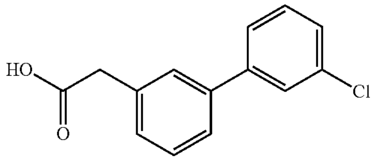 [SMILES: O=C(O)Cc1cccc(-c2cccc(Cl)c2)c1] | INT-4-14 | 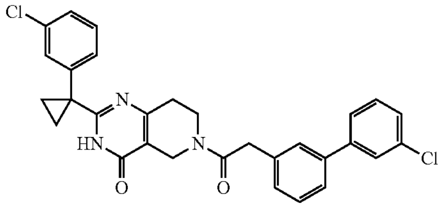 [SMILES: O=C(Cc1cccc(-c2cccc(Cl)c2)c1)N1CCc2nc(C3(c4cccc(Cl)c4)CC3)[nH]c(=O)c2C1] | 2.17 min | 530.4 |
| 14-115 | INT-26-5 | INT-4-14 | 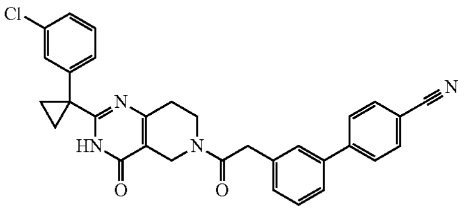 [SMILES: N#Cc1ccc(-c2cccc(CC(=O)N3CCc4nc(C5(c6cccc(Cl)c6)CC5)[nH]c(=O)c4C3)c2)cc1] | 1.99 min | 521.4 |
| 14-116 | INT-26-6 | INT-4-14 | 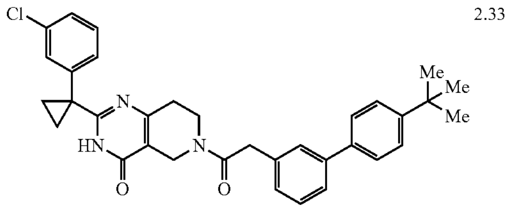 | 2.33 min | 552.5 |
TABLE 45-18
| | | | | | |
|---|---|---|---|---|---|
| 14-117 | INT-26-7 | INT-4-14 | 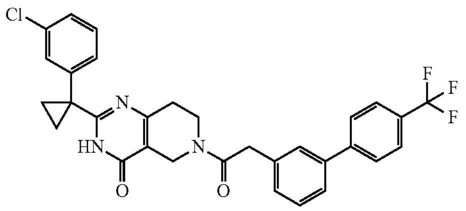 [SMILES: O=C(Cc1cccc(-c2ccc(C(F)(F)F)cc2)c1)N1CCc2nc(C3(c4cccc(Cl)c4)CC3)[nH]c(=O)c2C1] | 2.18 min | 564.4 |
| 14-118 | INT-26-8 | INT-4-14 | 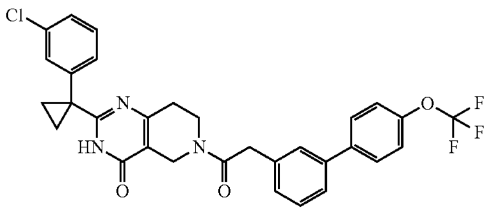 [SMILES: O=C(Cc1cccc(-c2ccc(OC(F)(F)F)cc2)c1)N1CCc2nc(C3(c4cccc(Cl)c4)CC3)[nH]c(=O)c2C1] | 2.21 min | 580.4 |

TABLE 45-18-continued

| | | | | | |
|---|---|---|---|---|---|
| 14-119 | INT-26-9 | INT-4-14 | 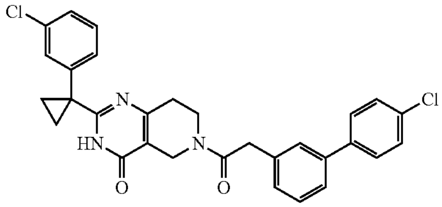 [SMILES: O=C(Cc1cccc(-c2ccc(Cl)cc2)c1)N1CCc2nc(C3(c4cccc(Cl)c4)CC3)[nH]c(=O)c2C1] | 2.17 min | 530.4 |
| 14-120 | INT-26-3 | INT-4-14 | 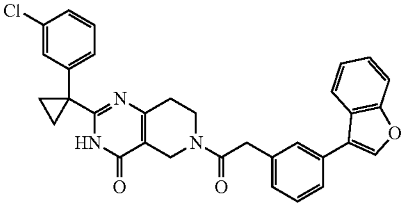 [SMILES: O=C(Cc1cccc(-c2coc3ccccc23)c1)N1CCc2nc(C3(c4cccc(Cl)c4)CC3)[nH]c(=O)c2C1] | 2.14 min | 536.4 |
| 14-121 | INT-26-4 | INT-4-14 | 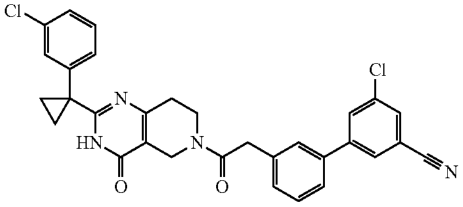 [SMILES: N#Cc1cc(Cl)cc(-c2cccc(CC(=O)N3CCc4nc(C5(c6cccc(Cl)c6)CC5)[nH]c(=O)c4C3)c2)c1] | 2.11 min | 555.4 |
| 14-122 | 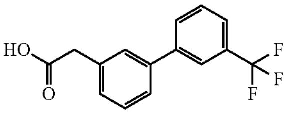 [SMILES: O=C(O)Cc1cccc(-c2cccc(C(F)(F)F)c2)c1] | INT-4-14 | 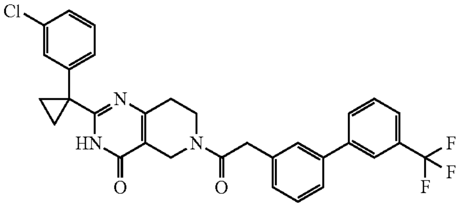 [SMILES: O=C(Cc1cccc(-c2cccc(C(F)(F)F)c2)c1)N1CCc2nc(C3(c4cccc(Cl)c4)CC3)[nH]c(=O)c2C1] | 2.18 min | 564.5 |

The following amide derivatives (Ex-15-1 to Ex-15-31) are prepared according to the procedure of Ex-1 or the general synthesis in scheme-1 from the synthesized amine drivatives and the known or synthesized acid derivatives in Tables 46-1 to 46-5. The further purification is carried out by preparative LC-MS or SFC-MS system in usual manner. The retention time and observed MS by HPLC-QC method are summarized in Tables 46-1 to 46-5.

TABLE 46-1

| Ex. | Acid (INT or Reagent) | Amine (INT) | Structure | Retention time | Observed MS |
|---|---|---|---|---|---|
| 15-1 | 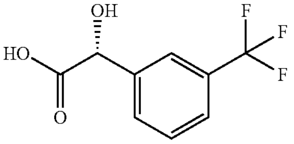 | INT-8-9 | 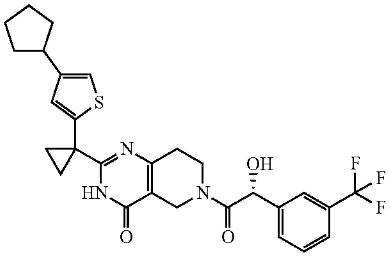 [SMILES: O=C([C@H](O)c1cccc(C(F)(F)F)c1)N1CCc2nc(C3(c4cc(C5CCCC5)cs4)CC3)[nH]c(=O)c2C1] | 2.03 min | 544.2 |

TABLE 46-1-continued
| Ex. | Acid (INT or Reagent) | Amine (INT) | Structure | Retention time | Observed MS |
|---|---|---|---|---|---|
| 15-2 | 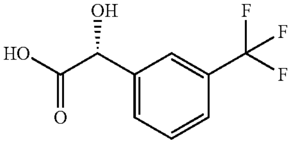 | INT-8-8 | 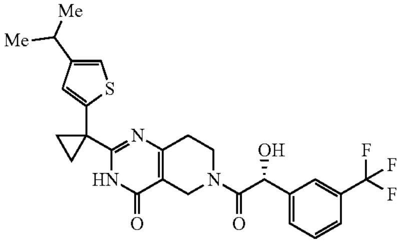 [SMILES: CC(C)c1csc(C2(c3nc4c(c(=O)[nH]3)CN(C(=O)[C@H](O)c3cccc(C(F)(F)F)c3)CC4)CC2)c1] | 1.89 min | 518.1 |
| 15-3 | 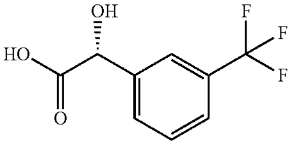 [SMILES: O=C(O)[C@H](O)c1cccc(C(F)(F)F)c1] | INT-8-12 | 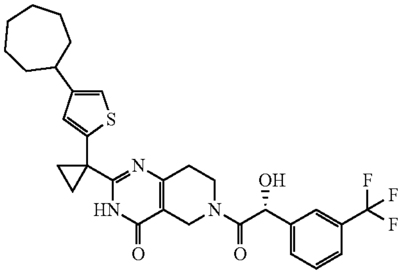 [SMILES: O=C([C@H](O)c1cccc(C(F)(F)F)c1)N1CCc2nc(C3(c4cc(C5CCCCCC5)cs4)CC3)[nH]c(=O)c2C1] | 2.19 min | 572.2 |
| 15-4 | 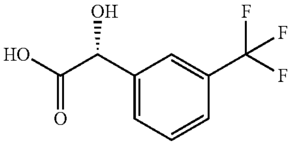 [SMILES: O=C(O)[C@H](O)c1cccc(C(F)(F)F)c1] | INT-8-10 | 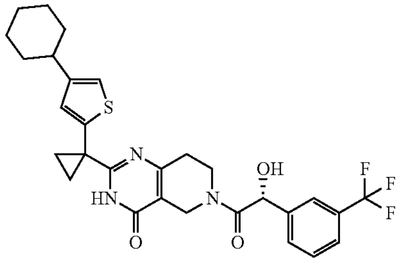 [SMILES: O=C([C@H](O)c1cccc(C(F)(F)F)c1)N1CCc2nc(C3(c4cc(C5CCCCC5)cs4)CC3)[nH]c(=O)c2C1] | 2.11 min | 558.2 |
| 15-5 | 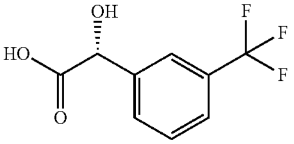 [SMILES: O=C(O)[C@H](O)c1cccc(C(F)(F)F)c1] | INT-8-7 | 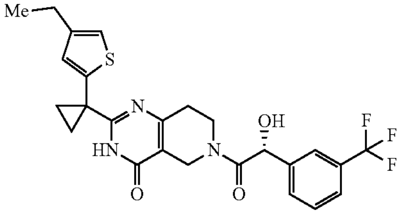 [SMILES: CCc1csc(C2(c3nc4c(c(=O)[nH]3)CN(C(=O)[C@H](O)c3cccc(C(F)(F)F)c3)CC4)CC2)c1] | 1.81 min | 504.1 |
| 15-6 | INT-25-2 | INT-4-6 | 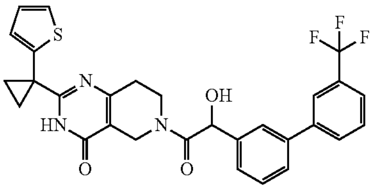 [SMILES: O=C(C(O)c1cccc(-c2cccc(C(F)(F)F)c2)c1)N1CCc2nc(C3(c4cccs4)CC3)[nH]c(=O)c2C1] | 1.87 min | 552.2 |
| 15-7 | 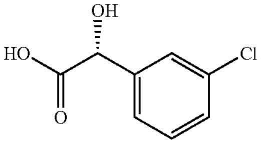 [SMILES: O=C(O)[C@H](O)c1cccc(Cl)c1] | INT-8-10 | 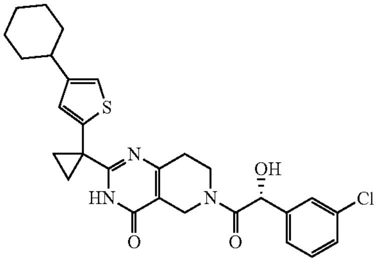 [SMILES: O=C([C@H](O)c1cccc(Cl)c1)N1CCc2nc(C3(c4cc(C5CCCCC5)cs4)CC3)[nH]c(=O)c2C1] | 2.11 min | 524.2 |

TABLE 46-2
| | | | | | |
|---|---|---|---|---|---|
| 15-8 | 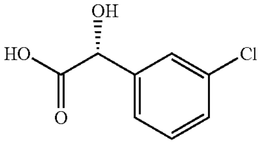 | INT-8-8 | 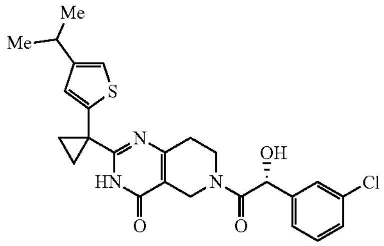 [SMILES: CC(C)c1csc(C2(c3nc4c(c(=O)[nH]3)CN(C(=O)[C@H](O)c3cccc(Cl)c3)CC4)CC2)c1] | 1.85 min | 484.2 |
| 15-9 | 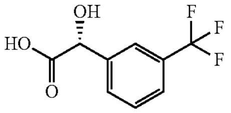 [SMILES: O=C(O)[C@H](O)c1cccc(C(F)(F)F)c1] | INT-4-19 | 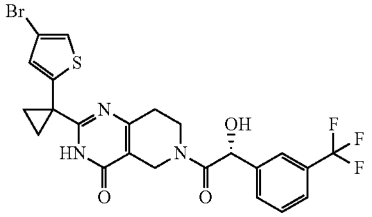 [SMILES: O=C([C@H](O)c1cccc(C(F)(F)F)c1)N1CCc2nc(C3(c4cc(Br)cs4)CC3)[nH]c(=O)c2C1] | 1.73 min | 554.0 |
| 15-10 | INT-25-5 | INT-4-6 | 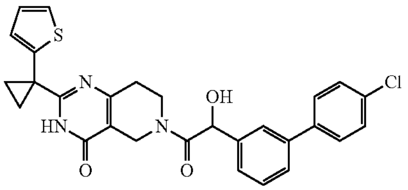 [SMILES: O=C(C(O)c1cccc(-c2ccc(Cl)cc2)c1)N1CCc2nc(C3(c4cccs4)CC3)[nH]c(=O)c2C1] | 1.84 min | 517.9 |
| 15-11 | INT-25-1 | INT-4-6 | 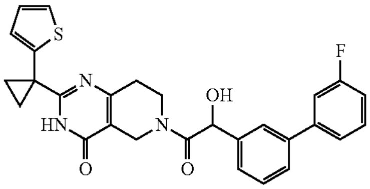 [SMILES: O=C(C(O)c1cccc(-c2cccc(F)c2)c1)N1CCc2nc(C3(c4cccs4)CC3)[nH]c(=O)c2C1] | 1.73 min | 502.0 |
| 15-12 | 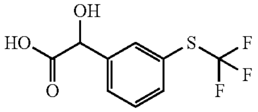 [SMILES: O=C(O)C(O)c1cccc(SC(F)(F)F)c1] | INT-4-6 | 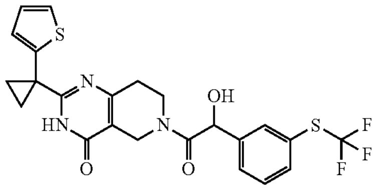 [SMILES: O=C(C(O)c1cccc(SC(F)(F)F)c1)N1CCc2nc(C3(c4cccs4)CC3)[nH]c(=O)c2C1] | 1.71 min | 508.1 |
| 15-13 | 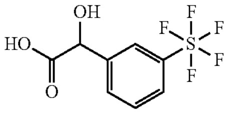 [SMILES: O=C(O)C(O)c1cccc(S(F)(F)(F)(F)F)c1] | INT-4-6 | 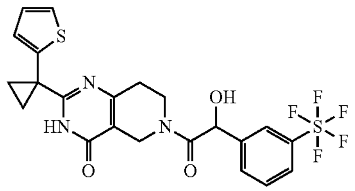 | 1.67 min | 534.0 |
| 15-14 | 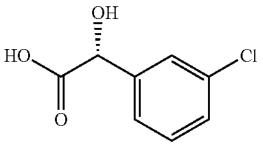 | INT-4-34 | 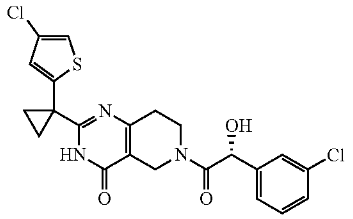 [SMILES: O=C([C@H](O)c1cccc(Cl)c1)N1CCc2nc(C3(c4cc(Cl)cs4)CC3)[nH]c(=O)c2C1] | 1.65 min | 476.0 |

TABLE 46-2-continued
| | | | | | |
|---|---|---|---|---|---|
| 15-15 | 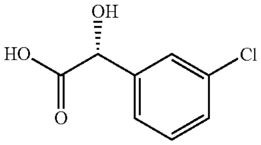 | INT-8-11 | 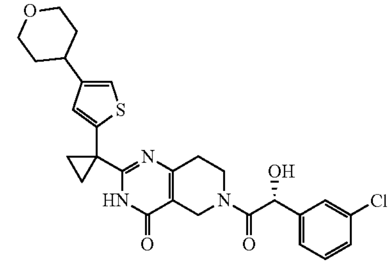 [SMILES: O=C([C@H](O)c1cccc(Cl)c1)N1CCc2nc(C3(c4cc(C5CCOCC5)cs4)CC3)[nH]c(=O)c2C1] | 1.62 min | 526.1 |
TABLE 46-3
| | | | | | |
|---|---|---|---|---|---|
| 15-16 | 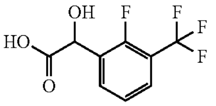 [SMILES: O=C(O)C(O)c1cccc(C(F)(F)F)c1F] | INT-4-6 | 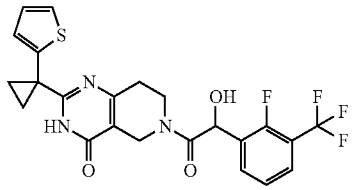 [SMILES: O=C(C(O)c1cccc(C(F)(F)F)c1F)N1CCc2nc(C3(c4cccs4)CC3)[nH]c(=O)c2C1] | 1.63 min | 494.1 |
| 15-17 | 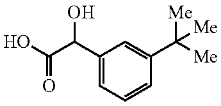 [SMILES: CC(C)(C)c1cccc(C(O)C(=O)O)c1] | INT-4-6 | 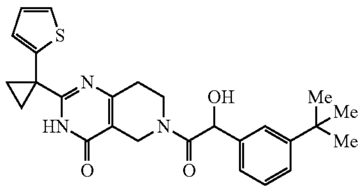 [SMILES: CC(C)(C)c1cccc(C(O)C(=O)N2CCc3nc(C4(c5cccs5)CC4)[nH]c(=O)c3C2)c1] | 1.75 min | 464.2 |
| 15-18 | 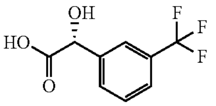 [SMILES: O=C(O)[C@H](O)c1cccc(C(F)(F)F)c1] | INT-4-6 | 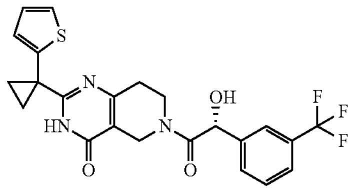 [SMILES: O=C([C@H](O)c1cccc(C(F)(F)F)c1)N1CCc2nc(C3(c4cccs4)CC3)[nH]c(=O)c2C1] | 1.60 min | 476.1 |
| 15-19 | 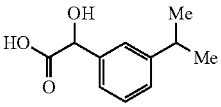 [SMILES: CC(C)c1cccc(C(O)C(=O)O)c1] | INT-4-6 | 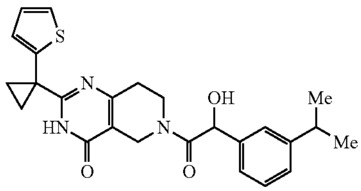 [SMILES: CC(C)c1cccc(C(O)C(=O)N2CCc3nc(C4(c5cccs5)CC4)[nH]c(=O)c3C2)c1] | 1.68 min | 450.1 |
| 15-20 | 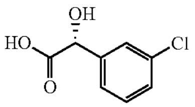 | INT-4-33 | 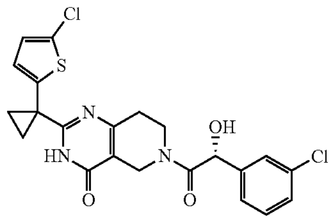 [SMILES: O=C([C@H](O)c1cccc(Cl)c1)N1CCc2nc(C3(c4ccc(Cl)s4)CC3)[nH]c(=O)c2C1] | 1.71 min | 476.0 |
| 15-21 | 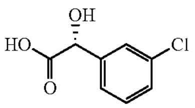 | INT-4-27 | 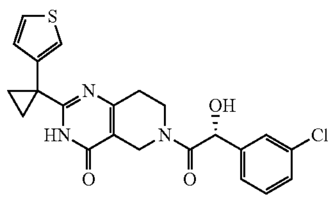 [SMILES: O=C([C@H](O)c1cccc(Cl)c1)N1CCc2nc(C3(c4ccsc4)CC3)[nH]c(=O)c2C1] | 1.51 min | 442.0 |

TABLE 46-3-continued
| | | | | | |
|---|---|---|---|---|---|
| 15-22 | 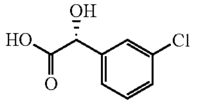 | INT-4-28 | 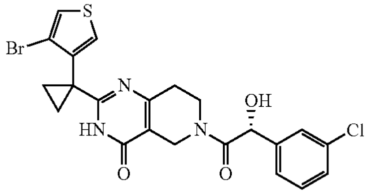 [SMILES: O=C([C@H](O)c1cccc(Cl)c1)N1CCc2nc(C3(c4cscc4Br)CC3)[nH]c(=O)c2C1] | 1.72 min | 520.0 |
TABLE 46-4
| | | | | | |
|---|---|---|---|---|---|
| 15-23 | 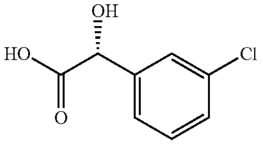 | INT-10-3 | 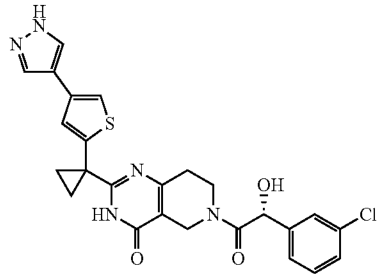 [SMILES: O=C([C@H](O)c1cccc(Cl)c1)N1CCc2nc(C3(c4cc(-c5cn[nH]c5)cs4)CC3)[nH]c(=O)c2C1] | 1.37 min | 508.1 |
| 15-24 | 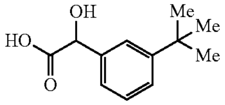 | INT-8-8 | 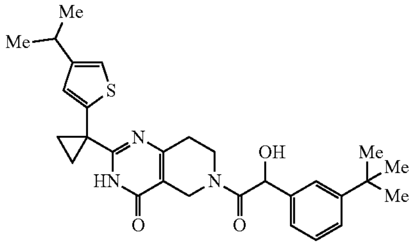 [SMILES: CC(C)c1csc(C2(c3nc4c(c(=O)[nH]3)CN(C(=O)C(O)c3cccc(C(C)(C)C)c3)CC4)CC2)c1] | 2.01 min | 506.0 |
| 15-25 | 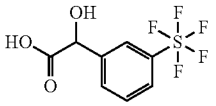 [SMILES: O=C(O)C(O)c1cccc(S(F)(F)(F)(F)F)c1] | INT-8-8 | 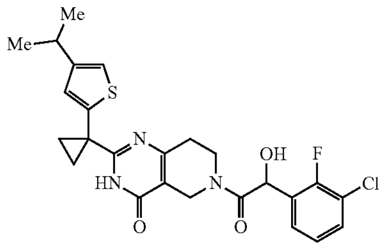 [SMILES: CC(C)c1csc(C2(c3nc4c(c(=O)[nH]3)CN(C(=O)C(O)c3cccc(Cl)c3F)CC4)CC2)c1] | 1.92 min | 575.9 |
| 15-26 | 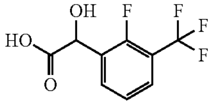 [SMILES: O=C(O)C(O)c1cccc(C(F)(F)F)c1F] | INT-8-8 | 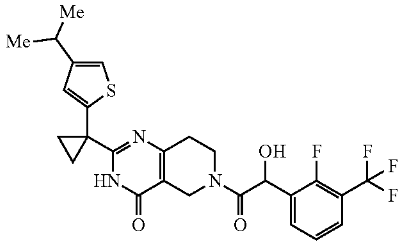 [SMILES: CC(C)c1csc(C2(c3nc4c(c(=O)[nH]3)CN(C(=O)C(O)c3cccc(C(F)(F)F)c3F)CC4)CC2)c1] | 1.89 min | 535.9 |
| 15-27 | 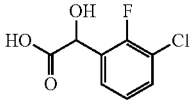 | INT-8-8 | 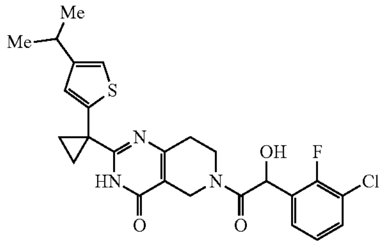 [SMILES: CC(C)c1csc(C2(c3nc4c(c(=O)[nH]3)CN(C(=O)C(O)c3cccc(Cl)c3F)CC4)CC2)c1] | 1.85 min | 501.9 |

TABLE 46-4-continued

| | | | | |
|---|---|---|---|---|
| 15-28 | INT-25-3 | INT-4-6 | 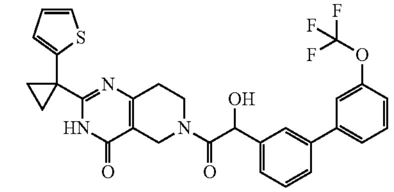 [SMILES: O=C(C(O)c1cccc(-c2cccc(OC(F)(F)F)c2)c1)N1CCc2nc(C3(c4cccs4)CC3)[nH]c(=O)c2C1] | 1.90 min 568.2 |

TABLE 46-5

| | | | | |
|---|---|---|---|---|
| 15-29 | 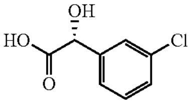 [SMILES: O=C(O)[C@H](O)c1cccc(Cl)c1] | INT-9-12 | 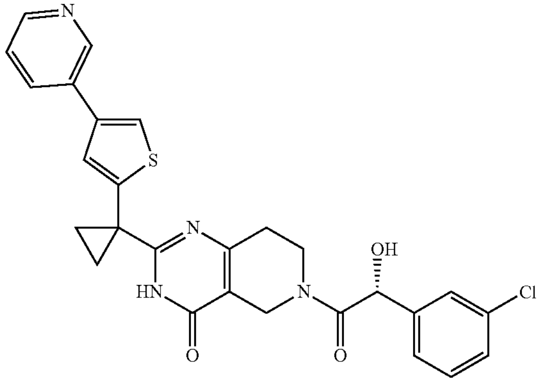 [SMILES: O=C([C@H](O)c1cccc(Cl)c1)N1CCc2nc(C3(c4cc(-c5cccnc5)cs4)CC3)[nH]c(=O)c2C1] | 1.50 min 519.1 |
| 15-30 | 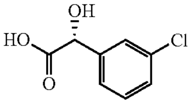 [SMILES: O=C(O)[C@H](O)c1cccc(Cl)c1] | INT-9-13 | 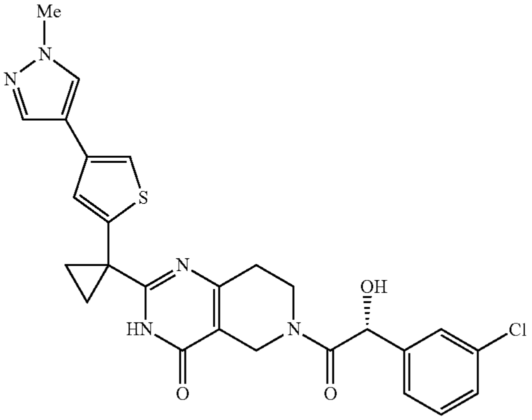 [SMILES: Cn1cc(-c2csc(C3(c4nc5c(c(=O)[nH]4)CN(C(=O)[C@H](O)c4cccc(Cl)c4)CC5)CC3)c2)cn1] | 1.47 min 522.1 |
| 15-31 | 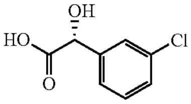 | INT-9-14 | 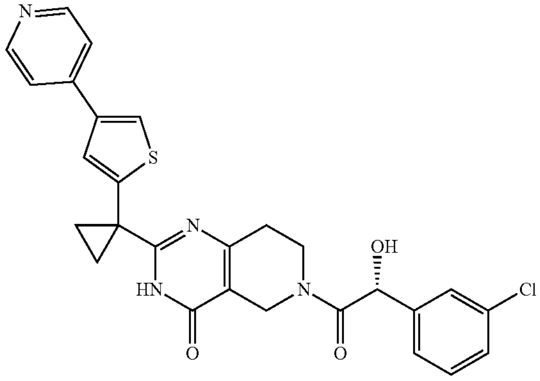 [SMILES: O=C([C@H](O)c1cccc(Cl)c1)N1CCc2nc(C3(c4cc(-c5ccncc5)cs4)CC3)[nH]c(=O)c2C1] | 1.48 min 519.1 |

The following amide derivatives (Ex-16-1 and Ex-16-2) are prepared according to the procedure of Ex-1 or the general synthesis in scheme-1 from the synthesized amine drivatives and the known or synthesized acid derivatives in Table 47. The further purification is carried out by preparative LC-MS or SFC-MS system in usual manner. The retention time and observed MS by HPLC-QC method are summarized in Table 47.

TABLE 47

| Ex | Acid (Reagent) | Amine (INT) | Structure | Retention time | Observed MS |
|---|---|---|---|---|---|
| 16-1 | 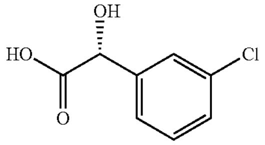 | INT-10-6 | 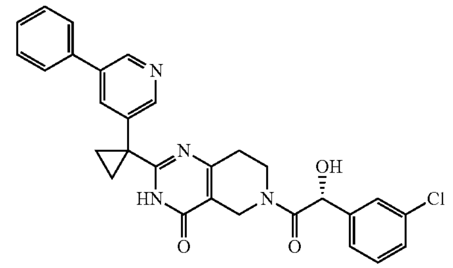 [SMILES: O=C([C@H](O)c1cccc(Cl)c1)N1CCc2nc(C3(c4cncc(-c5ccccc5)c4)CC3)[nH]c(=O)c2C1] | 1.55 min | 513.1 |
| 16-2 | 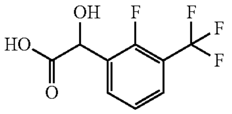 [SMILES: O=C(O)C(O)c1cccc(C(F)(F)F)c1F] | INT-10-6 | 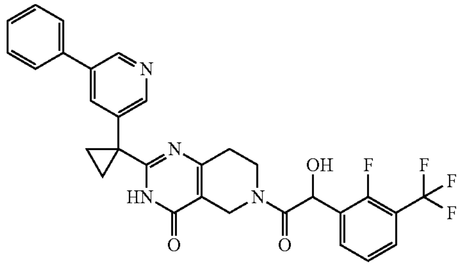 [SMILES: O=C(C(O)c1cccc(C(F)(F)F)c1F)N1CCc2nc(C3(c4cncc(-c5ccccc5)c4)CC3)[nH]c(=O)c2C1] | 1.62 min | 565.0 |

The following amide derivatives (Ex-17-1 to Ex-17-147) are prepared according to the procedure of Ex-1 or the general synthesis in scheme-1 from the synthesized amine drivatives and the known or synthesized acid derivatives in Tables 48-1 to 48-23. The further purification is carried out by preparative LC-MS or SFC-MS system in usual manner. The retention time and observed MS by HPLC-QC method are summarized in Tables 48-1 to 48-23.

TABLE 48-1

| Ex. | Acid (INT or Reagent) | Amine (INT) | Structure | Retention time | Observed MS |
|---|---|---|---|---|---|
| 17-1 | 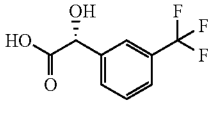 [SMILES: O=C(O)[C@H](O)c1cccc(C(F)(F)F)c1] | INT-8-20 | 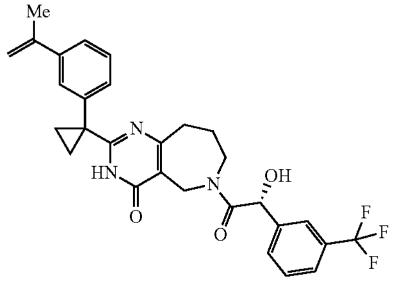 [SMILES: C=C(C)c1cccc(C2(c3nc4c(c(=O)[nH]3)CN(C(=O)[C@H](O)c3cccc(C(F)(F)F)c3)CCC4)CC2)c1] | 1.90 min | 524.2 |
| 17-2 | 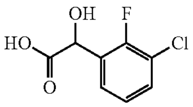 [SMILES: O=C(O)C(O)c1cccc(Cl)c1F] | INT-8-19 | 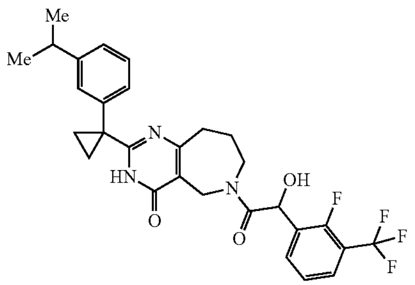 [SMILES: CC(C)c1cccc(C2(c3nc4c(c(=O)[nH]3)CN(C(=O)C(O)c3cccc(C(F)(F)F)c3F)CCC4)CC2)c1] | 1.90 min | 510.0 |

TABLE 48-1-continued
| Ex. | Acid (INT or Reagent) | Amine (INT) | Structure | Retention time | Observed MS |
|---|---|---|---|---|---|
| 17-3 | 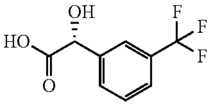 [SMILES: O=C(O)[C@H](O)c1cccc(C(F)(F)F)c1] | INT-8-16 | 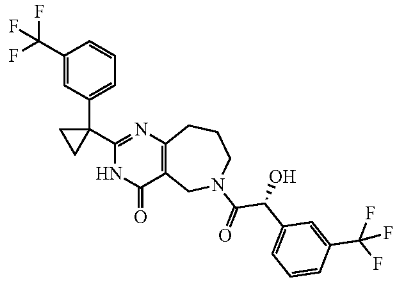 [SMILES: O=C([C@H](O)c1cccc(C(F)(F)F)c1)N1CCCc2nc(C3(c4cccc(C(F)(F)F)c4)CC3)[nH]c(=O)c2C1] | 1.80 min | 552.0 |
| 17-4 | 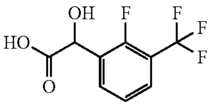 [SMILES: O=C(O)C(O)c1cccc(C(F)(F)F)c1F] | INT-8-14 | 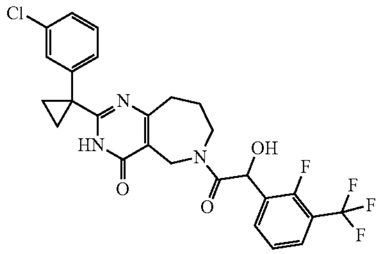 [SMILES: O=C(C(O)c1cccc(C(F)(F)F)c1F)N1CCCc2nc(C3(c4cccc(Cl)c4)CC3)[nH]c(=O)c2C1] | 1.78 min | 536.1 |
| 17-5 | INT-25-1 | INT-8-14 | 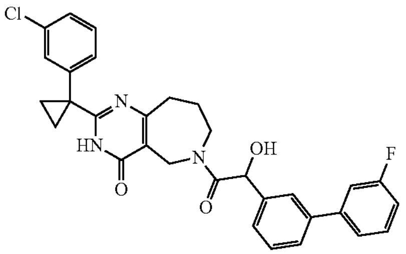 [SMILES: O=C(C(O)c1cccc(-c2cccc(F)c2)c1)N1CCCc2nc(C3(c4cccc(Cl)c4)CC3)[nH]c(=O)c2C1] | 1.90 min | 544.1 |
| 17-6 | 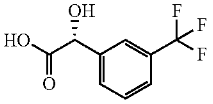 [SMILES: O=C(O)[C@H](O)c1cccc(C(F)(F)F)c1] | INT-8-18 | 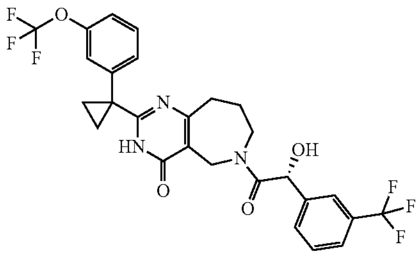 [SMILES: O=C([C@H](O)c1cccc(C(F)(F)F)c1)N1CCCc2nc(C3(c4cccc(OC(F)(F)F)c4)CC3)[nH]c(=O)c2C1] | 1.84 min | 568.0 |
TABLE 48-2
| | | | | | |
|---|---|---|---|---|---|
| 17-7 | 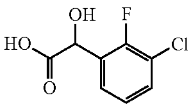 [SMILES: O=C(O)C(O)c1cccc(Cl)c1F] | INT-8-14 | 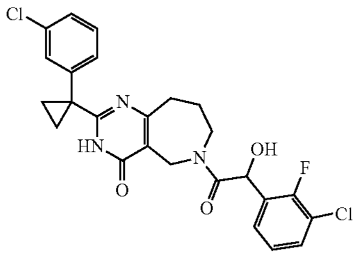 [SMILES: O=C(C(O)c1cccc(Cl)c1F)N1CCCc2nc(C3(c4cccc(Cl)c4)CC3)[nH]c(=O)c2C1] | 1.71 min | 502.1 |

TABLE 48-2-continued
| | | | | | |
|---|---|---|---|---|---|
| 17-8 | 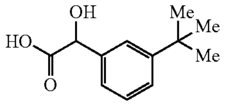 | INT-8-19 | 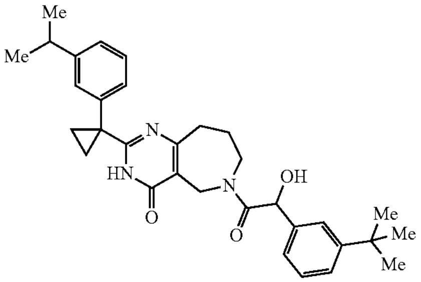 [SMILES: CC(C)c1cccc(C2(c3nc4c(c(=O)[nH]3)CN(C(=O)C(O)c3cccc(C(C)(C)C)c3)CCC4)CC2)c1] | 2.12 min | 514.1 |
| 17-9 | 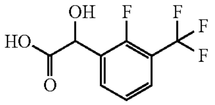 | INT-8-19 | 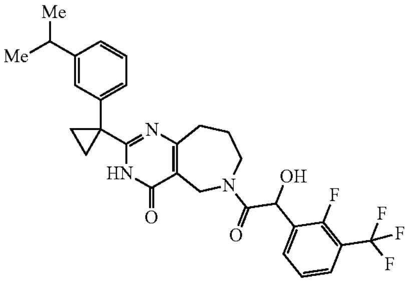 [SMILES: CC(C)c1cccc(C2(c3nc4c(c(=O)[nH]3)CN(C(=O)C(O)c3cccc(C(F)(F)F)c3F)CCC4)CC2)c1] | 1.96 min | 544.1 |
| 17-10 | 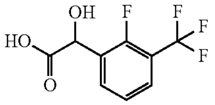 [SMILES: O=C(O)C(O)c1cccc(C(F)(F)F)c1F] | INT-8-13 | 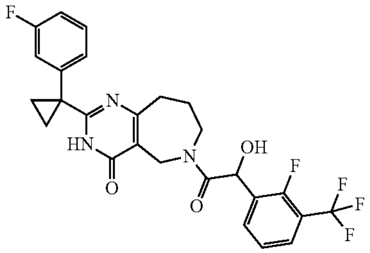 [SMILES: O=C(C(O)c1cccc(C(F)(F)F)c1F)N1CCCc2nc(C3(c4cccc(F)c4)CC3)[nH]c(=O)c2C1] | 1.69 min | 520.1 |
| 17-11 | 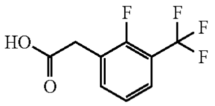 [SMILES: O=C(O)Cc1cccc(C(F)(F)F)c1F] | INT-8-3 | 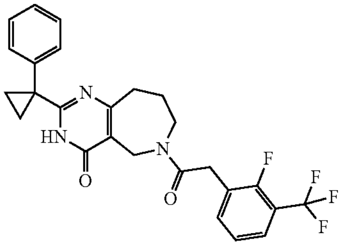 [SMILES: O=C(Cc1cccc(C(F)(F)F)c1F)N1CCCc2nc(C3(c4ccccc4)CC3)[nH]c(=O)c2C1] | 1.79 min | 486.1 |
| 17-12 | 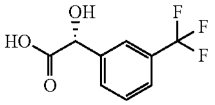 | INT-8-14 | 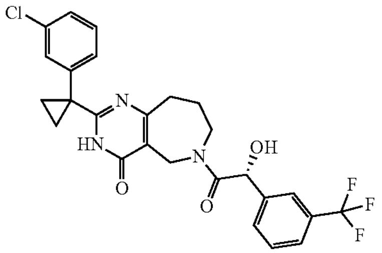 [SMILES: O=C([C@H](O)c1cccc(C(F)(F)F)c1)N1CCCc2nc(C3(c4cccc(Cl)c4)CC3)[nH]c(=O)c2C1] | 1.78 min | 518.1 |
| 17-13 | 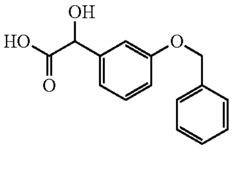 [SMILES: O=C(O)C(O)c1cccc(OCc2ccccc2)c1] | INT-8-14 | 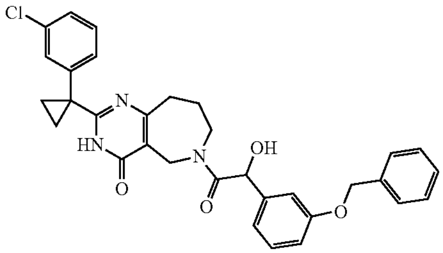 [SMILES: O=C(C(O)c1cccc(OCc2ccccc2)c1)N1CCCc2nc(C3(c4cccc(Cl)c4)CC3)[nH]c(=O)c2C1] | 1.90 min | 556.1 |

TABLE 48-3
| | | | | | |
|---|---|---|---|---|---|
| 17-14 | INT-25-2 | INT-8-13 | 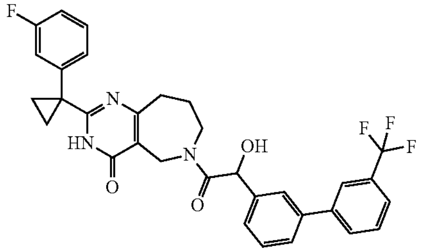 [SMILES: O=C(C(O)c1cccc(-c2cccc(C(F)(F)F)c2)c1)N1CCCc2nc(C3(c4cccc(F)c4)CC3)[nH]c(=O)c2C1] | 1.93 min | 578.2 |
| 17-15 | INT-25-3 | INT-8-13 | 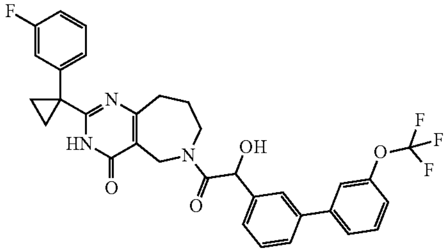 [SMILES: O=C(C(O)c1cccc(-c2cccc(OC(F)(F)F)c2)c1)N1CCCc2nc(C3(c4cccc(F)c4)CC3)[nH]c(=O)c2C1] | 1.97 min | 594.2 |
| 17-16 | INT-25-2 | INT-8-14 | 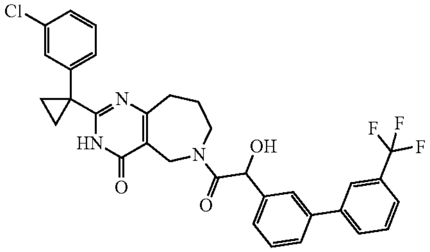 [SMILES: O=C(C(O)c1cccc(-c2cccc(C(F)(F)F)c2)c1)N1CCCc2nc(C3(c4cccc(Cl)c4)CC3)[nH]c(=O)c2C1] | 2.01 min | 594.2 |
| 17-17 | INT-25-5 | INT-8-14 | 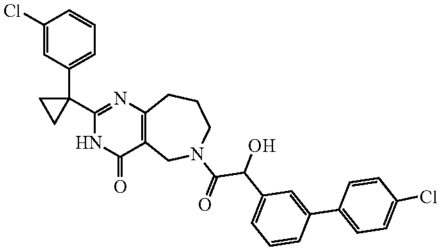 [SMILES: O=C(C(O)c1cccc(-c2ccc(Cl)cc2)c1)N1CCCc2nc(C3(c4cccc(Cl)c4)CC3)[nH]c(=O)c2C1] | 2.00 min | 560.0 |
| 17-18 | 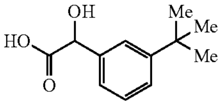 [SMILES: CC(C)(C)c1cccc(C(O)C(=O)O)c1] | INT-8-14 | 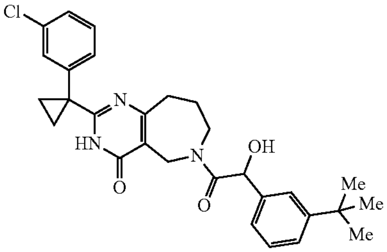 [SMILES: CC(C)(C)c1cccc(C(O)C(=O)N2CCCc3nc(C4(c5cccc(Cl)c5)CC4)[nH]c(=O)c3C2)c1] | 1.94 min | 506.2 |
| 17-19 | INT-25-4 | INT-8-14 | 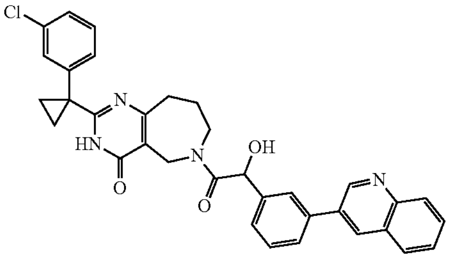 [SMILES: O=C(C(O)c1cccc(-c2cnc3ccccc3c2)c1)N1CCCc2nc(C3(c4cccc(Cl)c4)CC3)[nH]c(=O)c2C1] | 1.75 min | 577.0 |

TABLE 48-3-continued
| | | | | | |
|---|---|---|---|---|---|
| 17-20 | 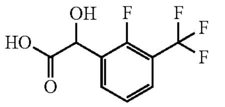 [SMILES: O=C(O)C(O)c1cccc(C(F)(F)F)c1F] | INT-8-3 | 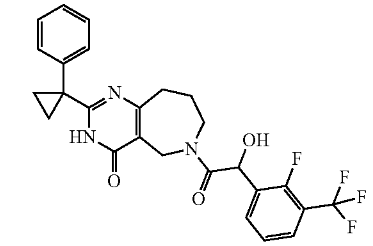 [SMILES: O=C(C(O)c1cccc(C(F)(F)F)c1F)N1CCCc2nc(C3(c4ccccc4)CC3)[nH]c(=O)c2C1] | 1.68 min | 502.2 |
TABLE 48-4
| | | | | | |
|---|---|---|---|---|---|
| 17-21 | 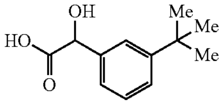 | INT-8-13 | 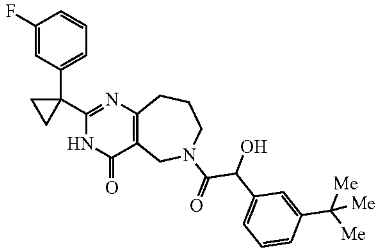 [SMILES: CC(C)(C)c1cccc(C(O)C(=O)N2CCCc3nc(C4(c5cccc(F)c5)CC4)[nH]c(=O)c3C2)c1] | 1.84 min | 490.3 |
| 17-22 | 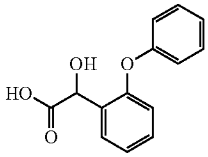 [SMILES: O=C(O)C(O)c1ccccc1Oc1ccccc1] | INT-8-14 | 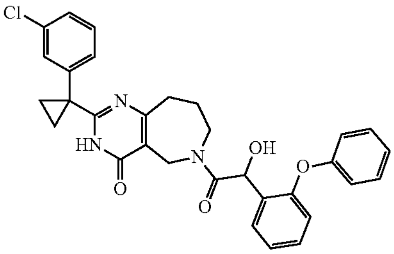 [SMILES: O=C(C(O)c1ccccc1Oc1ccccc1)N1CCCc2nc(C3(c4cccc(Cl)c4)CC3)[nH]c(=O)c2C1] | 1.87 min | 542.0 |
| 17-23 | INT-25-3 | INT-8-14 | 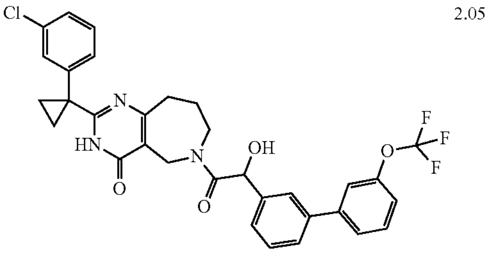 | 2.05 min | 610.1 |
| 17-24 | 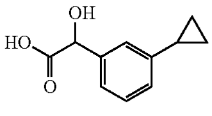 [SMILES: O=C(O)C(O)c1cccc(C2CC2)c1] | INT-8-14 | 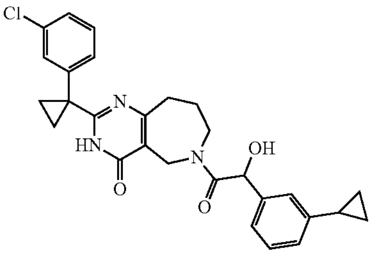 [SMILES: O=C(C(O)c1cccc(C2CC2)c1)N1CCCc2nc(C3(c4cccc(Cl)c4)CC3)[nH]c(=O)c2C1] | 1.78 min | 490.1 |

TABLE 48-4-continued
| | | | | | |
|---|---|---|---|---|---|
| 17-25 | 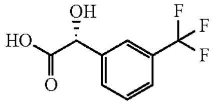 [SMILES: O=C(O)[C@H](O)c1cccc(C(F)(F)F)c1] | INT-8-21 | 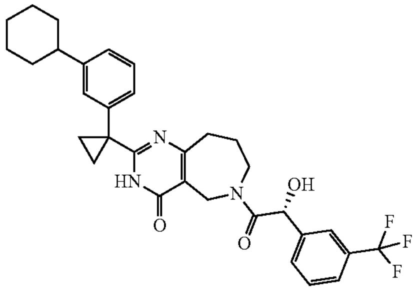 [SMILES: O=C([C@H](O)c1cccc(C(F)(F)F)c1)N1CCCc2nc(C3(c4cccc(C5CCCCC5)c4)CC3)[nH]c(=O)c2C1] | 2.20 min | 566.3 |
| 17-26 | 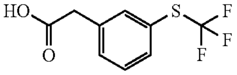 [SMILES: O=C(O)Cc1cccc(SC(F)(F)F)c1] | INT-8-3 | 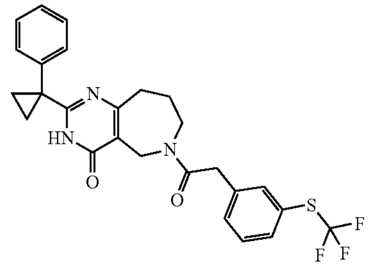 [SMILES: O=C(Cc1cccc(SC(F)(F)F)c1)N1CCCc2nc(C3(c4ccccc4)CC3)[nH]c(=O)c2C1] | 1.89 min | 500.1 |
| 17-27 | 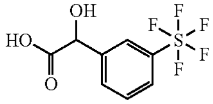 | INT-8-14 | 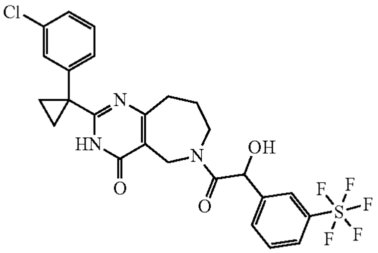 [SMILES: O=C(C(O)c1cccc(S(F)(F)(F)(F)F)c1)N1CCCc2nc(C3(c4cccc(Cl)c4)CC3)[nH]c(=O)c2C1] | 1.86 min | 576.1 |
TABLE 48-5
| | | | | | |
|---|---|---|---|---|---|
| 17-28 | 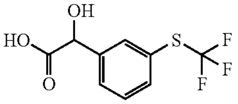 [SMILES: O=C(O)C(O)c1cccc(SC(F)(F)F)c1] | INT-8-14 | 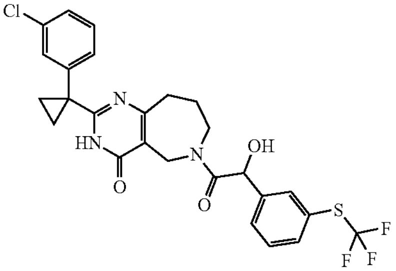 [SMILES: O=C(C(O)c1cccc(SC(F)(F)F)c1)N1CCCc2nc(C3(c4cccc(Cl)c4)CC3)[nH]c(=O)c2C1] | 1.89 min | 550.1 |
| 17-29 | 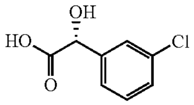 | INT-8-14 | 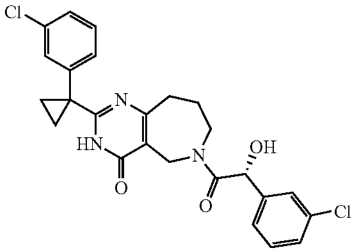 [SMILES: O=C([C@H](O)c1cccc(Cl)c1)N1CCCc2nc(C3(c4cccc(Cl)c4)CC3)[nH]c(=O)c2C1] | 1.71 min | 484.0 |

TABLE 48-5-continued
| | | | | | |
|---|---|---|---|---|---|
| 17-30 | 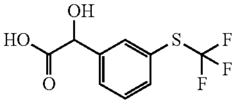 [SMILES: O=C(O)C(O)c1cccc(SC(F)(F)F)c1] | INT-8-13 | 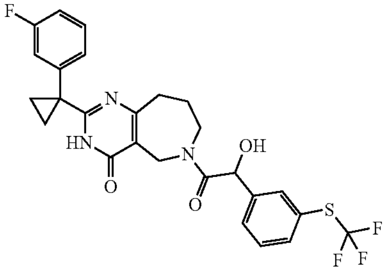 [SMILES: O=C(C(O)c1cccc(SC(F)(F)F)c1)N1CCCc2nc(C3(c4cccc(F)c4)CC3)[nH]c(=O)c2C1] | 1.80 min | 534.1 |
| 17-31 | 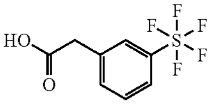 [SMILES: O=C(O)Cc1cccc(S(F)(F)(F)(F)F)c1] | INT-8-3 | 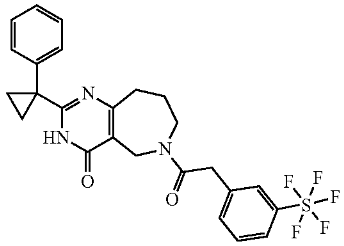 [SMILES: O=C(Cc1cccc(S(F)(F)(F)(F)F)c1)N1CCCc2nc(C3(c4ccccc4)CC3)[nH]c(=O)c2C1] | 1.85 min | 526.1 |
| 17-32 | 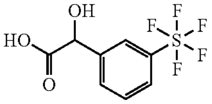 [SMILES: O=C(O)C(O)c1cccc(S(F)(F)(F)(F)F)c1] | INT-8-13 | 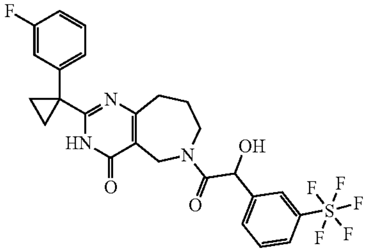 [SMILES: O=C(C(O)c1cccc(S(F)(F)(F)(F)F)c1)N1CCCc2nc(C3(c4cccc(F)c4)CC3)[nH]c(=O)c2C1] | 1.76 min | 560.2 |
| 17-33 | 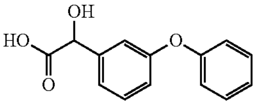 [SMILES: O=C(O)C(O)c1cccc(Oc2ccccc2)c1] | INT-8-14 | 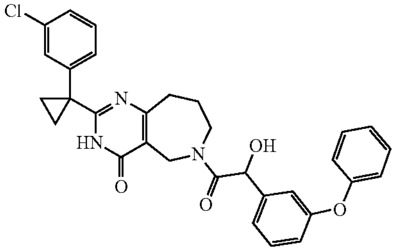 [SMILES: O=C(C(O)c1cccc(Oc2ccccc2)c1)N1CCCc2nc(C3(c4cccc(Cl)c4)CC3)[nH]c(=O)c2C1] | 1.90 min | 542.1 |
TABLE 48-6
| | | | | | |
|---|---|---|---|---|---|
| 17-34 | INT-25-5 | INT-8-13 | 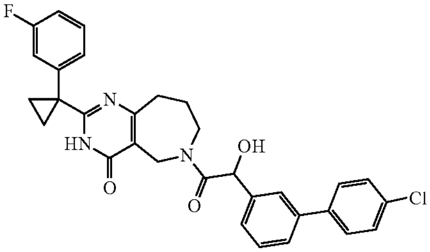 [SMILES: O=C(C(O)c1cccc(-c2ccc(Cl)cc2)c1)N1CCCc2nc(C3(c4cccc(F)c4)CC3)[nH]c(=O)c2C1] | 1.91 min | 544.1 |

TABLE 48-6-continued
| | | | | |
|---|---|---|---|---|
| 17-35 | 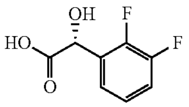 | INT-8-14 | 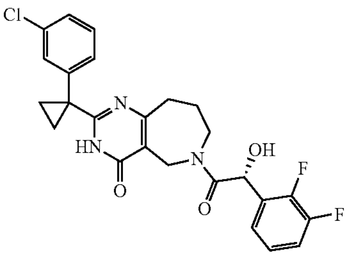 [SMILES: O=C([C@H](O)c1cccc(F)c1F)N1CCCc2nc(C3(c4cccc(Cl)c4)CC3)[nH]c(=O)c2C1] | 1.64 min 486.1 |
| 17-36 | 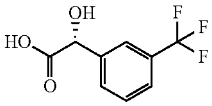 [SMILES: O=C(O)[C@H](O)c1cccc(C(F)(F)F)c1] | INT-8-13 | 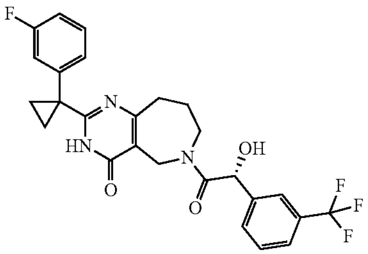 [SMILES: O=C([C@H](O)c1cccc(C(F)(F)F)c1)N1CCCc2nc(C3(c4cccc(F)c4)CC3)[nH]c(=O)c2C1] | 1.69 min 502.2 |
| 17-37 | 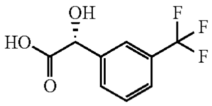 | INT-8-3 | 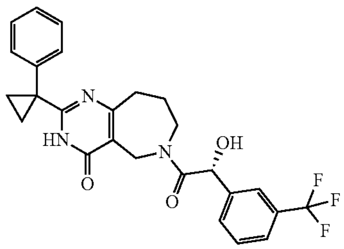 [SMILES: O=C([C@H](O)c1cccc(C(F)(F)F)c1)N1CCCc2nc(C3(c4ccccc4)CC3)[nH]c(=O)c2C1] | 1.68 min 484.1 |
| 17-38 | 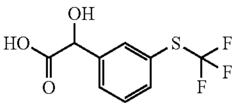 [SMILES: O=C(O)C(O)c1cccc(SC(F)(F)F)c1] | INT-8-3 | 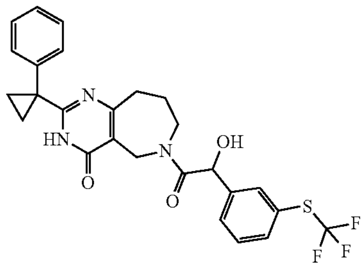 [SMILES: O=C(C(O)c1cccc(SC(F)(F)F)c1)N1CCCc2nc(C3(c4ccccc4)CC3)[nH]c(=O)c2C1] | 1.80 min 516.2 |
| 17-39 | 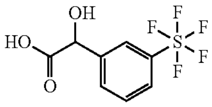 [SMILES: O=C(O)C(O)c1cccc(S(F)(F)(F)(F)F)c1] | INT-8-19 | 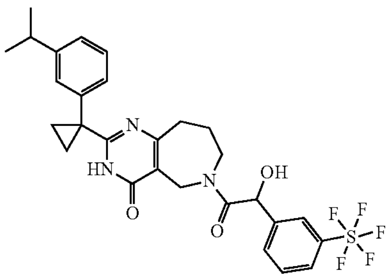 [SMILES: CC(C)c1cccc(C2(c3nc4c(c(=O)[nH]3)CN(C(=O)C(O)c3cccc(S(F)(F)(F)(F)F)c3)CCC4)CC2)c1] | 2.03 min 584.1 |

TABLE 48-7
| | | | | |
|---|---|---|---|---|
| 17-40 | 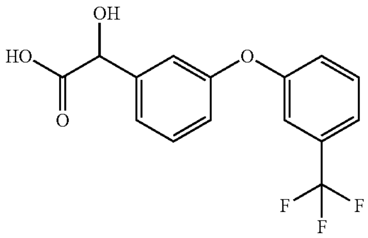 [SMILES: O=C(O)C(O)c1cccc(Oc2cccc(C(F)(F)F)c2)c1] | INT-8-14 | 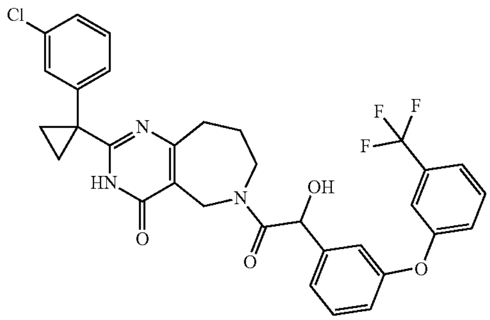 [SMILES: O=C(C(O)c1cccc(Oc2cccc(C(F)(F)F)c2)c1)N1CCCc2nc(C3(c4cccc(Cl)c4)CC3)[nH]c(=O)c2C1] | 2.02 min 610.0 |
| 17-41 | 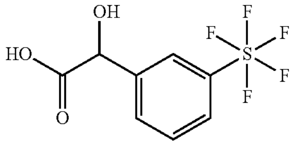 | INT-8-3 | 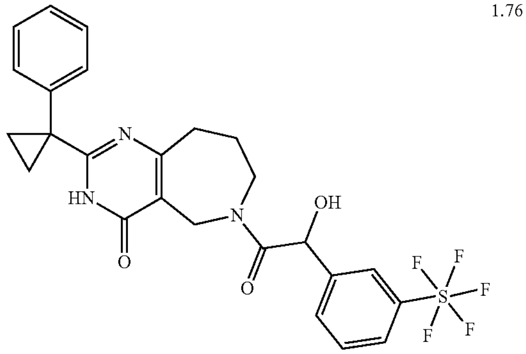 | 1.76 min 542.1 |
| 17-42 | 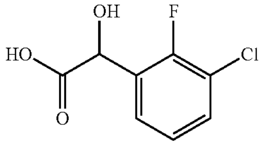 | INT-8-3 | 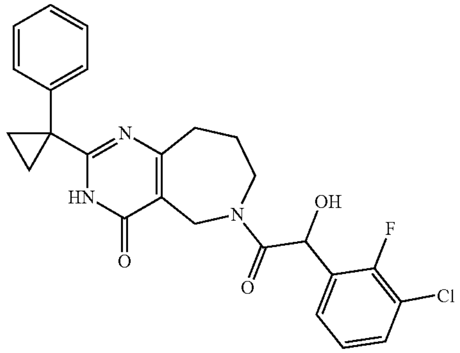 [SMILES: O=C(C(O)c1cccc(Cl)c1F)N1CCCc2nc(C3(c4ccccc4)CC3)[nH]c(=O)c2C1] | 1.59 min 468.1 |
| 17-43 | 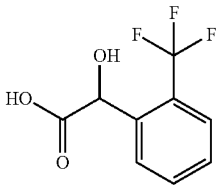 [SMILES: O=C(O)C(O)c1ccccc1C(F)(F)F] | INT-8-14 | 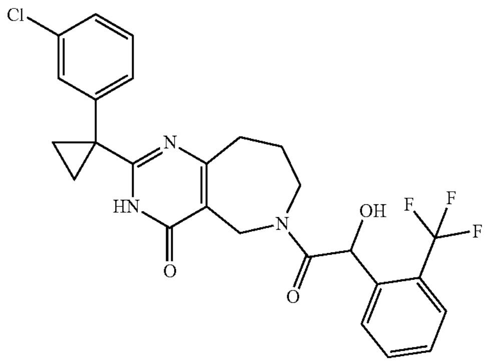 [SMILES: O=C(C(O)c1ccccc1C(F)(F)F)N1CCCc2nc(C3(c4cccc(Cl)c4)CC3)[nH]c(=O)c2C1] | 1.75 min 518.1 |

TABLE 48-7-continued
| | | | | |
|---|---|---|---|---|
| 17-44 | 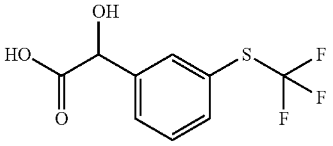 [SMILES: O=C(O)C(O)c1cccc(SC(F)(F)F)c1] | INT-8-19 | 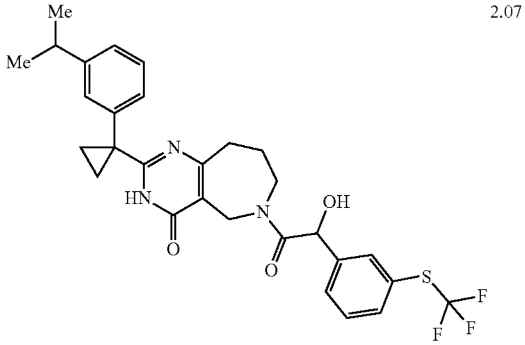 | 2.07 min 558.1 |
| 17-45 | INT-25-2 | INT-8-19 | 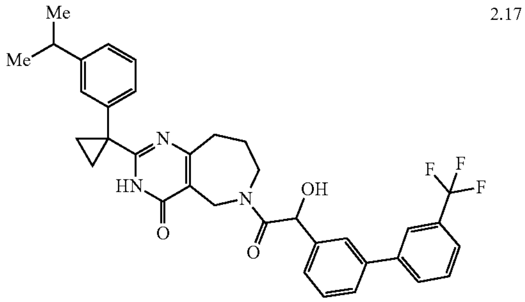 | 2.17 min 602.1 |
TABLE 48-8
| | | | | |
|---|---|---|---|---|
| 17-46 | 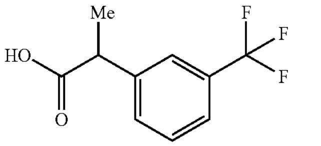 [SMILES: CC(C(=O)O)c1cccc(C(F)(F)F)c1] | INT-8-3 | 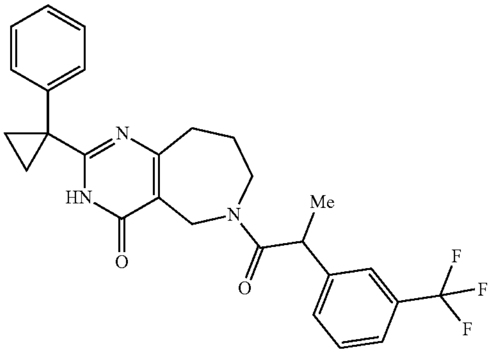 [SMILES: CC(C(=O)N1CCCc2nc(C3(c4ccccc4)CC3)[nH]c(=O)c2C1)c1cccc(C(F)(F)F)c1] | 1.86 min 482.2 |
| 17-47 | 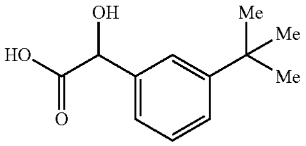 | INT-8-3 | 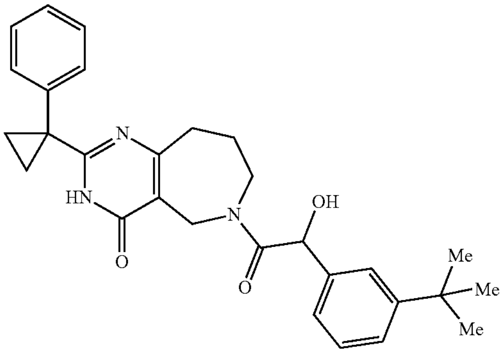 [SMILES: CC(C)(C)c1cccc(C(O)C(=O)N2CCCc3nc(C4(c5ccccc5)CC4)[nH]c(=O)c3C2)c1] | 1.85 min 472.2 |

TABLE 48-8-continued
| | | | | | |
|---|---|---|---|---|---|
| 17-48 | INT-25-1 | INT-8-13 | 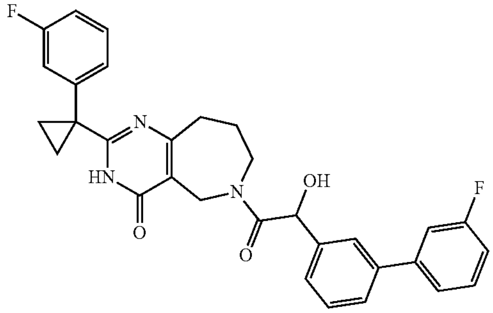 [SMILES: O=C(C(O)c1cccc(-c2cccc(F)c2)c1)N1CCCc2nc(C3(c4cccc(F)c4)CC3)[nH]c(=O)c2C1] | 1.81 min | 528.1 |
| 17-49 | INT-25-3 | INT-8-19 | 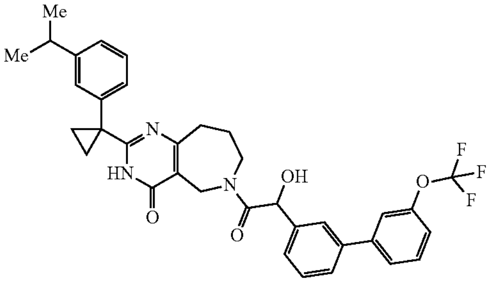 [SMILES: CC(C)c1cccc(C2(c3nc4c(c(=O)[nH]3)CN(C(=O)C(O)c3cccc(-c5cccc(OC(F)(F)F)c5)c3)CCC4)CC2)c1] | 2.20 min | 618.1 |
| 17-50 | 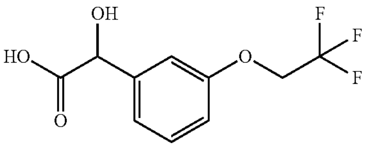 [SMILES: O=C(O)C(O)c1cccc(OCC(F)(F)F)c1] | INT-8-14 | 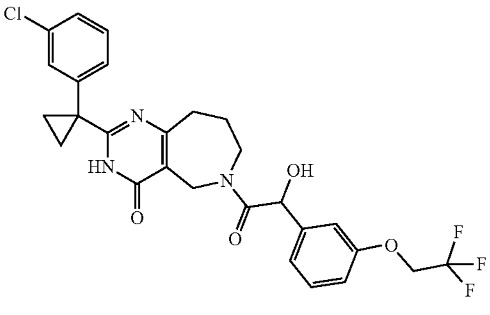 [SMILES: O=C(C(O)c1cccc(OCC(F)(F)F)c1)N1CCCc2nc(C3(c4cccc(Cl)c4)CC3)[nH]c(=O)c2C1] | 1.79 min | 548.1 |
| 17-51 | 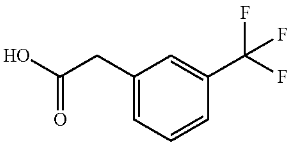 [SMILES: O=C(O)Cc1cccc(C(F)(F)F)c1] | INT-8-3 | 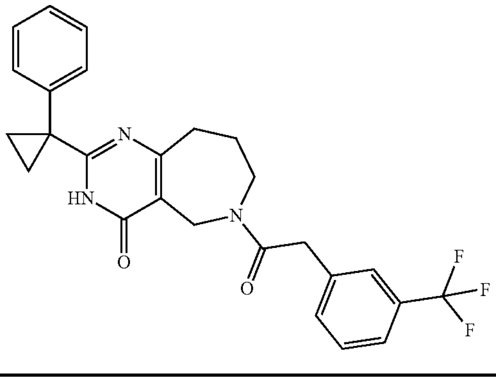 | 1.78 min | 468.2 |

TABLE 48-9
| | | | | |
|---|---|---|---|---|
| 17-52 | 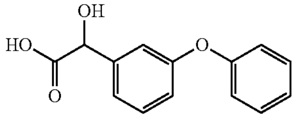 [SMILES: O=C(O)C(O)c1cccc(Oc2ccccc2)c1] | INT-8-13 | 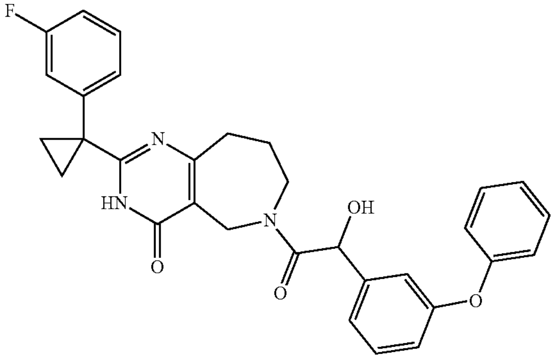 [SMILES: O=C(C(O)c1cccc(Oc2ccccc2)c1)N1CCCc2nc(C3(c4cccc(F)c4)CC3)[nH]c(=O)c2C1] | 1.81 min 526.2 |
| 17-53 | 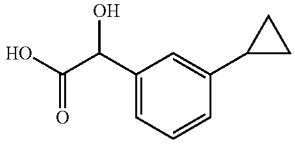 [SMILES: O=C(O)C(O)c1cccc(C2CC2)c1] | INT-8-13 | 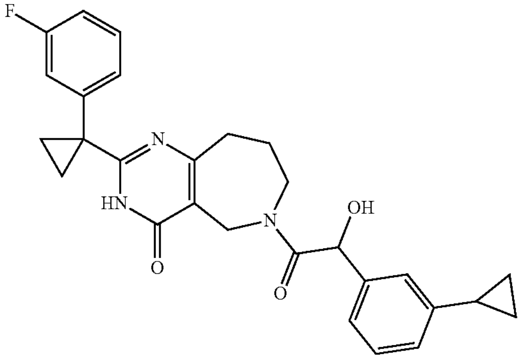 [SMILES: O=C(C(O)c1cccc(C2CC2)c1)N1CCCc2nc(C3(c4cccc(F)c4)CC3)[nH]c(=O)c2C1] | 1.68 min 474.2 |
| 17-54 | 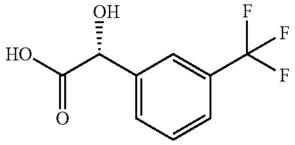 | INT-8-17 | 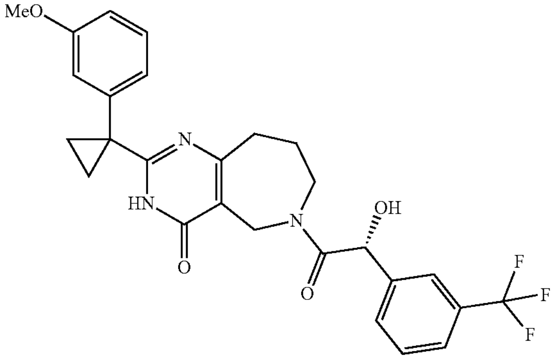 [SMILES: COc1cccc(C2(c3nc4c(c(=O)[nH]3)CN(C(=O)[C@H](O)c3cccc(C(F)(F)F)c3)CCC4)CC2)c1] | 1.69 min 514.2 |
| 17-55 | 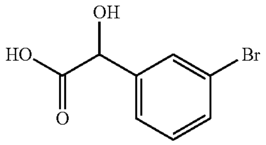 [SMILES: O=C(O)C(O)c1cccc(Br)c1] | INT-8-3 | 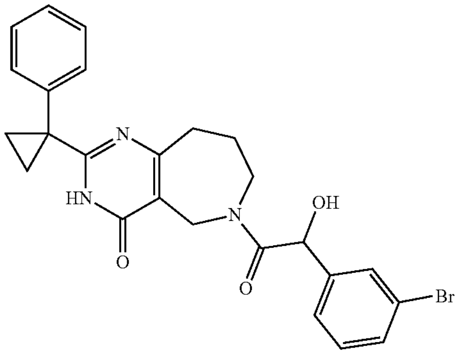 [SMILES: O=C(C(O)c1cccc(Br)c1)N1CCCc2nc(C3(c4ccccc4)CC3)[nH]c(=O)c2C1] | 1.62 min 494.0 |

TABLE 48-9-continued
| | | | | |
|---|---|---|---|---|
| 17-56 | 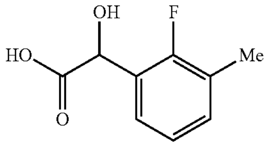 [SMILES: Cc1cccc(C(O)C(=O)O)c1F] | INT-8-3 | 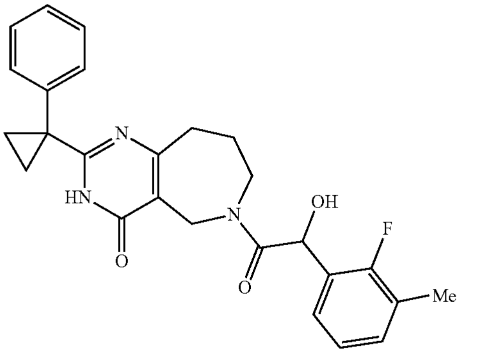 [SMILES: Cc1cccc(C(O)C(=O)N2CCCc3nc(C4(c5ccccc5)CC4)[nH]c(=O)c3C2)c1F] | 1.55 min 448.2 |
| 17-57 | 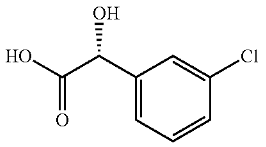 | INT-8-13 | 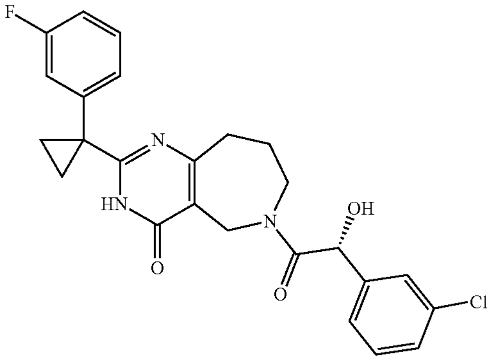 [SMILES: O=C([C@H](O)c1cccc(Cl)c1)N1CCCc2nc(C3(c4cccc(F)c4)CC3)[nH]c(=O)c2C1] | 1.61 min 468.1 |
TABLE 48-10
| | | | | |
|---|---|---|---|---|
| 17-58 | 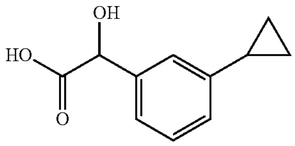 | INT-8-3 | 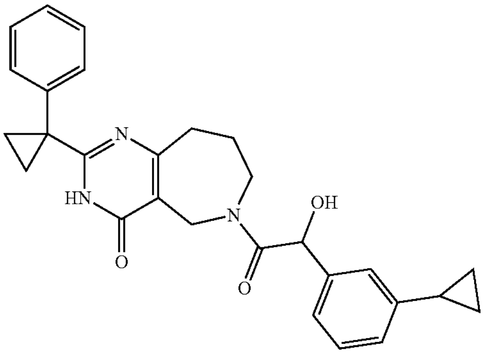 [SMILES: O=C(C(O)c1cccc(C2CC2)c1)N1CCCc2nc(C3(c4ccccc4)CC3)[nH]c(=O)c2C1] | 1.67 min 456.2 |
| 17-59 | 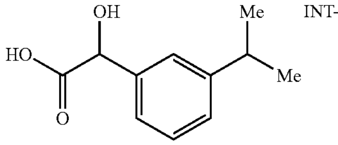 | INT-8-3 | 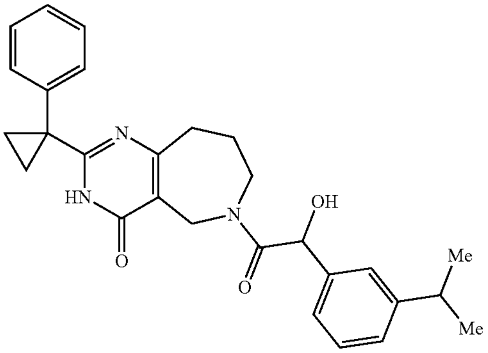 [SMILES: CC(C)c1cccc(C(O)C(=O)N2CCCc3nc(C4(c5ccccc5)CC4)[nH]c(=O)c3C2)c1] | 1.77 min 458.2 |

TABLE 48-10-continued
| | | | | |
|---|---|---|---|---|
| 17-60 | 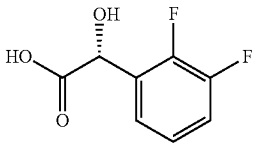 [SMILES: O=C(O)[C@H](O)c1cccc(F)c1F] | INT-8-13 | 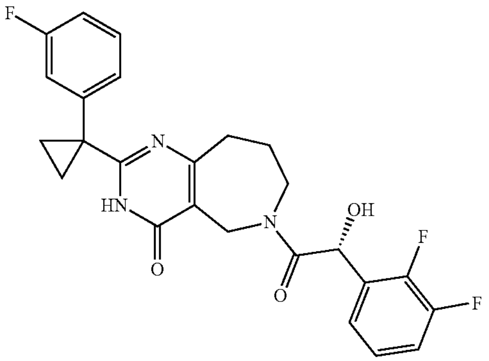 [SMILES: O=C([C@H](O)c1cccc(F)c1F)N1CCCc2nc(C3(c4cccc(F)c4)CC3)[nH]c(=O)c2C1] | 1.54 min 470.1 |
| 17-61 | 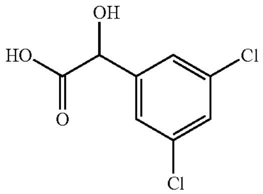 | INT-8-3 | 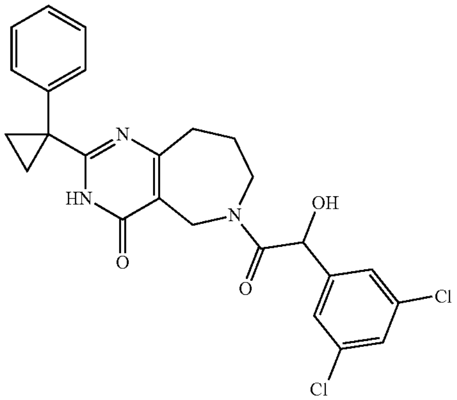 [SMILES: O=C(C(O)c1cc(Cl)cc(Cl)c1)N1CCCc2nc(C3(c4ccccc4)CC3)[nH]c(=O)c2C1] | 1.76 min 484.1 |
| 17-62 | 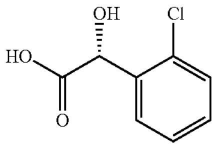 [SMILES: O=C(O)[C@H](O)c1ccccc1Cl] | INT-8-3 | 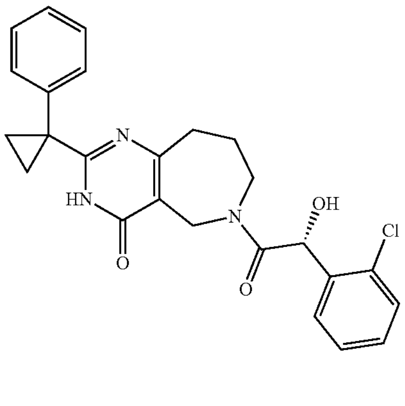 [SMILES: O=C([C@H](O)c1ccccc1Cl)N1CCCc2nc(C3(c4ccccc4)CC3)[nH]c(=O)c2C1] | 1.53 min 450.1 |
| 17-63 | 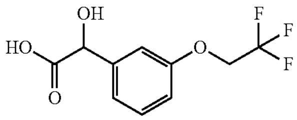 [SMILES: O=C(O)C(O)c1cccc(OCC(F)(F)F)c1] | INT-8-3 | 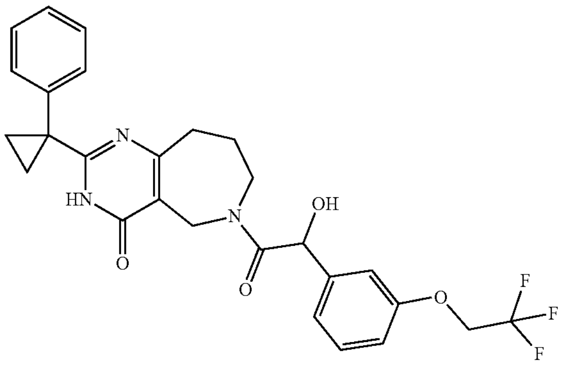 [SMILES: O=C(C(O)c1cccc(OCC(F)(F)F)c1)N1CCCc2nc(C3(c4ccccc4)CC3)[nH]c(=O)c2C1] | 1.69 min 514.1 |

TABLE 48-11
| | | | | |
|---|---|---|---|---|
| 17-64 | 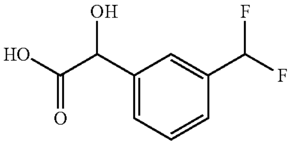 [SMILES: O=C(O)C(O)c1cccc(C(F)F)c1] | INT-8-3 | 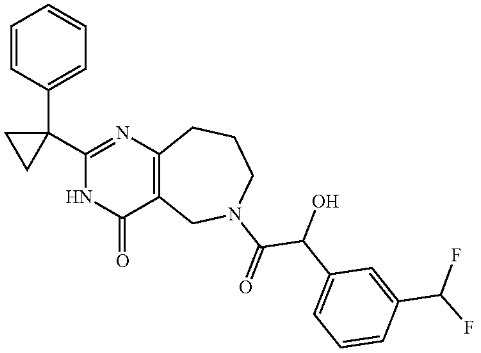 [SMILES: O=C(C(O)c1cccc(C(F)F)c1)N1CCCc2nc(C3(c4ccccc4)CC3)[nH]c(=O)c2C1] | 1.55 min 466.1 |
| 17-65 | 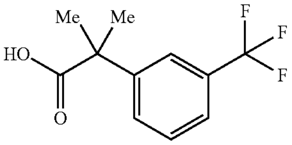 [SMILES: CC(C)(C(=O)O)c1cccc(C(F)(F)F)c1] | INT-8-3 | 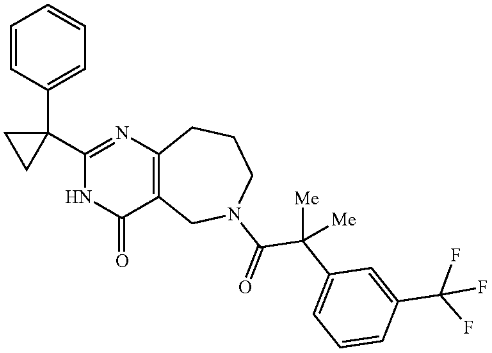 [SMILES: CC(C)(C(=O)N1CCCc2nc(C3(c4ccccc4)CC3)[nH]c(=O)c2C1)c1cccc(C(F)(F)F)c1] | 1.91 min 496.2 |
| 17-66 | 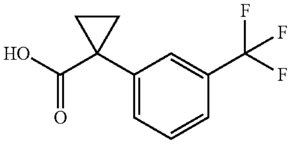 [SMILES: O=C(O)C1(c2cccc(C(F)(F)F)c2)CC1] | INT-8-3 | 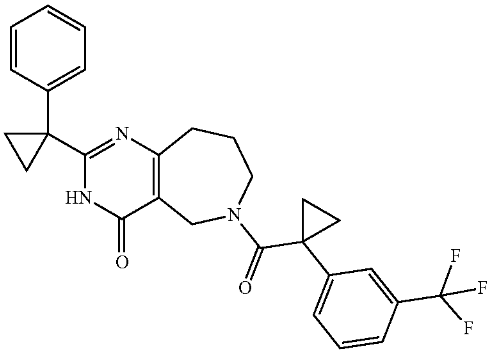 [SMILES: O=C(N1CCCc2nc(C3(c4ccccc4)CC3)[nH]c(=O)c2C1)C1(c2cccc(C(F)(F)F)c2)CC1] | 1.82 min 494.1 |
| 17-67 | 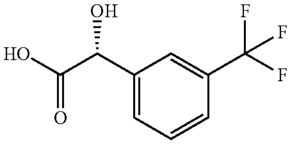 | INT-8-3 | 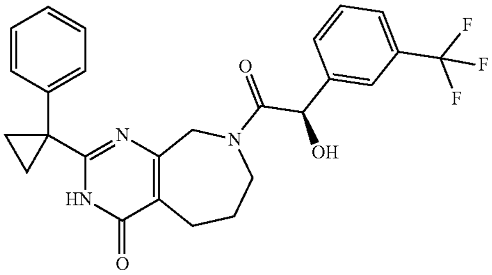 [SMILES: O=C([C@H](O)c1cccc(C(F)(F)F)c1)N1CCCc2c(nc(C3(c4ccccc4)CC3)[nH]c2=O)C1] | 1.67 min 484.1 |

TABLE 48-11-continued
| | | | | |
|---|---|---|---|---|
| 17-68 | 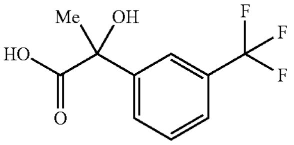 [SMILES: CC(O)(C(=O)O)c1cccc(C(F)(F)F)c1] | INT-8-3 | 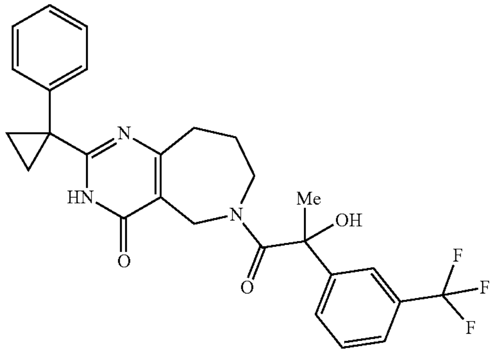 [SMILES: CC(O)(C(=O)N1CCCc2nc(C3(c4ccccc4)CC3)[nH]c(=O)c2C1)c1cccc(C(F)(F)F)c1] | 1.75 min 498.0 |
| 17-69 | 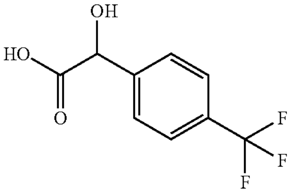 [SMILES: O=C(O)C(O)c1ccc(C(F)(F)F)cc1] | INT-8-14 | 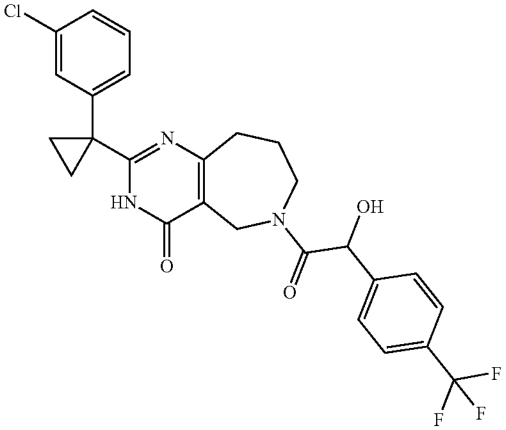 [SMILES: O=C(C(O)c1ccc(C(F)(F)F)cc1)N1CCCc2nc(C3(c4cccc(Cl)c4)CC3)[nH]c(=O)c2C1] | 1.82 min 518.1 |
TABLE 48-12
| | | | | |
|---|---|---|---|---|
| 17-70 | 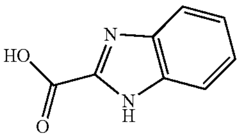 [SMILES: O=C(O)c1nc2ccccc2[nH]1] | INT-8-14 | 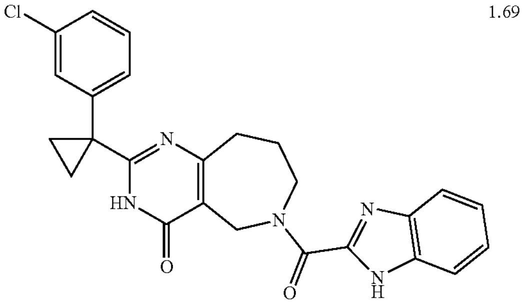 | 1.69 min 460.1 |
| 17-71 | 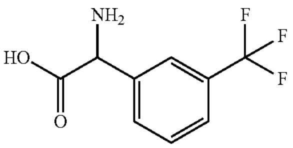 [SMILES: NC(C(=O)O)c1cccc(C(F)(F)F)c1] | INT-8-3 | 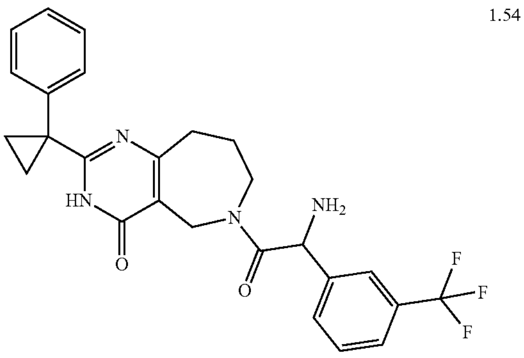 | 1.54 min 483.2 |

TABLE 48-12-continued
| | | | | |
|---|---|---|---|---|
| 17-72 | 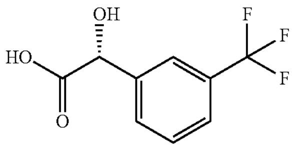 | INT-8-36 | 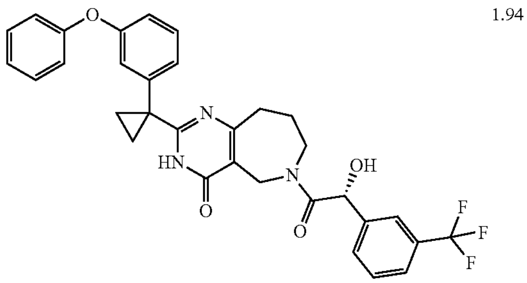 | 1.94 min 576.0 |
| 17-73 | 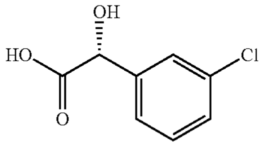 | INT-8-36 | 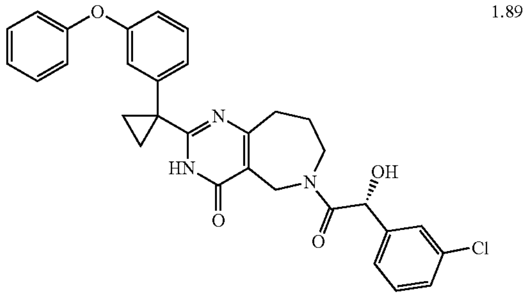 | 1.89 min 542.0 |
| 17-74 | INT-25-2 | INT-8-4 | 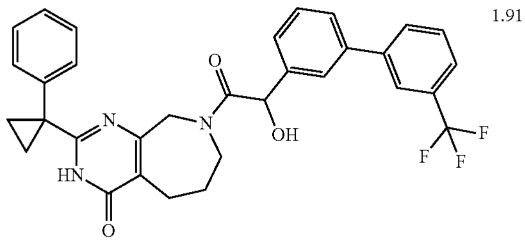 | 1.91 min 560.0 |
| 17-75 | 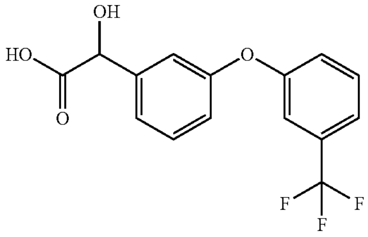 [SMILES: O=C(O)C(O)c1cccc(Oc2cccc(C(F)(F)F)c2)c1] | INT-8-3 | 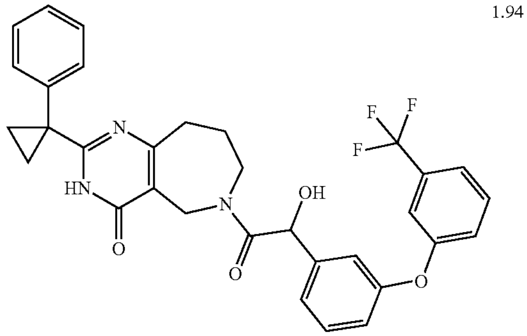 | 1.94 min 576.0 |
| 17-76 | 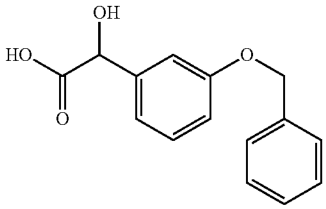 [SMILES: O=C(O)C(O)c1cccc(OCc2ccccc2)c1] | INT-8-3 | 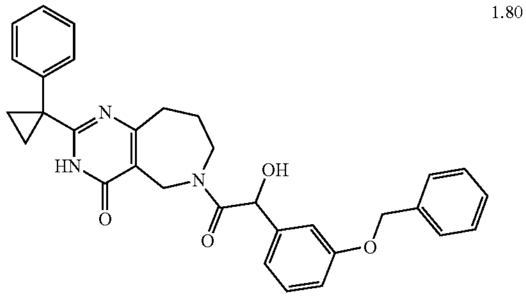 | 1.80 min 522.0 |

TABLE 48-13
| | | | | |
|---|---|---|---|---|
| 17-77 | 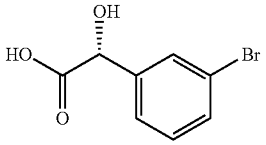 | INT-8-3 | 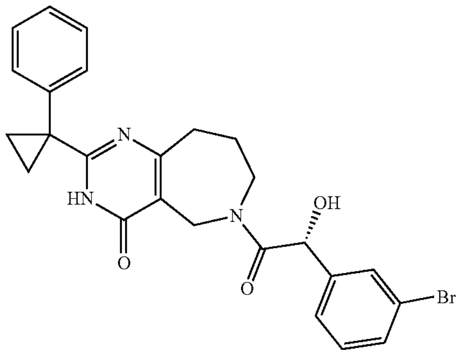 [SMILES: O=C([C@H](O)c1cccc(Br)c1)N1CCCc2nc(C3(c4ccccc4)CC3)[nH]c(=O)c2C1] | 1.60 min 493.9 |
| 17-78 | 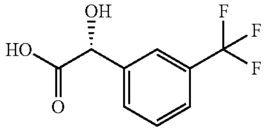 [SMILES: O=C(O)[C@H](O)c1cccc(C(F)(F)F)c1] | INT-8-37 | 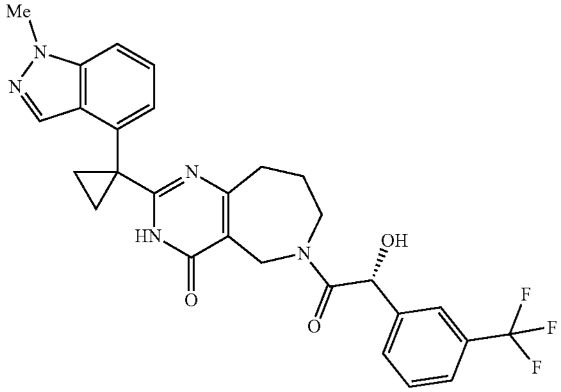 [SMILES: Cn1ncc2c(C3(c4nc5c(c(=O)[nH]4)CN(C(=O)[C@H](O)c4cccc(C(F)(F)F)c4)CCC5)CC3)cccc21] | 1.60 min 538.0 |
| 17-79 | 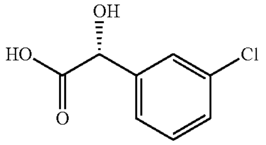 | INT-8-37 | 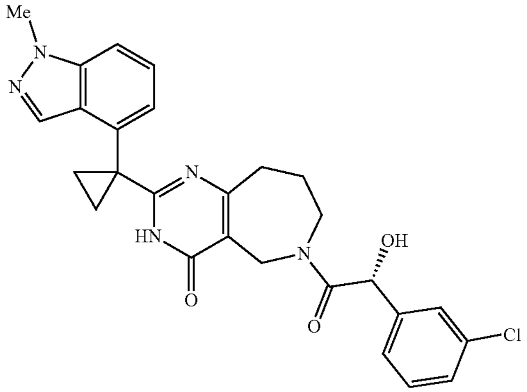 [SMILES: Cn1ncc2c(C3(c4nc5c(c(=O)[nH]4)CN(C(=O)[C@H](O)c4cccc(Cl)c4)CCC5)CC3)cccc21] | 1.52 min 503.9 |
| 17-80 | 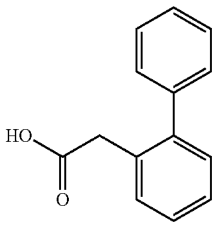 [SMILES: O=C(O)Cc1ccccc1-c1ccccc1] | INT-8-14 | 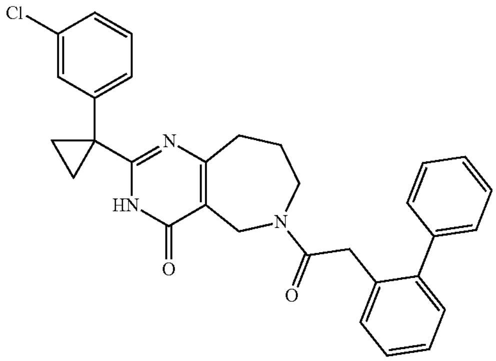 [SMILES: O=C(Cc1ccccc1-c1ccccc1)N1CCCc2nc(C3(c4cccc(Cl)c4)CC3)[nH]c(=O)c2C1] | 1.93 min 509.9 |

TABLE 48-13-continued
| | | | | | |
|---|---|---|---|---|---|
| 17-81 | 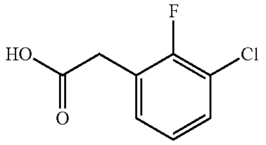 [SMILES: O=C(O)Cc1cccc(Cl)c1F] | INT-8-36 | 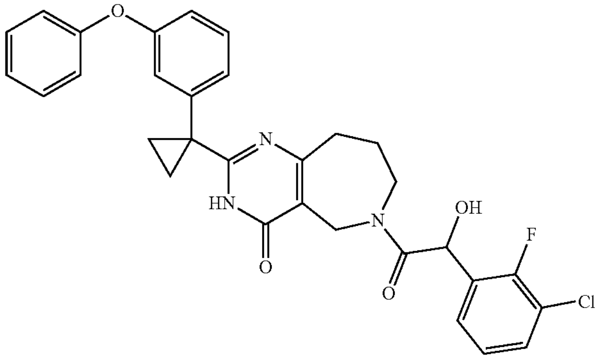 [SMILES: O=C(C(O)c1cccc(Cl)c1F)N1CCCc2nc(C3(c4cccc(Oc5ccccc5)c4)CC3)[nH]c(=O)c2C1] | 1.92 min | 559.9 |
| 17-82 | 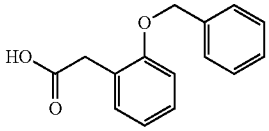 [SMILES: O=C(O)Cc1ccccc1OCc1ccccc1] | INT-8-14 | 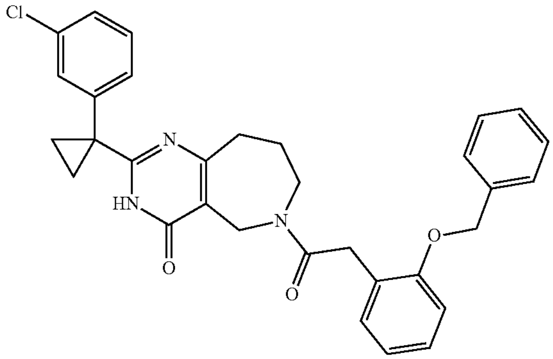 [SMILES: O=C(Cc1ccccc1OCc1ccccc1)N1CCCc2nc(C3(c4cccc(Cl)c4)CC3)[nH]c(=O)c2C1] | 1.96 min | 540.0 |
TABLE 48-14
| | | | | | |
|---|---|---|---|---|---|
| 17-83 | 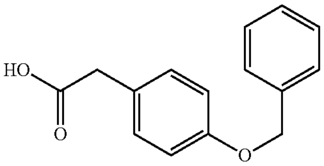 [SMILES: O=C(O)Cc1ccc(OCc2ccccc2)cc1] | INT-8-14 | 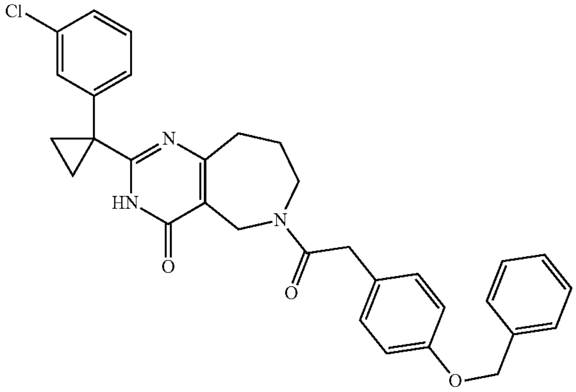 [SMILES: O=C(Cc1ccc(OCc2ccccc2)cc1)N1CCCc2nc(C3(c4cccc(Cl)c4)CC3)[nH]c(=O)c2C1] | 1.95 min | 540.0 |
| 17-84 | 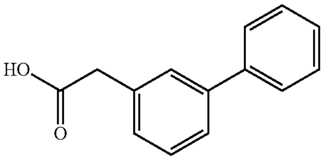 [SMILES: O=C(O)Cc1cccc(-c2ccccc2)c1] | INT-8-14 | 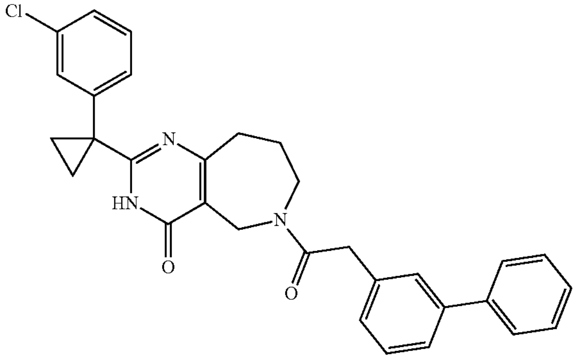 [SMILES: O=C(Cc1cccc(-c2ccccc2)c1)N1CCCc2nc(C3(c4cccc(Cl)c4)CC3)[nH]c(=O)c2C1] | 1.95 min | 509.9 |

TABLE 48-14-continued
| | | | | | |
|---|---|---|---|---|---|
| 17-85 | 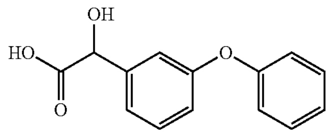 [SMILES: O=C(O)C(O)c1cccc(Oc2ccccc2)c1] | INT-8-3 | 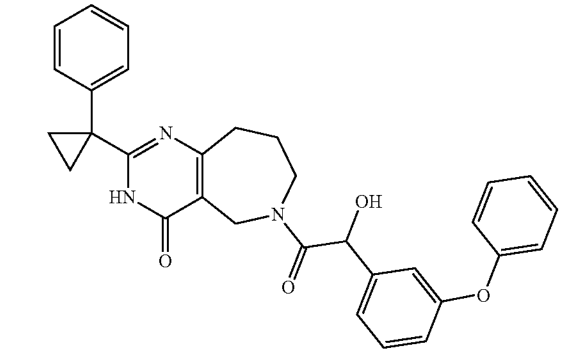 [SMILES: O=C(C(O)c1cccc(Oc2ccccc2)c1)N1CCCc2nc(C3(c4ccccc4)CC3)[nH]c(=O)c2C1] | 1.81 min | 508.2 |
| 17-86 | 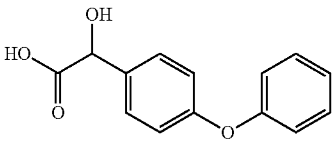 [SMILES: O=C(O)C(O)c1ccc(Oc2ccccc2)cc1] | INT-8-14 | 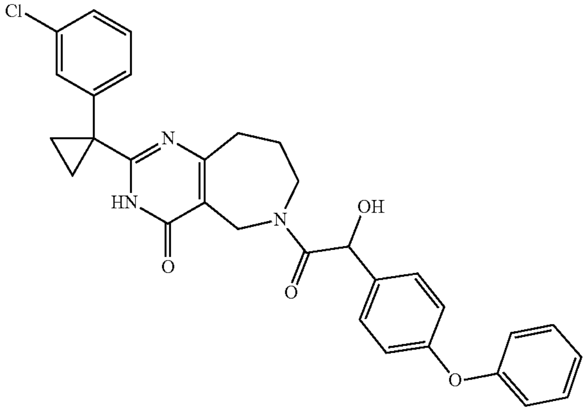 [SMILES: O=C(C(O)c1ccc(Oc2ccccc2)cc1)N1CCCc2nc(C3(c4cccc(Cl)c4)CC3)[nH]c(=O)c2C1] | 1.89 min | 542.0 |
| 17-87 | 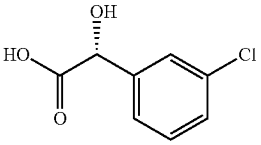 | INT-8-15 | 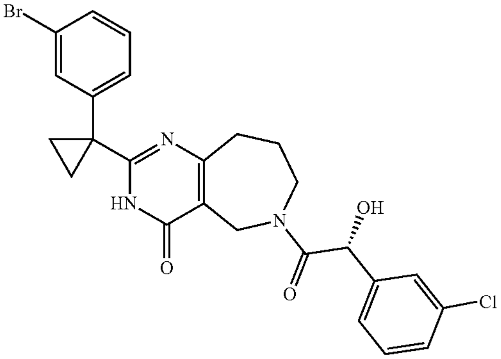 [SMILES: O=C([C@H](O)c1cccc(Cl)c1)N1CCCc2nc(C3(c4cccc(Br)c4)CC3)[nH]c(=O)c2C1] | 1.73 min | 527.9 |
| 17-88 | 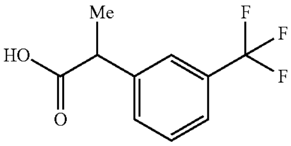 [SMILES: CC(C(=O)O)c1cccc(C(F)(F)F)c1] | INT-8-14 | 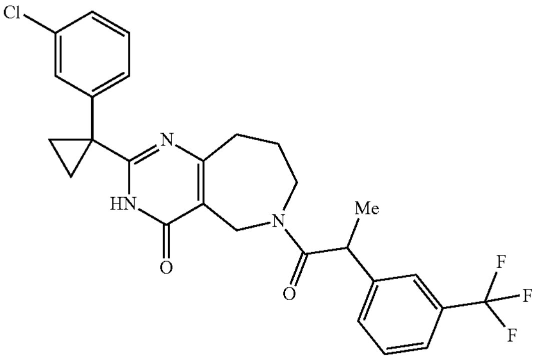 [SMILES: CC(C(=O)N1CCCc2nc(C3(c4cccc(Cl)c4)CC3)[nH]c(=O)c2C1)c1cccc(C(F)(F)F)c1] | 1.92 min | 515.9 |

TABLE 48-15
| | | | | | |
|---|---|---|---|---|---|
| 17-89 | 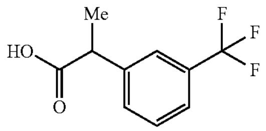 [SMILES: CC(C(=O)O)c1cccc(C(F)(F)F)c1] | INT-8-13 | 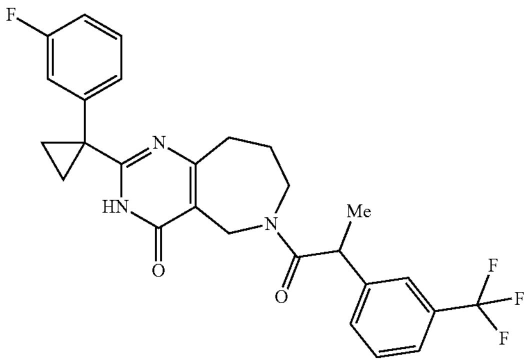 [SMILES: CC(C(=O)N1CCCc2nc(C3(c4cccc(F)c4)CC3)[nH]c(=O)c2C1)c1cccc(C(F)(F)F)c1] | 1.83 min | 499.9 |
| 17-90 | 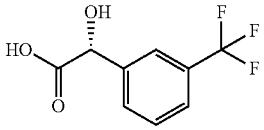 [SMILES: O=C(O)[C@H](O)c1cccc(C(F)(F)F)c1] | INT-8-41 | 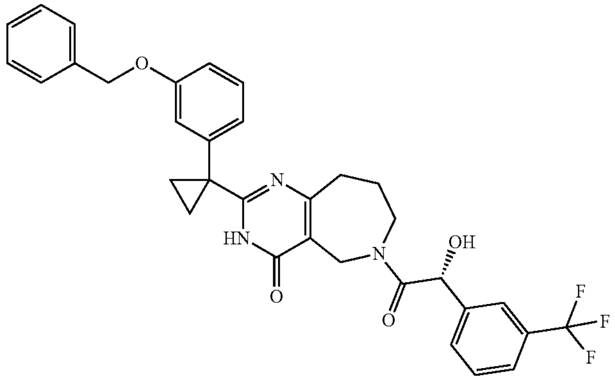 [SMILES: O=C([C@H](O)c1cccc(C(F)(F)F)c1)N1CCCc2nc(C3(c4cccc(OCc5ccccc5)c4)CC3)[nH]c(=O)c2C1] | 1.96 min | 590.0 |
| 17-91 | 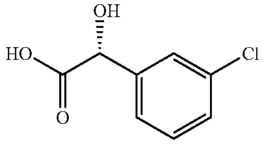 | INT-8-41 | 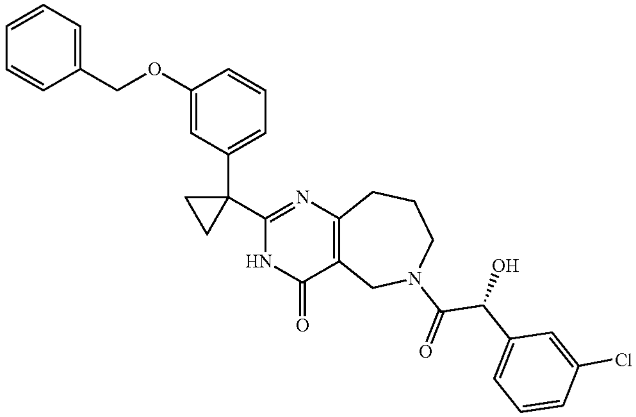 [SMILES: O=C([C@H](O)c1cccc(Cl)c1)N1CCCc2nc(C3(c4cccc(OCc5ccccc5)c4)CC3)[nH]c(=O)c2C1] | 1.92 min | 556.0 |
| 17-92 | 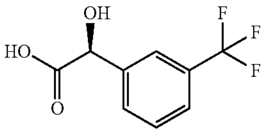 [SMILES: O=C(O)[C@@H](O)c1cccc(C(F)(F)F)c1] | INT-8-3 | 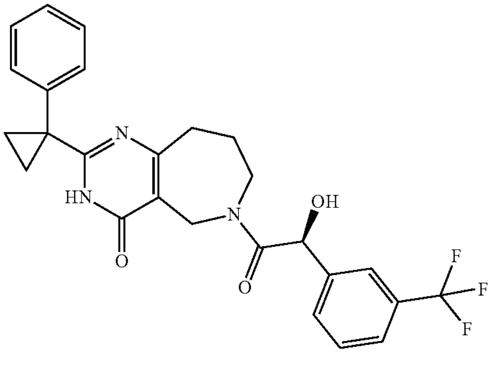 [SMILES: O=C([C@@H](O)c1cccc(C(F)(F)F)c1)N1CCCc2nc(C3(c4ccccc4)CC3)[nH]c(=O)c2C1] | 1.67 min | 483.9 |

TABLE 48-15-continued
| | | | | | |
|---|---|---|---|---|---|
| 17-93 | 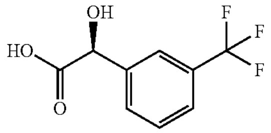 [SMILES: O=C(O)[C@@H](O)c1cccc(C(F)(F)F)c1] | INT-8-14 | 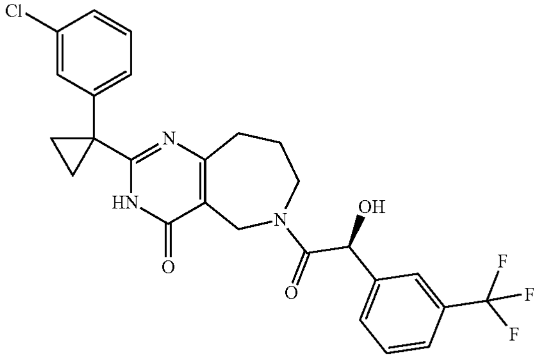 [SMILES: O=C([C@@H](O)c1cccc(C(F)(F)F)c1)N1CCCc2nc(C3(c4cccc(Cl)c4)CC3)[nH]c(=O)c2C1] | 1.78 min | 517.9 |
| 17-94 | 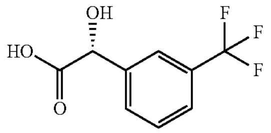 [SMILES: O=C(O)[C@H](O)c1cccc(C(F)(F)F)c1] | INT-10-12 | 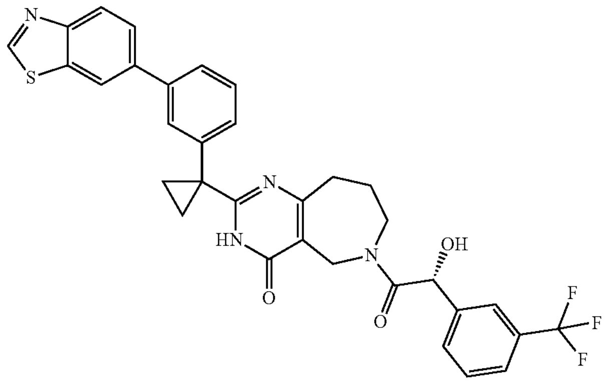 [SMILES: O=C([C@H](O)c1cccc(C(F)(F)F)c1)N1CCCc2nc(C3(c4cccc(-c5ccc6ncsc6c5)c4)CC3)[nH]c(=O)c2C1] | 3.54 min | 615.2 |
TABLE 48-16
| | | | | | |
|---|---|---|---|---|---|
| 17-95 | 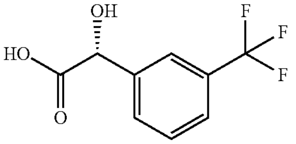 | INT-10-14 | 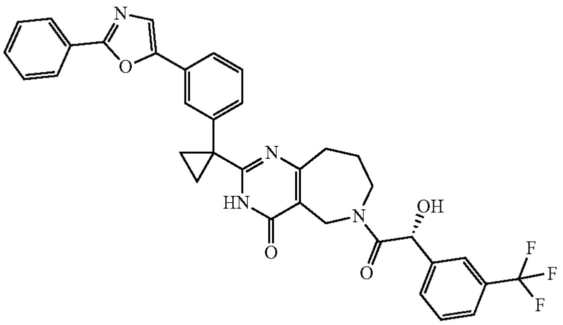 | 3.81 min | 625.2 |
| 17-96 | 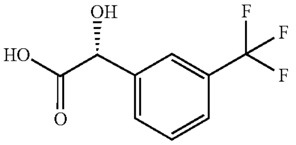 [SMILES: O=C(O)[C@H](O)c1cccc(C(F)(F)F)c1] | INT-10-11 | 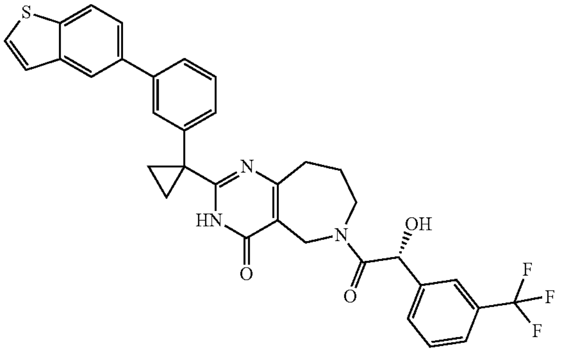 [SMILES: O=C([C@H](O)c1cccc(C(F)(F)F)c1)N1CCCc2nc(C3(c4cccc(-c5ccc6sccc6c5)c4)CC3)[nH]c(=O)c2C1] | 4.09 min | 614.2 |

TABLE 48-16-continued
| | | | | | |
|---|---|---|---|---|---|
| 17-97 | 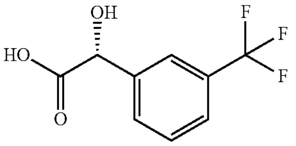 | INT-10-13 | 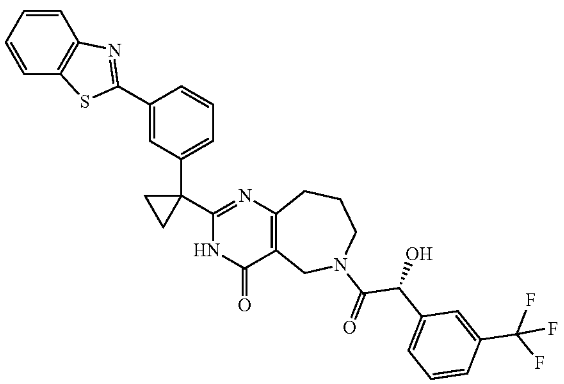 [SMILES: O=C([C@H](O)c1cccc(C(F)(F)F)c1)N1CCCc2nc(C3(c4cccc(-c5nc6ccccc6s5)c4)CC3)[nH]c(=O)c2C1] | 3.86 min | 615.2 |
| 17-98 | 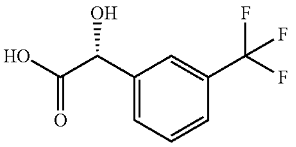 | INT-10-15 | 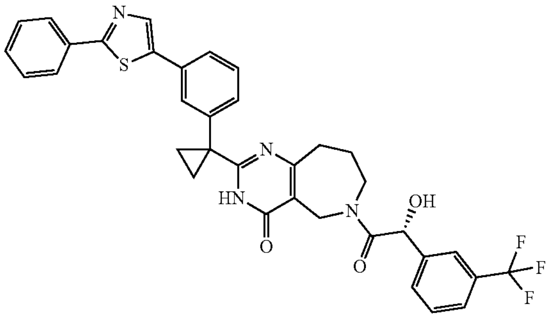 [SMILES: O=C([C@H](O)c1cccc(C(F)(F)F)c1)N1CCCc2nc(C3(c4cccc(-c5cnc(-c6ccccc6)s5)c4)CC3)[nH]c(=O)c2C1] | 4.08 min | 641.2 |
| 17-99 | 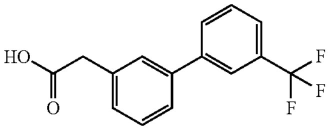 [SMILES: O=C(O)Cc1cccc(-c2cccc(C(F)(F)F)c2)c1] | INT-8-14 | 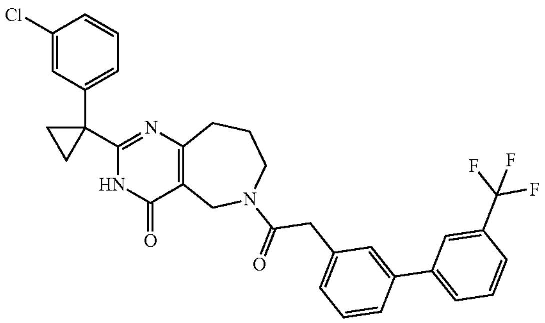 [SMILES: O=C(Cc1cccc(-c2cccc(C(F)(F)F)c2)c1)N1CCCc2nc(C3(c4cccc(Cl)c4)CC3)[nH]c(=O)c2C1] | 2.22 min | 578.5 |
| 17-100 | 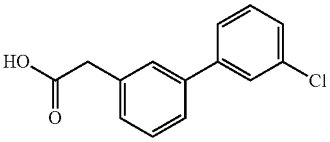 [SMILES: O=C(O)Cc1cccc(-c2cccc(Cl)c2)c1] | INT-8-14 | 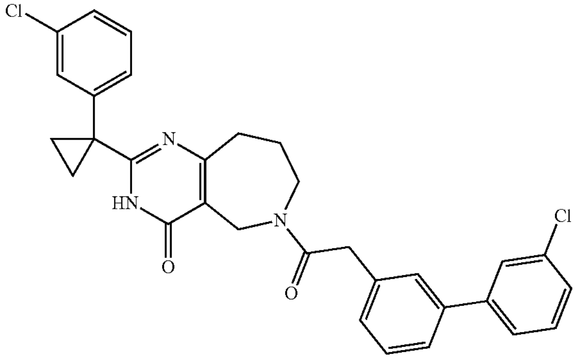 [SMILES: O=C(Cc1cccc(-c2cccc(Cl)c2)c1)N1CCCc2nc(C3(c4cccc(Cl)c4)CC3)[nH]c(=O)c2C1] | 2.21 min | 544.4 |

TABLE 48-17
| | | | | | |
|---|---|---|---|---|---|
| 17-101 | 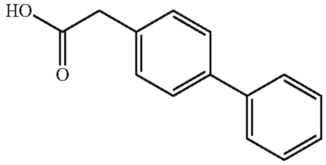 [SMILES: O=C(O)Cc1ccc(-c2ccccc2)cc1] | INT-8-14 | 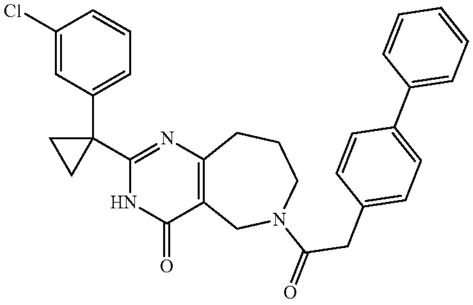 [SMILES: O=C(Cc1ccc(-c2ccccc2)cc1)N1CCCc2nc(C3(c4cccc(Cl)c4)CC3)[nH]c(=O)c2C1] | 2.12 min | 510.4 |
| 17-102 | 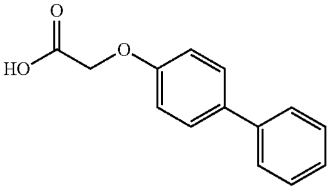 [SMILES: O=C(O)COc1ccc(-c2ccccc2)cc1] | INT-8-14 | 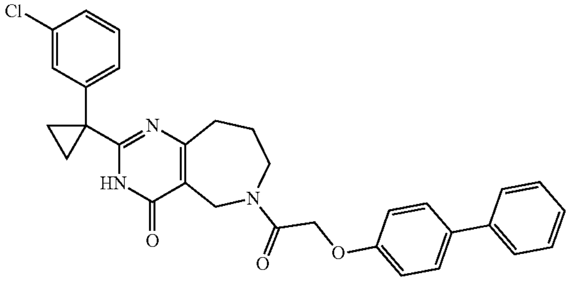 [SMILES: O=C(COc1ccc(-c2ccccc2)cc1)N1CCCc2nc(C3(c4cccc(Cl)c4)CC3)[nH]c(=O)c2C1] | 2.11 min | 526.5 |
| 17-103 | 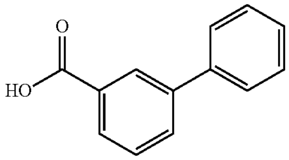 [SMILES: O=C(O)c1cccc(-c2ccccc2)c1] | INT-8-14 | 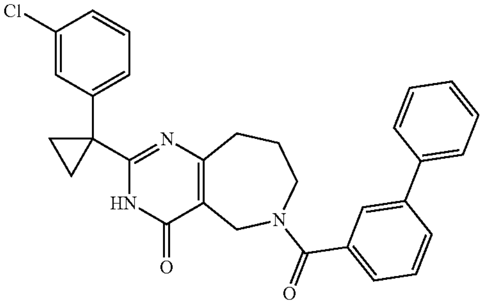 [SMILES: O=C(c1cccc(-c2ccccc2)c1)N1CCCc2nc(C3(c4cccc(Cl)c4)CC3)[nH]c(=O)c2C1] | 2.10 min | 496.5 |
| 17-104 | 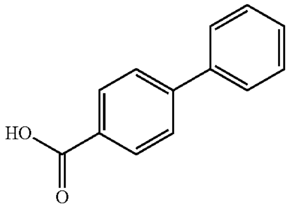 [SMILES: O=C(O)c1ccc(-c2ccccc2)cc1] | INT-8-14 | 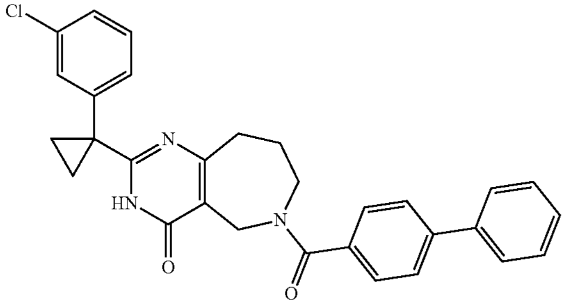 [SMILES: O=C(c1ccc(-c2ccccc2)cc1)N1CCCc2nc(C3(c4cccc(Cl)c4)CC3)[nH]c(=O)c2C1] | 2.11 min | 496.5 |
| 17-105 | 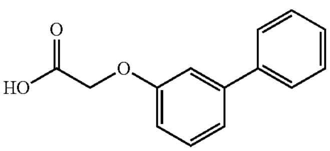 [SMILES: O=C(O)COc1cccc(-c2ccccc2)c1] | INT-8-14 | 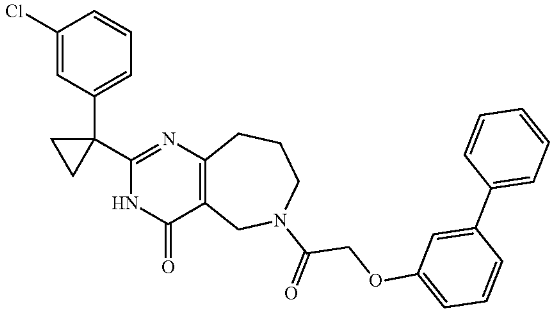 [SMILES: O=C(COc1cccc(-c2ccccc2)c1)N1CCCc2nc(C3(c4cccc(Cl)c4)CC3)[nH]c(=O)c2C1] | 2.12 min | 526.5 |

TABLE 48-17-continued
| | | | | | |
|---|---|---|---|---|---|
| 17-106 | 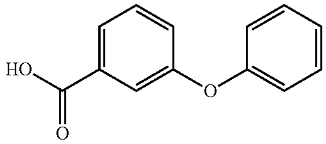 [SMILES: O=C(O)c1cccc(Oc2ccccc2)c1] | INT-8-14 | 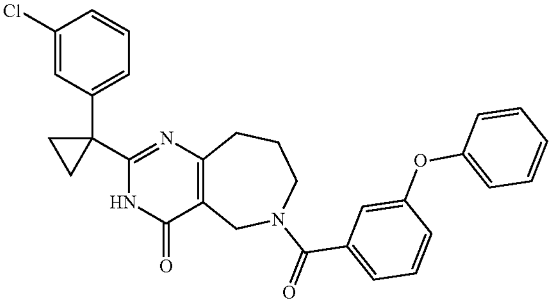 [SMILES: O=C(c1cccc(Oc2ccccc2)c1)N1CCCc2nc(C3(c4cccc(Cl)c4)CC3)[nH]c(=O)c2C1] | 2.10 min | 512.4 |
| 17-107 | 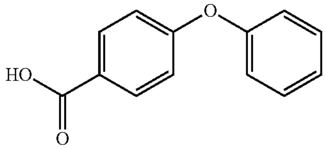 [SMILES: O=C(O)c1ccc(Oc2ccccc2)cc1] | INT-8-14 | 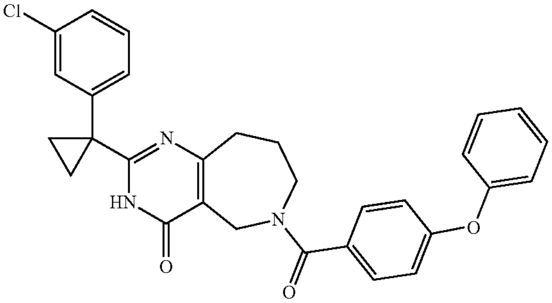 [SMILES: O=C(c1ccc(Oc2ccccc2)cc1)N1CCCc2nc(C3(c4cccc(Cl)c4)CC3)[nH]c(=O)c2C1] | 2.11 min | 512.5 |
TABLE 48-18
| | | | | | |
|---|---|---|---|---|---|
| 17-108 | 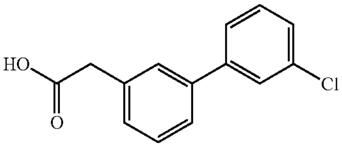 [SMILES: O=C(O)Cc1cccc(-c2cccc(Cl)c2)c1] | INT-8-4 | 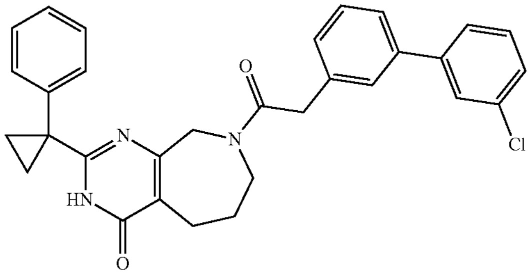 [SMILES: O=C(Cc1cccc(-c2cccc(Cl)c2)c1)N1CCCc2c(nc(C3(c4ccccc4)CC3)[nH]c2=O)C1] | 2.17 min | 510.5 |
| 17-109 | 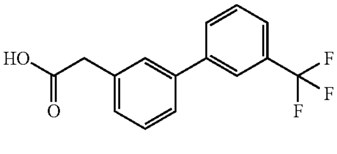 [SMILES: O=C(O)Cc1cccc(-c2cccc(C(F)(F)F)c2)c1] | INT-8-4 | 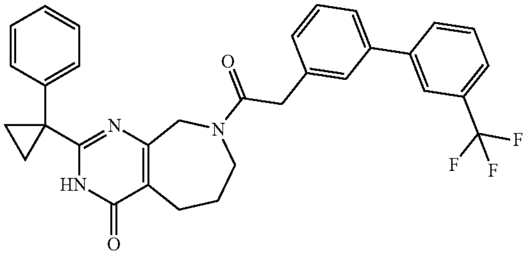 [SMILES: O=C(Cc1cccc(-c2cccc(C(F)(F)F)c2)c1)N1CCCc2c(nc(C3(c4ccccc4)CC3)[nH]c2=O)C1] | 2.17 min | 544.5 |

TABLE 48-18-continued
| | | | | | |
|---|---|---|---|---|---|
| 17-110 | 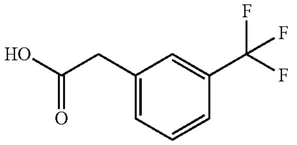 [SMILES: O=C(O)Cc1cccc(C(F)(F)F)c1] | INT-8-14 | 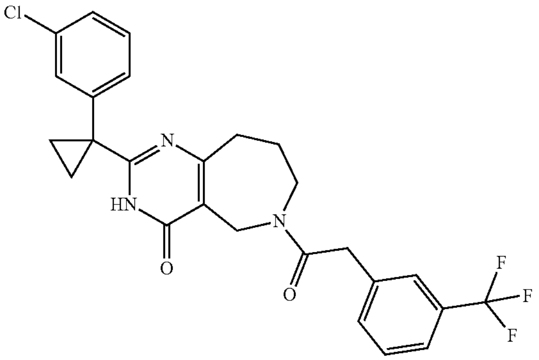 [SMILES: O=C(Cc1cccc(C(F)(F)F)c1)N1CCCc2nc(C3(c4cccc(Cl)c4)CC3)[nH]c(=O)c2C1] | 2.04 min | 502.3 |
| 17-111 | 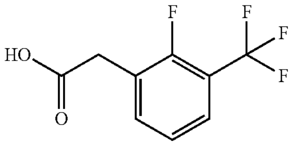 [SMILES: O=C(O)Cc1cccc(C(F)(F)F)c1F] | INT-8-14 | 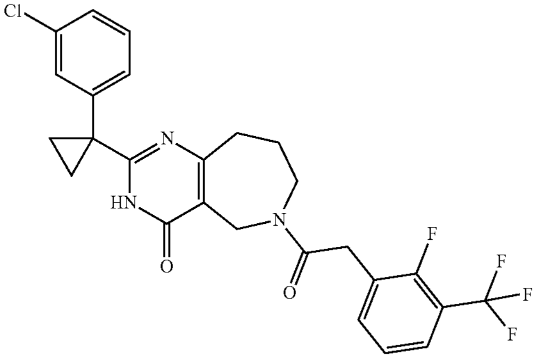 [SMILES: O=C(Cc1cccc(C(F)(F)F)c1F)N1CCCc2nc(C3(c4cccc(Cl)c4)CC3)[nH]c(=O)c2C1] | 2.04 min | 520.3 |
| 17-112 | 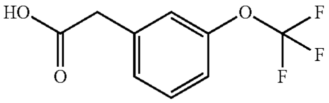 [SMILES: O=C(O)Cc1cccc(OC(F)(F)F)c1] | INT-8-14 | 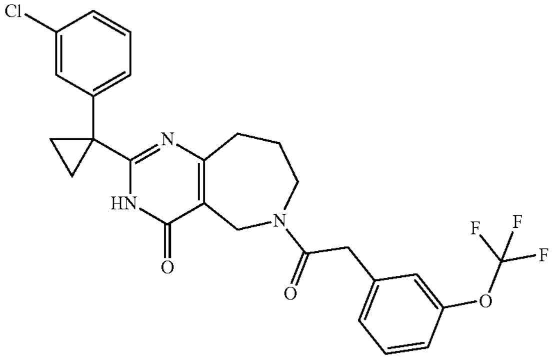 [SMILES: O=C(Cc1cccc(OC(F)(F)F)c1)N1CCCc2nc(C3(c4cccc(Cl)c4)CC3)[nH]c(=O)c2C1] | 2.07 min | 518.4 |
| 17-113 | 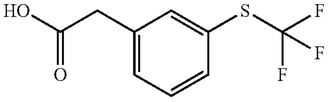 [SMILES: O=C(O)Cc1cccc(SC(F)(F)F)c1] | INT-8-14 | 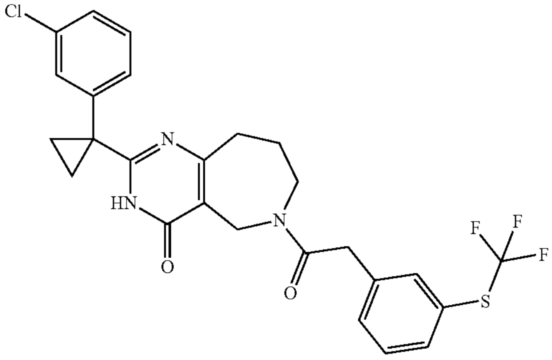 | 2.12 min | 534.3 |

TABLE 48-18-continued
| | | | | | |
|---|---|---|---|---|---|
| 17-114 | 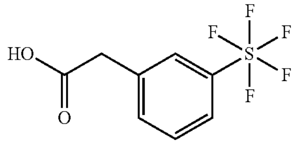 [SMILES: O=C(O)Cc1cccc(S(F)(F)(F)(F)F)c1] | INT-8-14 | 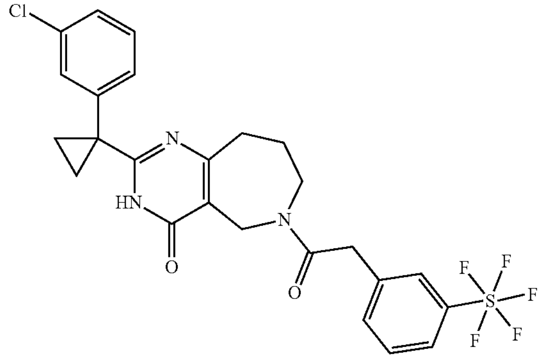 [SMILES: O=C(Cc1cccc(S(F)(F)(F)(F)F)c1)N1CCCc2nc(C3(c4cccc(Cl)c4)CC3)[nH]c(=O)c2C1] | 2.09 min | 560.3 |
| 17-115 | 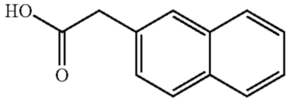 [SMILES: O=C(O)Cc1ccc2ccccc2c1] | INT-8-14 | 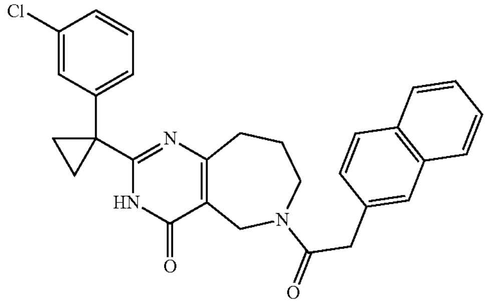 [SMILES: O=C(Cc1ccc2ccccc2c1)N1CCCc2nc(C3(c4cccc(Cl)c4)CC3)[nH]c(=O)c2C1] | 2.04 min | 484.4 |
| 17-116 | 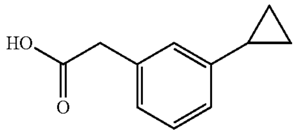 [SMILES: O=C(O)Cc1cccc(C2CC2)c1] | INT-8-14 | 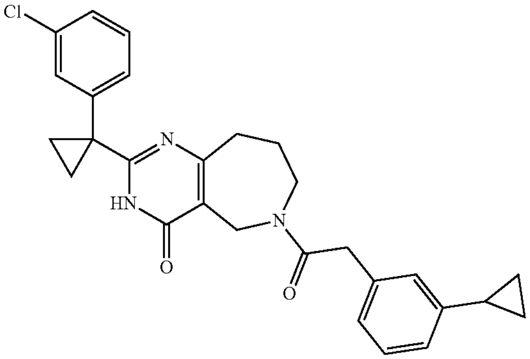 [SMILES: O=C(Cc1cccc(C2CC2)c1)N1CCCc2nc(C3(c4cccc(Cl)c4)CC3)[nH]c(=O)c2C1] | 2.05 min | 474.4 |
| 17-117 | 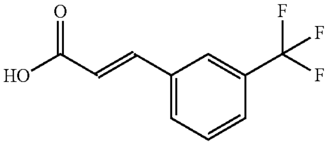 [SMILES: O=C(O)/C=C/c1cccc(C(F)(F)F)c1] | INT-8-14 | 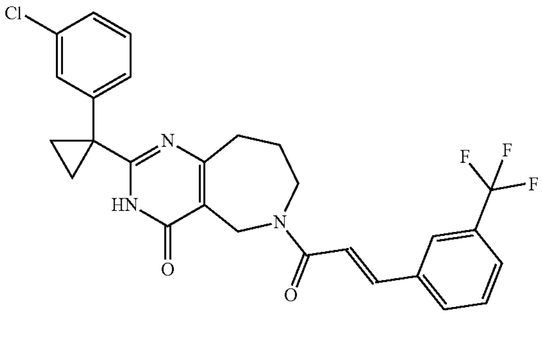 [SMILES: O=C(/C=C/c1cccc(C(F)(F)F)c1)N1CCCc2nc(C3(c4cccc(Cl)c4)CC3)[nH]c(=O)c2C1] | 2.13 min | 514.4 |

-continued
| | | | | | |
|---|---|---|---|---|---|
| 17-118 | INT-26-3 | INT-8-14 | 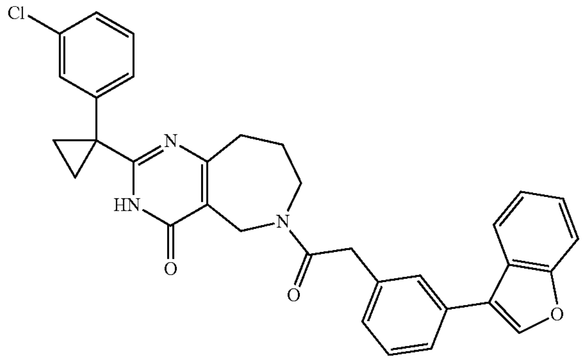 [SMILES: O=C(Cc1cccc(-c2coc3ccccc23)c1)N1CCCc2nc(C3(c4cccc(Cl)c4)CC3)[nH]c(=O)c2C1] | 2.18 min | 550.5 |
| 17-119 | INT-26-4 | INT-8-14 | 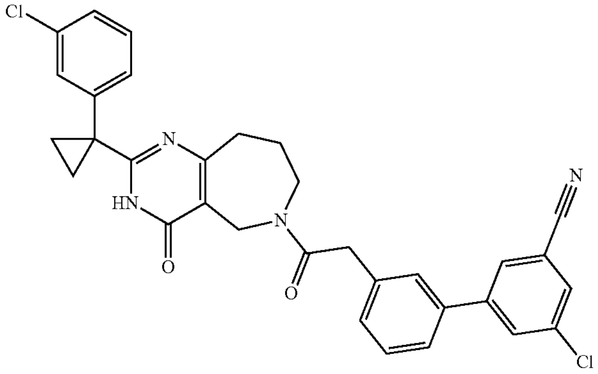 [SMILES: N#Cc1cc(Cl)cc(-c2cccc(CC(=O)N3CCCc4nc(C5(c6cccc(Cl)c6)CC5)[nH]c(=O)c4C3)c2)c1] | 2.15 min | 569.4 |
| 17-120 | 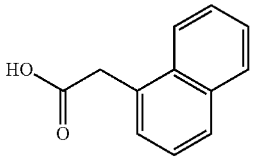 [SMILES: O=C(O)Cc1cccc2ccccc12] | INT-8-14 | 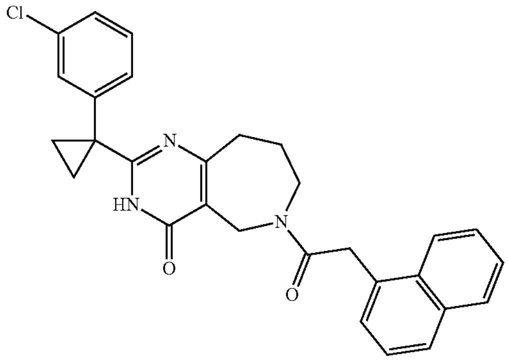 [SMILES: O=C(Cc1cccc2ccccc12)N1CCCc2nc(C3(c4cccc(Cl)c4)CC3)[nH]c(=O)c2C1] | 2.02 min | 484.4 |
| 17-121 | 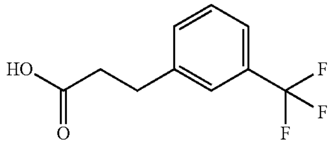 [SMILES: O=C(O)CCc1cccc(C(F)(F)F)c1] | INT-8-14 | 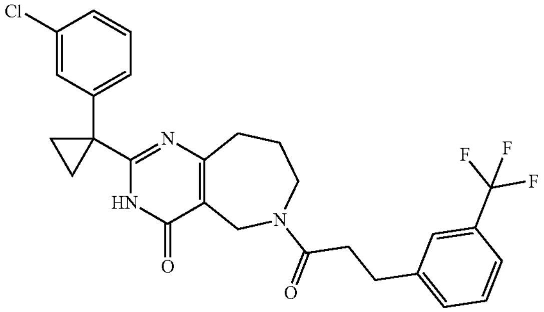 [SMILES: O=C(CCc1cccc(C(F)(F)F)c1)N1CCCc2nc(C3(c4cccc(Cl)c4)CC3)[nH]c(=O)c2C1] | 2.10 min | 516.4 |

TABLE 48-20
| | | | | | |
|---|---|---|---|---|---|
| 17-122 | 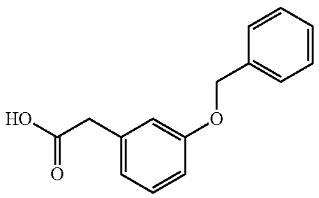 [SMILES: O=C(O)Cc1cccc(OCc2ccccc2)c1] | INT-8-14 | 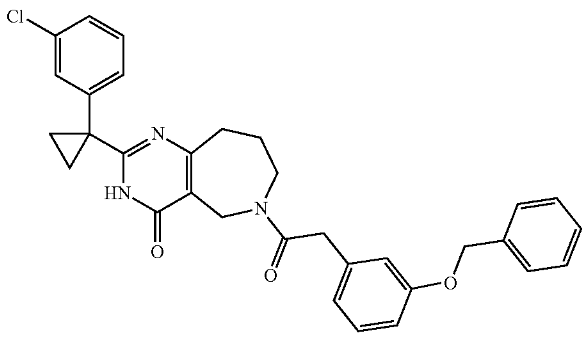 [SMILES: O=C(Cc1cccc(OCc2ccccc2)c1)N1CCCc2nc(C3(c4cccc(Cl)c4)CC3)[nH]c(=O)c2C1] | 2.13 min | 540.5 |
| 17-123 | 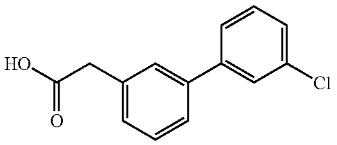 [SMILES: O=C(O)Cc1cccc(-c2cccc(Cl)c2)c1] | INT-10-20 | 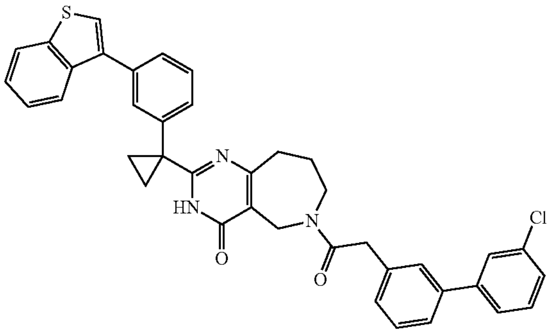 [SMILES: O=C(Cc1cccc(-c2cccc(Cl)c2)c1)N1CCCc2nc(C3(c4cccc(-c5csc6ccccc56)c4)CC3)[nH]c(=O)c2C1] | 2.45 min | 642.5 |
| 17-124 | 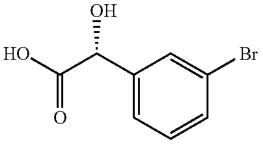 | INT-10-20 | 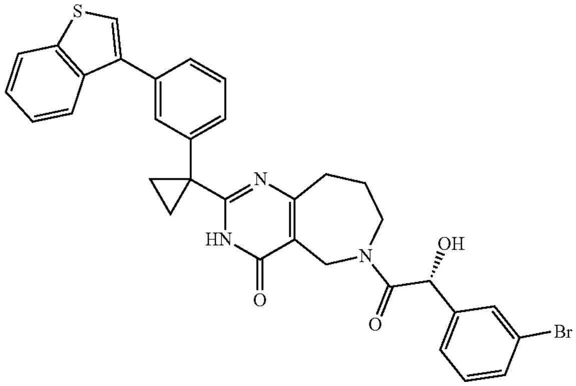 [SMILES: O=C([C@H](O)c1cccc(Br)c1)N1CCCc2nc(C3(c4cccc(-c5csc6ccccc56)c4)CC3)[nH]c(=O)c2C1] | 2.21 min | 626.3 |
| 17-125 | 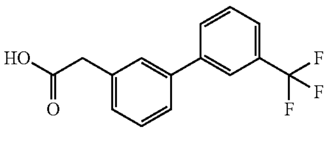 [SMILES: O=C(O)Cc1cccc(-c2cccc(C(F)(F)F)c2)c1] | INT-10-20 | 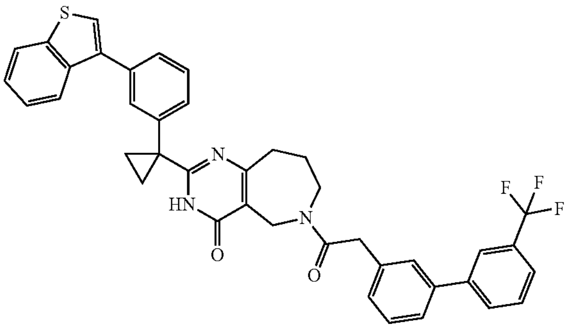 [SMILES: O=C(Cc1cccc(-c2cccc(C(F)(F)F)c2)c1)N1CCCc2nc(C3(c4cccc(-c5csc6ccccc56)c4)CC3)[nH]c(=O)c2C1] | 2.44 min | 676.5 |

TABLE 48-20-continued
| | | | | | |
|---|---|---|---|---|---|
| 17-126 | INT-26-5 | INT-8-14 | 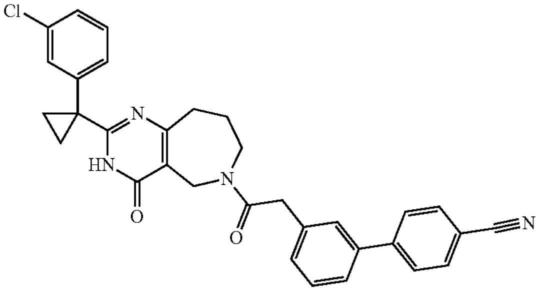 [SMILES: N#Cc1ccc(-c2cccc(CC(=O)N3CCCc4nc(C5(c6cccc(Cl)c6)CC5)[nH]c(=O)c4C3)c2)cc1] | 2.03 min | 535.5 |
| 17-127 | INT-26-6 | INT-8-14 | 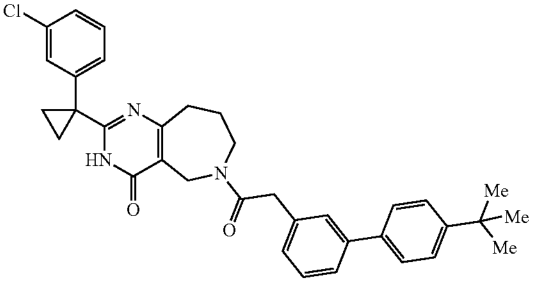 [SMILES: CC(C)(C)c1ccc(-c2cccc(CC(=O)N3CCCc4nc(C5(c6cccc(Cl)c6)CC5)[nH]c(=O)c4C3)c2)cc1] | 2.37 min | 566.6 |
TABLE 48-21
| | | | | | |
|---|---|---|---|---|---|
| 17-128 | INT-26-7 | INT-8-14 | 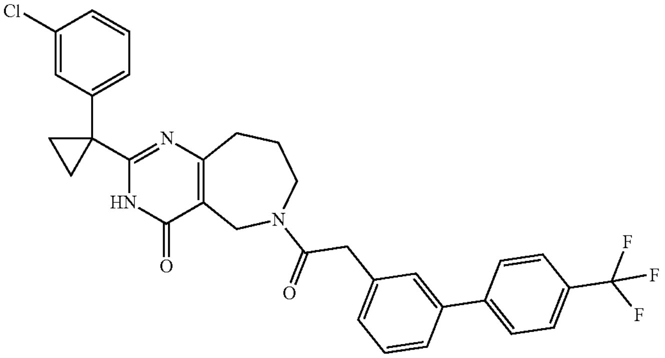 [SMILES: O=C(Cc1cccc(-c2ccc(C(F)(F)F)cc2)c1)N1CCCc2nc(C3(c4cccc(Cl)c4)CC3)[nH]c(=O)c2C1] | 2.23 min | 578.5 |
| 17-129 | INT-26-8 | INT-8-14 | 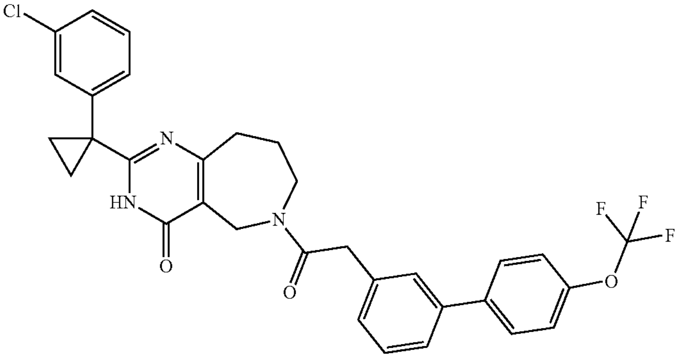 [SMILES: O=C(Cc1cccc(-c2ccc(OC(F)(F)F)cc2)c1)N1CCCc2nc(C3(c4cccc(Cl)c4)CC3)[nH]c(=O)c2C1] | 2.25 min | 594.5 |

TABLE 48-21-continued
| | | | | | |
|---|---|---|---|---|---|
| 17-130 | INT-26-9 | INT-8-14 | 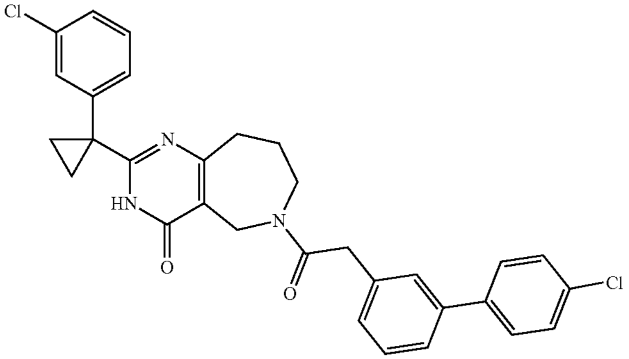 [SMILES: O=C(Cc1cccc(-c2ccc(Cl)cc2)c1)N1CCCc2nc(C3(c4cccc(Cl)c4)CC3)[nH]c(=O)c2C1] | 2.22 min | 544.4 |
| 17-131 | INT-26-5 | INT-8-3 | 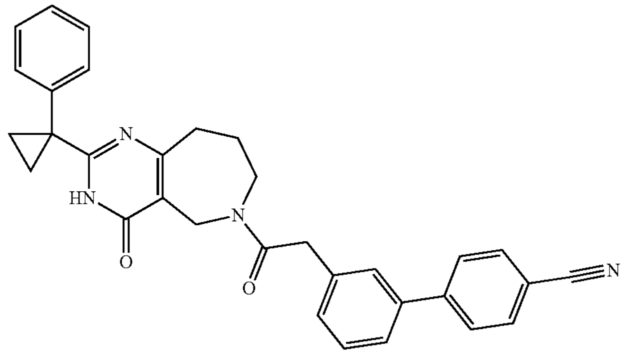 [SMILES: N#Cc1ccc(-c2cccc(CC(=O)N3CCCc4nc(C5(c6ccccc6)CC5)[nH]c(=O)c4C3)c2)cc1] | 1.96 min | 501.5 |
| 17-132 | INT-26-6 | INT-8-3 | 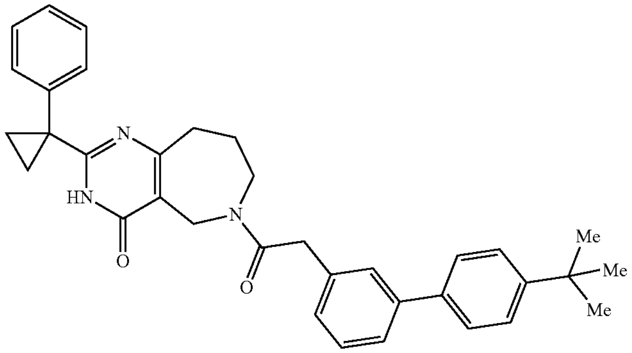 [SMILES: CC(C)(C)c1ccc(-c2cccc(CC(=O)N3CCCc4nc(C5(c6ccccc6)CC5)[nH]c(=O)c4C3)c2)cc1] | 2.32 min | 532.6 |
| 17-133 | INT-26-7 | INT-8-3 | 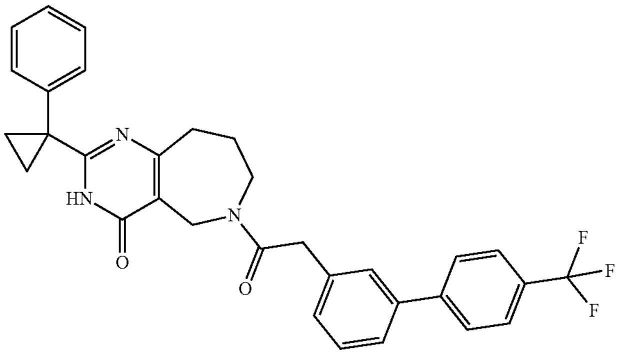 [SMILES: O=C(Cc1cccc(-c2ccc(C(F)(F)F)cc2)c1)N1CCCc2nc(C3(c4ccccc4)CC3)[nH]c(=O)c2C1] | 2.17 min | 544.5 |

TABLE 48-21-continued
| | | | | | |
|---|---|---|---|---|---|
| 17-134 | INT-26-8 | INT-8-3 | 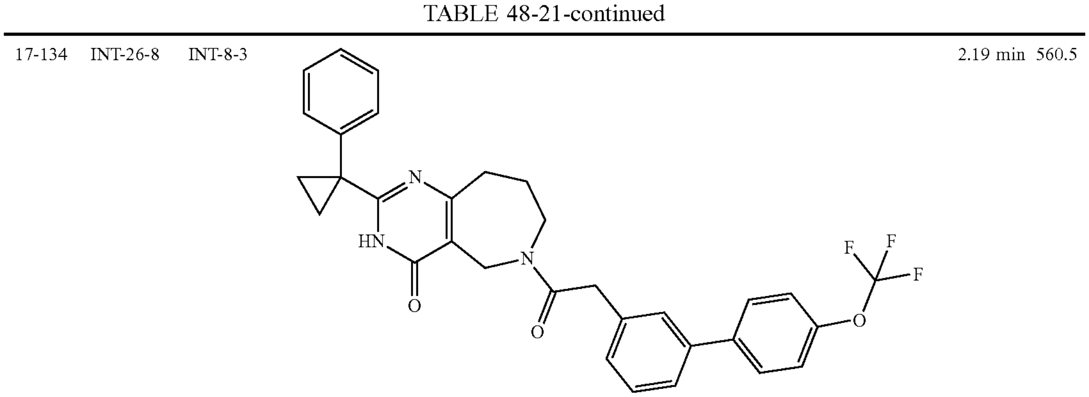 | 2.19 min | 560.5 |
TABLE 48-22
| | | | | | |
|---|---|---|---|---|---|
| 17-135 | INT-26-9 | INT-8-3 | 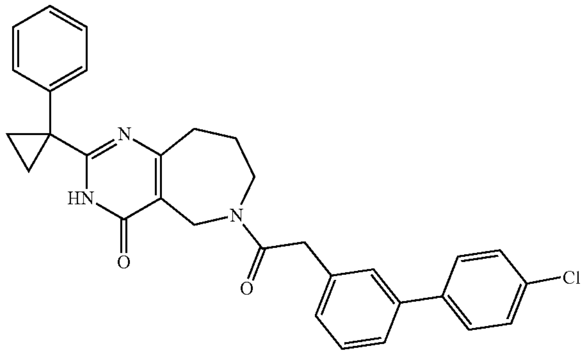 [SMILES: O=C(Cc1cccc(-c2ccc(Cl)cc2)c1)N1CCCc2nc(C3(c4ccccc4)CC3)[nH]c(=O)c2C1] | 2.16 min | 510.4 |
| 17-136 | 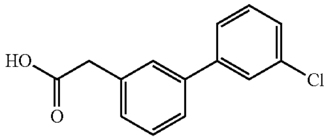 [SMILES: O=C(O)Cc1cccc(-c2cccc(Cl)c2)c1] | INT-8-3 | 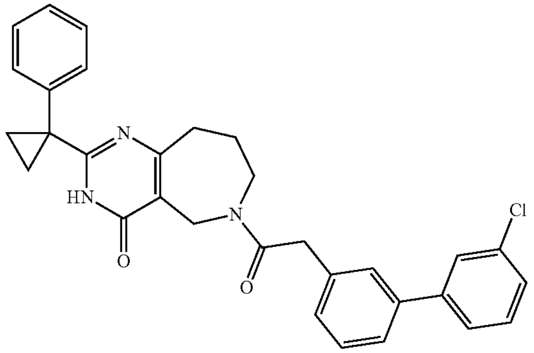 [SMILES: O=C(Cc1cccc(-c2cccc(Cl)c2)c1)N1CCCc2nc(C3(c4ccccc4)CC3)[nH]c(=O)c2C1] | 2.15 min | 510.4 |
| 17-137 | INT-26-3 | INT-8-3 | 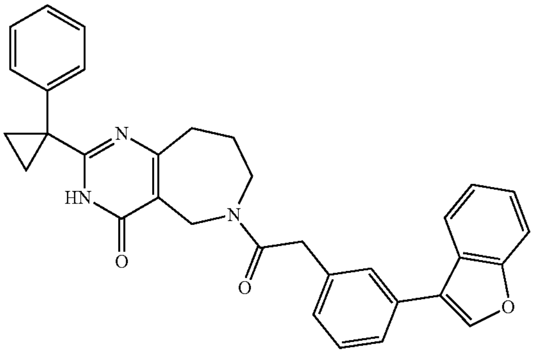 [SMILES: O=C(Cc1cccc(-c2coc3ccccc23)c1)N1CCCc2nc(C3(c4ccccc4)CC3)[nH]c(=O)c2C1] | 2.12 min | 516.5 |

TABLE 48-22-continued
| | | | | | |
|---|---|---|---|---|---|
| 17-138 | INT-26-4 | INT-8-3 | 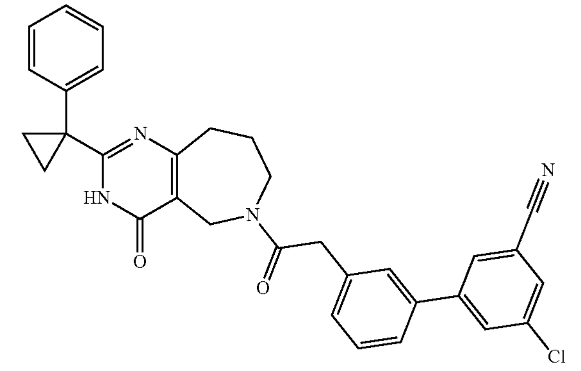 [SMILES: N#Cc1cc(Cl)cc(-c2cccc(CC(=O)N3CCCc4nc(C5(c6ccccc6)CC5)[nH]c(=O)c4C3)c2)c1] | 2.08 min | 535.4 |
| 17-139 | 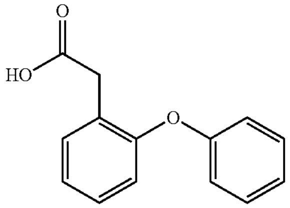 [SMILES: O=C(O)Cc1ccccc1Oc1ccccc1] | INT-8-14 | 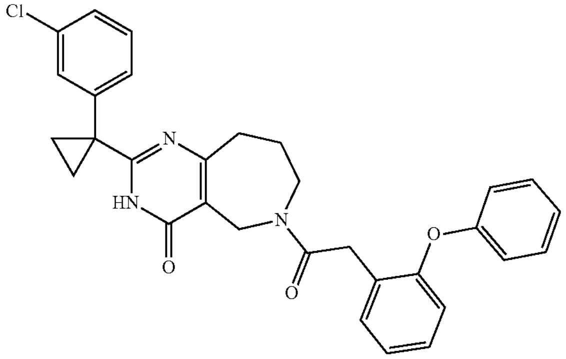 [SMILES: O=C(Cc1ccccc1Oc1ccccc1)N1CCCc2nc(C3(c4cccc(Cl)c4)CC3)[nH]c(=O)c2C1] | 2.11 min | 526.4 |
| 17-140 | 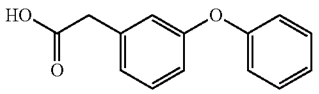 [SMILES: O=C(O)Cc1cccc(Oc2ccccc2)c1] | INT-8-14 | 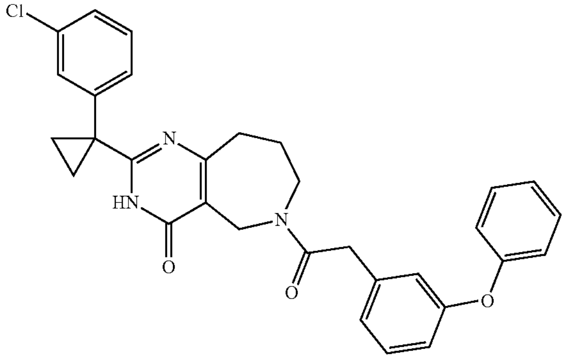 [SMILES: O=C(Cc1cccc(Oc2ccccc2)c1)N1CCCc2nc(C3(c4cccc(Cl)c4)CC3)[nH]c(=O)c2C1] | 2.12 min | 526.4 |
TABLE 48-23
| | | | | | |
|---|---|---|---|---|---|
| 17-141 | 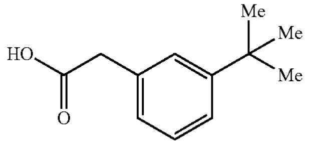 [SMILES: CC(C)(C)c1cccc(CC(=O)O)c1] | INT-8-14 | 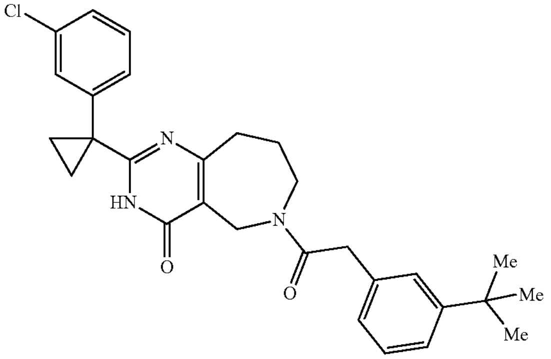 [SMILES: CC(C)(C)c1cccc(CC(=O)N2CCCc3nc(C4(c5cccc(Cl)c5)CC4)[nH]c(=O)c3C2)c1] | 2.17 min | 490.5 |

TABLE 48-23-continued
| | | | | | |
|---|---|---|---|---|---|
| 17-142 | 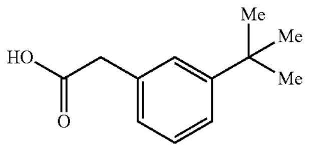 [SMILES: CC(C)(C)c1cccc(CC(=O)O)c1] | INT-8-3 | 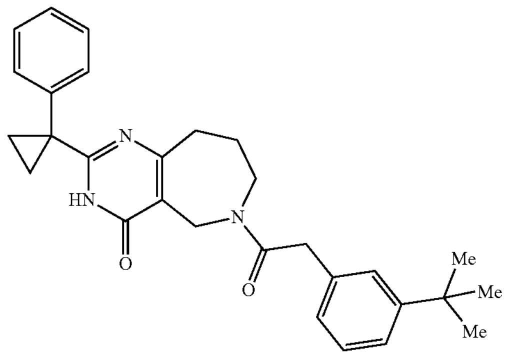 [SMILES: CC(C)(C)c1cccc(CC(=O)N2CCCc3nc(C4(c5ccccc5)CC4)[nH]c(=O)c3C2)c1] | 2.10 min | 456.5 |
| 17-143 | 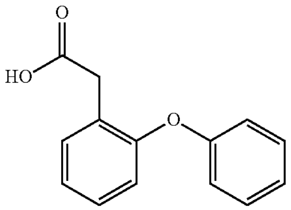 [SMILES: O=C(O)Cc1ccccc1Oc1ccccc1] | INT-8-3 | 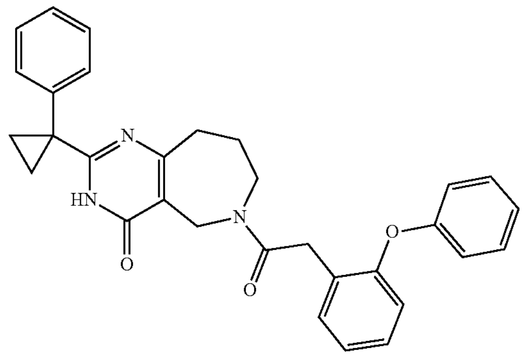 [SMILES: O=C(Cc1ccccc1Oc1ccccc1)N1CCCc2nc(C3(c4ccccc4)CC3)[nH]c(=O)c2C1] | 2.04 min | 492.5 |
| 17-144 | 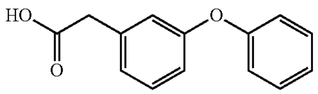 [SMILES: O=C(O)Cc1cccc(Oc2ccccc2)c1] | INT-8-3 | 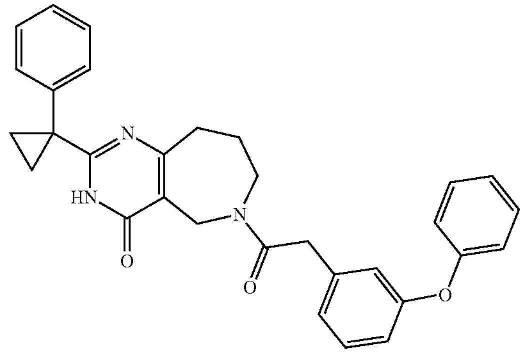 [SMILES: O=C(Cc1cccc(Oc2ccccc2)c1)N1CCCc2nc(C3(c4ccccc4)CC3)[nH]c(=O)c2C1] | 2.06 min | 492.4 |
| 17-145 | 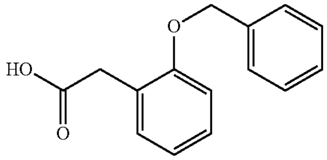 [SMILES: O=C(O)Cc1ccccc1OCc1ccccc1] | INT-8-3 | 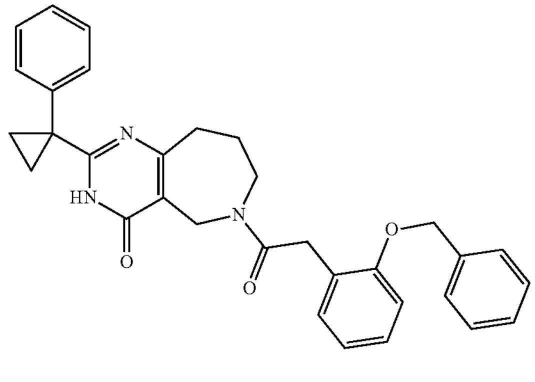 [SMILES: O=C(Cc1ccccc1OCc1ccccc1)N1CCCc2nc(C3(c4ccccc4)CC3)[nH]c(=O)c2C1] | 2.06 min | 506.5 |

TABLE 48-23-continued

| | | | | | |
|---|---|---|---|---|---|
| 17-146 | 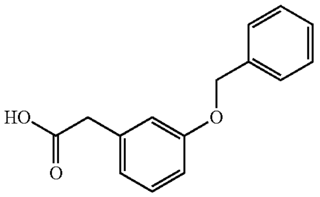 [SMILES: O=C(O)Cc1cccc(OCc2ccccc2)c1] | INT-8-3 | 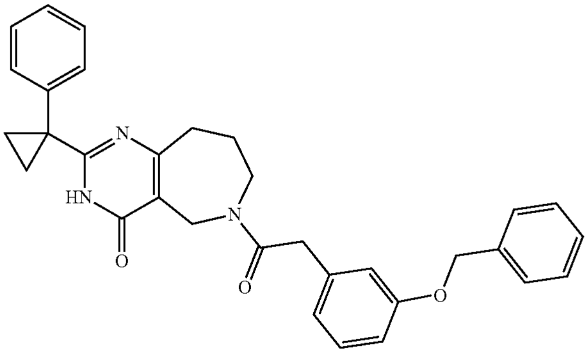 [SMILES: O=C(Cc1cccc(OCc2ccccc2)c1)N1CCCc2nc(C3(c4ccccc4)CC3)[nH]c(=O)c2C1] | 2.06 min | 506.5 |
| 17-147 | 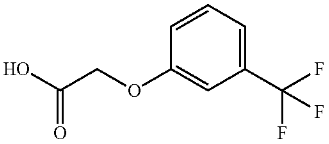 [SMILES: O=C(O)COc1cccc(C(F)(F)F)c1] | INT-8-14 | 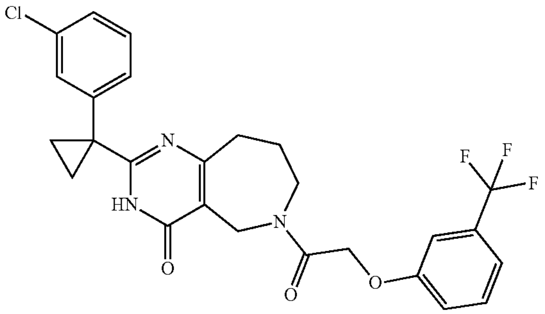 | 2.04 min | 518.4 |

The following amide derivatives (Ex-18-1 to Ex-18-31) are prepared according to the procedure of Ex-1 or the general synthesis in scheme-1 from the synthesized amine drivatives and the known or synthesized acid derivatives in Tables 49-1 to 49-5. The further purification is carried out by preparative LC-MS or SFC-MS system in usual manner. The retention time and observed MS by HPLC-QC method are summarized in Tables 49-1 to 49-5.

TABLE 49-1

| Ex. | Acid (INT or Reagent) | Amine (INT) | Structure | Retention time | Observed MS |
|---|---|---|---|---|---|
| 18-1 | 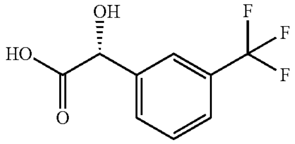 | INT-8-25 | 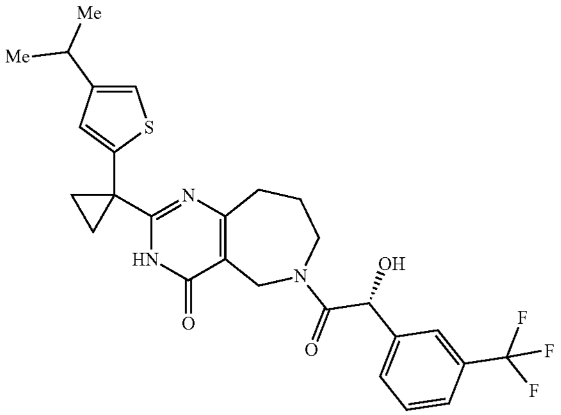 [SMILES: CC(C)c1csc(C2(c3nc4c(c(=O)[nH]3)CN(C(=O)[C@H](O)c3cccc(C(F)(F)F)c3)CCC4)CC2)c1] | 1.96 min | 532.2 |

TABLE 49-1-continued
| Ex. | Acid (INT or Reagent) | Amine (INT) | Structure | Reten-tion time | Ob-served MS |
|---|---|---|---|---|---|
| 18-2 | 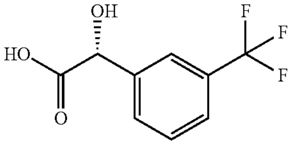 | INT-8-24 | 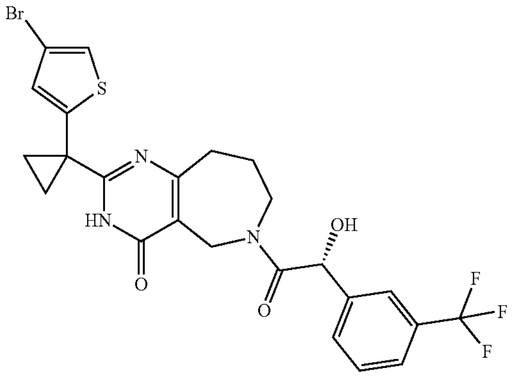 [SMILES: O=C([C@H](O)c1cccc(C(F)(F)F)c1)N1CCCc2nc(C3(c4cc(Br)cs4)CC3)[nH]c(=O)c2C1] | 1.78 min | 568.0 |
| 18-3 | 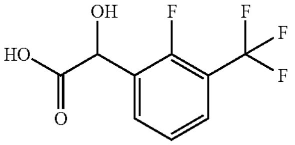 [SMILES: O=C(O)C(O)c1cccc(C(F)(F)F)c1F] | INT-8-22 | 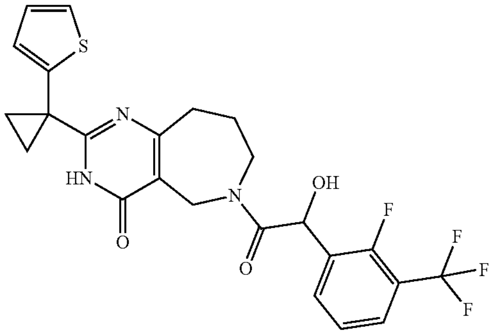 [SMILES: O=C(C(O)c1cccc(C(F)(F)F)c1F)N1CCCc2nc(C3(c4cccs4)CC3)[nH]c(=O)c2C1] | 1.66 min | 508.1 |
| 18-4 | 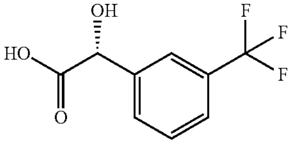 | INT-8-27 | 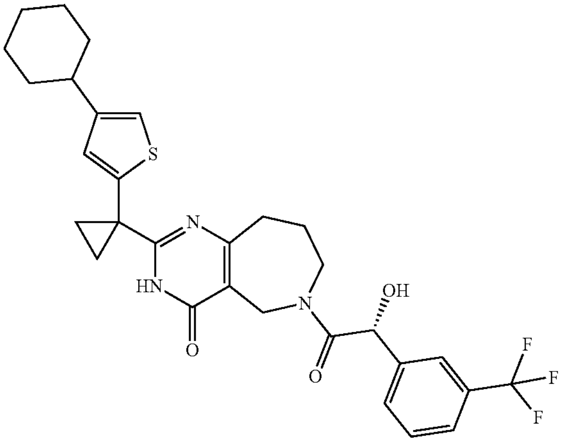 [SMILES: O=C([C@H](O)c1cccc(C(F)(F)F)c1)N1CCCc2nc(C3(c4cc(C5CCCCC5)cs4)CC3)[nH]c(=O)c2C1] | 2.19 min | 572.2 |
| 18-5 | INT-25-5 | INT-8-22 | 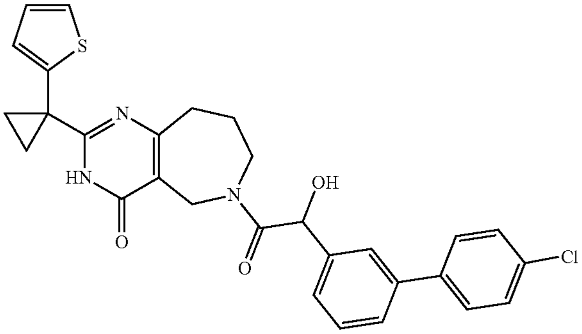 [SMILES: O=C(C(O)c1cccc(-c2ccc(Cl)cc2)c1)N1CCCc2nc(C3(c4cccs4)CC3)[nH]c(=O)c2C1] | 1.91 min | 532.0 |

TABLE 49-1-continued
| Ex. | Acid (INT or Reagent) | Amine (INT) | Structure | Reten-tion time | Ob-served MS |
|---|---|---|---|---|---|
| 18-6 | 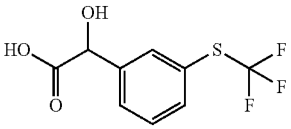 [SMILES: O=C(O)C(O)c1cccc(SC(F)(F)F)c1] | INT-8-22 | 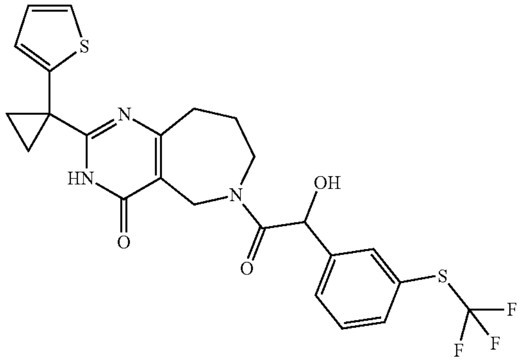 [SMILES: O=C(C(O)c1cccc(SC(F)(F)F)c1)N1CCCc2nc(C3(c4cccs4)CC3)[nH]c(=O)c2C1] | 1.79 min | 522.1 |
TABLE 49-2
| | | | | | |
|---|---|---|---|---|---|
| 18-7 | 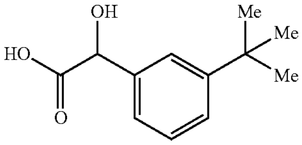 [SMILES: CC(C)(C)c1cccc(C(O)C(=O)O)c1] | INT-8-22 | 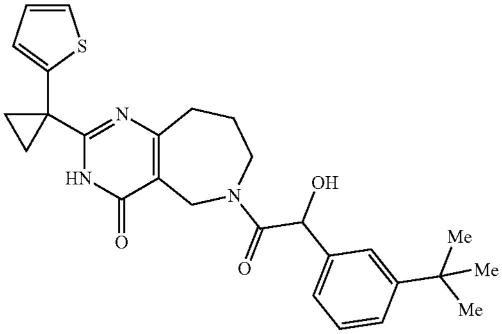 [SMILES: CC(C)(C)c1cccc(C(O)C(=O)N2CCCc3nc(C4(c5cccs5)CC4)[nH]c(=O)c3C2)c1] | 1.84 min | 478.2 |
| 18-8 | 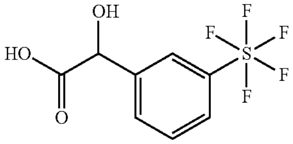 [SMILES: O=C(O)C(O)c1cccc(S(F)(F)(F)(F)F)c1] | INT-8-22 | 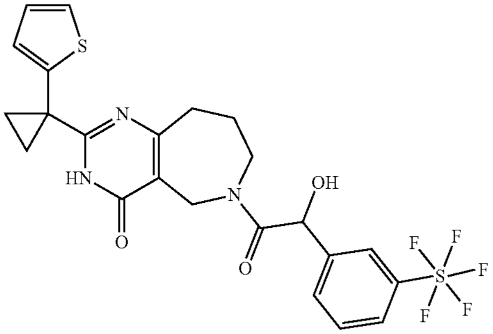 [SMILES: O=C(C(O)c1cccc(S(F)(F)(F)(F)F)c1)N1CCCc2nc(C3(c4cccs4)CC3)[nH]c(=O)c2C1] | 1.75 min | 548.1 |
| 18-9 | 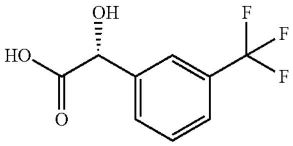 | INT-8-22 | 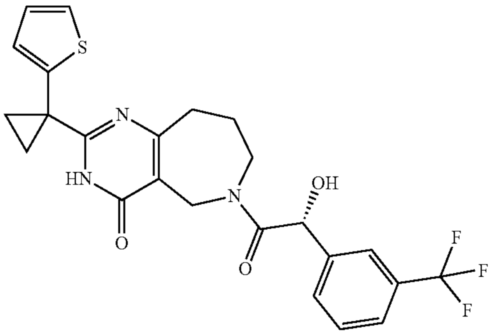 [SMILES: O=C([C@H](O)c1cccc(C(F)(F)F)c1)N1CCCc2nc(C3(c4cccs4)CC3)[nH]c(=O)c2C1] | 1.66 min | 490.1 |

TABLE 49-2-continued
| | | | | |
|---|---|---|---|---|
| 18-10 | 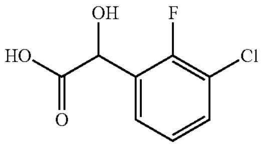 | INT-8-22 | 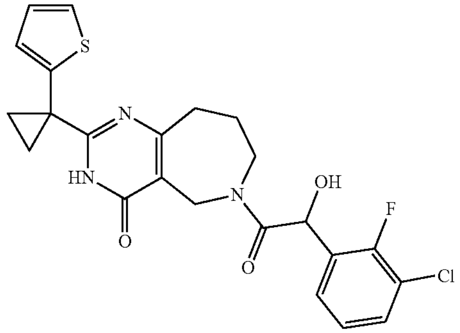 [SMILES: O=C(C(O)c1cccc(Cl)c1F)N1CCCc2nc(C3(c4cccs4)CC3)[nH]c(=O)c2C1] | 1.58 min 474.1 |
| 18-11 | 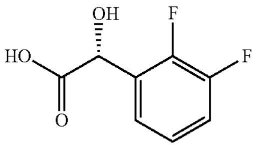 [SMILES: O=C(O)[C@H](O)c1cccc(F)c1F] | INT-8-22 | 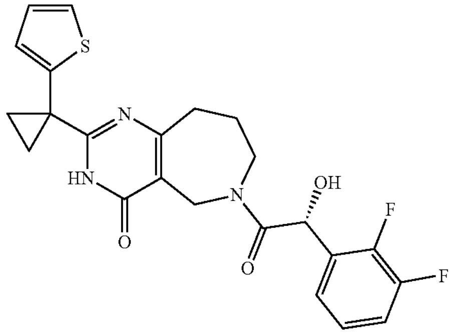 [SMILES: O=C([C@H](O)c1cccc(F)c1F)N1CCCc2nc(C3(c4cccs4)CC3)[nH]c(=O)c2C1] | 1.50 min 458.1 |
| 18-12 | 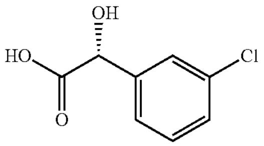 | INT-8-22 | 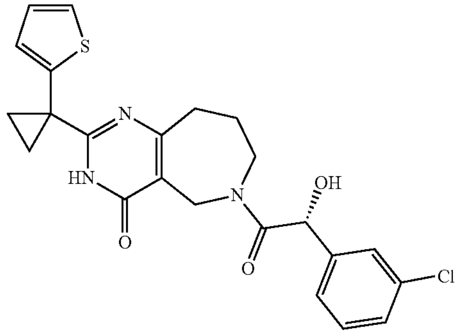 [SMILES: O=C([C@H](O)c1cccc(Cl)c1)N1CCCc2nc(C3(c4cccs4)CC3)[nH]c(=O)c2C1] | 1.58 min 456.0 |
| 18-13 | 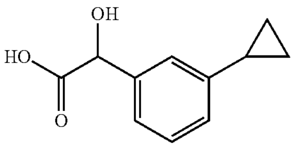 [SMILES: O=C(O)C(O)c1cccc(C2CC2)c1] | INT-8-22 | 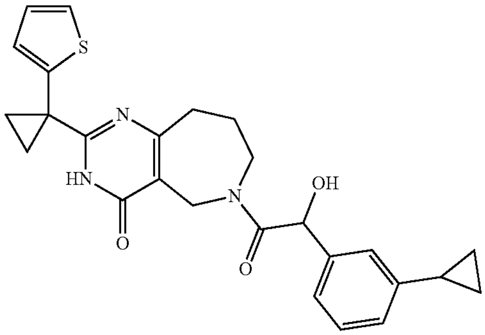 [SMILES: O=C(C(O)c1cccc(C2CC2)c1)N1CCCc2nc(C3(c4cccs4)CC3)[nH]c(=O)c2C1] | 1.65 min 462.2 |

TABLE 49-3
| | | | | | |
|---|---|---|---|---|---|
| 18-14 | 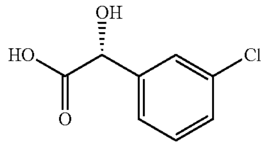 | INT-8-23 | 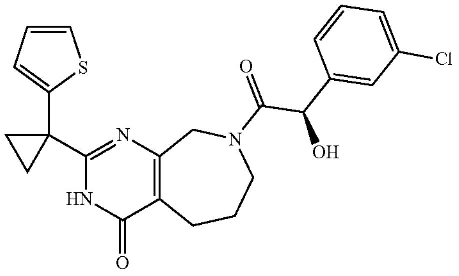 [SMILES: O=C([C@H](O)c1cccc(Cl)c1)N1CCCc2c(nc(C3(c4cccs4)CC3)[nH]c2=O)C1] | 1.58 min | 456.0 |
| 18-15 | 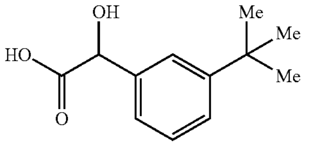 [SMILES: CC(C)(C)c1cccc(C(O)C(=O)O)c1] | INT-8-25 | 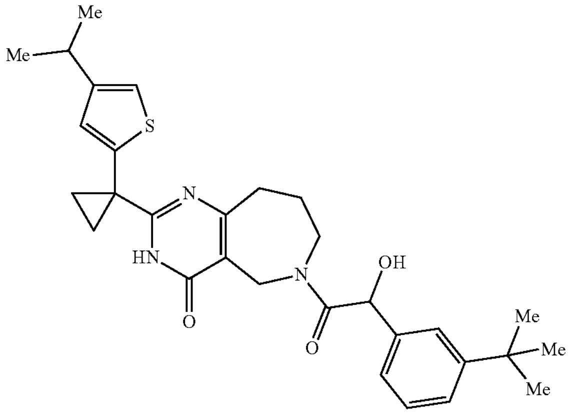 [SMILES: CC(C)c1csc(C2(c3nc4c(c(=O)[nH]3)CN(C(=O)C(O)c3cccc(C(C)(C)C)c3)CCC4)CC2)c1] | 2.09 min | 520.1 |
| 18-16 | 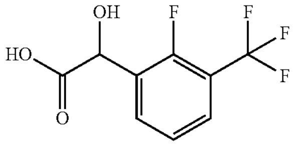 [SMILES: O=C(O)C(O)c1cccc(C(F)(F)F)c1F] | INT-8-25 | 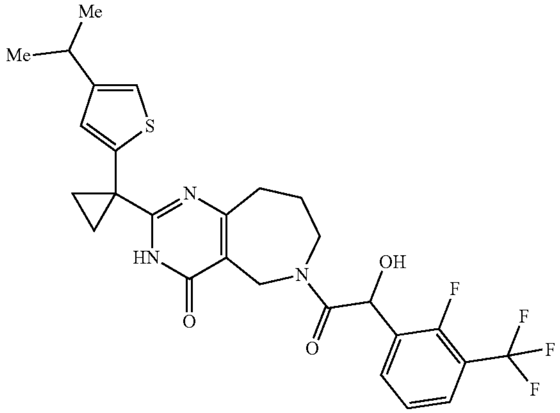 | 1.93 min | 550.0 |
| 18-17 | 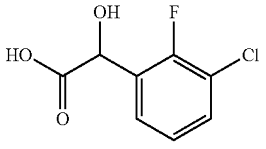 [SMILES: O=C(O)C(O)c1cccc(Cl)c1F] | INT-8-25 | 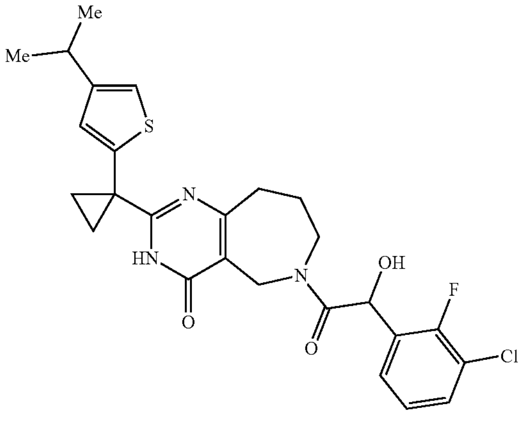 [SMILES: CC(C)c1csc(C2(c3nc4c(c(=O)[nH]3)CN(C(=O)C(O)c3cccc(Cl)c3F)CCC4)CC2)c1] | 1.87 min | 516.0 |

TABLE 49-3-continued
| | | | | |
|---|---|---|---|---|
| 18-18 | 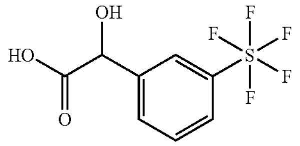 [SMILES: O=C(O)C(O)c1cccc(S(F)(F)(F)(F)F)c1] | INT-8-25 | 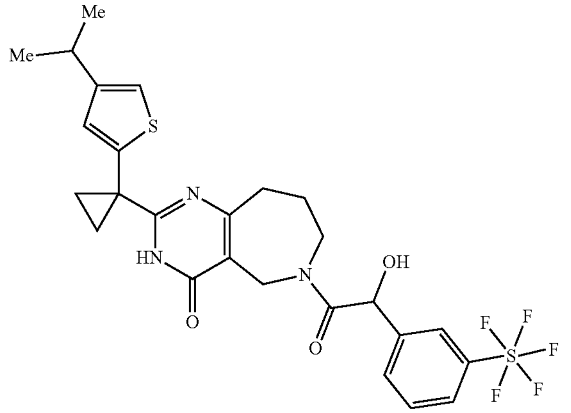 [SMILES: CC(C)c1csc(C2(c3nc4c(c(=O)[nH]3)CN(C(=O)C(O)c3cccc(S(F)(F)(F)(F)F)c3)CCC4)CC2)c1] | 2.00 min 590.0 |
| 18-19 | 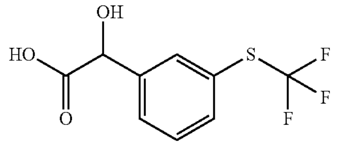 [SMILES: O=C(O)C(O)c1cccc(SC(F)(F)F)c1] | INT-8-25 | 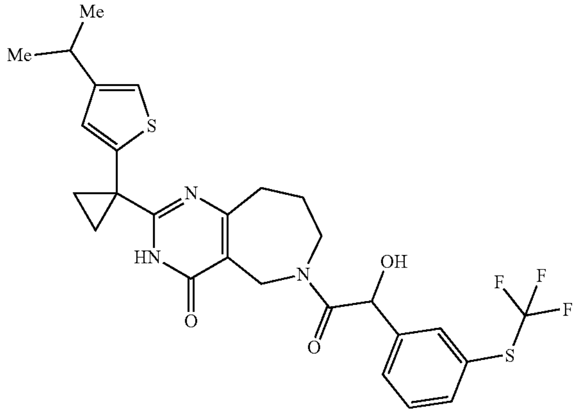 [SMILES: CC(C)c1csc(C2(c3nc4c(c(=O)[nH]3)CN(C(=O)C(O)c3cccc(SC(F)(F)F)c3)CCC4)CC2)c1] | 2.04 min 564.0 |
TABLE 49-4
| | | | | |
|---|---|---|---|---|
| 18-20 | INT-25-3 | INT-8-25 | 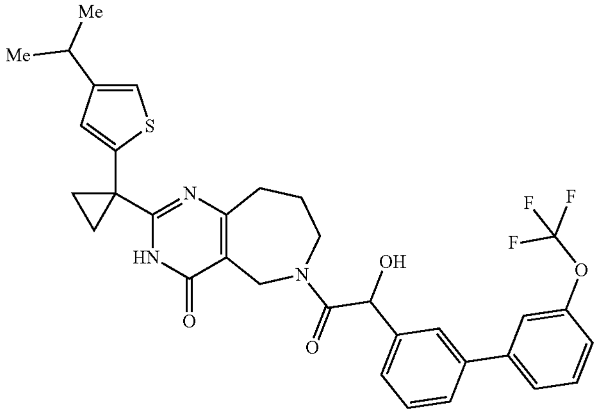 [SMILES: CC(C)c1csc(C2(c3nc4c(c(=O)[nH]3)CN(C(=O)C(O)c3cccc(-c5cccc(OC(F)(F)F)c5)c3)CCC4)CC2)c1] | 2.17 min 624.1 |

TABLE 49-4-continued
| | | | | |
|---|---|---|---|---|
| 18-21 | INT-25-2 | INT-8-25 | 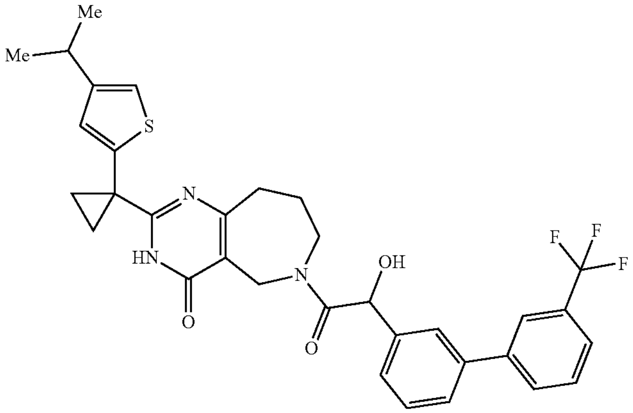 | 2.14 min 608.1 |
| 18-22 | 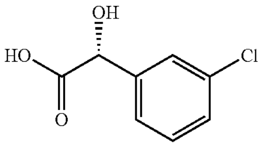 [SMILES: O=C(O)[C@H](O)c1cccc(Cl)c1] | INT-8-27 | 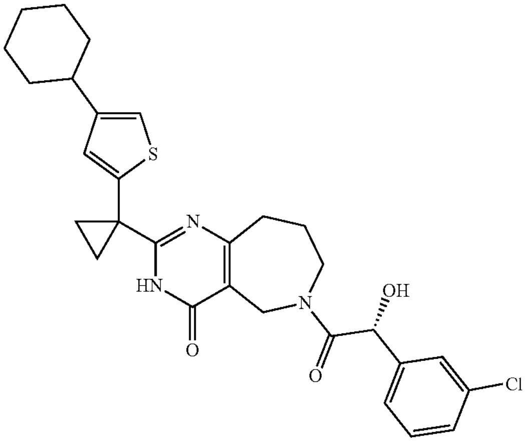 [SMILES: O=C([C@H](O)c1cccc(Cl)c1)N1CCCc2nc(C3(c4cc(C5CCCCC5)cs4)CC3)[nH]c(=O)c2C1] | 2.13 min 538.0 |
| 18-23 | 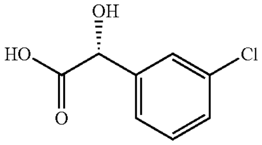 | INT-8-26 | 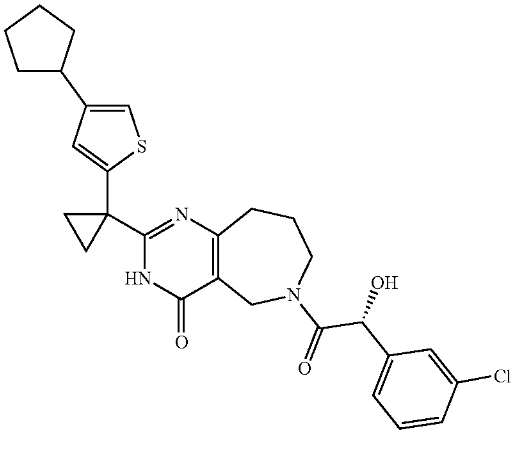 [SMILES: O=C([C@H](O)c1cccc(Cl)c1)N1CCCc2nc(C3(c4cc(C5CCCC5)cs4)CC3)[nH]c(=O)c2C1] | 2.04 min 523.9 |

TABLE 49-4-continued
| | | | | | |
|---|---|---|---|---|---|
| 18-24 | 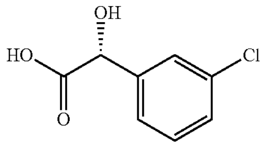 [SMILES: O=C(O)[C@H](O)c1cccc(Cl)c1] | INT-8-25 | 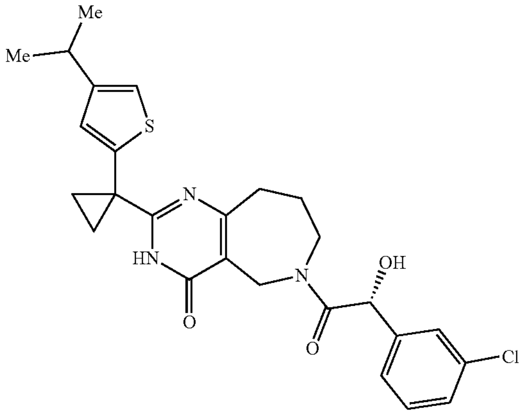 | 1.88 min | 497.9 |
| 18-25 | 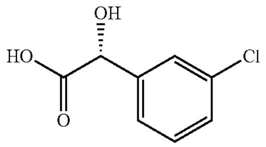 [SMILES: O=C(O)[C@H](O)c1cccc(Cl)c1] | INT-8-28 | 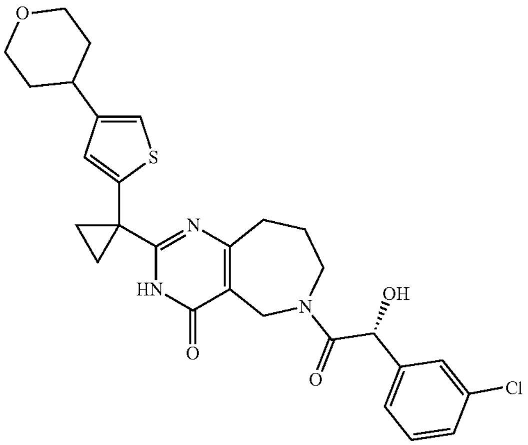 [SMILES: O=C([C@H](O)c1cccc(Cl)c1)N1CCCc2nc(C3(c4cc(C5CCOCC5)cs4)CC3)[nH]c(=O)c2C1] | 1.64 min | 540.0 |
TABLE 49-5
| | | | | | |
|---|---|---|---|---|---|
| 18-26 | INT-26-2 | INT-10-8 | 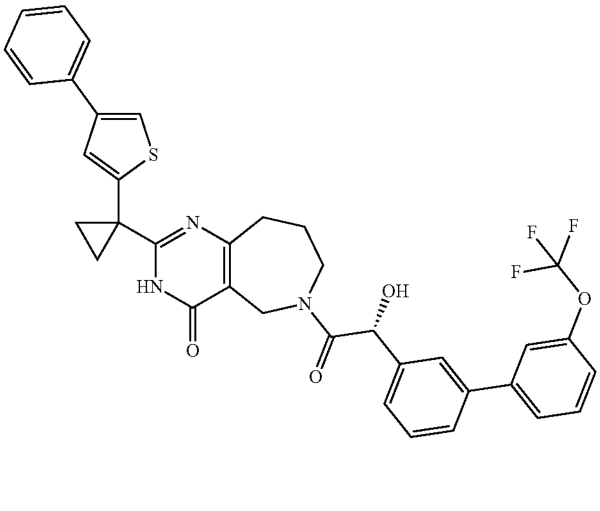 [SMILES: O=C([C@H](O)c1cccc(-c2cccc(OC(F)(F)F)c2)c1)N1CCCc2nc(C3(c4cc(-c5ccccc5)cs4)CC3)[nH]c(=O)c2C1] | 2.18 min | 658.0 |

TABLE 49-5-continued
| | | | | | |
|---|---|---|---|---|---|
| 18-27 | 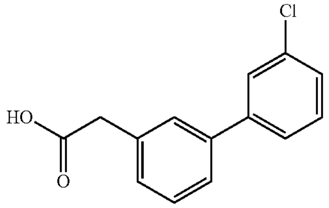 [SMILES: O=C(O)Cc1cccc(-c2cccc(Cl)c2)c1] | INT-10-8 | 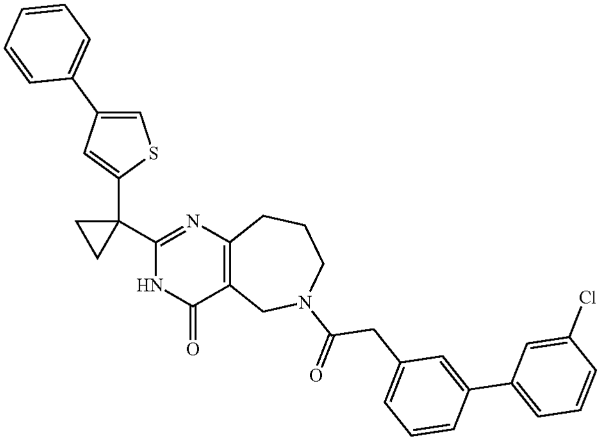 [SMILES: O=C(Cc1cccc(-c2cccc(Cl)c2)c1)N1CCCc2nc(C3(c4cc(-c5ccccc5)cs4)CC3)[nH]c(=O)c2C1] | 2.32 min | 592.5 |
| 18-28 | 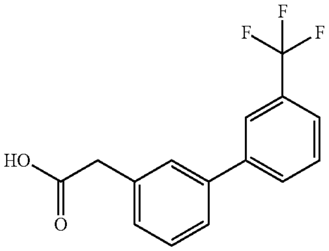 [SMILES: O=C(O)Cc1cccc(-c2cccc(C(F)(F)F)c2)c1] | INT-10-8 | 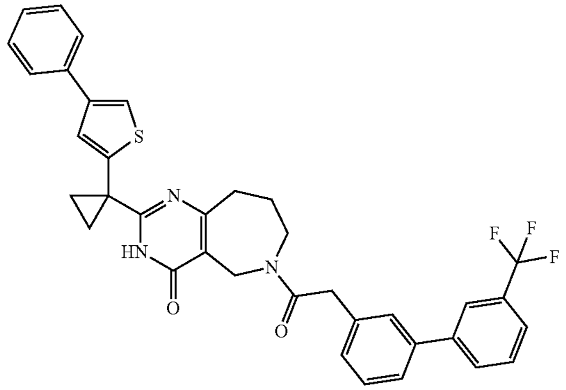 [SMILES: O=C(Cc1cccc(-c2cccc(C(F)(F)F)c2)c1)N1CCCc2nc(C3(c4cc(-c5ccccc5)cs4)CC3)[nH]c(=O)c2C1] | 2.32 min | 626.5 |
| 18-29 | 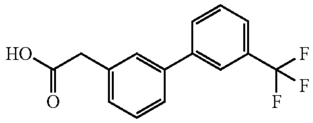 [SMILES: O=C(O)Cc1cccc(-c2cccc(C(F)(F)F)c2)c1] | INT-8-25 | 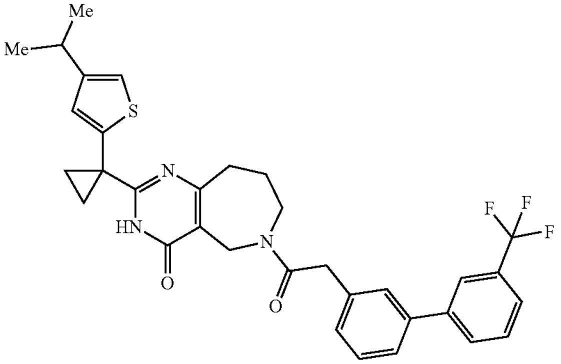 [SMILES: CC(C)c1csc(C2(c3nc4c(c(=O)[nH]3)CN(C(=O)Cc3cccc(-c5cccc(C(F)(F)F)c5)c3)CCC4)CC2)c1] | 2.36 min | 592.4 |
| 18-30 | 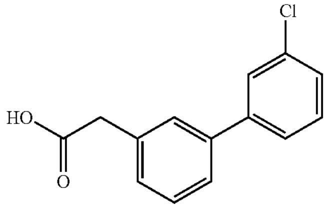 [SMILES: O=C(O)Cc1cccc(-c2cccc(Cl)c2)c1] | INT-8-25 | 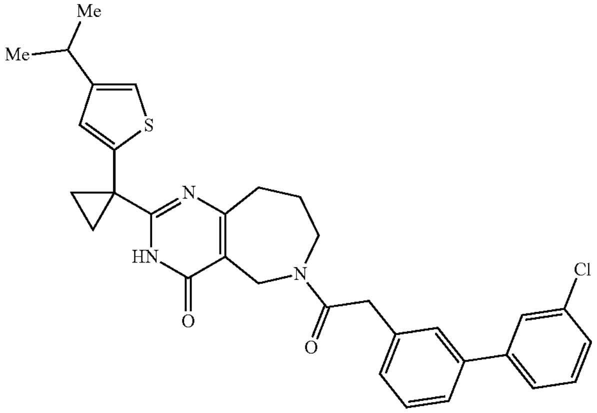 [SMILES: CC(C)c1csc(C2(c3nc4c(c(=O)[nH]3)CN(C(=O)Cc3cccc(-c5cccc(Cl)c5)c3)CCC4)CC2)c1] | 2.36 min | 558.4 |

TABLE 49-5-continued

| | | | | | |
|---|---|---|---|---|---|
| 18-31 | 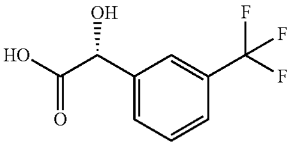 [SMILES: O=C(O)[C@H](O)c1cccc(C(F)(F)F)c1] | INT-8-39 | 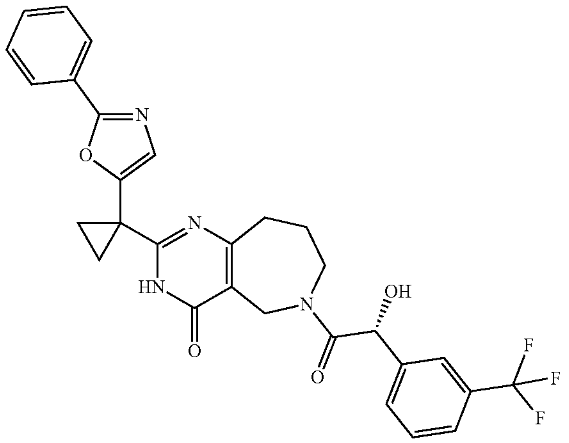 [SMILES: O=C([C@H](O)c1cccc(C(F)(F)F)c1)N1CCCc2nc(C3(c4cnc(-c5ccccc5)o4)CC3)[nH]c(=O)c2C1] | 1.69 min | 550.9 |

The following amide derivatives (Ex-19-1 to Ex-19-15) are prepared according to the procedure of Ex-1 or the general synthesis in scheme-1 from the synthesized amine drivatives and the known or synthesized acid derivatives in Tables 50-1 to 50-3. The further purification is carried out by preparative LC-MS or SFC-MS system in usual manner. The retention time and observed MS by HPLC-QC method are summarized in Tables 50-1 to 50-3.

TABLE 50-1

| Ex. | Acid (INT or Reagent) | Amine (INT) | Structure | Retention time | Observed MS |
|---|---|---|---|---|---|
| 19-1 | 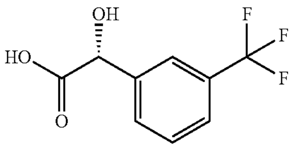 [SMILES: O=C(O)[C@H](O)c1cccc(C(F)(F)F)c1] | INT-8-34 | 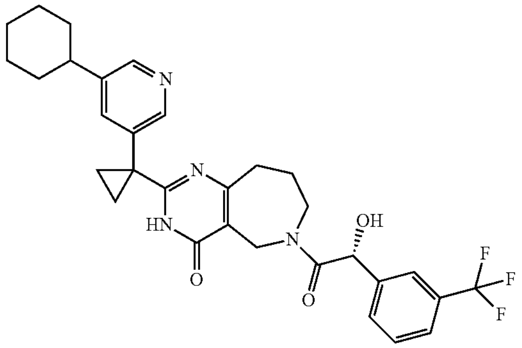 [SMILES: O=C([C@H](O)c1cccc(C(F)(F)F)c1)N1CCCc2nc(C3(c4cncc(C5CCCCC5)c4)CC3)[nH]c(=O)c2C1] | 1.83 min | 567.3 |
| 19-2 | 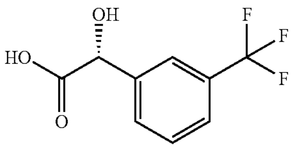 [SMILES: O=C(O)[C@H](O)c1cccc(C(F)(F)F)c1] | INT-8-33 | 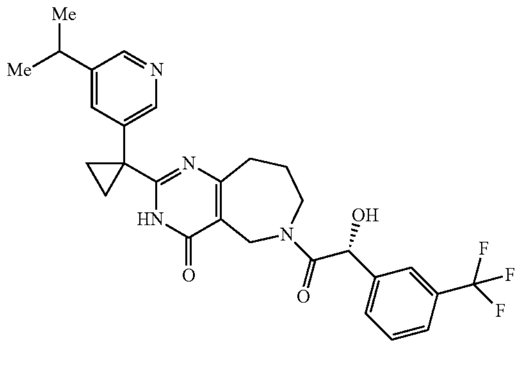 | 1.59 min | 527.2 |

TABLE 50-1-continued
| Ex. | Acid (INT or Reagent) | Amine (INT) | Structure | Retention time | Observed MS |
|---|---|---|---|---|---|
| 19-3 | 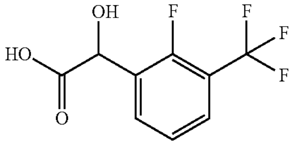 [SMILES: O=C(O)C(O)c1cccc(C(F)(F)F)c1F] | INT-10-9 | 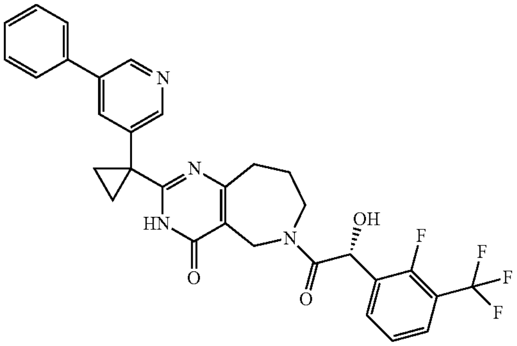 [SMILES: O=C([C@H](O)c1cccc(C(F)(F)F)c1F)N1CCCc2nc(C3(c4cncc(-c5ccccc5)c4)CC3)[nH]c(=O)c2C1] | 1.65 min | 579.2 |
| 19-4 | 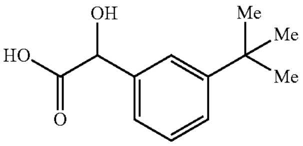 [SMILES: CC(C)(C)c1cccc(C(O)C(=O)O)c1] | INT-8-33 | 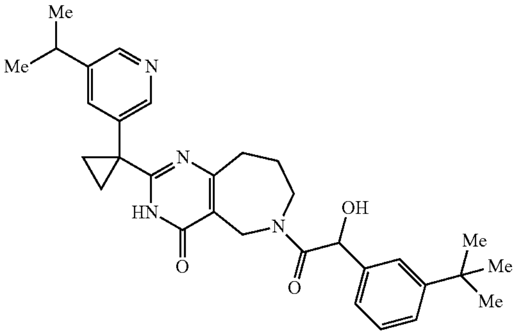 [SMILES: CC(C)c1cncc(C2(c3nc4c(c(=O)[nH]3)CN(C(=O)C(O)c3cccc(C(C)(C)C)c3)CCC4)CC2)c1] | 1.74 min | 515.1 |
| 19-5 | 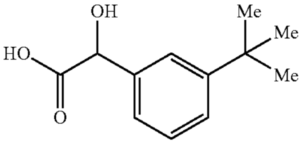 [SMILES: CC(C)(C)c1cccc(C(O)C(=O)O)c1] | INT-10-9 | 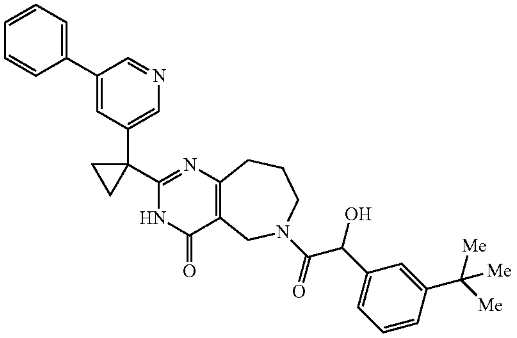 [SMILES: CC(C)(C)c1cccc(C(O)C(=O)N2CCCc3nc(C4(c5cncc(-c6ccccc6)c5)CC4)[nH]c(=O)c3C2)c1] | 1.79 min | 549.3 |
| 19-6 | 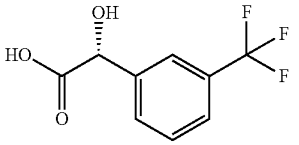 | INT-8-31 | 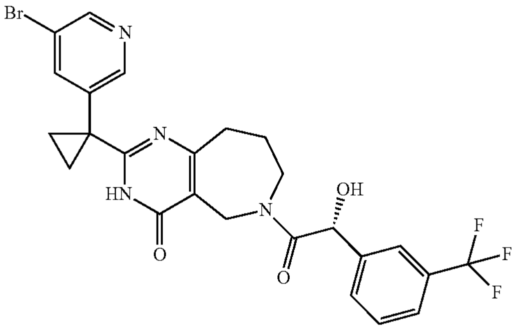 [SMILES: O=C([C@H](O)c1cccc(C(F)(F)F)c1)N1CCCc2nc(C3(c4cncc(Br)c4)CC3)[nH]c(=O)c2C1] | 1.53 min | 563.1 |

TABLE 50-2
| | | | | |
|---|---|---|---|---|
| 19-7 | 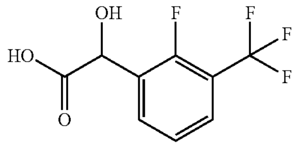 [SMILES: O=C(O)C(O)c1cccc(C(F)(F)F)c1F] | INT-8-33 | 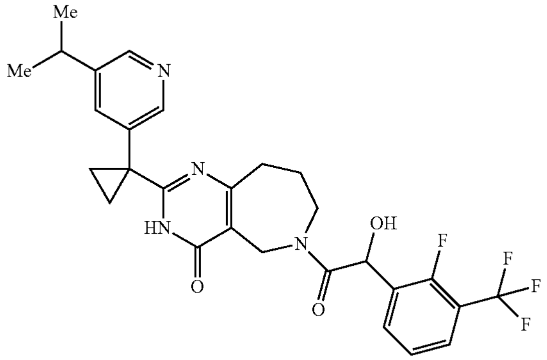 [SMILES: CC(C)c1cncc(C2(c3nc4c(c(=O)[nH]3)CN(C(=O)C(O)c3cccc(C(F)(F)F)c3F)CCC4)CC2)c1] | 1.59 min 545.1 |
| 19-8 | 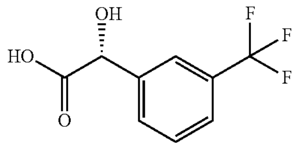 [SMILES: O=C(O)[C@H](O)c1cccc(C(F)(F)F)c1] | INT-8-35 | 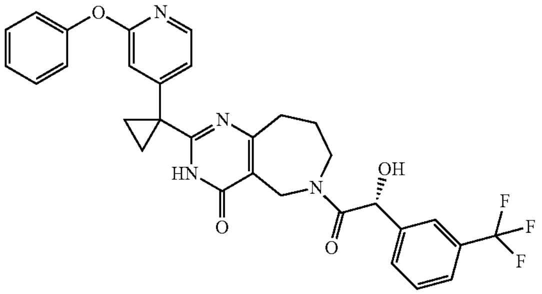 [SMILES: O=C([C@H](O)c1cccc(C(F)(F)F)c1)N1CCCc2nc(C3(c4ccnc(Oc5ccccc5)c4)CC3)[nH]c(=O)c2C1] | 1.73 min 577.0 |
| 19-9 | 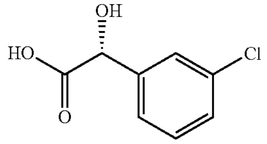 [SMILES: O=C(O)[C@H](O)c1cccc(Cl)c1] | INT-8-35 | 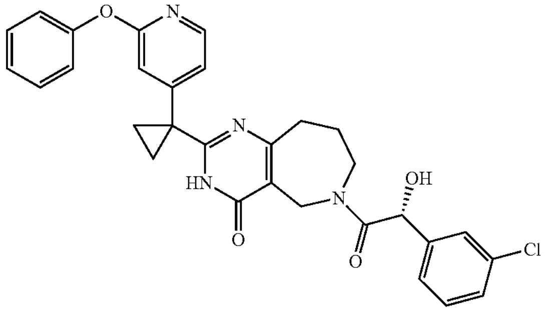 [SMILES: O=C([C@H](O)c1cccc(Cl)c1)N1CCCc2nc(C3(c4ccnc(Oc5ccccc5)c4)CC3)[nH]c(=O)c2C1] | 1.68 min 542.9 |
| 19-10 | 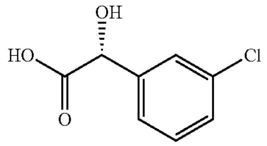 [SMILES: O=C(O)[C@H](O)c1cccc(Cl)c1] | INT-10-10 | 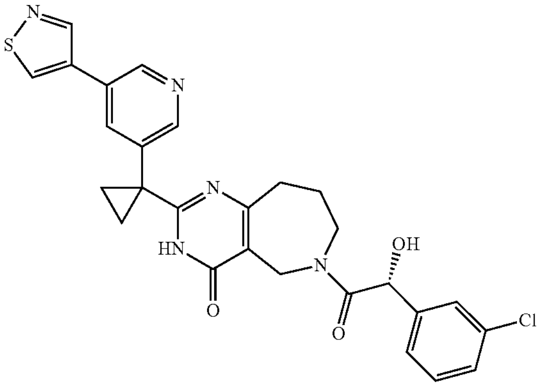 [SMILES: O=C([C@H](O)c1cccc(Cl)c1)N1CCCc2nc(C3(c4cncc(-c5cnsc5)c4)CC3)[nH]c(=O)c2C1] | 1.33 min 533.9 |

TABLE 50-2-continued
| | | | | |
|---|---|---|---|---|
| 19-11 | 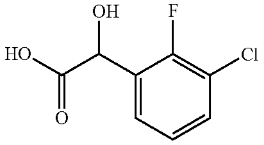 [SMILES: O=C(O)C(O)c1cccc(Cl)c1F] | INT-10-9 | 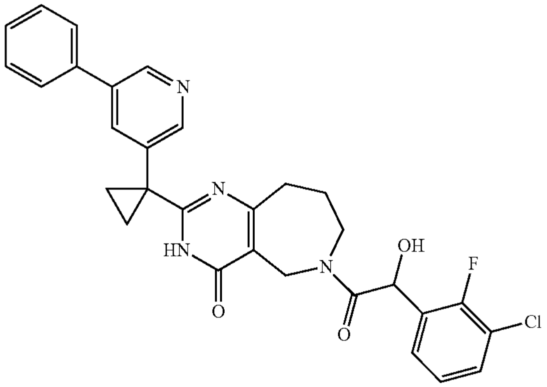 [SMILES: O=C(C(O)c1cccc(Cl)c1F)N1CCCc2nc(C3(c4cncc(-c5ccccc5)c4)CC3)[nH]c(=O)c2C1] | 1.57 min 544.9 |
| 19-12 | 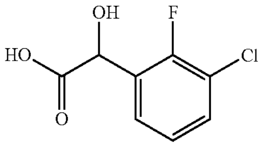 [SMILES: O=C(O)C(O)c1cccc(Cl)c1F] | INT-8-33 | 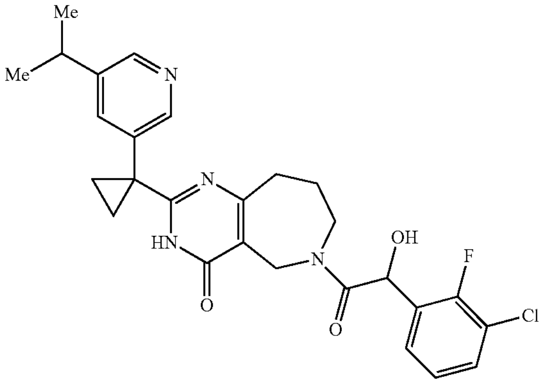 [SMILES: CC(C)c1cncc(C2(c3nc4c(c(=O)[nH]3)CN(C(=O)C(O)c3cccc(Cl)c3F)CCC4)CC2)c1] | 1.49 min 510.9 |
TABLE 50-3
| | | | | |
|---|---|---|---|---|
| 19-13 | 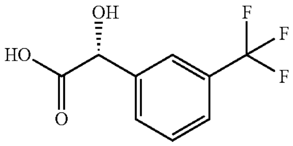 [SMILES: O=C(O)[C@H](O)c1cccc(C(F)(F)F)c1] | INT-8-40 | 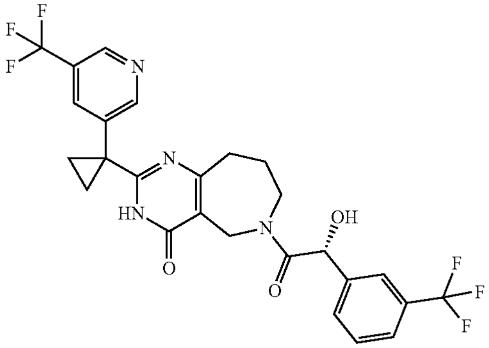 [SMILES: O=C([C@H](O)c1cccc(C(F)(F)F)c1)N1CCCc2nc(C3(c4cncc(C(F)(F)F)c4)CC3)[nH]c(=O)c2C1] | 1.57 min 552.9 |
| 19-14 | 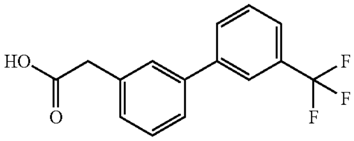 [SMILES: O=C(O)Cc1cccc(-c2cccc(C(F)(F)F)c2)c1] | INT-10-9 | 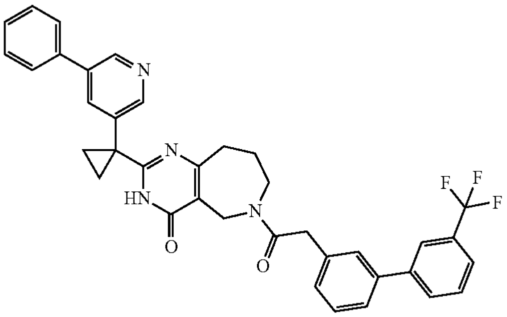 [SMILES: O=C(Cc1cccc(-c2cccc(C(F)(F)F)c2)c1)N1CCCc2nc(C3(c4cncc(-c5ccccc5)c4)CC3)[nH]c(=O)c2C1] | 2.13 min 621.5 |

TABLE 50-3-continued

| | | | | |
|---|---|---|---|---|
| 19-15 | 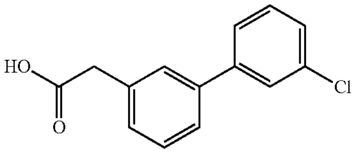 [SMILES: O=C(O)Cc1cccc(-c2cccc(Cl)c2)c1] | INT-10-9 | 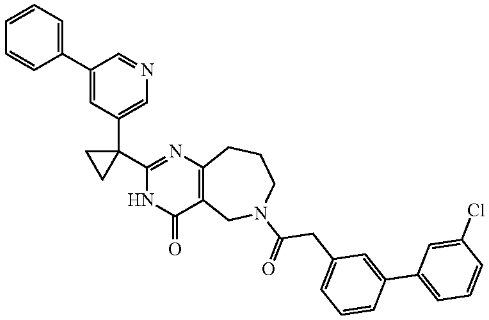 [SMILES: O=C(Cc1cccc(-c2cccc(Cl)c2)c1)N1CCCc2nc(C3(c4cncc(-c5ccccc5)c4)CC3)[nH]c(=O)c2C1] | 2.11 min 587.5 |

The following amide derivatives (Ex-20-1 to Ex-20-15) are prepared according to the procedure of Ex-1 or the general synthesis in scheme-1 from the synthesized amine drivatives and the known or synthesized acid derivatives in Tables 51-1 to 51-2. The further purification is carried out by preparative LC-MS or SFC-MS system in usual manner. The retention time and observed MS by HPLC-QC method are summarized in Tables 51-1 to 51-2.

TABLE 51-1

| Ex. | Acid (INT or Reagent) | Amine (INT) | Structure | Retention time | Observed MS |
|---|---|---|---|---|---|
| 20-1 | 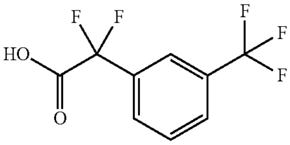 [SMILES: O=C(O)C(F)(F)c1cccc(C(F)(F)F)c1] | INT-8-3 | 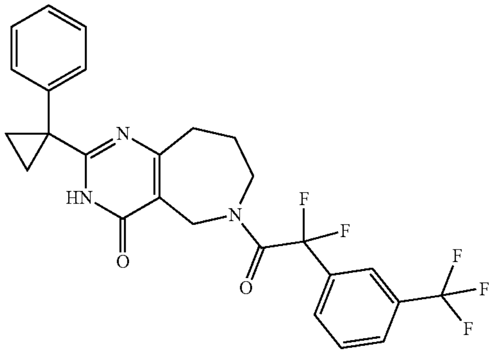 [SMILES: O=C(N1CCCc2nc(C3(c4ccccc4)CC3)[nH]c(=O)c2C1)C(F)(F)c1cccc(C(F)(F)F)c1] | 1.91 min | 504.1 |
| 20-2 | 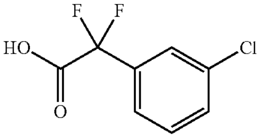 [SMILES: O=C(O)C(F)(F)c1cccc(Cl)c1] | INT-8-14 | 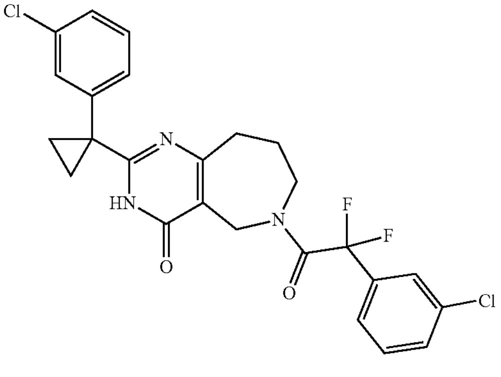 [SMILES: O=C(N1CCCc2nc(C3(c4cccc(Cl)c4)CC3)[nH]c(=O)c2C1)C(F)(F)c1cccc(Cl)c1] | 1.95 min | 504.0 |

TABLE 51-1-continued
| Ex. | Acid (INT or Reagent) | Amine (INT) | Structure | Retention time | Observed MS |
|---|---|---|---|---|---|
| 20-3 | 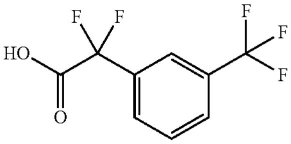 [SMILES: O=C(O)C(F)(F)c1cccc(C(F)(F)F)c1] | INT-8-13 | 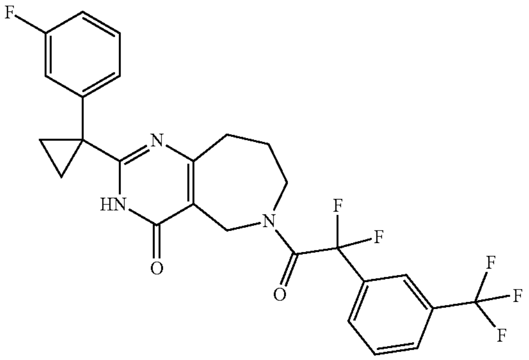 [SMILES: O=C(N1CCCc2nc(C3(c4cccc(F)c4)CC3)[nH]c(=O)c2C1)C(F)(F)c1cccc(C(F)(F)F)c1] | 1.90 min | 522.1 |
| 20-4 | 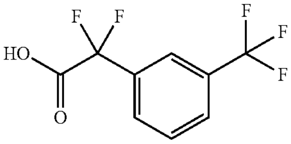 [SMILES: O=C(O)C(F)(F)c1cccc(C(F)(F)F)c1] | INT-8-14 | 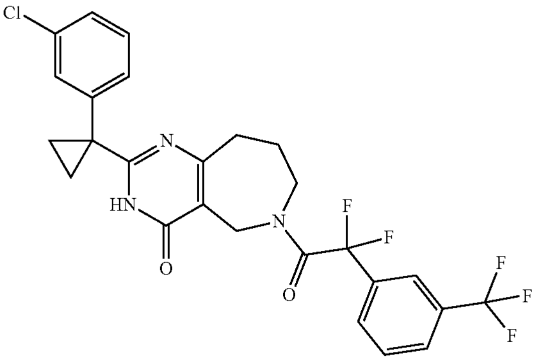 [SMILES: O=C(N1CCCc2nc(C3(c4cccc(Cl)c4)CC3)[nH]c(=O)c2C1)C(F)(F)c1cccc(C(F)(F)F)c1] | 1.99 min | 538.1 |
| 20-5 | 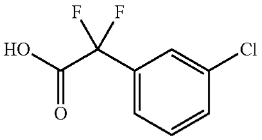 | INT-8-13 | 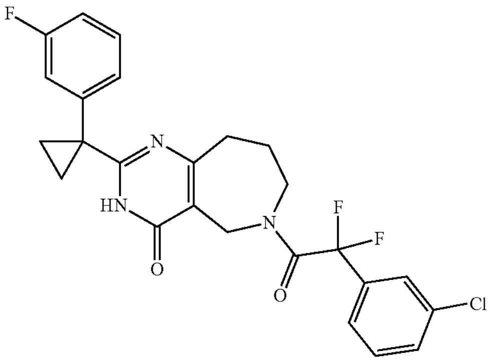 [SMILES: O=C(N1CCCc2nc(C3(c4cccc(F)c4)CC3)[nH]c(=O)c2C1)C(F)(F)c1cccc(Cl)c1] | 1.86 min | 488.1 |
| 20-6 | 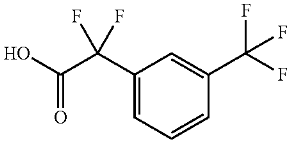 [SMILES: O=C(O)C(F)(F)c1cccc(C(F)(F)F)c1] | INT-8-19 | 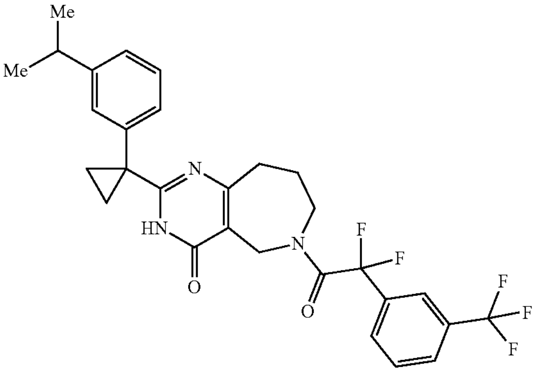 [SMILES: CC(C)c1cccc(C2(c3nc4c(c(=O)[nH]3)CN(C(=O)C(F)(F)c3cccc(C(F)(F)F)c3)CCC4)CC2)c1] | 2.14 min | 546.0 |

TABLE 51-1-continued
| Ex. | Acid (INT or Reagent) | Amine (INT) | Structure | Retention time | Observed MS |
|---|---|---|---|---|---|
| 20-7 | 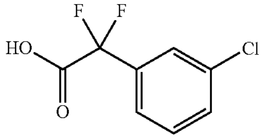 | INT-8-3 | 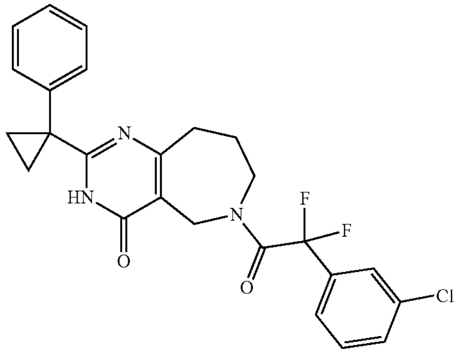 [SMILES: O=C(N1CCCc2nc(C3(c4ccccc4)CC3)[nH]c(=O)c2C1)C(F)(F)c1cccc(Cl)c1] | 1.86 min | 470.1 |
TABLE 51-2
| | | | | | |
|---|---|---|---|---|---|
| 20-8 | 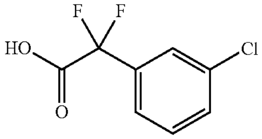 [SMILES: O=C(O)C(F)(F)c1cccc(Cl)c1] | INT-8-19 | 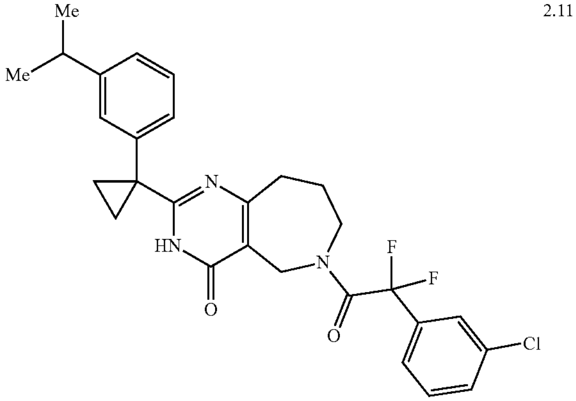 | 2.11 min | 512.0 |
| 20-9 | 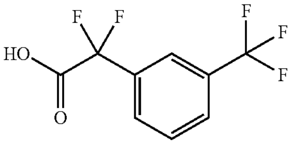 [SMILES: O=C(O)C(F)(F)c1cccc(C(F)(F)F)c1] | INT-1 | 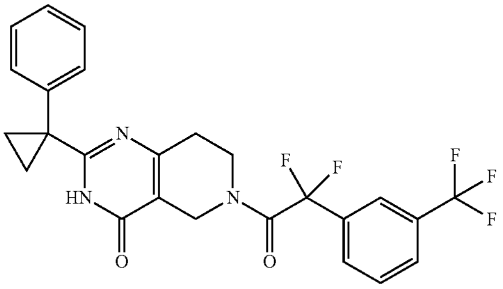 [SMILES: O=C(N1CCc2nc(C3(c4ccccc4)CC3)[nH]c(=O)c2C1)C(F)(F)c1cccc(C(F)(F)F)c1] | 1.90 min | 490.1 |
| 20-10 | 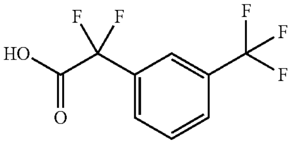 [SMILES: O=C(O)C(F)(F)c1cccc(C(F)(F)F)c1] | INT-4-14 | 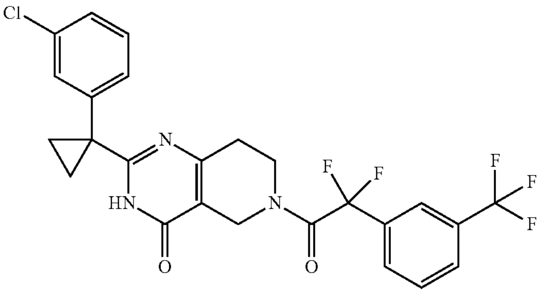 [SMILES: O=C(N1CCc2nc(C3(c4cccc(Cl)c4)CC3)[nH]c(=O)c2C1)C(F)(F)c1cccc(C(F)(F)F)c1] | 1.98 min | 524.1 |

TABLE 51-2-continued
| | | | | | |
|---|---|---|---|---|---|
| 20-11 | 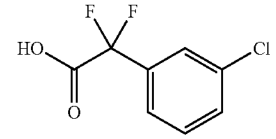 | INT-4-14 | 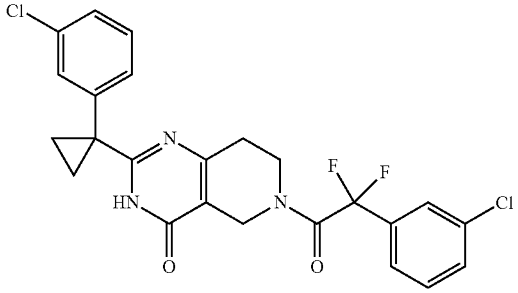 [SMILES: O=C(N1CCc2nc(C3(c4cccc(Cl)c4)CC3)[nH]c(=O)c2C1)C(F)(F)c1cccc(Cl)c1] | 1.95 min | 490.0 |
| 20-12 | 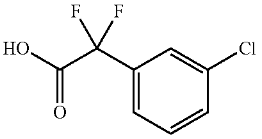 [SMILES: O=C(O)C(F)(F)c1cccc(Cl)c1] | INT-1 | 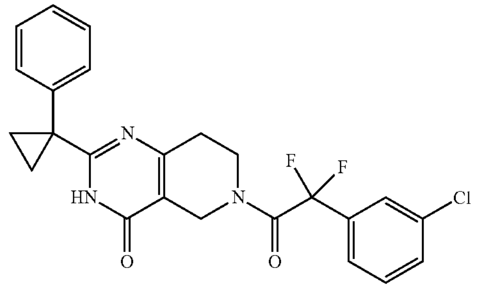 [SMILES: O=C(N1CCc2nc(C3(c4ccccc4)CC3)[nH]c(=O)c2C1)C(F)(F)c1cccc(Cl)c1] | 1.87 min | 456.1 |
| 20-13 | 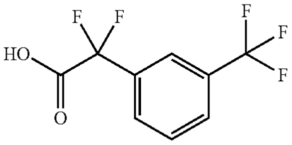 [SMILES: O=C(O)C(F)(F)c1cccc(C(F)(F)F)c1] | INT-8-5 | 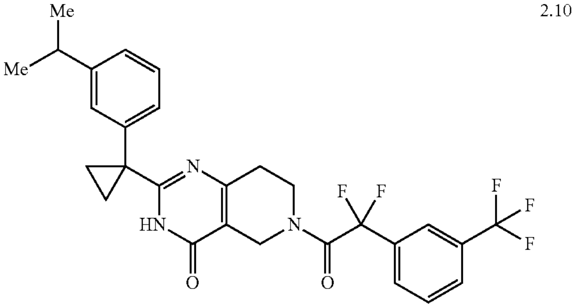 | 2.10 min | 532.0 |
| 20-14 | 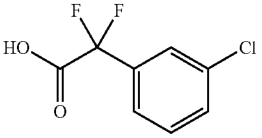 [SMILES: O=C(O)C(F)(F)c1cccc(Cl)c1] | INT-8-5 | 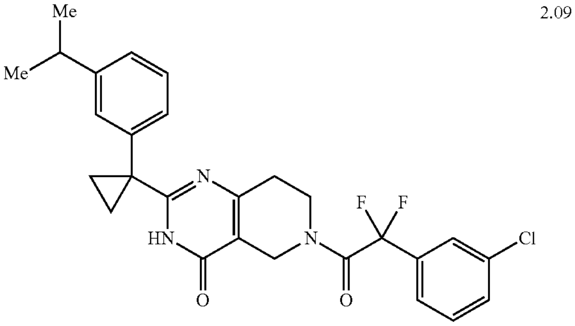 | 2.09 min | 498.0 |
| 20-15 | 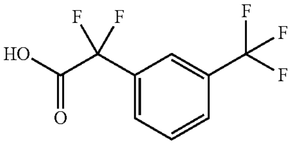 [SMILES: O=C(O)C(F)(F)c1cccc(C(F)(F)F)c1] | INT-10-20 | 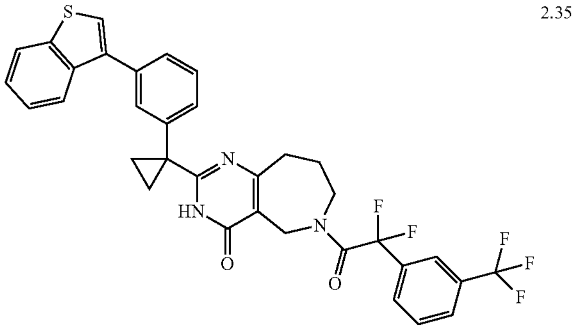 | 2.35 min | 636.5 |
The following amide derivatives (Ex-21-1 to Ex-21-6) are prepared according to the procedure of Ex-1 or the general synthesis in scheme-1 from the synthesized amine drivatives and the known or synthesized acid derivatives in Table 52.

The further purification is carried out by preparative LC-MS or SFC-MS system in usual manner. The retention time and observed MS by HPLC-QC method are summarized in Table 52.
TABLE 52
| Ex. | Acid (INT or Reagent) | Amine (INT) | Structure | Retention time | Observed MS |
|---|---|---|---|---|---|
| 21-1 | 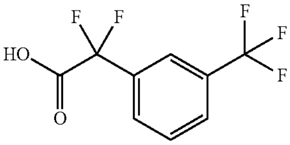 | INT-8-22 | 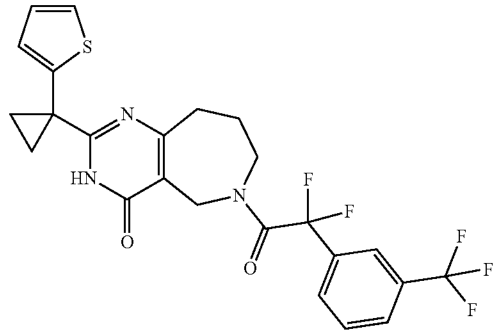 [SMILES: O=C(N1CCCc2nc(C3(c4cccs4)CC3)[nH]c(=O)c2C1)C(F)(F)c1cccc(C(F)(F)F)c1] | 1.89 min | 510.1 |
| 21-2 | 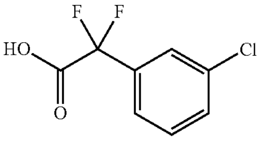 [SMILES: O=C(O)C(F)(F)c1cccc(Cl)c1] | INT-8-22 | 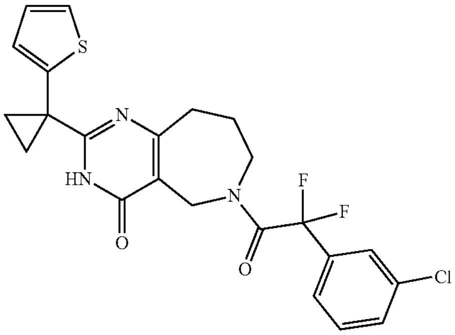 [SMILES: O=C(N1CCCc2nc(C3(c4cccs4)CC3)[nH]c(=O)c2C1)C(F)(F)c1cccc(Cl)c1] | 1.85 min | 476.1 |
| 21-3 | 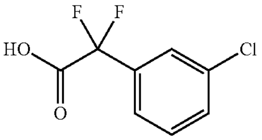 | INT-8-25 | 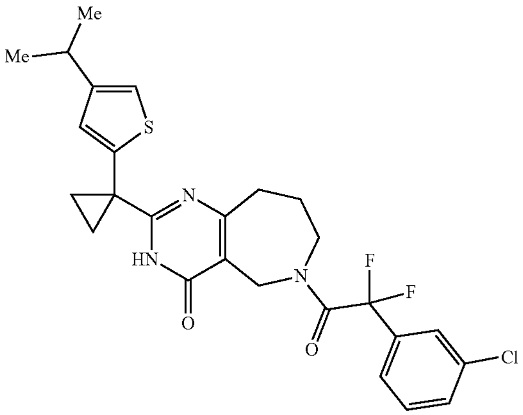 [SMILES: CC(C)c1csc(C2(c3nc4c(c(=O)[nH]3)CN(C(=O)C(F)(F)c3cccc(Cl)c3)CCC4)CC2)c1] | 2.08 min | 517.9 |
| 21-4 | 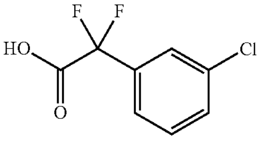 [SMILES: O=C(O)C(F)(F)c1cccc(Cl)c1] | INT-8-8 | 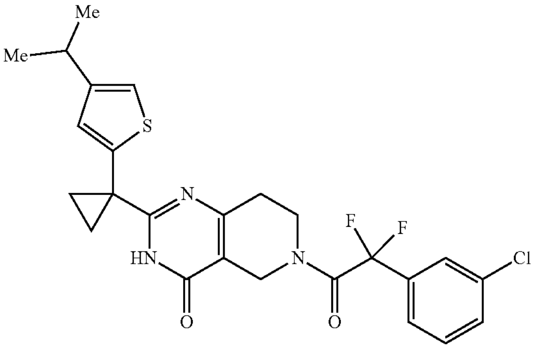 [SMILES: CC(C)c1csc(C2(c3nc4c(c(=O)[nH]3)CN(C(=O)C(F)(F)c3cccc(Cl)c3)CC4)CC2)c1] | 2.09 min | 503.9 |

TABLE 52-continued

| Ex. | Acid (INT or Reagent) | Amine (INT) | Structure | Retention time | Observed MS |
|---|---|---|---|---|---|
| 21-5 | 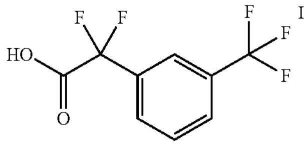 | INT-8-8 | 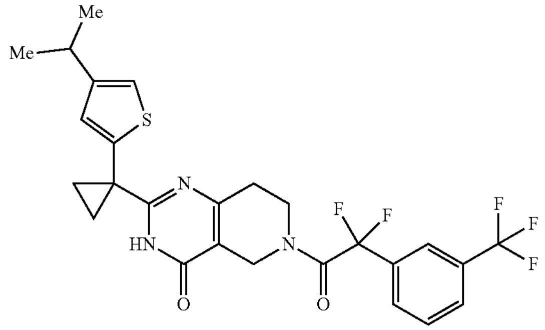 [SMILES: CC(C)c1csc(C2(c3nc4c(c(=O)[nH]3)CN(C(=O)C(F)(F)c3cccc(C(F)(F)F)c3)CC4)CC2)c1] | 2.09 min | 537.9 |
| 21-6 | 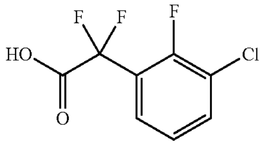 [SMILES: O=C(O)C(F)(F)c1cccc(Cl)c1F] | INT-8-25 | 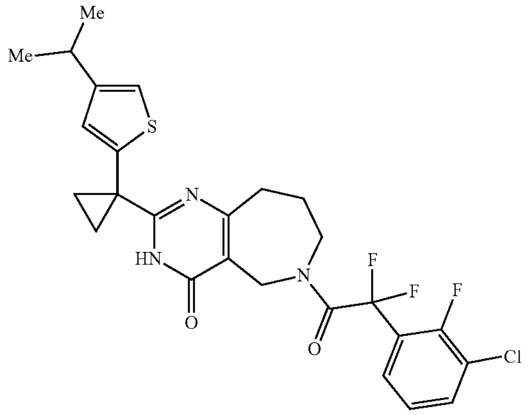 [SMILES: CC(C)c1csc(C2(c3nc4c(c(=O)[nH]3)CN(C(=O)C(F)(F)c3cccc(Cl)c3F)CCC4)CC2)c1] | 2.12 min | 535.9 |

The following amide derivatives (Ex-22-1 to Ex-22-10) are prepared according to the procedure of Ex-1 or the general synthesis in scheme-1 from the synthesized amine drivatives and the known or synthesized acid derivatives in Tables 53-1 to 53-2. The further purification is carried out by preparative LC-MS or SFC-MS system in usual manner. The retention time and observed MS by HPLC-QC method are summarized in Tables 53-1 to 53-2.

TABLE 53-1

| Ex. | Acid (INT or Reagent) | Amine (INT) | Structure | Retention time | Observed MS |
|---|---|---|---|---|---|
| 22-1 | 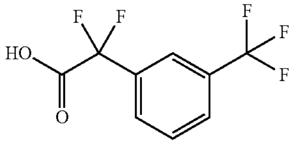 | INT-8-33 | 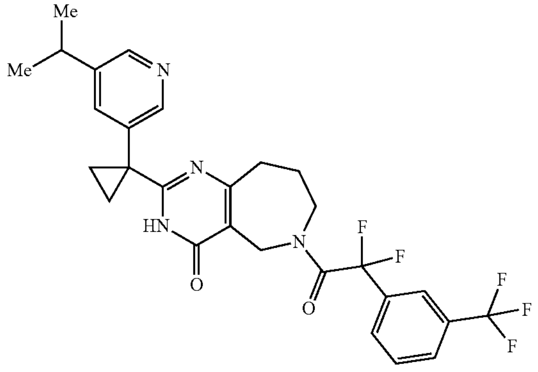 [SMILES: CC(C)c1cncc(C2(c3nc4c(c(=O)[nH]3)CN(C(=O)C(F)(F)c3cccc(C(F)(F)F)c3)CCC4)CC2)c1] | 1.82 min | 547.1 |

TABLE 53-1-continued
| Ex. | Acid (INT or Reagent) | Amine (INT) | Structure | Retention time | Observed MS |
|---|---|---|---|---|---|
| 22-2 | 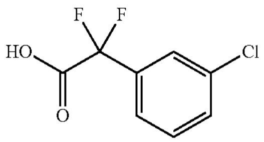 | INT-10-9 | 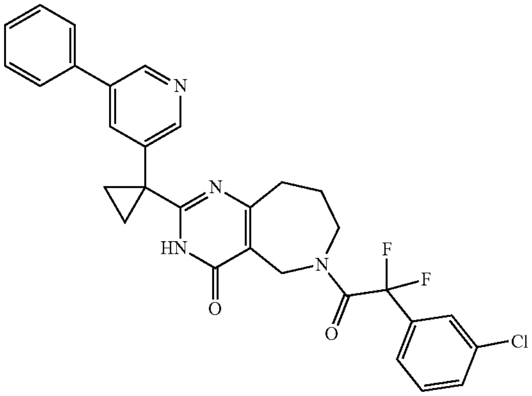 [SMILES: O=C(N1CCCc2nc(C3(c4cncc(-c5ccccc5)c4)CC3)[nH]c(=O)c2C1)C(F)(F)c1cccc(Cl)c1] | 1.81 min | 547.0 |
| 22-3 | 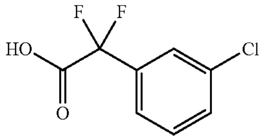 | INT-8-33 | 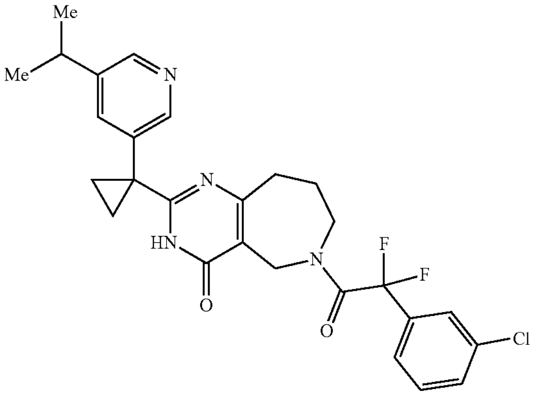 | 1.77 min | 513.0 |
| 22-4 | 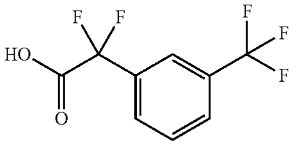 [SMILES: O=C(O)C(F)(F)c1cccc(C(F)(F)F)c1] | INT-10-9 | 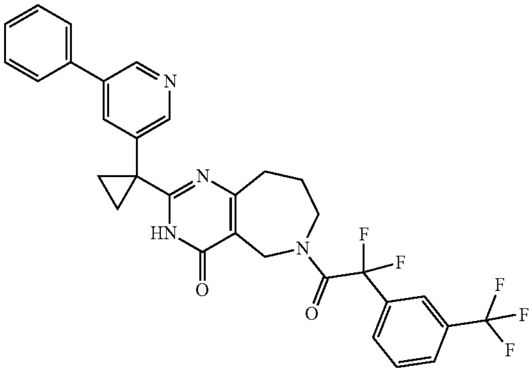 [SMILES: O=C(N1CCCc2nc(C3(c4cncc(-c5ccccc5)c4)CC3)[nH]c(=O)c2C1)C(F)(F)c1cccc(C(F)(F)F)c1] | 1.87 min | 581.2 |
| 22-5 | 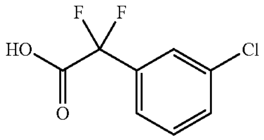 | INT-10-6 | 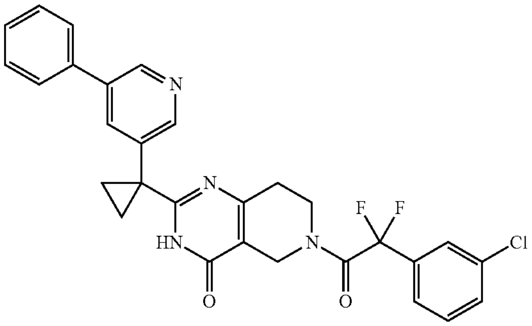 [SMILES: O=C(N1CCc2nc(C3(c4cncc(-c5ccccc5)c4)CC3)[nH]c(=O)c2C1)C(F)(F)c1cccc(Cl)c1] | 1.82 min | 532.9 |

TABLE 53-1-continued
| Ex. | Acid (INT or Reagent) | Amine (INT) | Structure | Retention time | Observed MS |
|---|---|---|---|---|---|
| 22-6 | 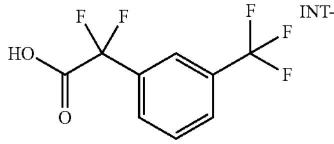 | INT-10-6 | 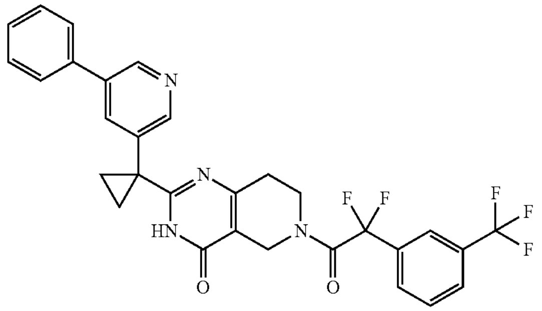 [SMILES: O=C(N1CCc2nc(C3(c4cncc(-c5ccccc5)c4)CC3)[nH]c(=O)c2C1)C(F)(F)c1cccc(C(F)(F)F)c1] | 1.85 min | 567.0 |
TABLE 53-2
| | | | | | |
|---|---|---|---|---|---|
| 22-7 | 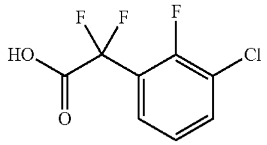 [SMILES: O=C(O)C(F)(F)c1cccc(Cl)c1F] | INT-10-9 | 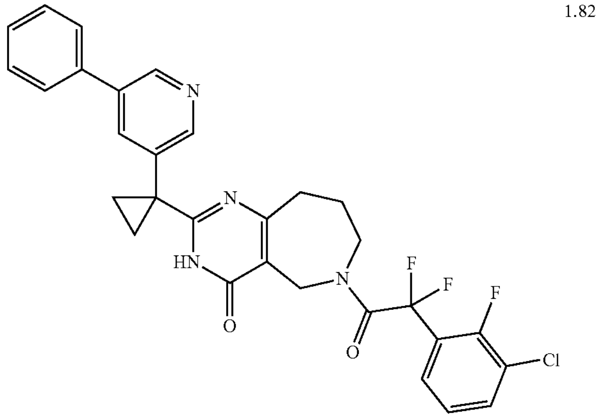 | 1.82 min | 564.9 |
| 22-8 | 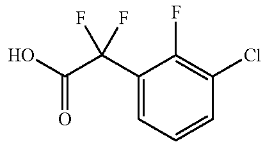 [SMILES: O=C(O)C(F)(F)c1cccc(Cl)c1F] | INT-8-33 | 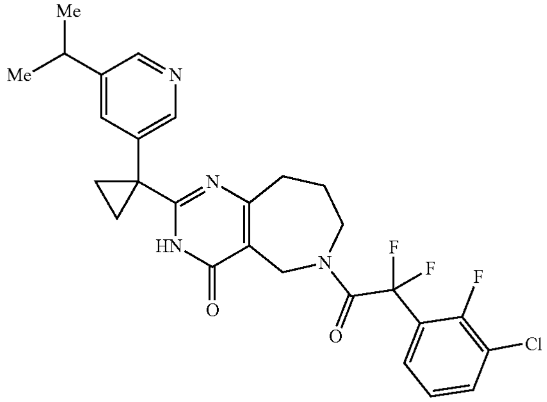 [SMILES: CC(C)c1cncc(C2(c3nc4c(c(=O)[nH]3)CN(C(=O)C(F)(F)c3cccc(Cl)c3F)CCC4)CC2)c1] | 1.76 min | 530.9 |
| 22-9 | 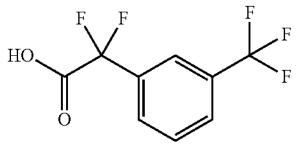 [SMILES: O=C(O)C(F)(F)c1cccc(C(F)(F)F)c1] | INT-8-29 | 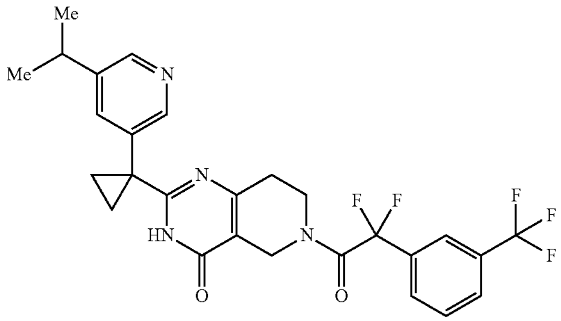 [SMILES: CC(C)c1cncc(C2(c3nc4c(c(=O)[nH]3)CN(C(=O)C(F)(F)c3cccc(C(F)(F)F)c3)CC4)CC2)c1] | 1.80 min | 533.0 |

TABLE 53-2-continued

| | | | | |
|---|---|---|---|---|
| 22-10 | 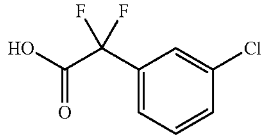 [SMILES: O=C(O)C(F)(F)c1cccc(Cl)c1] | INT-8-29 | 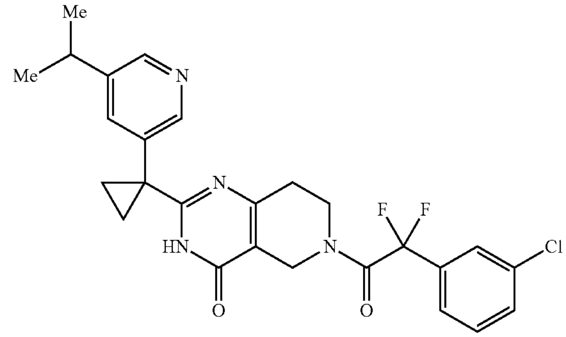 [SMILES: CC(C)c1cncc(C2(c3nc4c(c(=O)[nH]3)CN(C(=O)C(F)(F)c3cccc(Cl)c3)CC4)CC2)c1] | 1.76 min 499.0 |

Example-23-1

(R)-6-(2-(3-chlorophenyl)-2-hydroxyacetyl)-2-(1-(4-(4,4-difluorocyclohexyl)thiophen-2-yl)cyclopropyl)-5,6,7,8-tetrahydropyrido[4,3-d]pyrimidin-4(3H)-one (Ex-23-1)

{Chem. 103}

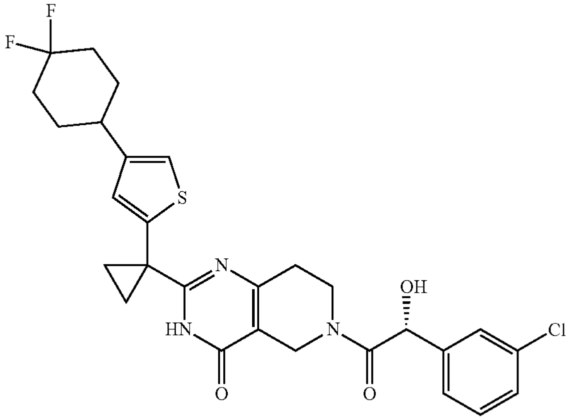

A mixture of INT-12-2 (17.3 mg, 0.031 mmol) in MeOH (1 mL) is hydrogenated in the presence of $PtO_2$ (4 mg) at rt under hydrogen atmosphere until the disappearance of starting meterial. The mixture is filtered through a pad of celite and the filtrate and washings are evaporated in vacuo to give the crude titled compound (13.5 mg) as a brown solid. The further purification is carried out by preparative LC-MS or SFC-MS system in the usual manner. The retention time and observed MS by HPLC-QC method is noted in Table 54.

The following pyrimidin-4(3H)-one derivative (Ex-23-2) is prepared according to the procedure of Ex-23-1 or the general synthesis in scheme-7 from INT-12-1. The further purification is carried out by preparative LC-MS or SFC-MS system in usual manner. The retention time and observed MS by HPLC-QC method is summarized in Table 54.

TABLE 54

| Ex. | Intermediate (INT) | Structure | Retention time (min.) | Observed MS |
|---|---|---|---|---|
| 23-1 | INT-12-2 | 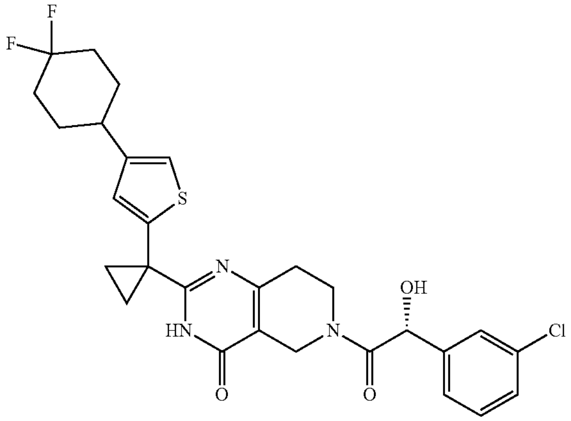 [SMILES: O=C([C@H](O)c1cccc(Cl)c1)N1CCc2nc(C3(c4cc(C5CCC(F)(F)CC5)cs4)CC3)[nH]c(=O)c2C1] | 1.86 min | 560.0 |

TABLE 54-continued

| Ex. | Intermediate (INT) | Structure | Retention time (min.) | Observed MS |
|---|---|---|---|---|
| 23-2 | INT-12-1 | 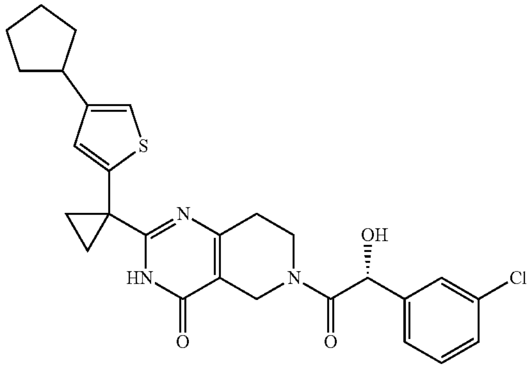 [SMILES: O=C([C@H](O)c1cccc(Cl)c1)N1CCc2nc(C3(c4cc(C5CCCC5)cs4)CC3)[nH]c(=O)c2C1] | 1.99 min | 510.0 |

The following pyrimidin-4(3H)-one derivative (Ex-24-1) is prepared according to the procedure of Ex-23-1 or the general synthesis in scheme-7 from INT-13-1. The further purification is carried out by preparative LC-MS or SFC-MS system in usual manner. The retention time and observed MS by HPLC-QC method is summarized in Table 55.

TABLE 55

| Ex. | Intermediate (INT) | Structure | Retention time | Observed MS |
|---|---|---|---|---|
| 24-1 | INT-13-1 | 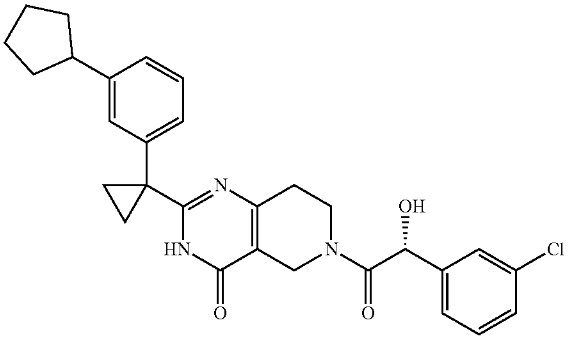 [SMILES: O=C([C@H](O)c1cccc(Cl)c1)N1CCc2nc(C3(c4cccc(C5CCCC5)c4)CC3)[nH]c(=O)c2C1] | 1.99 min | 504.0 |

The following pyrimidin-4(3H)-one derivatives (Ex-25-1 to Ex-25-5) are prepared according to the procedure of Ex-23-1 or the general synthesis in scheme-7 from the corresponding intermediates. The further purification is carried out by preparative LC-MS system in usual manner. The retention time and observed MS by HPLC-QC method are summarized in Table 56.

TABLE 56
| Ex. | Intermediate (INT) | Structure | Retention time | Observed MS |
|---|---|---|---|---|
| 25-1 | INT-14-2 | 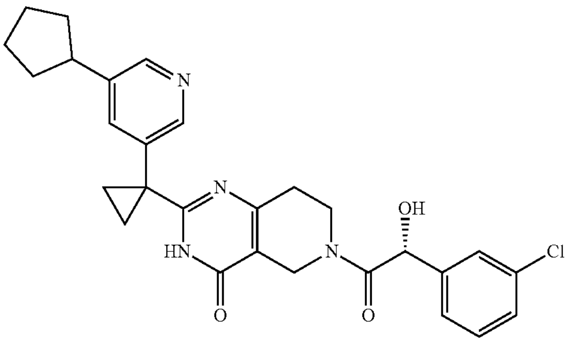 [SMILES: O=C([C@H](O)c1cccc(Cl)c1)N1CCc2nc(C3(c4cncc(C5CCCC5)c4)CC3)[nH]c(=O)c2C1] | 1.62 min | 505.0 |
| 25-2 | INT-14-3 | 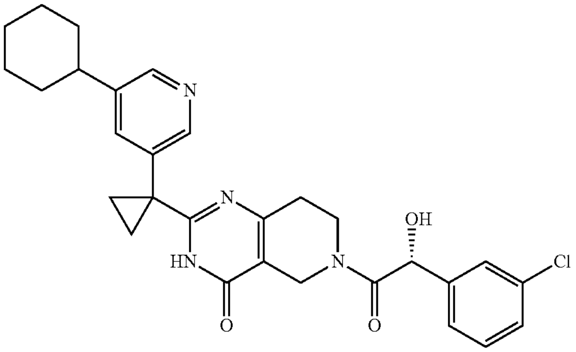 [SMILES: O=C([C@H](O)c1cccc(Cl)c1)N1CCc2nc(C3(c4cncc(C5CCCCC5)c4)CC3)[nH]c(=O)c2C1] | 1.72 min | 519.2 |
| 25-3 | INT-14-1 | 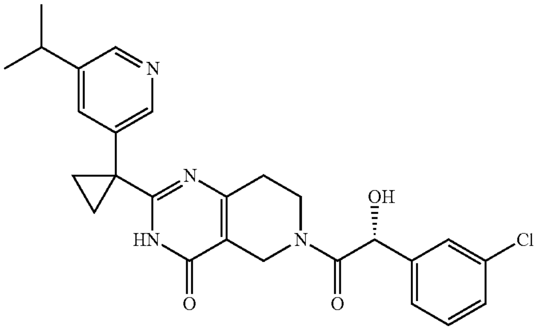 [SMILES: CC(C)c1cncc(C2(c3nc4c(c(=O)[nH]3)CN(C(=O)[C@H](O)c3cccc(Cl)c3)CC4)CC2)c1] | 1.47 min | 479.2 |
| 25-4 | INT-14-4 | 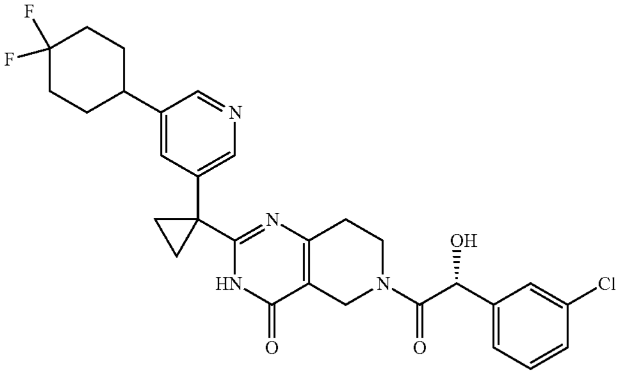 [SMILES: O=C([C@H](O)c1cccc(Cl)c1)N1CCc2nc(C3(c4cncc(C5CCC(F)(F)CC5)c4)CC3)[nH]c(=O)c2C1] | 1.55 min | 555.0 |

TABLE 56-continued

| Ex. | Intermediate (INT) | Structure | Retention time | Observed MS |
|---|---|---|---|---|
| 25-5 | INT-14-5 | 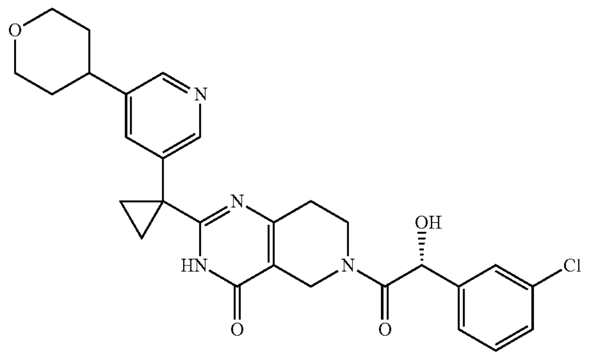 [SMILES: O=C([C@H](O)c1cccc(Cl)c1)N1CCc2nc(C3(c4cncc(C5CCOCC5)c4)CC3)[nH]c(=O)c2C1] | 1.29 min | 521.0 |

The following pyrimidin-4(3H)-one derivative (Ex-26-1 and Ex-26-2) are prepared according to the procedure of Ex-23-1 or the general synthesis in scheme-7 from the corresponding intermediates. The further purification is carried out by preparative LC-MS or SFC-MS system in usual manner. The retention time and observed MS by HPLC-QC method are summarized in Table 57.

The following pyrimidin-4(3H)-one derivative (Ex-27-1 to Ex-27-8) are prepared according to the procedure of Ex-23-1 or the general synthesis in scheme-7 from the corresponding intermediates. The further purification is carried out by preparative LC-MS or SFC-MS system in usual manner. The retention time and observed MS by HPLC-QC method are summarized in Tables 58-1 to 58-2.

TABLE 57

| Ex. | Intermediate (INT) | Structure | Retention time | Observed MS |
|---|---|---|---|---|
| 26-1 | INT-15-2 | 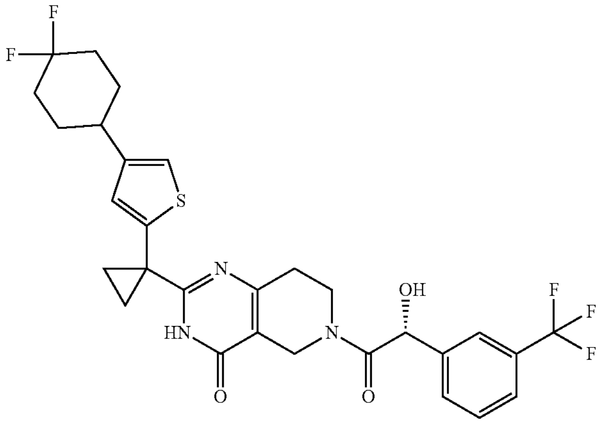 [SMILES: O=C([C@H](O)c1cccc(C(F)(F)F)c1)N1CCc2nc(C3(c4cc(C5CCC(F)(F)CC5)cs4)CC3)[nH]c(=O)c2C1] | 1.89 min | 594.0 |
| 26-2 | INT-15-3 | 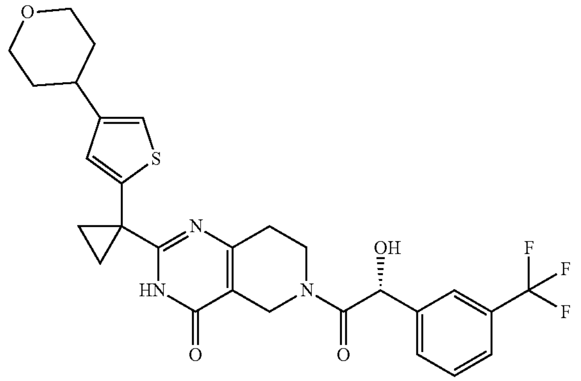 [SMILES: O=C([C@H](O)c1cccc(C(F)(F)F)c1)N1CCc2nc(C3(c4cc(C5CCOCC5)cs4)CC3)[nH]c(=O)c2C1] | 1.66 min | 560.0 |

TABLE 58-1
| Ex. | Intermediate (INT) | Structure | Retention time | Observed MS |
|---|---|---|---|---|
| 27-1 | INT-16-1 | 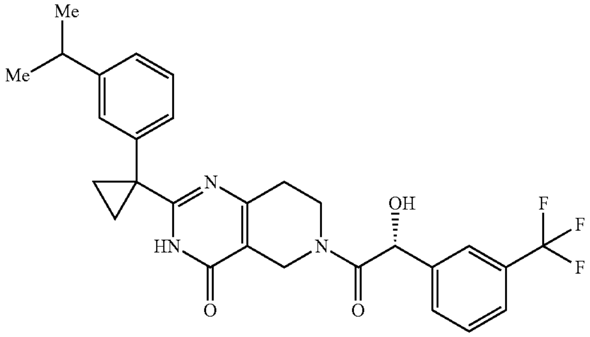 [SMILES: CC(C)c1cccc(C2(c3nc4c(c(=O)[nH]3)CN(C(=O)[C@H](O)c3cccc(C(F)(F)F)c3)CC4)CC2)c1] | 1.88 min | 512.0 |
| 27-2 | INT-16-2 | 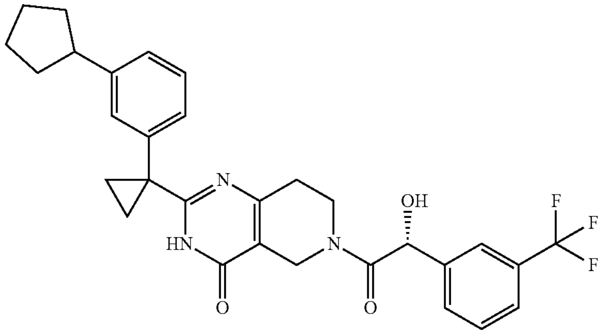 [SMILES: O=C([C@H](O)c1cccc(C(F)(F)F)c1)N1CCc2nc(C3(c4cccc(C5CCCC5)c4)CC3)[nH]c(=O)c2C1] | 2.01 min | 538.0 |
| 27-3 | INT-16-3 | 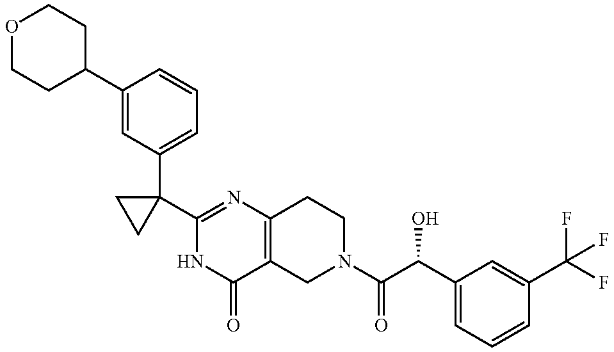 | 1.66 min | 554.0 |
| 27-4 | INT-21-18 | 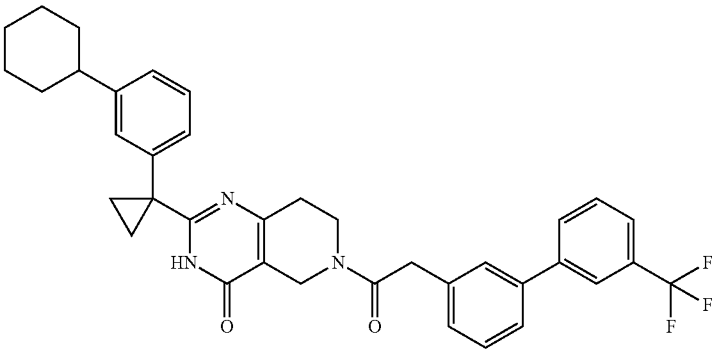 [SMILES: O=C(Cc1cccc(-c2cccc(C(F)(F)F)c2)c1)N1CCc2nc(C3(c4cccc(C5CCCCC5)c4)CC3)[nH]c(=O)c2C1] | 2.49 min | 612.5 |

TABLE 58-1-continued

| Ex. | Intermediate (INT) | Structure | Retention time | Observed MS |
|---|---|---|---|---|
| 27-5 | INT-21-13 | 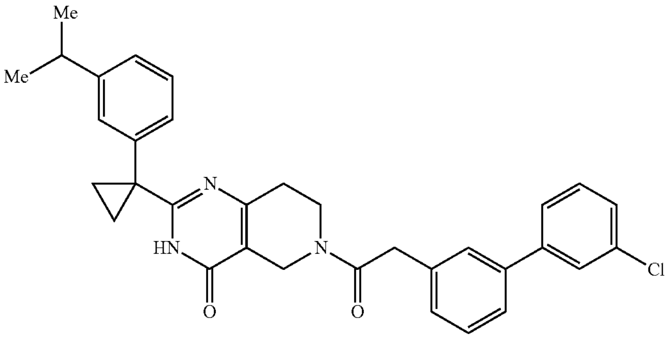 [SMILES: CC(C)c1cccc(C2(c3nc4c(c(=O)[nH]3)CN(C(=O)Cc3cccc(-c5cccc(Cl)c5)c3)CC4)CC2)c1] | 2.31 min | 538.5 |

TABLE 58-2

| | | | | |
|---|---|---|---|---|
| 27-6 | INT-21-17 | 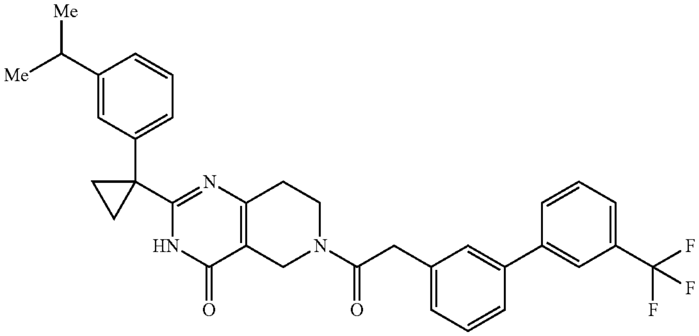 [SMILES: CC(C)c1cccc(C2(c3nc4c(c(=O)[nH]3)CN(C(=O)Cc3cccc(-c5cccc(C(F)(F)F)c5)c3)CC4)CC2)c1] | 2.31 min | 572.5 |
| 27-7 | INT-21-14 | 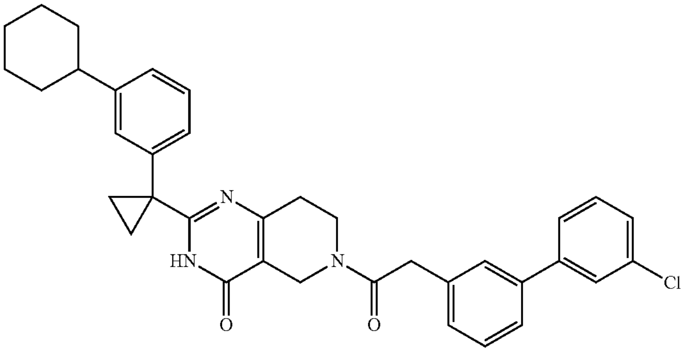 [SMILES: O=C(Cc1cccc(-c2cccc(Cl)c2)c1)N1CCc2nc(C3(c4cccc(C5CCCCC5)c4)CC3)[nH]c(=O)c2C1] | 2.51 min | 578.5 |
| 27-8 | Ex-48-12 | 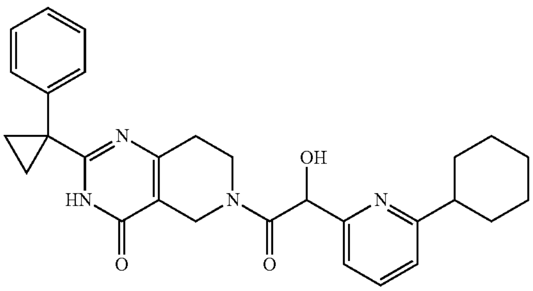 [SMILES: O=C(C(O)c1cccc(C2CCCCC2)n1)N1CCc2nc(C3(c4ccccc4)CC3)[nH]c(=O)c2C1] | 1.85 min | 485.2 |

The following pyrimidin-4(3H)-one derivatives (Ex-28-1 to Ex-28-5) are prepared according to the procedure of Ex-23-1 or the general synthesis in scheme-7 from the corresponding intermediates. The further purification is carried out by preparative LC-MS or SFC-MS system in usual manner. The retention time and observed MS by HPLC-QC method are summarized in Table 59.

TABLE 59
| Ex. | Intermediate (INT) | Structure | Retention time | Observed MS |
|---|---|---|---|---|
| 28-1 | INT-17-5 | 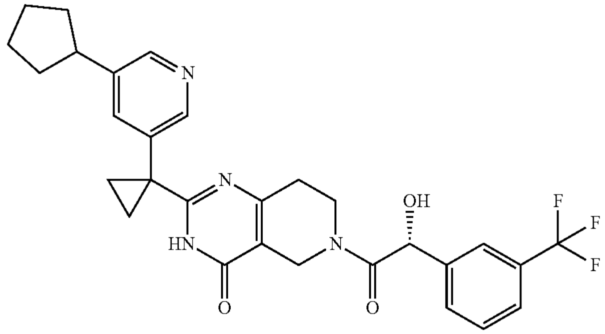 [SMILES: O=C([C@H](O)c1cccc(C(F)(F)F)c1)N1CCc2nc(C3(c4cncc(C5CCCC5)c4)CC3)[nH]c(=O)c2C1] | 1.67 min | 539.1 |
| 28-2 | INT-17-2 | 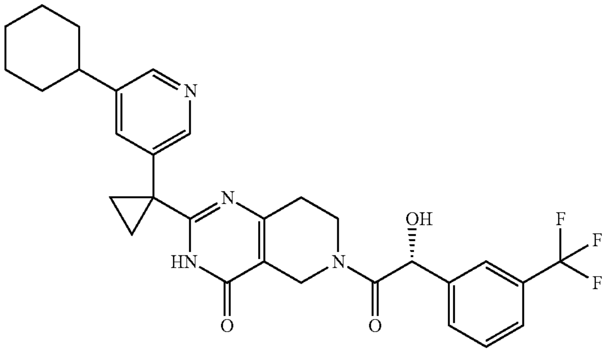 [SMILES: O=C([C@H](O)c1cccc(C(F)(F)F)c1)N1CCc2nc(C3(c4cncc(C5CCCCC5)c4)CC3)[nH]c(=O)c2C1] | 1.77 min | 553.3 |
| 28-3 | INT-17-1 | 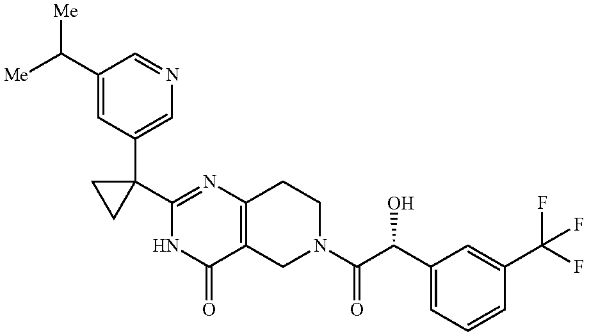 [SMILES: CC(C)c1cncc(C2(c3nc4c(c(=O)[nH]3)CN(C(=O)[C@H](O)c3cccc(C(F)(F)F)c3)CC4)CC2)c1] | 1.54 min | 513.2 |
| 28-4 | INT-17-3 | 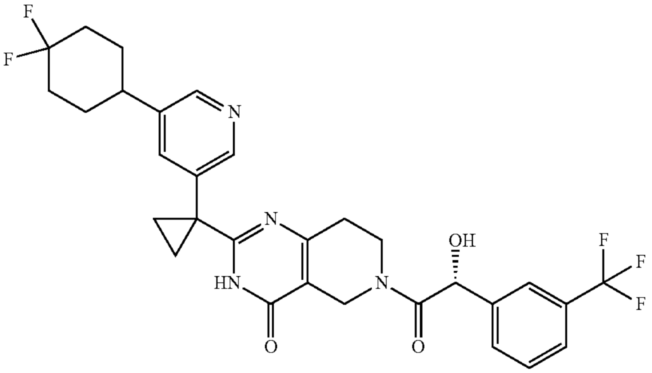 [SMILES: O=C([C@H](O)c1cccc(C(F)(F)F)c1)N1CCc2nc(C3(c4cncc(C5CCC(F)(F)CC5)c4)CC3)[nH]c(=O)c2C1] | 1.60 min | 589.0 |

TABLE 59-continued

| Ex. | Intermediate (INT) | Structure | Retention time | Observed MS |
|---|---|---|---|---|
| 28-5 | INT-17-4 | 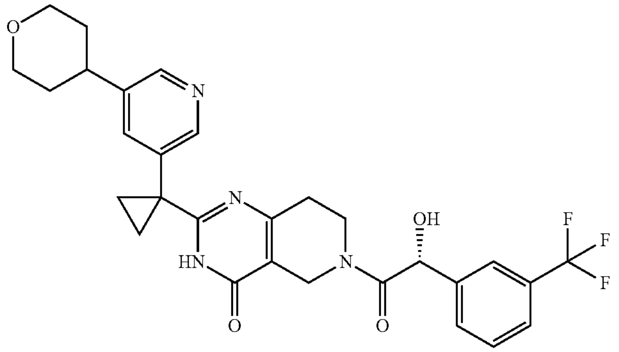 [SMILES: O=C([C@H](O)c1cccc(C(F)(F)F)c1)N1CCc2nc(C3(c4cncc(C5CCOCC5)c4)CC3)[nH]c(=O)c2C1] | 1.36 min | 555.0 |

Example-29-2 (Ex-29-2)

(R)-6-(2-(3-chlorophenyl)-2-hydroxyacetyl)-2-(1-(3-cyclohexylphenyl)cyclopropyl)-3,5,6,7,8,9-hexahydro-4H-pyrimido[5,4-c]azepin-4-one (Ex-29-2)

{Chem. 104}

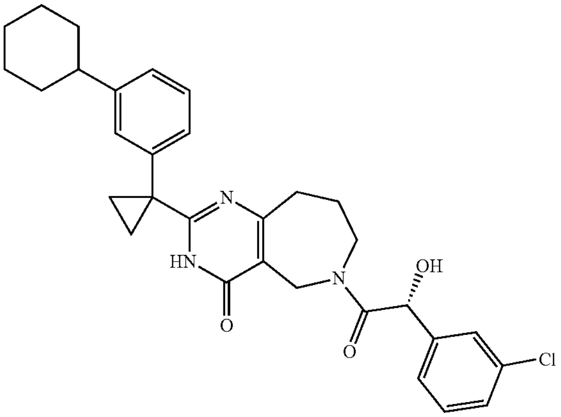

A mixtute of INT-18-2 (30 mg) in MeOH (3 mL) is hydrogenated in the presence of 10% Pd—C (8 mg) at rt for 3 hrs under hydrogen atmosphere. The mixture is filtered through a pad of celite and the filter cake is washed with methanol. The filtrate and washings are evaporated in vauo to give the crude titled compound (26 mg; ratio of product/starting material=72/28) as a slightly black viscous oil.

The further purification is carried out by preparative LC-MS or SFC-MS system in the usual manner. The retention time and observed MS by HPLC-QC method are summarized in Table 60.

The following pyrimidin-4(3H)-one derivatives (Ex-29-1 to Ex-29-4) are prepared according to the procedure of Ex-29-2 or the general synthesis in scheme-7 from the corresponding intermediates. The further purification is carried out by preparative LC-MS or SFC-MS system in usual manner. The retention time and observed MS by HPLC-QC method are summarized in Table 60.

TABLE 60

| Ex. | Intermediate (INT) | Structure | Retention time | Observed MS |
|---|---|---|---|---|
| 29-1 | INT-18-1 | 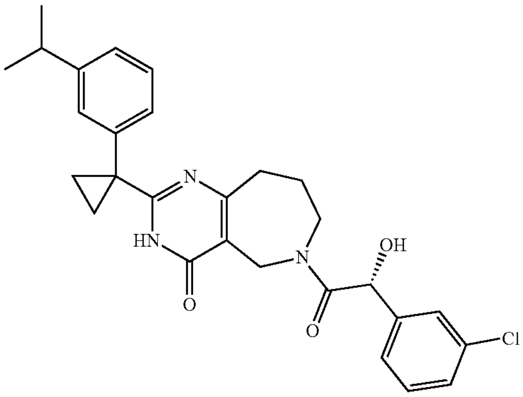 [SMILES: CC(C)c1cccc(C2(c3nc4c(c(=O)[nH]3)CN(C(=O)[C@H](O)c3cccc(Cl)c3)CCC4)CC2)c1] | 1.90 min | 492.0 |

TABLE 60-continued

| Ex. | Intermediate (INT) | Structure | Retention time | Observed MS |
| --- | --- | --- | --- | --- |
| 29-2 | INT-18-2 | 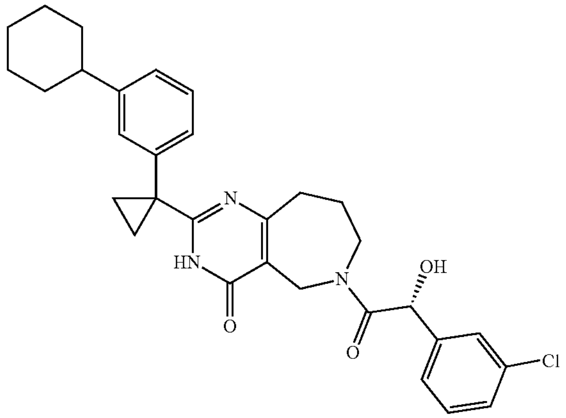 [SMILES: O=C([C@H](O)c1cccc(Cl)c1)N1CCCc2nc(C3(c4cccc(C5CCCCC5)c4)CC3)[nH]c(=O)c2C1] | 2.15 min | 532.0 |
| 29-3 | INT-18-3 | 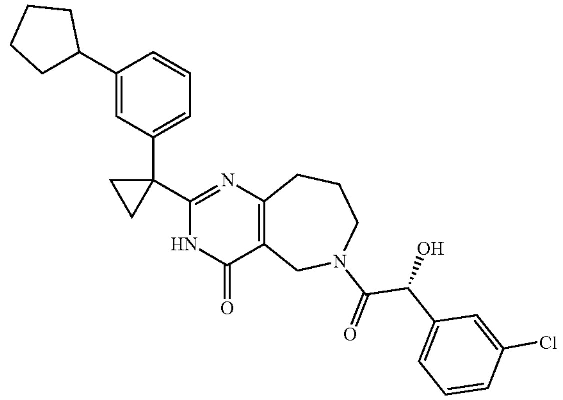 [SMILES: O=C([C@H](O)c1cccc(Cl)c1)N1CCCc2nc(C3(c4cccc(C5CCCC5)c4)CC3)[nH]c(=O)c2C1] | 2.05 min | 518.0 |
| 29-4 | INT-18-4 | 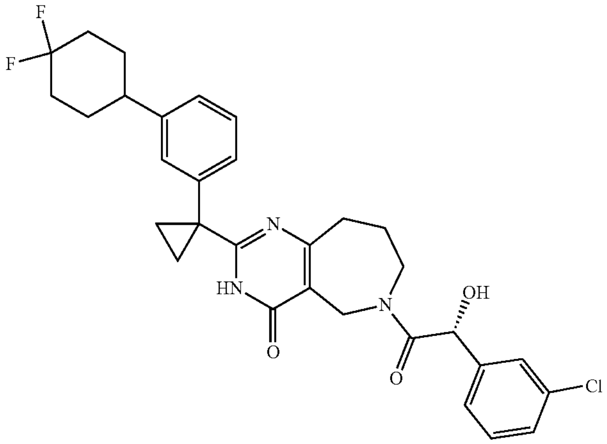 [SMILES: O=C([C@H](O)c1cccc(Cl)c1)N1CCCc2nc(C3(c4cccc(C5CCC(F)(F)CC5)c4)CC3)[nH]c(=O)c2C1] | 1.93 min | 568.0 |

The following pyrimidin-4(3H)-one derivatives (Ex-30-1 to Ex-30-14) are prepared according to the procedure of Ex-29-2 or the general synthesis in scheme-7 from the corresponding intermediates. The further purification is carried out by preparative LC-MS system in usual manner. The retention time and observed MS by HPLC-QC method are summarized in Tables 61-1 to 61-3.

TABLE 61-1
| Ex. | Intermediate (INT) | Structure | Retention time | Observed MS |
|---|---|---|---|---|
| 30-1 | INT-19-1 | 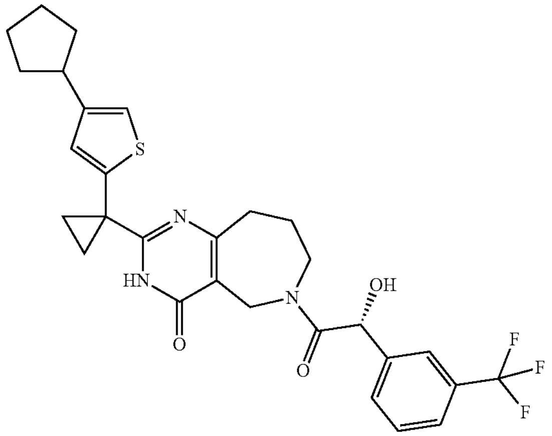 [SMILES: O=C([C@H](O)c1cccc(C(F)(F)F)c1)N1CCCc2nc(C3(c4cc(C5CCCC5)cs4)CC3)[nH]c(=O)c2C1] | 2.10 min | 558.2 |
| 30-2 | INT-19-2 | 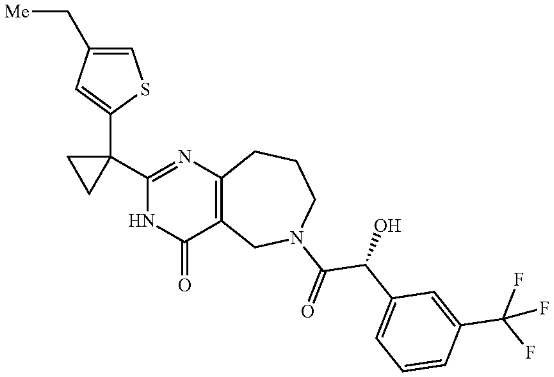 [SMILES: CCc1csc(C2(c3nc4c(c(=O)[nH]3)CN(C(=O)[C@H](O)c3cccc(C(F)(F)F)c3)CCC4)CC2)c1] | 1.88 min | 518.1 |
| 30-3 | INT-19-3 | 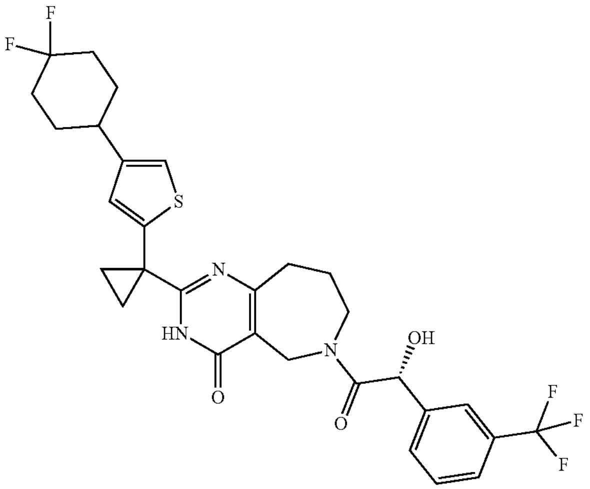 [SMILES: O=C([C@H](O)c1cccc(C(F)(F)F)c1)N1CCCc2nc(C3(c4cc(C5CCC(F)(F)CC5)cs4)CC3)[nH]c(=O)c2C1] | 1.95 min | 608.0 |

TABLE 61-1-continued
| Ex. | Intermediate (INT) | Structure | Retention time | Observed MS |
|---|---|---|---|---|
| 30-4 | INT-20-2 | 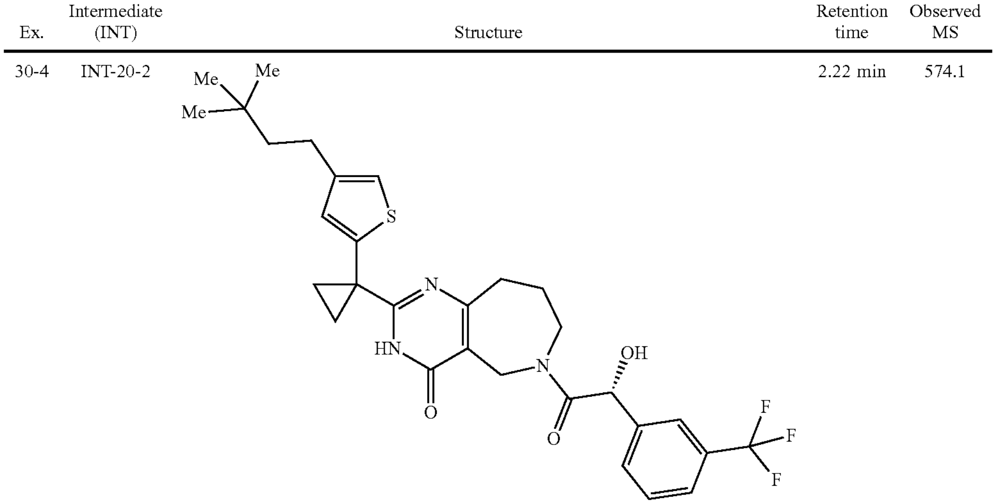 | 2.22 min | 574.1 |
| 30-5 | INT-20-1 | 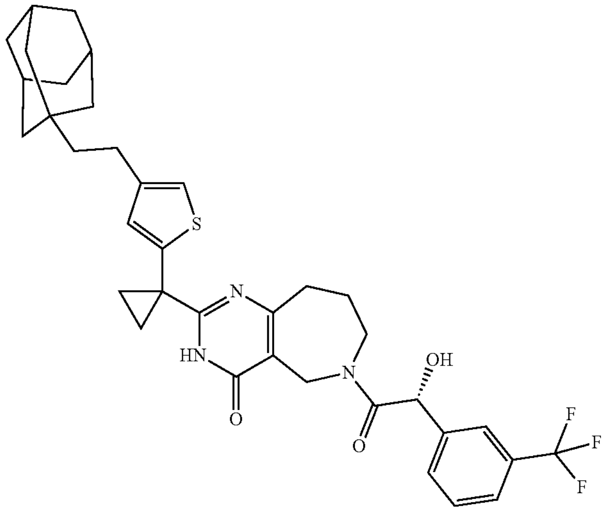 [SMILES: O=C([C@H](O)c1cccc(C(F)(F)F)c1)N1CCCc2nc(C3(c4cc(CCC56CC7CC(CC(C7)C5)C6)cs4)CC3)[nH]c(=O)c2C1] | 2.63 min | 652.2 |
TABLE 61-2
| | | | | |
|---|---|---|---|---|
| 30-6 | INT-20-3 | 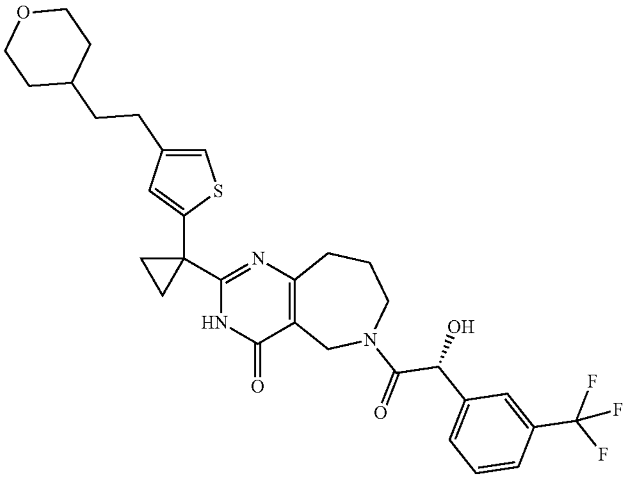 [SMILES: O=C([C@H](O)c1cccc(C(F)(F)F)c1)N1CCCc2nc(C3(c4cc(CCC5CCOCC5)cs4)CC3)[nH]c(=O)c2C1] | 1.92 min | 602.2 |

TABLE 61-2-continued
| | | | | |
|---|---|---|---|---|
| 30-7 | INT-19-4 | 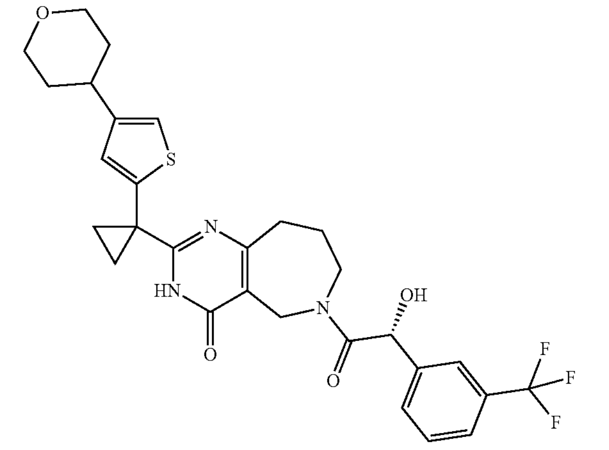 [SMILES: O=C([C@H](O)c1cccc(C(F)(F)F)c1)N1CCCc2nc(C3(c4cc(C5CCOCC5)cs4)CC3)[nH]c(=O)c2C1] | 1.73 min | 574.0 |
| 30-8 | INT-20-4 | 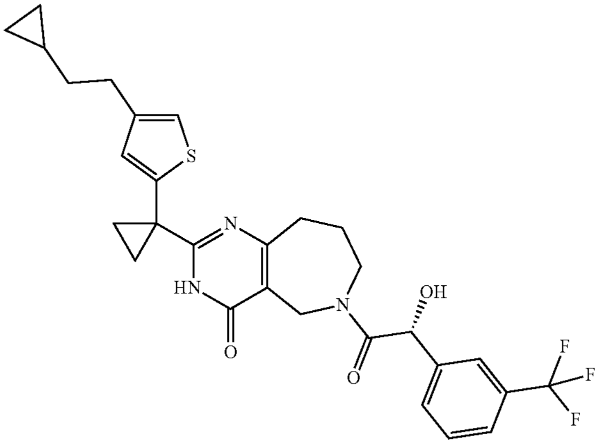 [SMILES: O=C([C@H](O)c1cccc(C(F)(F)F)c1)N1CCCc2nc(C3(c4cc(CCC5CC5)cs4)CC3)[nH]c(=O)c2C1] | 2.08 min | 558.1 |
| 30-9 | INT-20-5 | 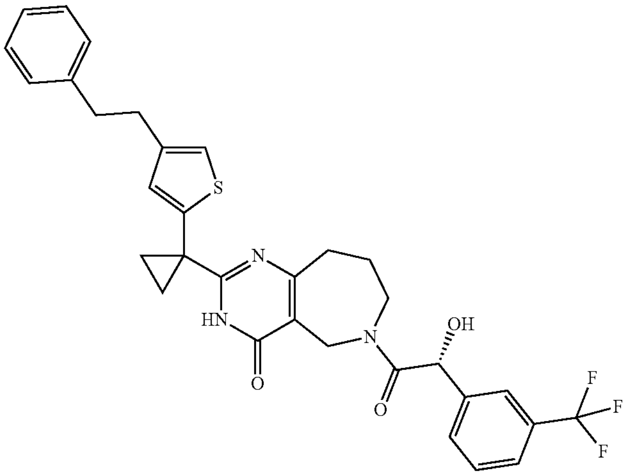 [SMILES: O=C([C@H](O)c1cccc(C(F)(F)F)c1)N1CCCc2nc(C3(c4cc(CCc5ccccc5)cs4)CC3)[nH]c(=O)c2C1] | 2.08 min | 594.2 |

TABLE 61-2-continued
| | | | | |
|---|---|---|---|---|
| 30-10 | INT-20-7 | 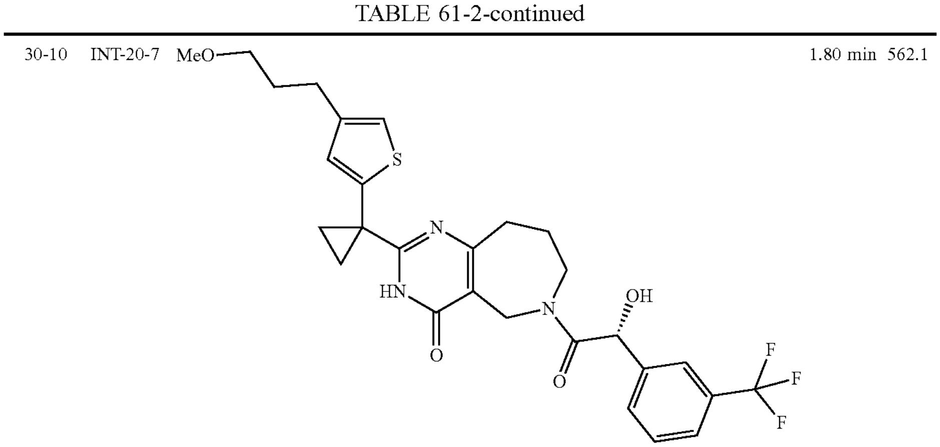 | 1.80 min | 562.1 |
TABLE 61-3
| | | | | |
|---|---|---|---|---|
| 30-11 | INT-20-6 | 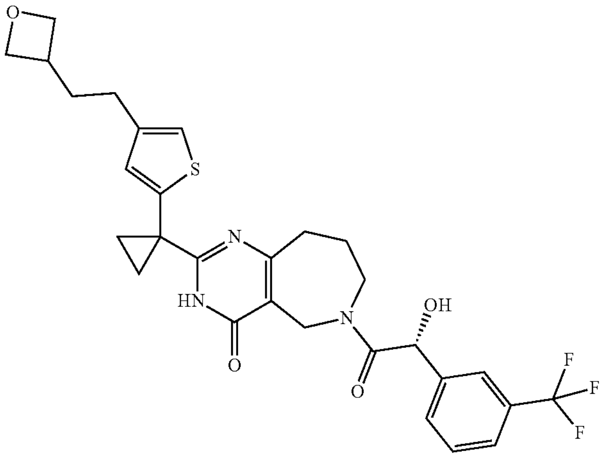 [SMILES: O=C([C@H](O)c1cccc(C(F)(F)F)c1)N1CCCc2nc(C3(c4cc(CCC5COC5)cs4)CC3)[nH]c(=O)c2C1] | 1.70 min | 574.1 |
| 30-12 | INT-20-8 | 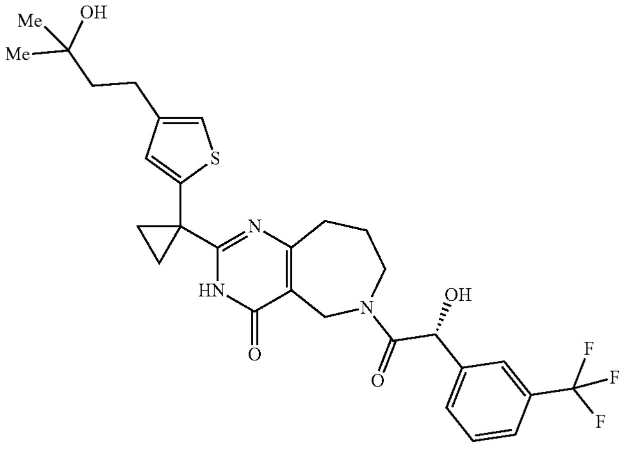 [SMILES: CC(C)(O)CCc1csc(C2(c3nc4c(c(=O)[nH]3)CN(C(=O)[C@H](O)c3cccc(C(F)(F)F)c3)CCC4)CC2)c1] | 1.67 min | 576.1 |

TABLE 61-3-continued

| | | | | |
|---|---|---|---|---|
| 30-13 | INT-19-5 | 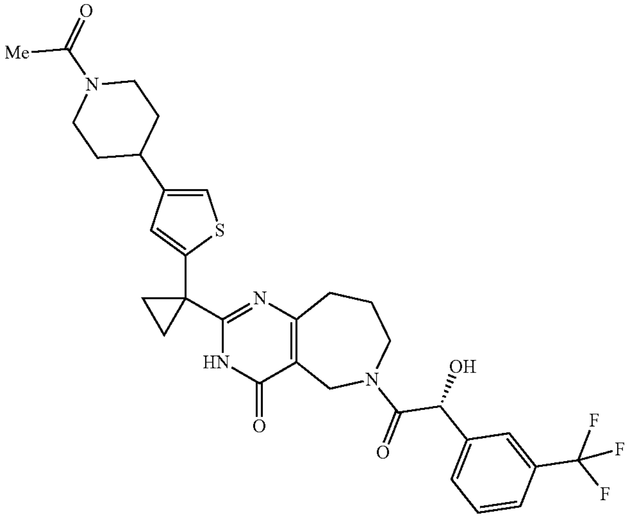 [SMILES: CC(=O)N1CCC(c2csc(C3(c4nc5c(c(=O)[nH]4)CN(C(=O)[C@H](O)c4cccc(C(F)(F)F)c4)CCC5)CC3)c2)CC1] | 1.57 min | 615.2 |
| 30-14 | INT-20-9 | 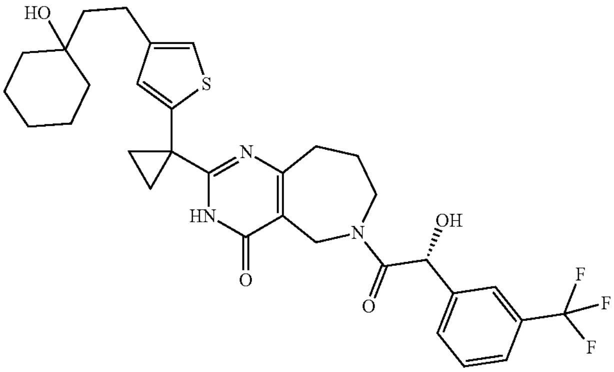 [SMILES: O=C([C@H](O)c1cccc(C(F)(F)F)c1)N1CCCc2nc(C3(c4cc(CCC5(O)CCCCC5)cs4)CC3)[nH]c(=O)c2C1] | 1.91 min | 616.1 |

The following pyrimidin-4(3H)-one derivatives (Ex-31-1 to Ex-31-16) are prepared according to the procedure of Ex-29-2 or the general synthesis in scheme-7 from the corresponding intermediates. The further purification is carried out by preparative LC-MS system in usual manner. The retention time and observed MS by HPLC-QC method are summarized in Tables 62-1 to 62-4.

TABLE 62-1

| Ex. | Intermediate (INT) | Structure | Retention time | Observed MS |
|---|---|---|---|---|
| 31-1 | INT-21-7 | 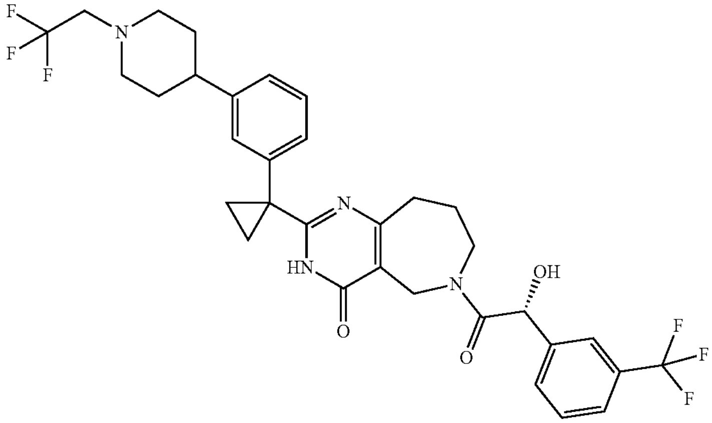 | 2.02 min | 649.3 |

TABLE 62-1-continued
| Ex. | Intermediate (INT) | Structure | Retention time | Observed MS |
|---|---|---|---|---|
| 31-2 | INT-21-6 | 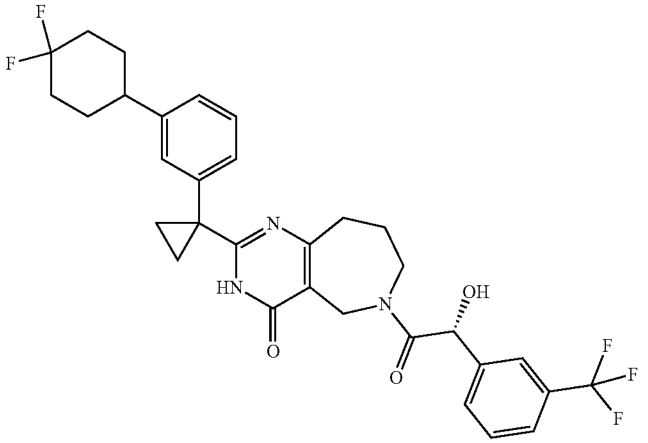 [SMILES: O=C([C@H](O)c1cccc(C(F)(F)F)c1)N1CCCc2nc(C3(c4cccc(C5CCC(F)(F)CC5)c4)CC3)[nH]c(=O)c2C1] | 1.97 min | 602.3 |
| 31-3 | INT-21-5 | 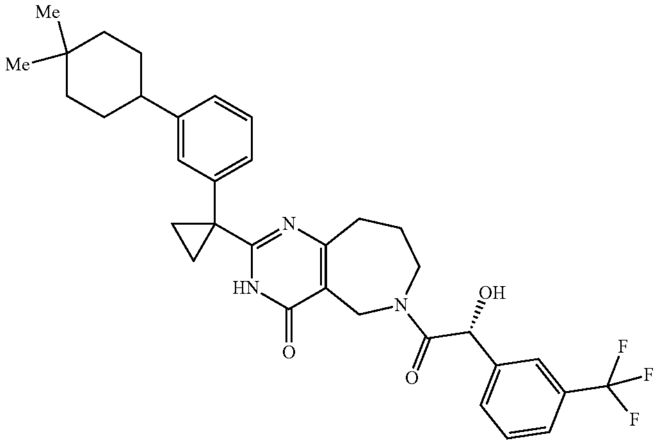 [SMILES: CC1(C)CCC(c2cccc(C3(c4nc5c(c(=O)[nH]4)CN(C(=O)[C@H](O)c4cccc(C(F)(F)F)c4)CCC5)CC3)c2)CC1] | 2.33 min | 594.2 |
| 31-4 | INT-21-3 | 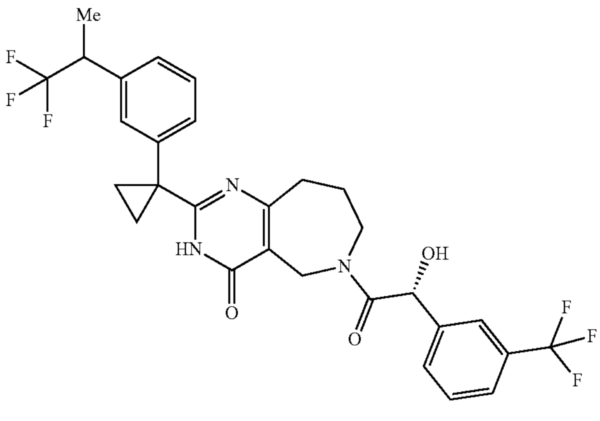 [SMILES: CC(c1cccc(C2(c3nc4c(c(=O)[nH]3)CN(C(=O)[C@H](O)c3cccc(C(F)(F)F)c3)CCC4)CC2)c1)C(F)(F)F] | 1.88 min | 580.1 |

TABLE 62-1-continued
| Ex. | Intermediate (INT) | Structure | Retention time | Observed MS |
|---|---|---|---|---|
| 31-5 | INT-21-1 | 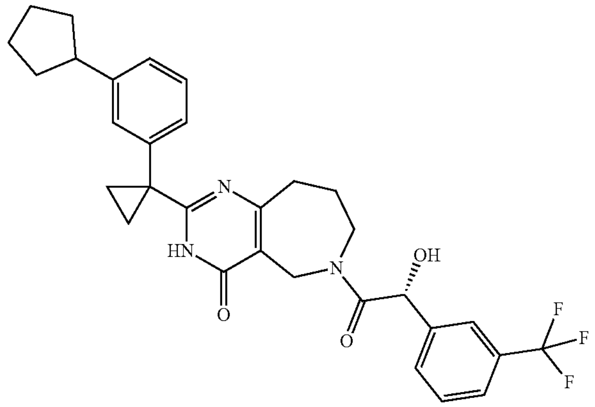 [SMILES: O=C([C@H](O)c1cccc(C(F)(F)F)c1)N1CCCc2nc(C3(c4cccc(C5CCCC5)c4)CC3)[nH]c(=O)c2C1] | 2.10 min | 552.1 |
TABLE 62-2
| | | | | |
|---|---|---|---|---|
| 31-6 | INT-21-2 | 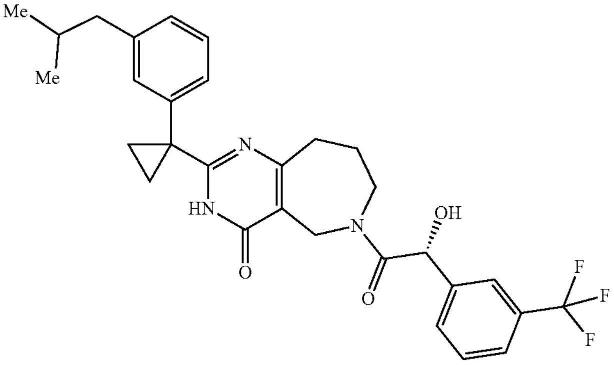 [SMILES: CC(C)Cc1cccc(C2(c3nc4c(c(=O)[nH]3)CN(C(=O)[C@H](O)c3cccc(C(F)(F)F)c3)CCC4)CC2)c1] | 2.08 min | 540.1 |
| 31-7 | INT-21-4 | 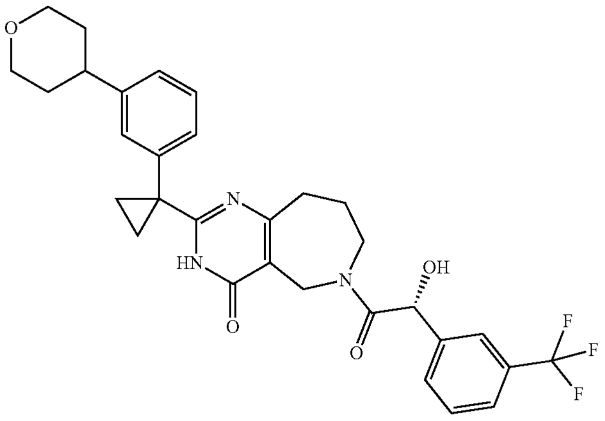 [SMILES: O=C([C@H](O)c1cccc(C(F)(F)F)c1)N1CCCc2nc(C3(c4cccc(C5CCOCC5)c4)CC3)[nH]c(=O)c2C1] | 1.73 min | 568.0 |

TABLE 62-2-continued
| | | | | |
|---|---|---|---|---|
| 31-8 | Ex-17-1 | 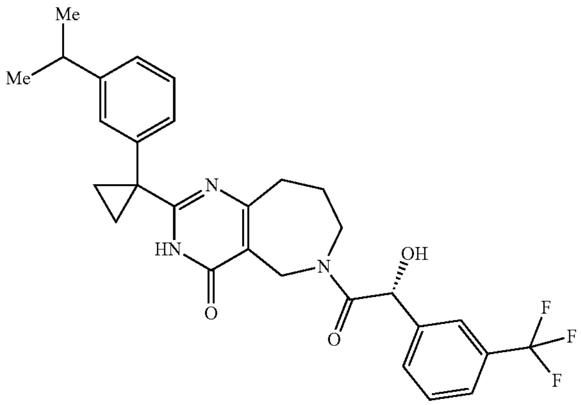 [SMILES: CC(C)c1cccc(C2(c3nc4c(c(=O)[nH]3)CN(C(=O)[C@H](O)c3cccc(C(F)(F)F)c3)CCC4)CC2)c1] | 1.97 min | 526.2 |
| 31-9 | INT-21-8 | 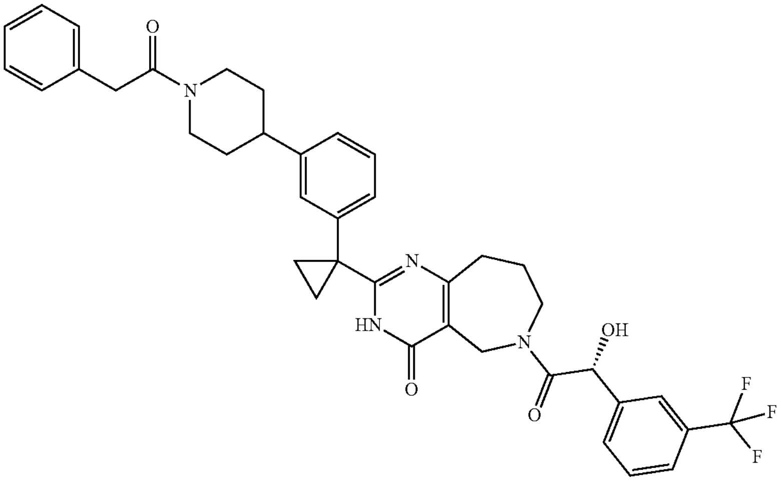 [SMILES: O=C(Cc1ccccc1)N1CCC(c2cccc(C3(c4nc5c(c(=O)[nH]4)CN(C(=O)[C@H](O)c4cccc(C(F)(F)F)c4)CCC5)CC3)c2)CC1] | 1.83 min | 685.1 |
| 31-10 | INT-21-9 | 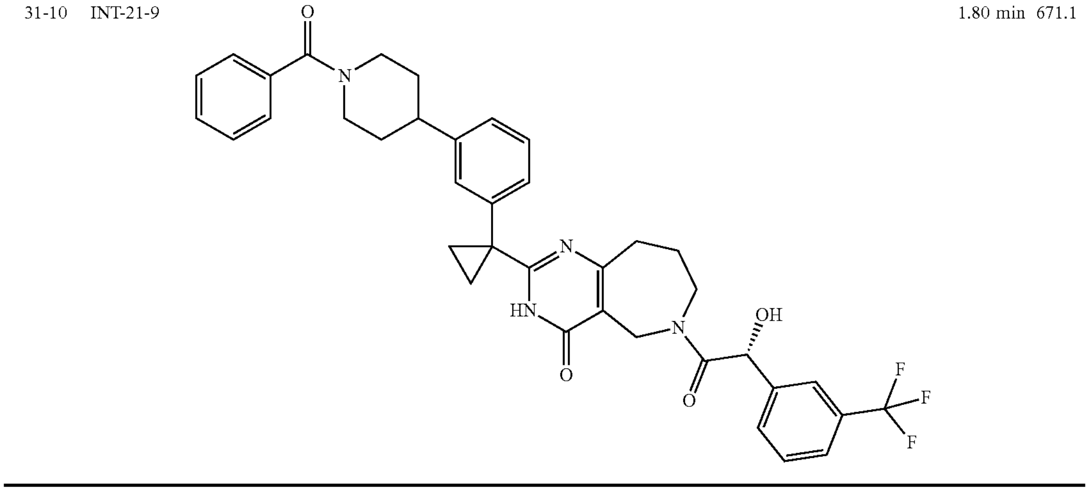 | 1.80 min | 671.1 |

TABLE 62-3
| | | | | |
|---|---|---|---|---|
| 31-11 | INT-21-10 | 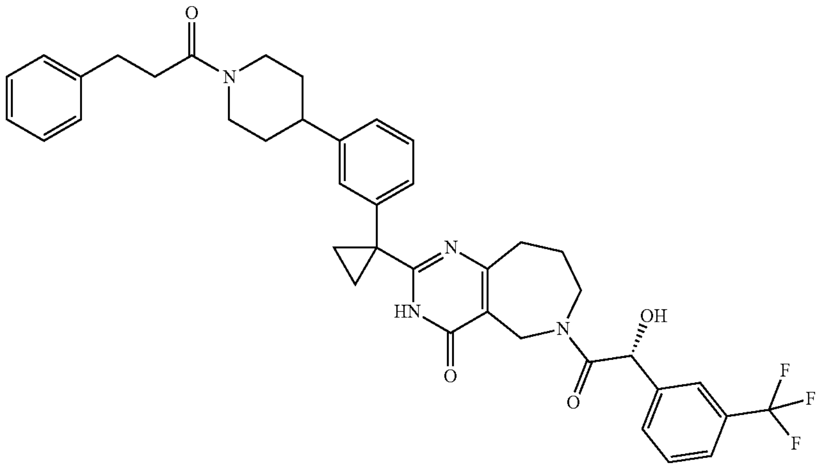 [SMILES: O=C(CCc1ccccc1)N1CCC(c2cccc(C3(c4nc5c(c(=O)[nH]4)CN(C(=O)[C@H](O)c4cccc(C(F)(F)F)c4)CCC5)CC3)c2)CC1] | 1.90 min | 699.2 |
| 31-12 | INT-21-11 | 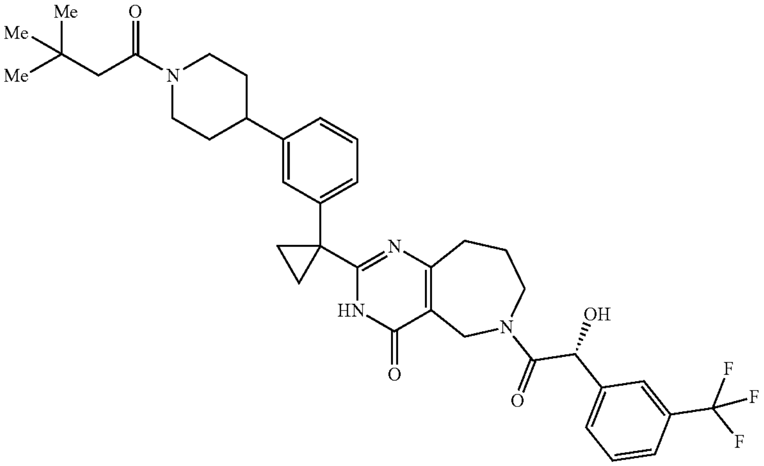 [SMILES: CC(C)(C)CC(=O)N1CCC(c2cccc(C3(c4nc5c(c(=O)[nH]4)CN(C(=O)[C@H](O)c4cccc(C(F)(F)F)c4)CCC5)CC3)c2)CC1] | 1.91 min | 665.2 |
| 31-13 | INT-21-19 | 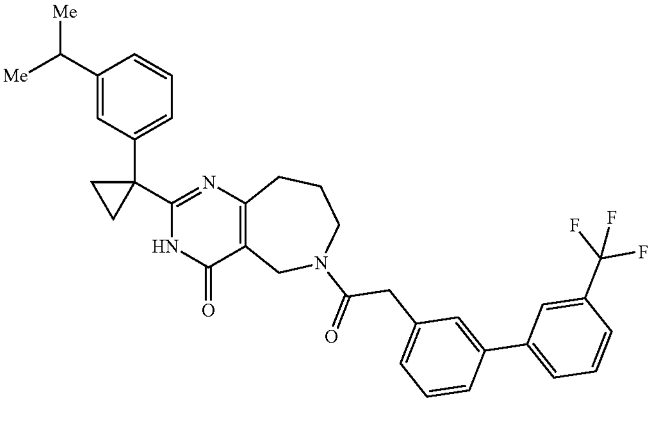 [SMILES: CC(C)c1cccc(C2(c3nc4c(c(=O)[nH]3)CN(C(=O)Cc3cccc(-c5cccc(C(F)(F)F)c5)c3)CCC4)CC2)c1] | 2.36 min | 586.5 |

TABLE 62-3-continued

| | | | | |
|---|---|---|---|---|
| 31-14 | Ex.42-70 | 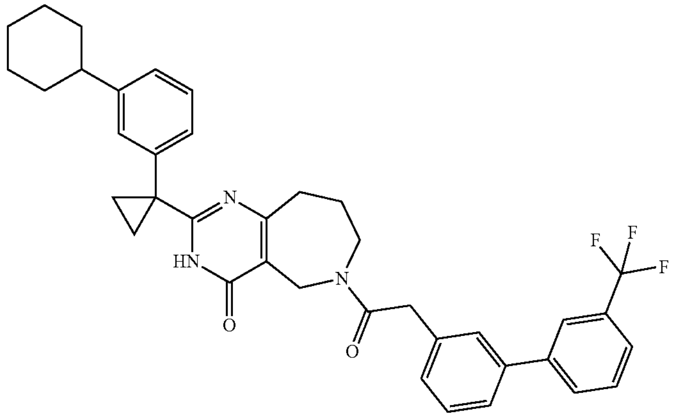 [SMILES: O=C(Cc1cccc(-c2cccc(C(F)(F)F)c2)c1)N1CCCc2nc(C3(c4cccc(C5CCCCC5)c4)CC3)[nH]c(=O)c2C1] | 2.55 min | 626.6 |
| 31-15 | INT-21-15 | 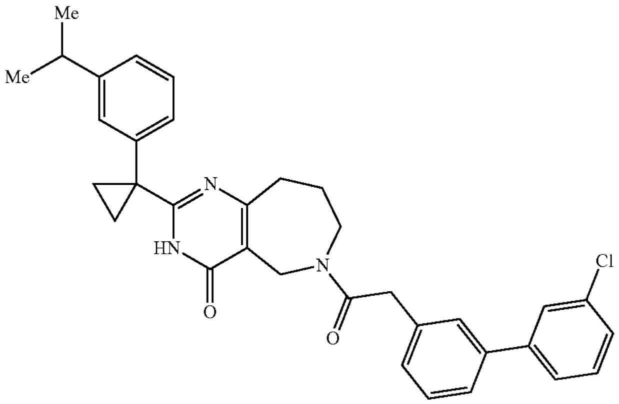 [SMILES: CC(C)c1cccc(C2(c3nc4c(c(=O)[nH]3)CN(C(=O)Cc3cccc(-c5cccc(Cl)c5)c3)CCC4)CC2)c1] | 2.36 min | 552.5 |

TABLE 62-4

| | | | | |
|---|---|---|---|---|
| 31-16 | INT-21-16 | 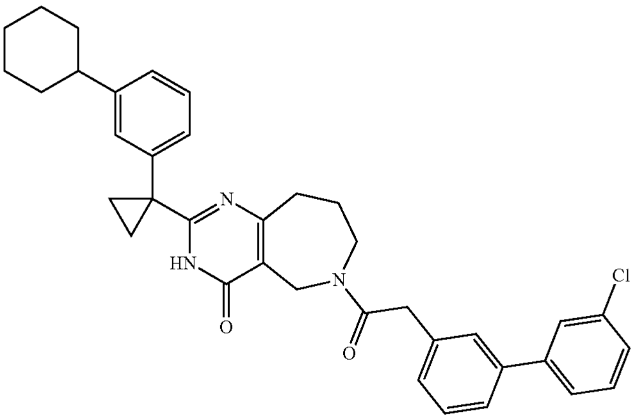 [SMILES: O=C(Cc1cccc(-c2cccc(Cl)c2)c1)N1CCCc2nc(C3(c4cccc(C5CCCCC5)c4)CC3)[nH]c(=O)c2C1] | 2.57 min | 592.6 |

The following pyrimidin-4(3H)-one derivatives (Ex-32-1 and Ex-32-2) are prepared according to the procedure of Ex-29-2 or the general synthesis in scheme-7 from the corresponding intermediates. The further purification is carried out by preparative LC-MS or SFC-MS system in usual manner. The retention time and observed MS by HPLC-QC method are summarized in Table 63.

TABLE 63

| Ex. | Intermediate (INT) | Structure | Retention time | Observed MS |
|---|---|---|---|---|
| 32-1 | INT-23-1 | 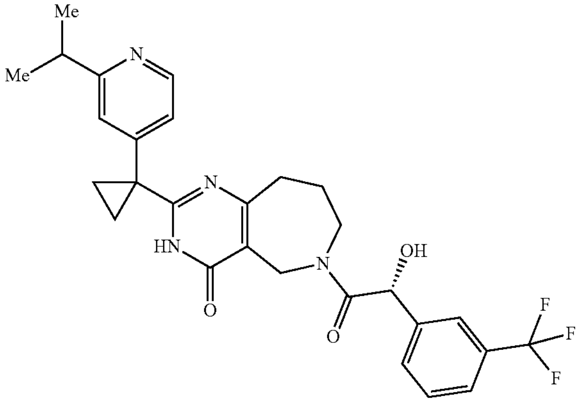 [SMILES: CC(C)c1cc(C2(c3nc4c(c(=O)[nH]3)CN(C(=O)[C@H](O)c3cccc(C(F)(F)F)c3)CCC4)CC2)ccn1] | 1.56 min | 527.2 |
| 32-2 | INT-22-1 | 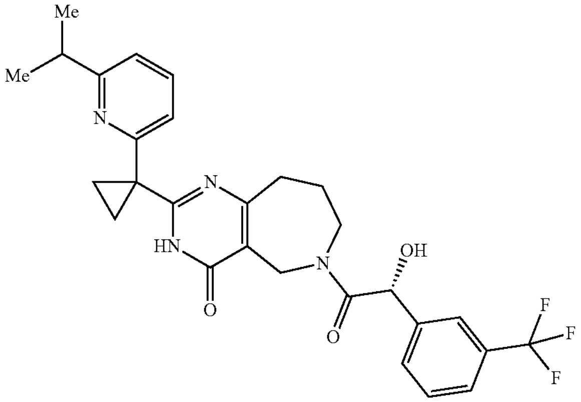 [SMILES: CC(C)c1cccc(C2(c3nc4c(c(=O)[nH]3)CN(C(=O)[C@H](O)c3cccc(C(F)(F)F)c3)CCC4)CC2)n1] | 1.91 min | 527.2 |

Example 33-1 (Ex-33-1)

(R)-6-(2-(3-chlorophenyl)-2-hydroxyacetyl)-2-(1-(4-(thiazol-5-yl)thiophen-2-yl)cyclopropyl)-5,6,7,8-tetrahydropyrido[4,3-d]pyrimidin-4(3H)-one (Ex-33-1)

{Chem. 105}

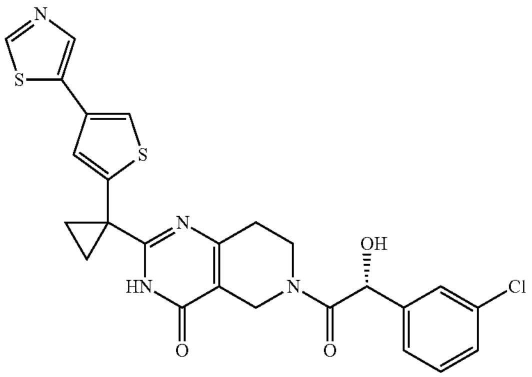

A mixture of INT-11-1 (25 mg, 0.041 mmol), 5-(tetramethyl-1,3,2-dioxaborolan-2-yl)-1,3-thiazole (12.1 mg, 0.057 mmol), palladium (II) acetate (1.8 mg, 0.0082 mmol) and triphenylphosphine (4.3 mg, 0.016 mmol) in 1,4-dioxane (1 mL) and saturated aqueous sodium bicarbonate (0.5 mL) is stirred at 100° C. for 1 hr. After the filtration through a pad of celite, the mixture is extracted with EOAc. The separated organic layer is washed with brine, dried over magnesium sulfate, filtered and concentrated in vacuo to give crude compound, which is purified with SCX (washing with MeOH and release with 1 M $NH_3$-MeOH) to give the titled compound (10.5 mg) as a brown solid.

The further purification is carried out by preparative LC-MS or SFC-MS system in the usual manner. The retention time and observed MS by HPLC-QC method are summarized in Table 64.

The following pyrimidin-4(3H)-one derivative (Ex-33-1) is prepared according to the procedure of Ex-33-1 from INT-11-1 and the known boronic acid derivatives. Ex-33-2 is prepared according to the procedure of INT-9-1-B from INT-11-1 and zinc cyanide.

TABLE 64

| Ex. | Intermediate (INT) | Structure | Retention time | Observed MS |
|---|---|---|---|---|
| 33-1 | INT-11-1 | 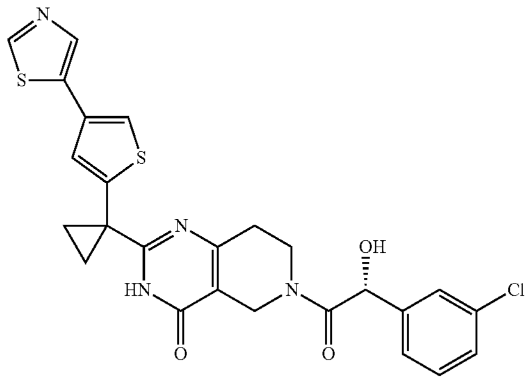 [SMILES: O=C([C@H](O)c1cccc(Cl)c1)N1CCc2nc(C3(c4cc(-c5cncs5)cs4)CC3)[nH]c(=O)c2C1] | 1.52 min | 524.9 |
| 33-2 | INT-11-1 | 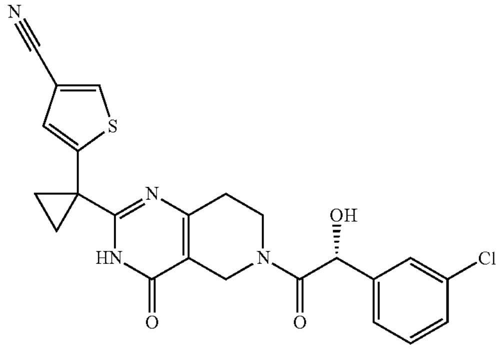 [SMILES: N#Cc1csc(C2(c3nc4c(c(=O)[nH]3)CN(C(=O)[C@H](O)c3cccc(Cl)c3)CC4)CC2)c1] | 1.47 min | 465.2 |

The following pyrimidin-4(3H)-one derivatives (Ex-34-1 and Ex-34-2) are prepared according to the procedure of Ex-33-1 or the general synthesis in scheme-6 from INT-11-2 and the known boronic acid derivatives. The further purification is carried out by preparative LC-MS or SFC-MS system in usual manner. The retention time and observed MS by HPLC-QC method are summarized in Table 65.

TABLE 65

| Ex. | Intermediate (INT) | Structure | Retention time | Observed MS |
|---|---|---|---|---|
| 34-1 | INT-11-2 | 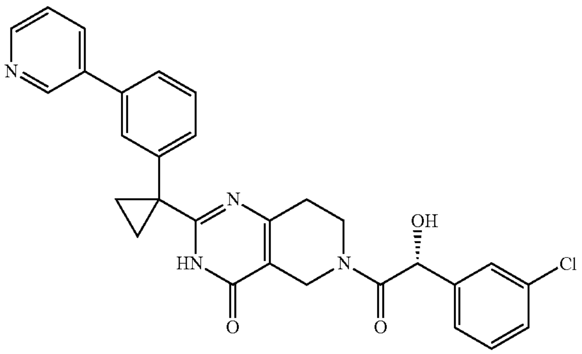 [SMILES: O=C([C@H](O)c1cccc(Cl)c1)N1CCc2nc(C3(c4cccc(-c5cccnc5)c4)CC3)[nH]c(=O)c2C1] | 1.50 min | 513.0 |

TABLE 65-continued

| Ex. | Intermediate (INT) | Structure | Retention time | Observed MS |
|---|---|---|---|---|
| 34-2 | INT-11-2 | 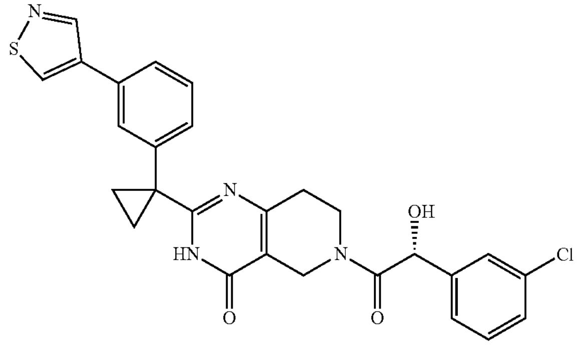 [SMILES: O=C([C@H](O)c1cccc(Cl)c1)N1CCc2nc(C3(c4cccc(-c5cnsc5)c4)CC3)[nH]c(=O)c2C1] | 1.59 min | 519.0 |

The following pyrimidin-4(3H)-one derivatives (Ex-35-1 and Ex-35-2) are prepared according to the procedure of Ex-33-1 or the general synthesis in scheme-6 from INT-11-3 and the known boronic acid derivatives. The further purification is carried out by preparative LC-MS or SFC-MS system in usual manner. The retention time and observed MS by HPLC-QC method are summarized in Table 66.

The following pyrimidin-4(3H)-one derivatives (Ex-36-1 and Ex-36-2) are prepared according to the procedure of Ex-33-1 or the general synthesis in scheme-6 from INT-11-4 and the known boronic acid derivatives. The further purification is carried out by preparative LC-MS or SFC-MS system in usual manner. The retention time and observed MS by HPLC-QC method are summarized in Table 67.

TABLE 66

| Ex. | Intermediate (INT) | Structure | Retention time | Observed MS |
|---|---|---|---|---|
| 35-1 | INT-11-3 | 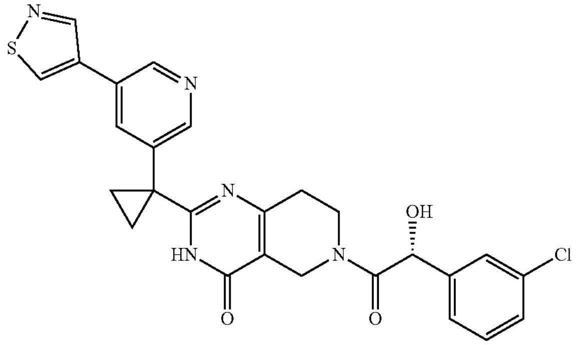 [SMILES: O=C([C@H](O)c1cccc(Cl)c1)N1CCc2nc(C3(c4cncc(-c5cnsc5)c4)CC3)[nH]c(=O)c2C1] | 1.32 min | 520.0 |
| 35-2 | INT-11-3 | 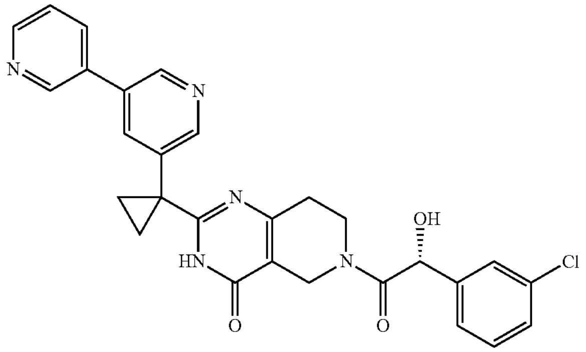 [SMILES: O=C([C@H](O)c1cccc(Cl)c1)N1CCc2nc(C3(c4cncc(-c5cccnc5)c4)CC3)[nH]c(=O)c2C1] | 1.24 min | 514.0 |

TABLE 67

| Ex. | Intermediate (INT) | Structure | Retention time | Observed MS |
|---|---|---|---|---|
| 36-1 | INT-11-4 | 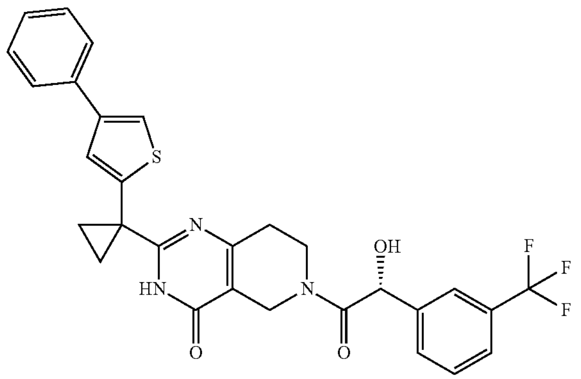 [SMILES: O=C([C@H](O)c1cccc(C(F)(F)F)c1)N1CCc2nc(C3(c4cc(-c5ccccc5)cs4)CC3)[nH]c(=O)c2C1] | 1.88 min | 552.0 |
| 36-2 | INT-11-4 | 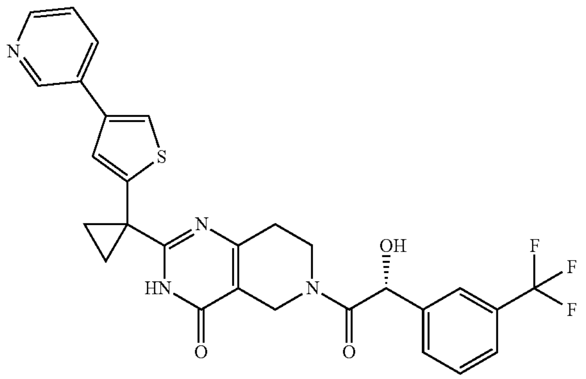 [SMILES: O=C([C@H](O)c1cccc(C(F)(F)F)c1)N1CCc2nc(C3(c4cc(-c5cccnc5)cs4)CC3)[nH]c(=O)c2C1] | 1.55 min | 553.0 |

The following pyrimidin-4(3H)-one derivative (Ex-37-1 to Ex-37-3) are prepared according to the procedure of Ex-33-1 or the general synthesis in scheme-6 from INT-11-5 and the known boronic acid derivatives. The further purification is carried out by preparative LC-MS or SFC-MS system in usual manner. The retention time and observed MS by HPLC-QC method are summarized in Table 68.

TABLE 68

| Ex. | Intermediate (INT) | Structure | Retention time | Observed MS |
|---|---|---|---|---|
| 37-1 | INT-11-5 | 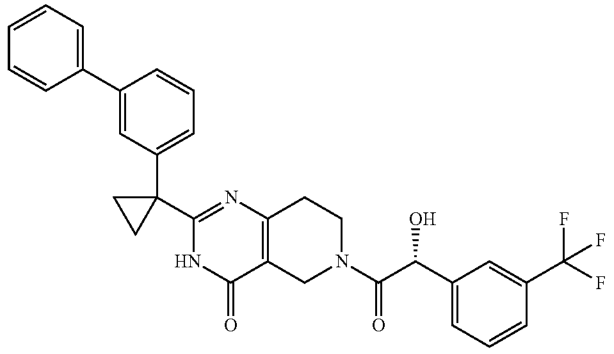 [SMILES: O=C([C@H](O)c1cccc(C(F)(F)F)c1)N1CCc2nc(C3(c4cccc(-c5ccccc5)c4)CC3)[nH]c(=O)c2C1] | 1.88 min | 546.0 |

TABLE 68-continued

| Ex. | Intermediate (INT) | Structure | Retention time | Observed MS |
|---|---|---|---|---|
| 37-2 | INT-11-5 | 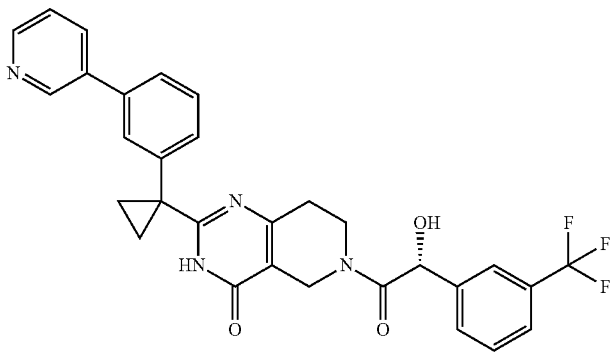 [SMILES: O=C([C@H](O)c1cccc(C(F)(F)F)c1)N1CCc2nc(C3(c4cccc(-c5cccnc5)c4)CC3)[nH]c(=O)c2C1] | 1.56 min | 547.0 |
| 37-3 | INT-11-5 | 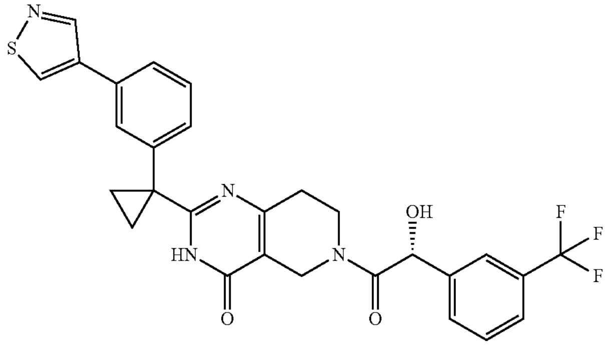 [SMILES: O=C([C@H](O)c1cccc(C(F)(F)F)c1)N1CCc2nc(C3(c4cccc(-c5cnsc5)c4)CC3)[nH]c(=O)c2C1] | 1.64 min | 553.0 |

The following pyrimidin-4(3H)-one derivatives (Ex-38-1 to Ex-38-3) are prepared according to the procedure of Ex-33-1 or the general synthesis in scheme-6 from INT-11-6 and the known boronic acid derivatives. The further purification is carried out by preparative LC-MS or SFC-MS system in usual manner. The retention time and observed MS by HPLC-QC method are summarized in Table 69.

TABLE 69

| Ex. | Intermediate (INT) | Structure | Retention time | Observed MS |
|---|---|---|---|---|
| 38-1 | INT-11-6 | 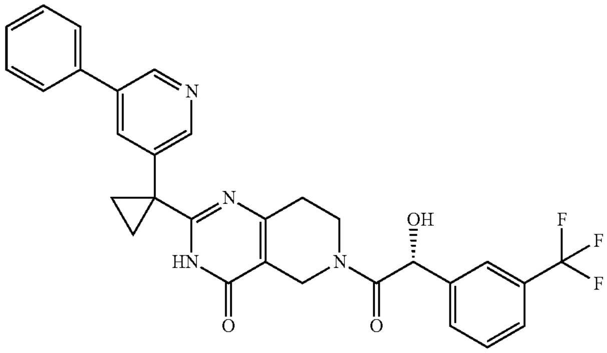 [SMILES: O=C([C@H](O)c1cccc(C(F)(F)F)c1)N1CCc2nc(C3(c4cncc(-c5ccccc5)c4)CC3)[nH]c(=O)c2C1] | 1.60 min | 547.0 |

TABLE 69-continued

| Ex. | Intermediate (INT) | Structure | Retention time | Observed MS |
|---|---|---|---|---|
| 38-2 | INT-11-6 | 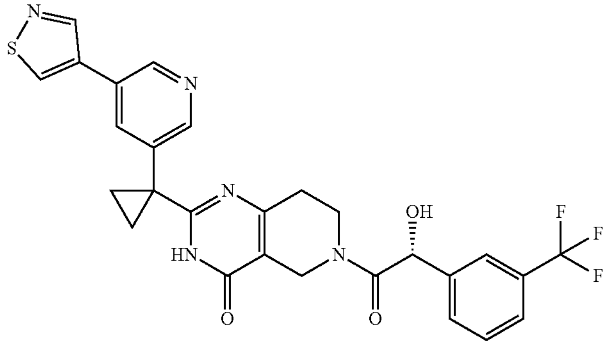 [SMILES: O=C([C@H](O)c1cccc(C(F)(F)F)c1)N1CCc2nc(C3(c4cncc(-c5cnsc5)c4)CC3)[nH]c(=O)c2C1] | 1.39 min | 554.0 |
| 38-3 | INT-11-6 | 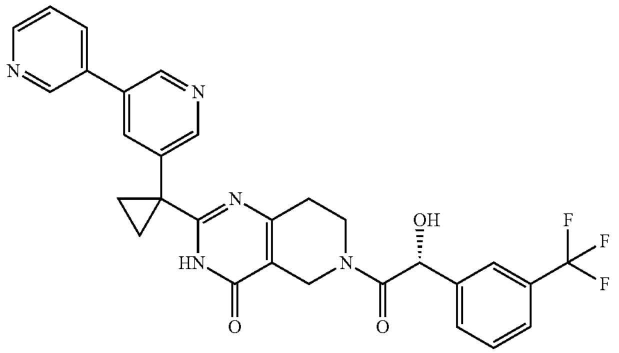 [SMILES: O=C([C@H](O)c1cccc(C(F)(F)F)c1)N1CCc2nc(C3(c4cncc(-c5cccnc5)c4)CC3)[nH]c(=O)c2C1] | 1.31 min | 548.0 |

The following pyrimidin-4(3H)-one derivatives (Ex-39-1 to Ex-39-3) are prepared according to the procedure of Ex-33-1 or the general synthesis in scheme-6 from INT-11-7 and the known boronic acid derivatives. The further purification is carried out by preparative LC-MS or SFC-MS system in usual manner. The retention time and observed MS by HPLC-QC method are summarized in Table 70.

TABLE 70

| Ex. | Intermediate (INT) | Structure | Retention time | Observed MS |
|---|---|---|---|---|
| 39-1 | INT-11-7 | 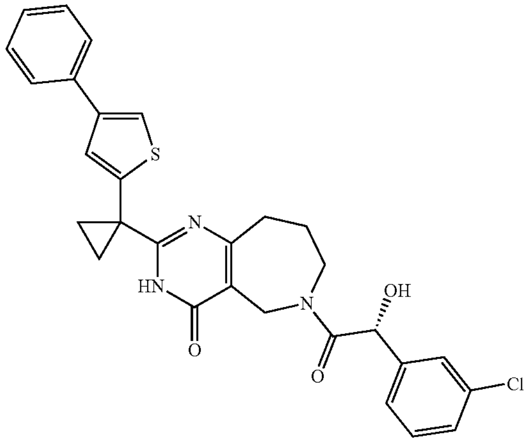 [SMILES: O=C([C@H](O)c1cccc(Cl)c1)N1CCCc2nc(C3(c4cc(-c5ccccc5)cs4)CC3)[nH]c(=O)c2C1] | 1.89 min | 531.9 |

TABLE 70-continued

| Ex. | Intermediate (INT) | Structure | Retention time | Observed MS |
|---|---|---|---|---|
| 39-2 | INT-11-7 | 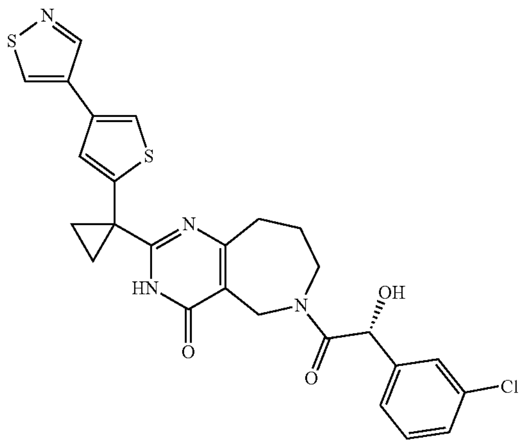 [SMILES: O=C([C@H](O)c1cccc(Cl)c1)N1CCCc2nc(C3(c4cc(-c5cnsc5)cs4)CC3)[nH]c(=O)c2C1] | 1.62 min | 538.9 |
| 39-3 | INT-11-7 | 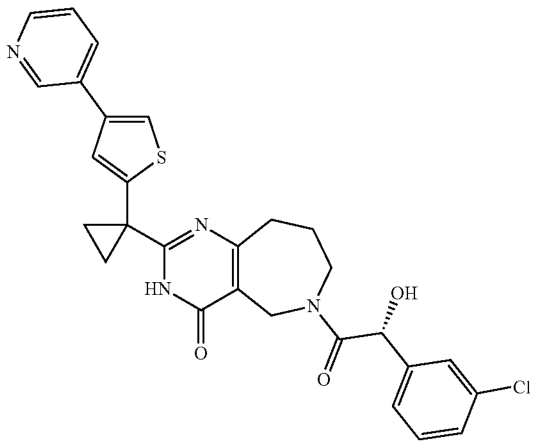 [SMILES: O=C([C@H](O)c1cccc(Cl)c1)N1CCCc2nc(C3(c4cc(-c5cccnc5)cs4)CC3)[nH]c(=O)c2C1] | 1.52 min | 533.0 |

40

The following pyrimidin-4(3H)-one derivatives (Ex-40-1 to Ex-40-22) are prepared according to the procedure of Ex-33-1 or the general synthesis in scheme-6 from INT-11-8 and the known boronic acid derivatives. The further purification is carried out by preparative LC-MS system in usual manner. The retention time and observed MS by HPLC-QC method are summarized in Table 71-1 to 71-5.

TABLE 71-1

| Ex. | Intermediate (INT) | Structure | Retention time | Observed MS |
|---|---|---|---|---|
| 40-1 | INT-11-8 | 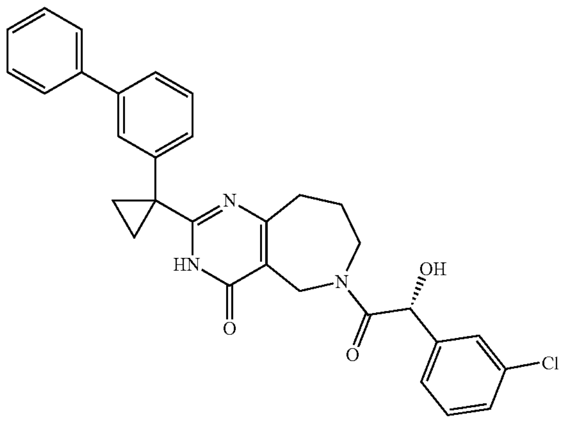 [SMILES: O=C([C@H](O)c1cccc(Cl)c1)N1CCCc2nc(C3(c4cccc(-c5ccccc5)c4)CC3)[nH]c(=O)c2C1] | 1.90 min | 526.0 |

TABLE 71-1-continued
| Ex. | Intermediate (INT) | Structure | Retention time | Observed MS |
| --- | --- | --- | --- | --- |
| 40-2 | INT-11-8 | 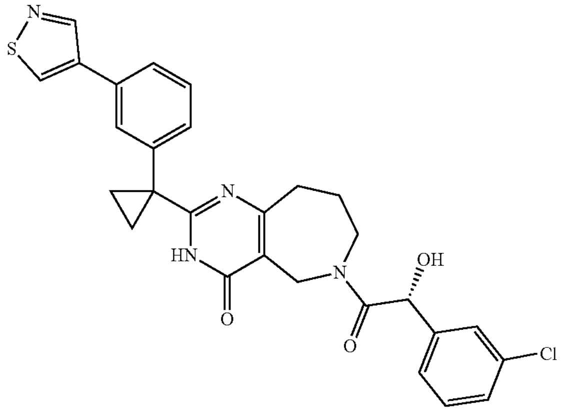 [SMILES: O=C([C@H](O)c1cccc(Cl)c1)N1CCCc2nc(C3(c4cccc(-c5cnsc5)c4)CC3)[nH]c(=O)c2C1] | 1.62 min | 533.0 |
| 40-3 | INT-11-8 | 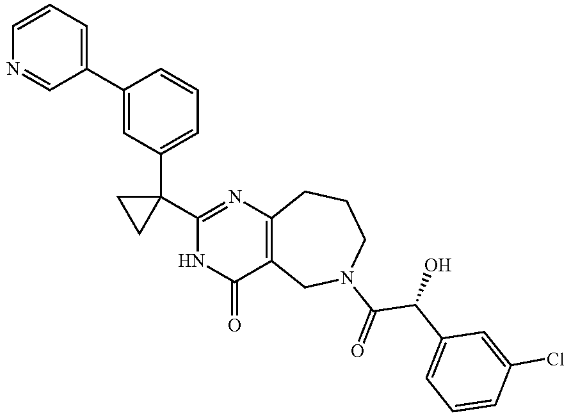 [SMILES: O=C([C@H](O)c1cccc(Cl)c1)N1CCCc2nc(C3(c4cccc(-c5cccnc5)c4)CC3)[nH]c(=O)c2C1] | 1.53 min | 527.0 |
| 40-4 | INT-11-8 | 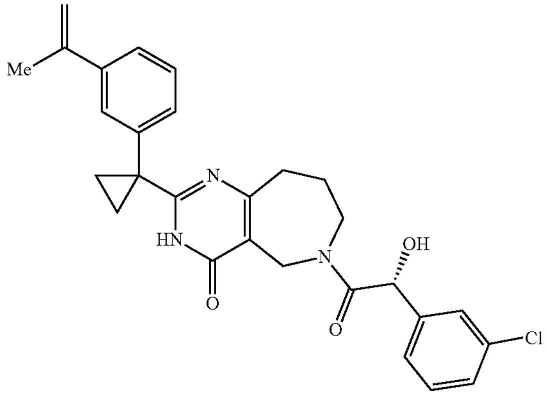 [SMILES: C=C(C)c1cccc(C2(c3nc4c(c(=O)[nH]3)CN(C(=O)[C@H](O)c3cccc(Cl)c3)CCC4)CC2)c1] | 1.83 min | 490.0 |

TABLE 71-1-continued
| Ex. | Intermediate (INT) | Structure | Retention time | Observed MS |
|---|---|---|---|---|
| 40-5 | INT-11-8 | 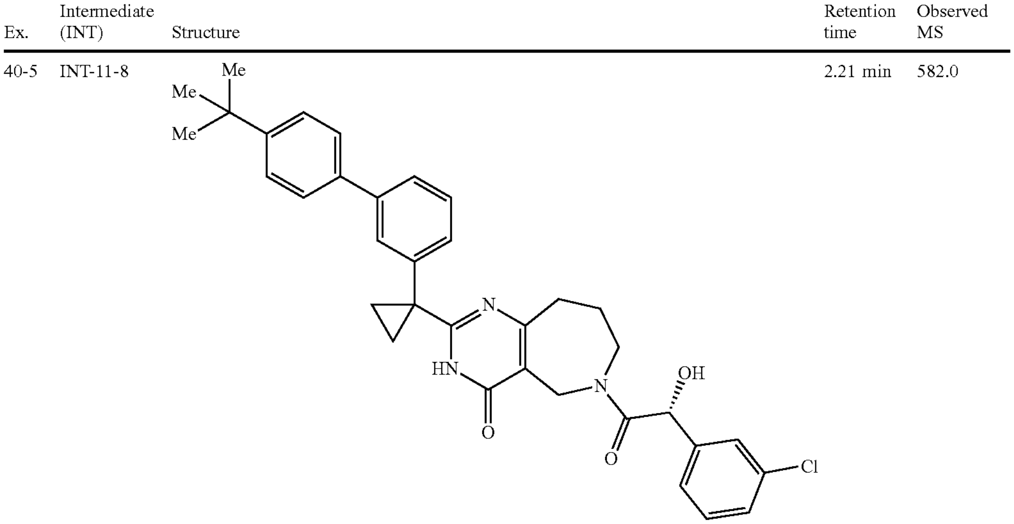 | 2.21 min | 582.0 |
TABLE 71-2
| | | | | |
|---|---|---|---|---|
| 40-6 | INT-11-8 | 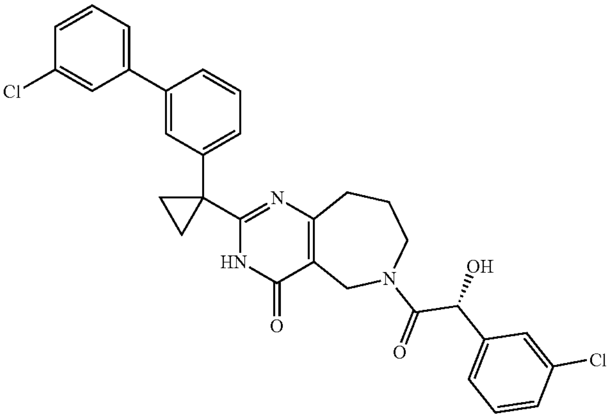 [SMILES: O=C([C@H](O)c1cccc(Cl)c1)N1CCCc2nc(C3(c4cccc(-c5cccc(Cl)c5)c4)CC3)[nH]c(=O)c2C1] | 2.01 min | 559.9 |
| 40-7 | INT-11-8 | 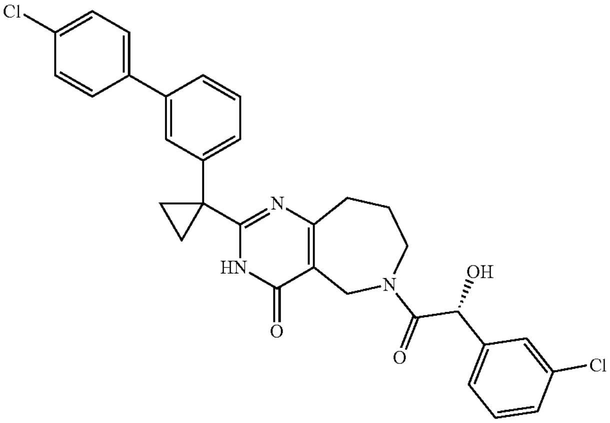 [SMILES: O=C([C@H](O)c1cccc(Cl)c1)N1CCCc2nc(C3(c4cccc(-c5ccc(Cl)cc5)c4)CC3)[nH]c(=O)c2C1] | 2.01 min | 559.9 |

TABLE 71-2-continued
| | | | |
|---|---|---|---|
| 40-8 | INT-11-8 | 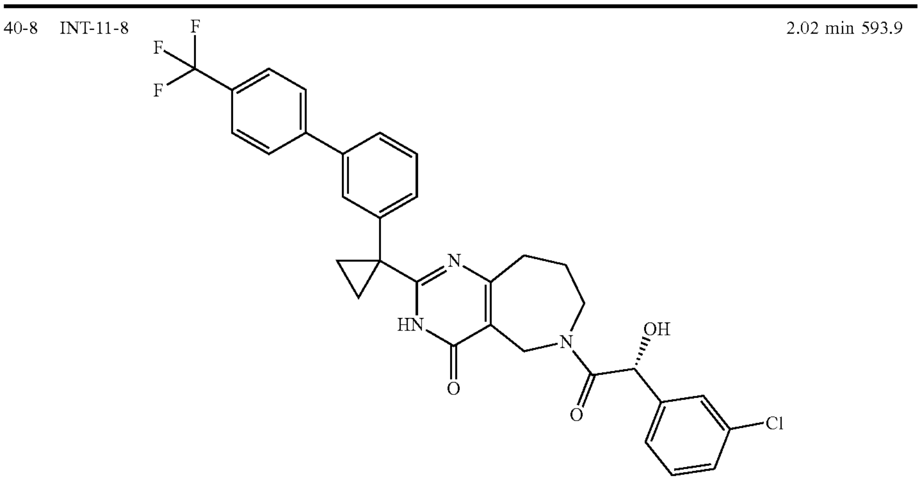 | 2.02 min 593.9 |
| 40-9 | INT-11-8 | 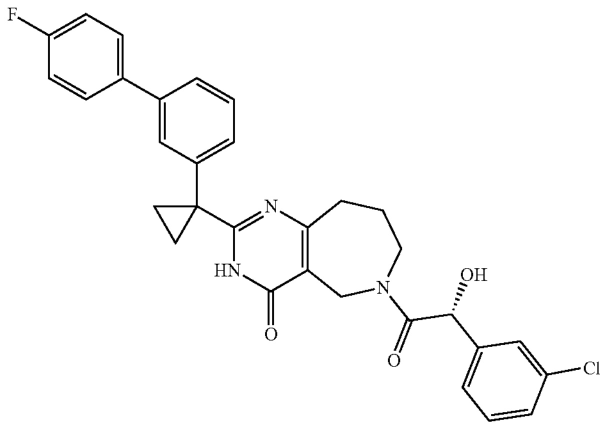 [SMILES: O=C([C@H](O)c1cccc(Cl)c1)N1CCCc2nc(C3(c4cccc(-c5ccc(F)cc5)c4)CC3)[nH]c(=O)c2C1] | 1.90 min 543.9 |
| 40-10 | INT-11-8 | 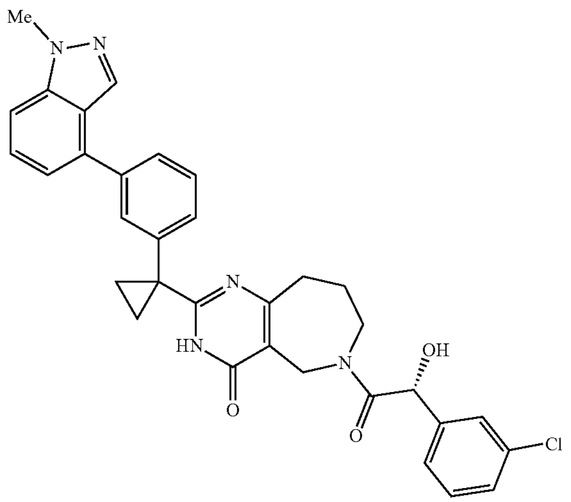 [SMILES: Cn1ncc2c(-c3cccc(C4(c5nc6c(c(=O)[nH]5)CN(C(=O)[C@H](O)c5cccc(Cl)c5)CCC6)CC4)c3)cccc21] | 1.77 min 579.9 |

TABLE 71-3
| | | | |
|---|---|---|---|
| 40-11 | INT-11-8 | 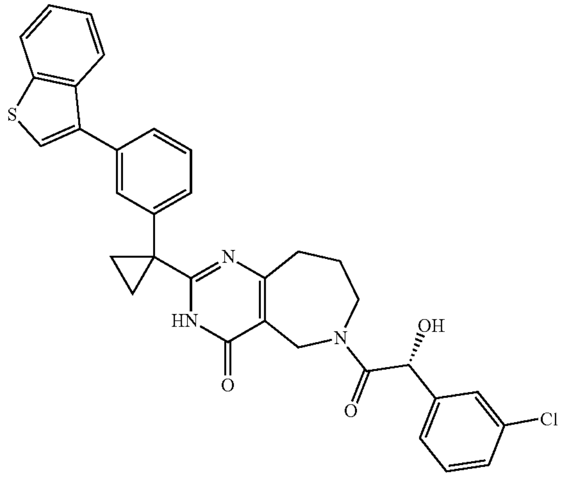 [SMILES: O=C([C@H](O)c1cccc(Cl)c1)N1CCCc2nc(C3(c4cccc(-c5csc6ccccc56)c4)CC3)[nH]c(=O)c2C1] | 2.08 min 581.9 |
| 40-12 | INT-11-8 | 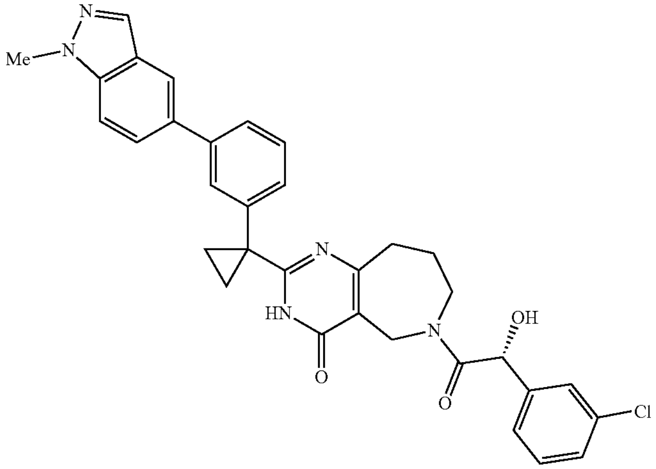 [SMILES: Cn1ncc2cc(-c3cccc(C4(c5nc6c(c(=O)[nH]5)CN(C(=O)[C@H](O)c5cccc(Cl)c5)CCC6)CC4)c3)ccc21] | 1.75 min 579.9 |
| 40-13 | INT-11-8 | 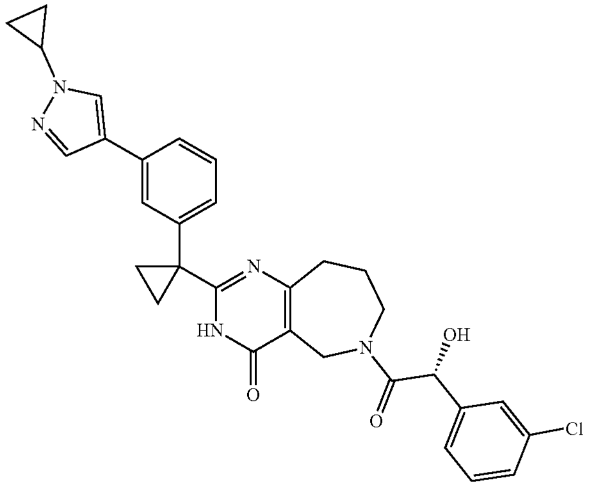 [SMILES: O=C([C@H](O)c1cccc(Cl)c1)N1CCCc2nc(C3(c4cccc(-c5cnn(C6CC6)c5)c4)CC3)[nH]c(=O)c2C1] | 1.62 min 556.0 |

TABLE 71-3-continued
| | | | |
|---|---|---|---|
| 40-14 | INT-11-8 | 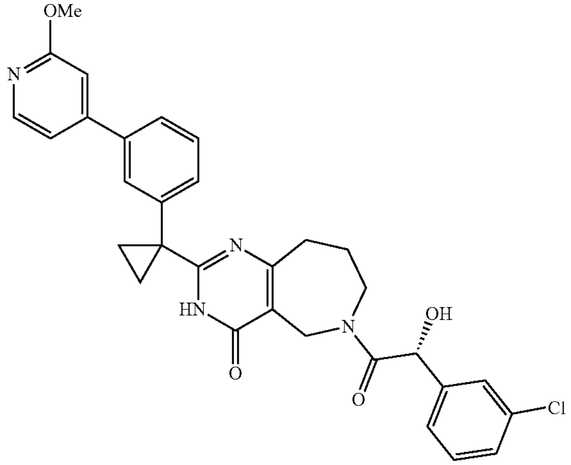 [SMILES: COc1cc(-c2cccc(C3(c4nc5c(c(=O)[nH]4)CN(C(=O)[C@H](O)c4cccc(Cl)c4)CCC5)CC3)c2)ccn1] | 1.73 min 557.0 |
TABLE 71-4
| | | | |
|---|---|---|---|
| 40-15 | INT-11-8 | 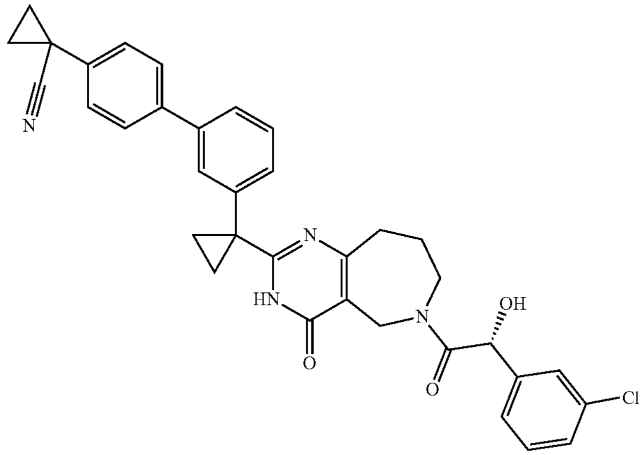 [SMILES: N#CC1(c2ccc(-c3cccc(C4(c5nc6c(c(=O)[nH]5)CN(C(=O)[C@H](O)c5cccc(Cl)c5)CCC6)CC4)c3)cc2)CC1] | 1.88 min 591.0 |
| 40-16 | INT-11-8 | 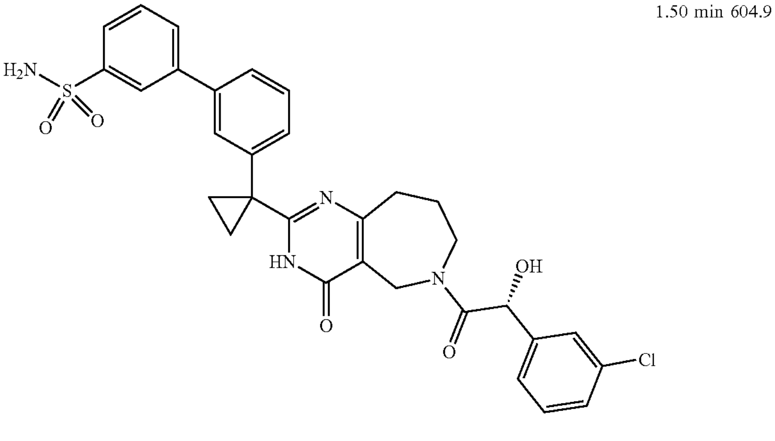 | 1.50 min 604.9 |

TABLE 71-4-continued
| | | | |
|---|---|---|---|
| 40-17 | INT-11-8 | 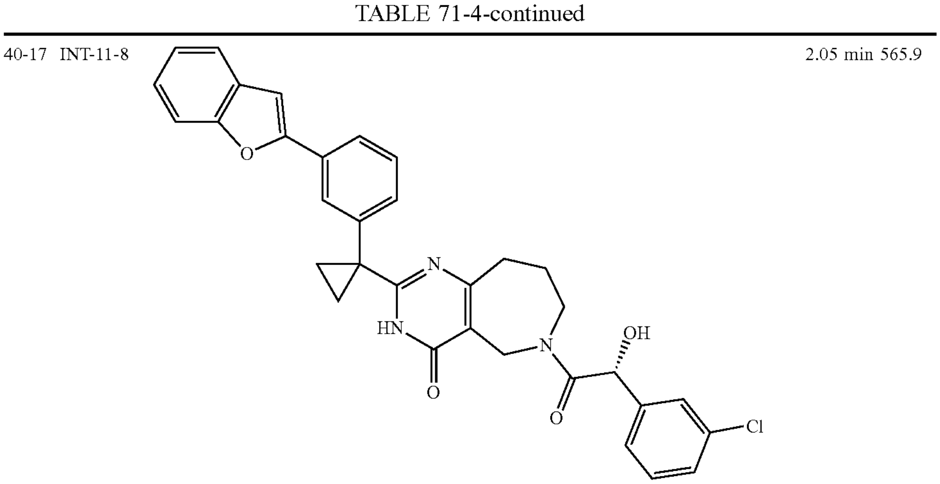 | 2.05 min 565.9 |
| 40-18 | INT-11-8 | 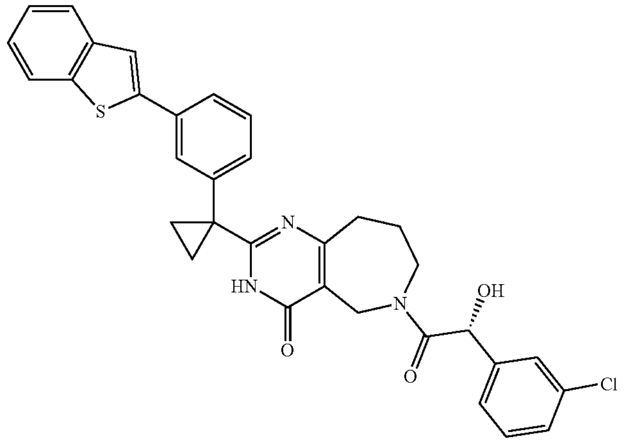 [SMILES: O=C([C@H](O)c1cccc(Cl)c1)N1CCCc2nc(C3(c4cccc(-c5cc6ccccc6s5)c4)CC3)[nH]c(=O)c2C1] | 2.10 min 581.9 |
TABLE 71-5
| | | | |
|---|---|---|---|
| 40-19 | INT-11-8 | 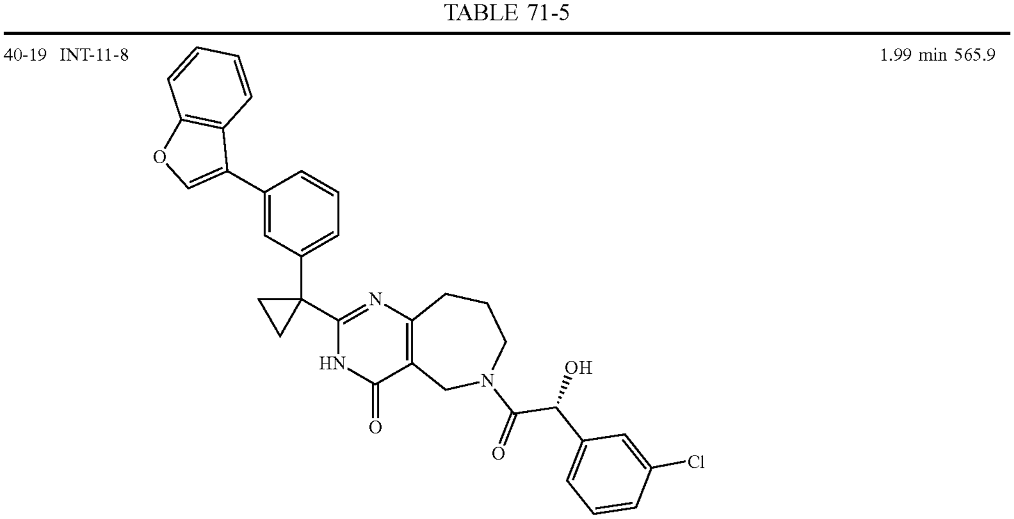 | 1.99 min 565.9 |

TABLE 71-5-continued

| | | | |
|---|---|---|---|
| 40-20 | INT-11-8 | 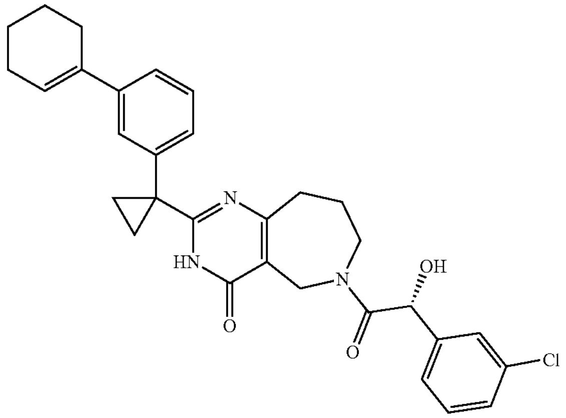 [SMILES: O=C([C@H](O)c1cccc(Cl)c1)N1CCCc2nc(C3(c4cccc(C5=CCCCC5)c4)CC3)[nH]c(=O)c2C1] | 2.10 min 530.1 |
| 40-21 | INT-11-8 | 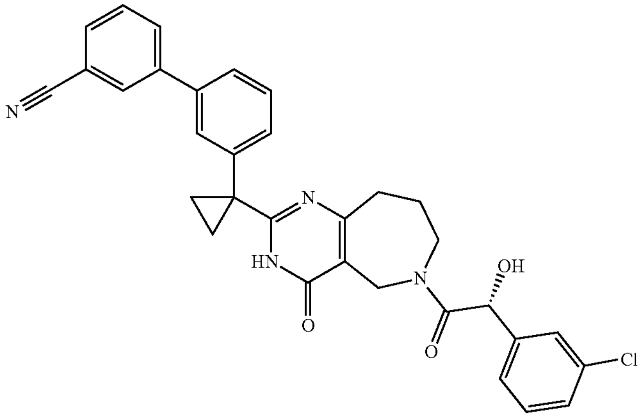 [SMILES: N#Cc1cccc(-c2cccc(C3(c4nc5c(c(=O)[nH]4)CN(C(=O)[C@H](O)c4cccc(Cl)c4)CCC5)CC3)c2)c1] | 1.78 min 550.9 |
| 40-22 | INT-11-8 | 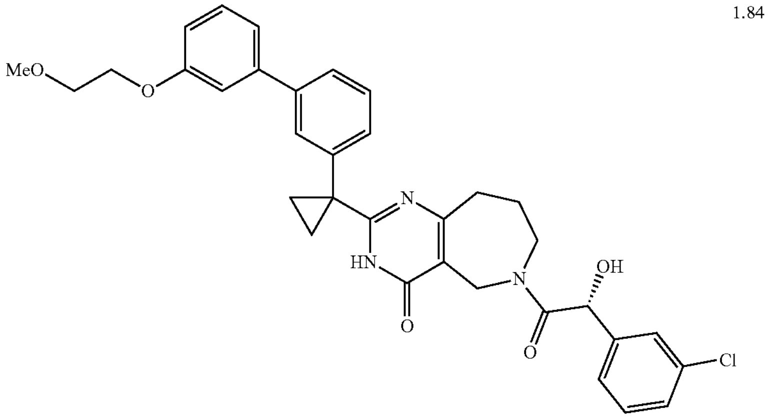 | 1.84 min 600.0 |

The following pyrimidin-4(3H)-one derivatives (Ex-41-1 to Ex-41-3) are prepared according to the procedure of Ex-33-1 or the general synthesis in scheme-6 from INT-11-9 and the known boronic acid derivatives. The further purification is carried out by preparative LC-MS or SFC-MS system in usual manner. The retention time and observed MS by HPLC-QC method are summarized in Table 72.

TABLE 72

| Ex. | Intermediate (INT) | Structure | Retention time | Observed MS |
|---|---|---|---|---|
| 41-1 | INT-11-9 | 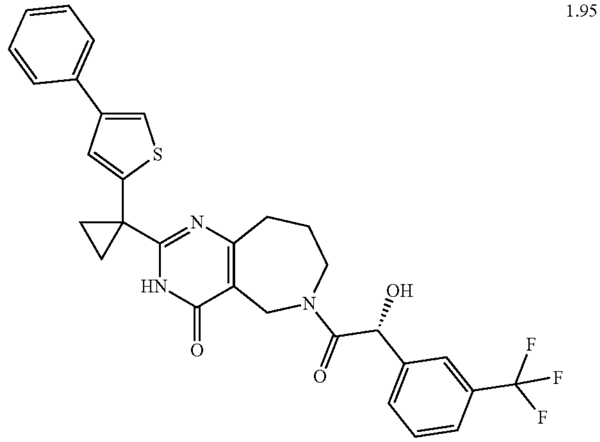 | 1.95 min | 566.2 |
| 41-2 | INT-11-9 | 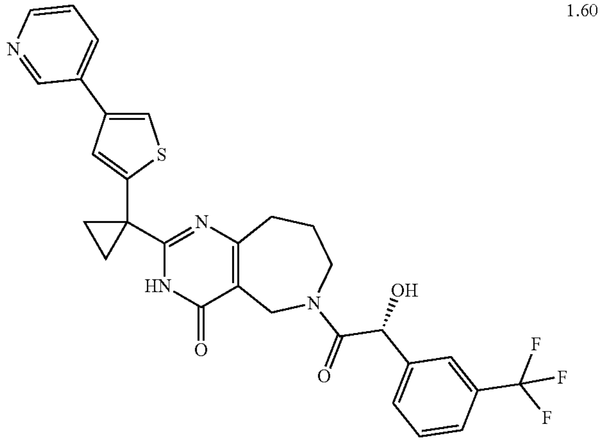 | 1.60 min | 567.0 |
| 41-3 | INT-11-9 | 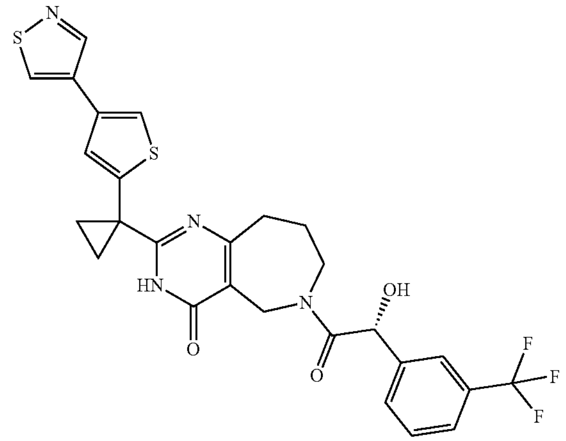 [SMILES: O=C([C@H](O)c1cccc(C(F)(F)F)c1)N1CCCc2nc(C3(c4cc(-c5cnsc5)cs4)CC3)[nH]c(=O)c2C1] | 1.71 min | 572.9 |

The following pyrimidin-4(3H)-one derivatives (Ex-42-1 to Ex-42-71) are prepared according to the procedure of Ex-33-1 or the general synthesis in scheme-6 from INT-11-10 and the known boronic acid derivatives or INT-11-38 and the known halide derivatives. The further purification is carried out by preparative LC-MS or SFC-MS system in usual manner. The retention time and observed MS by HPLC-QC method are summarized in Tables 73-1 to 73-15.

TABLE 73-1
| Ex. | Intermediate (INT) | Structure | Retention time | Observed MS |
|---|---|---|---|---|
| 42-1 | INT-11-10 | 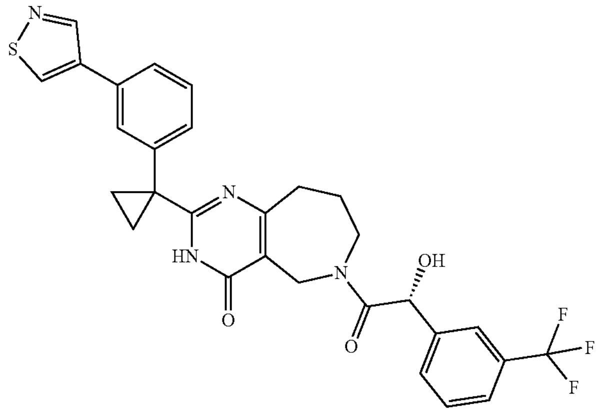 [SMILES: O=C([C@H](O)c1cccc(C(F)(F)F)c1)N1CCCc2nc(C3(c4cccc(-c5cnsc5)c4)CC3)[nH]c(=O)c2C1] | 1.71 min | 567.0 |
| 42-2 | INT-11-10 | 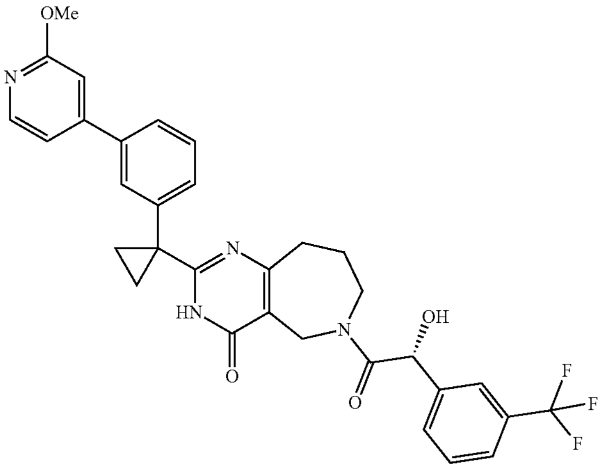 [SMILES: COc1cc(-c2cccc(C3(c4nc5c(c(=O)[nH]4)CN(C(=O)[C@H](O)c4cccc(C(F)(F)F)c4)CCC5)CC3)c2)ccn1] | 1.81 min | 591.1 |
| 42-3 | INT-11-10 | 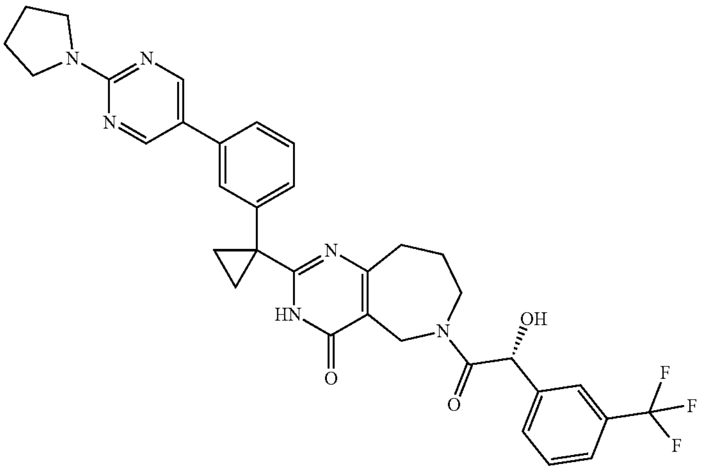 [SMILES: O=C([C@H](O)c1cccc(C(F)(F)F)c1)N1CCCc2nc(C3(c4cccc(-c5cnc(N6CCCC6)nc5)c4)CC3)[nH]c(=O)c2C1] | 1.85 min | 631.3 |

TABLE 73-1-continued
| Ex. | Intermediate (INT) | Structure | Retention time | Observed MS |
|---|---|---|---|---|
| 42-4 | INT-11-10 | 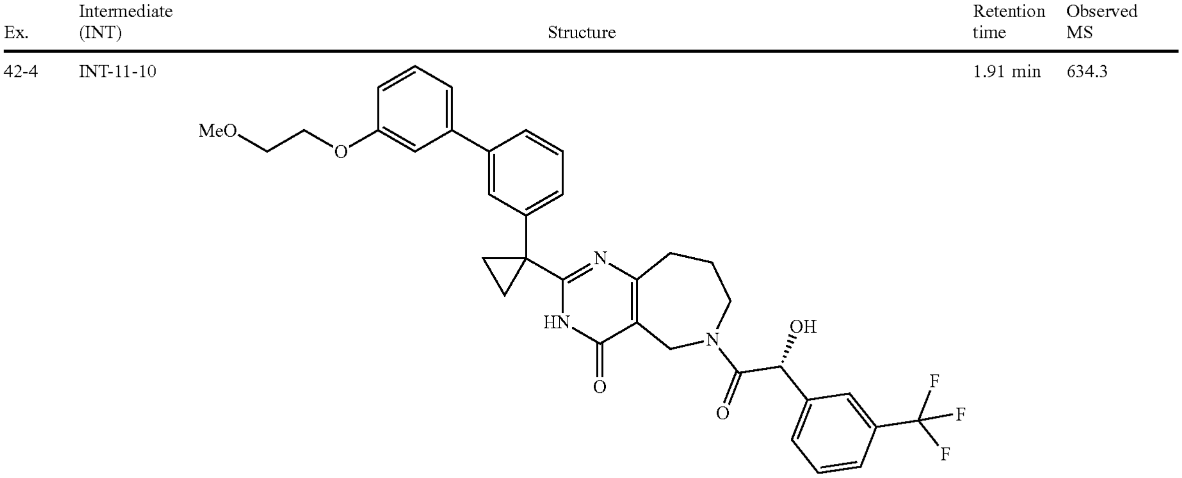 | 1.91 min | 634.3 |
| 42-5 | INT-11-10 | 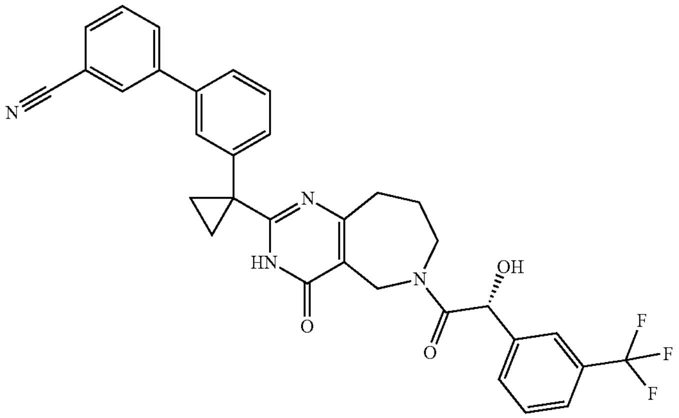 [SMILES: N#Cc1cccc(-c2cccc(C3(c4nc5c(c(=O)[nH]4)CN(C(=O)[C@H](O)c4cccc(C(F)(F)F)c4)CCC5)CC3)c2)c1] | 1.86 min | 585.2 |
TABLE 73-2
| | | | | |
|---|---|---|---|---|
| 42-6 | INT-11-10 | 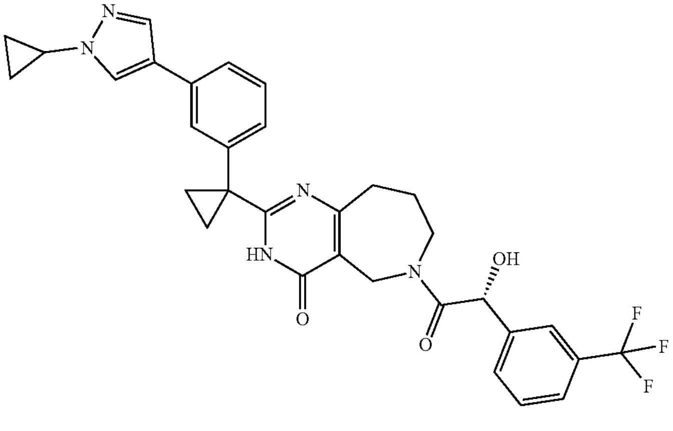 [SMILES: O=C([C@H](O)c1cccc(C(F)(F)F)c1)N1CCCc2nc(C3(c4cccc(-c5cnn(C6CC6)c5)c4)CC3)[nH]c(=O)c2C1] | 1.70 min | 590.2 |

TABLE 73-2-continued
| | | | |
|---|---|---|---|
| 42-7 | INT-11-10 | 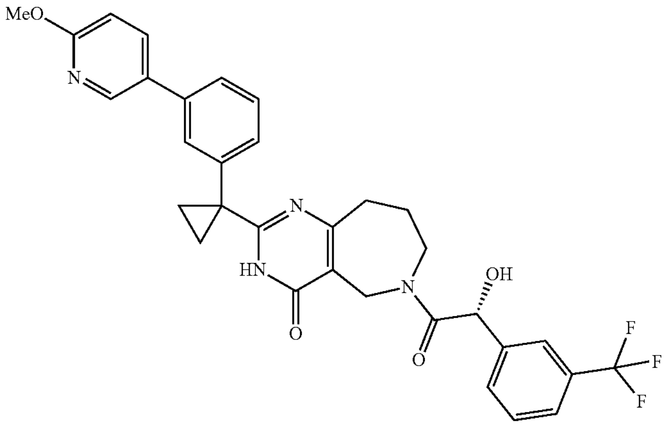 [SMILES: COc1ccc(-c2cccc(C3(c4nc5c(c(=O)[nH]4)CN(C(=O)[C@H](O)c4cccc(C(F)(F)F)c4)CCC5)CC3)c2)cn1] | 1.83 min 591.1 |
| 42-8 | INT-11-10 | 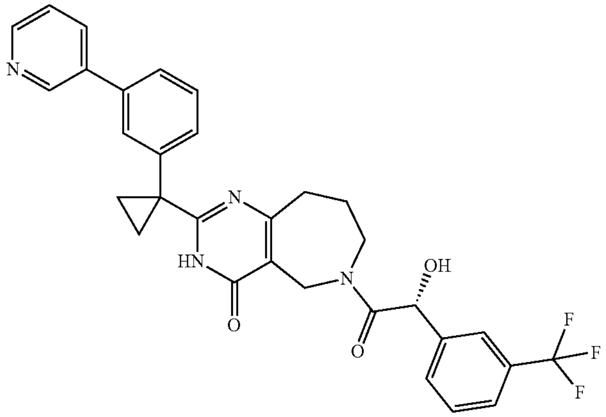 [SMILES: O=C([C@H](O)c1cccc(C(F)(F)F)c1)N1CCCc2nc(C3(c4cccc(-c5cccnc5)c4)CC3)[nH]c(=O)c2C1] | 1.61 min 561.1 |
| 42-9 | INT-11-10 | 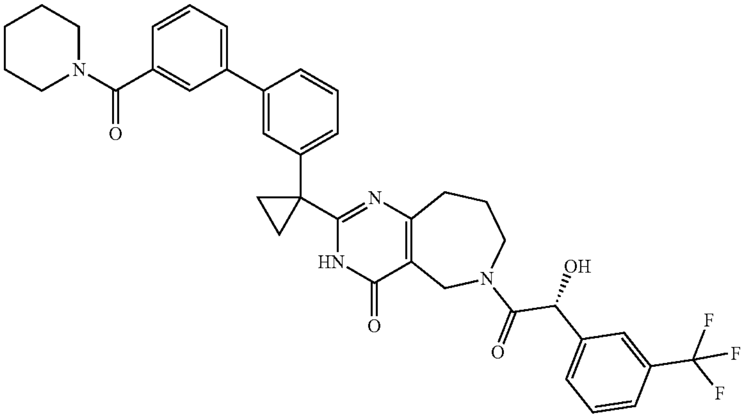 [SMILES: O=C(c1cccc(-c2cccc(C3(c4nc5c(c(=O)[nH]4)CN(C(=O)[C@H](O)c4cccc(C(F)(F)F)c4)CCC5)CC3)c2)c1)N1CCCCC1] | 1.87 min 671.4 |

TABLE 73-2-continued
| | | | |
|---|---|---|---|
| 42-10 | INT-11-10 | 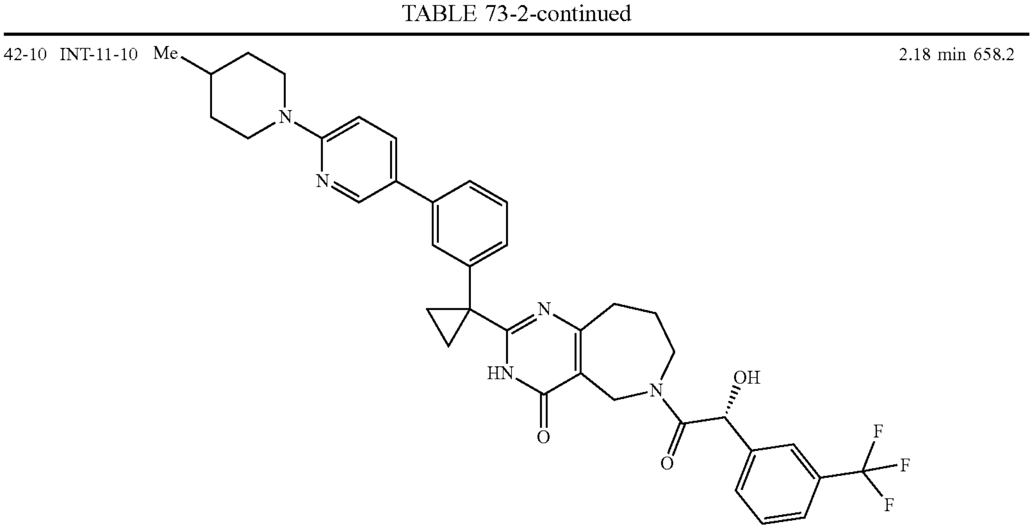 | 2.18 min 658.2 |
TABLE 73-3
| | | | |
|---|---|---|---|
| 42-11 | INT-11-10 | 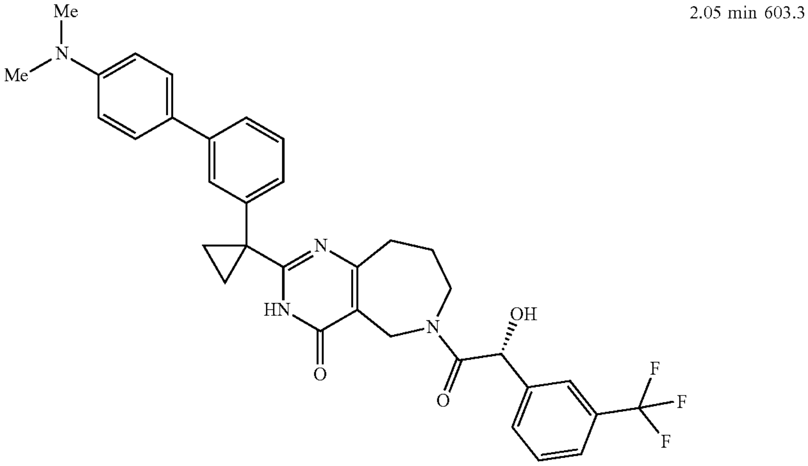 | 2.05 min 603.3 |
| 42-12 | INT-11-10 | 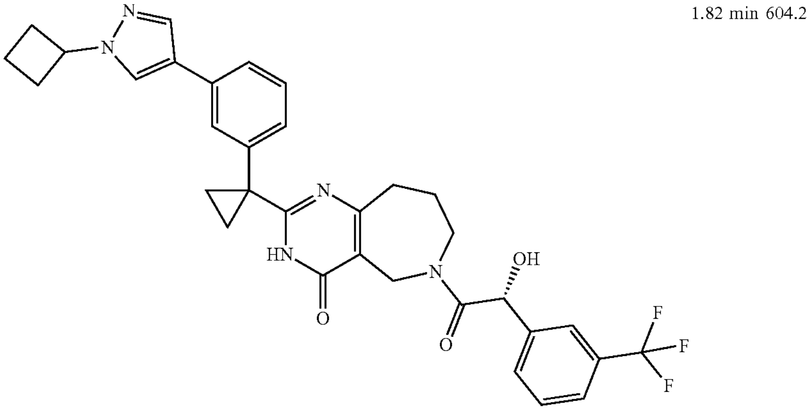 | 1.82 min 604.2 |

TABLE 73-3-continued
| | | | |
|---|---|---|---|
| 42-13 | INT-11-10 | 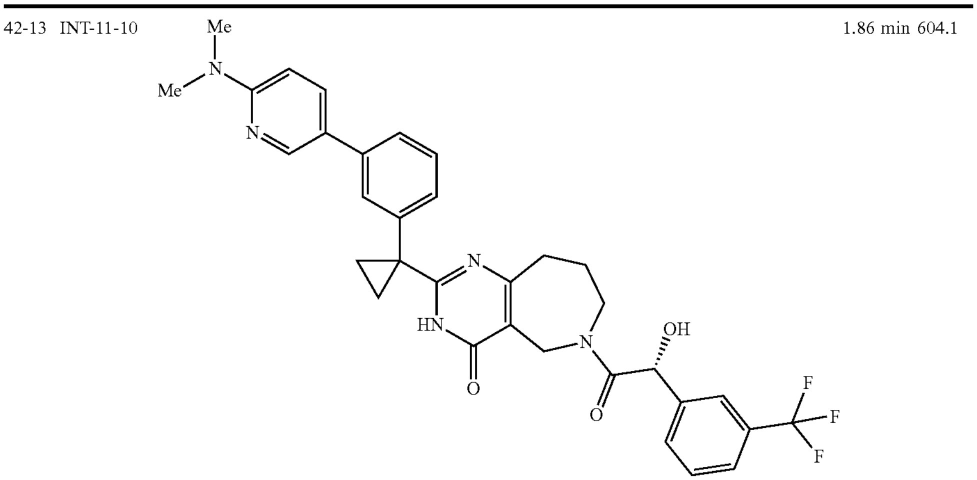 | 1.86 min 604.1 |
| 42-14 | INT-11-10 | 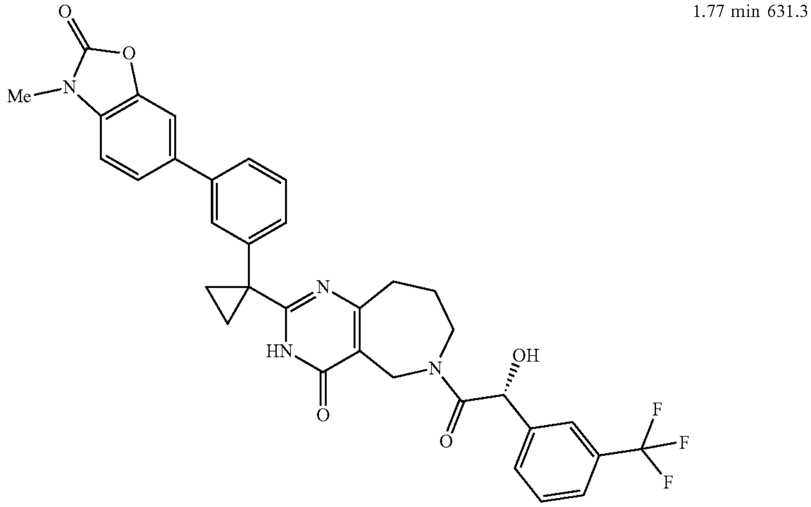 | 1.77 min 631.3 |
| 42-15 | INT-11-10 | 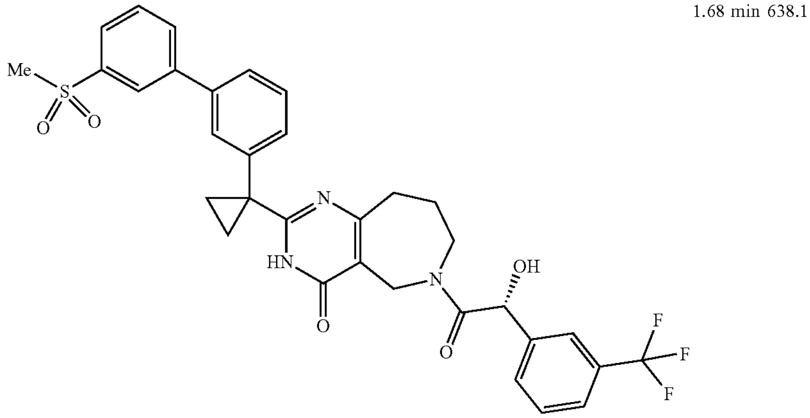 | 1.68 min 638.1 |

TABLE 73-4
| | | | |
|---|---|---|---|
| 42-16 | INT-11-10 | 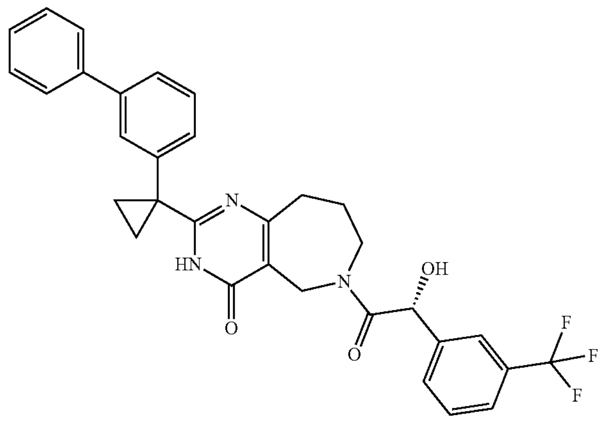 [SMILES: O=C([C@H](O)c1cccc(C(F)(F)F)c1)N1CCCc2nc(C3(c4cccc(-c5ccccc5)c4)CC3)[nH]c(=O)c2C1] | 1.96 min 560.2 |
| 42-17 | INT-11-10 | 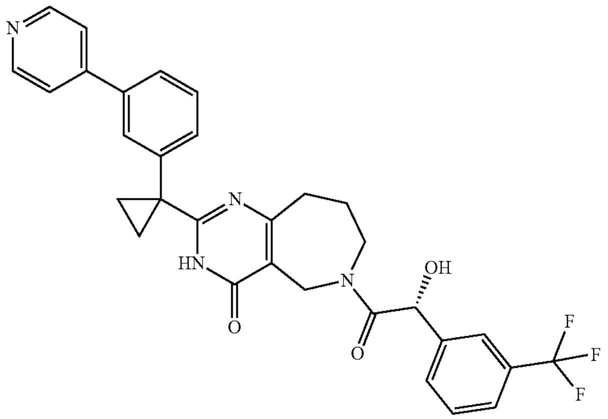 [SMILES: O=C([C@H](O)c1cccc(C(F)(F)F)c1)N1CCCc2nc(C3(c4cccc(-c5ccncc5)c4)CC3)[nH]c(=O)c2C1] | 1.58 min 561.1 |
| 42-18 | INT-11-10 | 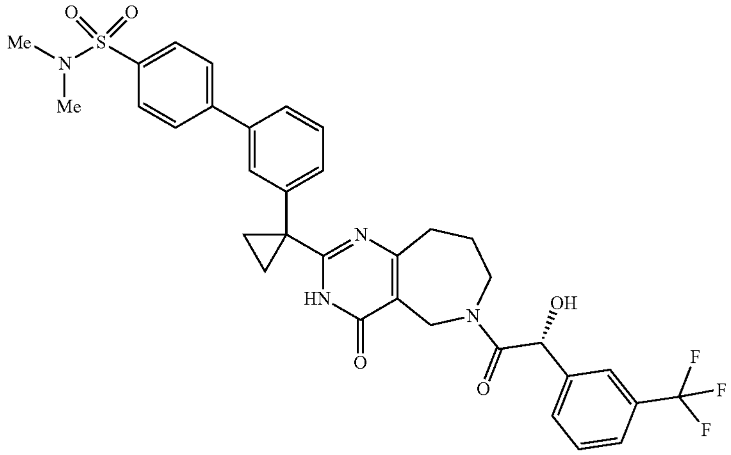 [SMILES: CN(C)S(=O)(=O)c1ccc(-c2cccc(C3(c4nc5c(c(=O)[nH]4)CN(C(=O)[C@H](O)c4cccc(C(F)(F)F)c4)CCC5)CC3)c2)cc1] | 1.81 min 667.2 |

TABLE 73-4-continued
| | | | |
|---|---|---|---|
| 42-19 | INT-11-10 | 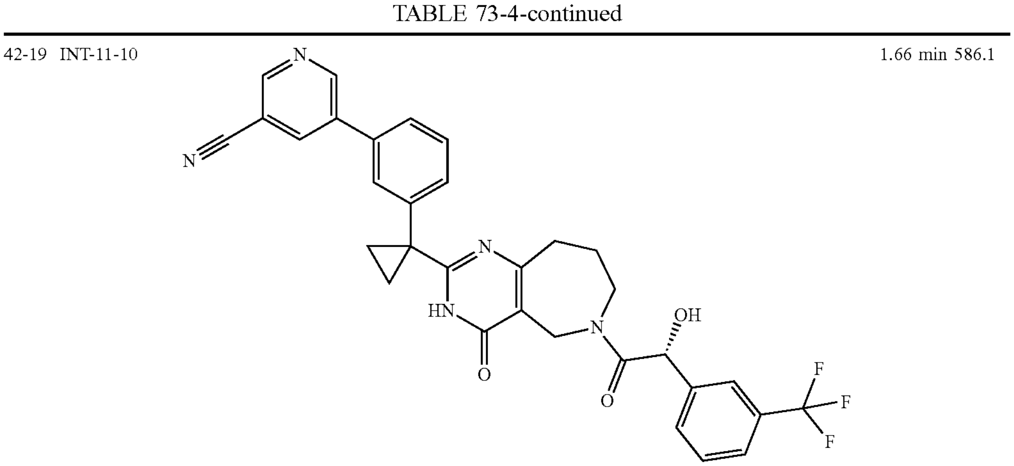 | 1.66 min 586.1 |
| 42-20 | INT-11-10 | 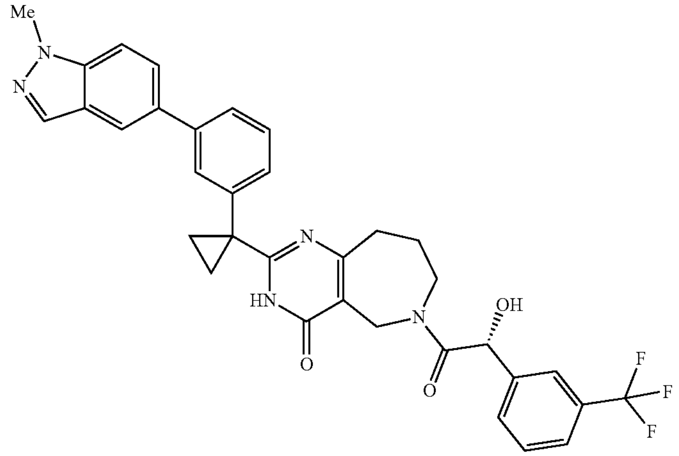 [SMILES: Cn1ncc2cc(-c3cccc(C4(c5nc6c(c(=O)[nH]5)CN(C(=O)[C@H](O)c5cccc(C(F)(F)F)c5)CCC6)CC4)c3)ccc21] | 1.81 min 614.1 |
TABLE 73-5
| | | | |
|---|---|---|---|
| 42-21 | INT-11-10 | 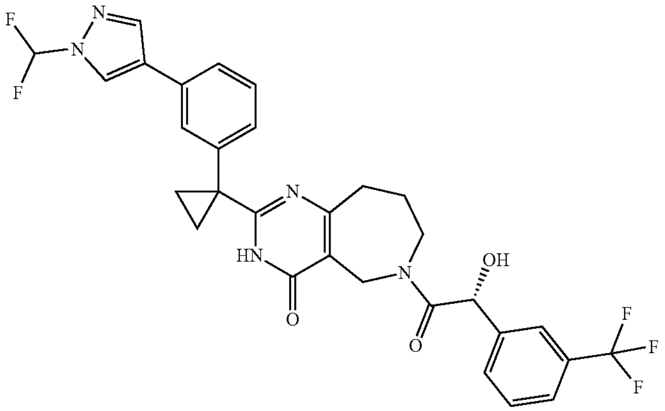 [SMILES: O=C([C@H](O)c1cccc(C(F)(F)F)c1)N1CCCc2nc(C3(c4cccc(-c5cnn(C(F)F)c5)c4)CC3)[nH]c(=O)c2C1] | 1.72 min 600.2 |

TABLE 73-5-continued
| | | | |
|---|---|---|---|
| 42-22 | INT-11-10 | 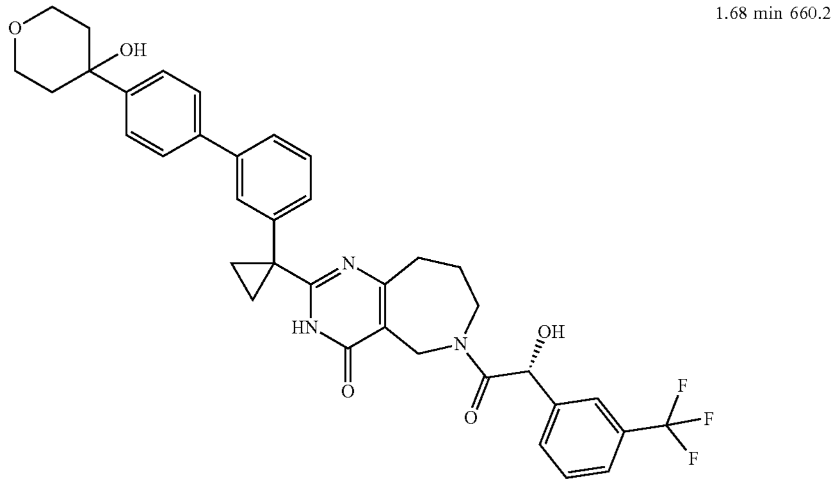 | 1.68 min 660.2 |
| 42-23 | INT-11-10 | 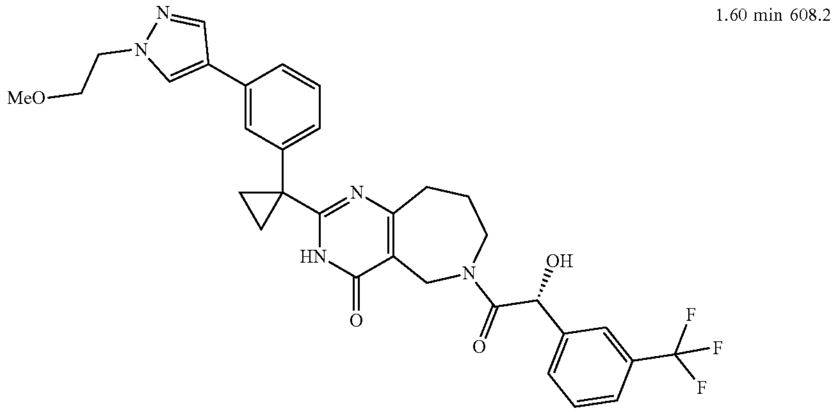 | 1.60 min 608.2 |
| 42-24 | INT-11-10 | 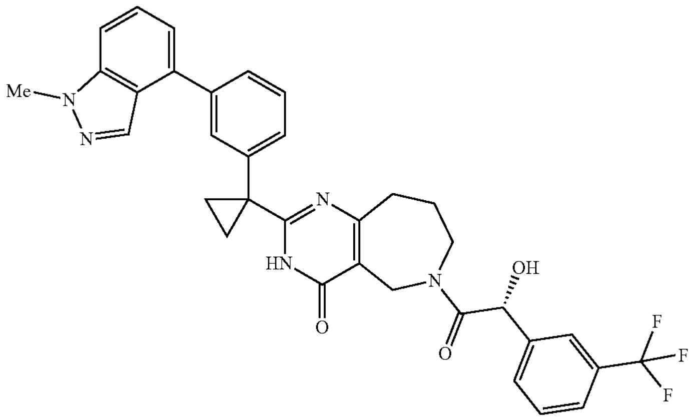 [SMILES: Cn1ncc2c(-c3cccc(C4(c5nc6c(c(=O)[nH]5)CN(C(=O)[C@H](O)c5cccc(C(F)(F)F)c5)CCC6)CC4)c3)cccc21] | 1.82 min 614.1 |

TABLE 73-5-continued
| | | | |
|---|---|---|---|
| 42-25 | INT-11-10 | 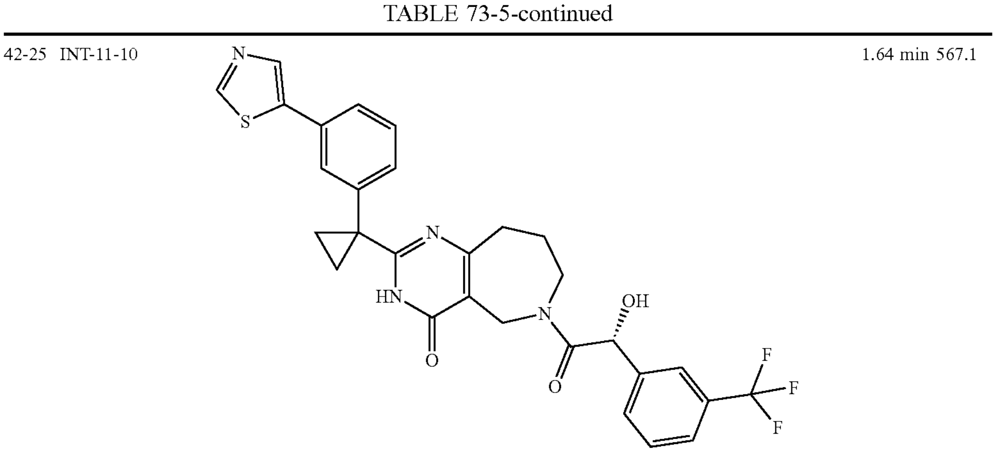 | 1.64 min 567.1 |
TABLE 73-6
| | | | |
|---|---|---|---|
| 42-26 | INT-11-10 | 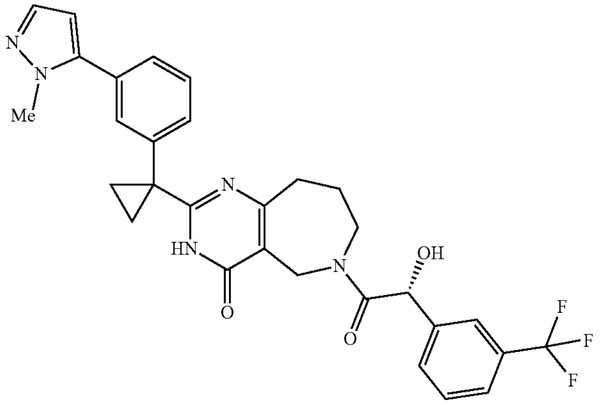 [SMILES: Cn1nccc1-c1cccc(C2(c3nc4c(c(=O)[nH]3)CN(C(=O)[C@H](O)c3cccc(C(F)(F)F)c3)CCC4)CC2)c1] | 1.58 min 564.1 |
| 42-27 | INT-11-10 | 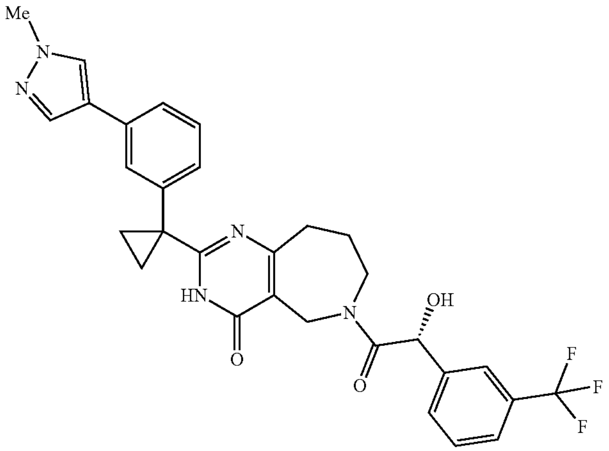 [SMILES: Cn1cc(-c2cccc(C3(c4nc5c(c(=O)[nH]4)CN(C(=O)[C@H](O)c4cccc(C(F)(F)F)c4)CCC5)CC3)c2)cn1] | 1.57 min 564.1 |

TABLE 73-6-continued
| | | | |
|---|---|---|---|
| 42-28 | INT-11-10 | 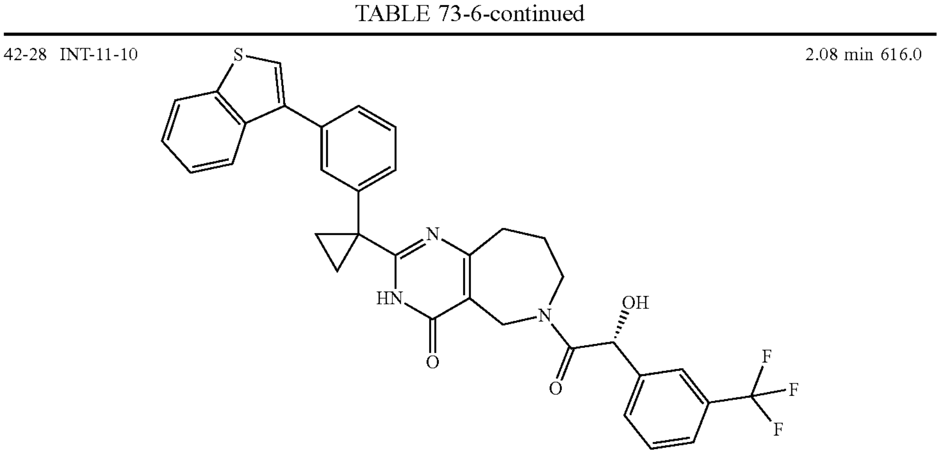 | 2.08 min 616.0 |
| 42-29 | INT-11-10 | 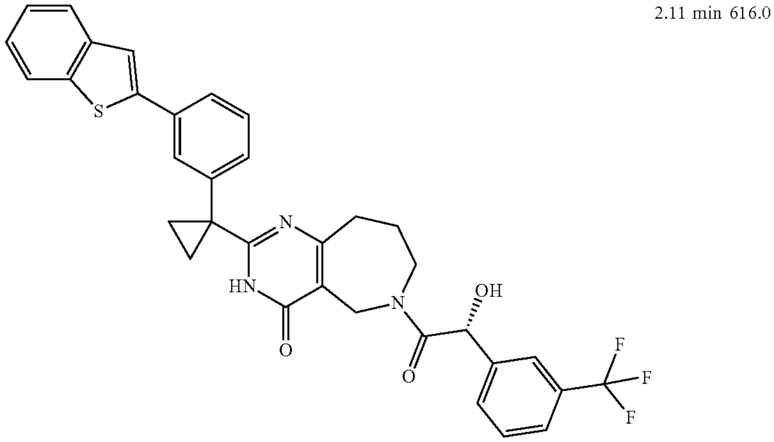 | 2.11 min 616.0 |
| 42-30 | INT-11-10 | 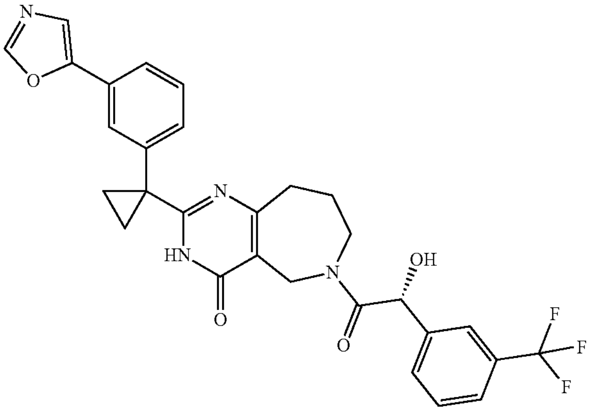 | 1.57 min 551.1 |

TABLE 73-7
| | | | |
|---|---|---|---|
| 42-31 | INT-11-10 | 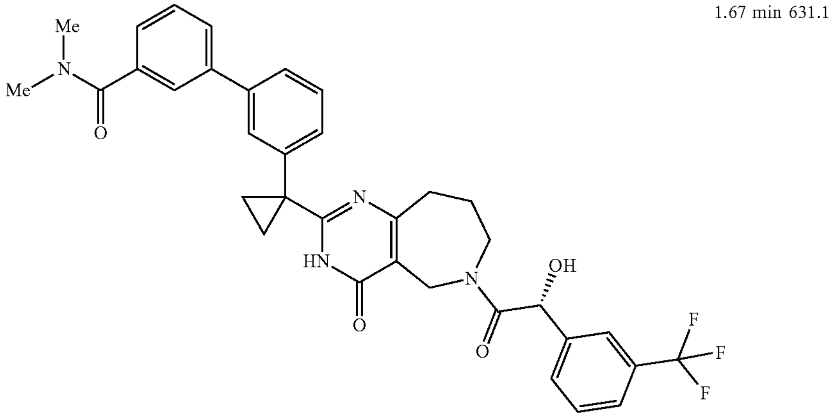 | 1.67 min 631.1 |
| 42-32 | INT-11-10 | 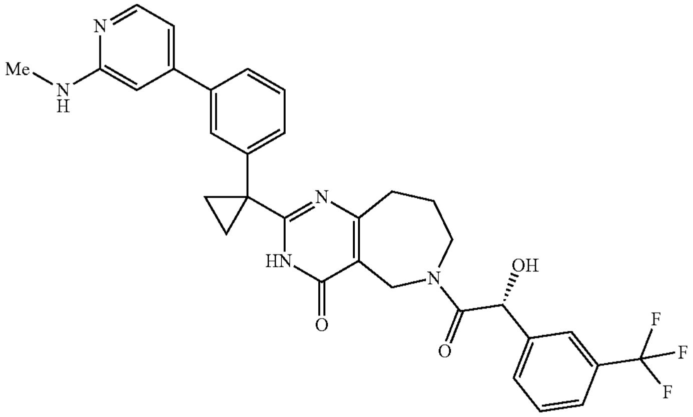 [SMILES: CNc1cc(-c2cccc(C3(c4nc5c(c(=O)[nH]4)CN(C(=O)[C@H](O)c4cccc(C(F)(F)F)c4)CCC5)CC3)c2)ccn1] | 1.62 min 590.3 |
| 42-33 | INT-11-10 | 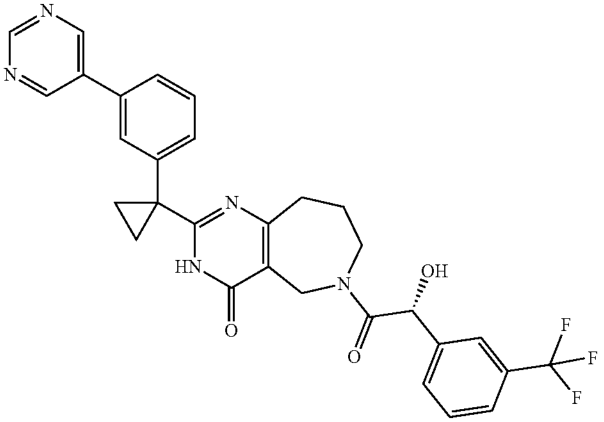 [SMILES: O=C([C@H](O)c1cccc(C(F)(F)F)c1)N1CCCc2nc(C3(c4cccc(-c5cncnc5)c4)CC3)[nH]c(=O)c2C1] | 1.49 min 562.1 |

TABLE 73-7-continued
| | | | |
|---|---|---|---|
| 42-34 | INT-11-10 | 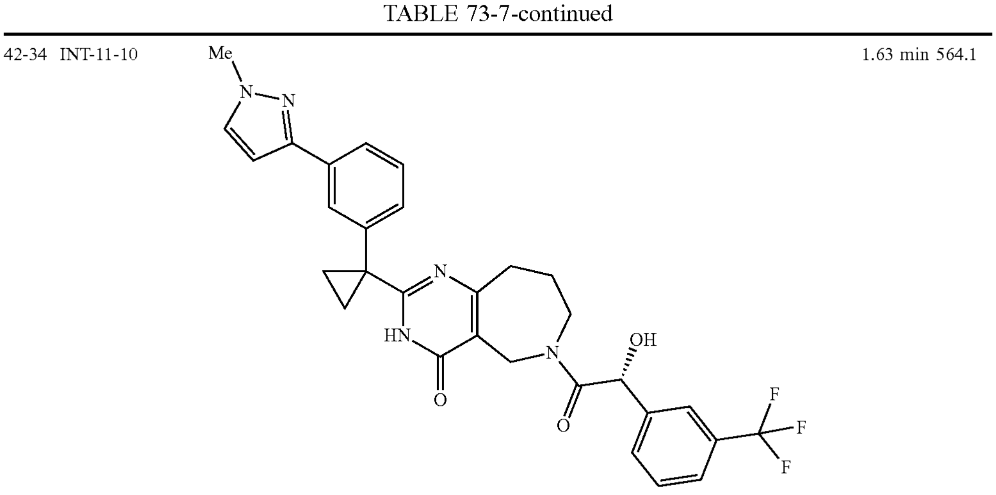 | 1.63 min 564.1 |
| 42-35 | INT-11-10 | 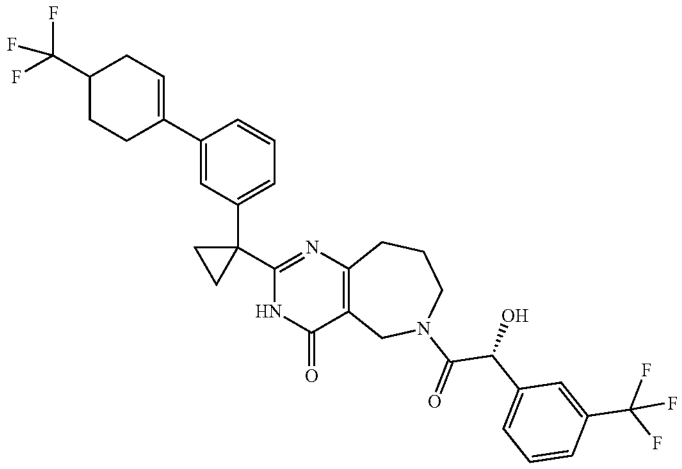 [SMILES: O=C([C@H](O)c1cccc(C(F)(F)F)c1)N1CCCc2nc(C3(c4cccc(C5=CCC(C(F)(F)F)CC5)c4)CC3)[nH]c(=O)c2C1] | 2.11 min 632.1 |
TABLE 73-8
| | | | |
|---|---|---|---|
| 42-36 | INT-11-10 | 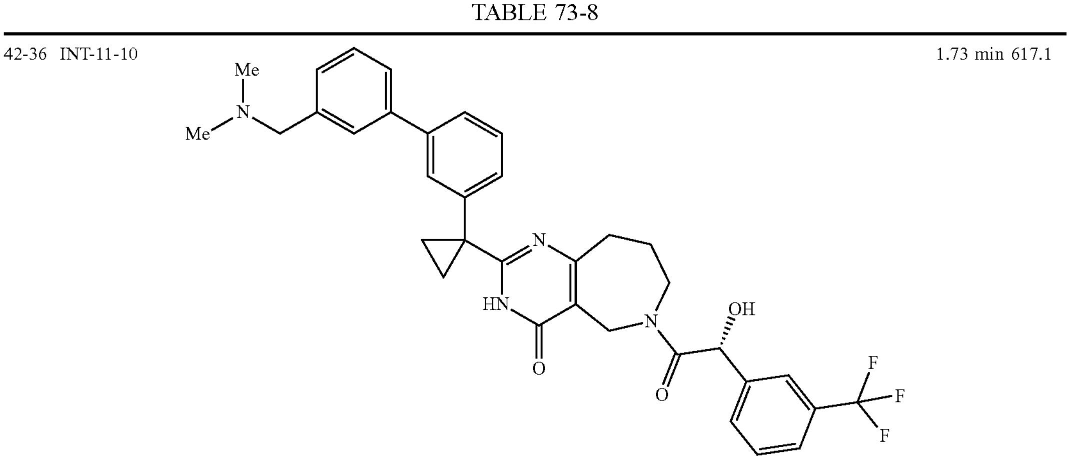 | 1.73 min 617.1 |

TABLE 73-8-continued
| | | | |
|---|---|---|---|
| 42-37 | INT-11-10 | 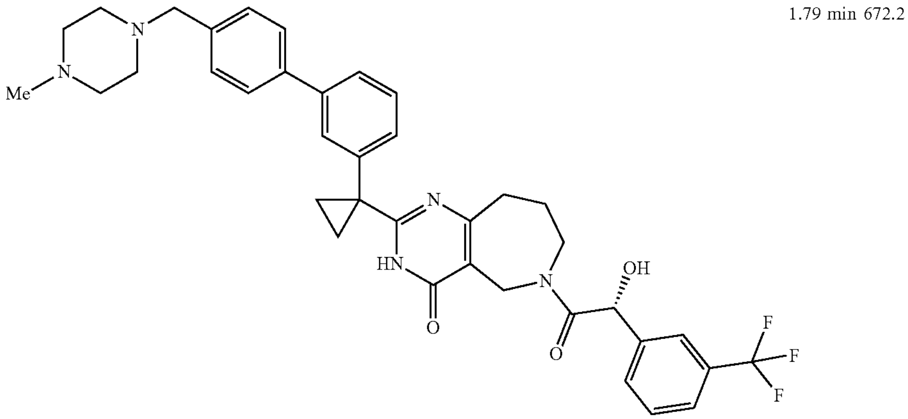 | 1.79 min 672.2 |
| 42-38 | INT-11-10 | 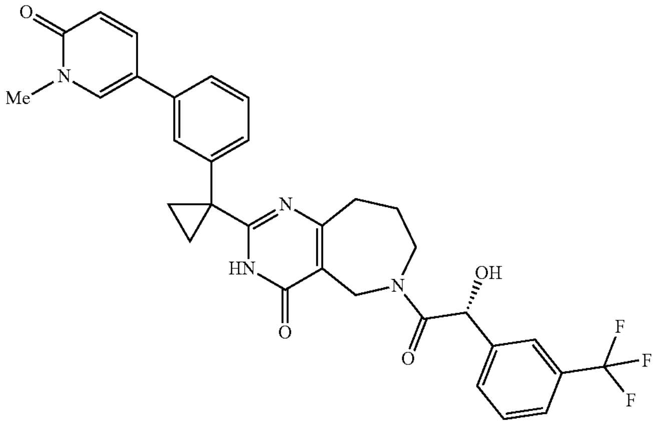 [SMILES: Cn1cc(-c2cccc(C3(c4nc5c(c(=O)[nH]4)CN(C(=O)[C@H](O)c4cccc(C(F)(F)F)c4)CCC5)CC3)c2)ccc1=O] | 1.45 min 591.1 |
| 42-39 | INT-11-10 | 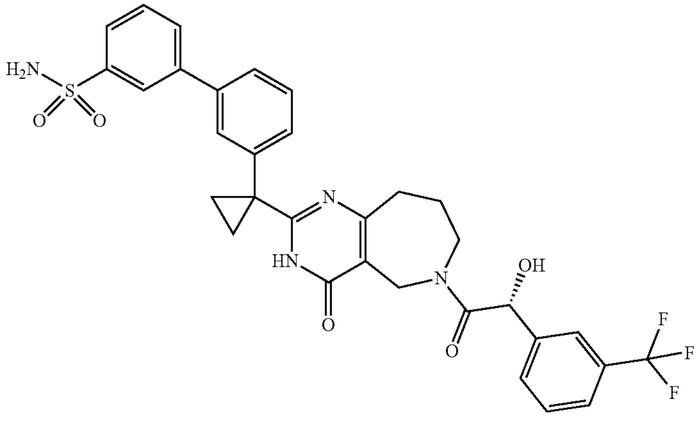 [SMILES: NS(=O)(=O)c1cccc(-c2cccc(C3(c4nc5c(c(=O)[nH]4)CN(C(=O)[C@H](O)c4cccc(C(F)(F)F)c4)CCC5)CC3)c2)c1] | 1.57 min 639.2 |

TABLE 73-8-continued
| | | | |
|---|---|---|---|
| 42-40 | INT-11-10 | 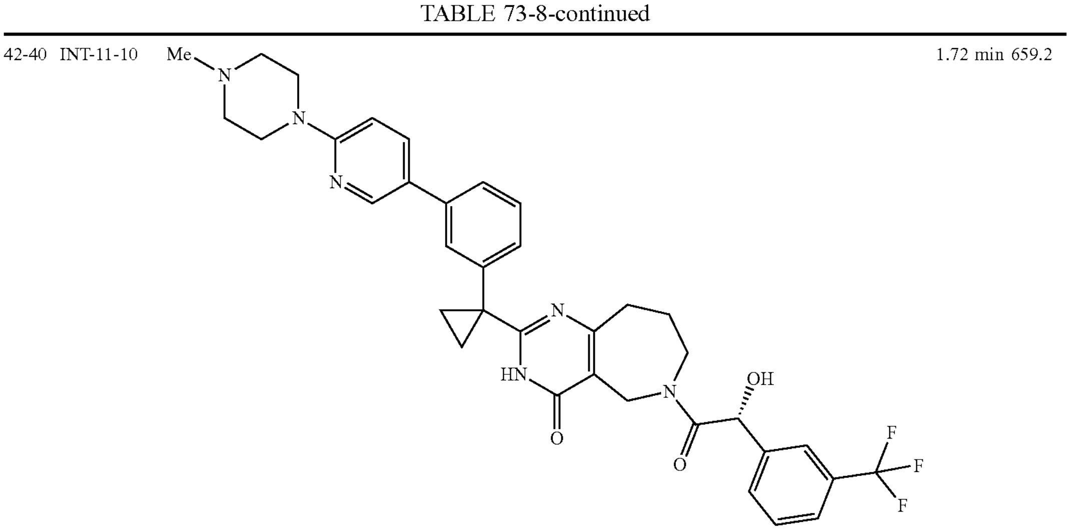 | 1.72 min 659.2 |
TABLE 73-9
| | | | |
|---|---|---|---|
| 42-41 | INT-11-10 | 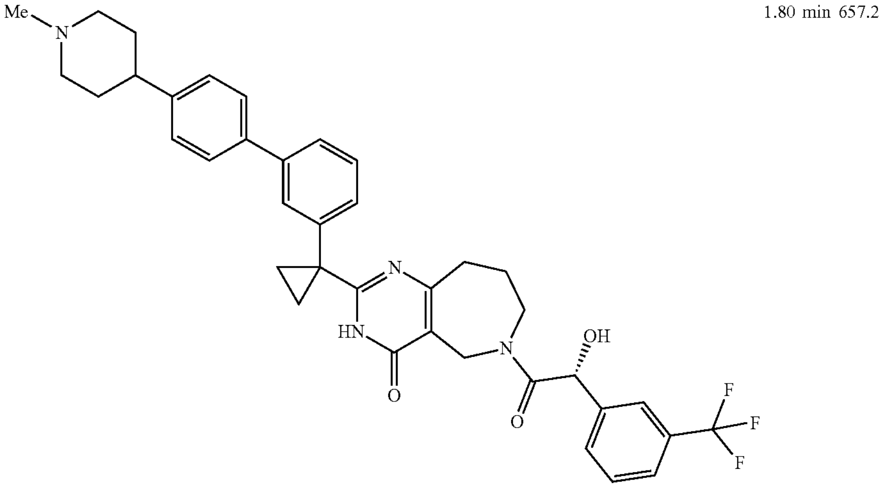 | 1.80 min 657.2 |
| 42-42 | INT-11-10 | 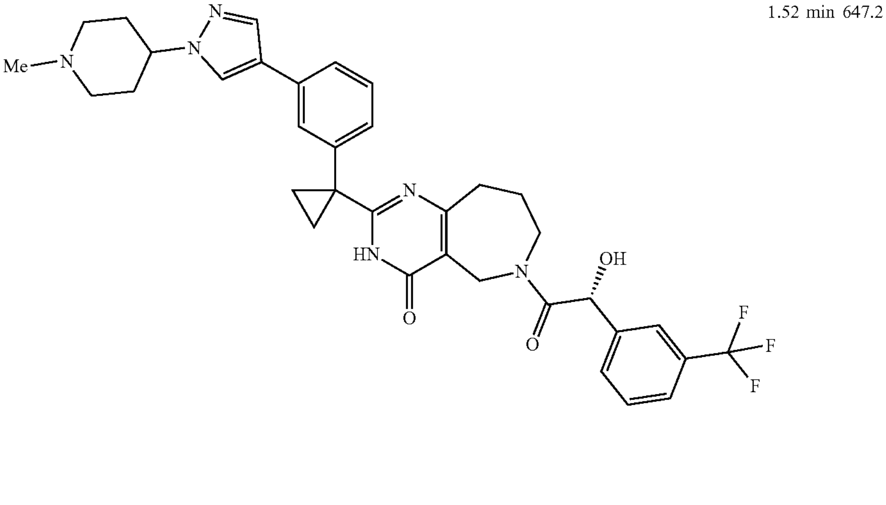 | 1.52 min 647.2 |

TABLE 73-9-continued
| | | | | |
|---|---|---|---|---|
| 42-43 | INT-11-10 | 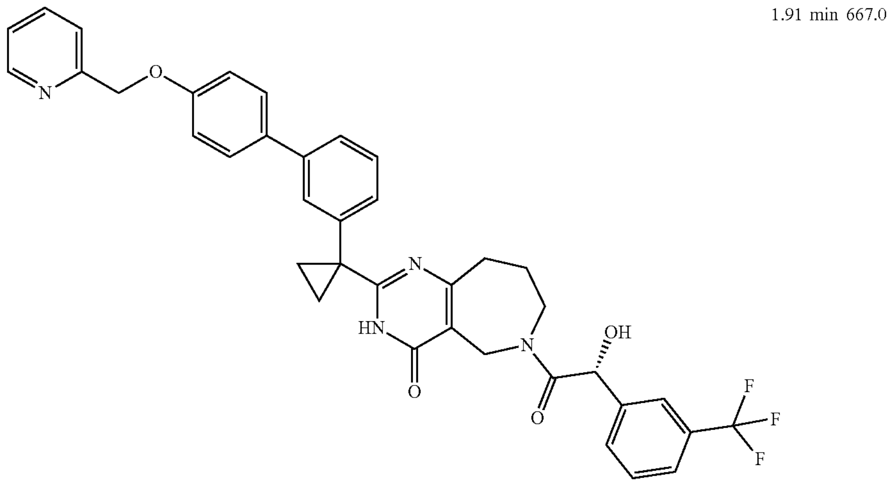 | 1.91 min | 667.0 |
| 42-44 | INT-11-10 | 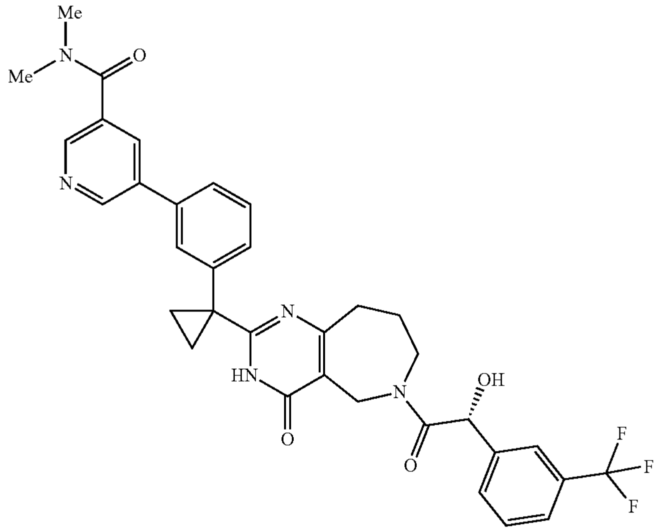 [SMILES: CN(C)C(=O)c1cncc(-c2cccc(C3(c4nc5c(c(=O)[nH]4)CN(C(=O)[C@H](O)c4cccc(C(F)(F)F)c4)CCC5)CC3)c2)c1] | 1.45 min | 632.0 |
| 42-45 | INT-11-10 | 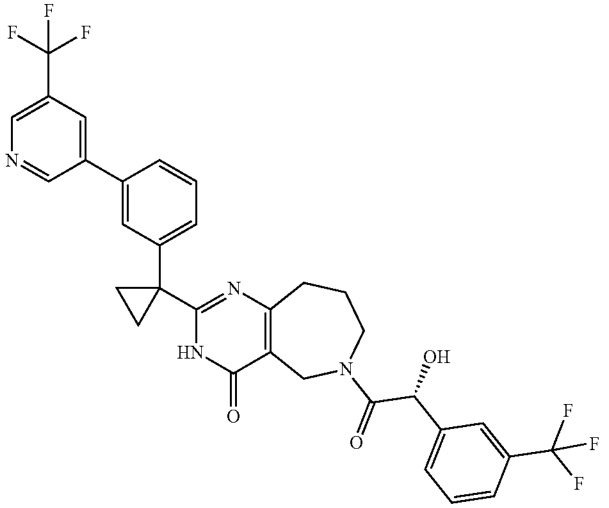 [SMILES: O=C([C@H](O)c1cccc(C(F)(F)F)c1)N1CCCc2nc(C3(c4cccc(-c5cncc(C(F)(F)F)c5)c4)CC3)[nH]c(=O)c2C1] | 1.86 min | 629.0 |

TABLE 73-10
| | | | |
|---|---|---|---|
| 42-46 | INT-11-10 | 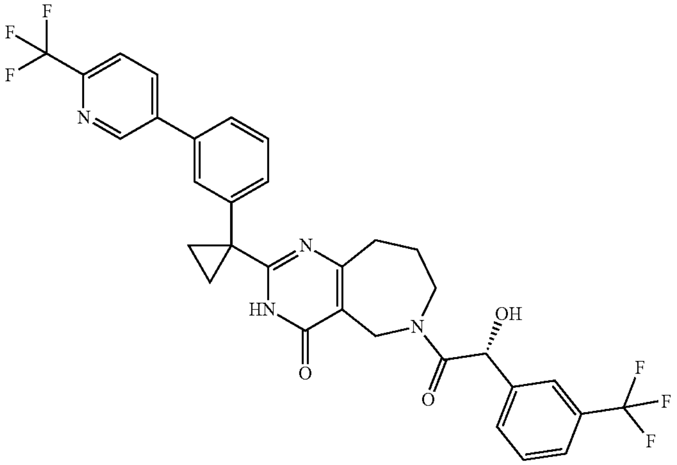 [SMILES: O=C([C@H](O)c1cccc(C(F)(F)F)c1)N1CCCc2nc(C3(c4cccc(-c5ccc(C(F)(F)F)nc5)c4)CC3)[nH]c(=O)c2C1] | 1.89 min 629.0 |
| 42-47 | INT-11-10 | 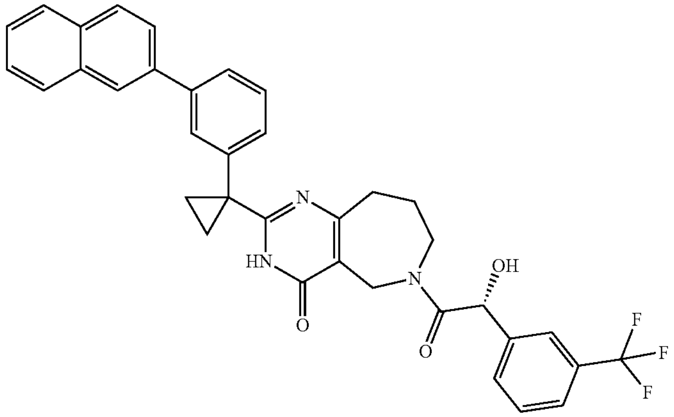 [SMILES: O=C([C@H](O)c1cccc(C(F)(F)F)c1)N1CCCc2nc(C3(c4cccc(-c5ccc6ccccc6c5)c4)CC3)[nH]c(=O)c2C1] | 2.14 min 610.1 |
| 42-48 | INT-11-10 | 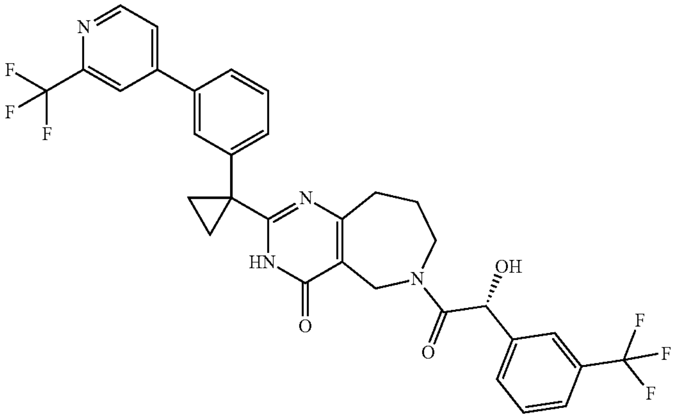 [SMILES: O=C([C@H](O)c1cccc(C(F)(F)F)c1)N1CCCc2nc(C3(c4cccc(-c5ccnc(C(F)(F)F)c5)c4)CC3)[nH]c(=O)c2C1] | 1.87 min 629.0 |

TABLE 73-10-continued
| | | | |
|---|---|---|---|
| 42-49 | INT-11-10 | 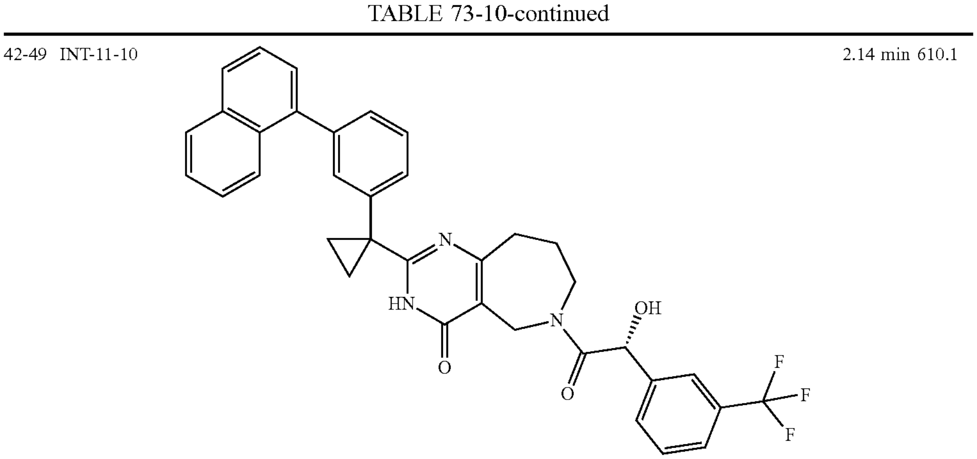 | 2.14 min 610.1 |
| 42-50 | INT-11-10 | 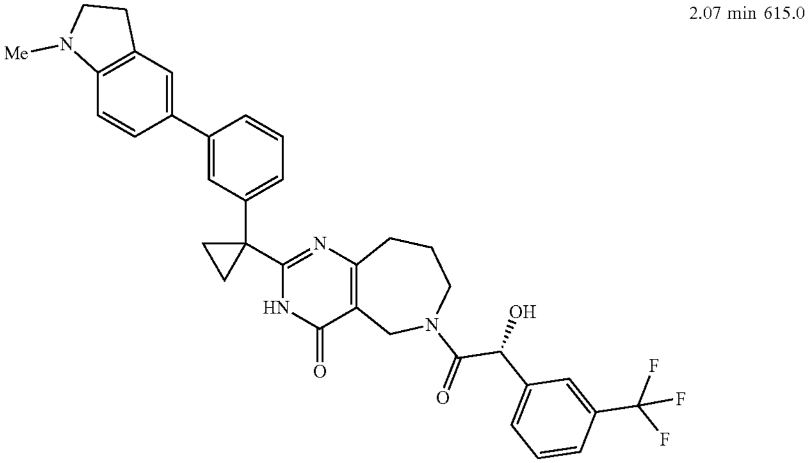 | 2.07 min 615.0 |
TABLE 73-11
| | | | |
|---|---|---|---|
| 42-51 | INT-11-10 | 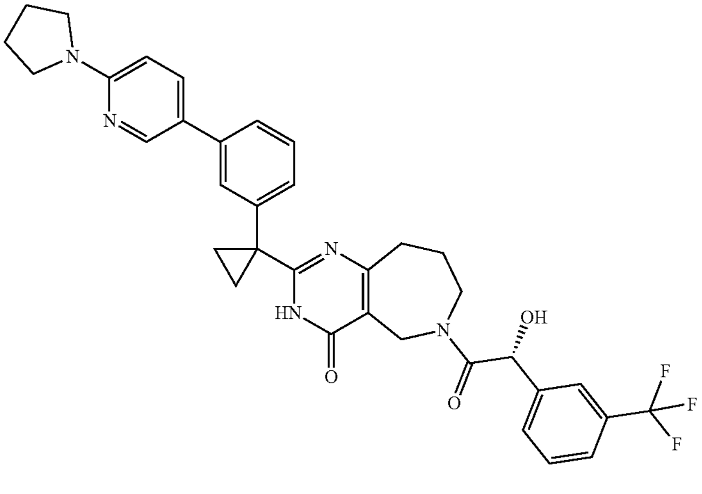 [SMILES: O=C([C@H](O)c1cccc(C(F)(F)F)c1)N1CCCc2nc(C3(c4cccc(-c5ccc(N6CCCC6)nc5)c4)CC3)[nH]c(=O)c2C1] | 1.94 min 630.1 |

TABLE 73-11-continued
| | | | |
|---|---|---|---|
| 42-52 | INT-11-10 | 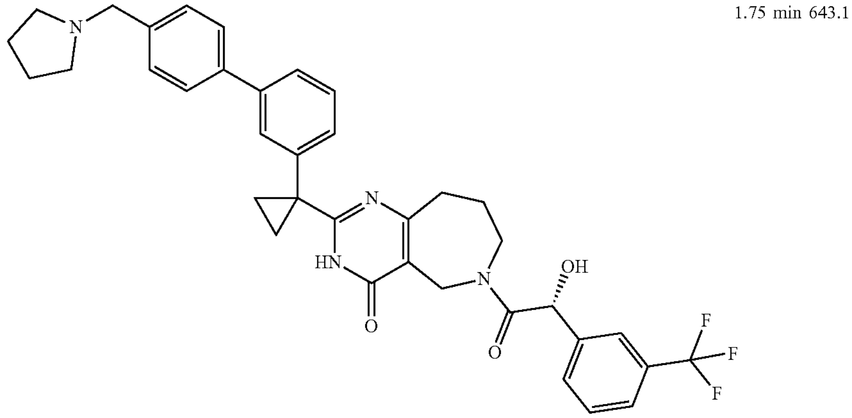 | 1.75 min 643.1 |
| 42-53 | INT-11-10 | 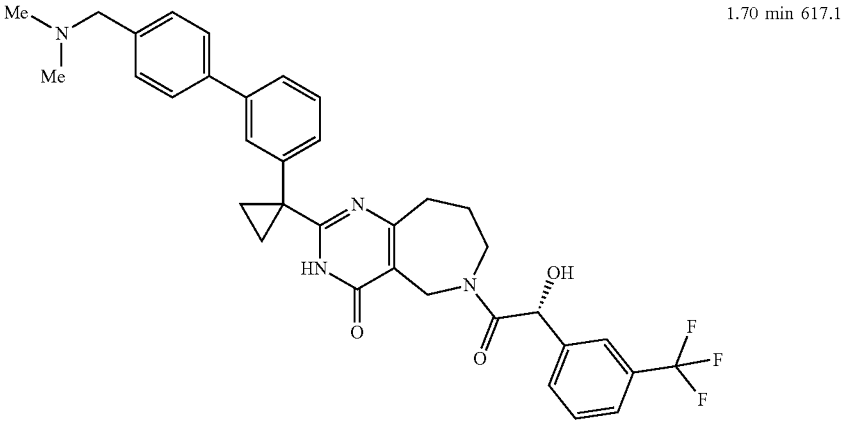 | 1.70 min 617.1 |
| 42-54 | INT-11-10 | 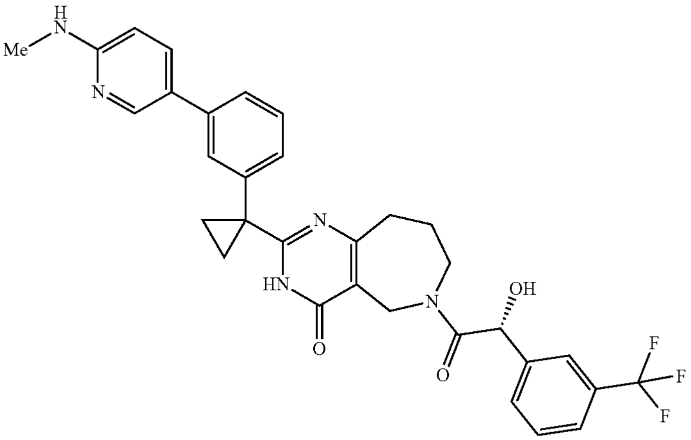 [SMILES: CNc1ccc(-c2cccc(C3(c4nc5c(c(=O)[nH]4)CN(C(=O)[C@H](O)c4cccc(C(F)(F)F)c4)CCC5)CC3)c2)cn1] | 1.64 min 590.1 |

TABLE 73-11-continued
| | | | |
|---|---|---|---|
| 42-55 | INT-11-10 | 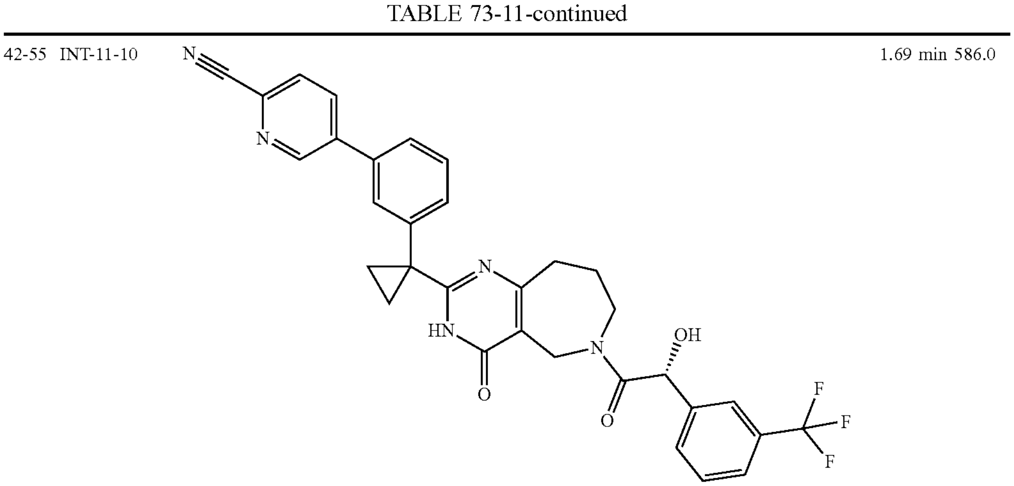 | 1.69 min 586.0 |
TABLE 73-12
| | | | |
|---|---|---|---|
| 42-56 | INT-11-10 | 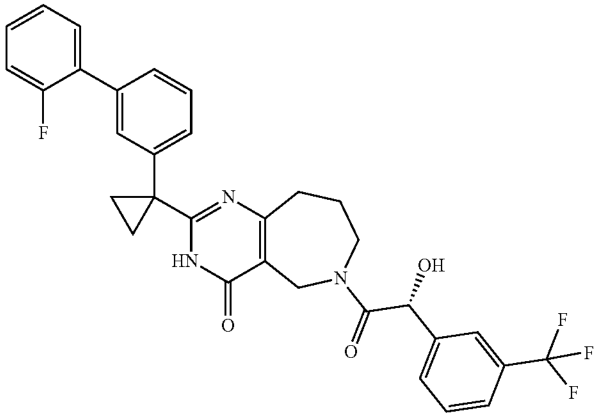 [SMILES: O=C([C@H](O)c1cccc(C(F)(F)F)c1)N1CCCc2nc(C3(c4cccc(-c5ccccc5F)c4)CC3)[nH]c(=O)c2C1] | 3.76 min 576.2 |
| 42-57 | INT-11-10 | 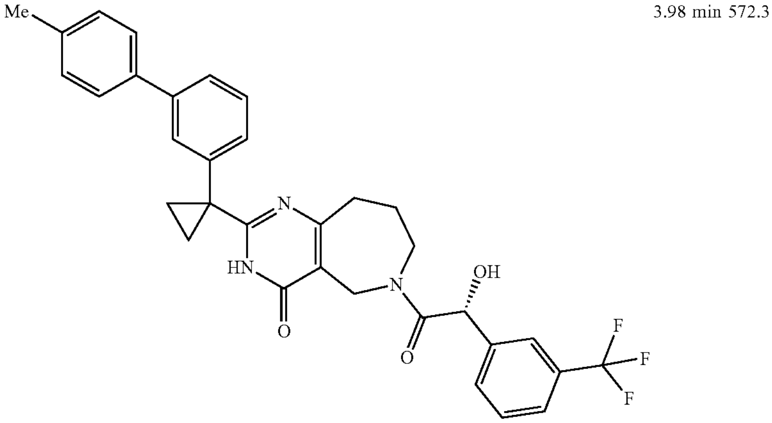 | 3.98 min 572.3 |

TABLE 73-12-continued
| | | | |
|---|---|---|---|
| 42-58 | INT-11-10 | 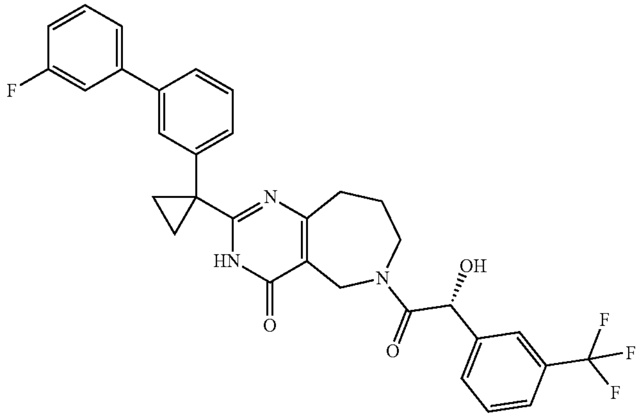 [SMILES: O=C([C@H](O)c1cccc(C(F)(F)F)c1)N1CCCc2nc(C3(c4cccc(-c5cccc(F)c5)c4)CC3)[nH]c(=O)c2C1] | 3.79 min 576.2 |
| 42-59 | INT-11-10 | 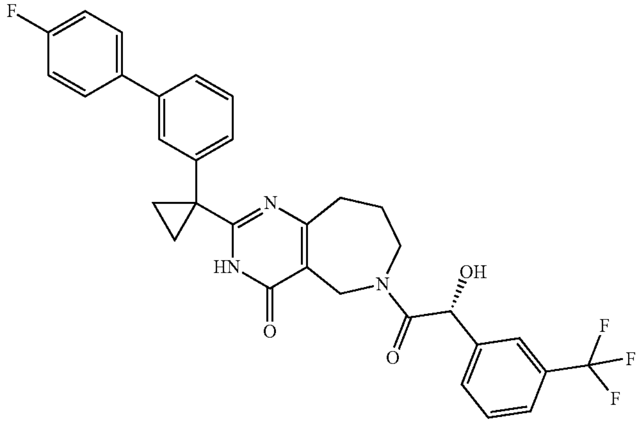 [SMILES: O=C([C@H](O)c1cccc(C(F)(F)F)c1)N1CCCc2nc(C3(c4cccc(-c5ccc(F)cc5)c4)CC3)[nH]c(=O)c2C1] | 3.78 min 576.2 |
| 42-60 | INT-11-10 | 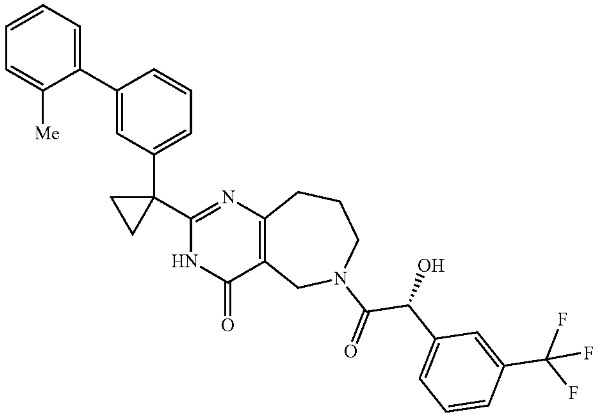 [SMILES: Cc1ccccc1-c1cccc(C2(c3nc4c(c(=O)[nH]3)CN(C(=O)[C@H](O)c3cccc(C(F)(F)F)c3)CCC4)CC2)c1] | 3.94 min 572.2 |

TABLE 73-13
| | | | |
|---|---|---|---|
| 42-61 | INT-11-10 | 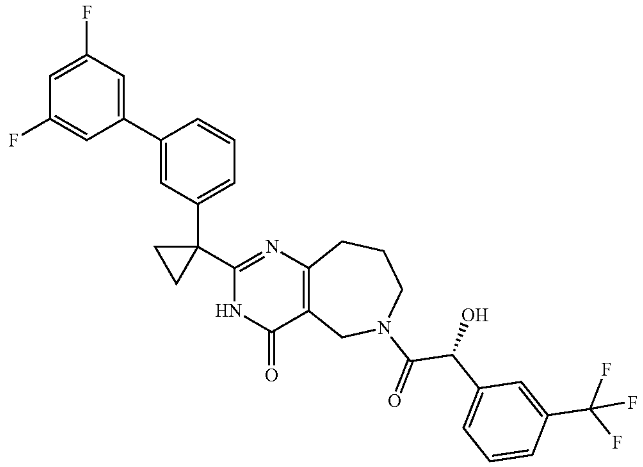 [SMILES: O=C([C@H](O)c1cccc(C(F)(F)F)c1)N1CCCc2nc(C3(c4cccc(-c5cc(F)cc(F)c5)c4)CC3)[nH]c(=O)c2C1] | 3.89 min 594.2 |
| 42-62 | INT-11-10 | 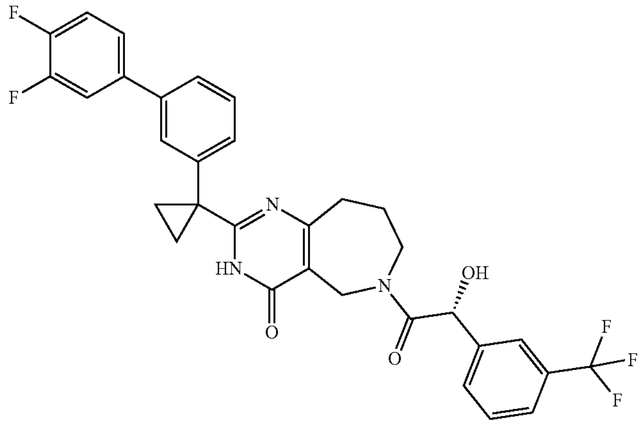 [SMILES: O=C([C@H](O)c1cccc(C(F)(F)F)c1)N1CCCc2nc(C3(c4cccc(-c5ccc(F)c(F)c5)c4)CC3)[nH]c(=O)c2C1] | 3.84 min 594.2 |
| 42-63 | INT-11-10 | 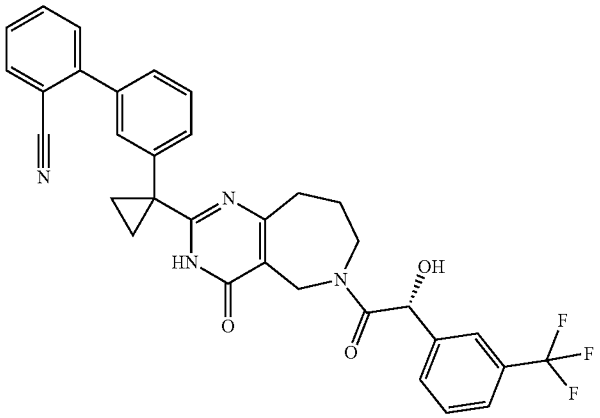 [SMILES: N#Cc1ccccc1-c1cccc(C2(c3nc4c(c(=O)[nH]3)CN(C(=O)[C@H](O)c3cccc(C(F)(F)F)c3)CCC4)CC2)c1] | 3.46 min 583.2 |

TABLE 73-13-continued
| | | | |
|---|---|---|---|
| 42-64 | INT-11-10 | 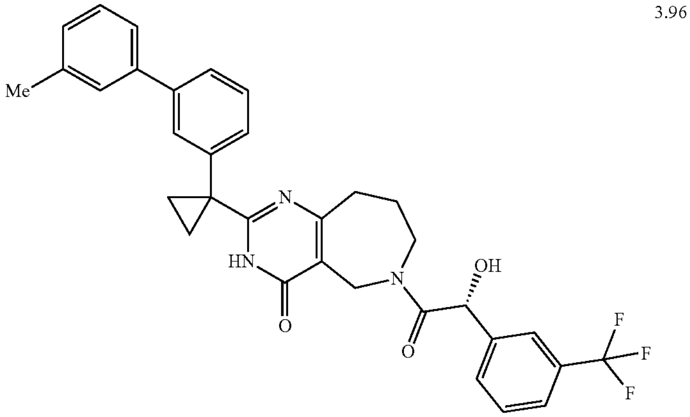 | 3.96 min 572.2 |
TABLE 73-14
| | | | |
|---|---|---|---|
| 42-65 | INT-11-10 | 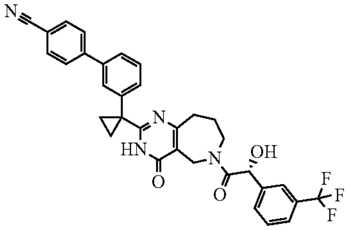 [SMILES: N#Cc1ccc(-c2cccc(C3(c4nc5c(c(=O)[nH]4)CN(C(=O)[C@H](O)c4cccc(C(F)(F)F)c4)CCC5)CC3)c2)cc1] | 3.56 min 583.2 |
| 42-66 | INT-11-10 | 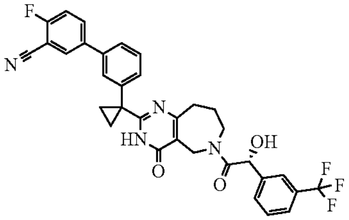 [SMILES: N#Cc1cc(-c2cccc(C3(c4nc5c(c(=O)[nH]4)CN(C(=O)[C@H](O)c4cccc(C(F)(F)F)c4)CCC5)CC3)c2)ccc1F] | 2.04 min 603.5 |
| 42-67 | INT-11-10 | 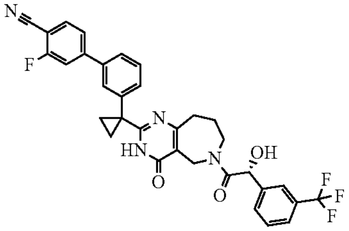 [SMILES: N#Cc1ccc(-c2cccc(C3(c4nc5c(c(=O)[nH]4)CN(C(=O)[C@H](O)c4cccc(C(F)(F)F)c4)CCC5)CC3)c2)cc1F] | 2.03 min 603.5 |
| 42-68 | 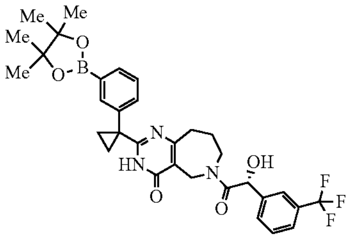 [SMILES: CC1(C)OB(c2cccc(C3(c4nc5c(c(=O)[nH]4)CN(C(=O)[C@H](O)c4cccc(C(F)(F)F)c4)CCC5)CC3)c2)OC1(C)C] INT-11-38 | 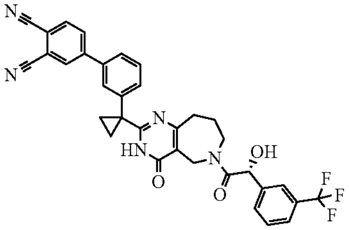 [SMILES: N#Cc1ccc(-c2cccc(C3(c4nc5c(c(=O)[nH]4)CN(C(=O)[C@H](O)c4cccc(C(F)(F)F)c4)CCC5)CC3)c2)cc1C#N] | 1.97 min 610.5 |

TABLE 73-15
| | | | | |
|---|---|---|---|---|
| 42-69 | INT-11-10 | 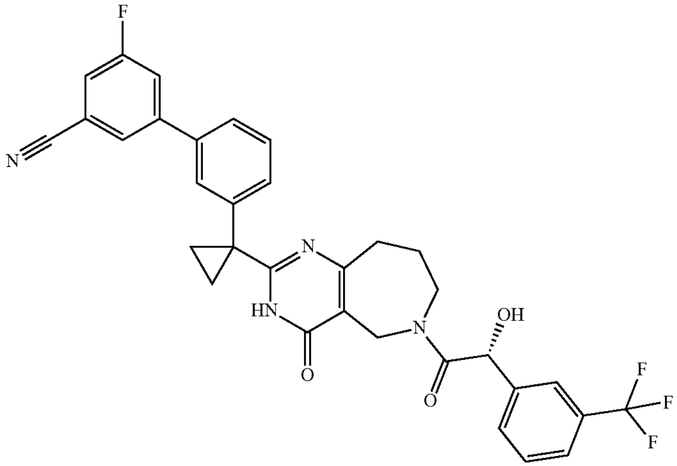 [SMILES: N#Cc1cc(F)cc(-c2cccc(C3(c4nc5c(c(=O)[nH]4)CN(C(=O)[C@H](O)c4cccc(C(F)(F)F)c4)CCC5)CC3)c2)c1] | 2.05 min | 603.5 |
| 42-70 | INT-11-10 | 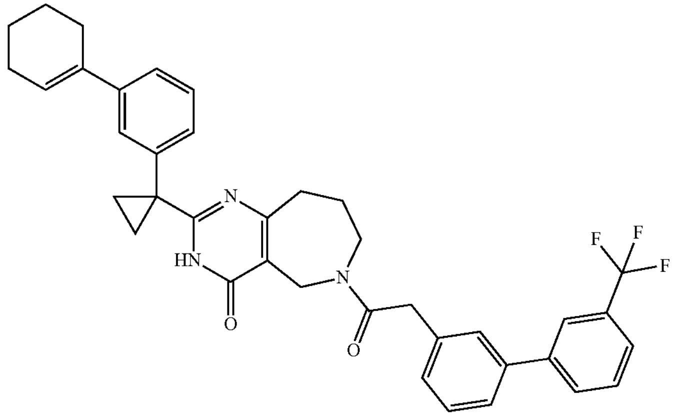 [SMILES: O=C(Cc1cccc(-c2cccc(C(F)(F)F)c2)c1)N1CCCc2nc(C3(c4cccc(C5=CCCCC5)c4)CC3)[nH]c(=O)c2C1] | 2.50 min | 624.5 |

TABLE 73-15-continued
| | | | | |
|---|---|---|---|---|
| 42-71 | 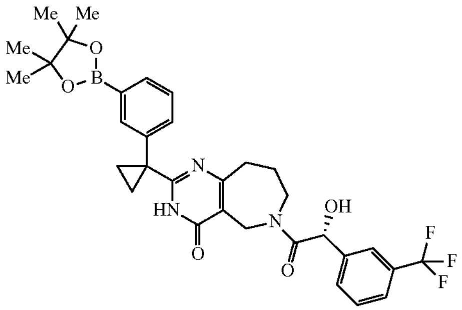 [SMILES: CC1(C)OB(c2cccc(C3(c4nc5c(c(=O)[nH]4)CN(C(=O)[C@H](O)c4cccc(C(F)(F)F)c4)CCC5)CC3)c2)OC1(C)C]<br>INT-11-38 | 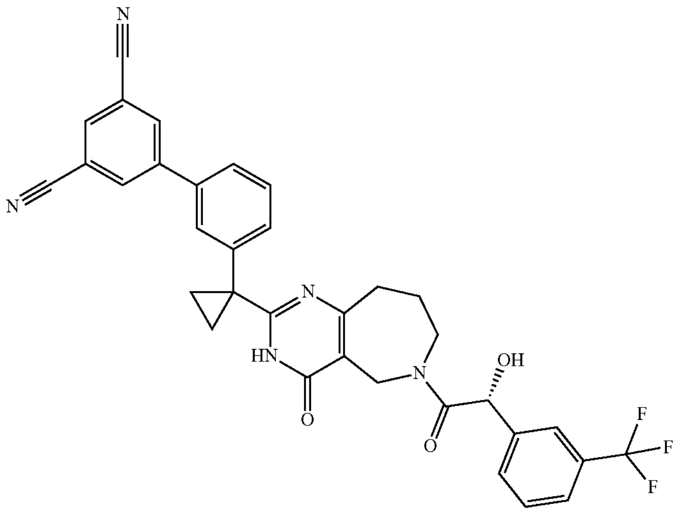 [SMILES: N#Cc1cc(C#N)cc(-c2cccc(C3(c4nc5c(c(=O)[nH]4)CN(C(=O)[C@H](O)c4cccc(C(F)(F)F)c4)CCC5)CC3)c2)c1] | 1.97 min | 610.5 |

The following pyrimidin-4(3H)-one derivatives (Ex-42-72 to Ex-42-84) are prepared according to the procedure of Ex-33-1 or the general synthesis in scheme-6 from INT-11-10 and the known or synthesized boronic acid derivatives. The further purification is carried out by preparative LC-MS or SFC-MS system in usual manner. The retention time and observed MS by HPLC-QC method are summarized in Tables 74-1 to 74-3.

TABLE 74-1

| Ex. | Inter-mediate (INT) | Rea-gent | Structure | Reten-tion time | Ob-served MS |
|---|---|---|---|---|---|
| 42-72 | INT-11-10 | INT-28-7 | 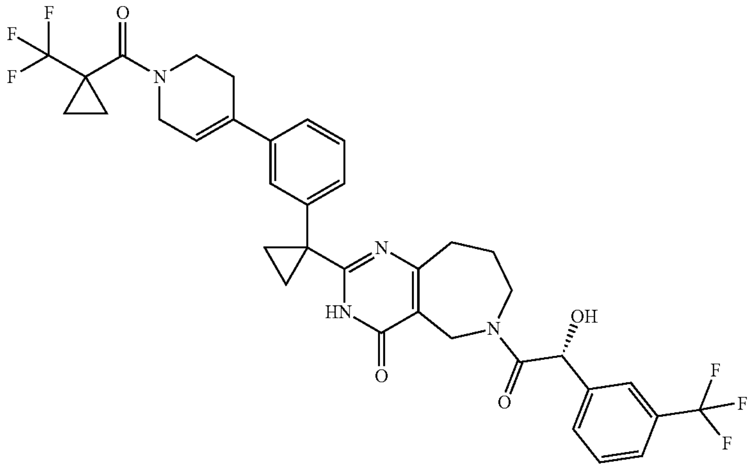 [SMILES: O=C([C@H](O)c1cccc(C(F)(F)F)c1)N1CCCc2nc(C3(c4cccc(C5=CCN(C(=O)C6(C(F)(F)F)CC6)CC5)c4)CC3)[nH]c(=O)c2C1] | 1.81 min | 701.0 |
| 42-73 | INT-11-10 | INT-29-1 | 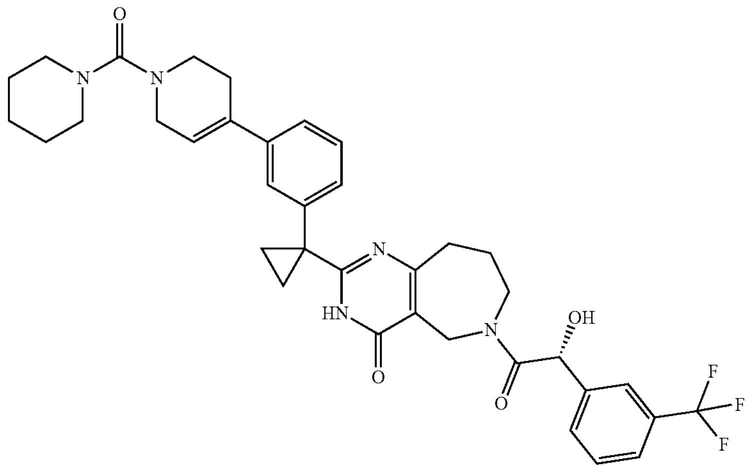 [SMILES: O=C([C@H](O)c1cccc(C(F)(F)F)c1)N1CCCc2nc(C3(c4cccc(C5=CCN(C(=O)N6CCCCC6)CC5)c4)CC3)[nH]c(=O)c2C1] | 1.91 min | 676.1 |
| 42-74 | INT-11-10 | INT-28-2 | 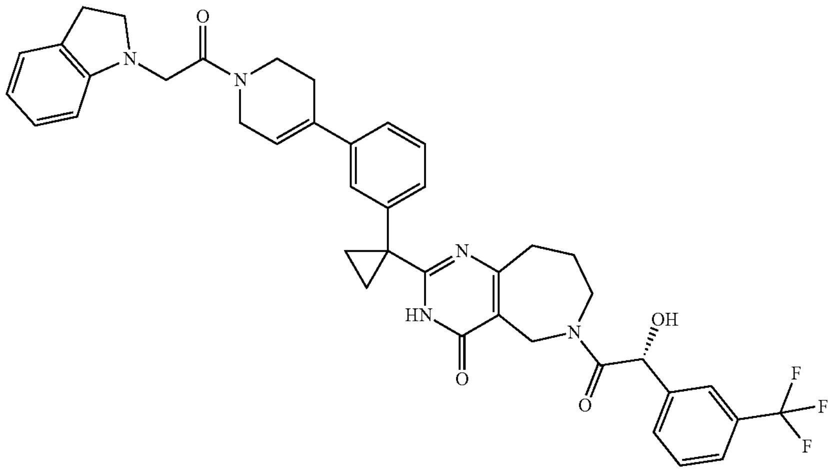 [SMILES: O=C(CN1CCc2ccccc21)N1CC=C(c2cccc(C3(c4nc5c(c(=O)[nH]4)CN(C(=O)[C@H](O)c4cccc(C(F)(F)F)c4)CCC5)CC3)c2)CC1] | 1.93 min | 724.1 |

TABLE 74-1-continued
| Ex. | Inter-mediate (INT) | Rea-gent | Structure | Reten-tion time | Ob-served MS |
|---|---|---|---|---|---|
| 42-75 | INT-11-10 | INT-31-1 | 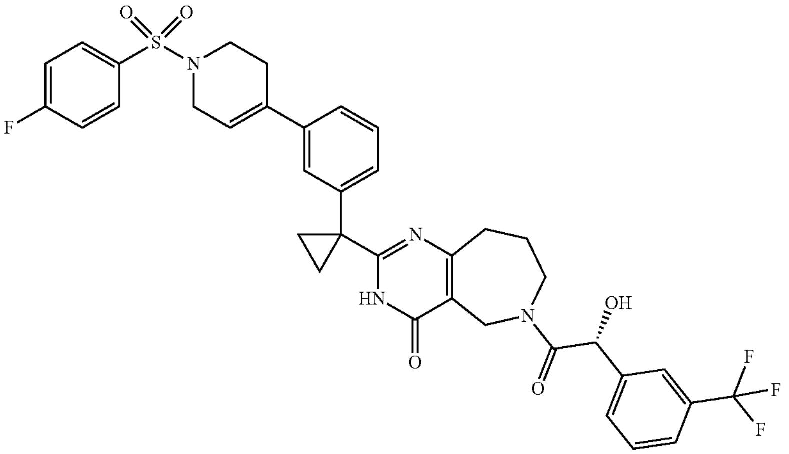 [SMILES: O=C([C@H](O)c1cccc(C(F)(F)F)c1)N1CCCc2nc(C3(c4cccc(C5=CCN(S(=O)(=O)c6ccc(F)cc6)CC5)c4)CC3)[nH]c(=O)c2C1] | 1.94 min | 723.0 |
| 42-76 | INT-11-10 | INT-31-2 | 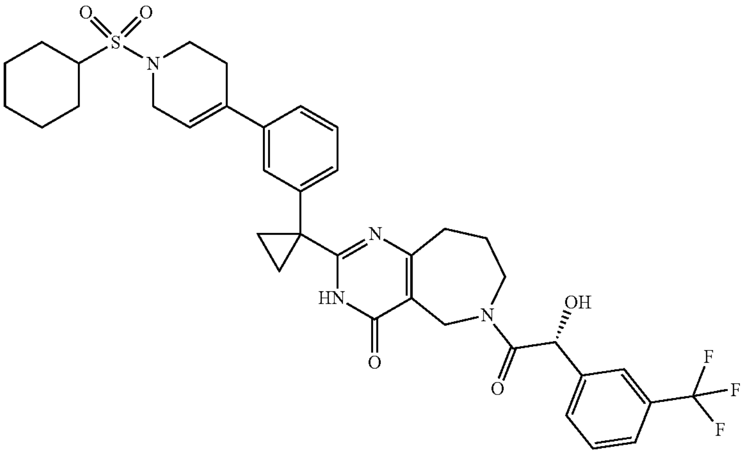 [SMILES: O=C([C@H](O)c1cccc(C(F)(F)F)c1)N1CCCc2nc(C3(c4cccc(C5=CCN(S(=O)(=O)C6CCCCC6)CC5)c4)CC3)[nH]c(=O)c2C1] | 2.00 min | 711.1 |
TABLE 74-2
| | | | | | |
|---|---|---|---|---|---|
| 42-77 | INT-11-10 | INT-28-3 | 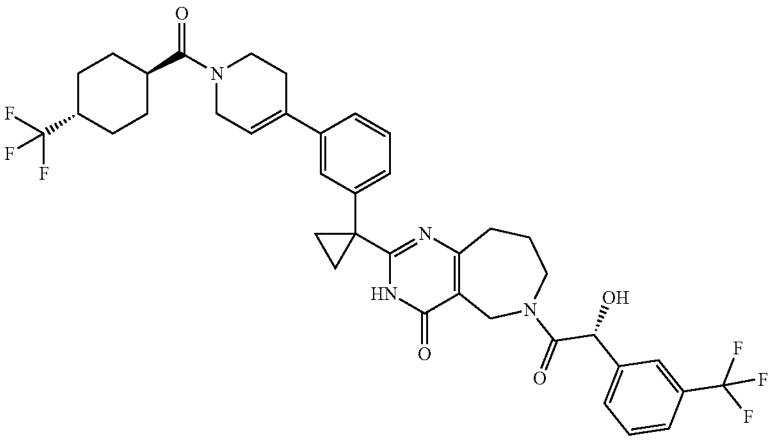 [SMILES: O=C([C@H](O)c1cccc(C(F)(F)F)c1)N1CCCc2nc(C3(c4cccc(C5=CCN(C(=O)[C@H]6CC[C@H](C(F)(F)F)CC6)CC5)c4)CC3)[nH]c(=O)c2C1] | 1.97 min | 743.0 |

TABLE 74-2-continued
| | | | | | |
|---|---|---|---|---|---|
| 42-78 | INT-11-10 | INT-31-3 | 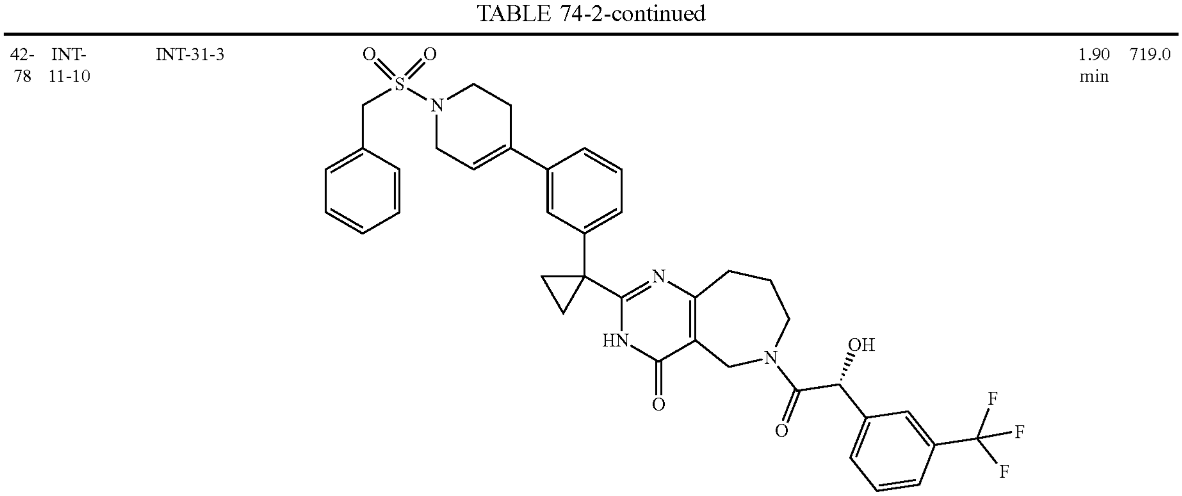 | 1.90 min | 719.0 |
| 42-79 | INT-11-10 | INT-28-4 | 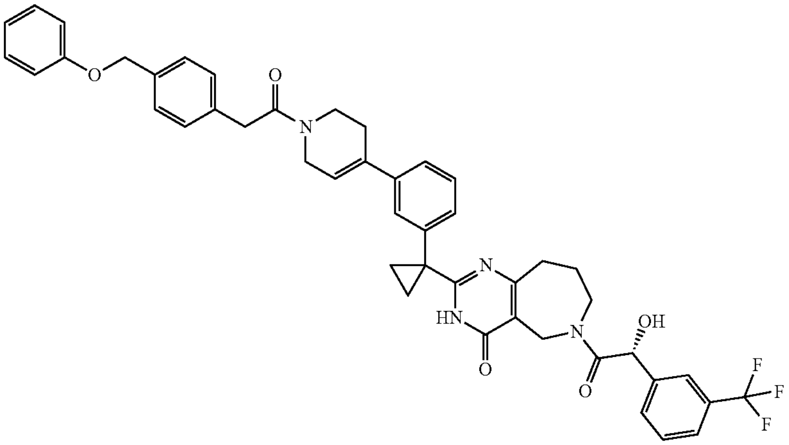 [SMILES: O=C(Cc1ccc(COc2ccccc2)cc1)N1CC=C(c2cccc(C3(c4nc5c(c(=O)[nH]4)CN(C(=O)[C@H](O)c4cccc(C(F)(F)F)c4)CCC5)CC3)c2)CC1] | 2.04 min | 789.1 |
| 42-80 | INT-11-10 | INT-28-5 | 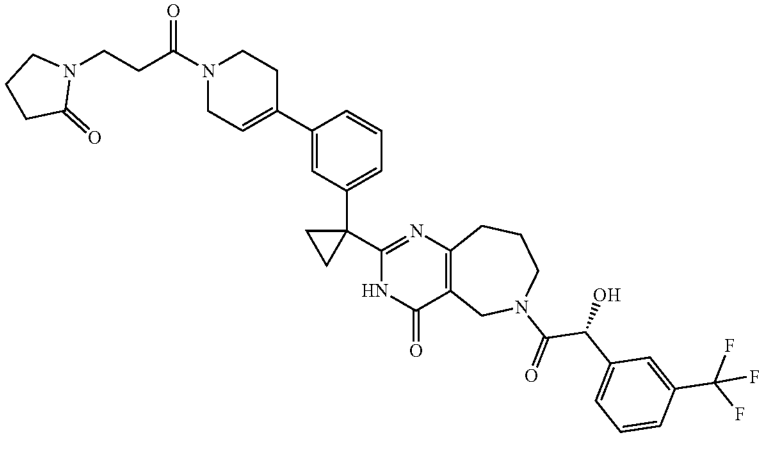 [SMILES: O=C(CCN1CCCC1=O)N1CC=C(c2cccc(C3(c4nc5c(c(=O)[nH]4)CN(C(=O)[C@H](O)c4cccc(C(F)(F)F)c4)CCC5)CC3)c2)CC1] | 1.47 min | 704.1 |

TABLE 74-2-continued
| | | | | | |
|---|---|---|---|---|---|
| 42-81 | INT-11-10 | 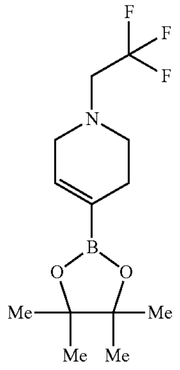 | 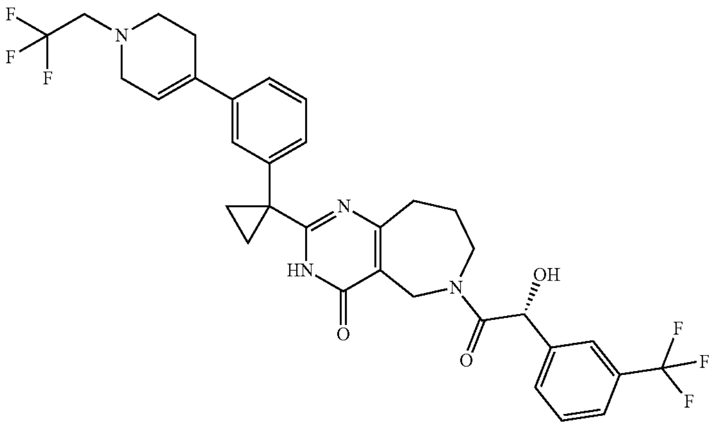 [SMILES: O=C([C@H](O)c1cccc(C(F)(F)F)c1)N1CCCc2nc(C3(c4cccc(C5=CCN(CC(F)(F)F)CC5)c4)CC3)[nH]c(=O)c2C1] | 2.17 min | 689.0 |
TABLE 74-3
| | | | | | |
|---|---|---|---|---|---|
| 42-82 | INT-11-10 | INT-28-6 | 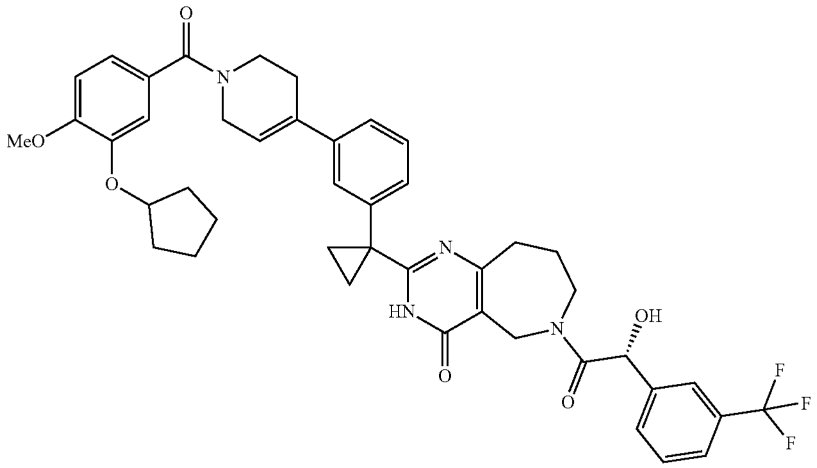 [SMILES: COc1ccc(C(=O)N2CC=C(c3cccc(C4(c5nc6c(c(=O)[nH]5)CN(C(=O)[C@H](O)c5cccc(C(F)(F)F)c5)CCC6)CC4)c3)CC2)cc1OC1CCCC1] | 1.99 min | 783.1 |
| 42-83 | INT-11-10 | INT-28-7 | 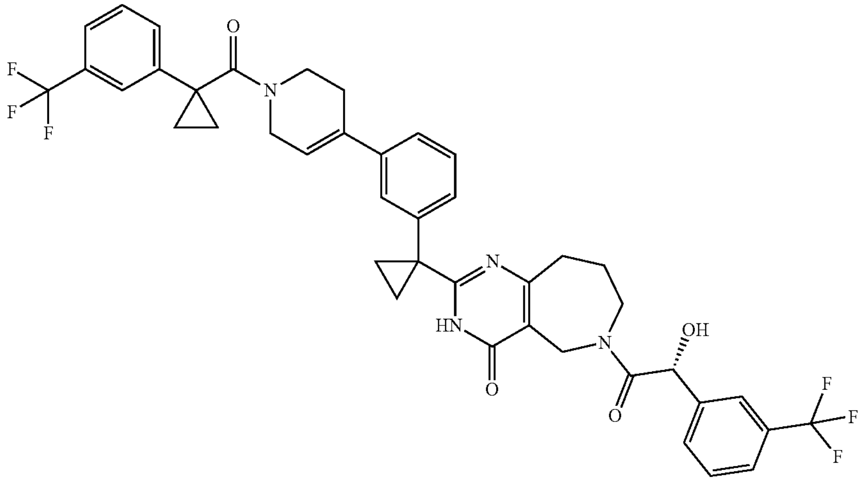 [SMILES: O=C([C@H](O)c1cccc(C(F)(F)F)c1)N1CCCc2nc(C3(c4cccc(C5=CCN(C(=O)C6(c7cccc(C(F)(F)F)c7)CC6)CC5)c4)CC3)[nH]c(=O)c2C1] | 2.02 min | 777.1 |

TABLE 74-3-continued

| | | | | | |
|---|---|---|---|---|---|
| 42-84 | INT-11-10 | INT-30-1 | 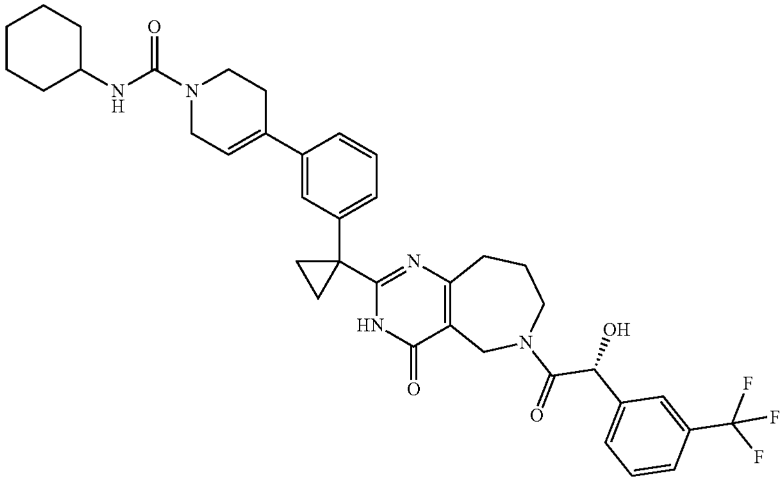 [SMILES: O=C(NC1CCCCC1)N1CC=C(c2cccc(C3(c4nc5c(c(=O)[nH]4)CN(C(=O)[C@H](O)c4cccc(C(F)(F)F)c4)CCC5)CC3)c2)CC1] | 1.87 min | 690.1 |

The following pyrimidin-4(3H)-one derivatives (Ex-42-85 to Ex-42-90) are prepared according to the procedure of Ex-33-1 or the general synthesis in scheme-6 from INT-11-10 and the synthesized boronic acid derivatives. The further purification is carried out by preparative LC-MS or SFC-MS system in usual manner. The retention time and observed MS by HPLC-QC method are summarized in Tables 75-1 to 75-2.

TABLE 75-1

| Ex. | Intermediate (INT) | Reagent | Structure | Retention time | Observed MS |
|---|---|---|---|---|---|
| 42-85 | INT-11-10 | INT-32-1 | 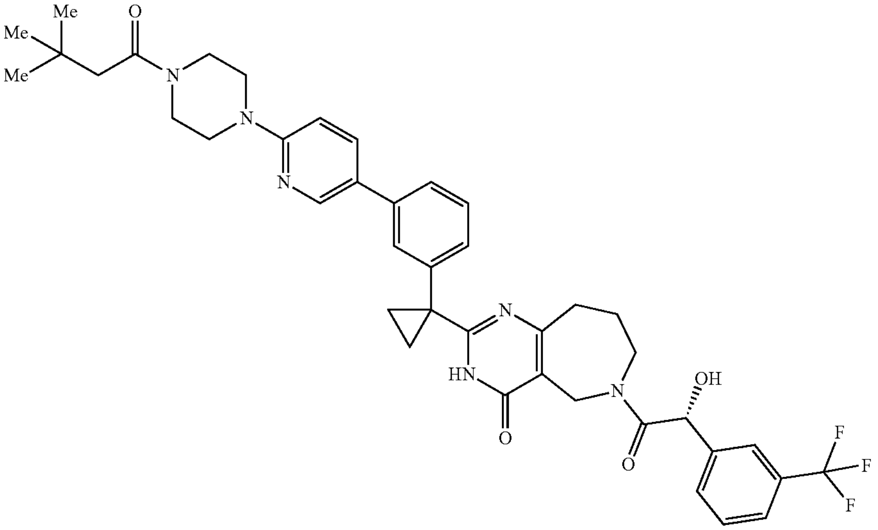 [SMILES: CC(C)(C)CC(=O)N1CCN(c2ccc(-c3cccc(C4(c5nc6c(c(=O)[nH]5)CN(C(=O)[C@H](O)c5cccc(C(F)(F)F)c5)CCC6)CC4)c3)cn2)CC1] | 1.93 min | 743.1 |

TABLE 75-1-continued
| Ex. | Intermediate (INT) | Reagent | Structure | Retention time | Observed MS |
|---|---|---|---|---|---|
| 42-86 | INT-11-10 | INT-32-2 | 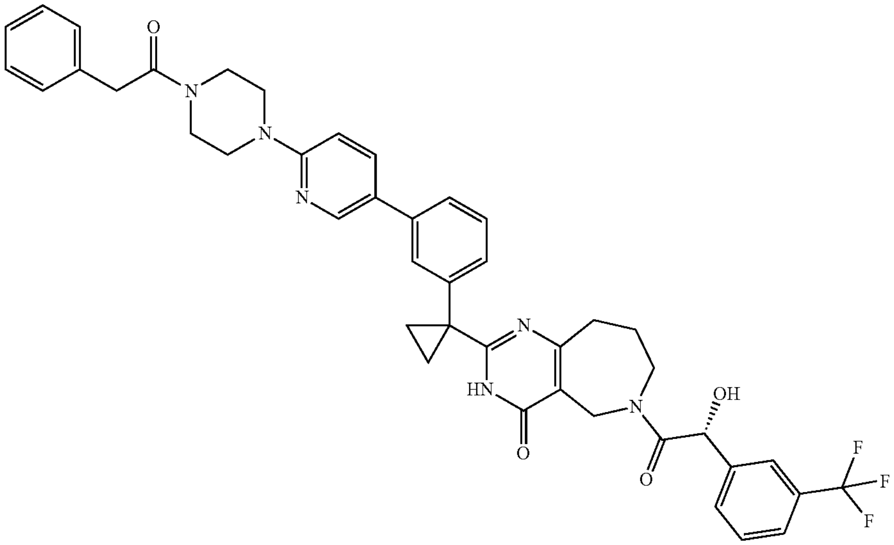 [SMILES: O=C(Cc1ccccc1)N1CCN(c2ccc(-c3cccc(C4(c5nc6c(c(=O)[nH]5)CN(C(=O)[C@H](O)c5cccc(C(F)(F)F)c5)CCC6)CC4)c3)cn2)CC1] | 1.86 min | 763.1 |
| 42-87 | INT-11-10 | INT-37-1 | 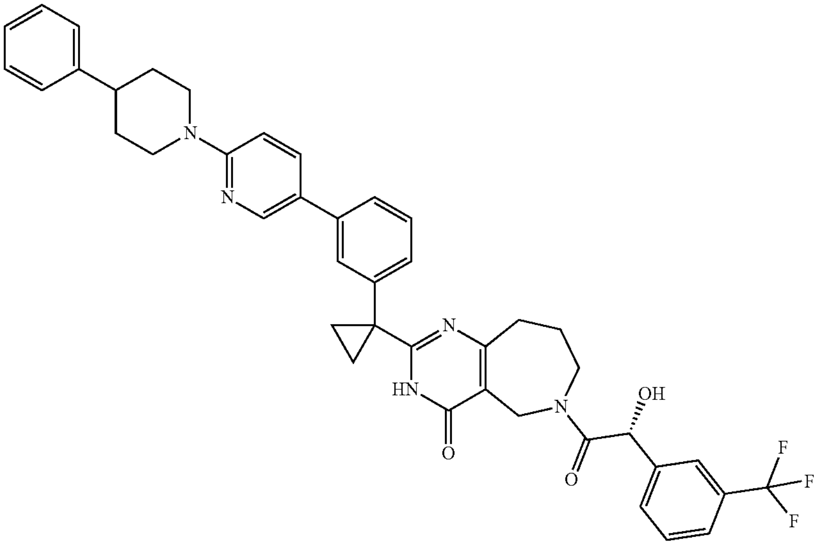 [SMILES: O=C([C@H](O)c1cccc(C(F)(F)F)c1)N1CCCc2nc(C3(c4cccc(-c5ccc(N6CCC(c7ccccc7)CC6)nc5)c4)CC3)[nH]c(=O)c2C1] | 2.26 min | 720.1 |

TABLE 75-1-continued
| Ex. | Intermediate (INT) | Reagent | Structure | Retention time | Observed MS |
|---|---|---|---|---|---|
| 42-88 | INT-11-10 | INT-37-2 | 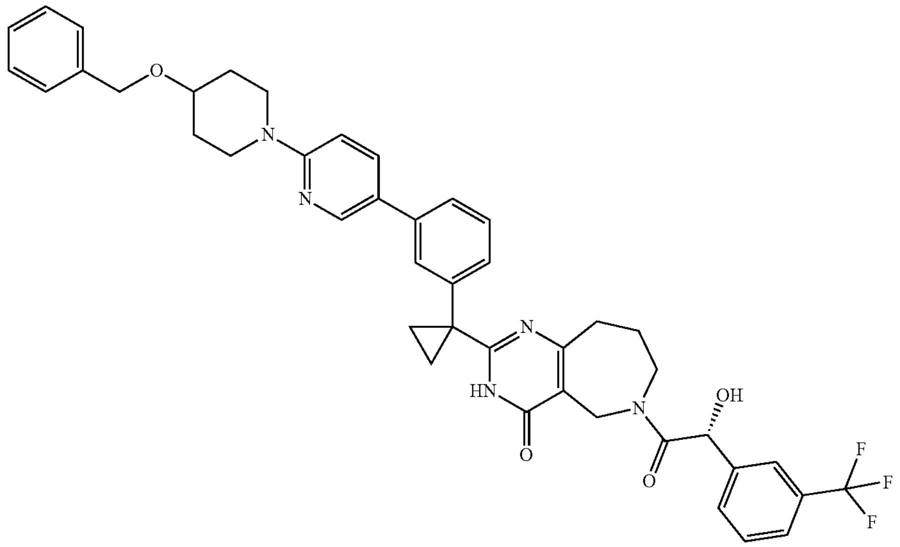 [SMILES: O=C([C@H](O)c1cccc(C(F)(F)F)c1)N1CCCc2nc(C3(c4cccc(-c5ccc(N6CCC(OCc7ccccc7)CC6)nc5)c4)CC3)[nH]c(=O)c2C1] | 2.20 min | 750.1 |
TABLE 75-2
| | | | | | |
|---|---|---|---|---|---|
| 42-89 | INT-11-10 | INT-32-3 | 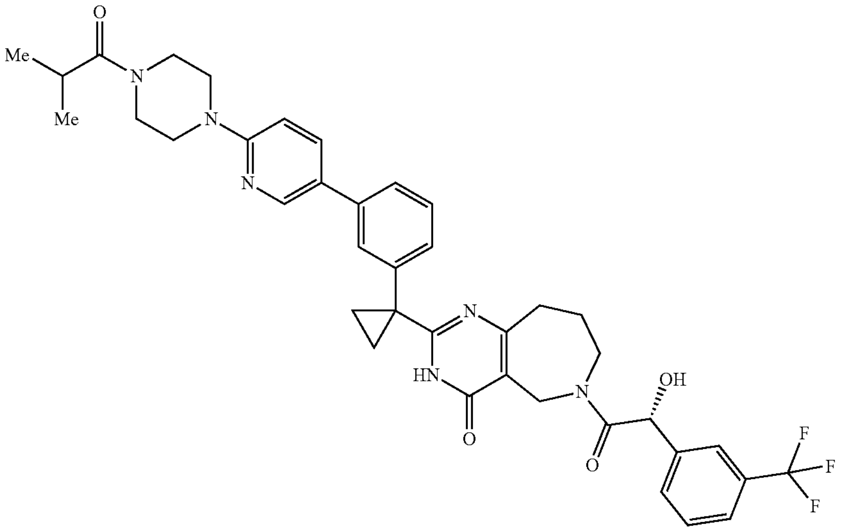 [SMILES: CC(C)C(=O)N1CCN(c2ccc(-c3cccc(C4(c5nc6c(c(=O)[nH]5)CN(C(=O)[C@H](O)c5cccc(C(F)(F)F)c5)CCC6)CC4)c3)cn2)CC1] | 1.78 min | 715.1 |

TABLE 75-2-continued

| | | | | | |
|---|---|---|---|---|---|
| 42-90 | INT-11-10 | INT-32-4 | 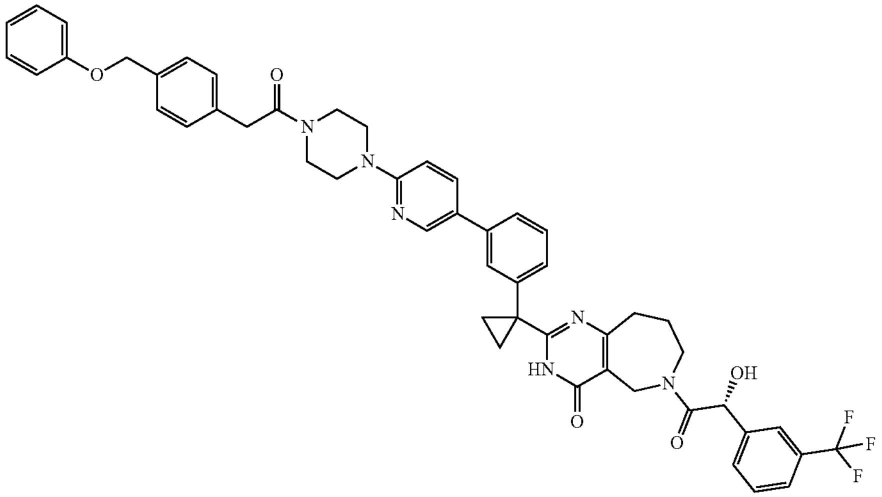 [SMILES: O=C(Cc1ccc(COc2ccccc2)cc1)N1CCN(c2ccc(-c3cccc(C4(c5nc6c(c(=O)[nH]5)CN(C(=O)[C@H](O)c5cccc(C(F)(F)F)c5)CCC6)CC4)c3)cn2)CC1] | 2.06 min | 869.2 |

The following pyrimidin-4(3H)-one derivatives (Ex-42-91 to Ex-42-97) are prepared according to the procedure of Ex-33-1 or the general synthesis in scheme-6 from INT-11-10 and the synthesized boronic acid derivatives. The derivatives of Ex-42-92, 42-94 and 42-97 are isolated as the corresponding carboxylic acd derivarives by hydrolysis in situ. The further purification is carried out by preparative LC-MS or SFC-MS system in usual manner. The retention time and observed MS by HPLC-QC method are summarized in Tables 76-1 to 76-2.

TABLE 76-1

| Ex. | Intermediate (INT) | Reagent | Structure | Retention time | Observed MS |
|---|---|---|---|---|---|
| 42-91 | INT-11-10 | INT-33-1 | 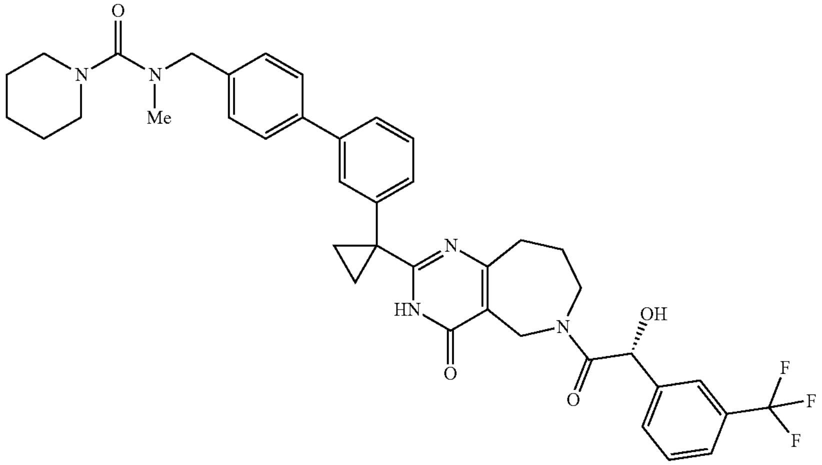 [SMILES: CN(Cc1ccc(-c2cccc(C3(c4nc5c(c(=O)[nH]4)CN(C(=O)[C@H](O)c4cccc(C(F)(F)F)c4)CCC5)CC3)c2)cc1)C(=O)N1CCCCC1] | 2.03 min | 714.1 |

TABLE 76-1-continued
| Ex. | Inter-me-diate (INT) | Rea-gent | Structure | Reten-tion time | Ob-served MS |
|---|---|---|---|---|---|
| 42-92 | INT-11-10 | INT-35-1 | 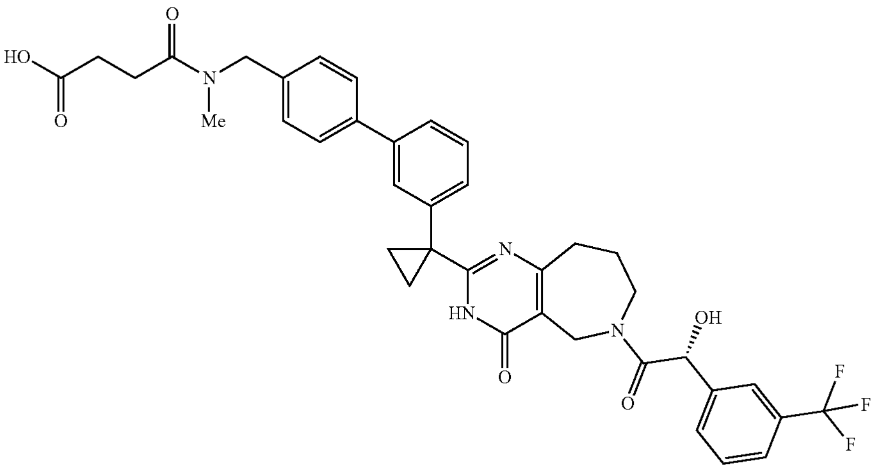 [SMILES: CN(Cc1ccc(-c2cccc(C3(c4nc5c(c(=O)[nH]4)CN(C(=O)[C@H](O)c4cccc(C(F)(F)F)c4)CCC5)CC3)c2)cc1)C(=O)CCC(=O)O] | 1.29 min | 703.0 |
| 42-93 | INT-11-10 | INT-34-1 | 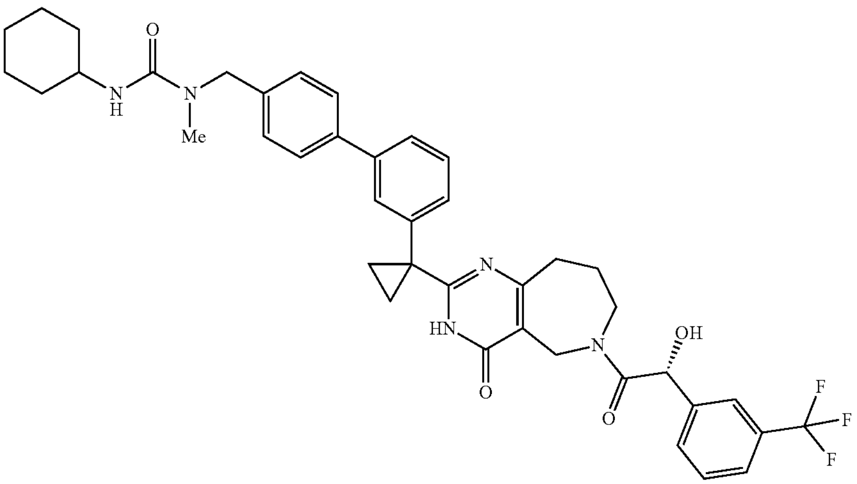 [SMILES: CN(Cc1ccc(-c2cccc(C3(c4nc5c(c(=O)[nH]4)CN(C(=O)[C@H](O)c4cccc(C(F)(F)F)c4)CCC5)CC3)c2)cc1)C(=O)NC1CCCCC1] | 1.96 min | 728.1 |
| 42-94 | INT-11-10 | INT-35-2 | 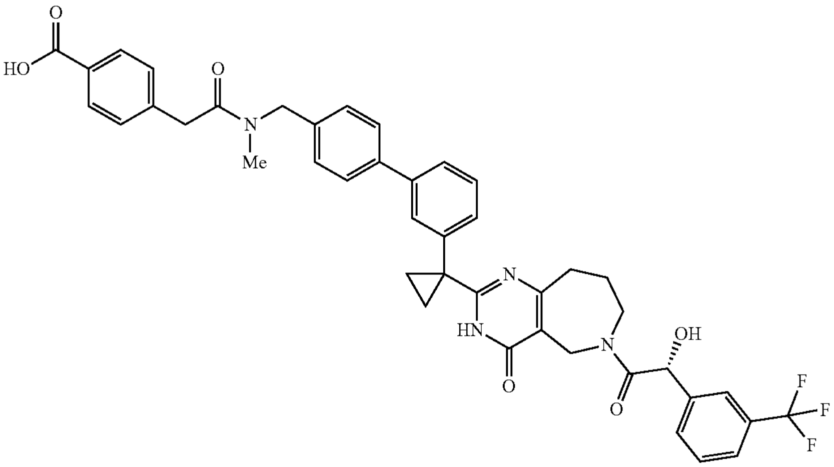 [SMILES: CN(Cc1ccc(-c2cccc(C3(c4nc5c(c(=O)[nH]4)CN(C(=O)[C@H](O)c4cccc(C(F)(F)F)c4)CCC5)CC3)c2)cc1)C(=O)Cc1ccc(C(=O)O)cc1] | 1.34 min | 765.1 |

TABLE 76-2

| | | | | | |
|---|---|---|---|---|---|
| 42-95 | INT-11-10 | INT-36-1 | 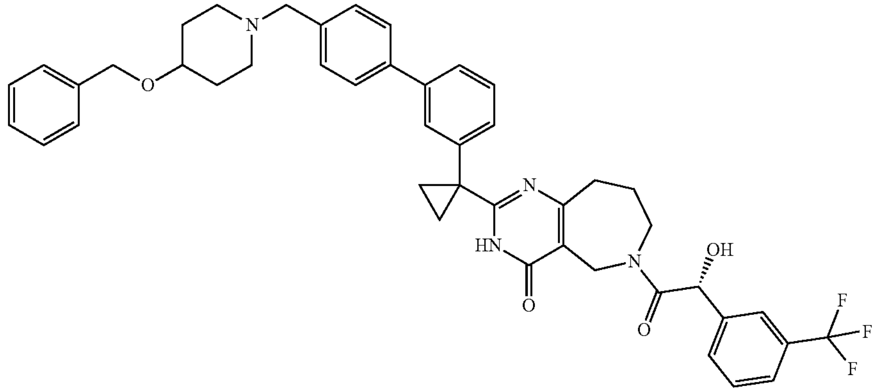 [SMILES: O=C([C@H](O)c1cccc(C(F)(F)F)c1)N1CCCc2nc(C3(c4cccc(-c5ccc(CN6CCC(OCc7ccccc7)CC6)cc5)c4)CC3)[nH]c(=O)c2C1] | 2.35 min | 762.9 |
| 42-96 | INT-11-10 | INT-36-2 | 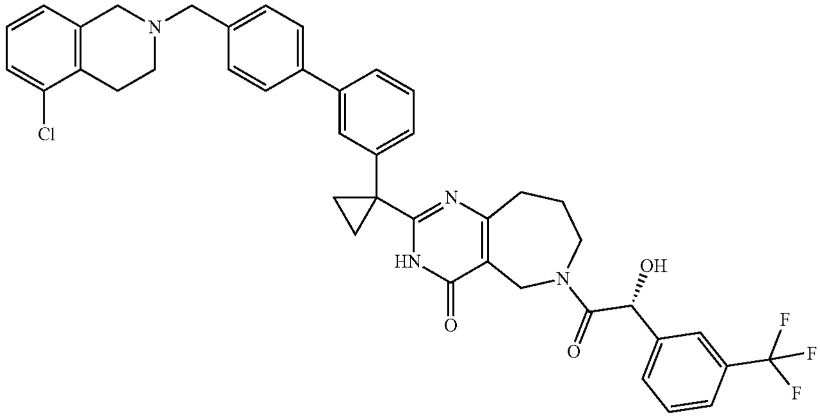 [SMILES: O=C([C@H](O)c1cccc(C(F)(F)F)c1)N1CCCc2nc(C3(c4cccc(-c5ccc(CN6CCc7c(Cl)cccc7C6)cc5)c4)CC3)[nH]c(=O)c2C1] | 2.41 min | 738.9 |
| 42-97 | INT-11-10 | INT-35-3 | 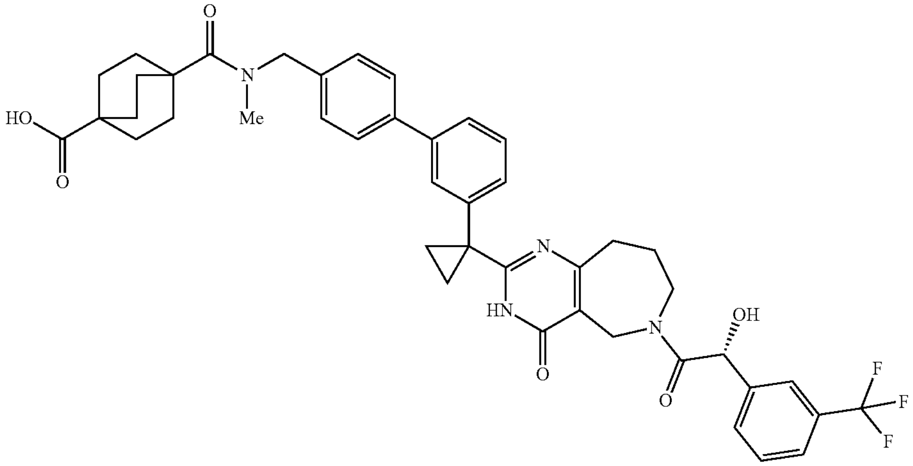 [SMILES: CN(Cc1ccc(-c2cccc(C3(c4nc5c(c(=O)[nH]4)CN(C(=O)[C@H](O)c4cccc(C(F)(F)F)c4)CCC5)CC3)c2)cc1)C(=O)C12CCC(C(=O)O)(CC1)CC2] | 1.47 min | 783.1 |

The following pyrimidin-4(3H)-one derivatives (Ex-43-1 and Ex-43-2) are prepared according to the procedure of Ex-33-1 or the general synthesis in scheme-6 from INT-11-11 and the known boronic acid derivatives. The further purification is carried out by preparative LC-MS or SFC-MS system in usual manner. The retention time and observed MS by HPLC-QC method are summarized in Table 77.

TABLE 77

| Ex. | Intermediate (INT) | Structure | Retention time | Observed MS |
| --- | --- | --- | --- | --- |
| 43-1 | INT-11-11 | 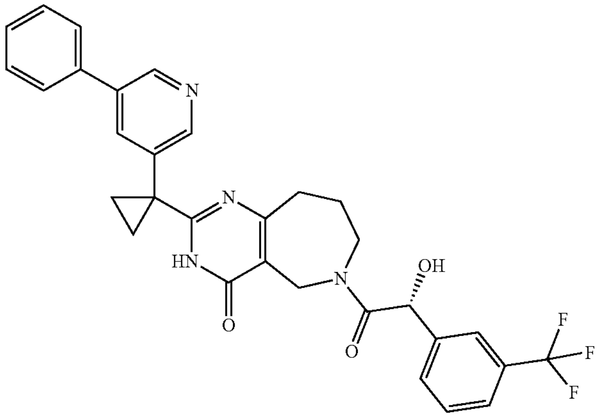 | 1.65 min | 561.2 |
| 43-2 | INT-11-11 | 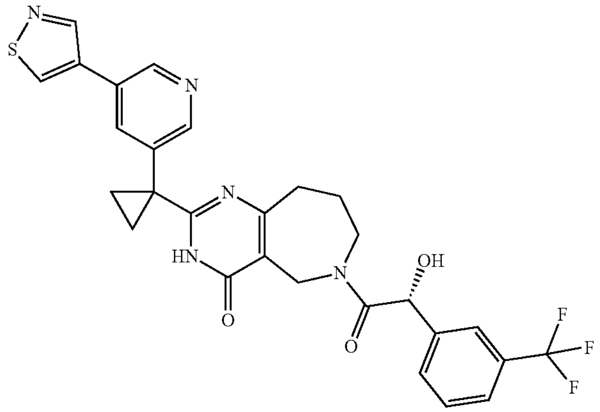 | 1.42 min | 568.0 |

Example 44-1 (Ex-44-1)

6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one (Ex-44-1)

{Chem. 106}

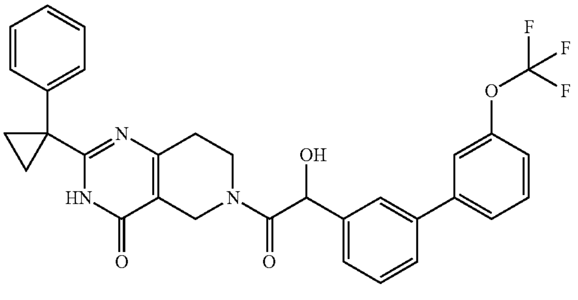 [SMILES: O=C(C(O)c1cccc(-c2cccc(OC(F)(F)F)c2)c1)N1CCc2nc(C3(c4ccccc4)CC3)[nH]c(=O)c2C1]

A mixture of INT-11-14 (23 mg, 0.048 mmol), 3-(trifluoromethoxy)phenylboronic acid (19.7 mg, 0.096 mmol), Pd(amphos)$Cl_2$ (10.2 mg, 0.014 mmol) and potassium carbonate (26.5 mg, 0.192 mmol) in 1,4-dioxane (1 mL) is stirred at 90° C. for 14 hrs. The mixture is diluted with EtOAc and washed with water. The organic fraction is dried over sodium sulfate. After the filtration and removal of solvent, the residue is purified by the filtration through a pad of amine silica gel and SCX (washing with MeOH and release with 1 M $NH_3$-MeOH) to give the titled compound (10.5 mg) as a brown solid.

The further purification is carried out by preparative LC-MS or SFC-MS system in the usual manner. The retention time and observed MS by HPLC-QC method are summarized in Tables 78-1 to 78-17.

The following pyrimidin-4(3H)-one derivatives (Ex-44-1 to Ex-44-119) are prepared according to the procedure of Ex-44-1 or the general synthesis in scheme-5 from INT-11-14, 11-15, 11-16 or 11-7 and the known boronic acid derivatives. The further purification is carried out by preparative LC-MS or SFC-MS system in usual manner. The retention time and observed MS by HPLC-QC method are summarized in Tables 78-1 to 78-17.

TABLE 78-1
| Ex. | Intermediate (INT) | Structure | Retention time | Observed MS |
|---|---|---|---|---|
| 44-1 | INT-11-14 | 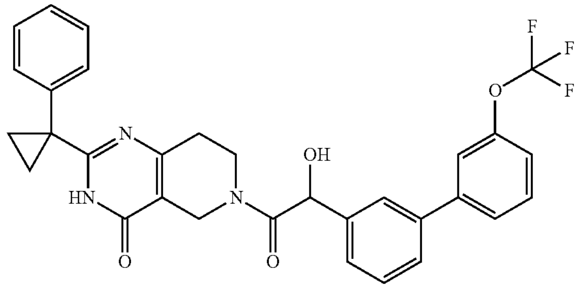 | 1.92 min | 562.2 |
| 44-2 | INT-11-15 | 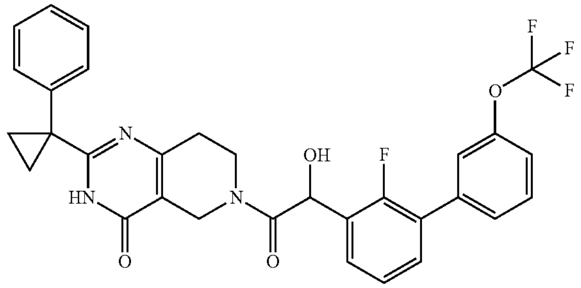 [SMILES: O=C(C(O)c1cccc(-c2cccc(OC(F)(F)F)c2)c1F)N1CCc2nc(C3(c4ccccc4)CC3)[nH]c(=O)c2C1] | 1.93 min | 580.2 |
| 44-3 | INT-11-14 | 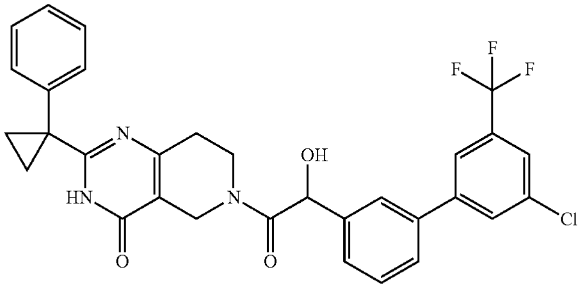 [SMILES: O=C(C(O)c1cccc(-c2cc(Cl)cc(C(F)(F)F)c2)c1)N1CCc2nc(C3(c4ccccc4)CC3)[nH]c(=O)c2C1] | 2.02 min | 580.2 |
| 44-4 | INT-11-14 | 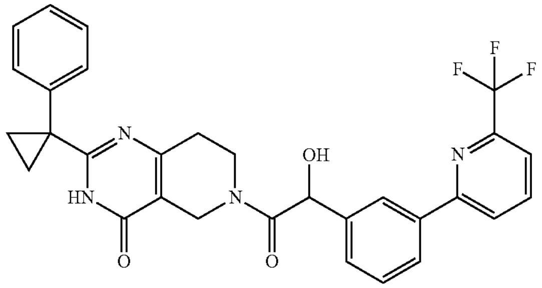 | 1.77 min | 547.2 |
| 44-5 | INT-11-14 | 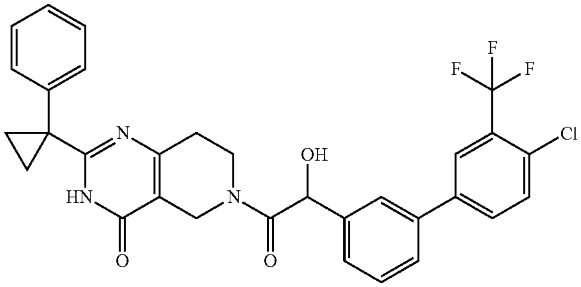 | 1.98 min | 580.2 |

TABLE 78-1-continued
| Ex. | Intermediate (INT) | Structure | Retention time | Observed MS |
|---|---|---|---|---|
| 44-6 | INT-11-14 | 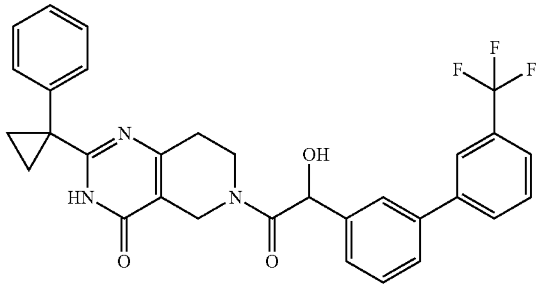 [SMILES: O=C(C(O)c1cccc(-c2cccc(C(F)(F)F)c2)c1)N1CCc2nc(C3(c4ccccc4)CC3)[nH]c(=O)c2C1] | 1.88 min | 546.2 |
| 44-7 | INT-11-14 | 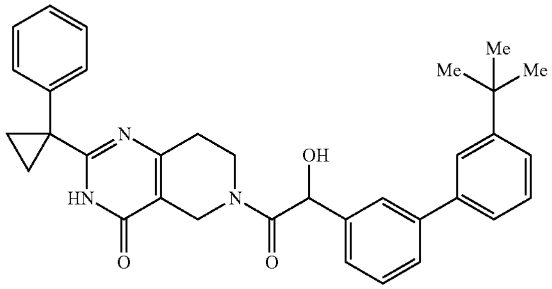 [SMILES: CC(C)(C)c1cccc(-c2cccc(C(O)C(=O)N3CCc4nc(C5(c6ccccc6)CC5)[nH]c(=O)c4C3)c2)c1] | 2.06 min | 534.3 |
TABLE 78-2
| | | | | |
|---|---|---|---|---|
| 44-8 | INT-11-14 | 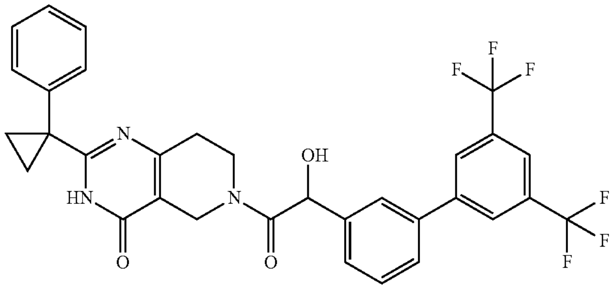 [SMILES: O=C(C(O)c1cccc(-c2cc(C(F)(F)F)cc(C(F)(F)F)c2)c1)N1CCc2nc(C3(c4ccccc4)CC3)[nH]c(=O)c2C1] | 2.01 min | 614.2 |
| 44-9 | INT-11-14 | 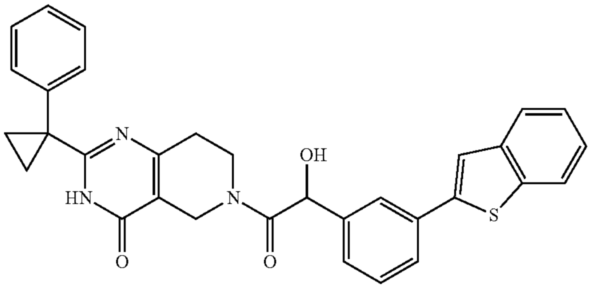 [SMILES: O=C(C(O)c1cccc(-c2cc3ccccc3s2)c1)N1CCc2nc(C3(c4ccccc4)CC3)[nH]c(=O)c2C1] | 1.91 min | 534.2 |
| 44-10 | INT-11-14 | 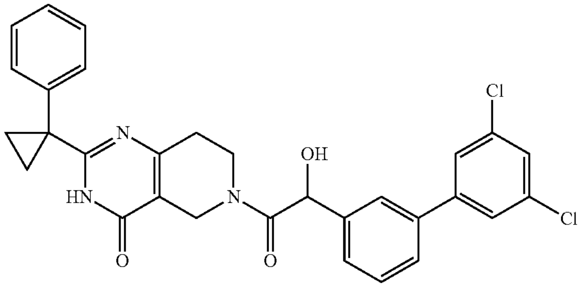 [SMILES: O=C(C(O)c1cccc(-c2cc(Cl)cc(Cl)c2)c1)N1CCc2nc(C3(c4ccccc4)CC3)[nH]c(=O)c2C1] | 2.01 min | 546.1 |

TABLE 78-2-continued
| | | | | |
|---|---|---|---|---|
| 44-11 | INT-11-14 | 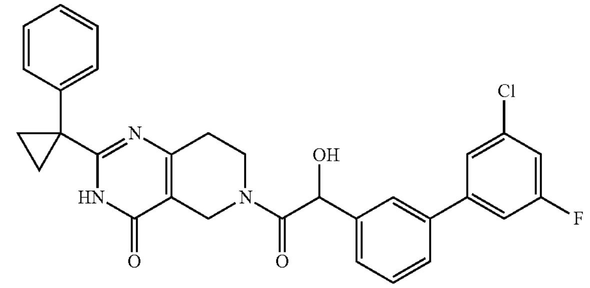 [SMILES: O=C(C(O)c1cccc(-c2cc(F)cc(Cl)c2)c1)N1CCc2nc(C3(c4ccccc4)CC3)[nH]c(=O)c2C1] | 1.90 min | 530.2 |
| 44-12 | INT-11-14 | 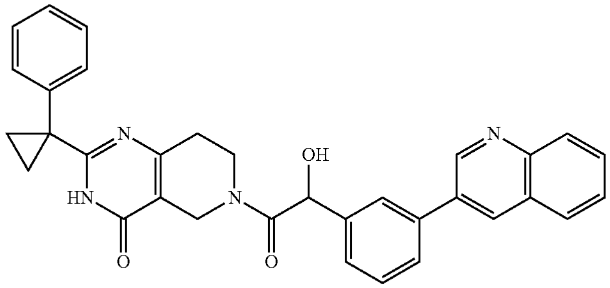 [SMILES: O=C(C(O)c1cccc(-c2cnc3ccccc3c2)c1)N1CCc2nc(C3(c4ccccc4)CC3)[nH]c(=O)c2C1] | 1.62 min | 529.2 |
| 44-13 | INT-11-14 | 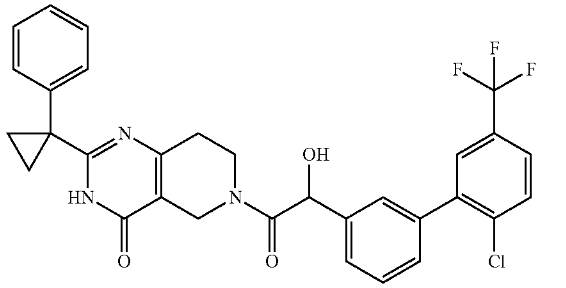 [SMILES: O=C(C(O)c1cccc(-c2cc(C(F)(F)F)ccc2Cl)c1)N1CCc2nc(C3(c4ccccc4)CC3)[nH]c(=O)c2C1] | 1.95 min | 580.2 |
| 44-14 | INT-11-14 | 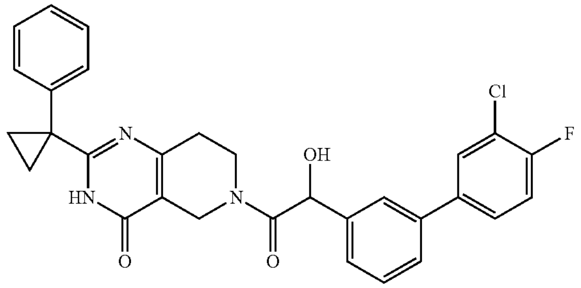 [SMILES: O=C(C(O)c1cccc(-c2ccc(F)c(Cl)c2)c1)N1CCc2nc(C3(c4ccccc4)CC3)[nH]c(=O)c2C1] | 1.87 min | 530.2 |
TABLE 78-3
| | | | | |
|---|---|---|---|---|
| 44-15 | INT-11-14 | 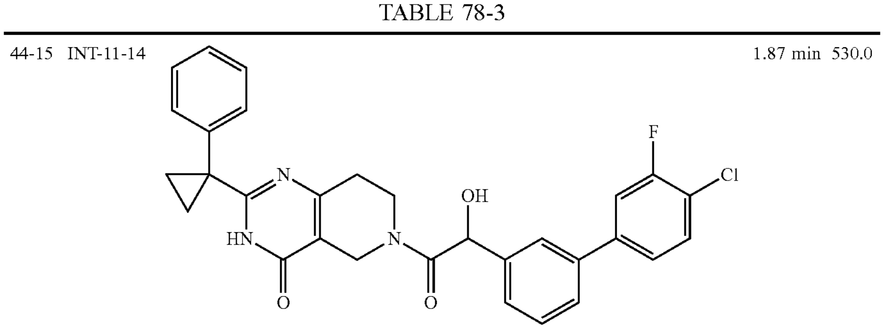 | 1.87 min | 530.0 |

TABLE 78-3-continued
| | | | | |
|---|---|---|---|---|
| 44-16 | INT-11-14 | 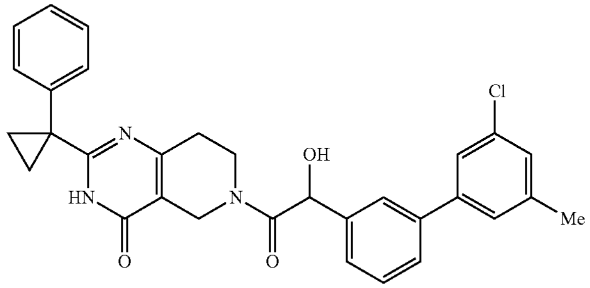 [SMILES: Cc1cc(Cl)cc(-c2cccc(C(O)C(=O)N3CCc4nc(C5(c6ccccc6)CC5)[nH]c(=O)c4C3)c2)c1] | 1.96 min | 526.2 |
| 44-17 | INT-11-14 | 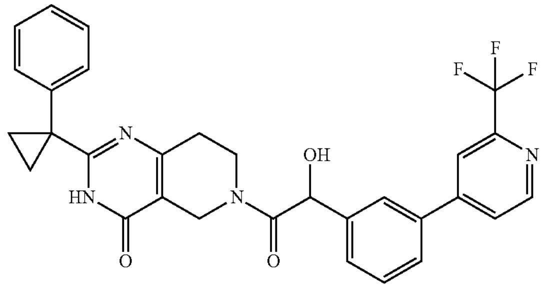 [SMILES: O=C(C(O)c1cccc(-c2ccnc(C(F)(F)F)c2)c1)N1CCc2nc(C3(c4ccccc4)CC3)[nH]c(=O)c2C1] | 1.66 min | 547.2 |
| 44-18 | INT-11-14 | 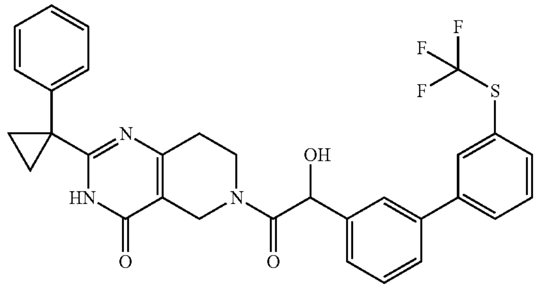 [SMILES: O=C(C(O)c1cccc(-c2cccc(SC(F)(F)F)c2)c1)N1CCc2nc(C3(c4ccccc4)CC3)[nH]c(=O)c2C1] | 1.98 min | 578.2 |
| 44-19 | INT-11-14 | 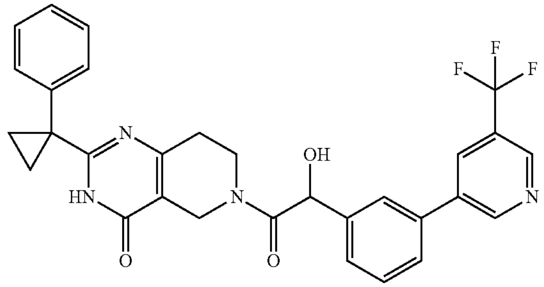 [SMILES: O=C(C(O)c1cccc(-c2cncc(C(F)(F)F)c2)c1)N1CCc2nc(C3(c4ccccc4)CC3)[nH]c(=O)c2C1] | 1.65 min | 547.0 |
| 44-20 | INT-11-14 | 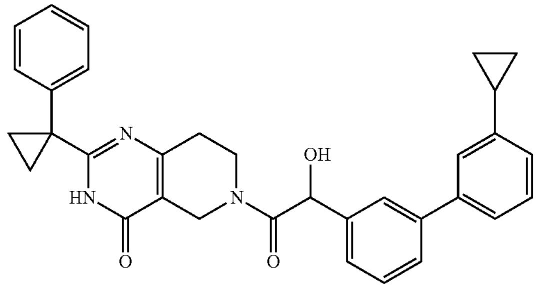 [SMILES: O=C(C(O)c1cccc(-c2cccc(C3CC3)c2)c1)N1CCc2nc(C3(c4ccccc4)CC3)[nH]c(=O)c2C1] | 1.91 min | 518.2 |

TABLE 78-3-continued
| | | | | |
|---|---|---|---|---|
| 44-21 | INT-11-14 | 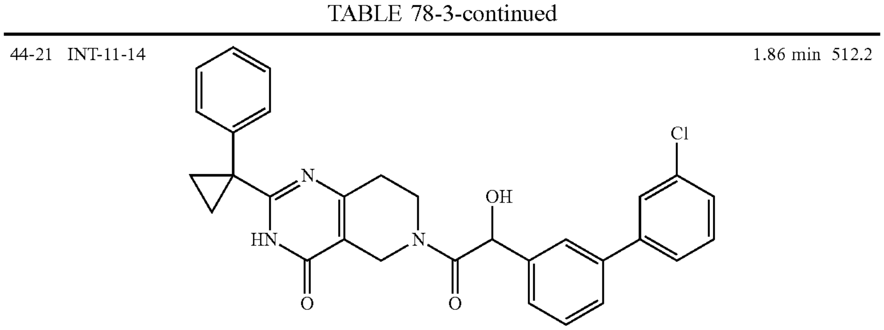 | 1.86 min | 512.2 |
TABLE 78-4
| | | | | |
|---|---|---|---|---|
| 44-22 | INT-11-15 | 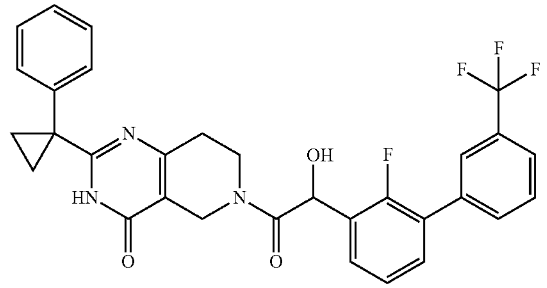 [SMILES: O=C(C(O)c1cccc(-c2cccc(C(F)(F)F)c2)c1F)N1CCc2nc(C3(c4ccccc4)CC3)[nH]c(=O)c2C1] | 1.89 min | 564.2 |
| 44-23 | INT-11-15 | 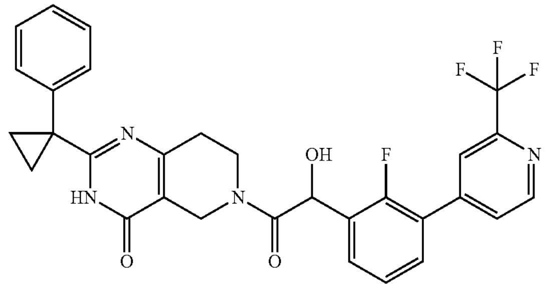 [SMILES: O=C(C(O)c1cccc(-c2ccnc(C(F)(F)F)c2)c1F)N1CCc2nc(C3(c4ccccc4)CC3)[nH]c(=O)c2C1] | 1.69 min | 565.2 |
| 44-24 | INT-11-14 | 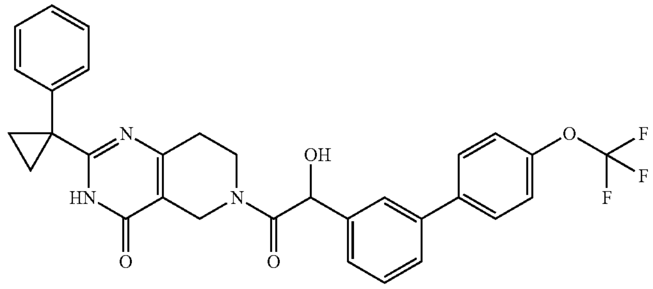 [SMILES: O=C(C(O)c1cccc(-c2ccc(OC(F)(F)F)cc2)c1)N1CCc2nc(C3(c4ccccc4)CC3)[nH]c(=O)c2C1] | 1.92 min | 562.2 |
| 44-25 | INT-11-14 | 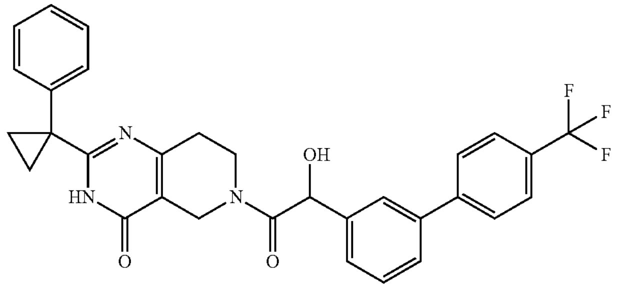 [SMILES: O=C(C(O)c1cccc(-c2ccc(C(F)(F)F)cc2)c1)N1CCc2nc(C3(c4ccccc4)CC3)[nH]c(=O)c2C1] | 1.89 min | 546.2 |

TABLE 78-4-continued
| | | | | |
|---|---|---|---|---|
| 44-26 | INT-11-14 | 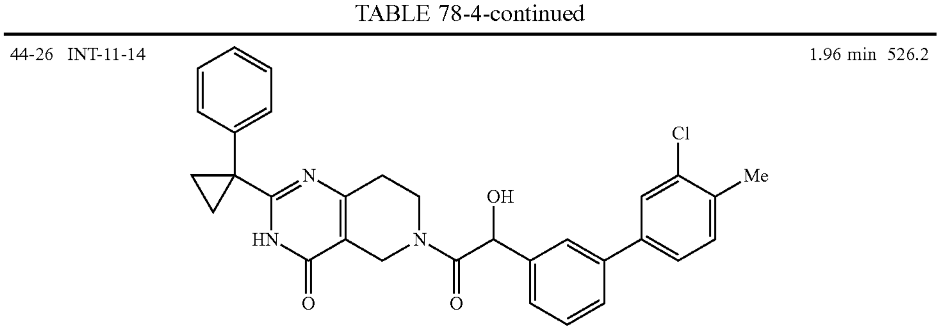 | 1.96 min | 526.2 |
| 44-27 | INT-11-14 | 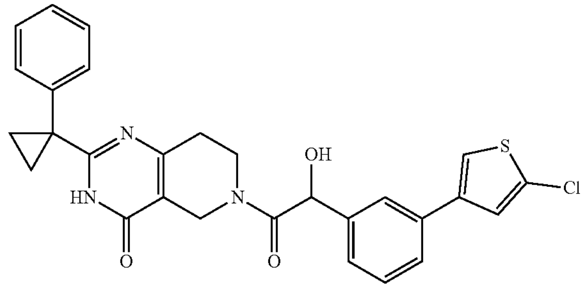 [SMILES: O=C(C(O)c1cccc(-c2csc(Cl)c2)c1)N1CCc2nc(C3(c4ccccc4)CC3)[nH]c(=O)c2C1] | 1.85 min | 518.1 |
| 44-28 | INT-11-14 | 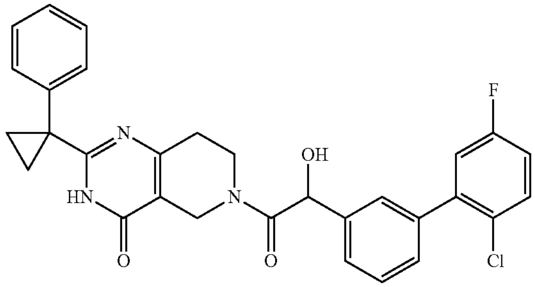 [SMILES: O=C(C(O)c1cccc(-c2cc(F)ccc2Cl)c1)N1CCc2nc(C3(c4ccccc4)CC3)[nH]c(=O)c2C1] | 1.83 min | 530.0 |
TABLE 78-5
| | | | | |
|---|---|---|---|---|
| 44-29 | INT-11-14 | 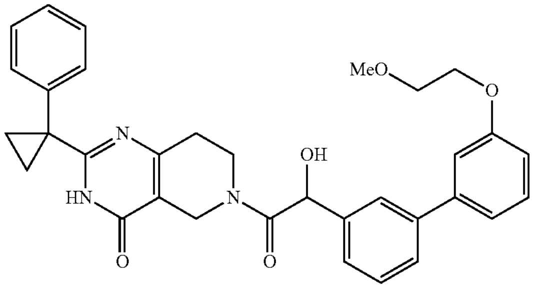 [SMILES: COCCOc1cccc(-c2cccc(C(O)C(=O)N3CCc4nc(C5(c6ccccc6)CC5)[nH]c(=O)c4C3)c2)c1] | 1.69 min | 552.2 |
| 44-30 | INT-11-14 | 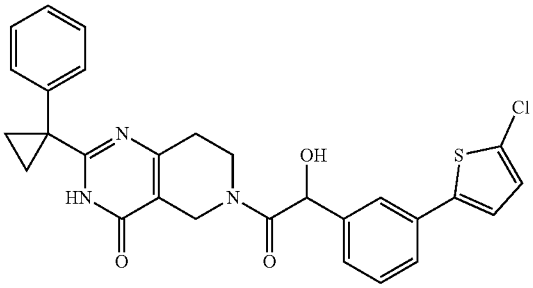 [SMILES: O=C(C(O)c1cccc(-c2ccc(Cl)s2)c1)N1CCc2nc(C3(c4ccccc4)CC3)[nH]c(=O)c2C1] | 1.87 min | 518.1 |

TABLE 78-5-continued
| | | | | |
|---|---|---|---|---|
| 44-31 | INT-11-14 | 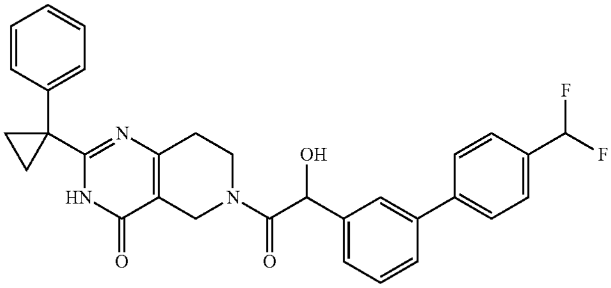 [SMILES: O=C(C(O)c1cccc(-c2ccc(C(F)F)cc2)c1)N1CCc2nc(C3(c4ccccc4)CC3)[nH]c(=O)c2C1] | 1.75 min | 528.2 |
| 44-32 | INT-11-14 | 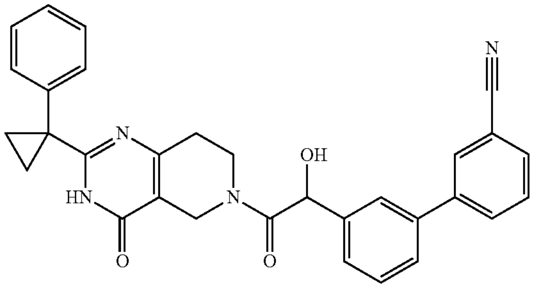 [SMILES: N#Cc1cccc(-c2cccc(C(O)C(=O)N3CCc4nc(C5(c6ccccc6)CC5)[nH]c(=O)c4C3)c2)c1] | 1.64 min | 503.2 |
| 44-33 | INT-11-15 | 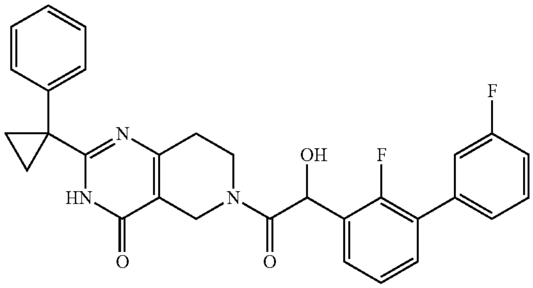 [SMILES: O=C(C(O)c1cccc(-c2cccc(F)c2)c1F)N1CCc2nc(C3(c4ccccc4)CC3)[nH]c(=O)c2C1] | 1.78 min | 514.2 |
| 44-34 | INT-11-14 | 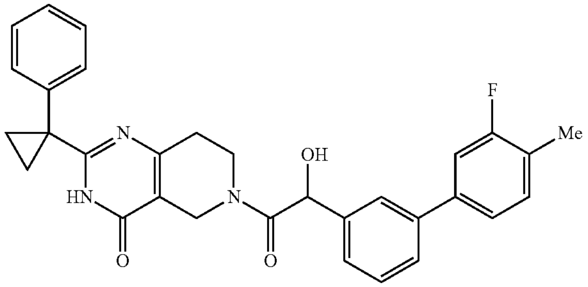 [SMILES: Cc1ccc(-c2cccc(C(O)C(=O)N3CCc4nc(C5(c6ccccc6)CC5)[nH]c(=O)c4C3)c2)cc1F] | 1.85 min | 510.1 |
| 44-35 | INT-11-14 | 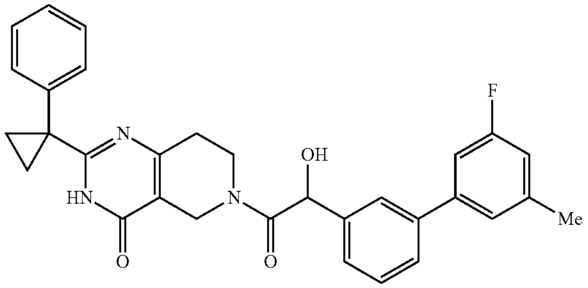 [SMILES: Cc1cc(F)cc(-c2cccc(C(O)C(=O)N3CCc4nc(C5(c6ccccc6)CC5)[nH]c(=O)c4C3)c2)c1] | 1.85 min | 510.0 |

TABLE 78-6
| | | | | |
|---|---|---|---|---|
| 44-36 | INT-11-14 | 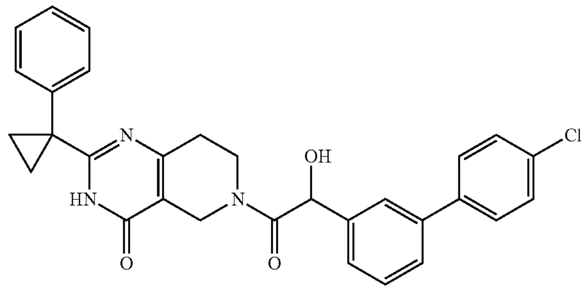 [SMILES: O=C(C(O)c1cccc(-c2ccc(Cl)cc2)c1)N1CCc2nc(C3(c4ccccc4)CC3)[nH]c(=O)c2C1] | 1.86 min | 512.1 |
| 44-37 | INT-11-14 | 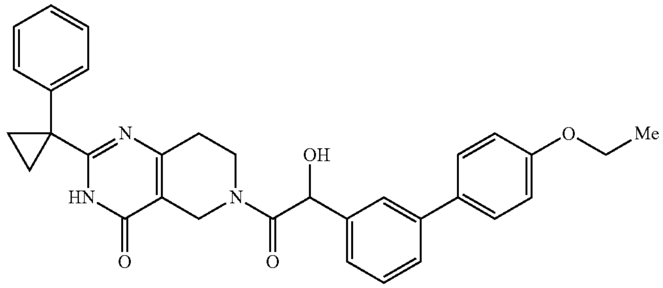 [SMILES: CCOc1ccc(-c2cccc(C(O)C(=O)N3CCc4nc(C5(c6ccccc6)CC5)[nH]c(=O)c4C3)c2)cc1] | 1.82 min | 522.2 |
| 44-38 | INT-11-14 | 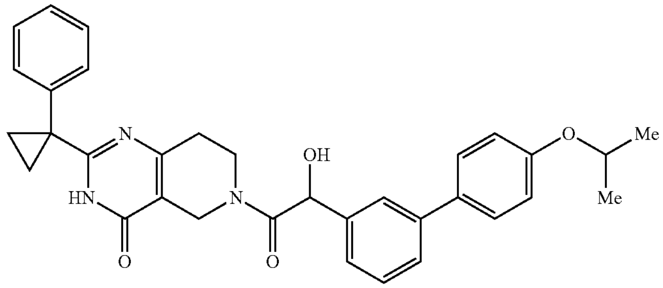 [SMILES: CC(C)Oc1ccc(-c2cccc(C(O)C(=O)N3CCc4nc(C5(c6ccccc6)CC5)[nH]c(=O)c4C3)c2)cc1] | 1.89 min | 536.2 |
| 44-39 | INT-11-14 | 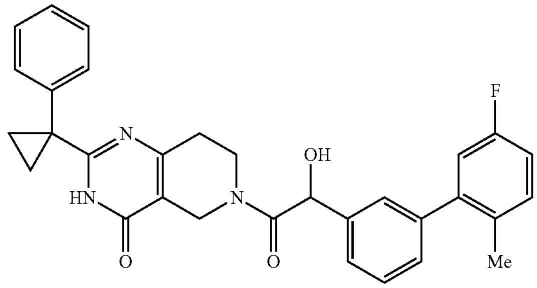 [SMILES: Cc1ccc(F)cc1-c1cccc(C(O)C(=O)N2CCc3nc(C4(c5ccccc5)CC4)[nH]c(=O)c3C2)c1] | 1.83 min | 510.0 |
| 44-40 | INT-11-14 | 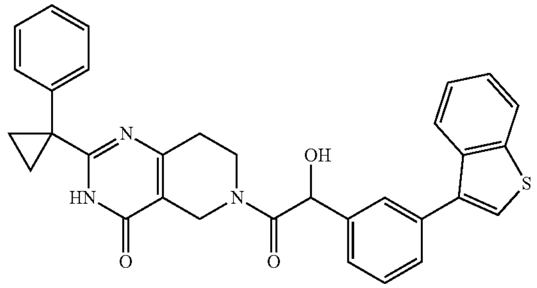 [SMILES: O=C(C(O)c1cccc(-c2csc3ccccc23)c1)N1CCc2nc(C3(c4ccccc4)CC3)[nH]c(=O)c2C1] | 1.90 min | 534.2 |

TABLE 78-6-continued
| | | | | |
|---|---|---|---|---|
| 44-41 | INT-11-14 | 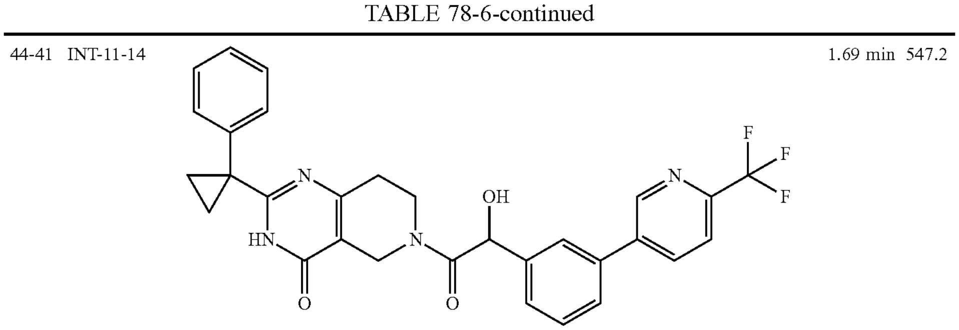 | 1.69 min | 547.2 |
| 44-42 | INT-11-14 | 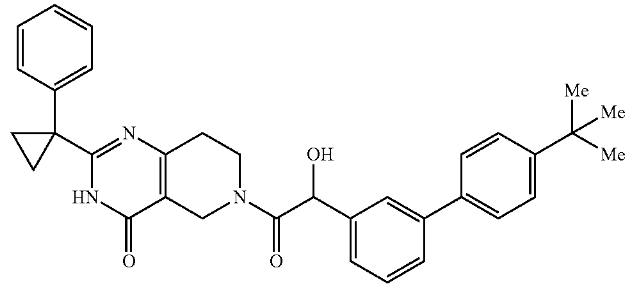 [SMILES: CC(C)(C)c1ccc(-c2cccc(C(O)C(=O)N3CCc4nc(C5(c6ccccc6)CC5)[nH]c(=O)c4C3)c2)cc1] | 2.07 min | 534.3 |
TABLE 78-7
| | | | | |
|---|---|---|---|---|
| 44-43 | INT-11-14 | 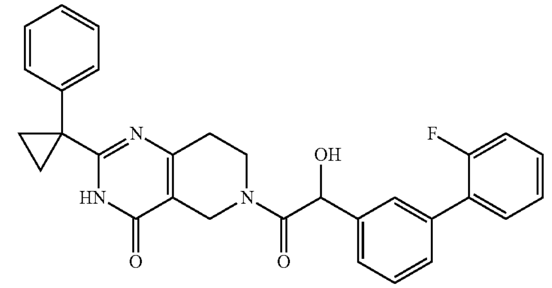 [SMILES: O=C(C(O)c1cccc(-c2ccccc2F)c1)N1CCc2nc(C3(c4ccccc4)CC3)[nH]c(=O)c2C1] | 1.73 min | 496.1 |
| 44-44 | INT-11-14 | 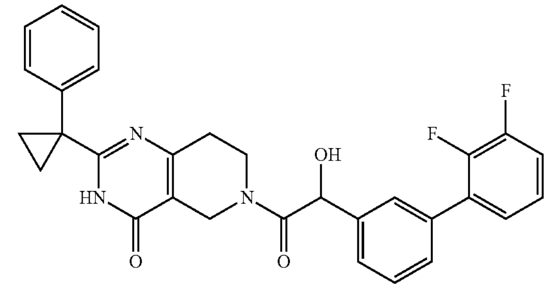 [SMILES: O=C(C(O)c1cccc(-c2cccc(F)c2F)c1)N1CCc2nc(C3(c4ccccc4)CC3)[nH]c(=O)c2C1] | 1.76 min | 514.0 |
| 44-45 | INT-11-14 | 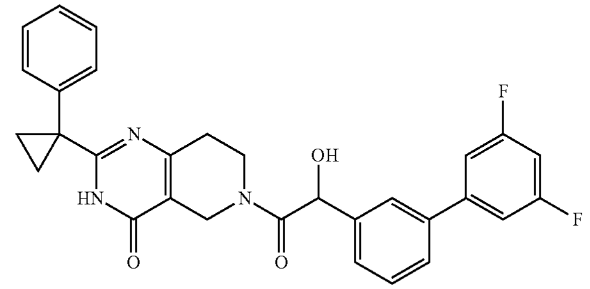 [SMILES: O=C(C(O)c1cccc(-c2cc(F)cc(F)c2)c1)N1CCc2nc(C3(c4ccccc4)CC3)[nH]c(=O)c2C1] | 1.79 min | 514.1 |

TABLE 78-7-continued
| | | | | |
|---|---|---|---|---|
| 44-46 | INT-11-14 | 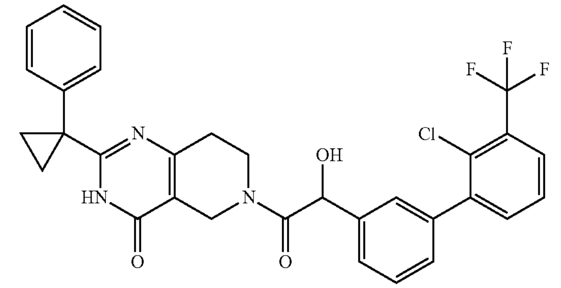 [SMILES: O=C(C(O)c1cccc(-c2cccc(C(F)(F)F)c2Cl)c1)N1CCc2nc(C3(c4ccccc4)CC3)[nH]c(=O)c2C1] | 1.92 min | 580.2 |
| 44-47 | INT-11-14 | 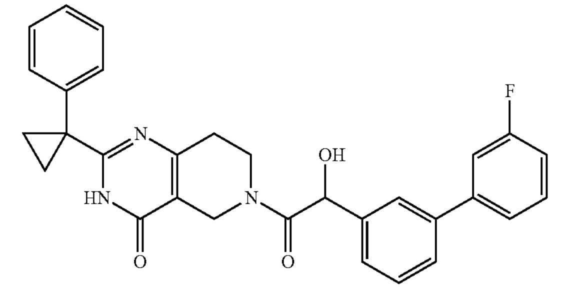 [SMILES: O=C(C(O)c1cccc(-c2cccc(F)c2)c1)N1CCc2nc(C3(c4ccccc4)CC3)[nH]c(=O)c2C1] | 1.75 min | 496.2 |
| 44-48 | INT-11-14 | 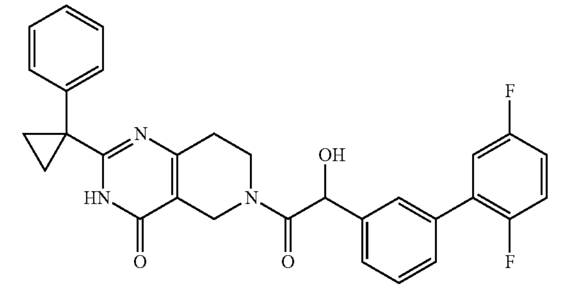 [SMILES: O=C(C(O)c1cccc(-c2cc(F)ccc2F)c1)N1CCc2nc(C3(c4ccccc4)CC3)[nH]c(=O)c2C1] | 1.76 min | 514.1 |
| 44-49 | INT-11-14 | 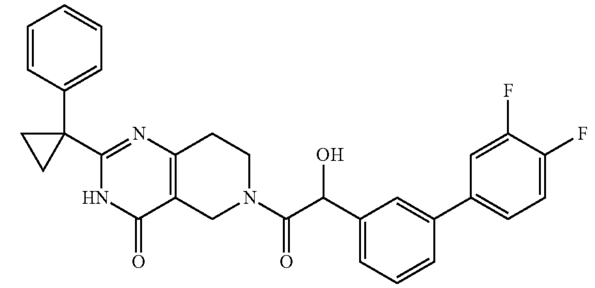 [SMILES: O=C(C(O)c1cccc(-c2ccc(F)c(F)c2)c1)N1CCc2nc(C3(c4ccccc4)CC3)[nH]c(=O)c2C1] | 1.78 min | 514.1 |
TABLE 78-8
| | | | | |
|---|---|---|---|---|
| 44-50 | INT-11-14 | 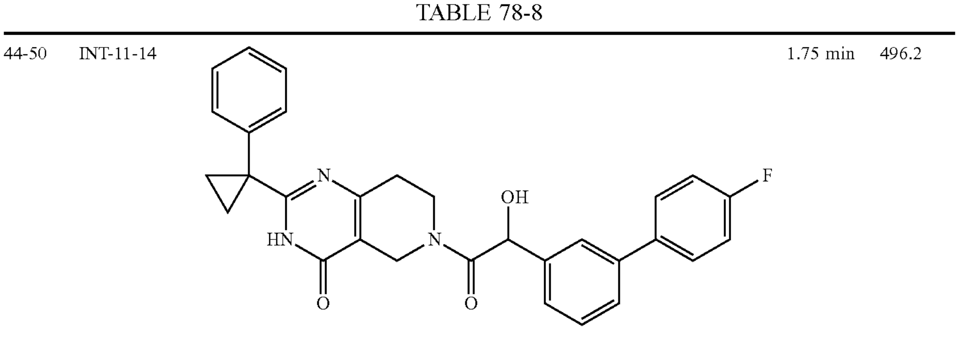 | 1.75 min | 496.2 |

TABLE 78-8-continued
| | | | | |
|---|---|---|---|---|
| 44-51 | INT-11-14 | 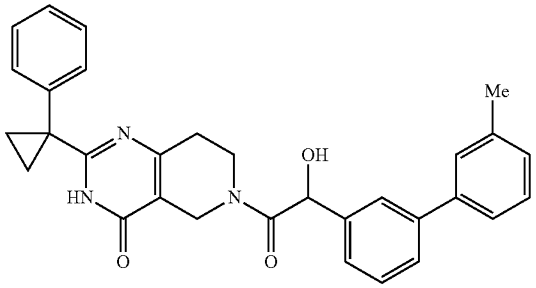 [SMILES: Cc1cccc(-c2cccc(C(O)C(=O)N3CCc4nc(C5(c6ccccc6)CC5)[nH]c(=O)c4C3)c2)c1] | 1.83 min | 492.2 |
| 44-52 | INT-11-14 | 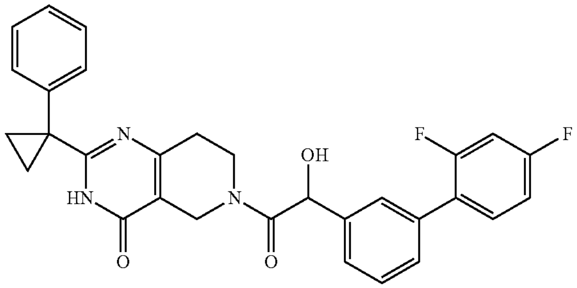 [SMILES: O=C(C(O)c1cccc(-c2ccc(F)cc2F)c1)N1CCc2nc(C3(c4ccccc4)CC3)[nH]c(=O)c2C1] | 1.76 min | 514.0 |
| 44-53 | INT-11-14 | 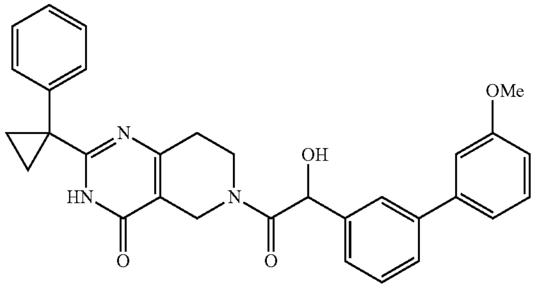 [SMILES: COc1cccc(-c2cccc(C(O)C(=O)N3CCc4nc(C5(c6ccccc6)CC5)[nH]c(=O)c4C3)c2)c1] | 1.73 min | 508.2 |
| 44-54 | INT-11-14 | 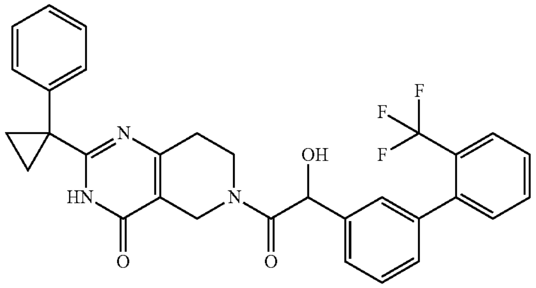 [SMILES: O=C(C(O)c1cccc(-c2ccccc2C(F)(F)F)c1)N1CCc2nc(C3(c4ccccc4)CC3)[nH]c(=O)c2C1] | 1.85 min | 546.2 |
| 44-55 | INT-11-14 | 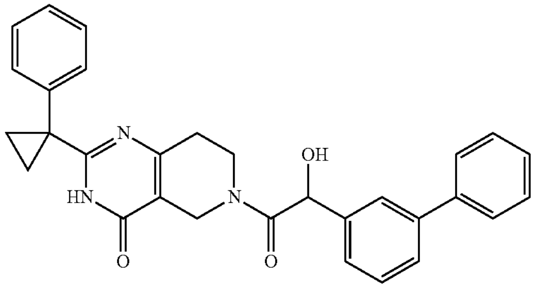 [SMILES: O=C(C(O)c1cccc(-c2ccccc2)c1)N1CCc2nc(C3(c4ccccc4)CC3)[nH]c(=O)c2C1] | 1.73 min | 478.0 |

TABLE 78-8-continued
| | | | | |
|---|---|---|---|---|
| 44-56 | INT-11-14 | 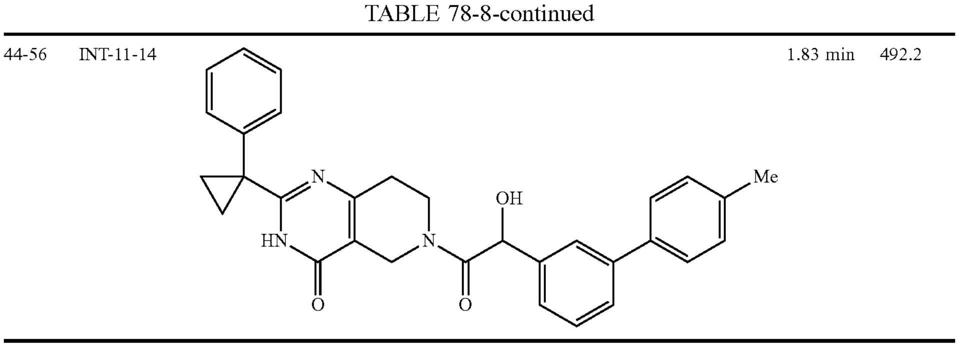 | 1.83 min | 492.2 |
TABLE 78-9
| | | | | |
|---|---|---|---|---|
| 44-57 | INT-11-14 | 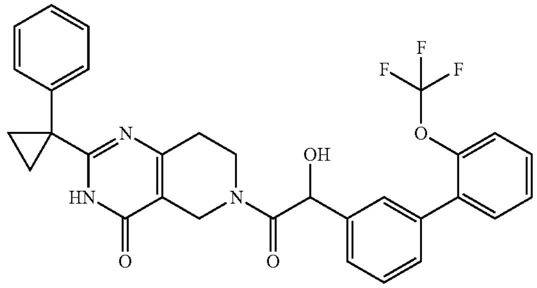 [SMILES: O=C(C(O)c1cccc(-c2ccccc2OC(F)(F)F)c1)N1CCc2nc(C3(c4ccccc4)CC3)[nH]c(=O)c2C1] | 1.88 min | 562.1 |
| 44-58 | INT-11-14 | 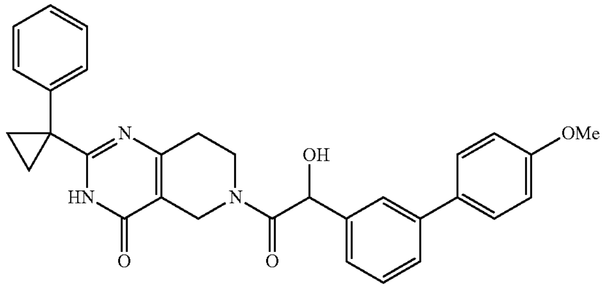 [SMILES: COc1ccc(-c2cccc(C(O)C(=O)N3CCc4nc(C5(c6ccccc6)CC5)[nH]c(=O)c4C3)c2)cc1] | 1.71 min | 508.2 |
| 44-59 | INT-11-14 | 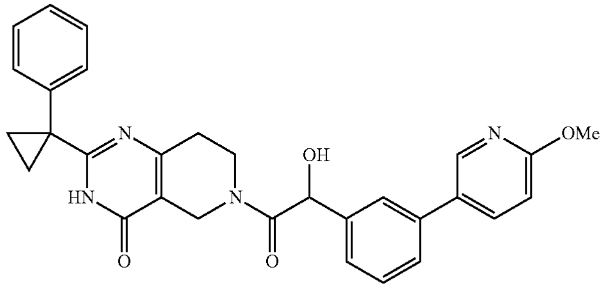 [SMILES: COc1ccc(-c2cccc(C(O)C(=O)N3CCc4nc(C5(c6ccccc6)CC5)[nH]c(=O)c4C3)c2)cn1] | 1.59 min | 509.2 |
| 44-60 | INT-11-14 | 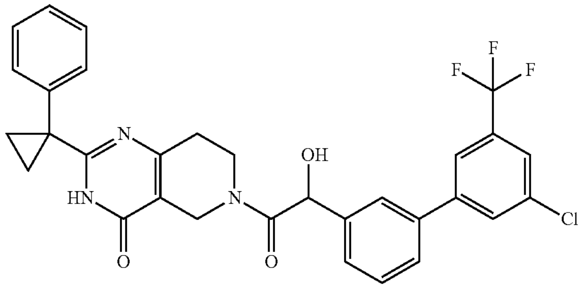 [SMILES: O=C(C(O)c1cccc(-c2cc(Cl)cc(C(F)(F)F)c2)c1)N1CCc2nc(C3(c4ccccc4)CC3)[nH]c(=O)c2C1] | 1.70 min | 562.2 |

TABLE 78-9-continued
| | | | | |
|---|---|---|---|---|
| 44-61 | INT-11-14 | 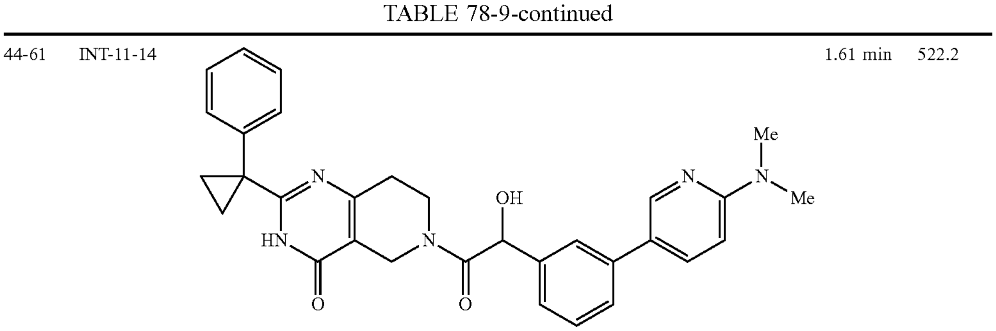 | 1.61 min | 522.2 |
| 44-62 | INT-11-14 | 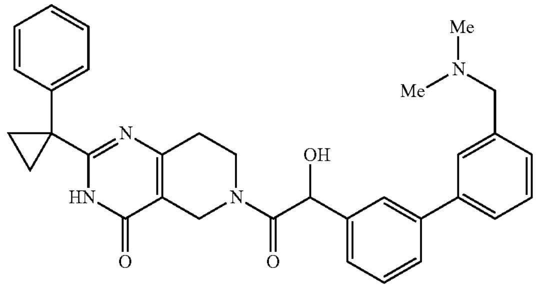 [SMILES: CN(C)Cc1cccc(-c2cccc(C(O)C(=O)N3CCc4nc(C5(c6ccccc6)CC5)[nH]c(=O)c4C3)c2)c1] | 1.39 min | 535.3 |
| 44-63 | INT-11-14 | 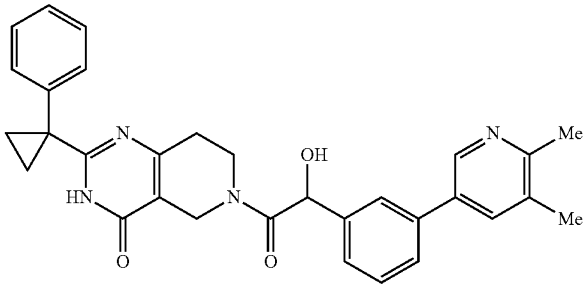 [SMILES: Cc1cc(-c2cccc(C(O)C(=O)N3CCc4nc(C5(c6ccccc6)CC5)[nH]c(=O)c4C3)c2)cnc1C] | 1.53 min | 507.2 |
TABLE 78-10
| | | | | |
|---|---|---|---|---|
| 44-64 | INT-11-14 | 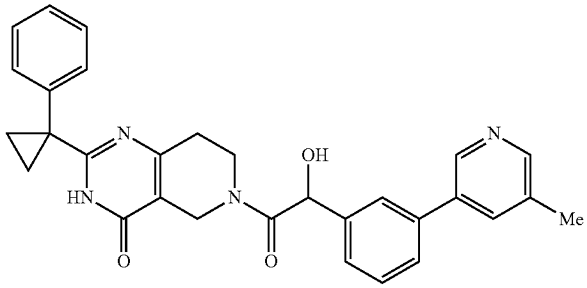 [SMILES: Cc1cncc(-c2cccc(C(O)C(=O)N3CCc4nc(C5(c6ccccc6)CC5)[nH]c(=O)c4C3)c2)c1] | 1.47 min | 493.2 |
| 44-65 | INT-11-14 | 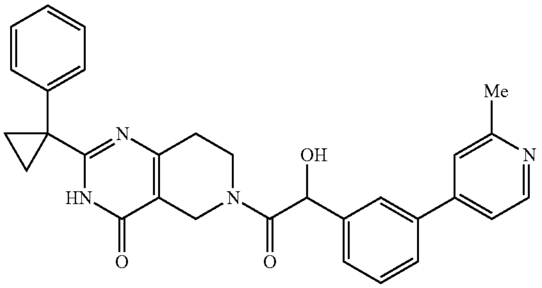 [SMILES: Cc1cc(-c2cccc(C(O)C(=O)N3CCc4nc(C5(c6ccccc6)CC5)[nH]c(=O)c4C3)c2)ccn1] | 1.42 min | 493.2 |

TABLE 78-10-continued
| | | | | |
|---|---|---|---|---|
| 44-66 | INT-11-14 | 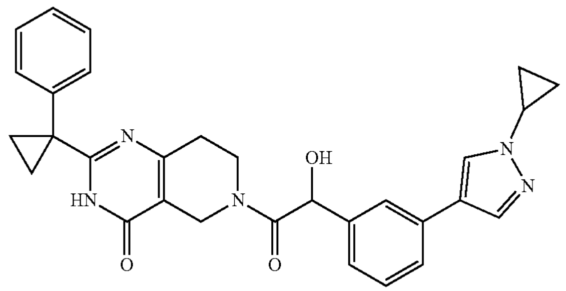 [SMILES: O=C(C(O)c1cccc(-c2cnn(C3CC3)c2)c1)N1CCc2nc(C3(c4ccccc4)CC3)[nH]c(=O)c2C1] | 1.46 min | 508.2 |
| 44-67 | INT-11-14 | 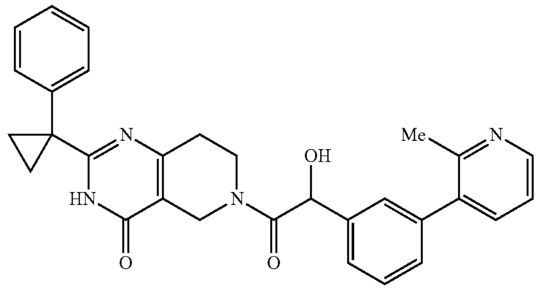 [SMILES: Cc1ncccc1-c1cccc(C(O)C(=O)N2CCc3nc(C4(c5ccccc5)CC4)[nH]c(=O)c3C2)c1] | 1.42 min | 493.2 |
| 44-68 | INT-11-14 | 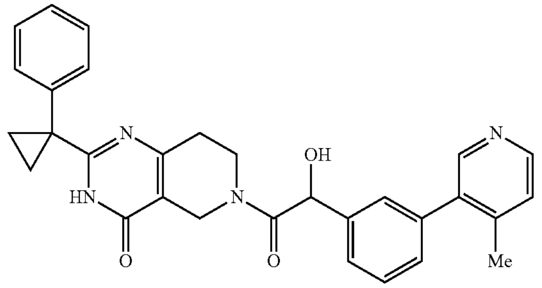 [SMILES: Cc1ccncc1-c1cccc(C(O)C(=O)N2CCc3nc(C4(c5ccccc5)CC4)[nH]c(=O)c3C2)c1] | 1.44 min | 493.2 |
| 44-69 | INT-11-14 | 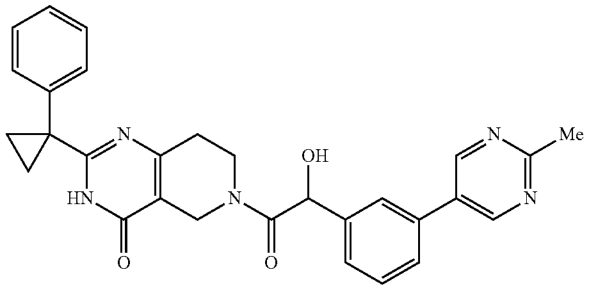 [SMILES: Cc1ncc(-c2cccc(C(O)C(=O)N3CCc4nc(C5(c6ccccc6)CC5)[nH]c(=O)c4C3)c2)cn1] | 1.30 min | 494.2 |
| 44-70 | INT-11-16 | 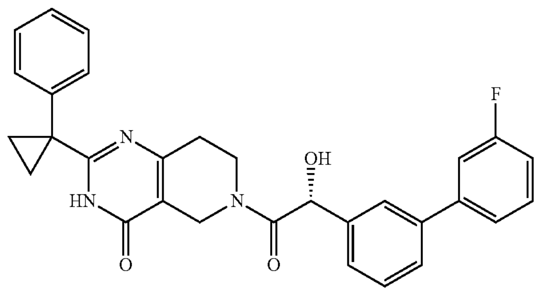 | 1.73 min | 496.0 |

TABLE 78-11
| | | | | |
|---|---|---|---|---|
| 44-71 | INT-11-16 | 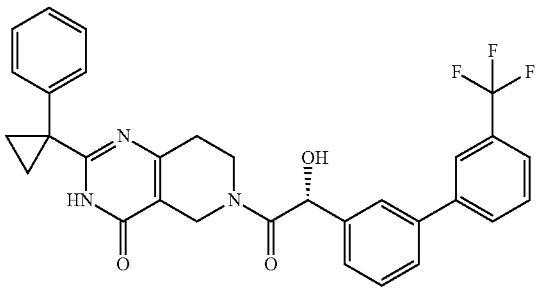 | 1.86 min | 546.0 |
| 44-72 | INT-11-16 | 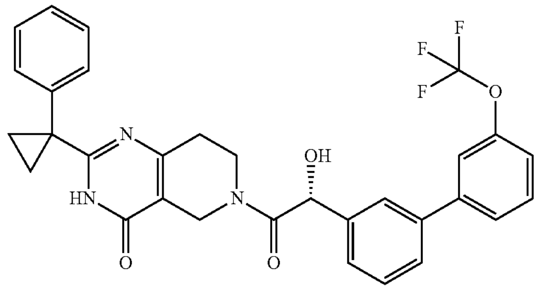 | 1.89 min | 562.0 |
| 44-73 | INT-11-16 | 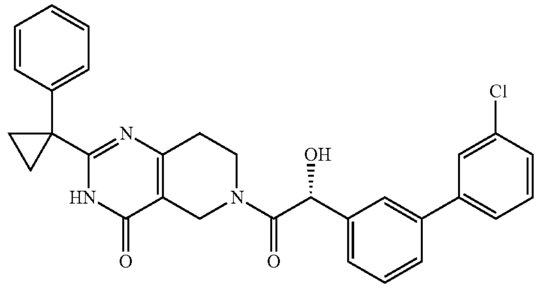 [SMILES: O=C([C@H](O)c1cccc(-c2cccc(Cl)c2)c1)N1CCc2nc(C3(c4ccccc4)CC3)[nH]c(=O)c2C1] | 1.84 min | 512.0 |
| 44-74 | INT-11-16 | 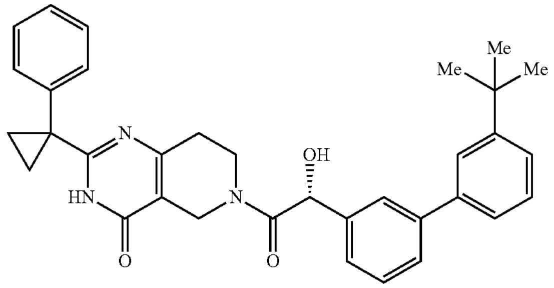 | 2.03 min | 534.1 |
| 44-75 | INT-11-17 | 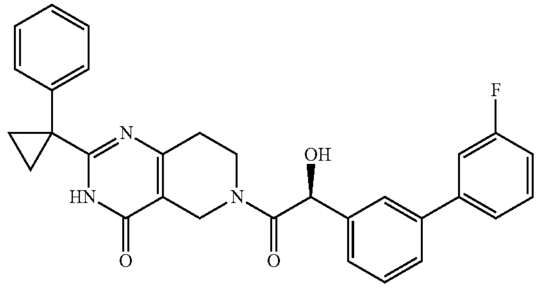 [SMILES: O=C([C@@H](O)c1cccc(-c2cccc(F)c2)c1)N1CCc2nc(C3(c4ccccc4)CC3)[nH]c(=O)c2C1] | 1.73 min | 496.0 |

TABLE 78-11-continued
| | | | | |
|---|---|---|---|---|
| 44-76 | INT-11-17 | 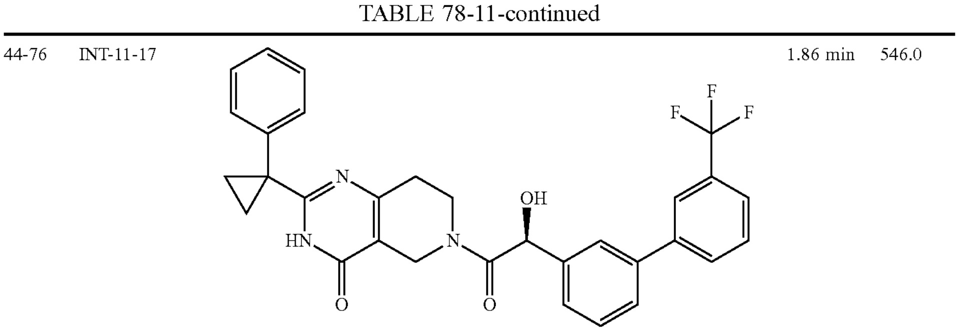 | 1.86 min | 546.0 |
| 44-77 | INT-11-16 | 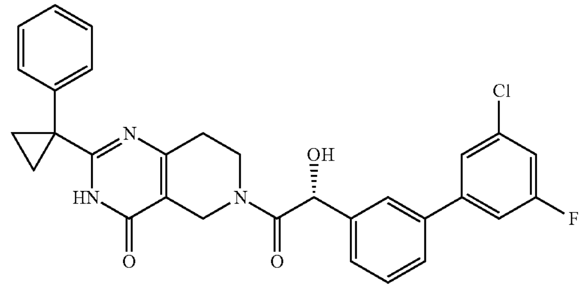 | 1.88 min | 530.0 |
TABLE 78-12
| | | | | |
|---|---|---|---|---|
| 44-78 | INT-11-16 | 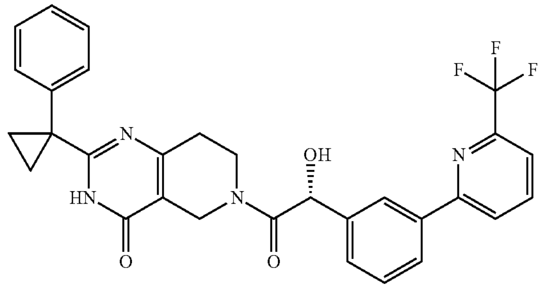 | 1.75 min | 547.0 |
| 44-79 | INT-11-16 | 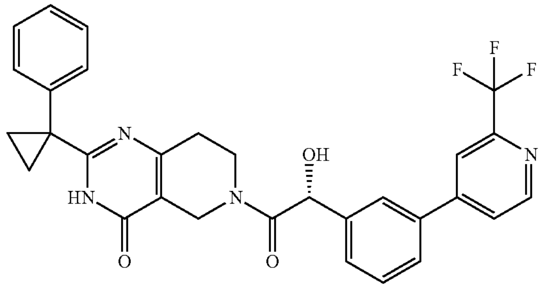 | 1.64 min | 547.0 |
| 44-80 | INT-11-17 | 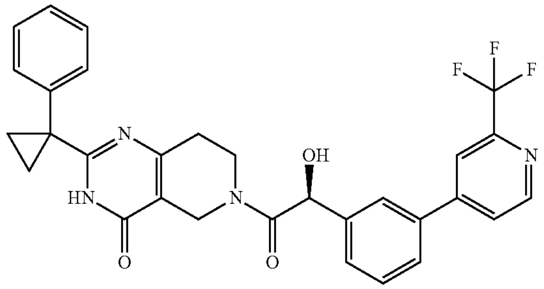 [SMILES: O=C([C@@H](O)c1cccc(-c2ccnc(C(F)(F)F)c2)c1)N1CCc2nc(C3(c4ccccc4)CC3)[nH]c(=O)c2C1] | 1.64 min | 547.0 |

TABLE 78-12-continued
| | | | | |
|---|---|---|---|---|
| 44-81 | INT-11-16 | 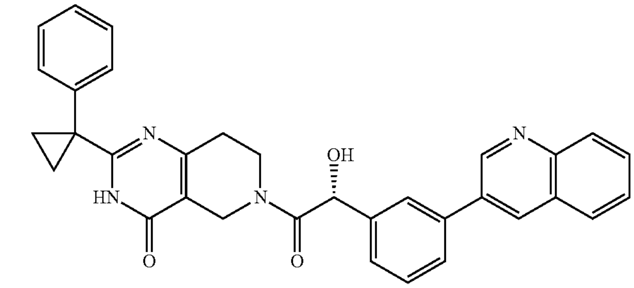 | 1.60 min | 529.0 |
| 44-82 | INT-11-16 | 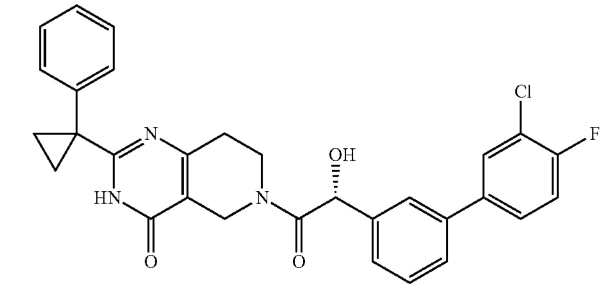 | 1.84 min | 529.9 |
| 44-83 | INT-11-16 | 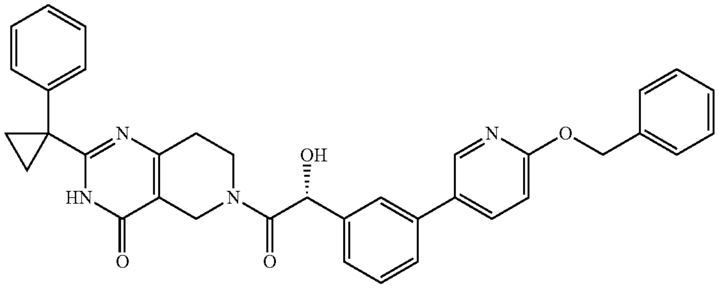 [SMILES: O=C([C@H](O)c1cccc(-c2ccc(OCc3ccccc3)nc2)c1)N1CCc2nc(C3(c4ccccc4)CC3)[nH]c(=O)c2C1] | 1.90 min | 585.0 |
| 44-84 | INT-11-16 | 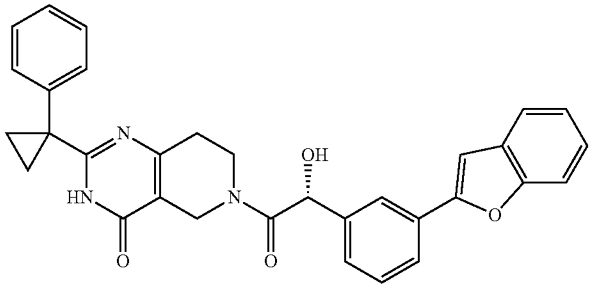 | 1.84 min | 518.0 |
TABLE 78-13
| | | | | |
|---|---|---|---|---|
| 44-85 | INT-11-16 | 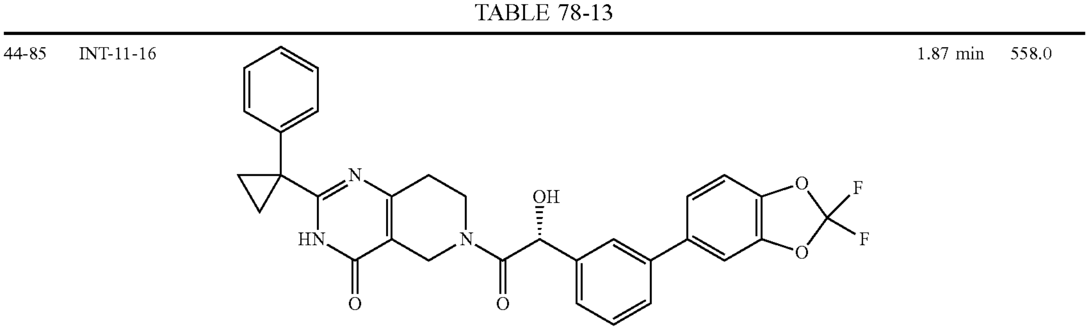 | 1.87 min | 558.0 |

TABLE 78-13-continued
| | | | | |
|---|---|---|---|---|
| 44-86 | INT-11-16 | 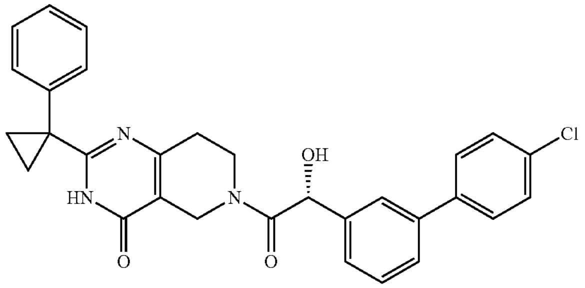 | 1.84 min | 512.0 |
| 44-87 | INT-11-16 | 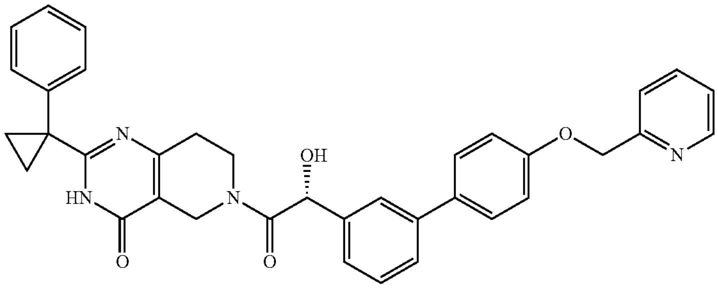 [SMILES: O=C([C@H](O)c1cccc(-c2ccc(OCc3ccccn3)cc2)c1)N1CCc2nc(C3(c4ccccc4)CC3)[nH]c(=O)c2C1] | 1.70 min | 585.1 |
| 44-88 | INT-11-16 | 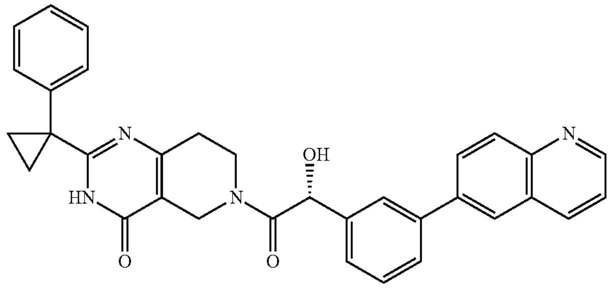 [SMILES: O=C([C@H](O)c1cccc(-c2ccc3ncccc3c2)c1)N1CCc2nc(C3(c4ccccc4)CC3)[nH]c(=O)c2C1] | 1.55 min | 529.0 |
| 44-89 | INT-11-16 | 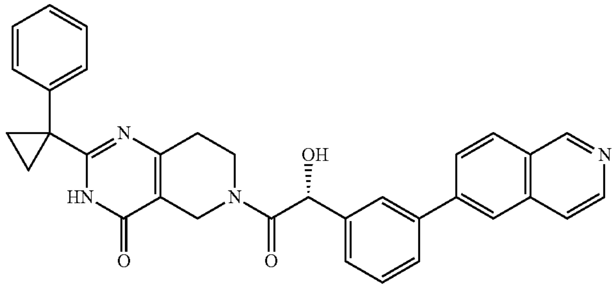 [SMILES: O=C([C@H](O)c1cccc(-c2ccc3cnccc3c2)c1)N1CCc2nc(C3(c4ccccc4)CC3)[nH]c(=O)c2C1] | 1.54 min | 529.0 |
| 44-90 | INT-11-16 | 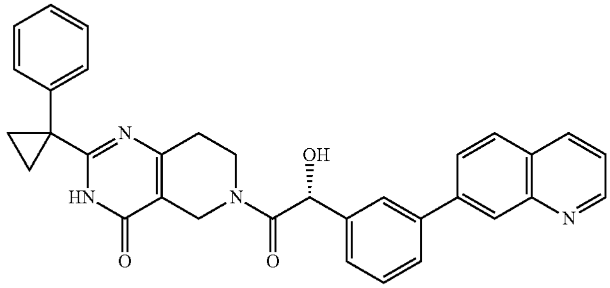 [SMILES: O=C([C@H](O)c1cccc(-c2ccc3cccnc3c2)c1)N1CCc2nc(C3(c4ccccc4)CC3)[nH]c(=O)c2C1] | 1.57 min | 529.0 |

TABLE 78-13-continued
| | | | | |
|---|---|---|---|---|
| 44-91 | INT-11-16 | 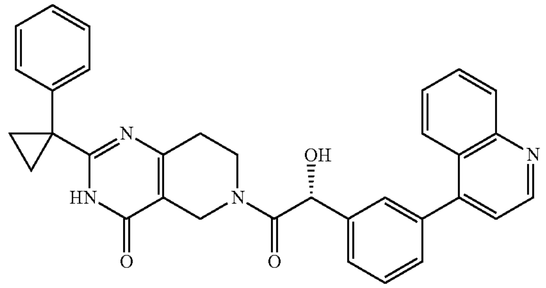 [SMILES: O=C([C@H](O)c1cccc(-c2ccnc3ccccc23)c1)N1CCc2nc(C3(c4ccccc4)CC3)[nH]c(=O)c2C1] | 1.57 min | 529.0 |
TABLE 78-14
| | | | | |
|---|---|---|---|---|
| 44-92 | INT-11-16 | 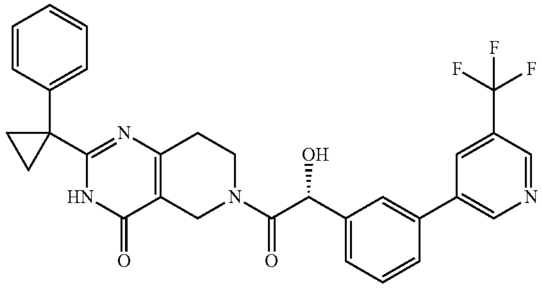 | 1.63 min | 547.0 |
| 44-93 | INT-11-16 | 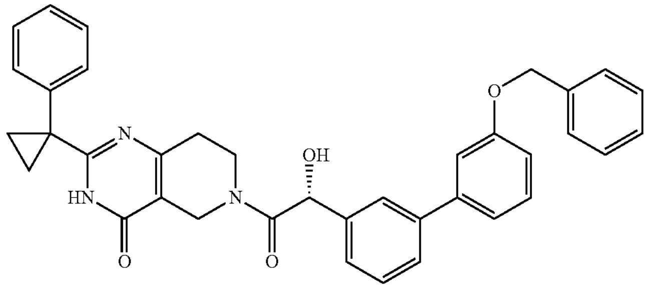 | 2.00 min | 584.1 |
| 44-94 | INT-11-16 | 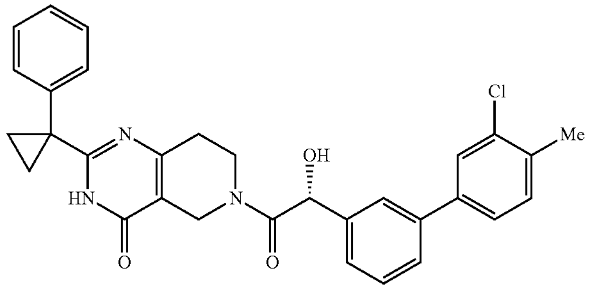 [SMILES: Cc1ccc(-c2cccc([C@@H](O)C(=O)N3CCc4nc(C5(c6ccccc6)CC5)[nH]c(=O)c4C3)c2)cc1Cl] | 1.97 min | 526.0 |
| 44-95 | INT-11-16 | 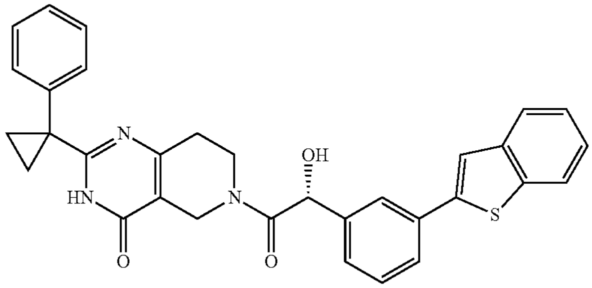 [SMILES: O=C([C@H](O)c1cccc(-c2cc3ccccc3s2)c1)N1CCc2nc(C3(c4ccccc4)CC3)[nH]c(=O)c2C1] | 1.92 min | 534.0 |

TABLE 78-14-continued
| | | | | |
|---|---|---|---|---|
| 44-96 | INT-11-16 | 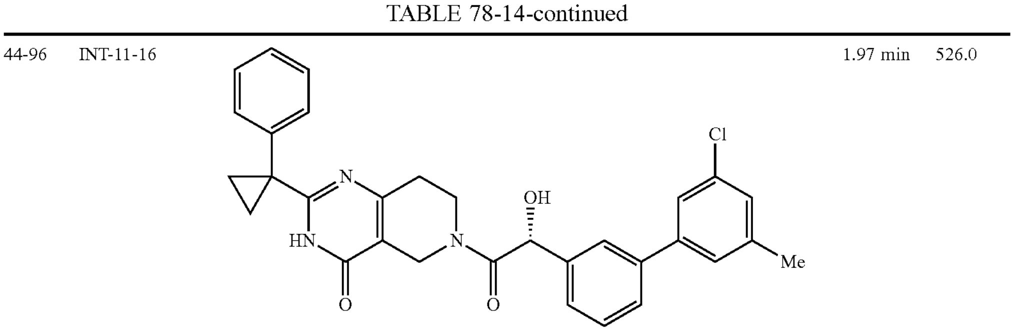 | 1.97 min | 526.0 |
| 44-97 | INT-11-16 | 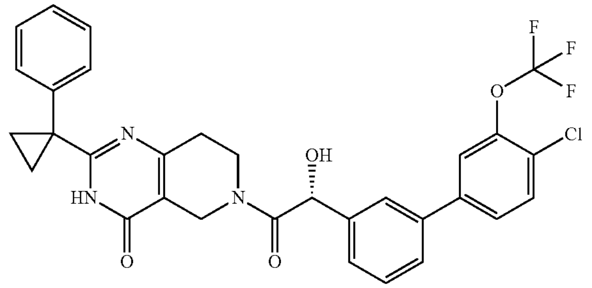 [SMILES: O=C([C@H](O)c1cccc(-c2ccc(Cl)c(OC(F)(F)F)c2)c1)N1CCc2nc(C3(c4ccccc4)CC3)[nH]c(=O)c2C1] | 2.03 min | 596.0 |
| 44-98 | INT-11-16 | 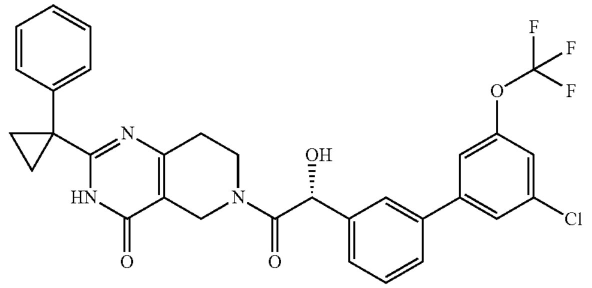 [SMILES: O=C([C@H](O)c1cccc(-c2cc(Cl)cc(OC(F)(F)F)c2)c1)N1CCc2nc(C3(c4ccccc4)CC3)[nH]c(=O)c2C1] | 2.06 min | 596.0 |
TABLE 78-15
| | | | | |
|---|---|---|---|---|
| 44-99 | INT-11-16 | 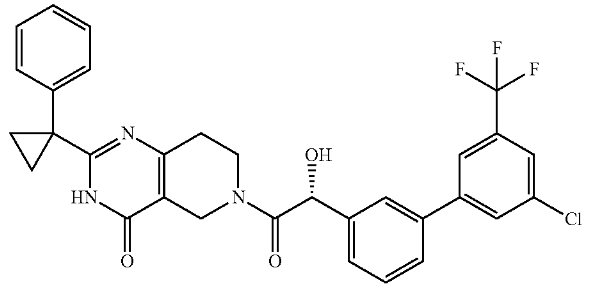 [SMILES: O=C([C@H](O)c1cccc(-c2cc(Cl)cc(C(F)(F)F)c2)c1)N1CCc2nc(C3(c4ccccc4)CC3)[nH]c(=O)c2C1] | 2.03 min | 579.9 |
| 44-100 | INT-11-16 | 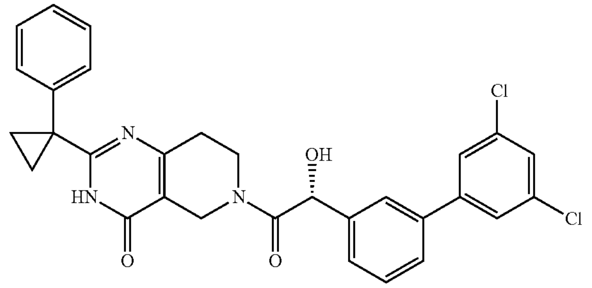 | 2.02 min | 545.9 |

TABLE 78-15-continued
| | | | | |
|---|---|---|---|---|
| 44-101 | INT-11-16 | 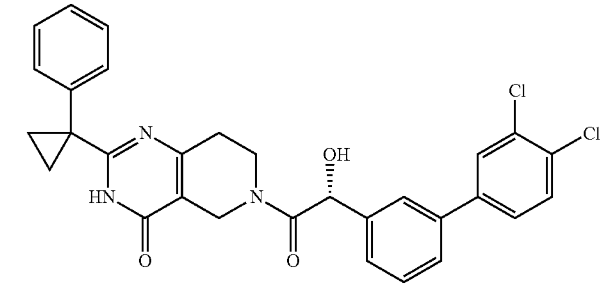 [SMILES: O=C([C@H](O)c1cccc(-c2ccc(Cl)c(Cl)c2)c1)N1CCc2nc(C3(c4ccccc4)CC3)[nH]c(=O)c2C1] | 1.98 min | 545.9 |
| 44-102 | INT-11-16 | 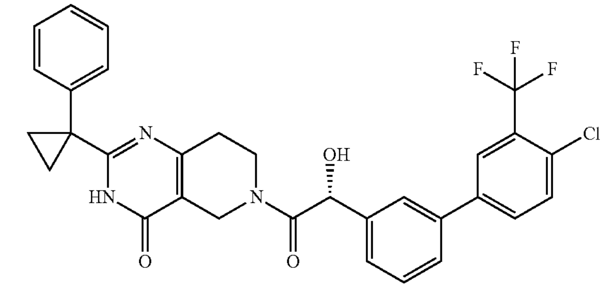 [SMILES: O=C([C@H](O)c1cccc(-c2ccc(Cl)c(C(F)(F)F)c2)c1)N1CCc2nc(C3(c4ccccc4)CC3)[nH]c(=O)c2C1] | 1.99 min | 579.9 |
| 44-103 | INT-11-16 | 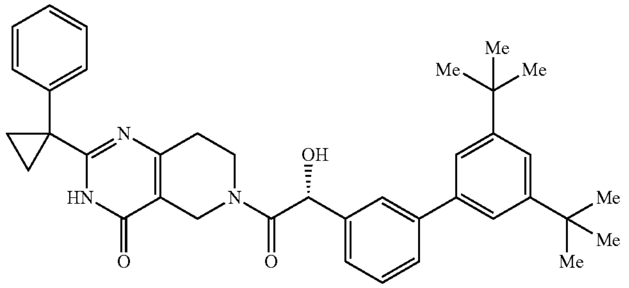 [SMILES: CC(C)(C)c1cc(-c2cccc([C@@H](O)C(=O)N3CCc4nc(C5(c6ccccc6)CC5)[nH]c(=O)c4C3)c2)cc(C(C)(C)C)c1] | 2.32 min | 590.1 |
| 44-104 | INT-11-16 | 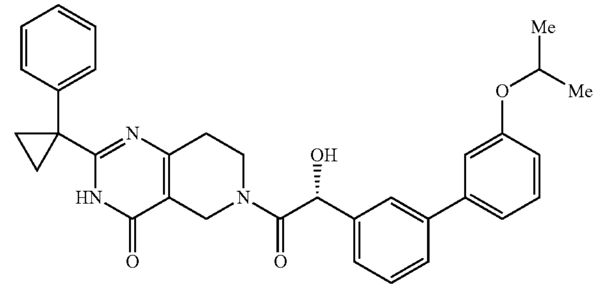 [SMILES: CC(C)Oc1cccc(-c2cccc([C@@H](O)C(=O)N3CCc4nc(C5(c6ccccc6)CC5)[nH]c(=O)c4C3)c2)c1] | 1.91 min | 536.0 |
| 44-105 | INT-11-16 | 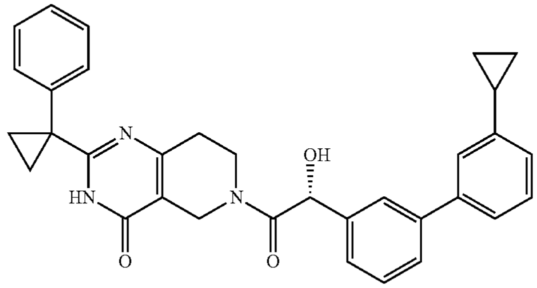 [SMILES: O=C([C@H](O)c1cccc(-c2cccc(C3CC3)c2)c1)N1CCc2nc(C3(c4ccccc4)CC3)[nH]c(=O)c2C1] | 1.92 min | 518.0 |

TABLE 78-16
| | | | | |
|---|---|---|---|---|
| 44-106 | INT-11-16 | 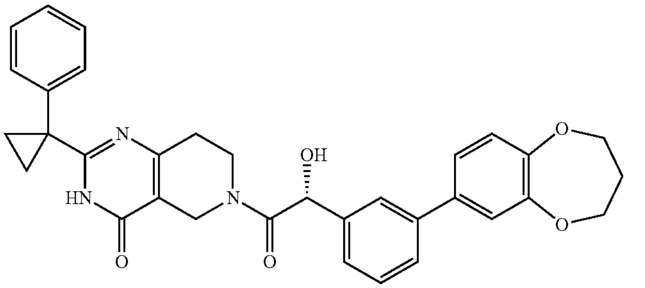 [SMILES: O=C([C@H](O)c1cccc(-c2ccc3c(c2)OCCCO3)c1)N1CCc2nc(C3(c4ccccc4)CC3)[nH]c(=O)c2C1] | 1.72 min | 550.0 |
| 44-107 | INT-11-16 | 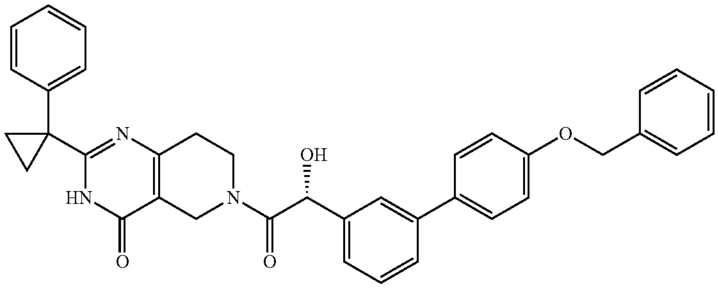 [SMILES: O=C([C@H](O)c1cccc(-c2ccc(OCc3ccccc3)cc2)c1)N1CCc2nc(C3(c4ccccc4)CC3)[nH]c(=O)c2C1] | 1.99 min | 584.0 |
| 44-108 | INT-11-16 | 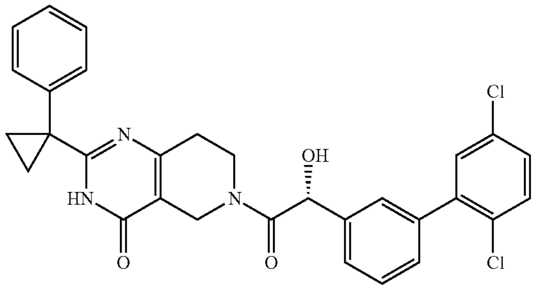 | 1.95 min | 545.9 |
| 44-109 | INT-11-16 | 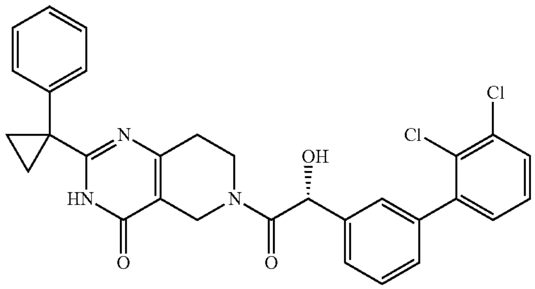 [SMILES: O=C([C@H](O)c1cccc(-c2cccc(Cl)c2Cl)c1)N1CCc2nc(C3(c4ccccc4)CC3)[nH]c(=O)c2C1] | 1.93 min | 545.9 |
| 44-110 | INT-11-16 | 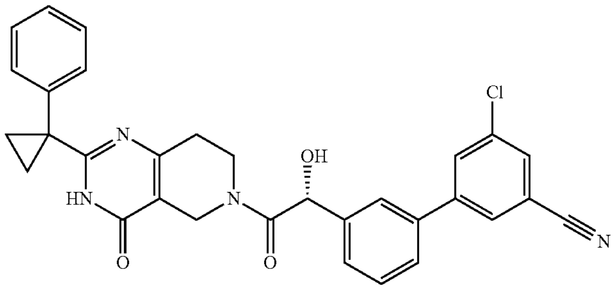 [SMILES: N#Cc1cc(Cl)cc(-c2cccc([C@@H](O)C(=O)N3CCc4nc(C5(c6ccccc6)CC5)[nH]c(=O)c4C3)c2)c1] | 1.79 min | 536.9 |

TABLE 78-16-continued
| | | | | |
|---|---|---|---|---|
| 44-111 | INT-11-16 | 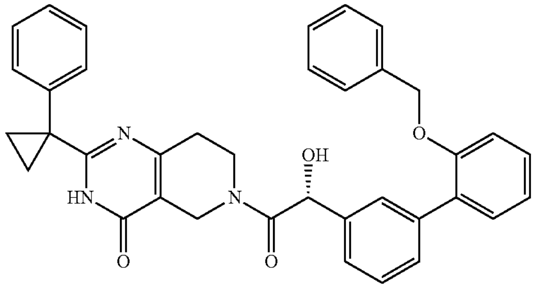 [SMILES: O=C([C@H](O)c1cccc(-c2ccccc2OCc2ccccc2)c1)N1CCc2nc(C3(c4ccccc4)CC3)[nH]c(=O)c2C1] | 1.99 min | 584.0 |
| 44-112 | INT-11-16 | 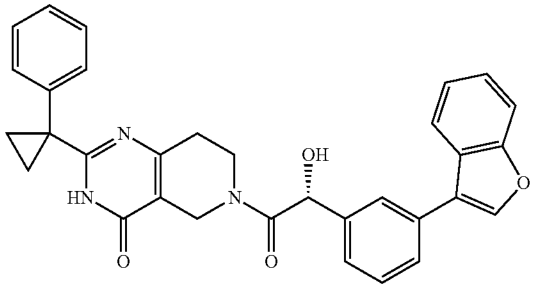 [SMILES: O=C([C@H](O)c1cccc(-c2coc3ccccc23)c1)N1CCc2nc(C3(c4ccccc4)CC3)[nH]c(=O)c2C1] | 1.82 min | 517.9 |
TABLE 78-17
| | | | | |
|---|---|---|---|---|
| 44-113 | INT-11-16 | 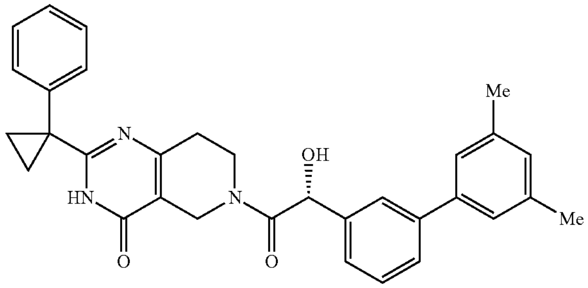 | 1.94 min | 506.0 |
| 44-114 | INT-11-16 | 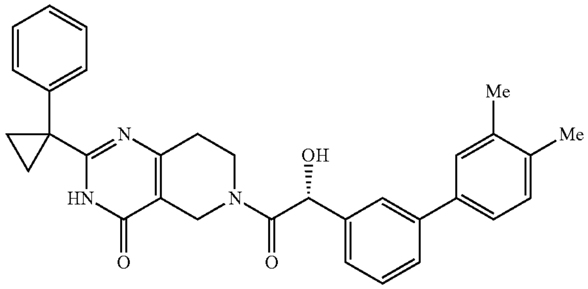 [SMILES: Cc1ccc(-c2cccc([C@@H](O)C(=O)N3CCc4nc(C5(c6ccccc6)CC5)[nH]c(=O)c4C3)c2)cc1C] | 1.92 min | 506.0 |
| 44-115 | INT-11-16 | 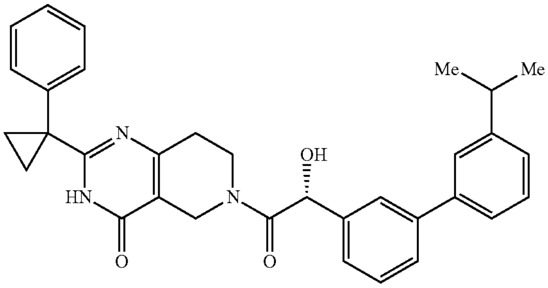 [SMILES: CC(C)c1cccc(-c2cccc([C@@H](O)C(=O)N3CCc4nc(C5(c6ccccc6)CC5)[nH]c(=O)c4C3)c2)c1] | 2.01 min | 520.0 |

TABLE 78-17-continued

| | | | | |
|---|---|---|---|---|
| 44-116 | INT-11-16 | 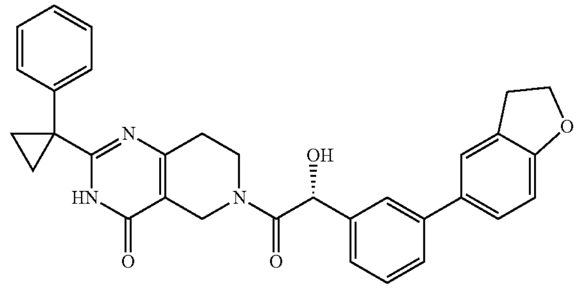 [SMILES: O=C([C@H](O)c1cccc(-c2ccc3c(c2)CCO3)c1)N1CCc2nc(C3(c4ccccc4)CC3)[nH]c(=O)c2C1] | 1.71 min | 520.0 |
| 44-117 | INT-11-16 | 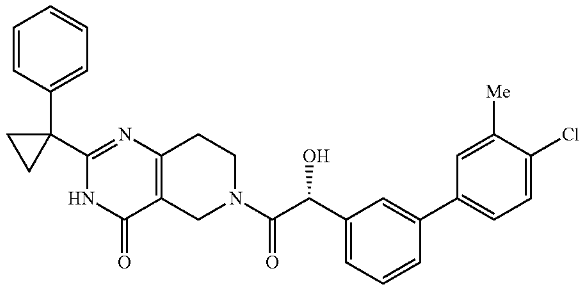 [SMILES: Cc1cc(-c2cccc([C@@H](O)C(=O)N3CCc4nc(C5(c6ccccc6)CC5)[nH]c(=O)c4C3)c2)ccc1Cl] | 1.97 min | 525.9 |
| 44-118 | INT-11-14 | 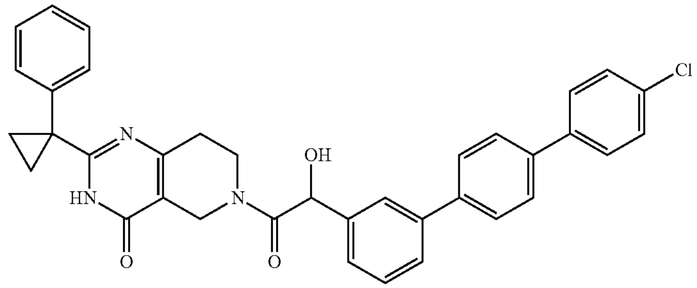 [SMILES: O=C(C(O)c1cccc(-c2ccc(-c3ccc(Cl)cc3)cc2)c1)N1CCc2nc(C3(c4ccccc4)CC3)[nH]c(=O)c2C1] | 2.12 min | 588.1 |
| 44-119 | INT-11-14 | 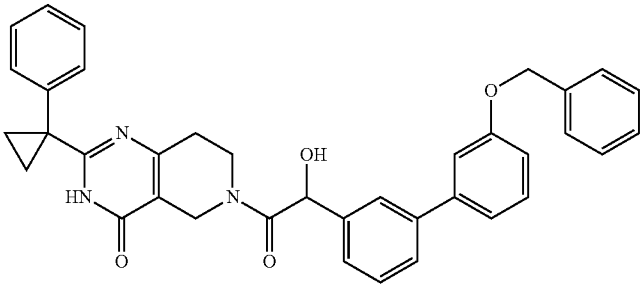 [SMILES: O=C(C(O)c1cccc(-c2cccc(OCc3ccccc3)c2)c1)N1CCc2nc(C3(c4ccccc4)CC3)[nH]c(=O)c2C1] | 1.99 min | 584.3 |

The following pyrimidin-4(3H)-one derivatives (Ex-45-1 to Ex-45-13) are prepared according to the procedure of Ex-44-1 or the general synthesis in scheme-5 from INT-11-35 or INT-11-45 and the known boronic acid derivatives. The further purification is carried out by preparative LC-MS or SFC-MS system in usual manner. The retention time and observed MS by HPLC-QC method are summarized in Tables 79-1 to 79-2.

TABLE 79-1
| Ex. | Intermediate (INT) | Structure | Retention time | Observed MS |
|---|---|---|---|---|
| 45-1 | INT-11-35 | 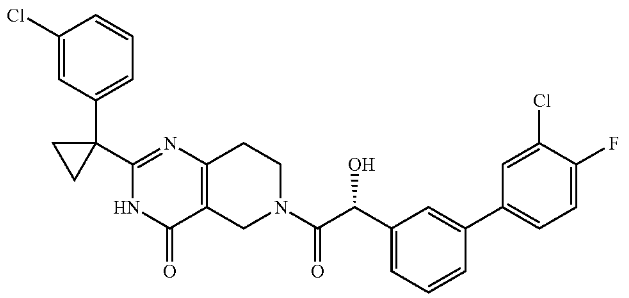 [SMILES: O=C([C@H](O)c1cccc(-c2ccc(F)c(Cl)c2)c1)N1CCc2nc(C3(c4cccc(Cl)c4)CC3)[nH]c(=O)c2C1] | 3.78 min | 562.1 |
| 45-2 | INT-11-35 | 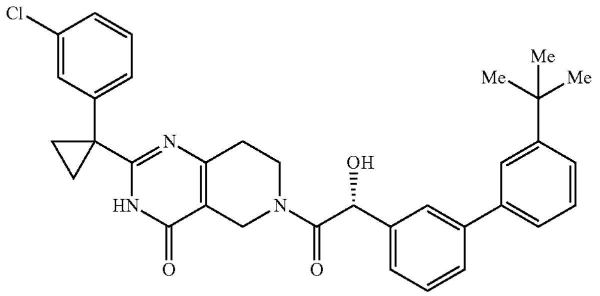 [SMILES: CC(C)(C)c1cccc(-c2cccc([C@@H](O)C(=O)N3CCc4nc(C5(c6cccc(Cl)c6)CC5)[nH]c(=O)c4C3)c2)c1] | 4.19 min | 566.3 |
| 45-3 | INT-11-35 | 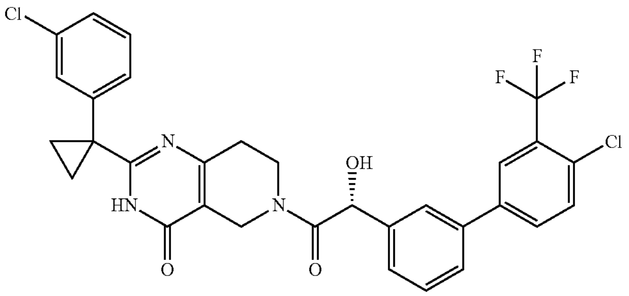 [SMILES: O=C([C@H](O)c1cccc(-c2ccc(Cl)c(C(F)(F)F)c2)c1)N1CCc2nc(C3(c4cccc(Cl)c4)CC3)[nH]c(=O)c2C1] | 4.03 min | 612.1 |
| 45-4 | INT-11-35 | 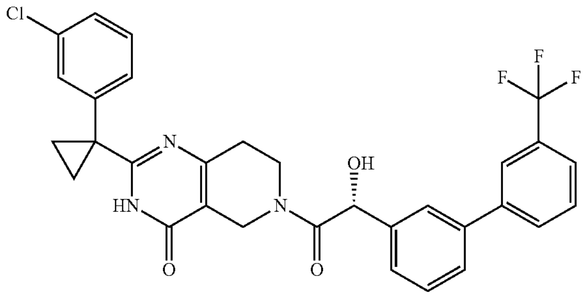 [SMILES: O=C([C@H](O)c1cccc(-c2cccc(C(F)(F)F)c2)c1)N1CCc2nc(C3(c4cccc(Cl)c4)CC3)[nH]c(=O)c2C1] | 3.83 min | 578.2 |
| 45-5 | INT-11-35 | 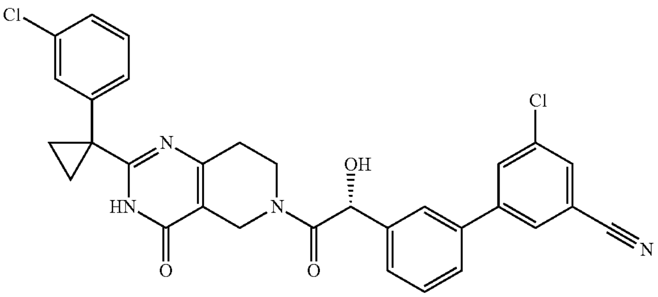 [SMILES: N#Cc1cc(Cl)cc(-c2cccc([C@@H](O)C(=O)N3CCc4nc(C5(c6cccc(Cl)c6)CC5)[nH]c(=O)c4C3)c2)c1] | 3.61 min | 569.1 |

TABLE 79-1-continued
| Ex. | Intermediate (INT) | Structure | Retention time | Observed MS |
|---|---|---|---|---|
| 45-6 | INT-11-35 | 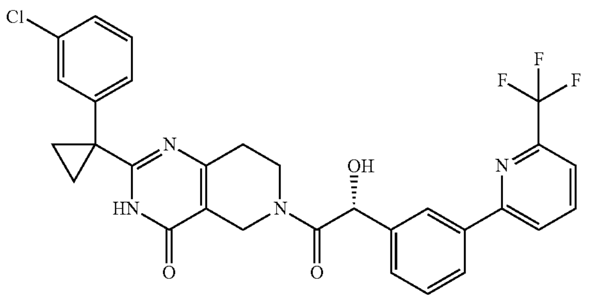 [SMILES: O=C([C@H](O)c1cccc(-c2cccc(C(F)(F)F)n2)c1)N1CCc2nc(C3(c4cccc(Cl)c4)CC3)[nH]c(=O)c2C1] | 3.63 min | 579.2 |
TABLE 79-2
| | | | | |
|---|---|---|---|---|
| 45-7 | INT-11-35 | 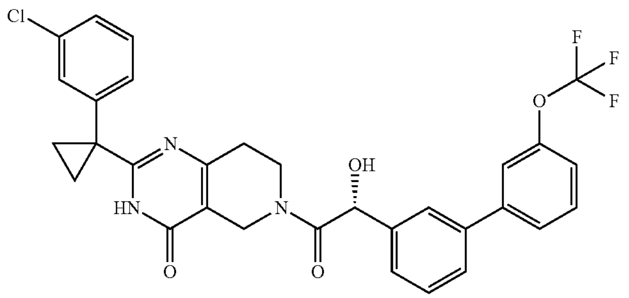 [SMILES: O=C([C@H](O)c1cccc(-c2cccc(OC(F)(F)F)c2)c1)N1CCc2nc(C3(c4cccc(Cl)c4)CC3)[nH]c(=O)c2C1] | 3.93 min | 594.2 |
| 45-8 | INT-11-35 | 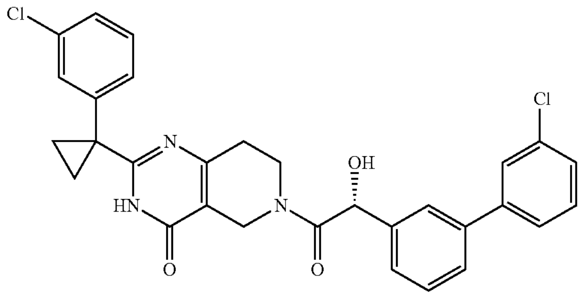 [SMILES: O=C([C@H](O)c1cccc(-c2cccc(Cl)c2)c1)N1CCc2nc(C3(c4cccc(Cl)c4)CC3)[nH]c(=O)c2C1] | 3.74 min | 544.1 |
| 45-9 | INT-11-35 | 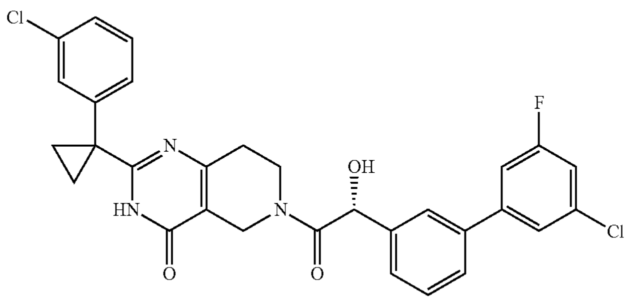 [SMILES: O=C([C@H](O)c1cccc(-c2cc(F)cc(Cl)c2)c1)N1CCc2nc(C3(c4cccc(Cl)c4)CC3)[nH]c(=O)c2C1] | 3.83 min | 562.1 |

TABLE 79-2-continued

| | | | | |
|---|---|---|---|---|
| 45-10 | INT-11-35 | 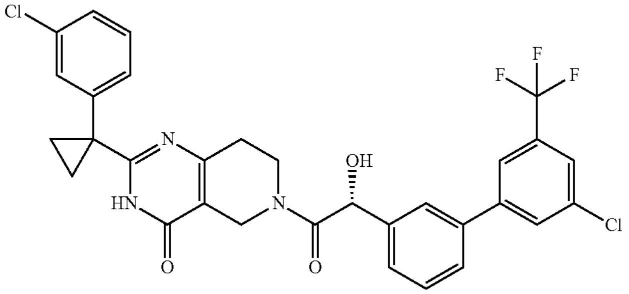 [SMILES: O=C([C@H](O)c1cccc(-c2cc(Cl)cc(C(F)(F)F)c2)c1)N1CCc2nc(C3(c4cccc(Cl)c4)CC3)[nH]c(=O)c2C1] | 4.11 min | 612.1 |
| 45-11 | INT-11-35 | 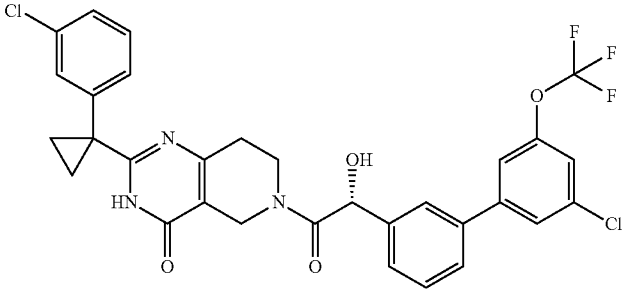 [SMILES: O=C([C@H](O)c1cccc(-c2cc(Cl)cc(OC(F)(F)F)c2)c1)N1CCc2nc(C3(c4cccc(Cl)c4)CC3)[nH]c(=O)c2C1] | 4.21 min | 628.1 |
| 45-12 | INT-11-45 | 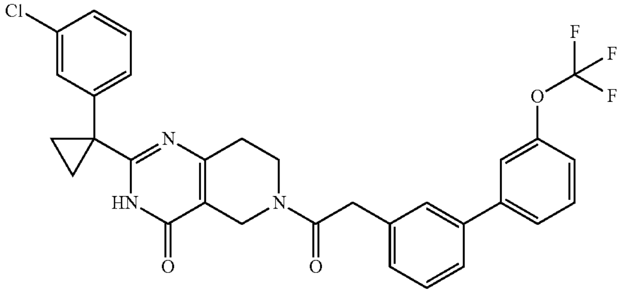 [SMILES: O=C(Cc1cccc(-c2cccc(OC(F)(F)F)c2)c1)N1CCc2nc(C3(c4cccc(Cl)c4)CC3)[nH]c(=O)c2C1] | 2.20 min | 580.4 |
| 45-13 | INT-11-45 | 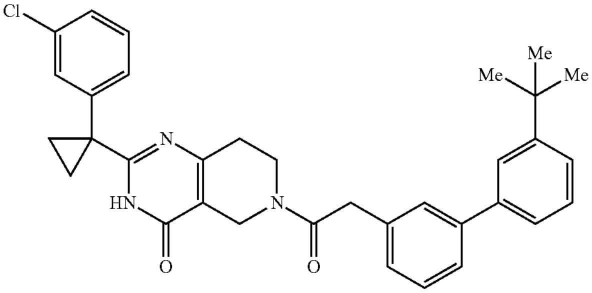 [SMILES: CC(C)(C)c1cccc(-c2cccc(CC(=O)N3CCc4nc(C5(c6cccc(Cl)c6)CC5)[nH]c(=O)c4C3)c2)c1] | 2.32 min | 552.5 |

The following pyrimidin-4(3H)-one derivatives (Ex-46-1 to Ex-46-6) are prepared according to the procedure of Ex-44-1 or the general synthesis in scheme-5 from INT-11-18 and the known boronic acid derivatives. The further purification is carried out by preparative LC-MS or SFC-MS system in usual manner. The retention time and observed MS by HPLC-QC method are summarized in Table 80.

TABLE 80
| Ex. | Intermediate (INT) | Structure | Retention time | Observed MS |
|---|---|---|---|---|
| 46-1 | INT-11-18 | 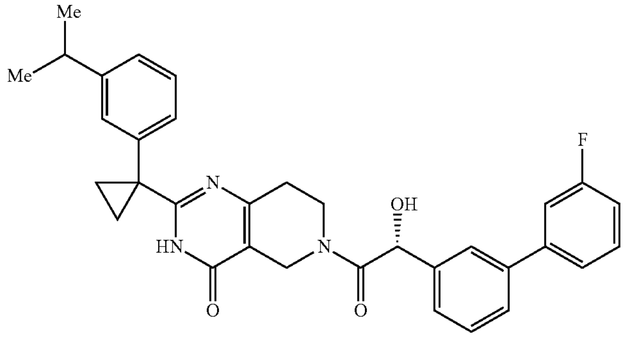 [SMILES: CC(C)c1cccc(C2(c3nc4c(c(=O)[nH]3)CN(C(=O)[C@H](O)c3cccc(-c5cccc(F)c5)c3)CC4)CC2)c1] | 1.99 min | 538.0 |
| 46-2 | INT-11-18 | 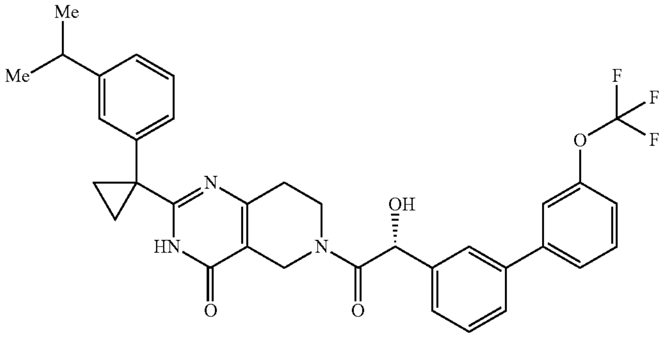 [SMILES: CC(C)c1cccc(C2(c3nc4c(c(=O)[nH]3)CN(C(=O)[C@H](O)c3cccc(-c5cccc(OC(F)(F)F)c5)c3)CC4)CC2)c1] | 2.12 min | 604.0 |
| 46-3 | INT-11-18 | 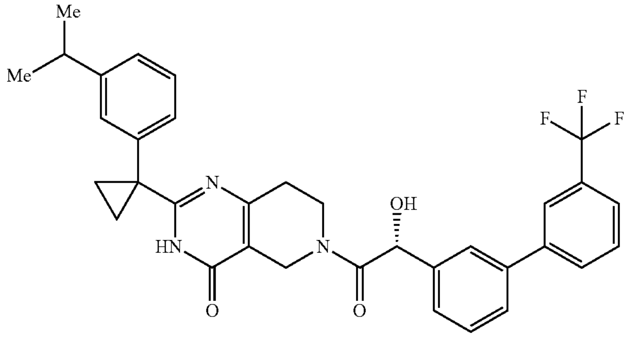 [SMILES: CC(C)c1cccc(C2(c3nc4c(c(=O)[nH]3)CN(C(=O)[C@H](O)c3cccc(-c5cccc(C(F)(F)F)c5)c3)CC4)CC2)c1] | 2.09 min | 588.0 |
| 46-4 | INT-11-18 | 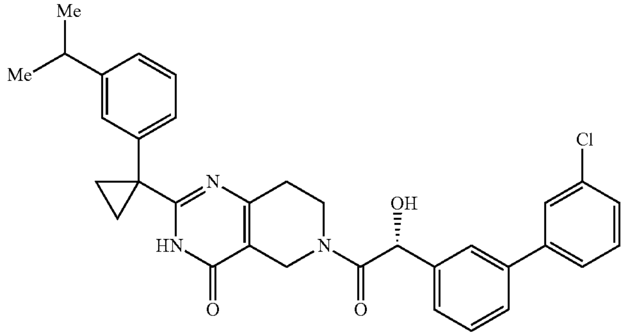 | 2.09 min | 554.0 |

TABLE 80-continued

| Ex. | Intermediate (INT) | Structure | Retention time | Observed MS |
|---|---|---|---|---|
| 46-5 | INT-11-18 | 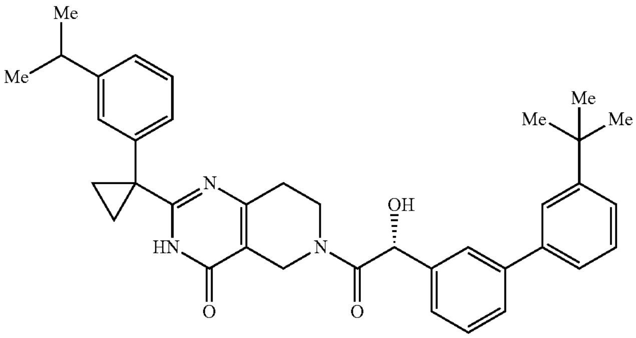 [SMILES: CC(C)c1cccc(C2(c3nc4c(c(=O)[nH]3)CN(C(=O)[C@H](O)c3cccc(-c5cccc(C(C)(C)C)c5)c3)CC4)CC2)c1] | 2.25 min | 576.1 |
| 46-6 | INT-11-18 | 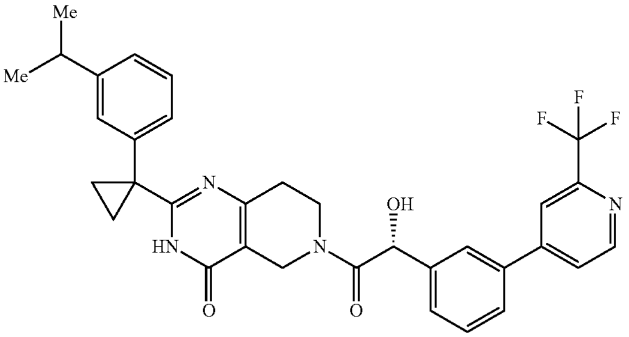 [SMILES: CC(C)c1cccc(C2(c3nc4c(c(=O)[nH]3)CN(C(=O)[C@H](O)c3cccc(-c5ccnc(C(F)(F)F)c5)c3)CC4)CC2)c1] | 1.90 min | 589.0 |

The following pyrimidin-4(3H)-one derivatives (Ex-47-1 to Ex-47-6) are prepared according to the procedure of Ex-44-1 or the general synthesis in scheme-5 from INT-11-19 and the known boronic acid derivatives. The further purification is carried out by preparative LC-MS or SFC-MS system in usual manner. The retention time and observed MS by HPLC-QC method are summarized in Table 81.

TABLE 81

| Ex. | Intermediate (INT) | Structure | Retention time | Observed MS |
|---|---|---|---|---|
| 47-1 | INT-11-19 | 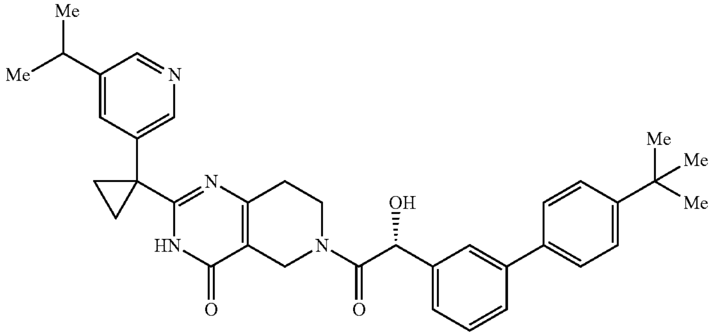 [SMILES: CC(C)c1cncc(C2(c3nc4c(c(=O)[nH]3)CN(C(=O)[C@H](O)c3cccc(-c5ccc(C(C)(C)C)cc5)c3)CC4)CC2)c1] | 1.96 min | 577.1 |

TABLE 81-continued
| Ex. | Intermediate (INT) | Structure | Retention time | Observed MS |
|---|---|---|---|---|
| 47-2 | INT-11-19 | 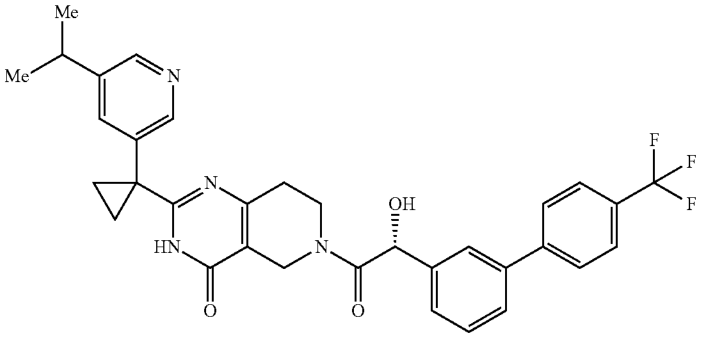 [SMILES: CC(C)c1cncc(C2(c3nc4c(c(=O)[nH]3)CN(C(=O)[C@H](O)c3cccc(-c5ccc(C(F)(F)F)cc5)c3)CC4)CC2)c1] | 1.79 min | 589.0 |
| 47-3 | INT-11-19 | 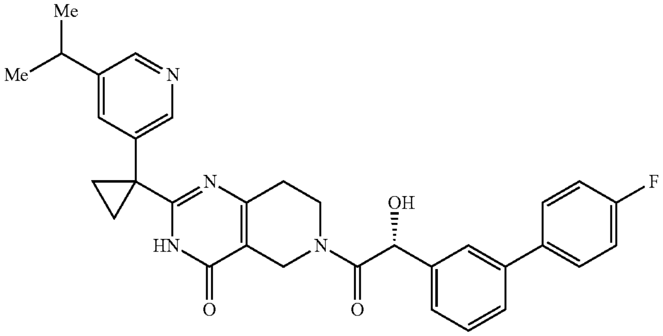 [SMILES: CC(C)c1cncc(C2(c3nc4c(c(=O)[nH]3)CN(C(=O)[C@H](O)c3cccc(-c5ccc(F)cc5)c3)CC4)CC2)c1] | 1.66 min | 539.0 |
| 47-4 | INT-11-19 | 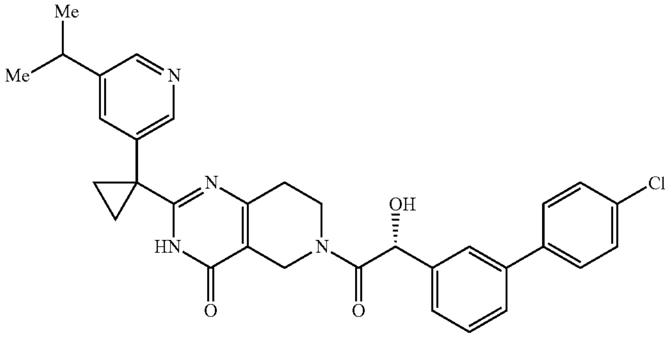 [SMILES: CC(C)c1cncc(C2(c3nc4c(c(=O)[nH]3)CN(C(=O)[C@H](O)c3cccc(-c5ccc(Cl)cc5)c3)CC4)CC2)c1] | 1.76 min | 555.0 |
| 47-5 | INT-11-19 | 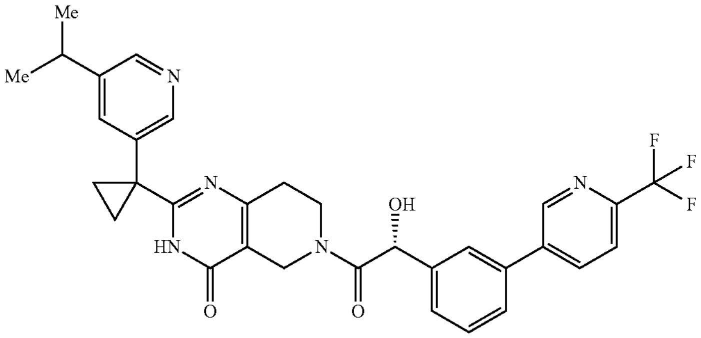 [SMILES: CC(C)c1cncc(C2(c3nc4c(c(=O)[nH]3)CN(C(=O)[C@H](O)c3cccc(-c5ccc(C(F)(F)F)nc5)c3)CC4)CC2)c1] | 1.58 min | 590.0 |

TABLE 81-continued

| Ex. | Intermediate (INT) | Structure | Retention time | Observed MS |
|---|---|---|---|---|
| 47-6 | INT-11-19 | 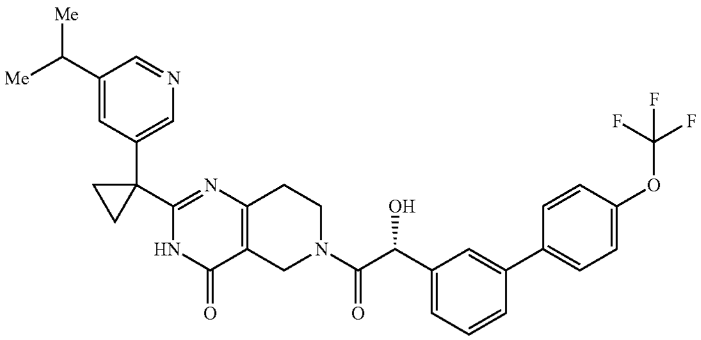 [SMILES: CC(C)c1cncc(C2(c3nc4c(c(=O)[nH]3)CN(C(=O)[C@H](O)c3cccc(-c5ccc(OC(F)(F)F)cc5)c3)CC4)CC2)c1] | 1.82 min | 605.0 |

The following pyrimidin-4(3H)-one derivatives (Ex-48-1 to Ex-48-15) are prepared according to the procedure of Ex-44-1 or the general synthesis in scheme-5 from INT-11-20, 11-21 or 11-22 and the known boronic acid derivatives. The further purification is carried out by preparative LC-MS or SFC-MS system in usual manner. The retention time and observed MS by HPLC-QC method are summarized in Tables 82-1 to 82-3.

TABLE 82-1

| Ex. | Intermediate (INT) | Structure | Retention time | Observed MS |
|---|---|---|---|---|
| 48-1 | INT-11-20 | 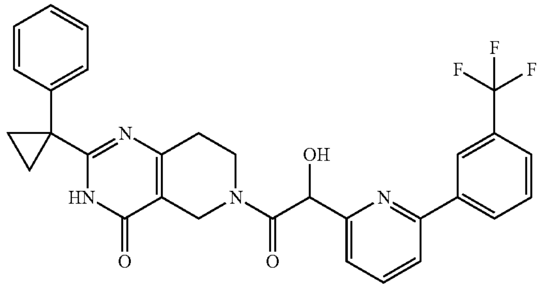 [SMILES: O=C(C(O)c1cccc(-c2cccc(C(F)(F)F)c2)n1)N1CCc2nc(C3(c4ccccc4)CC3)[nH]c(=O)c2C1] | 1.82 min | 547.2 |
| 48-2 | INT-11-20 | 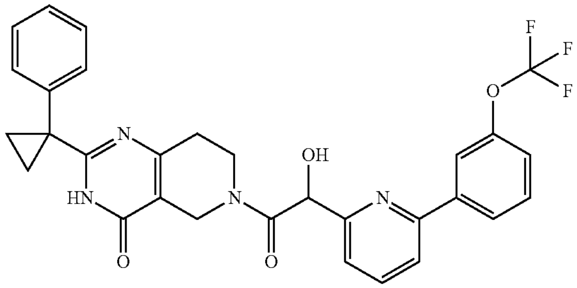 [SMILES: O=C(C(O)c1cccc(-c2cccc(OC(F)(F)F)c2)n1)N1CCc2nc(C3(c4ccccc4)CC3)[nH]c(=O)c2C1] | 1.86 min | 563.1 |
| 48-3 | INT-11-20 | 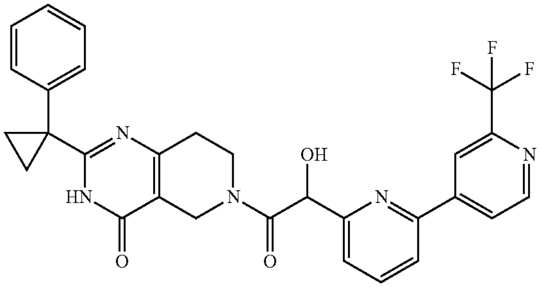 [SMILES: O=C(C(O)c1cccc(-c2ccnc(C(F)(F)F)c2)n1)N1CCc2nc(C3(c4ccccc4)CC3)[nH]c(=O)c2C1] | 1.61 min | 548.1 |

TABLE 82-1-continued
| Ex. | Intermediate (INT) | Structure | Retention time | Observed MS |
|---|---|---|---|---|
| 48-4 | INT-11-21 | 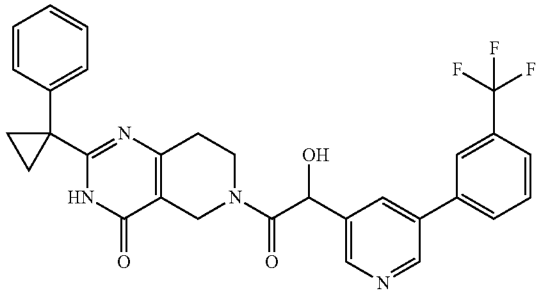 [SMILES: O=C(C(O)c1cncc(-c2cccc(C(F)(F)F)c2)c1)N1CCc2nc(C3(c4ccccc4)CC3)[nH]c(=O)c2C1] | 1.65 min | 547.0 |
| 48-5 | INT-11-21 | 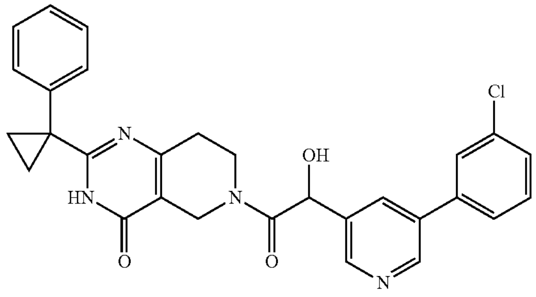 [SMILES: O=C(C(O)c1cncc(-c2cccc(Cl)c2)c1)N1CCc2nc(C3(c4ccccc4)CC3)[nH]c(=O)c2C1] | 1.61 min | 513.0 |
| 48-6 | INT-11-20 | 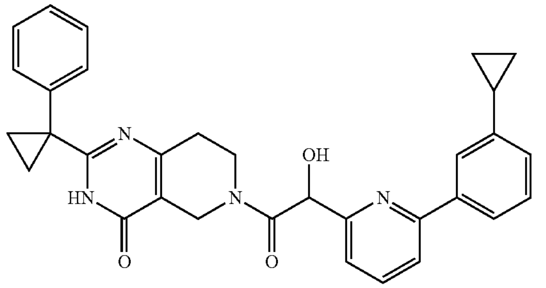 [SMILES: O=C(C(O)c1cccc(-c2cccc(C3CC3)c2)n1)N1CCc2nc(C3(c4ccccc4)CC3)[nH]c(=O)c2C1] | 1.85 min | 519.1 |
TABLE 82-2
| | | | | |
|---|---|---|---|---|
| 48-7 | INT-11-21 | 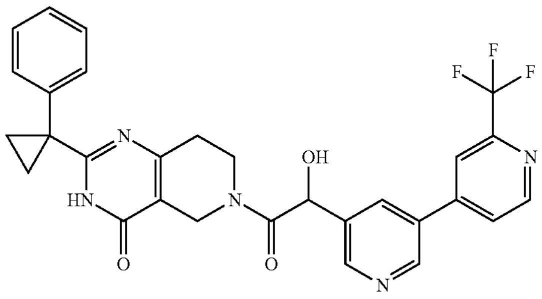 [SMILES: O=C(C(O)c1cncc(-c2ccnc(C(F)(F)F)c2)c1)N1CCc2nc(C3(c4ccccc4)CC3)[nH]c(=O)c2C1] | 1.46 min | 548.1 |

TABLE 82-2-continued
| | | | | |
|---|---|---|---|---|
| 48-8 | INT-11-20 | 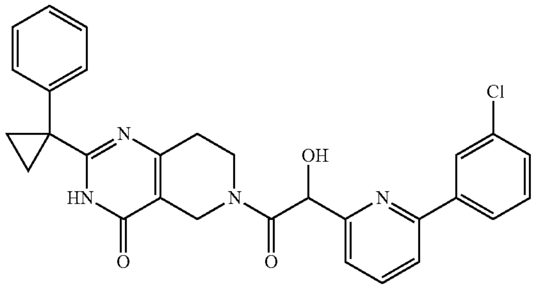 [SMILES: O=C(C(O)c1cccc(-c2cccc(Cl)c2)n1)N1CCc2nc(C3(c4ccccc4)CC3)[nH]c(=O)c2C1] | 1.78 min | 513.1 |
| 48-9 | INT-11-20 | 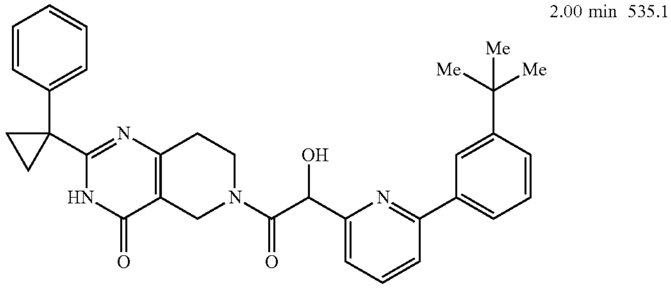 | 2.00 min | 535.1 |
| 48-10 | INT-11-20 | 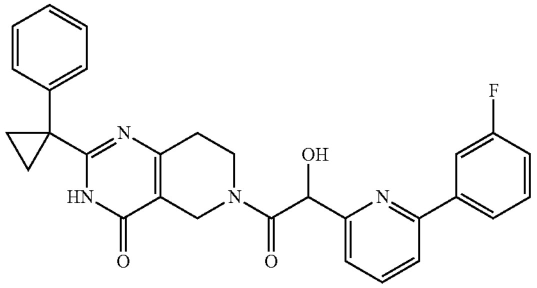 | 1.68 min | 497.1 |
| 48-11 | INT-11-21 | 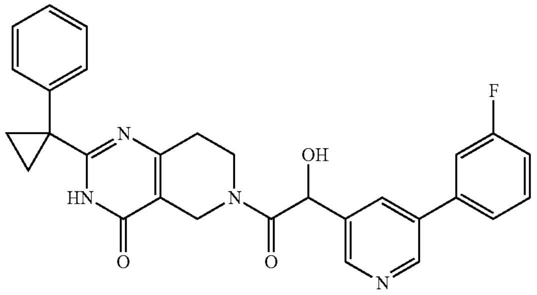 [SMILES: O=C(C(O)c1cncc(-c2cccc(F)c2)c1)N1CCc2nc(C3(c4ccccc4)CC3)[nH]c(=O)c2C1] | 1.51 min | 497.1 |
| 48-12 | INT-11-20 | 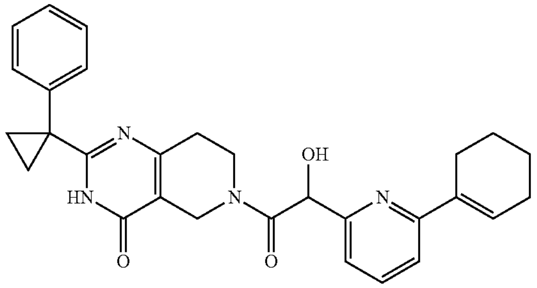 [SMILES: O=C(C(O)c1cccc(C2=CCCCC2)n1)N1CCc2nc(C3(c4ccccc4)CC3)[nH]c(=O)c2C1] | 1.82 min | 483.2 |

TABLE 82-2-continued

| | | | | |
|---|---|---|---|---|
| 48-13 | INT-11-22 | 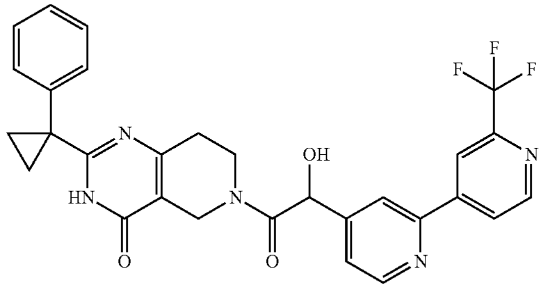 | 1.58 min | 548.2 |

TABLE 82-3

| | | | | |
|---|---|---|---|---|
| 48-14 | INT-11-20 | 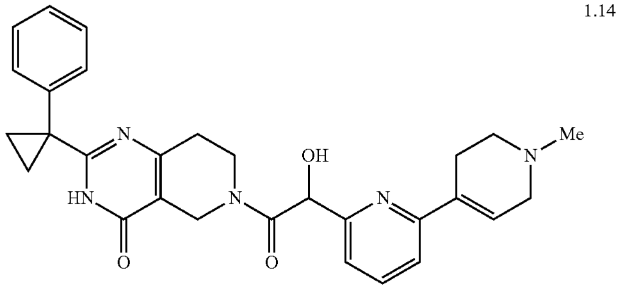 | 1.14 min | 498.2 |
| 48-15 | INT-11-22 | 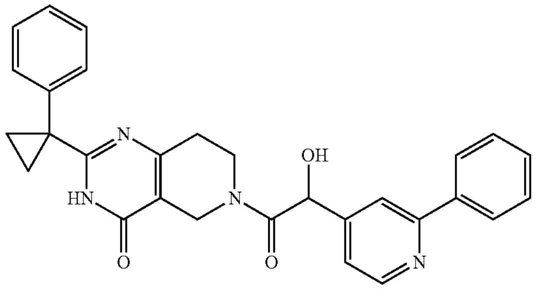 [SMILES: O=C(C(O)c1ccnc(-c2ccccc2)c1)N1CCc2nc(C3(c4ccccc4)CC3)[nH]c(=O)c2C1] | 1.52 min | 479.1 |

The following pyrimidin-4(3H)-one derivatives (Ex-49-1 to Ex-49-57) are prepared according to the procedure of Ex-44-1 or the general synthesis in scheme-5 from INT-11-23, 11-24, 11-32 or INT-11-34 and the known boronic acid derivatives. The further purification is carried out by preparative LC-MS or SFC-MS system in usual manner. The retention time and observed MS by HPLC-QC method are summarized in Tables 83-1 to 83-10.

TABLE 83-1

| Ex. | Intermediate (INT) | Structure | Retention time | Observed MS |
|---|---|---|---|---|
| 49-1 | INT-11-23 | 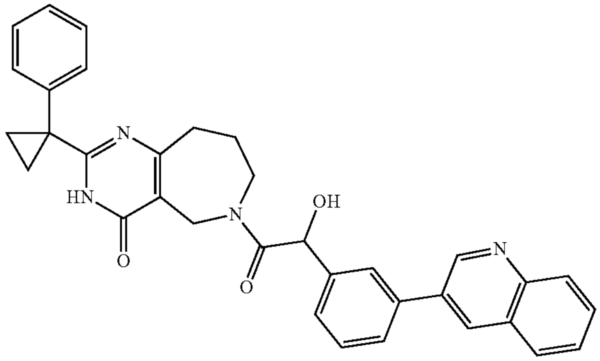 [SMILES: O=C(C(O)c1cccc(-c2cnc3ccccc3c2)c1)N1CCCc2nc(C3(c4ccccc4)CC3)[nH]c(=O)c2C1] | 1.65 min | 543.1 |

TABLE 83-1-continued
| Ex. | Intermediate (INT) | Structure | Retention time | Observed MS |
|---|---|---|---|---|
| 49-2 | INT-11-23 | 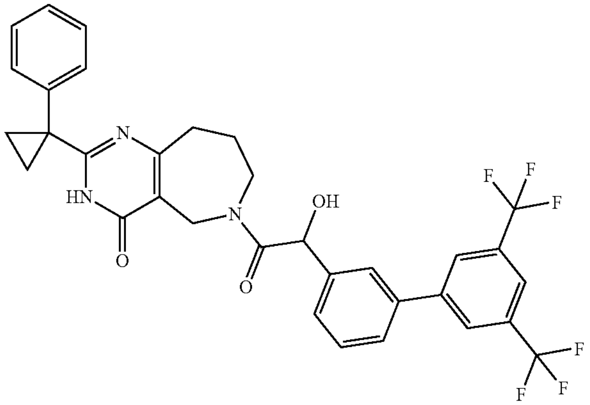 [SMILES: O=C(C(O)c1cccc(-c2cc(C(F)(F)F)cc(C(F)(F)F)c2)c1)N1CCCc2nc(C3(c4ccccc4)CC3)[nH]c(=O)c2C1] | 2.07 min | 628.1 |
| 49-3 | INT-11-23 | 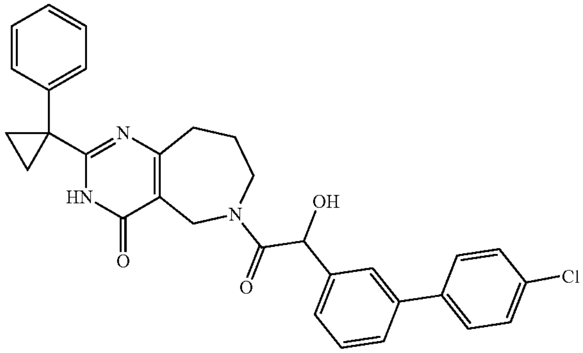 [SMILES: O=C(C(O)c1cccc(-c2ccc(Cl)cc2)c1)N1CCCc2nc(C3(c4ccccc4)CC3)[nH]c(=O)c2C1] | 1.92 min | 526.1 |
| 49-4 | INT-11-23 | 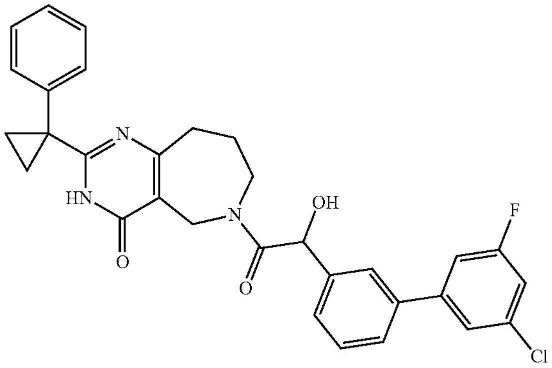 [SMILES: O=C(C(O)c1cccc(-c2cc(F)cc(Cl)c2)c1)N1CCCc2nc(C3(c4ccccc4)CC3)[nH]c(=O)c2C1] | 1.95 min | 544.1 |
| 49-5 | INT-11-23 | 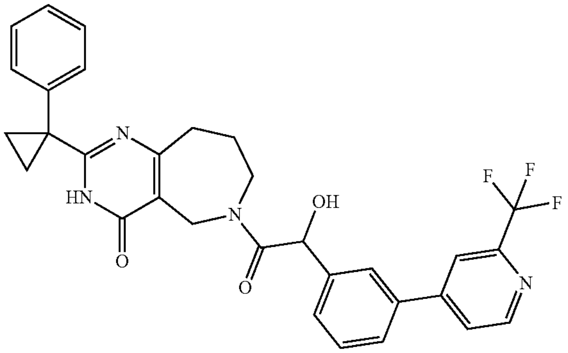 [SMILES: O=C(C(O)c1cccc(-c2ccnc(C(F)(F)F)c2)c1)N1CCCc2nc(C3(c4ccccc4)CC3)[nH]c(=O)c2C1] | 1.71 min | 561.1 |

TABLE 83-1-continued
| Ex. | Intermediate (INT) | Structure | Retention time | Observed MS |
|---|---|---|---|---|
| 49-6 | INT-11-23 | 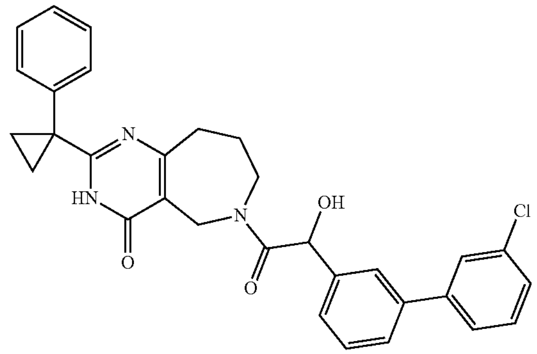 [SMILES: O=C(C(O)c1cccc(-c2cccc(Cl)c2)c1)N1CCCc2nc(C3(c4ccccc4)CC3)[nH]c(=O)c2C1] | 1.91 min | 526.0 |
TABLE 83-2
| | | | | |
|---|---|---|---|---|
| 49-7 | INT-11-23 | 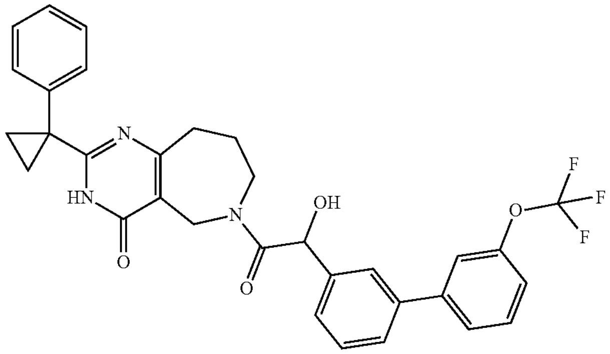 [SMILES: O=C(C(O)c1cccc(-c2cccc(OC(F)(F)F)c2)c1)N1CCCc2nc(C3(c4ccccc4)CC3)[nH]c(=O)c2C1] | 1.98 min | 576.1 |
| 49-8 | INT-11-23 | 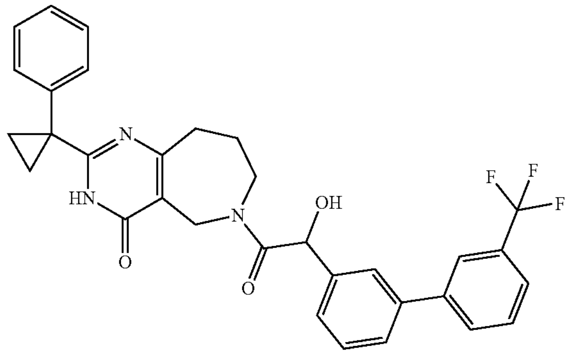 [SMILES: O=C(C(O)c1cccc(-c2cccc(C(F)(F)F)c2)c1)N1CCCc2nc(C3(c4ccccc4)CC3)[nH]c(=O)c2C1] | 1.94 min | 560.1 |
| 49-9 | INT-11-23 | 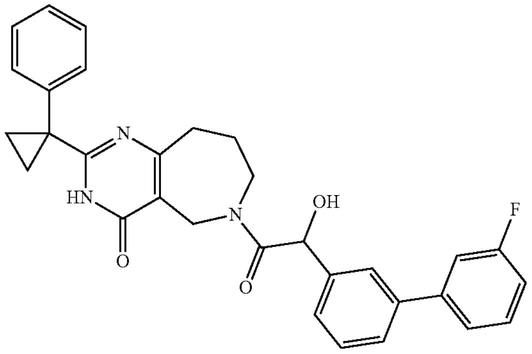 [SMILES: O=C(C(O)c1cccc(-c2cccc(F)c2)c1)N1CCCc2nc(C3(c4ccccc4)CC3)[nH]c(=O)c2C1] | 1.81 min | 510.1 |

TABLE 83-2-continued
| | | | | |
|---|---|---|---|---|
| 49-10 | INT-11-23 | 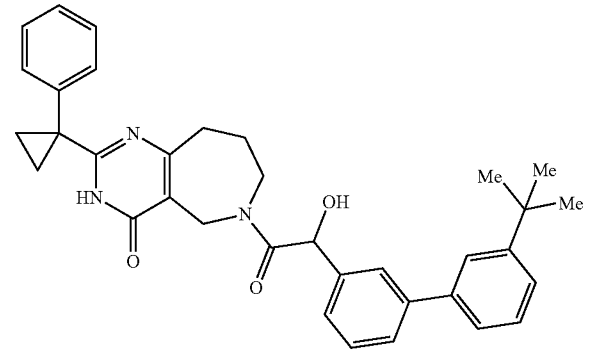 [SMILES: CC(C)(C)c1cccc(-c2cccc(C(O)C(=O)N3CCCc4nc(C5(c6ccccc6)CC5)[nH]c(=O)c4C3)c2)c1] | 2.13 min | 548.2 |
| 49-11 | INT-11-23 | 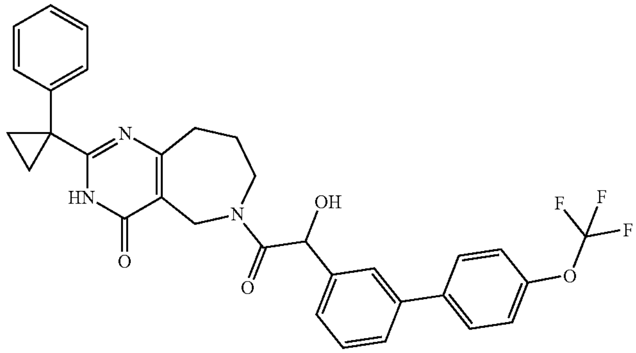 [SMILES: O=C(C(O)c1cccc(-c2ccc(OC(F)(F)F)cc2)c1)N1CCCc2nc(C3(c4ccccc4)CC3)[nH]c(=O)c2C1] | 1.97 min | 576.1 |
| 49-12 | INT-11-24 | 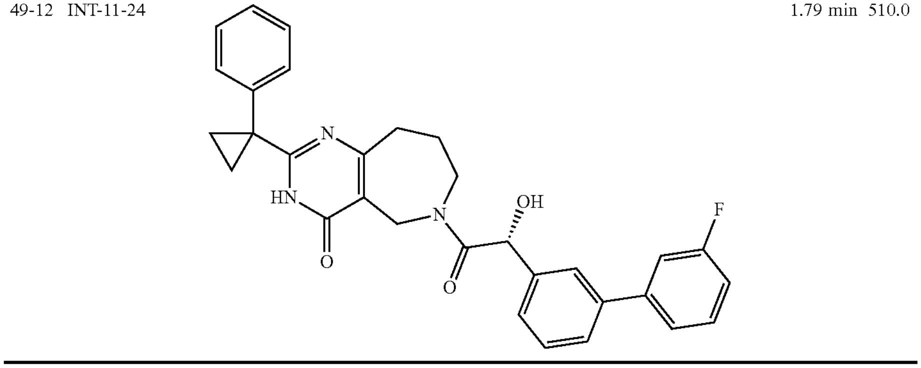 | 1.79 min | 510.0 |
TABLE 83-3
| | | | | |
|---|---|---|---|---|
| 49-13 | INT-11-24 | 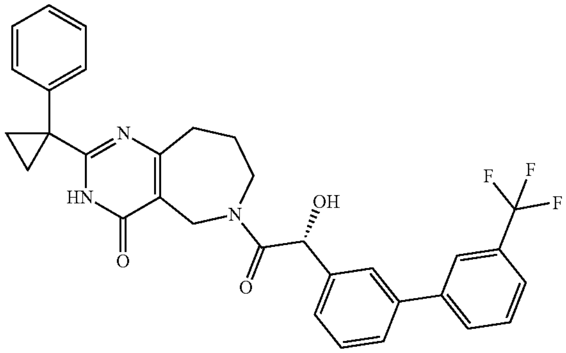 [SMILES: O=C([C@H](O)c1cccc(-c2cccc(C(F)(F)F)c2)c1)N1CCCc2nc(C3(c4ccccc4)CC3)[nH]c(=O)c2C1] | 1.91 min | 560.0 |

TABLE 83-3-continued
| | | | | |
|---|---|---|---|---|
| 49-14 | INT-11-24 | 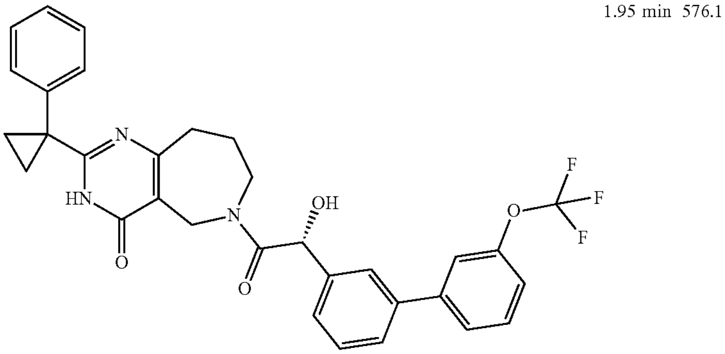 | 1.95 min | 576.1 |
| 49-15 | INT-11-24 | 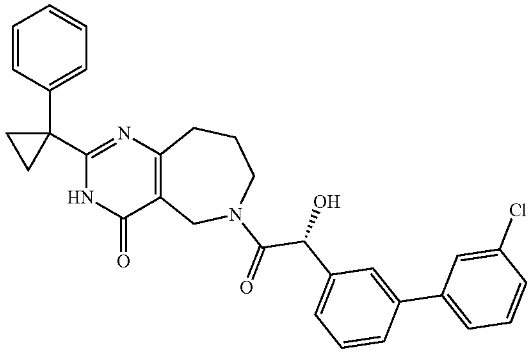 [SMILES: O=C([C@H](O)c1cccc(-c2cccc(Cl)c2)c1)N1CCCc2nc(C3(c4ccccc4)CC3)[nH]c(=O)c2C1] | 1.89 min | 526.0 |
| 49-16 | INT-11-24 | 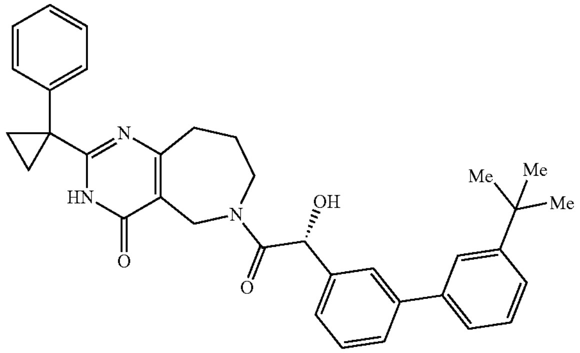 [SMILES: CC(C)(C)c1cccc(-c2cccc([C@@H](O)C(=O)N3CCCc4nc(C5(c6ccccc6)CC5)[nH]c(=O)c4C3)c2)c1] | 2.11 min | 548.1 |
| 49-17 | INT-11-24 | 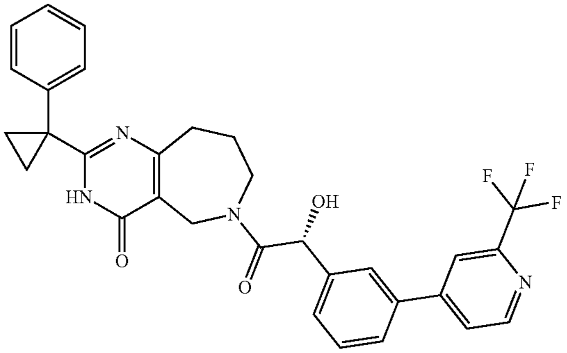 [SMILES: O=C([C@H](O)c1cccc(-c2ccnc(C(F)(F)F)c2)c1)N1CCCc2nc(C3(c4ccccc4)CC3)[nH]c(=O)c2C1] | 1.69 min | 561.0 |

TABLE 83-3-continued
| | | | | |
|---|---|---|---|---|
| 49-18 | INT-11-24 | 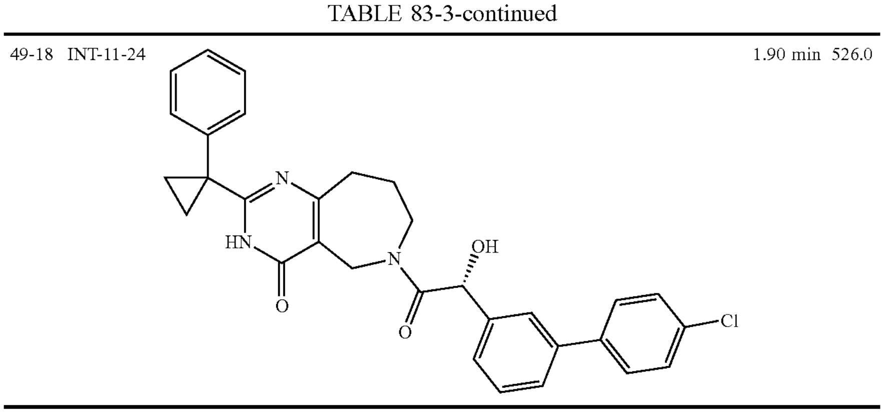 | 1.90 min | 526.0 |
TABLE 83-4
| | | | | |
|---|---|---|---|---|
| 49-19 | INT-11-34 | 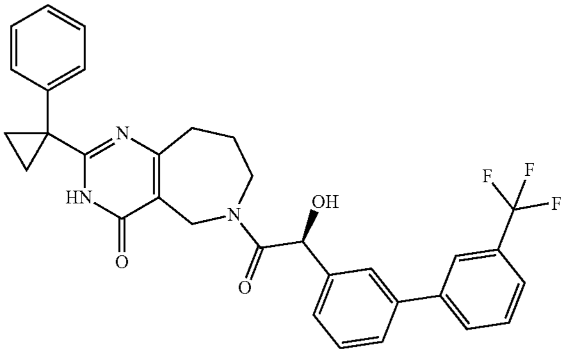 [SMILES: O=C([C@@H](O)c1cccc(-c2cccc(C(F)(F)F)c2)c1)N1CCCc2nc(C3(c4ccccc4)CC3)[nH]c(=O)c2C1] | 1.91 min | 560.0 |
| 49-20 | INT-11-34 | 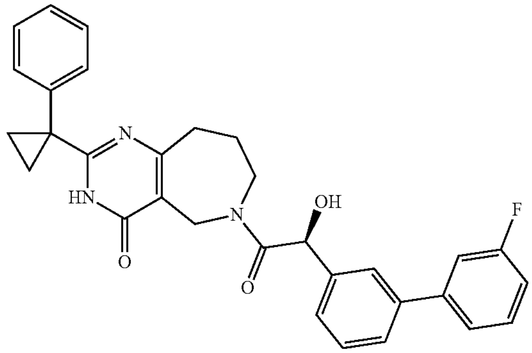 [SMILES: O=C([C@@H](O)c1cccc(-c2cccc(F)c2)c1)N1CCCc2nc(C3(c4ccccc4)CC3)[nH]c(=O)c2C1] | 1.79 min | 510.0 |
| 49-21 | INT-11-24 | 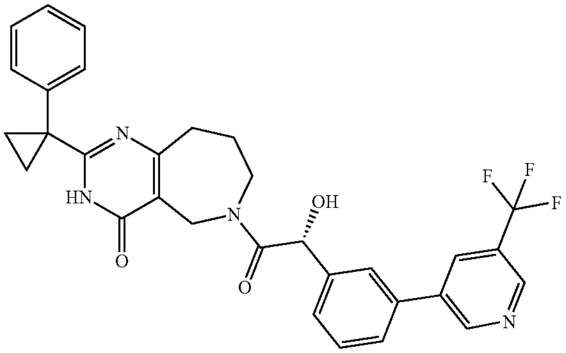 [SMILES: O=C([C@H](O)c1cccc(-c2cncc(C(F)(F)F)c2)c1)N1CCCc2nc(C3(c4ccccc4)CC3)[nH]c(=O)c2C1] | 1.68 min | 561.0 |

TABLE 83-4-continued
| | | | |
|---|---|---|---|
| 49-22 | INT-11-24 | 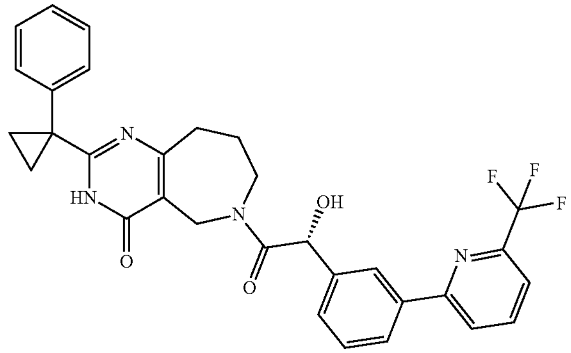 [SMILES: O=C([C@H](O)c1cccc(-c2cccc(C(F)(F)F)n2)c1)N1CCCc2nc(C3(c4ccccc4)CC3)[nH]c(=O)c2C1] | 1.79 min 561.0 |
| 49-23 | INT-11-34 | 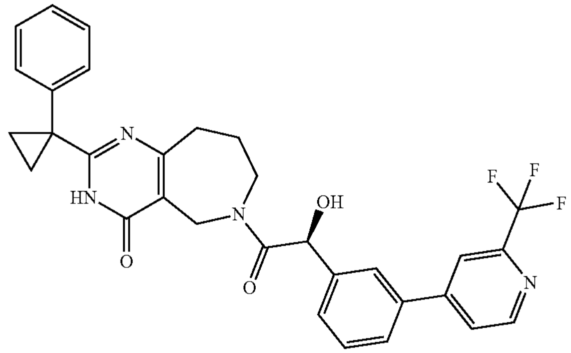 [SMILES: O=C([C@@H](O)c1cccc(-c2ccnc(C(F)(F)F)c2)c1)N1CCCc2nc(C3(c4ccccc4)CC3)[nH]c(=O)c2C1] | 1.69 min 561.0 |
| 49-24 | INT-11-24 | 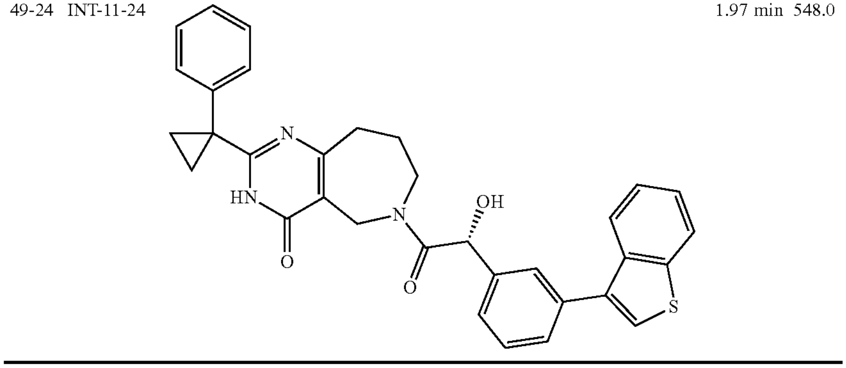 | 1.97 min 548.0 |
TABLE 83-5
| | | | |
|---|---|---|---|
| 49-25 | INT-11-24 | 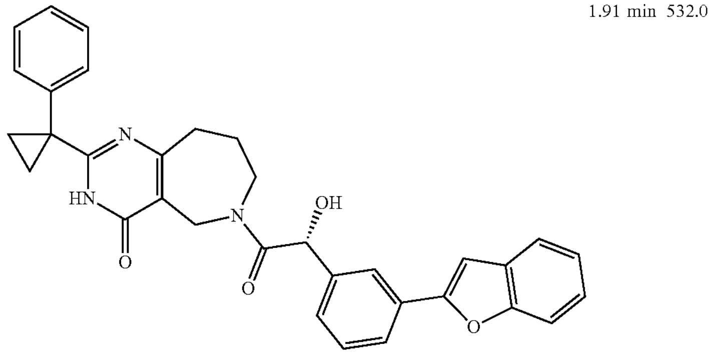 | 1.91 min 532.0 |

TABLE 83-5-continued
| | | | | |
|---|---|---|---|---|
| 49-26 | INT-11-24 | 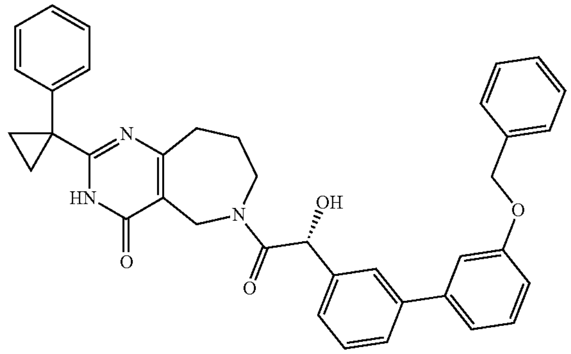 [SMILES: O=C([C@H](O)c1cccc(-c2cccc(OCc3ccccc3)c2)c1)N1CCCc2nc(C3(c4ccccc4)CC3)[nH]c(=O)c2C1] | 2.05 min | 598.0 |
| 49-27 | INT-11-24 | 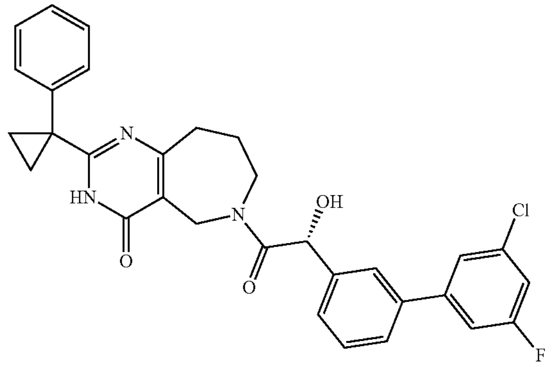 [SMILES: O=C([C@H](O)c1cccc(-c2cc(F)cc(Cl)c2)c1)N1CCCc2nc(C3(c4ccccc4)CC3)[nH]c(=O)c2C1] | 1.96 min | 543.9 |
| 49-28 | INT-11-24 | 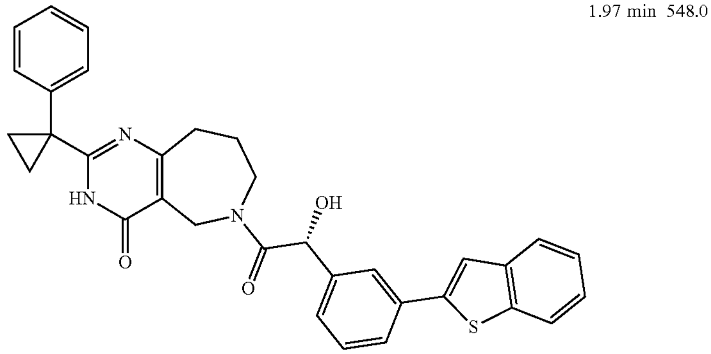 | 1.97 min | 548.0 |
| 49-29 | INT-11-24 | 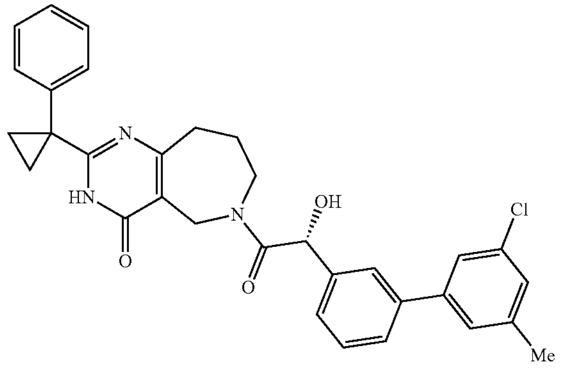 [SMILES: Cc1cc(Cl)cc(-c2cccc([C@@H](O)C(=O)N3CCCc4nc(C5(c6ccccc6)CC5)[nH]c(=O)c4C3)c2)c1] | 2.03 min | 540.0 |

TABLE 83-5-continued
| | | | |
|---|---|---|---|
| 48-30 | INT-11-24 | 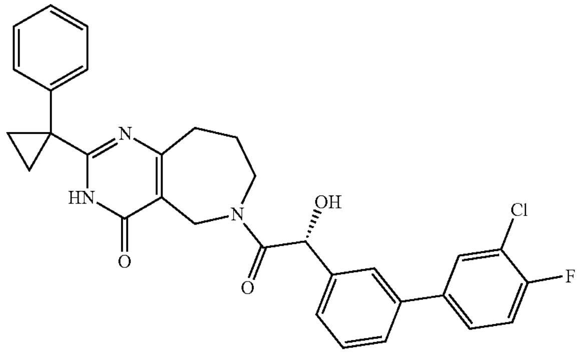 [SMILES: O=C([C@H](O)c1cccc(-c2ccc(F)c(Cl)c2)c1)N1CCCc2nc(C3(c4ccccc4)CC3)[nH]c(=O)c2C1] | 1.93 min 543.9 |
| 49-31 | INT-11-24 | 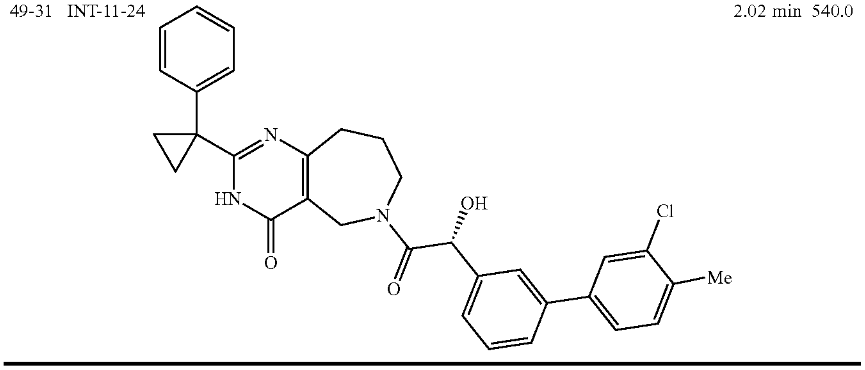 | 2.02 min 540.0 |
TABLE 83-6
| | | | |
|---|---|---|---|
| 49-32 | INT-11-24 | 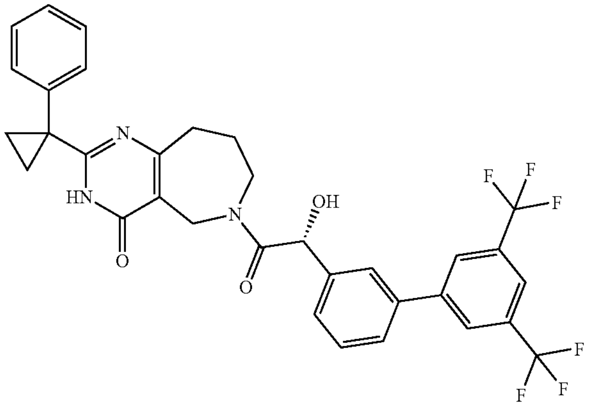 [SMILES: O=C([C@H](O)c1cccc(-c2cc(C(F)(F)F)cc(C(F)(F)F)c2)c1)N1CCCc2nc(C3(c4ccccc4)CC3)[nH]c(=O)c2C1] | 2.08 min 628.0 |
| 49-33 | INT-11-24 | 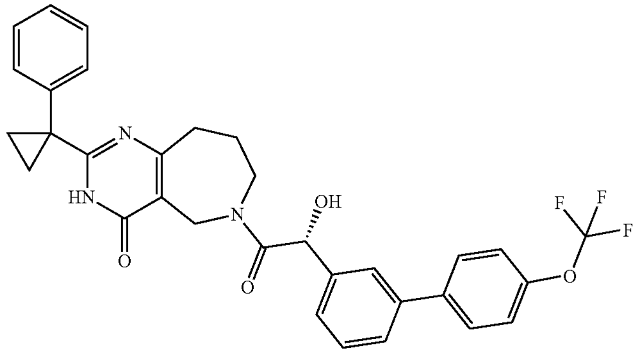 [SMILES: O=C([C@H](O)c1cccc(-c2ccc(OC(F)(F)F)cc2)c1)N1CCCc2nc(C3(c4ccccc4)CC3)[nH]c(=O)c2C1] | 1.98 min 576.0 |

TABLE 83-6-continued
| | | | | |
|---|---|---|---|---|
| 49-34 | INT-11-24 | 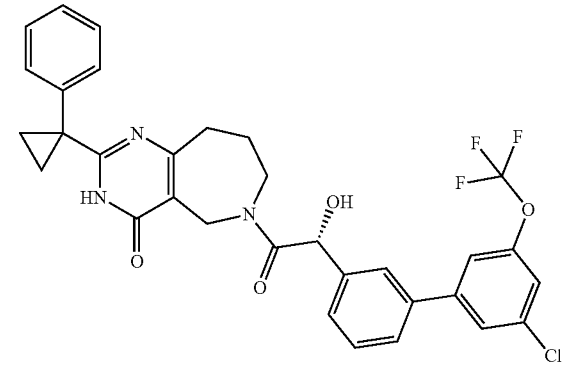 [SMILES: O=C([C@H](O)c1cccc(-c2cc(Cl)cc(OC(F)(F)F)c2)c1)N1CCCc2nc(C3(c4ccccc4)CC3)[nH]c(=O)c2C1] | 2.11 min | 610.0 |
| 49-35 | INT-11-24 | 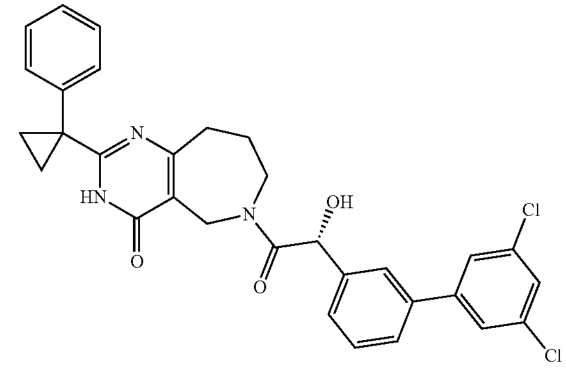 [SMILES: O=C([C@H](O)c1cccc(-c2cc(Cl)cc(Cl)c2)c1)N1CCCc2nc(C3(c4ccccc4)CC3)[nH]c(=O)c2C1] | 2.07 min | 559.9 |
| 49-36 | INT-11-24 | 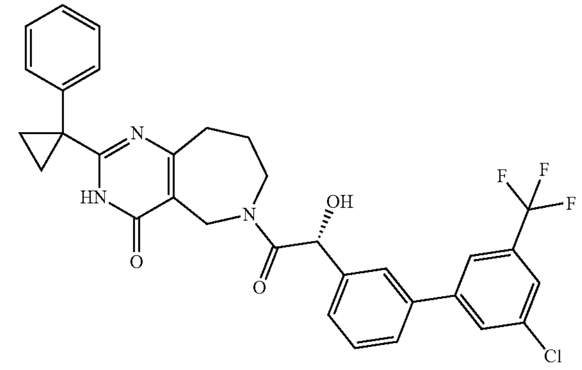 [SMILES: O=C([C@H](O)c1cccc(-c2cc(Cl)cc(C(F)(F)F)c2)c1)N1CCCc2nc(C3(c4ccccc4)CC3)[nH]c(=O)c2C1] | 2.08 min | 593.9 |
| 49-37 | INT-11-24 | 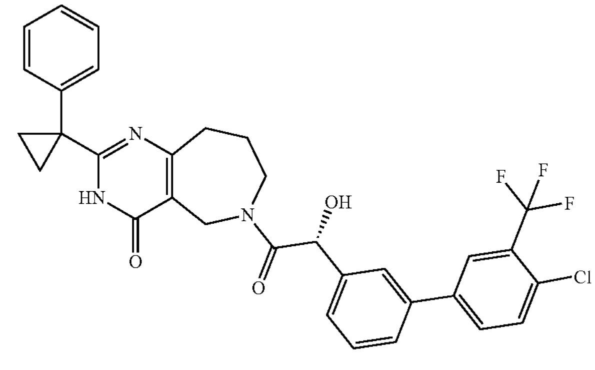 [SMILES: O=C([C@H](O)c1cccc(-c2ccc(Cl)c(C(F)(F)F)c2)c1)N1CCCc2nc(C3(c4ccccc4)CC3)[nH]c(=O)c2C1] | 2.04 min | 593.9 |

TABLE 83-7
| | | | | |
|---|---|---|---|---|
| 49-38 | INT-11-24 | 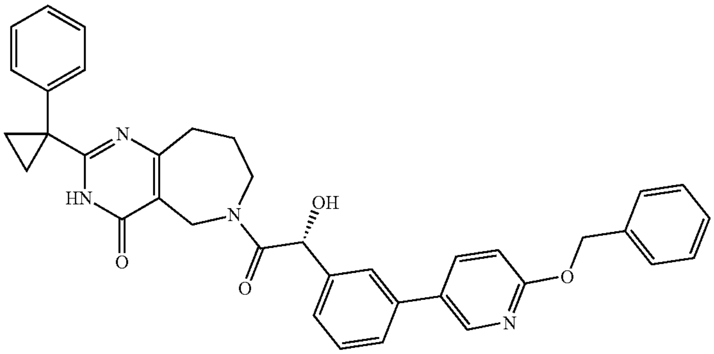 [SMILES: O=C([C@H](O)c1cccc(-c2ccc(OCc3ccccc3)nc2)c1)N1CCCc2nc(C3(c4ccccc4)CC3)[nH]c(=O)c2C1] | 1.98 min | 599.0 |
| 49-39 | INT-11-24 | 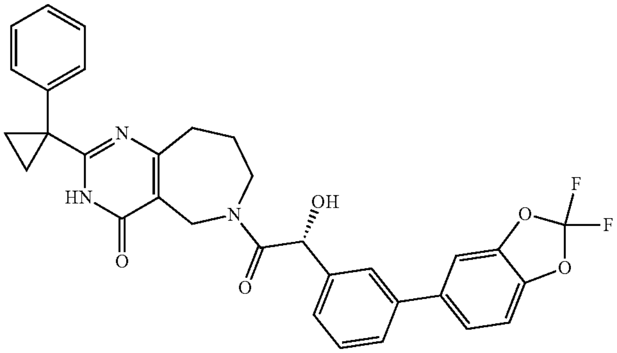 [SMILES: O=C([C@H](O)c1cccc(-c2ccc3c(c2)OC(F)(F)O3)c1)N1CCCc2nc(C3(c4ccccc4)CC3)[nH]c(=O)c2C1] | 1.96 min | 572.0 |
| 49-40 | INT-11-24 | 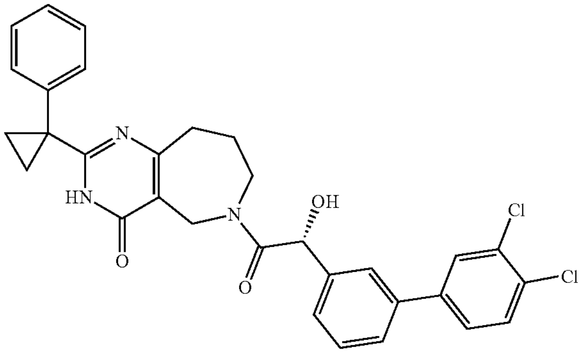 [SMILES: O=C([C@H](O)c1cccc(-c2ccc(Cl)c(Cl)c2)c1)N1CCCc2nc(C3(c4ccccc4)CC3)[nH]c(=O)c2C1] | 2.03 min | 559.9 |
| 49-41 | INT-11-24 | 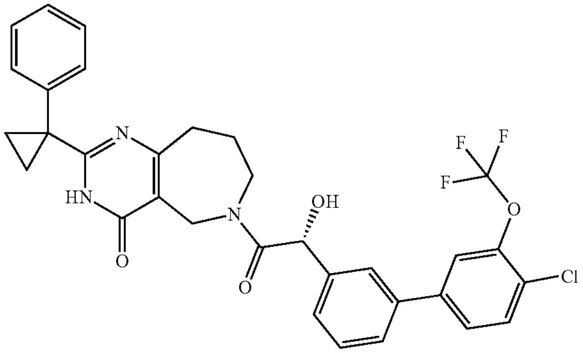 [SMILES: O=C([C@H](O)c1cccc(-c2ccc(Cl)c(OC(F)(F)F)c2)c1)N1CCCc2nc(C3(c4ccccc4)CC3)[nH]c(=O)c2C1] | 2.08 min | 609.9 |

TABLE 83-7-continued
| | | | |
|---|---|---|---|
| 49-42 | INT-11-24 | 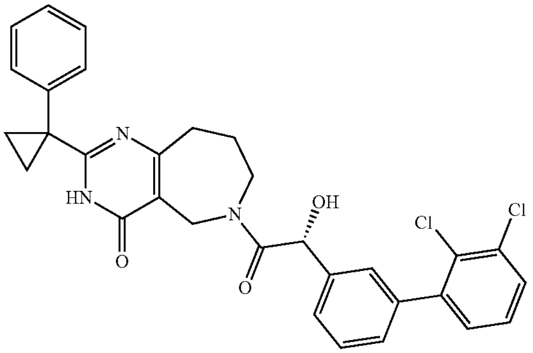 [SMILES: O=C([C@H](O)c1cccc(-c2cccc(Cl)c2Cl)c1)N1CCCc2nc(C3(c4ccccc4)CC3)[nH]c(=O)c2C1] | 1.99 min 559.9 |
| 49-43 | INT-11-24 | 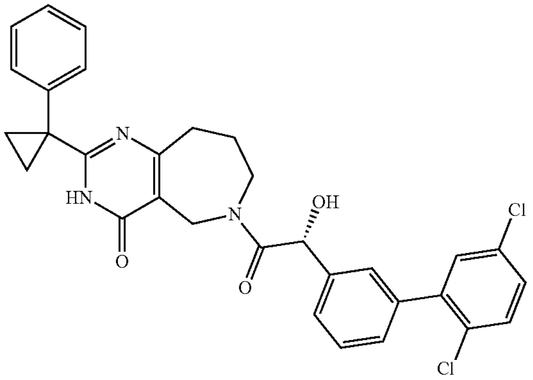 [SMILES: O=C([C@H](O)c1cccc(-c2cc(Cl)ccc2Cl)c1)N1CCCc2nc(C3(c4ccccc4)CC3)[nH]c(=O)c2C1] | 2.01 min 559.9 |
TABLE 83-8
| | | | |
|---|---|---|---|
| 49-44 | INT-11-24 | 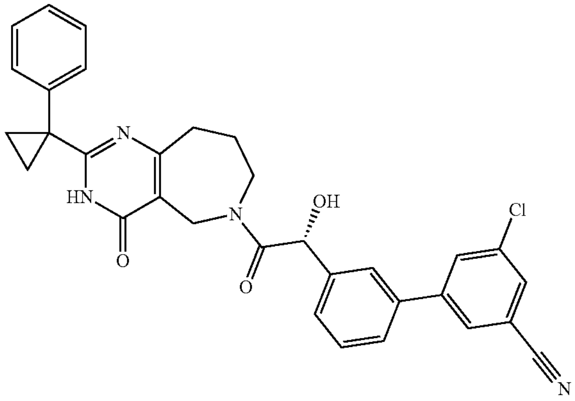 [SMILES: N#Cc1cc(Cl)cc(-c2cccc([C@@H](O)C(=O)N3CCCc4nc(C5(c6ccccc6)CC5)[nH]c(=O)c4C3)c2)c1] | 1.84 min 550.9 |
| 49-45 | INT-11-24 | 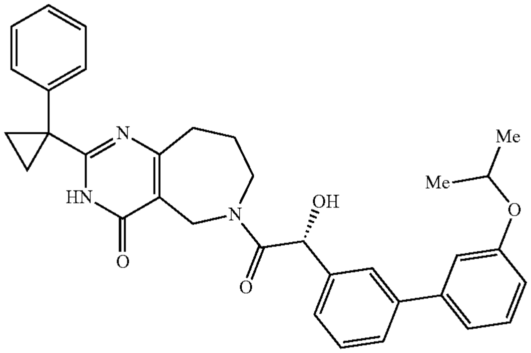 [SMILES: CC(C)Oc1cccc(-c2cccc([C@@H](O)C(=O)N3CCCc4nc(C5(c6ccccc6)CC5)[nH]c(=O)c4C3)c2)c1] | 1.97 min 550.0 |

TABLE 83-8-continued
| | | | | |
|---|---|---|---|---|
| 49-46 | INT-11-24 | 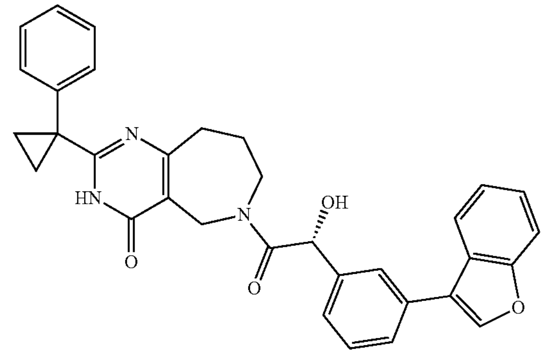 [SMILES: O=C([C@H](O)c1cccc(-c2coc3ccccc23)c1)N1CCCc2nc(C3(c4ccccc4)CC3)[nH]c(=O)c2C1] | 1.88 min | 531.9 |
| 49-47 | INT-11-24 | 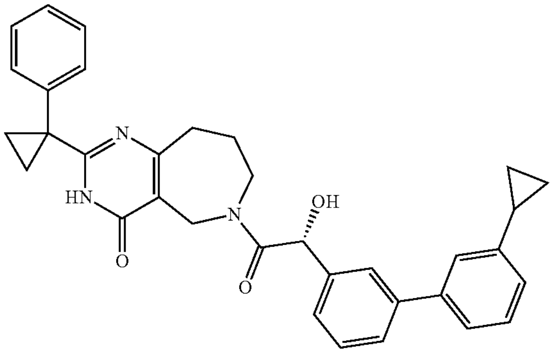 [SMILES: O=C([C@H](O)c1cccc(-c2cccc(C3CC3)c2)c1)N1CCCc2nc(C3(c4ccccc4)CC3)[nH]c(=O)c2C1] | 1.98 min | 532.0 |
| 49-48 | INT-11-24 | 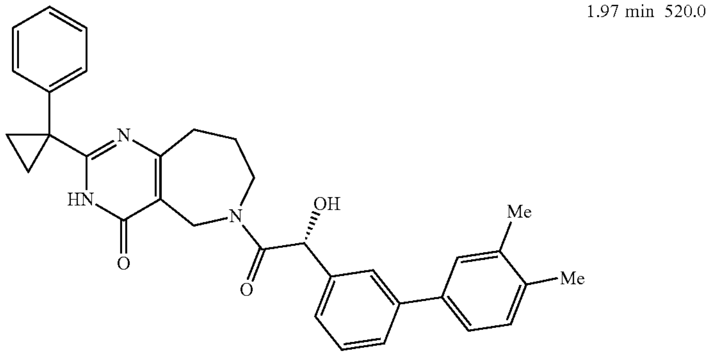 | 1.97 min | 520.0 |
| 49-49 | INT-11-24 | 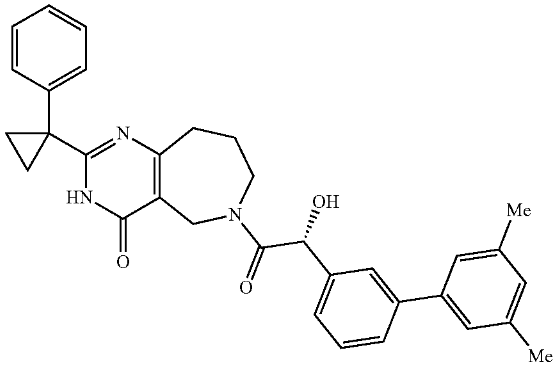 [SMILES: Cc1cc(C)cc(-c2cccc([C@@H](O)C(=O)N3CCCc4nc(C5(c6ccccc6)CC5)[nH]c(=O)c4C3)c2)c1] | 1.99 min | 520.0 |

TABLE 83-9
| | | | | |
|---|---|---|---|---|
| 49-50 | INT-11-24 | 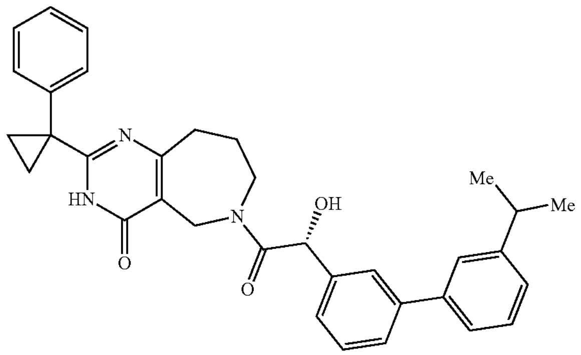 [SMILES: CC(C)c1cccc(-c2cccc([C@@H](O)C(=O)N3CCCc4nc(C5(c6ccccc6)CC5)[nH]c(=O)c4C3)c2)c1] | 2.07 min | 534.0 |
| 49-51 | INT-11-24 | 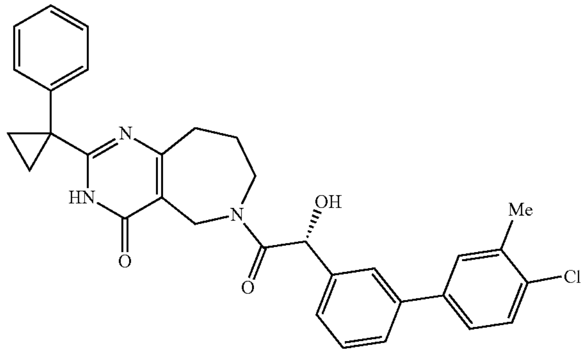 [SMILES: Cc1cc(-c2cccc([C@@H](O)C(=O)N3CCCc4nc(C5(c6ccccc6)CC5)[nH]c(=O)c4C3)c2)ccc1Cl] | 2.02 min | 540.0 |
| 49-52 | INT-11-24 | 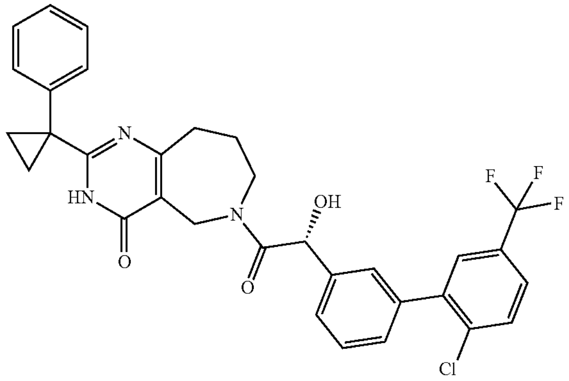 [SMILES: O=C([C@H](O)c1cccc(-c2cc(C(F)(F)F)ccc2Cl)c1)N1CCCc2nc(C3(c4ccccc4)CC3)[nH]c(=O)c2C1] | 2.02 min | 593.9 |
| 49-53 | INT-11-24 | 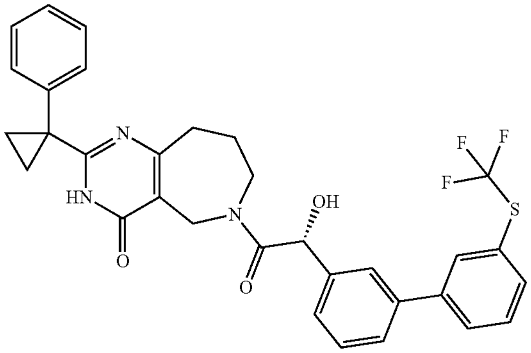 [SMILES: O=C([C@H](O)c1cccc(-c2cccc(SC(F)(F)F)c2)c1)N1CCCc2nc(C3(c4ccccc4)CC3)[nH]c(=O)c2C1] | 2.05 min | 591.9 |

TABLE 83-9-continued

| | | | |
|---|---|---|---|
| 49-54 | INT-11-32 | 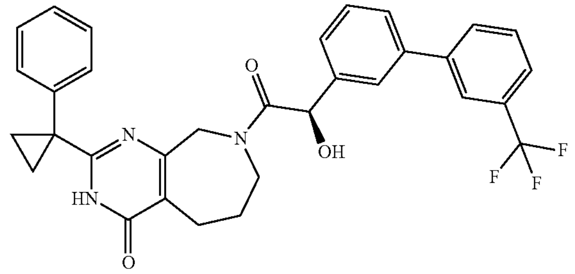 [SMILES: O=C([C@H](O)c1cccc(-c2cccc(C(F)(F)F)c2)c1)N1CCCc2c(nc(C3(c4ccccc4)CC3)[nH]c2=O)C1] | 1.93 min 559.9 |
| 49-55 | INT-11-32 | 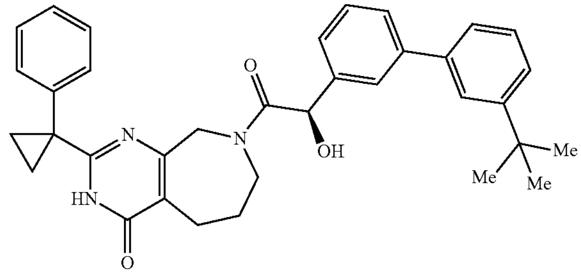 [SMILES: CC(C)(C)c1cccc(-c2cccc([C@@H](O)C(=O)N3CCCc4c(nc(C5(c6ccccc6)CC5)[nH]c4=O)C3)c2)c1] | 2.10 min 548.0 |

TABLE 83-10

| | | | |
|---|---|---|---|
| 49-56 | INT-11-32 | 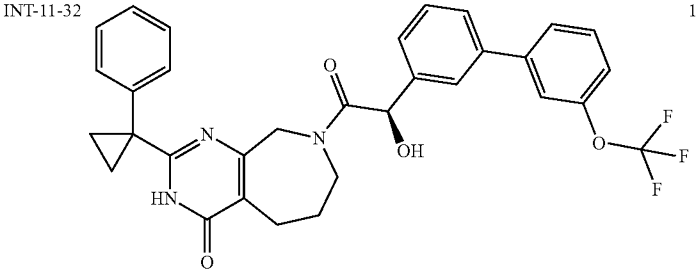 | 1.96 min 576.0 |
| 49-57 | INT-11-32 | 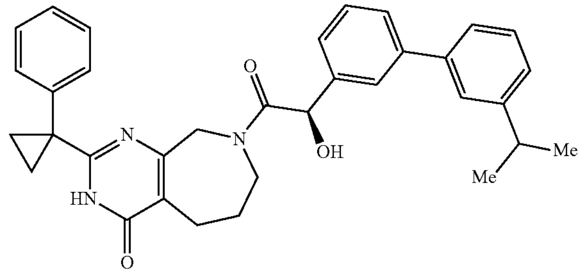 [SMILES: CC(C)c1cccc(-c2cccc([C@@H](O)C(=O)N3CCCc4c(nc(C5(c6ccccc6)CC5)[nH]c4=O)C3)c2)c1] | 2.05 min 534.0 |

The following pyrimidin-4(3H)-one derivatives (Ex-50-1 to Ex-50-26) are prepared according to the procedure of Ex-44-1 or the general synthesis in scheme-5 from INT-11-25 and the known boronic acid derivatives. The further purification is carried out by preparative LC-MS or SFC-MS system in usual manner. The retention time and observed MS by HPLC-QC method are summarized in Tables 84-1 to 84-5.

TABLE 84-1
| Ex. | Intermediate (INT) | Structure | Retention time | Observed MS |
|---|---|---|---|---|
| 50-1 | INT-11-25 | 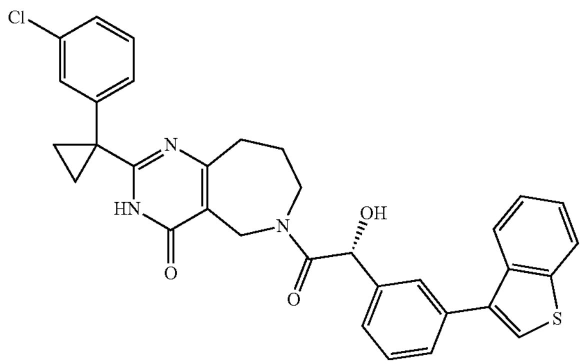 | 2.06 min | 581.9 |
| 50-2 | INT-11-25 | 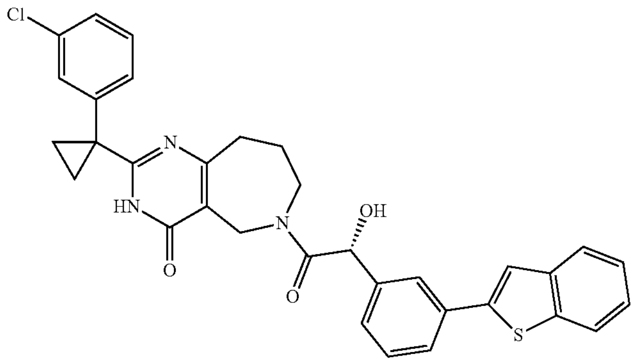 [SMILES: O=C([C@H](O)c1cccc(-c2cc3ccccc3s2)c1)N1CCCc2nc(C3(c4cccc(Cl)c4)CC3)[nH]c(=O)c2C1] | 2.06 min | 581.9 |
| 50-3 | INT-11-25 | 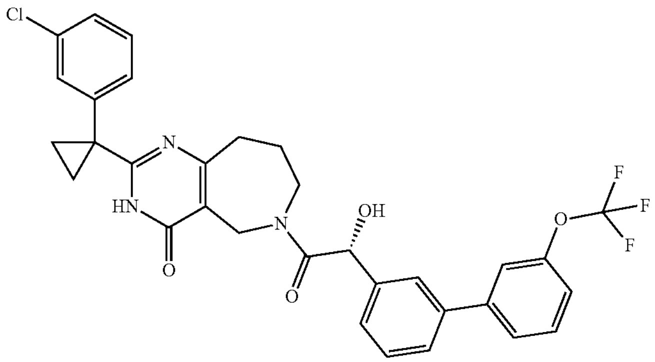 [SMILES: O=C([C@H](O)c1cccc(-c2cccc(OC(F)(F)F)c2)c1)N1CCCc2nc(C3(c4cccc(Cl)c4)CC3)[nH]c(=O)c2C1] | 2.06 min | 609.9 |
| 50-4 | INT-11-25 | 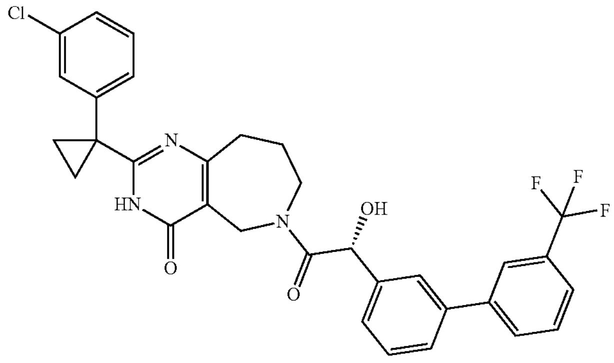 [SMILES: O=C([C@H](O)c1cccc(-c2cccc(C(F)(F)F)c2)c1)N1CCCc2nc(C3(c4cccc(Cl)c4)CC3)[nH]c(=O)c2C1] | 2.02 min | 593.9 |

TABLE 84-1-continued
| Ex. | Intermediate (INT) | Structure | Retention time | Observed MS |
|---|---|---|---|---|
| 50-5 | INT-11-25 | 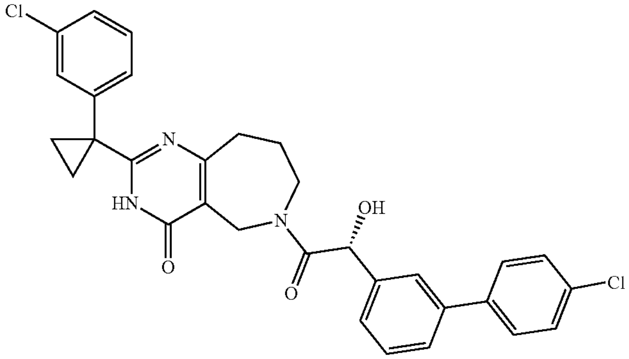 [SMILES: O=C([C@H](O)c1cccc(-c2ccc(Cl)cc2)c1)N1CCCc2nc(C3(c4cccc(Cl)c4)CC3)[nH]c(=O)c2C1] | 2.01 min | 559.9 |
| 50-6 | INT-11-25 | 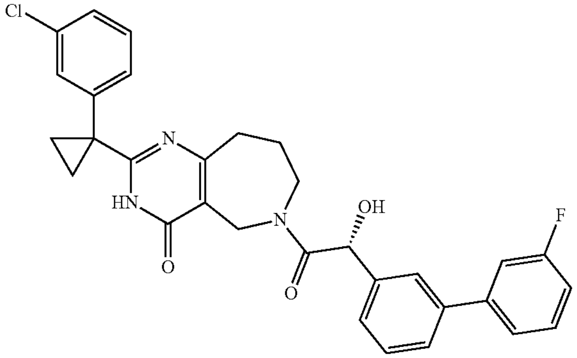 [SMILES: O=C([C@H](O)c1cccc(-c2cccc(F)c2)c1)N1CCCc2nc(C3(c4cccc(Cl)c4)CC3)[nH]c(=O)c2C1] | 1.91 min | 543.9 |
TABLE 84-2
| | | | | |
|---|---|---|---|---|
| 50-7 | INT-11-25 | 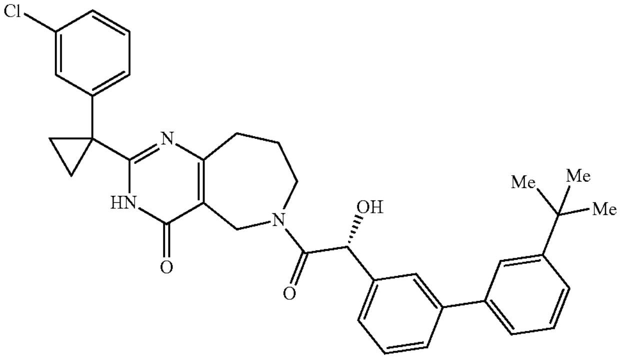 [SMILES: CC(C)(C)c1cccc(-c2cccc([C@@H](O)C(=O)N3CCCc4nc(C5(c6cccc(Cl)c6)CC5)[nH]c(=O)c4C3)c2)c1] | 2.21 min | 582.0 |
| 50-8 | INT-11-25 | 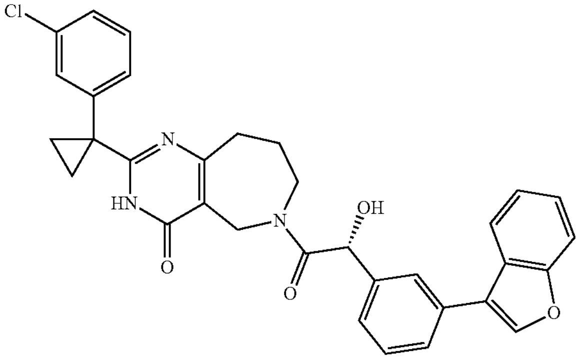 [SMILES: O=C([C@H](O)c1cccc(-c2coc3ccccc23)c1)N1CCCc2nc(C3(c4cccc(Cl)c4)CC3)[nH]c(=O)c2C1] | 1.98 min | 565.9 |

TABLE 84-2-continued
| | | | | |
|---|---|---|---|---|
| 50-9 | INT-11-25 | 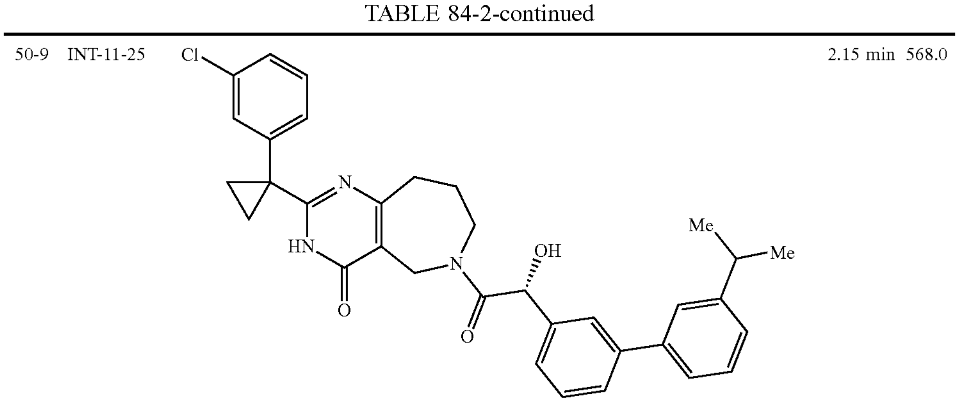 | 2.15 min | 568.0 |
| 50-10 | INT-11-25 | 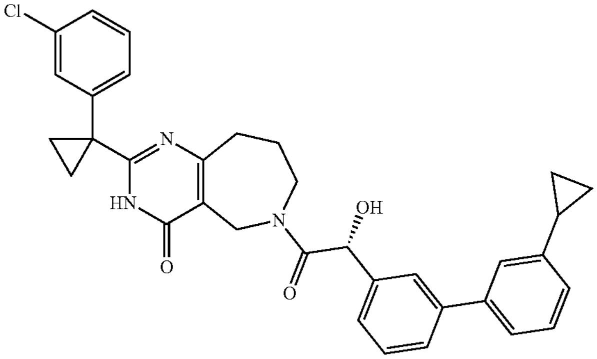 [SMILES: O=C([C@H](O)c1cccc(-c2cccc(C3CC3)c2)c1)N1CCCc2nc(C3(c4cccc(Cl)c4)CC3)[nH]c(=O)c2C1] | 2.06 min | 566.0 |
| 50-11 | INT-11-25 | 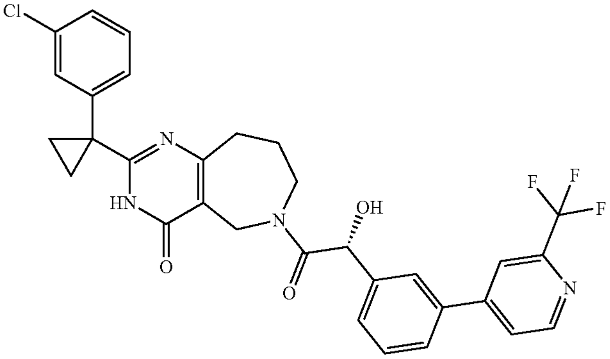 [SMILES: O=C([C@H](O)c1cccc(-c2ccnc(C(F)(F)F)c2)c1)N1CCCc2nc(C3(c4cccc(Cl)c4)CC3)[nH]c(=O)c2C1] | 1.81 min | 594.9 |
| 50-12 | INT-11-25 | 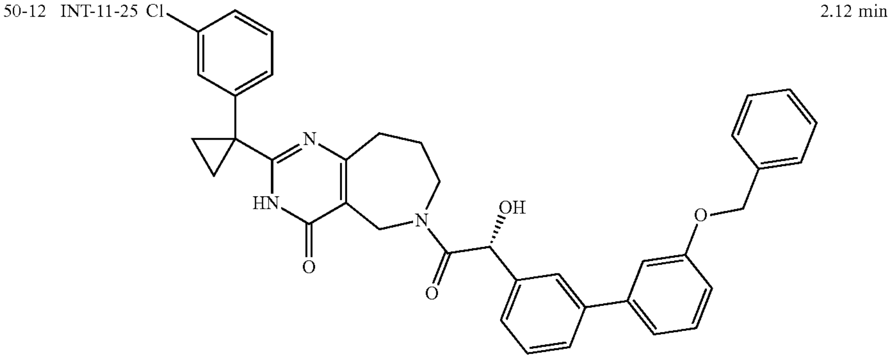 | 2.12 min | 632.0 |

TABLE 84-3
| | | | | |
|---|---|---|---|---|
| 50-13 | INT-11-25 | 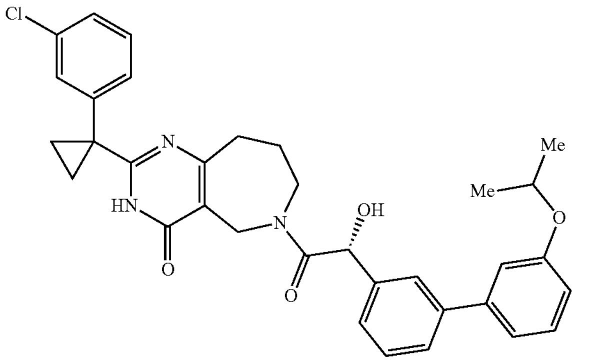 [SMILES: CC(C)Oc1cccc(-c2cccc([C@@H](O)C(=O)N3CCCc4nc(C5(c6cccc(Cl)c6)CC5)[nH]c(=O)c4C3)c2)c1] | 2.18 min | 584.5 |
| 50-14 | INT-11-25 | 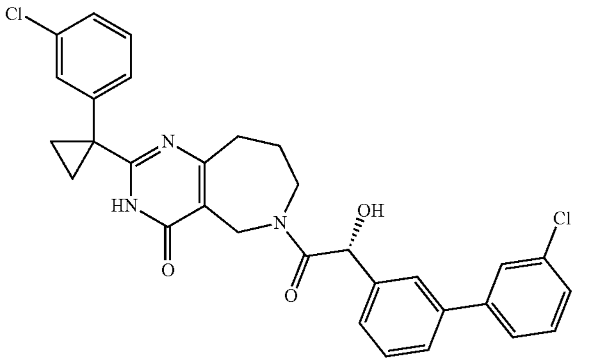 [SMILES: O=C([C@H](O)c1cccc(-c2cccc(Cl)c2)c1)N1CCCc2nc(C3(c4cccc(Cl)c4)CC3)[nH]c(=O)c2C1] | 2.14 min | 560.4 |
| 50-15 | INT-11-25 | 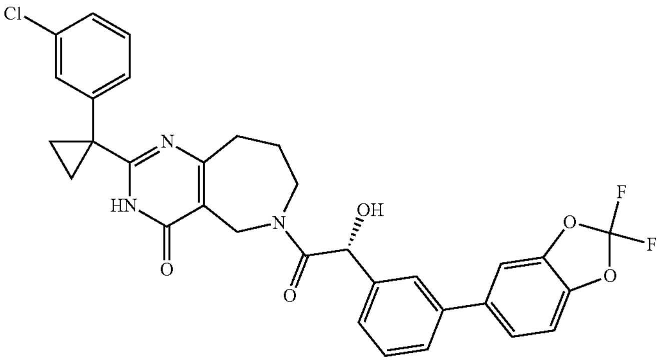 [SMILES: O=C([C@H](O)c1cccc(-c2ccc3c(c2)OC(F)(F)O3)c1)N1CCCc2nc(C3(c4cccc(Cl)c4)CC3)[nH]c(=O)c2C1] | 2.16 min | 606.5 |
| 50-16 | INT-11-25 | 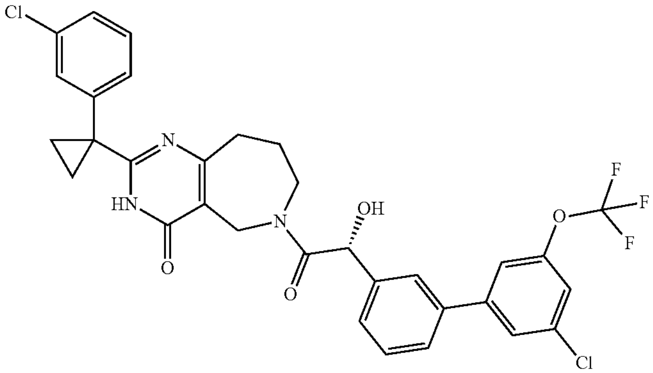 [SMILES: O=C([C@H](O)c1cccc(-c2cc(Cl)cc(OC(F)(F)F)c2)c1)N1CCCc2nc(C3(c4cccc(Cl)c4)CC3)[nH]c(=O)c2C1] | 2.29 min | 644.4 |

TABLE 84-3-continued
| | | | | |
|---|---|---|---|---|
| 50-17 | INT-11-25 | 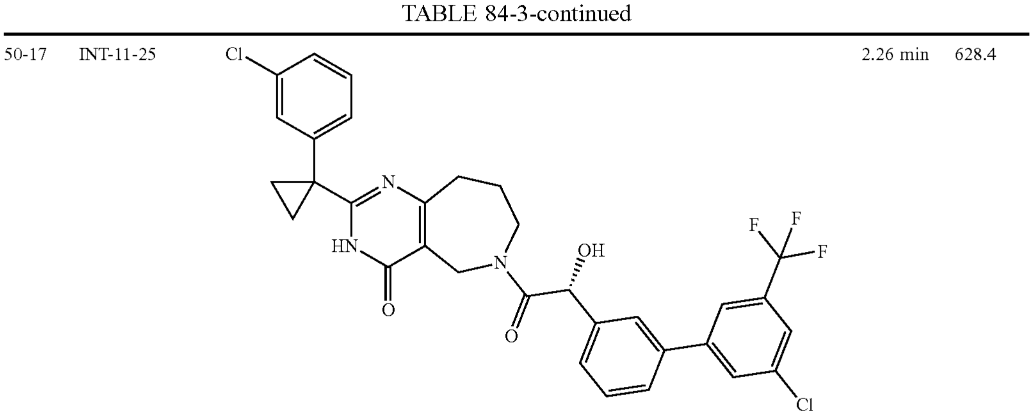 | 2.26 min | 628.4 |
| 50-18 | INT-11-25 | 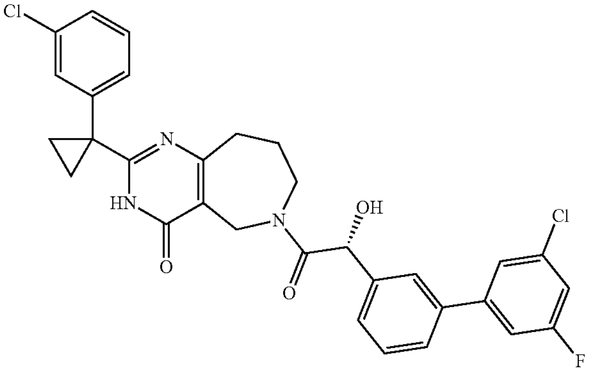 [SMILES: O=C([C@H](O)c1cccc(-c2cc(F)cc(Cl)c2)c1)N1CCCc2nc(C3(c4cccc(Cl)c4)CC3)[nH]c(=O)c2C1] | 2.17 min | 578.4 |
TABLE 84-4
| | | | | |
|---|---|---|---|---|
| 50-19 | INT-11-25 | 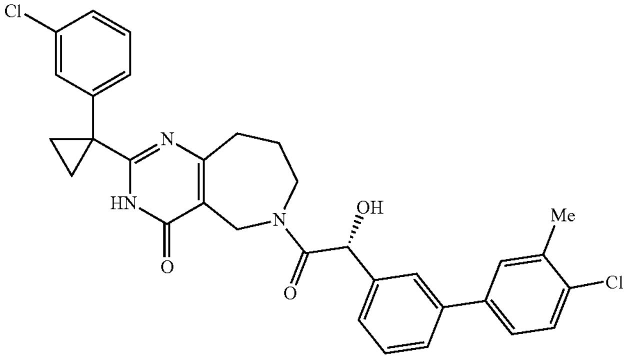 [SMILES: Cc1cc(-c2cccc([C@@H](O)C(=O)N3CCCc4nc(C5(c6cccc(Cl)c6)CC5)[nH]c(=O)c4C3)c2)ccc1Cl] | 2.22 min | 574.5 |
| 50-20 | INT-11-25 | 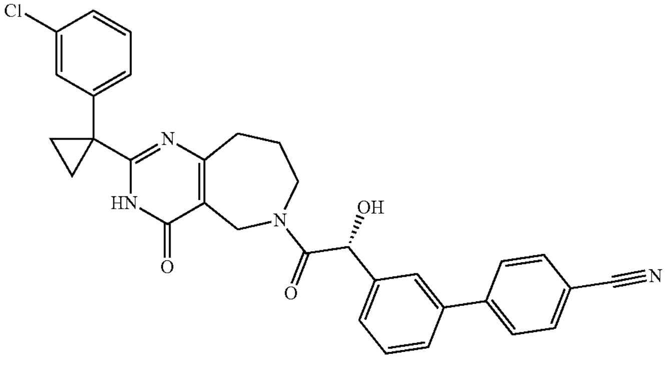 [SMILES: N#Cc1ccc(-c2cccc([C@@H](O)C(=O)N3CCCc4nc(C5(c6cccc(Cl)c6)CC5)[nH]c(=O)c4C3)c2)cc1] | 1.95 min | 551.5 |

TABLE 84-4-continued
| | | | | |
|---|---|---|---|---|
| 50-21 | INT-11-25 | 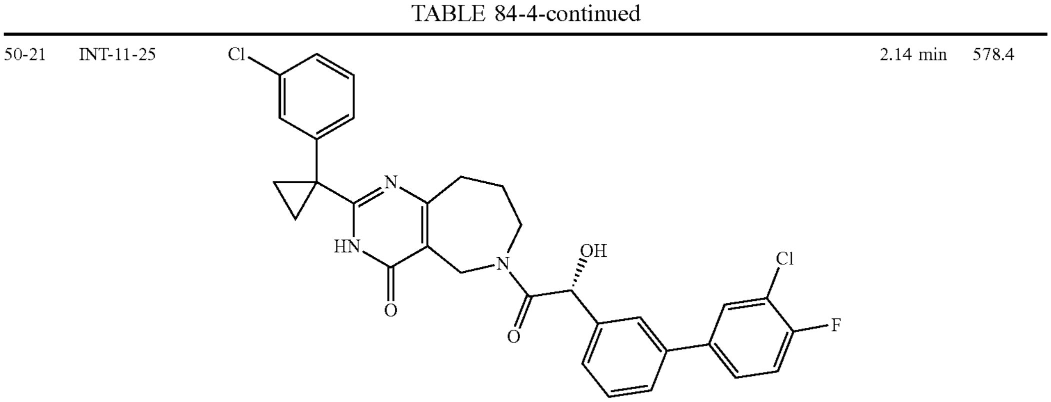 | 2.14 min | 578.4 |
| 50-22 | INT-11-25 | 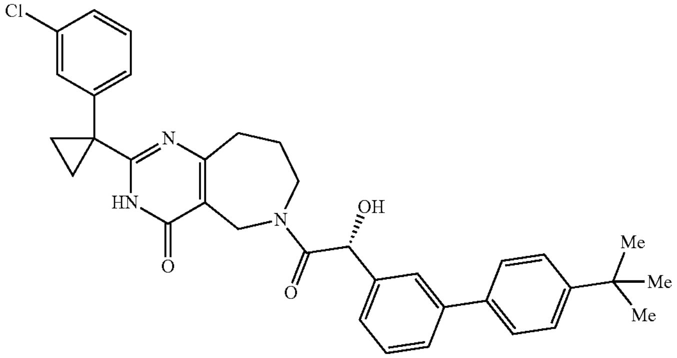 [SMILES: CC(C)(C)c1ccc(-c2cccc([C@@H](O)C(=O)N3CCCc4nc(C5(c6cccc(Cl)c6)CC5)[nH]c(=O)c4C3)c2)cc1] | 2.31 min | 582.6 |
| 50-23 | INT-11-25 | 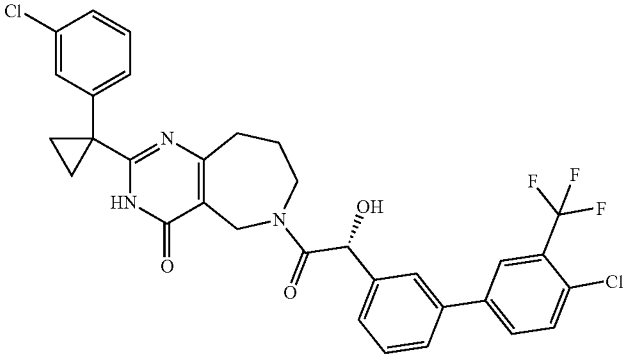 [SMILES: O=C([C@H](O)c1cccc(-c2ccc(Cl)c(C(F)(F)F)c2)c1)N1CCCc2nc(C3(c4cccc(Cl)c4)CC3)[nH]c(=O)c2C1] | 2.23 min | 628.4 |
TABLE 84-5
| | | | | |
|---|---|---|---|---|
| 50-24 | INT-11-25 | 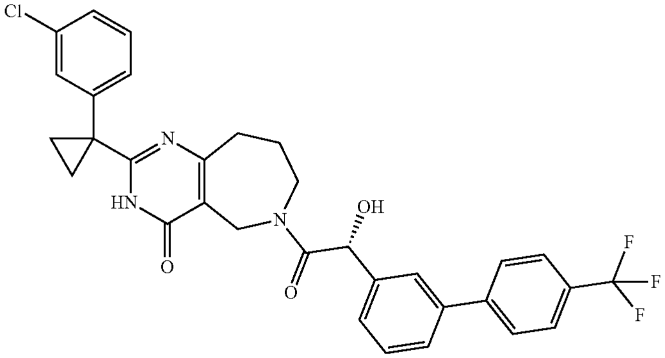 [SMILES: O=C([C@H](O)c1cccc(-c2ccc(C(F)(F)F)cc2)c1)N1CCCc2nc(C3(c4cccc(Cl)c4)CC3)[nH]c(=O)c2C1] | 2.16 min | 594.5 |

TABLE 84-5-continued

| | | | | |
|---|---|---|---|---|
| 50-25 | INT-11-25 | 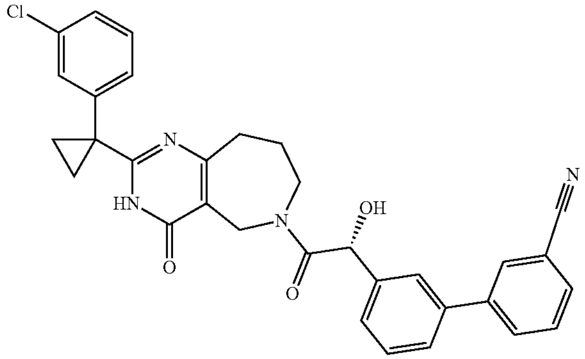 [SMILES: N#Cc1cccc(-c2cccc([C@@H](O)C(=O)N3CCCc4nc(C5(c6cccc(Cl)c6)CC5)[nH]c(=O)c4C3)c2)c1] | 1.96 min | 551.5 |
| 50-26 | INT-11-25 | 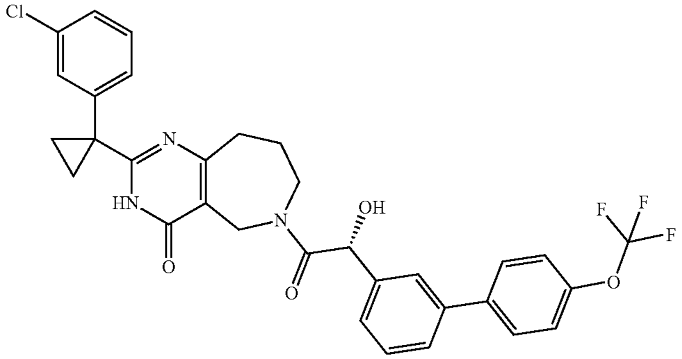 [SMILES: O=C([C@H](O)c1cccc(-c2ccc(OC(F)(F)F)cc2)c1)N1CCCc2nc(C3(c4cccc(Cl)c4)CC3)[nH]c(=O)c2C1] | 2.18 min | 610.4 |

The following pyrimidin-4(3H)-one derivatives (Ex-51-1 to Ex-51-8) are prepared according to the procedure of Ex-44-1 or the general synthesis in scheme-5 from INT-11-26 or INT-11-49 and the known boronic acid derivatives. The further purification is carried out by preparative LC-MS or SFC-MS system in usual manner. The retention time and observed MS by HPLC-QC method are summarized in Tables 85-1 and 85-2.

TABLE 85-1

| Ex. | Intermediate (INT) | Structure | Retention time | Observed MS |
|---|---|---|---|---|
| 51-1 | INT-11-49 | 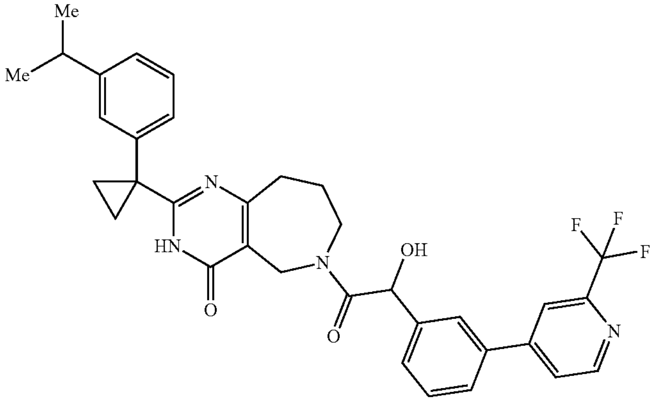 [SMILES: CC(C)c1cccc(C2(c3nc4c(c(=O)[nH]3)CN(C(=O)C(O)c3cccc(-c5ccnc(C(F)(F)F)c5)c3)CCC4)CC2)c1] | 1.98 min | 603.1 |

TABLE 85-1-continued
| Ex. | Intermediate (INT) | Structure | Retention time | Observed MS |
|---|---|---|---|---|
| 51-2 | INT-11-26 | 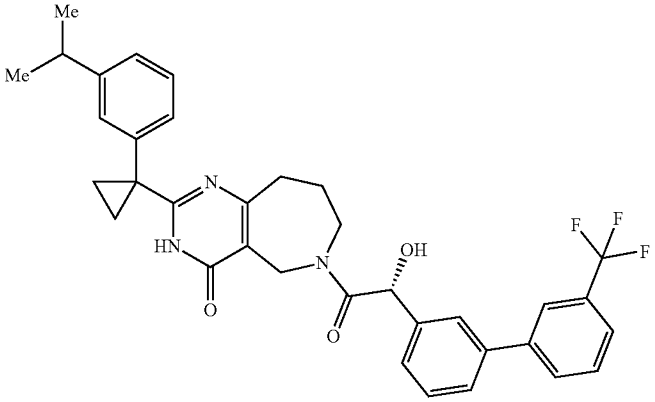 [SMILES: CC(C)c1cccc(C2(c3nc4c(c(=O)[nH]3)CN(C(=O)[C@H](O)c3cccc(-c5cccc(C(F)(F)F)c5)c3)CCC4)CC2)c1] | 2.20 min | 602.0 |
| 51-3 | INT-11-26 | 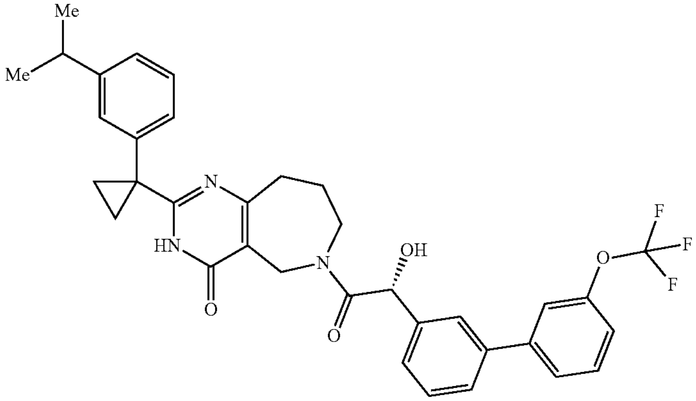 [SMILES: CC(C)c1cccc(C2(c3nc4c(c(=O)[nH]3)CN(C(=O)[C@H](O)c3cccc(-c5cccc(OC(F)(F)F)c5)c3)CCC4)CC2)c1] | 2.23 min | 618.0 |
| 51-4 | INT-11-26 | 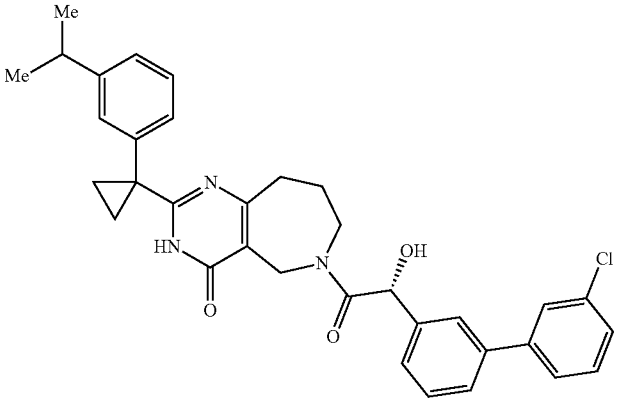 [SMILES: CC(C)c1cccc(C2(c3nc4c(c(=O)[nH]3)CN(C(=O)[C@H](O)c3cccc(-c5cccc(Cl)c5)c3)CCC4)CC2)c1] | 2.19 min | 568.0 |

TABLE 85-1-continued
| Ex. | Intermediate (INT) | Structure | Retention time | Observed MS |
|---|---|---|---|---|
| 51-5 | INT-11-26 | 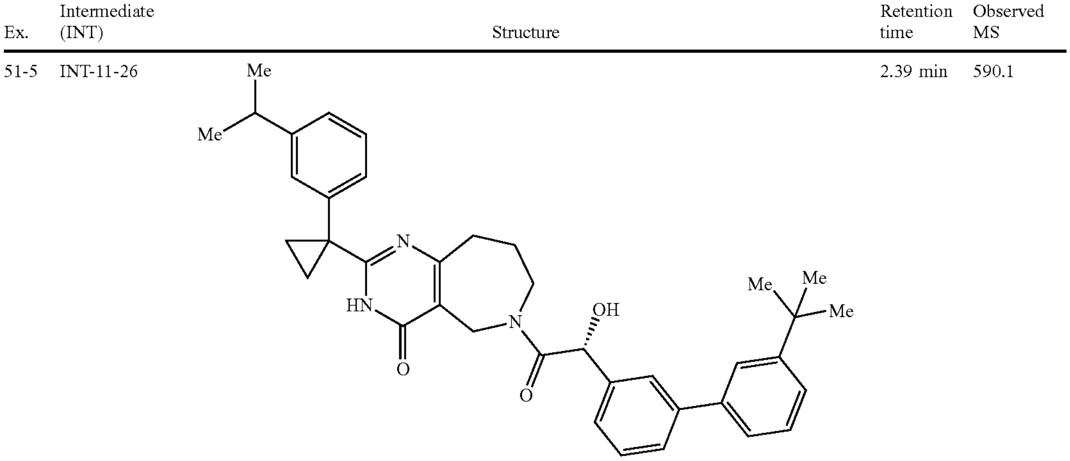 | 2.39 min | 590.1 |
TABLE 85-2
| | | | | |
|---|---|---|---|---|
| 51-6 | INT-11-26 | 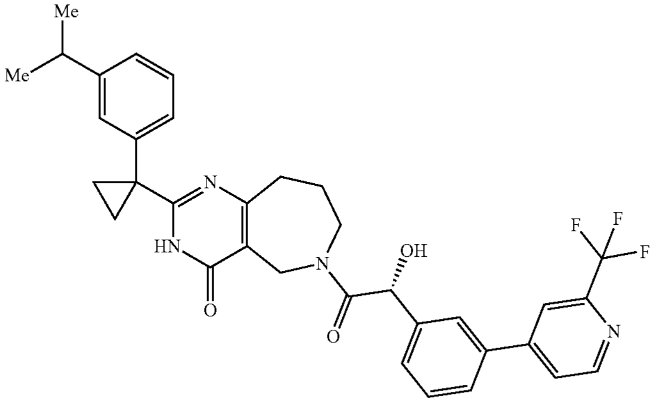 [SMILES: CC(C)c1cccc(C2(c3nc4c(c(=O)[nH]3)CN(C(=O)[C@H](O)c3cccc(-c5ccnc(C(F)(F)F)c5)c3)CCC4)CC2)c1] | 2.00 min | 603.0 |
| 51-7 | INT-11-26 | 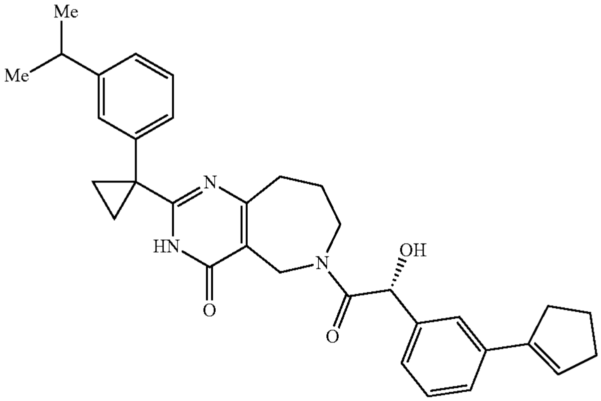 [SMILES: CC(C)c1cccc(C2(c3nc4c(c(=O)[nH]3)CN(C(=O)[C@H](O)c3cccc(C5=CCCC5)c3)CCC4)CC2)c1] | 2.16 min | 524.1 |

TABLE 85-2-continued

| | | | | |
|---|---|---|---|---|
| 51-8 | INT-11-26 | 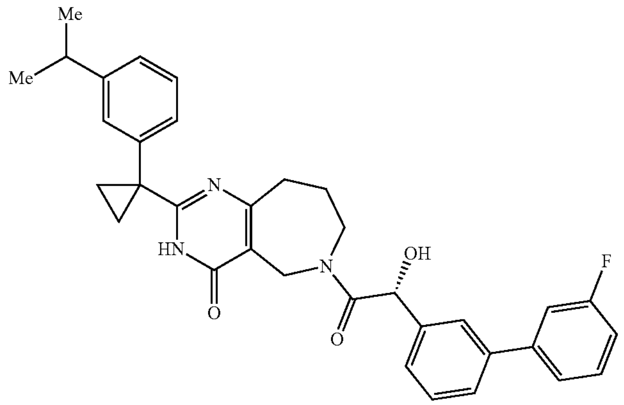 [SMILES: CC(C)c1cccc(C2(c3nc4c(c(=O)[nH]3)CN(C(=O)[C@H](O)c3cccc(-c5cccc(F)c5)c3)CCC4)CC2)c1] | 2.09 min | 552.0 |

The following pyrimidin-4(3H)-one derivatives (Ex-52-1 to Ex-52-15) are prepared according to the procedure of Ex-44-1 or the general synthesis in scheme-5 from INT-11-31, 11-37 or 11-44 and the known boronic acid derivatives. The further purification is carried out by preparative LC-MS or SFC-MS system in usual manner. The retention time and observed MS by HPLC-QC method are summarized in Tables 86-1 to 86-3.

TABLE 86-1

| Ex. | Intermediate (INT) | Structure | Retention time | Observed MS |
|---|---|---|---|---|
| 52-1 | INT-11-31 | 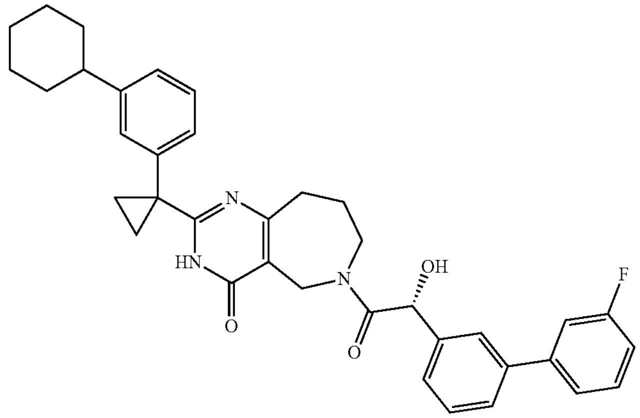 | 2.30 min | 592.0 |
| 52-2 | INT-11-31 | 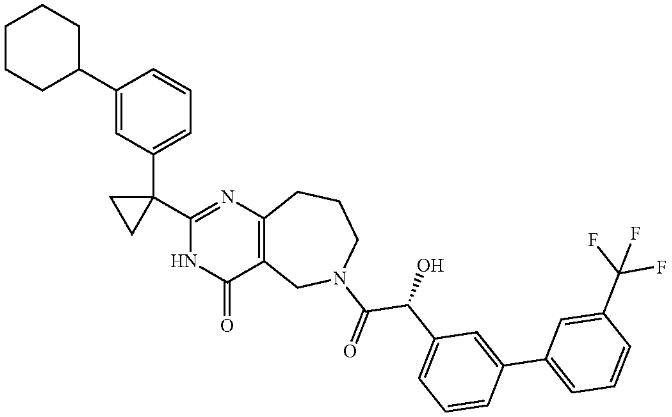 [SMILES: O=C([C@H](O)c1cccc(-c2cccc(C(F)(F)F)c2)c1)N1CCCc2nc(C3(c4cccc(C5CCCCC5)c4)CC3)[nH]c(=O)c2C1] | 2.39 min | 642.0 |

TABLE 86-1-continued
| Ex. | Intermediate (INT) | Structure | Retention time | Observed MS |
|---|---|---|---|---|
| 52-3 | INT-11-31 | 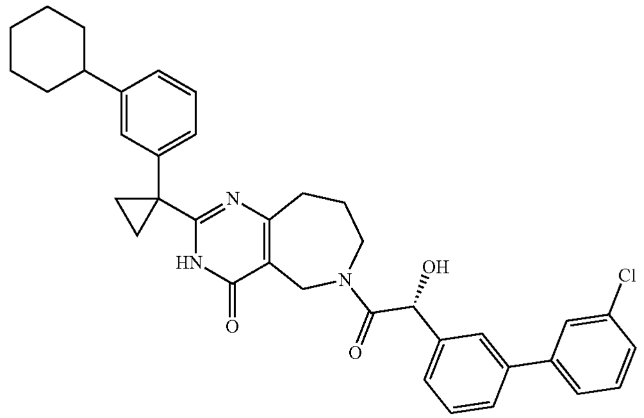 [SMILES: O=C([C@H](O)c1cccc(-c2cccc(Cl)c2)c1)N1CCCc2nc(C3(c4cccc(C5CCCCC5)c4)CC3)[nH]c(=O)c2C1] | 2.40 min | 608.0 |
| 52-4 | INT-11-31 | 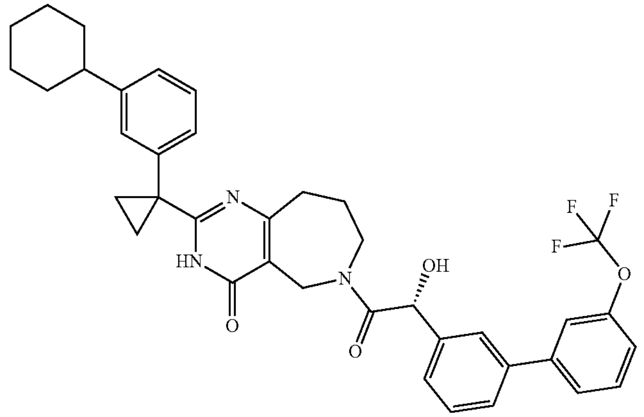 [SMILES: O=C([C@H](O)c1cccc(-c2cccc(OC(F)(F)F)c2)c1)N1CCCc2nc(C3(c4cccc(C5CCCCC5)c4)CC3)[nH]c(=O)c2C1] | 2.42 min | 658.1 |
| 52-5 | INT-11-31 | 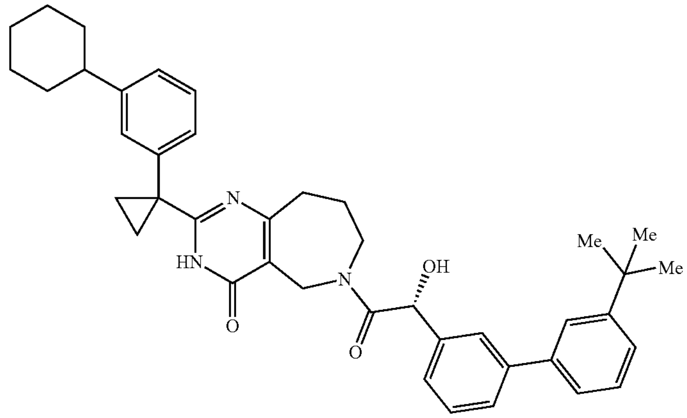 | 5.16 min | 628.3 |

TABLE 86-2
| | | | | |
|---|---|---|---|---|
| 52-6 | INT-11-31 | 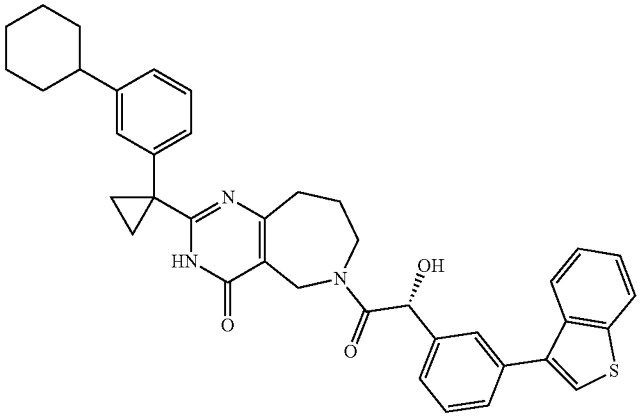 [SMILES: O=C([C@H](O)c1cccc(-c2csc3ccccc23)c1)N1CCCc2nc(C3(c4cccc(C5CCCCC5)c4)CC3)[nH]c(=O)c2C1] | 4.78 min | 628.3 |
| 52-7 | INT-11-31 | 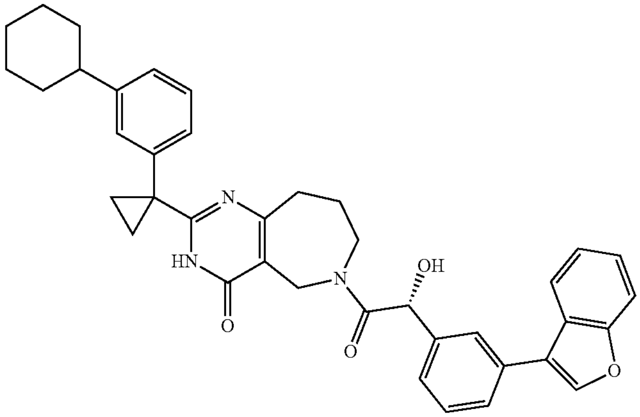 [SMILES: O=C([C@H](O)c1cccc(-c2coc3ccccc23)c1)N1CCCc2nc(C3(c4cccc(C5CCCCC5)c4)CC3)[nH]c(=O)c2C1] | 4.66 min | 612.3 |
| 52-8 | INT-11-37 | 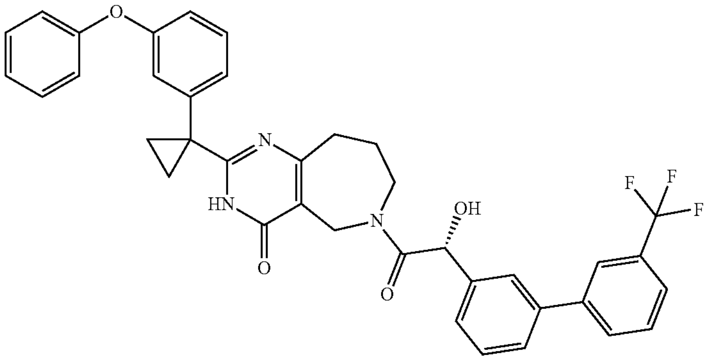 [SMILES: O=C([C@H](O)c1cccc(-c2cccc(C(F)(F)F)c2)c1)N1CCCc2nc(C3(c4cccc(Oc5ccccc5)c4)CC3)[nH]c(=O)c2C1] | 2.26 min | 652.5 |
| 52-9 | INT-11-44 | 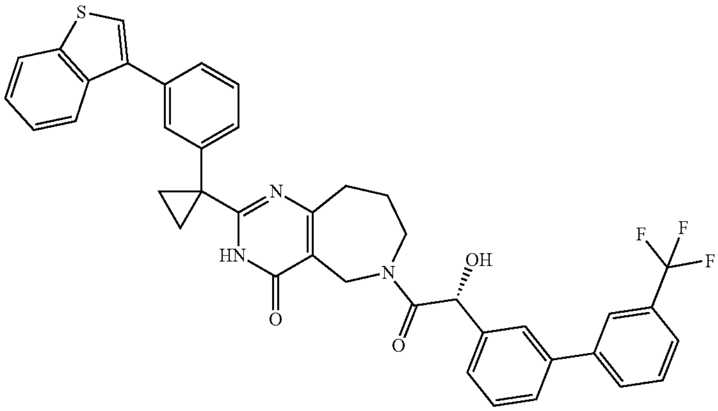 [SMILES: O=C([C@H](O)c1cccc(-c2cccc(C(F)(F)F)c2)c1)N1CCCc2nc(C3(c4cccc(-c5csc6ccccc56)c4)CC3)[nH]c(=O)c2C1] | 2.37 min | 692.5 |

TABLE 86-2-continued
| | | | | |
|---|---|---|---|---|
| 52-10 | INT-11-44 | 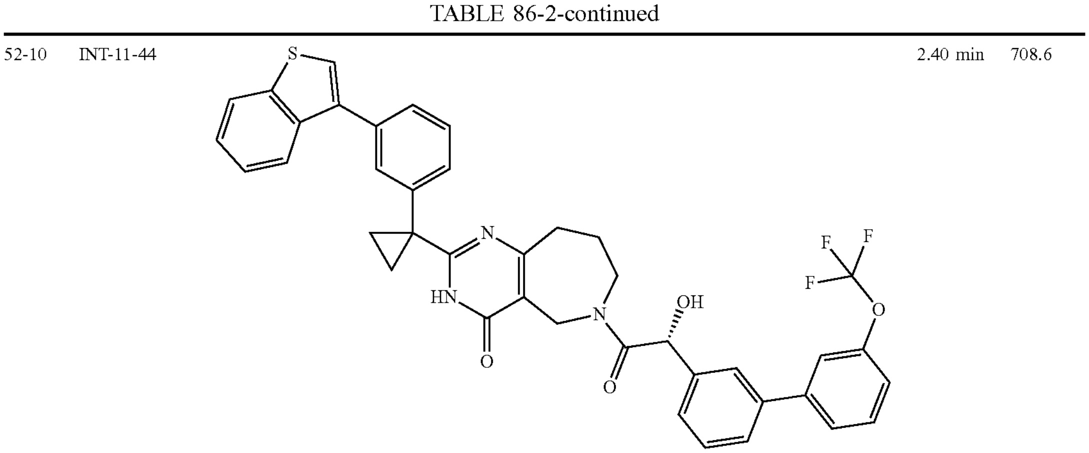 | 2.40 min | 708.6 |
TABLE 86-3
| | | | | |
|---|---|---|---|---|
| 52-11 | INT-11-44 | 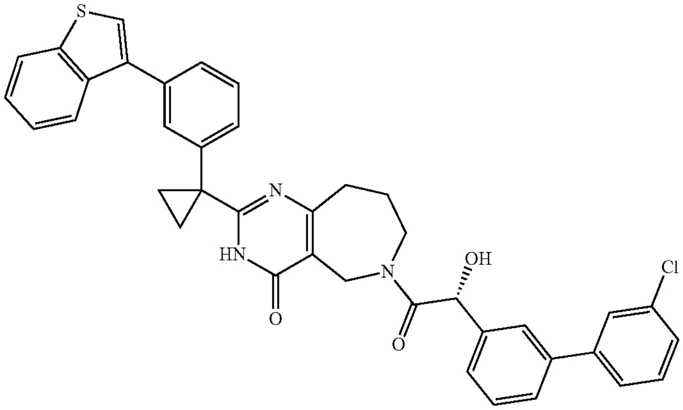 [SMILES: O=C([C@H](O)c1cccc(-c2cccc(Cl)c2)c1)N1CCCc2nc(C3(c4cccc(-c5csc6ccccc56)c4)CC3)[nH]c(=O)c2C1] | 2.38 min | 658.5 |
| 52-12 | INT-11-44 | 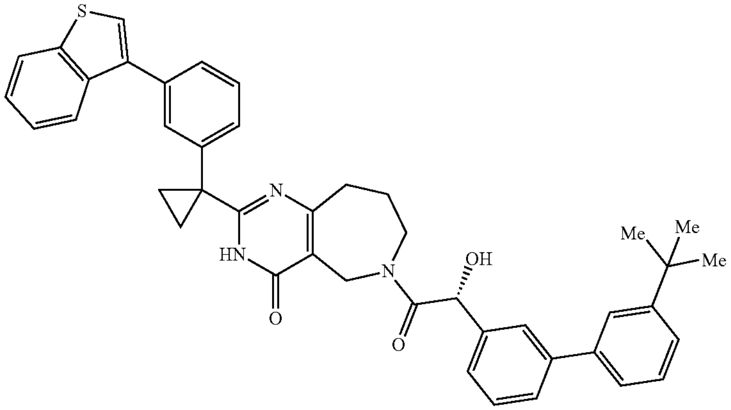 [SMILES: CC(C)(C)c1cccc(-c2cccc([C@@H](O)C(=O)N3CCCc4nc(C5(c6cccc(-c7csc8ccccc78)c6)CC5)[nH]c(=O)c4C3)c2)c1] | 2.53 min | 680.6 |

TABLE 86-3-continued

| | | | | |
|---|---|---|---|---|
| 52-13 | INT-11-44 | 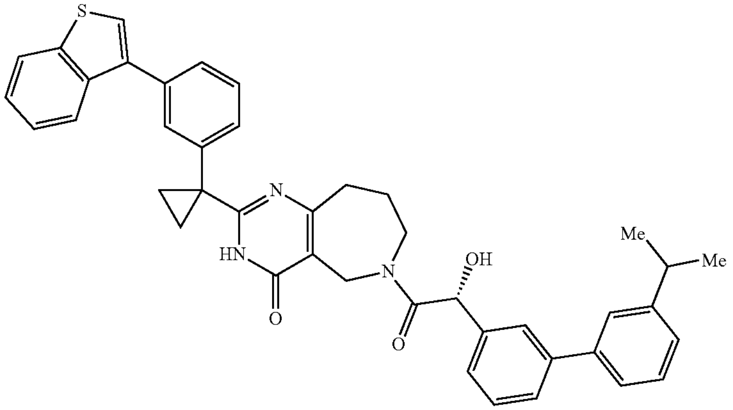 [SMILES: CC(C)c1cccc(-c2cccc([C@@H](O)C(=O)N3CCCc4nc(C5(c6cccc(-c7csc8ccccc78)c6)CC5)[nH]c(=O)c4C3)c2)c1] | 2.48 min | 666.6 |
| 52-14 | INT-11-44 | 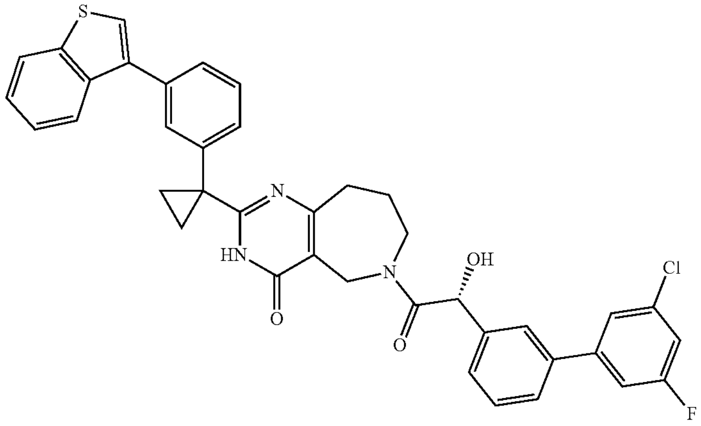 [SMILES: O=C([C@H](O)c1cccc(-c2cc(F)cc(Cl)c2)c1)N1CCCc2nc(C3(c4cccc(-c5csc6ccccc56)c4)CC3)[nH]c(=O)c2C1] | 2.40 min | 676.5 |
| 52-15 | INT-11-44 | 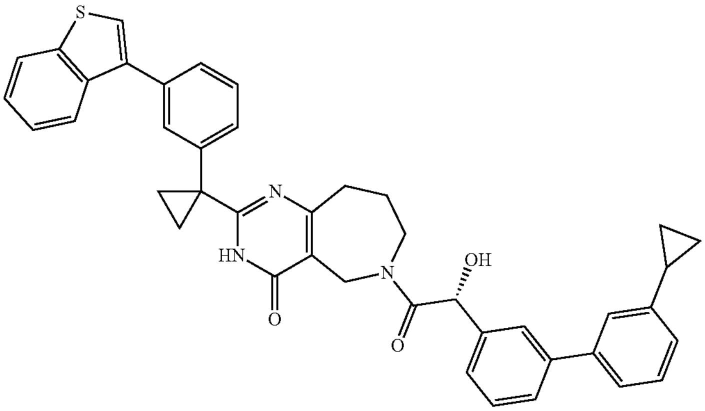 [SMILES: O=C([C@H](O)c1cccc(-c2cccc(C3CC3)c2)c1)N1CCCc2nc(C3(c4cccc(-c5csc6ccccc56)c4)CC3)[nH]c(=O)c2C1] | 2.42 min | 664.6 |

The following pyrimidin-4(3H)-one derivatives (Ex-53-1 to Ex-53-6) are prepared according to the procedure of Ex-44-1 or the general synthesis in scheme-5 from INT-11-36 and the known boronic acid derivatives. The further purification is carried out by preparative LC-MS or SFC-MS system in usual manner. The retention time and observed MS by HPLC-QC method are summarized in Table 87.

TABLE 87
| Ex. | Intermediate (INT) | Structure | Retention time | Observed MS |
|---|---|---|---|---|
| 53-1 | INT-11-36 | 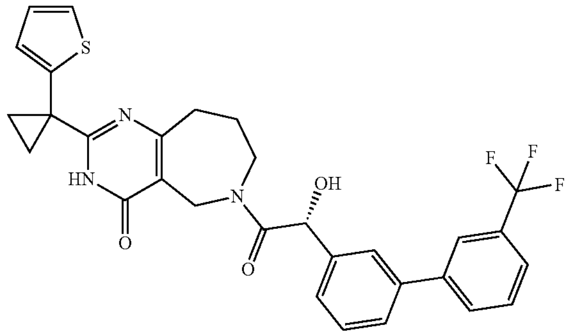 [SMILES: O=C([C@H](O)c1cccc(-c2cccc(C(F)(F)F)c2)c1)N1CCCc2nc(C3(c4cccs4)CC3)[nH]c(=O)c2C1] | 2.07 min | 566.4 |
| 53-2 | INT-11-36 | 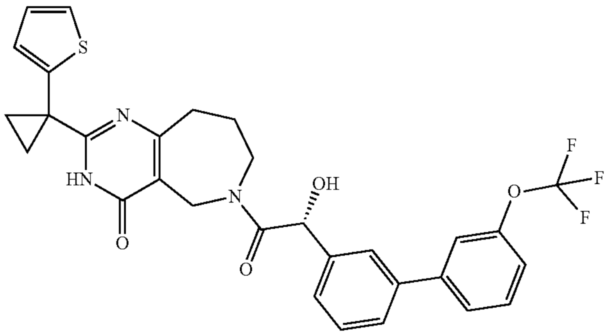 [SMILES: O=C([C@H](O)c1cccc(-c2cccc(OC(F)(F)F)c2)c1)N1CCCc2nc(C3(c4cccs4)CC3)[nH]c(=O)c2C1] | 2.11 min | 582.4 |
| 53-3 | INT-11-36 | 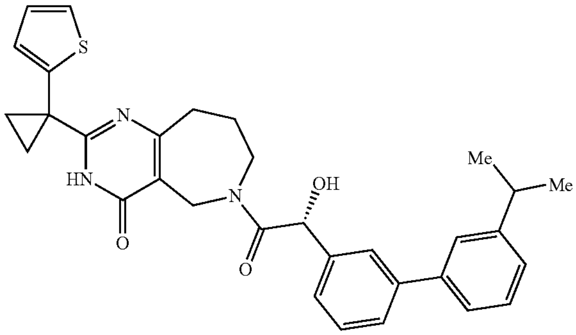 [SMILES: CC(C)c1cccc(-c2cccc([C@@H](O)C(=O)N3CCCc4nc(C5(c6cccs6)CC5)[nH]c(=O)c4C3)c2)c1] | 2.18 min | 540.5 |
| 53-4 | INT-11-36 | 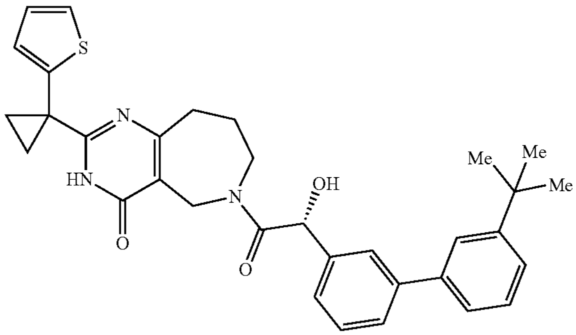 [SMILES: CC(C)(C)c1cccc(-c2cccc([C@@H](O)C(=O)N3CCCc4nc(C5(c6cccs6)CC5)[nH]c(=O)c4C3)c2)c1] | 2.24 min | 554.5 |

TABLE 87-continued

| Ex. | Intermediate (INT) | Structure | Retention time | Observed MS |
|---|---|---|---|---|
| 53-5 | INT-11-36 | 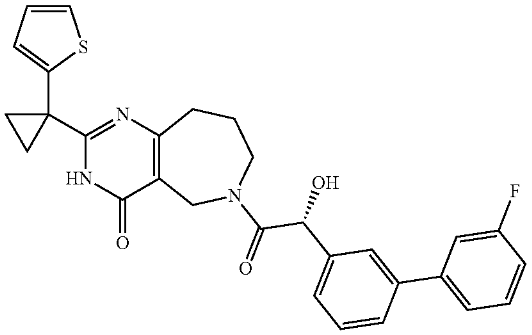 [SMILES: O=C([C@H](O)c1cccc(-c2cccc(F)c2)c1)N1CCCc2nc(C3(c4cccs4)CC3)[nH]c(=O)c2C1] | 1.97 min | 516.4 |
| 53-6 | INT-11-36 | 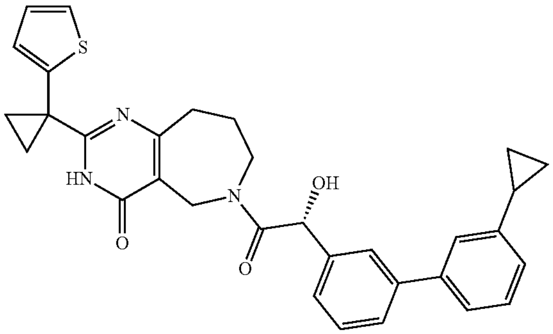 [SMILES: O=C([C@H](O)c1cccc(-c2cccc(C3CC3)c2)c1)N1CCCc2nc(C3(c4cccs4)CC3)[nH]c(=O)c2C1] | 2.11 min | 538.5 |

The following pyrimidin-4(3H)-one derivatives (Ex-54-1 to Ex-54-14) are prepared according to the procedure of Ex-44-1 or the general synthesis in scheme-5 from INT-11-27, 11-39 or 11-42 and the known boronic acid derivatives. The further purification is carried out by preparative LC-MS or SFC-MS system in usual manner. The retention time and observed MS by HPLC-QC method are summarized in Tables 88-1 to 88-3.

TABLE 88-1

| Ex. | Intermediate (INT) | Structure | Retention time | Observed MS |
|---|---|---|---|---|
| 54-1 | INT-11-27 | 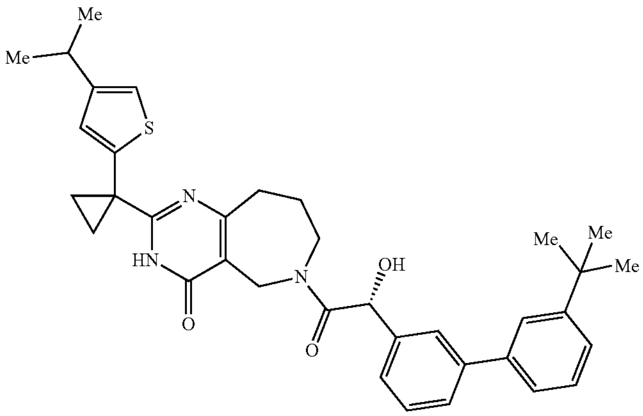 [SMILES: CC(C)c1csc(C2(c3nc4c(c(=O)[nH]3)CN(C(=O)[C@H](O)c3cccc(-c5cccc(C(C)(C)C)c5)c3)CCC4)CC2)c1] | 2.32 min | 596.1 |

TABLE 88-1-continued
| Ex. | Intermediate (INT) | Structure | Retention time | Observed MS |
|---|---|---|---|---|
| 54-2 | INT-11-27 | 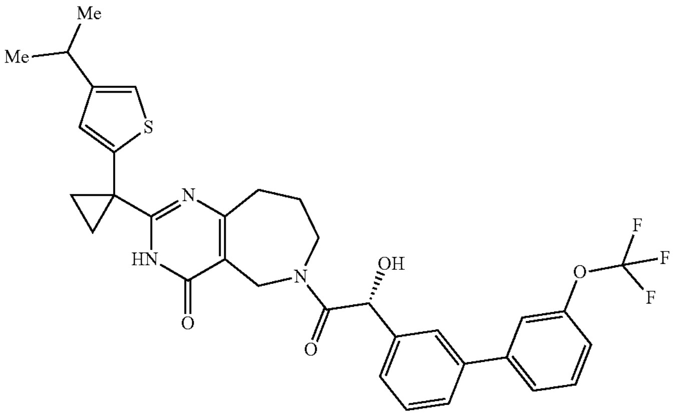 [SMILES: CC(C)c1csc(C2(c3nc4c(c(=O)[nH]3)CN(C(=O)[C@H](O)c3cccc(-c5cccc(OC(F)(F)F)c5)c3)CCC4)CC2)c1] | 2.18 min | 624.0 |
| 54-3 | INT-11-27 | 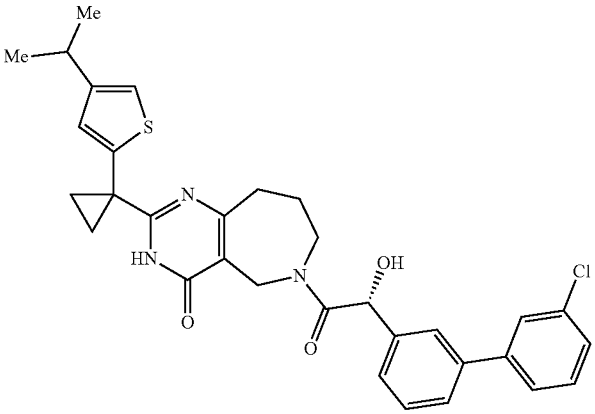 [SMILES: CC(C)c1csc(C2(c3nc4c(c(=O)[nH]3)CN(C(=O)[C@H](O)c3cccc(-c5cccc(Cl)c5)c3)CCC4)CC2)c1] | 2.14 min | 574.0 |
| 54-4 | INT-11-27 | 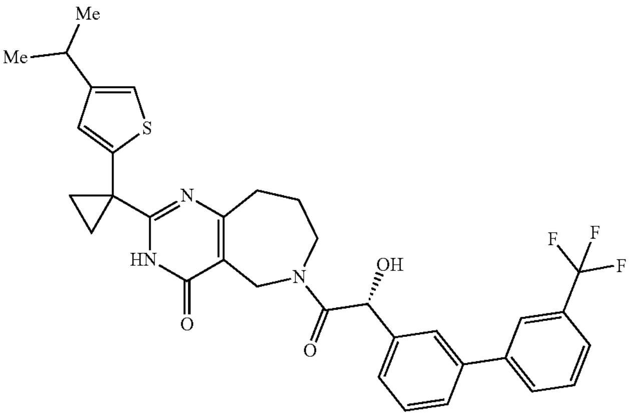 [SMILES: CC(C)c1csc(C2(c3nc4c(c(=O)[nH]3)CN(C(=O)[C@H](O)c3cccc(-c5cccc(C(F)(F)F)c5)c3)CCC4)CC2)c1] | 2.14 min | 608.0 |

TABLE 88-1-continued
| Ex. | Intermediate (INT) | Structure | Retention time | Observed MS |
|---|---|---|---|---|
| 54-5 | INT-11-27 | 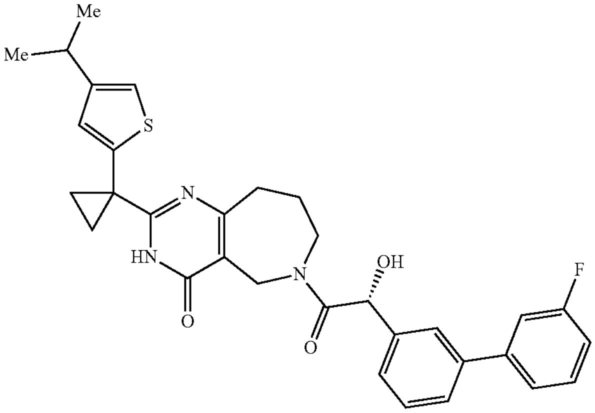 | 2.05 min | 558.0 |
TABLE 88-2
| | | | | |
|---|---|---|---|---|
| 54-6 | INT-11-27 | 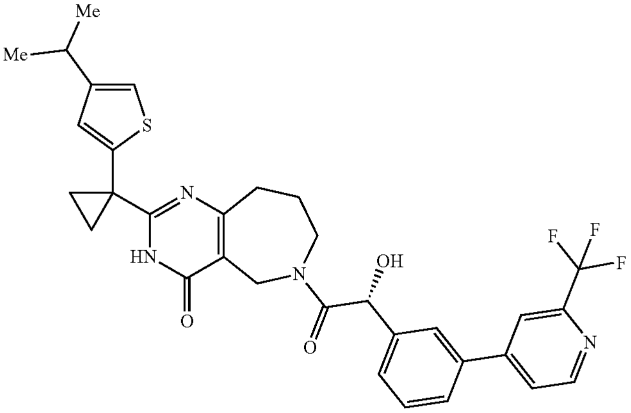 [SMILES: CC(C)c1csc(C2(c3nc4c(c(=O)[nH]3)CN(C(=O)[C@H](O)c3cccc(-c5ccnc(C(F)(F)F)c5)c3)CCC4)CC2)c1] | 1.96 min | 609.0 |
| 54-7 | INT-11-42 | 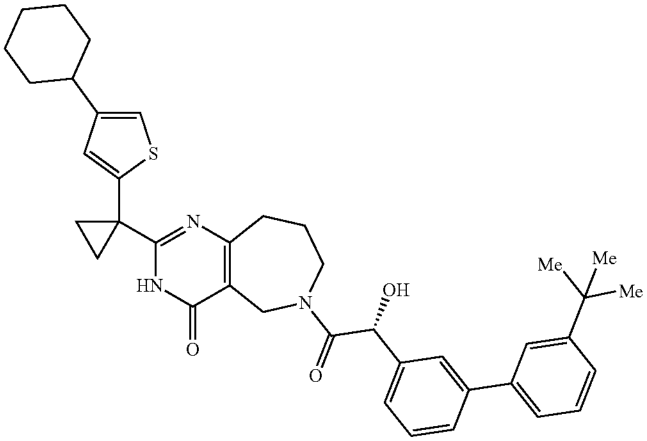 [SMILES: CC(C)(C)c1cccc(-c2cccc([C@@H](O)C(=O)N3CCCc4nc(C5(c6cc(C7CCCCC7)cs6)CC5)[nH]c(=O)c4C3)c2)c1] | 2.65 min | 636.6 |

TABLE 88-2-continued
| | | | | |
|---|---|---|---|---|
| 54-8 | INT-11-42 | 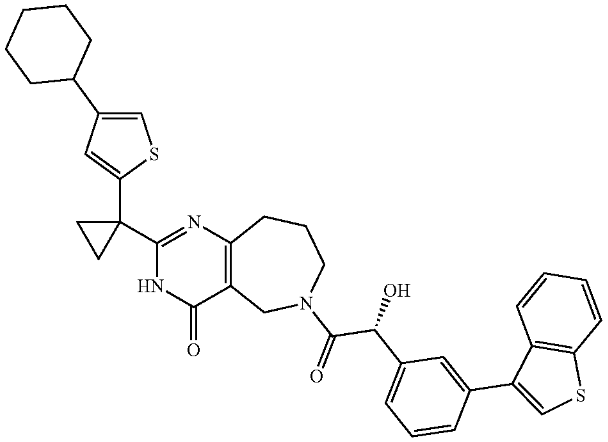 [SMILES: O=C([C@H](O)c1cccc(-c2csc3ccccc23)c1)N1CCCc2nc(C3(c4cc(C5CCCCC5)cs4)CC3)[nH]c(=O)c2C1] | 2.51 min | 636.4 |
| 54-9 | INT-11-42 | 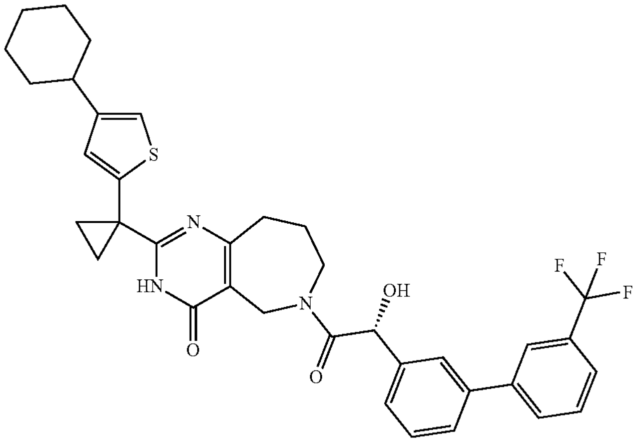 [SMILES: O=C([C@H](O)c1cccc(-c2cccc(C(F)(F)F)c2)c1)N1CCCc2nc(C3(c4cc(C5CCCCC5)cs4)CC3)[nH]c(=O)c2C1] | 2.46 min | 648.5 |
| 54-10 | INT-11-42 | 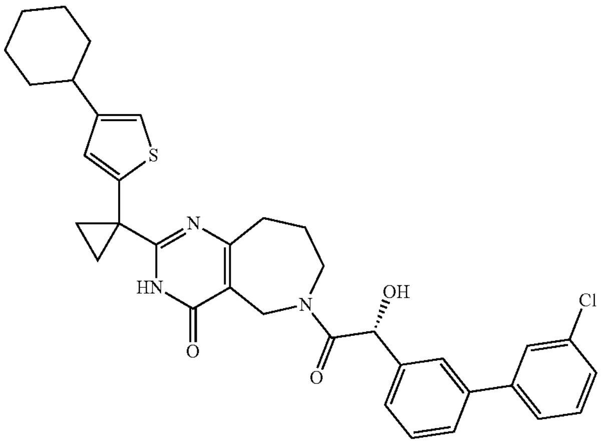 [SMILES: O=C([C@H](O)c1cccc(-c2cccc(Cl)c2)c1)N1CCCc2nc(C3(c4cc(C5CCCCC5)cs4)CC3)[nH]c(=O)c2C1] | 2.47 min | 614.5 |

TABLE 88-3
| | | | | |
|---|---|---|---|---|
| 54-11 | INT-11-42 | 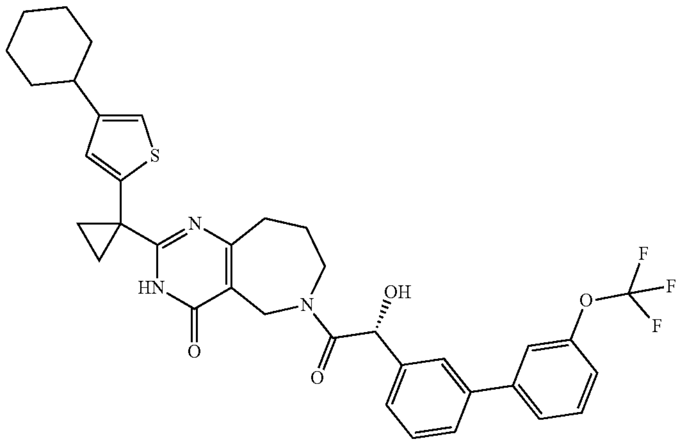 [SMILES: O=C([C@H](O)c1cccc(-c2cccc(OC(F)(F)F)c2)c1)N1CCCc2nc(C3(c4cc(C5CCCCC5)cs4)CC3)[nH]c(=O)c2C1] | 2.49 min | 664.5 |
| 54-12 | INT-11-39 | 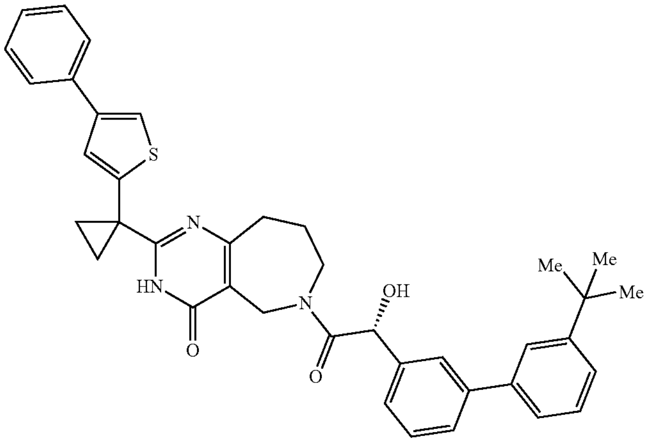 [SMILES: CC(C)(C)c1cccc(-c2cccc([C@@H](O)C(=O)N3CCCc4nc(C5(c6cc(-c7ccccc7)cs6)CC5)[nH]c(=O)c4C3)c2)c1] | 4.59 min | 628.3 |
| 54-13 | INT-11-39 | 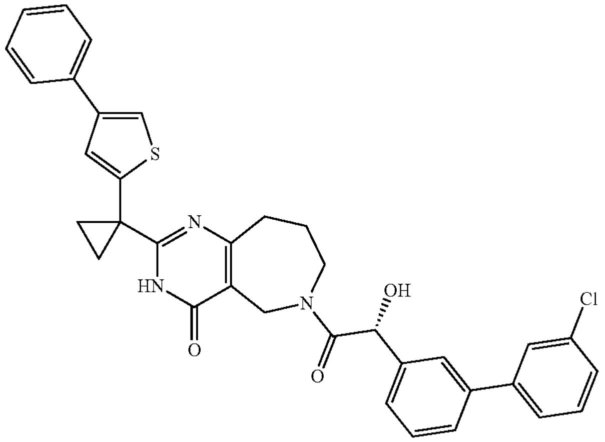 [SMILES: O=C([C@H](O)c1cccc(-c2cccc(Cl)c2)c1)N1CCCc2nc(C3(c4cc(-c5ccccc5)cs4)CC3)[nH]c(=O)c2C1] | 4.13 min | 606.2 |

TABLE 88-3-continued

| | | | | |
|---|---|---|---|---|
| 54-14 | INT-11-39 | 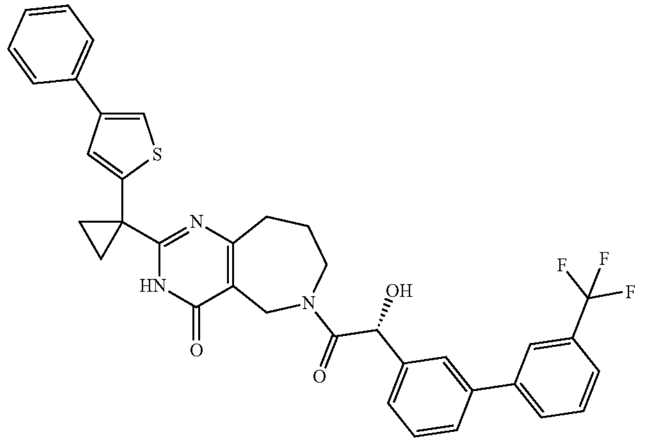 [SMILES: O=C([C@H](O)c1cccc(-c2cccc(C(F)(F)F)c2)c1)N1CCCc2nc(C3(c4cc(-c5ccccc5)cs4)CC3)[nH]c(=O)c2C1] | 2.26 min | 642.50 |

The following pyrimidin-4(3H)-one derivatives (Ex-55-1 to Ex-55-14) are prepared according to the procedure of Ex-44-1 or the general synthesis in scheme-5 from INT-11-28, 11-43 or INT-11-50 and the known boronic acid derivatives. The further purification is carried out by preparative LC-MS or SFC-MS system in usual manner. The retention time and observed MS by HPLC-QC method are summarized in Tables 89-1 to 89-3.

TABLE 89-1

| Ex. | Intermediate (INT) | Structure | Retention time | Observed MS |
|---|---|---|---|---|
| 55-1 | INT-11-50 | 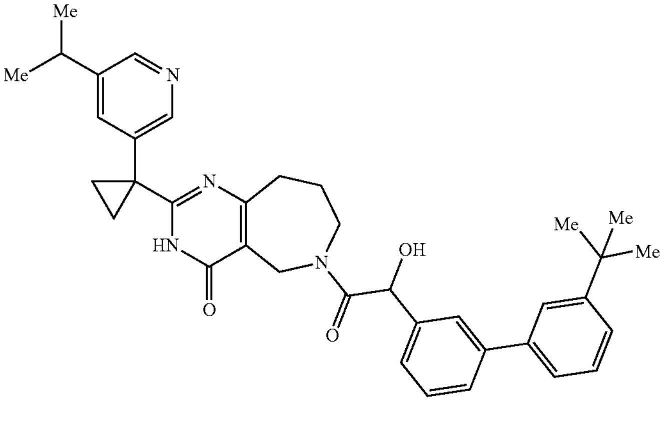 [SMILES: CC(C)c1cncc(C2(c3nc4c(c(=O)[nH]3)CN(C(=O)C(O)c3cccc(-c5cccc(C(C)(C)C)c5)c3)CCC4)CC2)c1] | 2.03 min | 591.2 |
| 55-2 | INT-11-50 | 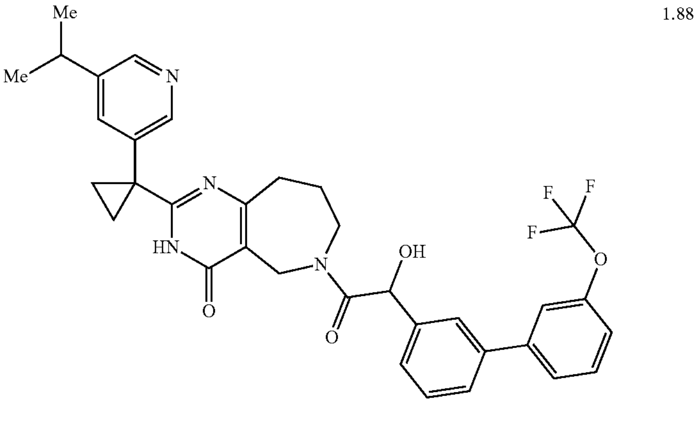 | 1.88 min | 619.2 |

TABLE 89-1-continued
| Ex. | Intermediate (INT) | Structure | Retention time | Observed MS |
|---|---|---|---|---|
| 55-3 | INT-11-50 | 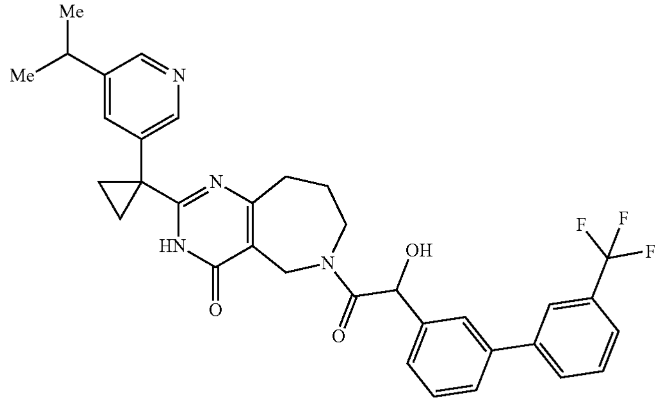 [SMILES: CC(C)c1cncc(C2(c3nc4c(c(=O)[nH]3)CN(C(=O)C(O)c3cccc(-c5cccc(C(F)(F)F)c5)c3)CCC4)CC2)c1] | 1.84 min | 603.1 |
| 55-4 | INT-11-28 | 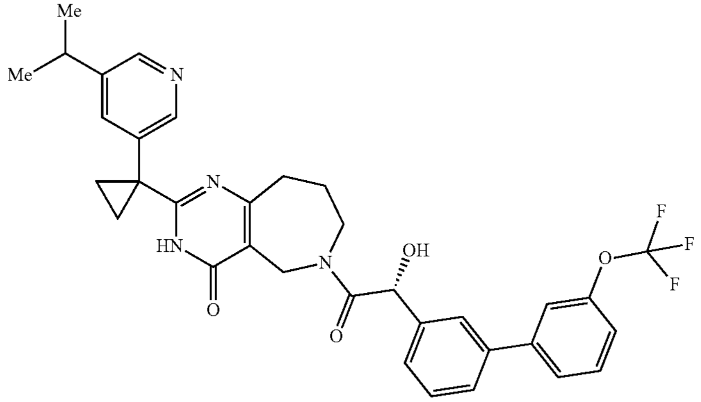 [SMILES: CC(C)c1cncc(C2(c3nc4c(c(=O)[nH]3)CN(C(=O)[C@H](O)c3cccc(-c5cccc(OC(F)(F)F)c5)c3)CCC4)CC2)c1] | 1.87 min | 619.1 |
| 55-5 | INT-11-28 | 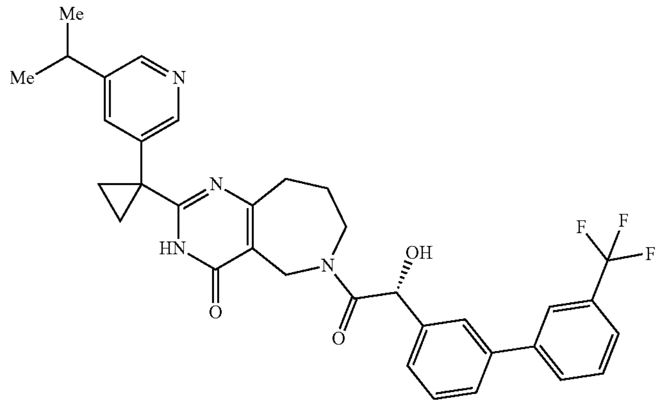 [SMILES: CC(C)c1cncc(C2(c3nc4c(c(=O)[nH]3)CN(C(=O)[C@H](O)c3cccc(-c5cccc(C(F)(F)F)c5)c3)CCC4)CC2)c1] | 1.83 min | 603.0 |

TABLE 89-2
| | | | | |
|---|---|---|---|---|
| 55-6 | INT-11-28 | 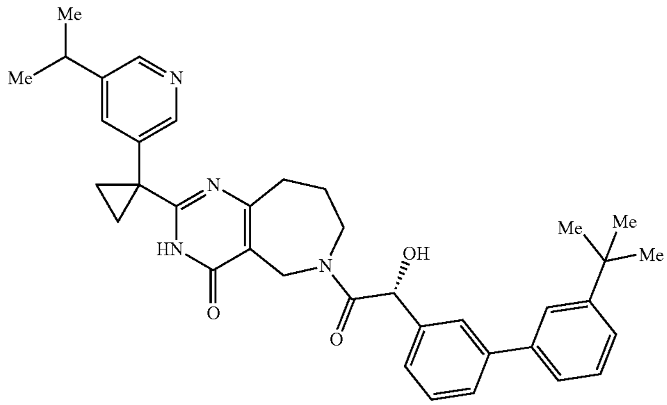 [SMILES: CC(C)c1cncc(C2(c3nc4c(c(=O)[nH]3)CN(C(=O)[C@H](O)c3cccc(-c5cccc(C(C)(C)C)c5)c3)CCC4)CC2)c1] | 2.01 min | 591.1 |
| 55-7 | INT-11-28 | 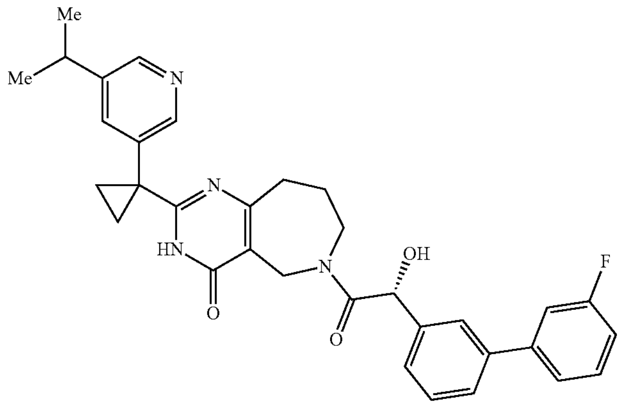 [SMILES: CC(C)c1cncc(C2(c3nc4c(c(=O)[nH]3)CN(C(=O)[C@H](O)c3cccc(-c5cccc(F)c5)c3)CCC4)CC2)c1] | 1.70 min | 553.0 |
| 55-8 | INT-11-28 | 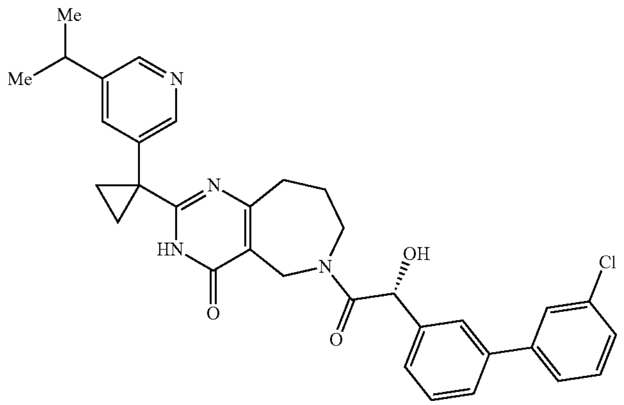 [SMILES: CC(C)c1cncc(C2(c3nc4c(c(=O)[nH]3)CN(C(=O)[C@H](O)c3cccc(-c5cccc(Cl)c5)c3)CCC4)CC2)c1] | 1.80 min | 569.0 |
| 55-9 | INT-11-28 | 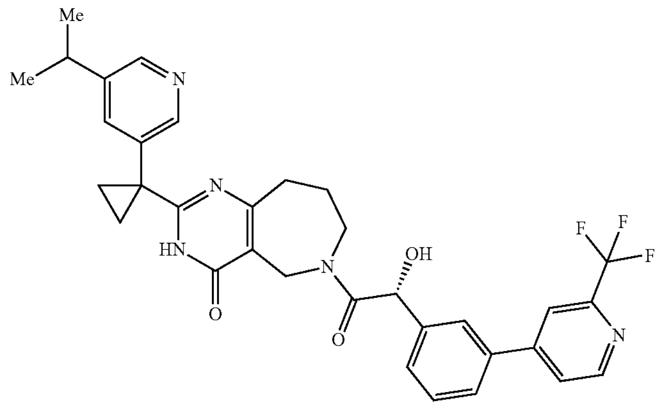 [SMILES: CC(C)c1cncc(C2(c3nc4c(c(=O)[nH]3)CN(C(=O)[C@H](O)c3cccc(-c5ccnc(C(F)(F)F)c5)c3)CCC4)CC2)c1] | 1.62 min | 604.1 |

TABLE 89-2-continued
| | | | | |
|---|---|---|---|---|
| 55-10 | INT-11-43 | 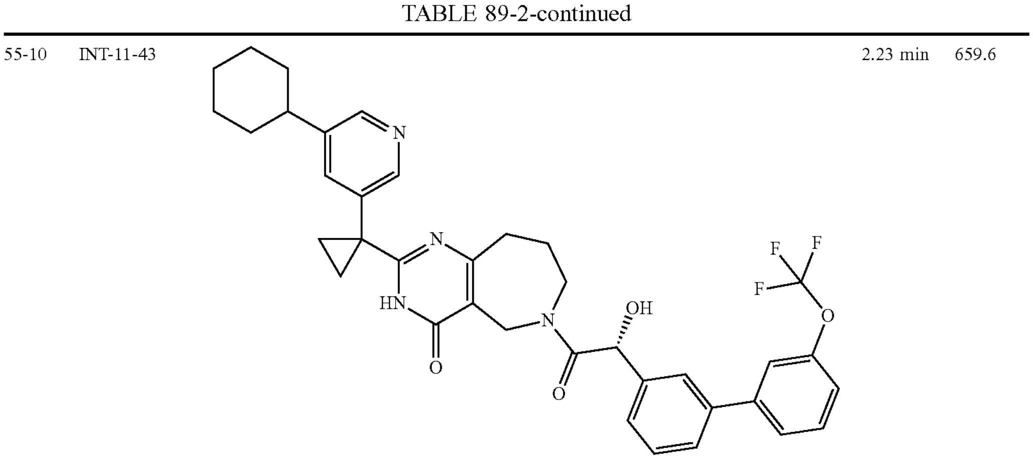 | 2.23 min | 659.6 |
TABLE 89-3
| | | | | |
|---|---|---|---|---|
| 55-11 | INT-11-43 | 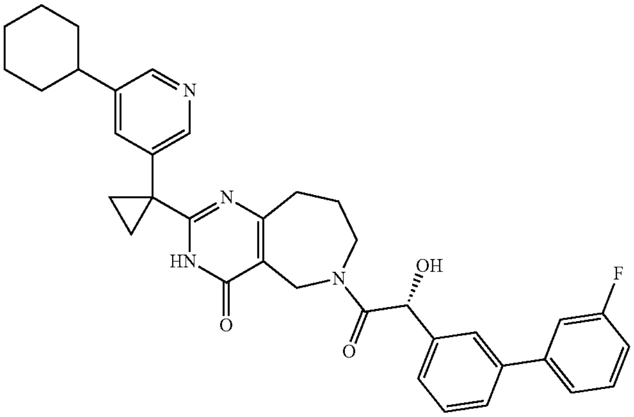 [SMILES: O=C([C@H](O)c1cccc(-c2cccc(F)c2)c1)N1CCCc2nc(C3(c4cncc(C5CCCCC5)c4)CC3)[nH]c(=O)c2C1] | 2.11 min | 593.6 |
| 55-12 | INT-11-43 | 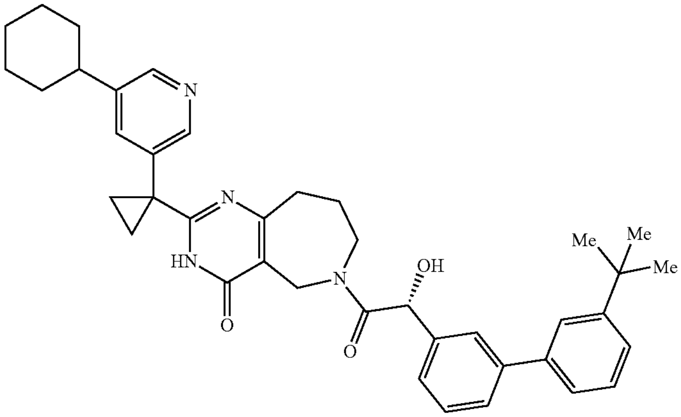 [SMILES: CC(C)(C)c1cccc(-c2cccc([C@@H](O)C(=O)N3CCCc4nc(C5(c6cncc(C7CCCCC7)c6)CC5)[nH]c(=O)c4C3)c2)c1] | 2.35 min | 631.7 |

TABLE 89-3-continued

| | | | | |
|---|---|---|---|---|
| 55-13 | INT-11-43 | 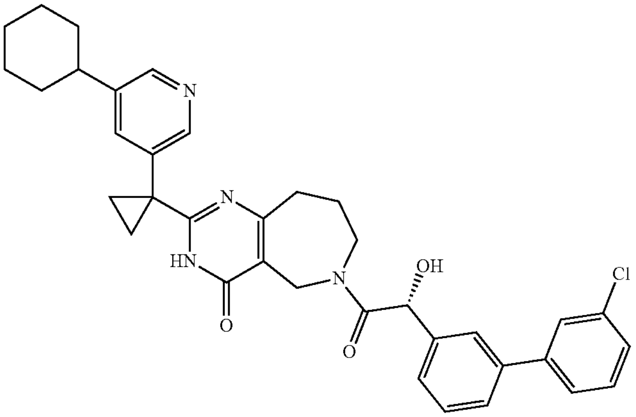 [SMILES: O=C([C@H](O)c1cccc(-c2cccc(Cl)c2)c1)N1CCCc2nc(C3(c4cncc(C5CCCCC5)c4)CC3)[nH]c(=O)c2C1] | 2.19 min | 609.5 |
| 55-14 | INT-11-43 | 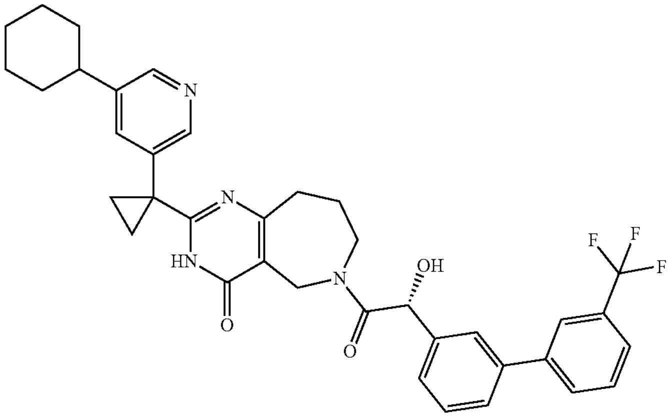 [SMILES: O=C([C@H](O)c1cccc(-c2cccc(C(F)(F)F)c2)c1)N1CCCc2nc(C3(c4cncc(C5CCCCC5)c4)CC3)[nH]c(=O)c2C1] | 2.20 min | 643.6 |

The following pyrimidin-4(3H)-one derivatives (Ex-56-1 to Ex-56-6) are prepared according to the procedure of Ex-44-1 or the general synthesis in scheme-5 from INT-11-29 or INT-11-51 and the known boronic acid derivatives. The further purification is carried out by preparative LC-MS system in usual manner. The retention time and observed MS by HPLC-QC method are summarized in Table 90.

TABLE 90

| Ex. | Intermediate (INT) | Structure | Retention time | Observed MS |
|---|---|---|---|---|
| 56-1 | INT-11-51 | 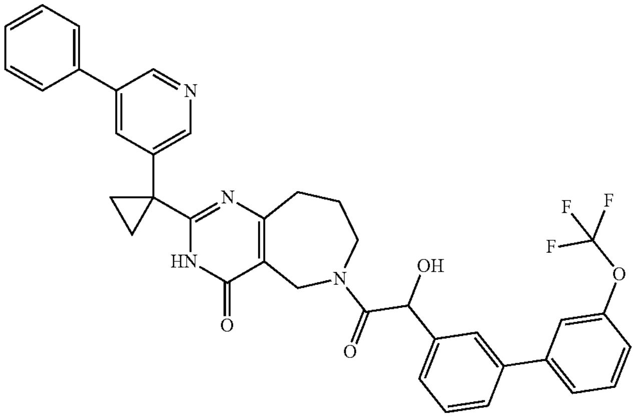 [SMILES: O=C(C(O)c1cccc(-c2cccc(OC(F)(F)F)c2)c1)N1CCCc2nc(C3(c4cncc(-c5ccccc5)c4)CC3)[nH]c(=O)c2C1] | 1.92 min | 653.3 |

TABLE 90-continued
| Ex. | Intermediate (INT) | Structure | Retention time | Observed MS |
|---|---|---|---|---|
| 56-2 | INT-11-51 | 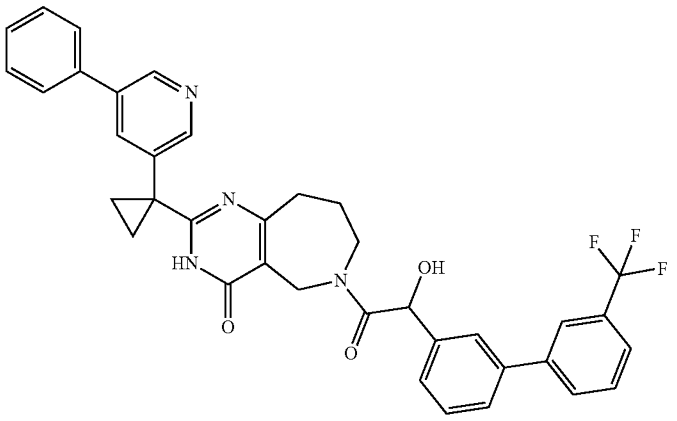 [SMILES: O=C(C(O)c1cccc(-c2cccc(C(F)(F)F)c2)c1)N1CCCc2nc(C3(c4cncc(-c5ccccc5)c4)CC3)[nH]c(=O)c2C1] | 1.89 min | 637.3 |
| 56-3 | INT-11-51 | 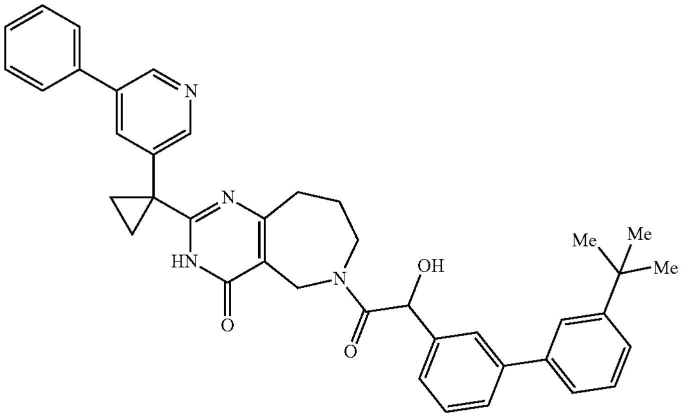 [SMILES: CC(C)(C)c1cccc(-c2cccc(C(O)C(=O)N3CCCc4nc(C5(c6cncc(-c7ccccc7)c6)CC5)[nH]c(=O)c4C3)c2)c1] | 2.06 min | 625.3 |
| 56-4 | INT-11-29 | 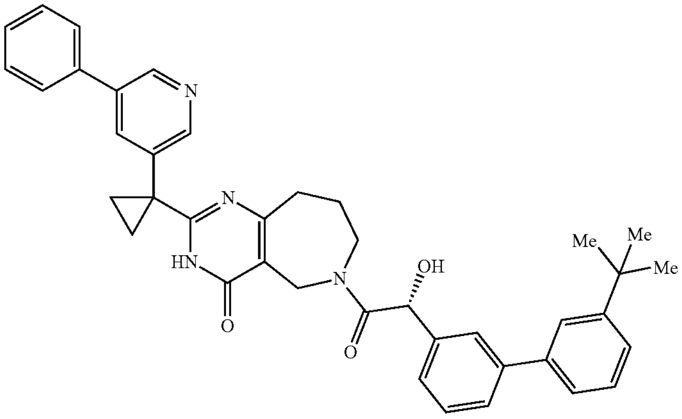 [SMILES: CC(C)(C)c1cccc(-c2cccc([C@@H](O)C(=O)N3CCCc4nc(C5(c6cncc(-c7ccccc7)c6)CC5)[nH]c(=O)c4C3)c2)c1] | 2.07 min | 625.1 |

TABLE 90-continued

| Ex. | Intermediate (INT) | Structure | Retention time | Observed MS |
|---|---|---|---|---|
| 56-5 | INT-11-29 | 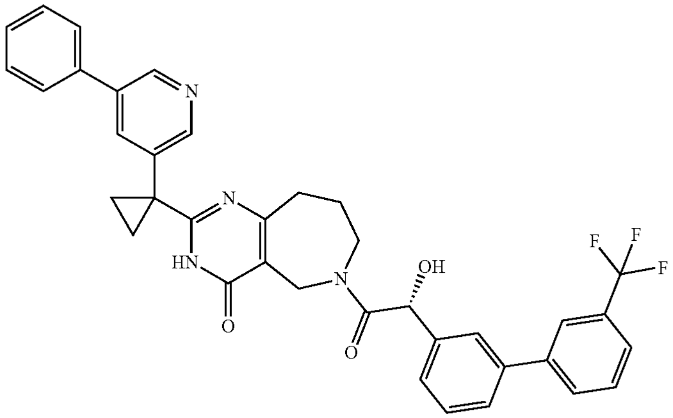 [SMILES: O=C([C@H](O)c1cccc(-c2cccc(C(F)(F)F)c2)c1)N1CCCc2nc(C3(c4cncc(-c5ccccc5)c4)CC3)[nH]c(=O)c2C1] | 1.89 min | 637.0 |
| 56-6 | INT-11-29 | 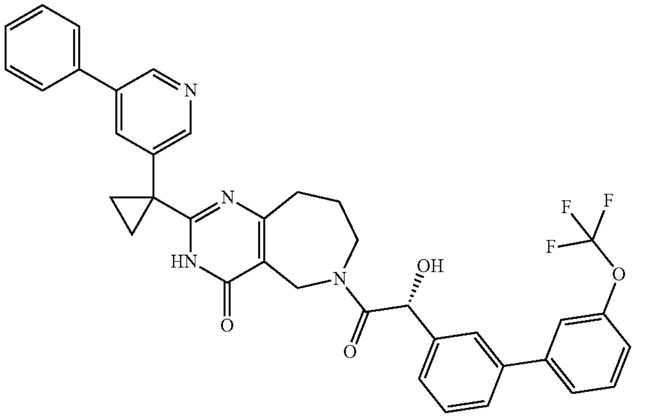 [SMILES: O=C([C@H](O)c1cccc(-c2cccc(OC(F)(F)F)c2)c1)N1CCCc2nc(C3(c4cncc(-c5ccccc5)c4)CC3)[nH]c(=O)c2C1] | 1.93 min | 653.0 |

The following pyrimidin-4(3H)-one derivatives (Ex-57-1 to Ex-57-9) are prepared according to the procedure of Ex-44-1 or the general synthesis in scheme-5 from INT-11-30 or 11-40 and the known boronic acid derivatives. The further purification is carried out by preparative LC-MS or SFC-MS system in usual manner. The retention time and observed MS by HPLC-QC method are summarized in Tables 91-1 to 91-2.

TABLE 91-1

| Ex. | Intermediate (INT) | Structure | Retention time | Observed MS |
|---|---|---|---|---|
| 57-1 | INT-11-30 | 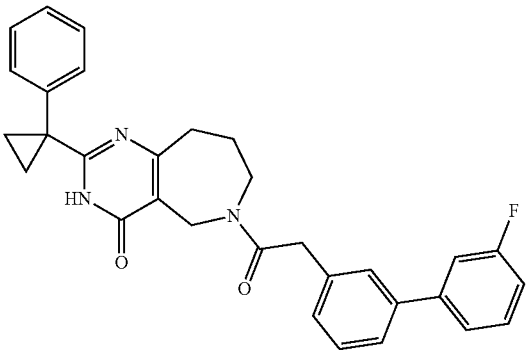 [SMILES: O=C(Cc1cccc(-c2cccc(F)c2)c1)N1CCCc2nc(C3(c4ccccc4)CC3)[nH]c(=O)c2C1] | 1.91 min | 494.0 |

TABLE 91-1-continued
| Ex. | Intermediate (INT) | Structure | Retention time | Observed MS |
|---|---|---|---|---|
| 57-2 | INT-11-30 | 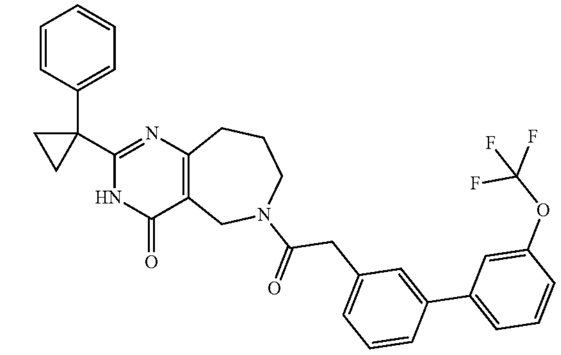 [SMILES: O=C(Cc1cccc(-c2cccc(OC(F)(F)F)c2)c1)N1CCCc2nc(C3(c4ccccc4)CC3)[nH]c(=O)c2C1] | 2.06 min | 559.9 |
| 57-3 | INT-11-30 | 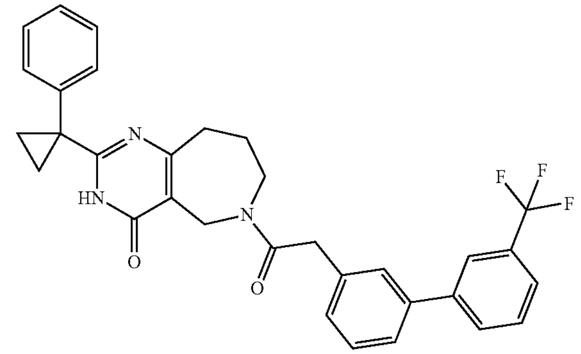 [SMILES: O=C(Cc1cccc(-c2cccc(C(F)(F)F)c2)c1)N1CCCc2nc(C3(c4ccccc4)CC3)[nH]c(=O)c2C1] | 2.03 min | 543.9 |
| 57-4 | INT-11-30 | 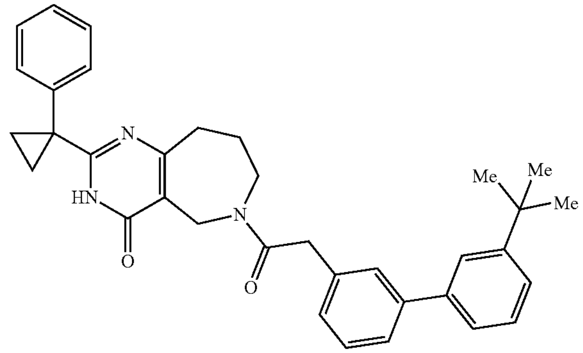 [SMILES: CC(C)(C)c1cccc(-c2cccc(CC(=O)N3CCCc4nc(C5(c6ccccc6)CC5)[nH]c(=O)c4C3)c2)c1] | 2.21 min | 531.9 |
| 57-5 | INT-11-40 | 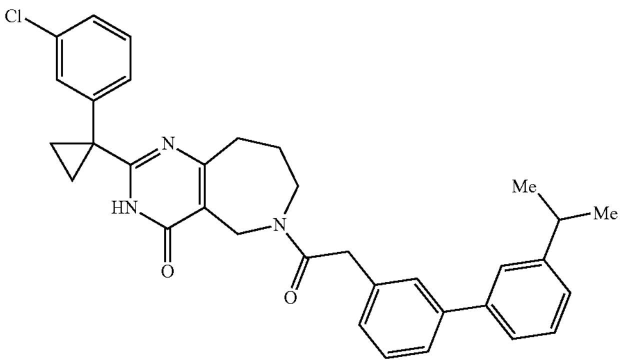 [SMILES: CC(C)c1cccc(-c2cccc(CC(=O)N3CCCc4nc(C5(c6cccc(Cl)c6)CC5)[nH]c(=O)c4C3)c2)c1] | 2.32 min | 552.5 |

TABLE 91-1-continued
| Ex. | Intermediate (INT) | Structure | Retention time | Observed MS |
|---|---|---|---|---|
| 57-6 | INT-11-40 | 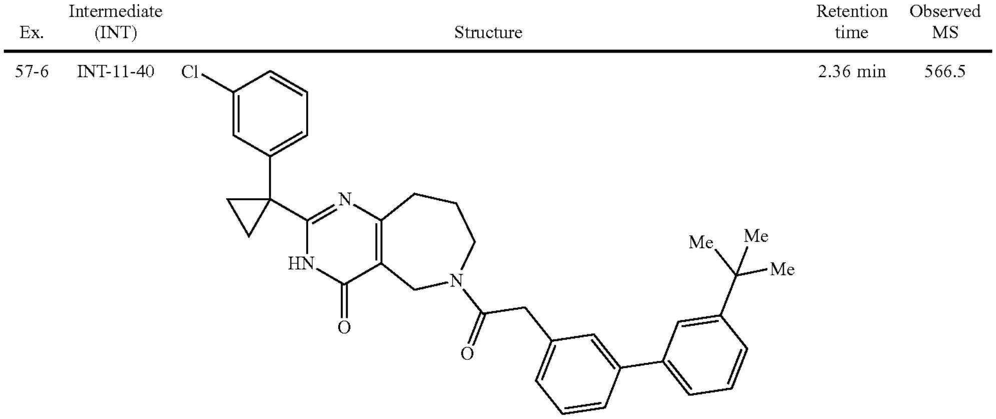 | 2.36 min | 566.5 |
TABLE 91-2
| | | | | |
|---|---|---|---|---|
| 57-7 | INT-11-40 | 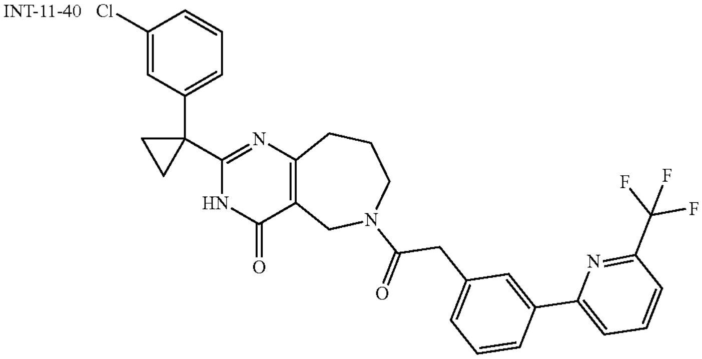 | 2.13 min | 579.4 |
| 57-8 | INT-11-40 | 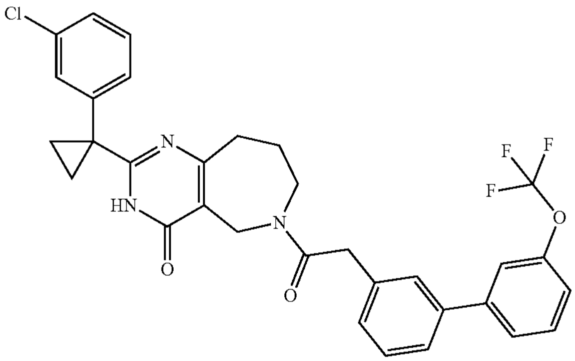 [SMILES: O=C(Cc1cccc(-c2cccc(OC(F)(F)F)c2)c1)N1CCCc2nc(C3(c4cccc(Cl)c4)CC3)[nH]c(=O)c2C1] | 2.24 min | 594.4 |

TABLE 91-2-continued

| | | | | |
|---|---|---|---|---|
| 57-9 | INT-11-40 | 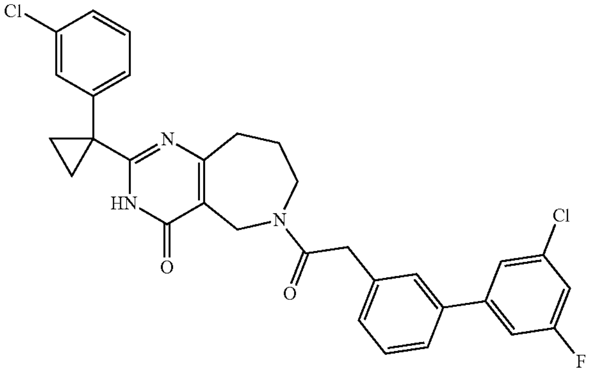 [SMILES: O=C(Cc1cccc(-c2cc(F)cc(Cl)c2)c1)N1CCCc2nc(C3(c4cccc(Cl)c4)CC3)[nH]c(=O)c2C1] | 2.24 min | 562.4 |

The following pyrimidin-4(3H)-one derivatives (Ex-58-1 to Ex-58-5) are prepared according to the procedure of Ex-44-1 or the general synthesis in scheme-5 from INT-11-33 and the known boronic acid derivatives. The further purification is carried out by preparative LC-MS or SFC-MS system in usual manner. The retention time and observed MS by HPLC-QC method are summarized in Table 92.

TABLE 92

| Ex. | Intermediate (INT) | Structure | Retention time | Observed MS |
|---|---|---|---|---|
| 58-1 | INT-11-33 | 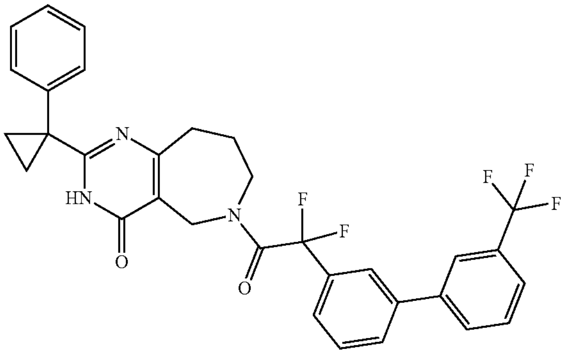 [SMILES: O=C(N1CCCc2nc(C3(c4ccccc4)CC3)[nH]c(=O)c2C1)C(F)(F)c1cccc(-c2cccc(C(F)(F)F)c2)c1] | 4.11 min | 578.2 |
| 58-2 | INT-11-33 | 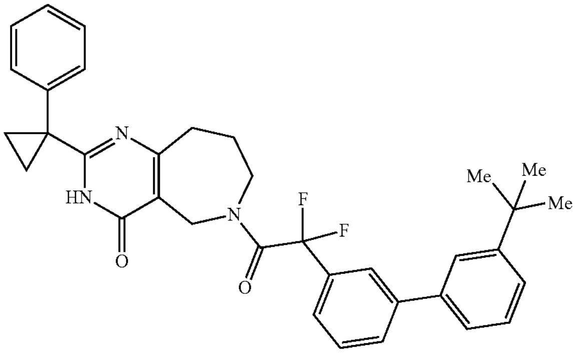 [SMILES: CC(C)(C)c1cccc(-c2cccc(C(F)(F)C(=O)N3CCCc4nc(C5(c6ccccc6)CC5)[nH]c(=O)c4C3)c2)c1] | 4.51 min | 566.3 |

TABLE 92-continued
| Ex. | Intermediate (INT) | Structure | Retention time | Observed MS |
|---|---|---|---|---|
| 58-3 | INT-11-33 | 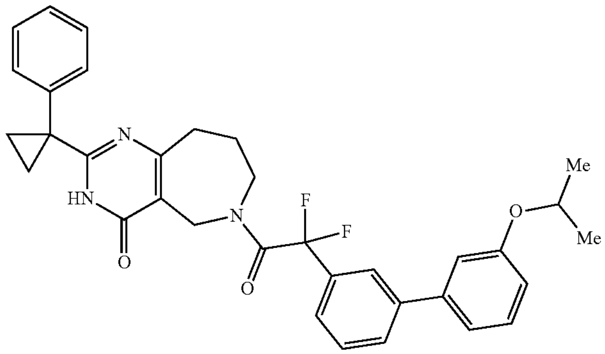 [SMILES: CC(C)Oc1cccc(-c2cccc(C(F)(F)C(=O)N3CCCc4nc(C5(c6ccccc6)CC5)[nH]c(=O)c4C3)c2)c1] | 4.18 min | 568.3 |
| 58-4 | INT-11-33 | 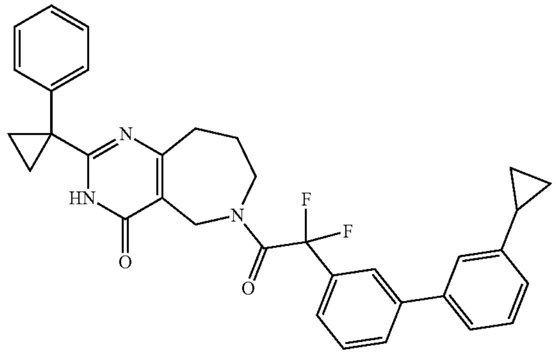 [SMILES: O=C(N1CCCc2nc(C3(c4ccccc4)CC3)[nH]c(=O)c2C1)C(F)(F)c1cccc(-c2cccc(C3CC3)c2)c1] | 4.19 min | 550.2 |
| 58-5 | INT-11-33 | 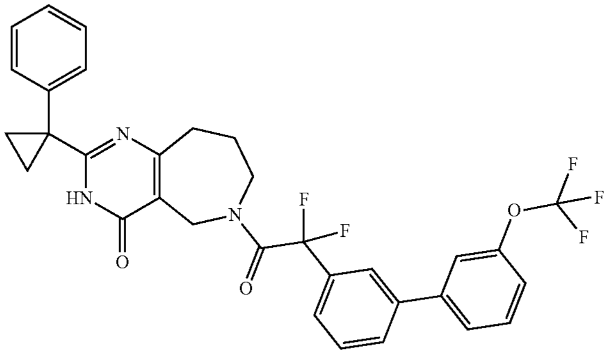 [SMILES: O=C(N1CCCc2nc(C3(c4ccccc4)CC3)[nH]c(=O)c2C1)C(F)(F)c1cccc(-c2cccc(OC(F)(F)F)c2)c1] | 4.21 min | 594.2 |

Example-59-14

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-diisopropylthiophene-3-carboxamide (Ex-59-14)

{Chem. 107}

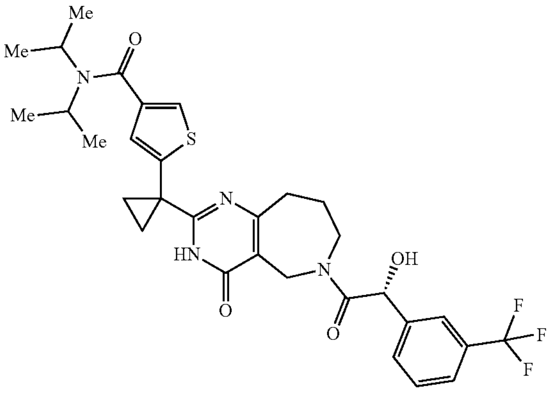

To the solution of INT-27-1 (15 mg, 0.028 mmol), diisopropylamine (0.0060 mL, 0.042 mmol), HATU (16.0 mg, 0.042 mmol) in 20% DMF in MeCN (1.2 mL) is added triethylamine (0.020 mL, 0.141 mmol). The reaction mixture is stirred at rt overnight. After concentrated in vacuo, the mixture is purified by a strong anion exchange cartridge (ISOLUTE (registered trademark) SCX-2, 1 g/6 mL, Biotage) and the extracted fraction is concentrated in vacuo to give the titled compound (12.5 mg) as a yellow viscous oil.

LC-MS (Method-F) m/z: M+1 obs 616.89, tR=2.79 min.

The further purification is carried out by preparative LC-MS or SFC-MS system in the usual manner. The retention time and observed MS by HPLC-QC method are summarized in Tables 93-1 to 93-4.

The following pyrimidin-4(3H)-one derivatives (Ex-59-1 to Ex-59-19) are prepared according to the procedure of Ex-59-14 or the general synthesis in scheme-1 from INT-27-1 and the known amine derivatives. The further purification is carried out by preparative LC-MS or SFC-MS system in usual manner. The retention time and observed MS by HPLC-QC method are summarized in Tables 93-1 to 93-4.

TABLE 93-1

| Ex. | Intermediate (INT) | Structure | Retention time | Observed MS |
|---|---|---|---|---|
| 59-1 | INT-27-1 | 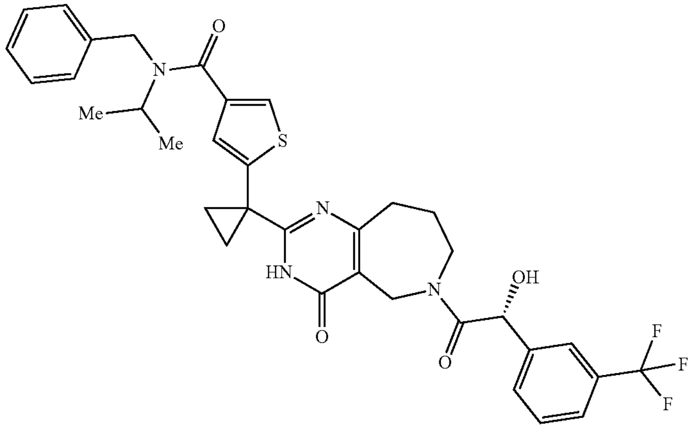 [SMILES: CC(C)N(Cc1ccccc1)C(=O)c1csc(C2(c3nc4c(c(=O)[nH]3)CN(C(=O)[C@H](O)c3cccc(C(F)(F)F)c3)CCC4)CC2)c1] | 1.87 min | 665.1 |
| 59-2 | INT-27-1 | 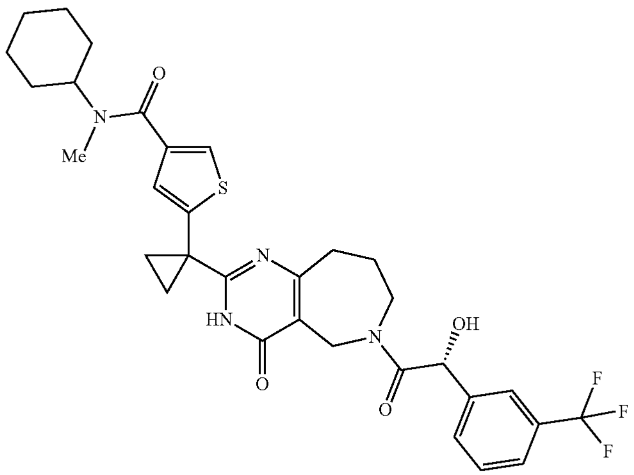 | 1.81 min | 629.1 |

TABLE 93-1-continued
| Ex. | Intermediate (INT) | Structure | Retention time | Observed MS |
| --- | --- | --- | --- | --- |
| 59-3 | INT-27-1 | 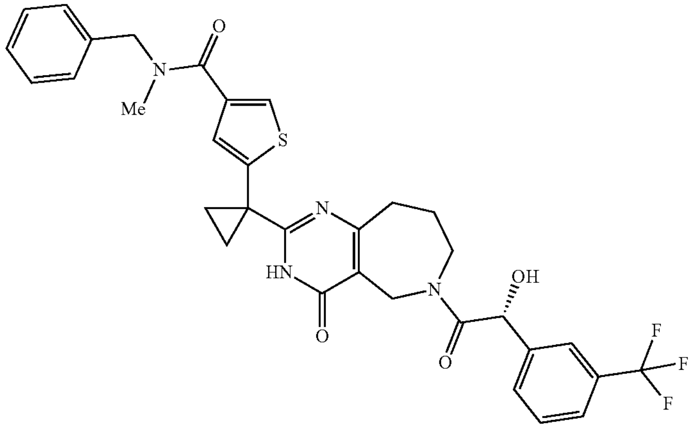 [SMILES: CN(Cc1ccccc1)C(=O)c1csc(C2(c3nc4c(c(=O)[nH]3)CN(C(=O)[C@H](O)c3cccc(C(F)(F)F)c3)CCC4)CC2)c1] | 1.74 min | 637.1 |
| 59-4 | INT-27-1 | 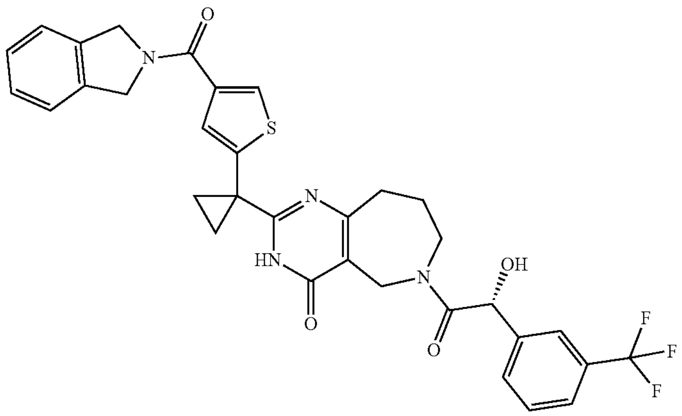 [SMILES: O=C(c1csc(C2(c3nc4c(c(=O)[nH]3)CN(C(=O)[C@H](O)c3cccc(C(F)(F)F)c3)CCC4)CC2)c1)N1Cc2ccccc2C1] | 1.72 min | 635.1 |
| 59-5 | INT-27-1 | 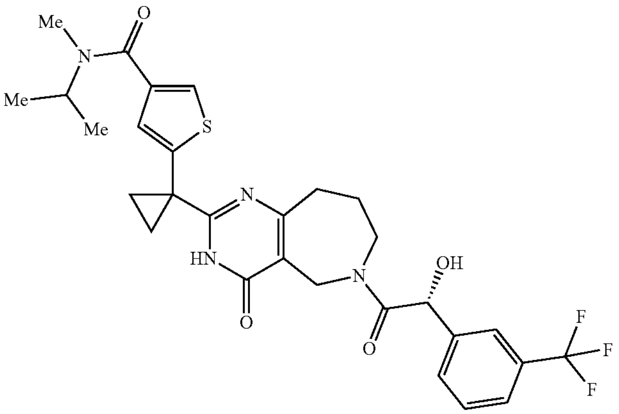 [SMILES: CC(C)N(C)C(=O)c1csc(C2(c3nc4c(c(=O)[nH]3)CN(C(=O)[C@H](O)c3cccc(C(F)(F)F)c3)CCC4)CC2)c1] | 1.59 min | 589.0 |

TABLE 93-2
| | | | | |
|---|---|---|---|---|
| 59-6 | INT-27-1 | 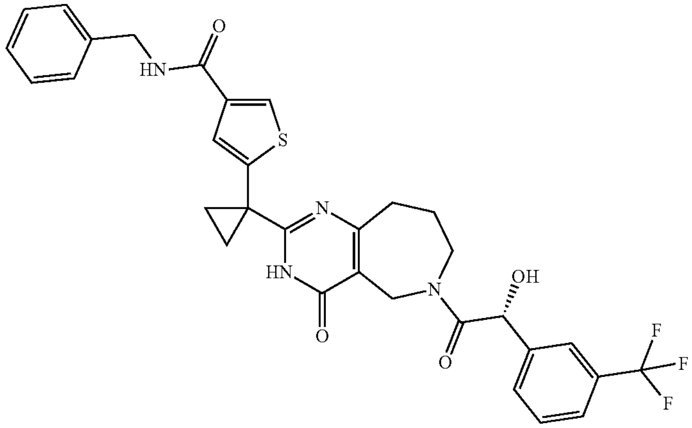 [SMILES: O=C(NCc1ccccc1)c1csc(C2(c3nc4c(c(=O)[nH]3)CN(C(=O)[C@H](O)c3cccc(C(F)(F)F)c3)CCC4)CC2)c1] | 1.64 min | 623.1 |
| 59-7 | INT-27-1 | 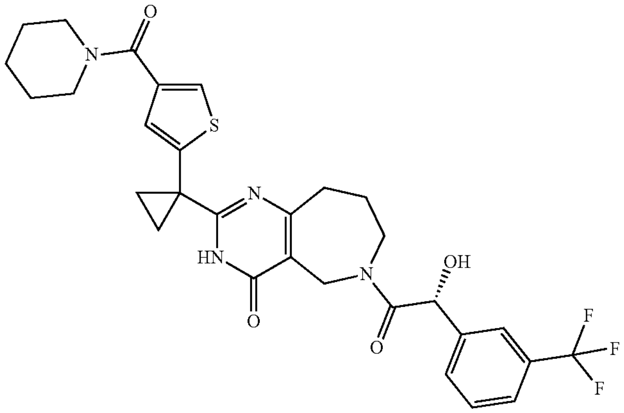 [SMILES: O=C(c1csc(C2(c3nc4c(c(=O)[nH]3)CN(C(=O)[C@H](O)c3cccc(C(F)(F)F)c3)CCC4)CC2)c1)N1CCCCC1] | 1.63 min | 601.0 |
| 59-8 | INT-27-1 | 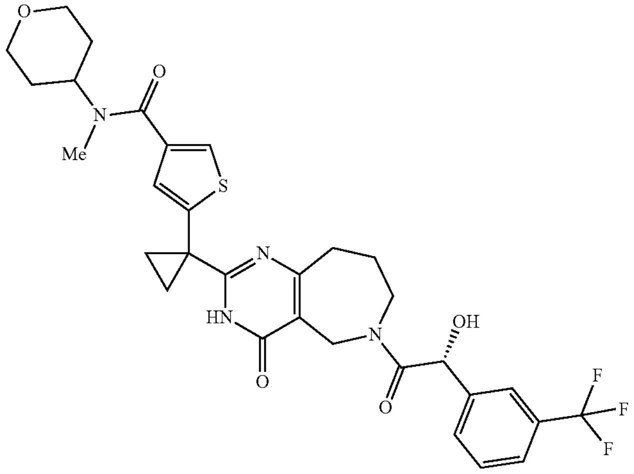 [SMILES: CN(C(=O)c1csc(C2(c3nc4c(c(=O)[nH]3)CN(C(=O)[C@H](O)c3cccc(C(F)(F)F)c3)CCC4)CC2)c1)C1CCOCC1] | 1.45 min | 631.1 |

TABLE 93-2-continued
| | | | | |
|---|---|---|---|---|
| 59-9 | INT-27-1 | 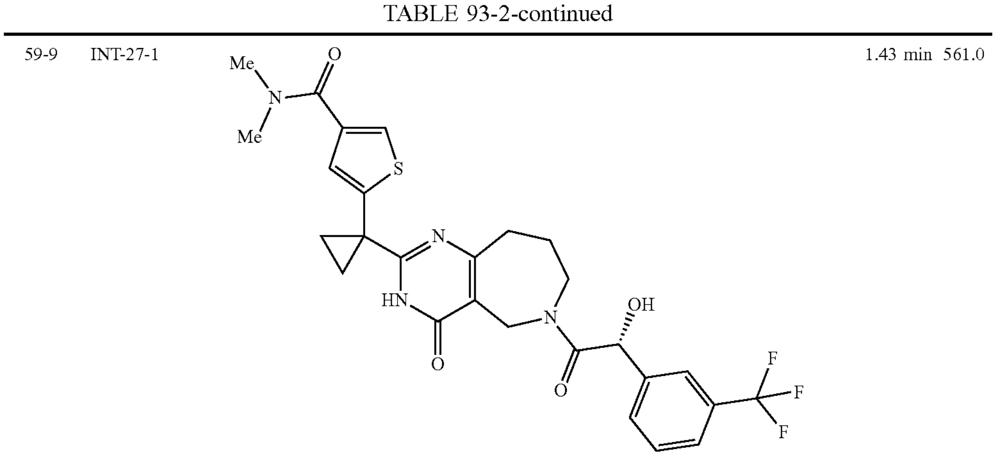 | 1.43 min | 561.0 |
| 59-10 | INT-27-1 | 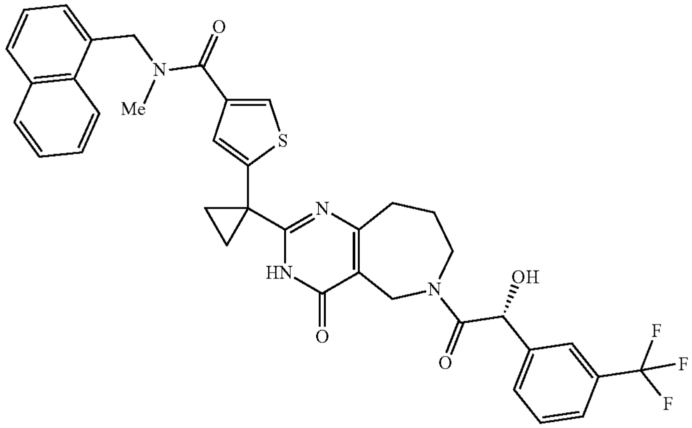 [SMILES: CN(Cc1cccc2ccccc12)C(=O)c1csc(C2(c3nc4c(c(=O)[nH]3)CN(C(=O)[C@H](O)c3cccc(C(F)(F)F)c3)CCC4)CC2)c1] | 1.90 min | 687.0 |
TABLE 93-3
| | | | | |
|---|---|---|---|---|
| 59-11 | INT-27-1 | 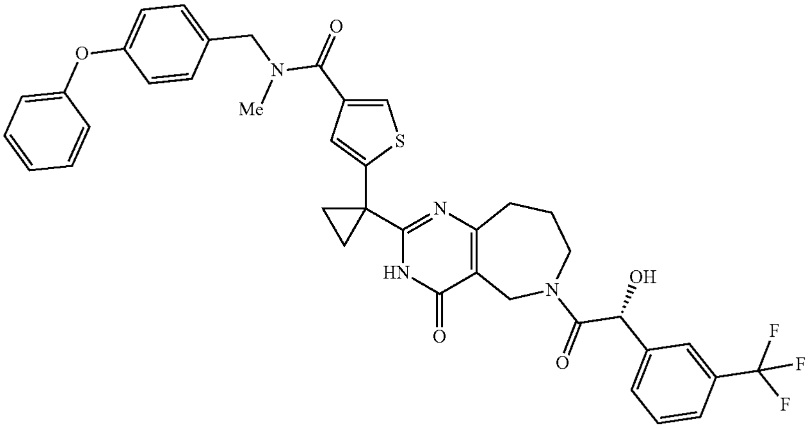 [SMILES: CN(Cc1ccc(Oc2ccccc2)cc1)C(=O)c1csc(C2(c3nc4c(c(=O)[nH]3)CN(C(=O)[C@H](O)c3cccc(C(F)(F)F)c3)CCC4)CC2)c1] | 1.98 min | 729.0 |

TABLE 93-3-continued
| | | | | |
|---|---|---|---|---|
| 59-12 | INT-27-1 | 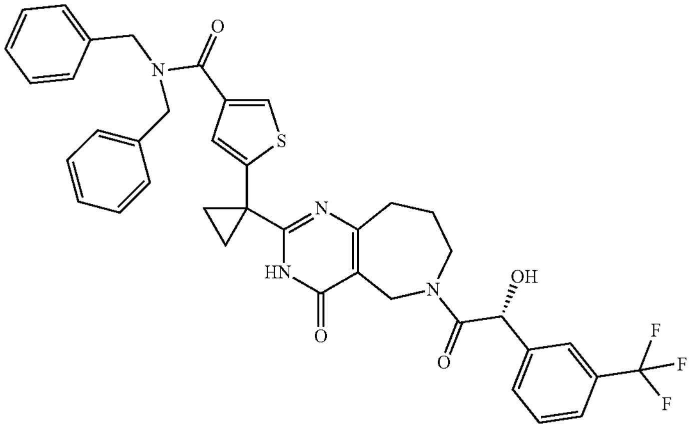 [SMILES: O=C(c1csc(C2(c3nc4c(c(=O)[nH]3)CN(C(=O)[C@H](O)c3cccc(C(F)(F)F)c3)CCC4)CC2)c1)N(Cc1ccccc1)Cc1ccccc1] | 2.01 min | 713.1 |
| 59-13 | INT-27-1 | 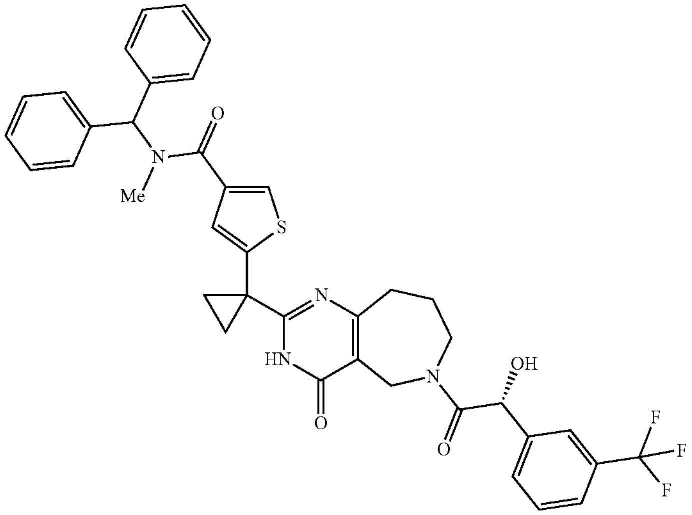 [SMILES: CN(C(=O)c1csc(C2(c3nc4c(c(=O)[nH]3)CN(C(=O)[C@H](O)c3cccc(C(F)(F)F)c3)CCC4)CC2)c1)C(c1ccccc1)c1ccccc1] | 2.01 min | 713.1 |
| 59-14 | INT-27-1 | 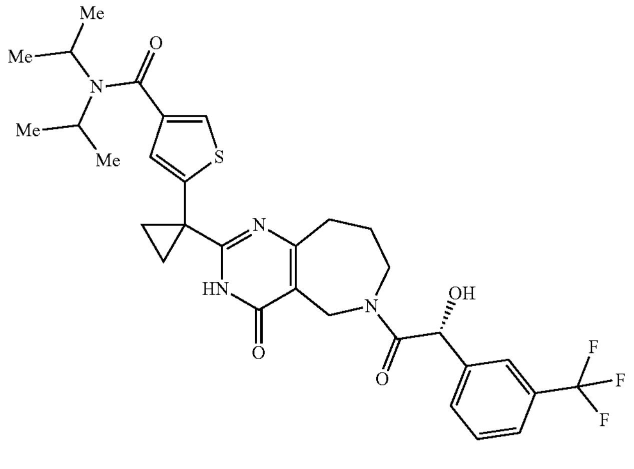 [SMILES: CC(C)N(C(=O)c1csc(C2(c3nc4c(c(=O)[nH]3)CN(C(=O)[C@H](O)c3cccc(C(F)(F)F)c3)CCC4)CC2)c1)C(C)C] | 1.81 min | 617.1 |

TABLE 93-3-continued
| | | | | |
|---|---|---|---|---|
| 59-15 | INT-27-1 | 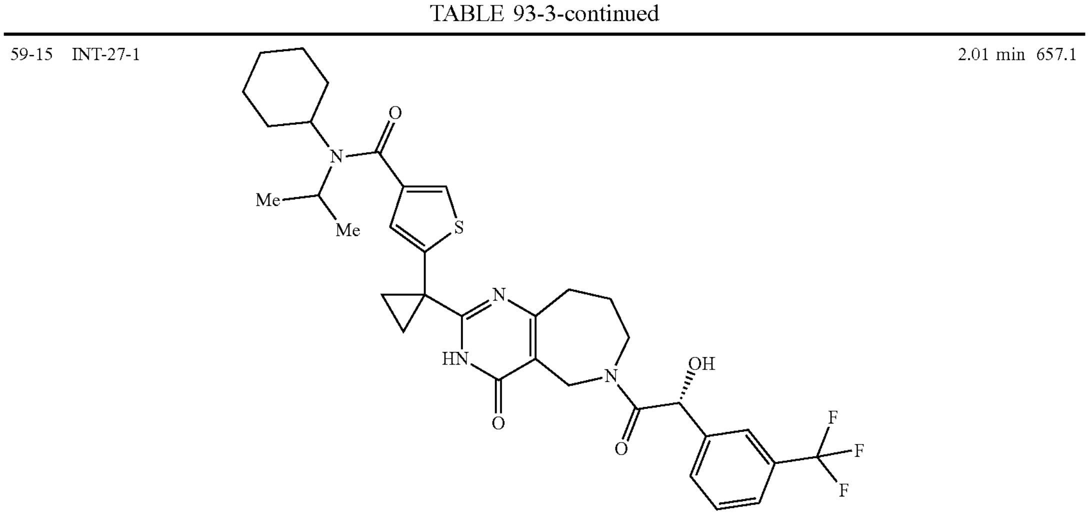 | 2.01 min | 657.1 |
TABLE 93-4
| | | | | |
|---|---|---|---|---|
| 59-16 | INT-27-1 | 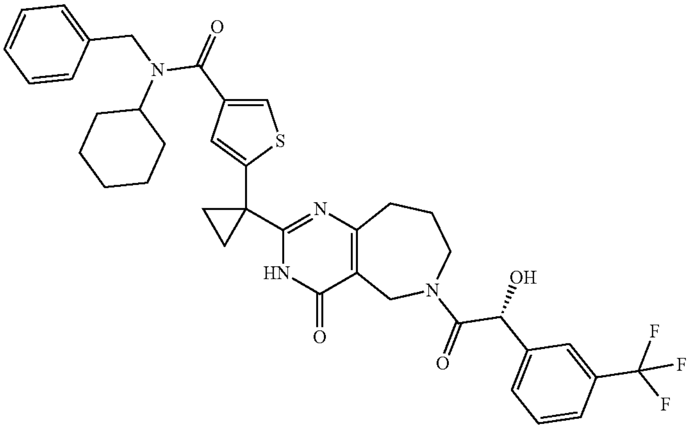 [SMILES: O=C([C@H](O)c1cccc(C(F)(F)F)c1)N1CCCc2nc(C3(c4cc(C(=O)N(Cc5ccccc5)C5CCCCC5)cs4)CC3)[nH]c(=O)c2C1] | 2.06 min | 705.0 |
| 59-17 | INT-27-1 | 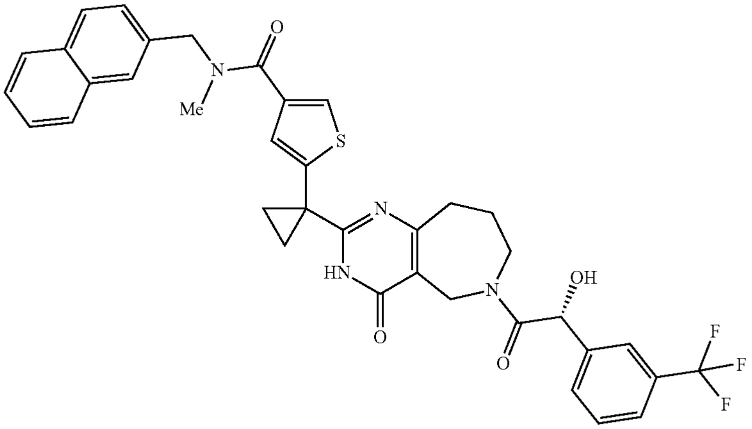 [SMILES: CN(Cc1ccc2ccccc2c1)C(=O)c1csc(C2(c3nc4c(c(=O)[nH]3)CN(C(=O)[C@H](O)c3cccc(C(F)(F)F)c3)CCC4)CC2)c1] | 1.90 min | 686.9 |

TABLE 93-4-continued

| | | | | |
|---|---|---|---|---|
| 59-18 | INT-27-1 | 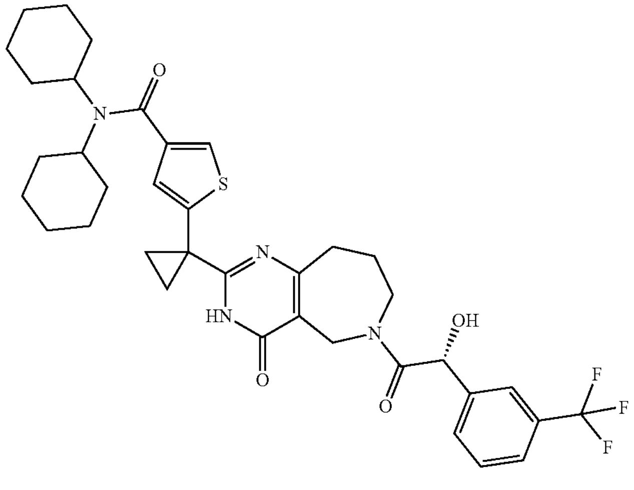 [SMILES: O=C([C@H](O)c1cccc(C(F)(F)F)c1)N1CCCc2nc(C3(c4cc(C(=O)N(C5CCCCC5)C5CCCCC5)cs4)CC3)[nH]c(=O)c2C1] | 2.23 min | 697.1 |
| 59-19 | INT-27-1 | 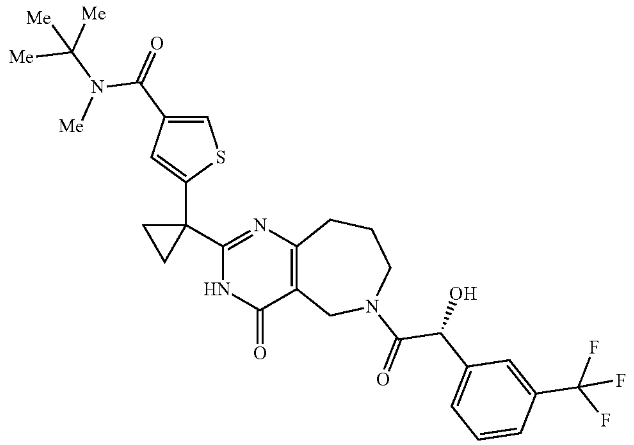 [SMILES: CN(C(=O)c1csc(C2(c3nc4c(c(=O)[nH]3)CN(C(=O)[C@H](O)c3cccc(C(F)(F)F)c3)CCC4)CC2)c1)C(C)(C)C] | 1.76 min | 603.0 |

Example-60-1 (Ex-60-1)

(R)-2-(1-(3-acetylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one (Ex-60-1)

{Chem. 108}

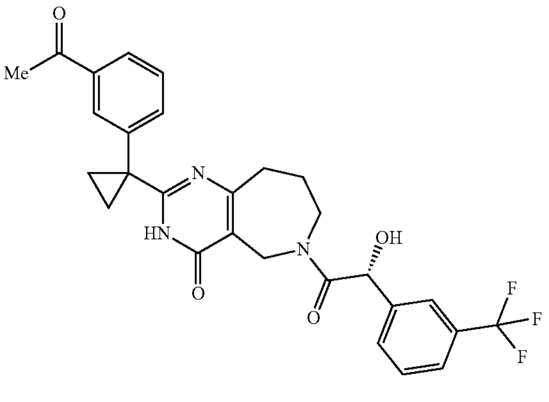

Ozone ($O_3$) gas is bubbled into a solution of Ex-17-1 (35 mg) in dichloromethane (3 mL) at −78° C. until reaction solution turnes to pale blue solution. Nitrogen gas is bubbled to dissipate bule color and dimethyl sulfide (0.098 mL, 1.337 mmol) was added to the reaction mixture and stirred for 20 min. at −78° C., then stirred overnight at rt. After removal of solvent, the residue is diluted with water and extracted with ethyl acetate. The organic layer is washed with brine, dried over sodium sulfate. The resulting solution is filtrated and concentrated in vacuo. The crude product is purified by column chromatography on silica gel eluting with a gradient of 0-100% ethyl acetate in n-hexan to give the titled compound (36 mg).

LC-MS (Method-K) m/z: M+1 obs 526.2, tR=0.53 min.

The further purification is carried out by preparative LC-MS or SFC-MS system in the usual manner.

LC-MS (Method-HPLC-QC) m/z: M+1 obs 526.2, tR=1.56 min.

Example-61-1 (Ex-61-1)

(R)-6-(2-hydroxy-2-(3-(trifluoromethyl)phenyl)acetyl)-2-(1-(3-(hydroxymethyl)phenyl)cyclopropyl)-3,5,6,7,8,9-hexahydro-4H-pyrimido[5,4-c]azepin-4-one (Ex-61-1)

{Chem. 109}

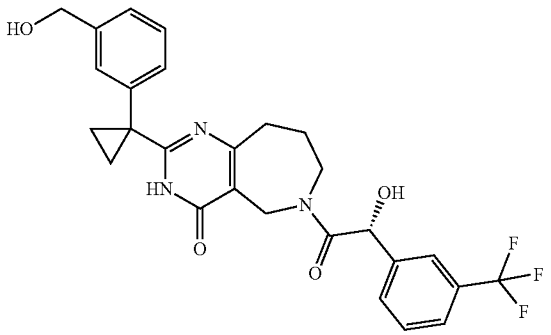

Step-61-1-A: (R)-3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)benzaldehyde (INT-61-1-A)

{Chem. 110}

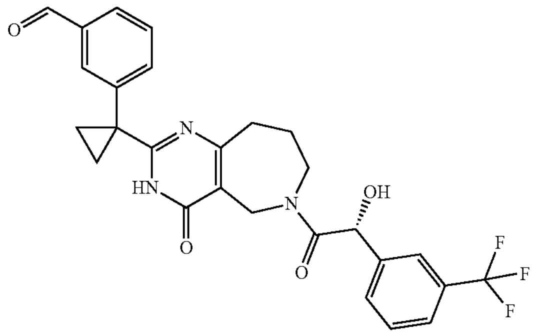

$O_3$ was bubbled in a solution of INT-21-12 (83 mg) in dichlromethane (5 mL) at −78° C. until reaction solution turned to pale blue solution. $N_2$ gas is bubbled to dissipate bule color, and dimethyl sulfide (0.238 mL, 3.26 mmol) is added to the reaction mixture and stirred for 20 min. at −78° C., then stirred over night at rt. After removal of solvent, the residue is diluted with water and extracted with ethyl acetate. The organic layer is washed with brine, dried over sodium sulfate. The resulting solution is filtrated and concentrated in vacuo. The crude product was purified by column chromatography on silica gel eluting with a gradient of 0-100% ethyl acetate in n-hexan to give the titled compound (36 mg).

LC-MS (Method-K) m/z: M+1 obs 512.2, tR=0.50 min.

Step-61-1-B: (R)-6-(2-hydroxy-2-(3-(trifluoromethyl)phenyl)acetyl)-2-(1-(3-(hydroxymethyl)phenyl)cyclopropyl)-3,5,6,7,8,9-hexahydro-4H-pyrimido[5,4-c]azepin-4-one (Ex-61-1)

To a stirred solution of INT-61-1-A (20 mg) in ethanol (1 mL) is added sodium borohydride (10 mg, 0.264 mmol) portionwise at room temperature and the mixture is stirred for 2 hrs. The reaction mixture is quenched with saturated $NH_4Cl$ aqueous solution and extracted with etyl acetate. The organic layer is c$^{oc}$entrated in vacuo to the crude product, which is purified by SCX cartridge to give the titled compound (17 mg).

LC-MS (Method-K) m/z: M+1 obs 514.2, tR=0.49 min.

The further purification is carried out by preparative LC-MS system in the usual manner.

LC-MS (Method-HPLC-QC) m/z: M+1 obs 514.1, tR=1.42 min.

Example-62-1 (Ex-62-1)

(R)-6-(2-hydroxy-2-(3-(trifluoromethyl)phenyl)acetyl)-2-(1-(3-(piperidin-1-ylmethyl)phenyl)cyclopropyl)-3,5,6,7,8,9-hexahydro-4H-pyrimido[5,4-c]azepin-4-one (Ex-62-1)

{Chem. 111}

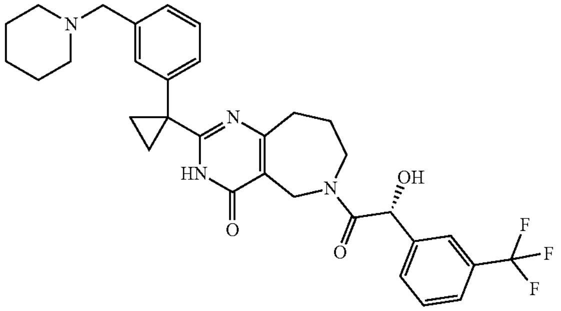

To a mixture of INT-61-1-A (20 mg, 0.039 mmol) and piperidine (6.7 mg, 0.078 mmol) in DCM (1 mL) is added sodium triacetoxyborohydride (33.1 mg, 0.156 mmol) at rt. The mixture was stirred at rt overnight. The reaction mixture is quenched with saturated sodium bicarbonate aqueous solution and extracted with DCM (5 mL). The separated organic layer is dried over sodium sulfate, filtered and concentrated in vacuo. The residue was purified by SCX column to give the titled compound (7 mg, 30.8% yield).

LC-MS (Method-K) m/z: M+1 obs 581.3, tR=0.59 min.

The further purification is carried out by preparative LC-MS or SFC-MS system in the usual manner.

LC-MS (Method-HPLC-QC) m/z: M+1 obs 581.2, tR=1.56 min.

Example-63-1 (Ex-63-1)

Synthesis of (R)-6-(2-hydroxy-2-(3-(trifluoromethyl)phenyl)acetyl)-2-(1-(4-(piperidin-4-yl)thiophen-2-yl)cyclopropyl)-3,5,6,7,8,9-hexahydro-4H-pyrimido[5,4-c]azepin-4-one (Ex-63-1)

{Chem. 112}

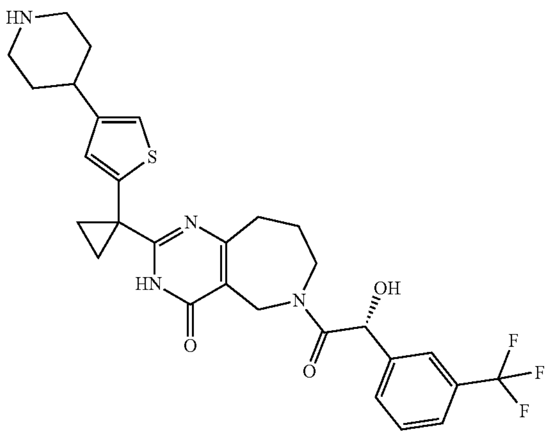

The mixture of INT-19-6 (36.8 mg, 0.055 mmol) in MeOH (1 mL) is hydrogenated in the presence of 10% Pd/C (29 mg) at rt for 24 hrs under hydrogen atmosphere. The reaction mixture is filtered through celite pad (eluting with MeOH). To the obtained MeOH solution is added 10% HCl-MeOH solution (3.0 mL) at room temperature. The mixture is heated at 50° C. for 2 hrs. The reaction mixture is concentrated to give the titled compound (35 mg) as a black solid.

LC-MS (Method-1) m/z: M+1 obs 573.2, tR=0.49 min.

The further purification is carried out by preparative LC-MS or SFC-MS system in the usual manner.

LC-MS (Method-HPLC-QC) m/z: M+1 obs 573.2, tR=1.28 min.

Example-64-1 (Ex-64-1)

Synthesis of (R)-6-(2-hydroxy-2-(3-(trifluoromethyl)phenyl)acetyl)-2-(1-(4-(1-methylpiperidin-4-yl)thiophen-2-yl)cyclopropyl)-3,5,6,7,8,9-hexahydro-4H-pyrimido[5,4-c]azepin-4-one (Ex-64-1)

{Chem. 113}

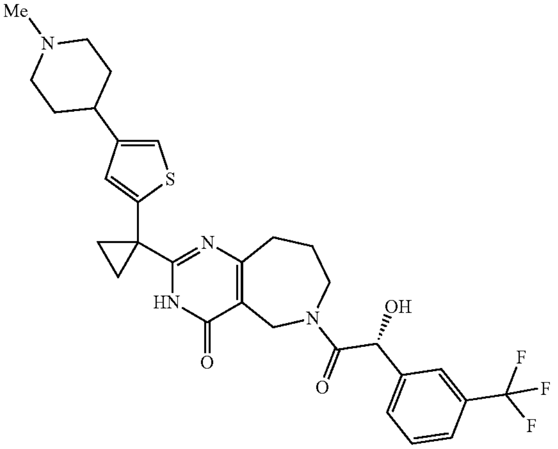

To the solution of Ex-63-1 (17.5 mg, 0.029 mmol), 37% Formalin aqueous solution (0.0032 mL, 0.043 mmol) and acetic acid (0.2 mL) in DMF/DCM (1/5 v/v, 1.2 mL) is added sodium triacetoxyborohydride (18.3 mg, 0.086 mmol). The reaction mixture is stirred overnight at room temperature. After concentrated in vacuo, the mixture is purified by a strong anion exchange cartridge (ISOLUTE (registered trademark) SCX-2) to give the titled compound (14.5 mg).

LC-MS (Method-1) m/z: M+1 obs 587.27, tR=0.50 min.

The further purification is carried out by preparative LC-MS or SFC-MS system in the usual manner.

LC-MS (Method-HPLC-QC) m/z: M+1 obs 587.2, tR=1.35 min.

Tables 94-1 to 94-7 are the List of compounds of Example-1 to Example-13-4

TABLE 94-1

| Examples |
| --- |
| 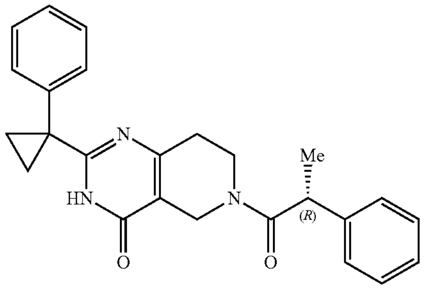 |
| Ex-1 |
| 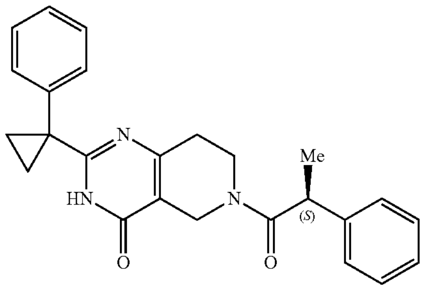 |
| Ex-2-1 |
| 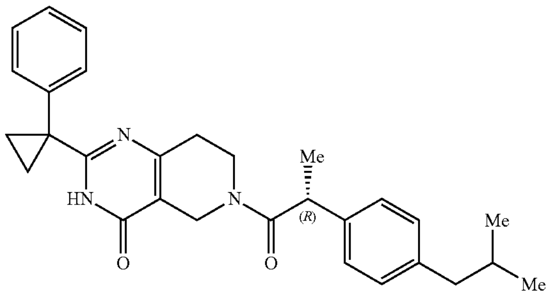 |
| Ex-2-2 |

TABLE 94-1-continued
| Examples |
| --- |
| 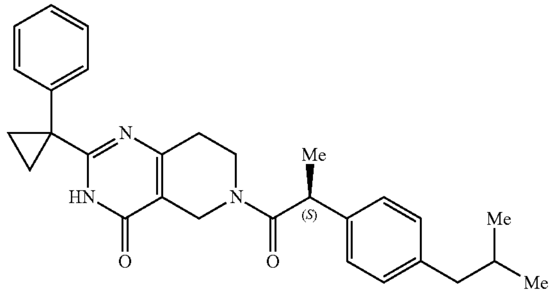 |
| Ex-2-3 |
| 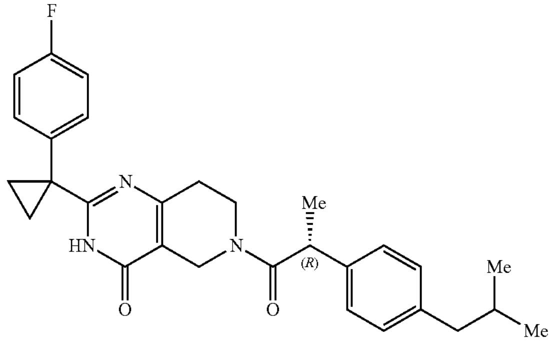 |
| Ex-2-4 |
| 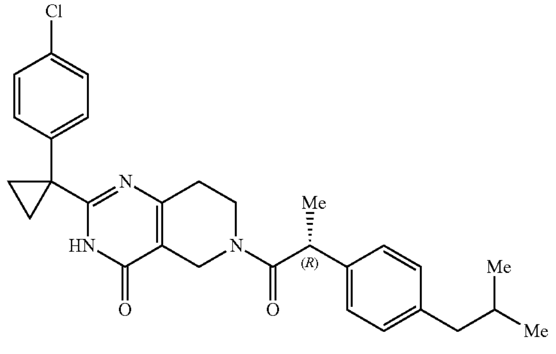 |
| Ex-2-5 |
| 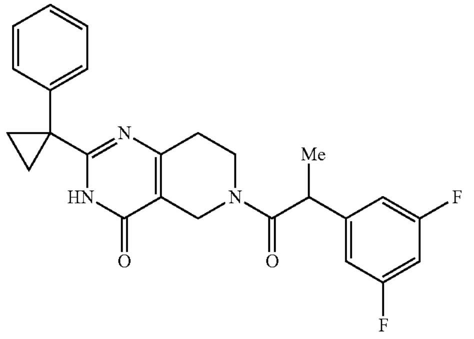 [SMILES: CC(C(=O)N1CCc2nc(C3(c4ccccc4)CC3)[nH]c(=O)c2C1)c1cc(F)cc(F)c1] |
| Ex-2-6 |
TABLE 94-1-continued
| Examples |
| --- |
| 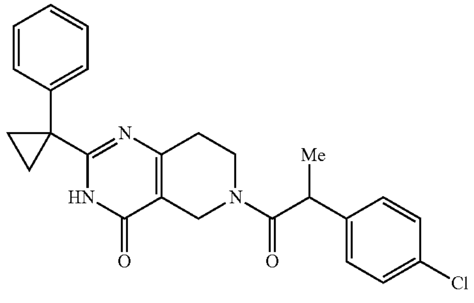 [SMILES: CC(C(=O)N1CCc2nc(C3(c4ccccc4)CC3)[nH]c(=O)c2C1)c1ccc(Cl)cc1] |
| Ex-2-7 |
| 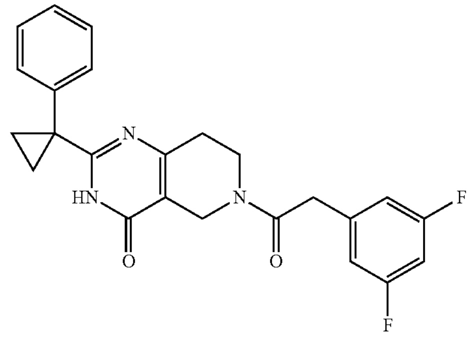 [SMILES: O=C(Cc1cc(F)cc(F)c1)N1CCc2nc(C3(c4ccccc4)CC3)[nH]c(=O)c2C1] |
| Ex-2-8 |
| 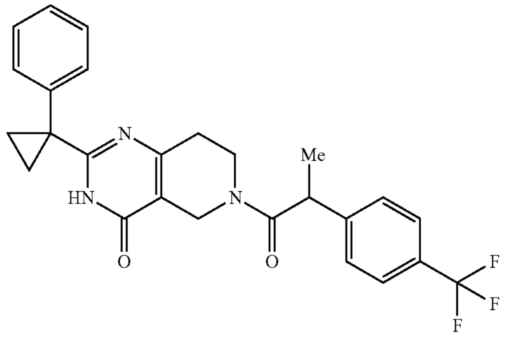 |
| Ex-2-9 |
| 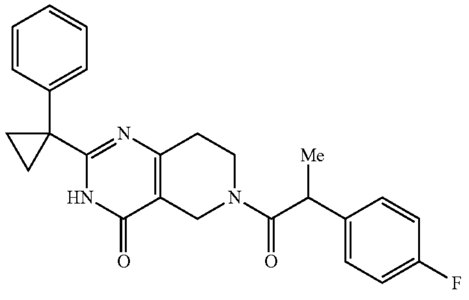 [SMILES: CC(C(=O)N1CCc2nc(C3(c4ccccc4)CC3)[nH]c(=O)c2C1)c1ccc(F)cc1] |
| Ex-2-10 |

TABLE 94-1-continued
| Examples |
| --- |
| 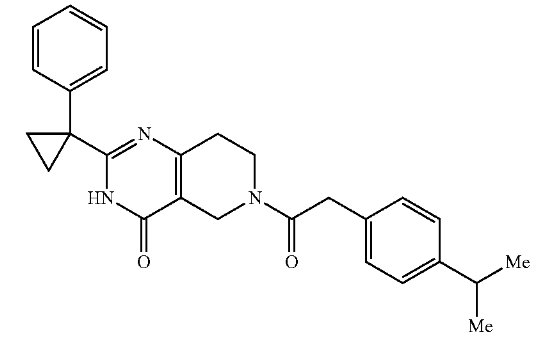 [SMILES: CC(C)c1ccc(CC(=O)N2CCc3nc(C4(c5ccccc5)CC4)[nH]c(=O)c3C2)cc1] |
| Ex-2-11 |
| 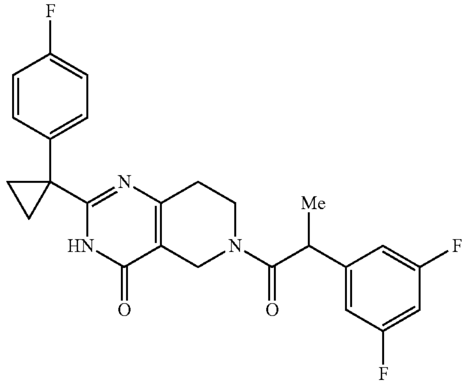 [SMILES: CC(C(=O)N1CCc2nc(C3(c4ccc(F)cc4)CC3)[nH]c(=O)c2C1)c1cc(F)cc(F)c1] |
| Ex-2-12 |
| 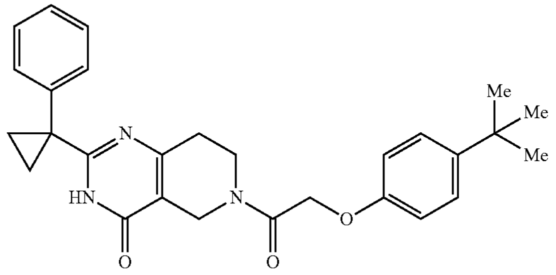 [SMILES: CC(C)(C)c1ccc(OCC(=O)N2CCc3nc(C4(c5ccccc5)CC4)[nH]c(=O)c3C2)cc1] |
| Ex-2-13 |
| 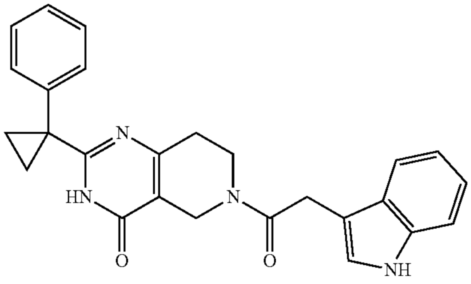 [SMILES: O=C(Cc1c[nH]c2ccccc12)N1CCc2nc(C3(c4ccccc4)CC3)[nH]c(=O)c2C1] |
| Ex-2-14 |
TABLE 94-1-continued
| Examples |
| --- |
| 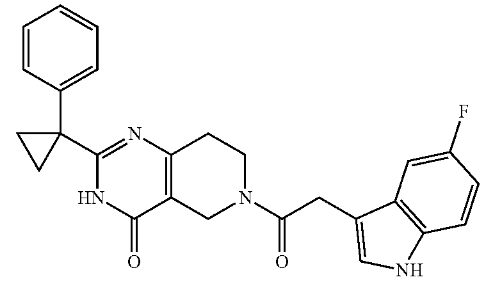 [SMILES: O=C(Cc1c[nH]c2ccc(F)cc12)N1CCc2nc(C3(c4ccccc4)CC3)[nH]c(=O)c2C1] |
| Ex-2-15 |
| 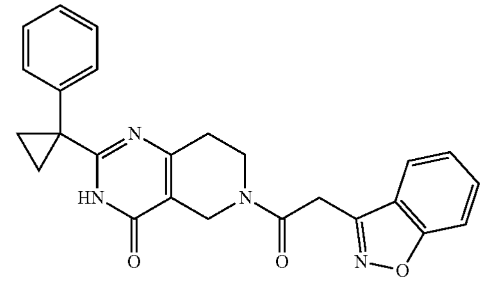 [SMILES: O=C(Cc1noc2ccccc12)N1CCc2nc(C3(c4ccccc4)CC3)[nH]c(=O)c2C1] |
| Ex-2-16 |
| 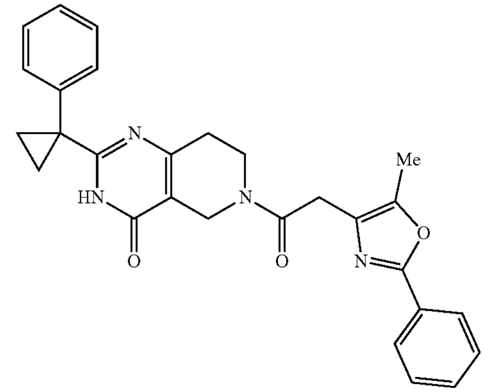 [SMILES: Cc1oc(-c2ccccc2)nc1CC(=O)N1CCc2nc(C3(c4ccccc4)CC3)[nH]c(=O)c2C1] |
| Ex-2-17 |
| 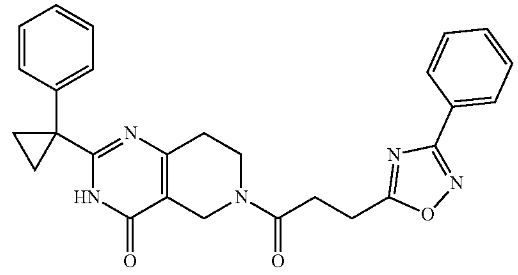 [SMILES: O=C(CCc1nc(-c2ccccc2)no1)N1CCc2nc(C3(c4ccccc4)CC3)[nH]c(=O)c2C1] |
| Ex-2-18 |

TABLE 94-1-continued
| Examples |
|---|
| 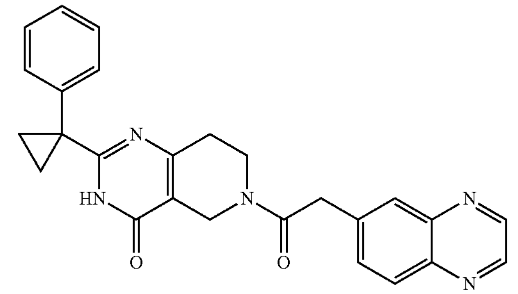 [SMILES: O=C(Cc1ccc2nccnc2c1)N1CCc2nc(C3(c4ccccc4)CC3)[nH]c(=O)c2C1] |
| Ex-2-19 |
| 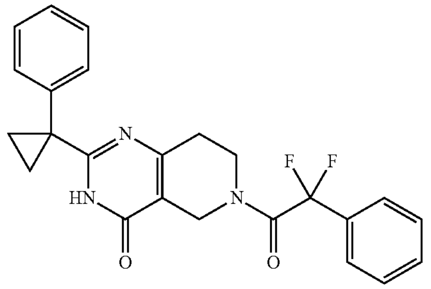 [SMILES: O=C(N1CCc2nc(C3(c4ccccc4)CC3)[nH]c(=O)c2C1)C(F)(F)c1ccccc1] |
| Ex-2-20 |
| 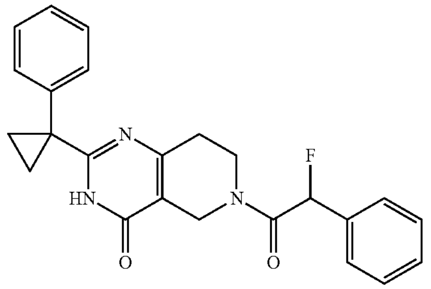 [SMILES: O=C(C(F)c1ccccc1)N1CCc2nc(C3(c4ccccc4)CC3)[nH]c(=O)c2C1] |
| Ex-2-21 |
| 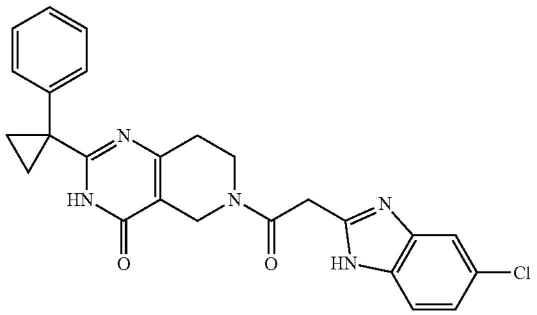 [SMILES: O=C(Cc1nc2cc(Cl)ccc2[nH]1)N1CCc2nc(C3(c4ccccc4)CC3)[nH]c(=O)c2C1] |
| Ex-2-22 |
TABLE 94-1-continued
| Examples |
|---|
| 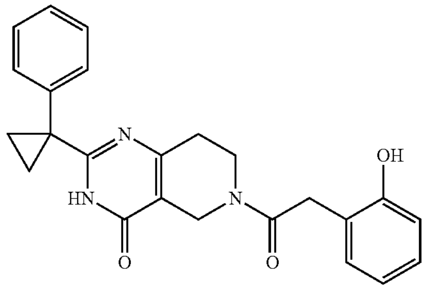 [SMILES: O=C(Cc1ccccc1O)N1CCc2nc(C3(c4ccccc4)CC3)[nH]c(=O)c2C1] |
| Ex-2-23 |
| 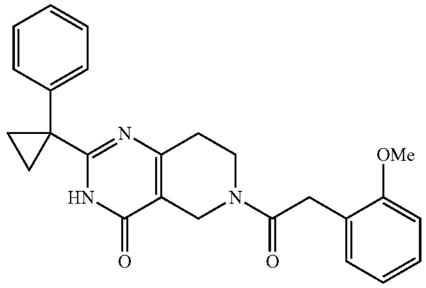 [SMILES: COc1ccccc1CC(=O)N1CCc2nc(C3(c4ccccc4)CC3)[nH]c(=O)c2C1] |
| Ex-2-24 |
| 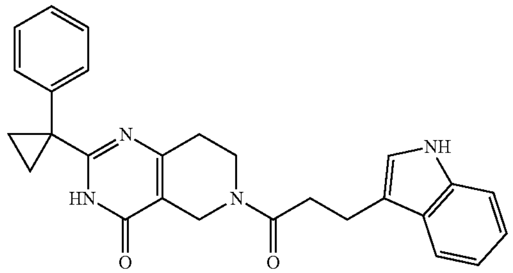 [SMILES: O=C(CCc1c[nH]c2ccccc12)N1CCc2nc(C3(c4ccccc4)CC3)[nH]c(=O)c2C1] |
| Ex-2-25 |
| 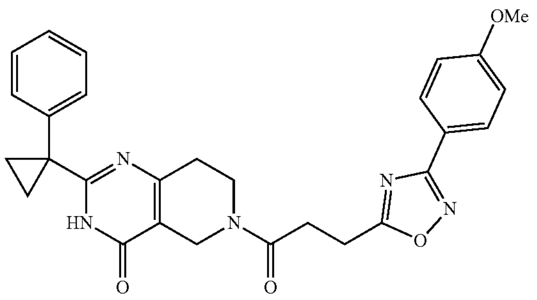 [SMILES: COc1ccc(-c2noc(CCC(=O)N3CCc4nc(C5(c6ccccc6)CC5)[nH]c(=O)c4C3)n2)cc1] |
| Ex-2-26 |

TABLE 94-1-continued
| Examples |
| --- |
| 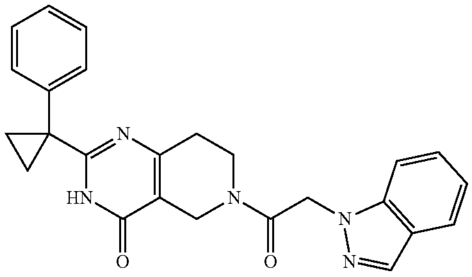 [SMILES: O=C(Cn1ncc2ccccc21)N1CCc2nc(C3(c4ccccc4)CC3)[nH]c(=O)c2C1] Ex-2-27 |
TABLE 94-2
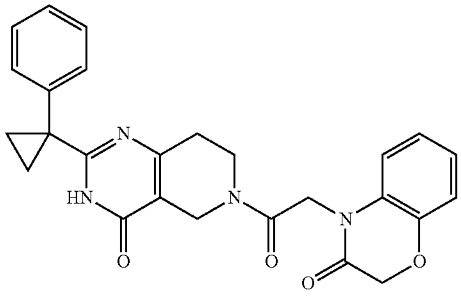 [SMILES: O=C(CN1C(=O)COc2ccccc21)N1CCc2nc(C3(c4ccccc4)CC3)[nH]c(=O)c2C1]
Ex-2-28
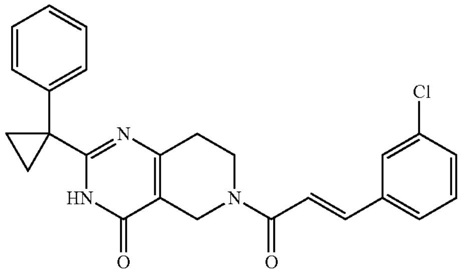 [SMILES: O=C(/C=C/c1cccc(Cl)c1)N1CCc2nc(C3(c4ccccc4)CC3)[nH]c(=O)c2C1]
Ex-2-29
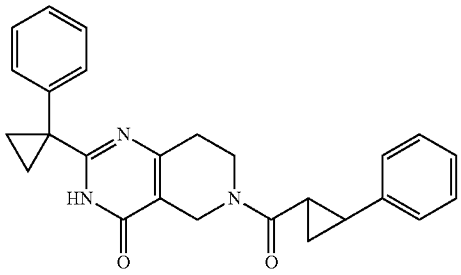 [SMILES: O=C(C1CC1c1ccccc1)N1CCc2nc(C3(c4ccccc4)CC3)[nH]c(=O)c2C1]
Ex-2-30
TABLE 94-2-continued
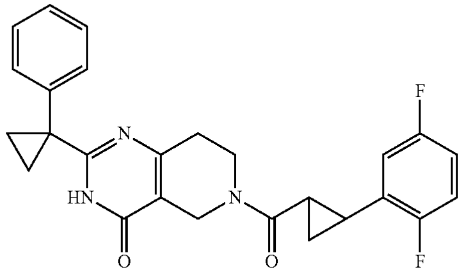 [SMILES: O=C(C1CC1c1cc(F)ccc1F)N1CCc2nc(C3(c4ccccc4)CC3)[nH]c(=O)c2C1]
Ex-2-31
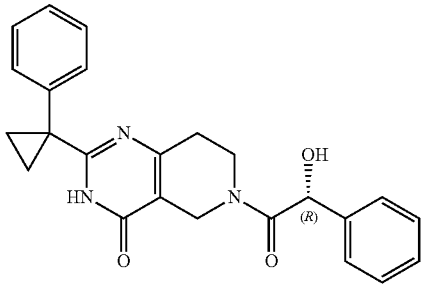
Ex-2-32
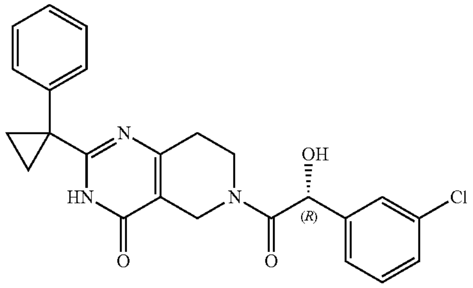
Ex-2-33
(–)-
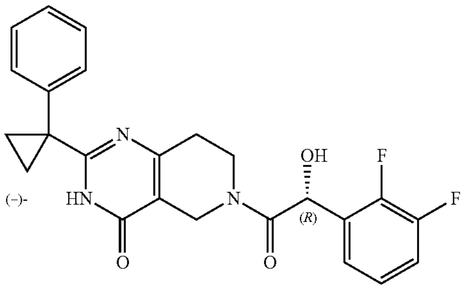
Ex-2-34

TABLE 94-2-continued
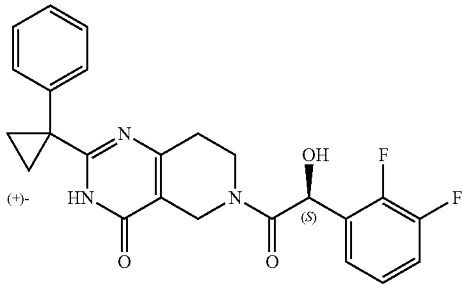
Ex-2-35
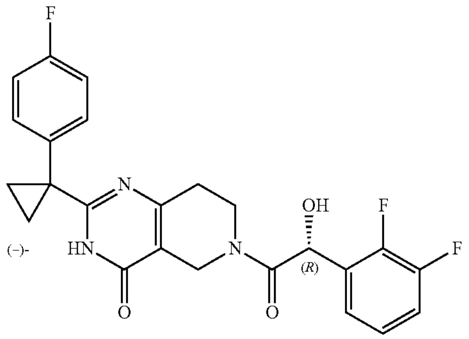
Ex-2-36
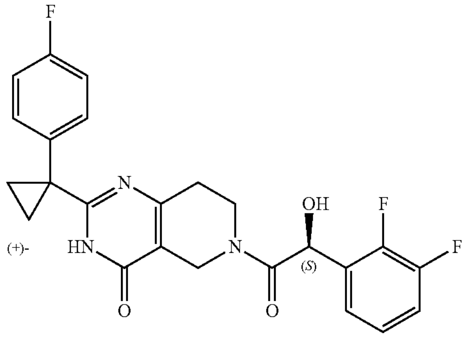
Ex-2-37
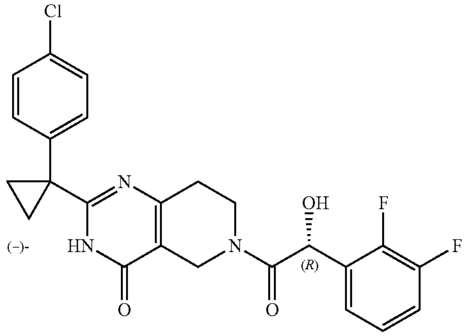
Ex-2-38
TABLE 94-2-continued
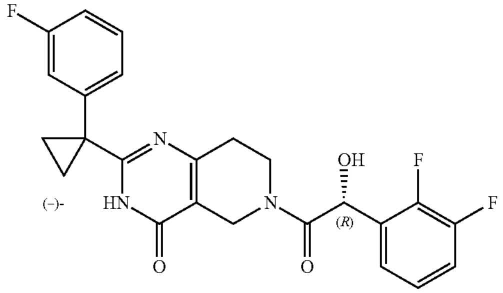
Ex-2-39
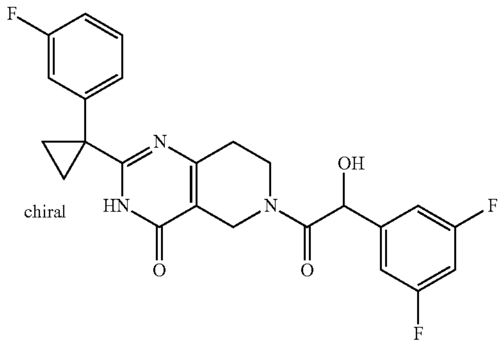 [SMILES: O=C(C(O)c1cc(F)cc(F)c1)N1CCc2nc(C3(c4cccc(F)c4)CC3)[nH]c(=O)c2C1]
Ex-2-40
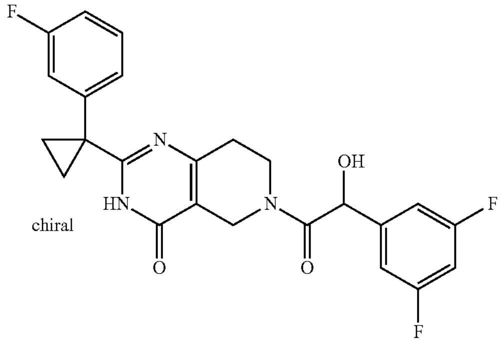 [SMILES: O=C(C(O)c1cc(F)cc(F)c1)N1CCc2nc(C3(c4cccc(F)c4)CC3)[nH]c(=O)c2C1]
Ex-2-41
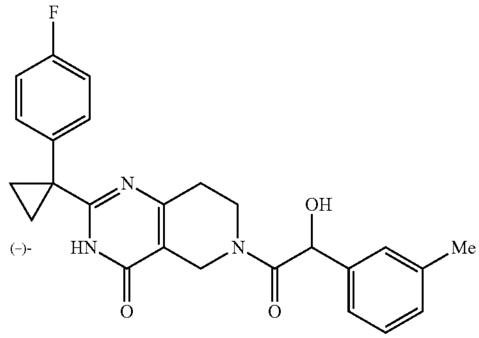 [SMILES: Cc1cccc(C(O)C(=O)N2CCc3nc(C4(c5ccc(F)cc5)CC4)[nH]c(=O)c3C2)c1]
Ex-2-42

TABLE 94-2-continued
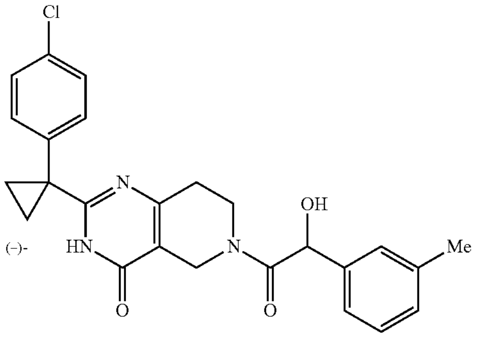 [SMILES: Cc1cccc(C(O)C(=O)N2CCc3nc(C4(c5ccc(Cl)cc5)CC4)[nH]c(=O)c3C2)c1]
Ex-2-43
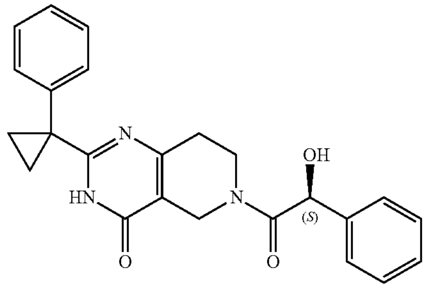
Ex-3-1
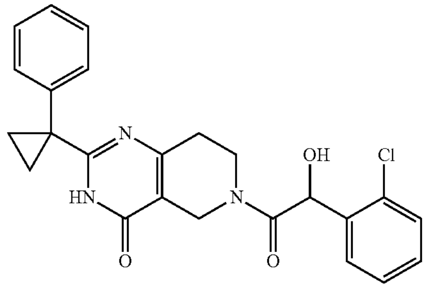 [SMILES: O=C(C(O)c1ccccc1Cl)N1CCc2nc(C3(c4ccccc4)CC3)[nH]c(=O)c2C1]
Ex-3-2
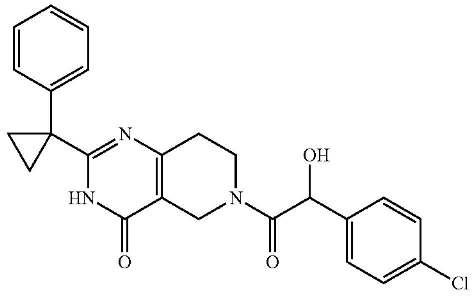 [SMILES: O=C(C(O)c1ccc(Cl)cc1)N1CCc2nc(C3(c4ccccc4)CC3)[nH]c(=O)c2C1]
Ex-3-3
TABLE 94-2-continued
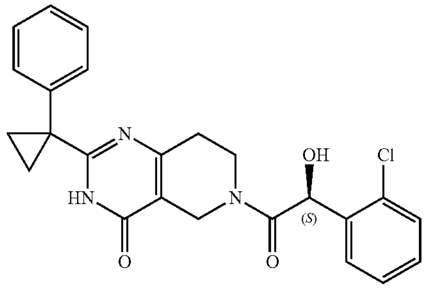
Ex-3-4
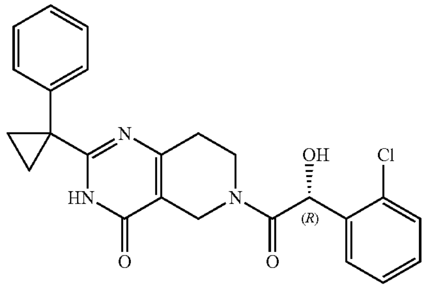
Ex-3-5
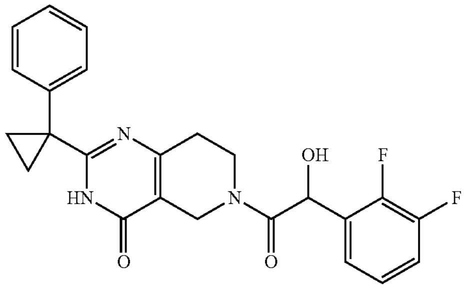 [SMILES: O=C(C(O)c1cccc(F)c1F)N1CCc2nc(C3(c4ccccc4)CC3)[nH]c(=O)c2C1]
Ex-3-6
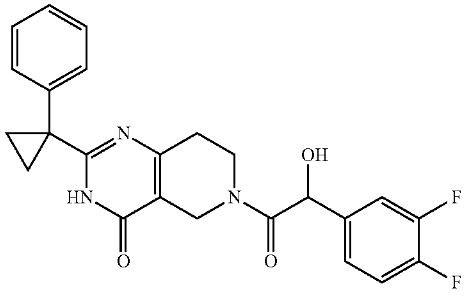 [SMILES: O=C(C(O)c1ccc(F)c(F)c1)N1CCc2nc(C3(c4ccccc4)CC3)[nH]c(=O)c2C1]
Ex-3-7

TABLE 94-2-continued
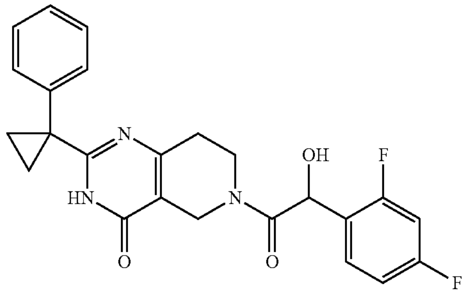 [SMILES: O=C(C(O)c1ccc(F)cc1F)N1CCc2nc(C3(c4ccccc4)CC3)[nH]c(=O)c2C1]
Ex-3-8
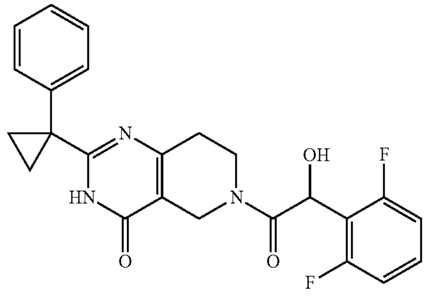 [SMILES: O=C(C(O)c1c(F)cccc1F)N1CCc2nc(C3(c4ccccc4)CC3)[nH]c(=O)c2C1]
Ex-3-9
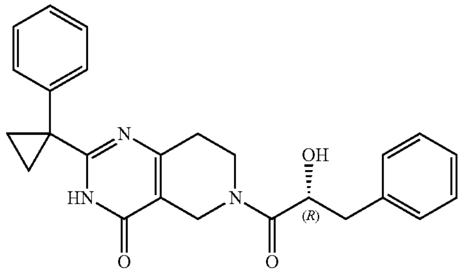
Ex-3-10
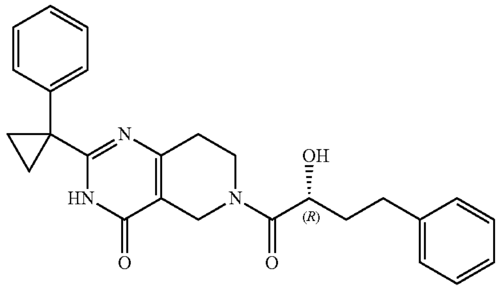
Ex-3-11
TABLE 94-2-continued
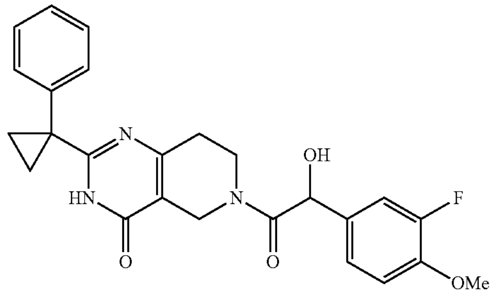 [SMILES: COc1ccc(C(O)C(=O)N2CCc3nc(C4(c5ccccc5)CC4)[nH]c(=O)c3C2)cc1F]
Ex-3-12
TABLE 94-3
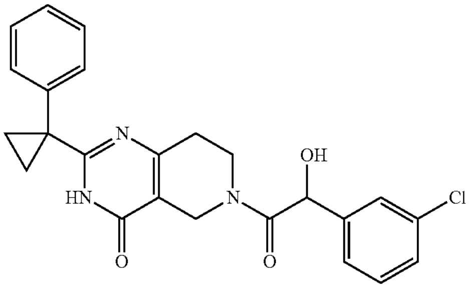 [SMILES: O=C(C(O)c1cccc(Cl)c1)N1CCc2nc(C3(c4ccccc4)CC3)[nH]c(=O)c2C1]
Ex-3-13
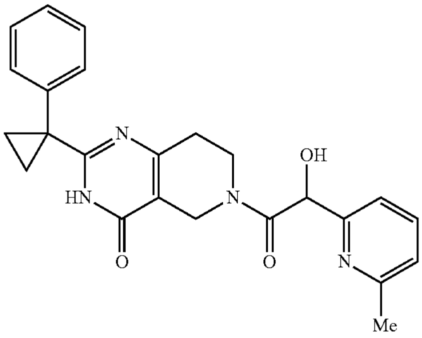 [SMILES: Cc1cccc(C(O)C(=O)N2CCc3nc(C4(c5ccccc5)CC4)[nH]c(=O)c3C2)n1]
Ex-3-14
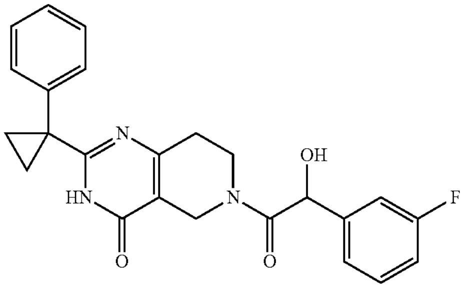 [SMILES: O=C(C(O)c1cccc(F)c1)N1CCc2nc(C3(c4ccccc4)CC3)[nH]c(=O)c2C1]
Ex-3-15

TABLE 94-3-continued
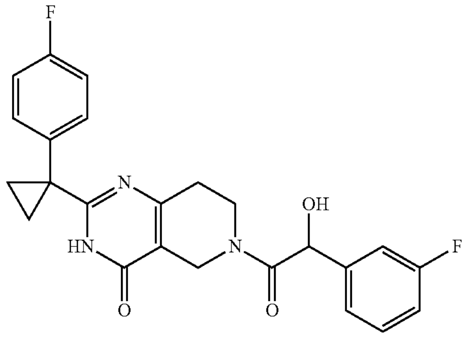 [SMILES: O=C(C(O)c1cccc(F)c1)N1CCc2nc(C3(c4ccc(F)cc4)CC3)[nH]c(=O)c2C1]
Ex-3-16
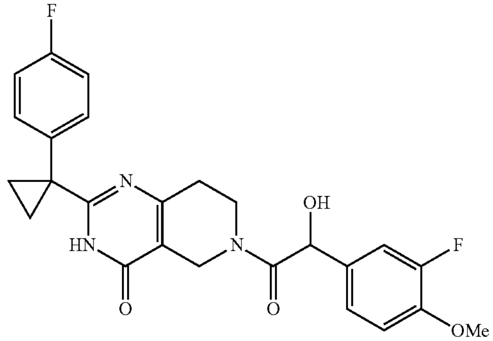 [SMILES: COc1ccc(C(O)C(=O)N2CCc3nc(C4(c5ccc(F)cc5)CC4)[nH]c(=O)c3C2)cc1F]
Ex-3-17
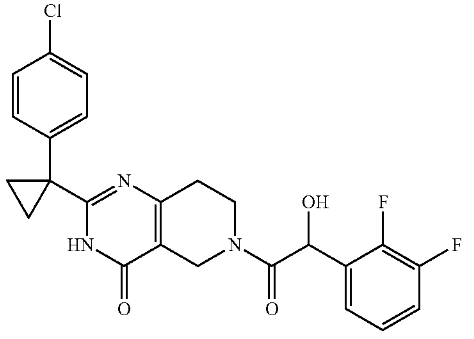
Ex-3-18
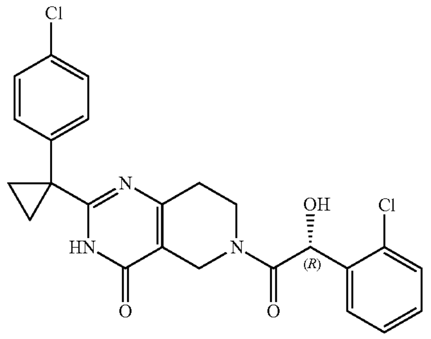
Ex-3-19
TABLE 94-3-continued
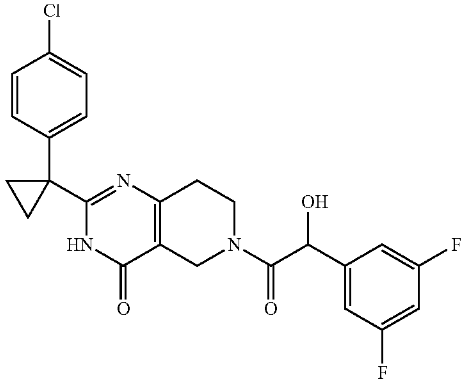
Ex-3-20
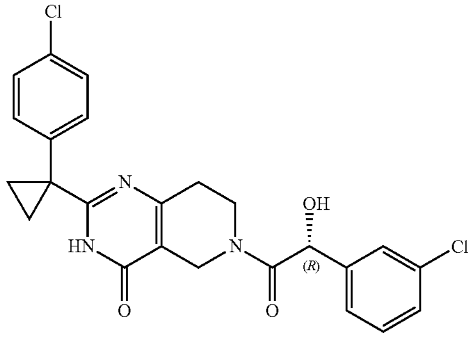
Ex-3-21
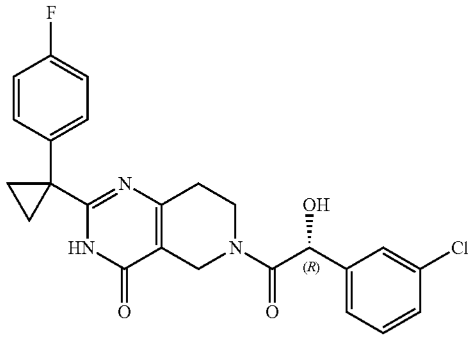
Ex-3-22
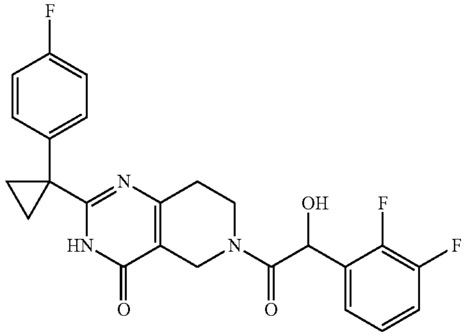 [SMILES: O=C(C(O)c1cccc(F)c1F)N1CCc2nc(C3(c4ccc(F)cc4)CC3)[nH]c(=O)c2C1]
Ex-3-23

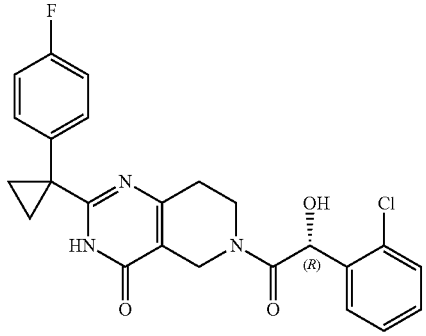
Ex-3-24
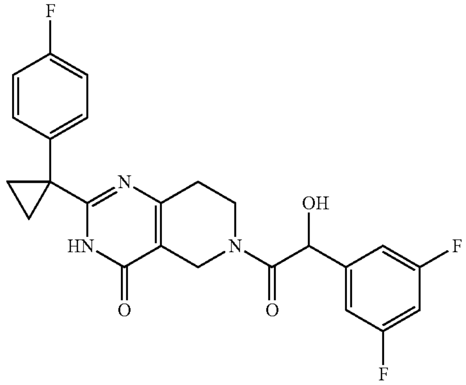 [SMILES: O=C(C(O)c1cc(F)cc(F)c1)N1CCc2nc(C3(c4ccc(F)cc4)CC3)[nH]c(=O)c2C1]
Ex-3-25
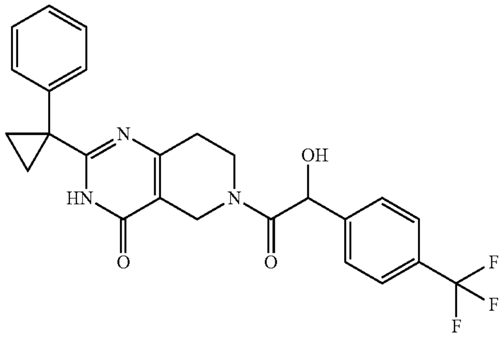 [SMILES: O=C(C(O)c1ccc(C(F)(F)F)cc1)N1CCc2nc(C3(c4ccccc4)CC3)[nH]c(=O)c2C1]
Ex-3-26
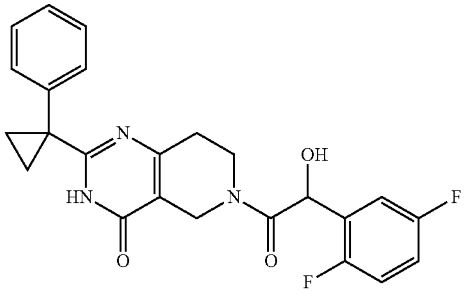 [SMILES: O=C(C(O)c1cc(F)ccc1F)N1CCc2nc(C3(c4ccccc4)CC3)[nH]c(=O)c2C1]
Ex-3-27
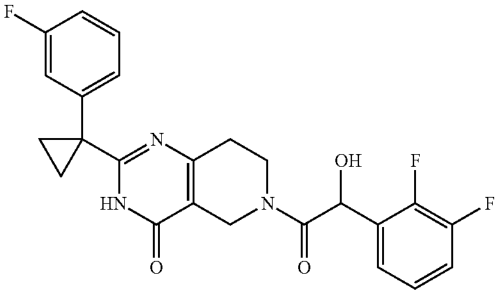 [SMILES: O=C(C(O)c1cccc(F)c1F)N1CCc2nc(C3(c4cccc(F)c4)CC3)[nH]c(=O)c2C1]
Ex-3-28
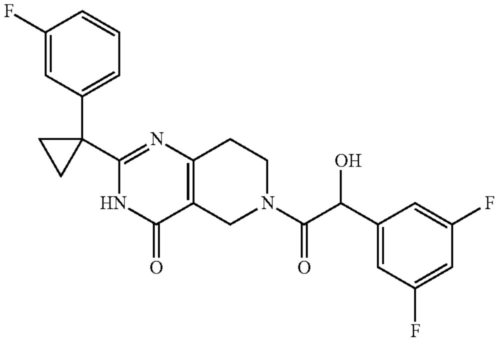 [SMILES: O=C(C(O)c1cc(F)cc(F)c1)N1CCc2nc(C3(c4cccc(F)c4)CC3)[nH]c(=O)c2C1]
Ex-3-29
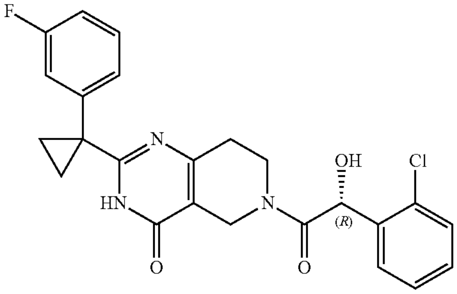
Ex-3-30
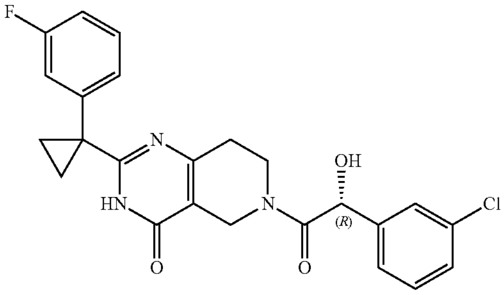
Ex-3-31

TABLE 94-3-continued
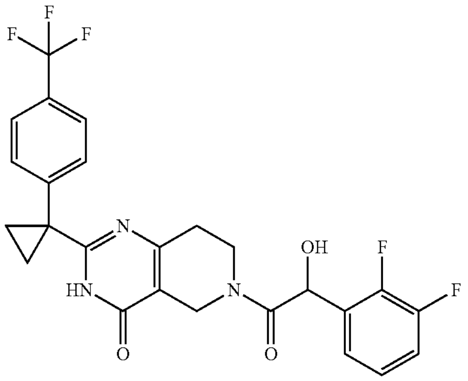 [SMILES: O=C(C(O)c1cccc(F)c1F)N1CCc2nc(C3(c4ccc(C(F)(F)F)cc4)CC3)[nH]c(=O)c2C1]
Ex-3-32
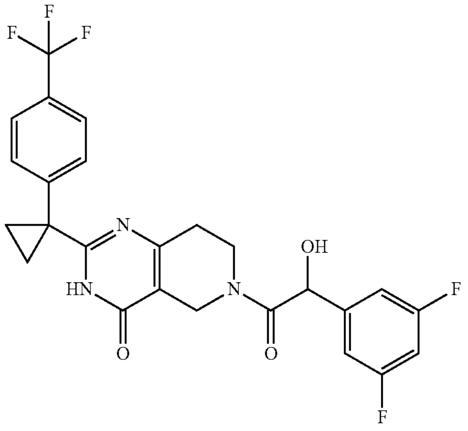 [SMILES: O=C(C(O)c1cc(F)cc(F)c1)N1CCc2nc(C3(c4ccc(C(F)(F)F)cc4)CC3)[nH]c(=O)c2C1]
Ex-3-33
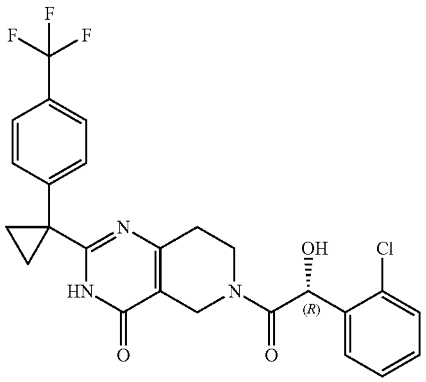
Ex-3-34
TABLE 94-3-continued
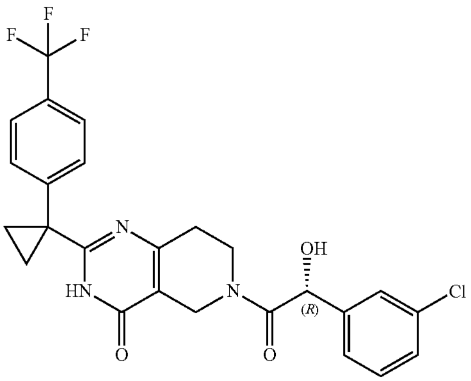
Ex-3-35
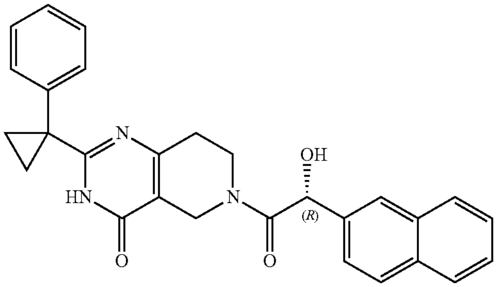
Ex-3-36
TABLE 94-4
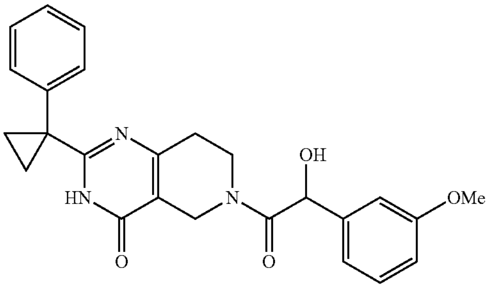 [SMILES: COc1cccc(C(O)C(=O)N2CCc3nc(C4(c5ccccc5)CC4)[nH]c(=O)c3C2)c1]
Ex-3-37
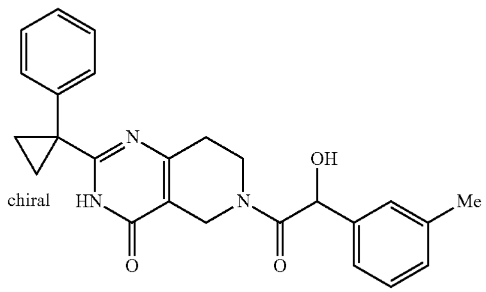 [SMILES: Cc1cccc(C(O)C(=O)N2CCc3nc(C4(c5ccccc5)CC4)[nH]c(=O)c3C2)c1]
Ex-3-38

TABLE 94-4-continued
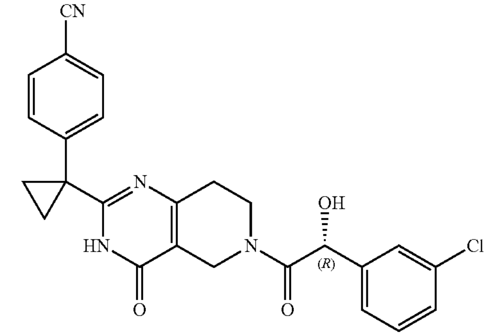
Ex-3-39
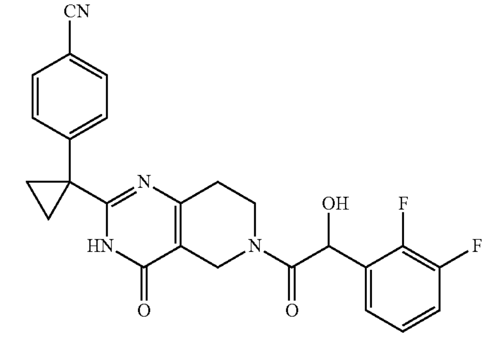 [SMILES: N#Cc1ccc(C2(c3nc4c(c(=O)[nH]3)CN(C(=O)C(O)c3cccc(F)c3F)CC4)CC2)cc1]
Ex-3-40
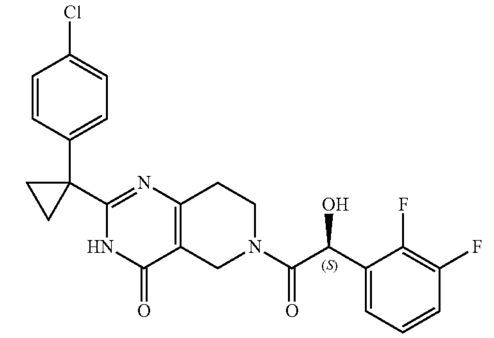
Ex-3-41
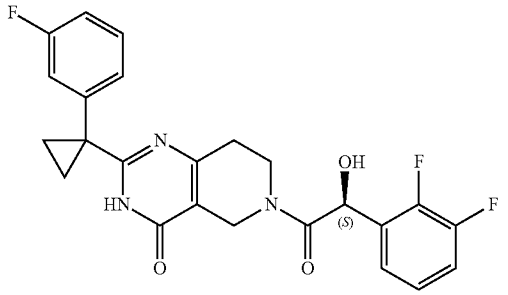
Ex-3-42
TABLE 94-4-continued
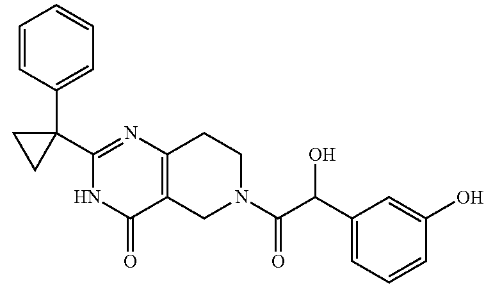 [SMILES: O=C(C(O)c1cccc(O)c1)N1CCc2nc(C3(c4ccccc4)CC3)[nH]c(=O)c2C1]
Ex-3-43
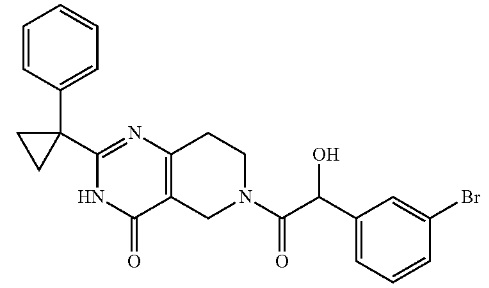 [SMILES: O=C(C(O)c1cccc(Br)c1)N1CCc2nc(C3(c4ccccc4)CC3)[nH]c(=O)c2C1]
Ex-3-44
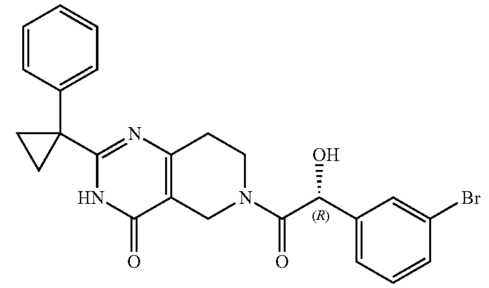
Ex-3-45
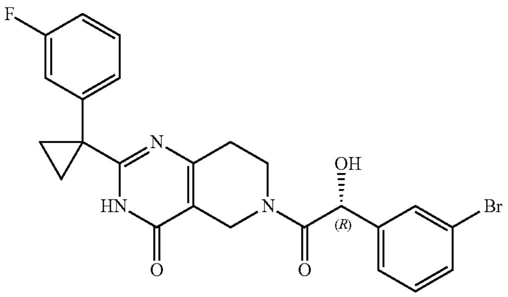
Ex-3-46

TABLE 94-4-continued
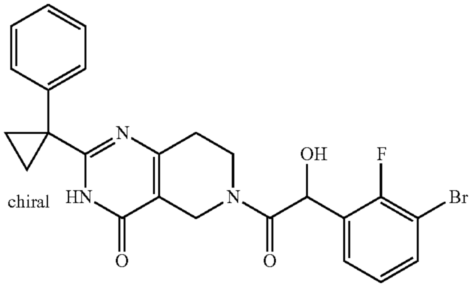 [SMILES: O=C(C(O)c1cccc(Br)c1F)N1CCc2nc(C3(c4ccccc4)CC3)[nH]c(=O)c2C1]
Ex-3-47
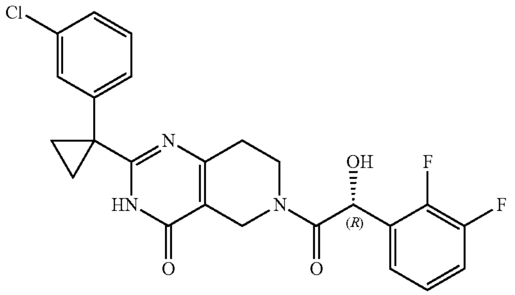
Ex-3-48
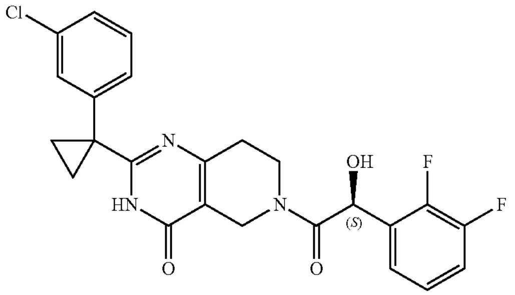
Ex-3-49
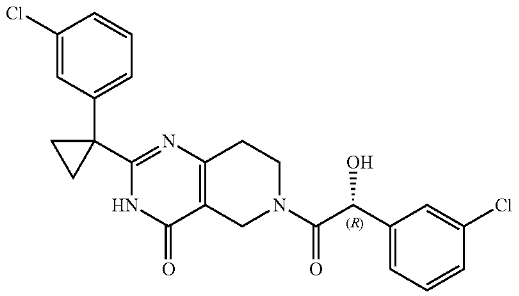
Ex-3-50
TABLE 94-4-continued
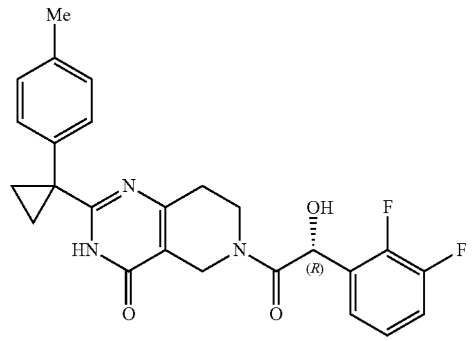
Ex-3-51
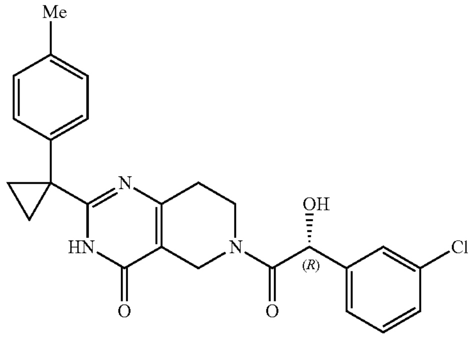
Ex-3-52
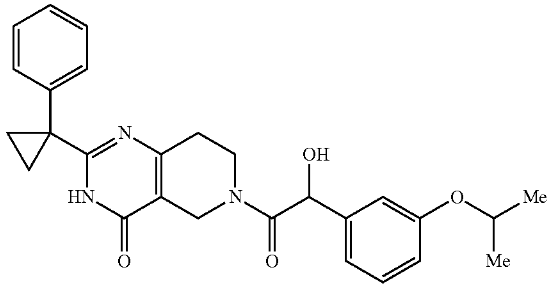 [SMILES: CC(C)Oc1cccc(C(O)C(=O)N2CCc3nc(C4(c5ccccc5)CC4)[nH]c(=O)c3C2)c1]
Ex-3-53
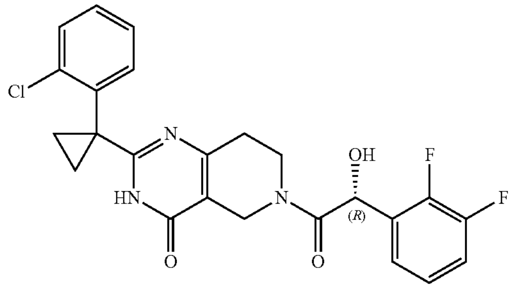
Ex-3-54

TABLE 94-4-continued
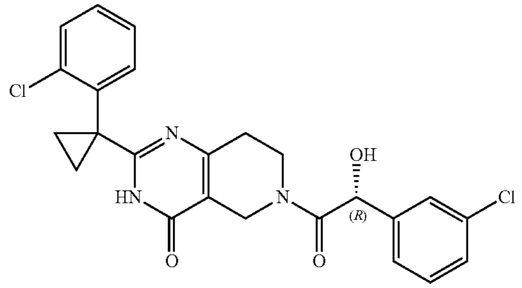
Ex-3-55
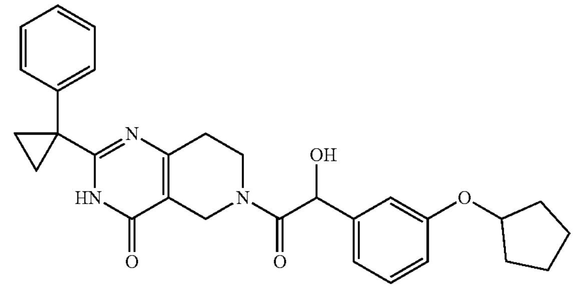 [SMILES: O=C(C(O)c1cccc(OC2CCCC2)c1)N1CCc2nc(C3(c4ccccc4)CC3)[nH]c(=O)c2C1]
Ex-3-56
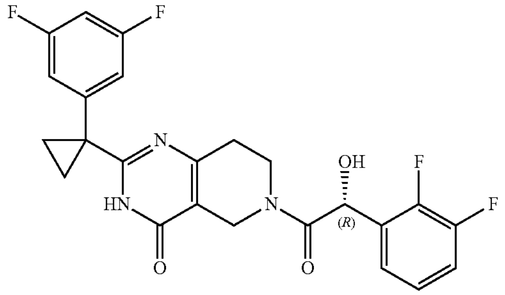
Ex-3-57
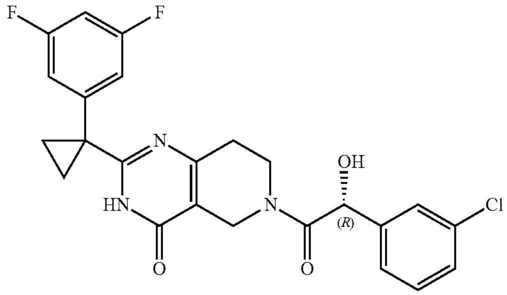
Ex-3-58
TABLE 94-4-continued
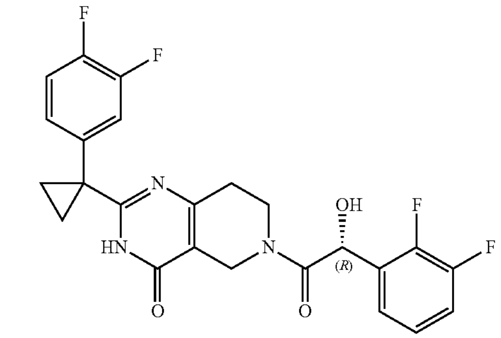
Ex-3-59
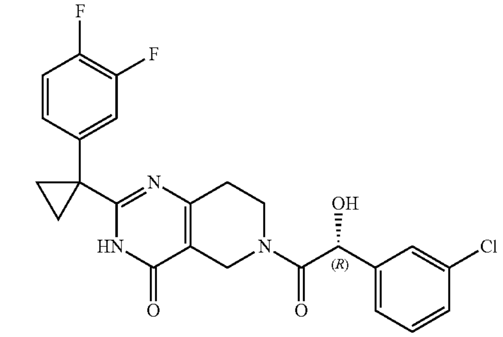
Ex-3-60
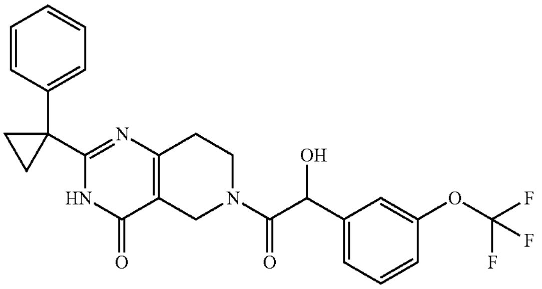
Ex-3-61
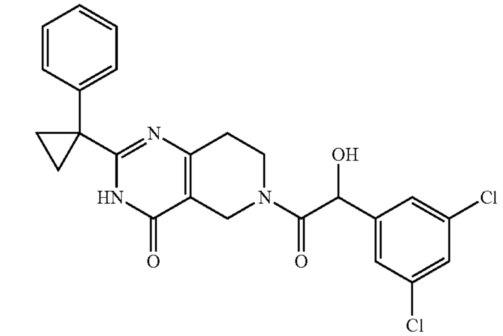 [SMILES: O=C(C(O)c1cc(Cl)cc(Cl)c1)N1CCc2nc(C3(c4ccccc4)CC3)[nH]c(=O)c2C1]
Ex-3-62

TABLE 94-4-continued
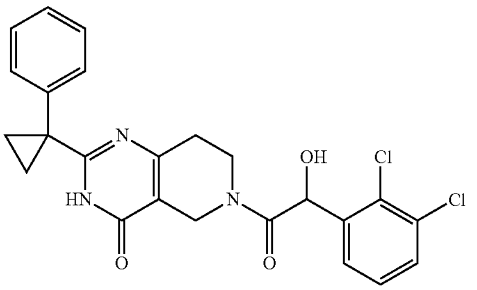 [SMILES: O=C(C(O)c1cccc(Cl)c1Cl)N1CCc2nc(C3(c4ccccc4)CC3)[nH]c(=O)c2C1]
Ex-3-63
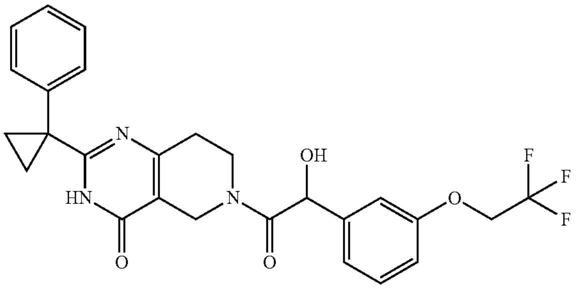 [SMILES: O=C(C(O)c1cccc(OCC(F)(F)F)c1)N1CCc2nc(C3(c4ccccc4)CC3)[nH]c(=O)c2C1]
Ex-3-64
TABLE 94-5
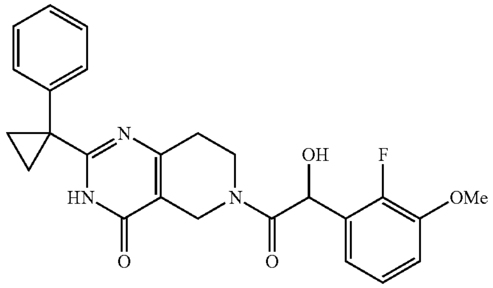 [SMILES: COc1cccc(C(O)C(=O)N2CCc3nc(C4(c5ccccc5)CC4)[nH]c(=O)c3C2)c1F]
Ex-3-65
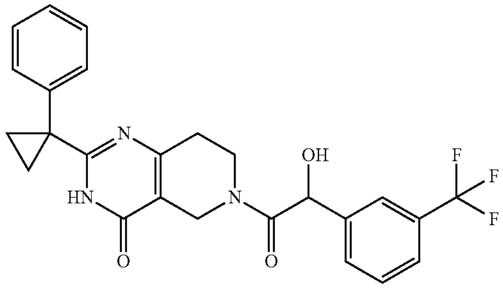
Ex-3-66
TABLE 94-5-continued
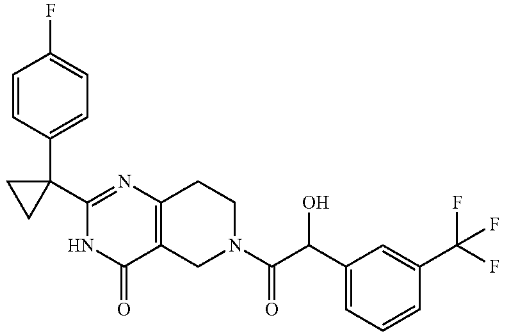 [SMILES: O=C(C(O)c1cccc(C(F)(F)F)c1)N1CCc2nc(C3(c4ccc(F)cc4)CC3)[nH]c(=O)c2C1]
Ex-3-67
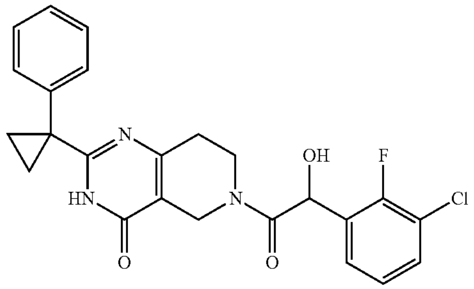 [SMILES: O=C(C(O)c1cccc(Cl)c1F)N1CCc2nc(C3(c4ccccc4)CC3)[nH]c(=O)c2C1]
Ex-3-68
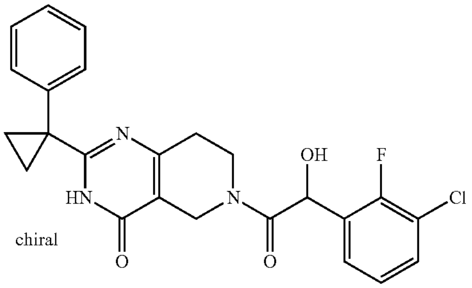 [SMILES: O=C(C(O)c1cccc(Cl)c1F)N1CCc2nc(C3(c4ccccc4)CC3)[nH]c(=O)c2C1]
Ex-3-69
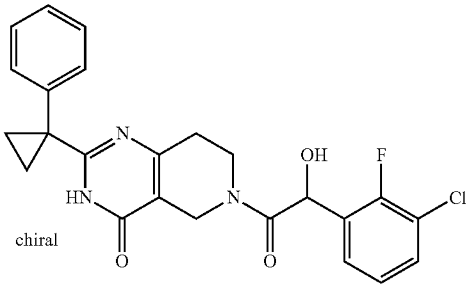 [SMILES: O=C(C(O)c1cccc(Cl)c1F)N1CCc2nc(C3(c4ccccc4)CC3)[nH]c(=O)c2C1]
Ex-3-70

TABLE 94-5-continued
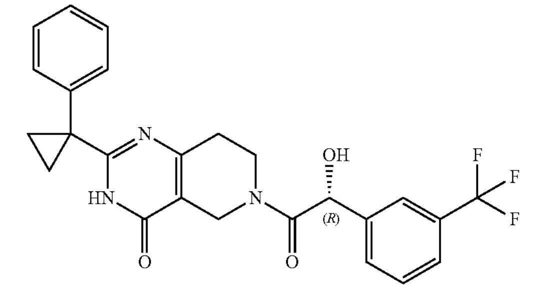
Ex-3-71
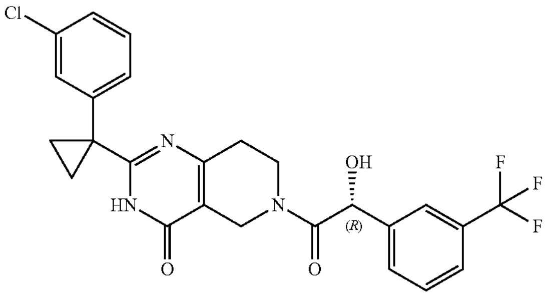
Ex-3-72
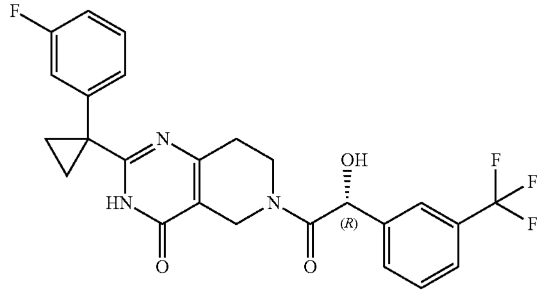
Ex-3-73
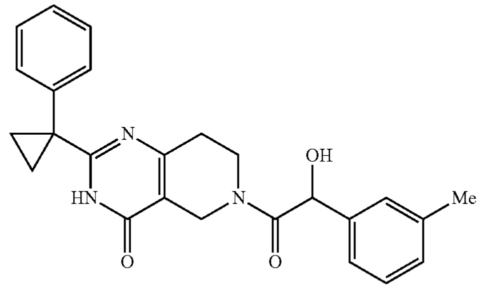 [SMILES: Cc1cccc(C(O)C(=O)N2CCc3nc(C4(c5ccccc5)CC4)[nH]c(=O)c3C2)c1]
Ex-4-1
TABLE 94-5-continued
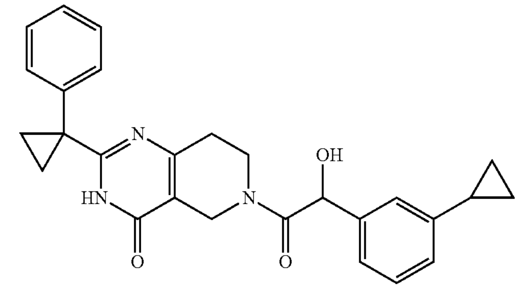 [SMILES: O=C(C(O)c1cccc(C2CC2)c1)N1CCc2nc(C3(c4ccccc4)CC3)[nH]c(=O)c2C1]
Ex-4-2
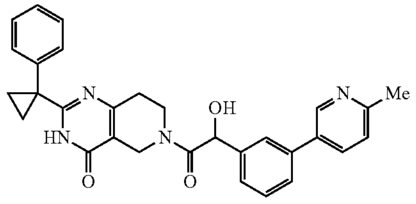 [SMILES: Cc1ccc(-c2cccc(C(O)C(=O)N3CCc4nc(C5(c6ccccc6)CC5)[nH]c(=O)c4C3)c2)cn1]
Ex-4-3
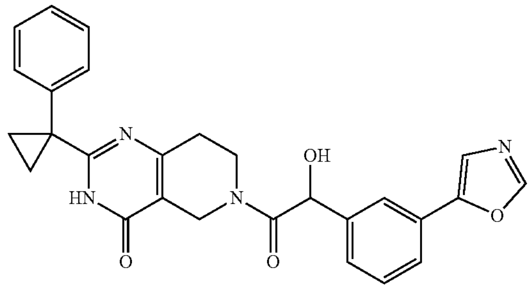 [SMILES: O=C(C(O)c1cccc(-c2cnco2)c1)N1CCc2nc(C3(c4ccccc4)CC3)[nH]c(=O)c2C1]
Ex-4-4
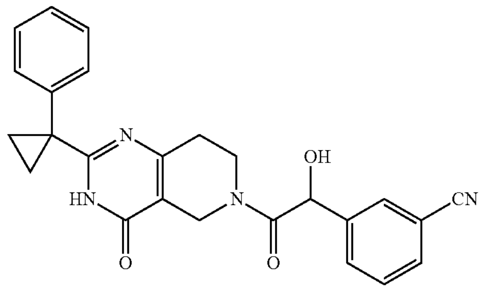 [SMILES: N#Cc1cccc(C(O)C(=O)N2CCc3nc(C4(c5ccccc5)CC4)[nH]c(=O)c3C2)c1]
Ex-4-5
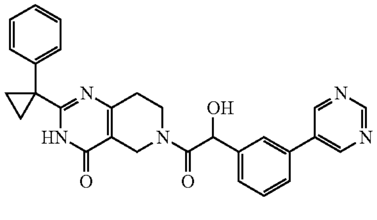 [SMILES: O=C(C(O)c1cccc(-c2cncnc2)c1)N1CCc2nc(C3(c4ccccc4)CC3)[nH]c(=O)c2C1]
Ex-4-6

TABLE 94-5-continued
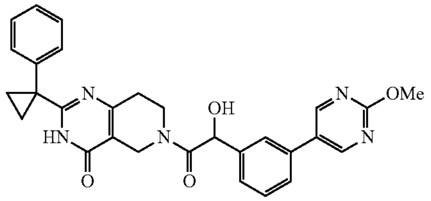 [SMILES: COc1ncc(-c2cccc(C(O)C(=O)N3CCc4nc(C5(c6ccccc6)CC5)[nH]c(=O)c4C3)c2)cn1]
Ex-4-7
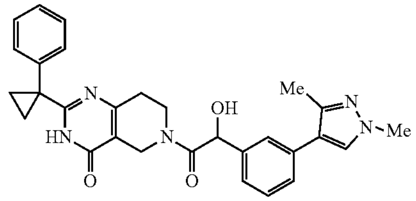 [SMILES: Cc1nn(C)cc1-c1cccc(C(O)C(=O)N2CCc3nc(C4(c5ccccc5)CC4)[nH]c(=O)c3C2)c1]
Ex-4-8
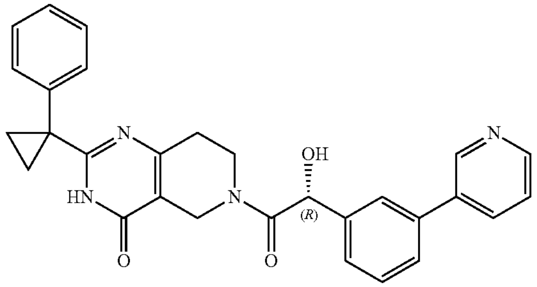
Ex-4-9
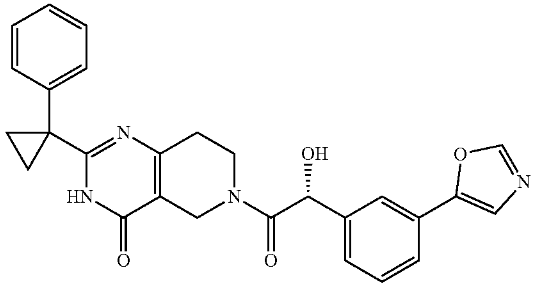 [SMILES: O=C([C@H](O)c1cccc(-c2cnco2)c1)N1CCc2nc(C3(c4ccccc4)CC3)[nH]c(=O)c2C1]
Ex-4-10
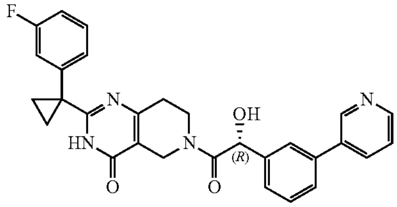
Ex-4-11
TABLE 94-5-continued
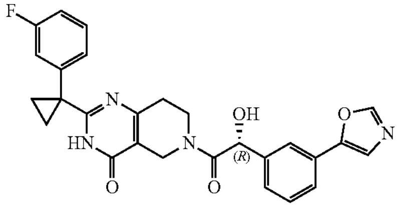
Ex-4-12
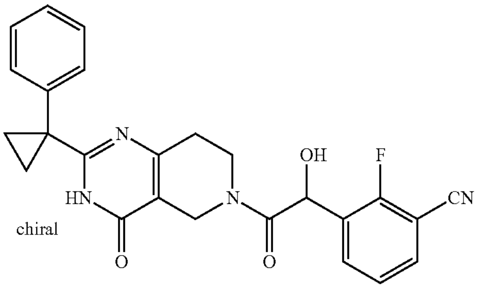 [SMILES: N#Cc1cccc(C(O)C(=O)N2CCc3nc(C4(c5ccccc5)CC4)[nH]c(=O)c3C2)c1F]
Ex-4-13
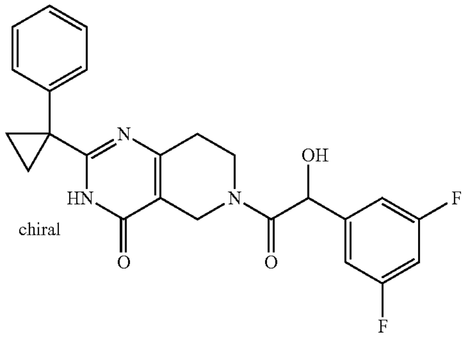 [SMILES: O=C(C(O)c1cc(F)cc(F)c1)N1CCc2nc(C3(c4ccccc4)CC3)[nH]c(=O)c2C1]
Ex-4-14
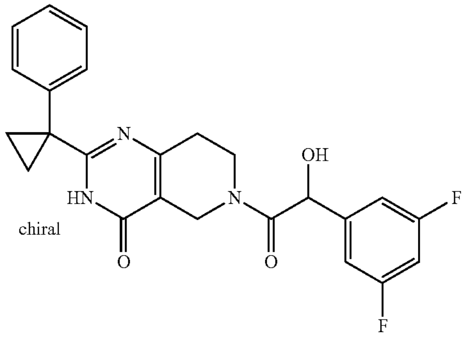 [SMILES: O=C(C(O)c1cc(F)cc(F)c1)N1CCc2nc(C3(c4ccccc4)CC3)[nH]c(=O)c2C1]
Ex-4-15

TABLE 94-5-continued
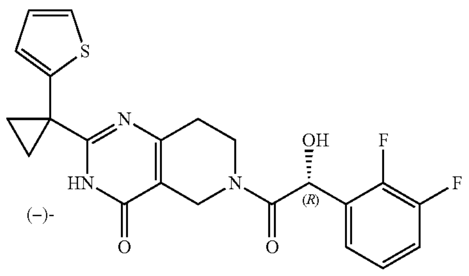
Ex-5-1
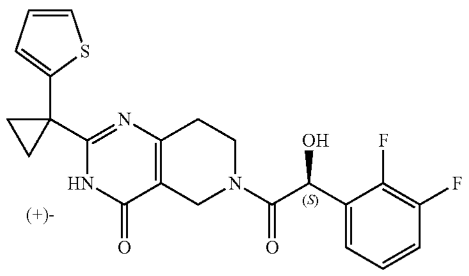
Ex-5-2
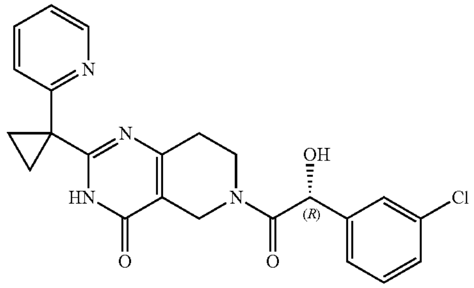
Ex-6-1
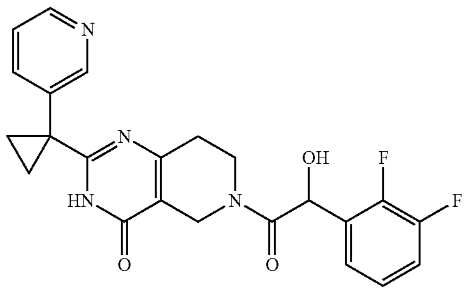 [SMILES: O=C(C(O)c1cccc(F)c1F)N1CCc2nc(C3(c4cccnc4)CC3)[nH]c(=O)c2C1]
Ex-6-2
TABLE 94-6
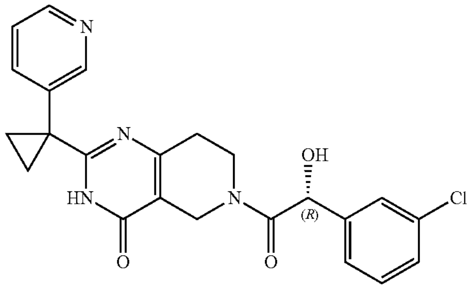
Ex-6-3
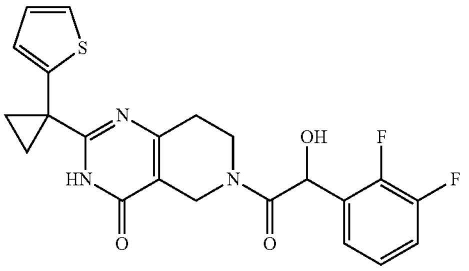 [SMILES: O=C(C(O)c1cccc(F)c1F)N1CCc2nc(C3(c4cccs4)CC3)[nH]c(=O)c2C1]
Ex-6-4
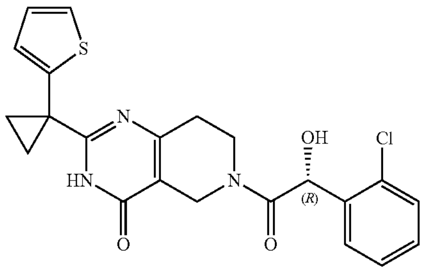
Ex-6-5
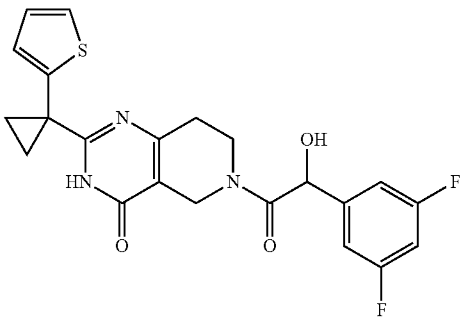 [SMILES: O=C(C(O)c1cc(F)cc(F)c1)N1CCc2nc(C3(c4cccs4)CC3)[nH]c(=O)c2C1]
Ex-6-6
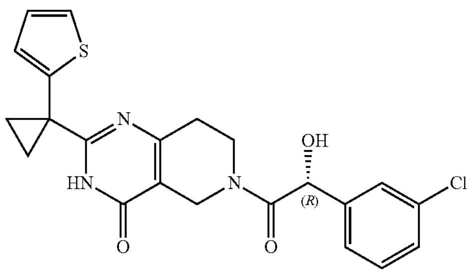
Ex-6-7

TABLE 94-6-continued
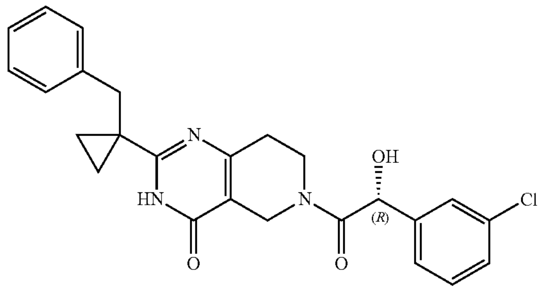
Ex-6-8
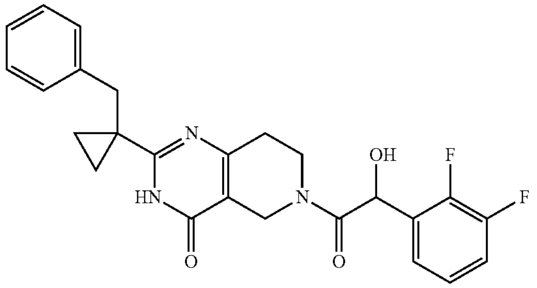 [SMILES: O=C(C(O)c1cccc(F)c1F)N1CCc2nc(C3(Cc4ccccc4)CC3)[nH]c(=O)c2C1]
Ex-6-9
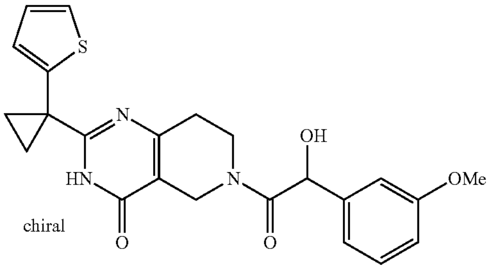 [SMILES: COc1cccc(C(O)C(=O)N2CCc3nc(C4(c5cccs5)CC4)[nH]c(=O)c3C2)c1]
Ex-6-10
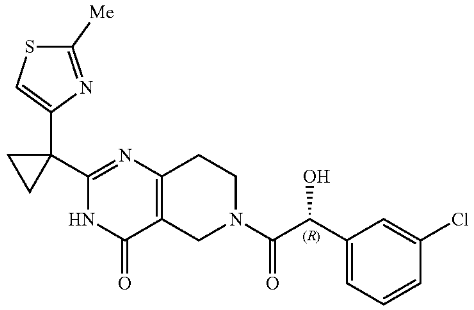
Ex-6-11
TABLE 94-6-continued
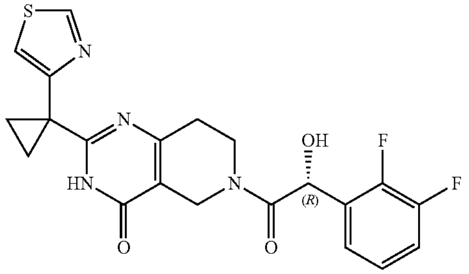
Ex-6-12
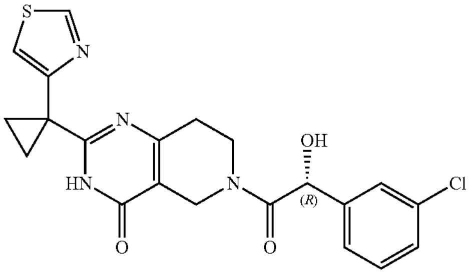
Ex-6-13
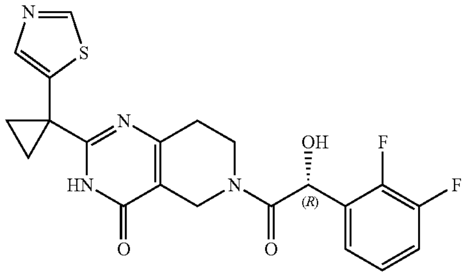
Ex-6-14
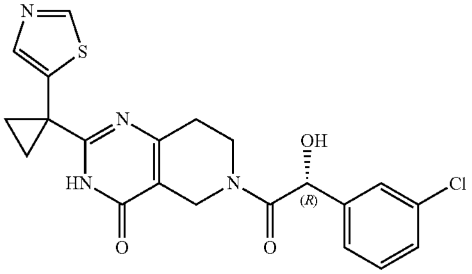
Ex-6-15
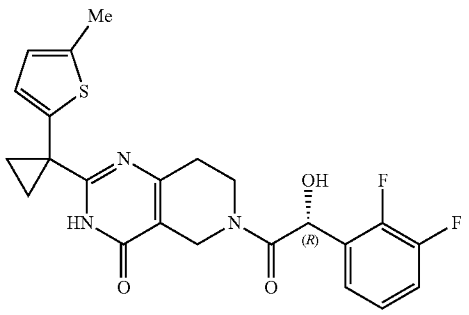
Ex-6-16

TABLE 94-6-continued
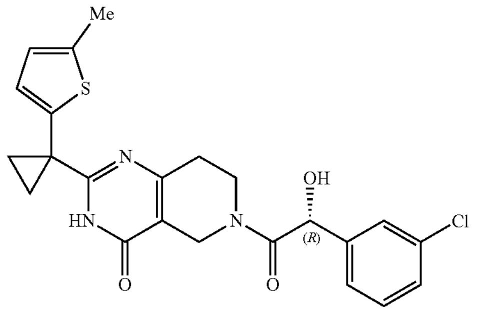
Ex-6-17
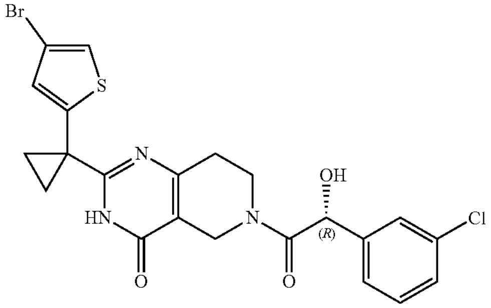
Ex-6-18
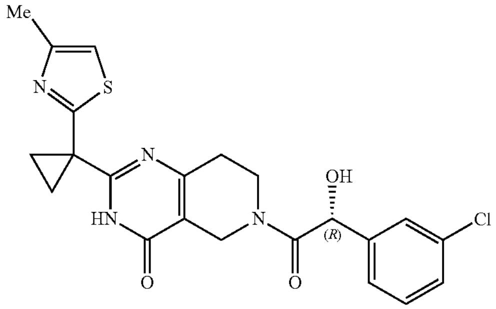
Ex-6-19
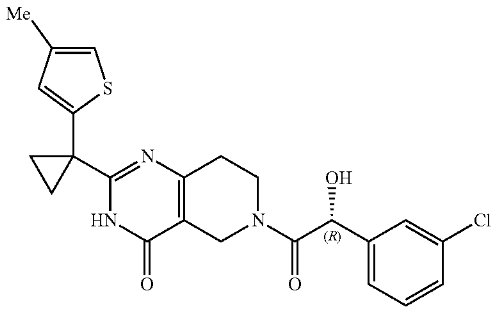
Ex-6-20
TABLE 94-6-continued
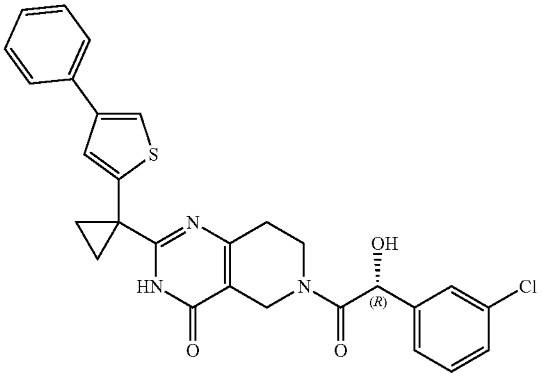
Ex-6-21
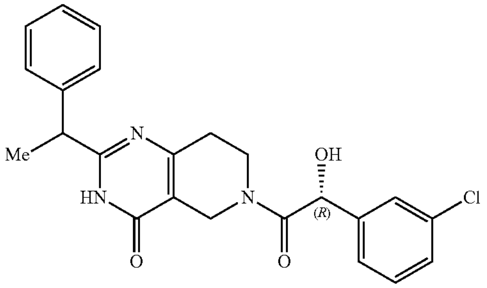
Ex-7-1
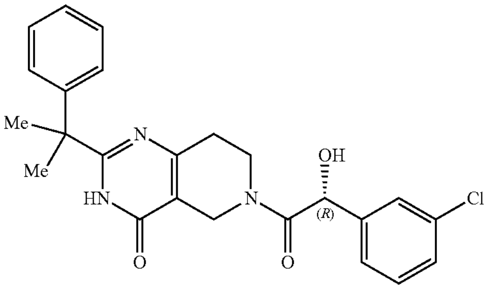
Ex-8-1
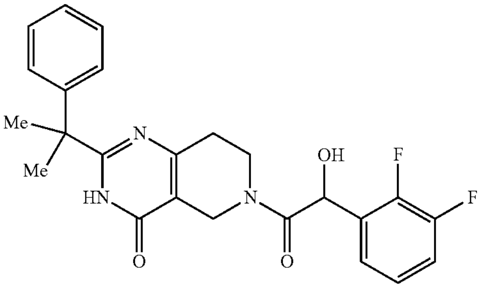 [SMILES: CC(C)(c1ccccc1)c1nc2c(c(=O)[nH]1)CN(C(=O)C(O)c1cccc(F)c1F)CC2]
Ex-9-1

TABLE 94-6-continued
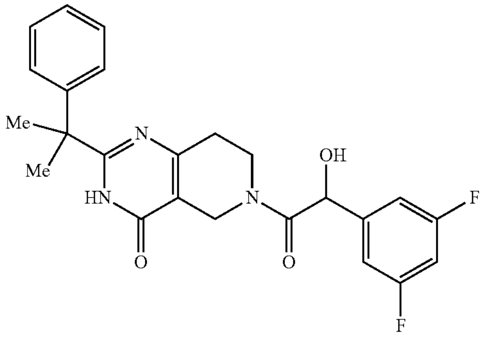 [SMILES: CC(C)(c1ccccc1)c1nc2c(c(=O)[nH]1)CN(C(=O)C(O)c1cc(F)cc(F)c1)CC2]
Ex-9-2
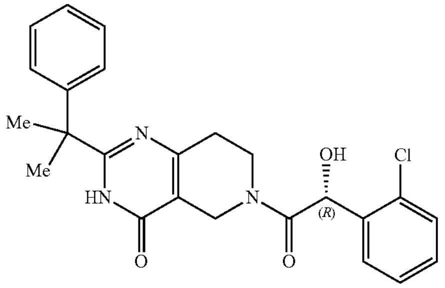
Ex-9-3
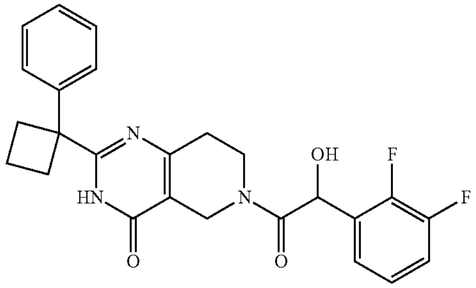 [SMILES: O=C(C(O)c1cccc(F)c1F)N1CCc2nc(C3(c4ccccc4)CCC3)[nH]c(=O)c2C1]
Ex-9-4
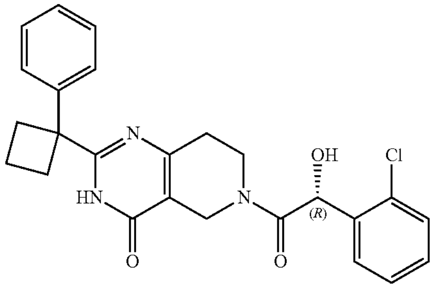
Ex-9-5
TABLE 94-6-continued
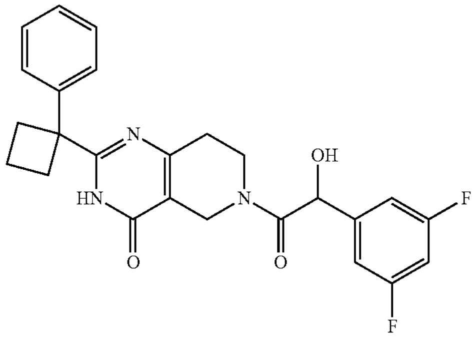 [SMILES: O=C(C(O)c1cc(F)cc(F)c1)N1CCc2nc(C3(c4ccccc4)CCC3)[nH]c(=O)c2C1]
Ex-9-6
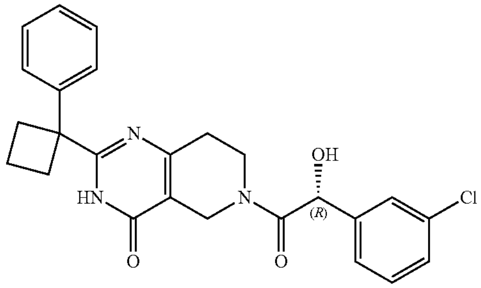
Ex-9-7
TABLE 94-7
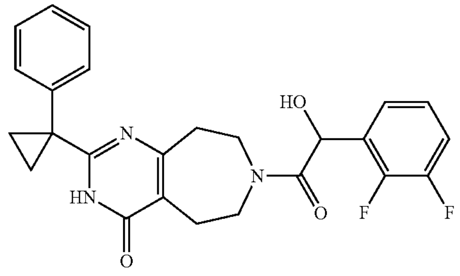 [SMILES: O=C(C(O)c1cccc(F)c1F)N1CCc2nc(C3(c4ccccc4)CC3)[nH]c(=O)c2CC1]
Ex-10-1
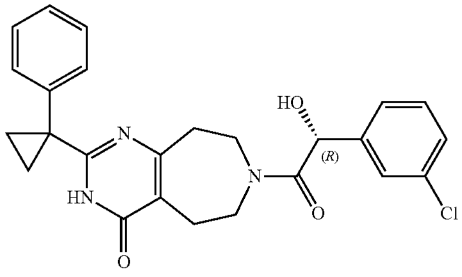
Ex-10-2

TABLE 94-7-continued
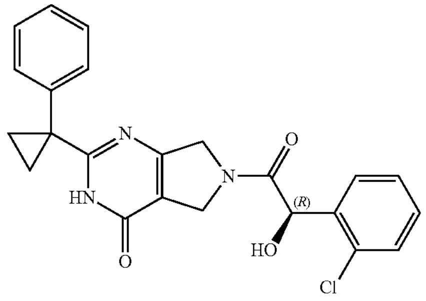
Ex-10-3
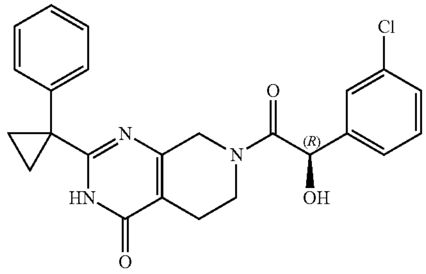
Ex-10-4
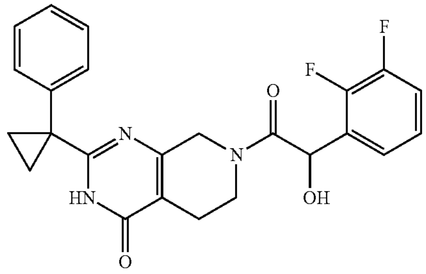 [SMILES: O=C(C(O)c1cccc(F)c1F)N1CCc2c(nc(C3(c4ccccc4)CC3)[nH]c2=O)C1]
Ex-10-5
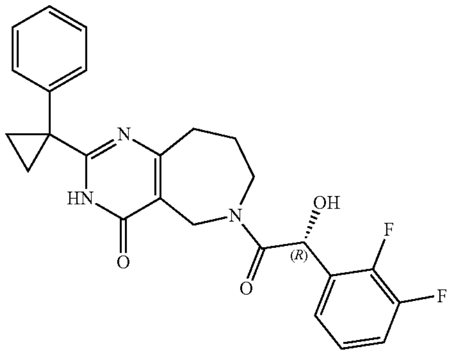
Ex-10-6
TABLE 94-7-continued
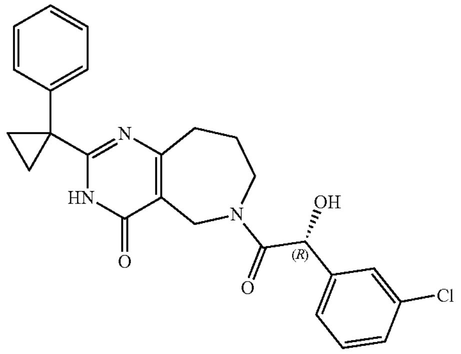
Ex-10-7
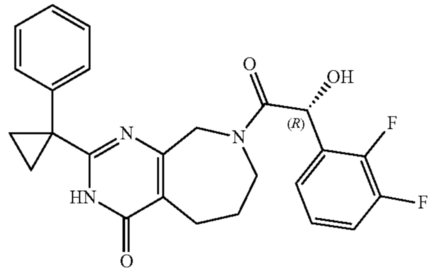
Ex-10-8
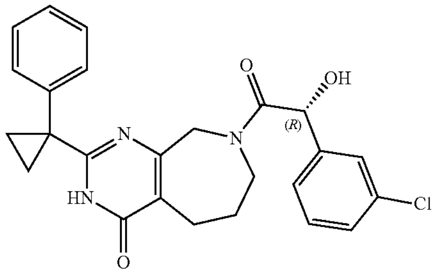
Ex-10-9
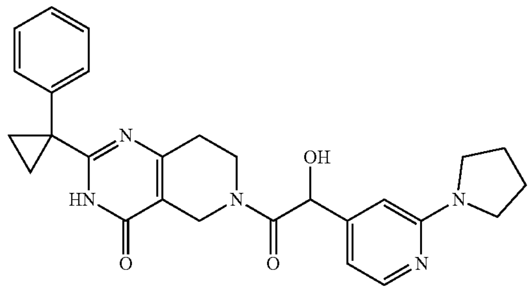 [SMILES: O=C(C(O)c1ccnc(N2CCCC2)c1)N1CCc2nc(C3(c4ccccc4)CC3)[nH]c(=O)c2C1]
Ex-11-1

TABLE 94-7-continued

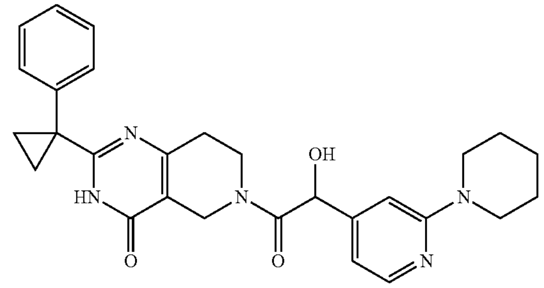 [SMILES: O=C(C(O)c1ccnc(N2CCCCC2)c1)N1CCc2nc(C3(c4ccccc4)CC3)[nH]c(=O)c2C1]

Ex-11-2

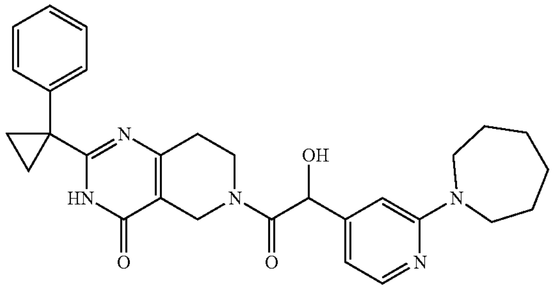 [SMILES: O=C(C(O)c1ccnc(N2CCCCCC2)c1)N1CCc2nc(C3(c4ccccc4)CC3)[nH]c(=O)c2C1]

Ex-11-3

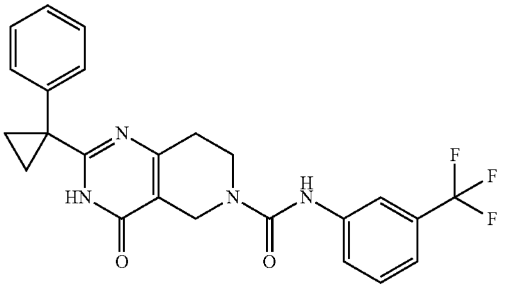 [SMILES: O=C(Nc1cccc(C(F)(F)F)c1)N1CCc2nc(C3(c4ccccc4)CC3)[nH]c(=O)c2C1]

Ex-12-1

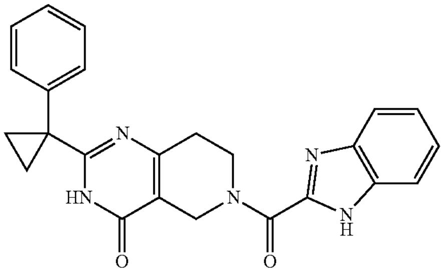 [SMILES: O=C(c1nc2ccccc2[nH]1)N1CCc2nc(C3(c4ccccc4)CC3)[nH]c(=O)c2C1]

Ex-13-1

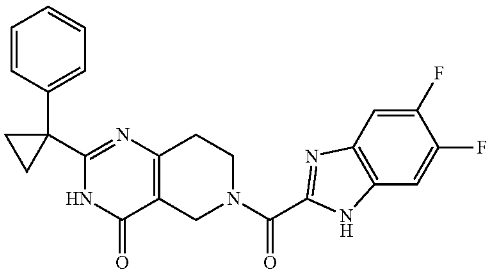 [SMILES: O=C(c1nc2cc(F)c(F)cc2[nH]1)N1CCc2nc(C3(c4ccccc4)CC3)[nH]c(=O)c2C1]

Ex-13-2

TABLE 94-7-continued

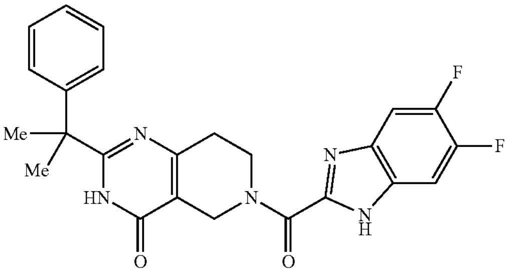 [SMILES: CC(C)(c1ccccc1)c1nc2c(c(=O)[nH]1)CN(C(=O)c1nc3cc(F)c(F)cc3[nH]1)CC2]

Ex-13-3

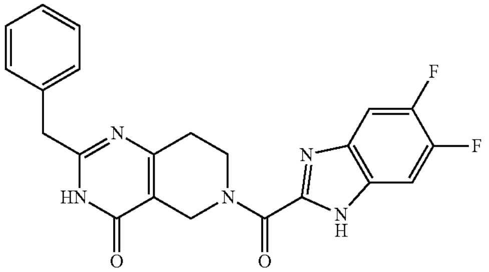 [SMILES: O=C(c1nc2cc(F)c(F)cc2[nH]1)N1CCc2nc(Cc3ccccc3)[nH]c(=O)c2C1]

Ex-13-4

Hypotonicity-Induced $Ca^{2+}$ Influx

TRPV4 channel activation/opening results in an influx of $Ca^{2+}$ (Liedtke, W. et al., 2000 (NPL 1)). The resulting changes in intracellular calcium are monitored using a $Ca^{2+}$ sensitive fluorescent dye Fluo-4 (Invitrogen). Dye loaded cells are treated with the test compounds for 5 minutes prior to the addition of a hypotonic solution and the inhibition of the hypotonicity-induced activation is recorded.

Forty microL of tetracycline-inducible Flp-In T-REx 293 cells (Invitrogen) stably expressing human TRPV4 are seeded onto the poly-D-lysine coated 384-well plate (Corning) at a density of 10,000 cells per well. The following day, TRPV4 expression is induced by adding 0.5 microg/mL tetracycline for 20-24 hours. On the day of the experiment, the media is removed and replaced with 40 microL of dye loading buffer [1 microM Fluo-4 AM (Invitrogen), 0.01% Pluronic F-127, and 20 mM HEPES in Hanks' balanced salt solutions (HBSS; Invitrogen)] and then the cells are incubated for 60 minutes at 25° C. Dye is then removed and replaced with 20 microL of assay buffer (20 mM HEPES in HBSS). Five minutes prior to the fluorescence measurement, 10 microL of test compound is added to the cells. Using the FDSS instrument (Hamamatsu Photonics), 30 microL of hypotonic solution (90 mM D-mannitol and 1.26 mM $CaCl_2$ in ultrapure water) is added 30 seconds after the start of measurement. The calcium flux signal is recorded for a total of 4.5 minutes.

The human $IC_{50}$ values of all example show below 3000 nM. The preferred examples showing below 3 nM, 10 nM and 50 nM of human $IC_{50}$ are summarized in Tables 95-1 to 95-3, Tables 96-1 to 96-2 and Table 97.

Human $IC_{50}$<50 nM

TABLE 95-1

| | | | | | | | | | |
|---|---|---|---|---|---|---|---|---|---|
| 2-21 | 3-62 | 6-21 | 14-7 | 14-17 | 14-27 | 14-110 | 14-122 | 15-10 | 15-25 |
| 2-33 | 3-66 | 10-6 | 14-8 | 14-18 | 14-28 | 14-111 | 15-1 | 15-11 | 15-26 |
| 2-34 | 3-67 | 10-7 | 14-9 | 14-19 | 14-29 | 14-114 | 15-2 | 15-12 | 15-27 |
| 3-21 | 3-69 | 11-3 | 14-10 | 14-20 | 14-30 | 14-115 | 15-3 | 15-13 | 15-28 |
| 3-22 | 3-71 | 14-1 | 14-11 | 14-21 | 14-31 | 14-116 | 15-4 | 15-14 | 16-1 |
| 3-28 | 3-72 | 14-2 | 14-12 | 14-22 | 14-32 | 14-117 | 15-5 | 15-15 | 16-2 |
| 3-31 | 3-73 | 14-3 | 14-13 | 14-23 | 14-105 | 14-118 | 15-6 | 15-16 | 17-1 |
| 3-48 | 6-7 | 14-4 | 14-14 | 14-24 | 14-106 | 14-119 | 15-7 | 15-17 | 17-2 |
| 3-50 | 6-18 | 14-5 | 14-15 | 14-25 | 14-107 | 14-120 | 15-8 | 15-18 | 17-3 |
| 3-58 | 6-20 | 14-6 | 14-16 | 14-26 | 14-109 | 14-121 | 15-9 | 15-24 | 17-4 |
| 17-5 | 17-15 | 17-25 | 17-35 | 17-45 | 17-55 | 17-75 | 17-89 | 17-100 | 17-116 |
| 17-6 | 17-16 | 17-26 | 17-36 | 17-46 | 17-56 | 17-76 | 17-90 | 17-102 | 17-117 |
| 17-7 | 17-17 | 17-27 | 17-37 | 17-47 | 17-57 | 17-77 | 17-91 | 17-105 | 17-118 |
| 17-8 | 17-18 | 17-28 | 17-38 | 17-48 | 17-58 | 17-80 | 17-93 | 17-109 | 17-119 |
| 17-9 | 17-19 | 17-29 | 17-39 | 17-49 | 17-59 | 17-81 | 17-94 | 17-110 | 17-120 |
| 17-10 | 17-20 | 17-30 | 17-40 | 17-50 | 17-60 | 17-82 | 17-95 | 17-111 | 17-121 |
| 17-11 | 17-21 | 17-31 | 17-41 | 17-51 | 17-61 | 17-84 | 17-96 | 17-112 | 17-122 |
| 17-12 | 17-22 | 17-32 | 17-42 | 17-52 | 17-72 | 17-85 | 17-97 | 17-113 | 17-123 |
| 17-13 | 17-23 | 17-33 | 17-43 | 17-53 | 17-73 | 17-87 | 17-98 | 17-114 | 17-124 |
| 17-14 | 17-24 | 17-34 | 17-44 | 17-54 | 17-74 | 17-88 | 17-99 | 17-115 | 17-125 |
| 17-126 | 17-136 | 17-146 | 18-9 | 18-20 | 18-30 | 19-9 | 20-4 | 21-1 | 22-5 |
| 17-127 | 17-137 | 17-147 | 18-10 | 18-21 | 18-31 | 19-10 | 20-5 | 21-2 | 22-6 |
| 17-128 | 17-138 | 18-1 | 18-11 | 18-22 | 19-1 | 19-11 | 20-6 | 21-3 | 22-7 |
| 17-129 | 17-139 | 18-2 | 18-12 | 18-23 | 19-2 | 19-12 | 20-7 | 21-4 | 22-8 |
| 17-130 | 17-140 | 18-3 | 18-13 | 18-24 | 19-3 | 19-13 | 20-8 | 21-5 | 22-9 |
| 17-131 | 17-141 | 18-4 | 18-15 | 18-25 | 19-4 | 19-14 | 20-9 | 21-6 | 22-10 |
| 17-132 | 17-142 | 18-5 | 18-16 | 18-26 | 19-5 | 19-15 | 20-10 | 22-1 | 23-1 |
| 17-133 | 17-143 | 18-6 | 18-17 | 18-27 | 19-6 | 20-1 | 20-13 | 22-2 | 23-2 |
| 17-134 | 17-144 | 18-7 | 18-18 | 18-28 | 19-7 | 20-2 | 20-14 | 22-3 | 24-1 |
| 17-135 | 17-145 | 18-8 | 18-19 | 18-29 | 19-8 | 20-3 | 20-15 | 22-4 | 25-1 |

TABLE 95-2

| | | | | | | | | | |
|---|---|---|---|---|---|---|---|---|---|
| 25-2 | 27-6 | 29-4 | 30-10 | 31-6 | 31-16 | 39-1 | 40-8 | 40-19 | 42-4 |
| 25-3 | 27-7 | 30-1 | 30-11 | 31-7 | 32-1 | 39-2 | 40-9 | 40-20 | 42-5 |
| 25-4 | 28-1 | 30-2 | 30-12 | 31-8 | 34-1 | 39-3 | 40-10 | 40-21 | 42-6 |
| 26-1 | 28-2 | 30-3 | 30-13 | 31-9 | 34-2 | 40-1 | 40-11 | 40-22 | 42-7 |
| 26-2 | 28-3 | 30-4 | 30-14 | 31-10 | 36-1 | 40-2 | 40-12 | 41-1 | 42-8 |
| 27-1 | 28-4 | 30-5 | 31-1 | 31-11 | 36-2 | 40-3 | 40-13 | 41-2 | 42-9 |
| 27-2 | 28-5 | 30-6 | 31-2 | 31-12 | 37-1 | 40-4 | 40-14 | 41-3 | 42-10 |
| 27-3 | 29-1 | 30-7 | 31-3 | 31-13 | 37-2 | 40-5 | 40-15 | 42-1 | 42-11 |
| 27-4 | 29-2 | 30-8 | 31-4 | 31-14 | 37-3 | 40-6 | 40-17 | 42-2 | 42-12 |
| 27-5 | 29-3 | 30-9 | 31-5 | 31-15 | 38-1 | 40-7 | 40-18 | 42-3 | 42-13 |
| 42-14 | 42-24 | 42-34 | 42-49 | 42-59 | 42-69 | 42-79 | 42-90 | 44-4 | 44-14 |
| 42-15 | 42-25 | 42-35 | 42-50 | 42-60 | 42-70 | 42-81 | 42-91 | 44-5 | 44-15 |
| 42-16 | 42-26 | 42-36 | 42-51 | 42-61 | 42-71 | 42-82 | 42-93 | 44-6 | 44-16 |
| 42-17 | 42-27 | 42-37 | 42-52 | 42-62 | 42-72 | 42-83 | 42-95 | 44-7 | 44-17 |
| 42-18 | 42-28 | 42-38 | 42-53 | 42-63 | 42-73 | 42-84 | 42-96 | 44-8 | 44-18 |
| 42-19 | 42-29 | 42-43 | 42-54 | 42-64 | 42-74 | 42-85 | 43-1 | 44-9 | 44-19 |
| 42-20 | 42-30 | 42-45 | 42-55 | 42-65 | 42-75 | 42-86 | 43-2 | 44-10 | 44-20 |
| 42-21 | 42-31 | 42-46 | 42-56 | 42-66 | 42-76 | 42-87 | 44-1 | 44-11 | 44-21 |
| 42-22 | 42-32 | 42-47 | 42-57 | 42-67 | 42-77 | 42-88 | 44-2 | 44-12 | 44-22 |
| 42-23 | 42-33 | 42-48 | 42-58 | 42-68 | 42-78 | 42-89 | 44-3 | 44-13 | 44-23 |
| 44-24 | 44-34 | 44-44 | 44-54 | 44-77 | 44-88 | 44-99 | 44-109 | 44-119 | 45-10 |
| 44-25 | 44-35 | 44-45 | 44-55 | 44-78 | 44-89 | 44-100 | 44-110 | 45-1 | 45-11 |
| 44-26 | 44-36 | 44-46 | 44-56 | 44-79 | 44-90 | 44-101 | 44-111 | 45-2 | 45-12 |
| 44-27 | 44-37 | 44-47 | 44-57 | 44-81 | 44-92 | 44-102 | 44-112 | 45-3 | 45-13 |
| 44-28 | 44-38 | 44-48 | 44-58 | 44-82 | 44-93 | 44-103 | 44-113 | 45-4 | 45-1 |
| 44-29 | 44-39 | 44-49 | 44-70 | 44-83 | 44-94 | 44-104 | 44-114 | 45-5 | 45-2 |
| 44-30 | 44-40 | 44-50 | 44-71 | 44-84 | 44-95 | 44-105 | 44-115 | 45-6 | 45-3 |
| 44-31 | 44-41 | 44-51 | 44-72 | 44-85 | 44-96 | 44-106 | 44-116 | 45-7 | 45-4 |
| 44-32 | 44-42 | 44-52 | 44-73 | 44-86 | 44-97 | 44-107 | 44-117 | 45-8 | 45-5 |
| 44-33 | 44-43 | 44-53 | 44-74 | 44-87 | 44-98 | 44-108 | 44-118 | 45-9 | 45-6 |

TABLE 95-3

| | | | | | | | | | |
|---|---|---|---|---|---|---|---|---|---|
| 47-1 | 48-5 | 49-4 | 49-14 | 49-27 | 49-37 | 49-47 | 49-57 | 50-10 | 50-20 |
| 47-2 | 48-6 | 49-5 | 49-15 | 49-28 | 49-38 | 49-48 | 50-1 | 50-11 | 50-21 |
| 47-3 | 48-7 | 49-6 | 49-16 | 49-29 | 49-39 | 49-49 | 50-2 | 50-12 | 50-22 |
| 47-4 | 48-8 | 49-7 | 49-17 | 49-30 | 49-40 | 49-50 | 50-3 | 50-13 | 50-23 |
| 47-5 | 48-9 | 49-8 | 49-18 | 49-31 | 49-41 | 49-51 | 50-4 | 50-14 | 50-24 |

TABLE 95-3-continued

| | | | | | | | | | |
|---|---|---|---|---|---|---|---|---|---|
| 47-6 | 48-10 | 49-9 | 49-21 | 49-32 | 49-42 | 49-52 | 50-5 | 50-15 | 50-25 |
| 48-1 | 48-11 | 49-10 | 49-22 | 49-33 | 49-43 | 49-53 | 50-6 | 50-16 | 50-26 |
| 48-2 | 49-1 | 49-11 | 49-24 | 49-34 | 49-44 | 49-54 | 50-7 | 50-17 | 51-1 |
| 48-3 | 49-2 | 49-12 | 49-25 | 49-35 | 49-45 | 49-55 | 50-8 | 50-18 | 51-2 |
| 48-4 | 49-3 | 49-13 | 49-26 | 49-36 | 49-46 | 49-56 | 50-9 | 50-19 | 51-3 |

TABLE 95-3-continued

| | | | | | | | | | |
|---|---|---|---|---|---|---|---|---|---|
| 51-4 | 52-6 | 53-1 | 54-5 | 55-1 | 55-11 | 57-1 | 58-2 | 59-10 | 60-1 |
| 51-5 | 52-7 | 53-2 | 54-6 | 55-2 | 55-12 | 57-2 | 58-3 | 59-11 | |
| 51-6 | 52-8 | 53-3 | 54-7 | 55-3 | 55-13 | 57-3 | 58-4 | 59-12 | |
| 51-7 | 52-9 | 53-4 | 54-8 | 55-4 | 55-14 | 57-4 | 58-5 | 59-13 | |
| 51-8 | 52-10 | 53-5 | 54-9 | 55-5 | 56-1 | 57-5 | 59-1 | 59-14 | |
| 52-1 | 52-11 | 53-6 | 54-10 | 55-6 | 56-2 | 57-6 | 59-2 | 59-15 | |

TABLE 95-3-continued

| | | | | | | | | |
|---|---|---|---|---|---|---|---|---|
| 52-2 | 52-12 | 54-1 | 54-11 | 55-7 | 56-3 | 57-7 | 59-3 | 59-16 |
| 52-3 | 52-13 | 54-2 | 54-12 | 55-8 | 56-4 | 57-8 | 59-4 | 59-17 |
| 52-4 | 52-14 | 54-3 | 54-13 | 55-9 | 56-5 | 57-9 | 59-5 | 59-18 |
| 52-5 | 52-15 | 54-4 | 54-14 | 55-10 | 56-6 | 58-1 | 59-6 | 59-19 |

Human $IC_{50}$<10 nM

TABLE 96-1

| | | | | | | | | | |
|---|---|---|---|---|---|---|---|---|---|
| 14-1 | 14-11 | 15-3 | 15-27 | 17-7 | 17-17 | 17-27 | 17-37 | 17-77 | 17-95 |
| 14-2 | 14-12 | 15-4 | 15-28 | 17-8 | 17-18 | 17-28 | 17-38 | 17-81 | 17-96 |
| 14-3 | 14-13 | 15-5 | 16-1 | 17-9 | 17-19 | 17-29 | 17-39 | 17-82 | 17-97 |
| 14-4 | 14-106 | 15-6 | 16-2 | 17-10 | 17-20 | 17-30 | 17-40 | 17-84 | 17-98 |
| 14-5 | 14-107 | 15-7 | 17-1 | 17-11 | 17-21 | 17-31 | 17-41 | 17-87 | 17-99 |
| 14-6 | 14-109 | 15-8 | 17-2 | 17-12 | 17-22 | 17-32 | 17-72 | 17-88 | 17-100 |
| 14-7 | 14-110 | 15-9 | 17-3 | 17-13 | 17-23 | 17-33 | 17-73 | 17-89 | 17-110 |
| 14-8 | 14-122 | 15-24 | 17-4 | 17-14 | 17-24 | 17-34 | 17-74 | 17-90 | 17-111 |
| 14-9 | 15-1 | 15-25 | 17-5 | 17-15 | 17-25 | 17-35 | 17-75 | 17-91 | 17-113 |
| 14-10 | 15-2 | 15-26 | 17-6 | 17-16 | 17-26 | 17-36 | 17-76 | 17-94 | 17-114 |
| 17-116 | 17-127 | 17-139 | 18-7 | 18-22 | 19-2 | 20-2 | 21-3 | 22-7 | 26-1 |
| 17-117 | 17-128 | 17-141 | 18-8 | 18-23 | 19-3 | 20-3 | 21-4 | 22-8 | 27-1 |
| 17-118 | 17-129 | 17-145 | 18-9 | 18-24 | 19-4 | 20-4 | 21-5 | 22-9 | 27-2 |
| 17-119 | 17-130 | 17-146 | 18-15 | 18-25 | 19-5 | 20-5 | 21-6 | 23-1 | 27-3 |
| 17-120 | 17-133 | 18-1 | 18-16 | 18-26 | 19-11 | 20-6 | 22-1 | 23-2 | 27-4 |
| 17-122 | 17-134 | 18-2 | 18-17 | 18-27 | 19-12 | 20-7 | 22-2 | 24-1 | 27-6 |
| 17-123 | 17-135 | 18-3 | 18-18 | 18-28 | 19-13 | 20-8 | 22-3 | 25-1 | 27-7 |
| 17-124 | 17-136 | 18-4 | 18-19 | 18-29 | 19-14 | 20-15 | 22-4 | 25-2 | 28-1 |
| 17-125 | 17-137 | 18-5 | 18-20 | 18-30 | 19-15 | 21-1 | 22-5 | 25-3 | 28-2 |
| 17-126 | 17-138 | 18-6 | 18-21 | 19-1 | 20-1 | 21-2 | 22-6 | 25-4 | 28-3 |
| 28-4 | 30-6 | 31-4 | 31-14 | 39-1 | 40-9 | 40-20 | 42-6 | 42-16 | 42-26 |
| 29-1 | 30-7 | 31-5 | 31-15 | 39-2 | 40-10 | 40-21 | 42-7 | 42-17 | 42-27 |
| 29-2 | 30-8 | 31-6 | 31-16 | 40-1 | 40-11 | 40-22 | 42-8 | 42-18 | 42-28 |
| 29-3 | 30-9 | 31-7 | 32-1 | 40-2 | 40-12 | 41-1 | 42-9 | 42-19 | 42-29 |
| 29-4 | 30-10 | 31-8 | 34-2 | 40-3 | 40-13 | 41-3 | 42-10 | 42-20 | 42-30 |
| 30-1 | 30-11 | 31-9 | 36-1 | 40-4 | 40-14 | 42-1 | 42-11 | 42-21 | 42-31 |
| 30-2 | 30-14 | 31-10 | 37-1 | 40-5 | 40-15 | 42-2 | 42-12 | 42-22 | 42-32 |
| 30-3 | 31-1 | 31-11 | 37-2 | 40-6 | 40-17 | 42-3 | 42-13 | 42-23 | 42-35 |
| 30-4 | 31-2 | 31-12 | 37-3 | 40-7 | 40-18 | 42-4 | 42-14 | 42-24 | 42-43 |
| 30-5 | 31-3 | 31-13 | 38-1 | 40-8 | 40-19 | 42-5 | 42-15 | 42-25 | 42-45 |

TABLE 96-2

| | | | | | | | | | |
|---|---|---|---|---|---|---|---|---|---|
| 42-46 | 42-58 | 42-68 | 42-78 | 42-89 | 44-4 | 44-14 | 44-78 | 44-95 | 44-105 |
| 42-47 | 42-59 | 42-69 | 42-79 | 42-90 | 44-5 | 44-15 | 44-79 | 44-96 | 44-107 |
| 42-48 | 42-60 | 42-70 | 42-81 | 42-91 | 44-6 | 44-16 | 44-81 | 44-97 | 44-108 |
| 42-49 | 42-61 | 42-71 | 42-82 | 42-93 | 44-7 | 44-17 | 44-82 | 44-98 | 44-110 |
| 42-50 | 42-62 | 42-72 | 42-83 | 42-95 | 44-8 | 44-18 | 44-83 | 44-99 | 44-112 |
| 42-51 | 42-63 | 42-73 | 42-84 | 42-96 | 44-9 | 44-71 | 44-84 | 44-100 | 44-115 |
| 42-54 | 42-64 | 42-74 | 42-85 | 43-1 | 44-10 | 44-72 | 44-85 | 44-101 | 44-117 |
| 42-55 | 42-65 | 42-75 | 42-86 | 44-1 | 44-11 | 44-73 | 44-86 | 44-102 | 44-118 |
| 42-56 | 42-66 | 42-76 | 42-87 | 44-2 | 44-12 | 44-74 | 44-93 | 44-103 | 44-119 |
| 42-57 | 42-67 | 42-77 | 42-88 | 44-3 | 44-13 | 44-77 | 44-94 | 44-104 | 45-1 |
| 45-2 | 45-12 | 47-3 | 49-1 | 49-11 | 49-25 | 49-35 | 49-45 | 49-55 | 50-9 |
| 45-3 | 45-13 | 47-4 | 49-2 | 49-12 | 49-26 | 49-36 | 49-46 | 49-56 | 50-10 |
| 45-4 | 45-1 | 47-5 | 49-3 | 49-13 | 49-27 | 49-37 | 49-47 | 50-1 | 50-11 |
| 45-5 | 45-2 | 47-6 | 49-4 | 49-14 | 49-28 | 49-38 | 49-48 | 50-2 | 50-12 |
| 45-6 | 45-3 | 48-1 | 49-5 | 49-15 | 49-29 | 49-39 | 49-49 | 50-3 | 50-13 |
| 45-7 | 45-4 | 48-2 | 49-6 | 49-16 | 49-30 | 49-40 | 49-50 | 50-4 | 50-14 |
| 45-8 | 45-5 | 48-3 | 49-7 | 49-17 | 49-31 | 49-41 | 49-51 | 50-5 | 50-15 |
| 45-9 | 45-6 | 48-4 | 49-8 | 49-18 | 49-32 | 49-42 | 49-52 | 50-6 | 50-16 |
| 45-10 | 47-1 | 48-5 | 49-9 | 49-22 | 49-33 | 49-43 | 49-53 | 50-7 | 50-17 |
| 45-11 | 47-2 | 48-6 | 49-10 | 49-24 | 49-34 | 49-44 | 49-54 | 50-8 | 50-18 |
| 50-19 | 51-3 | 52-5 | 52-15 | 54-4 | 54-14 | 55-10 | 56-6 | 58-1 | 59-12 |
| 50-20 | 51-4 | 52-6 | 53-1 | 54-5 | 55-1 | 55-11 | 57-1 | 58-2 | 59-13 |
| 50-21 | 51-5 | 52-7 | 53-2 | 54-6 | 55-2 | 55-12 | 57-2 | 58-3 | 59-14 |
| 50-22 | 51-6 | 52-8 | 53-3 | 54-7 | 55-3 | 55-13 | 57-3 | 58-4 | 59-15 |
| 50-23 | 51-7 | 52-9 | 53-4 | 54-8 | 55-4 | 55-14 | 57-4 | 58-5 | 59-16 |
| 50-24 | 51-8 | 52-10 | 53-5 | 54-9 | 55-5 | 56-1 | 57-5 | 59-1 | 59-17 |
| 50-25 | 52-1 | 52-11 | 53-6 | 54-10 | 55-6 | 56-2 | 57-6 | 59-2 | 59-18 |
| 50-26 | 52-2 | 52-12 | 54-1 | 54-11 | 55-7 | 56-3 | 57-7 | 59-3 | |
| 51-1 | 52-3 | 52-13 | 54-2 | 54-12 | 55-8 | 56-4 | 57-8 | 59-10 | |
| 51-2 | 52-4 | 52-14 | 54-3 | 54-13 | 55-9 | 56-5 | 57-9 | 59-11 | |

Human $IC_{50}$<3 nM

TABLE 97

| | | | | | | | | | |
|---|---|---|---|---|---|---|---|---|---|
| 14-1 | 17-3 | 17-100 | 19-11 | 22-3 | 30-3 | 37-3 | 40-14 | 42-3 | 42-13 |
| 15-1 | 17-4 | 17-119 | 20-1 | 22-4 | 31-1 | 38-1 | 40-15 | 42-4 | 42-14 |
| 15-2 | 17-5 | 18-1 | 20-2 | 22-7 | 31-2 | 39-1 | 40-17 | 42-5 | 42-15 |
| 15-3 | 17-6 | 18-2 | 20-3 | 25-1 | 31-3 | 40-1 | 40-19 | 42-6 | 42-43 |
| 15-4 | 17-7 | 18-3 | 20-4 | 28-1 | 31-4 | 40-2 | 40-20 | 42-7 | 42-46 |
| 15-27 | 17-8 | 18-17 | 20-5 | 29-2 | 31-5 | 40-4 | 40-21 | 42-8 | 42-48 |
| 15-28 | 17-73 | 18-22 | 21-1 | 29-3 | 31-6 | 40-9 | 40-22 | 42-9 | 42-55 |
| 16-1 | 17-75 | 18-23 | 21-3 | 29-4 | 31-8 | 40-10 | 41-1 | 42-10 | 42-66 |
| 17-1 | 17-91 | 18-24 | 22-1 | 30-1 | 31-11 | 40-11 | 42-1 | 42-11 | 42-77 |
| 17-2 | 17-98 | 19-1 | 22-2 | 30-2 | 37-1 | 40-12 | 42-2 | 42-12 | 42-82 |
| 42-83 | 44-81 | 45-1 | 49-27 | 49-45 | 50-11 | 53-6 | | | |
| 42-84 | 44-82 | 45-6 | 49-28 | 49-46 | 50-15 | 54-1 | | | |
| 42-88 | 44-84 | 49-13 | 49-30 | 49-50 | 50-18 | 54-5 | | | |
| 42-93 | 44-85 | 49-14 | 49-31 | 49-51 | 50-19 | 54-6 | | | |
| 43-1 | 44-95 | 49-15 | 49-33 | 49-52 | 50-20 | 55-7 | | | |
| 44-71 | 44-98 | 49-16 | 49-36 | 50-4 | 50-25 | 55-8 | | | |
| 44-72 | 44-102 | 49-17 | 49-38 | 50-5 | 51-6 | 56-1 | | | |
| 44-74 | 44-104 | 49-18 | 49-39 | 50-6 | 51-7 | 56-2 | | | |
| 44-78 | 44-110 | 49-22 | 49-40 | 50-8 | 52-3 | 56-3 | | | |
| 44-79 | 45-5 | 49-25 | 49-44 | 50-9 | 53-2 | 57-2 | | | |

Human Dofetilide Binding Assay

Human HERG transfected HEK293S cells are prepared and grown in-house. The collected cells are suspended in 50 mM Tris-HCl (pH 7.4 at 4° C.) and homogenized using a hand held Polytron PT 1200 disruptor set at full power for 20 sec on ice. The homogenates are centrifuged at 48,000×g at 4° C. for 20 min. The pellets are then resuspended, homogenized, and centrifuged once more in the same manner. The final pellets are resuspended in an appropriate volume of 50 mM Tris-HCl, 10 mM KCl, 1 mM $MgCl_2$ (pH 7.4 at 4° C.), homogenized, aliquoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microg protein) for 120 minutes at room temperature. Nonspecific binding is determined by 10 microM E4031 at the final concentration.

All tested compounds of the invention show low affinity to human dofetilide binding site. The low affinity to human dofetilide binding site leads to reducing the risk of cardiovascular adverse events.

Metabolic Stability Assay:

Half-Life in Human Liver Microsomes (HLM)

Test compounds (1 microM) are incubated with 3.3 mM $MgCl_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture is split into two groups, a non-P450 group and a P450 group. NADPH is only added to the reaction mixture of the P450 group. (NADPH generation system is also used instead of NADPH.) An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yields the rate of metabolism (k). This is converted to a half-life value using following equations: Half-life=ln 2/k The compounds of this invention show preferable stability, which shows the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam (ULTRAFINE UC-429) 2 microM) at 3 microM of the each compound.

More specifically, the assay is carried out as follows. The compounds (60 microM, 10 microL) are pre-incubated in 170 microL of mixture including 0.1 mg protein/mL human liver microsomes, 100 mM potassium phosphate buffer (pH 7.4), 1 mM $MgCl_2$ and probes as substrate for 5 min. Reaction is started by adding a 20 microL of 10 mM NADPH (20 microL of NADPH generating system, which consist of 10 mM $NADP^+$, 50 mM DL-Isocitric acid and 10 U/ml Isocitric Dehydrogenase, is also used). The assay plate is incubated at 37° C. Acetonitrile is added to the incubate solution at appropriate time (e.g. 8 min).

The metabolites' concentration in the supernatant is measured by LC/MS/MS system.

The degree of drug-drug interaction is interpreted based on generation % of metabolites in the presence or absence of test compound.

The compounds of this invention show preferable results, which shows the above-mentioned practical use.

Plasma Protein Binding Assay

Plasma protein binding of the test compound (1 microM) is measured by the method of equilibrium dialysis using 96-well plate type equipment. HTD96a (registered trademark), regenerated cellulose membranes (molecular weight cut-off 12,000-14,000, 22 mm×120 mm) are soaked for overnight in distilled water, then for 15 minutes in 30% ethanol, and finally for 20 minutes in dialysis buffer (Dulbecco's phosphate buffered saline, pH 7.4). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 rpm, aliquots of plasma and buffer are sampled. The compound in plasma and buffer are extracted with 300 microL of acetonitrile containing internal standard compounds for analysis. The concentration of the compound is determined with LC/MS/MS analysis. The fraction of the compound unbound is calculated by the following equation (A) or (B):

{Math. 1}

$$fu=1-\{([plasma]_{eq}-[buffer]_{eq})/([plasma]_{eq})\} \quad (A)$$

wherein $[plasma]_{eq}$ and $[buffer]_{eq}$ are the concentrations of the compound in plasma and buffer, respectively.

[Math. 2]

$$fu\ (\%) = \frac{Cb/Cis,\ b \times 4}{Cp/Cis,\ p \times 4/3} \times 100 \quad (B)$$

wherein Cp is the peak area of the compound in plasma sample;

Cis,p is the peak area of the internal standard in plasma sample;

Cb is the peak area of the compound in buffer sample;

Cis,b is the peak area of the internal standard in buffer sample;

4 and 4/3 is the reciprocal of the dilution rate in plasma and buffer, respectively.

The compounds of this invention show preferable plasma protein binding, which shows the above-mentioned practical use.

INDUSTRIAL APPLICABILITY

The compounds of the present invention can be used for, for example, the treatment of inflammatory, pain and urological diseases or disorders.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of formula (I):

(I)

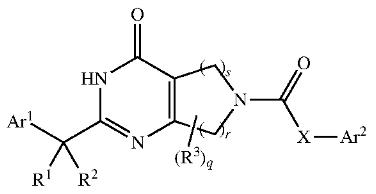

or a pharmaceutically acceptable salt, stereoisomer, or tautomer thereof, wherein:

$Ar^1$ is aryl or heteroaryl;

wherein the aryl or heteroaryl is optionally substituted with 1, 2, 3, 4, 5, or 6 substituents independently selected from the group consisting of halogen, CN, $NO_2$, $C_1$-$C_6$ alkyl, $C_1$-$C_4$ alkylene-heterocyclyl, $C_1$-$C_4$ alkylene-aryl, $C_1$-$C_4$ alkylene-heteroaryl, $C_2$-$C_6$ alkenyl, $C(O)R^7$, $C(O)NR^7R^8$, $NR^7R^8$, $NHS(O)_2R^7$, OH, $OC_1$—$C_6$ alkyl, $OC_1$—$C_6$ alkylene-heterocyclyl, $OC_1$—$C_6$ alkylene-aryl, $OC_1$—$C_6$ alkylene-heteroaryl, $OC_3$—$C_7$ cycloalkyl, Oheterocyclyl, Oaryl, Oheteroaryl, $Si(C_1$-$C_6$ alkyl$)_3$, $SC_1$—$C_6$ alkyl, $SC_1$—$C_6$ haloalkyl, $S(O)C_1$-$C_6$ alkyl, $S(O)_2C_1$-$C_6$ alkyl, $S(O)_2NR^7R^8$, $C_3$-$C_7$ cycloalkyl, heterocyclyl, aryl, heteroaryl, and substituent group Q;

wherein each $C_1$-$C_6$ alkyl, $C_1$-$C_4$ alkylene-heterocyclyl, $C_1$-$C_4$ alkylene-aryl, $C_1$-$C_4$ alkylene-heteroaryl, $C_2$-$C_6$ alkenyl, $OC_1$—$C_6$ alkyl, $OC_1$—$C_6$ alkylene-heterocyclyl, $OC_1$—$C_6$ alkylene-aryl, $OC_1$—$C_6$ alkylene-heteroaryl, $OC_3$—$C_7$ cycloalkyl, Oheterocyclyl, Oaryl, Oheteroaryl, $C_3$-$C_7$ cycloalkyl, heterocyclyl, aryl, and heteroaryl is optionally and independently substituted with 1, 2, 3, 4, 5, or 6 substituents independently selected from the group consisting of halogen, CN, $C_1$-$C_6$ alkyl, $C_1$-$C_6$ haloalkyl, $C_1$-$C_6$ alkylene-$NR^aR^b$, $C_1$-$C_6$ alkylene-$OC_1$—$C_6$ alkyl, $C(O)R^a$, $C(O)NR^aR^b$, $NR^aR^b$, OH, $OC_1$—$C_6$ alkyl, $OC_1$—$C_6$ haloalkyl, $OC_1$—$C_6$ alkylene-$C(O)NR^aR^b$, $OC_1$—$C_6$ alkylene-$NR^aR^b$, $OC_1$—$C_6$ alkylene-$OC_1$—$C_6$ alkyl, $S(O)_2C_1$-$C_6$ alkyl, $S(O)_2NR^aR^b$, and $C_3$-$C_7$ cycloalkyl;

wherein each $C_3$-$C_7$ cycloalkyl substituent of each $C_1$-$C_6$ alkyl, $C_1$-$C_4$ alkylene-heterocyclyl, $C_1$-$C_4$ alkylene-aryl, $C_1$-$C_4$ alkylene-heteroaryl, $C_2$-$C_6$ alkenyl, $OC_1$—$C_6$ alkyl, $OC_1$—$C_6$ alkylene-heterocyclyl, $OC_1$—$C_6$ alkylene-aryl, $OC_1$—$C_6$ alkylene-heteroaryl, $OC_3$—$C_7$ cycloalkyl, Oheterocyclyl, Oaryl, Oheteroaryl, $C_3$-$C_7$ cycloalkyl, heterocyclyl, aryl, and heteroaryl is optionally and independently substituted with 1 substituent selected from the group consisting of CN and phenyl; and wherein each substituent group Q is independently:

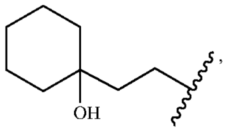,
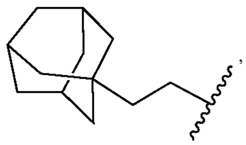,
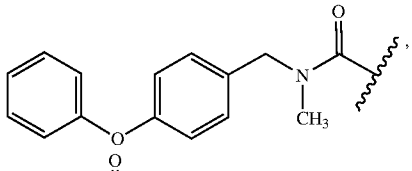,
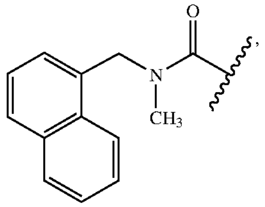,
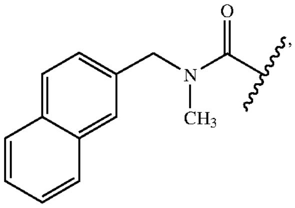,
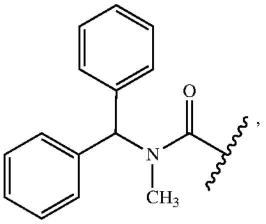,
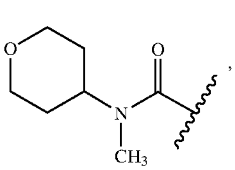,
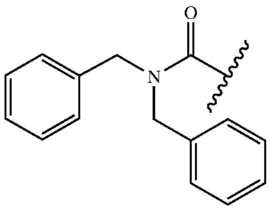,
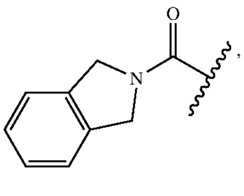, -continued
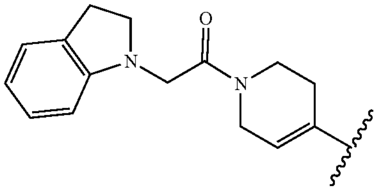
,
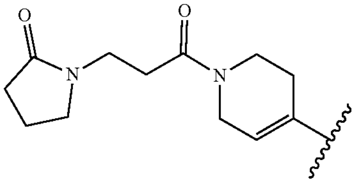
,
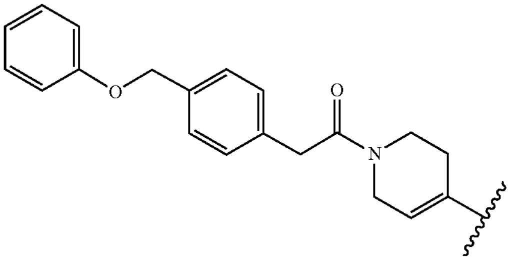
,
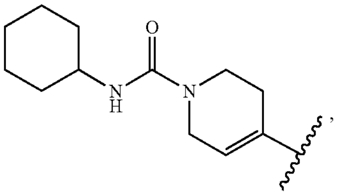
,
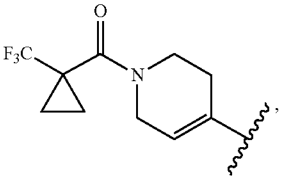
,
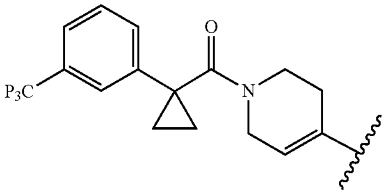
,
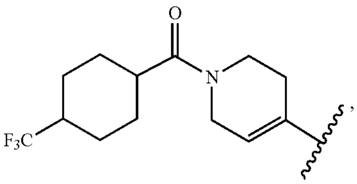
,
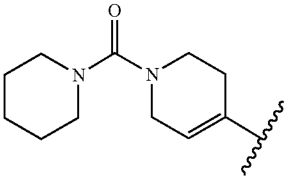
,
-continued
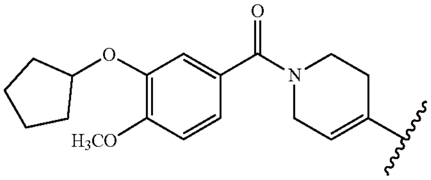
,
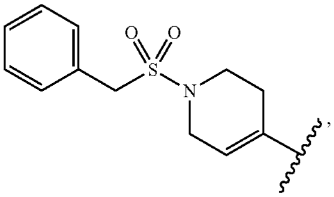
,
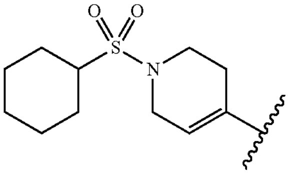
,
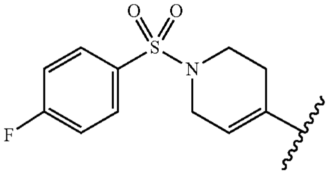
,
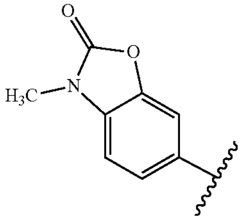
,
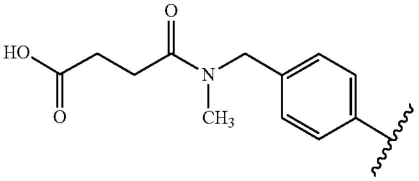
,
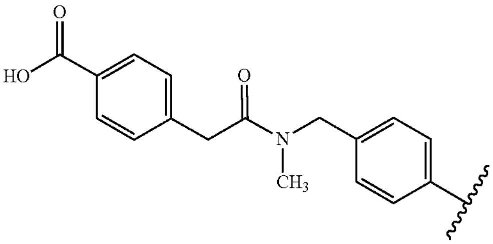
,
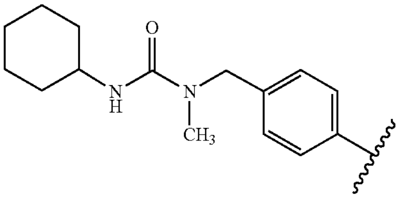
, -continued

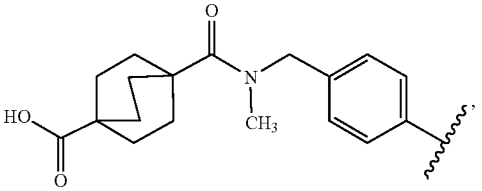

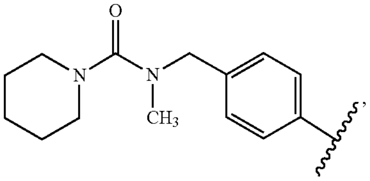

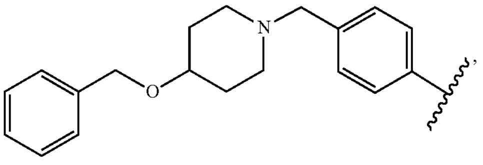

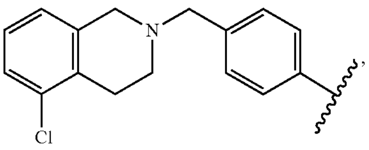

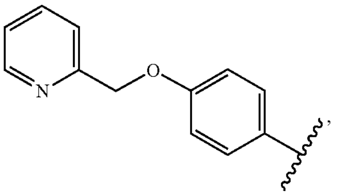

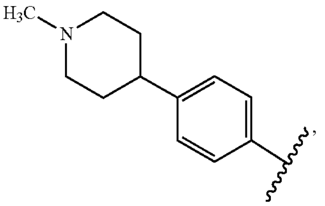

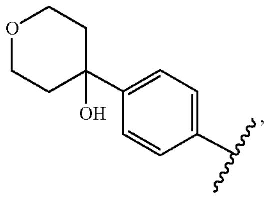

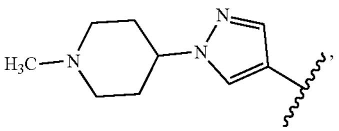

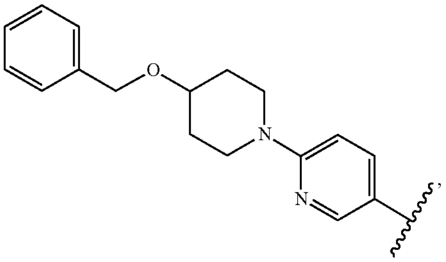

-continued

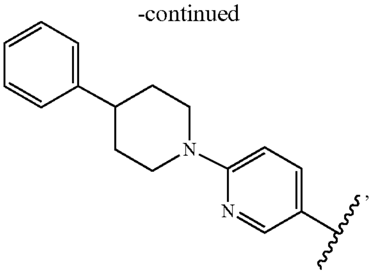

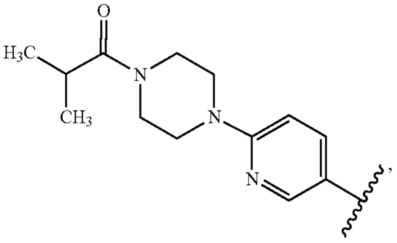

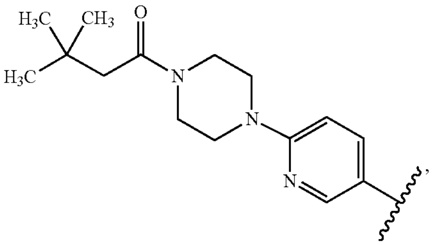

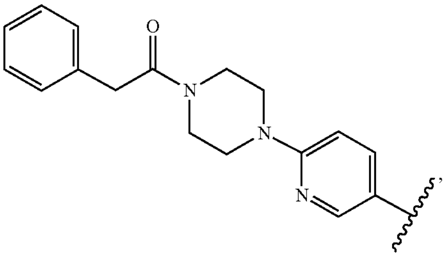

or

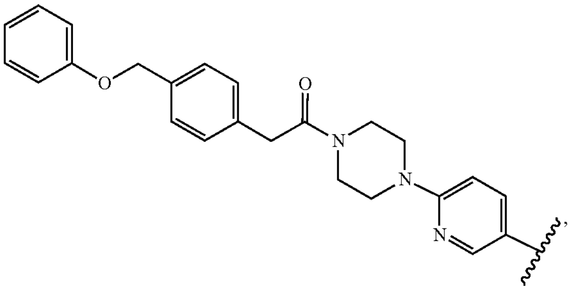

wherein each substituent group Q is optionally and independently substituted with 1 substituent selected from the group consisting of halogen, $C_1$-$C_6$ alkyl, and OH;

each $R^7$ is independently H, halogen, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-N($C_1$-$C_6$ alkyl)$_2$, $C_1$-$C_6$ hydroxyalkyl, $C_1$-$C_6$ alkylene-$OC_1$—$C_6$ alkyl, $C_1$-$C_6$ alkylene-$OC_1$—$C_6$ haloalkyl, $CH_2$-phenyl, OH, $OC_1$—$C_6$ alkyl, $OC_1$—$C_6$ haloalkyl, $C_3$-$C_7$ cycloalkyl, or heterocyclyl;

each $R^8$ is independently H, halogen, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-N($C_1$-$C_6$ alkyl)$_2$, $C_1$-$C_6$ hydroxyalkyl, $C_1$-$C_6$ alkylene-$OC_1$—$C_6$ alkyl, $C_1$-$C_6$ alkylene-$OC_1$—$C_6$ haloalkyl, $CH_2$- phenyl, OH, $OC_1$—$C_6$ alkyl, $OC_1$—$C_6$ haloalkyl, $C_3$-$C_7$ cycloalkyl, or heterocyclyl; or any $R^7$ and $R^8$, together with the nitrogen atom to which they are attached, independently forms a 3- to 10-membered ring;

wherein each 3- to 10-membered ring optionally and independently contains 1 additional heteroatom selected from the group consisting of nitrogen, oxygen, and sulfur; and wherein each 3- to 10-membered ring is optionally and independently substituted with 1, 2, 3, 4, 5, or 6 substituents independently selected from the group consisting of halogen, $C_1$-$C_6$ alkyl, $C_1$-$C_6$ haloalkyl, $C(O)C_1$-$C_6$ alkyl, $C(O)C_1$-$C_6$ haloalkyl, OH, $OC_1$—$C_6$ alkyl, =O, $S(O)_2C_1$-$C_6$ alkyl, and $S(O)_2C_1$-$C_6$ haloalkyl;

each $R^a$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-$N(C_1$-$C_6$ alkyl$)_2$, $C_1$-$C_6$ hydroxyalkyl, $C_1$-$C_6$ alkylene-$OC_1$—$C_6$ alkyl, $C_1$-$C_6$ alkylene-$OC_1$—$C_6$ haloalkyl, $C_1$-$C_6$ alkylene-phenyl, $C_3$-$C_7$ cycloalkyl, or phenyl;

each $R^b$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-$N(C_1$-$C_6$ alkyl$)_2$, $C_1$-$C_6$ hydroxyalkyl, $C_1$-$C_6$ alkylene-$OC_1$—$C_6$ alkyl, $C_1$-$C_6$ alkylene-$OC_1$—$C_6$ haloalkyl, $C_1$-$C_6$ alkylene-phenyl, $C_3$-$C_7$ cycloalkyl, or phenyl; or any $R^a$ and $R^b$, together with the nitrogen atom to which they are attached, independently forms a 3- to 7-membered ring;

wherein each 3- to 7-membered ring optionally and independently contains 1 additional heteroatom selected from the group consisting of nitrogen, oxygen, and sulfur; and wherein each 3- to 7-membered ring is optionally and independently substituted with 1, 2, or 3 independently selected $C_1$-$C_6$ alkyl substituents;

$R^1$ is H, halogen, $C_1$-$C_6$ alkyl, $C_1$-$C_6$ haloalkyl, $C_1$-$C_4$ alkylene-phenyl, OH, $OC_1$—$C_6$ alkyl, $OC_1$—$C_6$ haloalkyl, $C_3$-$C_7$ cycloalkyl, or phenyl, wherein the $C_3$-$C_7$ cycloalkyl, $C_1$-$C_4$ alkylene-phenyl, or phenyl is optionally substituted with 1, 2, 3, or 4 substituents independently selected from the group consisting of halogen, $C_1$-$C_6$ alkyl, $C_1$-$C_6$ haloalkyl, OH, $OC_1$—$C_6$ alkyl, and $OC_1$—$C_6$ haloalkyl;

$R^2$ is H, halogen, $C_1$-$C_6$ alkyl, $C_1$-$C_6$ haloalkyl, $C_1$-$C_4$ alkylene-phenyl, OH, $OC_1$—$C_6$ alkyl, $OC_1$—$C_6$ haloalkyl, $C_3$-$C_7$ cycloalkyl, or phenyl, wherein the $C_3$-$C_7$ cycloalkyl, $C_1$-$C_4$ alkylene-phenyl, or phenyl is optionally substituted with 1, 2, 3, or 4 substituents independently selected from the group consisting of halogen, $C_1$-$C_6$ alkyl, $C_1$-$C_6$ haloalkyl, OH, $OC_1$—$C_6$ alkyl, and $OC_1$—$C_6$ haloalkyl; or $R^1$ and $R^2$, together with the carbon atom to which they are attached, form a 3- to 8-membered ring;

wherein the 3- to 8-membered ring optionally contains 1, 2, 3, or 4 heteroatoms independently selected from the group consisting of nitrogen, oxygen, and sulfur; and wherein the 3- to 8-membered ring is optionally substituted with 1, 2, 3, 4, 5, or 6 substituents independently selected from the group consisting of halogen, $C_1$-$C_6$ alkyl, $C_1$-$C_6$ haloalkyl, $C(O)C_1$-$C_6$ alkyl, $C(O)C_1$-$C_6$ haloalkyl, OH, $S(O)_2C_1$-$C_6$ alkyl, and $S(O)_2C_1$-$C_6$ haloalkyl;

each $R^3$ is independently H, F, $CH_3$, $CH_2CH_3$, or $C_1$-$C_6$ haloalkyl;

X is a chemical bond, —$(CR^5R^6)_n$—, —$CR^4NR^5R^6$—, —$(CR^5R^6)_nNR^4$—, —$(CR^5R^6)_nO$—, —$(CR^5R^6)_nS$—, —$CR^5$=$CR^6$—, —C(O)—, —$NR^4$—, —$NR^4(CR^5R^6)_n$—, or $C_3$-$C_8$ cycloalkylene;

$R^4$ is H or $C_1$-$C_6$ alkyl;

each $R^5$ is independently H, halogen, $C_1$-$C_6$ alkyl, $C_1$-$C_6$ haloalkyl, $C_1$-$C_6$ hydroxyalkyl, $C_1$-$C_6$ alkylene-$OC_1$—$C_6$ alkyl, OH, $OC_1$—$C_6$ alkyl, or $OC_1$—$C_6$ haloalkyl;

each $R^6$ is independently H, halogen, $C_1$-$C_6$ alkyl, $C_1$-$C_6$ haloalkyl, $C_1$-$C_6$ hydroxyalkyl, $C_1$-$C_6$ alkylene-$OC_1$—$C_6$ alkyl, OH, $OC_1$—$C_6$ alkyl, or $OC_1$—$C_6$ haloalkyl;

n is 1, 2, 3, or 4;

$Ar^2$ is aryl or heteroaryl;

wherein the aryl or heteroaryl is optionally substituted with 1, 2, 3, 4, 5, or 6 substituents independently selected from the group consisting of halogen, CN, $NO_2$, $C_1$-$C_6$ alkyl, $C_1$-$C_4$ alkylene-heterocyclyl, $C_1$-$C_4$ alkylene-aryl, $C_1$-$C_4$ alkylene-heteroaryl, $C(O)R^9$, $C(O)NR^9R^{10}$, $NR^9R^{10}$, $NHS(O)_2R^9$, OH, $OC_1$—$C_6$ alkyl, $OC_1$—$C_6$ alkylene-heterocyclyl, $OC_1$—$C_6$ alkylene-aryl, $OC_1$—$C_6$ alkylene-heteroaryl, $OC_3$—$C_7$ cycloalkyl, Oheterocyclyl, Oaryl, Oheteroaryl, $Si(C_1$-$C_6$ alkyl$)_3$, $SC_1$—$C_6$ alkyl, $SC_1$—$C_6$ haloalkyl, $SF_5$, $S(O)C_1$-$C_6$ alkyl, $S(O)_2C_1$-$C_6$ alkyl, $S(O)_2NR^9R^{10}$, $C_3$-$C_7$ cycloalkyl, heterocyclyl, aryl, and heteroaryl; and wherein each $C_1$-$C_6$ alkyl, $C_1$-$C_4$ alkylene-heterocyclyl, $C_1$-$C_4$ alkylene-aryl, $C_1$-$C_4$ alkylene-heteroaryl, $OC_1$—$C_6$ alkyl, $OC_1$—$C_6$ alkylene-heterocyclyl, $OC_1$—$C_6$ alkylene-aryl, $OC_1$—$C_6$ alkylene-heteroaryl, $OC_3$—$C_7$ cycloalkyl, Oheterocyclyl, Oaryl, Oheteroaryl, $C_3$-$C_7$ cycloalkyl, heterocyclyl, aryl, and heteroaryl is optionally and independently substituted with 1, 2, 3, 4, 5, or 6 substituents independently selected from the group consisting of halogen, CN, $C_1$-$C_6$ alkyl, $C_1$-$C_6$ haloalkyl, $C_1$-$C_6$ alkylene-$NR^cR^d$, $C(O)NR^cR^d$, $NR^cR^d$, OH, $OC_1$—$C_6$ alkyl, $OC_1$—$C_6$ haloalkyl, $OC_1$—$C_6$ alkylene-$C(O)NR^cR^d$, $OC_1$—$C_6$ alkylene-$NR^cR^d$, $OC_1$—$C_6$ alkylene-$OC_1$—$C_6$ alkyl, $OCH_2$-phenyl, $SCF_3$, $SF_5$, and $C_3$-$C_7$ cycloalkyl;

each $R^9$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-$N(C_1$-$C_6$ alkyl$)_2$, $C_1$-$C_6$ hydroxyalkyl, $C_1$-$C_6$ alkylene-$OC_1$—$C_6$ alkyl, or $C_1$-$C_6$ alkylene-$OC_1$—$C_6$ haloalkyl;

each $R^{10}$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-$N(C_1$-$C_6$ alkyl$)_2$, $C_1$-$C_6$ hydroxyalkyl, $C_1$-$C_6$ alkylene-$OC_1$—$C_6$ alkyl, or $C_1$-$C_6$ alkylene-$OC_1$—$C_6$ haloalkyl; or any $R^9$ and $R^{10}$, together with the nitrogen atom to which they are attached, independently forms a 3- to 10-membered ring;

wherein each 3- to 10-membered ring optionally and independently contains 1 additional heteroatom selected from the group consisting of nitrogen, oxygen, and sulfur; and wherein each 3- to 10-membered ring is optionally and independently substituted with 1, 2, 3, 4, 5, or 6 substituents independently selected from the group consisting of halogen, $C_1$-$C_6$ alkyl, $C_1$-$C_6$ haloalkyl, $C(O)C_1$-$C_6$ alkyl, $C(O)C_1$-$C_6$ haloalkyl, OH, $OC_1$—$C_6$ alkyl, =O, $S(O)_2C_1$-$C_6$ alkyl, and $S(O)_2C_1$-$C_6$ haloalkyl;

each $R^c$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-N($C_1$-$C_6$ alkyl)$_2$, $C_1$-$C_6$ hydroxyalkyl, $C_1$-$C_6$ alkylene-$OC_1$—$C_6$ alkyl, or $C_1$-$C_6$ alkylene-$OC_1$—$C_6$ haloalkyl;

each $R^d$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-N($C_1$-$C_6$ alkyl)$_2$, $C_1$-$C_6$ hydroxyalkyl, $C_1$-$C_6$ alkylene-$OC_1$—$C_6$ alkyl, or $C_1$-$C_6$ alkylene-$OC_1$—$C_6$ haloalkyl; or any $R^c$ and $R^d$, together with the nitrogen atom to which they are attached, independently forms a 3- to 7-membered ring, wherein each 3- to 7-membered ring optionally and independently contains 1 additional heteroatom selected from the group consisting of nitrogen, oxygen, and sulfur;

q is 1, 2, 3, or 4;

r is 1, 2, 3, or 4; and s is 1, 2, 3, or 4.

2. The compound according to claim 1, or a pharmaceutically acceptable salt, stereoisomer, or tautomer thereof, wherein:

$R^1$ is H, $C_1$-$C_6$ alkyl, $C_1$-$C_6$ haloalkyl, $OC_1$—$C_6$ alkyl, $OC_1$—$C_6$ haloalkyl, or $C_3$-$C_7$ cycloalkyl;

$R^2$ is H, $C_1$-$C_6$ alkyl, $C_1$-$C_6$ haloalkyl, $OC_1$—$C_6$ alkyl, $OC_1$—$C_6$ haloalkyl, or $C_3$-$C_7$ cycloalkyl; or $R^1$ and $R^2$, together with the carbon atom to which they are attached, form a 3- to 8-membered carbocyclyl;

X is a chemical bond, —$CR^5R^6$—$(CH_2)_m$—, —$CH_2O$—, —CH=CH—, or $C_3$-$C_8$ cycloalkylene;

$R^5$ is H, halogen, $C_1$-$C_6$ alkyl, or OH;

$R^6$ is H, halogen, $C_1$-$C_6$ alkyl, or OH; and m is 0, 1, 2, or 3.

3. The compound according to claim 1, or a pharmaceutically acceptable salt, stereoisomer, or tautomer thereof, wherein:

$Ar^1$ is aryl or heteroaryl;

wherein the aryl or heteroaryl is optionally substituted with 1, 2, 3, 4, 5, or 6 substituents independently selected from the group consisting of halogen, CN, $C_1$-$C_6$ alkyl, $C(O)R^7$, $C(O)NR^7R^8$, $NR^7R^8$, $NHS(O)_2R^7$, OH, $OC_1$—$C_6$ alkyl, $OCH_2$-phenyl, Ophenyl, $S(O)_2NR^7R^8$, $C_3$-$C_7$ cycloalkyl, heterocyclyl, phenyl, and heteroaryl; and wherein each $C_1$-$C_6$ alkyl, $OC_1$—$C_6$ alkyl, $OCH_2$-phenyl, Ophenyl, $C_3$-$C_7$ cycloalkyl, heterocyclyl, phenyl, and heteroaryl is optionally and independently substituted with 1, 2, 3, 4, 5, or 6 substituents independently selected from the group consisting of halogen, CN, $C_1$-$C_6$ alkyl, $C_1$-$C_6$ haloalkyl, $C(O)R^a$, $C(O)NR^aR^b$, $NR^aR^b$, OH, $OC_1$—$C_6$ alkyl, and $C_3$-$C_7$ cycloalkyl;

each $R^7$ is independently H, $C_1$-$C_6$ alkyl, $C_1$-$C_6$ haloalkyl, OH, or $C_3$-$C_7$ cycloalkyl;

each $R^8$ is independently H, $C_1$-$C_6$ alkyl, $C_1$-$C_6$ haloalkyl, OH, or $C_3$-$C_7$ cycloalkyl; or any $R^7$ and $R^8$, together with the nitrogen atom to which they are attached, independently forms a 3- to 7-membered ring;

wherein each 3- to 7-membered ring optionally and independently contains 1 additional heteroatom selected from the group consisting of nitrogen, oxygen, and sulfur; and wherein each 3- to 7-membered ring is optionally and independently substituted with 1, 2, 3, 4, 5, or 6 substituents independently selected from the group consisting of halogen, $C_1$-$C_6$ alkyl, $C_1$-$C_6$ haloalkyl, OH, and $OC_1$—$C_6$ alkyl;

each $R^a$ is independently H, $C_1$-$C_6$ alkyl, $C_1$-$C_6$ haloalkyl, or $C_3$-$C_7$ cycloalkyl;

each $R^b$ is independently H, $C_1$-$C_6$ alkyl, $C_1$-$C_6$ haloalkyl, or $C_3$-$C_7$ cycloalkyl; or any $R^a$ and $R^b$, together with the nitrogen atom to which they are attached, independently forms a 3- to 7-membered ring;

wherein each 3- to 7-membered ring optionally and independently contains 1 additional heteroatom selected from the group consisting of nitrogen, oxygen, and sulfur; and wherein each 3- to 7-membered ring is optionally and independently substituted with 1, 2, or 3 substituents independently selected from the group consisting of $CH_3$ and $CH_2CH_3$;

$R^1$ is H, $C_1$-$C_6$ alkyl, $C_1$-$C_6$ haloalkyl, $OC_1$—$C_6$ alkyl, $OC_1$—$C_6$ haloalkyl, or $C_3$-$C_7$ cycloalkyl;

$R^2$ is H, $C_1$-$C_6$ alkyl, $C_1$-$C_6$ haloalkyl, $OC_1$—$C_6$ alkyl, $OC_1$—$C_6$ haloalkyl, or $C_3$-$C_7$ cycloalkyl; or $R^1$ and $R^2$, together with the carbon atom to which they are attached, form a 3- to 8-membered carbocyclyl;

X is a chemical bond or —$CR^5R^6$—;

$R^5$ is H, halogen, $C_1$-$C_6$ alkyl, OH, or $OC_1$—$C_6$ alkyl;

$R^6$ is H, halogen, $C_1$-$C_6$ alkyl, OH, or $OC_1$—$C_6$ alkyl;

$Ar^2$ is aryl or heteroaryl;

wherein the aryl or heteroaryl is optionally substituted with 1, 2, 3, 4, 5, or 6 substituents independently selected from the group consisting of halogen, CN, $C_1$-$C_6$ alkyl, $C(O)R^9$, $C(O)NR^9R^{10}$, $NR^9R^{10}$, $NHS(O)_2R^9$, OH, $OC_1$—$C_6$ alkyl, $OCH_2$-phenyl, $OC_3$—$C_7$ cycloalkyl, Ophenyl, $SC_1$—$C_6$ haloalkyl, $SF_5$, $S(O)_2NR^9R^{10}$, $C_3$-$C_7$ cycloalkyl, heterocyclyl, phenyl, and heteroaryl; and wherein each $C_1$-$C_6$ alkyl, $OC_1$—$C_6$ alkyl, $OCH_2$-phenyl, $OC_3$—$C_7$ cycloalkyl, Ophenyl, $C_3$-$C_7$ cycloalkyl, heterocyclyl, phenyl, and heteroaryl is optionally and independently substituted with 1, 2, 3, 4, 5, or 6 substituents independently selected from the group consisting of halogen, $C_1$-$C_6$ alkyl, $C_1$-$C_6$ haloalkyl, $C(O)NR^cR^d$, $NR^cR^d$, OH, $OC_1$—$C_6$ alkyl, $OC_1$—$C_6$ haloalkyl, and $C_3$-$C_7$ cycloalkyl;

each $R^c$ is independently H, $C_1$-$C_6$ alkyl, $C_1$-$C_6$ haloalkyl, or $C_1$-$C_6$ hydroxyalkyl;

each $R^d$ is independently H, $C_1$-$C_6$ alkyl, $C_1$-$C_6$ haloalkyl, or $C_1$-$C_6$ hydroxyalkyl; or any $R^c$ and $R^d$, together with the nitrogen atom to which they are attached, independently forms a 3- to 7-membered ring, wherein each 3- to 7-membered ring optionally and independently contains 1 additional heteroatom selected from the group consisting of nitrogen, oxygen, and sulfur;

q is 1, 2, or 3;

r is 1, 2, or 3; and s is 1, 2, or 3.

4. The compound according to claim 1, or a pharmaceutically acceptable salt, stereoisomer, or tautomer thereof, wherein:

$Ar^1$ is phenyl, naphthalenyl, pyrrolyl, furanyl, thiophenyl, pyrazolyl, imidazolyl, isoxazolyl, oxazolyl, isothiazolyl, thiazolyl, oxadiazolyl, pyridinyl, pyridazinyl, pyrimidinyl, pyrazinyl, indolyl, benzofuranyl, benzothiophenyl, indazolyl, benzimidazolyl, benzoisoxazolyl, quinolinyl, isoquinolinyl, quinazolinyl, quinoxalinyl, or imidazopyridinyl;

wherein the phenyl, naphthalenyl, pyrrolyl, furanyl, thiophenyl, pyrazolyl, imidazolyl, isoxazolyl, oxazolyl, isothiazolyl, thiazolyl, oxadiazolyl, pyridinyl, pyridazinyl, pyrimidinyl, pyrazinyl, indolyl, benzofuranyl, benzothiophenyl, indazolyl, benzimidazolyl, benzoisoxazolyl, quinolinyl, isoquinolinyl, quinazolinyl, quinoxalinyl, or imidazopyridinyl is optionally substituted with 1, 2, 3, 4, 5, or 6 substituents independently selected from the group consisting of halogen, CN, $C_1$-$C_6$ alkyl, $C(O)R^7$, $C(O)NR^7R^8$, $NR^7R^8$, $NHS(O)_2R^7$, OH, $OC_1$—$C_6$ alkyl, $OCH_2$-phenyl, Ophenyl, $S(O)_2NR^7R^8$, $C_3$-$C_7$ cycloalkyl, aziridinyl, azetidinyl, oxetanyl, pyrrolidinyl, piperidinyl, tetrahydrofuranyl, tetrahydropyranyl, piperazinyl, morpholinyl, phenyl, naphthalenyl, pyrrolyl, furanyl, thiophenyl, pyrazolyl, imidazolyl, isoxazolyl, oxazolyl, isothiazolyl, thiazolyl, pyridinyl, pyridazinyl, pyrimidinyl, pyrazinyl, indolyl, indazolyl, benzofuranyl, benzothiophenyl, benzimidazolyl, and benzothiazolyl; and wherein each $C_1$-$C_6$ alkyl, $OC_1$—$C_6$ alkyl, $OCH_2$-phenyl, Ophenyl, $S(O)_2NR^7R^8$, $C_3$-$C_7$ cycloalkyl, aziridinyl, azetidinyl, oxetanyl, pyrrolidinyl, piperidinyl, tetrahydrofuranyl, tetrahydropyranyl, piperazinyl, morpholinyl, phenyl, naphthalenyl, pyrrolyl, furanyl, thiophenyl, pyrazolyl, imidazolyl, isoxazolyl, oxazolyl, isothiazolyl, thiazolyl, pyridinyl, pyridazinyl, pyrimidinyl, pyrazinyl, indolyl, indazolyl, benzofuranyl, benzothiophenyl, benzimidazolyl, and benzothiazolyl is optionally and independently substituted with 1, 2, 3, 4, 5, or 6 substituents independently selected from the group consisting of halogen, CN, $C_1$-$C_6$ alkyl, $C_1$-$C_6$ haloalkyl, and OH;

each $R^7$ is independently H, $C_1$-$C_6$ alkyl, $C_1$-$C_6$ haloalkyl, OH, $OC_1$—$C_6$ alkyl, $OC_1$—$C_6$ haloalkyl, or $C_3$-$C_7$ cycloalkyl;

each $R^8$ is independently H, $C_1$-$C_6$ alkyl, $C_1$-$C_6$ haloalkyl, OH, $OC_1$—$C_6$ alkyl, $OC_1$—$C_6$ haloalkyl, or $C_3$-$C_7$ cycloalkyl;

$R^1$ is H, $CH_3$, or $CH_2CH_3$;

$R^2$ is H, $CH_3$, or $CH_2CH_3$; or $R^1$ and $R^2$, together with the carbon atom to which they are attached, form a 3- to 6-membered carbocyclyl; and $Ar^2$ is phenyl, naphthalenyl, pyrrolyl, furanyl, thiophenyl, pyrazolyl, imidazolyl, oxazolyl, isoxazoloyl, thiazolyl, isothiazolyl, oxadiazolyl, pyridinyl, pyridazinyl, pyrimidinyl, pyrazinyl, indolyl, benzofuranyl, benzothiophenyl, indazolyl, benzimidazolyl, benzoisoxazolyl, quinolinyl, isoquinolinyl, quinazolinyl, quinoxalinyl, or imidazopyridinyl;

wherein the phenyl, naphthalenyl, pyrrolyl, furanyl, thiophenyl, pyrazolyl, imidazolyl, oxazolyl, isoxazoloyl, thiazolyl, isothiazolyl, oxadiazolyl, pyridinyl, pyridazinyl, pyrimidinyl, pyrazinyl, indolyl, benzofuranyl, benzothiophenyl, indazolyl, benzimidazolyl, benzoisoxazolyl, quinolinyl, isoquinolinyl, quinazolinyl, quinoxalinyl, or imidazopyridinyl is optionally substituted with 1, 2, 3, 4, 5, or 6 substituents independently selected from the group consisting of halogen, CN, $C_1$-$C_6$ alkyl, $C_1$-$C_6$ haloalkyl, OH, $OC_1$—$C_6$ alkyl, $OC_1$—$C_6$ haloalkyl, $OCH_2$-phenyl, Ophenyl, $SCF_3$, $SF_5$, phenyl, naphthalenyl, pyrrolyl, furanyl, thiophenyl, pyrazolyl, imidazolyl, oxazolyl, pyridinyl, pyridazinyl, pyrimidinyl, pyrazinyl, indolyl, benzofuranyl, benzothiophenyl, benzimidazolyl, quinolinyl, and isoquinolinyl; and wherein each $OCH_2$-phenyl, Ophenyl, phenyl, naphthalenyl, pyrrolyl, furanyl, thiophenyl, pyrazolyl, imidazolyl, oxazolyl, pyridinyl, pyridazinyl, pyrimidinyl, pyrazinyl, indolyl, benzofuranyl, benzothiophenyl, benzimidazolyl, quinolinyl, and isoquinolinyl is optionally and independently substituted with 1, 2, 3, 4, 5, or 6 substituents independently selected from the group consisting of halogen, CN, $C_1$-$C_6$ alkyl, $C_1$-$C_6$ haloalkyl, OH, $OC_1$—$C_6$ alkyl, $OC_1$—$C_6$ haloalkyl, $SCF_3$, and $SF_5$.

5. The compound according to claim 1, wherein the compound is represented by formula (I-a):

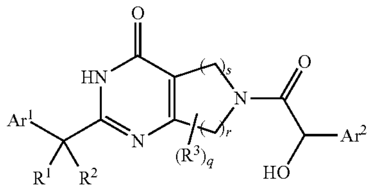

(I-a)

or a pharmaceutically acceptable salt, stereoisomer, or tautomer thereof, wherein:

each $R^7$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-$N(C_1$-$C_6$ alkyl$)_2$, $C_1$-$C_6$ hydroxyalkyl, $C_1$-$C_6$ alkylene-$OC_1$—$C_6$ alkyl, $C_1$-$C_6$ alkylene-$OC_1$—$C_6$ haloalkyl, $CH_2$-phenyl, OH, $OC_1$—$C_6$ alkyl, $C_3$-$C_7$ cycloalkyl, or heterocyclyl;

each $R^8$ is independently H, $C_1$-$C_6$ alkyl, $C_1$-$C_6$ haloalkyl, $C_1$-$C_6$ alkylene-$NH_2$, $C_1$-$C_6$ alkylene-$NHC_1$—$C_6$ alkyl, $C_1$-$C_6$ alkylene-$N(C_1$-$C_6$ alkyl$)_2$, $C_1$-$C_6$ hydroxyalkyl, $C_1$-$C_6$ alkylene-$OC_1$—$C_6$ alkyl, $C_1$-$C_6$ alkylene-$OC_1$—$C_6$ haloalkyl, $CH_2$-phenyl, OH, $OC_1$—$C_6$ alkyl, $C_3$-$C_7$ cycloalkyl, or heterocyclyl; or any $R^7$ and $R^8$, together with the nitrogen atom to which they are attached, independently forms a 3- to 10-membered ring;

wherein each 3- to 10-membered ring optionally and independently contains 1 additional heteroatom selected from the group consisting of nitrogen, oxygen, and sulfur; and wherein each 3- to 10-membered ring is optionally and independently substituted with 1, 2, 3, 4, 5, or 6 substituents independently selected from the group consisting of halogen, $C_1$-$C_6$ alkyl, $C_1$-$C_6$ haloalkyl, $C(O)C_1$-$C_6$ alkyl, $C(O)C_1$-$C_6$ haloalkyl, OH, $OC_1$—$C_6$ alkyl, =O, $S(O)_2C_1$-$C_6$ alkyl, and $S(O)_2C_1$-$C_6$ haloalkyl;

$R^1$ is H, halogen, $C_1$-$C_6$ alkyl, $C_1$-$C_6$ haloalkyl, $C_1$-$C_4$ alkylene-phenyl, OH, $OC_1$—$C_6$ alkyl, $OC_1$—$C_6$ haloalkyl, $C_3$-$C_7$ cycloalkyl, or phenyl, wherein the $C_3$-$C_7$ cycloalkyl, $C_1$-$C_4$ alkylene-phenyl, or phenyl is optionally substituted with 1, 2, 3, or 4 substituents independently selected from the group consisting of halogen, $C_1$-$C_6$ alkyl, $C_1$-$C_6$ haloalkyl, OH, $OC_1$—$C_6$ alkyl, and $OC_1$—$C_6$ haloalkyl; and $R^2$ is H, halogen, $C_1$-$C_6$ alkyl, $C_1$-$C_6$ haloalkyl, $C_1$-$C_4$ alkylene-phenyl, OH, $OC_1$—$C_6$ alkyl, $OC_1$—$C_6$ haloalkyl, $C_3$-$C_7$ cycloalkyl, or phenyl, wherein the $C_3$-$C_7$ cycloalkyl, $C_1$-$C_4$ alkylene-phenyl, or phenyl is optionally substituted with 1, 2, 3, or 4 substituents independently selected from the group consisting of halogen, $C_1$-$C_6$ alkyl, $C_1$-$C_6$ haloalkyl, OH, $OC_1$—$C_6$ alkyl, and $OC_1$—$C_6$ haloalkyl; or $R^1$ and $R^2$, together with the carbon atom to which they are attached, form a 3- to 8-membered carbocyclyl, wherein the 3- to 8-membered carbocyclyl is optionally substituted with 1, 2, 3, 4, 5, or 6 substituents independently selected from the group consisting of halogen, $C_1$-$C_6$ alkyl, $C_1$-$C_6$ haloalkyl, $C(O)C_1$-$C_6$ alkyl, $C(O)C_1$-$C_6$ haloalkyl, OH, $S(O)_2C_1$-$C_6$ alkyl, and $S(O)_2C_1$-$C_6$ haloalkyl.

6. The compound according to claim 1, or a pharmaceutically acceptable salt, stereoisomer, or tautomer thereof, wherein the compound, stereoisomer or tautomer is selected from the group consisting of:

(R)-2-(1-phenylcyclopropyl)-6-(2-phenylpropanoyl)-5,6,7,8-tetrahydropyrido[4,3-d]pyrimidin-4(3H)-one;

(S)-2-(1-phenylcyclopropyl)-6-(2-phenylpropanoyl)-5,6,7,8-tetrahydropyrido[4,3-d]pyrimidin-4(3H)-one;

(R)-6-(2-(4-isobutylphenyl)propanoyl)-2-(1-phenylcyclopropyl)-5,6,7,8-tetrahydropyrido[4,3-d]pyrimidin-4(3H)-one;

(S)-6-(2-(4-isobutylphenyl)propanoyl)-2-(1-phenylcyclopropyl)-5,6,7,8-tetrahydropyrido[4,3-d]pyrimidin-4(3H)-one;

(R)-2-(1-(4-fluorophenyl)cyclopropyl)-6-(2-(4-isobutylphenyl)propanoyl)-5,6,7,8-tetrahydropyrido[4,3-d]pyrimidin-4(3H)-one;

(R)-2-(1-(4-chlorophenyl)cyclopropyl)-6-(2-(4-isobutylphenyl)propanoyl)-5,6,7,8-tetrahydropyrido[4,3-d]pyrimidin-4(3H)-one;

6-(2-(3,5-difluorophenyl)propanoyl)-2-(1-phenylcyclopropyl)-5,6,7,8-tetrahydropyrido[4,3-d]pyrimidin-4(3H)-one;

6-(2-(4-chlorophenyl)propanoyl)-2-(1-phenylcyclopropyl)-5,6,7,8-tetrahydropyrido[4,3-d]pyrimidin-4(3H)-one;

6-(2-(3,5-difluorophenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(4-(trifluoromethyl)phenyl)propanoyl)-5,6,7,8-tetrahydropyrido[4,3-d]pyrimidin-4(3H)-one;

6-(2-(4-fluorophenyl)propanoyl)-2-(1-phenylcyclopropyl)-5,6,7,8-tetrahydropyrido[4,3-d]pyrimidin-4(3H)-one;

6-(2-(4-isopropylphenyl)acetyl)-2-(1-phenylcyclopropyl)-5,6,7,8-tetrahydropyrido[4,3-d]pyrimidin-4(3H)-one;

6-(2-(3,5-difluorophenyl)propanoyl)-2-(1-(4-fluorophenyl)cyclopropyl)-5,6,7,8-tetrahydropyrido[4,3-d]pyrimidin-4(3H)-one;

6-(2-(4-(tert-butyl)phenoxy)acetyl)-2-(1-phenylcyclopropyl)-5,6,7,8-tetrahydropyrido[4,3-d]pyrimidin-4(3H)-one;

6-(2-(1H-indol-3-yl)acetyl)-2-(1-phenylcyclopropyl)-5,6,7,8-tetrahydropyrido[4,3-d]pyrimidin-4(3H)-one;

6-(2-(5-fluoro-1H-indol-3-yl)acetyl)-2-(1-phenylcyclopropyl)-5,6,7,8-tetrahydropyrido[4,3-d]pyrimidin-4(3H)-one;

6-(2-(benzo[d]isoxazol-3-yl)acetyl)-2-(1-phenylcyclopropyl)-5,6,7,8-tetrahydropyrido[4,3-d]pyrimidin-4(3H)-one;

6-(2-(5-methyl-2-phenyloxazol-4-yl)acetyl)-2-(1-phenylcyclopropyl)-5,6,7,8-tetrahydropyrido[4,3-d]pyrimidin-4(3H)-one;

6-(3-(3-phenyl-1,2,4-oxadiazol-5-yl)propanoyl)-2-(1-phenylcyclopropyl)-5,6,7,8-tetrahydropyrido[4,3-d]pyrimidin-4(3H)-one;

2-(1-phenylcyclopropyl)-6-(2-(quinoxalin-6-yl)acetyl)-5,6,7,8-tetrahydropyrido[4,3-d]pyrimidin-4(3H)-one;

6-(2,2-difluoro-2-phenylacetyl)-2-(1-phenylcyclopropyl)-5,6,7,8-tetrahydropyrido[4,3-d]pyrimidin-4(3H)-one;

6-(2-fluoro-2-phenylacetyl)-2-(1-phenylcyclopropyl)-5,6,7,8-tetrahydropyrido[4,3-d]pyrimidin-4(3H)-one;

6-(2-(5-chloro-1H-benzo[d]imidazol-2-yl)acetyl)-2-(1-phenylcyclopropyl)-5,6,7,8-tetrahydropyrido[4,3-d]pyrimidin-4(3H)-one;

6-(2-(2-hydroxyphenyl)acetyl)-2-(1-phenylcyclopropyl)-5,6,7,8-tetrahydropyrido[4,3-d]pyrimidin-4(3H)-one;

6-(2-(2-methoxyphenyl)acetyl)-2-(1-phenylcyclopropyl)-5,6,7,8-tetrahydropyrido[4,3-d]pyrimidin-4(3H)-one;

6-(3-(1H-indol-3-yl)propanoyl)-2-(1-phenylcyclopropyl)-5,6,7,8-tetrahydropyrido[4,3-d]pyrimidin-4(3H)-one;

6-(3-(3-(4-methoxyphenyl)-1,2,4-oxadiazol-5-yl)propanoyl)-2-(1-phenylcyclopropyl)-5,6,7,8-tetrahydropyrido[4,3-d]pyrimidin-4(3H)-one;

6-(2-(1H-indazol-1-yl)acetyl)-2-(1-phenylcyclopropyl)-5,6,7,8-tetrahydropyrido[4,3-d]pyrimidin-4(3H)-one;

4-(2-oxo-2-(4-oxo-2-(1-phenylcyclopropyl)-3,5,7,8-tetrahydropyrido[4,3-d]pyrimidin-6(4H)-yl)ethyl)-2H-benzo[b][1,4]oxazin-3(4H)-one;

(E)-6-(3-(3-chlorophenyl)acryloyl)-2-(1-phenylcyclopropyl)-5,6,7,8-tetrahydropyrido[4,3-d]pyrimidin-4(3H)-one;

6-((1R*,2R*)-2-phenylcyclopropane-1-carbonyl)-2-(1-phenylcyclopropyl)-5,6,7,8-tetrahydropyrido[4,3-d]pyrimidin-4(3H)-one;

6-((1R*,2R*)-2-(2,5-difluorophenyl)cyclopropane-1-carbonyl)-2-(1-phenylcyclopropyl)-5,6,7,8-tetrahydropyrido[4,3-d]pyrimidin-4(3H)-one;

(R)-6-(2-hydroxy-2-phenylacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-phenylcyclopropyl)-5,6,7,8-tetrahydropyrido[4,3-d]pyrimidin-4(3H)-one;

(R)-(−)-6-(2-(2,3-difluorophenyl)-2-hydroxyacetyl)-2-(1-phenylcyclopropyl)-5,6,7,8-tetrahydropyrido[4,3-d]pyrimidin-4(3H)-one;

(S)-(+)-6-(2-(2,3-difluorophenyl)-2-hydroxyacetyl)-2-(1-phenylcyclopropyl)-5,6,7,8-tetrahydropyrido[4,3-d]pyrimidin-4(3H)-one;

(R)-(−)-6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one;

(S)-(+)-6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one;

(R)-(−)-2-(1-(4-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-(−)-6-(2-(2,3-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one;

(−)-2-(1-(4-fluorophenyl)cyclopropyl)-6-(2-hydroxy-2-(m-tolyl)acetyl)-5,6,7,8-tetrahydropyrido[4,3-d]pyrimidin-4(3H)-one;

(−)-2-(1-(4-chlorophenyl)cyclopropyl)-6-(2-hydroxy-2-(m-tolyl)acetyl)-5,6,7,8-tetrahydropyrido[4,3-d]pyrimidin-4(3H)-one;

(S)-6-(2-hydroxy-2-phenylacetyl)-2-(1-phenylcyclopropyl)-5,6,7,8-tetrahydropyrido[4,3-d]pyrimidin-4(3H)-one;

6-(2-(2-chlorophenyl)-2-hydroxyacetyl)-2-(1-phenylcyclopropyl)-5,6,7,8-tetrahydropyrido[4,3-d]pyrimidin-4(3H)-one;

6-(2-(4-chlorophenyl)-2-hydroxyacetyl)-2-(1-phenylcyclopropyl)-5,6,7,8-tetrahydropyrido[4,3-d]pyrimidin-4(3H)-one;

(S)-6-(2-(2-chlorophenyl)-2-hydroxyacetyl)-2-(1-phenylcyclopropyl)-5,6,7,8-tetrahydropyrido[4,3-d]pyrimidin-4(3H)-one;

(R)-6-(2-(2-chlorophenyl)-2-hydroxyacetyl)-2-(1-phenylcyclopropyl)-5,6,7,8-tetrahydropyrido[4,3-d]pyrimidin-4(3H)-one;

6-(2-(2,3-difluorophenyl)-2-hydroxyacetyl)-2-(1-phenylcyclopropyl)-5,6,7,8-tetrahydropyrido[4,3-d]pyrimidin-4(3H)-one;

6-(2-(3,4-difluorophenyl)-2-hydroxyacetyl)-2-(1-phenylcyclopropyl)-5,6,7,8-tetrahydropyrido[4,3-d]pyrimidin-4(3H)-one;

6-(2-(2,4-difluorophenyl)-2-hydroxyacetyl)-2-(1-phenylcyclopropyl)-5,6,7,8-tetrahydropyrido[4,3-d]pyrimidin-4(3H)-one;

6-(2-(2,6-difluorophenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-3-phenylpropanoyl)-2-(1-phenylcyclopropyl)-5,6,7,8-tetrahydropyrido[4,3-d]pyrimidin-4(3H)-one;

(R)-6-(2-hydroxy-4-phenylbutanoyl)-2-(1-phenylcyclopropyl)-5,6,7,8-tetrahydropyrido[4,3-d]pyrimidin-4(3H)-one;

6-(2-(3-fluoro-4-methoxyphenyl)-2-hydroxyacetyl)-2-(1-phenylcyclopropyl)-5,6,7,8-tetrahydropyrido[4,3-d]pyrimidin-4(3H)-one;

6-(2-(3-chlorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(6-methylpyridin-2-yl)acetyl)-2-(1-phenylcyclopropyl)-5,6,7,8-tetrahydropyrido[4,3-d]pyrimidin-4(3H)-one;

6-(2-(3-fluorophenyl)-2-hydroxyacetyl)-2-(1-phenylcyclopropyl)-5,6,7,8-tetrahydropyrido[4,3-d]pyrimidin-4(3H)-one;

6-(2-(3-fluorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-(3-fluoro-4-methoxyphenyl)-2-hydroxyacetyl)-2-(1-(4-fluorophenyl)cyclopropyl)-5,6,7,8-tetrahydropyrido[4,3-d]pyrimidin-4(3H)-one;

2-(1-(4-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-6-(2-(2-chlorophenyl)-2-hydroxyacetyl)-2-(1-(4-chlorophenyl)cyclopropyl)-5,6,7,8-tetrahydropyrido[4,3-d]pyrimidin-4(3H)-one;

2-(1-(4-chlorophenyl)cyclopropyl)-6-(2-(3,5-difluorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(4-chlorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-(2,3-difluorophenyl)-2-hydroxyacetyl)-2-(1-(4-fluorophenyl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(4-fluorophenyl)cyclopropyl)-5,6,7,8-tetrahydropyrido[4,3-d]pyrimidin-4(3H)-one;

6-(2-hydroxy-2-(4-(trifluoromethyl)phenyl)acetyl)-2-(1-phenylcyclopropyl)-5,6,7,8-tetrahydropyrido[4,3-d]pyrimidin-4(3H)-one;

6-(2-(2,5-difluorophenyl)-2-hydroxyacetyl)-2-(1-phenylcyclopropyl)-5,6,7,8-tetrahydropyrido[4,3-d]pyrimidin-4(3H)-one;

6-(2-(2,3-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(3-fluorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(2,3-difluorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

6-(2-(3,5-difluorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-(trifluoromethyl)phenyl)cyclopropyl)-5,6,7,8-tetrahydropyrido[4,3-d]pyrimidin-4(3H)-one;

(R)-6-(2-hydroxy-2-(naphthalen-2-yl)acetyl)-2-(1-phenylcyclopropyl)-5,6,7,8-tetrahydropyrido[4,3-d]pyrimidin-4(3H)-one;

6-(2-hydroxy-2-(3-methoxyphenyl)acetyl)-2-(1-phenylcyclopropyl)-5,6,7,8-tetrahydropyrido[4,3-d]pyrimidin-4(3H)-one;

6-(2-hydroxy-2-(m-tolyl)acetyl)-2-(1-phenylcyclopropyl)-5,6,7,8-tetrahydropyrido[4,3-d]pyrimidin-4(3H)-one;

(R)-4-(1-(6-(2-(3-chlorophenyl)-2-hydroxyacetyl)-4-oxo-3,4,5,6,7,8-hexahydropyrido[4,3-d]pyrimidin-2-yl)cyclopropyl)benzonitrile;

4-(1-(6-(2-(2,3-difluorophenyl)-2-hydroxyacetyl)-4-oxo-3,4,5,6,7,8-hexahydropyrido[4,3-d]pyrimidin-2-yl)cyclopropyl)benzonitrile;

(S)-2-(1-(4-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(S)-6-(2-(2,3-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-hydroxy-2-(3-hydroxyphenyl)acetyl)-2-(1-phenylcyclopropyl)-5,6,7,8-tetrahydropyrido[4,3-d]pyrimidin-4(3H)-one;

6-(2-(3-bromophenyl)-2-hydroxyacetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3-bromo-2-fluorophenyl)-2-hydroxyacetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(S)-2-(1-(3-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(p-tolyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(p-tolyl)cyclopropyl)-5,6,7,8-tetrahydropyrido[4,3-d]pyrimidin-4(3H)-one;

6-(2-hydroxy-2-(3-isopropoxyphenyl)acetyl)-2-(1-phenylcyclopropyl)-5,6,7,8-tetrahydropyrido[4,3-d]pyrimidin-4(3H)-one;

(R)-2-(1-(2-chlorophenyl)cyclopropyl)-6-(2-(2,3-difluorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(2-chlorophenyl)cyclopropyl)-5,6,7,8-tetrahydropyrido[4,3-d]pyrimidin-4(3H)-one;

6-(2-(3-(cyclopentyloxy)phenyl)-2-hydroxyacetyl)-2-(1-phenylcyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(3,5-difluorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3,5-difluorophenyl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(3,4-difluorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3,4-difluorophenyl)cyclopropyl)-5,6,7,8-tetrahydropyrido[4,3-d]pyrimidin-4(3H)-one;

6-(2-hydroxy-2-(3-(trifluoromethoxy)phenyl)acetyl)-2-(1-phenylcyclopropyl)-5,6,7,8-tetrahydropyrido[4,3-d]pyrimidin-4(3H)-one;

6-(2-(3,5-dichlorophenyl)-2-hydroxyacetyl)-2-(1-phenylcyclopropyl)-5,6,7,8-tetrahydropyrido[4,3-d]pyrimidin-4(3H)-one;

6-(2-(2,3-dichlorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(2,2,2-trifluoroethoxy)phenyl)acetyl)-2-(1-phenylcyclopropyl)-5,6,7,8-tetrahydropyrido[4,3-d]pyrimidin-4(3H)-one;

6-(2-(2-fluoro-3-methoxyphenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(trifluoromethyl)phenyl)acetyl)-2-(1-phenylcyclopropyl)-5,6,7,8-tetrahydropyrido[4,3-d]pyrimidin-4(3H)-one;

2-(1-(4-fluorophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-hydroxy-2-(m-tolyl)acetyl)-2-(1-phenylcyclopropyl)-5,6,7,8-tetrahydropyrido[4,3-d]pyrimidin-4(3H)-one;

6-(2-(3-cyclopropylphenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(6-methylpyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(oxazol-5-yl)phenyl)acetyl)-2-(1-phenylcyclopropyl)-5,6,7,8-tetrahydropyrido[4,3-d]pyrimidin-4(3H)-one;

3-(1-hydroxy-2-oxo-2-(4-oxo-2-(1-phenylcyclopropyl)-3,5,7,8-tetrahydropyrido[4,3-d]pyrimidin-6(4H)-yl)ethyl)benzonitrile;

6-(2-hydroxy-2-(3-(pyrimidin-5-yl)phenyl)acetyl)-2-(1-phenylcyclopropyl)-5,6,7,8-tetrahydropyrido[4,3-d]pyrimidin-4(3H)-one;

6-(2-hydroxy-2-(3-(2-methoxypyrimidin-5-yl)phenyl)acetyl)-2-(1-phenylcyclopropyl)-5,6,7,8-tetrahydropyrido[4,3-d]pyrimidin-4(3H)-one;

6-(2-(3-(1,3-dimethyl-1H-pyrazol-4-yl)phenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(pyridin-3-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(oxazol-5-yl)phenyl)acetyl)-2-(1-phenylcyclopropyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(pyridin-3-yl)phenyl)acetyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(oxazol-5-yl)phenyl)acetyl)-5,6,7,8-tetrahydropyrido[4,3-d]pyrimidin-4(3H)-one;

2-fluoro-3-(1-hydroxy-2-oxo-2-(4-oxo-2-(1-phenylcyclopropyl)-3,5,7,8-tetrahydropyrido[4,3-d]pyrimidin-6(4H)-yl)ethyl)benzonitrile;

6-(2-(3,5-difluorophenyl)-2-hydroxyacetyl)-2-(1-phenylcyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one;

(S)-6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(pyridin-2-yl)cyclopropyl)-5,6,7,8-tetrahydropyrido[4,3-d]pyrimidin-4(3H)-one;

6-(2-(2,3-difluorophenyl)-2-hydroxyacetyl)-2-(1-(pyridin-3-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(pyridin-3-yl)cyclopropyl)-5,6,7,8-tetrahydropyrido[4,3-d]pyrimidin-4(3H)-one;

6-(2-(2,3-difluorophenyl)-2-hydroxyacetyl)-2-(1-(thiophen-2-yl)cyclopropyl)-5,6,7,8-tetrahydropyrido[4,3-d]pyrimidin-4(3H)-one;

(R)-6-(2-(2-chlorophenyl)-2-hydroxyacetyl)-2-(1-(thiophen-2-yl)cyclopropyl)-5,6,7,8-tetrahydropyrido[4,3-d]pyrimidin-4(3H)-one;

6-(2-(3,5-difluorophenyl)-2-hydroxyacetyl)-2-(1-(thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(thiophen-2-yl)cyclopropyl)-5,6,7,8-tetrahydropyrido[4,3-d]pyrimidin-4(3H)-one;

6-(2-hydroxy-2-(m-tolyl)acetyl)-2-(1-(thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(2-methylthiazol-4-yl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(thiazol-4-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(thiazol-4-yl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(thiazol-5-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(thiazol-5-yl)cyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(5-methylthiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-methylthiophen-2-yl)cyclopropyl)-5,6,7,8-tetrahydropyrido[4,3-d]pyrimidin-4(3H)-one;

(R)-2-(1-(4-bromothiophen-2-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(4-methylthiazol-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-methylthiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-phenylthiophen-2-yl)cyclopropyl)-5,6,7,8-tetrahydropyrido[4,3-d]pyrimidin-4(3H)-one;

6-((R)-2-(3-chlorophenyl)-2-hydroxyacetyl)-2-((R/S)-1-phenylethyl)-5,6,7,8-tetrahydropyrido[4,3-d]pyrimidin-4(3H)-one;

(R)-6-(2-(3-chlorophenyl)-2-hydroxyacetyl)-2-(2-phenylpropan-2-yl)-5,6,7,8-tetrahydropyrido[4,3-d]pyrimidin-4(3H)-one;

6-(2-(2,3-difluorophenyl)-2-hydroxyacetyl)-2-(2-phenylpropan-2-yl)-5,6,7,8-tetrahydropyrido[4,3-d]pyrimidin-4(3H)-one;

6-(2-(3,5-difluorophenyl)-2-hydroxyacetyl)-2-(2-phenylpropan-2-yl)-5,6,7,8-tetrahydropyrido[4,3-d]pyrimidin-4(3H)-one;

(R)-6-(2-(2-chlorophenyl)-2-hydroxyacetyl)-2-(2-phenylpropan-2-yl)-5,6,7,8-tetrahydropyrido[4,3-d]pyrimidin-4(3H)-one;

6-(2-(2,3-difluorophenyl)-2-hydroxyacetyl)-2-(1-phenylcyclobutyl)-5,6,7,8-tetrahydropyrido[4,3-d]pyrimidin-4(3H)-one;

(R)-6-(2-(2-chlorophenyl)-2-hydroxyacetyl)-2-(1-phenylcyclobutyl)-5,6,7,8-tetrahydropyrido[4,3-d]pyrimidin-4(3H)-one;

6-(2-(3,5-difluorophenyl)-2-hydroxyacetyl)-2-(1-phenylcyclobutyl)-5,6,7,8-tetrahydropyrido[4,3-d]pyrimidin-4(3H)-one;

(R)-6-(2-(3-chlorophenyl)-2-hydroxyacetyl)-2-(1-phenylcyclobutyl)-5,6,7,8-tetrahydropyrido[4,3-d]pyrimidin-4(3H)-one;

7-(2-(2,3-difluorophenyl)-2-hydroxyacetyl)-2-(1-phenylcyclopropyl)-3,5,6,7,8,9-hexahydro-4H-pyrimido[4,5-d]azepin-4-one;

(R)-7-(2-(3-chlorophenyl)-2-hydroxyacetyl)-2-(1-phenylcyclopropyl)-3,5,6,7,8,9-hexahydro-4H-pyrimido[4,5-d]azepin-4-one;

(R)-6-(2-(2-chlorophenyl)-2-hydroxyacetyl)-2-(1-phenylcyclopropyl)-3,5,6,7-tetrahydro-4H-pyrrolo[3,4-d]pyrimidin-4-one;

(R)-7-(2-(3-chlorophenyl)-2-hydroxyacetyl)-2-(1-phenylcyclopropyl)-5,6,7,8-tetrahydropyrido[3,4-d]pyrimidin-4(3H)-one;

7-(2-(2,3-difluorophenyl)-2-hydroxyacetyl)-2-(1-phenylcyclopropyl)-5,6,7,8-tetrahydropyrido[3,4-d]pyrimidin-4(3H)-one;

(R)-6-(2-(2,3-difluorophenyl)-2-hydroxyacetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-phenylcyclopropyl)-3,5,6,7,8,9-hexahydro-4H-pyrimido[5,4-c]azepin-4-one;

(R)-8-(2-(2,3-difluorophenyl)-2-hydroxyacetyl)-2-(1-phenylcyclopropyl)-3,5,6,7,8,9-hexahydro-4H-pyrimido[4,5-c]azepin-4-one;

(R)-8-(2-(3-chlorophenyl)-2-hydroxyacetyl)-2-(1-phenylcyclopropyl)-3,5,6,7,8,9-hexahydro-4H-pyrimido[4,5-c]azepin-4-one;

6-(2-hydroxy-2-(2-(pyrrolidin-1-yl)pyridin-4-yl)acetyl)-2-(1-phenylcyclopropyl)-5,6,7,8-tetrahydropyrido[4,3-d]pyrimidin-4(3H)-one;

6-(2-hydroxy-2-(2-(piperidin-1-yl)pyridin-4-yl)acetyl)-2-(1-phenylcyclopropyl)-5,6,7,8-tetrahydropyrido[4,3-d]pyrimidin-4(3H)-one;

6-(2-(2-(azepan-1-yl)pyridin-4-yl)-2-hydroxyacetyl)-2-(1-phenylcyclopropyl)-5,6,7,8-tetrahydropyrido[4,3-d]pyrimidin-4(3H)-one;

(R)-5-(1-(6-(2-(3-chlorophenyl)-2-hydroxyacetyl)-4-oxo-3,4,5,6,7,8-hexahydropyrido[4,3-d]pyrimidin-2-yl)cyclopropyl)thiophene-3-carbonitrile;

4-oxo-2-(1-phenylcyclopropyl)-N-(3-(trifluoromethyl)phenyl)-3,5,7,8-tetrahydropyrido[4,3-d]pyrimidine-6(4H)-carboxamide;

6-(1H-benzo[d]imidazole-2-carbonyl)-2-(1-phenylcyclopropyl)-5,6,7,8-tetrahydropyrido[4,3-d]pyrimidin-4(3H)-one;

6-(5,6-difluoro-1H-benzo[d]imidazole-2-carbonyl)-2-(1-phenylcyclopropyl)-5,6,7,8-tetrahydropyrido[4,3-d]pyrimidin-4(3H)-one;

6-(5,6-difluoro-1H-benzo[d]imidazole-2-carbonyl)-2-(2-phenylpropan-2-yl)-5,6,7,8-tetrahydropyrido[4,3-d]pyrimidin-4(3H)-one;

2-benzyl-6-(5,6-difluoro-1H-benzo[d]imidazole-2-carbonyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(thiophen-2-yl)cyclopropyl)-5,6,7,8-tetrahydropyrido[4,3-d]pyrimidin-4(3H)-one;

(R)-2-(1-(4-bromothiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-phenylcyclopropyl)-3,5,6,7,8,9-hexahydro-4H-pyrimido[5,4-c]azepin-4-one;

6-(2-(5-chloro-2-fluorophenyl)-2-hydroxyacetyl)-2-(1-phenylcyclopropyl)-5,6,7,8-tetrahydropyrido[4,3-d]pyrimidin-4(3H)-one;

6-(2-(3-chloro-5-fluorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-isopropylphenyl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-cyclohexylthiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-(pyridin-4-yl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-(pyridin-3-yl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-phenylcyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-fluorophenyl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(thiophen-2-yl)cyclopropyl)-5,6,7,8-tetrahydropyrido[4,3-d]pyrimidin-4(3H)-one;

6-(2-hydroxy-2-(3-((trifluoromethyl)thio)phenyl)acetyl)-2-(1-phenylcyclopropyl)-5,6,7,8-tetrahydropyrido[4,3-d]pyrimidin-4(3H)-one;

6-(2-(3-bromophenyl)-2-hydroxyacetyl)-2-(1-phenylcyclopropyl)-5,6,7,8-tetrahydropyrido[4,3-d]pyrimidin-4(3H)-one;

6-(2-(2-chloro-3-fluorophenyl)-2-hydroxyacetyl)-2-(1-phenylcyclopropyl)-5,6,7,8-tetrahydropyrido[4,3-d]pyrimidin-4(3H)-one;

(R)-2-(1-(4-(benzyloxy)phenyl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(4-(tetrahydro-2H-pyran-4-yl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-phenylcyclopropyl)-3,5,6,7,8,9-hexahydro-4H-pyrimido[5,4-c]azepin-4-one;

(R)-2-(1-(3-fluorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(4-(1-methyl-1H-pyrazol-4-yl)thiophen-2-yl)cyclopropyl)-5,6,7,8-tetrahydropyrido[4,3-d]pyrimidin-4(3H)-one;

6-(4-hydroxy-2-naphthoyl)-2-(1-phenylcyclopropyl)-5,6,7,8-tetrahydropyrido[4,3-d]pyrimidin-4(3H)-one;

6-(2-hydroxy-2-(2-(trifluoromethyl)phenyl)acetyl)-2-(1-phenylcyclopropyl)-5,6,7,8-tetrahydropyrido[4,3-d]pyrimidin-4(3H)-one;

6-(2-(2,3-dihydrobenzofuran-7-yl)-2-hydroxyacetyl)-2-(1-phenylcyclopropyl)-5,6,7,8-tetrahydropyrido[4,3-d]pyrimidin-4(3H)-one;

6-(2-(2-fluoro-3-methylphenyl)-2-hydroxyacetyl)-2-(1-phenylcyclopropyl)-5,6,7,8-tetrahydropyrido[4,3-d]pyrimidin-4(3H)-one;

6-(2-(3-chloro-4-fluorophenyl)-2-hydroxyacetyl)-2-(1-phenylcyclopropyl)-5,6,7,8-tetrahydropyrido[4,3-d]pyrimidin-4(3H)-one;

6-(2-(3-chloro-2,4-difluorophenyl)-2-hydroxyacetyl)-2-(1-phenylcyclopropyl)-5,6,7,8-tetrahydropyrido[4,3-d]pyrimidin-4(3H)-one;

6-(3-(1H-indol-1-yl)propanoyl)-2-(1-phenylcyclopropyl)-5,6,7,8-tetrahydropyrido[4,3-d]pyrimidin-4(3H)-one;

6-(2-(5-chlorothiophen-2-yl)-2-hydroxyacetyl)-2-(1-phenylcyclopropyl)-5,6,7,8-tetrahydropyrido[4,3-d]pyrimidin-4(3H)-one;

6-(2-(4-cyclopropylphenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(4-(trifluoromethyl)phenyl)acetyl)-5,6,7,8-tetrahydropyrido[4,3-d]pyrimidin-4(3H)-one;

6-(2-(4-chlorophenyl)acetyl)-2-(1-phenylcyclopropyl)-5,6,7,8-tetrahydropyrido[4,3-d]pyrimidin-4(3H)-one;

6-(2-(3-chlorophenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(3-(trifluoromethyl)phenyl)acetyl)-5,6,7,8-tetrahydropyrido[4,3-d]pyrimidin-4(3H)-one;

(R)-6-(3-hydroxy-3-phenylpropanoyl)-2-(1-phenylcyclopropyl)-5,6,7,8-tetrahydropyrido[4,3-d]pyrimidin-4(3H)-one;

6-(2-(3-(difluoromethyl)phenyl)-2-hydroxyacetyl)-2-(1-phenylcyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-phenylcyclopropyl)-5,6,7,8-tetrahydropyrido[4,3-d]pyrimidin-4(3H)-one;

6-(2-(4-(tert-butyl)phenyl)acetyl)-2-(1-phenylcyclopropyl)-5,6,7,8-tetrahydropyrido[4,3-d]pyrimidin-4(3H)-one;

(R)-6-(2-(2,3-difluorophenyl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3,5-dichlorophenyl)-2-hydroxyacetyl)-2-(1-phenylcyclopropyl)-3,5,6,7,8,9-hexahydro-4H-pyrimido[5,4-c]azepin-4-one;

(R)-2-(1-(4-(1H-pyrazol-4-yl)thiophen-2-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(thiophen-3-yl)cyclopropyl)-5,6,7,8-tetrahydropyrido[4,3-d]pyrimidin-4(3H)-one;

6-(2-(3-chlorophenyl)-2,2-difluoroacetyl)-2-(1-phenylcyclopropyl)-5,6,7,8-tetrahydropyrido[4,3-d]pyrimidin-4(3H)-one;

6-(2-(4-chloro-2-fluorophenyl)-2-hydroxyacetyl)-2-(1-phenylcyclopropyl)-5,6,7,8-tetrahydropyrido[4,3-d]pyrimidin-4(3H)-one;

6-(2-hydroxy-2-(5-(trifluoromethyl)pyridin-3-yl)acetyl)-2-(1-phenylcyclopropyl)-5,6,7,8-tetrahydropyrido[4,3-d]pyrimidin-4(3H)-one;

6-(2-(2-fluoro-5-(trifluoromethyl)phenyl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(naphthalen-1-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(naphthalen-1-ylmethyl)-5,6,7,8-tetrahydropyrido[4,3-d]pyrimidin-4(3H)-one;

(R)-6-(2-(3-chlorophenyl)-2-hydroxyacetyl)-2-(1-(naphthalen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;

(R)-8-(2-(3-chlorophenyl)-2-hydroxyacetyl)-2-(1-(thiophen-2-yl)cyclopropyl)-3,5,6,7,8,9-hexahydro-4H-pyrimido[4,5-c]azepin-4-one;

(R)-8-(2-hydroxy-2-(3-(trifluoromethyl)phenyl)acetyl)-2-(1-phenylcyclopropyl)-3,5,6,7,8,9-hexahydro-4H-pyrimido[4,5-c]azepin-4-one;

(R)-6-(2-(2,3-difluorophenyl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(2-chlorophenyl)-2-hydroxyacetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-hydroxy-2-(6-(trifluoromethyl)pyridin-2-yl)acetyl)-2-(1-phenylcyclopropyl)-5,6,7,8-tetrahydropyrido[4,3-d]pyrimidin-4(3H)-one;

6-(2-hydroxy-2-(2-(trifluoromethyl)pyridin-4-yl)acetyl)-2-(1-phenylcyclopropyl)-5,6,7,8-tetrahydropyrido[4,3-d]pyrimidin-4(3H)-one;

6-(6-chloro-1H-indole-2-carbonyl)-2-(1-phenylcyclopropyl)-5,6,7,8-tetrahydropyrido[4,3-d]pyrimidin-4(3H)-one;

2-(1-phenylcyclopropyl)-6-(5-(trifluoromethyl)-1H-benzo[d]imidazole-2-carbonyl)-5,6,7,8-tetrahydropyrido[4,3-d]pyrimidin-4(3H)-one;

6-(3-(2-fluorophenyl)-1H-pyrazole-5-carbonyl)-2-(1-phenylcyclopropyl)-5,6,7,8-tetrahydropyrido[4,3-d]pyrimidin-4(3H)-one;

6-(2-(2-chlorophenyl)acetyl)-2-(1-phenylcyclopropyl)-5,6,7,8-tetrahydropyrido[4,3-d]pyrimidin-4(3H)-one;

6-(3-(2-chlorophenyl)propanoyl)-2-(1-phenylcyclopropyl)-5,6,7,8-tetrahydropyrido[4,3-d]pyrimidin-4(3H)-one;

6-(2-(2-chlorophenoxy)acetyl)-2-(1-phenylcyclopropyl)-5,6,7,8-tetrahydropyrido[4,3-d]pyrimidin-4(3H)-one;

2-(1-phenylcyclopropyl)-6-(2-(2-(trifluoromethyl)phenyl)acetyl)-5,6,7,8-tetrahydropyrido[4,3-d]pyrimidin-4(3H)-one;

6-(3-(3-chlorophenyl)propanoyl)-2-(1-phenylcyclopropyl)-5,6,7,8-tetrahydropyrido[4,3-d]pyrimidin-4(3H)-one;

6-(2-(3-chlorophenoxy)acetyl)-2-(1-phenylcyclopropyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-phenylcyclopropyl)-5,6,7,8-tetrahydropyrido[4,3-d]pyrimidin-4(3H)-one;

6-(2-(4-chloro-3-fluorophenyl)-2-hydroxyacetyl)-2-(1-phenylcyclopropyl)-5,6,7,8-tetrahydropyrido[4,3-d]pyrimidin-4(3H)-one;

6-(2-hydroxy-3-(o-tolyloxy)propanoyl)-2-(1-phenylcyclopropyl)-5,6,7,8-tetrahydropyrido[4,3-d]pyrimidin-4(3H)-one;

6-(2-(3,4-dichlorophenyl)-2-hydroxyacetyl)-2-(1-phenylcyclopropyl)-5,6,7,8-tetrahydropyrido[4,3-d]pyrimidin-4(3H)-one;

6-(2-(3-acetylphenyl)-2-hydroxyacetyl)-2-(1-phenylcyclopropyl)-5,6,7,8-tetrahydropyrido[4,3-d]pyrimidin-4(3H)-one;

6-(2-(3-ethylphenyl)-2-hydroxyacetyl)-2-(1-phenylcyclopropyl)-5,6,7,8-tetrahydropyrido[4,3-d]pyrimidin-4(3H)-one;

(R)-2-(1-(3-bromothiophen-2-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(6-phenylpyridin-3-yl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-3,5,6,7,8,9-hexahydro-4H-pyrimido[5,4-c]azepin-4-one;

6-(2-(2-fluoro-3-methylphenyl)-2-hydroxyacetyl)-2-(1-phenylcyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-chlorophenyl)cyclopropyl)-5,6,7,8-tetrahydropyrido[4,3-d]pyrimidin-4(3H)-one;

(R)-2-(1-(3-bromophenyl)cyclopropyl)-6-(2-(3-chlorophenyl)-2-hydroxyacetyl)-5,6,7,8-tetrahydropyrido[4,3-d]pyrimidin-4(3H)-one;

6-(2-(2,5-dichlorophenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(p-tolyl)acetyl)-2-(1-phenylcyclopropyl)-5,6,7,8-tetrahydropyrido[4,3-d]pyrimidin-4(3H)-one;

6-(2-hydroxy-2-(3-isopropylphenyl)acetyl)-2-(1-phenylcyclopropyl)-3,5,6,7,8,9-hexahydro-4H-pyrimido[5,4-c]azepin-4-one;

6-(2-(3-(difluoromethyl)phenyl)-2-hydroxyacetyl)-2-(1-phenylcyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-phenylcyclopropyl)-3,5,6,7,8,9-hexahydro-4H-pyrimido[5,4-c]azepin-4-one;

2-(1-phenylcyclopropyl)-6-(2-(4-(trifluoromethoxy)phenyl)acetyl)-5,6,7,8-tetrahydropyrido[4,3-d]pyrimidin-4(3H)-one;

6-(2-(4-phenoxyphenyl)acetyl)-2-(1-phenylcyclopropyl)-5,6,7,8-tetrahydropyrido[4,3-d]pyrimidin-4(3H)-one;

6-(2-(3-chloro-2-methoxyphenyl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-phenylpyridin-3-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-chlorothiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-chlorothiophen-2-yl)cyclopropyl)-5,6,7,8-tetrahydropyrido[4,3-d]pyrimidin-4(3H)-one;

(R)-2-(1-([1,1'-biphenyl]-3-yl)cyclopropyl)-6-(2-(3-chlorophenyl)-2-hydroxyacetyl)-5,6,7,8-tetrahydropyrido[4,3-d]pyrimidin-4(3H)-one;

(R)-2-(1-(4-bromophenyl)cyclopropyl)-6-(2-(3-chlorophenyl)-2-hydroxyacetyl)-5,6,7,8-tetrahydropyrido[4,3-d]pyrimidin-4(3H)-one;

(R)-2-(1-([1,1'-biphenyl]-4-yl)cyclopropyl)-6-(2-(3-chlorophenyl)-2-hydroxyacetyl)-5,6,7,8-tetrahydropyrido[4,3-d]pyrimidin-4(3H)-one;

6-(2-hydroxy-2-(naphthalen-1-yl)acetyl)-2-(1-phenylcyclopropyl)-5,6,7,8-tetrahydropyrido[4,3-d]pyrimidin-4(3H)-one;

6-(2-(3-chloro-2-methylphenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(2-methylpyridin-3-yl)phenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(quinolin-3-yl)acetyl)-5,6,7,8-tetrahydropyrido[4,3-d]pyrimidin-4(3H)-one;

2-(1-phenylcyclopropyl)-6-(2-(4-(pyridin-2-yl)phenyl)acetyl)-5,6,7,8-tetrahydropyrido[4,3-d]pyrimidin-4(3H)-one;

2-(1-phenylcyclopropyl)-6-(2-(3-(trifluoromethoxy)phenyl)acetyl)-5,6,7,8-tetrahydropyrido[4,3-d]pyrimidin-4(3H)-one;

6-(2-([1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-phenoxyphenyl)cyclopropyl)-5,6,7,8-tetrahydropyrido[4,3-d]pyrimidin-4(3H)-one;

6-(2-hydroxy-2-(3-(5-methylpyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(4-methylpyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(6-methoxypyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(4'-methyl-[1,1'-biphenyl]-3-yl)acetyl)-2-(1-phenylcyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(2-methylpyridin-4-yl)phenyl)acetyl)-2-(1-phenylcyclopropyl)-5,6,7,8-tetrahydropyrido[4,3-d]pyrimidin-4(3H)-one;

6-(2-hydroxy-2-(3-(2-methylpyrimidin-5-yl)phenyl)acetyl)-2-(1-phenylcyclopropyl)-5,6,7,8-tetrahydropyrido[4,3-d]pyrimidin-4(3H)-one;

6-(2-(3-(6-(dimethylamino)pyridin-3-yl)phenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(6-(trifluoromethyl)pyridin-3-yl)phenyl)acetyl)-2-(1-phenylcyclopropyl)-5,6,7,8-tetrahydropyrido[4,3-d]pyrimidin-4(3H)-one;

6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

6-(2-(3-(1-cyclopropyl-1H-pyrazol-4-yl)phenyl)-2-hydroxyacetyl)-2-(1-phenylcyclopropyl)-5,6,7,8-tetrahydropyrido[4,3-d]pyrimidin-4(3H)-one;

6-(2-(3-(5-chlorothiophen-2-yl)phenyl)-2-hydroxyacetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-hydroxy-2-(3-isopropylphenyl)acetyl)-5,6,7,8-tetrahydropyrido[4,3-d]pyrimidin-4(3H)-one;

2-(1-(3-chlorophenyl)cyclopropyl)-6-(2-hydroxy-2-(3-isopropylphenyl)acetyl)-5,6,7,8-tetrahydropyrido[4,3-d]pyrimidin-4(3H)-one;

6-(2-hydroxy-2-(3-isopropylphenyl)acetyl)-2-(1-(thiophen-2-yl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(3-fluorophenyl)cyclopropyl)-5,6,7,8-tetrahydropyrido[4,3-d]pyrimidin-4(3H)-one;

2-(1-(3-chlorophenyl)cyclopropyl)-6-(2-(2-fluoro-3-(trifluoromethyl)phenyl)-2-hydroxyacetyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(thiophen-2-yl)cyclopropyl)-5,6,7,8-tetrahydropyrido[4,3-d]pyrimidin-4(3H)-one;

2-(1-(3-fluorophenyl)cyclopropyl)-6-(2-hydroxy-2-(3-((trifluoromethyl)thio)phenyl)acetyl)-5,6,7,8-tetrahydropyrido[4,3-d]pyrimidin-4(3H)-one;

2-(1-(3-chlorophenyl)cyclopropyl)-6-(2-hydroxy-2-(3-((trifluoromethyl)thio)phenyl)acetyl)-5,6,7,8-tetrahydropyrido[4,3-d]pyrimidin-4(3H)-one;

6-(2-hydroxy-2-(3-((trifluoromethyl)thio)phenyl)acetyl)-2-(1-(thiophen-2-yl)cyclopropyl)-5,6,7,8-tetrahydropyrido[4,3-d]pyrimidin-4(3H)-one;

6-(2-hydroxy-2-(3-((trifluoromethyl)thio)phenyl)acetyl)-2-(1-phenylcyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3-(pentafluoro-(lambda)$^6$-sulfaneyl)phenyl)acetyl)-5,6,7,8-tetrahydropyrido[4,3-d]pyrimidin-4(3H)-one;

2-(1-(3-chlorophenyl)cyclopropyl)-6-(2-hydroxy-2-(3-(pentafluoro-(lambda)$^6$-sulfaneyl)phenyl)acetyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-(thiophen-2-yl)cyclopropyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;

6-(2-hydroxy-2-(2-phenylpyridin-4-yl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(3-cyclohexylphenyl)cyclopropyl)-5,6,7,8-tetrahydropyrido[4,3-d]pyrimidin-4(3H)-one;

6-(2-(2-fluoro-3-(trifluoromethyl)phenyl)acetyl)-2-(1-phenylcyclopropyl)-5,6,7,8-tetrahydropyrido[4,3-d]pyrimidin-4(3H)-one;

6-(2-(3-cyclopropylphenyl)acetyl)-2-(1-phenylcyclopropyl)-5,6,7,8-tetrahydropyrido[4,3-d]pyrimidin-4(3H)-one;

6-(2-hydroxy-2-(1-methyl-1H-indol-3-yl)acetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

(R)-2-(1-(4-ethylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(4-cyclopentylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(2-methyl-3-(trifluoromethyl)phenyl)acetyl)-2-(1-phenylcyclopropyl)-5,6,7,8-tetrahydropyrido[4,3-d]pyrimidin-4(3H)-one;

6-(2-(2-chloro-3-(trifluoromethyl)phenyl)-2-hydroxyacetyl)-2-(1-phenylcyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(thiophen-2-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3-fluoro-5-(trifluoromethyl)phenyl)-2-hydroxyacetyl)-2-(1-phenylcyclopropyl)-5,6,7,8-tetrahydropyrido[4,3-d]pyrimidin-4(3H)-one;

6-(2-(3-chloro-5-(trifluoromethyl)phenyl)-2-hydroxyacetyl)-2-(1-phenylcyclopropyl)-5,6,7,8-tetrahydropyrido[4,3-d]pyrimidin-4(3H)-one;

2-(1-phenylcyclopropyl)-6-(2-(3-(trifluoromethyl)phenyl)acetyl)-3,5,6,7,8,9-hexahydro-4H-pyrimido[5,4-c]azepin-4-one;

6-(2-(3-chlorophenyl)-2,2-difluoroacetyl)-2-(1-phenylcyclopropyl)-3,5,6,7,8,9-hexahydro-4H-pyrimido[5,4-c]azepin-4-one;

6-(2-hydroxy-2-(3-((trifluoromethyl)thio)phenyl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-phenoxyphenyl)cyclopropyl)-5,6,7,8-tetrahydropyrido[4,3-d]pyrimidin-4(3H)-one;

(R)-2-(1-(4-cycloheptylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-hydroxy-2-(2'-(trifluoromethyl)-[2,4'-bipyridin]-4-yl)acetyl)-2-(1-phenylcyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-chlorophenyl)cyclopropyl)-5,6,7,8-tetrahydropyrido[4,3-d]pyrimidin-4(3H)-one;

6-(2-(4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(4'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(4'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3'-methyl-[1,1'-biphenyl]-3-yl)acetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(4'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;

6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

6-(2-(3-(5-chlorothiophen-3-yl)phenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-methyl-5-(trifluoromethyl)phenyl)acetyl)-2-(1-phenylcyclopropyl)-5,6,7,8-tetrahydropyrido[4,3-d]pyrimidin-4(3H)-one;

2-(1-phenylcyclopropyl)-6-(2-(3-(trifluoromethyl)phenyl)propanoyl)-3,5,6,7,8,9-hexahydro-4H-pyrimido[5,4-c]azepin-4-one;

6-(2-hydroxy-2-(3'-methoxy-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(4'-methoxy-[1,1'-biphenyl]-3-yl)acetyl)-2-(1-phenylcyclopropyl)-5,6,7,8-tetrahydropyrido[4,3-d]pyrimidin-4(3H)-one;

6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

3'-(1-hydroxy-2-oxo-2-(4-oxo-2-(1-phenylcyclopropyl)-3,5,7,8-tetrahydropyrido[4,3-d]pyrimidin-6(4H)-yl)ethyl)-[1,1'-biphenyl]-3-carbonitrile;

6-(2-(4'-ethoxy-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(4'-isopropoxy-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(2'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

6-(2-(3-(benzo[b]thiophen-3-yl)phenyl)-2-hydroxyacetyl)-2-(1-phenylcyclopropyl)-5,6,7,8-tetrahydropyrido[4,3-d]pyrimidin-4(3H)-one;

6-(2-(3-(5,6-dimethylpyridin-3-yl)phenyl)-2-hydroxy-acetyl)-2-(1-phenylcyclopropyl)-5,6,7,8-tetrahydro-pyrido[4,3-d]pyrimidin-4(3H)-one;
6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(4'-(difluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-chloro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;
(R)-2-(1-(5-cyclohexylpyridin-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(5-bromopyridin-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(4-bromothiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(prop-1-en-2-yl)phenyl)cyclopropyl)-3,5,6,7,8,9-hexahydro-4H-pyrimido[5,4-c]azepin-4-one;
(R)-2-(1-(3-cyclohexylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
6-(2-(3-chlorophenyl)-2,2-difluoroacetyl)-2-(1-(thiophen-2-yl)cyclopropyl)-3,5,6,7,8,9-hexahydro-4H-pyrimido[5,4-c]azepin-4-one;
6-(2-(2-fluoro-3-(trifluoromethyl)phenyl)acetyl)-2-(1-phenylcyclopropyl)-3,5,6,7,8,9-hexahydro-4H-pyrimido[5,4-c]azepin-4-one;
6-(2,2-difluoro-2-(3-(trifluoromethyl)phenyl)acetyl)-2-(1-phenylcyclopropyl)-5,6,7,8-tetrahydropyrido[4,3-d]pyrimidin-4(3H)-one;
6-(2,2-difluoro-2-(3-(trifluoromethyl)phenyl)acetyl)-2-(1-phenylcyclopropyl)-3,5,6,7,8,9-hexahydro-4H-pyrimido[5,4-c]azepin-4-one;
6-(2,2-difluoro-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;
6-(2-(2-fluoro-3-(trifluoromethyl)phenyl)-2-hydroxy-acetyl)-2-(1-(3-fluorophenyl)cyclopropyl)-3,5,6,7,8,9-hexahydro-4H-pyrimido[5,4-c]azepin-4-one;
2-(1-(3-fluorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;
2-(1-(3-fluorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;
6-(2-(3-chlorophenyl)-2,2-difluoroacetyl)-2-(1-(3-chlorophenyl)cyclopropyl)-5,6,7,8-tetrahydropyrido[4,3-d]pyrimidin-4(3H)-one;
6-(2-(3-chlorophenyl)-2,2-difluoroacetyl)-2-(1-(3-fluorophenyl)cyclopropyl)-3,5,6,7,8,9-hexahydro-4H-pyrimido[5,4-c]azepin-4-one;
2-(1-(3-chlorophenyl)cyclopropyl)-6-(2,2-difluoro-2-(3-(trifluoromethyl)phenyl)acetyl)-5,6,7,8-tetrahydro-pyrido[4,3-d]pyrimidin-4(3H)-one;
6-(2,2-difluoro-2-(3-(trifluoromethyl)phenyl)acetyl)-2-(1-(3-fluorophenyl)cyclopropyl)-3,5,6,7,8,9-hexahydro-4H-pyrimido[5,4-c]azepin-4-one;
2-(1-(3-chlorophenyl)cyclopropyl)-6-(2-(3-cyclopropylphenyl)-2-hydroxyacetyl)-5,6,7,8-tetrahydropyrido[4,3-d]pyrimidin-4(3H)-one;
6-(2-(3-cyclopropylphenyl)-2-hydroxyacetyl)-2-(1-phenylcyclopropyl)-3,5,6,7,8,9-hexahydro-4H-pyrimido[5,4-c]azepin-4-one;
6-(2-(3-cyclopropylphenyl)-2-hydroxyacetyl)-2-(1-(thiophen-2-yl)cyclopropyl)-3,5,6,7,8,9-hexahydro-4H-pyrimido[5,4-c]azepin-4-one;
6-(2-(3-cyclopropylphenyl)-2-hydroxyacetyl)-2-(1-(3-fluorophenyl)cyclopropyl)-3,5,6,7,8,9-hexahydro-4H-pyrimido[5,4-c]azepin-4-one;
(R)-2-(1-(4-ethylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(4-cyclopentylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
2-(1-(3-chlorophenyl)cyclopropyl)-6-(2-(2-fluoro-3-(trifluoromethyl)phenyl)-2-hydroxyacetyl)-3,5,6,7,8,9-hexahydro-4H-pyrimido[5,4-c]azepin-4-one;
2-(1-(3-chlorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;
2-(1-(3-chlorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;
6-(2-(3-chlorophenyl)-2,2-difluoroacetyl)-2-(1-(3-chlorophenyl)cyclopropyl)-3,5,6,7,8,9-hexahydro-4H-pyrimido[5,4-c]azepin-4-one;
2-(1-(3-chlorophenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one;
(R)-2-(1-(4-(1-acetylpiperidin-4-yl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;
(R)-2-(1-(3-(4,4-difluorocyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
6-(2-(6-chloropyridin-2-yl)-2-hydroxyacetyl)-2-(1-phenylcyclopropyl)-5,6,7,8-tetrahydropyrido[4,3-d]pyrimidin-4(3H)-one;
6-(2-hydroxy-2-(6-(3-(trifluoromethyl)phenyl)pyridin-2-yl)acetyl)-2-(1-phenylcyclopropyl)-5,6,7,8-tetrahydro-pyrido[4,3-d]pyrimidin-4(3H)-one;
6-(2-hydroxy-2-(2'-(trifluoromethyl)-[2,4'-bipyridin]-6-yl)acetyl)-2-(1-phenylcyclopropyl)-5,6,7,8-tetrahydro-pyrido[4,3-d]pyrimidin-4(3H)-one;
6-(2-(6-(3-chlorophenyl)pyridin-2-yl)-2-hydroxyacetyl)-2-(1-phenylcyclopropyl)-5,6,7,8-tetrahydropyrido[4,3-d]pyrimidin-4(3H)-one;

6-(2-hydroxy-2-(6-(3-(trifluoromethoxy)phenyl)pyridin-2-yl)acetyl)-2-(1-phenylcyclopropyl)-5,6,7,8-tetrahydropyrido[4,3-d]pyrimidin-4(3H)-one;
(R)-2-(1-(3-chlorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-(3-chlorophenyl)-2-hydroxyacetyl)-2-(1-(3-chlorophenyl)cyclopropyl)-3,5,6,7,8,9-hexahydro-4H-pyrimido[5,4-c]azepin-4-one;
6-(2-(3-chloro-2-fluorophenyl)-2-hydroxyacetyl)-2-(1-(3-chlorophenyl)cyclopropyl)-3,5,6,7,8,9-hexahydro-4H-pyrimido[5,4-c]azepin-4-one;
6-(2-(3-(tert-butyl)phenyl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(piperidin-4-yl)thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(1-methylpiperidin-4-yl)thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(2-isopropylpyridin-4-yl)cyclopropyl)-3,5,6,7,8,9-hexahydro-4H-pyrimido[5,4-c]azepin-4-one;
2-(1-(3-chlorophenyl)cyclopropyl)-6-(2-(3-cyclopropylphenyl)-2-hydroxyacetyl)-3,5,6,7,8,9-hexahydro-4H-pyrimido[5,4-c]azepin-4-one;
6-(2-(2'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3',5'-bis(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-((dimethylamino)methyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-2-(1-(3-acetylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-methoxyphenyl)cyclopropyl)-3,5,6,7,8,9-hexahydro-4H-pyrimido[5,4-c]azepin-4-one;
6-(1H-benzo[d]imidazole-2-carbonyl)-2-(1-(3-chlorophenyl)cyclopropyl)-3,5,6,7,8,9-hexahydro-4H-pyrimido[5,4-c]azepin-4-one;
6-(2-(6-(cyclohex-1-en-1-yl)pyridin-2-yl)-2-hydroxyacetyl)-2-(1-phenylcyclopropyl)-5,6,7,8-tetrahydropyrido[4,3-d]pyrimidin-4(3H)-one;
6-(2-hydroxy-2-(3-(2,2,2-trifluoroethoxy)phenyl)acetyl)-2-(1-phenylcyclopropyl)-3,5,6,7,8,9-hexahydro-4H-pyrimido[5,4-c]azepin-4-one;
6-(2-hydroxy-2-(1'-methyl-1',2',3',6'-tetrahydro-[2,4'-bipyridin]-6-yl)acetyl)-2-(1-phenylcyclopropyl)-5,6,7,8-tetrahydropyrido[4,3-d]pyrimidin-4(3H)-one;
(R)-2-(1-(3-chlorophenyl)cyclopropyl)-6-(2-(2,3-difluorophenyl)-2-hydroxyacetyl)-3,5,6,7,8,9-hexahydro-4H-pyrimido[5,4-c]azepin-4-one;
6-(2-(6-cyclohexylpyridin-2-yl)-2-hydroxyacetyl)-2-(1-phenylcyclopropyl)-5,6,7,8-tetrahydropyrido[4,3-d]pyrimidin-4(3H)-one;
2-(1-(3-chlorophenyl)cyclopropyl)-6-(2-hydroxy-2-(3-(2,2,2-trifluoroethoxy)phenyl)acetyl)-3,5,6,7,8,9-hexahydro-4H-pyrimido[5,4-c]azepin-4-one;
6-(2-(2'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(6-isopropylpyridin-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-phenylthiophen-2-yl)cyclopropyl)-3,5,6,7,8,9-hexahydro-4H-pyrimido[5,4-c]azepin-4-one;
2-(1-phenylcyclopropyl)-6-(2-(3-((trifluoromethyl)thio)phenyl)acetyl)-3,5,6,7,8,9-hexahydro-4H-pyrimido[5,4-c]azepin-4-one;
6-(2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;
6-(2-amino-2-(3-(trifluoromethyl)phenyl)acetyl)-2-(1-phenylcyclopropyl)-3,5,6,7,8,9-hexahydro-4H-pyrimido[5,4-c]azepin-4-one;
2-(1-(3-chlorophenyl)cyclopropyl)-6-(2-hydroxy-2-(2-(trifluoromethyl)phenyl)acetyl)-3,5,6,7,8,9-hexahydro-4H-pyrimido[5,4-c]azepin-4-one;
2-(1-(3-chlorophenyl)cyclopropyl)-6-(2-hydroxy-2-(4-(trifluoromethyl)phenyl)acetyl)-3,5,6,7,8,9-hexahydro-4H-pyrimido[5,4-c]azepin-4-one;
6-(2-methyl-2-(3-(trifluoromethyl)phenyl)propanoyl)-2-(1-phenylcyclopropyl)-3,5,6,7,8,9-hexahydro-4H-pyrimido[5,4-c]azepin-4-one;
6-(2-hydroxy-2-(3'-hydroxy-5'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;
6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-hydroxy-2-(3'-((trifluoromethyl)thio)-[1,1'-biphenyl]-3-yl)acetyl)-2-(1-phenylcyclopropyl)-5,6,7,8-tetrahydropyrido[4,3-d]pyrimidin-4(3H)-one;
6-(2-hydroxy-2-(2'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;
(R)-2-(1-([1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(thiazol-5-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(3-methoxypropyl)thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-phenethylthiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;
6-(2-(6-(3-(tert-butyl)phenyl)pyridin-2-yl)-2-hydroxyacetyl)-2-(1-phenylcyclopropyl)-5,6,7,8-tetrahydropyrido[4,3-d]pyrimidin-4(3H)-one;
6-(2-(6-(3-cyclopropylphenyl)pyridin-2-yl)-2-hydroxyacetyl)-2-(1-phenylcyclopropyl)-5,6,7,8-tetrahydropyrido[4,3-d]pyrimidin-4(3H)-one;
6-(2-(3-bromophenyl)-2-hydroxyacetyl)-2-(1-phenylcyclopropyl)-3,5,6,7,8,9-hexahydro-4H-pyrimido[5,4-c]azepin-4-one;

2-(1-phenylcyclopropyl)-6-(1-(3-(trifluoromethyl)phenyl)cyclopropane-1-carbonyl)-3,5,6,7,8,9-hexahydro-4H-pyrimido[5,4-c]azepin-4-one;
6-(2-hydroxy-2-(3-(trifluoromethyl)phenyl)propanoyl)-2-(1-phenylcyclopropyl)-3,5,6,7,8,9-hexahydro-4H-pyrimido[5,4-c]azepin-4-one;
6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;
6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;
6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(2-(tetrahydro-2H-pyran-4-yl)ethyl)thiophen-2-yl)cyclopropyl)-3,5,6,7,8,9-hexahydro-4H-pyrimido[5,4-c]azepin-4-one;
(R)-2-(1-(4-(2-cyclopropylethyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(pyridin-3-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(pyrimidin-5-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-methyl-1H-pyrazol-4-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(isothiazol-4-yl)phenyl)cyclopropyl)-3,5,6,7,8,9-hexahydro-4H-pyrimido[5,4-c]azepin-4-one;
6-((R)-2-hydroxy-2-(3-(trifluoromethyl)phenyl)acetyl)-2-(1-(4'-(trifluoromethyl)-2',3',4',5'-tetrahydro-[1,1'-biphenyl]-3-yl)cyclopropyl)-3,5,6,7,8,9-hexahydro-4H-pyrimido[5,4-c]azepin-4-one;
6-((R)-2-hydroxy-2-(3-(trifluoromethyl)phenyl)acetyl)-2-(1-(3-(1,1,1-trifluoropropan-2-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-isobutylphenyl)cyclopropyl)-3,5,6,7,8,9-hexahydro-4H-pyrimido[5,4-c]azepin-4-one;
(R)-2-(1-(3-(4,4-dimethylcyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(3-hydroxy-3-methylbutyl)thiophen-2-yl)cyclopropyl)-3,5,6,7,8,9-hexahydro-4H-pyrimido[5,4-c]azepin-4-one;
(R)-2-(1-(4-(3,3-dimethylbutyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;
(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;
(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-dimethylthiophene-3-carboxamide;
1-(2-(1-(3-chlorophenyl)cyclopropyl)-4-oxo-3,5,7,8-tetrahydropyrido[4,3-d]pyrimidin-6(4H)-yl)-2-(3-(trifluoromethyl)phenyl)ethane-1,2-dione;
(R)-6-(2-hydroxy-2-(3-(trifluoromethyl)phenyl)acetyl)-2-(1-(3-(hydroxymethyl)phenyl)cyclopropyl)-3,5,6,7,8,9-hexahydro-4H-pyrimido[5,4-c]azepin-4-one;
6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2-(3',4'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3',5'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(2',5'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-fluoro-[1,1'-biphenyl]-3-yl)-2-hydroxyacetyl)-2-(1-(3-fluorophenyl)cyclopropyl)-5,6,7,8-tetrahydropyrido[4,3-d]pyrimidin-4(3H)-one;
2-(1-(3-chlorophenyl)cyclopropyl)-6-(2-(3'-fluoro-[1,1'-biphenyl]-3-yl)-2-hydroxyacetyl)-5,6,7,8-tetrahydropyrido[4,3-d]pyrimidin-4(3H)-one;
6-(2-(3'-fluoro-[1,1'-biphenyl]-3-yl)-2-hydroxyacetyl)-2-(1-(thiophen-2-yl)cyclopropyl)-5,6,7,8-tetrahydropyrido[4,3-d]pyrimidin-4(3H)-one;
6-(2-(3'-fluoro-[1,1'-biphenyl]-3-yl)-2-hydroxyacetyl)-2-(1-(3-fluorophenyl)cyclopropyl)-3,5,6,7,8,9-hexahydro-4H-pyrimido[5,4-c]azepin-4-one;
2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;
6-(2-hydroxy-2-(3-phenoxyphenyl)acetyl)-2-(1-phenylcyclopropyl)-5,6,7,8-tetrahydropyrido[4,3-d]pyrimidin-4(3H)-one;
2-(1-(3-chlorophenyl)cyclopropyl)-6-(2-hydroxy-2-(3-phenoxyphenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-(2-(oxetan-3-yl)ethyl)thiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(trifluoromethyl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(piperidin-1-ylmethyl)phenyl)cyclopropyl)-3,5,6,7,8,9-hexahydro-4H-pyrimido[5,4-c]azepin-4-one;
(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)nicotinonitrile;
(R)-2-(1-(3-(6-(dimethylamino)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-dimethyl-[1,1'-biphenyl]-3-carboxamide;
6-(2-(3-chlorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;
6-(2-(3'-fluoro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(3'-fluoro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(5'-fluoro-2'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(2',3'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(4'-chloro-3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(2'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-([1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(2'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;
6-(2-(2',4'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
6-(2-(5-bromopyridin-3-yl)-2-hydroxyacetyl)-2-(1-phenylcyclopropyl)-5,6,7,8-tetrahydropyrido[4,3-d]pyrimidin-4(3H)-one;
6-(2-hydroxy-2-(5-(3-(trifluoromethyl)phenyl)pyridin-3-yl)acetyl)-2-(1-phenylcyclopropyl)-5,6,7,8-tetrahydropyrido[4,3-d]pyrimidin-4(3H)-one;
6-(2-(5-(3-chlorophenyl)pyridin-3-yl)-2-hydroxyacetyl)-2-(1-phenylcyclopropyl)-5,6,7,8-tetrahydropyrido[4,3-d]pyrimidin-4(3H)-one;
6-(2-(2-fluoro-3-(trifluoromethyl)phenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;
2-(1-(4-(2-((3S,5S)-adamantan-1-yl)ethyl)thiophen-2-yl)cyclopropyl)-6-((RS)-2-hydroxy-2-(3-(trifluoromethyl)phenyl)acetyl)-3,5,6,7,8,9-hexahydro-4H-pyrimido[5,4-c]azepin-4-one;
6-(2,2-difluoro-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;
6-(2-(3-(tert-butyl)phenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(trifluoromethoxy)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(2-methoxypyridin-4-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-methyl-6-oxo-1,6-dihydropyridin-3-yl)phenyl)cyclopropyl)-3,5,6,7,8,9-hexahydro-4H-pyrimido[5,4-c]azepin-4-one;
(R)-2-(1-(3'-((dimethylamino)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
6-(2-(5-(3-fluorophenyl)pyridin-3-yl)-2-hydroxyacetyl)-2-(1-phenylcyclopropyl)-5,6,7,8-tetrahydropyrido[4,3-d]pyrimidin-4(3H)-one;
6-(2-hydroxy-2-(2'-(trifluoromethyl)-[3,4'-bipyridin]-5-yl)acetyl)-2-(1-phenylcyclopropyl)-5,6,7,8-tetrahydropyrido[4,3-d]pyrimidin-4(3H)-one;
6-(2-(6-(3-fluorophenyl)pyridin-2-yl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-(1-(2,2,2-trifluoroethyl)piperidin-4-yl)phenyl)cyclopropyl)-3,5,6,7,8,9-hexahydro-4H-pyrimido[5,4-c]azepin-4-one;
(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-sulfonamide;
(R)-6-(2-hydroxy-2-(3-(trifluoromethyl)phenyl)acetyl)-2-(1-(4'-(4-hydroxytetrahydro-2H-pyran-4-yl)-[1,1'-biphenyl]-3-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-methyl-1H-pyrazol-5-yl)phenyl)cyclopropyl)-3,5,6,7,8,9-hexahydro-4H-pyrimido[5,4-c]azepin-4-one;
(R)-2-(1-(3-(1-cyclopropyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(3-(1-(difluoromethyl)-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-methyl-1H-pyrazol-3-yl)phenyl)cyclopropyl)-3,5,6,7,8,9-hexahydro-4H-pyrimido[5,4-c]azepin-4-one;
(R)-2-(1-(3-(1-cyclobutyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-(2-methoxyethyl)-1H-pyrazol-4-yl)phenyl)cyclopropyl)-3,5,6,7,8,9-hexahydro-4H-pyrimido[5,4-c]azepin-4-one;
(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-3'-(1-(6-(2-hydroxy-2-(3-(trifluoromethyl)phenyl) acetyl)-4-oxo-4,5,6,7,8,9-hexahydro-3H-pyrimido[5,4-c]azepin-2-yl)cyclopropyl)-N,N-dimethyl-[1,1'-biphenyl]-4-sulfonamide;

6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(oxazol-5-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3'-(methylsulfonyl)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(pyridin-4-yl)phenyl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)-6-(2-hydroxy-2-(3-(trifluoromethyl)phenyl)acetyl)-2-(1-(4-(isoindoline-2-carbonyl)thiophen-2-yl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-fluorophenyl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(thiophen-2-yl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(3-fluorophenyl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

6-(2-(2-fluoro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2,3'-difluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(2-fluoro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(2-(methylamino)pyridin-4-yl)phenyl)cyclopropyl)-3,5,6,7,8,9-hexahydro-4H-pyrimido[5,4-c]azepin-4-one;

(R)-2-(1-(4'-(dimethylamino)-[1,1'-biphenyl]-3-yl)cyclopropyl)-6-(2-hydroxy-2-(3-(trifluoromethyl)phenyl) acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-(pyrrolidin-1-yl)pyrimidin-5-yl)phenyl)cyclopropyl)-3,5,6,7,8,9-hexahydro-4H-pyrimido[5,4-c] azepin-4-one;

(R)-2-(1-(5-cyclohexylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(3-(1-(6-(2-hydroxy-2-(3-(trifluoromethyl)phenyl) acetyl)-4-oxo-4,5,6,7,8,9-hexahydro-3H-pyrimido[5,4-c]azepin-2-yl)cyclopropyl)phenyl)-3-methylbenzo[d] oxazol-2(3H)-one;

(R)-6-(2-hydroxy-2-(3-(trifluoromethyl)phenyl)acetyl)-2-(1-(3'-(piperidine-1-carbonyl)-[1,1'-biphenyl]-3-yl) cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

6-(2-hydroxy-2-(3'-(2-methoxyethoxy)-[1,1'-biphenyl]-3-yl)acetyl)-2-(1-phenylcyclopropyl)-5,6,7,8-tetrahydropyrido[4,3-d]pyrimidin-4(3H)-one;

6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;

6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

6-(2-hydroxy-2-(3'-(trifluoromethyl)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

2-(1-(3-fluorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

6-(2-hydroxy-2-(3'-(trifluoromethoxy)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

2-(1-(3-chlorophenyl)cyclopropyl)-6-(2-hydroxy-2-(3-phenoxyphenyl)acetyl)-5,6,7,8-tetrahydropyrido[4,3-d]pyrimidin-4(3H)-one;

6-(2-hydroxy-2-(3-phenoxyphenyl)acetyl)-2-(1-phenylcyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3-phenoxyphenyl)acetyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(2-fluoro-3-(2-(trifluoromethyl)pyridin-4-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-cyclohexylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-methylpiperidin-1-yl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-methylpiperazin-1-yl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-((4-methylpiperazin-1-yl)methyl)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-methoxypyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(1-methylpiperidin-4-yl)-1H-pyrazol-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(1-methylpiperidin-4-yl)-[1,1'-biphenyl]-3-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-cyclopentylpyridin-3-yl)cyclopropyl)-5,6,7,8-tetrahydropyrido[4,3-d]pyrimidin-4(3H)-one;

(R)-2-(1-(5-cyclopentylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(3-cyclopentylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(3-isopropylphenyl)cyclopropyl)-3,5,6,7,8,9-hexahydro-4H-pyrimido[5,4-c]azepin-4-one;

6-(2-hydroxy-2-(3-((trifluoromethyl)thio)phenyl)acetyl)-2-(1-(3-isopropylphenyl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(thiazol-5-yl)thiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-phenylthiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(pyridin-3-yl)thiophen-2-yl)cyclopropyl)-5,6,7,8-tetrahydropyrido[4,3-d]pyrimidin-4(3H)-one;

6-(2-hydroxy-2-(3-(2-(trifluoromethyl)pyridin-4-yl)phenyl)acetyl)-2-(1-(3-isopropylphenyl)cyclopropyl)-3,5,6,7,8,9-hexahydro-4H-pyrimido[5,4-c]azepin-4-one;

(R)-2-(1-([3,3'-bipyridin]-5-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-(isothiazol-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

6-(2-hydroxy-2-(2-phenoxyphenyl)acetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-hydroxy-2-(2-phenoxyphenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-phenylacetyl)piperidin-4-yl)phenyl)cyclopropyl)-3,5,6,7,8,9-hexahydro-4H-pyrimido[5,4-c]azepin-4-one;

(R)-2-(1-(3-(1-(3,3-dimethylbutanoyl)piperidin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(1-benzoylpiperidin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(3-phenylpropanoyl)piperidin-4-yl)phenyl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(4-phenoxyphenyl)acetyl)-3,5,6,7,8,9-hexahydro-4H-pyrimido[5,4-c]azepin-4-one;

6-(2-(3-(benzyloxy)phenyl)-2-hydroxyacetyl)-2-(1-phenylcyclopropyl)-5,6,7,8-tetrahydropyrido[4,3-d]pyrimidin-4(3H)-one;

6-(2-(3-(benzyloxy)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(pyridin-3-yl)thiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-2-(1-(3-bromophenyl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-([1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3-(isothiazol-4-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(pyridin-3-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(2',3',4',5'-tetrahydro-[1,1'-biphenyl]-3-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(prop-1-en-2-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-(tetrahydro-2H-pyran-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-(tetrahydro-2H-pyran-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(tetrahydro-2H-pyran-4-yl)phenyl)cyclopropyl)-3,5,6,7,8,9-hexahydro-4H-pyrimido[5,4-c]azepin-4-one;

(R)-2-(1-([3,3'-bipyridin]-5-yl)cyclopropyl)-6-(2-(3-chlorophenyl)-2-hydroxyacetyl)-5,6,7,8-tetrahydropyrido[4,3-d]pyrimidin-4(3H)-one;

(R)-6-(2-(3-chlorophenyl)-2-hydroxyacetyl)-2-(1-(5-(isothiazol-4-yl)pyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(6-(methylamino)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(pyrrolidin-1-yl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(pyrrolidin-1-ylmethyl)-[1,1'-biphenyl]-3-yl)cyclopropyl)-3,5,6,7,8,9-hexahydro-4H-pyrimido[5,4-c]azepin-4-one;

6-(2-hydroxy-2-(3-(3-(trifluoromethyl)phenoxy)phenyl)acetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-hydroxy-2-(3-(3-(trifluoromethyl)phenoxy)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(4-(4,4-difluorocyclohexyl)thiophen-2-yl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-cyclopentylthiophen-2-yl)cyclopropyl)-5,6,7,8-tetrahydropyrido[4,3-d]pyrimidin-4(3H)-one;

(R)-2-(1-(4-(4,4-difluorocyclohexyl)thiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(tetrahydro-2H-pyran-4-yl)thiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(pyridin-3-yl)thiophen-2-yl)cyclopropyl)-3,5,6,7,8,9-hexahydro-4H-pyrimido[5,4-c]azepin-4-one;

(R)-2-(1-(4-(4,4-difluorocyclohexyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(3-isopropylphenyl)cyclopropyl)-3,5,6,7,8,9-hexahydro-4H-pyrimido[5,4-c]azepin-4-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(tetrahydro-2H-pyran-4-yl)thiophene-3-carboxamide;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropyl-N-methylthiophene-3-carboxamide;

(R)-6-(2-hydroxy-2-(3-(trifluoromethyl)phenyl)acetyl)-2-(1-(4-(piperidine-1-carbonyl)thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(2-(1-hydroxycyclohexyl)ethyl)thiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-isopropylphenyl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-(quinolin-3-yl)phenyl)acetyl)-5,6,7,8-tetrahydropyrido[4,3-d]pyrimidin-4(3H)-one;

6-(2-hydroxy-2-(3-(quinolin-3-yl)phenyl)acetyl)-2-(1-phenylcyclopropyl)-3,5,6,7,8,9-hexahydro-4H-pyrimido[5,4-c]azepin-4-one;
2-(1-(3-chlorophenyl)cyclopropyl)-6-(2-hydroxy-2-(3-(quinolin-3-yl)phenyl)acetyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-methyl-1H-indazol-5-yl)phenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-methyl-1H-indazol-4-yl)phenyl)cyclopropyl)-3,5,6,7,8,9-hexahydro-4H-pyrimido[5,4-c]azepin-4-one;
(R)-2-(1-(3-(benzo[b]thiophen-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(3-(benzo[b]thiophen-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-(3-chlorophenyl)-2-hydroxyacetyl)-2-(1-(5-(4,4-difluorocyclohexyl)pyridin-3-yl)cyclopropyl)-5,6,7,8-tetrahydropyrido[4,3-d]pyrimidin-4(3H)-one;
(R)-2-(1-(5-(4,4-difluorocyclohexyl)pyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;
(R)-6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;
(R)-6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;
(R)-6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(S)-6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(S)-6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;
(R)-6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;
(R)-6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;
(R)-6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
(R)-6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(3-cyclopentylphenyl)cyclopropyl)-5,6,7,8-tetrahydropyrido[4,3-d]pyrimidin-4(3H)-one;
(R)-6-(2-(3-chlorophenyl)-2-hydroxyacetyl)-2-(1-(3-(pyridin-3-yl)phenyl)cyclopropyl)-5,6,7,8-tetrahydropyrido[4,3-d]pyrimidin-4(3H)-one;
(R)-6-(2-(3-chlorophenyl)-2-hydroxyacetyl)-2-(1-(3-(isothiazol-4-yl)phenyl)cyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-isopropylphenyl)cyclopropyl)-5,6,7,8-tetrahydropyrido[4,3-d]pyrimidin-4(3H)-one;
(R)-2-(1-(3-cyclopentylphenyl)cyclopropyl)-6-(2-hydroxy-2-(3-(trifluoromethyl)phenyl)acetyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-(tetrahydro-2H-pyran-4-yl)phenyl)cyclopropyl)-5,6,7,8-tetrahydropyrido[4,3-d]pyrimidin-4(3H)-one;
(R)-2-(1-([1,1'-biphenyl]-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-(pyridin-3-yl)phenyl)cyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-(isothiazol-4-yl)phenyl)cyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-phenoxyphenyl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(3-phenoxyphenyl)cyclopropyl)-3,5,6,7,8,9-hexahydro-4H-pyrimido[5,4-c]azepin-4-one;
6-(2-(3-(tert-butyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;
6-(2-(2-fluoro-3-(trifluoromethyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;
6-(2-(3-chloro-2-fluorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;
6-(2-(3-chlorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;
6-(2-hydroxy-2-(3-(pentafluoro-(lambda)$^6$-sulfaneyl)phenyl)acetyl)-2-(1-(4-isopropylthiophen-2-yl)cyclopropyl)-3,5,6,7,8,9-hexahydro-4H-pyrimido[5,4-c]azepin-4-one;
6-(2-hydroxy-2-(3-((trifluoromethyl)thio)phenyl)acetyl)-2-(1-(4-isopropylthiophen-2-yl)cyclopropyl)-3,5,6,7,8,9-hexahydro-4H-pyrimido[5,4-c]azepin-4-one;
6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;
6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;
6-(2-hydroxy-2-(4-phenoxyphenyl)acetyl)-2-(1-phenylcyclopropyl)-5,6,7,8-tetrahydropyrido[4,3-d]pyrimidin-4(3H)-one;

(R)-6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

(S)-6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;

(R)-6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2-phenoxypyridin-4-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

6-(2-(3-chlorophenyl)-2,2-difluoroacetyl)-2-(1-(4-isopropylthiophen-2-yl)cyclopropyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-(4-isopropylthiophen-2-yl)cyclopropyl)-5,6,7,8-tetrahydropyrido[4,3-d]pyrimidin-4(3H)-one;

(S)-6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(S)-6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(5-(trifluoromethyl)pyridin-3-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(6-(trifluoromethyl)pyridin-2-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(quinolin-6-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(isoquinolin-6-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(quinolin-7-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(quinolin-4-yl)phenyl)acetyl)-2-(1-phenylcyclopropyl)-5,6,7,8-tetrahydropyrido[4,3-d]pyrimidin-4(3H)-one;

(R)-6-(2-(3-(benzofuran-2-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(3-(2,2-difluorobenzo[d][1,3]dioxol-5-yl)phenyl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclopentylphenyl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-(6-(benzyloxy)pyridin-3-yl)phenyl)-2-hydroxyacetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-hydroxy-2-(3-(3-(trifluoromethyl)phenoxy)phenyl)acetyl)-5,6,7,8-tetrahydropyrido[4,3-d]pyrimidin-4(3H)-one;

6-(2-hydroxy-2-(3-(3-(trifluoromethyl)phenoxy)phenyl)acetyl)-2-(1-phenylcyclopropyl)-3,5,6,7,8,9-hexahydro-4H-pyrimido[5,4-c]azepin-4-one;

6-(2-(3-(benzyloxy)phenyl)-2-hydroxyacetyl)-2-(1-phenylcyclopropyl)-3,5,6,7,8,9-hexahydro-4H-pyrimido[5,4-c]azepin-4-one;

(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-N,N-dimethylnicotinamide;

(R)-6-(2-hydroxy-2-(3-(trifluoromethyl)phenyl)acetyl)-2-(1-(3-(1-(1-(trifluoromethyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-hydroxy-2-(3'-(trifluoromethyl)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

(R)-2-(1-(4'-(tert-butyl)-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(4'-fluoro-[1,1'-biphenyl]-3-yl)cyclopropyl)-3,5,6,7,8,9-hexahydro-4H-pyrimido[5,4-c]azepin-4-one;

(R)-2-(1-(4'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-cyclopropyl-1H-pyrazol-4-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(2-methoxypyridin-4-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4'-(trifluoromethyl)-[1,1'-biphenyl]-3-yl)cyclopropyl)-3,5,6,7,8,9-hexahydro-4H-pyrimido[5,4-c]azepin-4-one;

8-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[4,5-c]azepin-4-one;

(R)-6-(2-(3-chlorophenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-cyclopentylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

6-(2-(3-(benzyloxy)phenyl)-2-hydroxyacetyl)-2-(1-(3-chlorophenyl)cyclopropyl)-5,6,7,8-tetrahydropyrido[4,3-d]pyrimidin-4(3H)-one;

(R)-2-(1-(3'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one;

(R)-3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-3-carbonitrile;

2-(1-(3-chlorophenyl)cyclopropyl)-6-(2-(3-(trifluoromethyl)phenyl)propanoyl)-3,5,6,7,8,9-hexahydro-4H-pyrimido[5,4-c]azepin-4-one;

2-(1-(3-fluorophenyl)cyclopropyl)-6-(2-(3-(trifluoromethyl)phenyl)propanoyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-isobutyrylpiperazin-1-yl)pyridin-3-yl)phenyl)cyclopropyl)-3,5,6,7,8,9-hexahydro-4H-pyrimido[5,4-c]azepin-4-one;

(R)-2-(1-(3-(6-(4-(3,3-dimethylbutanoyl)piperazin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-(2-phenylacetyl)piperazin-1-yl)pyridin-3-yl)phenyl)cyclopropyl)-3,5,6,7,8,9-hexahydro-4H-pyrimido[5,4-c]azepin-4-one;

(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)picolinonitrile;

(R)-2-(1-(4'-((dimethylamino)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(pyridin-2-ylmethoxy)-[1,1'-biphenyl]-3-yl)cyclopropyl)-3,5,6,7,8,9-hexahydro-4H-pyrimido[5,4-c]azepin-4-one;

(R)-6-(2-hydroxy-2-(4'-(trifluoromethoxy)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(4'-(trifluoromethyl)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;

(R)-6-(2-(4'-(tert-butyl)-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-(4'-fluoro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-(4'-chloro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3-(6-(trifluoromethyl)pyridin-3-yl)phenyl)acetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(5-isopropylpyridin-3-yl)cyclopropyl)-3,5,6,7,8,9-hexahydro-4H-pyrimido[5,4-c]azepin-4-one;

6-(2-(2-(benzyloxy)phenyl)acetyl)-2-(1-(3-chlorophenyl)cyclopropyl)-3,5,6,7,8,9-hexahydro-4H-pyrimido[5,4-c]azepin-4-one;

6-(2-(4-(benzyloxy)phenyl)acetyl)-2-(1-(3-chlorophenyl)cyclopropyl)-3,5,6,7,8,9-hexahydro-4H-pyrimido[5,4-c]azepin-4-one;

6-(2-([1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(3-isopropylphenyl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-chlorophenyl)-2,2-difluoroacetyl)-2-(1-(3-isopropylphenyl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(5-phenylpyridin-3-yl)cyclopropyl)-5,6,7,8-tetrahydropyrido[4,3-d]pyrimidin-4(3H)-one;

6-(2-(3-chlorophenyl)-2,2-difluoroacetyl)-2-(1-(5-phenylpyridin-3-yl)cyclopropyl)-5,6,7,8-tetrahydropyrido[4,3-d]pyrimidin-4(3H)-one;

6-(2,2-difluoro-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

6-(2-(3-chlorophenyl)-2,2-difluoroacetyl)-2-(1-(5-isopropylpyridin-3-yl)cyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-hydroxy-2-(3-(2-(trifluoromethyl)pyridin-4-yl)phenyl)acetyl)-2-(1-(3-isopropylphenyl)cyclopropyl)-5,6,7,8-tetrahydropyrido[4,3-d]pyrimidin-4(3H)-one;

6-(2,2-difluoro-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(1-methyl-1H-indazol-4-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(1-methyl-1H-indazol-4-yl)cyclopropyl)-3,5,6,7,8,9-hexahydro-4H-pyrimido[5,4-c]azepin-4-one;

(S)-6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;

6-(2-([1,1'-biphenyl]-2-yl)acetyl)-2-(1-(3-chlorophenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-methyl-1H-indazol-4-yl)phenyl)cyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-methyl-1H-indazol-5-yl)phenyl)cyclopropyl)-3,5,6,7,8,9-hexahydro-4H-pyrimido[5,4-c]azepin-4-one;

(R)-1-(3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-4-yl)cyclopropane-1-carbonitrile;

(R)-3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-3-sulfonamide;

(R)-6-(2-(3-chlorophenyl)-2-hydroxyacetyl)-2-(1-(3-(4,4-difluorocyclohexyl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(indolin-1-yl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(3-isopropylphenyl)cyclopropyl)-3,5,6,7,8,9-hexahydro-4H-pyrimido[5,4-c]azepin-4-one;

(R)-4-(((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)(methyl)amino)-4-oxobutanoic acid;

(R)-6-(2-(3-chlorophenyl)-2-hydroxyacetyl)-2-(1-(2-phenoxypyridin-4-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-(isothiazol-4-yl)pyridin-3-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-(isothiazol-4-yl)pyridin-3-yl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-(trifluoromethyl)pyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(trifluoromethyl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(5-(trifluoromethyl)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(piperidine-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)—N-((3'-(1-(6-(2-hydroxy-2-(3-(trifluoromethyl)phenyl)acetyl)-4-oxo-4,5,6,7,8,9-hexahydro-3H-pyrimido

[5,4-c]azepin-2-yl)cyclopropyl)-[1,1'-biphenyl]-4-yl) methyl)-N-methylpiperidine-1-carboxamide;

(R)-6-(2-(3-(cyclopent-1-en-1-yl)phenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(naphthalen-1-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(naphthalen-2-yl)phenyl)cyclopropyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3',4'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-5'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

8,8-difluoro-2-(1-phenylcyclopropyl)-6-(2-(3-(trifluoromethyl)phenyl)acetyl)-5,6,7,8-tetrahydropyrido[4,3-d]pyrimidin-4(3H)-one;

(R)—N,N-dibenzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

(R)—N-benzhydryl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)-5-(1-(6-(2-hydroxy-2-(3-(trifluoromethyl)phenyl) acetyl)-4-oxo-4,5,6,7,8,9-hexahydro-3H-pyrimido[5,4-c]azepin-2-yl)cyclopropyl)-N-methyl-N-(4-phenoxybenzyl)thiophene-3-carboxamide;

(R)-5-(1-(6-(2-hydroxy-2-(3-(trifluoromethyl)phenyl) acetyl)-4-oxo-4,5,6,7,8,9-hexahydro-3H-pyrimido[5,4-c]azepin-2-yl)cyclopropyl)-N-methyl-N-(naphthalen-1-ylmethyl)thiophene-3-carboxamide;

(R)-5-(1-(6-(2-hydroxy-2-(3-(trifluoromethyl)phenyl) acetyl)-4-oxo-4,5,6,7,8,9-hexahydro-3H-pyrimido[5,4-c]azepin-2-yl)cyclopropyl)-N,N-diisopropylthiophene-3-carboxamide;

6-((R)-2-hydroxy-2-(3-(trifluoromethyl)phenyl)acetyl)-2-(1-(3-(1-((trans)-4-(trifluoromethyl)cyclohexane-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(4-(phenoxymethyl)phenyl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methylindolin-5-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(3-(2-oxopyrrolidin-1-yl)propanoyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-(1-(2,2,2-trifluoroethyl)-1,2,3,6-tetrahydropyridin-4-yl)phenyl)cyclopropyl)-3,5,6,7,8,9-hexahydro-4H-pyrimido[5,4-c]azepin-4-one;

(R)-2-(1-(3-(1-(benzylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(1-(cyclohexylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(1-((4-fluorophenyl)sulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(2',3'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(2',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-5-chloro-3'-(1-hydroxy-2-oxo-2-(4-oxo-2-(1-phenylcyclopropyl)-3,5,7,8-tetrahydropyrido[4,3-d]pyrimidin-6(4H)-yl)ethyl)-[1,1'-biphenyl]-3-carbonitrile;

(R)-6-(2-hydroxy-2-(3'-isopropoxy-[1,1'-biphenyl]-3-yl) acetyl)-2-(1-phenylcyclopropyl)-5,6,7,8-tetrahydropyrido[4,3-d]pyrimidin-4(3H)-one;

(R)-6-(2-(3',5'-di-tert-butyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(3,4-dihydro-2H-benzo[b][1,4]dioxepin-7-yl) phenyl)-2-hydroxyacetyl)-2-(1-phenylcyclopropyl)-5,6,7,8-tetrahydropyrido[4,3-d]pyrimidin-4(3H)-one;

(R)-6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3-(benzo[b]thiophen-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3-(benzo[b]thiophen-2-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-phenoxyphenyl)cyclopropyl)-3,5,6,7,8,9-hexahydro-4H-pyrimido[5,4-c]azepin-4-one;
6-(2-(3-chloro-2-fluorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;
6-(2-(3-chloro-2-fluorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;
6-(2-(3-chloro-2-fluorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;
(R)-2-(1-(3-(benzofuran-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;
(R)-2-(1-(3-(benzo[b]thiophen-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;
(R)-2-(1-(3-(benzofuran-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;
(R)-6-(2-(3'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-(3-(benzofuran-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;
(R)-2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;
(R)-6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-(3-(benzofuran-3-yl)phenyl)-2-hydroxyacetyl)-2-(1-phenylcyclopropyl)-5,6,7,8-tetrahydropyrido[4,3-d]pyrimidin-4(3H)-one;
(R)-6-(2-(2'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-(3',4'-dimethyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-(3',5'-dimethyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-(3-(2,3-dihydrobenzofuran-5-yl)phenyl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3'-isopropyl-[1,1'-biphenyl]-3-yl)acetyl)-2-(1-phenylcyclopropyl)-5,6,7,8-tetrahydropyrido[4,3-d]pyrimidin-4(3H)-one;
(R)-6-(2-(4'-chloro-3'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-hydroxy-2-(3'-(trifluoromethoxy)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-(1-(3-(trifluoromethyl)phenyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;
(R)-2-(1-(3-(1-(3-(cyclopentyloxy)-4-methoxybenzoyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)—N-cyclohexyl-4-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-3,6-dihydropyridine-1(2H)-carboxamide;
(R)-3-cyclohexyl-1-((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)-1-methylurea;
(R)-6-(2-hydroxy-2-(3-(trifluoromethyl)phenyl)acetyl)-2-(1-(3-(6-(4-phenylpiperidin-1-yl)pyridin-3-yl)phenyl)cyclopropyl)-3,5,6,7,8,9-hexahydro-4H-pyrimido[5,4-c]azepin-4-one;
(R)-2-(1-(3-(6-(4-(benzyloxy)piperidin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-4-(2-(((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)(methyl)amino)-2-oxoethyl)benzoic acid;
(R)-4-(((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)(methyl)carbamoyl)bicyclo[2.2.2]octane-1-carboxylic acid;
(R)-6-(2-hydroxy-2-(3-(trifluoromethyl)phenyl)acetyl)-2-(1-(3-(6-(4-(2-(4-(phenoxymethyl)phenyl)acetyl)piperazin-1-yl)pyridin-3-yl)phenyl)cyclopropyl)-3,5,6,7,8,9-hexahydro-4H-pyrimido[5,4-c]azepin-4-one;
(R)-2-(1-(3-chlorophenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;
(R)-2-(1-(3-chlorophenyl)cyclopropyl)-6-(2-hydroxy-2-(3-(2-(trifluoromethyl)pyridin-4-yl)phenyl)acetyl)-3,5,6,7,8,9-hexahydro-4H-pyrimido[5,4-c]azepin-4-one;
(R)-6-(2-(3'-(benzyloxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;
(R)-2-(1-(3-chlorophenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;
(R)-6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3'-chloro-5'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3-(benzo[b]thiophen-3-yl)phenyl)-2-hydroxyacetyl)-2-(1-phenylcyclopropyl)-3,5,6,7,8,9-hexahydro-4H-pyrimido[5,4-c]azepin-4-one;
(R)-6-(2-(3-(6-(benzyloxy)pyridin-3-yl)phenyl)-2-hydroxyacetyl)-2-(1-phenylcyclopropyl)-3,5,6,7,8,9-hexahydro-4H-pyrimido[5,4-c]azepin-4-one;
(R)-6-(2-(3'-chloro-4'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(3-(benzo[b]thiophen-2-yl)phenyl)-2-hydroxyacetyl)-2-(1-phenylcyclopropyl)-3,5,6,7,8,9-hexahydro-4H-pyrimido[5,4-c]azepin-4-one;
(R)-6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
(R)-6-(2-(3-(2,2-difluorobenzo[d][1,3]dioxol-5-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3-(benzofuran-2-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-4'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-(benzyloxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-(trifluoromethyl)pyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2-phenyloxazol-5-yl)cyclopropyl)-3,5,6,7,8,9-hexahydro-4H-pyrimido[5,4-c]azepin-4-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)—N-benzyl-N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

(R)—N,N-dicyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(naphthalen-2-ylmethyl)thiophene-3-carboxamide;

(R)—N-(tert-butyl)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

6-(2-(3'-fluoro-[1,1'-biphenyl]-3-yl)acetyl)-2-(1-phenylcyclopropyl)-3,5,6,7,8,9-hexahydro-4H-pyrimido[5,4-c]azepin-4-one;

2-(1-phenylcyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

2-(1-phenylcyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-2-(1-(3-cyclohexylphenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-2-(1-(3-cyclohexylphenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-2-(1-(3-cyclohexylphenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzyloxy)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(benzyloxy)phenyl)cyclopropyl)-6-(2-(3-chlorophenyl)-2-hydroxyacetyl)-3,5,6,7,8,9-hexahydro-4H-pyrimido[5,4-c]azepin-4-one;

(S)-6-(2-hydroxy-2-(3-(trifluoromethyl)phenyl)acetyl)-2-(1-phenylcyclopropyl)-5,6,7,8-tetrahydropyrido[4,3-d]pyrimidin-4(3H)-one;

(S)-6-(2-hydroxy-2-(3-(trifluoromethyl)phenyl)acetyl)-2-(1-phenylcyclopropyl)-3,5,6,7,8,9-hexahydro-4H-pyrimido[5,4-c]azepin-4-one;

(S)-2-(1-(3-chlorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3',4'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(4'-chloro-3'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(2',3'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(2',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-5-chloro-3'-(1-hydroxy-2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

(R)-6-(2-hydroxy-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-phenylcyclopropyl)-3,5,6,7,8,9-hexahydro-4H-pyrimido[5,4-c]azepin-4-one;

(R)-6-(2-(3'-cyclopropyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',4'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3',5'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3'-isopropyl-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(4'-chloro-3'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(2'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3'-((trifluoromethyl)thio)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-8-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[4,5-c]azepin-4-one;

(R)-8-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[4,5-c]azepin-4-one;

(R)-8-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[4,5-c]azepin-4-one;

(R)-8-(2-hydroxy-2-(3'-isopropyl-[1,1'-biphenyl]-3-yl)acetyl)-2-(1-phenylcyclopropyl)-3,5,6,7,8,9-hexahydro-4H-pyrimido[4,5-c]azepin-4-one;

(R)-2-(1-(4'-((5-chloro-3,4-dihydroisoquinolin-2(1H)-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4'-((4-(benzyloxy)piperidin-1-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-6-(2-(3-(benzo[b]thiophen-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;

(R)-2-(1-(3-(benzo[b]thiophen-5-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(benzo[d]thiazol-6-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3-(benzo[d]thiazol-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-phenyloxazol-5-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(5-phenylthiazol-2-yl)phenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3-(6-(trifluoromethyl)pyridin-2-yl)phenyl)acetyl)-5,6,7,8-tetrahydropyrido[4,3-d]pyrimidin-4(3H)-one;

(R)-5-chloro-3'-(2-(2-(1-(3-chlorophenyl)cyclopropyl)-4-oxo-3,5,7,8-tetrahydropyrido[4,3-d]pyrimidin-6(4H)-yl)-1-hydroxy-2-oxoethyl)-[1,1'-biphenyl]-3-carbonitrile;

(R)-2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-6-(2-(3'-chloro-4'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

(R)-6-(2-(3'-chloro-5'-(trifluoromethoxy)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-chloro-5'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

6-(2,2-difluoro-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

6-(2,2-difluoro-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-(tert-butyl)-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

6-(2,2-difluoro-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-cyclopropyl-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

(R)-2-(1-(2'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-2-carbonitrile;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;

(R)-6-(2-hydroxy-2-(3-(trifluoromethyl)phenyl)acetyl)-2-(1-(2'-methyl-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3'-methyl-[1,1'-biphenyl]-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-methyl-[1,1'-biphenyl]-3-yl)cyclopropyl)-3,5,6,7,8,9-hexahydro-4H-pyrimido[5,4-c]azepin-4-one;

(R)-2-(1-(3',4'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(3',5'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3'-isopropyl-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3'-cyclopropyl-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(3-phenoxyphenyl)cyclopropyl)-3,5,6,7,8,9-hexahydro-4H-pyrimido[5,4-c]azepin-4-one;

(R)-4-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-3-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,4-dicarbonitrile;

2-(1-(3-chlorophenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-isopropoxy-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

2-(1-(5-phenylpyridin-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(2',3',4',5'-tetrahydro-[1,1'-biphenyl]-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-isopropylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-5-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,5-dicarbonitrile;

(R)-2-(1-(4-cyclohexylthiophen-2-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(4-cyclohexylthiophen-2-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3-(benzo[b]thiophen-3-yl)phenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

2-(1-(3-chlorophenyl)cyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(2-(3'-isopropyl-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-(3-(6-(trifluoromethyl)pyridin-2-yl)phenyl)acetyl)-3,5,6,7,8,9-hexahydro-4H-pyrimido[5,4-c]azepin-4-one;

6-(2-(3'-chloro-5'-fluoro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

6-(2-([1,1'-biphenyl]-4-yl)acetyl)-2-(1-(3-chlorophenyl)cyclopropyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

(R)-2-(1-(5-cyclohexylpyridin-3-yl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(4'-chloro-3'-methyl-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-(3-(2,2-difluorobenzo[d][1,3]dioxol-5-yl)phenyl)-2-hydroxyacetyl)-3,5,6,7,8,9-hexahydro-4H-pyrimido[5,4-c]azepin-4-one;

(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-3-carbonitrile;

(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-4-carbonitrile;

(R)-2-(1-(3-chlorophenyl)cyclopropyl)-6-(2-hydroxy-2-(4'-(trifluoromethyl)-[1,1'-biphenyl]-3-yl)acetyl)-3,5,6,7,8,9-hexahydro-4H-pyrimido[5,4-c]azepin-4-one;

(R)-2-(1-(3-chlorophenyl)cyclopropyl)-6-(2-hydroxy-2-(4'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(4'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

6-(2-([1,1'-biphenyl]-4-yloxy)acetyl)-2-(1-(3-chlorophenyl)cyclopropyl)-3,5,6,7,8,9-hexahydro-4H-pyrimido[5,4-c]azepin-4-one;

6-([1,1'-biphenyl]-3-carbonyl)-2-(1-(3-chlorophenyl)cyclopropyl)-3,5,6,7,8,9-hexahydro-4H-pyrimido[5,4-c]azepin-4-one;

6-([1,1'-biphenyl]-4-carbonyl)-2-(1-(3-chlorophenyl)cyclopropyl)-3,5,6,7,8,9-hexahydro-4H-pyrimido[5,4-c]azepin-4-one;

6-(2-([1,1'-biphenyl]-3-yloxy)acetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(3-phenoxybenzoyl)-3,5,6,7,8,9-hexahydro-4H-pyrimido[5,4-c]azepin-4-one;

2-(1-(3-chlorophenyl)cyclopropyl)-6-(4-phenoxybenzoyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

2-(1-(4-phenylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

8-(2-(3'-chloro-[1,1'-biphenyl]-3-yl)acetyl)-2-(1-phenylcyclopropyl)-3,5,6,7,8,9-hexahydro-4H-pyrimido[4,5-c]azepin-4-one;

2-(1-phenylcyclopropyl)-8-(2-(3'-(trifluoromethyl)-[1,1'-biphenyl]-3-yl)acetyl)-3,5,6,7,8,9-hexahydro-4H-pyrimido[4,5-c]azepin-4-one;

2-(1-(4-isopropylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

6-(2-(3'-chloro-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

2-(1-(3-isopropylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-(3-(trifluoromethyl)phenyl)acetyl)-3,5,6,7,8,9-hexahydro-4H-pyrimido[5,4-c]azepin-4-one;

2-(1-(3-chlorophenyl)cyclopropyl)-6-(2-(2-fluoro-3-(trifluoromethyl)phenyl)acetyl)-3,5,6,7,8,9-hexahydro-4H-pyrimido[5,4-c]azepin-4-one;

2-(1-(3-chlorophenyl)cyclopropyl)-6-(2-(3-(trifluoromethoxy)phenyl)acetyl)-3,5,6,7,8,9-hexahydro-4H-pyrimido[5,4-c]azepin-4-one;

2-(1-(3-chlorophenyl)cyclopropyl)-6-(2-(3-((trifluoromethyl)thio)phenyl)acetyl)-3,5,6,7,8,9-hexahydro-4H-pyrimido[5,4-c]azepin-4-one;

2-(1-(3-chlorophenyl)cyclopropyl)-6-(2-(3-(pentafluoro-(lambda)$^6$-sulfaneyl)phenyl)acetyl)-3,5,6,7,8,9-hexahydro-4H-pyrimido[5,4-c]azepin-4-one;

2-(1-(3-chlorophenyl)cyclopropyl)-6-(2-(naphthalen-2-yl)acetyl)-3,5,6,7,8,9-hexahydro-4H-pyrimido[5,4-c]azepin-4-one;

2-(1-(3-chlorophenyl)cyclopropyl)-6-(2-(3-cyclopropylphenyl)acetyl)-3,5,6,7,8,9-hexahydro-4H-pyrimido[5,4-c]azepin-4-one;

(E)-2-(1-(3-chlorophenyl)cyclopropyl)-6-(3-(3-(trifluoromethyl)phenyl)acryloyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-cyclohexylphenyl)cyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-cyclohexylphenyl)cyclopropyl)-5,6,7,8-tetrahydropyrido[4,3-d]pyrimidin-4(3H)-one;

6-(2-(3-(benzofuran-3-yl)phenyl)acetyl)-2-(1-(3-chlorophenyl)cyclopropyl)-3,5,6,7,8,9-hexahydro-4H-pyrimido[5,4-c]azepin-4-one;

5-chloro-3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-3-carbonitrile;

2-(1-(3-chlorophenyl)cyclopropyl)-6-(2-(naphthalen-1-yl)acetyl)-3,5,6,7,8,9-hexahydro-4H-pyrimido[5,4-c]azepin-4-one;

2-(1-(3-chlorophenyl)cyclopropyl)-6-(3-(3-(trifluoromethyl)phenyl)propanoyl)-3,5,6,7,8,9-hexahydro-4H-pyrimido[5,4-c]azepin-4-one;

6-(2-(3-(benzyloxy)phenyl)acetyl)-2-(1-(3-chlorophenyl)cyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-chloro-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3-bromophenyl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-(benzo[b]thiophen-3-yl)phenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-[1,1'-biphenyl]-3-yl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-(tert-butyl)-[1,1'-biphenyl]-3-yl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-5'-fluoro-[1,1'-biphenyl]-3-yl)-2-hydroxyacetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;

3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-4-carbonitrile;

6-(2-(4'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

6-(2-(4'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

3'-(2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-4-carbonitrile;

6-(2-(4'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

2-(1-phenylcyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

2-(1-phenylcyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

6-(2-(4'-chloro-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3-(benzofuran-3-yl)phenyl)acetyl)-2-(1-phenylcyclopropyl)-3,5,6,7,8,9-hexahydro-4H-pyrimido[5,4-c]azepin-4-one;

5-chloro-3'-(2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

2-(1-(3-chlorophenyl)cyclopropyl)-6-(2-(2-phenoxyphenyl)acetyl)-3,5,6,7,8,9-hexahydro-4H-pyrimido[5,4-c]azepin-4-one;

2-(1-(3-chlorophenyl)cyclopropyl)-6-(2-(3-phenoxyphenyl)acetyl)-3,5,6,7,8,9-hexahydro-4H-pyrimido[5,4-c]azepin-4-one;

6-(2-(3-(tert-butyl)phenyl)acetyl)-2-(1-(3-chlorophenyl)cyclopropyl)-3,5,6,7,8,9-hexahydro-4H-pyrimido[5,4-c]azepin-4-one;

6-(2-(3-(tert-butyl)phenyl)acetyl)-2-(1-phenylcyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-(3'-(trifluoromethoxy)-[1,1'-biphenyl]-3-yl)acetyl)-5,6,7,8-tetrahydropyrido[4,3-d]pyrimidin-4(3H)-one;

6-(2-(3'-(tert-butyl)-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

3'-(2-(2-(1-(3-chlorophenyl)cyclopropyl)-4-oxo-3,5,7,8-tetrahydropyrido[4,3-d]pyrimidin-6(4H)-yl)-2-oxoethyl)-[1,1'-biphenyl]-4-carbonitrile;

6-(2-(4'-(tert-butyl)-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-(4'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-(4'-(trifluoromethoxy)-[1,1'-biphenyl]-3-yl)acetyl)-5,6,7,8-tetrahydropyrido[4,3-d]pyrimidin-4(3H)-one;

6-(2-(4'-chloro-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

6-(2-(3-(benzofuran-3-yl)phenyl)acetyl)-2-(1-(3-chlorophenyl)cyclopropyl)-5,6,7,8-tetrahydropyrido[4,3-d]pyrimidin-4(3H)-one;

5-chloro-3'-(2-(2-(1-(3-chlorophenyl)cyclopropyl)-4-oxo-3,5,7,8-tetrahydropyrido[4,3-d]pyrimidin-6(4H)-yl)-2-oxoethyl)-[1,1'-biphenyl]-3-carbonitrile;

6-(2-(2-phenoxyphenyl)acetyl)-2-(1-phenylcyclopropyl)-3,5,6,7,8,9-hexahydro-4H-pyrimido[5,4-c]azepin-4-one;

6-(2-(3-phenoxyphenyl)acetyl)-2-(1-phenylcyclopropyl)-3,5,6,7,8,9-hexahydro-4H-pyrimido[5,4-c]azepin-4-one;

6-(2-(2-(benzyloxy)phenyl)acetyl)-2-(1-phenylcyclopropyl)-3,5,6,7,8,9-hexahydro-4H-pyrimido[5,4-c]azepin-4-one;

6-(2-(3-(benzyloxy)phenyl)acetyl)-2-(1-phenylcyclopropyl)-3,5,6,7,8,9-hexahydro-4H-pyrimido[5,4-c]azepin-4-one;

2-(1-(3-chlorophenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

2-(1-(3-chlorophenyl)cyclopropyl)-6-(2-(3-(trifluoromethyl)phenoxy)acetyl)-3,5,6,7,8,9-hexahydro-4H-pyrimido[5,4-c]azepin-4-one; and (R)-6-(2-hydroxy-2-(3-(trifluoromethyl)phenyl)acetyl)-2-(1-(4-(phenylethynyl)thiophen-2-yl)cyclopropyl)-3,5,6,7,8,9-hexahydro-4H-pyrimido[5,4-c]azepin-4-one.

7. The compound according to claim 6, or a pharmaceutically acceptable salt, stereoisomer, or tautomer thereof, wherein the compound, stereoisomer or tautomer is selected from the group consisting of:

(R)-6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-phenoxyphenyl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(2-methoxypyridin-4-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(1-methyl-1H-indazol-5-yl)phenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;

(R)-2-(1-([1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(prop-1-en-2-yl)phenyl)cyclopropyl)-3,5,6,7,8,9-hexahydro-4H-pyrimido[5,4-c]azepin-4-one;

(R)-3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-3-carbonitrile;

(R)-6-(2-hydroxy-2-(3-(trifluoromethyl)phenyl)acetyl)-2-(1-(3-(isothiazol-4-yl)phenyl)cyclopropyl)-3,5,6,7,8,9-hexahydro-4H-pyrimido[5,4-c]azepin-4-one;

(R)-2-(1-(3-(6-(4-(benzyloxy)piperidin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(6-(trifluoromethyl)pyridin-2-yl)phenyl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-methoxypyridin-4-yl)phenyl)cyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

(R)-5-chloro-3'-(1-hydroxy-2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

(R)-6-(2-hydroxy-2-(3-(trifluoromethyl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-4-carbonitrile;

6-(2-(3-chlorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2,2,2-trifluoroethyl)piperidin-4-yl)phenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-phenylcyclopropyl)-3,5,6,7,8,9-hexahydro-4H-pyrimido[5,4-c]azepin-4-one;

(R)-5-chloro-3'-(1-hydroxy-2-oxo-2-(4-oxo-2-(1-phenylcyclopropyl)-3,5,7,8-tetrahydropyrido[4,3-d]pyrimidin-6(4H)-yl)ethyl)-[1,1'-biphenyl]-3-carbonitrile;

(R)-2-(1-(3-(4,4-difluorocyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(2',3',4',5'-tetrahydro-[1,1'-biphenyl]-3-yl)cyclopropyl)-3,5,6,7,8,9-hexahydro-4H-pyrimido[5,4-c]azepin-4-one;

(R)-1-(3'-(1-(6-(2-(3-chlorophenyl)-2-hydroxyacetyl)-4-oxo-4,5,6,7,8,9-hexahydro-3H-pyrimido[5,4-c]azepin-2-yl)cyclopropyl)-[1,1'-biphenyl]-4-yl)cyclopropane-1-carbonitrile;

(R)-6-(2-hydroxy-2-(3-(trifluoromethyl)phenyl)acetyl)-2-(1-(3-(6-(trifluoromethyl)pyridin-3-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4'-fluoro-[1,1'-biphenyl]-3-yl)cyclopropyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2-(3-chlorophenyl)-2,2-difluoroacetyl)-2-(1-(3-chlorophenyl)cyclopropyl)-3,5,6,7,8,9-hexahydro-4H-pyrimido[5,4-c]azepin-4-one;
(R)-6-(2-(3'-(tert-butyl)-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(trifluoromethyl)phenyl)cyclopropyl)-3,5,6,7,8,9-hexahydro-4H-pyrimido[5,4-c]azepin-4-one;
(R)—N-cyclohexyl-4-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-3,6-dihydropyridine-1(2H)-carboxamide;
(R)-2-(1-(4-cyclopentylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(3-(4,4-dimethylcyclohexyl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;
6-(2,2-difluoro-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;
(R)-6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;
(R)-6-(2-hydroxy-2-(3'-isopropyl-[1,1'-biphenyl]-3-yl)acetyl)-2-(1-phenylcyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;
6-(2-(3-chlorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(isothiazol-4-yl)phenyl)cyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-(2-(pyrrolidin-1-yl)pyrimidin-5-yl)phenyl)cyclopropyl)-3,5,6,7,8,9-hexahydro-4H-pyrimido[5,4-c]azepin-4-one;
(R)-6-(2-(3-(2,2-difluorobenzo[d][1,3]dioxol-5-yl)phenyl)-2-hydroxyacetyl)-2-(1-phenylcyclopropyl)-3,5,6,7,8,9-hexahydro-4H-pyrimido[5,4-c]azepin-4-one;
(R)-2-(1-(5-cyclopentylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3'-(2-methoxyethoxy)-[1,1'-biphenyl]-3-yl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(4-phenylthiophen-2-yl)cyclopropyl)-3,5,6,7,8,9-hexahydro-4H-pyrimido[5,4-c]azepin-4-one;
(R)-6-(2-(3'-chloro-4'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
6-(2,2-difluoro-2-(3-(trifluoromethyl)phenyl)acetyl)-2-(1-(3-fluorophenyl)cyclopropyl)-3,5,6,7,8,9-hexahydro-4H-pyrimido[5,4-c]azepin-4-one;
2-(1-(3-chlorophenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one;
(R)-6-(2-(3-chlorophenyl)-2-hydroxyacetyl)-2-(1-(3-(1-methyl-1H-indazol-4-yl)phenyl)cyclopropyl)-3,5,6,7,8,9-hexahydro-4H-pyrimido[5,4-c]azepin-4-one;
(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;
(R)-6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;
(R)-6-(2-(3-(benzo[b]thiophen-2-yl)phenyl)-2-hydroxyacetyl)-2-(1-phenylcyclopropyl)-3,5,6,7,8,9-hexahydro-4H-pyrimido[5,4-c]azepin-4-one;
(R)-6-(2-(3'-chloro-5'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-(3-(benzofuran-2-yl)phenyl)-2-hydroxyacetyl)-2-(1-phenylcyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-(1-(3-(trifluoromethyl)phenyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;
(R)-2-(1-(3-chlorophenyl)cyclopropyl)-6-(2-(3-(2,2-difluorobenzo[d][1,3]dioxol-5-yl)phenyl)-2-hydroxyacetyl)-3,5,6,7,8,9-hexahydro-4H-pyrimido[5,4-c]azepin-4-one;
(R)-6-(2-(3-chlorophenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(3-(prop-1-en-2-yl)phenyl)cyclopropyl)-3,5,6,7,8,9-hexahydro-4H-pyrimido[5,4-c]azepin-4-one;
(R)-6-(2-(3-(benzofuran-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(4-phenylthiophen-2-yl)cyclopropyl)-3,5,6,7,8,9-hexahydro-4H-pyrimido[5,4-c]azepin-4-one;
(R)-2-(1-(4-ethylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-(3'-cyclopropyl-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;
(R)-6-(2-(3',4'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(4'-chloro-3'-methyl-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;
(R)-2-(1-(4-bromothiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-(3'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-((R)-2-hydroxy-2-(3-(trifluoromethyl)phenyl)acetyl)-2-(1-(3-(1,1,1-trifluoropropan-2-yl)phenyl)cyclopropyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-phenylcyclopropyl)-3,5,6,7,8,9-hexahydro-4H-pyrimido[5,4-c]azepin-4-one;

(R)-2-(1-(3-(1-cyclopropyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-methoxypyridin-3-yl)phenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3-(2-(trifluoromethyl)pyridin-4-yl)phenyl)acetyl)-3,5,6,7,8,9-hexahydro-4H-pyrimido[5,4-c]azepin-4-one;

(R)-2-(1-(3-cyclopentylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(pyridin-3-yl)phenyl)cyclopropyl)-3,5,6,7,8,9-hexahydro-4H-pyrimido[5,4-c]azepin-4-one;

2-(1-phenylcyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3'-(piperidine-1-carbonyl)-[1,1'-biphenyl]-3-yl)cyclopropyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

6-(2-(3-chloro-2-fluorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-2-(1-(5-cyclohexylpyridin-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4-cyclopentylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-(3-chlorophenyl)-2-hydroxyacetyl)-2-(1-(3-cyclopentylphenyl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

(R)-2-(1-(4-cycloheptylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(6-(4-methylpiperidin-1-yl)pyridin-3-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(isothiazol-4-yl)phenyl)cyclopropyl)-3,5,6,7,8,9-hexahydro-4H-pyrimido[5,4-c]azepin-4-one;

2-(1-(3-chlorophenyl)cyclopropyl)-6-(2-(2-fluoro-3-(trifluoromethyl)phenyl)-2-hydroxyacetyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

(R)-6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(pyridin-2-ylmethoxy)-[1,1'-biphenyl]-3-yl)cyclopropyl)-3,5,6,7,8,9-hexahydro-4H-pyrimido[5,4-c]azepin-4-one;

(R)-5-chloro-3'-(2-(2-(1-(3-chlorophenyl)cyclopropyl)-4-oxo-3,5,7,8-tetrahydropyrido[4,3-d]pyrimidin-6(4H)-yl)-1-hydroxy-2-oxoethyl)-[1,1'-biphenyl]-3-carbonitrile;

(R)-6-(2-hydroxy-2-(3-(trifluoromethyl)phenyl)acetyl)-2-(1-(3-(trifluoromethoxy)phenyl)cyclopropyl)-3,5,6,7,8,9-hexahydro-4H-pyrimido[5,4-c]azepin-4-one;

(R)-2-(1-(4-cyclohexylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-(3-chlorophenyl)-2-hydroxyacetyl)-2-(1-(4-cyclopentylthiophen-2-yl)cyclopropyl)-3,5,6,7,8,9-hexahydro-4H-pyrimido[5,4-c]azepin-4-one;

(R)-6-(2-(4'-chloro-3'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-hydroxy-2-(3-(3-(trifluoromethyl)phenoxy)phenyl)acetyl)-2-(1-phenylcyclopropyl)-3,5,6,7,8,9-hexahydro-4H-pyrimido[5,4-c]azepin-4-one;

(R)-2-(1-(3-(benzofuran-3-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3-(1-(3-(cyclopentyloxy)-4-methoxybenzoyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-(cyclopent-1-en-1-yl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;

(R)-2-(1-(4'-(dimethylamino)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclohexylphenyl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(thiophen-2-yl)cyclopropyl)-3,5,6,7,8,9-hexahydro-4H-pyrimido[5,4-c]azepin-4-one;
(R)-6-(2-(3-(benzofuran-2-yl)phenyl)-2-hydroxyacetyl)-2-(1-phenylcyclopropyl)-5,6,7,8-tetrahydropyrido[4,3-d]pyrimidin-4(3H)-one;
(R)-6-(2-(3-chlorophenyl)-2-hydroxyacetyl)-2-(1-(3-(4,4-difluorocyclohexyl)phenyl)cyclopropyl)-3,5,6,7,8,9-hexahydro-4H-pyrimido[5,4-c]azepin-4-one;
(R)-4-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;
(R)-6-(2-(3-chlorophenyl)-2-hydroxyacetyl)-2-(1-(3-cyclohexylphenyl)cyclopropyl)-5,6,7,8-tetrahydropyrido[4,3-d]pyrimidin-4(3H)-one;
(R)-6-(2-hydroxy-2-(3-(trifluoromethyl)phenyl)acetyl)-2-(1-(3-isobutylphenyl)cyclopropyl)-3,5,6,7,8,9-hexahydro-4H-pyrimido[5,4-c]azepin-4-one;
(R)-6-(2-hydroxy-2-(3-(trifluoromethyl)phenyl)acetyl)-2-(1-(3-(1-(3-phenylpropanoyl)piperidin-4-yl)phenyl)cyclopropyl)-3,5,6,7,8,9-hexahydro-4H-pyrimido[5,4-c]azepin-4-one;
(R)-2-(1-(3-(1-cyclobutyl-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-2-(1-(3-(6-(dimethylamino)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
(R)-6-(2-hydroxy-2-(3'-(trifluoromethoxy)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;
(R)-6-(2-(3-chlorophenyl)-2-hydroxyacetyl)-2-(1-(5-phenylpyridin-3-yl)cyclopropyl)-5,6,7,8-tetrahydropyrido[4,3-d]pyrimidin-4(3H)-one;
(R)-3-cyclohexyl-1-((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)-1-methylurea;
6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;
(R)-6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;
(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)picolinonitrile;
(R)-6-(2-(3-(2,2-difluorobenzo[d][1,3]dioxol-5-yl)phenyl)-2-hydroxyacetyl)-2-(1-phenylcyclopropyl)-5,6,7,8-tetrahydropyrido[4,3-d]pyrimidin-4(3H)-one;
(R)-3'-(2-(2-(1-(3-chlorophenyl)cyclopropyl)-4-oxo-3,4,5,7,8,9-hexahydro-6H-pyrimido[5,4-c]azepin-6-yl)-1-hydroxy-2-oxoethyl)-[1,1'-biphenyl]-3-carbonitrile;
(R)-6-(2-hydroxy-2-(3-(trifluoromethyl)phenyl)acetyl)-2-(1-(3-(5-phenylthiazol-2-yl)phenyl)cyclopropyl)-3,5,6,7,8,9-hexahydro-4H-pyrimido[5,4-c]azepin-4-one;
(R)-2-(1-(3-(benzofuran-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;
(R)-6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;
(R)-2-(1-(3-chlorophenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;
(R)-6-(2-hydroxy-2-(3-(2-(trifluoromethyl)pyridin-4-yl)phenyl)acetyl)-2-(1-(3-isopropylphenyl)cyclopropyl)-3,5,6,7,8,9-hexahydro-4H-pyrimido[5,4-c]azepin-4-one;
(R)-2-(1-(3-(benzyloxy)phenyl)cyclopropyl)-6-(2-(3-chlorophenyl)-2-hydroxyacetyl)-3,5,6,7,8,9-hexahydro-4H-pyrimido[5,4-c]azepin-4-one;
6-(2-(3'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;
(R)-6-(2-(3-(6-(benzyloxy)pyridin-3-yl)phenyl)-2-hydroxyacetyl)-2-(1-phenylcyclopropyl)-3,5,6,7,8,9-hexahydro-4H-pyrimido[5,4-c]azepin-4-one;
(R)-6-(2-(3'-chloro-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;
(R)-6-(2-(3'-fluoro-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;
6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;
(R)-2-(1-(4-(4,4-difluorocyclohexyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;
6-((R)-2-hydroxy-2-(3-(trifluoromethyl)phenyl)acetyl)-2-(1-(3-(1-((trans)-4-(trifluoromethyl)cyclohexane-1-carbonyl)-1,2,3,6-tetrahydropyridin-4-yl)phenyl)cyclopropyl)-3,5,6,7,8,9-hexahydro-4H-pyrimido[5,4-c]azepin-4-one;
(R)-6-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)-3-methylbenzo[d]oxazol-2(3H)-one;
(R)-6-(2-hydroxy-2-(3-(trifluoromethyl)phenyl)acetyl)-2-(1-(5-phenylpyridin-3-yl)cyclopropyl)-3,5,6,7,8,9-hexahydro-4H-pyrimido[5,4-c]azepin-4-one;
(R)-6-(2-(3'-chloro-5'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;
(R)-6-(2-(3'-fluoro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;
(R)-6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;
(R)-6-(2-(3'-chloro-4'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-6-(2-(2'-chloro-5'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;
(R)-2-(1-(3-chlorophenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;
6-(2-(3-chlorophenyl)-2,2-difluoroacetyl)-2-(1-(3-fluorophenyl)cyclopropyl)-3,5,6,7,8,9-hexahydro-4H-pyrimido[5,4-c]azepin-4-one;
(R)-6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-cyclopentylpyridin-3-yl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(3-isopropylphenyl)cyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3-chloro-2-fluorophenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-2-(1-([1,1'-biphenyl]-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(2-(trifluoromethyl)pyridin-4-yl)phenyl)cyclopropyl)-3,5,6,7,8,9-hexahydro-4H-pyrimido[5,4-c]azepin-4-one;

6-(2-(3-chloro-2-fluorophenyl)-2,2-difluoroacetyl)-2-(1-(5-phenylpyridin-3-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

5-chloro-3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-3-carbonitrile;

(R)-6-(2-hydroxy-2-(3-(trifluoromethyl)phenyl)acetyl)-2-(1-(3'-(methylsulfonyl)-[1,1'-biphenyl]-3-yl)cyclopropyl)-3,5,6,7,8,9-hexahydro-4H-pyrimido[5,4-c]azepin-4-one;

(R)-6-(2-hydroxy-2-(3'-isopropoxy-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-hydroxy-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-isopropylphenyl)cyclopropyl)-3,5,6,7,8,9-hexahydro-4H-pyrimido[5,4-c]azepin-4-one;

6-((R)-2-hydroxy-2-(3-(trifluoromethyl)phenyl)acetyl)-2-(1-(4'-(trifluoromethyl)-2',3',4',5'-tetrahydro-[1,1'-biphenyl]-3-yl)cyclopropyl)-3,5,6,7,8,9-hexahydro-4H-pyrimido[5,4-c]azepin-4-one;

(R)-6-(2-(3'-(benzyloxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-hydroxy-2-(3-(2-(trifluoromethyl)pyridin-4-yl)phenyl)acetyl)-2-(1-(3-isopropylphenyl)cyclopropyl)-3,5,6,7,8,9-hexahydro-4H-pyrimido[5,4-c]azepin-4-one;

(R)-2-(1-(3-(benzo[d]thiazol-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)-6-(2-hydroxy-2-(3-(trifluoromethyl)phenyl)acetyl)-2-(1-(3-isopropylphenyl)cyclopropyl)-5,6,7,8-tetrahydropyrido[4,3-d]pyrimidin-4(3H)-one;

5-chloro-3'-(2-oxo-2-(4-oxo-2-(1-phenylcyclopropyl)-3,4,5,7,8,9-hexahydro-6H-pyrimido[5,4-c]azepin-6-yl)ethyl)-[1,1'-biphenyl]-3-carbonitrile;

(R)-6-(2-(3-(benzo[b]thiophen-3-yl)phenyl)-2-hydroxyacetyl)-2-(1-phenylcyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(4-isopropylthiophen-2-yl)cyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(3-isopropylphenyl)cyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-fluorophenyl)cyclopropyl)-3,5,6,7,8,9-hexahydro-4H-pyrimido[5,4-c]azepin-4-one;

(R)-2-(1-(3-(benzo[b]thiophen-2-yl)phenyl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-2-(1-(3-(1-(benzylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-phenoxyphenyl)cyclopropyl)-3,5,6,7,8,9-hexahydro-4H-pyrimido[5,4-c]azepin-4-one;

6-(2-(2-fluoro-3-(trifluoromethyl)phenyl)acetyl)-2-(1-phenylcyclopropyl)-3,5,6,7,8,9-hexahydro-4H-pyrimido[5,4-c]azepin-4-one;

6-(2-(4'-chloro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(4-(phenoxymethyl)phenyl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(3',5'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(isothiazol-4-yl)phenyl)cyclopropyl)-5,6,7,8-tetrahydropyrido[4,3-d]pyrimidin-4(3H)-one;

(R)-2-(1-(5-cyclohexylpyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-2-(1-(4-(3,3-dimethylbutyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(2'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-chlorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(pyrrolidin-1-yl)pyridin-3-yl)phenyl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(4'-(tert-butyl)-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

6-(2-(3-(benzyloxy)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(tetrahydro-2H-pyran-4-yl)phenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(5-isopropylpyridin-3-yl)cyclopropyl)-3,5,6,7,8,9-hexahydro-4H-pyrimido[5,4-c]azepin-4-one;

(R)-2-(1-([1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3-chlorophenyl)-2,2-difluoroacetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(piperidine-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-diisopropylthiophene-3-carboxamide;

(R)-2-(1-(3-bromophenyl)cyclopropyl)-6-(2-(3-chlorophenyl)-2-hydroxyacetyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3'-cyclopropyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

2-(1-(3-chlorophenyl)cyclopropyl)-6-(2-(3-(6-(trifluoromethyl)pyridin-2-yl)phenyl)acetyl)-3,5,6,7,8,9-hexahydro-4H-pyrimido[5,4-c]azepin-4-one;

2-(1-(3-chlorophenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3-chlorophenyl)-2,2-difluoroacetyl)-2-(1-phenylcyclopropyl)-3,5,6,7,8,9-hexahydro-4H-pyrimido[5,4-c]azepin-4-one;

2-(1-(4-(2-((3S,5S)-adamantan-1-yl)ethyl)thiophen-2-yl)cyclopropyl)-6-((RS)-2-hydroxy-2-(3-(trifluoromethyl)phenyl)acetyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,4-dicarbonitrile;

6-(2-hydroxy-2-(3-(quinolin-3-yl)phenyl)acetyl)-2-(1-phenylcyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(3-(benzyloxy)phenyl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3'-((trifluoromethyl)thio)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

6-(2-hydroxy-2-(6-(3-(trifluoromethyl)phenyl)pyridin-2-yl)acetyl)-2-(1-phenylcyclopropyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;

(R)-3-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-carbonitrile;

6-(2-(3-(benzyloxy)phenyl)acetyl)-2-(1-(3-chlorophenyl)cyclopropyl)-3,5,6,7,8,9-hexahydro-4H-pyrimido[5,4-c]azepin-4-one;

6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

2-(1-(3-chlorophenyl)cyclopropyl)-6-(2-(2-fluoro-3-(trifluoromethyl)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-phenylpiperidin-1-yl)pyridin-3-yl)phenyl)cyclopropyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-(2-(4-(phenoxymethyl)phenyl)acetyl)piperazin-1-yl)pyridin-3-yl)phenyl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(2-(tetrahydro-2H-pyran-4-yl)ethyl)thiophen-2-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(3-phenoxyphenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(pyridin-4-yl)phenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-dimethyl-[1,1'-biphenyl]-4-sulfonamide;

(R)-6-(2-(3-chlorophenyl)-2-hydroxyacetyl)-2-(1-(3-(1-cyclopropyl-1H-pyrazol-4-yl)phenyl)cyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzyloxy)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(3-chloro-2-fluorophenyl)-2,2-difluoroacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3',4'-dimethyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

2-(1-phenylcyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

8-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[4,5-c]azepin-4-one;

6-(2-hydroxy-2-(6-(3-(trifluoromethoxy)phenyl)pyridin-2-yl)acetyl)-2-(1-phenylcyclopropyl)-5,6,7,8-tetrahydropyrido[4,3-d]pyrimidin-4(3H)-one;

(R)-2-(1-(3-cyclohexylphenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-phenoxyphenyl)cyclopropyl)-5,6,7,8-tetrahydropyrido[4,3-d]pyrimidin-4(3H)-one;

(R)-2-(1-(4'-((4-(benzyloxy)piperidin-1-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3-chlorophenyl)-2,2-difluoroacetyl)-2-(1-(3-isopropylphenyl)cyclopropyl)-3,5,6,7,8,9-hexahydro-4H-pyrimido[5,4-c]azepin-4-one;

(R)-6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(naphthalen-1-ylmethyl)thiophene-3-carboxamide;

2-(1-(3-chlorophenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-cyclopropyl-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

6-(2-([1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

6-(2,2-difluoro-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-5-(3-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)phenyl)nicotinonitrile;

6-(2-(2-fluoro-3-(trifluoromethyl)phenyl)-2-hydroxyacetyl)-2-(1-(5-phenylpyridin-3-yl)cyclopropyl)-5,6,7,8-tetrahydropyrido[4,3-d]pyrimidin-4(3H)-one;

(R)-6-(2-hydroxy-2-(3'-isopropyl-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

6-(2-(3'-chloro-5'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-phenylacetyl)piperidin-4-yl)phenyl)cyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-2-(1-(4-ethylthiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(3-cyclopentylphenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4'-methyl-[1,1'-biphenyl]-3-yl)cyclopropyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-(quinolin-3-yl)phenyl)acetyl)-5,6,7,8-tetrahydropyrido[4,3-d]pyrimidin-4(3H)-one;

6-(2-(2-(benzyloxy)phenyl)acetyl)-2-(1-(3-chlorophenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(5-cyclohexylpyridin-3-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(1-methyl-1H-indazol-5-yl)phenyl)cyclopropyl)-3,5,6,7,8,9-hexahydro-4H-pyrimido[5,4-c]azepin-4-one;

(R)-2-(1-(3-(1-(difluoromethyl)-1H-pyrazol-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3'-isopropyl-[1,1'-biphenyl]-3-yl)acetyl)-2-(1-(thiophen-2-yl)cyclopropyl)-3,5,6,7,8,9-hexahydro-4H-pyrimido[5,4-c]azepin-4-one;

(R)-2-(1-(3-(1-benzoylpiperidin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3-(tert-butyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-2-(1-(3-cyclohexylphenyl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4'-(4-hydroxytetrahydro-2H-pyran-4-yl)-[1,1'-biphenyl]-3-yl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(4'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-methoxyethyl)-1H-pyrazol-4-yl)phenyl)cyclopropyl)-3,5,6,7,8,9-hexahydro-4H-pyrimido[5,4-c]azepin-4-one;

3'-(2-(2-(1-(3-chlorophenyl)cyclopropyl)-4-oxo-3,4,5,7,8,9-hexahydro-6H-pyrimido[5,4-c]azepin-6-yl)-2-oxoethyl)-[1,1'-biphenyl]-4-carbonitrile;

(R)-6-(2-hydroxy-2-(3-(trifluoromethyl)phenyl)acetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4'-(trifluoromethyl)-[1,1'-biphenyl]-3-yl)cyclopropyl)-3,5,6,7,8,9-hexahydro-4H-pyrimido[5,4-c]azepin-4-one;

(R)-2-(1-(4-(2-cyclopropylethyl)thiophen-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-(benzo[b]thiophen-2-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-indazol-4-yl)phenyl)cyclopropyl)-3,5,6,7,8,9-hexahydro-4H-pyrimido[5,4-c]azepin-4-one;

(R)-6-(2-hydroxy-2-(4'-(trifluoromethoxy)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3'-(trifluoromethyl)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

(R)-2-(1-(5-cyclohexylpyridin-3-yl)cyclopropyl)-6-(2-(3'-fluoro-[1,1'-biphenyl]-3-yl)-2-hydroxyacetyl)-3,5,6,7,8,9-hexahydro-4H-pyrimido[5,4-c]azepin-4-one;

(R)-2-(1-(3-chlorophenyl)cyclopropyl)-6-(2-hydroxy-2-(4'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(1-(cyclohexylsulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(2-fluoro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(4'-(trifluoromethyl)-[1,1'-biphenyl]-3-yl)acetyl)-2-(1-(5-isopropylpyridin-3-yl)cyclopropyl)-5,6,7,8-tetrahydropyrido[4,3-d]pyrimidin-4(3H)-one;

(R)-6-(2-hydroxy-2-(3'-(trifluoromethyl)-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-(2',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3'-(tert-butyl)-[1,1'-biphenyl]-3-yl)-2,2-difluoroacetyl)-2-(1-phenylcyclopropyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2'-methyl-[1,1'-biphenyl]-3-yl)cyclopropyl)-3,5,6,7,8,9-hexahydro-4H-pyrimido[5,4-c]azepin-4-one;

(R)-6-(2-(3',5'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2,2-difluoro-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(tetrahydro-2H-pyran-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(methylamino)pyridin-3-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methylindolin-5-yl)phenyl)cyclopropyl)-3,5,6,7,8,9-hexahydro-4H-pyrimido[5,4-c]azepin-4-one;

(R)-2-(1-(4'-((5-chloro-3,4-dihydroisoquinolin-2(1H)-yl)methyl)-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-phenethylthiophen-2-yl)cyclopropyl)-3,5,6,7,8,9-hexahydro-4H-pyrimido[5,4-c]azepin-4-one;

6-(2-(3-(benzyloxy)phenyl)acetyl)-2-(1-phenylcyclopropyl)-3,5,6,7,8,9-hexahydro-4H-pyrimido[5,4-c]azepin-4-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(4-phenoxybenzyl)thiophene-3-carboxamide;

(R)—N-benzyl-N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

2-(1-(3-chlorophenyl)cyclopropyl)-6-(2-hydroxy-2-(3-(quinolin-3-yl)phenyl)acetyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3,5-dicarbonitrile;

(R)-6-(2-(3-(benzo[b]thiophen-3-yl)phenyl)-2-hydroxyacetyl)-2-(1-(3-chlorophenyl)cyclopropyl)-3,5,6,7,8,9-hexahydro-4H-pyrimido[5,4-c]azepin-4-one;

6-(2-(3'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(4-(2-(1-hydroxycyclohexyl)ethyl)thiophen-2-yl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3-(6-(trifluoromethyl)pyridin-2-yl)phenyl)acetyl)-5,6,7,8-tetrahydropyrido[4,3-d]pyrimidin-4(3H)-one;

(R)-6-(2-(3-chlorophenyl)-2-hydroxyacetyl)-2-(1-(3-phenoxyphenyl)cyclopropyl)-5,6,7,8-tetrahydropyrido[4,3-d]pyrimidin-4(3H)-one;

6-(2-hydroxy-2-(3-((trifluoromethyl)thio)phenyl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-2-(1-(3-(benzo[d]thiazol-6-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

6-(2-hydroxy-2-(3-(6-(trifluoromethyl)pyridin-2-yl)phenyl)acetyl)-2-(1-phenylcyclopropyl)-5,6,7,8-tetrahydropyrido[4,3-d]pyrimidin-4(3H)-one;

(R)—N-((3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-4-yl)methyl)-N-methylpiperidine-1-carboxamide;

6-(2-(2-fluoro-3-(trifluoromethyl)phenyl)-2-hydroxyacetyl)-2-(1-phenylcyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-isopropoxy-[1,1'-biphenyl]-3-yl)acetyl)-3,5,6,7,8,9-hexahydro-4H-pyrimido[5,4-c]azepin-4-one;

(R)-5-fluoro-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-3-carbonitrile;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(4'-chloro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-5'-methyl-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(4'-(trifluoromethyl)-[1,1'-biphenyl]-3-yl)acetyl)-3,5,6,7,8,9-hexahydro-4H-pyrimido[5,4-c]azepin-4-one;

(R)—N-benzhydryl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)-6-(2-hydroxy-2-(3-(trifluoromethyl)phenyl)acetyl)-2-(1-(3-(naphthalen-2-yl)phenyl)cyclopropyl)-3,5,6,7,8,9-hexahydro-4H-pyrimido[5,4-c]azepin-4-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-isopropylthiophene-3-carboxamide;

(R)-2-(1-(3-cyclohexylphenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-(benzyloxy)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-2-(1-(3-(1-(3,3-dimethylbutanoyl)piperidin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3-(6-(trifluoromethyl)pyridin-3-yl)phenyl)acetyl)-2-(1-(5-isopropylpyridin-3-yl)cyclopropyl)-5,6,7,8-tetrahydropyrido[4,3-d]pyrimidin-4(3H)-one;

(R)-6-(2-(3-(benzo[b]thiophen-3-yl)phenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

6-(2,2-difluoro-2-(3'-isopropoxy-[1,1'-biphenyl]-3-yl)acetyl)-2-(1-phenylcyclopropyl)-3,5,6,7,8,9-hexahydro-4H-pyrimido[5,4-c]azepin-4-one;

6-(2-hydroxy-2-(3-(2-(trifluoromethyl)pyridin-4-yl)phenyl)acetyl)-2-(1-phenylcyclopropyl)-3,5,6,7,8,9-hexahydro-4H-pyrimido[5,4-c]azepin-4-one;

(R)-2-(1-(3-(1-((4-fluorophenyl)sulfonyl)-1,2,3,6-tetrahydropyridin-4-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(4'-(tert-butyl)-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3'-chloro-[1,1'-biphenyl]-3-yl)cyclopropyl)-6-(2-(3-chlorophenyl)-2-hydroxyacetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-isopropylphenyl)cyclopropyl)-3,5,6,7,8,9-hexahydro-4H-pyrimido[5,4-c]azepin-4-one;

6-(2-hydroxy-2-(2'-(trifluoromethyl)-[2,4'-bipyridin]-6-yl)acetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(5-(trifluoromethyl)pyridin-3-yl)phenyl)cyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3'-chloro-[1,1'-biphenyl]-3-yl)acetyl)-2-(1-phenylcyclopropyl)-3,5,6,7,8,9-hexahydro-4H-pyrimido[5,4-c]azepin-4-one;

(R)—N,N-dibenzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

2-(1-(4-isopropylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-phenylcyclopropyl)-5,6,7,8-tetrahydropyrido[4,3-d]pyrimidin-4(3H)-one;

(R)-2-(1-(3-(6-(4-(3,3-dimethylbutanoyl)piperazin-1-yl)pyridin-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3-(tert-butyl)phenyl)-2-hydroxyacetyl)-2-(1-(3-fluorophenyl)cyclopropyl)-3,5,6,7,8,9-hexahydro-4H-pyrimido[5,4-c]azepin-4-one;

(R)-2-(1-(3-chlorophenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-hydroxy-2-(2-phenoxyphenyl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-5-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(4'-chloro-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-chloro-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

(R)-2-(1-(4-cyclohexylthiophen-2-yl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(3-cyclohexylphenyl)cyclopropyl)-5,6,7,8-tetrahydropyrido[4,3-d]pyrimidin-4(3H)-one;

6-(2-(3'-(tert-butyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-(3-cyclopropylphenyl)-2-hydroxyacetyl)-3,5,6,7,8,9-hexahydro-4H-pyrimido[5,4-c]azepin-4-one;

(R)-6-(2-(3-chlorophenyl)-2-hydroxyacetyl)-2-(1-(3-cyclopentylphenyl)cyclopropyl)-5,6,7,8-tetrahydropyrido[4,3-d]pyrimidin-4(3H)-one;

6-(2-(3'-chloro-5'-fluoro-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(thiazol-5-yl)phenyl)cyclopropyl)-3,5,6,7,8,9-hexahydro-4H-pyrimido[5,4-c]azepin-4-one;

(R)—N,N-dicyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)thiophene-3-carboxamide;

6-(2,2-difluoro-2-(3-(trifluoromethyl)phenyl)acetyl)-2-(1-(5-isopropylpyridin-3-yl)cyclopropyl)-5,6,7,8-tetrahydropyrido[4,3-d]pyrimidin-4(3H)-one;

(R)-6-(2-(3',5'-bis(trifluoromethyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3-(benzofuran-3-yl)phenyl)acetyl)-2-(1-phenylcyclopropyl)-3,5,6,7,8,9-hexahydro-4H-pyrimido[5,4-c]azepin-4-one;

6-(2-(3-chloro-2-fluorophenyl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-chloro-2-fluorophenyl)-2-hydroxyacetyl)-2-(1-(3-phenoxyphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-(pyridin-3-yl)phenyl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-isopropylphenyl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-2-(1-(3-chlorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-6-(2-(3-chlorophenyl)-2-hydroxyacetyl)-2-(1-(4-(4,4-difluorocyclohexyl)thiophen-2-yl)cyclopropyl)-5,6,7,8-tetrahydropyrido[4,3-d]pyrimidin-4(3H)-one;

(R)-2-(1-(3-(benzo[b]thiophen-3-yl)phenyl)cyclopropyl)-6-(2-(3-bromophenyl)-2-hydroxyacetyl)-3,5,6,7,8,9-hexahydro-4H-pyrimido[5,4-c]azepin-4-one;

6-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

(R)-2-(1-(4-(4,4-difluorocyclohexyl)thiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-(3',5'-bis(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-isopropylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-[1,1'-biphenyl]-2-carbonitrile;

(R)-6-(2-(3-chlorophenyl)-2-hydroxyacetyl)-2-(1-(4-(isothiazol-4-yl)thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(2-(indolin-1-yl)acetyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(4'-chloro-3'-(trifluoromethoxy)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2,2-difluoro-2-(3-(trifluoromethyl)phenyl)acetyl)-2-(1-(4-isopropylthiophen-2-yl)cyclopropyl)-5,6,7,8-tetrahydropyrido[4,3-d]pyrimidin-4(3H)-one;

(R)-6-(2-(4'-chloro-3'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)—N-cyclohexyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

2-(1-(3-chlorophenyl)cyclopropyl)-6-(2-(3-((trifluoromethyl)thio)phenyl)acetyl)-3,5,6,7,8,9-hexahydro-4H-pyrimido[5,4-c]azepin-4-one;

2-(1-(3-chlorophenyl)cyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-phenylthiophen-2-yl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3'-methyl-[1,1'-biphenyl]-3-yl)cyclopropyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(thiophen-2-yl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(3-cyclohexylphenyl)cyclopropyl)-3,5,6,7,8,9-hexahydro-4H-pyrimido[5,4-c]azepin-4-one;

6-(2-hydroxy-2-(5-(3-(trifluoromethyl)phenyl)pyridin-3-yl)acetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-hydroxy-2-(3'-(trifluoromethoxy)-[1,1'-biphenyl]-3-yl)acetyl)-5,6,7,8-tetrahydropyrido[4,3-d]pyrimidin-4(3H)-one;

(R)-2-(1-(3-cyclohexylphenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-hydroxy-2-(3'-(trifluoromethoxy)-[1,1'-biphenyl]-3-yl)acetyl)-2-(1-(5-isopropylpyridin-3-yl)cyclopropyl)-3,5,6,7,8,9-hexahydro-4H-pyrimido[5,4-c]azepin-4-one;

6-(2-(3-(benzofuran-3-yl)phenyl)acetyl)-2-(1-(3-chlorophenyl)cyclopropyl)-3,5,6,7,8,9-hexahydro-4H-pyrimido[5,4-c]azepin-4-one;

6-(2-(3-(benzo[b]thiophen-2-yl)phenyl)-2-hydroxyacetyl)-2-(1-phenylcyclopropyl)-5,6,7,8-tetrahydropyrido[4,3-d]pyrimidin-4(3H)-one;

6-(2-hydroxy-2-(3-(pentafluoro-(lambda)$^6$-sulfaneyl)phenyl)acetyl)-2-(1-(4-isopropylthiophen-2-yl)cyclopropyl)-5,6,7,8-tetrahydropyrido[4,3-d]pyrimidin-4(3H)-one;

(R)-6-(2-(4'-fluoro-[1,1'-biphenyl]-3-yl)-2-hydroxyacetyl)-2-(1-(5-isopropylpyridin-3-yl)cyclopropyl)-5,6,7,8-tetrahydropyrido[4,3-d]pyrimidin-4(3H)-one;

6-(2-(4'-chloro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

6-(2-(3-chlorophenyl)-2,2-difluoroacetyl)-2-(1-(5-phenylpyridin-3-yl)cyclopropyl)-5,6,7,8-tetrahydropyrido[4,3-d]pyrimidin-4(3H)-one;

2-(1-(3-chlorophenyl)cyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3-(benzofuran-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3'-(trifluoromethyl)-[1,1'-biphenyl]-3-yl)acetyl)-5,6,7,8-tetrahydropyrido[4,3-d]pyrimidin-4(3H)-one;

2-(1-phenylcyclopropyl)-6-(2-(3-((trifluoromethyl)thio)phenyl)acetyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;

(R)-2-(1-(3'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(5-cyclohexylpyridin-3-yl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(3'-fluoro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(3-methoxypropyl)thiophen-2-yl)cyclopropyl)-3,5,6,7,8,9-hexahydro-4H-pyrimido[5,4-c]azepin-4-one;

(R)-6-(2-(3'-chloro-4'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

(R)—N-benzyl-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methylthiophene-3-carboxamide;

(R)-6-(2-(4'-(tert-butyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

(R)-5-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N-methyl-N-(naphthalen-2-ylmethyl)thiophene-3-carboxamide;

6-(2-(3',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(5-(trifluoromethyl)pyridin-3-yl)cyclopropyl)-3,5,6,7,8,9-hexahydro-4H-pyrimido[5,4-c]azepin-4-one;

2-(1-(3-chlorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(4-(2-(oxetan-3-yl)ethyl)thiophen-2-yl)cyclopropyl)-3,5,6,7,8,9-hexahydro-4H-pyrimido[5,4-c]azepin-4-one;

(R)-2-(1-(3',5'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-hydroxy-2-(3'-(trifluoromethyl)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-(1-(trifluoromethyl)cyclopropane-1-carbonyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-(4'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-8-(2-hydroxy-2-(3'-(trifluoromethoxy)-[1,1'-biphenyl]-3-yl)acetyl)-2-(1-phenylcyclopropyl)-3,5,6,7,8,9-hexahydro-4H-pyrimido[4,5-c]azepin-4-one;

(R)-2-(1-(3',4'-difluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-chlorophenyl)-2-hydroxyacetyl)-2-(1-(3-chlorophenyl)cyclopropyl)-3,5,6,7,8,9-hexahydro-4H-pyrimido[5,4-c]azepin-4-one;

6-(2-(3-(tert-butyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-6-(2-(4'-chloro-3'-(trifluoromethoxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(4'-fluoro-[1,1'-biphenyl]-3-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(4-phenylthiophen-2-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-[1,1'-biphenyl]-3-yl)-2-hydroxyacetyl)-3,5,6,7,8,9-hexahydro-4H-pyrimido[5,4-c]azepin-4-one;

6-(2-(3'-chloro-5'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-phenylcyclopropyl)-6-(2-(4'-(trifluoromethoxy)-[1,1'-biphenyl]-3-yl)acetyl)-3,5,6,7,8,9-hexahydro-4H-pyrimido[5,4-c]azepin-4-one;

6-(2-(4'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(5-phenylpyridin-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-8-(2-hydroxy-2-(3'-(trifluoromethyl)-[1,1'-biphenyl]-3-yl)acetyl)-2-(1-phenylcyclopropyl)-3,5,6,7,8,9-hexahydro-4H-pyrimido[4,5-c]azepin-4-one;

(R)-6-(2-hydroxy-2-(3-(trifluoromethyl)phenyl)acetyl)-2-(1-(3-(pyridin-3-yl)phenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(6-(4-isobutyrylpiperazin-1-yl)pyridin-3-yl)phenyl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(1-methyl-1H-pyrazol-5-yl)phenyl)cyclopropyl)-3,5,6,7,8,9-hexahydro-4H-pyrimido[5,4-c]azepin-4-one;

(R)-6-(2-(3'-chloro-5'-(trifluoromethoxy)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(3-(2-phenyloxazol-5-yl)phenyl)cyclopropyl)-3,5,6,7,8,9-hexahydro-4H-pyrimido[5,4-c]azepin-4-one;

6-(2-(2-(benzyloxy)phenyl)acetyl)-2-(1-phenylcyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-cyclopropyl-[1,1'-biphenyl]-3-yl)-2-hydroxyacetyl)-3,5,6,7,8,9-hexahydro-4H-pyrimido[5,4-c]azepin-4-one;

(R)-6-(2-(3'-(tert-butyl)-[1,1'-biphenyl]-3-yl)-2-hydroxyacetyl)-2-(1-(5-isopropylpyridin-3-yl)cyclopropyl)-3,5,6,7,8,9-hexahydro-4H-pyrimido[5,4-c]azepin-4-one;

6-(2-(3'-(tert-butyl)-[1,1'-biphenyl]-3-yl)acetyl)-2-(1-(3-chlorophenyl)cyclopropyl)-3,5,6,7,8,9-hexahydro-4H-pyrimido[5,4-c]azepin-4-one;

2-(1-(3-fluorophenyl)cyclopropyl)-6-(2-hydroxy-2-(3-((trifluoromethyl)thio)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(1-methyl-1H-pyrazol-4-yl)phenyl)cyclopropyl)-3,5,6,7,8,9-hexahydro-4H-pyrimido[5,4-c]azepin-4-one;

6-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

6-(2-(3-chlorophenyl)-2,2-difluoroacetyl)-2-(1-(4-isopropylthiophen-2-yl)cyclopropyl)-5,6,7,8-tetrahydropyrido[4,3-d]pyrimidin-4(3H)-one;

6-(2-(2-fluoro-3-(trifluoromethyl)phenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(4-(tetrahydro-2H-pyran-4-yl)thiophen-2-yl)cyclopropyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(5-phenylpyridin-3-yl)cyclopropyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3'-(trifluoromethoxy)-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

2-(1-(3-isopropylphenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3'-chloro-[1,1'-biphenyl]-3-yl)-2-hydroxyacetyl)-2-(1-(3-(1-(2,2,2-trifluoroethyl)-1,2,3,6-tetrahydropyridin-4-yl)phenyl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(6-(4-(2-phenylacetyl)piperazin-1-yl)pyridin-3-yl)phenyl)cyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(3-(tert-butyl)phenyl)acetyl)-2-(1-(3-chlorophenyl)cyclopropyl)-3,5,6,7,8,9-hexahydro-4H-pyrimido[5,4-c]azepin-4-one;

(R)-6-(2-(2',3'-dichloro-[1,1'-biphenyl]-3-yl)-2-hydroxyacetyl)-2-(1-phenylcyclopropyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-chloro-5'-fluoro-[1,1'-biphenyl]-3-yl)-2-hydroxyacetyl)-3,5,6,7,8,9-hexahydro-4H-pyrimido[5,4-c]azepin-4-one;

6-(2-(2-fluoro-3-(trifluoromethyl)phenyl)-2-hydroxyacetyl)-2-(1-(3-isopropylphenyl)cyclopropyl)-5,6,7,8-tetrahydropyrido[4,3-d]pyrimidin-4(3H)-one;

2-(1-(3-chlorophenyl)cyclopropyl)-6-(2-(3-(trifluoromethyl)phenyl)acetyl)-3,5,6,7,8,9-hexahydro-4H-pyrimido[5,4-c]azepin-4-one;

6-(2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;

6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-(3-(trifluoromethyl)phenyl)propanoyl)-3,5,6,7,8,9-hexahydro-4H-pyrimido[5,4-c]azepin-4-one;

6-(2-(3-(tert-butyl)phenyl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-cyclohexylthiophen-2-yl)cyclopropyl)-5,6,7,8-tetrahydropyrido[4,3-d]pyrimidin-4(3H)-one;

6-(2-hydroxy-2-(3-(quinolin-3-yl)phenyl)acetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)acetyl)-2-(1-(3-cyclohexylphenyl)cyclopropyl)-3,5,6,7,8,9-hexahydro-4H-pyrimido[5,4-c]azepin-4-one;

6-(2-(2'-chloro-5'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(4'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(2',5'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-hydroxy-2-(4'-(trifluoromethoxy)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-chloro-4'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-(benzyloxy)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-(tert-butyl)-[1,1'-biphenyl]-3-yl)acetyl)-2-(1-(3-chlorophenyl)cyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-isopropylpyridin-3-yl)cyclopropyl)-5,6,7,8-tetrahydropyrido[4,3-d]pyrimidin-4(3H)-one;

2-(1-(3-chlorophenyl)cyclopropyl)-6-(2-(3'-(trifluoromethoxy)-[1,1'-biphenyl]-3-yl)acetyl)-3,5,6,7,8,9-hexahydro-4H-pyrimido[5,4-c]azepin-4-one;

(R)-6-(2-(3',5'-di-tert-butyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-(benzo[b]thiophen-2-yl)phenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

6-(2-(4'-chloro-3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(4-isopropylthiophen-2-yl)cyclopropyl)-5,6,7,8-tetrahydropyrido[4,3-d]pyrimidin-4(3H)-one;

(R)-6-(2-(3'-chloro-5'-(trifluoromethyl)-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

2-(1-(3-chlorophenyl)cyclopropyl)-6-(2-(3'-isopropyl-[1,1'-biphenyl]-3-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(2-isopropylpyridin-4-yl)cyclopropyl)-3,5,6,7,8,9-hexahydro-4H-pyrimido[5,4-c]azepin-4-one;

(R)-2-(1-([1,1'-biphenyl]-3-yl)cyclopropyl)-6-(2-(3-chlorophenyl)-2-hydroxyacetyl)-5,6,7,8-tetrahydropyrido[4,3-d]pyrimidin-4(3H)-one;

2-(1-phenylcyclopropyl)-6-(2-(4'-(trifluoromethyl)-[1,1'-biphenyl]-3-yl)acetyl)-3,5,6,7,8,9-hexahydro-4H-pyrimido[5,4-c]azepin-4-one;

6-(2-(3-(tert-butyl)phenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(oxazol-5-yl)phenyl)cyclopropyl)-3,5,6,7,8,9-hexahydro-4H-pyrimido[5,4-c]azepin-4-one;

2-(1-(3-chlorophenyl)cyclopropyl)-6-(2-(2-phenoxyphenyl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-hydroxy-2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-fluorophenyl)cyclopropyl)-6-(2-hydroxy-2-(3-(pentafluoro-(lambda)$^6$-sulfaneyl)phenyl)acetyl)-3,5,6,7,8,9-hexahydro-4H-pyrimido[5,4-c]azepin-4-one;

2-(1-(3-chlorophenyl)cyclopropyl)-6-(2-hydroxy-2-(3-phenoxyphenyl)acetyl)-3,5,6,7,8,9-hexahydro-4H-pyrimido[5,4-c]azepin-4-one;

(R)-6-(2-hydroxy-2-(3'-(trifluoromethyl)-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

2-(1-(3-chlorophenyl)cyclopropyl)-6-(2-(3-cyclopropylphenyl)acetyl)-3,5,6,7,8,9-hexahydro-4H-pyrimido[5,4-c]azepin-4-one;

6-(2-(3'-chloro-[1,1'-biphenyl]-3-yl)acetyl)-2-(1-(4-phenylthiophen-2-yl)cyclopropyl)-3,5,6,7,8,9-hexahydro-4H-pyrimido[5,4-c]azepin-4-one;

(R)-6-(2-hydroxy-2-(3-(2-(trifluoromethyl)pyridin-4-yl)phenyl)acetyl)-2-(1-(5-isopropylpyridin-3-yl)cyclopropyl)-3,5,6,7,8,9-hexahydro-4H-pyrimido[5,4-c]azepin-4-one;

6-(2-(4'-chloro-[1,1'-biphenyl]-3-yl)-2-hydroxyacetyl)-2-(1-(3-fluorophenyl)cyclopropyl)-3,5,6,7,8,9-hexahydro-4H-pyrimido[5,4-c]azepin-4-one;

6-(2-(3'-fluoro-[1,1'-biphenyl]-3-yl)acetyl)-2-(1-phenylcyclopropyl)-3,5,6,7,8,9-hexahydro-4H-pyrimido[5,4-c]azepin-4-one;

(R)-8-(2-(3'-(tert-butyl)-[1,1'-biphenyl]-3-yl)-2-hydroxyacetyl)-2-(1-phenylcyclopropyl)-3,5,6,7,8,9-hexahydro-4H-pyrimido[4,5-c]azepin-4-one;

6-(2-hydroxy-2-(3-((trifluoromethyl)thio)phenyl)acetyl)-2-(1-(thiophen-2-yl)cyclopropyl)-3,5,6,7,8,9-hexahydro-4H-pyrimido[5,4-c]azepin-4-one;

(R)-2-(1-(3-chlorophenyl)cyclopropyl)-6-(2-(2,3-difluorophenyl)-2-hydroxyacetyl)-3,5,6,7,8,9-hexahydro-4H-pyrimido[5,4-c]azepin-4-one;

6-(2-(3'-chloro-5'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(3-fluorophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

2-(1-(3-cyclohexylphenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

(R)-2-(1-(3-(benzo[b]thiophen-3-yl)phenyl)cyclopropyl)-6-(2-hydroxy-2-(3'-isopropyl-[1,1'-biphenyl]-3-yl)acetyl)-3,5,6,7,8,9-hexahydro-4H-pyrimido[5,4-c]azepin-4-one;

(R)-2-(1-(3-(benzo[b]thiophen-3-yl)phenyl)cyclopropyl)-6-(2-(3'-(tert-butyl)-[1,1'-biphenyl]-3-yl)-2-hydroxyacetyl)-3,5,6,7,8,9-hexahydro-4H-pyrimido[5,4-c]azepin-4-one;

2-(1-(2',3',4',5'-tetrahydro-[1,1'-biphenyl]-3-yl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

6-(2-hydroxy-2-(3-(2-(trifluoromethyl)pyridin-4-yl)phenyl)acetyl)-2-(1-phenylcyclopropyl)-5,6,7,8-tetrahydropyrido[4,3-d]pyrimidin-4(3H)-one;

(R)-6-(2-(3-(6-(benzyloxy)pyridin-3-yl)phenyl)-2-hydroxyacetyl)-2-(1-phenylcyclopropyl)-5,6,7,8-tetrahydropyrido[4,3-d]pyrimidin-4(3H)-one;

(E)-2-(1-(3-chlorophenyl)cyclopropyl)-6-(3-(3-(trifluoromethyl)phenyl)acryloyl)-3,5,6,7,8,9-hexahydro-4H-pyrimido[5,4-c]azepin-4-one;

(R)-6-(2-(3-chlorophenyl)-2-hydroxyacetyl)-2-(1-(4-cyclopentylthiophen-2-yl)cyclopropyl)-5,6,7,8-tetrahydropyrido[4,3-d]pyrimidin-4(3H)-one;

6-(2-(3-(tert-butyl)phenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3-(benzo[b]thiophen-3-yl)phenyl)-2-hydroxyacetyl)-2-(1-(3-cyclohexylphenyl)cyclopropyl)-3,5,6,7,8,9-hexahydro-4H-pyrimido[5,4-c]azepin-4-one;

2-(1-(3-chlorophenyl)cyclopropyl)-6-(2-(3-(pentafluoro-(lambda)$^6$-sulfaneyl)phenyl)acetyl)-3,5,6,7,8,9-hexahydro-4H-pyrimido[5,4-c]azepin-4-one;

(R)-2-(1-(5-(4,4-difluorocyclohexyl)pyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2,2-difluoro-2-(3-(trifluoromethyl)phenyl)acetyl)-2-(1-(5-phenylpyridin-3-yl)cyclopropyl)-5,6,7,8-tetrahydropyrido[4,3-d]pyrimidin-4(3H)-one;

2-(1-(3-chlorophenyl)cyclopropyl)-6-(2-(3'-fluoro-[1,1'-biphenyl]-3-yl)-2-hydroxyacetyl)-5,6,7,8-tetrahydropyrido[4,3-d]pyrimidin-4(3H)-one;

6-(2-(3-chloro-2-fluorophenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-(thiophen-2-yl)cyclopropyl)-3,5,6,7,8,9-hexahydro-4H-pyrimido[5,4-c]azepin-4-one;

2-(1-(3-chlorophenyl)cyclopropyl)-6-(2-(3'-(trifluoromethoxy)-[1,1'-biphenyl]-3-yl)acetyl)-5,6,7,8-tetrahydropyrido[4,3-d]pyrimidin-4(3H)-one;

(R)-6-(2-(3-(benzofuran-3-yl)phenyl)-2-hydroxyacetyl)-2-(1-phenylcyclopropyl)-5,6,7,8-tetrahydropyrido[4,3-d]pyrimidin-4(3H)-one;

(R)-2-(1-(3-(benzo[b]thiophen-3-yl)phenyl)cyclopropyl)-6-(2-hydroxy-2-(3'-(trifluoromethoxy)-[1,1'-biphenyl]-3-yl)acetyl)-3,5,6,7,8,9-hexahydro-4H-pyrimido[5,4-c]azepin-4-one;

6-(2-(3-(tert-butyl)phenyl)-2-hydroxyacetyl)-2-(1-(thiophen-2-yl)cyclopropyl)-3,5,6,7,8,9-hexahydro-4H-pyrimido[5,4-c]azepin-4-one;

6-(2-(5-(3-chlorophenyl)pyridin-3-yl)-2-hydroxyacetyl)-2-(1-phenylcyclopropyl)-5,6,7,8-tetrahydropyrido[4,3-d]pyrimidin-4(3H)-one;

(R)-6-(2-(3'-chloro-4'-methyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

2-(1-(3-fluorophenyl)cyclopropyl)-6-(2-(3-(trifluoromethyl)phenyl)propanoyl)-3,5,6,7,8,9-hexahydro-4H-pyrimido[5,4-c]azepin-4-one;

(R)-3'-(1-(6-(2-hydroxy-2-(3-(trifluoromethyl)phenyl)acetyl)-4-oxo-4,5,6,7,8,9-hexahydro-3H-pyrimido[5,4-c]azepin-2-yl)cyclopropyl)-N,N-dimethyl-[1,1'-biphenyl]-3-carboxamide;

6-(2-(3-chloro-2-fluorophenyl)-2,2-difluoroacetyl)-2-(1-(5-isopropylpyridin-3-yl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(thiophen-2-yl)cyclopropyl)-3,5,6,7,8,9-hexahydro-4H-pyrimido[5,4-c]azepin-4-one;

6-(2-hydroxy-2-(3'-((trifluoromethyl)thio)-[1,1'-biphenyl]-3-yl)acetyl)-2-(1-phenylcyclopropyl)-5,6,7,8-tetrahydropyrido[4,3-d]pyrimidin-4(3H)-one;

(R)-6-(2-(3-chlorophenyl)-2-hydroxyacetyl)-2-(1-(5-(4,4-difluorocyclohexyl)pyridin-3-yl)cyclopropyl)-5,6,7,8-tetrahydropyrido[4,3-d]pyrimidin-4(3H)-one;

(R)-6-(2-(3'-(tert-butyl)-[1,1'-biphenyl]-3-yl)-2-hydroxyacetyl)-2-(1-(4-phenylthiophen-2-yl)cyclopropyl)-3,5,6,7,8,9-hexahydro-4H-pyrimido[5,4-c]azepin-4-one;

6-(2-(3-(benzyloxy)phenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3-bromophenyl)-2-hydroxyacetyl)-2-(1-phenylcyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

2-(1-(3-chlorophenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one;

(R)-6-(2-(3'-chloro-5'-fluoro-[1,1'-biphenyl]-3-yl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-phenylcyclopropyl)-3,5,6,7,8,9-hexahydro-4H-pyrimido[5,4-c]azepin-4-one;

2-(1-(3-(benzo[b]thiophen-3-yl)phenyl)cyclopropyl)-6-(2,2-difluoro-2-(3-(trifluoromethyl)phenyl)acetyl)-3,5,6,7,8,9-hexahydro-4H-pyrimido[5,4-c]azepin-4-one 6-(2-hydroxy-2-(3-((trifluoromethyl)thio)phenyl)acetyl)-2-(1-phenylcyclopropyl)-3,5,6,7,8,9-hexahydro-4H-pyrimido[5,4-c]azepin-4-one;

(R)-6-(2-(4'-chloro-3'-(trifluoromethyl)-[1,1'-biphenyl]-3-yl)-2-hydroxyacetyl)-2-(1-(3-chlorophenyl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-(3-isopropylphenyl)cyclopropyl)-3,5,6,7,8,9-hexahydro-4H-pyrimido[5,4-c]azepin-4-one;

(R)-6-(2-(3-chlorophenyl)-2-hydroxyacetyl)-2-(1-(3-isopropylphenyl)cyclopropyl)-5,6,7,8-tetrahydropyrido[4,3-d]pyrimidin-4(3H)-one;

2-(1-(3-chlorophenyl)cyclopropyl)-6-(2-hydroxy-2-(3-(3-(trifluoromethyl)phenoxy)phenyl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(naphthalen-1-yl)phenyl)cyclopropyl)-3,5,6,7,8,9-hexahydro-4H-pyrimido[5,4-c]azepin-4-one;

6-(2-(6-(3-cyclopropylphenyl)pyridin-2-yl)-2-hydroxyacetyl)-2-(1-phenylcyclopropyl)-5,6,7,8-tetrahydropyrido[4,3-d]pyrimidin-4(3H)-one;

2-(1-(3-chlorophenyl)cyclopropyl)-6-(2-(naphthalen-1-yl)acetyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(2-(methylamino)pyridin-4-yl)phenyl)cyclopropyl)-3,5,6,7,8,9-hexahydro-4H-pyrimido[5,4-c]azepin-4-one;

6-(2-hydroxy-2-(3-(pentafluoro-(lambda)$^6$-sulfaneyl)phenyl)acetyl)-2-(1-phenylcyclopropyl)-3,5,6,7,8,9-hexahydro-4H-pyrimido[5,4-c]azepin-4-one;

(R)-6-(2-(3',4'-dichloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-2-(1-(4-bromothiophen-2-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

6-(2-hydroxy-2-(3-(3-(trifluoromethyl)phenoxy)phenyl)acetyl)-2-(1-phenylcyclopropyl)-5,6,7,8-tetrahydropyrido[4,3-d]pyrimidin-4(3H)-one;

6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)acetyl)-2-(1-(3-isopropylphenyl)cyclopropyl)-5,6,7,8-tetrahydropyrido[4,3-d]pyrimidin-4(3H)-one;

2-(1-phenylcyclopropyl)-8-(2-(3'-(trifluoromethyl)-[1,1'-biphenyl]-3-yl)acetyl)-3,5,6,7,8,9-hexahydro-4H-pyrimido[4,5-c]azepin-4-one;

6-(2-(3-chloro-2-fluorophenyl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-hydroxy-2-(3-(trifluoromethyl)phenyl)acetyl)-2-(1-(3-(pyrimidin-5-yl)phenyl)cyclopropyl)-3,5,6,7,8,9-hexahydro-4H-pyrimido[5,4-c]azepin-4-one;

(R)-6-(2-(3'-fluoro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(5-(trifluoromethyl)pyridin-3-yl)phenyl)acetyl)-2-(1-phenylcyclopropyl)-3,5,6,7,8,9-hexahydro-4H-pyrimido[5,4-c]azepin-4-one;

6-(2-(4'-(tert-butyl)-[1,1'-biphenyl]-3-yl)acetyl)-2-(1-phenylcyclopropyl)-3,5,6,7,8,9-hexahydro-4H-pyrimido[5,4-c]azepin-4-one;

6-(2-(3'-cyclopropyl-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3'-chloro-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

(R)-6-(2-hydroxy-2-(3-(5-(trifluoromethyl)pyridin-3-yl)phenyl)acetyl)-2-(1-phenylcyclopropyl)-5,6,7,8-tetrahydropyrido[4,3-d]pyrimidin-4(3H)-one;

(R)-6-(2-hydroxy-2-(3-(trifluoromethyl)phenyl)acetyl)-2-(1-(2-phenoxypyridin-4-yl)cyclopropyl)-3,5,6,7,8,9-hexahydro-4H-pyrimido[5,4-c]azepin-4-one;

6-(2-(2-fluoro-3'-(trifluoromethyl)-[1,1'-biphenyl]-3-yl)-2-hydroxyacetyl)-2-(1-phenylcyclopropyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-3,5,6,7,8,9-hexahydro-4H-pyrimido[5,4-c]azepin-4-one; and 6-(2-(2-fluoro-3-(2-(trifluoromethyl)pyridin-4-yl)phenyl)-2-hydroxyacetyl)-2-(1-phenylcyclopropyl)-5,6,7,8-tetrahydropyrido[4,3-d]pyrimidin-4(3H)-one.

8. The compound according to claim 1, or a pharmaceutically acceptable salt, stereoisomer, or tautomer thereof, wherein the compound, stereoisomer or tautomer is selected from the group consisting of:

6-(2-(3,5-difluorophenyl)-2-hydroxyacetyl)-2-(1-(3-fluorophenyl)cyclopropyl)-5,6,7,8-tetrahydropyrido[4,3-d]pyrimidin-4(3H)-one;

6-(2-hydroxy-2-(m-tolyl)acetyl)-2-(1-phenylcyclopropyl)-5,6,7,8-tetrahydropyrido[4,3-d]pyrimidin-4(3H)-one;

6-(2-(3-bromo-2-fluorophenyl)-2-hydroxyacetyl)-2-(1-phenylcyclopropyl)-5,6,7,8-tetrahydropyrido[4,3-d]pyrimidin-4(3H)-one;

6-(2-(3-chloro-2-fluorophenyl)-2-hydroxyacetyl)-2-(1-phenylcyclopropyl)-5,6,7,8-tetrahydropyrido[4,3-d]pyrimidin-4(3H)-one;

2-fluoro-3-(1-hydroxy-2-oxo-2-(4-oxo-2-(1-phenylcyclopropyl)-3,5,7,8-tetrahydropyrido[4,3-d]pyrimidin-6(4H)-yl)ethyl)benzonitrile;

6-(2-(3,5-difluorophenyl)-2-hydroxyacetyl)-2-(1-phenylcyclopropyl)-5,6,7,8-tetrahydropyrido[4,3-d]pyrimidin-4(3H)-one; and 6-(2-hydroxy-2-(m-tolyl)acetyl)-2-(1-(thiophen-2-yl)cyclopropyl)-5,6,7,8-tetrahydropyrido[4,3-d]pyrimidin-4(3H)-one.

9. The compound according to claim 1, or a pharmaceutically acceptable salt, stereoisomer, or tautomer thereof, wherein the compound, stereoisomer or tautomer is selected from the group consisting of:

(R)-2-(1-(5-bromopyridin-3-yl)cyclopropyl)-6-(2-(3-chlorophenyl)-2-hydroxyacetyl)-5,6,7,8-tetrahydropyrido[4,3-d]pyrimidin-4(3H)-one;

(R)-2-(1-(3-bromophenyl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(5-bromopyridin-3-yl)cyclopropyl)-6-(2-hydroxy-2-(3-(trifluoromethyl)phenyl)acetyl)-5,6,7,8-tetrahydropyrido[4,3-d]pyrimidin-4(3H)-one;

(R)-2-(1-(4-bromothiophen-2-yl)cyclopropyl)-6-(2-(3-chlorophenyl)-2-hydroxyacetyl)-3,5,6,7,8,9-hexahydro-4H-pyrimido[5,4-c]azepin-4-one;

(R)-2-(1-(3-bromophenyl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(2-bromopyridin-4-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-2-(1-(6-bromopyridin-2-yl)cyclopropyl)-6-(2-hydroxy-2-(3-(trifluoromethyl)phenyl)acetyl)-3,5,6,7,8,9-hexahydro-4H-pyrimido[5,4-c]azepin-4-one;

(R)-6-(2-(3-bromophenyl)-2-hydroxyacetyl)-2-(1-phenylcyclopropyl)-5,6,7,8-tetrahydropyrido[4,3-d]pyrimidin-4(3H)-one;

(R)-6-(2-(3-bromophenyl)-2-hydroxyacetyl)-2-(1-(3-isopropylphenyl)cyclopropyl)-5,6,7,8-tetrahydropyrido[4,3-d]pyrimidin-4(3H)-one;

(R)-6-(2-(3-bromophenyl)-2-hydroxyacetyl)-2-(1-(5-isopropylpyridin-3-yl)cyclopropyl)-5,6,7,8-tetrahydropyrido[4,3-d]pyrimidin-4(3H)-one;

(R)-6-(2-(3-bromophenyl)-2-hydroxyacetyl)-2-(1-(3-chlorophenyl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-isopropylphenyl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(4-isopropylthiophen-2-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(5-isopropylpyridin-3-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(5-phenylpyridin-3-yl)cyclopropyl)-3,5,6,7,8,9-hexahydro-4H-pyrimido[5,4-c]azepin-4-one;

6-(2-(3-bromophenyl)acetyl)-2-(1-phenylcyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-cyclohexylphenyl)cyclopropyl)-3,5,6,7,8,9-hexahydro-4H-pyrimido[5,4-c]azepin-4-one;

6-(2-(3-bromophenyl)-2,2-difluoroacetyl)-2-(1-phenylcyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-chlorophenyl)cyclopropyl)-5,6,7,8-tetrahydropyrido[4,3-d]pyrimidin-4(3H)-one;

(R)-6-(2-(3-bromophenyl)-2-hydroxyacetyl)-2-(1-(thiophen-2-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(3-phenoxyphenyl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(4-phenylthiophen-2-yl)cyclopropyl)-3,5,6,7,8,9-hexahydro-4H-pyrimido[5,4-c]azepin-4-one;

6-(2-(3-bromophenyl)acetyl)-2-(1-(3-chlorophenyl)cyclopropyl)-3,5,6,7,8,9-hexahydro-4H-pyrimido[5,4-c]azepin-4-one;

2-(1-(3-bromophenyl)cyclopropyl)-6-(2-(3'-(trifluoromethyl)-[1,1'-biphenyl]-3-yl)acetyl)-3,5,6,7,8,9-hexahydro-4H-pyrimido[5,4-c]azepin-4-one;

(R)-6-(2-(3-bromophenyl)-2-hydroxyacetyl)-2-(1-(4-cyclohexylthiophen-2-yl)cyclopropyl)-3,5,6,7,8,9-hexahydro-4H-pyrimido[5,4-c]azepin-4-one;

(R)-6-(2-(3-bromophenyl)-2-hydroxyacetyl)-2-(1-(5-cyclohexylpyridin-3-yl)cyclopropyl)-3,5,6,7,8,9-hexahydro-4H-pyrimido[5,4-c]azepin-4-one;

6-(2-(3-bromophenyl)acetyl)-2-(1-(3-chlorophenyl)cyclopropyl)-5,6,7,8-tetrahydropyrido[4,3-d]pyrimidin-4(3H)-one;

2-(1-(3-bromophenyl)cyclopropyl)-6-(2-(3'-chloro-[1,1'-biphenyl]-3-yl)acetyl)-3,5,6,7,8,9-hexahydro-4H-pyrimido[5,4-c]azepin-4-one;

2-(1-(3-bromophenyl)cyclopropyl)-6-(2-(3'-(trifluoromethyl)-[1,1'-biphenyl]-3-yl)acetyl)-5,6,7,8-tetrahydropyrido[4,3-d]pyrimidin-4(3H)-one; and 2-(1-(3-bromophenyl)cyclopropyl)-6-(2-(3'-chloro-[1,1'-biphenyl]-3-yl)acetyl)-5,6,7,8-tetrahydropyrido[4,3-d]pyrimidin-4(3H)-one.

10. A pharmaceutical composition comprising a pharmaceutically acceptable carrier or excipient and a compound according to claim 1, or a pharmaceutically acceptable salt, stereoisomer, or tautomer thereof.

11. The pharmaceutical composition according to claim 10, wherein the pharmaceutical composition further comprises another pharmacologically active agent.

12. A method for antagonizing transient receptor potential 4 (TRPV4) activity in an animal or a human, wherein the method comprises administering to the animal or the human in need thereof a therapeutically effective amount of a compound according to claim 1, or a pharmaceutically acceptable salt, stereoisomer, or tautomer thereof.

13. The method according to claim 12, wherein the animal or the human suffers from at least one condition, disease, or disorder selected from the group consisting of algesia, cancer pain, a cluster and tension headache, chronic pain, fibromyalgia, an inflammatory disorder, irritable bowel syndrome, ischemia, an itch, migraine, a neuropathy, osteoarthritis, postoperative pain, a psychiatric disorder, pulmonary hypertension, rheumatoid arthritic pain, a stroke, a urological disease, and a urological disorder.

14. The method according to claim 13, wherein the inflammatory disorder is selected from the group consisting of asthma, chronic obstructive airway disease (COAD), chronic obstructive pulmonary disease (COPD), and inflammatory bowel disease, or a combination thereof.

15. The method according to claim 13, wherein the neuropathy is selected from the group consisting of a nerve injury, neuralgia, neurodegeneration, and neuropathic pain.

16. The method according to claim 15, wherein the neuropathy is diabetic neuropathy.

17. The method according to claim 13, wherein the psychiatric disorder is anxiety or depression.

18. The method according to claim 17, wherein the anxiety is anxiety caused by or related to another stress-related disorder.

19. The method according to claim 13, wherein the urological disease or urological disorder is selected from the group consisting of benign prostatic hyperplasia, detrusor hyperflexia, detrusor instability, detrusor overactivity, a lower urinary tract symptom, overactive bladder, and urinary incontinence, or a combination thereof.

20. The method according to claim 19, wherein the detrusor overactivity is idiopathic detrusor overactivity or neurogenic detrusor overactivity.

21. The method according to claim 12, wherein the animal or the human suffers from at least one condition, disease, or disorder selected from the group consisting of inflammation, pain, a urological disease, and a urological disorder.

22. A process for preparing the pharmaceutical composition according to claim 10, wherein the process comprises admixing a pharmaceutically acceptable carrier or excipient with a compound according to claim 1, or a pharmaceutically acceptable salt, stereoisomer, or tautomer thereof.

23. A compound or a pharmaceutically acceptable salt, stereoisomer, or tautomer thereof, wherein the compound, stereoisomer or tautomer is selected from the group consisting of:

(R)-2-(1-benzylcyclopropyl)-6-(2-(3-chlorophenyl)-2-hydroxyacetyl)-5,6,7,8-tetrahydropyrido[4,3-d]pyrimidin-4(3H)-one;

2-(1-benzylcyclopropyl)-6-(2-(2,3-difluorophenyl)-2-hydroxyacetyl)-5,6,7,8-tetrahydropyrido[4,3-d]pyrimidin-4(3H)-one;

(R)-6-(2-hydroxy-2-(4'-(pyridin-2-ylmethoxy)-[1,1'-biphenyl]-3-yl)acetyl)-2-(1-phenylcyclopropyl)-5,6,7,8-tetrahydropyrido[4,3-d]pyrimidin-4(3H)-one; and 6-(2-(4"-chloro-[1,1':4',1"-terphenyl]-3-yl)-2-hydroxyacetyl)-2-(1-phenylcyclopropyl)-5,6,7,8-tetrahydropyrido[4,3-d]pyrimidin-4(3H)-one.

* * * * *